US012319925B2

(12) United States Patent
Getts et al.

(10) Patent No.: US 12,319,925 B2
(45) Date of Patent: Jun. 3, 2025

(54) METHODS AND COMPOSITIONS FOR GENOMIC INTEGRATION

(71) Applicant: Myeloid Therapeutics, Inc., Cambridge, MA (US)

(72) Inventors: Daniel Getts, Stow, MA (US); Yuxiao Wang, Belmont, MA (US); Namita Bisaria, Somerville, MA (US); Inna Shcherbakova, Holliston, MA (US); Socheata Ly, North Billerica, MA (US)

(73) Assignee: MYELOID THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 18/157,052

(22) Filed: Jan. 19, 2023

(65) Prior Publication Data

US 2023/0141052 A1 May 11, 2023

Related U.S. Application Data

(63) Continuation of application No. PCT/US2022/028831, filed on May 11, 2022.

(60) Provisional application No. 63/274,907, filed on Nov. 2, 2021, provisional application No. 63/254,791, filed on Oct. 12, 2021, provisional application No. 63/187,117, filed on May 11, 2021.

(51) Int. Cl.

| | |
|---|---|
| ***C12N 15/85*** | (2006.01) |
| ***A61K 31/713*** | (2006.01) |
| ***C12N 15/90*** | (2006.01) |

(52) U.S. Cl.

CPC ............ *C12N 15/85* (2013.01); *A61K 31/713* (2013.01); *C12N 15/90* (2013.01); *C07K 2319/03* (2013.01); *C07K 2319/09* (2013.01); *C07K 2319/30* (2013.01); *C07K 2319/33* (2013.01); *C12N 2310/20* (2017.05); *C12N 2800/80* (2013.01); *C12N 2800/90* (2013.01); *C12N 2830/50* (2013.01); *C12N 2840/203* (2013.01)

(58) Field of Classification Search

CPC ........ C12N 15/85; C12N 9/1276; C12N 9/22; C12N 15/11; C12N 15/113; C12N 15/907; C12N 2310/14; C12N 2310/20; C12N 2320/31; C12N 2800/80; C12N 2800/90; C12N 2830/50; C12N 2840/203; A61K 31/711; A61K 31/713; A61K 38/1774; A61K 38/45; A61K 38/465; A61K 39/39558; A61K 48/00; C07K 14/7051; C07K 16/32; C07K 2319/03; C07K 2319/09; C07K 2319/30; C07K 2319/33; C12Y 207/07049

See application file for complete search history.

(56) References Cited

U.S. PATENT DOCUMENTS

| | | | |
|---|---|---|---|
| 4,470,461 | A | 9/1984 | Stapp |
| 4,522,811 | A | 6/1985 | Eppstein et al. |
| 5,122,464 | A | 6/1992 | Wilson et al. |
| 5,225,539 | A | 7/1993 | Winter |
| 5,571,894 | A | 11/1996 | Wels et al. |
| 5,580,859 | A | 12/1996 | Felgner et al. |
| 5,585,089 | A | 12/1996 | Queen et al. |
| 5,587,458 | A | 12/1996 | King et al. |
| 5,591,828 | A | 1/1997 | Bosslet et al. |
| 5,633,234 | A | 5/1997 | August et al. |
| 5,639,642 | A | 6/1997 | Kjeldsen et al. |
| 5,641,870 | A | 6/1997 | Rinderknecht et al. |
| 5,693,761 | A | 12/1997 | Queen et al. |
| 5,766,903 | A | 6/1998 | Sarnow et al. |
| 5,773,244 | A | 6/1998 | Ares, Jr. et al. |
| 5,776,910 | A | 7/1998 | Schreiber et al. |
| 5,869,046 | A | 2/1999 | Presta et al. |
| 6,150,160 | A | 11/2000 | Kazazian, Jr. et al. |
| 6,210,931 | B1 | 4/2001 | Feldstein et al. |
| 6,210,963 | B1 | 4/2001 | Haddada et al. |
| 6,248,516 | B1 | 6/2001 | Winter et al. |
| 6,455,299 | B1 | 9/2002 | Steinman et al. |
| 6,468,798 | B1 | 10/2002 | Debs et al. |
| 6,602,709 | B1 | 8/2003 | Albert et al. |
| 6,734,014 | B1 | 5/2004 | Hwu et al. |
| 6,806,080 | B2 | 10/2004 | Kasahara et al. |
| 6,936,468 | B2 | 8/2005 | Robbins et al. |
| 7,833,789 | B2 | 11/2010 | Naldini et al. |
| 7,926,300 | B2 | 4/2011 | Roberts et al. |
| 8,198,020 | B2 | 6/2012 | Francois et al. |
| 8,709,412 | B2 | 4/2014 | Jones et al. |
| 8,932,860 | B2 | 1/2015 | Rozwadowski et al. |
| 9,045,541 | B2 | 6/2015 | Eckelman et al. |
| 9,149,519 | B2 | 10/2015 | Landau et al. |
| 9,206,479 | B2 | 12/2015 | Maquat et al. |
| 9,221,908 | B2 | 12/2015 | Frazier et al. |
| 9,353,370 | B2 | 5/2016 | Carninci et al. |

(Continued)

FOREIGN PATENT DOCUMENTS

| | | |
|---|---|---|
| CA | 2850380 C | 8/2015 |
| CN | 1951499 A | 4/2007 |

(Continued)

OTHER PUBLICATIONS

Ade et al. Gene 2018, vol. 642, pp. 188-198. (Year: 2018).*

(Continued)

*Primary Examiner* — Michael D Burkhart

(74) *Attorney, Agent, or Firm* — Wilson Sonsini Goodrich & Rosati

(57) ABSTRACT

Methods and composition for modulating a target genome and stable integration of a transgene of interest into the genome of a cell are disclosed.

21 Claims, 70 Drawing Sheets

Specification includes a Sequence Listing.

(56) References Cited

U.S. PATENT DOCUMENTS 9,428,569 B2 8/2016 Spencer et al.
9,481,892 B2 11/2016 Schumann et al.
9,518,116 B2 12/2016 Frazier et al.
9,663,575 B2 5/2017 Eckelman et al.
9,745,368 B2 8/2017 Milone et al.
9,820,350 B2 11/2017 Pyshos et al.
9,845,345 B2 12/2017 Ring et al.
9,850,312 B2 12/2017 Agatsuma et al.
9,913,920 B2 3/2018 Movahedi et al.
10,034,900 B2 7/2018 Senju
10,081,680 B2 9/2018 Weiskopf et al.
10,106,609 B2 10/2018 Yang et al.
10,125,193 B2 11/2018 Cooper et al.
10,155,038 B2 12/2018 Rabinovich et al.
10,166,255 B2 1/2019 Moriarity et al.
10,172,880 B2 1/2019 Osborn et al.
10,174,095 B2 1/2019 Brogdon et al.
10,174,309 B2 1/2019 Grawunder
10,184,122 B2 1/2019 Grunenwald et al.
10,189,903 B2 1/2019 Jensen
10,214,591 B1 * 2/2019 Spadafora .............. C07K 16/34
10,259,859 B2 4/2019 Pons et al.
10,259,873 B2 4/2019 Frazier et al.
10,299,335 B2 5/2019 Pyshos et al.
10,415,017 B2 9/2019 O'Neill
10,428,143 B2 10/2019 Krummel et al.
10,602,584 B2 3/2020 Pyshos et al.
10,617,749 B1 4/2020 Hanks et al.
10,774,125 B2 9/2020 Ring et al.
10,925,944 B2 2/2021 De Vries et al.
10,980,836 B1 4/2021 Getts et al.
11,013,764 B2 5/2021 Getts et al.
11,026,973 B2 6/2021 Getts et al.
11,034,749 B2 6/2021 Gill et al.
11,041,023 B2 6/2021 Vale et al.
11,517,589 B2 12/2022 Wagner et al.
11,572,557 B2 2/2023 Velema et al.
11,672,874 B2 6/2023 Getts et al.
2002/0103152 A1 8/2002 Kay et al.
2002/0132224 A1 9/2002 Poznansky et al.
2003/0121063 A1 6/2003 Kazazian, Jr. et al.
2003/0130496 A1 7/2003 Winter et al.
2004/0053873 A1 3/2004 Barman et al.
2005/0031628 A1 2/2005 George et al.
2006/0018889 A1 1/2006 Li et al.
2006/0183226 A1 8/2006 Fujiwara et al.
2006/0188891 A1 8/2006 Bickmore, Jr. et al.
2007/0037759 A1 2/2007 Deininger et al.
2008/0254027 A1 10/2008 Bernett et al.
2011/0045591 A1 * 2/2011 Schumann ............. C12N 15/85
435/320.1
2011/0171729 A1 7/2011 Wang et al.
2011/0250203 A1 10/2011 Klitgaard et al.
2011/0287038 A1 11/2011 Slawin et al.
2011/0293603 A1 12/2011 Saraiva et al.
2012/0045389 A1 * 2/2012 Gassull Duro ........ C12N 15/86
977/773
2013/0280285 A1 10/2013 Schonfeld et al.
2014/0037606 A1 2/2014 Amiel
2014/0134142 A1 5/2014 Smith et al.
2014/0140989 A1 5/2014 Eckelman et al.
2014/0141046 A1 5/2014 Karlsson-Parra et al.
2014/0161805 A1 6/2014 Jamieson et al.
2014/0242701 A1 8/2014 Shiku et al.
2015/0057161 A1 2/2015 Schultze et al.
2015/0274826 A1 10/2015 Frazier et al.
2016/0038541 A1 2/2016 Stripecke et al.
2016/0045551 A1 2/2016 Brentjens et al.
2016/0137733 A1 5/2016 Frazier et al.
2016/0145348 A1 5/2016 Stephan
2016/0250258 A1 9/2016 Delaney et al.
2016/0251435 A1 9/2016 Eckelman et al.
2017/0087185 A1 3/2017 Crane et al.
2017/0151281 A1 6/2017 Wagner et al.
2017/0151282 A1 6/2017 Discher et al.
2017/0166657 A1 6/2017 O'Neill et al.
2017/0204422 A1 7/2017 Nelson et al.
2017/0226183 A1 8/2017 Schiffer-Mannioui
2017/0233452 A1 8/2017 Mcivor et al.
2017/0246278 A1 8/2017 Vera Valdes et al.
2017/0275665 A1 9/2017 Silas et al.
2017/0283498 A1 10/2017 Frazier et al.
2017/0292118 A1 10/2017 Duchateau et al.
2017/0369890 A1 12/2017 Henriksen
2018/0000899 A1 1/2018 Francois et al.
2018/0030553 A1 2/2018 Tang et al.
2018/0057592 A1 3/2018 Frazier et al.
2018/0104308 A1 4/2018 Mamonkin et al.
2018/0105600 A1 4/2018 Pons et al.
2018/0133252 A9 5/2018 Wilson et al.
2018/0135032 A1 5/2018 Izsvak et al.
2018/0142019 A1 5/2018 Manning et al.
2018/0155405 A1 6/2018 Ring et al.
2018/0171021 A1 6/2018 Karlsson et al.
2018/0186855 A1 7/2018 Rosenthal
2018/0186878 A1 7/2018 Rosenthal
2018/0221503 A1 8/2018 Kadiyala et al.
2018/0244748 A1 8/2018 Gill et al.
2018/0250395 A1 9/2018 Pietsch et al.
2018/0265890 A1 9/2018 Qian et al.
2018/0319883 A1 11/2018 Weiskopf et al.
2018/0325953 A1 11/2018 Poznansky et al.
2018/0334653 A1 11/2018 O'Neill
2018/0355011 A1 12/2018 Lim et al.
2019/0008897 A1 1/2019 Scatena et al.
2019/0010219 A1 1/2019 Short
2019/0023761 A1 1/2019 Pule et al.
2019/0038671 A1 2/2019 Fan et al.
2019/0040453 A1 2/2019 Bibillo et al.
2019/0055297 A1 2/2019 Zhao et al.
2019/0062450 A1 2/2019 De Palma et al.
2019/0070277 A1 3/2019 O'Neill et al.
2019/0112373 A1 4/2019 Manning et al.
2019/0119379 A1 4/2019 Gottschalk et al.
2019/0119396 A1 4/2019 Liu et al.
2019/0144522 A1 5/2019 Bari et al.
2019/0144863 A1 5/2019 Lee et al.
2019/0169266 A1 6/2019 Pons et al.
2019/0169637 A1 6/2019 Hudecek et al.
2019/0169638 A1 6/2019 Izsvak et al.
2019/0185880 A1 6/2019 Shedlock et al.
2019/0233496 A1 8/2019 Rosenthal
2019/0240343 A1 8/2019 Ahmed et al.
2019/0248892 A1 8/2019 Frazier et al.
2019/0263928 A1 8/2019 Watanabe et al.
2019/0275150 A1 9/2019 Pincetic et al.
2019/0323037 A1 10/2019 Buerckstuemmer et al.
2019/0336615 A1 11/2019 Thompson et al.
2019/0345217 A1 11/2019 Ma et al.
2019/0381158 A1 12/2019 Gunn
2020/0101147 A1 4/2020 Zeng
2020/0109398 A1 * 4/2020 Rubens ................ C12N 15/102
2020/0239592 A1 7/2020 Vale et al.
2020/0247870 A1 8/2020 Gill et al.
2020/0345773 A1 11/2020 Getts et al.
2020/0345774 A1 11/2020 Getts et al.
2020/0390072 A1 12/2020 Kotin et al.
2021/0002377 A1 1/2021 Brogdon et al.
2021/0038702 A1 2/2021 De Vries et al.
2021/0046110 A1 2/2021 Gill et al.
2021/0095001 A1 4/2021 Gill et al.
2021/0222163 A1 7/2021 Wu et al.
2021/0252053 A1 8/2021 Wagner et al.
2021/0277140 A1 9/2021 Vale et al.
2021/0285009 A1 9/2021 Schaffer et al.
2021/0299172 A1 9/2021 Getts et al.
2021/0361703 A1 11/2021 Getts et al.
2022/0000917 A1 1/2022 Klichinsky et al.
2022/0000918 A1 1/2022 Klichinsky et al.
2022/0001021 A1 1/2022 Uhl et al.
2022/0001031 A1 1/2022 Getts et al.
2022/0002375 A1 1/2022 Gill et al.
2022/0002376 A1 1/2022 Gill et al.
2022/0002377 A1 1/2022 Gill et al.

(56) References Cited

U.S. PATENT DOCUMENTS

| | | | |
|---|---|---|---|
| 2022/0002675 | A1 | 1/2022 | Klichinsky et al. |
| 2022/0033465 | A1 | 2/2022 | Gill et al. |
| 2022/0033466 | A1 | 2/2022 | Gill et al. |
| 2022/0033467 | A1 | 2/2022 | Gill et al. |
| 2022/0033468 | A1 | 2/2022 | Gill et al. |
| 2022/0041688 | A1 | 2/2022 | Gill et al. |
| 2022/0073639 | A1 | 3/2022 | Ruella et al. |
| 2022/0098273 | A1 | 3/2022 | Corey |
| 2022/0118010 | A1 | 4/2022 | Wagner et al. |
| 2022/0152199 | A1 | 5/2022 | Getts et al. |
| 2022/0175830 | A1 | 6/2022 | Wagner et al. |
| 2022/0175831 | A1 | 6/2022 | Wagner et al. |
| 2022/0184230 | A1 | 6/2022 | Getts et al. |
| 2022/0202856 | A1 | 6/2022 | Wagner et al. |
| 2022/0233586 | A1 | 7/2022 | Wagner et al. |
| 2022/0241428 | A1 | 8/2022 | Getts et al. |
| 2022/0364110 | A1 | 11/2022 | Getts et al. |
| 2022/0378824 | A1 | 12/2022 | Getts et al. |
| 2022/0411817 | A1 | 12/2022 | Getts et al. |
| 2023/0046472 | A1 | 2/2023 | Getts et al. |
| 2023/0277659 | A1 | 9/2023 | Getts et al. |
| 2023/0364265 | A1 | 11/2023 | Getts et al. |
| 2023/0364266 | A1 | 11/2023 | Getts et al. |

FOREIGN PATENT DOCUMENTS

| | | | | |
|---|---|---|---|---|
| EP | 0404097 | A2 | 12/1990 | |
| EP | 0338841 | B1 | 3/1995 | |
| EP | 2205750 | B1 | 3/2012 | |
| EP | 2626415 | A2 | 8/2013 | |
| EP | 2953643 | A1 | 12/2015 | |
| EP | 2242512 | B1 | 4/2016 | |
| EP | 3197495 | A1 | 8/2017 | |
| EP | 3328402 | A1 | 6/2018 | |
| EP | 3350335 | A1 | 7/2018 | |
| EP | 3414333 | A1 | 12/2018 | |
| EP | 3504244 | A1 | 7/2019 | |
| EP | 3519441 | A1 | 8/2019 | |
| EP | 3574018 | A2 | 12/2019 | |
| EP | 4025686 | A2 | 7/2022 | |
| EP | 4337268 | A1 | 3/2024 | |
| GB | 2572005 | A | 9/2019 | |
| WO | WO-9201813 | A1 | 2/1992 | |
| WO | WO-9301161 | A1 | 1/1993 | |
| WO | WO-9425591 | A1 | 11/1994 | |
| WO | WO-9505835 | A1 | 3/1995 | |
| WO | WO-1995005835 | A1 | 3/1995 | |
| WO | WO-02077029 | A2 | 10/2002 | |
| WO | WO-2004050855 | A2 | 6/2004 | |
| WO | WO-2004072290 | A1 | 8/2004 | |
| WO | WO-2006069812 | A2 * | 7/2006 | ............. A61P 35/00 |
| WO | WO-2007113572 | A1 | 10/2007 | |
| WO | WO-2008011599 | A2 | 1/2008 | |
| WO | WO-2009056321 | A1 | 5/2009 | |
| WO | WO-2012005763 | A1 | 1/2012 | |
| WO | WO-2012170930 | A1 | 12/2012 | |
| WO | WO-2013123088 | A1 | 8/2013 | |
| WO | WO-2013185552 | A1 | 12/2013 | |
| WO | WO-2014055668 | A1 | 4/2014 | |
| WO | WO-2014123580 | A1 | 8/2014 | |
| WO | WO-2014153114 | A1 | 9/2014 | |
| WO | WO-2016030501 | A1 * | 3/2016 | ......... A61K 48/0058 |
| WO | WO-2016033331 | A1 | 3/2016 | |
| WO | WO-2016040441 | A1 | 3/2016 | |
| WO | WO-2016049641 | A1 | 3/2016 | |
| WO | WO-2016070136 | A1 | 5/2016 | |
| WO | WO-2016126213 | A1 | 8/2016 | |
| WO | WO-2016126608 | A1 | 8/2016 | |
| WO | WO-2016138491 | A1 | 9/2016 | |
| WO | WO-2016149254 | A1 | 9/2016 | |
| WO | WO-2016172606 | A1 | 10/2016 | |
| WO | WO-2016205749 | A1 | 12/2016 | |
| WO | WO-2017019848 | A1 | 2/2017 | |
| WO | WO-2017025944 | A2 | 2/2017 | |
| WO | WO-2017044487 | A1 | 3/2017 | |
| WO | WO-2017050884 | A1 | 3/2017 | |
| WO | WO-2017136633 | A1 | 8/2017 | |
| WO | WO-2017172981 | A2 | 10/2017 | |
| WO | WO-2017219027 | A1 | 12/2017 | |
| WO | WO-2017219934 | A1 | 12/2017 | |
| WO | WO-2018038684 | A1 | 3/2018 | |
| WO | WO-2018064076 | A1 | 4/2018 | |
| WO | WO-2018073394 | A1 | 4/2018 | |
| WO | WO-2018083126 | A1 | 5/2018 | |
| WO | WO-2018107129 | A1 | 6/2018 | |
| WO | WO-2018140831 | A3 | 8/2018 | |
| WO | WO-2018169948 | A1 | 9/2018 | |
| WO | WO-2018170340 | A1 | 9/2018 | |
| WO | WO-2018231871 | A1 | 12/2018 | |
| WO | WO-2019005641 | A1 | 1/2019 | |
| WO | WO-2019010551 | A1 | 1/2019 | |
| WO | WO-2019020089 | A1 | 1/2019 | |
| WO | WO-2019020090 | A1 | 1/2019 | |
| WO | WO-2019032624 | A1 | 2/2019 | |
| WO | WO-2019050948 | A1 | 3/2019 | |
| WO | WO-2019051424 | A2 | 3/2019 | |
| WO | WO-2019055946 | A1 | 3/2019 | |
| WO | WO-2019067328 | A1 | 4/2019 | |
| WO | WO-2019070704 | A1 | 4/2019 | |
| WO | WO-2019070843 | A1 | 4/2019 | |
| WO | WO-2019086512 | A1 | 5/2019 | |
| WO | WO-2019090175 | A1 | 5/2019 | |
| WO | WO-2019129146 | A1 | 7/2019 | |
| WO | WO-2019191332 | A1 | 10/2019 | |
| WO | WO-2019191334 | A1 | 10/2019 | |
| WO | WO-2019191340 | A1 | 10/2019 | |
| WO | WO-2019201995 | A1 | 10/2019 | |
| WO | WO-2020006049 | A1 | 1/2020 | |
| WO | WO-2020047124 | A1 | 3/2020 | |
| WO | WO-2020095044 | A1 | 5/2020 | |
| WO | WO-2020097193 | A1 | 5/2020 | |
| WO | WO-2020131662 | A1 | 6/2020 | |
| WO | WO-2020131862 | A1 | 6/2020 | |
| WO | WO-2020150534 | A9 * | 8/2020 | ............. A61K 35/17 |
| WO | WO-2020223550 | A1 | 11/2020 | |
| WO | WO-2020252208 | A2 | 12/2020 | |
| WO | WO-2020257727 | A1 | 12/2020 | |
| WO | WO-2021016075 | A1 | 1/2021 | |
| WO | WO-2021046243 | A2 | 3/2021 | |
| WO | WO-2021102042 | A1 | 5/2021 | |
| WO | WO-2021119538 | A1 | 6/2021 | |
| WO | WO-2021178709 | A1 | 9/2021 | |
| WO | WO-2021178717 | A2 | 9/2021 | |
| WO | WO-2021178720 | A2 | 9/2021 | |
| WO | WO-2021178898 | A1 | 9/2021 | |
| WO | WO-2021263152 | A1 | 12/2021 | |
| WO | WO-2022036265 | A1 | 2/2022 | |
| WO | WO-2022067033 | A1 | 3/2022 | |
| WO | WO-2022241029 | A1 | 11/2022 | |

OTHER PUBLICATIONS

Kines et al. Mobile DNA vol. 7, Article No. 8 (2016) (Year: 2016).*

Ade et al.: Evaluating different DNA binding domains to modulate L1 ORF2p-driven site-specific retrotransposition events in human cells. Gene. (2018); 642:188-198. Epub (2018).

Ahl et al.: Retrotransposition and Crystal Structure of an Alu RNP in the Ribosome-Stalling Conformation. Mol Cell. 60(5):715-727 doi:10.1016/j.molcel.2015.10.003 (2015).

Ali et al.: Induction of neoantigen-reactive T cells from healthy donors. Nature Protocols (2019).

Altschul et al., Basic local alignment search tool. J. Mol. Biol. 215:403-410 (1990).

Alvey el al.: SIRPA-Inhibited, Marrow-Derived macrophages engorge, accumulate, and differentiate in Antibody-Targeted regression of solid tumors. Current Biology 27:2065-2077 (2017).

Alvey et al. Engineering macrophages to eat Cancer: from "marker of self" CD47 and phagocytosis to differentiation. Journal of Leukocyte Biology 102:31-40 (2017).

Ancuta et al.: (BMC Genomics 10:403, pp. 1-19 (2009 )).

Andreesen et al.: Adoptive transfer of tumor cytotoxic macrophages generated in vitro from circulating blood monocytes: a new approach to Cancer immunotherapy. Cancer Research 50:7450-7456 (1990).

(56) References Cited

OTHER PUBLICATIONS

Andreu el al.: Primary macrophages and J774 cells respond differently to infection with *Mycobacterium tuberculosis*. Scientific Reports 7:42225 (2017).
Application as filed for U.S. Appl. No. 17/202,018, filed Mar. 15, 2021.
Auffray et al.: Blood monocytes: development, heterogeneity, and relationship with dendritic cells, Annual Rev. Immunol. 27:669-92 (2009).
Batista et al.: B cells acquire antigen from target cells after synapse formation. Nature 411:489-494 (2001).
Baxter et al.: Engineering domain fusion chimeras from I-Onul family LAGLIDADG homing endonucleases. Nucleic Acids Res. 40(16):7985-8000 doi:10.1093/nar/gks502 (2012).
Beck et al.: LINE-1 Elements in Structural Variation and Disease. Annual Review of Genomics and Human Genetics vol. 12:187-215 (Volume publication date Sep. 2011). https://doi.org/10.1146/annurev-genom-082509-141802.
Beningo et al.: Fc-receptor-mediated phagocytosis is regulated by mechanical properties of the target. Journal of Cell Science 115:849-856 (2002).
Benton et al.: Screening lambdagt recombinant clones by hybridization to single plaques in situ. Science. 196(4286):80-182 (1977).
Berger et al.: Efficient Elutriation of monocytes within a closed system (Elutra ™). Journal of Immunological Methods 298:61-72 (2005).
Bhattacharjee et al.: Monocytes isolated by positive and negative magnetic sorting techniques show different molecular characteristics and immunophenotypic behaviour. F100Research p. 1-13 (2018).
Biglari et al.: Human monocytes expressing a CEA-specific chimeric CD64 receptor specifically target CEA-expressing tumour cells in vitro and in vivo. Gene Therapy 13, 602-610 (2006).
Blumenthal et al.: Development and Characterization of Chimeric Antigen Receptor Monocytes (CAR Mono), a Novel Cell Therapy Platform for Solid Tumor Immunotherapy. Poster Presentation. Society for Immunotherapy of Cancer (SITC) Meeting, Washington, DC, United States (2021). https://secureservercdn.net/45.40.149.113/74d.fcf.myftpupload.com/wp-content/uploads/2021/11/Poster-104-Daniel-Blumenthal-Carisma-Therapeutics.pdf.
Blumenthal et al.: Pre-clinical development of CAR Monocytes (CAR Mono) for solid tumor immunotherapy. Poster Presentation. The American Association for Cancer Research (AACR) Annual Meeting, New Orleans, LA, United States (2022) https://secureservercdn.net/45.40.149.113/74d.fcf.myftpupload.com/wp-content/uploads/2022/07/Poster-5000-Daniel-Blumenthal-Carisma-Therapeutics.pdf.
Bournazos et al.: The Role and Function of Fcy Receptors on Myeloid Cells. Microbiol Spectr 4(6) (2016).
Brooks et al.: Binding of cytoplasmic proteins to the CD19 intracellular domain is high affinity, competitive, and multimeric. The Journal of Immunology 172:7556-7564 (2004).
Bu el al.: Analysis of the interaction of ZAP-70 and syk protein-tyrosine kinases with the T-cell antigen receptor by plasmon resonance. PNAS 92:5106-5110 (1995).
Bucheton et al.: The molecular basis of I-R hybrid Dysgenesis in drosophila melanogaster: Identification, cloning, and properties of the I factor. 38(1):153-163 (1984). Abstract. DOI: https://doi.org/10.1016/0092-8674(84)90536-1.
Burgueño-Bucio E. et al.: The multiple faces of CD5. J Leukoc Biol. 105(5):891-904. Epub (2019).
Calderwood, David: Integrin Activation. Journal of Cell Science 117:657-666 (2004).
Callahan et al.: Polymerization and nucleic acid-binding properties of human L1 ORF1 protein. Nucleic Acids Research 40(2):813-827 (2012).
Cebrian-Serrano et al.: CRISPR-Cas orthologues and variants: optimizing the repertoire, specificity and delivery of genome engineering tools. Mammalian Genome 28:247-261 (2017).
Chadwick et al.: Safety of a single aerosol administration of escalating doses of the cationic lipid GL-67/DOPE/DMPE-PEG5000 formulation to the lungs of normal volunteers. Gene Therapy 4(9):937-42 (1997). doi: 10.1038/sj.gt.3300481.
Chao et al.: Anti-CD47 antibody synergizes with rituximab to promote phagocytosis and eradicate non-Hodgkin lymphoma. Cell 142:699-713 (2010).
Chen et al.: Functional Interrogation of Primary Human T Cells via CRISPR Genetic Editing. The Journal of Immunology 201:1586-1598 (2018).
Chen et al.: SLAMF7 is critical for phagocytosis of haematopoietic tumour cells via Mac-1 integrin. Nature 544:493-497 (2017).
Christian et al.: Involvement of Conserved Amino Acids in the C-Terminal Region of LINE-1 ORF2p in Retrotransposition. Genetics 205(3):1139-1149 (2017). Epub (2017).
Corresponding PCT Application No. PCT/US2019/060052, filed Nov. 6, 2011.
Cros et al.: Human CD14dim) Monocytes Patrol and Sense Nucleic Acids and viruses via TLR7 and TLR8 Receptors. Immunity 33:375-386, (2010).
Cross et al.: Nanomechanical analysis of cells from cancer patients. Nature Nanotechnology 2:780-783 (2007).
Daeron et al.: Fc Receptors. Current Topics in Microbiology and Immunology, vol. 382 (2014).
Davis et al.: The kinetic-segregation model: TCR triggering and beyond. Nature Immunology 7:803-809 (2006).
De Kleer et al.: Ontogeny of myeloid cells. frontiers in Immunology 5(423):1-11 (2014).
De Koning et al.: Repetitive Elements May Comprise Over two= Thirds of the Human Genome. PLoS 7(2) 1-12 (2011).
De Oliveria et al.: Modification of Hematopoietic Stem/Progenitor Cells with CD19-Specific Chimeric Antigen Receptros as a Novel Approach for Cancer Immunotherapy. Human Gene Therapy 24:824-839 (2013).
Deininger: Alu elements: know the SINEs. Genome Biol. 12(12):236, pp. 1-21 doi:10.1186/GB-2011-12-12-236 (2011).
Devereux et al., A comprehensive set of sequence analysis programs for the VAX. Nucleic Acids Res. Jan. 11, 1984;12(1 Pt 1):387-95.
Dewannieux et al.: Endogenous retroviruses: acquisition, amplification and taming of genome invaders. Science Direct, Current Opinion in Virology 3:646-656 (2013).
Dewannieux et al.: L1-mediated Retrotransposition of Murine B1 and B2 SINEs Recapitulated in Cultured Cells. J. Mol. Bio. 349:241-247 (2005).
Dewannieux et al.: LINE-mediated retrotransposition of marked Alu sequences. Nature Genetics 35(1):41-48 (2003).
Dong et al.: LINE-Like Retrotransposition in Saccharomyces cerevsiae. The Genetics Society of America (2008). DOI: 10.1534/genetics.108.096636.
Dotti et al. Design and Development of Therapies using Chimeric Antigen Receptor-Expressing T cells. Immunol Rev. 257(1):35 pgs (2014).
Doucet et al.: A 3' Poly(A) Tract Is Required for LINE-1 Retrotransposition. Mol Cell 60(5):728-741 doi:10.1016/j.molcel.2015.10.012 (2015).
Douse et al.: TASOR is a pseudo-PARP that directs HUSH complex assembly and epigenetic transposon control. Nature Communications 11(4940):1-16 (2020).
Edelstein et al.: Computer control of microscopes using mmanager. Current Protocols in Molecular Biology 14:14.20 (2010).
Eickbush et al.: Evolution of the R2 Retrotransposon Ribozyme and Its self-Cleavage Site. PLoS 8(9): 1-16 (2013).
Engel et al.: Abnormal B lymphocyte development, activation, and differentiation in mice that lack or overexpress the CD19 signal transduction molecule. Immunity 3:39-50 (1995).
Faulkner et al.: L1 retrotransposition in the soma: a field jumping ahead. Mob DNA 9:22, pp. 1-18 doi:10.1186/s13100-018-0128-1 (2018).
Fesnak et al.: Engineered T cells: the promise and challenges of cancer immunotherapy. Nature Reviews Cancer 16:566-581 (2016).
Final Office Action issued in counterpart U.S. Appl. No. 17/499,232 dated Dec. 8, 2022.
Final Office Action issued in counterpart U.S. Appl. No. 17/499,232 dated Jul. 7, 2022.
Fingl et al.: Chapter 1: General Principles. The Pharmacological Basis of Therapeutics (49 pgs) (1975).

(56) References Cited

OTHER PUBLICATIONS

Floor et al.: Get in LINE: Competition for Newly Minted Retrotransposon Proteins at the Ribosome. Molecular Cell 60(5):712-714 http://dx.doi.org/10.1016/j.molcel.2015.11.014 (2015).
Flynn et al.: Mammalian Y RNAs are modified at discrete guanosine residues with N-glycans. bioRxiv 787614 doi:https://doi.org/10.1101/787614 [1-31] (2019).
Fraser et al.: Development, functional characterization and validation of methodology for GMP-compliant manufacture of phagocytic macrophages: A novel cellular therapeutic for liver cirrhosis. Cyotherapy ISSN 1465-3249 (2017).
Frassinelli et al.: The RNA editing enzyme ADAR2 restricts L1 mobility. RNA Biol, pp. 1-13 doi:10.1080/15476286.2021.1940020 (2021).
Freeman et al.: Integrins Form an Expanding Diffusional Barrier that Coordinates Phagocytosis. Cell 164:128-140 (2016).
Freeman et al.: Phagocytosis: receptors, signal integration, and the cytoskeleton. Immunological Reviews 262:193-215 (2014).
Fujiwara et al.: Site-specific non-LTR retrotransposons. Microbiology Spectrum, p. 1-16 (2014).
Gabitova et al.: Anti-HER2 CAR monocytes demonstrate targeted anti-tumor activity and enable a single day cell manufacturing process. Poster Presentation. The American Association for Cancer Research (AACR) Annual Meeting, Philadelphia, PA, United States (2021). https://secureservercdn.net/45.40.149.113/74d.fcf.myftpupload.com/wp-content/uploads/2021/09/Anti-HER2-CAR-monocytes_AACR2021.pdf.
Gao et al.: Cationic liposome-mediated gene transfer. Gene Therapy 2(10):710-722 (1995). Abstract.
Gardai et al.: Cell-surface calreticulin initiates clearance of viable or apoptotic cells through trans-activation of LRP on the phagocyte. Cell 123:321-334 (2005).
Geissmann et al.: Blood Monocytes Consist of Two Principal Subsets with Distinct Migratory Properties. Immunity (19):71-82 (2003).
Getts et al.: Harnessing nanoparticles for immune modulation. Trends Immunol 36(7):419-427 (2015).
Getts et al.: Microparticles bearing encephalitogenic peptides induce T-cell tolerance and ameliorate experimental autoimmune encephalomyelitis. Nat Biotechnol 30(12):1217-1224 (2012).
Goddard et al.: A second dose of a CFTR cDNA-liposome complex is as effective as the first dose in restoring cAMP-dependent chloride secretion to null CF mice trachea. Gene Therapy 4:1231-1236 (1997).
Gokhale et al.: Antisense raf oligodeoxyribonucleotide is protected by liposomal encapsulation and inhibits Raf-1 protein expression in vitro and in vivo: implication for gene therapy of radioresistant cancer. Gene Therapy 4:1289-1299 (1997).
Gordon: Phagocytosis: An Immunobiologic Process. Immunity 44 (2016).
Gorman et al.: Efficient in vivo delivery of DNA to pulmonary cells using the novel lipid EDMPC. Gene Therapy 4:983-992 (1997).
Goudot et al.: Aryl Hydrocarbon Receptro Controls Monocyte Differentiation into Dendritic Cells versus Macrophages. Immunity 47: 582-596 (2017).
Grechishnikova et al.: Conserved 3' UTR stem-loop structure in L1 and Alu transposons in human genome: possible role in retrotransposition. BMC Genomics 17(1):992, pp. 1-17 doi:10.1186/s12864-016-3344-4 (2016).
Grunstein et al.: Colony hybridization: a method for the isolation of cloned DNAs that contain a specific gene. Proc Natl Acad Sci 72, (10):3961-3965 (1975).
Guatelli et al.: Isothermal, in vitro amplification of nucleic acids by a multienzyme reaction modeled after retroviral replication. Proc Natl Acad. Sci. 87(5)1874-1878 (1990).
Hackett et al.: A Transposon and Transposase System for Human Application. Mol Ther. 18(4):674-683 doi:10.1038/mt.2010.2 (2010).
Han et al.: Development of miniature base editors using engineered IscB nickase. Nature Methods (2022). https://doi.org/10.1038/s41592-023-0189809.
Harburger et al.: Integrin signalling at a glance. Journal of Cell Sciences 122 (2009).
Harland et al.: Stability of RNA in developing Xenopus embryos and identification of a destabilizing sequence in TFIIIA messenger RNA. Development 102(4):837-852 (1988).
Harshyne et al.: A Role for Class A Scavenger Receptor in Dendritic Cell Nibbling from Live Cells. The Journal of Immunology 170:2302-2309 (2003).
Harshyne et al.: Dendritic cells acquire antigens from live cells for Cross-Presentation to CTL. The Journal of Immunology 166:3717-3723 (2001).
Haso et al.: Anti-CD22-chimeric antigen receptors targeting B-cell precursor acute lymphoblastic leukemia. Blood 121:1165-1174 (2013).
Hollinger P. et al.: Diabodies: small bivalent and bispecific antibody fragments. Proc Natl Acad Sci 90(14):6444-6448 (1993).
Hsu et al.: Electron microscopic evidence for the circular form of RNA in the cytoplasm of eukaryotic cells. Nature 280:339-340 (1979).
Huang et al.: Antigen-loaded monocyte administration induces potent therapeutic antitumor T cell responses, The Journal of Clinical Investigation, p. 1-15 (2020).
Hudson et al.: Engineered antibodies. Nature Medicine 9(1):129-134 (2003).
Hui et al.: In vitro membrane reconstitution of the T-cell receptor proximal signaling network. Nature Structural & Molecular Biology 21:133-142 (2014).
Hui et al.: T cell constimulatory receptor CD28 is a primary target for PD-1-mediated inhibition. Science 355(6332):1428-1433 (2017).
Ingersoll et al.: Brief Report: Pilot Randomized Controlled Trial of Reciprocal Imitation Training for Teaching Elicited and Spontaneous Imitation to Children with Autism, J Autism Dev Disord 40(9):1154-1160 (2010).
Italiani et al.: From Monocytes to M1/M2 Macrophages: Phenotypical vs. Functional Differentiation. Front Immunol 17(5):514 (2014).
Ivancevic et al.: LINEs between Species: Evolutionary Dynamics of LINE-1 Retrotransposons across the Eukaryotic Tree of Life. Genome Biology and Evolution 8(11):3301-3322 (2016). https://doi.org/10.1093/gbe/evw243.
Ivic et al.: Molecular Reconstruction of Sleeping Beauty, a Tc1-like Transposon from Fish, and Its Transposition in Human Cells. Cell 91:501-510 (1997).
Ivics et al.: Transposon-medicated Genome Manipulations in Vertebrates. Nat Methods 6(6):415-422 (2009).
Jadus et al.: Macrophages can recognize and kill tumor cells bearing the membrane isoform of macrophage colony-stimulating factor. Blood 87:5232-5241 (1996).
Jaeger et al.: TectoRNA: modular assembly units for the construction of RNA nano-objects. Nucleic Acids Res. 29(2):455-463 doi:10.1093/nar/29.2.455 (2001).
Jaiswal et al.: CD47 is upregulated on circulating hematopoietic stem cells and leukemia cells to avoid phagocytosis. Cell 138:271-285 (2009).
Jamburuthugoda et al.: Identification of RNA binding motifs in the R2 retrotransposon-encoded reverse transcriptase. Nucleic Acids Res. 42(13):8405-8415 doi: 10.1093/nar/gku514 (2014).
James et al.: Biophysical mechanism of T-cell receptor triggering in a reconstituted system. Nature 487:64-69 (2012).
Jarrosson-Wuilleme et al.: Transduction of nondividing human macrophages with gammaretrovirus-derived vectors. J Virol. 80(3):1152-1159 doi:10.1128/JVI.80.3.1152-1159.2006 (2006).
Jeck et al.: Circular RNAs are abundant, conserved, and associated with ALU repeats. RNA 19:41-157 (2013).
Joly et al.: What is trogocytosis and what is its purpose? Nature Immunology 4:815 (2003).
Kamber et al.: Inter-cellular CRISPR screens reveal regulators of cancer cell phagocytosis. Nature 597(7877):549-554 doi:10.1038/s41586-021-03879-4 (2021).
Kao et al.: The role of the laminin beta subunit in laminin heterotrimer assembly and basement membrane function and development in C. elegans. Developmental Biology 290:211-219 (2006).
Kapitonov et al.: ISC, a Novel Group of Bacterial and Archaeal DNA Transposons That Encode Cas9 Homologs. Journal of Bac-

(56) References Cited

OTHER PUBLICATIONS teriology, American Society for Microbiology 198:5 (2022). DOI: https://doi.org/10.1128/jb.00783-15.
Khazina et al.: Human LINE-1 retrotransposition requires a metastable coiled coil and a positively charged N-terminus in L1ORF1p. Elife 7:e34960 (2018).
Kievits et al.: NASBATM isothermal enzymatic in vitro nucleic acid amplification optimized for the diagnosis of HIV-1 infection. J. Virol. Methods 35:273-286 (1991).
Kim et al.: Monocyte Enrichment from Leukapheresis products by using the Elutra cell separator. Transfusion 47:2290-2296 (2007).
Kimmel et al.: Preparation of cDNA and the generation of cDNA libraries: overview. Methods Enzymol 152:307-316 (1987).
Kines KJ. et al., The endonuclease domain of the LINE-1 ORF2 protein can tolerate multiple mutations. Mob DNA. Apr. 19, 2016;7:8.
Kinsey, J. A.: Tad, a LINE-Like Transposable Element of Neurospora, Can Transpose Between Nuclei in Heterokaryons. Genetics 126:317-326 (1990).
Klichinsky et al.: Human chimeric antigen receptor macrophages for cancer immunotherapy. Nat Biotechnol. 38(8):947-953 (2020); Epub (2020).
Klichinsky M. et al., "CAR-Macrophage for Cancer Immunotherapy: Latest Findings from the CT-0508 Clinical Trial" YouTube, https://youtu.be/2Ag7SVM-fPg, published Jun. 27, 2022, https://carismatx.com/programs/ct-0508/.
Kochenderfer et al.: Construction and preclinical evaluation of an anti-CD19 chimeric antigen receptor. Journal of Immunotherapy 32:689-702 (2009).
Kowalski et al.: Delivering the Messenger: Advances in Technologies for Therapeutic mRNA Delivery. Mol. Ther 27(4):710-728 (2019).
Kwoh et al.: Transcription-based amplification system and detection of amplified human immunodeficiency virus type 1 with a bead-based sandwich hybridization format. Proc Natl Acad Sci 86(4):1173-1177 (1989).
Lacerna et al.: Adoptive cancer immunotherapy utilizing lymphokine activated killer cells and gamma interferon activated killer monocytes. Pharmacology & Therapeutics 38:453-465 (1988).
Laird et al.: (J. Leukocyte Biology 85: 966-977 (2009)).
Larson et al.: Spliced integrated retrotransposed element (SpIRE) formation in the human genome. PLoS Biology 16(3):e2003067, pp. 1-37 (2018).
Lee et al.: Macrophage-based cell therapies: the long and winding road. Journal of Controlled Release 240:527-540 (2016).
Levine et al.: Global Manufacturing of CAR T Cell Therapy. Mol Ther Methods Clin Dev. 4:92-101 (2016).
Lim, et al., "Antisense oligonucleotide modulation of non-productive alternative splicing upregulates gene expression" (2020) Nature Communication.
Lim et al.: The Principles of Engineering Immune Cells to Treat Cancer. Cell 168:724-740 (2017).
Liu et al.: CD47 blockade triggers T cell-mediated destruction of immunogenic tumors. Nature Medicine 21:1209-1215 (2015).
Liu et al.: Ouroboros resembling competitive endogenous loop (ORCEL) in revealed through transcriptome sequencing dataset analysis. BMC Genomics 19(Suppl 2):171, pp. 87-95 doi:10.1186/s12864-018-4456-9 (2018).
Liu Q et al.: Nuclear localization of the ORF2 protein encoded by porcine circovirus type 2. Virology 285(1):91-9 (2001).
Lloyd et al. Modelling the human immune response: performance of a 1011 human antibody repertoire against a broad panel of therapeutically relevant antigens. Protein Eng Des Sel 22(3):159-168 (2009).
Loannidi et al.: Drag-and-drop genome insertion without DNA cleavage with CRISPR-directed integrases. bioRxiv (2021). doi: https://doi.org/10.1101/2021.11.01.466786.
Luan et al.: Reverse Transcription of R2Bm RNA Is Primed by a Nick at the Chromosomal Target Site: A Mechanism for Non-LTR Retrotransposition Cell 72:595-605 (1993).
Macia et al.: Engineered LINE-1 retrotransposition in nondividing human neurons. Genome Res. 27(3):335-348 doi:10.1101/gr.206805.116 (2017).
Majeti et al.: CD47 is an adverse prognostic factor and therapeutic antibody target on human acute myeloid leukemia stem cells. Cell 138:286-299 (2009).
Manoj et al: Targeted insertion of large genetic payloads using ca directed LINE-1 reverse transcriptase. Scientific Reports—Nature Portfolio p. 1-9 (2021).
Matsuyoshi et al.: Enchanced Priming of Antigen-Specific CTL's In Vivo by Embryonic Stem Cell-Derived Dendritic Cells Expressing Chemokine Along with Antigenic Protein: Application to Antitumor Vaccination. The Journal of Immunology 172:776-786 (2004).
Mayordomo et al.: Bone marrow-derived dendritic cells pulsed with synthetic tumour peptides elicit protective and therapeutic antitumour immunity. Nature Medicine 1:1297-1302 (1995).
Mccaffrey et al.: RNA Interference in Adult Mice. Nature 418:38-39 (2002).
Mcever et al.: Selectins: initiators of leucocyte adhesion and signalling at the vascular wall. Cardovascular Research 107:331-339 (2015).
Medzihradszky, K.F.: Lessons in de novo peptide sequencing by tandem mass spectrometry. Mass Spectrom Rev 34(1):43-63 (2015).
Memczak et al.: Circular RNAs are a large class of animal RNAs with regulatory potency. Nature 495:333-338 (2013).
Mildner et al.: Distinct and Non-Redundant Roles of Microglia and Myeloid Subsets in Mouse Models of Alzheimer's Disease. Neurobiology of Disease, J. Neurosci. 31(31):11159-11171 (2011).
Mita et al.: BRCA1 and S phase DNA repair pathways restrict LINE-1 retrotransposition in human cells. Nat Struct Mol Biol. 27(2):179-191 doi:10.1038/s41594-020-0374-z (2020).
Monahan et al.: Direct intramuscular injection with recombinant AAV vectors results in sustained expression in a dog model of hemophilia. Gene Therapy 5:40-49 (1998).
Morrissey et al.: Chimeric antigen receptors that trigger phagocytosis. eLife p. 1-21 (2018).
Muckenfuss et al.: APOBEC3 proteins inhibit human LINE-1 retrotransposition. J Biol Chem. 281(31):22161-22172 doi:10.1074/jbc.M601716200 (2006).
Mukherjee et al.: Non-Classical monocytes display inflammatory features: Validation in Sepsis and Systemic Lupus Erythematous. Scientific Reports p. 1-14 (2015).
Murshid et al: Hsp90-peptide complexes stimulate antigen presentation through the class II pathway after binding scavenger receptor SREC-1. Immunobiology 219(12):924-931 (2014).
Ni et al.: Transposon tools hopping in vertebrates. Briefings in Functional Genomics and proteomics 7(6):444-453 (2008).
Non-Final Office Action issued in counterpart U.S. Appl. No. 17/499,232 dated May 4. 2022.
Non-Final Office Action issued in counterpart U.S. Appl. No. 17/499,232 dated Sep. 26. 2022.
Non-Final Office Action issued in counterpart U.S. Appl. No. 17/855,230 dated Oct. 26, 2022.
Non-Final Office Action issued in counterpart U.S. Appl. No. 17/855,423 dated Nov. 7, 2022.
Novikova et al.: Engineering cooperative tecto-RNA complexes having programmable stoichiometries. Nucleic Acids Res. 39(7):2903-2917 doi:10.1093/nar/gkq1231 (2011).
Olingy et al.: Monocyte heterogeneity and functions in cancer. J Leukoc Biol. 106(2):309-322 (2019). doi: 10.1002/JLB.4RI0818-311R. Epub (2019).
Onodera et al.: Successful Peripheral T-Lymphocyte-Directed Gene Transfer for a Patient With Severe Combined Immune Deficiency Caused by Adenosine Deaminase Deficiency. Blood 91(1):30-36 (1998). https://doi.org/10.1182/blood.V91.1.30.
Orecchioni et al.: Macrophage Polarization: Different Gene Signatures in M1(LPS+) vs. Classically and M2(LPS-) vs. Alternatively Activated Macrophages. Front Immunol. (2019);10:1084. Erratum in: Front Immunol. 25;11:234 (2020).
Orechini et al.: ADAR1 restricts LINE-1 retrotransposition. Nucleic Acids Res. 45(1):155-168 doi:10.1093/nar/gkw834 (2017).

(56) References Cited

OTHER PUBLICATIONS

Oshi et al.: M1 Macrophage and M1/M2 ratio defined by transcriptomic signatures resemble only part of their conventional clinical characteristics in breast cancer. Sci Rep. 10(1):16554 (2020).
Oviedo-Boyso et al.: The Phosphoinositide-3-Kinase-Akt Signaling Pathway Is Important for *Staphylococcus aureus* Internalization by Endothelial Cells Infection and Immunity 79(11):4569-4577 (2011).
Ozcan et al.: Programmable RNA targeting with the single-protein CRISPR effector Cas7-11. Nature 597(7878):720-725 doi: 10.1038/s41586-021-03886-5 (2021).
Pascolo S.: Messenger RNA-based vaccines. Expert Opin Biol Ther. 4(8):1285-94 (2004).
Passlick et al.: Identification and Characterization of a Novel Monocyte Subpopulation in Human Peripheral Blood. Article in Blood 74:2527-2534 (1989).
Patel et al.: The fate and lifespan of human monocyte subsets in steady state and systemic inflammation. J. Exp. Med. 214(7):1913-1923 (2017).
PCT/US2019/060052 International Preliminary Report on Patentability May 11, 2021.
PCT/US2019/060052 International Search Report and Written Opinion dated Apr. 30, 2020.
PCT/US2020/030837 International Search Report and Written Opinion dated Sep. 1, 2020.
PCT/US2020/037312 International Search Report dated Nov. 30, 2020.
PCT/US2020/049240 International Search Report and Written Opinion dated Mar. 26, 2021.
PCT/US2020/064686 International Preliminary Report on Patentability mailed Jun. 23, 2022.
PCT/US2020/064686 International Search Report and Written Opinion dated Apr. 6, 2021.
PCT/US2022/028831 International Search Report and Written Opinion dated Sep. 2, 2022.
Penberthy et al.: Apoptotic cell recognition receptors and scavenger receptors. Immunological Reviews 269:44-59 (2016).
Pierini et al.: Chimeric antigen receptor macrophages (CAR-M) elicit a systemic anti-tumor immune response and synergize with PD-1 blockade in immunocompetent mouse models of HER2+ solid tumors. Poster Presentation. Society for Immunotherapy of Cancer (SITC) Meeting, Virtual (2020). https://secureservercdn.net/45.40.149.113/74d.fcf.myftpupload.com/wp-content/uploads/2021/09/CAR-M-syngeneic-model_SITC2020.pdf.
Piskareva et al.: The carboxy-terminal segment of the human LINE-1 ORF2 protein is involved in RNA binding. FEBS Open Bio. 3:433-437 (2013).
Pluckthun et al.: The Pharmacology of Monoclonal Antibodies. Springer-Verlag 11:69-315 (1994).
Putnam. Antisense strategies and therapeutic applications. Am. J. Health Syst. Pharm. 53:151-160 (1996), erratum at Am. J. Health Syst. Pharm. 53:325 (1996).
Ralston et al.: Trogocytosis by Entamoeba histolytica contributes to cell killing and tissue invasion. Nature 508:526-530 (2014).
Reiss et al.: A Phase 1, First-In-Human (FIH) Study of the Anti-HER2 CAR Macrophage CT-0508 in Participants with HER2 Overexpressing Solid Tumors. Poster Presentation. American Society of Clinical Oncology (ASCO) Annual Meeting, New Chicago, IL, United States (2022). https://secureservercdn.net/45.40.149.113/74d.fcf.myftpupload.com/wp-content/uploads/2022/07/ASCO-Data-In-Person-2022.final_.pdf.
Reiss et al.: LBA (951): A Phase 1 first in human study of adenovirally transduced anti-HER2 CAR Macrophages in subjects with HER2 overexpressing solid tumors: preliminary safety, pharmacokinetics, and TME reprogramming data. Poster Presentation. Society for Immunotherapy of Cancer (SITC) Meeting, Washington, DC, United States (2021). https://secureservercdn.net/45.40.149.113/74d.fcf.myftpupload.com/wp-content/uploads/2021/11/Poster-LBA951-CT-0508-Study-101-SITC-FINAL.pdf.
Richardson et al.: The Influence of LINE-1 and SINE Retrotransposons on Mammalian Genomes. Microbiol Spectr. 3(2):MDNA3-0061-2014, pp. 1-63 doi:10.1128/microbiolspec.MDNA3-0061-2014 (2015).
Roberts et al.: Antigen-Specific Cytolysis by Neutrophils and NK Cells Expressing Chimeric Immune Receptros Bearing xx Signaling Domains. J Immunol 161:375-384 (1998).
Roberts et al.: Critical Role for CD103(+)/CD141(+) Dendritic Cells Bearing CCR7 for Tumor Antigen Trafficking and Priming of T Cell Immunity in Melanoma. Cancer Cell 30:324-336 (2016).
Rosales et al.: Phagocytosis: A Fundamental Process in Immunity. BioMed Research International, Article ID 9042851 (2017).
Ruiz-Aguilar et al.: Human CD16+ and CD16+ monocyte subsets display unique effector properties in inflammatory conditions in vivo. Journal of Leukocyte Biology 90:1119-1131 (2011).
Russell, D.G.: Mycobacterium tuberculosis and the intimate discourse of a chronic infection. Immunol Rev 240(1):252-268 (2011).
Scherberich et al.: CD14++ monocytes, CD14+/CD16+ subset and soluble CD14 as biological markers of inflammatory systemic diseases and monitoring immunosuppressive therapy. Clin Chem Lab Med. 37(3):209-13 (1999).
Schlam et al.: Phosphoinositide 3-kinase enables phagocytosis of large particles by terminating actin assembly through Rac/Cdc42 GTPase-activating proteins. Nature Communications 6:8623 (2015).
Schroers R, et al. Transduction of human PBMC-derived dendritic cells and macrophages by an HIV-1-based lentiviral vector system. Mol Ther. Feb. 2000;1(2):171-9.
Segel et al.: Mammalian retrovirus-like protein PEG10 packages its own mRNA and can be pseudotyped for mRNA delivery. Science 373(6557):882-889 (2021).
Senju et al.: Generation and genetic modification of dendritic cells derived from mouse embryonic stem cells derived from mouse embryonics stem cells. Blood 101(9):3501-3508 (2003).
Senju et al.: Generation of dendritic cells and macrophages from human induced pluripotent stem cells aiming at cell therapy. Gene Therapy 18:874-883 (2011).
Shein et al.: Recognition of 3'-end L1, Alu, processed pseudogenes, and mRNA stem-loops in the human genome using sequence-based and structure-based machine-learning models. Sci Rep. 9(1):7211, pp. 1-16 doi:10.1038/s41598-019-43403-3 (2019).
Shumann et al.: The impact of transposable element activity on therapeutically relevant human stem cells. Mob DNA 10:9, pp. 1-23 doi:10.1186/s13100-019-0151-x (2019).
Sloas et al.: SIRPα-Deficient CAR-Macrophages Exhibit Enhanced Anti-Tumor Function and Bypass the CD47 Immune Checkpoint. Poster Presentation. Society for Immunotherapy of Cancer (SITC) Meeting, Washington, DC, United States (2021). https://secureservercdn.net/45.40.149.113/74d.fcf.myftpupload.com/wp-content/uploads/2021/11/CRISPR_CAR-M_Poster_101721_share-Read-Only.pdf.
Soderberg et al. (J. Virology 67(6): 3166-3175 (1993)).
Strauss et al.: The immunophenotype of antigen presenting cells of the mononuclear phagocyte system in a normal human liver—A systematic review. Journal of Hepatology 62:458-468 (2015).
Su et al.: Phase separation of signaling molecules promotes T cell receptor signal transduction. Science 352(6285):595-599 (2016).
Takahashi et al.: A new family of site-specific retrotransposons, SART1, is inserted into telomeric repeats of the silkworm, Bombyx mori. Nucleic acids Research 25(8):1-7 (1997).
Taylor et al.: A DNA-Based T Cell Receptor Reveals a Role for Receptor Clustering in Ligand Discrimination. Cell 169(1):108-119 doi:10.1016/j.cell.2017.03.006 (2017).
Tippet et al.: (J. Leukocyte Biology 93:913-920 (2013)).
Tristan-Ramos et al.: The tumor suppressor microRNA let-7 inhibits human LINE-1 retrotransposition. Nat Commun. 11(1):5712 doi:10.1038/s41467-020-19430-4 [1-14] (2020).
Tseng et al.: Anti-CD47 antibody-mediated phagocytosis of cancer by macrophages primes an effective antitumor T-cell response. PNAS 110:11103-11108 (2013).
Tsutsui et al. The use of microbubbles to target drug delivery. Cardiovascular Ultrasound 2:23 (2004).
Tuveson et al.: CD19 of B cells as a surrogate kinase insert region to bindphosphatidylinositol 3-kinase. Science 260:986-989 (1993).
Villanueva MT. Macrophages get a CAR. Nat Rev Drug Discov. 19(5):308 (2020).

(56) References Cited

OTHER PUBLICATIONS

Wahl et al.: Molecular hybridization of immobilized nucleic acids: theoretical concepts and practical considerations. Methods Enzymol 152:399-407 (1987).
Walker et al.: Strand displacement amplification—an isothermal, in vitro DNA amplification technique. Nucleic Acids Res 20(7):1691-1696 (1992).
Wei et al.: Human L1 retrotransposition: cis preference versus trans complementation. Mol Cell Biol. 21(4):1429-1439 doi:10.1128/MCB.21.4.1429-1439.2001 (2001).
Weischenfeldt et al.: Bone Marrow-Derived Macrophages (BMM): Isolation and Applications. Cold Spring Harbor Protocols 2008:pdb.prot5080.
Wilkinson et al. (Med. Microbio. Immunol. 204:273-284 (2015)).
Wong et al.: The three human monocyte subsets: implications for health and disease. Immunol Res. 2012; 53(1-3):41-57. Epub (2012).
Xia et al.: siRNA-mediated gene silencing in vitro and in vivo. Nat Biotechnol. 20:1006-1010 (2002).
Xiao et al.: Electrophysiological Characteristics of Primary Afferent Fibers After Systemic Administration of Anti-GC2 Ganglioside Antibody, Pain69: 145-151 (1997).
Xiao et al.: Identification and characterization of fully human anti-CD22 monoclonal antibodies. mAbs 1:297-303 (2009).
Yarnall et al.: Drag-and-drop genome insertion of large sequences without double-strand DNA cleavage using CRISPR-directed integrases. nature biotechnology (2022). https://doi.org/10.1038/s41587-022-01527-4.
Yeh et al.: In vivo base editing of post-mitotic sensory cells. Nat Commun. 9(1):2184, pp. 1-10 doi:10.1038/s41467-018-04580-3 (2018).
Yesselman et al.: RNA tertiary structure energetics predicted by an ensemble model of the RNA double helix.bioRxiv 341107, pp. 1-31 DOI:10.1101/341107 (2018).
Yong et al.: A role for multiple chimeric antigen receptor-expressing leukocytes in antigen-specific responses to cancer. Oncotarget 7(23):34582-34598 (2016).
Yong et al.: Using electroporation to determine function of a chimeric antigen receptor in T cell and macrophage cell lines. The Open Gene Therapy Journal 23:5(1) (2013).
Zhang et al.: Homologous 2',5'-phosphodiesterases from disparate RNA viruses antagonize antiviral innate immunity. PNAS USA 110(32):13114-13119 doi:10.1073/pnas.1306917110 (2013).
Zhang et al.: The structure and retrotransposition mechanism of LTR-retrotransposons in the asexual yeast *Candida albicans*. Virulence 5(6):655-664 doi:10.4161/viru.32180 (2014).
1-(3,4-dichlorophenyl)-3-(4-methoxyphenyl)-4-(4-morpholinyl)-1H-pyrrole-2,5-dione (CAS 1417162) 1 page, Retrieved URL https://www.caymanchem.com/product/18397/ri-2.
6-hydroxyDL-dopa (CAS 21373-30-8). 3 Pages. Retrived URL: https://www.rndsystems.com/products/6-hydroxy-dl-dopa_5740.
B02 (CAS 1290541-46-6). 4 Pages. Retrived URL: https://www.rndsystems.com/products/b02_6392.
Benzamide for synthesis. CAS No. 55-21-0, EC No. 200-227-7. 3 Pages. Retrived URL: https://www.merckmillipore.com/IN/en/product/Benzamide,MDA_CHEM-802191.
Bucheton, A et al. The Molecular Basis of I-R Hybrid Dysgenesis in *Drosophila Melanogaster*: Identification, Cloning, and Properties of the I Factor. Cell vol. 38,1: 153-163 (1984).
Camptothecin (CPT) (CAS 7689-03-4). 8 Pages. Retrived URL: https://www.tcichemicals.com/IN/en/p/C1495.
Carisma Therapeutics. “Carisma Therapeutics Corporate Overview.” Nov. 2018.
Chadwick, SL et al. Safety of a Single Aerosol Administration of Escalating Doses of the Cationic Lipid GL-67/Dope/empe-peg 5000 Formulation to the Lungs of Normal Volunteers. Gene Therapy vol. 4,9: 937-942 (1997).
Dids (Cas 67483-13-0). 4 Pages. Retrived URL: https://www.tocris.com/products/dids_4523.
EP20861388 European Extended Search Report dated Aug. 11, 2023.
European Patent Application No. 20861388.5 Extended European Search Report dated Aug. 11, 2023.
Gao, X et al. Cationic Liposome-medicated Gene Transfer. Gene Therapy vol. 2,10: 710-722 (1995).
GenBank Accession No. AAC51261. Version No. AAC51261.1. Putative p150 [*Homo sapiens*]. 2 pages. Retrieved from URL: https://www.ncbi.nlm.nih.gov/protein/AAC51261.
GenBank Accession No. AAC51262. Version No. AAC51262.1. p40 [*Homo sapiens*]. 2 pages. Retrieved from URL: https://www.ncbi.nlm.nih.gov/protein/AAC51262.
GenBank Accession No. AAC51263. Version No. AAC51263.1. Putative p150 [*Homo sapiens*]. 2 pages. Retrieved from URL: https://www.ncbi.nlm.nih.gov/protein/AAC51263.
GenBank Accession No. AAC51264. Version No. AAC51264.1. Putative p150 [*Homo sapiens*]. 2 pages. Retrieved from URL: https://www.ncbi.nlm.nih.gov/protein/AAC51264.
GenBank Accession No. AAC51265. Version No. AAC51265.1. p40 [*Homo sapiens*]. 2 pages. Retrieved from URL: https://www.ncbi.nlm.nih.gov/protein/AAC51265.
GenBank Accession No. AAC51266. Version No. AAC51266.1. p40 [*Homo sapiens*]. 2 pages. Retrieved from URL: https://www.ncbi.nlm.nih.gov/protein/AAC51266.
GenBank Accession No. AAC51267. Version No. AAC51267.1. Putative p150 [*Homo sapiens*]. 2 pages. Retrieved from URL: https://www.ncbi.nlm.nih.gov/protein/AAC51267.
GenBank Accession No. AAC51268. Version No. AAC51268.1. p40 [*Homo sapiens*]. 2 pages. Retrieved from URL: https://www.ncbi.nlm.nih.gov/protein/AAC51268.
GenBank Accession No. AAC51269. Version No. AAC51269.1. Putative p150 [*Homo sapiens*]. 2 pages. Retrieved from URL: https://www.ncbi.nlm.nih.gov/protein/AAC51269.
GenBank Accession No. AAC51270. Version No. AAC51270.1. p40 [*Homo sapiens*]. 2 pages. Retrieved from URL: https://www.ncbi.nlm.nih.gov/protein/AAC51270.
GenBank Accession No. AAC51271. Version No. AAC51271.1. Putative p150 [*Homo sapiens*]. 2 pages. Retrieved from URL: https://www.ncbi.nlm.nih.gov/protein/AAC51271.
GenBank Accession No. AAC51272. Version No. AAC51272.1. p40 [*Homo sapiens*]. 1 page. Retrieved from URL: https://www.ncbi.nlm.nih.gov/protein/AAC51272.
GenBank Accession No. AAC51273. Version No. AAC51273.1. Putative p150 [*Homo sapiens*]. 2 pages. Retrieved from URL: https://www.ncbi.nlm.nih.gov/protein/AAC51273.
GenBank Accession No. AAC51274. Version No. AAC51274.1. p40 [*Homo sapiens*]. 2 page. Retrieved from URL: https://www.ncbi.nlm.nih.gov/protein/AAC51274.
GenBank Accession No. AAC51275. Version No. AAC51275.1. p40 [*Homo sapiens*]. 1 page. Retrieved from URL: https://www.ncbi.nlm.nih.gov/protein/AAC51275.
GenBank Accession No. AAC51276. Version No. AAC51276.1. Putative p150 [*Homo sapiens*]. 2 pages. Retrieved from URL: https://www.ncbi.nlm.nih.gov/protein/AAC51276.
GenBank Accession No. AAC51277. Version No. AAC51277.1. p40 [*Homo sapiens*]. 2 page. Retrieved from URL: https://www.ncbi.nlm.nih.gov/protein/AAC51277.
GenBank Accession No. AAC51278. Version No. AAC51278.1. p40 [*Homo sapiens*]. 2 page. Retrieved from URL: https://www.ncbi.nlm.nih.gov/protein/AAC51278.
GenBank Accession No. AAC51279. Version No. AAC51279.1. Putative p150 [*Homo sapiens*]. 2 pages. Retrieved from URL: https://www.ncbi.nlm.nih.gov/protein/AAC51279.
Gordon, S., Phagocytosis an immunobiologic process. Immunity 44, Mar. 15, 2016 p. 463-475.
Great Britain Patent Application No. GB2203647.9 Examination Report dated Jan. 24, 2024.
International Search Report and Written Opinion for PCT/US2020/030837 issued Oct. 1, 2020.
Irinotecan (CAS 100286-90-6). 7 Pages. Retrived URL: https://www.sigmaaldrich.com/IN/en/product/sigma/i1406.
Laborde, Rebecca R. et al.: Cancer Vaccines in the World of Immune Suppressive Monocytes (CD14+HLA-DRIo/neg Cells): The Gateway to Improved Responses. Frontiers in Immunology vol. 5 (2014). https://doi.org/10.3389/fimmu.2014.00147.

(56) References Cited

OTHER PUBLICATIONS

Li et al.: The dicistronic RNA from the mouse LINE-1 retrotransposon contains an internal ribosome entry site upstream of each ORF: implications for retrotransposition. Nucleic Acids Research 34(3):853-864 (2006).
ML216 (CAS 1430213-30-1). 2 Pages. Retrived URL: https://www.scbt.com/p/ml-216-1430213-30-1.
Nakamizo et al.: Single-cell analysis of human skin identifies CD14+ type 3 dendritic cells co-producing IL1B and IL23A in psoriasis. J Exp Med 218(9):e20202345 (2021). https://doi.org/10.1084/jem.20202345.
Niraparib (MK-827 Tesaro) CAS 1038915-60-4). 2 Pages. Retrived URL: https://www.bldpharm.com/products/1038915-60-4.html.
NSC 19630 (CAS 72835-26-8). 2 Pages. Retrived URL: https://www.merckmillipore.com/IN/en/product/WRN-Helicase-Inhibitor-NSC-19630-CAS-72835-26-8-Calbiochem, EMD_BIO-681647.
NSC 617145 (CAS 203115-63-3). 3 Pages. Retrived URL: https://www.rndsystems.com/products/nsc-617145_5340.
Oates et al.: Characterizing the polarization continuum of macrophage subtypes M1, M2a and M2c. bioRxiv (2022). doi: https://doi.org/10.1101/2022.06.13.495868.
Office Action dated Dec. 8, 2022 issued in U.S. Appl. No. 17/499,232.
Office Action dated Oct. 7, 2022 issued in U.S. Appl. No. 17/855,423.
Olaparib (Lynparza) (CAS 763113-22-0). 54 Pages. Retrived URL: https://pubchem.ncbi.nlm.nih.gov/compound/Olaparib.
Onodera, Masafumi et al. Successful Peripheral T-Lymphocyte-Directed Gene Transfer for a Patient With Severe Combined Immune Deficiency Caused by Adenosine Deaminase Deficiency. Blood vol. 91,1: 30-36 (1998).
PCT/US2020/049240 International Search Report dated Mar. 26, 2021.
PF-01367338 Pfizer. 3 Pages. Retrived URL: https://www.pfizer.com/news/press-release/press-release-detail/clovis-oncology-inc-receives-license-worldwide-development.
Pierini et al.: Chimeric antigen receptor macrophages (CAR-M) sensitize solid tumors to anti-PD1 immunotherapy. Poster Presentation. The American Association for Cancer Research (AACR) Annual Meeting, New Orleans, LA, United States (2022). https://secureservercdn.net/45.40.149.113/74d.fcf.myftpupload.com/wp-content/uploads/2022/07/AACR2022_CARMaPD11.pdf.
RI-1 (CAS 415713-60-9). 3 Pages. Retrived URL: https://www.rndsystems.com/products/ri-1_6168.
Sambrook, Joseph et al.: Molecular Cloning: A Laboratory Manual, 2nd Edition. Cold Spring Harbor Laboratory Press : pp. 1-30 (1989).
Sica, F., Fingolimod Immune Effects Beyond Its Sequestration Ability, Neurol Ther (2019) 8:231-240.
Silverstein RL., Mechanisms of Cell Signaling By the Scavenger Receptor CD36: Implications in Atherosclerosis and Thrombosis, Transactions of the American Clinical and Climatological Association, vol. 121, 2010.
Streptonigrin (SN) (CAS 3930-19-6). 2 Pages. Retrived URL: https://medkoo.com/products/15240.
Supplementary European Search Report dated Dec. 16, 2022 issued in European Patent Application 20798060.
Topotecan (Hycamtin® GlaxoSmithKline) (CAS 123948-87-8). 2 Pages. Retrived URL: https://www.scbt.com/p/topotecan-123948-87-8.
U.S. Appl. No. 18/313,087 Office Action dated Feb. 12, 2024.
U.S. Appl. No. 18/313,087 Office Action dated Jun. 27, 2024.
U.S. Appl. No. 18/313,126 Office Action dated Feb. 1, 2024.
U.S. Serial No. 18/313, 126 Office Action dated May 31, 2024.
Veliparib (ABT-888 Abbvie) (CAS 912444-00-9). 4 Pages. Retrieved URL: https://www.selleckchem.com/products/ABT-888.html.
www.kazusa.orjp/codon.
Anzalone, Andrew V. et al.: Search-and-replace Genome Editing Without Double-strand Breaks or Donor DNA. Nature 576(7785):149-157 (2019).
Kuroki-Kami, Azusa et al.: Targeted gene knockin in zebrafish using the 28S rDNA-specific non-LTRretrotransposon R2O1. Mobile DNA 10:23 (2019).
Meyer, Thomas J. et al.: Heads or tails: L1 insertion-associated 5' homopolymeric sequences. Mob DNA 1(1):7 (2010).
Nigumann, Pilvi et al.: Many human genes are transcribed from the antisense promoter of L1 retrotransposon. Genomics 79(5):628-34 (2002). doi: 10.1006/geno.2002.6758 (Abstract).
U.S. Appl. No. 17/855,230 Office Action dated Oct. 26, 2022.
Wang; Yuxiao et al.: CRISPR-Enabled Autonomous Transposable Element (CREATE) for RNA-based gene editing and delivery. Cold Spring Harbor Laboratory May 4, 2024. bioRxiv preprint doi: https://doi.org/10.1101/2024.01.29.577809.

* cited by examiner

SEQUENCE LISTING

```
Sequence total quantity: 113
SEQ ID NO: 1            moltype = AA  length = 116
FEATURE                 Location/Qualifiers
REGION                  1..116
                        note = Description of Artificial Sequence: Synthetic
                         polypeptide
source                  1..116
                        mol_type = protein
                        organism = synthetic construct
SEQUENCE: 1
EIQLVQSGGG LVKPGGSVRI SCAASGYTFT NYGMNWVRQA PGKGLEWMGW INTHTGEPTY  60
ADSFKGRFTF SLDDSKNTAY LQINSLRAED TAVYFCTRRG YDWYFDVWGQ GTTVTV      116

SEQ ID NO: 2            moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 2
DIQMTQSPSS LSASVGDRVT ITCRASQDIN SYLSWFQQKP GKAPKTLIYR ANRLESGVPS  60
RFSGSGSGTD YTLTISSLQY EDFGIYYCQQ YDESPWTFGG GTKLEIK                107

SEQ ID NO: 3            moltype = AA  length = 46
FEATURE                 Location/Qualifiers
REGION                  1..46
                        note = Description of Artificial Sequence: Synthetic
                         polypeptide
source                  1..46
                        mol_type = protein
                        organism = synthetic construct
SEQUENCE: 3
LYCRRLKIQV RKAAITSYEK SDGVYTGLST RNQETYETLK HEKPPQ                 46

SEQ ID NO: 4            moltype = AA  length = 35
FEATURE                 Location/Qualifiers
REGION                  1..35
                        note = Description of Artificial Sequence: Synthetic
                         polypeptide
source                  1..35
                        mol_type = protein
                        organism = synthetic construct
SEQUENCE: 4
YEDMRGILYA APQLRSIRGQ PGPNHEEDAD SYENM                             35

SEQ ID NO: 5            moltype = AA  length = 62
FEATURE                 Location/Qualifiers
REGION                  1..62
                        note = Description of Artificial Sequence: Synthetic
                         polypeptide
source                  1..62
                        mol_type = protein
                        organism = synthetic construct
SEQUENCE: 5
KKVAKKPTNK APHPKQEPQE INFPDDLPGS NTAAPVQETL HGCQPVTQED GKESRISVQE  60
RQ                                                                 62

SEQ ID NO: 6            moltype = AA  length = 21
FEATURE                 Location/Qualifiers
REGION                  1..21
                        note = Description of Artificial Sequence: Synthetic peptide
source                  1..21
                        mol_type = protein
                        organism = synthetic construct
SEQUENCE: 6
IYIWAPLAGT CGVLLLSLVI T                                            21

SEQ ID NO: 7            moltype = AA  length = 62
FEATURE                 Location/Qualifiers
REGION                  1..62
                        note = Description of Artificial Sequence: Synthetic
                         polypeptide
source                  1..62
                        mol_type = protein
                        organism = synthetic construct
SEQUENCE: 7
```

```
ALSNSIMYFS HFVPVFLPAK PTTTPAPRPP TPAPTIASQP LSLRPEACRP AAGGAVHTRG  60
LD                                                                62

SEQ ID NO: 8            moltype = AA  length = 130
FEATURE                 Location/Qualifiers
REGION                  1..130
                        note = Description of Artificial Sequence: Synthetic
                         polypeptide
source                  1..130
                        mol_type = protein
                        organism = synthetic construct
SEQUENCE: 8
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYTTPPTFGQ GTKVEIKRTG STSGSGKPGS  120
GEGSEVQLVE                                                        130

SEQ ID NO: 9            moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 9
LVQPGGSLRL SCAASGFNIK DTYIHWVRQA PGKGLEWVAR IYPTNGYTRY ADSVKGRFTI  60
SADTSKNTAY LQMNSLRAED TAVYYCSRWG GDGFYAMDVW GQGTLVTV              108

SEQ ID NO: 10           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 10
SSGGGGSGGG GSGGGGS                                                17

SEQ ID NO: 11           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 11
SGGGGSG                                                           7

SEQ ID NO: 12           moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 12
SGGG                                                              4

SEQ ID NO: 13           moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 13
GSGS                                                              4

SEQ ID NO: 14           moltype = AA  length = 432
FEATURE                 Location/Qualifiers
REGION                  1..432
                        note = Description of Artificial Sequence: Synthetic
                         polypeptide
source                  1..432
                        mol_type = protein
                        organism = synthetic construct
SEQUENCE: 14
MWLQSLLLLG TVACSISEIQ LVQSGGGLVK PGGSVRISCA ASGYTFTNYG MNWVRQAPGK  60
GLEWMGWINT HTGEPTYADS FKGRFTFSLD DSKNTAYLQI NSLRAEDTAV YFCTRRGYDW  120
```

```
-continued

YFDVWGQGTT VTVSSGGGGS GGGGSGGGGS DIQMTQSPSS LSASVGDRVT ITCRASQDIN    180
SYLSWFQQKP GKAPKTLIYR ANRLESGVPS RFSGSGSGTD YTLTISSLQY EDFGIYYCQQ    240
YDESPWTFGG GTKLEIKSGG GGSGALSNSI MYFSHFVPVF LPAKPTTTPA PRPPTPAPTI    300
ASQPLSLRPE ACRPAAGGAV HTRGLDIYIW APLAGTCGVL LLSLVITLYC RRLKIQVRKA    360
AITSYEKSDG VYTGLSTRNQ ETYETLKHEK PPQGSGSYED MRGILYAAPQ LRSIRGQPGP    420
NHEEDADSYE NM                                                       432

SEQ ID NO: 15           moltype = AA  length = 436
FEATURE                 Location/Qualifiers
REGION                  1..436
                        note = Description of Artificial Sequence: Synthetic
                         polypeptide
source                  1..436
                        mol_type = protein
                        organism = synthetic construct
SEQUENCE: 15
MWLQSLLLLG TVACSISDIQ MTQSPSSLSA SVGDRVTITC RASQDVNTAV AWYQQKPGKA     60
PKLLIYSASF LYSGVPSRFS GSRSGTDFTL TISSLQPEDF ATYYCQQHYT TPPTFGQGTK    120
VEIKRTGSTS GSGKPGSGEG SEVQLVESGG GLVQPGGSLR LSCAASGFNI KDTYIHWVRQ    180
APGKGLEWVA RIYPTNGYTR YADSVKGRFT ISADTSKNTA YLQMNSLRAE DTAVYYCSRW    240
GGDGFYAMDV WGQGTLVTVS SSGGGGSGAL SNSIMYFSHF VPVFLPAKPT TTPAPRPPTP    300
APTIASQPLS LRPEACRPAA GGAVHTRGLD IYIWAPLAGT CGVLLLSLVI TLYCRRLKIQ    360
VRKAAITSYE KSDGVYTGLS TRNQETYETL KHEKPPQGSG SYEDMRGILY AAPQLRSIRG    420
QPGPNHEEDA DSYENM                                                   436

SEQ ID NO: 16           moltype = AA  length = 454
FEATURE                 Location/Qualifiers
REGION                  1..454
                        note = Description of Artificial Sequence: Synthetic
                         polypeptide
source                  1..454
                        mol_type = protein
                        organism = synthetic construct
SEQUENCE: 16
MWLQSLLLLG TVACSISEIQ LVQSGGGLVK PGGSVRISCA ASGYTFTNYG MNWVRQAPGK     60
GLEWMGWINT HTGEPTYADS FKGRFTFSLD DSKNTAYLQI NSLRAEDTAV YFCTRRGYDW    120
YFDVWGQGTT VTVSSGGGGS GGGGSGGGGS DIQMTQSPSS LSASVGDRVT ITCRASQDIN    180
SYLSWFQQKP GKAPKTLIYR ANRLESGVPS RFSGSGSGTD YTLTISSLQY EDFGIYYCQQ    240
YDESPWTFGG GTKLEIKSGG GGSGALSNSI MYFSHFVPVF LPAKPTTTPA PRPPTPAPTI    300
ASQPLSLRPE ACRPAAGGAV HTRGLDIYIW APLAGTCGVL LLSLVITLYC RLKIQVRKAA    360
ITSYEKSDGV YTGLSTRNQE TYETLKHEKP PQKKVAKKPT NKAPHPKQEP QEINFPDDLP    420
GSNTAAPVQE TLHGCQPVTQ EDGKESRISV QERQ                               454

SEQ ID NO: 17           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 17
MWLQSLLLLG TVACSIS                                                    17

SEQ ID NO: 18           moltype = AA  length = 27
FEATURE                 Location/Qualifiers
REGION                  1..27
                        note = Description of Artificial Sequence: Synthetic peptide
source                  1..27
                        mol_type = protein
                        organism = synthetic construct
SEQUENCE: 18
FWVLVVVGGV LACYSLLVTV AFIIFWV                                         27

SEQ ID NO: 19           moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 19
ILLPLIIGLI LLGLLALVLI AFCII                                           25

SEQ ID NO: 20           moltype = AA  length = 45
FEATURE                 Location/Qualifiers
REGION                  1..45
                        note = Description of Artificial Sequence: Synthetic
                         polypeptide
source                  1..45
```

```
                      mol_type = protein
                      organism = synthetic construct
SEQUENCE: 20
LYCRLKIQVR KAAITSYEKS DGVYTGLSTR NQETYETLKH EKPPQ                  45

SEQ ID NO: 21         moltype = AA  length = 219
FEATURE               Location/Qualifiers
REGION                1..219
                      note = Description of Artificial Sequence: Synthetic
                       polypeptide
source                1..219
                      mol_type = protein
                      organism = synthetic construct
SEQUENCE: 21
QRWKSKLYSI VCGKSTPEKE GELEGTTTKP LAPNPSFSPT PGFTPTLGFS PVPSSTFTSS  60
STYTPGDCPN FAAPRREVAP PYQGADPILA TALASDPIPN PLQKWEDSAH KPQSLDTDDP  120
ATLYAVVENV PPLRWKEFVR RLGLSDHEID RLELQNGRCL REAQYSMLAT WRRRTPRREA  180
TLELLGRVLR DMDLLGCLED IEEALCGPAA LPPAPSLLR                         219

SEQ ID NO: 22         moltype = AA  length = 171
FEATURE               Location/Qualifiers
REGION                1..171
                      note = Description of Artificial Sequence: Synthetic
                       polypeptide
source                1..171
                      mol_type = protein
                      organism = synthetic construct
SEQUENCE: 22
PLCLQREAKV PHLPADKARG TQGPEQQHLL ITAPSSSSSS LESSASALDR RAPTRNQPQA  60
PGVEASGAGE ARASTGSSDS SPGGHGTQVN VTCIVNVCSS SDHSSQCSSQ ASSTMGDTDS  120
SPSESPKDEQ VPFSKEECAF RSQLETPETL LGSTEEKPLP LGVPDAGMKP S           171

SEQ ID NO: 23         moltype = AA  length = 211
FEATURE               Location/Qualifiers
REGION                1..211
                      note = Description of Artificial Sequence: Synthetic
                       polypeptide
source                1..211
                      mol_type = protein
                      organism = synthetic construct
SEQUENCE: 23
MSNGYSTDEN FRYLISCFRA RVKMYIQVEP VLDYLTFLPA EVKEQIQRTV ATSGNMQAVE  60
LLLSTLEKGV WHLGWTREFV EALRRTGSPL AARYMNPELT DLPSPSFENA HDEYLQLLNL  120
LQPTLVDKLL VRDVLDKCME EELLTIEDRN RIAAAENNGN ESGVRELLKR IVQKENWFSA  180
FLNVLRQTGN NELVQELTGS DCSESNAEIE N                                 211

SEQ ID NO: 24         moltype = AA  length = 607
FEATURE               Location/Qualifiers
REGION                1..607
                      note = Description of Artificial Sequence: Synthetic
                       polypeptide
source                1..607
                      mol_type = protein
                      organism = synthetic construct
SEQUENCE: 24
MWLQSLLLLG TVACSISEIQ LVQSGGGLVK PGGSVRISCA ASGYTFTNYG MNWVRQAPGK  60
GLEWMGWINT HTGEPTYADS FKGRFTFSLD DSKNTAYLQI NSLRAEDTAV YFCTRRGYDW  120
YFDVWGQGTT VTVSSGGGGS GGGGSGGGGS DIQMTQSPSS LSASVGDRVT ITCRASQDIN  180
SYLSWFQQKP GKAPKTLIYR ANRLESGVPS RFSGSGSGTD YTLTISSLQY EDFGIYYCQQ  240
YDESPWTFGG GTKLEIKSGG GGSGALSNSI MYFSHFVPVF LPAKPTTTPA PRPPTPAPTI  300
ASQPLSLRPE ACRPAAGGAV HTRGLDIYIW APLAGTCGVL LLSLVITLYC RLKIQVRKAA  360
ITSYEKSDGV YTGLSTRNQE TYETLKHEKP PQGSGSMSNG YSTDENFRYL ISCFRARVKM  420
YIQVEPVLDY LTFLPAEVKE QIQRTVATSG NMQAVELLLS TLEKGVWHLG WTREFVEALR  480
RTGSPLAARY MNPELTDLPS PSFENAHDEY LQLLNLLQPT LVDKLLVRDV LDKCMEEELL  540
TIEDRNRIAA AENNGNESGV RELLKRIVQK ENWFSAFLNV LRQTGNNELV QELTGSDCSE  600
SNAEIEN                                                            607

SEQ ID NO: 25         moltype = AA  length = 615
FEATURE               Location/Qualifiers
REGION                1..615
                      note = Description of Artificial Sequence: Synthetic
                       polypeptide
source                1..615
                      mol_type = protein
                      organism = synthetic construct
SEQUENCE: 25
MWLQSLLLLG TVACSISEIQ LVQSGGGLVK PGGSVRISCA ASGYTFTNYG MNWVRQAPGK  60
GLEWMGWINT HTGEPTYADS FKGRFTFSLD DSKNTAYLQI NSLRAEDTAV YFCTRRGYDW  120
YFDVWGQGTT VTVSSGGGGS GGGGSGGGGS DIQMTQSPSS LSASVGDRVT ITCRASQDIN  180
```

-continued

```
SYLSWFQQKP GKAPKTLIYR ANRLESGVPS RFSGSGSGTD YTLTISSLQY EDFGIYYCQQ  240
YDESPWTFGG GTKLEIKSGG GGSGALSNSI MYFSHFVPVF LPAKPTTTPA PRPPTPAPTI  300
ASQPLSLRPE ACRPAAGGAV HTRGLDIYIW APLAGTCGVL LLSLVITLYC RLKIQVRKAA  360
ITSYEKSDGV YTGLSTRNQE TYETLKHEKP PQGSGSQRWK SKLYSIVCGK STPEKEGELE  420
GTTTKPLAPN PSFSPTPGFT PTLGFSPVPS STFTSSSTYT PGDCPNFAAP RREVAPPYQG  480
ADPILATALA SDPIPNPLQK WEDSAHKPQS LDTDDPATLY AVVENVPPLR WKEFVRRLGL  540
SDHEIDRLEL QNGRCLREAQ YSMLATWRRR TPRREATLEL LGRVLRDMDL LGCLEDIEEA  600
LCGPAALPPA PSLLR                                                   615

SEQ ID NO: 26          moltype = AA  length = 567
FEATURE                Location/Qualifiers
REGION                 1..567
                       note = Description of Artificial Sequence: Synthetic
                        polypeptide
source                 1..567
                       mol_type = protein
                       organism = synthetic construct
SEQUENCE: 26
MWLQSLLLLG TVACSISEIQ LVQSGGGLVK PGGSVRISCA ASGYTFTNYG MNWVRQAPGK  60
GLEWMGWINT HTGEPTYADS FKGRFTFSLD DSKNTAYLQI NSLRAEDTAV YFCTRRGYDW  120
YFDVWGQGTT VTVSSGGGGS GGGGSGGGGS DIQMTQSPSS LSASVGDRVT ITCRASQDIN  180
SYLSWFQQKP GKAPKTLIYR ANRLESGVPS RFSGSGSGTD YTLTISSLQY EDFGIYYCQQ  240
YDESPWTFGG GTKLEIKSGG GGSGALSNSI MYFSHFVPVF LPAKPTTTPA PRPPTPAPTI  300
ASQPLSLRPE ACRPAAGGAV HTRGLDIYIW APLAGTCGVL LLSLVITLYC RLKIQVRKAA  360
ITSYEKSDGV YTGLSTRNQE TYETLKHEKP PQGSGSPLCL QREAKVPHLP ADKARGTQGP  420
EQQHLLITAP SSSSSSLESS ASALDRRAPT RNQPQAPGVE ASGAGEARAS TGSSDSSPGG  480
HGTQVNVTCI VNVCSSSDHS SQCSSQASST MGDTDSSPSE SPKDEQVPFS KEECAFRSQL  540
ETPETLLGST EEKPLPLGVP DAGMKPS                                      567

SEQ ID NO: 27          moltype = AA  length = 42
FEATURE                Location/Qualifiers
REGION                 1..42
                       note = Description of Artificial Sequence: Synthetic
                        polypeptide
source                 1..42
                       mol_type = protein
                       organism = synthetic construct
SEQUENCE: 27
RLKIQVRKAA ITSYEKSDGV YTGLSTRNQE TYETLKHEKP PQ                     42

SEQ ID NO: 28          moltype = AA  length = 42
FEATURE                Location/Qualifiers
REGION                 1..42
                       note = Description of Artificial Sequence: Synthetic
                        polypeptide
source                 1..42
                       mol_type = protein
                       organism = synthetic construct
SEQUENCE: 28
RLKIQVRKAA ITSYEKSDGV YTGLSTRNQE TYETLKHEKP PQ                     42

SEQ ID NO: 29          moltype = AA  length = 24
FEATURE                Location/Qualifiers
REGION                 1..24
                       note = Description of Artificial Sequence: Synthetic peptide
source                 1..24
                       mol_type = protein
                       organism = synthetic construct
SEQUENCE: 29
IYIWAPLAGT CGVLLLSLVI TLYC                                         24

SEQ ID NO: 30          moltype = AA  length = 86
FEATURE                Location/Qualifiers
REGION                 1..86
                       note = Description of Artificial Sequence: Synthetic
                        polypeptide
source                 1..86
                       mol_type = protein
                       organism = synthetic construct
SEQUENCE: 30
ALSNSIMYFS HFVPVFLPAK PTTTPAPRPP TPAPTIASQP LSLRPEACRP AAGGAVHTRG  60
LDIYIWAPLA GTCGVLLLSL VITLYC                                       86

SEQ ID NO: 31          moltype = AA  length = 83
FEATURE                Location/Qualifiers
REGION                 1..83
                       note = Description of Artificial Sequence: Synthetic
                        polypeptide
source                 1..83
```

```
                         mol_type = protein
                         organism = synthetic construct
SEQUENCE: 31
ALSNSIMYFS HFVPVFLPAK PTTTPAPRPP TPAPTIASQP LSLRPEACRP AAGGAVHTRG  60
LDIYIWAPLA GTCGVLLLSL VIT                                          83

SEQ ID NO: 32            moltype = AA  length = 255
FEATURE                  Location/Qualifiers
REGION                   1..255
                         note = Description of Artificial Sequence: Synthetic
                          polypeptide
source                   1..255
                         mol_type = protein
                         organism = synthetic construct
SEQUENCE: 32
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYTTPPTFGQ GTKVEIKRTG STSGSGKPGS  120
GEGSEVQLVE SSGGGGSGGG GSGGGGSLVQ PGGSLRLSCA ASGFNIKDTY IHWVRQAPGK  180
GLEWVARIYP TNGYTRYADS VKGRFTISAD TSKNTAYLQM NSLRAEDTAV YYCSRWGGDG  240
FYAMDVWGQG TLVTV                                                   255

SEQ ID NO: 33            moltype = AA  length = 240
FEATURE                  Location/Qualifiers
REGION                   1..240
                         note = Description of Artificial Sequence: Synthetic
                          polypeptide
source                   1..240
                         mol_type = protein
                         organism = synthetic construct
SEQUENCE: 33
EIQLVQSGGG LVKPGGSVRI SCAASGYTFT NYGMNWVRQA PGKGLEWMGW INTHTGEPTY  60
ADSFKGRFTF SLDDSKNTAY LQINSLRAED TAVYFCTRRG YDWYFDVWGQ GTTVTVSSGG  120
GGSGGGGSGG GGSDIQMTQS PSSLSASVGD RVTITCRASQ DINSYLSWFQ QKPGKAPKTL  180
IYRANRLESG VPSRFSGSGS GTDYTLTISS LQYEDFGIYY CQQYDESPWT FGGGTKLEIK  240

SEQ ID NO: 34            moltype = AA  length = 26
FEATURE                  Location/Qualifiers
REGION                   1..26
                         note = Description of Artificial Sequence: Synthetic peptide
source                   1..26
                         mol_type = protein
                         organism = synthetic construct
SEQUENCE: 34
IYLIIGICGG GSLLMVFVAL LVFYIT                                       26

SEQ ID NO: 35            moltype = DNA  length = 1075
FEATURE                  Location/Qualifiers
misc_feature             1..1075
                         note = Description of Artificial Sequence: Synthetic
                          polynucleotide
source                   1..1075
                         mol_type = other DNA
                         organism = synthetic construct
SEQUENCE: 35
taatacgact cactataggg agaaagacgc caccatgggc aagaagcaaa atcgcaagac  60
ggggaattcc aagacacaat ccgctagccc accacctaaa gagcgttcta gctcccctgc  120
tactgagcag tcctggatgg aaaacgactt cgatgaactc cgggaagagg gatttaggcg  180
atccaactat tcagaactcc gcgaagatat ccagacaaag gggaaggaag tcgagaattt  240
cgagaagaac ctcgaggagt gcatcacccg tatcacaaac actgagaaat gtctcaaaga  300
actcatggaa cttaagacaa aagccaggga gcttcgagag gagtgtcgga gtctgagatc  360
caggtgtgac cagctcgagg agcgcgtgag cgcgatggaa gacgagatga acgagatgaa  420
aagagagggc aaattcaggg agaagcgcat taagaggaac gaacagagtc tgcaggagat  480
ttgggattac gtcaagaggc ctaacctgcg gttgatcggc gtccccgaga gcgacgtaga  540
aaacgggact aaactggaga atacacttca agacatcatt caagaaaatt ttccaaacct  600
ggctcggcaa gctaatgtgc aaatccaaga gatccaacgc acaccccagc ggtatagctc  660
tcggcgtgcc accccctaggc atattatcgt gcgctttact aaggtggaga tgaaagagaa  720
gatgctgcga gccgctcggg aaaagggaag ggtgactttg aagggcaaac ctattcggct  780
gacggttgac cttagcgccg agacactcca ggcacgccgg gaatggggcc ccatctttaa  840
tatcctgaag gagaagaact tccagccacg aatctcttac cctgcaaagt tgagttttat  900
ctccgagggt gagattaagt atttcatcga taaacagatg ctgcgagact tcgtgacaac  960
tcgcccagct ctcaaggaac tgctcaaaga ggctcttaat atggagcgca ataatagata  1020
tcaacccttg cagaaccacg caaagatgga ttataaggat gacgatgata aatga       1075

SEQ ID NO: 36            moltype = DNA  length = 5751
FEATURE                  Location/Qualifiers
misc_feature             1..5751
                         note = Description of Artificial Sequence: Synthetic
                          polynucleotide
source                   1..5751
```

mol_type = other DNA
organism = synthetic construct
SEQUENCE: 36
taatacgact cactataggg agaaagacgc caccatgaca ggttcaaata gtcacattac 60
gattctcact ctgaatataa atgggctgaa ttctgcaatt aaacggcaca ggcttgcttc 120
ctggataaag tctcaagacc cctcagtgtg ctgtattcag gaaacgcatc tcacgtgcag 180
ggacacccat cggctgaaaa taaaaggctg gcggaagatc taccaagcca atggaaaaca 240
aaagaaggct ggggtggcga tacttgtaag cgataaaaca gactttaaac caactaagat 300
caaacgggac aaagagggcc attacatcat ggtaaagggt agtattcaac aagaggagct 360
gactatcctg aatatttatg cacctaatac tggagccccc agattcataa agcaagtgtt 420
gagtgacctt caacgcgacc tcgactccca cactctgatc atgggagact ttaacacccc 480
gctgtccact ctcgacagat ctactagaca gaaagtcaac aaggatacac aggaactgaa 540
cagtgctctc caccaagcgg accttatcga catctacaga acactccacc ccaaaagcac 600
agaatatacc ttcttttcag cccctcacca cacctattcc aaaattgacc acattgtggg 660
gagtaaagcc cttctctcca aatgtaaacg gaccgaaatt atcactaact atctctccga 720
ccacagtgca ataaaacttg aattgcgaat taagaatctc actcaaagta gatccacgac 780
atggaaactg aacaatctcc tcttgaatga ctactgggtg cataacgaaa tgaaggctga 840
aataaagatg ttctttgaga ccaacgaaaa caaagacacc acgtaccaga atctctggga 900
cgctttcaaa gcagtgtgtc gaggaaaatt tattgcactg aatgcttaca agcggaagca 960
ggaaagatcc aaaatagaca ccctgactag ccaacttaaa gaactggaaa agcaagagca 1020
aactcatagc aaagctagcc gtcgccaaga aattacgaaa atcagagctg aactgaagga 1080
aattgagaca cagaaaaccc tgcaaaagat aaatgaaagc cgcagctggt tctttgaacg 1140
catcaacaaa atcgataggc cacttgctcg ccttatcaag aagaaaaggg agaagaatca 1200
aatcgacact ataaagaatg ataaaggcga tataaccacc gatcccacag aaattcaaac 1260
aaccatacgc gaatactaca aacacctcta cgccaataaa ctcgaaaatc tcgaggaaat 1320
ggatacattc ctcgacacgt acacccttcc caggctgaac caggaagaag ttgaatcact 1380
gaatcggcct atcacgggga gtgaaatagt agctatcatc aattcactcc ctaccaagaa 1440
gtcacccgga cctgatggat tcaccgccga attctaccag agatacatgg aagaactggt 1500
gcccttcttg ctgaaacttt tccaaagtat tgagaaagag ggaatacttc caaactcatt 1560
ttatgaggca tccatcattc tgatcccgaa gcccggcagg gacacgacca agaaagagaa 1620
ttttcgacca atctcattga tgaacattga tgcaaagatc ctcaataaaa tactggcaaa 1680
tcggattcag cagcacataa agaagctgat ccaccatgat caagtaggct tcatccccgg 1740
tatgcaaggt tggttcaata tacgaaaatc aatcaatgtt atccagcata taaaccgggc 1800
caaagacaag aaccacatga ttattagtat cgatgctgag aaagcctttg acaaaataca 1860
acaacccttc atgctgaaaa cattgaataa gctgggaatt gatggcacct acttcaaaat 1920
catcagagcc atatatgaca aaccaacagc aaatatcatt ctgaatggtc agaaattgga 1980
agcattcccc ttgaaaaccg gcacacggca gggttgccct ctgtcaccac tcctcttcaa 2040
catcgtgttg gaagttcttg cccgcgcaat ccggcaggaa aaggaaatca agggcattca 2100
actgggcaaa gaggaagtta aattgagcct gtttgcagac gacatgatcg tctatttgga 2160
aaaccccata gttagtgcac aaaatctgct gaagttgatc agtaatttct ccaaagtgag 2220
tgggtacaaa atcaatgtgc aaaagagcca agctttcttg tacaccaaca acaggcaaac 2280
tgagtctcaa atcatgggcg aactcccctt cgtgattgca tccaagcgga tcaaatacct 2340
ggggattcaa ttgactcgtg atgtgaagga cctcttcaag gagaactaca aacccctgct 2400
caaggaaatc aaagaggaca caaacaaatg gaagaacatt ccatgctctt gggtgggaag 2460
gatcaatatc gtcaaaatgg ccatcctgcc caaggtaatt tacaggttca atgctatacc 2520
catcaagctc cccatgacat tcttcacaga acttgaaaag acgacgctga agttcatttg 2580
gaaccagaaa cgtgccagga ttgctaaatc tattctctcc caaaagaaca aagctggcgg 2640
aatcacactc ccagacttca aactttacta caaggcgacc gtgacgaaaa cggcttggta 2700
ctggtaccaa aacagggata tagatcaatg gaaccgaacg gagcccagcg aaattatgcc 2760
tcatatatac aactatctga tctttgacaa accggagaag aacaagcaat ggggaaagga 2820
tagtctgttt aataaatggt gctgggaaaa ctggctcgca atctgtagga agctgaaact 2880
ggatccattc ttgacgcctt atacaaagat aaattcccga tggattaaag atctcaacgt 2940
gaaacccaaa acaattaaaa ccctcgagga aaacctgggt attacgattc aggacattgg 3000
ggtgggaaag gacttcatgt ccaaaacccc aaaagcgatg gcaaccaaag acaaaatcga 3060
caaatgggat ctcataaaac ttaagtcatt ttgcacagct aaagaaacga caattagggt 3120
gaaccgacaa ccgaccactt gggagaaaat cttcgcaaca tacagttctg acaaaggcct 3180
gatttccagg atctacaatg aattgaaaca aatttacaag aagaagacga acaaccctat 3240
aaagaaatgg gccaaggaca tgaacagaca cttctctaag gaagacattt atgcagccaa 3300
gaaacacatg aagaaatgca gctcttcact ggcaatcagg gaaatgcaaa tcaaaacaac 3360
aatgagatat catctcacac ccgtcagaat ggccatcatt aagaagagcg gaaacaaccg 3420
gtgctggcgt ggttgcggag aaatcggtac tctccttcac tgttggtggg actgtaaact 3480
cgttcaacca ctgtggaagt ctgtgtggcg gttcctcaga gatctggaac tcgaaatccc 3540
atttgaccca gccatccctc tcctgggtat atacccgaat gagtataaat cctgctgcta 3600
taaagacacc tgcacaagga tgtttattgc agctctcttc acaatcgcga agacgtggaa 3660
ccaacccaaa tgtccgacta tgattgactg gattaagaag atgtggcaca tatacactat 3720
ggaatactat gctgcgatca agaacgatga gttcatatca tttgtgggca catggatgaa 3780
actcgaaacc atcatactct ctaaattgag tcaagaacag aaaactaaac accgtatatt 3840
ttccctgatc ggtgggaatt agctacaaag acgatgacga caaggaccat ggagacggtg 3900
agagacacaa aaaattccaa cacactattg caatgaaaat aaatttcctt tattagccag 3960
aagtcagatg ctcaaggggc ttcatgatgt ccccataatt tttggcagag ggaaaaagat 4020
ctcagtggta tttgtgagcc agggcattgg ccttctgata ggcagcctgc acctgaggag 4080
tgcggccgct ttacttgtac agctcgtcca tgccgagagt gatcccggcg gcggtcacga 4140
actccagcag gaccatgtga tcgcgcttct cgttggggtc tttgctcagg gcggactggg 4200
tgctcaggta gtggttgtcg ggcagcagca cggggccgtc gccgatgggg gtgttctgct 4260
ggtagtggtc ggcgagctgc acgctgccgt cctcgatgtt gtggcggatc ttgaagttca 4320
ccttgatgcc gttcttctgc ttgtcggcca tgatatagac gttgtggctg ttgtagttgt 4380
actccagctt gtgccccagg atgttgccgt cctccttgaa gtcgatgccc ttcagctcga 4440
tgcggttcac cagggtgtcg ccctcgaact tcacctcggc gcgggtcttg tagttgccgt 4500
cgtccttgaa gaagatggtg cgctcctgga cgtagccttc gggcatggcg gacttgaaga 4560

```
agtcgtgctg cttcatgtgg tcggggtagc ggctgaagca ctgcacgccg taggtcaggg  4620
tggtcacgag ggtgggccag ggcacgggca gcttgccggt ggtgcagatg aacttcaggg  4680
tcagcttgcc gtaggtggca tcgccctcgc cctcgccgga cacgctgaac ttgtggccgt  4740
ttacgtcgcc gtccagctcg accaggatgg gcaccacccc ggtgaacagc tcctcgccct  4800
tgctcaccat ggtggcggga tctgacggtt cactaaacca gctctgctta tatagacctc  4860
ccaccgtaca cgcctaccgc ccatttgcgt caatggggcg gagttgttac gacattttgg  4920
aaagtcccgt tgattttggt gccaaaacaa actcccattg acgtcaatgg ggtggagact  4980
tggaaatccc cgtgagtcaa accgctatcc acgcccattg atgtactgcc aaaaccgcat  5040
caccatggta atagcgatga ctaatacgta gatgtactgc caagtaggaa agtcccataa  5100
ggtcatgtac tgggcataat gccaggcggg ccatttaccg tcattgacgt caatagggg   5160
cgtacttggc atatgataca cttgatgtac tgccaagtgg gcagtttacc gtaaatactc  5220
cacccattga cgtcaatgga aagtccctat tggcgttact atgggaacat acgtcattat  5280
tgacgtcaat gggcgggggt cgttgggcgg tcagccaggc gggccattta ccgtaagtta  5340
tgtaacgacg tctcagctga caatgagatc acatggacac aggaagggga atatcacact  5400
ctggggactg tggtggggtc gggggagggg ggagggatag cattgggaga tatacctaat  5460
gctagatgac acattagtgg gtgcagcgca ccagcatggc acatgtatac atatgtaact  5520
aacctgcaca atgtgcacat gtaccctaaa acttagagta taatggatcc gcaggcctct  5580
gctagcttga ctgactgaga tacagcgtac cttcagctca cagacatgat aagatacatt  5640
gatgagtttg gacaaaccac aactagaatg cagtgaaaaa aatgctttat ttgtgaaatt  5700
tgtgatgcta ttgctttatt tgtaaccatt ataagctgca ataaacaagt t           5751

SEQ ID NO: 37           moltype = DNA  length = 18285
FEATURE                 Location/Qualifiers
misc_feature            1..18285
                        note = Description of Artificial Sequence: Synthetic
                         polynucleotide
source                  1..18285
                        mol_type = other DNA
                        organism = synthetic construct
SEQUENCE: 37
cggccgcggg gggaggagcc aagatggccg aataggaaca gctccggtct acagctccca  60
gcgtgagcga cgcagaagac ggtgatttct gcatttccat ctgaggtacc gggttcatct  120
cactagggag tgccagacag tgggcgcagg ccagtgtgtg tgcgcaccgt gcgcgagccg  180
aagcagggcg aggcattgcc tcacctggga agcgcaaggg gtcagggagt tccctttccg  240
agtcaaagaa aggggtgacg gacgcacctg gaaaatcggg tcactcccac ccgaatattg  300
cgcttttcag accggcttaa gaaacggcgc accacgagac tatatcccac acctggctcg  360
gagggtccta cgcccacgga atctcgctga ttgctagcac agcagtctga gatcaaactg  420
caaggcggca acgaggctgg gggaggggcg cccgccattg cccaggcttg cttaggtaaa  480
caaagcagca gggaagctcg aactgggtgg agcccaccac agctcaagga ggcctgcctg  540
cctctgtagg ctccacctct gggggcaggg cacagacaaa caaaaagaca gcagtaacct  600
ctgcagactt aagtgtccct gtctgacagc tttgaagaga gcagtggttc tcccagcacg  660
cagctggaga tctgagaacg ggcagactgc ctcctcaagt gggtccctga cccctgaccc  720
ccgagcagcc taactgggag gcaccccccca gcaggggcac actgacacct cacacggcag  780
ggtattccaa cagacctgca gctgagggtc ctgtctgtta gaaggaaaac taacaaccag  840
aaaggacatc tacaccgaaa acccatctgt acatcaccat catcaaagac caaaagtaga  900
taaaaccaca aagatgggga aaaaacagaa cagaaaaact ggaaactcta aaacgcagag  960
cgcctctcct cctccaaagg aacgcagttc ctcaccagca acagaacaaa gctggatgga  1020
gaatgatttt gatgagctga gagaagaagg cttcagacga tcaaattact ctgagctacg  1080
ggaggacatt caaaccaaag gcaaagaagt tgaaaacttt gaaaaaaatt tagaagaatg  1140
tataactaga ataaccaata cagagaagtg cttaaaggag ctgatggagc tgaaaaccaa  1200
ggctcgagaa ctacgtgaag aatgcagaag cctcaggagc cgatgcgatc aactggaaga  1260
aagggtatca gcaatggaag atgaaatgaa tgaaatgaag cgagaaggga agtttagaga  1320
aaaaagaata aaaagaaatg agcaaagcct ccaagaaata tgggactatg tgaaaagacc  1380
aaatctacgt ctgattggtg tacctgaaag tgatgtggag aatggaacca agttggaaaa  1440
cactctgcag gatattatcc aggagaactt ccccaatcta gcaaggcagg ccaacgttca  1500
gattcaggaa atacagagaa cgccacaaag atactcctcg agaagagcaa ctccaagaca  1560
cataattgtc agattcacca aagttgaaat gaaggaaaaa atgttaaggg cagccagaga  1620
gaaaggtcgg gttaccctca aaggaaagcc catcagacta acagcggatc tctcggcaga  1680
aaccctacaa gccagaagag agtgggggcc aatattcaac attcttaaag aaaagaattt  1740
tcaacccaga atttcatatc cagccaaact aagcttcata agtgaaggag aaataaaata  1800
ctttatagac aagcaaatgt tgagagattt tgtcaccacc aggcctgccc taaaagagct  1860
cctgaaggaa gcgctaaaca tggaaaggaa caaccggtac cagccgctgc aaaatcatgc  1920
caaaatgtaa agaccatcaa gactaggaag aaactgcatc aactaatgag caaaatcacc  1980
agctaacatc ataatgacag gatcaacttc acacataaca atattaactt taaatataaa  2040
tggactaaat tctgcaatta aaagacacag actggcaagt tggataaaga gtcaagaccc  2100
atcagtgtgc tgtattcagg aaacccatct cacgtgcaga gacacacata ggctcaaaat  2160
aaaaggatgg aggaagatct accaagccaa tggaaaacaa aaaaaggcag gggttgcaat  2220
cctagtctct gataaaacag actttaaacc aacaaagatc aaaagagaca aagaaggcca  2280
ttacataatg gtaaagggat caattcaaca agaggagcta actatcctaa atatttatgc  2340
acccaataca ggagcaccca gattcataaa gcaagtcctc agtgacctac aaagagactt  2400
agactcccac acattaataa tgggagactt taacacccca ctgtcaacat tagacagatc  2460
aacgagacag aaagtcaaca aggataccca ggaattgaac tcagctctgc accaagcaga  2520
cctaatagac atctacagaa ctctccaccc caaatcaaca gaatatacat ttttttcagc  2580
accacaccac acctattcca aaattgacca catagttgga agtaaagctc tcctcagcaa  2640
atgtaaaaga acagaaatta taacaaacta tctctcagac cacagtgcaa tcaaactaga  2700
actcaggatt aagaatctca ctcaaagccg ctcaactaca tggaaactga acaacctgct  2760
cctgaatgac tactgggtac ataacgaaat gaaggcagaa ataaagatgt tctttgaaac  2820
caacgagaac aaagacacca cataccagaa tctctgggac gcattcaaag cagtgtgtag  2880
agggaaattt atagcactaa atgcctacaa gagaaagcag gaaagatcca aaattgacac  2940
```

-continued

```
cctaacatca caattaaaag aactagaaaa gcaagagcaa acacattcaa aagctagcag  3000
aaggcaagaa ataactaaaa tcagagcaga actgaaggaa atagagacac aaaaaaccct  3060
tcaaaaaatc aatgaatcca ggagctggtt ttttgaaagg atcaacaaaa ttgatagacc  3120
gctagcaaga ctaataaaga aaaaaagaga gaagaatcaa atagacacaa taaaaaatga  3180
taaaggggat atcaccaccg atcccacaga aatacaaact accatcagag aatactacaa  3240
acacctctac gcaaataaac tagaaaatct agaagaaatg gatacattcc tcgacacata  3300
cactctccca agactaaacc aggaagaagt tgaatctctg aatcgaccaa taacaggctc  3360
tgaaattgtg gcaataatca atagtttacc aaccaaaaag agtccaggac cagatggatt  3420
cacagccgaa ttctaccaga ggtacaagga ggaactggta ccattccttc tgaaactatt  3480
ccaatcaata gaaaaagagg gaatcctccc taactcattt tatgaggcca gcatcattct  3540
gataccaaag ccgggcagag acacaaccaa aaaagagaat tttagaccaa tatccttgat  3600
gaacattgat gcaaaaatcc tcaataaaat actggcaaac cgaatccagc agcacatcaa  3660
aaagcttatc caccatgatc aagtgggctt catccctggg atgcaaggct ggttcaatat  3720
acgcaaatca ataaatgtaa tccagcatat aaacagagcc aaagacaaaa accacatgat  3780
tatctcaata gatgcagaaa aagcctttga caaaattcaa caacccttca tgctaaaaac  3840
tctcaataaa ttaggtattg atgggacgta tttcaaaata ataagagcta tctatgacaa  3900
acccacagcc aatatcatac tgaatgggca aaaactggaa gcattccctt tgaaaaccgg  3960
cacaagacag ggatgccctc tctcaccgct cctattcaac atagtgttgg aagttctggc  4020
cagggcaatc aggcaggaga aggaaataaa gggtattcaa ttaggaaaag aggaagtcaa  4080
attgtccctg tttgcagacg acatgattgt ttatctagaa aaccccatcg tctcagccca  4140
aaatctcctt aagctgataa gcaacttcag caaagtctca ggatacaaaa tcaatgtaca  4200
aaaatcacaa gcattcttat acaccaacaa cagacaaaca gagagccaaa tcatgggtga  4260
actcccattc acaattgctt caaagagaat aaaataccta ggaatccaac ttacaaggga  4320
tgtgaaggac ctcttcaagg agaactacaa accactgctc aaggaaataa aagaggagac  4380
aaacaaatgg aagaacattc catgctcatg ggtaggaaga atcaatatcg tgaaaatggc  4440
catactgccc aaggtaattt acagattcaa tgccatcccc atcaagctac caatgacttt  4500
cttcacagaa ttggaaaaaa ctactttaaa gttcatatgg aaccaaaaaa gagcccgcat  4560
tgccaagtca atcctaagcc aaaagaacaa agctggaggc atcacactac ctgacttcaa  4620
actatactac aaggctacag taaccaaaac agcatggtac tggtaccaaa acagagatat  4680
agatcaatgg aacagaacag agccctcaga aataatgccg catatctaca actatctgat  4740
ctttgacaaa cctgagaaaa acaagcaatg gggaaaggat tccctattta ataaatggtg  4800
ctgggaaaac tggctagcca tatgtagaaa gctgaaactg gatcccttcc ttacacctta  4860
tacaaaaatc aattcaagat ggattaaaga tttaaacgtt aaacctaaaa ccataaaaac  4920
cctagaagaa aacctaggca ttaccattca ggacataggc gtgggcaagg acttcatgtc  4980
caaaacacca aaagcaatgg caacaaaaga caaaattgac aaatgggatc taattaaact  5040
aaagagcttc tgcacagcaa aagaaactac catcagagtg aacaggcaac ctacaacatg  5100
ggagaaaatt tttgcaacct actcatctga caaagggcta atatccagaa tctacaatga  5160
actcaaacaa atttacaaga aaaaaacaaa caaccccatc aaaaagtggg cgaaggacat  5220
gaacagacac ttctcaaaag aagacattta tgcagccaaa aaacacatga agaaatgctc  5280
atcatcactg gccatcagag aaatgcaaat caaaaccact atgagatatc atctcacacc  5340
agttagaatg gcaatcatta aaaagtcagg aaacaacagg tgctggagag gatgcggaga  5400
aataggaaca cttttacact gttggtggga ctgtaaacta gttcaaccat tgtggaagtc  5460
agtgtggcga ttcctcaggg atctagaact agaaatacca tttgacccag ccatcccatt  5520
actgggtata tacccaaatg agtataaatc atgctgctat aaagacacat gcacacgtat  5580
gtttattgcg gcactattca caatagcaaa gacttggaac caacccaaat gtccaacaat  5640
gatagactgg attaagaaaa tgtggcacat atacaccatg gaatactatg cagccataaa  5700
aaatgatgag ttcatatcct ttgtagggac atggatgaaa ttggaaacca tcattctcag  5760
taaactatcg caagaacaaa aaaccaaaca ccgcatattc tcactcatag gtgggaattg  5820
aacaatgaga tcacatggac acaggaaggg gaatatcaca ctctggggac tgtggtgggg  5880
tcgggggagg ggggagggat agcattggga gatataccta atgctagatg acacattagt  5940
gggtgcagcg caccagcatg gcacatgtat acggatccga attctcgacg gatcgatccg  6000
aacaaacgac ccaacacccg tgcgttttat tctgtctttt tattgccgat cccctcagaa  6060
gaactcgtca agaaggcgat agaaggcgat gcgctgcgaa tcgggagcgg cgataccgta  6120
aagcacgagg aagcggtcag cccattcgcc gccaagctct tcagcaatat cacgggtagc  6180
caacgctatg tcctgatagc ggtcggccgc tttacttgta cagctcgtcc atgccgagag  6240
tgatcccggc ggcggtcacg aactccagca ggaccatgtg atcgcgcttc tcgttggggt  6300
ctttgctcag ggcggactgg gtgctcaggt agtggttgtc gggcagcagc acggggccgt  6360
cgccgatggg ggtgttctgc tggtagtggt cggccaggtg agtccaggag atgtttcagc  6420
actgttgcct ttagtctcga ggcaacttag acaactgagt attgatctga gcacagcagg  6480
gtgtgagctg tttgaagata ctggggttgg gggtgaagaa actgcagagg actaactggg  6540
ctgagaccca gtggcaatgt tttagggcct aaggaatgcc tctgaaaatc tagatggaca  6600
actttgactt tgagaaaaga gaggtggaaa tgaggaaaat gacttttctt tattagattt  6660
cggtagaaag aactttcatc tttcccctat ttttgttatt cgttttaaaa catctatctg  6720
gaggcaggac aagtatggtc attaaaaaga tgcaggcaga aggcatatat tggctcagtc  6780
aaagtgggga actttggtgg ccaaacatac attgctaagg ctattcctat atcagctgga  6840
cacatataaa atgctgctaa tgcttcatta caaacttata tcctttaatt ccagatgggg  6900
gcaaagtatg tccaggggtg aggaacaatt gaaacatttg ggctggagta gatttgaaaa  6960
gtcagctctg tgtgtgtgtg tgtgtgtgtg tgtgtgagag cgtgtgtttc ttttaacgtt  7020
ttcagcctac agcatacagg gttcatggtg gcaagaagat aacaagattt aaattatggc  7080
cagtgactag tgctgcaaga agaacaacta cctgcattta atgggaaagc aaaatctcag  7140
gctttgaggg aagttaacat aggcttgatt ctgggtggaa gctgggtgtg tagttatctg  7200
gaggccaggc tggagctctc agctcactat gggttcatct ttattgtctc ctttcatctc  7260
aacagctgca cgctgccgtc ctcgatgttg tggcggatct tgaagttcac cttgatgccg  7320
ttcttctgct tgtcggccat gatatagacg ttgtggctgt tgtagttgta ctccagcttg  7380
tgccccagga tgttgccgtc ctccttgaag tcgatgccct tcagctcgat gcggttcacc  7440
agggtgtcgc cctcgaactt cacctcggcg cgggtcttgt agttgccgtc gtccttgaag  7500
aagatggtgc gctcctggac gtagccttcg ggcatggcgg acttgaagaa gtcgtgctgc  7560
ttcatgtggt cggggtagcg gctgaagcac tgcacgccgt aggtcagggt ggtcacgagg  7620
gtgggccagg gcacgggcag cttgccggtg gtgcagatga acttcagggt cagcttgccg  7680
```

-continued taggtggcat cgccctcgcc ctcgccggac acgctgaact tgtggccgtt tacgtcgccg 7740
tccagctcga ccaggatggg caccaccccg gtgaacagct cctcgccctt gctcaccatg 7800
gtggcgaatt cgaagcttga gctcgagatc tgagtccggt agcgctagcg gatctgacgg 7860
ttcactaaac cagctctgct tatatagacc tcccaccgta cacgcctacc gcccatttgc 7920
gtcaatgggg cggagttgtt acgacatttt ggaaagtccc gttgattttg gtgccaaaac 7980
aaactcccat tgacgtcaat ggggtggaga cttggaaatc cccgtgagtc aaaccgctat 8040
ccacgcccat tgatgtactg ccaaaaccgc atcaccatgg taatagcgat gactaatacg 8100
tagatgtact gccaagtagg aaagtcccat aaggtcatgt actgggcata atgccaggcg 8160
ggccatttac cgtcattgac gtcaataggg ggcgtacttg gcatatgata cacttgatgt 8220
actgccaagt gggcagttta ccgtaaatac tccacccatt gacgtcaatg gaaagtccct 8280
attggcgtta ctatgggaac atacgtcatt attgacgtca atgggcgggg gtcgttgggc 8340
ggtcagccag gcgggccatt taccgtaagt tatgtaacgc ggaactccat atatgggcta 8400
tgaactaatg accccgtaat tgattactat tagcccgggg gatccagaca tgataagata 8460
cattgatgag tttggacaaa ccacaactag aatgcagtga aaaaaatgct ttatttgtga 8520
aatttgtgat gctattgctt tatttgtaac cattataagc tgcaataaac aagttaacaa 8580
caacaattgc attcatttta tgtttcaggt tcagggggag gtgtgggagg tttttaaag 8640
caagtaaaac ctctacaaat gtggtatggc tgattatgat ccggctgcct cgcgcgtttc 8700
ggtgatgacg gtgaaaacct ctgacacatg cagctcccgg agacggtcac agcttgtctg 8760
taagcggatg ccgggagcag acaagcccgt cagggcgcgt cagcgggtgt tggcgggtgt 8820
cggggcgcag ccatgaggtc gatcgactct agaggatcga tccccgcccc ggacgaacta 8880
aacctgacta cgacatctct gccccttctt cgcggggcag tgcatgtaat cccttcagtt 8940
ggttggtaca acttgccaac tgggccctgt tccacatgtg acacgggggg ggaccaaaca 9000
caaaggggtt ctctgactgt agttgacatc cttataaatg gatgtgcaca tttgccaaca 9060
ctgagtggct ttcatcctgg agcagacttt gcagtctgtg gactgcaaca caacattgcc 9120
tttatgtgta actcttggct gaagctctta caccaatgct gggggacatg tacctcccag 9180
gggcccagga agactacggg aggctacacc aacgtcaatc agaggggcct gtgtagctac 9240
cgataagcgg accctcaaga gggcattagc aatagtgttt ataaggcccc cttgttaacc 9300
ctaaacgggt agcatatgct tcccgggtag tagtatatac tatccagact aaccctaatt 9360
caatagcata tgttacccaa cgggaagcat atgctatcga attagggtta gtaaaagggt 9420
cctaaggaac agcgatatct cccaccccat gagctgtcac ggttttattt acatggggtc 9480
aggattccac gagggtagtg aaccatttta gtcacaaggg cagtggctga agatcaagga 9540
gcgggcagtg aactctcctg aatcttcgcc tgcttcttca ttctccttcg tttagctaat 9600
agaataactg ctgagttgtg aacagtaagg tgtatgtgag gtgctcgaaa acaaggtttc 9660
aggtgacgcc cccagaataa aatttggacg gggggttcag tggtggcatt gtgctatgac 9720
accaatataa ccctcacaaa ccccttgggc aataaatact agtgtaggaa tgaaacattc 9780
tgaatatctt taacaataga aatccatggg gtggggacaa gccgtaaaga ctggatgtcc 9840
atctcacacg aatttatggc tatgggcaac acataatcct agtgcaatat gatactgggg 9900
ttattaagat gtgtcccagg cagggaccaa gacaggtgaa ccatgttgtt acactctatt 9960
tgtaacaagg ggaaagagag tggacgccga cagcagcgga ctccactggt tgtctctaac 10020
acccccgaaa attaaacggg gctccacgcc aatggggccc ataaacaaag acaagtggcc 10080
actctttttt ttgaaattgt ggagtggggg cacgcgtcag cccccacacg ccgccctgcg 10140
gttttggact gtaaaataag ggtgtaataa cttggctgat tgtaaccccg ctaaccactg 10200
cggtcaaacc acttgcccac aaaaccacta atggcacccc ggggaatacc tgcataagta 10260
ggtgggcggg ccaagatagg ggcgcgattg ctgcgatctg gaggacaaat tacacacact 10320
tgcgcctgag cgccaagcac agggttgttg gtcctcatat tcacgaggtc gctgagagca 10380
cggtgggcta atgttgccat gggtagcata tactacccaa atatctggat agcatatgct 10440
atcctaatct atatctgggt agcataggct atcctaatct atatctgggt agcatatgct 10500
atcctaatct atatctgggt agtatatgct atcctaattt atatctgggt agcataggct 10560
atcctaatct atatctgggt agcatatgct atcctaatct atatctgggt agtatatgct 10620
atcctaatct gtatccgggt agcatatgct atcctaatag agattagggt agtatatgct 10680
atcctaattt atatctgggt agcatatact acccaaatat ctggatagca tatgctatcc 10740
taatctatat ctgggtagca tatgctatcc taatctatat ctgggtagca taggctatcc 10800
taatctatat ctgggtagca tatgctatcc taatctatat ctgggtagta tatgctatcc 10860
taatttatat ctgggtagca taggctatcc taatctatat ctgggtagca tatgctatcc 10920
taatctatat ctgggtagta tatgctatcc taatctgtat ccgggtagca tatgctatcc 10980
tcatgcatat acagtcagca tatgataccc agtagtagag tgggagtgct atcctttgca 11040
tatgccgcca cctcccaagg gggcgtgaat tttcgctgct tgtccttttc ctgcatgctg 11100
gttgctccca ttcttaggtg aatttaagga ggccaggcta aagccgtcgc atgtctgatt 11160
gctcaccagg taaatgtcgc taatgttttc caacgcgaga aggtgttgag cgcggagctg 11220
agtgacgtga caacatgggt atgcccaatt gccccatgtt gggaggacga aaatggtgac 11280
aagacagatg gccagaaata caccaacagc acgcatgatg tctactgggg atttattctt 11340
tagtgcgggg gaatacacgg cttttaatac gattgagggc gtctcctaac aagttacatc 11400
actcctgccc ttcctcaccc tcatctccat cacctccttc atctccgtca tctccgtcat 11460
caccctccgc ggcagcccct tccaccatag gtggaaacca gggaggcaaa tctactccat 11520
cgtcaaagct gcacacagtc accctgatat tgcaggtagg agcgggcttt gtcataacaa 11580
ggtccttaat cgcatccttc aaaacctcag caaatatatg agtttgtaaa aagaccatga 11640
aataacagac aatggactcc cttagcgggc caggttgtgg gccgggtcca ggggccattc 11700
caaaggggag acgactcaat ggtgtaagac gacattgtgg aatagcaagg gcagttcctc 11760
gccttaggtt gtaaagggag gtcttactac ctccatatac gaacacaccg gcgacccaag 11820
ttccttcgtc ggtagtcctt tctacgtgac tcctagccag gagagctctt aaaccttctg 11880
caatgttctc aaatttcggg ttggaacctc cttgaccacg atgctttcca aaccaccctc 11940
ctttttgcg cctgcctcca tcaccctgac cccggggtcc agtgcttggg ccttctcctg 12000
ggtcatctgc ggggccctgc tctatcgctc ccgggggcac gtcaggctca ccatctgggc 12060
caccttcttg gtggtattca aaataatcgg cttcccctac agggtggaaa aatggccttc 12120
tacctggagg gggcctgcgc ggtggagacc cggatgatga tgactgacta ctgggactcc 12180
tgggcctctt ttctccacgt ccacgacctc tcccccctggc tctttcacga cttccccccc 12240
tggctctttc acgtcctcta ccccggcggc ctccactacc tcctcgaccc cggcctccac 12300
tacctcctcg accccggcct ccactgcctc ctcgaccccg gcctccacct cctgctcctg 12360
cccctcctgc tcctgcccct cctcctgctc ctgcccctcc tgcccctcct gctcctgccc 12420

```
ctcctgcccc tcctgctcct gcccctcctg cccctcctgc tcctgcccct cctgcccctc  12480
ctcctgctcc tgcccctcct gcccctcctc ctgctcctgc ccctcctgcc cctcctgctc  12540
ctgcccctcc tgcccctcct gctcctgccc ctcctgcccc tcctgctcct gcccctcctg  12600
ctcctgcccc tcctgctcct gcccctcctg ctcctgcccc tcctgcccct cctgcccctc  12660
ctcctgctcc tgcccctcct gctcctgccc ctcctgcccc tcctgcccct cctgctcctg  12720
cccctcctcc tgctcctgcc cctcctgccc ctcctgcccc tcctcctgct cctgcccctc  12780
ctgcccctcc tcctgctcct gcccctcctc ctgctcctgc ccctcctgcc cctcctgccc  12840
ctcctcctgc tcctgcccct cctgcccctc ctcctgctcc tgcccctcct cctgctcctg  12900
cccctcctgc ccctcctgcc cctcctcctg ctcctgcccc tcctcctgct cctgcccctc  12960
ctgcccctcc tgcccctcct gcccctcctc ctgctcctgc ccctcctcct gctcctgccc  13020
ctcctgctcc tgcccctccc gctcctgctc ctgctcctgt tccaccgtgg gtccctttgc  13080
agccaatgca acttggacgt ttttggggtc tccggacacc atctctatgt cttggccctg  13140
atcctgagcc gcccggggct cctggtcttc cgcctcctcg tcctcgtcct cttccccgtc  13200
ctcgtccatg gttatcaccc cctcttcttt gaggtccact gccgccggag ccttctggtc  13260
cagatgtgtc tcccttctct cctaggccat ttccaggtcc tgtacctggc ccctcgtcag  13320
acatgattca cactaaaaga gatcaataga catctttatt agacgacgct cagtgaatac  13380
agggagtgca gactcctgcc ccctccaaca gcccccccac cctcatcccc ttcatggtcg  13440
ctgtcagaca gatccaggtc tgaaaattcc ccatcctccg aaccatcctc gtcctcatca  13500
ccaattactc gcagcccgga aaactcccgc tgaacatcct caagatttgc gtcctgagcc  13560
tcaagccagg cctcaaattc ctcgtccccc tttttgctgg acggtaggga tggggattct  13620
cgggacccct cctcttcctc ttcaaggtca ccagacagag atgctactgg ggcaacggaa  13680
gaaaagctgg gtgcggcctg tgaggatcag cttatcgatg ataagctgtc aaacatgaga  13740
attcttgaag acgaaagggc ctcgtgatac gcctattttt ataggttaat gtcatgataa  13800
taatggtttc ttagacgtca ggtggcactt ttcggggaaa tgtgcgcgga acccctattt  13860
gtttattttt ctaaatacat tcaaatatgt atccgctcat gagacaataa ccctgataaa  13920
tgcttcaata atattgaaaa aggaagagta tgagtattca acatttccgt gtcgccctta  13980
ttcccttttt tgcggcattt tgccttcctg tttttgctca cccagaaacg ctggtgaaag  14040
taaaagatgc tgaagatcag ttgggtgcac gagtgggtta catcgaactg gatctcaaca  14100
gcggtaagat ccttgagagt tttcgccccg aagaacgttt tccaatgatg agcactttta  14160
aagttctgct atgtggcgcg gtattatccc gtgttgacgc cgggcaagag caactcggtc  14220
gccgcataca ctattctcag aatgacttgg ttgagtactc accagtcaca gaaaagcatc  14280
ttacggatgg catgacagta agagaattat gcagtgctgc cataaccatg agtgataaca  14340
ctgcggccaa cttacttctg acaacgatcg gaggaccgaa ggagctaacc gcttttttgc  14400
acaacatggg ggatcatgta actcgccttg atcgttggga accggagctg aatgaagcca  14460
taccaaacga cgagcgtgac accacgatgc ctgcagcaat ggcaacaacg ttgcgcaaac  14520
tattaactgg cgaactactt actctagctt cccggcaaca attaatagac tggatggagg  14580
cggataaagt tgcaggacca cttctgcgct cggcccttcc ggctggctgg tttattgctg  14640
ataaatctgg agccggtgag cgtgggtctc gcggtatcat tgcagcactg gggccagatg  14700
gtaagccctc ccgtatcgta gttatctaca cgacggggag tcaggcaact atggatgaac  14760
gaaatagaca gatcgctgag ataggtgcct cactgattaa gcattggtaa ctgtcagacc  14820
aagtttactc atatatactt tagattgatt taaaacttca tttttaattt aaaaggatct  14880
aggtgaagat cctttttgat aatctcatga ccaaaatccc ttaacgtgag ttttcgttcc  14940
actgagcgtc agaccccgta gaaaagatca aaggatcttc ttgagatcct ttttttctgc  15000
gcgtaatctg ctgcttgcaa acaaaaaaac caccgctacc agcggtggtt tgtttgccgg  15060
atcaagagct accaactctt tttccgaagg taactggctt cagcagagcg cagataccaa  15120
atactgtcct tctagtgtag ccgtagttag gccaccactt caagaactct gtagcaccgc  15180
ctacatacct cgctctgcta atcctgttac cagtggctgc tgccagtggc gataagtcgt  15240
gtcttaccgg gttggactca agacgatagt taccggataa ggcgcagcgg tcgggctgaa  15300
cggggggttc gtgcacacag cccagcttgg agcgaacgac ctacaccgaa ctgagatacc  15360
tacagcgtga gctatgagaa agcgccacgc ttcccgaagg gagaaaggcg gacaggtatc  15420
cggtaagcgg cagggtcgga acaggagagc gcacgaggga gcttccaggg ggaaacgcct  15480
ggtatcttta tagtcctgtc gggtttcgcc acctctgact tgagcgtcga tttttgtgat  15540
gctcgtcagg ggggcggagc ctatggaaaa acgccagcaa cgcggccttt ttacggttcc  15600
tggccttttg ctggcctttt gctcacatgt tctttcctgc gttatcccct gattctgtgg  15660
ataaccgtat taccgccttt gagtgagctg ataccgctcg ccgcagccga acgaccgagc  15720
gcagcgagtc agtgagcgag gaagcggaag agcgcctgat gcggtatttt ctccttacgc  15780
atctgtgcgg tatttcacac cgcatatggt gcactctcag tacaatctgc tctgatgccg  15840
catagttaag ccagctgtgg aatgtgtgtc agttagggtg tggaaagtcc ccaggctccc  15900
cagcaggcag aagtatgcaa agcatgcatc tcaattagtc agcaaccagg tgtggaaagt  15960
ccccaggctc cccagcaggc agaagtatgc aaagcatgca tctcaattag tcagcaacca  16020
tagtcccgcc cctaactccg cccatcccgc ccctaactcc gcccagttcc gcccattctc  16080
cgccccatgg ctgactaatt ttttttattt atgcagaggc cgaggccgcc tcggcctctg  16140
agctattcca gaagtagtga ggaggctttt ttggaggcct aggcttttgc aaaaagcttg  16200
catgcctgca ggtcggccgc cacgaccggt gccgccacca tcccctgacc cacgcccctg  16260
acccctcaca aggagacgac cttccatgac cgagtacaag cccacggtgc gcctcgccac  16320
ccgcgacgac gtcccccggg ccgtacgcac cctcgccgcc gcgttcgccg actaccccgc  16380
cacgcgccac accgtcgacc cggaccgcca catcgagcgg gtcaccgagc tgcaagaact  16440
cttcctcacg cgcgtcgggc tcgacatcgg caaggtgtgg gtcgcggacg acggcgccgc  16500
ggtggcggtc tggaccacgc cggagagcgt cgaagcgggg gcggtgttcg ccgagatcgg  16560
cccgcgcatg gccgagttga gcggttcccg gctggccgcg cagcaacaga tggaaggcct  16620
cctggcgccg caccggccca aggagcccgc gtggttcctg gccaccgtcg gcgtctcgcc  16680
cgaccaccag ggcaagggtc tgggcagcgc cgtcgtgctc cccggagtgg aggcggccga  16740
gcgcgccggg gtgcccgcct tcctggagac ctccgcgccc cgcaacctcc ccttctacga  16800
gcggctcggc ttcaccgtca ccgccgacgt cgaggtgccc gaaggaccgc gcacctggtg  16860
catgacccgc aagcccggtg cctgacgccc gccccacgac ccgcagcgcc cgaccgaaag  16920
gagcgcacga ccccatggct ccgaccgaag ccgacccggg cggccccgcc gaccccgcac  16980
ccgcccccga ggcccaccga ctctagagga tcataatcag ccataccaca tttgtagagg  17040
ttttacttgc tttaaaaaac ctcccacacc tcccccctgaa cctgaaacat aaaatgaatg  17100
caattgttgt tgttaacttg tttattgcag cttataatgg ttacaaataa agcaatagca  17160
```

-continued

```
tcacaaattt cacaaataaa gcattttttt cactgcattc tagttgtggt ttgtccaaac  17220
tcatcaatgt atcttatcat gtctggatca ctcgccgata gtggaaaccg acgccccagc  17280
actcgtccga gggcaaagga ataggggaga tgggggaggc taactgaaac acggaaggag  17340
acaataccgg aaggaacccg cgctatgacg gcaataaaaa gacagaataa aacgcacggg  17400
tgttgggtcg tttgttcata aacgcggggt tcggtcccag ggctggcact ctgtcgatac  17460
cccaccgaga ccccattggg gccaatacgc ccgcgtttct tccttttccc caccccaccc  17520
cccaagttcg ggtgaaggcc cagggctcgc agccaacgtc ggggcggcag gccctgccat  17580
agccactggc cccgtgggtt agggacgggg tcccccatgg ggaatggttt atggttcgtg  17640
ggggttatta ttttgggcgt tgcgtggggt ctggtccacg actggactga gcagacagac  17700
ccatggtttt tggatggcct gggcatggac cgcatgtact ggcgcgacac gaacaccggg  17760
cgtctgtggc tgccaaacac ccccgacccc caaaaaccac cgcgcggatt tctggcgtgc  17820
caagctagtc gaccaattct catgtttgac agcttatcat cgcagatccg ggcaacgttg  17880
ttgcattgct gcaggcgcag aactggtagg tatggaagat ctctagaagc tgggtaccag  17940
ctgctagcaa gcttgctagc ggccggctcg agtttactcc ctatcagtga tagagaacgt  18000
atgtcgagtt tactccctat cagtgataga gaacgatgtc gagtttactc cctatcagtg  18060
atagagaacg tatgtcgagt ttactcccta tcagtgatag agaacgtatg tcgagtttac  18120
tccctatcag tgatagagaa cgtatgtcga gtttatccct atcagtgata gagaacgtat  18180
gtcgagttta ctccctatca gtgatagaga acgtatgtcg aggtaggcgt gtacggtggg  18240
aggcctatat aagcagagct cgtttagtga accgtcagat cgccg                  18285

SEQ ID NO: 38           moltype = DNA  length = 7264
FEATURE                 Location/Qualifiers
misc_feature            1..7264
                        note = Description of Artificial Sequence: Synthetic
                         polynucleotide
source                  1..7264
                        mol_type = other DNA
                        organism = synthetic construct
SEQUENCE: 38
taatacgact cactataggg agaagtactg ccaccatggg caagaagcaa aatcgcaaga  60
cggggaattc caagacacaa tccgctagcc caccacctaa agagcgttct agctcccctg  120
ctactgagca gtcctggatg gaaaacgact tcgatgaact ccgggaagag ggatttaggc  180
gatccaacta ttcagaactc cgcgaagata tccagacaaa ggggaaggaa gtcgagaatt  240
tcgagaagaa cctcgaggag tgcatcaccc gtatcacaaa cactgagaaa tgtctcaaag  300
aactcatgga acttaagaca aaagccaggg agcttcgaga ggagtgtcgg agtctgagat  360
ccaggtgtga ccagctcgag gagcgcgtga gcgcgatgga agacgagatg aacgagatga  420
aaagagaggg caaattcagg gagaagcgca ttaagaggaa cgaacagagt ctgcaggaga  480
tttgggatta cgtcaagagg cctaacctgc ggttgatcgg cgtccccgag agcgacgtag  540
aaaacgggac taaactggag aatacacttc aagacatcat tcaagaaaat tttccaaacc  600
tggctcggca agctaatgtg caaatccaag agatccaacg cacaccccag cggtatagct  660
ctcggcgtgc cacccctagg catattatcg tgcgctttac taaggtggag atgaaagaga  720
agatgctgcg agccgctcgg gaaaagggaa gggtgacttt gaagggcaaa cctattcggc  780
tgacggttga ccttagcgcc gagacactcc aggcacgccg ggaatggggc cccatcttta  840
atatcctgaa ggagaagaac ttccagccac gaatctctta ccctgcaaag ttgagtttta  900
tctccgaggg tgagattaag tatttcatcg ataaacagat gctgcgagac ttcgtgacaa  960
ctcgcccagc tctcaaggaa ctgctcaaag aggctcttaa tatggagcgc aataatagat  1020
atcaaccctt gcagaaccac gcaaagatgt gagacagccg tcagaccatc aagactagga  1080
agaaactgca tcaactaatg agcaaaatca ccagctaaca tcatagtata catgaccggc  1140
tctaactcac atatcaccat ccttacactt aacattaacg gcctcaactc agctatcaag  1200
cgccatcggc tggccagctg gatcaaatca caggatccaa gcgtttgttg catccaagag  1260
acccacctga cctgtagaga tactcaccgc ctcaagatca agggatggcg aaagatttat  1320
caggcgaacg gtaagcagaa gaaagccgga gtcgcaattc tggtctcaga caagacggat  1380
ttcaagccca ccaaaattaa gcgtgataag gaaggtcact atattatggt gaaaggcagc  1440
atacagcagg aagaacttac catattgaac atctacgcgc caaacaccgg cgcacctcgc  1500
tttatcaaac aggtcctgtc cgatctgcag cgagatctgg attctcatac gttgattatg  1560
ggtgatttca atacaccatt gagcaccctg gatcgcagca ccaggcaaaa ggtaaataaa  1620
gacacgcaag agctcaatag cgcactgcat caggcagatc tcattgatat ttatcgcact  1680
cttcatccta agagtaccga gtacacattc ttcagcgccc cacatcatac atactcaaag  1740
atcgatcata tcgtcggctc aaaggctctg ctgtcaaagt gcaagcgcac agagataatt  1800
acaaattacc tgtcagatca tagcgcgatc aagctcgagc tgagaatcaa gaacctgacc  1860
cagagccgga gtaccacttg gaagcttaat aacctgctgc tcaacgatta ttgggtccac  1920
aatgagatga aggcagagat taaaatgttc ttcgaaacaa atgagaataa ggatactacc  1980
tatcaaaacc tttgggatgc ctttaaggcc gtctgcagag gcaagttcat cgccctcaac  2040
gcctataaaa gaaaacaaga gagatctaag atcgatactc tcacctctca gctgaaggag  2100
ttggagaaac aggaacagac ccactccaag gcgtcaagac ggcaggagat cacaaagatt  2160
cgcgccgagt tgaaagagat cgaaacccaa aagactcttc agaaaattaa cgagtctcgt  2220
agttggttct tcgagcggat taataagata gacagacctc tggcacgact gattaagaag  2280
aagcgcgaaa agaaccagat tgataccatc aagaacgaca agggcgacat cactactgac  2340
ccgaccgaga tccagaccac tattcgggag tattataagc atttgtatgc taacaagctt  2400
gagaacctgg aagagatgga cacttttctg gatacctata ctctgccacg gcttaatcaa  2460
gaggaagtcg agtccctcaa ccgcccaatt acaggaagcg agattgtggc cataattaac  2520
tccctgccga caaagaaatc tcctggtccg gacgggttta cagctgagtt ttatcaacgg  2580
tatatggaag agcttgtacc gtttctgctc aagctctttc agtctataga aaaggaaggc  2640
atcttgccca attccttcta cgaagcttct ataatactta ttcccaaacc aggacgcgat  2700
accacaaaga aggaaaactt ccggcccatt agtctcatga atatcgacgc taaaatattg  2760
aacaagattc tcgccaacag aatccaacaa catattaaga aattgataca tcacgaccag  2820
gtggggttta tacctggcat gcagggctgg tttaacatcc ggaagagtat taacgtcatt  2880
caacacatta atagagctaa ggataagaat catatgatca tctctataga cgcggaaaag  2940
gcattcgata agattcagca gccatttatg ctcaagactc tgaacaaact cggcatcgac  3000
```

-continued

```
ggaacatatt ttaagattat tcgcgcaatt tacgataagc cgactgctaa cattatcctt  3060
aacggccaaa agctcgaggc ctttccgctc aagactggaa cccgccaagg ctgtcccctc  3120
tccccgcttt tgtttaatat tgtactcgag gtgctggcta gggctattcg tcaagagaaa  3180
gagattaaag ggatacagct cgggaaggaa gaggtcaagc tttccttgtt cgccgatgat  3240
atgattgtgt acctggagaa tcctattgtg tctgctcaga accttcttaa acttatttct  3300
aactttagca aggtcagcgg ctataagatt aacgtccaga aatctcaggc ctttctgtac  3360
acaaataatc gacagaccga atcccagata atgggtgagc ttccgtttgt catagccagc  3420
aaaaggataa agtatctcgg aatccagctg acacgagacg ttaaagattt gtttaaggaa  3480
aattacaagc ctctcctgaa agagattaag gaagatacta ataagtggaa gaatatcccc  3540
tgttcatggg ttggcagaat caacatagtg aagatggcaa tacttcctaa agtgatatat  3600
cgctttaacg ccatcccaat taaactgcct atgaccttct ttacggagct cgagaaaaca  3660
acccttaaat ttatatggaa tcaaaagaga gcaagaatag cgaagtccat cttgagccag  3720
aagaataagg ccggtgggat tactttgcct gattttaagt tgtattataa agccacagta  3780
actaagacag cctggtattg gtatcagaat agagacatcg accagtggaa tcggaccgaa  3840
ccatcagaga taatgcccca catctataat taccttatat tcgataagcc agaaaagaat  3900
aaacagtggg gcaaagacag cctcttcaac aagtggtgtt gggagaattg gctggccata  3960
tgccggaaac tcaagctcga ccccttttctt acaccctaca ctaaaatcaa cagtaggtgg  4020
atcaaggact tgaatgtcaa gccaaagact ataaagacac tggaagagaa tcttgggatc  4080
acaatacaag atataggcgt cggcaaagat tttatgtcaa agacgcccaa ggccatggcc  4140
actaaggata agattgataa gtgggacctt attaagctca aaagcttctg tactgccaag  4200
gagaccacga tcagagttaa taggcagccc actacatggg aaaagatttt cgccacttat  4260
tcatcagata aggggttgat aagcagaata tataacgagc tgaagcagat ctacaagaag  4320
aaaacgaata atcccatcaa gaagtgggca aaagatatga acaggcattt tagcaaagag  4380
gatatctacg ccgcgaagaa gcatatgaag aagtgtagtt caagcttggc cattcgtgag  4440
atgcagatta agacgaccat gcgataccac cttaccccag tgaggatggc aattatcaag  4500
aaatctggca ataatagatg ttggcggggc tgtggcgaga ttggcaccct gctccattgc  4560
tggtgggatt gcaagctggt gcagccgctt tggaaatcag tctggcgctt tctgagggac  4620
ctcgagcttg agattccctt cgatcccgca attcccttgc tcggaatcta tcctaacgaa  4680
tacaagagct gttgttacaa ggatacgtgt acccggatgt tcatcgcggc cttgtttacg  4740
atagctaaga cgtggaatca gcctaagtgc cccacaatga tcgattggat caagaaaatg  4800
tggcatattt ataccatgga gtattacgca gcaattaaga atgacgaatt tatttccttc  4860
gttgggacct ggatgaagct ggagactatt attctgagca agctgtctca ggagcaaaag  4920
acaaagcata gaatcttctc tctcattggt ggtaacgact acaaagacga tgacgacaag  4980
taaagcgctt ctagaagttg tctcctcctg cactgactga ctgatacaat cgatttctgg  5040
atccgcaggc ctaatcaacc tctggattac aaaatttgtg aaagattgac tggtattctt  5100
aactatgttg ctccttttac gctatgtgga tacgctgctt taatgccttt gtatcatgct  5160
attgcttccc gtatggcttt cattttctcc tccttgtata aatcctggtt gctgtctctt  5220
tatgaggagt tgtggcccgt tgtcaggcaa cgtggcgtgg tgtgcactgt gtttgctgac  5280
gcaaccccca ctggttgggg cattgccacc acctgtcagc tcctttccgg gactttcgct  5340
ttccccctcc ctattgccac ggcggaactc atcgccgcct gccttgcccg ctgctggaca  5400
ggggctcggc tgttgggcac tgacaattcc gtggtgttgt cggggaagct gacgtccttt  5460
ccatggctgc tcgcctgtgt tgccacctgg attctgcgcg ggacgtcctt ctgctacgtc  5520
ccttcggccc tcaatccagc ggaccttcct tcccgctgag agacacaaaa aattccaaca  5580
cactattgca atgaaaataa atttccttta ttagccagaa gtcagatgct caaggggctt  5640
catgatgtcc ccataatttt tggcagaggg aaaaagatct cagtggtatt tgtgagccag  5700
ggcattggcc ttctgatagg cagcctgcac ctgaggagtg cggccgcttt acttgtacag  5760
ctcgtccatg ccgagagtga tcccggcggc ggtcacgaac tccagcagga ccatgtgatc  5820
gcgcttctcg ttggggtctt tgctcagggc ggactgggtg ctcaggtagt ggttgtcggg  5880
cagcagcacg gggccgtcgc cgatgggggt gttctgctgg tagtggtcgg cgagctgcac  5940
gctgccgtcc tcgatgttgt ggcggatctt gaagttcacc ttgatgccgt tcttctgctt  6000
gtcggccatg atatagacgt tgtggctgtt gtagttgtac tccagcttgt gccccaggat  6060
gttgccgtcc tccttgaagt cgatgccctt cagctcgatg cggttcacca gggtgtcgcc  6120
ctcgaacttc acctcggcgc gggtcttgta gttgccgtcg tccttgaaga agatggtgcg  6180
ctcctggacg tagccttcgg gcatggcgga cttgaagaag tcgtgctgct tcatgtggtc  6240
ggggtagcgg ctgaagcact gcacgccgta ggtcagggtg gtcacgaggg tgggccaggg  6300
cacgggcagc ttgccggtgg tgcagatgaa cttcagggtc agcttgccgt aggtggcatc  6360
gccctcgccc tcgccggaca cgctgaactt gtggccgttt acgtcgccgt ccagctcgac  6420
caggatgggc accaccccgg tgaacagctc ctcgcccttg ctcaccatgg tggcgggatc  6480
tgacggttca ctaaaccagc tctgcttata tagacctccc accgtacacg cctaccgccc  6540
atttgcgtca atggggcgga gttgttacga cattttggaa agtcccgttg attttggtgc  6600
caaaacaaac tcccattgac gtcaatgggg tggagacttg gaaatccccg tgagtcaaac  6660
cgctatccac gcccattgat gtactgccaa aaccgcatca ccatggtaat agcgatgact  6720
aatacgtaga tgtactgcca agtaggaaag tcccataagg tcatgtactg ggcataatgc  6780
caggcgggcc atttaccgtc attgacgtca atagggggcg tacttggcat atgatacact  6840
tgatgtactg ccaagtgggc agtttaccgt aaatactcca cccattgacg tcaatggaaa  6900
gtccctattg gcgttactat gggaacatac gtcattattg acgtcaatgg gcgggggtcg  6960
ttgggcggtc agccaggcgg gccatttacc gtaagttatg taacgggcct gctgccggct  7020
ctgcggcctc ttccgcgtct tcgccttcgc cctcagacga gtcggatctc cctttgggcc  7080
gcctccccgc ctgtctagct tgactgactg agatacagcg taccttcagc tcacagacat  7140
gataagatac attgatgagt ttggacaaac cacaactaga atgcagtgaa aaaaatgctt  7200
tatttgtgaa atttgtgatg ctattgcttt atttgtaacc attataagct gcaataaaca  7260
agtt                                                              7264
```

```
SEQ ID NO: 39          moltype = DNA  length = 18852
FEATURE                Location/Qualifiers
misc_feature           1..18852
                       note = Description of Artificial Sequence: Synthetic
                        polynucleotide
source                 1..18852
```

```
                        mol_type = other DNA
                        organism = synthetic construct
SEQUENCE: 39
cggccgcggg gggaggagcc aagatggccg aataggaaca gctccggtct acagctccca  60
gcgtgagcga cgcagaagac ggtgatttct gcatttccat ctgaggtacc gggttcatct  120
cactagggag tgccagacag tgggcgcagg ccagtgtgtg tgcgcaccgt gcgcgagccg  180
aagcagggcg aggcattgcc tcacctggga agcgcaaggg gtcagggagt tccctttccg  240
agtcaaagaa aggggtgacg gacgcacctg gaaaatcggg tcactcccac ccgaatattg  300
cgcttttcag accggcttaa gaaacggcgc accacgagac tatatcccac acctggctcg  360
gagggtccta cgcccacgga atctcgctga ttgctagcac agcagtctga gatcaaactg  420
caaggcggca acgaggctgg gggaggggcg cccgccattg cccaggcttg cttaggtaaa  480
caaagcagca gggaagctcg aactgggtgg agcccaccac agctcaagga ggcctgcctg  540
cctctgtagg ctccacctct gggggcaggg cacagacaaa caaaaagaca gcagtaacct  600
ctgcagactt aagtgtccct gtctgacagc tttgaagaga gcagtggttc tcccagcacg  660
cagctggaga tctgagaacg ggcagactgc ctcctcaagt gggtccctga cccctgaccc  720
ccgagcagcc taactgggag gcaccccca gcaggggcac actgacacct cacacggcag  780
ggtattccaa cagacctgca gctgagggtc ctgtctgtta gaaggaaaac taacaaccag  840
aaaggacatc tacaccgaaa acccatctgt acatcaccat catcaaagac caaaagtaga  900
taaaaccaca aagatgggga aaaaacagaa cagaaaaact ggaaactcta aaacgcagag  960
cgcctctcct cctccaaagg aacgcagttc ctcaccagca acagaacaaa gctggatgga  1020
gaatgatttt gatgagctga gagaagaagg cttcagacga tcaaattact ctgagctacg  1080
ggaggacatt caaaccaaag gcaaagaagt tgaaaacttt gaaaaaaatt tagaagaatg  1140
tataactaga ataaccaata cagagaagtg cttaaaggag ctgatggagc tgaaaaccaa  1200
ggctcgagaa ctacgtgaag aatgcagaag cctcaggagc cgatgcgatc aactggaaga  1260
aagggtatca gcaatggaag atgaaatgaa tgaaatgaag cgagaaggga agtttagaga  1320
aaaaagaata aaaagaaatg agcaaagcct ccaagaaata tgggactatg tgaaaagacc  1380
aaatctacgt ctgattggtg tacctgaaag tgatgtggag aatggaacca agttggaaaa  1440
cactctgcag gatattatcc aggagaactt ccccaatcta gcaaggcagg ccaacgttca  1500
gattcaggaa atacagagaa cgccacaaag atactcctcg agaagagcaa ctccaagaca  1560
cataattgtc agattcacca aagttgaaat gaaggaaaaa atgttaaggg cagccagaga  1620
gaaaggtcgg gttaccctca aaggaaagcc catcagacta acagcggatc tctcggcaga  1680
aaccctacaa gccagaagag agtgggggcc aatattcaac attcttaaag aaaagaattt  1740
tcaacccaga atttcatatc cagccaaact aagcttcata agtgaaggag aaataaaata  1800
ctttatagac aagcaaatgt tgagagattt tgtcaccacc aggcctgccc taaaagagct  1860
cctgaaggaa gcgctaaaca tggaaaggaa caaccggtac cagccgctgc aaaatcatgc  1920
caaaatgtaa agaccatcaa gactaggaag aaactgcatc aactaatgag caaaatcacc  1980
agctaacatc ataatgacag gatcaacttc acacataaca atattaactt taaatataaa  2040
tggactaaat tctgcaatta aaagacacag actggcaagt tggataaaga gtcaagaccc  2100
atcagtgtgc tgtattcagg aaacccatct cacgtgcaga gacacacata ggctcaaaat  2160
aaaaggatgg aggaagatct accaagccaa tggaaaacaa aaaaaggcag gggttgcaat  2220
cctagtctct gataaaacag actttaaacc aacaaagatc aaaagagaca aagaaggcca  2280
ttacataatg gtaaagggat caattcaaca agaggagcta actatcctaa atatttatgc  2340
acccaataca ggagcaccca gattcataaa gcaagtcctc agtgacctac aaagagactt  2400
agactcccac acattaataa tgggagactt taacacccca ctgtcaacat tagacagatc  2460
aacgagacag aaagtcaaca aggataccca ggaattgaac tcagctctgc accaagcaga  2520
cctaatagac atctacagaa ctctccaccc caaatcaaca gaatatacat ttttttcagc  2580
accacaccac acctattcca aaattgacca catagttgga agtaaagctc tcctcagcaa  2640
atgtaaaaga acagaaatta taacaaacta tctctcagac cacagtgcaa tcaaactaga  2700
actcaggatt aagaatctca ctcaaagccg ctcaactaca tggaaactga acaacctgct  2760
cctgaatgac tactgggtac ataacgaaat gaaggcagaa ataaagatgt tctttgaaac  2820
caacgagaac aaagacacca cataccagaa tctctgggac gcattcaaag cagtgtgtag  2880
agggaaattt atagcactaa atgcctacaa gagaaagcag gaaagatcca aaattgacac  2940
cctaacatca caattaaaag aactagaaaa gcaagagcaa acacattcaa aagctagcag  3000
aaggcaagaa ataactaaaa tcagagcaga actgaaggaa atagagacac aaaaaaccct  3060
tcaaaaaatc aatgaatcca ggagctggtt ttttgaaagg atcaacaaaa ttgatagacc  3120
gctagcaaga ctaataaaga aaaaaagaga gaagaatcaa atagacacaa taaaaaatga  3180
taaaggggat atcaccaccg atcccacaga aatacaaact accatcagag aatactacaa  3240
acacctctac gcaaataaac tagaaaatct agaagaaatg gatacattcc tcgacacata  3300
cactctccca agactaaacc aggaagaagt tgaatctctg aatcgaccaa taacaggctc  3360
tgaaattgtg gcaataatca atagtttacc aaccaaaaag agtccaggac cagatggatt  3420
cacagccgaa ttctaccaga ggtacaagga ggaactggta ccattccttc tgaaactatt  3480
ccaatcaata gaaaaagagg gaatcctccc taactcattt tatgaggcca gcatcattct  3540
gataccaaag ccgggcagag acacaaccaa aaaagagaat tttagaccaa tatccttgat  3600
gaacattgat gcaaaaatcc tcaataaaat actggcaaac cgaatccagc agcacatcaa  3660
aaagcttatc caccatgatc aagtgggctt catccctggg atgcaaggct ggttcaatat  3720
acgcaaatca ataaatgtaa tccagcatat aaacagagcc aaagacaaaa accacatgat  3780
tatctcaata gatgcagaaa aagcctttga caaaattcaa caacccttca tgctaaaaac  3840
tctcaataaa ttaggtattg atgggacgta tttcaaaata ataagagcta tctatgacaa  3900
acccacagcc aatatcatac tgaatgggca aaaactggaa gcattccctt tgaaaaccgg  3960
cacaagacag ggatgccctc tctcaccgct cctattcaac atagtgttgg aagttctggc  4020
cagggcaatc aggcaggaga aggaaataaa gggtattcaa ttaggaaaag aggaagtcaa  4080
attgtccctg tttgcagacg acatgattgt ttatctagaa aaccccatcg tctcagccca  4140
aaatctcctt aagctgataa gcaacttcag caaagtctca ggatacaaaa tcaatgtaca  4200
aaaatcacaa gcattcttat acaccaacaa cagacaaaca gagagccaaa tcatgggtga  4260
actcccattc acaattgctt caaagagaat aaaataccta ggaatccaac ttacaaggga  4320
tgtgaaggac ctcttcaagg agaactacaa accactgctc aaggaaataa aagaggagac  4380
aaacaaatgg aagaacattc catgctcatg ggtaggaaga atcaatatcg tgaaaatggc  4440
catactgccc aaggtaattt acagattcaa tgccatcccc atcaagctac caatgacttt  4500
cttcacagaa ttggaaaaaa ctactttaaa gttcatatgg aaccaaaaaa gagcccgcat  4560
```

```
tgccaagtca atcctaagcc aaaagaacaa agctggaggc atcacactac ctgacttcaa  4620
actatactac aaggctacag taaccaaaac agcatggtac tggtaccaaa acagagatat  4680
agatcaatgg aacagaacag agccctcaga aataatgccg catatctaca actatctgat  4740
ctttgacaaa cctgagaaaa acaagcaatg ggaaaggat  tccctattta ataaatggtg  4800
ctgggaaaac tggctagcca tatgtagaaa gctgaaactg gatcccttcc ttacacctta  4860
tacaaaaatc aattcaagat ggattaaaga tttaaacgtt aaacctaaaa ccataaaaac  4920
cctagaagaa aacctaggca ttaccattca ggacataggc gtgggcaagg acttcatgtc  4980
caaaacacca aaagcaatgg caacaaaaga caaaattgac aaatgggatc taattaaact  5040
aaagagcttc tgcacagcaa aagaaactac catcagagtg aacaggcaac ctacaacatg  5100
ggagaaaatt tttgcaacct actcatctga caaagggcta atatccagaa tctacaatga  5160
actcaaacaa atttacaaga aaaaaacaaa caaccccatc aaaaagtggg cgaaggacat  5220
gaacagacac ttctcaaaag aagacattta tgcagccaaa aaacacatga agaaatgctc  5280
atcatcactg gccatcagag aaatgcaaat caaaaccact atgagatatc atctcacacc  5340
agttagaatg gcaatcatta aaaagtcagg aaacaacagg tgctggagag gatgcggaga  5400
aataggaaca cttttacact gttggtggga ctgtaaacta gttcaaccat tgtggaagtc  5460
agtgtggcga ttcctcaggg atctagaact agaaatacca tttgacccag ccatcccatt  5520
actgggtata tacccaaatg agtataaatc atgctgctat aaagacacat gcacacgtat  5580
gtttattgcg gcactattca caatagcaaa gacttggaac caacccaaat gtccaacaat  5640
gatagactgg attaagaaaa tgtggcacat atacaccatg gaatactatg cagccataaa  5700
aaatgatgag ttcatatcct ttgtagggac atggatgaaa ttggaaacca tcattctcag  5760
taaactatcg caagaacaaa aaaccaaaca ccgcatattc tcactcatag gtgggaattg  5820
aacaatgaga tcacatggac acaggaaggg gaatatcaca ctctggggac tgtggtgggg  5880
tcgggggagg ggggagggat agcattggga gatataccta atgctagatg acacattagt  5940
gggtgcagcg caccagcatg gcacatgtat acggatccga attctcgacg gatcgatccg  6000
aacaaacgac ccaacacccg tgcgttttat tctgtctttt tattgccgat cccctcagaa  6060
gaactcgtca agaaggcgat agaaggcgat gcgctgcgaa tcgggagcgg cgataccgta  6120
aagcacgagg aagcggtcag cccattcgcc gccaagctct tcagcaatat cacgggtagc  6180
caacgctatg tcctgatagc ggtcggccgc tcatgttctc gtaggagtcg gcgtcctctt  6240
cgtggttagg tccaggttgg cctctgatag accgcagctg aggagcggcg tacagaatgc  6300
ctctcatgtc ctcatagctg ccgctgcctt gtggaggctt ctcgtgcttc agtgtctcgt  6360
atgtctcttg attccgggtg ctcaggccgg tgtacacgcc atcagatttc tcgtagctgg  6420
tgatggcggc cttccgcact tggatcttca gccgtctgca gtacagggtg atgaccagag  6480
acagcagcag gacaccacat gtgccagcca gagggcccca aatgtagata tccaggcctc  6540
tggtatgcac agctccgcct gcagcaggtc tacaggcttc aggtctgaga gacagaggct  6600
ggctggcgat tgtaggagct ggtgtaggtg gtctaggagc gggtgttgtt gtaggcttgg  6660
cgggcagaaa cacgggcacg aagtggctga agtacatgat gctattgctc agggctccgc  6720
ttcctccgcc gcctgatttg atttccagct tggtgcctcc gccaaatgtc caagggctct  6780
cgtcgtactg ctggcagtag tagatgccga agtcctcgta ctgcaggctg ctgattgtca  6840
gggtgtagtc ggtgccagag ccgctgccag aaaatctgct tggcacgccg ctttccagtc  6900
tgttggcccg gtagatcagt gtcttagggg ccttgccagg cttctgctgg aaccagctca  6960
ggtagctgtt gatgtcctgg ctggctctac aggtgatggt cactctatcg ccccacagagg  7020
cagacaggct gctagggctc tgtgtcatct ggatatcaga gccaccaccg ccagatccac  7080
cgccacctga tcctccgcct ccgctagaaa ctgtcactgt ggtgccctgg ccccacacat  7140
cgaagtacca gtcgtagcct cttctggtgc agaagtacac ggcggtatcc tcggctctca  7200
ggctgttgat ctgcaggtag gcggtgttct tgctgtcgtc caggctgaag gtgaatctgc  7260
ccttaaagct atcggcgtag gttggctcgc cggtgtgggt attgatccag cccatccact  7320
caaggccagg tgagtccagg agatgtttca gcactgttgc ctttagtctc gaggcaactt  7380
agacaactga gtattgatct gagcacagca gggtgtgagc tgtttgaaga tactggggtt  7440
gggggtgaag aaactgcaga ggactaactg ggctgagacc cagtggcaat gttttagggc  7500
ctaaggaatg cctctgaaaa tctagatgga caactttgac tttgagaaaa gagaggtgga  7560
aatgaggaaa atgacttttc tttattagat ttcggtagaa agaactttca tctttcccct  7620
atttttgtta ttcgttttaa aacatctatc tggaggcagg acaagtatgg tcattaaaaa  7680
gatgcaggca gaaggcatat attggctcag tcaaagtggg gaactttggt ggccaaacat  7740
acattgctaa ggctattcct atatcagctg gacacatata aaatgctgct aatgcttcat  7800
tacaaactta tatcctttaa ttccagatgg gggcaaagta tgtccagggg tgaggaacaa  7860
ttgaaacatt tgggctggag tagattttga aagtcagctc tgtgtgtgtg tgtgtgtgtg  7920
tgtgtgtgag agcgtgtgtt tcttttaacg ttttcagcct acagcataca gggttcatgg  7980
tggcaagaag ataacaagat ttaaattatg gccagtgact agtgctgcaa gaagaacaac  8040
tacctgcatt taatgggaaa gcaaaatctc aggctttgag ggaagttaac ataggcttga  8100
ttctgggtgg aagctgggtg tgtagttatc tggaggccag gctggagctc tcagctcact  8160
atgggttcat ctttattgtc tcctttttcc aggggcctgt cggacccagt tcatgccgta  8220
gttggtgaag gtgtagccgc tggcggcaca gctgattctg acagatccgc caggtttcac  8280
aagtccgccg ccagactgaa ccagctggat ctcagagatg ctacaggcca ctgttcccag  8340
cagcagcaga gactgcagcc acatctggtg gcgaattcga agcttgagct cgagatctga  8400
gtccggtagc gctagcggat ctgacggttc actaaaccag ctctgcttat atagacctcc  8460
caccgtacac gcctaccgcc catttgcgtc aatggggcgg agttgttacg acattttgga  8520
aagtcccgtt gattttggtg ccaaaacaaa ctcccattga cgtcaatggg gtggagactt  8580
ggaaatcccc gtgagtcaaa ccgctatcca cgcccattga tgtactgcca aaaccgcatc  8640
accatggtaa tagcgatgac taatacgtag atgtactgcc aagtaggaaa gtcccataag  8700
gtcatgtact gggcataatg ccaggcgggc catttaccgt cattgacgtc aatagggggc  8760
gtacttggca tatgatacac ttgatgtact gccaagtggg cagtttaccg taaatactcc  8820
acccattgac gtcaatggaa agtccctatt ggcgttacta tgggaacata cgtcattatt  8880
gacgtcaatg ggcgggggtc gttgggcggt cagccaggcg ggccatttac cgtaagttat  8940
gtaacgcgga actccatata tgggctatga actaatgacc ccgtaattga ttactattag  9000
cccgggggat ccagacatga taagatacat tgatgagttt ggacaaacca caactagaat  9060
gcagtgaaaa aaatgcttta tttgtgaaat ttgtgatgct attgctttat ttgtaaccat  9120
tataagctgc aataaacaag ttaacaacaa caattgcatt cattttatgt ttcaggttca  9180
gggggaggtg tgggaggttt tttaaagcaa gtaaaacctc tacaaatgtg gtatggctga  9240
ttatgatccg gctgcctcgc gcgtttcggt gatgacggtg aaaacctctg acacatgcag  9300
```

-continued

```
ctcccggaga cggtcacagc ttgtctgtaa gcggatgccg ggagcagaca agcccgtcag  9360
ggcgcgtcag cgggtgttgg cgggtgtcgg ggcgcagcca tgaggtcgat cgactctaga  9420
ggatcgatcc ccgccccgga cgaactaaac ctgactacga catctctgcc ccttcttcgc  9480
ggggcagtgc atgtaatccc ttcagttggt tggtacaact tgccaactgg gccctgttcc  9540
acatgtgaca cggggggga ccaaacacaa aggggttctc tgactgtagt tgacatcctt  9600
ataaatggat gtgcacattt gccaacactg agtggctttc atcctggagc agactttgca  9660
gtctgtggac tgcaacacaa cattgccttt atgtgtaact cttggctgaa gctcttacac  9720
caatgctggg ggacatgtac ctcccagggg cccaggaaga ctacgggagg ctacaccaac  9780
gtcaatcaga ggggcctgtg tagctaccga taagcggacc ctcaagaggg cattagcaat  9840
agtgtttata aggcccctt gttaacccta aacgggtagc atatgcttcc cgggtagtag  9900
tatatactat ccagactaac cctaattcaa tagcatatgt tacccaacgg gaagcatatg  9960
ctatcgaatt agggttagta aaagggtcct aaggaacagc gatatctccc accccatgag  10020
ctgtcacggt tttatttaca tggggtcagg attccacgag ggtagtgaac cattttagtc  10080
acaagggcag tggctgaaga tcaaggagcg ggcagtgaac tctcctgaat cttcgcctgc  10140
ttcttcattc tccttcgttt agctaataga ataactgctg agttgtgaac agtaaggtgt  10200
atgtgaggtg ctcgaaaaca aggtttcagg tgacgccccc agaataaaat ttggacgggg  10260
ggttcagtgg tggcattgtg ctatgacacc aatataaccc tcacaaaccc cttgggcaat  10320
aaatactagt gtaggaatga aacattctga atatctttaa caatagaaat ccatggggtg  10380
gggacaagcc gtaaagactg gatgtccatc tcacacgaat ttatggctat gggcaacaca  10440
taatcctagt gcaatatgat actggggtta ttaagatgtg tcccaggcag ggaccaagac  10500
aggtgaacca tgttgttaca ctctatttgt aacaagggga aagagagtgg acgccgacag  10560
cagcggactc cactggttgt ctctaacacc cccgaaaatt aaacggggct ccacgccaat  10620
ggggcccata aacaaagaca agtggccact cttttttttg aaattgtgga gtgggggcac  10680
gcgtcagccc ccacacgccg ccctgcggtt ttggactgta aaataagggt gtaataactt  10740
ggctgattgt aaccccgcta accactgcgg tcaaaccact tgcccacaaa accactaatg  10800
gcaccccggg gaatacctgc ataagtaggt gggcgggcca agataggggc gcgattgctg  10860
cgatctggag gacaaattac acacacttgc gcctgagcgc caagcacagg gttgttggtc  10920
ctcatattca cgaggtcgct gagagcacgg tgggctaatg ttgccatggg tagcatatac  10980
tacccaaata tctggatagc atatgctatc ctaatctata tctgggtagc ataggctatc  11040
ctaatctata tctgggtagc atatgctatc ctaatctata tctgggtagt atatgctatc  11100
ctaatttata tctgggtagc ataggctatc ctaatctata tctgggtagc atatgctatc  11160
ctaatctata tctgggtagt atatgctatc ctaatctgta tccgggtagc atatgctatc  11220
ctaatagaga ttagggtagt atatgctatc ctaatttata tctgggtagc atatactacc  11280
caaatatctg gatagcatat gctatcctaa tctatatctg ggtagcatat gctatcctaa  11340
tctatatctg ggtagcatag gctatcctaa tctatatctg ggtagcatat gctatcctaa  11400
tctatatctg ggtagtatat gctatcctaa tttatatctg ggtagcatag gctatcctaa  11460
tctatatctg ggtagcatat gctatcctaa tctatatctg ggtagtatat gctatcctaa  11520
tctgtatccg ggtagcatat gctatcctca tgcatataca gtcagcatat gatacccagt  11580
agtagagtgg gagtgctatc ctttgcatat gccgccacct cccaaggggg cgtgaatttt  11640
cgctgcttgt ccttttcctg catgctggtt gctcccattc ttaggtgaat ttaaggaggc  11700
caggctaaag ccgtcgcatg tctgattgct caccaggtaa atgtcgctaa tgttttccaa  11760
cgcgagaagg tgttgagcgc ggagctgagt gacgtgacaa catgggtatg cccaattgcc  11820
ccatgttggg aggacgaaaa tggtgacaag acagatggcc agaaatacac caacagcacg  11880
catgatgtct actggggatt tattctttag tgcgggggaa tacacggctt ttaatacgat  11940
tgagggcgtc tcctaacaag ttacatcact cctgcccttc ctcaccctca tctccatcac  12000
ctccttcatc tccgtcatct ccgtcatcac cctccgcggc agccccttcc accataggtg  12060
gaaaccaggg aggcaaatct actccatcgt caaagctgca cacagtcacc ctgatattgc  12120
aggtaggagc gggctttgtc ataacaaggt ccttaatcgc atccttcaaa acctcagcaa  12180
atatatgagt ttgtaaaaag accatgaaat aacagacaat ggactccctt agcgggccag  12240
gttgtgggcc gggtccaggg gccattccaa aggggagacg actcaatggt gtaagacgac  12300
attgtggaat agcaagggca gttcctcgcc ttaggttgta aagggaggtc ttactacctc  12360
catatacgaa cacaccggcg acccaagttc cttcgtcggt agtcctttct acgtgactcc  12420
tagccaggag agctcttaaa ccttctgcaa tgttctcaaa tttcgggttg gaacctcctt  12480
gaccacgatg ctttccaaac caccctcctt ttttgcgcct gcctccatca ccctgacccc  12540
ggggtccagt gcttgggcct tctcctgggt catctgcggg gccctgctct atcgctcccg  12600
ggggcacgtc aggctcacca tctgggccac cttcttggtg gtattcaaaa taatcggctt  12660
cccctacagg gtggaaaaat ggccttctac ctggaggggg cctgcgcggt ggagacccgg  12720
atgatgatga ctgactactg ggactcctgg gcctcttttc tccacgtcca cgacctctcc  12780
ccctggctct ttcacgactt ccccccctgg ctctttcacg tcctctaccc cggcggcctc  12840
cactacctcc tcgaccccgg cctccactac ctcctcgacc ccggcctcca ctgcctcctc  12900
gaccccggcc tccacctcct gctcctgccc ctcctgctcc tgcccctcct cctgctcctg  12960
cccctcctgc ccctcctgct cctgcccctc ctgcccctcc tgctcctgcc cctcctgccc  13020
ctcctgctcc tgcccctcct gcccctcctc ctgctcctgc ccctcctgcc cctcctcctg  13080
ctcctgcccc tcctgcccct cctgctcctg cccctcctgc ccctcctgct cctgcccctc  13140
ctgcccctcc tgctcctgcc cctcctgctc ctgcccctcc tgctcctgcc cctcctgctc  13200
ctgcccctcc tgcccctcct gcccctcctc ctgctcctgc ccctcctgct cctgcccctc  13260
ctgcccctcc tgcccctcct gctcctgccc ctcctcctgc tcctgcccct cctgcccctc  13320
ctgcccctcc tcctgctcct gcccctcctg cccctcctcc tgctcctgcc cctcctcctg  13380
ctcctgcccc tcctgcccct cctgcccctc ctcctgctcc tgcccctcct gcccctcctc  13440
ctgctcctgc ccctcctcct gctcctgccc ctcctgcccc tcctgcccct cctcctgctc  13500
ctgcccctcc tcctgctcct gcccctcctg cccctcctgc ccctcctgcc cctcctcctg  13560
ctcctgcccc tcctcctgct cctgcccctc ctgctcctgc ccctcccgct cctgctcctg  13620
ctcctgttcc accgtgggtc cctttgcagc caatgcaact tggacgtttt tggggtctcc  13680
ggacaccatc tctatgtctt ggccctgatc ctgagccgcc cggggctcct ggtcttccgc  13740
ctcctcgtcc tcgtcctctt ccccgtcctc gtccatggtt atcacccct cttctttgag  13800
gtccactgcc gccggagcct tctggtccag atgtgtctcc cttctctcct aggccatttc  13860
caggtcctgt acctggcccc tcgtcagaca tgattcacac taaaagagat caatagacat  13920
ctttattaga cgacgctcag tgaatacagg gagtgcagac tcctgccccc tccaacagcc  13980
cccccaccct catccccttc atggtcgctg tcagacagat ccaggtctga aaattcccca  14040
```

-continued

```
tcctccgaac catcctcgtc ctcatcacca attactcgca gcccggaaaa ctcccgctga  14100
acatcctcaa gatttgcgtc ctgagcctca agccaggcct caaattcctc gtcccccttt  14160
ttgctggacg gtagggatgg ggattctcgg gacccctcct cttcctcttc aaggtcacca  14220
gacagagatg ctactggggc aacggaagaa aagctgggtg cggcctgtga ggatcagctt  14280
atcgatgata agctgtcaaa catgagaatt cttgaagacg aaagggcctc gtgatacgcc  14340
tatttttata ggttaatgtc atgataataa tggtttctta gacgtcaggt ggcacttttc  14400
ggggaaatgt gcgcggaacc cctatttgtt tatttttcta aatacattca aatatgtatc  14460
cgctcatgag acaataaccc tgataaatgc ttcaataata ttgaaaaagg aagagtatga  14520
gtattcaaca tttccgtgtc gcccttattc cctttttttgc ggcattttgc cttcctgttt  14580
ttgctcaccc agaaacgctg gtgaaagtaa aagatgctga agatcagttg ggtgcacgag  14640
tgggttacat cgaactggat ctcaacagcg gtaagatcct tgagagtttt cgccccgaag  14700
aacgttttcc aatgatgagc acttttaaag ttctgctatg tggcgcggta ttatcccgtg  14760
ttgacgccgg gcaagagcaa ctcggtcgcc gcatacacta ttctcagaat gacttggttg  14820
agtactcacc agtcacagaa aagcatctta cggatggcat gacagtaaga gaattatgca  14880
gtgctgccat aaccatgagt gataacactg cggccaactt acttctgaca acgatcggag  14940
gaccgaagga gctaaccgct tttttgcaca acatggggga tcatgtaact cgccttgatc  15000
gttgggaacc ggagctgaat gaagccatac caaacgacga gcgtgacacc acgatgcctg  15060
cagcaatggc aacaacgttg cgcaaactat taactggcga actacttact ctagcttccc  15120
ggcaacaatt aatagactgg atggaggcgg ataaagttgc aggaccactt ctgcgctcgg  15180
cccttccggc tggctggttt attgctgata aatctggagc cggtgagcgt gggtctcgcg  15240
gtatcattgc agcactgggg ccagatggta agccctcccg tatcgtagtt atctacacga  15300
cggggagtca ggcaactatg gatgaacgaa atagacagat cgctgagata ggtgcctcac  15360
tgattaagca ttggtaactg tcagaccaag tttactcata tatactttag attgatttaa  15420
aacttcattt ttaatttaaa aggatctagg tgaagatcct ttttgataat ctcatgacca  15480
aaatccctta acgtgagttt tcgttccact gagcgtcaga ccccgtagaa aagatcaaag  15540
gatcttcttg agatcctttt tttctgcgcg taatctgctg cttgcaaaca aaaaaaccac  15600
cgctaccagc ggtggtttgt ttgccggatc aagagctacc aactcttttt ccgaaggtaa  15660
ctggcttcag cagagcgcag ataccaaata ctgtccttct agtgtagccg tagttaggcc  15720
accacttcaa gaactctgta gcaccgccta catacctcgc tctgctaatc ctgttaccag  15780
tggctgctgc cagtggcgat aagtcgtgtc ttaccgggtt ggactcaaga cgatagttac  15840
cggataaggc gcagcggtcg ggctgaacgg ggggttcgtg cacacagccc agcttggagc  15900
gaacgaccta caccgaactg agatacctac agcgtgagct atgagaaagc gccacgcttc  15960
ccgaagggag aaaggcggac aggtatccgg taagcggcag ggtcggaaca ggagagcgca  16020
cgagggagct tccaggggga aacgcctggt atctttatag tcctgtcggg tttcgccacc  16080
tctgacttga gcgtcgattt ttgtgatgct cgtcaggggg gcggagccta tggaaaaacg  16140
ccagcaacgc ggccttttta cggttcctgg ccttttgctg gccttttgct cacatgttct  16200
ttcctgcgtt atcccctgat tctgtggata accgtattac cgcctttgag tgagctgata  16260
ccgctcgccg cagccgaacg accgagcgca gcgagtcagt gagcgaggaa gcggaagagc  16320
gcctgatgcg gtattttctc cttacgcatc tgtgcggtat ttcacaccgc atatggtgca  16380
ctctcagtac aatctgctct gatgccgcat agttaagcca gctgtggaat gtgtgtcagt  16440
tagggtgtgg aaagtcccca ggctccccag caggcagaag tatgcaaagc atgcatctca  16500
attagtcagc aaccaggtgt ggaaagtccc caggctcccc agcaggcaga agtatgcaaa  16560
gcatgcatct caattagtca gcaaccatag tcccgcccct aactccgccc atcccgcccc  16620
taactccgcc cagttccgcc cattctccgc cccatggctg actaattttt tttatttatg  16680
cagaggccga ggccgcctcg gcctctgagc tattccagaa gtagtgagga ggcttttttg  16740
gaggcctagg cttttgcaaa aagcttgcat gcctgcaggt cggccgccac gaccggtgcc  16800
gccaccatcc cctgacccac gcccctgacc cctcacaagg agacgacctt ccatgaccga  16860
gtacaagccc acggtgcgcc tcgccacccg cgacgacgtc ccccgggccg tacgcaccct  16920
cgccgccgcg ttcgccgact accccgccac gcgccacacc gtcgacccgg accgccacat  16980
cgagcgggtc accgagctgc aagaactctt cctcacgcgc gtcgggctcg acatcggcaa  17040
ggtgtgggtc gcggacgacg gcgccgcggt ggcggtctgg accacgccgg agagcgtcga  17100
agcgggggcg gtgttcgccg agatcggccc gcgcatggcc gagttgagcg gttcccggct  17160
ggccgcgcag caacagatgg aaggcctcct ggcgccgcac cggcccaagg agcccgcgtg  17220
gttcctggcc accgtcggcg tctcgcccga ccaccagggc aagggtctgg gcagcgccgt  17280
cgtgctcccc ggagtggagg cggccgagcg cgccggggtg cccgccttcc tggagacctc  17340
cgcgccccgc aacctcccct tctacgagcg gctcggcttc accgtcaccg ccgacgtcga  17400
ggtgcccgaa ggaccgcgca cctggtgcat gacccgcaag cccggtgcct gacgcccgcc  17460
ccacgacccg cagcgcccga ccgaaaggag cgcacgaccc catggctccg accgaagccg  17520
acccgggcgg ccccgccgac cccgcacccg cccccgaggc ccaccgactc tagaggatca  17580
taatcagcca taccacattt gtagaggttt tacttgcttt aaaaaacctc ccacacctcc  17640
ccctgaacct gaaacataaa atgaatgcaa ttgttgttgt taacttgttt attgcagctt  17700
ataatggtta caaataaagc aatagcatca caaatttcac aaataaagca ttttttttcac  17760
tgcattctag ttgtggtttg tccaaactca tcaatgtatc ttatcatgtc tggatcactc  17820
gccgatagtg gaaaccgacg ccccagcact cgtccgaggg caaaggaata ggggagatgg  17880
gggaggctaa ctgaaacacg gaaggagaca ataccggaag gaacccgcgc tatgacggca  17940
ataaaaagac agaataaaac gcacgggtgt tgggtcgttt gttcataaac gcggggttcg  18000
gtcccagggc tggcactctg tcgatacccc accgagaccc cattggggcc aatacgcccg  18060
cgtttcttcc ttttccccac cccacccccc aagttcgggt gaaggcccag ggctcgcagc  18120
caacgtcggg gcggcaggcc ctgccatagc cactggcccc gtgggttagg gacggggtcc  18180
cccatgggga atggtttatg gttcgtgggg gttattattt tgggcgttgc gtggggtctg  18240
gtccacgact ggactgagca gacagaccca tggtttttgg atggcctggg catggaccgc  18300
atgtactggc gcgacacgaa caccgggcgt ctgtggctgc caaacacccc cgacccccaa  18360
aaaccaccgc gcggatttct ggcgtgccaa gctagtcgac caattctcat gtttgacagc  18420
ttatcatcgc agatccgggc aacgttgttg cattgctgca ggcgcagaac tggtaggtat  18480
ggaagatctc tagaagctgg gtaccagctg ctagcaagct tgctagcggc cggctcgagt  18540
ttactcccta tcagtgatag agaacgtatg tcgagtttac tccctatcag tgatagagaa  18600
cgatgtcgag tttactccct atcagtgata gagaacgtat gtcgagttta ctccctatca  18660
gtgatagaga acgtatgtcg agtttactcc ctatcagtga tagagaacgt atgtcgagtt  18720
tatccctatc agtgatagag aacgtatgtc gagtttactc cctatcagtg atagagaacg  18780
```

```
tatgtcgagg taggcgtgta cggtgggagg cctatataag cagagctcgt ttagtgaacc  18840
gtcagatcgc cg                                                      18852

SEQ ID NO: 40          moltype = DNA  length = 19625
FEATURE                Location/Qualifiers
misc_feature           1..19625
                       note = Description of Artificial Sequence: Synthetic
                        polynucleotide
source                 1..19625
                       mol_type = other DNA
                       organism = synthetic construct
SEQUENCE: 40
cggccgcggg gggaggagcc aagatggccg aataggaaca gctccggtct acagctccca  60
gcgtgagcga cgcagaagac ggtgatttct gcatttccat ctgaggtacc gggttcatct  120
cactagggag tgccagacag tgggcgcagg ccagtgtgtg tgcgcaccgt gcgcgagccg  180
aagcagggcg aggcattgcc tcacctggga agcgcaaggg gtcagggagt tccctttccg  240
agtcaaagaa aggggtgacg gacgcacctg gaaaatcggg tcactcccac ccgaatattg  300
cgcttttcag accggcttaa gaaacggcgc accacgagac tatatcccac acctggctcg  360
gagggtccta cgcccacgga atctcgctga ttgctagcac agcagtctga gatcaaactg  420
caaggcggca acgaggctgg gggaggggcg cccgccattg cccaggcttg cttaggtaaa  480
caaagcagca gggaagctcg aactgggtgg agcccaccac agctcaagga ggcctgcctg  540
cctctgtagg ctccacctct gggggcaggg cacagacaaa caaaaagaca gcagtaacct  600
ctgcagactt aagtgtccct gtctgacagc tttgaagaga gcagtggttc tcccagcacg  660
cagctggaga tctgagaacg ggcagactgc ctcctcaagt gggtccctga cccctgaccc  720
ccgagcagcc taactgggag gcaccccca gcaggggcac actgacacct cacacggcag  780
ggtattccaa cagacctgca gctgagggtc ctgtctgtta gaaggaaaac taacaaccag  840
aaaggacatc tacaccgaaa acccatctgt acatcaccat catcaaagac caaaagtaga  900
taaaaccaca aagatgggga aaaaacagaa cagaaaaact ggaaactcta aaacgcagag  960
cgcctctcct cctccaaagg aacgcagttc ctcaccagca acagaacaaa gctggatgga  1020
gaatgatttt gatgagctga gagaagaagg cttcagacga tcaaattact ctgagctacg  1080
ggaggacatt caaaccaaag gcaaagaagt tgaaaacttt gaaaaaaatt tagaagaatg  1140
tataactaga ataaccaata cagagaagtg cttaaaggag ctgatggagc tgaaaaccaa  1200
ggctcgagaa ctacgtgaag aatgcagaag cctcaggagc cgatgcgatc aactggaaga  1260
aagggtatca gcaatggaag atgaaatgaa tgaaatgaag cgagaaggga agtttagaga  1320
aaaaagaata aaaagaaatg agcaaagcct ccaagaaata tgggactatg tgaaaagacc  1380
aaatctacgt ctgattggtg tacctgaaag tgatgtggag aatggaacca agttggaaaa  1440
cactctgcag gatattatcc aggagaactt ccccaatcta gcaaggcagg ccaacgttca  1500
gattcaggaa atacagagaa cgccacaaag atactcctcg agaagagcaa ctccaagaca  1560
cataattgtc agattcacca aagttgaaat gaaggaaaaa atgttaaggg cagccagaga  1620
gaaaggtcgg gttaccctca aaggaaagcc catcagacta acagcggatc tctcggcaga  1680
aaccctacaa gccagaagag agtgggggcc aatattcaac attcttaaag aaaagaattt  1740
tcaacccaga atttcatatc cagccaaact aagcttcata agtgaaggag aaataaaata  1800
ctttatagac aagcaaatgt tgagagattt tgtcaccacc aggcctgccc taaaagagct  1860
cctgaaggaa gcgctaaaca tggaaaggaa caaccggtac cagccgctgc aaaatcatgc  1920
caaaatgtaa agaccatcaa gactaggaag aaactgcatc aactaatgag caaaatcacc  1980
agctaacatc ataatgacag gatcaacttc acacataaca atattaactt taaatataaa  2040
tggactaaat tctgcaatta aaagacacag actggcaagt tggataaaga gtcaagaccc  2100
atcagtgtgc tgtattcagg aaacccatct cacgtgcaga gacacacata ggctcaaaat  2160
aaaaggatgg aggaagatct accaagccaa tggaaaacaa aaaaaggcag gggttgcaat  2220
cctagtctct gataaaacag actttaaacc aacaaagatc aaaagagaca aagaaggcca  2280
ttacataatg gtaaagggat caattcaaca agaggagcta actatcctaa atatttatgc  2340
acccaataca ggagcaccca gattcataaa gcaagtcctc agtgacctac aaagagactt  2400
agactcccac acattaataa tgggagactt taacacccca ctgtcaacat tagacagatc  2460
aacgagacag aaagtcaaca aggataccca ggaattgaac tcagctctgc accaagcaga  2520
cctaatagac atctacagaa ctctccaccc caaatcaaca gaatatacat ttttttcagc  2580
accacaccac acctattcca aaattgacca catagttgga agtaaagctc tcctcagcaa  2640
atgtaaaaga acagaaatta taacaaacta tctctcagac cacagtgcaa tcaaactaga  2700
actcaggatt aagaatctca ctcaaagccg ctcaactaca tggaaactga acaacctgct  2760
cctgaatgac tactgggtac ataacgaaat gaaggcagaa ataaagatgt tctttgaaac  2820
caacgagaac aaagacacca cataccagaa tctctgggac gcattcaaag cagtgtgtag  2880
agggaaattt atagcactaa atgcctacaa gagaaagcag gaaagatcca aaattgacac  2940
cctaacatca caattaaaag aactagaaaa gcaagagcaa acacattcaa aagctagcag  3000
aaggcaagaa ataactaaaa tcagagcaga actgaaggaa atagagacac aaaaaaccct  3060
tcaaaaaatc aatgaatcca ggagctggtt ttttgaaagg atcaacaaaa ttgatagacc  3120
gctagcaaga ctaataaaga aaaaaagaga gaagaatcaa atagacacaa taaaaaatga  3180
taaaggggat atcaccaccg atcccacaga aatacaaact accatcagag aatactacaa  3240
acacctctac gcaaataaac tagaaaatct agaagaaatg gatacattcc tcgacacata  3300
cactctccca agactaaacc aggaagaagt tgaatctctg aatcgaccaa taacaggctc  3360
tgaaattgtg gcaataatca atagtttacc aaccaaaaag agtccaggac cagatggatt  3420
cacagccgaa ttctaccaga ggtacaagga ggaactggta ccattccttc tgaaactatt  3480
ccaatcaata gaaaaagagg gaatcctccc taactcattt tatgaggcca gcatcattct  3540
gataccaaag ccgggcagag acacaaccaa aaaagagaat tttagaccaa tatccttgat  3600
gaacattgat gcaaaaatcc tcaataaaat actggcaaac cgaatccagc agcacatcaa  3660
aaagcttatc caccatgatc aagtgggctt catccctggg atgcaaggct ggttcaatat  3720
acgcaaatca ataaatgtaa tccagcatat aaacagagcc aaagacaaaa accacatgat  3780
tatctcaata gatgcagaaa aagcctttga caaaattcaa caacccttca tgctaaaaac  3840
tctcaataaa ttaggtattg atgggacgta tttcaaaata ataagagcta tctatgacaa  3900
acccacagcc aatatcatac tgaatgggca aaaactggaa gcattccctt tgaaaaccgg  3960
cacaagacag ggatgccctc tctcaccgct cctattcaac atagtgttgg aagttctggc  4020
```

```
cagggcaatc aggcaggaga aggaaataaa gggtattcaa ttaggaaaag aggaagtcaa  4080
attgtccctg tttgcagacg acatgattgt ttatctagaa aaccccatcg tctcagccca  4140
aaatctcctt aagctgataa gcaacttcag caaagtctca ggatacaaaa tcaatgtaca  4200
aaaatcacaa gcattcttat acaccaacaa cagacaaaca gagagccaaa tcatgggtga  4260
actcccattc acaattgctt caaagagaat aaaataccta ggaatccaac ttacaaggga  4320
tgtgaaggac ctcttcaagg agaactacaa accactgctc aaggaaataa aagaggagac  4380
aaacaaatgg aagaacattc catgctcatg ggtaggaaga atcaatatcg tgaaaatggc  4440
catactgccc aaggtaattt acagattcaa tgccatcccc atcaagctac caatgacttt  4500
cttcacagaa ttggaaaaaa ctactttaaa gttcatatgg aaccaaaaaa gagcccgcat  4560
tgccaagtca atcctaagcc aaaagaacaa agctggaggc atcacactac ctgacttcaa  4620
actatactac aaggctacag taaccaaaac agcatggtac tggtaccaaa acagagatat  4680
agatcaatgg aacagaacag agccctcaga aataatgccg catatctaca actatctgat  4740
ctttgacaaa cctgagaaaa acaagcaatg gggaaaggat tccctattta ataaatggtg  4800
ctgggaaaac tggctagcca tatgtagaaa gctgaaactg gatcccttcc ttacacctta  4860
tacaaaaatc aattcaagat ggattaaaga tttaaacgtt aaacctaaaa ccataaaaac  4920
cctagaagaa aacctaggca ttaccattca ggacataggc gtgggcaagg acttcatgtc  4980
caaaacacca aaagcaatgg caacaaaaga caaaattgac aaatgggatc taattaaact  5040
aaagagcttc tgcacagcaa aagaaactac catcagagtg aacaggcaac ctacaacatg  5100
ggagaaaatt tttgcaacct actcatctga caaagggcta atatccagaa tctacaatga  5160
actcaaacaa atttacaaga aaaaaacaaa caaccccatc aaaaagtggg cgaaggacat  5220
gaacagacac ttctcaaaag aagacattta tgcagccaaa aaacacatga agaaatgctc  5280
atcatcactg gccatcagag aaatgcaaat caaaaccact atgagatatc atctcacacc  5340
agttagaatg gcaatcatta aaaagtcagg aaacaacagg tgctggagag gatgcggaga  5400
aataggaaca cttttacact gttggtggga ctgtaaacta gttcaaccat tgtggaagtc  5460
agtgtggcga ttcctcaggg atctagaact agaaatacca tttgacccag ccatcccatt  5520
actgggtata tacccaaatg agtataaatc atgctgctat aaagacacat gcacacgtat  5580
gtttattgcg gcactattca caatagcaaa gacttggaac caacccaaat gtccaacaat  5640
gatagactgg attaagaaaa tgtggcacat atacaccatg gaatactatg cagccataaa  5700
aaatgatgag ttcatatcct ttgtagggac atggatgaaa ttggaaacca tcattctcag  5760
taaactatcg caagaacaaa aaaccaaaca ccgcatattc tcactcatag gtgggaattg  5820
aacaatgaga tcacatggac acaggaaggg gaatatcaca ctctggggac tgtggtgggg  5880
tcgggggagg ggggagggat agcattggga gatataccta atgctagatg acacattagt  5940
gggtgcagcg caccagcatg gcacatgtat acggatccga attctcgacg gatcgatccg  6000
aacaaacgac ccaacacccg tgcgttttat tctgtctttt tattgccgat cccctcagaa  6060
gaactcgtca agaaggcgat agaaggcgat gcgctgcgaa tcgggagcgg cgataccgta  6120
aagcacgagg aagcggtcag cccattcgcc gccaagctct tcagcaatat cacgggtagc  6180
caacgctatg tcctgatagc ggtcggccgc tttacttgta cagctcgtcc atgccgagag  6240
tgatcccggc ggcggtcacg aactccagca ggaccatgtg atcgcgcttc tcgttggggt  6300
ctttgctcag ggcggactgg gtgctcaggt agtggttgtc gggcagcagc acggggccgt  6360
cgccgatggg ggtgttctgc tggtagtggt cggccaggtg agtccaggag atgtttcagc  6420
actgttgcct ttagtctcga ggcaacttag acaactgagt attgatctga gcacagcagg  6480
gtgtgagctg tttgaagata ctggggttgg gggtgaagaa actgcagagg actaactggg  6540
ctgagaccca gtggcaatgt tttagggcct aaggaatgcc tctgaaaatc tagatggaca  6600
actttgactt tgagaaaaga gaggtggaaa tgaggaaaat gacttttctt tattagattt  6660
cggtagaaag aactttcatc tttcccctat ttttgttatt cgttttaaaa catctatctg  6720
gaggcaggac aagtatggtc attaaaaaga tgcaggcaga aggcatatat tggctcagtc  6780
aaagtgggga actttggtgg ccaaacatac attgctaagg ctattcctat atcagctgga  6840
cacatataaa atgctgctaa tgcttcatta caaacttata tcctttaatt ccagatgggg  6900
gcaaagtatg tccaggggtg aggaacaatt gaaacatttg ggctggagta gattttgaaa  6960
gtcagctctg tgtgtgtgtg tgtgtgtgtg tgtgtgagag cgtgtgtttc ttttaacgtt  7020
ttcagcctac agcatacagg gttcatggtg gcaagaagat aacaagattt aaattatggc  7080
cagtgactag tgctgcaaga agaacaacta cctgcattta atgggaaagc aaaatctcag  7140
gctttgaggg aagttaacat aggcttgatt ctgggtggaa gctgggtgtg tagttatctg  7200
gaggccaggc tggagctctc agctcactat gggttcatct ttattgtctc ctttcatctc  7260
aacagctgca cgctgccgtc ctcgatgttg tggcggatct tgaagttcac cttgatgccg  7320
ttcttctgct tgtcggccat gatatagacg ttgtggctgt tgtagttgta ctccagcttg  7380
tgccccagga tgttgccgtc ctccttgaag tcgatgccct tcagctcgat gcggttcacc  7440
agggtgtcgc cctcgaactt cacctcggcg cgggtcttgt agttgccgtc gtccttgaag  7500
aagatggtgc gctcctggac gtagccttcg ggcatggcgg acttgaagaa gtcgtgctgc  7560
ttcatgtggt cggggtagcg gctgaagcac tgcacgccgt aggtcagggt ggtcacgagg  7620
gtgggccagg gcacgggcag cttgccggtg gtgcagatga acttcagggt cagcttgccg  7680
taggtggcat cgccctcgcc ctcgccggac acgctgaact tgtggccgtt tacgtcgccg  7740
tccagctcga ccaggatggg caccaccccg gtgaacagct cctcgccctt gctcaccata  7800
gggccgggat tctcctccac gtcaccgcat gttagaagac ttcctctgcc ctccatgttc  7860
tcgtaggagt cggcgtcctc ttcgtggtta ggtccaggtt ggcctctgat agaccgcagc  7920
tgaggagcgg cgtacagaat gcctctcatg tcctcatagc tgccgctgcc ttgtggaggc  7980
ttctcgtgct tcagtgtctc gtatgtctct tgattccggg tgctcaggcc ggtgtacacg  8040
ccatcagatt tctcgtagct ggtgatggcg gccttccgca cttggatctt cagccgtctg  8100
cagtacaggg tgatgaccag agacagcagc aggacaccac atgtgccagc cagaggggcc  8160
caaatgtaga tatccaggcc tctggtatgc acagctccgc ctgcagcagg tctacaggct  8220
tcaggtctga gagacagagg ctggctggcg attgtaggag ctggtgtagg tggtctagga  8280
gcgggtgttg ttgtaggctt ggcgggcaga aacacgggca cgaagtggct gaagtacatg  8340
atgctattgc tcagggctcc gcttcctccg ccgcctgatt tgatttccag cttggtgcct  8400
ccgccaaatg tccaagggct ctcgtcgtac tgctggcagt agtagatgcc gaagtcctcg  8460
tactgcaggc tgctgattgt cagggtgtag tcggtgccag agccgctgcc agaaaatctg  8520
cttggcacgc cgctttccag tctgttggcc cggtagatca gtgtcttagg ggccttgcca  8580
ggcttctgct ggaaccagct caggtagctg ttgatgtcct ggctggctct acaggtgatg  8640
gtcactctat cgcccacaga ggcagacagg ctgctagggc tctgtgtcat ctggatatca  8700
gagccaccac cgccagatcc accgccacct gatcctccgc ctccgctaga aactgtcact  8760
```

-continued

```
gtggtgccct ggccccacac atcgaagtac cagtcgtagc ctcttctggt gcagaagtac  8820
acggcggtat cctcggctct caggctgttg atctgcaggt aggcggtgtt cttgctgtcg  8880
tccaggctga aggtgaatct gcccttaaag ctatcggcgt aggttggctc gccggtgtgg  8940
gtattgatcc agcccatcca ctcaaggcct tttccagggg cctgtcggac ccagttcatg  9000
ccgtagttgg tgaaggtgta gccgctggcg gcacagctga ttctgacaga tccgccaggt  9060
ttcacaagtc cgccgccaga ctgaaccagc tggatctcag agatgctaca ggccactgtt  9120
cccagcagca gcagagactg cagccacatt cgaagcttga gctcgagatc tgagtccggt  9180
agcgctagcg gatctgacgg ttcactaaac cagctctgct tatatagacc tcccaccgta  9240
cacgcctacc gcccatttgc gtcaatgggg cggagttgtt acgacatttt ggaaagtccc  9300
gttgattttg gtgccaaaac aaactcccat tgacgtcaat ggggtggaga cttggaaatc  9360
cccgtgagtc aaaccgctat ccacgcccat tgatgtactg ccaaaaccgc atcaccatgg  9420
taatagcgat gactaatacg tagatgtact gccaagtagg aaagtcccat aaggtcatgt  9480
actgggcata atgccaggcg ggccatttac cgtcattgac gtcaataggg ggcgtacttg  9540
gcatatgata cacttgatgt actgccaagt gggcagttta ccgtaaatac tccacccatt  9600
gacgtcaatg gaaagtccct attggcgtta ctatgggaac atacgtcatt attgacgtca  9660
atgggcgggg gtcgttgggc ggtcagccag gcgggccatt taccgtaagt tatgtaacgc  9720
ggaactccat atatgggcta tgaactaatg accccgtaat tgattactat tagcccgggg  9780
gatccagaca tgataagata cattgatgag tttggacaaa ccacaactag aatgcagtga  9840
aaaaaatgct ttatttgtga aatttgtgat gctattgctt tatttgtaac cattataagc  9900
tgcaataaac aagttaacaa caacaattgc attcatttta tgtttcaggt tcagggggag  9960
gtgtgggagg ttttttaaag caagtaaaac ctctacaaat gtggtatggc tgattatgat  10020
ccggctgcct cgcgcgtttc ggtgatgacg gtgaaaacct ctgacacatg cagctcccgg  10080
agacggtcac agcttgtctg taagcggatg ccgggagcag acaagcccgt cagggcgcgt  10140
cagcgggtgt tggcgggtgt cggggcgcag ccatgaggtc gatcgactct agaggatcga  10200
tccccgcccc ggacgaacta aacctgacta cgacatctct gccccttctt cgcggggcag  10260
tgcatgtaat cccttcagtt ggttggtaca acttgccaac tgggccctgt tccacatgtg  10320
acacgggggg ggaccaaaca caaaggggtt ctctgactgt agttgacatc cttataaatg  10380
gatgtgcaca tttgccaaca ctgagtggct ttcatcctgg agcagacttt gcagtctgtg  10440
gactgcaaca caacattgcc tttatgtgta actcttggct gaagctctta caccaatgct  10500
gggggacatg tacctcccag gggcccagga agactacggg aggctacacc aacgtcaatc  10560
agaggggcct gtgtagctac cgataagcgg accctcaaga gggcattagc aatagtgttt  10620
ataaggcccc cttgttaacc ctaaacgggt agcatatgct tcccgggtag tagtatatac  10680
tatccagact aaccctaatt caatagcata tgttacccaa cgggaagcat atgctatcga  10740
attagggtta gtaaaagggt cctaaggaac agcgatatct cccaccccat gagctgtcac  10800
ggttttattt acatggggtc aggattccac gagggtagtg aaccatttta gtcacaaggg  10860
cagtggctga agatcaagga gcgggcagtg aactctcctg aatcttcgcc tgcttcttca  10920
ttctccttcg tttagctaat agaataactg ctgagttgtg aacagtaagg tgtatgtgag  10980
gtgctcgaaa acaaggtttc aggtgacgcc cccagaataa aatttggacg gggggttcag  11040
tggtggcatt gtgctatgac accaatataa ccctcacaaa ccccttgggc aataaatact  11100
agtgtaggaa tgaaacattc tgaatatctt taacaataga aatccatggg gtggggacaa  11160
gccgtaaaga ctggatgtcc atctcacacg aatttatggc tatgggcaac acataatcct  11220
agtgcaatat gatactgggg ttattaagat gtgtcccagg cagggaccaa gacaggtgaa  11280
ccatgttgtt acactctatt tgtaacaagg ggaaagagag tggacgccga cagcagcgga  11340
ctccactggt tgtctctaac acccccgaaa attaaacggg gctccacgcc aatggggccc  11400
ataaacaaag acaagtggcc actctttttt ttgaaattgt ggagtggggg cacgcgtcag  11460
cccccacacg ccgccctgcg gttttggact gtaaaataag ggtgtaataa cttggctgat  11520
tgtaaccccg ctaaccactg cggtcaaacc acttgcccac aaaaccacta atggcacccc  11580
ggggaatacc tgcataagta ggtgggcggg ccaagatagg ggcgcgattg ctgcgatctg  11640
gaggacaaat tacacacact tgcgcctgag cgccaagcac agggttgttg gtcctcatat  11700
tcacgaggtc gctgagagca cggtgggcta atgttgccat gggtagcata tactacccaa  11760
atatctggat agcatatgct atcctaatct atatctgggt agcataggct atcctaatct  11820
atatctgggt agcatatgct atcctaatct atatctgggt agtatatgct atcctaattt  11880
atatctgggt agcataggct atcctaatct atatctgggt agcatatgct atcctaatct  11940
atatctgggt agtatatgct atcctaatct gtatccgggt agcatatgct atcctaatag  12000
agattagggt agtatatgct atcctaattt atatctgggt agcatatact acccaaatat  12060
ctggatagca tatgctatcc taatctatat ctgggtagca tatgctatcc taatctatat  12120
ctgggtagca taggctatcc taatctatat ctgggtagca tatgctatcc taatctatat  12180
ctgggtagta tatgctatcc taatttatat ctgggtagca taggctatcc taatctatat  12240
ctgggtagca tatgctatcc taatctatat ctgggtagta tatgctatcc taatctgtat  12300
ccgggtagca tatgctatcc tcatgcatat acagtcagca tatgataccc agtagtagag  12360
tgggagtgct atcctttgca tatgccgcca cctcccaagg gggcgtgaat tttcgctgct  12420
tgtccttttc ctgcatgctg gttgctccca ttcttaggtg aatttaagga ggccaggcta  12480
aagccgtcgc atgtctgatt gctcaccagg taaatgtcgc taatgttttc caacgcgaga  12540
aggtgttgag cgcggagctg agtgacgtga caacatgggt atgcccaatt gccccatgtt  12600
gggaggacga aaatggtgac aagacagatg gccagaaata caccaacagc acgcatgatg  12660
tctactgggg atttattctt tagtgcgggg gaatacacgg cttttaatac gattgagggc  12720
gtctcctaac aagttacatc actcctgccc ttcctcaccc tcatctccat cacctccttc  12780
atctccgtca tctccgtcat caccctccgc ggcagcccct tccaccatag gtggaaacca  12840
gggaggcaaa tctactccat cgtcaaagct gcacacagtc accctgatat tgcaggtagg  12900
agcgggcttt gtcataacaa ggtccttaat cgcatccttc aaaacctcag caaatatatg  12960
agtttgtaaa aagaccatga aataacagac aatggactcc cttagcgggc caggttgtgg  13020
gccgggtcca ggggccattc caaaggggag acgactcaat ggtgtaagac gacattgtgg  13080
aatagcaagg gcagttcctc gccttaggtt gtaaagggag gtcttactac ctccatatac  13140
gaacacaccg gcgacccaag ttccttcgtc ggtagtcctt tctacgtgac tcctagccag  13200
gagagctctt aaaccttctg caatgttctc aaatttcggg ttggaacctc cttgaccacg  13260
atgctttcca aaccaccctc ctttttttgcg cctgcctcca tcaccctgac cccggggtcc  13320
agtgcttggg ccttctcctg ggtcatctgc ggggccctgc tctatcgctc ccgggggcac  13380
gtcaggctca ccatctgggc caccttcttg gtggtattca aaataatcgg cttcccctac  13440
agggtggaaa aatggccttc tacctggagg gggcctgcgc ggtggagacc cggatgatga  13500
```

```
tgactgacta ctgggactcc tgggcctctt ttctccacgt ccacgacctc tccccctggc  13560
tctttcacga cttccccccc tggctctttc acgtcctcta ccccggcggc ctccactacc  13620
tcctcgaccc cggcctccac tacctcctcg accccggcct ccactgcctc ctcgaccccg  13680
gcctccacct cctgctcctg cccctcctgc tcctgcccct cctcctgctc ctgcccctcc  13740
tgcccctcct gctcctgccc ctcctgcccc tcctgctcct gcccctcctg cccctcctgc  13800
tcctgcccct cctgcccctc ctcctgctcc tgcccctcct gcccctcctc ctgctcctgc  13860
ccctcctgcc cctcctgctc ctgcccctcc tgcccctcct gctcctgccc ctcctgcccc  13920
tcctgctcct gcccctcctg ctcctgcccc tcctgctcct gcccctcctg ctcctgcccc  13980
tcctgcccct cctgcccctc ctcctgctcc tgcccctcct gctcctgccc ctcctgcccc  14040
tcctgcccct cctgctcctg cccctcctcc tgctcctgcc cctcctgccc ctcctgcccc  14100
tcctcctgct cctgcccctc ctgcccctcc tcctgctcct gcccctcctc ctgctcctgc  14160
ccctcctgcc cctcctgccc ctcctcctgc tcctgcccct cctgcccctc ctcctgctcc  14220
tgcccctcct cctgctcctg cccctcctgc ccctcctgcc cctcctcctg ctcctgcccc  14280
tcctcctgct cctgcccctc ctgcccctcc tgcccctcct gcccctcctc ctgctcctgc  14340
ccctcctcct gctcctgccc ctcctgctcc tgcccctccc gctcctgctc ctgctcctgt  14400
tccaccgtgg gtccctttgc agccaatgca acttggacgt tttggggtc tccggacacc  14460
atctctatgt cttggccctg atcctgagcc gcccggggct cctggtcttc cgcctcctcg  14520
tcctcgtcct cttccccgtc ctcgtccatg gttatcaccc cctcttcttt gaggtccact  14580
gccgccggag ccttctggtc cagatgtgtc tcccttctct cctaggccat ttccaggtcc  14640
tgtacctggc ccctcgtcag acatgattca cactaaaaga gatcaataga catctttatt  14700
agacgacgct cagtgaatac agggagtgca gactcctgcc ccctccaaca gcccccccac  14760
cctcatcccc ttcatggtcg ctgtcagaca gatccaggtc tgaaaattcc ccatcctccg  14820
aaccatcctc gtcctcatca ccaattactc gcagcccgga aaactcccgc tgaacatcct  14880
caagatttgc gtcctgagcc tcaagccagg cctcaaattc ctcgtccccc tttttgctgg  14940
acggtaggga tggggattct cgggacccct cctcttcctc ttcaaggtca ccagacagag  15000
atgctactgg ggcaacggaa gaaaagctgg gtgcggcctg tgaggatcag cttatcgatg  15060
ataagctgtc aaacatgaga attcttgaag acgaaagggc ctcgtgatac gcctattttt  15120
ataggttaat gtcatgataa taatggtttc ttagacgtca ggtggcactt ttcggggaaa  15180
tgtgcgcgga acccctattt gtttattttt ctaaatacat tcaaatatgt atccgctcat  15240
gagacaataa ccctgataaa tgcttcaata atattgaaaa aggaagagta tgagtattca  15300
acatttccgt gtcgccctta ttcccttttt tgcggcattt tgccttcctg tttttgctca  15360
cccagaaacg ctggtgaaag taaaagatgc tgaagatcag ttgggtgcac gagtgggtta  15420
catcgaactg gatctcaaca gcggtaagat ccttgagagt tttcgccccg aagaacgttt  15480
tccaatgatg agcactttta aagttctgct atgtggcgcg gtattatccc gtgttgacgc  15540
cgggcaagag caactcggtc gccgcataca ctattctcag aatgacttgg ttgagtactc  15600
accagtcaca gaaaagcatc ttacggatgg catgacagta agagaattat gcagtgctgc  15660
cataaccatg agtgataaca ctgcggccaa cttacttctg acaacgatcg gaggaccgaa  15720
ggagctaacc gcttttttgc acaacatggg ggatcatgta actcgccttg atcgttggga  15780
accggagctg aatgaagcca taccaaacga cgagcgtgac accacgatgc ctgcagcaat  15840
ggcaacaacg ttgcgcaaac tattaactgg cgaactactt actctagctt cccggcaaca  15900
attaatagac tggatggagg cggataaagt tgcaggacca cttctgcgct cggcccttcc  15960
ggctggctgg tttattgctg ataaatctgg agccggtgag cgtgggtctc gcggtatcat  16020
tgcagcactg gggccagatg gtaagccctc ccgtatcgta gttatctaca cgacggggag  16080
tcaggcaact atggatgaac gaaatagaca gatcgctgag ataggtgcct cactgattaa  16140
gcattggtaa ctgtcagacc aagtttactc atatatactt tagattgatt taaaacttca  16200
tttttaattt aaaaggatct aggtgaagat cctttttgat aatctcatga ccaaaatccc  16260
ttaacgtgag ttttcgttcc actgagcgtc agaccccgta gaaaagatca aaggatcttc  16320
ttgagatcct ttttttctgc gcgtaatctg ctgcttgcaa acaaaaaaac caccgctacc  16380
agcggtggtt tgtttgccgg atcaagagct accaactctt tttccgaagg taactggctt  16440
cagcagagcg cagataccaa atactgtcct tctagtgtag ccgtagttag gccaccactt  16500
caagaactct gtagcaccgc ctacatacct cgctctgcta atcctgttac cagtggctgc  16560
tgccagtggc gataagtcgt gtcttaccgg gttggactca agacgatagt taccggataa  16620
ggcgcagcgg tcgggctgaa cggggggttc gtgcacacag cccagcttgg agcgaacgac  16680
ctacaccgaa ctgagatacc tacagcgtga gctatgagaa agcgccacgc ttcccgaagg  16740
gagaaaggcg gacaggtatc cggtaagcgg cagggtcgga acaggagagc gcacgaggga  16800
gcttccaggg ggaaacgcct ggtatcttta tagtcctgtc gggtttcgcc acctctgact  16860
tgagcgtcga tttttgtgat gctcgtcagg ggggcggagc ctatggaaaa acgccagcaa  16920
cgcggccttt ttacggttcc tggccttttg ctggcctttt gctcacatgt tctttcctgc  16980
gttatcccct gattctgtgg ataaccgtat taccgccttt gagtgagctg ataccgctcg  17040
ccgcagccga acgaccgagc gcagcgagtc agtgagcgag gaagcggaag agcgcctgat  17100
gcggtatttt ctccttacgc atctgtgcgg tatttcacac cgcatatggt gcactctcag  17160
tacaatctgc tctgatgccg catagttaag ccagctgtgg aatgtgtgtc agttagggtg  17220
tggaaagtcc ccaggctccc cagcaggcag aagtatgcaa agcatgcatc tcaattagtc  17280
agcaaccagg tgtggaaagt ccccaggctc cccagcaggc agaagtatgc aaagcatgca  17340
tctcaattag tcagcaacca tagtcccgcc cctaactccg cccatcccgc ccctaactcc  17400
gcccagttcc gcccattctc cgccccatgg ctgactaatt ttttttattt atgcagaggc  17460
cgaggccgcc tcggcctctg agctattcca gaagtagtga ggaggctttt ttggaggcct  17520
aggcttttgc aaaaagcttg catgcctgca ggtcggccgc cacgaccggt gccgccacca  17580
tcccctgacc cacgcccctg acccctcaca aggagacgac cttccatgac cgagtacaag  17640
cccacggtgc gcctcgccac ccgcgacgac gtcccccggg ccgtacgcac cctcgccgcc  17700
gcgttcgccg actaccccgc cacgcgccac accgtcgacc cggaccgcca catcgagcgg  17760
gtcaccgagc tgcaagaact cttcctcacg cgcgtcgggc tcgacatcgg caaggtgtgg  17820
gtcgcggacg acggcgccgc ggtggcggtc tggaccacgc cggagagcgt cgaagcgggg  17880
gcggtgttcg ccgagatcgg cccgcgcatg gccgagttga gcggttcccg gctggccgcg  17940
cagcaacaga tggaaggcct cctggcgccg caccggccca aggagcccgc gtggttcctg  18000
gccaccgtcg gcgtctcgcc cgaccaccag ggcaagggtc tgggcagcgc cgtcgtgctc  18060
cccggagtgg aggcggccga gcgcgccggg gtgcccgcct tcctggagac ctccgcgccc  18120
cgcaacctcc ccttctacga gcggctcggc ttcaccgtca ccgccgacgt cgaggtgccc  18180
gaaggaccgc gcacctggtg catgacccgc aagcccggtg cctgacgccc gccccacgac  18240
```

```
ccgcagcgcc cgaccgaaag gagcgcacga ccccatggct ccgaccgaag ccgacccggg  18300
cggccccgcc gaccccgcac ccgcccccga ggcccaccga ctctagagga tcataatcag  18360
ccataccaca tttgtagagg ttttacttgc tttaaaaaac ctcccacacc tccccctgaa  18420
cctgaaacat aaaatgaatg caattgttgt tgttaacttg tttattgcag cttataatgg  18480
ttacaaataa agcaatagca tcacaaattt cacaaataaa gcattttttt cactgcattc  18540
tagttgtggt ttgtccaaac tcatcaatgt atcttatcat gtctggatca ctcgccgata  18600
gtggaaaccg acgccccagc actcgtccga gggcaaagga atagggggaga tgggggaggc  18660
taactgaaac acggaaggag acaataccgg aaggaacccg cgctatgacg gcaataaaaa  18720
gacagaataa aacgcacggg tgttgggtcg tttgttcata aacgcggggt tcggtcccag  18780
ggctggcact ctgtcgatac cccaccgaga ccccattggg gccaatacgc ccgcgtttct  18840
tccttttccc caccccaccc cccaagttcg ggtgaaggcc cagggctcgc agccaacgtc  18900
ggggcggcag gccctgccat agccactggc cccgtgggtt agggacgggg tcccccatgg  18960
ggaatggttt atggttcgtg ggggttatta ttttgggcgt tgcgtggggt ctggtccacg  19020
actggactga gcagacagac ccatggtttt tggatggcct gggcatggac cgcatgtact  19080
ggcgcgacac gaacaccggg cgtctgtggc tgccaaacac cccgacccc caaaaaccac  19140
cgcgcggatt tctggcgtgc caagctagtc gaccaattct catgtttgac agcttatcat  19200
cgcagatccg ggcaacgttg ttgcattgct gcaggcgcag aactggtagg tatggaagat  19260
ctctagaagc tgggtaccag ctgctagcaa gcttgctagc ggccggctcg agtttactcc  19320
ctatcagtga tagagaacgt atgtcgagtt tactccctat cagtgataga gaacgatgtc  19380
gagtttactc cctatcagtg atagagaacg tatgtcgagt ttactcccta tcagtgatag  19440
agaacgtatg tcgagtttac tccctatcag tgatagagaa cgtatgtcga gtttatccct  19500
atcagtgata gagaacgtat gtcgagttta ctccctatca gtgatagaga acgtatgtcg  19560
aggtaggcgt gtacggtggg aggcctatat aagcagagct cgtttagtga accgtcagat  19620
cgccg                                                             19625
```

```
SEQ ID NO: 41          moltype = DNA  length = 19730
FEATURE                Location/Qualifiers
misc_feature           1..19730
                       note = Description of Artificial Sequence: Synthetic
                        polynucleotide
source                 1..19730
                       mol_type = other DNA
                       organism = synthetic construct
SEQUENCE: 41
cggccgcggg gggaggagcc aagatggccg aataggaaca gctccggtct acagctccca  60
gcgtgagcga cgcagaagac ggtgatttct gcatttccat ctgaggtacc gggttcatct  120
cactagggag tgccagacag tgggcgcagg ccagtgtgtg tgcgcaccgt gcgcgagccg  180
aagcagggcg aggcattgcc tcacctggga agcgcaaggg gtcagggagt tccctttccg  240
agtcaaagaa aggggtgacg gacgcacctg gaaaatcggg tcactcccac ccgaatattg  300
cgcttttcag accggcttaa gaaacggcgc accacgagac tatatcccac acctggctcg  360
gagggtccta cgcccacgga atctcgctga ttgctagcac agcagtctga gatcaaactg  420
caaggcggca acgaggctgg gggaggggcg cccgccattg cccaggcttg cttaggtaaa  480
caaagcagca gggaagctcg aactgggtgg agcccaccac agctcaagga ggcctgcctg  540
cctctgtagg ctccacctct gggggcaggg cacagacaaa caaaaagaca gcagtaacct  600
ctgcagactt aagtgtccct gtctgacagc tttgaagaga gcagtggttc tcccagcacg  660
cagctggaga tctgagaacg ggcagactgc ctcctcaagt gggtccctga cccctgaccc  720
ccgagcagcc taactgggag gcaccccca gcaggggcac actgacacct cacacggcag  780
ggtattccaa cagacctgca gctgagggtc ctgtctgtta gaaggaaaac taacaaccag  840
aaaggacatc tacaccgaaa acccatctgt acatcaccat catcaaagac caaaagtaga  900
taaaaccaca aagatgggga aaaaacagaa cagaaaaact ggaaactcta aaacgcagag  960
cgcctctcct cctccaaagg aacgcagttc ctcaccagca acagaacaaa gctggatgga  1020
gaatgatttt gatgagctga gagaagaagg cttcagacga tcaaattact ctgagctacg  1080
ggaggacatt caaaccaaag gcaaagaagt tgaaaacttt gaaaaaaatt tagaagaatg  1140
tataactaga ataaccaata cagagaagtg cttaaaggag ctgatggagc tgaaaaccaa  1200
ggctcgagaa ctacgtgaag aatgcagaag cctcaggagc cgatgcgatc aactggaaga  1260
aagggtatca gcaatggaag atgaaatgaa tgaaatgaag cgagaaggga agtttagaga  1320
aaaaagaata aaaagaaatg agcaaagcct ccaagaaata tgggactatg tgaaaagacc  1380
aaatctacgt ctgattggtg tacctgaaag tgatgtggag aatggaacca agttggaaaa  1440
cactctgcag gatattatcc aggagaactt ccccaatcta gcaaggcagg ccaacgttca  1500
gattcaggaa atacagagaa cgccacaaag atactcctcg agaagagcaa ctccaagaca  1560
cataattgtc agattcacca aagttgaaat gaaggaaaaa atgttaaggg cagccagaga  1620
gaaaggtcgg gttaccctca aaggaaagcc catcagacta acagcggatc tctcggcaga  1680
aaccctacaa gccagaagag agtgggggcc aatattcaac attcttaaag aaaagaattt  1740
tcaacccaga atttcatatc cagccaaact aagcttcata agtgaaggag aaataaaata  1800
ctttatagac aagcaaatgt tgagagattt tgtcaccacc aggcctgccc taaaagagct  1860
cctgaaggaa gcgctaaaca tggaaaggaa caaccggtac cagccgctgc aaaatcatgc  1920
caaaatgtaa agaccatcaa gactaggaag aaactgcatc aactaatgag caaaatcacc  1980
agctaacatc ataatgacag gatcaacttc acacataaca atattaactt taaatataaa  2040
tggactaaat tctgcaatta aaagacacag actggcaagt tggataaaga gtcaagaccc  2100
atcagtgtgc tgtattcagg aaacccatct cacgtgcaga gacacacata ggctcaaaat  2160
aaaaggatgg aggaagatct accaagccaa tggaaaacaa aaaaaggcag gggttgcaat  2220
cctagtctct gataaaacag actttaaacc aacaaagatc aaaagagaca aagaaggcca  2280
ttacataatg gtaaagggat caattcaaca agaggagcta actatcctaa atatttatgc  2340
acccaataca ggagcaccca gattcataaa gcaagtcctc agtgacctac aaagagactt  2400
agactcccac acattaataa tgggagactt taacacccca ctgtcaacat tagacagatc  2460
aacgagacag aaagtcaaca aggataccca ggaattgaac tcagctctgc accaagcaga  2520
cctaatagac atctacagaa ctctccaccc caaatcaaca gaatatacat ttttttcagc  2580
accacaccac acctattcca aaattgacca catagttgga agtaaagctc tcctcagcaa  2640
atgtaaaaga acagaaatta taacaaacta tctctcagac cacagtgcaa tcaaactaga  2700
```

-continued

```
actcaggatt aagaatctca ctcaaagccg ctcaactaca tggaaactga acaacctgct  2760
cctgaatgac tactgggtac ataacgaaat gaaggcagaa ataaagatgt tctttgaaac  2820
caacgagaac aaagacacca cataccagaa tctctgggac gcattcaaag cagtgtgtag  2880
agggaaattt atagcactaa atgcctacaa gagaaagcag gaaagatcca aaattgacac  2940
cctaacatca caattaaaag aactagaaaa gcaagagcaa acacattcaa aagctagcag  3000
aaggcaagaa ataactaaaa tcagagcaga actgaaggaa atagagacac aaaaaaccct  3060
tcaaaaaatc aatgaatcca ggagctggtt ttttgaaagg atcaacaaaa ttgatagacc  3120
gctagcaaga ctaataaaga aaaaaagaga gaagaatcaa atagacacaa taaaaaatga  3180
taaaggggat atcaccaccg atcccacaga aatacaaact accatcagag aatactacaa  3240
acacctctac gcaaataaac tagaaaatct agaagaaatg gatacattcc tcgacacata  3300
cactctccca agactaaacc aggaagaagt tgaatctctg aatcgaccaa taacaggctc  3360
tgaaattgtg gcaataatca atagtttacc aaccaaaaag agtccaggac cagatggatt  3420
cacagccgaa ttctaccaga ggtacaagga ggaactggta ccattccttc tgaaactatt  3480
ccaatcaata gaaaaagagg gaatcctccc taactcattt tatgaggcca gcatcattct  3540
gataccaaag ccgggcagag acacaaccaa aaaagagaat tttagaccaa tatccttgat  3600
gaacattgat gcaaaaatcc tcaataaaat actggcaaac cgaatccagc agcacatcaa  3660
aaagcttatc caccatgatc aagtgggctt catccctggg atgcaaggct ggttcaatat  3720
acgcaaatca ataaatgtaa tccagcatat aaacagagcc aaagacaaaa accacatgat  3780
tatctcaata gatgcagaaa aagcctttga caaaattcaa caacccttca tgctaaaaac  3840
tctcaataaa ttaggtattg atgggacgta tttcaaaata ataagagcta tctatgacaa  3900
acccacagcc aatatcatac tgaatgggca aaaactggaa gcattccctt tgaaaaccgg  3960
cacaagacag ggatgccctc tctcaccgct cctattcaac atagtgttgg aagttctggc  4020
cagggcaatc aggcaggaga aggaaataaa gggtattcaa ttaggaaaag aggaagtcaa  4080
attgtccctg tttgcagacg acatgattgt ttatctagaa aaccccatcg tctcagccca  4140
aaatctcctt aagctgataa gcaacttcag caaagtctca ggatacaaaa tcaatgtaca  4200
aaaatcacaa gcattcttat acaccaacaa cagacaaaca gagagccaaa tcatgggtga  4260
actcccattc acaattgctt caaagagaat aaaataccta ggaatccaac ttacaaggga  4320
tgtgaaggac ctcttcaagg agaactacaa accactgctc aaggaaataa aagaggagac  4380
aaacaaatgg aagaacattc catgctcatg ggtaggaaga atcaatatcg tgaaaatggc  4440
catactgccc aaggtaattt acagattcaa tgccatcccc atcaagctac caatgacttt  4500
cttcacagaa ttggaaaaaa ctactttaaa gttcatatgg aaccaaaaaa gagcccgcat  4560
tgccaagtca atcctaagcc aaaagaacaa agctggaggc atcacactac ctgacttcaa  4620
actatactac aaggctacag taaccaaaac agcatggtac tggtaccaaa acagagatat  4680
agatcaatgg aacagaacag agccctcaga aataatgccg catatctaca actatctgat  4740
ctttgacaaa cctgagaaaa acaagcaatg gggaaaggat tccctattta ataaatggtg  4800
ctgggaaaac tggctagcca tatgtagaaa gctgaaactg gatcccttcc ttacacctta  4860
tacaaaaatc aattcaagat ggattaaaga tttaaacgtt aaacctaaaa ccataaaaac  4920
cctagaagaa aacctaggca ttaccattca ggacataggc gtgggcaagg acttcatgtc  4980
caaaacacca aaagcaatgg caacaaaaga caaaattgac aaatgggatc taattaaact  5040
aaagagcttc tgcacagcaa aagaaactac catcagagtg aacaggcaac ctacaacatg  5100
ggagaaaatt tttgcaacct actcatctga caaagggcta atatccagaa tctacaatga  5160
actcaaacaa atttacaaga aaaaaacaaa caaccccatc aaaaagtggg cgaaggacat  5220
gaacagacac ttctcaaaag aagacattta tgcagccaaa aaacacatga agaaatgctc  5280
atcatcactg gccatcagag aaatgcaaat caaaaccact atgagatatc atctcacacc  5340
agttagaatg gcaatcatta aaaagtcagg aaacaacagg tgctggagag gatgcggaga  5400
aataggaaca cttttacact gttggtggga ctgtaaacta gttcaaccat tgtggaagtc  5460
agtgtggcga ttcctcaggg atctagaact agaaatacca tttgacccag ccatcccatt  5520
actgggtata tacccaaatg agtataaatc atgctgctat aaagacacat gcacacgtat  5580
gtttattgcg gcactattca caatagcaaa gacttggaac caacccaaat gtccaacaat  5640
gatagactgg attaagaaaa tgtggcacat atacaccatg gaatactatg cagccataaa  5700
aaatgatgag ttcatatcct ttgtagggac atggatgaaa ttggaaacca tcattctcag  5760
taaactatcg caagaacaaa aaaccaaaca ccgcatattc tcactcatag gtgggaattg  5820
aacaatgaga tcacatggac acaggaaggg gaatatcaca ctctggggac tgtggtgggg  5880
tcgggggagg ggggagggat agcattggga gatataccta atgctagatg acacattagt  5940
gggtgcagcg caccagcatg gcacatgtat acggatccga attctcgacg gatcgatccg  6000
aacaaacgac ccaacacccg tgcgttttat tctgtctttt tattgccgat cccctcagaa  6060
gaactcgtca agaaggcgat agaaggcgat gcgctgcgaa tcgggagcgg cgataccgta  6120
aagcacgagg aagcggtcag cccattcgcc gccaagctct tcagcaatat cacgggtagc  6180
caacgctatg tcctgatagc ggtcggccgc tttacttgta cagctcgtcc atgccgagag  6240
tgatcccggc ggcggtcacg aactccagca ggaccatgtg atcgcgcttc tcgttggggt  6300
ctttgctcag ggcggactgg gtgctcaggt agtggttgtc gggcagcagc acggggccgt  6360
cgccgatggg ggtgttctgc tggtagtggt cggccaggtg agtccaggag atgtttcagc  6420
actgttgcct ttagtctcga ggcaacttag acaactgagt attgatctga gcacagcagg  6480
gtgtgagctg tttgaagata ctggggttgg gggtgaagaa actgcagagg actaactggg  6540
ctgagaccca gtggcaatgt tttagggcct aaggaatgcc tctgaaaatc tagatggaca  6600
actttgactt tgagaaaaga gaggtggaaa tgaggaaaat gacttttctt tattagattt  6660
cggtagaaag aactttcatc tttcccctat ttttgttatt cgttttaaaa catctatctg  6720
gaggcaggac aagtatggtc attaaaaaga tgcaggcaga aggcatatat tggctcagtc  6780
aaagtgggga actttggtgg ccaaacatac attgctaagg ctattcctat atcagctgga  6840
cacatataaa atgctgctaa tgcttcatta caaacttata tcctttaatt ccagatgggg  6900
gcaaagtatg tccaggggtg aggaacaatt gaaacatttg ggctggagta gattttgaaa  6960
gtcagctctg tgtgtgtgtg tgtgtgtgtg tgtgtgagag cgtgtgtttc ttttaacgtt  7020
ttcagcctac agcatacagg gttcatggtg gcaagaagat aacaagattt aaattatggc  7080
cagtgactag tgctgcaaga agaacaacta cctgcattta atgggaaagc aaaatctcag  7140
gctttgaggg aagttaacat aggcttgatt ctgggtggaa gctgggtgtg tagttatctg  7200
gaggccaggc tggagctctc agctcactat gggttcatct ttattgtctc ctttcatctc  7260
aacagctgca cgctgccgtc ctcgatgttg tggcggatct tgaagttcac cttgatgccg  7320
ttcttctgct tgtcggccat gatatagacg ttgtggctgt tgtagttgta ctccagcttg  7380
tgccccagga tgttgccgtc ctccttgaag tcgatgccct tcagctcgat gcggttcacc  7440
```

```
agggtgtcgc cctcgaactt cacctcggcg cgggtcttgt agttgccgtc gtccttgaag  7500
aagatggtgc gctcctggac gtagccttcg ggcatggcgg acttgaagaa gtcgtgctgc  7560
ttcatgtggt cggggtagcg gctgaagcac tgcacgccgt aggtcagggt ggtcacgagg  7620
gtgggccagg gcacgggcag cttgccggtg gtgcagatga acttcagggt cagcttgccg  7680
taggtggcat cgccctcgcc ctcgccggac acgctgaact tgtggccgtt tacgtcgccg  7740
tccagctcga ccaggatggg caccaccccg gtgaacagct cctcgccctt gctcaccata  7800
gggccgggat tctcctccac gtcaccgcat gttagaagac ttcctctgcc ctctcttgga  7860
ggcagggcct gcatgtgcag ggcatcgtag gtatccttgg tggctgtgct cagtccctgg  7920
tacagtccat cgtggccctt gcctcttctt ctctcgccct tcatgccgat ctcgctgtag  7980
gcctcggcca tcttgtcttt ctgcagctca ttatacaggc cctcttgagg attctttctc  8040
cgctggggct tgccgcccat ctcaggatct ctgcctctcc gcttatccag cacgtcgtac  8100
tcttctcttc tccccaggtt cagctcgttg tacagctgat tctggccctg ctggtaagca  8160
ggagcgtcgg cggatctgct gaacttcact ctgcagtaca gggtgatgac cagagagagc  8220
agcagaacgc cacatgtgcc agccagaggg gcccaaatgt agatatccag gcctctggta  8280
tgcacagctc cgccagctgc aggtctacag gcttcaggtc tgagagacag aggctggctg  8340
gcgattgtag gagctggtgt aggtggtcta ggagcgggtg ttgttgtagg cttggcgggc  8400
agaaacacgg gcacgaagtg gctgaagtac atgatgctat tgctcagggc tccgcttcct  8460
ccgcctccgc tagaagaaac tgtgaccagg gtgccctgtc cccaaacatc catggcgtag  8520
aagccgtcgc ctccccatct agaacagtag tacacggcgg tgtcctcggc tctcaggctg  8580
ttcatctgca ggtaggcggt gttcttgctg gtgtcggcgc tgatggtgaa tctgcccttc  8640
acgctatcgg cgtatctggt gtagccgttg gtggggtaga ttctggcgac ccattcaagt  8700
ccctttccag ggcctgtcg gacccagtgg atgtaggtgt ccttgatgtt gaagccgctg  8760
gcggcacaag acagtctcag agagccgcca ggctgaacaa gtcctccgcc agattcaacc  8820
agctgcacct cagatccttc gccagatcca ggctttccag agccgctggt gctgcctgtt  8880
ctcttgattt ccaccttggt gccctggcca aaggttggag gtgtggtgta gtgctgctgg  8940
cagtagtagg tggcgaagtc ctcaggctgc aggctagaga tggtcagggt gaagtcggtg  9000
ccagatctgc tgccgctgaa tctgcttggc acgccgctgt acagaaagct ggcgctgtag  9060
atcagcagct taggggcttt tccaggcttc tgctgatacc aggccacggc ggtattcaca  9120
tcctggctgg ctctacaggt gatggtcact ctatcgccca cagaggcaga caggctgcta  9180
gggctctgtg tcatctggat gtcgctgatg ctgcaggcca ctgttcccag cagcagcaga  9240
gactgcagcc acattcgaag cttgagctcg agatctgagt ccggtagcgc tagcggatct  9300
gacggttcac taaaccagct ctgcttatat agacctccca ccgtacacgc ctaccgccca  9360
tttgcgtcaa tggggcggag ttgttacgac attttggaaa gtcccgttga ttttggtgcc  9420
aaaacaaact cccattgacg tcaatggggt ggagacttgg aaatccccgt gagtcaaacc  9480
gctatccacg cccattgatg tactgccaaa accgcatcac catggtaata gcgatgacta  9540
atacgtagat gtactgccaa gtaggaaagt cccataaggt catgtactgg gcataatgcc  9600
aggcgggcca tttaccgtca ttgacgtcaa taggggcgt acttggcata tgatacactt  9660
gatgtactgc caagtgggca gtttaccgta aatactccac ccattgacgt caatggaaag  9720
tccctattgg cgttactatg ggaacatacg tcattattga cgtcaatggg cgggggtcgt  9780
tgggcggtca gccaggcggg ccatttaccg taagttatgt aacgcggaac tccatatatg  9840
ggctatgaac taatgacccc gtaattgatt actattagcc cgggggatcc agacatgata  9900
agatacattg atgagtttgg acaaaccaca actagaatgc agtgaaaaaa atgctttatt  9960
tgtgaaattt gtgatgctat tgctttattt gtaaccatta taagctgcaa taaacaagtt  10020
aacaacaaca attgcattca ttttatgttt caggttcagg gggaggtgtg ggaggttttt  10080
taaagcaagt aaaacctcta caaatgtggt atggctgatt atgatccggc tgcctcgcgc  10140
gtttcggtga tgacggtgaa aacctctgac acatgcagct cccggagacg gtcacagctt  10200
gtctgtaagc ggatgccggg agcagacaag cccgtcaggg cgcgtcagcg ggtgttggcg  10260
ggtgtcgggg cgcagccatg aggtcgatcg actctagagg atcgatcccc gccccggacg  10320
aactaaacct gactacgaca tctctgcccc ttcttcgcgg ggcagtgcat gtaatccctt  10380
cagttggttg gtacaacttg ccaactgggc cctgttccac atgtgacacg gggggggacc  10440
aaacacaaag gggttctctg actgtagttg acatccttat aaatggatgt gcacatttgc  10500
caacactgag tggctttcat cctggagcag actttgcagt ctgtggactg caacacaaca  10560
ttgcctttat gtgtaactct tggctgaagc tcttacacca atgctggggg acatgtacct  10620
cccaggggcc caggaagact acgggaggct acaccaacgt caatcagagg ggcctgtgta  10680
gctaccgata agcggaccct caagagggca ttagcaatag tgtttataag gcccccttgt  10740
taaccctaaa cgggtagcat atgcttcccg ggtagtagta tatactatcc agactaaccc  10800
taattcaata gcatatgtta cccaacggga agcatatgct atcgaattag ggttagtaaa  10860
agggtcctaa ggaacagcga tatctcccac cccatgagct gtcacggttt tatttacatg  10920
gggtcaggat tccacgaggg tagtgaacca ttttagtcac aagggcagtg gctgaagatc  10980
aaggagcggg cagtgaactc tcctgaatct tcgcctgctt cttcattctc cttcgtttag  11040
ctaatagaat aactgctgag ttgtgaacag taaggtgtat gtgaggtgct cgaaaacaag  11100
gtttcaggtg acgcccccag aataaaattt ggacgggggg ttcagtggtg gcattgtgct  11160
atgacaccaa tataaccctc acaaacccct tgggcaataa atactagtgt aggaatgaaa  11220
cattctgaat atctttaaca atagaaatcc atggggtggg gacaagccgt aaagactgga  11280
tgtccatctc acacgaattt atggctatgg gcaacacata atcctagtgc aatatgatac  11340
tggggttatt aagatgtgtc ccaggcaggg accaagacag gtgaaccatg ttgttacact  11400
ctatttgtaa caaggggaaa gagagtggac gccgacagca gcggactcca ctggttgtct  11460
ctaacacccc cgaaaattaa acggggctcc acgccaatgg ggcccataaa caaagacaag  11520
tggccactct ttttttgaa attgtggagt gggggcacgc gtcagccccc acacgccgcc  11580
ctgcggtttt ggactgtaaa ataagggtgt aataacttgg ctgattgtaa ccccgctaac  11640
cactgcggtc aaaccacttg cccacaaaac cactaatggc accccgggga atacctgcat  11700
aagtaggtgg gcgggccaag ataggggcgc gattgctgcg atctggagga caaattacac  11760
acacttgcgc ctgagcgcca agcacagggt tgttggtcct catattcacg aggtcgctga  11820
gagcacggtg ggctaatgtt gccatgggta gcatatacta cccaaatatc tggatagcat  11880
atgctatcct aatctatatc tgggtagcat aggctatcct aatctatatc tgggtagcat  11940
atgctatcct aatctatatc tgggtagtat atgctatcct aatttatatc tgggtagcat  12000
aggctatcct aatctatatc tgggtagcat atgctatcct aatctatatc tgggtagtat  12060
atgctatcct aatctgtatc cgggtagcat atgctatcct aatagagatt agggtagtat  12120
atgctatcct aatttatatc tgggtagcat atactaccca aatatctgga tagcatatgc  12180
```

-continued

```
tatcctaatc tatatctggg tagcatatgc tatcctaatc tatatctggg tagcataggc  12240
tatcctaatc tatatctggg tagcatatgc tatcctaatc tatatctggg tagtatatgc  12300
tatcctaatt tatatctggg tagcataggc tatcctaatc tatatctggg tagcatatgc  12360
tatcctaatc tatatctggg tagtatatgc tatcctaatc tgtatccggg tagcatatgc  12420
tatcctcatg catatacagt cagcatatga tacccagtag tagagtggga gtgctatcct  12480
ttgcatatgc cgccacctcc caagggggcg tgaattttcg ctgcttgtcc ttttcctgca  12540
tgctggttgc tcccattctt aggtgaattt aaggaggcca ggctaaagcc gtcgcatgtc  12600
tgattgctca ccaggtaaat gtcgctaatg ttttccaacg cgagaaggtg ttgagcgcgg  12660
agctgagtga cgtgacaaca tgggtatgcc caattgcccc atgttgggag gacgaaaatg  12720
gtgacaagac agatggccag aaatacacca acagcacgca tgatgtctac tggggattta  12780
ttctttagtg cgggggaata cacggctttt aatacgattg agggcgtctc ctaacaagtt  12840
acatcactcc tgcccttcct caccctcatc tccatcacct ccttcatctc cgtcatctcc  12900
gtcatcaccc tccgcggcag ccccttccac cataggtgga aaccagggag gcaaatctac  12960
tccatcgtca aagctgcaca cagtcaccct gatattgcag gtaggagcgg gctttgtcat  13020
aacaaggtcc ttaatcgcat ccttcaaaac ctcagcaaat atatgagttt gtaaaaagac  13080
catgaaataa cagacaatgg actcccttag cgggccaggt tgtgggccgg gtccaggggc  13140
cattccaaag gggagacgac tcaatggtgt aagacgacat tgtggaatag caagggcagt  13200
tcctcgcctt aggttgtaaa gggaggtctt actacctcca tatacgaaca caccggcgac  13260
ccaagttcct tcgtcggtag tcctttctac gtgactccta gccaggagag ctcttaaacc  13320
ttctgcaatg ttctcaaatt tcgggttgga acctccttga ccacgatgct ttccaaacca  13380
ccctcctttt ttgcgcctgc ctccatcacc ctgaccccgg ggtccagtgc ttgggccttc  13440
tcctgggtca tctgcggggc cctgctctat cgctcccggg ggcacgtcag gctcaccatc  13500
tgggccacct tcttggtggt attcaaaata atcggcttcc cctacagggt ggaaaaatgg  13560
ccttctacct ggagggggcc tgcgcggtgg agacccggat gatgatgact gactactggg  13620
actcctgggc ctcttttctc cacgtccacg acctctcccc ctggctcttt cacgacttcc  13680
ccccctggct ctttcacgtc ctctaccccg gcggcctcca ctacctcctc gaccccggcc  13740
tccactacct cctcgacccc ggcctccact gcctcctcga ccccggcctc cacctcctgc  13800
tcctgcccct cctgctcctg cccctcctcc tgctcctgcc cctcctgccc ctcctgctcc  13860
tgcccctcct gcccctcctg ctcctgcccc tcctgcccct cctgctcctg cccctcctgc  13920
ccctcctcct gctcctgccc ctcctgcccc tcctcctgct cctgcccctc ctgcccctcc  13980
tgctcctgcc cctcctgccc ctcctgctcc tgcccctcct gcccctcctg ctcctgcccc  14040
tcctgctcct gcccctcctg ctcctgcccc tcctgctcct gcccctcctg cccctcctgc  14100
ccctcctcct gctcctgccc ctcctgctcc tgcccctcct gcccctcctg cccctcctgc  14160
tcctgcccct cctcctgctc ctgcccctcc tgcccctcct gcccctcctc ctgctcctgc  14220
ccctcctgcc cctcctcctg ctcctgcccc tcctcctgct cctgcccctc ctgcccctcc  14280
tgcccctcct cctgctcctg cccctcctgc ccctcctcct gctcctgccc ctcctcctgc  14340
tcctgcccct cctgcccctc ctgcccctcc tcctgctcct gcccctcctc ctgctcctgc  14400
ccctcctgcc cctcctgccc ctcctgcccc tcctcctgct cctgcccctc ctcctgctcc  14460
tgcccctcct gctcctgccc ctcccgctcc tgctcctgct cctgttccac cgtgggtccc  14520
tttgcagcca atgcaacttg gacgtttttg gggtctccgg acaccatctc tatgtcttgg  14580
ccctgatcct gagccgcccg gggctcctgg tcttccgcct cctcgtcctc gtcctcttcc  14640
ccgtcctcgt ccatggttat cacccccctct tctttgaggt ccactgccgc cggagccttc  14700
tggtccagat gtgtctccct tctctcctag gccatttcca ggtcctgtac ctggcccctc  14760
gtcagacatg attcacacta aaagagatca atagacatct ttattagacg acgctcagtg  14820
aatacaggga gtgcagactc ctgcccccctc caacagcccc cccaccctca tcccccttcat  14880
ggtcgctgtc agacagatcc aggtctgaaa attccccatc ctccgaacca tcctcgtcct  14940
catcaccaat tactcgcagc ccggaaaact cccgctgaac atcctcaaga tttgcgtcct  15000
gagcctcaag ccaggcctca aattcctcgt cccccttttt gctggacggt agggatgggg  15060
attctcggga cccctcctct tcctcttcaa ggtcaccaga cagagatgct actggggcaa  15120
cggaagaaaa gctgggtgcg gcctgtgagg atcagcttat cgatgataag ctgtcaaaca  15180
tgagaattct tgaagacgaa agggcctcgt gatacgccta tttttatagg ttaatgtcat  15240
gataataatg gtttcttaga cgtcaggtgg cacttttcgg ggaaatgtgc gcggaacccc  15300
tatttgttta tttttctaaa tacattcaaa tatgtatccg ctcatgagac aataaccctg  15360
ataaatgctt caataatatt gaaaaaggaa gagtatgagt attcaacatt tccgtgtcgc  15420
ccttattccc ttttttgcgg cattttgcct tcctgttttt gctcacccag aaacgctggt  15480
gaaagtaaaa gatgctgaag atcagttggg tgcacgagtg ggttacatcg aactggatct  15540
caacagcggt aagatccttg agagttttcg ccccgaagaa cgttttccaa tgatgagcac  15600
ttttaaagtt ctgctatgtg gcgcggtatt atcccgtgtt gacgccgggc aagagcaact  15660
cggtcgccgc atacactatt ctcagaatga cttggttgag tactcaccag tcacagaaaa  15720
gcatcttacg gatggcatga cagtaagaga attatgcagt gctgccataa ccatgagtga  15780
taacactgcg gccaacttac ttctgacaac gatcggagga ccgaaggagc taaccgcttt  15840
tttgcacaac atgggggatc atgtaactcg ccttgatcgt tgggaaccgg agctgaatga  15900
agccatacca aacgacgagc gtgacaccac gatgcctgca gcaatggcaa caacgttgcg  15960
caaactatta actggcgaac tacttactct agcttcccgg caacaattaa tagactggat  16020
ggaggcggat aaagttgcag gaccacttct gcgctcggcc cttccggctg gctggtttat  16080
tgctgataaa tctggagccg gtgagcgtgg gtctcgcggt atcattgcag cactggggcc  16140
agatggtaag ccctcccgta tcgtagttat ctacacgacg gggagtcagg caactatgga  16200
tgaacgaaat agacagatcg ctgagatagg tgcctcactg attaagcatt ggtaactgtc  16260
agaccaagtt tactcatata tactttagat tgatttaaaa cttcattttt aatttaaaag  16320
gatctaggtg aagatccttt ttgataatct catgaccaaa atcccttaac gtgagttttc  16380
gttccactga gcgtcagacc ccgtagaaaa gatcaaagga tcttcttgag atcctttttt  16440
tctgcgcgta atctgctgct tgcaaacaaa aaaaccaccg ctaccagcgg tggtttgttt  16500
gccggatcaa gagctaccaa ctcttttttcc gaaggtaact ggcttcagca gagcgcagat  16560
accaaatact gtccttctag tgtagccgta gttaggccac cacttcaaga actctgtagc  16620
accgcctaca tacctcgctc tgctaatcct gttaccagtg gctgctgcca gtggcgataa  16680
gtcgtgtctt accgggttgg actcaagacg atagttaccg gataaggcgc agcggtcggg  16740
ctgaacgggg ggttcgtgca cacagcccag cttggagcga acgacctaca ccgaactgag  16800
atacctacag cgtgagctat gagaaagcgc cacgcttccc gaagggagaa aggcggacag  16860
gtatccggta agcggcaggg tcggaacagg agagcgcacg agggagcttc caggggggaaa  16920
```

-continued

```
cgcctggtat ctttatagtc ctgtcgggtt tcgccacctc tgacttgagc gtcgattttt  16980
gtgatgctcg tcaggggggc ggagcctatg gaaaaacgcc agcaacgcgg cctttttacg  17040
gttcctggcc ttttgctggc cttttgctca catgttcttt cctgcgttat cccctgattc  17100
tgtggataac cgtattaccg cctttgagtg agctgatacc gctcgccgca gccgaacgac  17160
cgagcgcagc gagtcagtga gcgaggaagc ggaagagcgc ctgatgcggt attttctcct  17220
tacgcatctg tgcggtattt cacaccgcat atggtgcact ctcagtacaa tctgctctga  17280
tgccgcatag ttaagccagc tgtggaatgt gtgtcagtta gggtgtggaa agtccccagg  17340
ctccccagca ggcagaagta tgcaaagcat gcatctcaat tagtcagcaa ccaggtgtgg  17400
aaagtcccca ggctccccag caggcagaag tatgcaaagc atgcatctca attagtcagc  17460
aaccatagtc ccgcccctaa ctccgcccat cccgccccta actccgccca gttccgccca  17520
ttctccgccc catggctgac taattttttt tatttatgca gaggccgagg ccgcctcggc  17580
ctctgagcta ttccagaagt agtgaggagg cttttttgga ggcctaggct tttgcaaaaa  17640
gcttgcatgc ctgcaggtcg gccgccacga ccggtgccgc caccatcccc tgacccacgc  17700
ccctgacccc tcacaaggag acgaccttcc atgaccgagt acaagcccac ggtgcgcctc  17760
gccacccgcg acgacgtccc ccgggccgta cgcaccctcg ccgccgcgtt cgccgactac  17820
cccgccacgc gccacaccgt cgacccggac cgccacatcg agcgggtcac cgagctgcaa  17880
gaactcttcc tcacgcgcgt cgggctcgac atcggcaagg tgtgggtcgc ggacgacggc  17940
gccgcggtgg cggtctggac cacgccggag agcgtcgaag cgggggcggt gttcgccgag  18000
atcggcccgc gcatggccga gttgagcggt tcccggctgg ccgcgcagca acagatggaa  18060
ggcctcctgg cgccgcaccg gcccaaggag cccgcgtggt tcctggccac cgtcggcgtc  18120
tcgcccgacc accagggcaa gggtctgggc agcgccgtcg tgctccccgg agtggaggcg  18180
gccgagcgcg ccggggtgcc cgccttcctg gagacctccg cgccccgcaa cctccccttc  18240
tacgagcggc tcggcttcac cgtcaccgcc gacgtcgagg tgcccgaagg accgcgcacc  18300
tggtgcatga cccgcaagcc cggtgcctga cgcccgcccc acgacccgca gcgcccgacc  18360
gaaaggagcg cacgacccca tggctccgac cgaagccgac ccgggcggcc ccgccgaccc  18420
cgcacccgcc cccgaggccc accgactcta gaggatcata atcagccata ccacatttgt  18480
agaggtttta cttgctttaa aaaacctccc acacctcccc ctgaacctga aacataaaat  18540
gaatgcaatt gttgttgtta acttgtttat tgcagcttat aatggttaca aataaagcaa  18600
tagcatcaca aatttcacaa ataaagcatt tttttcactg cattctagtt gtggtttgtc  18660
caaactcatc aatgtatctt atcatgtctg gatcactcgc cgatagtgga aaccgacgcc  18720
ccagcactcg tccgagggca aaggaatagg ggagatgggg gaggctaact gaaacacgga  18780
aggagacaat accggaagga acccgcgcta tgacggcaat aaaaagacag aataaaacgc  18840
acgggtgttg ggtcgtttgt tcataaacgc ggggttcggt cccagggctg gcactctgtc  18900
gataccccac cgagacccca ttggggccaa tacgcccgcg tttcttcctt ttccccaccc  18960
caccccccaa gttcgggtga aggcccaggg ctcgcagcca acgtcggggc ggcaggccct  19020
gccatagcca ctggccccgt gggttaggga cggggtcccc catggggaat ggtttatggt  19080
tcgtgggggt tattattttg ggcgttgcgt ggggtctggt ccacgactgg actgagcaga  19140
cagacccatg gtttttggat ggcctgggca tggaccgcat gtactggcgc gacacgaaca  19200
ccgggcgtct gtggctgcca aacacccccg acccccaaaa accaccgcgc ggatttctgg  19260
cgtgccaagc tagtcgacca attctcatgt ttgacagctt atcatcgcag atccgggcaa  19320
cgttgttgca ttgctgcagg cgcagaactg gtaggtatgg aagatctcta gaagctgggt  19380
accagctgct agcaagcttg ctagcggccg gctcgagttt actccctatc agtgatagag  19440
aacgtatgtc gagtttactc cctatcagtg atagagaacg atgtcgagtt tactccctat  19500
cagtgataga gaacgtatgt cgagtttact ccctatcagt gatagagaac gtatgtcgag  19560
tttactccct atcagtgata gagaacgtat gtcgagttta tccctatcag tgatagagaa  19620
cgtatgtcga gtttactccc tatcagtgat agagaacgta tgtcgaggta ggcgtgtacg  19680
gtgggaggcc tatataagca gagctcgttt agtgaaccgt cagatcgccg             19730

SEQ ID NO: 42           moltype = DNA  length = 7291
FEATURE                 Location/Qualifiers
misc_feature            1..7291
                        note = Description of Artificial Sequence: Synthetic
                         polynucleotide
source                  1..7291
                        mol_type = other DNA
                        organism = synthetic construct
SEQUENCE: 42
taatacgact cactataggg agaagtactg ccaccatggg caagaagcaa aatcgcaaga  60
cggggaattc caagacacaa tccgctagcc caccacctaa agagcgttct agctcccctg  120
ctactgagca gtcctggatg gaaaacgact tcgatgaact ccgggaagag ggatttaggc  180
gatccaacta ttcagaactc cgcgaagata tccagacaaa ggggaaggaa gtcgagaatt  240
tcgagaagaa cctcgaggag tgcatcaccc gtatcacaaa cactgagaaa tgtctcaaag  300
aactcatgga acttaagaca aaagccaggg agcttcgaga ggagtgtcgg agtctgagat  360
ccaggtgtga ccagctcgag gagcgcgtga gcgcgatgga agacgagatg aacgagatga  420
aaagagaggg caaattcagg gagaagcgca ttaagaggaa cgaacagagt ctgcaggaga  480
tttgggatta cgtcaagagg cctaacctgc ggttgatcgg cgtccccgag agcgacgtag  540
aaaacgggac taaactggag aatacacttc aagacatcat tcaagaaaat tttccaaacc  600
tggctcggca agctaatgtg caaatccaag agatccaacg cacaccccag cggtatagct  660
ctcggcgtgc caccccctagg catattatcg tgcgctttac taaggtggag atgaaagaga  720
agatgctgcg agccgctcgg gaaaagggaa gggtgacttt gaagggcaaa cctattcggc  780
tgacggttga ccttagcgcc gagacactcc aggcacgccg ggaatggggc cccatcttta  840
atatcctgaa ggagaagaac ttccagccac gaatctctta ccctgcaaag ttgagtttta  900
tctccgaggg tgagattaag tatttcatcg ataaacagat gctgcgagac ttcgtgacaa  960
ctcgcccagc tctcaaggaa ctgctcaaag aggctcttaa tatggagcgc aataatagat  1020
atcaaccctt gcagaaccac gcaaagatgt gagacagccg tcagaccatc aagactagga  1080
agaaactgca tcaactaatg agcaaaatca ccagctaaca tcatagtata catgaccggc  1140
tctaactcac atatcaccat ccttacactt aacattaacg gcctcaactc agctatcaag  1200
cgccatcggc tggccagctg gatcaaatca caggatccaa gcgtttgttg catccaagag  1260
acccacctga cctgtagaga tactcaccgc ctcaagatca agggatggcg aaagatttat  1320
```

-continued

```
caggcgaacg gtaagcagaa gaaagccgga gtcgcaattc tggtctcaga caagacggat 1380
ttcaagccca ccaaaattaa gcgtgataag gaaggtcact atattatggt gaaaggcagc 1440
atacagcagg aagaacttac catattgaac atctacgcgc caaacaccgg cgcacctcgc 1500
tttatcaaac aggtcctgtc cgatctgcag cgagatctgg attctcatac gttgattatg 1560
ggtgatttca atacaccatt gagcaccctg gatcgcagca ccaggcaaaa ggtaaataaa 1620
gacacgcaag agctcaatag cgcactgcat caggcagatc tcattgatat ttatcgcact 1680
cttcatccta agagtaccga gtacacattc ttcagcgccc cacatcatac atactcaaag 1740
atcgatcata tcgtcggctc aaaggctctg ctgtcaaagt gcaagcgcac agagataatt 1800
acaaattacc tgtcagatca tagcgcgatc aagctcgagc tgagaatcaa gaacctgacc 1860
cagagccgga gtaccacttg gaagcttaat aacctgctgc tcaacgatta ttgggtccac 1920
aatgagatga aggcagagat taaaatgttc ttcgaaacaa atgagaataa ggatactacc 1980
tatcaaaacc tttgggatgc ctttaaggcc gtctgcagag gcaagttcat cgccctcaac 2040
gcctataaaa gaaaacaaga gagatctaag atcgatactc tcacctctca gctgaaggag 2100
ttggagaaac aggaacagac ccactccaag gcgtcaagac ggcaggagat cacaaagatt 2160
cgcgccgagt tgaaagagat cgaaacccaa aagactcttc agaaaattaa cgagtctcgt 2220
agttggttct tcgagcggat taataagata gacagacctc tggcacgact gattaagaag 2280
aagcgcgaaa agaaccagat tgataccatc aagaacgaca agggcgacat cactactgac 2340
ccgaccgaga tccagaccac tattcgggag tattataagc atttgtatgc taacaagctt 2400
gagaacctgg aagagatgga cacttttctg gatacctata ctctgccacg gcttaatcaa 2460
gaggaagtcg agtccctcaa ccgcccaatt acaggaagcg agattgtggc cataattaac 2520
tccctgccga caaagaaatc tcctggtccg gacgggttta cagctgagtt ttatcaacgg 2580
tatatggaag agcttgtacc gtttctgctc aagctctttc agtctataga aaaggaaggc 2640
atcttgccca attccttcta cgaagcttct ataatactta ttcccaaacc aggacgcgat 2700
accacaaaga aggaaaactt ccggcccatt agtctcatga atatcgacgc taaaatattg 2760
aacaagattc tcgccaacag aatccaacaa catattaaga aattgataca tcacgaccag 2820
gtggggttta tacctggcat gcagggctgg tttaacatcc ggaagagtat taacgtcatt 2880
caacacatta atagagctaa ggataagaat catatgatca tctctataga cgcggaaaag 2940
gcattcgata agattcagca gccatttatg ctcaagactc tgaacaaact cggcatcgac 3000
ggaacatatt ttaagattat tcgcgcaatt tacgataagc cgactgctaa cattatcctt 3060
aacggccaaa agctcgaggc ctttccgctc aagactggaa cccgccaagg ctgtcccctc 3120
tccccgcttt tgtttaatat tgtactcgag gtgctggcta gggctattcg tcaagagaaa 3180
gagattaaag ggatacagct cgggaaggaa gaggtcaagc tttccttgtt cgccgatgat 3240
atgattgtgt acctggagaa tcctattgtg tctgctcaga accttcttaa acttatttct 3300
aactttagca aggtcagcgg ctataagatt aacgtccaga aatctcaggc ctttctgtac 3360
acaaataatc gacagaccga atcccagata atgggtgagc ttccgtttgt catagccagc 3420
aaaaggataa agtatctcgg aatccagctg acacgagacg ttaaagattt gtttaaggaa 3480
aattacaagc ctctcctgaa agagattaag gaagatacta ataagtggaa gaatatcccc 3540
tgttcatggg ttggcagaat caacatagtg aagatggcaa tacttcctaa agtgatatat 3600
cgctttaacg ccatcccaat taaactgcct atgaccttct ttacggagct cgagaaaaca 3660
acccttaaat ttatatggaa tcaaaagaga gcaagaatag cgaagtccat cttgagccag 3720
aagaataagg ccggtgggat tactttgcct gattttaagt tgtattataa agccacagta 3780
actaagacag cctggtattg gtatcagaat agagacatcg accagtggaa tcggaccgaa 3840
ccatcagaga taatgcccca catctataat taccttatat tcgataagcc agaaaagaat 3900
aaacagtggg gcaaagacag cctcttcaac aagtggtgtt gggagaattg gctggccata 3960
tgccggaaac tcaagctcga cccctttctt acaccctaca ctaaaatcaa cagtaggtgg 4020
atcaaggact tgaatgtcaa gccaaagact ataaagacac tggaagagaa tcttgggatc 4080
acaatacaag atataggcgt cggcaaagat tttatgtcaa agacgcccaa ggccatggcc 4140
actaaggata agattgataa gtgggacctt attaagctca aaagcttctg tactgccaag 4200
gagaccacga tcagagttaa taggcagccc actacatggg aaaagatttt cgccacttat 4260
tcatcagata aggggttgat aagcagaata tataacgagc tgaagcagat ctacaagaag 4320
aaaacgaata atcccatcaa gaagtgggca aaagatatga acaggcattt tagcaaagag 4380
gatatctacg ccgcgaagaa gcatatgaag aagtgtagtt caagcttggc cattcgtgag 4440
atgcagatta agacgaccat gcgataccac cttaccccag tgaggatggc aattatcaag 4500
aaatctggca ataatagatg ttggcggggc tgtggcgaga ttggcaccct gctccattgc 4560
tggtgggatt gcaagctggt gcagccgctt tggaaatcag tctggcgctt tctgagggac 4620
ctcgagcttg agattccctt cgatcccgca attcccttgc tcggaatcta tcctaacgaa 4680
tacaagagct gttgttacaa ggatacgtgt acccggatgt tcatcgcggc cttgtttacg 4740
atagctaaga cgtggaatca gcctaagtgc cccacaatga tcgattggat caagaaaatg 4800
tggcatattt ataccatgga gtattacgca gcaattaaga atgacgaatt tatttccttc 4860
gttgggacct ggatgaagct ggagactatt attctgagca agctgtctca ggagcaaaag 4920
acaaagcata gaatcttctc tctcattggt ggtaacgact acaaagacga tgacgacaag 4980
cccgccgcca agagggtgaa gctggactaa agcgcttcta gaagttgtct cctcctgcac 5040
tgactgactg atacaatcga tttctggatc cgcaggccta atcaacctct ggattacaaa 5100
atttgtgaaa gattgactgg tattcttaac tatgttgctc cttttacgct atgtggatac 5160
gctgctttaa tgcctttgta tcatgctatt gcttcccgta tggctttcat tttctcctcc 5220
ttgtataaat cctggttgct gtctctttat gaggagttgt ggcccgttgt caggcaacgt 5280
ggcgtggtgt gcactgtgtt tgctgacgca acccccactg gttggggcat tgccaccacc 5340
tgtcagctcc tttccgggac tttcgctttc cccctcccta ttgccacggc ggaactcatc 5400
gccgcctgcc ttgcccgctg ctggacaggg gctcggctgt tgggcactga caattccgtg 5460
gtgttgtcgg ggaagctgac gtcctttcca tggctgctcg cctgtgttgc cacctggatt 5520
ctgcgcggga cgtccttctg ctacgtccct tcggccctca atccagcgga ccttccttcc 5580
cgctgagaga cacaaaaaat tccaacacac tattgcaatg aaaataaatt tcctttatta 5640
gccagaagtc agatgctcaa ggggcttcat gatgtcccca taatttttgg cagagggaaa 5700
aagatctcag tggtatttgt gagccagggc attggccttc tgataggcag cctgcacctg 5760
aggagtgcgg ccgctttact tgtacagctc gtccatgccg agagtgatcc cggcggcggt 5820
cacgaactcc agcaggacca tgtgatcgcg cttctcgttg gggtctttgc tcagggcgga 5880
ctgggtgctc aggtagtggt tgtcgggcag cagcacgggg ccgtcgccga tgggggtgtt 5940
ctgctggtag tggtcggcga gctgcacgct gccgtcctcg atgttgtggc ggatcttgaa 6000
gttcaccttg atgccgttct tctgcttgtc ggccatgata tagacgttgt ggctgttgta 6060
```

```
gttgtactcc agcttgtgcc ccaggatgtt gccgtcctcc ttgaagtcga tgcccttcag  6120
ctcgatgcgg ttcaccaggg tgtcgccctc gaacttcacc tcggcgcggg tcttgtagtt  6180
gccgtcgtcc ttgaagaaga tggtgcgctc ctggacgtag ccttcgggca tggcggactt  6240
gaagaagtcg tgctgcttca tgtggtcggg gtagcggctg aagcactgca cgccgtaggt  6300
cagggtggtc acgagggtgg gccagggcac gggcagcttg ccggtggtgc agatgaactt  6360
cagggtcagc ttgccgtagg tggcatcgcc ctcgccctcg ccggacacgc tgaacttgtg  6420
gccgtttacg tcgccgtcca gctcgaccag gatgggcacc accccggtga acagctcctc  6480
gcccttgctc accatggtgg cgggatctga cggttcacta aaccagctct gcttatatag  6540
acctcccacc gtacacgcct accgcccatt tgcgtcaatg gggcggagtt gttacgacat  6600
tttggaaagt cccgttgatt ttggtgccaa aacaaactcc cattgacgtc aatggggtgg  6660
agacttggaa atccccgtga gtcaaaccgc tatccacgcc cattgatgta ctgccaaaac  6720
cgcatcacca tggtaatagc gatgactaat acgtagatgt actgccaagt aggaaagtcc  6780
cataaggtca tgtactgggc ataatgccag gcgggccatt taccgtcatt gacgtcaata  6840
gggggcgtac ttggcatatg atacacttga tgtactgcca agtgggcagt ttaccgtaaa  6900
tactccaccc attgacgtca atggaaagtc cctattggcg ttactatggg aacatacgtc  6960
attattgacg tcaatgggcg ggggtcgttg ggcggtcagc caggcgggcc atttaccgta  7020
agttatgtaa cgggcctgct gccggctctg cggcctcttc cgcgtcttcg ccttcgccct  7080
cagacgagtc ggatctccct ttgggccgcc tccccgcctg tctagcttga ctgactgaga  7140
tacagcgtac cttcagctca cagacatgat aagatacatt gatgagtttg gacaaaccac  7200
aactagaatg cagtgaaaaa aatgctttat ttgtgaaatt tgtgatgcta ttgctttatt  7260
tgtaaccatt ataagctgca ataaacaagt t                                 7291
```

```
SEQ ID NO: 43           moltype = DNA  length = 7376
FEATURE                 Location/Qualifiers
misc_feature            1..7376
                        note = Description of Artificial Sequence: Synthetic
                         polynucleotide
source                  1..7376
                        mol_type = other DNA
                        organism = synthetic construct
SEQUENCE: 43
taatacgact cactataggg agaagtactg ccaccatggg caagaagcaa aatcgcaaga  60
cggggaattc caagacacaa tccgctagcc caccacctaa agagcgttct agctcccctg  120
ctactgagca gtcctggatg gaaaacgact tcgatgaact ccgggaagag ggatttaggc  180
gatccaacta ttcagaactc cgcgaagata tccagacaaa ggggaaggaa gtcgagaatt  240
tcgagaagaa cctcgaggag tgcatcaccc gtatcacaaa cactgagaaa tgtctcaaag  300
aactcatgga acttaagaca aaagccaggg agcttcgaga ggagtgtcgg agtctgagat  360
ccaggtgtga ccagctcgag gagcgcgtga gcgcgatgga agacgagatg aacgagatga  420
aaagagaggg caaattcagg gagaagcgca ttaagaggaa cgaacagagt ctgcaggaga  480
tttgggatta cgtcaagagg cctaacctgc ggttgatcgg cgtccccgag agcgacgtag  540
aaaacgggac taaactggag aatacacttc aagacatcat tcaagaaaat tttccaaacc  600
tggctcggca agctaatgtg caaatccaag agatccaacg cacaccccag cggtatagct  660
ctcggcgtgc cacccctagg catattatcg tgcgctttac taaggtggag atgaaagaga  720
agatgctgcg agccgctcgg gaaaagggaa gggtgacttt gaagggcaaa cctattcggc  780
tgacggttga ccttagcgcc gagacactcc aggcacgccg ggaatggggc cccatcttta  840
atatcctgaa ggagaagaac ttccagccac gaatctctta ccctgcaaag ttgagtttta  900
tctccgaggg tgagattaag tatttcatcg ataaacagat gctgcgagac ttcgtgacaa  960
ctcgcccagc tctcaaggaa ctgctcaaag aggctcttaa tatggagcgc aataatagat  1020
atcaaccctt gcagaaccac gcaaagatgt gagacagccg tcagaccatc aagactagga  1080
agaaactgca tcaactaatg agcaaaatca ccagctaaca tcatagtata catgaccggc  1140
tctaactcac atatcaccat ccttacactt aacattaacg gcctcaactc agctatcaag  1200
cgccatcggc tggccagctg gatcaaatca caggatccaa gcgtttgttg catccaagag  1260
acccacctga cctgtagaga tactcaccgc ctcaagatca agggatggcg aaagatttat  1320
caggcgaacg gtaagcagaa gaaagccgga gtcgcaattc tggtctcaga caagacggat  1380
ttcaagccca ccaaaattaa gcgtgataag gaaggtcact atattatggt gaaaggcagc  1440
atacagcagg aagaacttac catattgaac atctacgcgc caaacaccgg cgcacctcgc  1500
tttatcaaac aggtcctgtc cgatctgcag cgagatctgg attctcatac gttgattatg  1560
ggtgatttca atacaccatt gagcaccctg gatcgcagca ccaggcaaaa ggtaaataaa  1620
gacacgcaag agctcaatag cgcactgcat caggcagatc tcattgatat ttatcgcact  1680
cttcatccta agagtaccga gtacacattc ttcagcgccc cacatcatac atactcaaag  1740
atcgatcata tcgtcggctc aaaggctctg ctgtcaaagt gcaagcgcac agagataatt  1800
acaaattacc tgtcagatca tagcgcgatc aagctcgagc tgagaatcaa gaacctgacc  1860
cagagccgga gtaccacttg gaagcttaat aacctgctgc tcaacgatta ttgggtccac  1920
aatgagatga aggcagagat taaaatgttc ttcgaaacaa atgagaataa ggatactacc  1980
tatcaaaacc tttgggatgc ctttaaggcc gtctgcagag gcaagttcat cgccctcaac  2040
gcctataaaa gaaaacaaga gagatctaag atcgatactc tcacctctca gctgaaggag  2100
ttggagaaac aggaacagac ccactccaag gcgtcaagac ggcaggagat cacaaagatt  2160
cgcgccgagt tgaaagagat cgaaacccaa aagactcttc agaaaattaa cgagtctcgt  2220
agttggttct tcgagcggat taataagata gacagacctc tggcacgact gattaagaag  2280
aagcgcgaaa agaaccagat tgataccatc aagaacgaca agggcgacat cactactgac  2340
ccgaccgaga tccagaccac tattcgggag tattataagc atttgtatgc taacaagctt  2400
gagaacctgg aagagatgga cacttttctg gatacctata ctctgccacg gcttaatcaa  2460
gaggaagtcg agtccctcaa ccgcccaatt acaggaagcg agattgtggc cataattaac  2520
tccctgccga caaagaaatc tcctggtccg gacgggttta cagctgagtt ttatcaacgg  2580
tatatggaag agcttgtacc gtttctgctc aagctctttc agtctataga aaaggaaggc  2640
atcttgccca attccttcta cgaagcttct ataatactta ttcccaaacc aggacgcgat  2700
accacaaaga aggaaaactt ccggcccatt agtctcatga atatcgacgc taaaatattg  2760
aacaagattc tcgccaacag aatccaacaa catattaaga aattgataca tcacgaccag  2820
gtggggttta tacctggcat gcagggctgg tttaacatcc ggaagagtat taacgtcatt  2880
```

-continued

```
caacacatta atagagctaa ggataagaat catatgatca tctctataga cgcggaaaag  2940
gcattcgata agattcagca gccatttatg ctcaagactc tgaacaaact cggcatcgac  3000
ggaacatatt ttaagattat tcgcgcaatt tacgataagc cgactgctaa cattatcctt  3060
aacggccaaa agctcgaggc ctttccgctc aagactggaa cccgccaagg ctgtcccctc  3120
tccccgcttt tgtttaatat tgtactcgag gtgctggcta gggctattcg tcaagagaaa  3180
gagattaaag ggatacagct cgggaaggaa gaggtcaagc tttccttgtt cgccgatgat  3240
atgattgtgt acctggagaa tcctattgtg tctgctcaga accttcttaa acttatttct  3300
aactttagca aggtcagcgg ctataagatt aacgtccaga aatctcaggc ctttctgtac  3360
acaaataatc gacagaccga atcccagata atgggtgagc ttccgtttgt catagccagc  3420
aaaaggataa agtatctcgg aatccagctg acacgagacg ttaaagattt gtttaaggaa  3480
aattacaagc ctctcctgaa agagattaag gaagatacta ataagtggaa gaatatcccc  3540
tgttcatggg ttggcagaat caacatagtg aagatggcaa tacttcctaa agtgatatat  3600
cgctttaacg ccatcccaat taaactgcct atgaccttct ttacggagct cgagaaaaca  3660
acccttaaat ttatatggaa tcaaaagaga gcaagaatag cgaagtccat cttgagccag  3720
aagaataagg ccggtgggat tactttgcct gattttaagt tgtattataa agccacagta  3780
actaagacag cctggtattg gtatcagaat agagacatcg accagtggaa tcggaccgaa  3840
ccatcagaga taatgcccca catctataat taccttatat tcgataagcc agaaaagaat  3900
aaacagtggg gcaaagacag cctcttcaac aagtggtgtt gggagaattg gctggccata  3960
tgccggaaac tcaagctcga ccccttttctt acaccctaca ctaaaatcaa cagtaggtgg  4020
atcaaggact tgaatgtcaa gccaaagact ataaagacac tggaagagaa tcttgggatc  4080
acaatacaag atataggcgt cggcaaagat tttatgtcaa agacgcccaa ggccatggcc  4140
actaaggata agattgataa gtgggacctt attaagctca aaagcttctg tactgccaag  4200
gagaccacga tcagagttaa taggcagccc actacatggg aaaagatttt cgccacttat  4260
tcatcagata aggggttgat aagcagaata tataacgagc tgaagcagat ctacaagaag  4320
aaaacgaata atcccatcaa gaagtgggca aaagatatga acaggcattt tagcaaagag  4380
gatatctacg ccgcgaagaa gcatatgaag aagtgtagtt caagcttggc cattcgtgag  4440
atgcagatta agacgaccat gcgataccac cttaccccag tgaggatggc aattatcaag  4500
aaatctggca ataatagatg ttggcggggc tgtggcgaga ttggcaccct gctccattgc  4560
tggtgggatt gcaagctggt gcagccgctt tggaaatcag tctggcgctt tctgagggac  4620
ctcgagcttg agattccctt cgatcccgca attcccttgc tcggaatcta tcctaacgaa  4680
tacaagagct gttgttacaa ggatacgtgt acccggatgt tcatcgcggc cttgtttacg  4740
atagctaaga cgtggaatca gcctaagtgc cccacaatga tcgattggat caagaaaatg  4800
tggcatattt ataccatgga gtattacgca gcaattaaga atgacgaatt tatttccttc  4860
gttgggacct ggatgaagct ggagactatt attctgagca agctgtctca ggagcaaaag  4920
acaaagcata gaatcttctc tctcattggt ggtaacgact acaaagacga tgacgacaag  4980
taaagcggcc gggcgcggtg gctcacgcct gtaatcccag cactttggga ggccgaggcg  5040
ggaggatcgc agttcgagac cagcgcgaga ccccgtctct acaaaaaatac aaaaaattagc  5100
ttctagaagt tgtctcctcc tgcactgact gactgataca atcgatttct ggatccgcag  5160
gcctaatcaa cctctggatt acaaaatttg tgaaagattg actggtattc ttaactatgt  5220
tgctcctttt acgctatgtg gatacgctgc tttaatgcct ttgtatcatg ctattgcttc  5280
ccgtatggct ttcattttct cctccttgta taaatcctgg ttgctgtctc tttatgagga  5340
gttgtggccc gttgtcaggc aacgtggcgt ggtgtgcact gtgtttgctg acgcaacccc  5400
cactggttgg ggcattgcca ccacctgtca gctcctttcc gggactttcg ctttcccccct  5460
ccctattgcc acggcggaac tcatcgccgc ctgccttgcc cgctgctgga caggggctcg  5520
gctgttgggc actgacaatt ccgtggtgtt gtcggggaag ctgacgtcct ttccatggct  5580
gctcgcctgt gttgccacct ggattctgcg cgggacgtcc ttctgctacg tcccttcggc  5640
cctcaatcca gcggaccttc cttcccgctg agagacacaa aaaattccaa cacactattg  5700
caatgaaaat aaatttcctt tattagccag aagtcagatg ctcaaggggc ttcatgatgt  5760
ccccataatt tttggcagag ggaaaaagat ctcagtggta tttgtgagcc agggcattgg  5820
ccttctgata ggcagcctgc acctgaggag tgcggccgct ttacttgtac agctcgtcca  5880
tgccgagagt gatcccggcg gcggtcacga actccagcag gaccatgtga tcgcgcttct  5940
cgttggggtc tttgctcagg gcggactggg tgctcaggta gtggttgtcg ggcagcagca  6000
cggggccgtc gccgatgggg gtgttctgct ggtagtggtc ggcgagctgc acgctgccgt  6060
cctcgatgtt gtggcggatc ttgaagttca ccttgatgcc gttcttctgc ttgtcggcca  6120
tgatatagac gttgtggctg ttgtagttgt actccagctt gtgccccagg atgttgccgt  6180
cctccttgaa gtcgatgccc ttcagctcga tgcggttcac cagggtgtcg ccctcgaact  6240
tcacctcggc gcgggtcttg tagttgccgt cgtccttgaa gaagatggtg cgctcctgga  6300
cgtagccttc gggcatggcg gacttgaaga agtcgtgctg cttcatgtgg tcggggtagc  6360
ggctgaagca ctgcacgccg taggtcaggg tggtcacgag ggtgggccag ggcacgggca  6420
gcttgccggt ggtgcagatg aacttcaggg tcagcttgcc gtaggtggca tcgccctcgc  6480
cctcgccgga cacgctgaac ttgtggccgt ttacgtcgcc gtccagctcg accaggatgg  6540
gcaccacccc ggtgaacagc tcctcgccct tgctcaccat ggtggcggga tctgacggtt  6600
cactaaacca gctctgctta tatagacctc ccaccgtaca cgcctaccgc ccatttgcgt  6660
caatggggcg gagttgttac gacattttgg aaagtcccgt tgattttggt gccaaaacaa  6720
actcccattg acgtcaatgg ggtggagact tggaaatccc cgtgagtcaa accgctatcc  6780
acgcccattg atgtactgcc aaaaccgcat caccatggta atagcgatga ctaatacgta  6840
gatgtactgc caagtaggaa agtcccataa ggtcatgtac tgggcataat gccaggcggg  6900
ccatttaccg tcattgacgt caatagggggg cgtacttggc atatgataca cttgatgtac  6960
tgccaagtgg gcagtttacc gtaaatactc cacccattga cgtcaatgga aagtccctat  7020
tggcgttact atgggaacat acgtcattat tgacgtcaat gggcgggggt cgttgggcgg  7080
tcagccaggc gggccattta ccgtaagtta tgtaacgggc ctgctgccgg ctctgcggcc  7140
tcttccgcgt cttcgccttc gccctcagac gagtcggatc tccctttggg ccgcctcccc  7200
gcctgtctag cttgactgac tgagatacag cgtaccttca gctcacagac atgataagat  7260
acattgatga gtttggacaa accacaacta gaatgcagtg aaaaaaatgc tttatttgtg  7320
aaatttgtga tgctattgct ttatttgtaa ccattataag ctgcaataaa caagtt      7376
```

SEQ ID NO: 44 moltype = DNA length = 14122
FEATURE Location/Qualifiers
misc_feature 1..14122

```
                       note = Description of Artificial Sequence: Synthetic
                        polynucleotide
source                 1..14122
                       mol_type = other DNA
                       organism = synthetic construct
SEQUENCE: 44
taatacgact cactataggg agaagtactg ccaccatggg caagaagcaa aatcgcaaga  60
cggggaattc caagacacaa tccgctagcc caccacctaa agagcgttct agctcccctg  120
ctactgagca gtcctggatg gaaaacgact tcgatgaact ccgggaagag ggatttaggc  180
gatccaacta ttcagaactc cgcgaagata tccagacaaa ggggaaggaa gtcgagaatt  240
tcgagaagaa cctcgaggag tgcatcaccc gtatcacaaa cactgagaaa tgtctcaaag  300
aactcatgga acttaagaca aaagccaggg agcttcgaga ggagtgtcgg agtctgagat  360
ccaggtgtga ccagctcgag gagcgcgtga gcgcgatgga agacgagatg aacgagatga  420
aaagagaggg caaattcagg gagaagcgca ttaagaggaa cgaacagagt ctgcaggaga  480
tttgggatta cgtcaagagg cctaacctgc ggttgatcgg cgtccccgag agcgacgtag  540
aaaacgggac taaactggag aatacacttc aagacatcat tcaagaaaat tttccaaacc  600
tggctcggca agctaatgtg caaatccaag agatccaacg cacaccccag cggtatagct  660
ctcggcgtgc caccccctagg catattatcg tgcgctttac taaggtggag atgaaagaga  720
agatgctgcg agccgctcgg gaaaagggaa gggtgacttt gaagggcaaa cctattcggc  780
tgacggttga ccttagcgcc gagacactcc aggcacgccg ggaatggggc cccatcttta  840
atatcctgaa ggagaagaac ttccagccac gaatctctta ccctgcaaag ttgagtttta  900
tctccgaggg tgagattaag tatttcatcg ataaacagat gctgcgagac ttcgtgacaa  960
ctcgcccagc tctcaaggaa ctgctcaaag aggctcttaa tatggagcgc aataatagat  1020
atcaaccctt gcagaaccac gcaaagatgt gagacagtta aaacagcctg tgggttgatc  1080
ccacccacag gcccattggg cgctagcact ctggtatcac ggtacctttg tgcgcctgtt  1140
ttataccccc tcccccaact gtaacttaga agtaacacac accgatcaac agtcagcgtg  1200
gcacaccagc cacgttttga tcaagcactt ctgttacccc ggactgagta tcaatagact  1260
gctcacgcgg ttgaaggaga aagcgttcgt tatccggcca actacttcga aaaacctagt  1320
aacaccgtgg aagttgcaga gtgtttcgct cagcactacc ccagtgtaga tcaggtcgat  1380
gagtcaccgc attccccacg ggcgaccgtg gcggtggctg cgttggcggc ctgcccatgg  1440
ggaaacccat gggacgctct aatacagaca tggtgcgaag agtctattga gctagttggt  1500
agtcctccgg cccctgaatg cggctaatcc taactgcgga gcacacaccc tcaagccaga  1560
gggcagtgtg tcgtaacggg caactctgca gcggaaccga ctactttggg tgtccgtgtt  1620
tcattttatt cctatactgg ctgcttatgg tgacaattga gagatcgtta ccatatagct  1680
attggattgg ccatccggtg actaatagag ctattatata tccctttgtt gggtttatac  1740
cacttagctt gaaagaggtt aaaacattac aattcattgt taagttgaat acagcaaata  1800
catgaccggc tctaactcac atatcaccat ccttacactt aacattaacg gcctcaactc  1860
agctatcaag cgccatcggc tggccagctg gatcaaatca caggatccaa gcgtttgttg  1920
catccaagag acccacctga cctgtagaga tactcaccgc ctcaagatca agggatggcg  1980
aaagatttat caggcgaacg gtaagcagaa gaaagccgga gtcgcaattc tggtctcaga  2040
caagacggat ttcaagccca ccaaaattaa gcgtgataag gaaggtcact atattatggt  2100
gaaaggcagc atacagcagg aagaacttac catattgaac atctacgcgc caaacaccgg  2160
cgcacctcgc tttatcaaac aggtcctgtc cgatctgcag cgagatctgg attctcatac  2220
gttgattatg ggtgatttca atacaccatt gagcaccctg gatcgcagca ccaggcaaaa  2280
ggtaaataaa gacacgcaag agctcaatag cgcactgcat caggcagatc tcattgatat  2340
ttatcgcact cttcatccta agagtaccga gtacacattc ttcagcgccc cacatcatac  2400
atactcaaag atcgatcata tcgtcggctc aaaggctctg ctgtcaaagt gcaagcgcac  2460
agagataatt acaaattacc tgtcagatca tagcgcgatc aagctcgagc tgagaatcaa  2520
gaacctgacc cagagccgga gtaccacttg gaagcttaat aacctgctgc tcaacgatta  2580
ttgggtccac aatgagatga aggcagagat taaaatgttc ttcgaaacaa atgagaataa  2640
ggatactacc tatcaaaacc tttgggatgc ctttaaggcc gtctgcagag gcaagttcat  2700
cgccctcaac gcctataaaa gaaaacaaga gagatctaag atcgatactc tcacctctca  2760
gctgaaggag ttggagaaac aggaacagac ccactccaag gcgtcaagac ggcaggagat  2820
cacaaagatt cgcgccgagt tgaaagagat cgaaacccaa aagactcttc agaaaattaa  2880
cgagtctcgt agttggttct tcgagcggat taataagata gacagacctc tggcacgact  2940
gattaagaag aagcgcgaaa agaaccagat tgataccatc aagaacgaca agggcgacat  3000
cactactgac ccgaccgaga tccagaccac tattcgggag tattataagc atttgtatgc  3060
taacaagctt gagaacctgg aagagatgga cacttttctg gatacctata ctctgccacg  3120
gcttaatcaa gaggaagtcg agtccctcaa ccgcccaatt acaggaagcg agattgtggc  3180
cataattaac tccctgccga caaagaaatc tcctggtccg gacgggttta cagctgagtt  3240
ttatcaacgg tatatggaag agcttgtacc gtttctgctc aagctctttc agtctataga  3300
aaaggaaggc atcttgccca attccttcta cgaagcttct ataatactta ttcccaaacc  3360
aggacgcgat accacaaaga aggaaaactt ccggcccatt agtctcatga atatcgacgc  3420
taaaatattg aacaagattc tcgccaacag aatccaacaa catattaaga aattgataca  3480
tcacgaccag gtggggttta tacctggcat gcagggctgg tttaacatcc ggaagagtat  3540
taacgtcatt caacacatta atagagctaa ggataagaat catatgatca tctctataga  3600
cgcggaaaag gcattcgata agattcagca gccatttatg ctcaagactc tgaacaaact  3660
cggcatcgac ggaacatatt ttaagattat tcgcgcaatt tacgataagc cgactgctaa  3720
cattatcctt aacggccaaa agctcgaggc ctttccgctc aagactggaa cccgccaagg  3780
ctgtcccctc tccccgcttt tgtttaatat tgtactcgag gtgctggcta gggctattcg  3840
tcaagagaaa gagattaaag ggatacagct cgggaaggaa gaggtcaagc tttccttgtt  3900
cgccgatgat atgattgtgt acctggagaa tcctattgtg tctgctcaga accttcttaa  3960
acttatttct aactttagca aggtcagcgg ctataagatt aacgtccaga aatctcaggc  4020
ctttctgtac acaaataatc gacagaccga atcccagata atgggtgagc ttccgtttgt  4080
catagccagc aaaaggataa agtatctcgg aatccagctg acacgagacg ttaaagattt  4140
gtttaaggaa aattacaagc ctctcctgaa agagattaag gaagatacta ataagtggaa  4200
gaatatcccc tgttcatggg ttggcagaat caacatagtg aagatggcaa tacttcctaa  4260
agtgatatat cgctttaacg ccatcccaat taaactgcct atgaccttct ttacggagct  4320
cgagaaaaca acccttaaat ttatatggaa tcaaaagaga gcaagaatag cgaagtccat  4380
```

```
cttgagccag aagaataagg ccggtgggat tactttgcct gattttaagt tgtattataa  4440
agccacagta actaagacag cctggtattg gtatcagaat agagacatcg accagtggaa  4500
tcggaccgaa ccatcagaga taatgcccca catctataat taccttatat tcgataagcc  4560
agaaaagaat aaacagtggg gcaaagacag cctcttcaac aagtggtgtt gggagaattg  4620
gctggccata tgccggaaac tcaagctcga cccctttctt acaccctaca ctaaaatcaa  4680
cagtaggtgg atcaaggact tgaatgtcaa gccaaagact ataaagacac tggaagagaa  4740
tcttgggatc acaatacaag atataggcgt cggcaaagat tttatgtcaa agacgcccaa  4800
ggccatggcc actaaggata agattgataa gtgggacctt attaagctca aagcttctg   4860
tactgccaag gagaccacga tcagagttaa taggcagccc actacatggg aaaagatttt  4920
cgccacttat tcatcagata aggggttgat aagcagaata tataacgagc tgaagcagat  4980
ctacaagaag aaaacgaata atcccatcaa gaagtgggca aaagatatga acaggcattt  5040
tagcaaagag gatatctacg ccgcgaagaa gcatatgaag aagtgtagtt caagcttggc  5100
cattcgtgag atgcagatta agacgaccat gcgataccac cttaccccag tgaggatggc  5160
aattatcaag aaatctggca ataatagatg ttggcggggc tgtggcgaga ttggcaccct  5220
gctccattgc tggtgggatt gcaagctggt gcagccgctt tggaaatcag tctggcgctt  5280
tctgagggac ctcgagcttg agattccctt cgatcccgca attcccttgc tcggaatcta  5340
tcctaacgaa tacaagagct gttgttacaa ggatacgtgt acccggatgt tcatcgcggc  5400
cttgtttacg atagctaaga cgtggaatca gcctaagtgc cccacaatga tcgattggat  5460
caagaaaatg tggcatattt ataccatgga gtattacgca gcaattaaga atgacgaatt  5520
tatttccttc gttgggacct ggatgaagct ggagactatt attctgagca agctgtctca  5580
ggagcaaaag acaaagcata gaatcttctc tctcattggt ggtaacgact acaaagacga  5640
tgacgacaag taaagcgctt ctagaagttg tctcctcctg cactgactga ctgatacaat  5700
cgatttctgg atccgcaggc ctaatcaacc tctggattac aaaatttgtg aaagattgac  5760
tggtattctt aactatgttg ctccttttac gctatgtgga tacgctgctt taatgccttt  5820
gtatcatgct attgcttccc gtatggcttt cattttctcc tccttgtata aatcctggtt  5880
gctgtctctt tatgaggagt tgtggcccgt tgtcaggcaa cgtggcgtgg tgtgcactgt  5940
gtttgctgac gcaaccccca ctggttgggg cattgccacc acctgtcagc tcctttccgg  6000
gactttcgct ttccccctcc ctattgccac ggcggaactc atcgccgcct gccttgcccg  6060
ctgctggaca ggggctcggc tgttgggcac tgacaattcc gtggtgttgt cggggaagct  6120
gacgtccttt ccatggctgc tcgcctgtgt tgccacctgg attctgcgcg ggacgtcctt  6180
ctgctacgtc ccttcggccc tcaatccagc ggaccttcct tcccgcgaac aaacgaccca  6240
acacccgtgc gttttattct gtctttttat tgccgatccc ctcagaagaa ctcgtcaaga  6300
aggcgataga aggcgatgcg ctgcgaatcg ggagcggcga taccgtaaag cacgaggaag  6360
cggtcagccc attcgccgcc aagctcttca gcaatatcac gggtagccaa cgctatgtcc  6420
tgatagcggt cggccgcttt acttgtacag ctcgtccatg ccgagagtga tcccggcggc  6480
ggtcacgaac tccagcagga ccatgtgatc gcgcttctcg ttggggtctt tgctcagggc  6540
ggactgggtg ctcaggtagt ggttgtcggg cagcagcacg gggccgtcgc cgatgggggt  6600
gttctgctgg tagtggtcgg ccaggtgagt ccaggagatg tttcagcact gttgccttta  6660
gtctcgaggc aacttagaca actgagtatt gatctgagca cagcagggtg tgagctgttt  6720
gaagatactg gggttggggg tgaagaaact gcagaggact aactgggctg agacccagtg  6780
gcaatgtttt agggcctaag gaatgcctct gaaaatctag atggacaact ttgactttga  6840
gaaaagagag gtggaaatga ggaaaatgac ttttctttat tagatttcgg tagaaagaac  6900
tttcatcttt cccctatttt tgttattcgt tttaaaacat ctatctggag gcaggacaag  6960
tatggtcatt aaaaagatgc aggcagaagg catatattgg ctcagtcaaa gtggggaact  7020
ttggtggcca aacatacatt gctaaggcta ttcctatatc agctggacac atataaaatg  7080
ctgctaatgc ttcattacaa acttatatcc tttaattcca gatgggggca aagtatgtcc  7140
aggggtgagg aacaattgaa acatttgggc tggagtagat tttgaaagtc agctctgtgt  7200
gtgtgtgtgt gtgtgtgtgt gtgagagcgt gtgtttcttt taacgttttc agcctacagc  7260
atacagggtt catggtggca agaagataac aagatttaaa ttatggccag tgactagtgc  7320
tgcaagaaga acaactacct gcatttaatg ggaaagcaaa atctcaggct ttgagggaag  7380
ttaacatagg cttgattctg ggtggaagct gggtgtgtag ttatctggag gccaggctgg  7440
agctctcagc tcactatggg ttcatcttta ttgtctcctt tcatctcaac agctgcacgc  7500
tgccgtcctc gatgttgtgg cggatcttga agttcacctt gatgccgttc ttctgcttgt  7560
cggccatgat atagacgttg tggctgttgt agttgtactc cagcttgtgc cccaggatgt  7620
tgccgtcctc cttgaagtcg atgcccttca gctcgatgcg gttcaccagg gtgtcgccct  7680
cgaacttcac ctcggcgcgg gtcttgtagt tgccgtcgtc cttgaagaag atggtgcgct  7740
cctggacgta gccttcgggc atggcggact tgaagaagtc gtgctgcttc atgtggtcgg  7800
ggtagcggct gaagcactgc acgccgtagg tcagggtggt cacgagggtg ggccagggca  7860
cgggcagctt gccggtggtg cagatgaact tcagggtcag cttgccgtag gtggcatcgc  7920
cctcgccctc gccggacacg ctgaacttgt ggccgtttac gtcgccgtcc agctcgacca  7980
ggatgggcac caccccggtg aacagctcct cgcccttgct caccatggtg gcgaattcga  8040
agcttgagca cgagatctga gtccggtagg cctagcggat ctgacggttc actaaaccag  8100
ctctgcttat atagacctcc caccgtacac gcctaccgcc catttgcgtc aatggggcgg  8160
agttgttacg acattttgga aagtcccgtt gattttggtg ccaaaacaaa ctcccattga  8220
cgtcaatggg gtggagactt ggaaatcccc gtgagtcaaa ccgctatcca cgcccattga  8280
tgtactgcca aaaccgcatc accatggtaa tagcgatgac taatacgtag atgtactgcc  8340
aagtaggaaa gtcccataag gtcatgtact gggcataatg ccaggcgggc catttaccgt  8400
cattgacgtc aatagggggc gtacttggca tatgatacac ttgatgtact gccaagtggg  8460
cagtttaccg taaatactcc acccattgac gtcaatggaa agtccctatt ggcgttacta  8520
tgggaacata cgtcattatt gacgtcaatg ggcgggggtc gttgggcggt cagccaggcg  8580
ggccatttac cgtaagttat gtaacgggcc tgctgccggc tctgcggcct cttccgcgtc  8640
ttcgccttcg ccctcagacg agtcggatct ccctttgggc cgcctccccg cctgtctagc  8700
ttgactgact gagatacagc gtaccttcag ctcacagaca tgataagata cattgatgag  8760
tttggacaaa ccacaactag aatgcagtga aaaaaatgct ttatttgtga aatttgtgat  8820
gctattgctt tatttgtaac cattataagc tgcaataaac aagttaacaa caacaattgc  8880
attcatttta tgtttcaggt tcagggggag gtgtgggagg ttttttaaag caagtaaaac  8940
ctctacaaat gtggtattgg cccatctcta tcggtatcgt agcataaccc cttggggcct  9000
ctaaacgggt cttgaggggt tttttgtgcc cctcgggccg gattgctatc taccggcatt  9060
ggcgcagaaa aaaatgcctg atgcgacgct gcgcgtctta tactcccaca tatgccagat  9120
```

-continued

```
tcagcaacgg atacggcttc cccaacttgc ccacttccat acgtgtcctc cttaccagaa  9180
atttatcctt aaggtcgtca gctatcctgc aggcgatctc tcgatttcga tcaagacatt  9240
cctttaatgg tcttttctgg acaccactag gggtcagaag tagttcatca aactttcttc  9300
cctccctaat ctcattggtt accttgggct atcgaaactt aattaagcga tctgcatctc  9360
aattagtcag caaccatagt cccgccccta actccgccca tcccgcccct aactccgccc  9420
agttccgccc attctccgcc ccatcgctga ctaatttttt ttatttatgc agaggccgag  9480
gccgcctcgg cctctgagct attccagaag tagtgaggag gcttttttgg aggcctaggc  9540
ttttgcaaag gaggtagcca acatgattga acaagatgga ttgcacgcag gttctcccgc  9600
cgcttgggtg gagaggctat tcggctatga ctgggcacaa cagacaatcg gctgctctga  9660
tgccgccgtg ttccggctgt cagcgcaggg gcgcccggtt ctttttgtca agaccgacct  9720
gtccggtgcc ctgaatgaac tccaggacga ggcagcgcgg ctatcgtggc tggccacgac  9780
gggcgttcct tgcgcagctg tgctcgacgt tgtcactgaa gcgggaaggg actggctgct  9840
attgggcgaa gtgccggggc aggatctcct gtcatctcac cttgctcctg ccgagaaagt  9900
atccatcatg gctgatgcaa tgcggcggct gcatacgctt gatccggcta cctgcccatt  9960
cgaccaccaa gcgaaacatc gcatcgagcg agcacgtact cggatggaag ccggtcttgt  10020
cgatcaggat gatctggacg aagagcatca ggggctcgcg ccagccgaac tgttcgccag  10080
gctcaaggcg cggatgcccg acggcgagga tctcgtcgtg acccacggcg atgcctgctt  10140
gccgaatatc atggtggaaa atggccgctt ttctggattc atcgactgtg gccggctggg  10200
tgtggcggac cgctatcagg acatagcgtt ggctacccgt gatattgctg aagagcttgg  10260
cggcgaatgg gctgaccgct tcctcgtgct ttacggtatc gccgctcccg attcgcagcg  10320
catcgccttc tatcgccttc ttgacgagtt cttctagtat gtaagccctg tgccttctag  10380
ttgccagcca tctgttgttt gcccctcccc cgtgccttcc ttgaccctgg aaggtgccac  10440
tcccactgtc ctttcctaat aaaatgagga aattgcatcg cattgtctga gtaggtgtca  10500
ttctattctg gggggtgggg tggggcagga cagcaagggg gaggattggg aagacaatag  10560
caggcatgct ggggatgcgg tgggctctat ggttaattaa ccagtcaagt cagctacttg  10620
gcgagatcga cttgtctggg tttcgactac gctcagaatt gcgtcagtca agttcgatct  10680
ggtccttgct attgcacccg ttctccgatt acgagtttca tttaaatcat gtgagcaaaa  10740
ggccagcaaa aggccaggaa ccgtaaaaag gccgcgttgc tggcgttttt ccataggctc  10800
cgcccccctg acgagcatca caaaaatcga cgctcaagtc agaggtggcg aaacccgaca  10860
ggactataaa gataccaggc gtttccccct ggaagctccc tcgtgcgctc tcctgttccg  10920
accctgccgc ttaccggata cctgtccgcc tttctccctt cgggaagcgt ggcgctttct  10980
catagctcac gctgtaggta tctcagttcg gtgtaggtcg ttcgctccaa gctgggctgt  11040
gtgcacgaac cccccgttca gcccgaccgc tgcgccttat ccggtaacta tcgtcttgag  11100
tccaacccgg taagacacga cttatcgcca ctggcagcag ccactggtaa caggattagc  11160
agagcgaggt atgtaggcgg tgctacagag ttcttgaagt ggtggcctaa ctacggctac  11220
actagaagaa cagtatttgg tatctgcgct ctgctgaagc cagttacctt cggaaaaaga  11280
gttggtagct cttgatccgg caaacaaacc accgctggta gcggtggttt ttttgtttgc  11340
aagcagcaga ttacgcgcag aaaaaaagga tctcaagaag atcctttgat cttttctacg  11400
gggtctgacg ctcagtggaa cgaaaactca cgttaaggga ttttggtcat gagattatca  11460
aaaaggatct tcacctagat ccttttaaat taaaaatgaa gttttaaatc aatctaaagt  11520
atatatgagt aaacttggtc tgacagttac caatgcttaa tcagtgaggc acctatctca  11580
gcgatctgtc tatttcgttc atccatagtt gcatttaaat ttccgaactc tccaaggccc  11640
tcgtcggaaa atcttcaaac ctttcgtccg atccatcttg caggctacct ctcgaacgaa  11700
ctatcgcaag tctcttggcc ggccttgcgc cttggctatt gcttggcagc gcctatcgcc  11760
aggtattact ccaatcccga atatccgaga tcgggatcac ccgagagaag ttcaacctac  11820
atcctcaatc ccgatctatc cgagatccga ggaatatcga aatcggggcg cgcctggtgt  11880
accgagaacg atcctctcag tgcgagtctc gacgatccat atcgttgctt ggcagtcagc  11940
cagtcggaat ccagcttggg acccaggaag tccaatcgtc agatattgta ctcaagcctg  12000
gtcacggcag cgtaccgatc tgtttaaacc tagatattga tagtctgatc ggtcaacgta  12060
taatcgagtc ctagcttttg caaacatcta tcaagagaca ggatcagcag gaggctttcg  12120
catgagtatt caacatttcc gtgtcgccct tattcccttt tttgcggcat tttgccttcc  12180
tgtttttgct cacccagaaa cgctggtgaa agtaaaagat gctgaagatc agttgggtgc  12240
gcgagtgggt tacatcgaac tggatctcaa cagcggtaag atccttgaga gttttcgccc  12300
cgaagaacgc tttccaatga tgagcacttt taaagttctg ctatgtggcg cggtattatc  12360
ccgtattgac gccgggcaag agcaactcgg tcgccgcata cactattctc agaatgactt  12420
ggttgagtat tcaccagtca cagaaaagca tcttacggat ggcatgacag taagagaatt  12480
atgcagtgct gccataacca tgagtgataa cactgcggcc aacttacttc tgacaacgat  12540
tggaggaccg aaggagctaa ccgctttttt gcacaacatg ggggatcatg taactcgcct  12600
tgatcgttgg gaaccggagc tgaatgaagc cataccaaac gacgagcgtg acaccacgat  12660
gcctgtagca atggcaacaa ccttgcgtaa actattaact ggcgaactac ttactctagc  12720
ttcccggcaa cagttgatag actggatgga ggcggataaa gttgcaggac cacttctgcg  12780
ctcggccctt ccggctggct ggtttattgc tgataaatct ggagccggtg agcgtgggtc  12840
tcgcggtatc attgcagcac tggggccaga tggtaagccc tcccgtatcg tagttatcta  12900
cacgacgggg agtcaggcaa ctatggatga acgaaataga cagatcgctg agataggtgc  12960
ctcactgatt aagcattggt aaccgattct aggtgcattg gcgcagaaaa aaatgcctga  13020
tgcgacgctg cgcgtcttat actcccacat atgccagatt cagcaacgga tacggcttcc  13080
ccaacttgcc cacttccata cgtgtcctcc ttaccagaaa tttatcctta agatcgttta  13140
aactcgactc tggctctatc gaatctccgt cgtttcgagc ttacgcgaac agccgtggcg  13200
ctcatttgct cgtcgggcat cgaatctcgt cagctatcgt cagcttacct ttttggcagc  13260
gatcgcggct cccgacatct tggaccatta gctccacagg tatcttcttc cctctagtgg  13320
tcataacagc agcttcagct acctctcaat tcaaaaaacc cctcaagacc cgtttagagg  13380
ccccaagggg ttatgctatc aatcgttgcg ttacacacac aaaaaaccaa cacacatcca  13440
tcttcgatgg atagcgattt tattatctaa ctgctgatcg agtgtagcca gatctagtaa  13500
tcaattacgg ggtcattagt tcatagccca tatatggagt tccgcgttac ataacttacg  13560
gtaaatggcc cgcctggctg accgcccaac gacccccgcc cattgacgtc aataatgacg  13620
tatgttccca tagtaacgcc aatagggact ttccattgac gtcaatgggt ggagtattta  13680
cggtaaactg cccacttggc agtacatcaa gtgtatcata tgccaagtac gccccctatt  13740
gacgtcaatg acggtaaatg gcccgcctgg cattatgccc agtacatgac cttatgggac  13800
tttcctactt ggcagtacat ctacgtatta gtcatcgcta ttaccatgct gatgcggttt  13860
```

```
tggcagtaca tcaatgggcg tggatagcgg tttgactcac ggggatttcc aagtctccac  13920
cccattgacg tcaatgggag tttgttttgg caccaaaatc aacgggactt tccaaaatgt  13980
cgtaacaact ccgccccatt gacgcaaatg ggcggtaggc gtgtacggtg ggaggtctat  14040
ataagcagag ctggtttagt gaaccgtcag atcagatctt tgtcgatcct accatccact  14100
cgacacaccc gccagcggcc gc                                           14122
```

```
SEQ ID NO: 45          moltype = DNA  length = 14124
FEATURE                Location/Qualifiers
misc_feature           1..14124
                       note = Description of Artificial Sequence: Synthetic
                        polynucleotide
source                 1..14124
                       mol_type = other DNA
                       organism = synthetic construct
SEQUENCE: 45
taatacgact cactataggg agaagtactg ccaccatggg caagaagcaa aatcgcaaga  60
cggggaattc caagacacaa tccgctagcc caccacctaa agagcgttct agctcccctg  120
ctactgagca gtcctggatg gaaaacgact tcgatgaact ccgggaagag ggatttaggc  180
gatccaacta ttcagaactc cgcgaagata tccagacaaa ggggaaggaa gtcgagaatt  240
tcgagaagaa cctcgaggag tgcatcaccc gtatcacaaa cactgagaaa tgtctcaaag  300
aactcatgga acttaagaca aaagccaggg agcttcgaga ggagtgtcgg agtctgagat  360
ccaggtgtga ccagctcgag gagcgcgtga gcgcgatgga agacgagatg aacgagatga  420
aaagagaggg caaattcagg gagaagcgca ttaagaggaa cgaacagagt ctgcaggaga  480
tttgggatta cgtcaagagg cctaacctgc ggttgatcgg cgtccccgag agcgacgtag  540
aaaacgggac taaactggag aatacacttc aagacatcat tcaagaaaat tttccaaacc  600
tggctcggca agctaatgtg caaatccaag agatccaacg cacaccccag cggtatagct  660
ctcggcgtgc cacccctagg catattatcg tgcgctttac taaggtggag atgaaagaga  720
agatgctgcg agccgctcgg gaaaagggaa gggtgacttt gaagggcaaa cctattcggc  780
tgacggttga ccttagcgcc gagacactcc aggcacgccg ggaatggggc cccatcttta  840
atatcctgaa ggagaagaac ttccagccac gaatctctta ccctgcaaag ttgagtttta  900
tctccgaggg tgagattaag tatttcatcg ataaacagat gctgcgagac ttcgtgacaa  960
ctcgcccagc tctcaaggaa ctgctcaaag aggctcttaa tatggagcgc aataatagat  1020
atcaaccctt gcagaaccac gcaaagatgt gagacagtta aaacagctgt gggttgtcac  1080
ccacccacag ggtccactgg gcgctagtac actggtatct cggtaccttt gtacgcctgt  1140
tttatacccc ctccctgatt tgcaacttag aagcaacgca aaccagatca atagtaggtg  1200
tgacatacca gtcgcatctt gatcaagcac ttctgtatcc ccggaccgag tatcaataga  1260
ctgtgcacac ggttgaagga gaaaacgtcc gttacccggc taactacttc gagaagccta  1320
gtaacgccat tgaagttgca gagtgtttcg ctcagcactc cccccgtgta gatcaggtcg  1380
atgagtcacc gcattcccca cgggcgaccg tggcggtggc tgcgttggcg gcctgcctat  1440
ggggtaaccc ataggacgct ctaatacgga catggcgtga agagtctatt gagctagtta  1500
gtagtcctcc ggcccctgaa tgcggctaat cctaactgcg gagcacatac ccttaatcca  1560
aagggcagtg tgtcgtaacg ggcaactctg cagcggaacc gactactttg ggtgtccgtg  1620
tttcttttta ttcttgtatt ggctgcttat ggtgacaatt aaagaattgt taccatatag  1680
ctattggatt ggccatccag tgtcaaacag agctattgta tatctctttg ttggattcac  1740
acctctcact cttgaaacgt tacacaccct caattacatt atactgctga acacgaagcg  1800
tacatgaccg gctctaactc acatatcacc atccttacac ttaacattaa cggcctcaac  1860
tcagctatca agcgccatcg gctggccagc tggatcaaat cacaggatcc aagcgtttgt  1920
tgcatccaag agacccacct gacctgtaga gatactcacc gcctcaagat caagggatgg  1980
cgaaagattt atcaggcgaa cggtaagcag aagaaagccg gagtcgcaat tctggtctca  2040
gacaagacgg atttcaagcc caccaaaatt aagcgtgata aggaaggtca ctatattatg  2100
gtgaaaggca gcatacagca ggaagaactt accatattga acatctacgc gccaaacacc  2160
ggcgcacctc gctttatcaa acaggtcctg tccgatctgc agcgagatct ggattctcat  2220
acgttgatta tgggtgattt caatacacca ttgagcaccc tggatcgcag caccaggcaa  2280
aaggtaaata aagacacgca agagctcaat agcgcactgc atcaggcaga tctcattgat  2340
atttatcgca ctcttcatcc taagagtacc gagtacacat tcttcagcgc cccacatcat  2400
acatactcaa agatcgatca tatcgtcggc tcaaaggctc tgctgtcaaa gtgcaagcgc  2460
acagagataa ttacaaatta cctgtcagat catagcgcga tcaagctcga gctgagaatc  2520
aagaacctga cccagagccg gagtaccact tggaagctta ataacctgct gctcaacgat  2580
tattgggtcc acaatgagat gaaggcagag attaaaatgt tcttcgaaac aaatgagaat  2640
aaggatacta cctatcaaaa cctttgggat gcctttaagg ccgtctgcag aggcaagttc  2700
atcgccctca acgcctataa aagaaaacaa gagagatcta agatcgatac tctcacctct  2760
cagctgaagg agttggagaa acaggaacag acccactcca aggcgtcaag acggcaggag  2820
atcacaaaga ttcgcgccga gttgaaagag atcgaaaccc aaaagactct tcagaaaatt  2880
aacgagtctc gtagttggtt cttcgagcgg attaataaga tagacagacc tctggcacga  2940
ctgattaaga agaagcgcga aaagaaccag attgatacca tcaagaacga caagggcgac  3000
atcactactg acccgaccga gatccagacc actattcggg agtattataa gcatttgtat  3060
gctaacaagc ttgagaacct ggaagagatg gacacttttc tggataccta tactctgcca  3120
cggcttaatc aagaggaagt cgagtccctc aaccgcccaa ttacaggaag cgagattgtg  3180
gccataatta actccctgcc gacaaagaaa tctcctggtc cggacgggtt tacagctgag  3240
ttttatcaac ggtatatgga agagcttgta ccgtttctgc tcaagctctt tcagtctata  3300
gaaaaggaag gcatcttgcc caattccttc tacgaagctt ctataatact tattcccaaa  3360
ccaggacgcg ataccacaaa gaaggaaaac ttccggccca ttagtctcat gaatatcgac  3420
gctaaaatat tgaacaagat tctcgccaac agaatccaac aacatattaa gaaattgata  3480
catcacgacc aggtggggtt tatacctggc atgcagggct ggtttaacat ccggaagagt  3540
attaacgtca ttcaacacat taatagagct aaggataaga atcatatgat catctctata  3600
gacgcggaaa aggcattcga taagattcag cagccattta tgctcaagac tctgaacaaa  3660
ctcggcatcg acggaacata ttttaagatt attcgcgcaa tttacgataa gccgactgct  3720
aacattatcc ttaacggcca aaagctcgag gcctttccgc tcaagactgg aacccgccaa  3780
ggctgtcccc tctccccgct tttgtttaat attgtactcg aggtgctggc tagggctatt  3840
```

-continued

```
cgtcaagaga aagagattaa agggatacag ctcgggaagg aagaggtcaa gctttccttg  3900
ttcgccgatg atatgattgt gtacctggag aatcctattg tgtctgctca gaaccttctt  3960
aaacttattt ctaactttag caaggtcagc ggctataaga ttaacgtcca gaaatctcag  4020
gcctttctgt acacaaataa tcgacagacc gaatcccaga taatgggtga gcttccgttt  4080
gtcatagcca gcaaaaggat aaagtatctc ggaatccagc tgacacgaga cgttaaagat  4140
ttgtttaagg aaaattacaa gcctctcctg aaagagatta aggaagatac taataagtgg  4200
aagaatatcc cctgttcatg ggttggcaga atcaacatag tgaagatggc aatacttcct  4260
aaagtgatat atcgctttaa cgccatccca attaaactgc ctatgacctt ctttacggag  4320
ctcgagaaaa caacccttaa atttatatgg aatcaaaaga gagcaagaat agcgaagtcc  4380
atcttgagcc agaagaataa ggccggtggg attactttgc ctgattttaa gttgtattat  4440
aaagccacag taactaagac agcctggtat tggtatcaga atagagacat cgaccagtgg  4500
aatcggaccg aaccatcaga gataatgccc cacatctata attaccttat attcgataag  4560
ccagaaaaga ataaacagtg gggcaaagac agcctcttca acaagtggtg ttgggagaat  4620
tggctggcca tatgccggaa actcaagctc gaccccttc ttacacccta cactaaaatc  4680
aacagtaggt ggatcaagga cttgaatgtc aagccaaaga ctataaagac actggaagag  4740
aatcttggga tcacaataca agatataggc gtcggcaaag attttatgtc aaagacgccc  4800
aaggccatgg ccactaagga taagattgat aagtgggacc ttattaagct caaaagcttc  4860
tgtactgcca aggagaccac gatcagagtt aataggcagc ccactacatg ggaaaagatt  4920
ttcgccactt attcatcaga taaggggttg ataagcagaa tatataacga gctgaagcag  4980
atctacaaga agaaaacgaa taatcccatc aagaagtggg caaaagatat gaacaggcat  5040
tttagcaaag aggatatcta cgccgcgaag aagcatatga agaagtgtag ttcaagcttg  5100
gccattcgtg agatgcagat taagacgacc atgcgatacc accttacccc agtgaggatg  5160
gcaattatca agaaatctgg caataataga tgttggcggg gctgtggcga gattggcacc  5220
ctgctccatt gctggtggga ttgcaagctg gtgcagccgc tttggaaatc agtctggcgc  5280
tttctgaggg acctcgagct tgagattccc ttcgatcccg caattccctt gctcggaatc  5340
tatcctaacg aatacaagag ctgttgttac aaggatacgt gtacccggat gttcatcgcg  5400
gccttgttta cgatagctaa gacgtggaat cagcctaagt gccccacaat gatcgattgg  5460
atcaagaaaa tgtggcatat ttataccatg gagtattacg cagcaattaa gaatgacgaa  5520
tttatttcct tcgttgggac ctggatgaag ctggagacta ttattctgag caagctgtct  5580
caggagcaaa agacaaagca tagaatcttc tctctcattg gtggtaacga ctacaaagac  5640
gatgacgaca agtaaagcgc ttctagaagt tgtctcctcc tgcactgact gactgataca  5700
atcgatttct ggatccgcag gcctaatcaa cctctggatt acaaaatttg tgaaagattg  5760
actggtattc ttaactatgt tgctcctttt acgctatgtg gatacgctgc tttaatgcct  5820
ttgtatcatg ctattgcttc ccgtatggct ttcattttct cctccttgta taaatcctgg  5880
ttgctgtctc tttatgagga gttgtggccc gttgtcaggc aacgtggcgt ggtgtgcact  5940
gtgtttgctg acgcaacccc cactggttgg ggcattgcca ccacctgtca gctcctttcc  6000
gggactttcg ctttccccct ccctattgcc acggcggaac tcatcgccgc ctgccttgcc  6060
cgctgctgga caggggctcg gctgttgggc actgacaatt ccgtggtgtt gtcggggaag  6120
ctgacgtcct ttccatggct gctcgcctgt gttgccacct ggattctgcg cgggacgtcc  6180
ttctgctacg tcccttcggc cctcaatcca gcggaccttc cttcccgcga acaaacgacc  6240
caacacccgt gcgttttatt ctgtcttttt attgccgatc ccctcagaag aactcgtcaa  6300
gaaggcgata gaaggcgatg cgctgcgaat cgggagcggc gataccgtaa agcacgagga  6360
agcggtcagc ccattcgccg ccaagctctt cagcaatatc acgggtagcc aacgctatgt  6420
cctgatagcg gtcggccgct ttacttgtac agctcgtcca tgccgagagt gatcccggcg  6480
gcggtcacga actccagcag gaccatgtga tcgcgcttct cgttggggtc tttgctcagg  6540
gcggactggg tgctcaggta gtggttgtcg ggcagcagca cggggccgtc gccgatgggg  6600
gtgttctgct ggtagtggtc ggccaggtga gtccaggaga tgtttcagca ctgttgcctt  6660
tagtctcgag gcaacttaga caactgagta ttgatctgag cacagcaggg tgtgagctgt  6720
ttgaagatac tggggttggg ggtgaagaaa ctgcagagga ctaactgggc tgagacccag  6780
tggcaatgtt ttagggccta aggaatgcct ctgaaaatct agatggacaa ctttgacttt  6840
gagaaaagag aggtggaaat gaggaaaatg actttttcttt attagatttc ggtagaaaga  6900
actttcatct ttcccctatt tttgttattc gttttaaaac atctatctgg aggcaggaca  6960
agtatggtca ttaaaaagat gcaggcagaa ggcatatatt ggctcagtca aagtggggaa  7020
ctttggtggc caaacataca ttgctaaggc tattcctata tcagctggac acatataaaa  7080
tgctgctaat gcttcattac aaacttatat cctttaattc cagatggggg caaagtatgt  7140
ccaggggtga ggaacaattg aaacatttgg gctggagtag attttgaaag tcagctctgt  7200
gtgtgtgtgt gtgtgtgtgt gtgtgagagc gtgtgtttct tttaacgttt tcagcctaca  7260
gcatacaggg ttcatggtgg caagaagata acaagattta aattatggcc agtgactagt  7320
gctgcaagaa gaacaactac ctgcatttaa tgggaaagca aaatctcagg ctttgaggga  7380
agttaacata ggcttgattc tgggtggaag ctgggtgtgt agttatctgg aggccaggct  7440
ggagctctca gctcactatg ggttcatctt tattgtctcc tttcatctca acagctgcac  7500
gctgccgtcc tcgatgttgt ggcggatctt gaagttcacc ttgatgccgt tcttctgctt  7560
gtcggccatg atatagacgt tgtggctgtt gtagttgtac tccagcttgt gccccaggat  7620
gttgccgtcc tccttgaagt cgatgccctt cagctcgatg cggttcacca gggtgtcgcc  7680
ctcgaacttc acctcggcgc gggtcttgta gttgccgtcg tccttgaaga agatggtgcg  7740
ctcctggacg tagccttcgg gcatggcgga cttgaagaag tcgtgctgct tcatgtggtc  7800
ggggtagcgg ctgaagcact gcacgccgta ggtcagggtg gtcacgaggg tgggccaggg  7860
cacgggcagc ttgccggtgg tgcagatgaa cttcagggtc agcttgccgt aggtggcatc  7920
gccctcgccc tcgccggaca cgctgaactt gtggccgttt acgtcgccgt ccagctcgac  7980
caggatgggc accaccccgg tgaacagctc ctcgcccttg ctcaccatgg tggcgaattc  8040
gaagcttgag cacgagatct gagtccggta ggcctagcgg atctgacggt tcactaaacc  8100
agctctgctt atatagacct cccaccgtac acgcctaccg cccatttgcg tcaatggggc  8160
ggagttgtta cgacattttg gaaagtcccg ttgattttgg tgccaaaaca aactcccatt  8220
gacgtcaatg gggtggagac ttggaaatcc ccgtgagtca aaccgctatc cacgcccatt  8280
gatgtactgc caaaaccgca tcaccatggt aatagcgatg actaatacgt agatgtactg  8340
ccaagtagga aagtcccata aggtcatgta ctgggcataa tgccaggcgg gccatttacc  8400
gtcattgacg tcaatagggg gcgtacttgg catatgatac acttgatgta ctgccaagtg  8460
ggcagtttac cgtaaatact ccacccattg acgtcaatgg aaagtcccta ttggcgttac  8520
tatgggaaca tacgtcatta ttgacgtcaa tgggcggggg tcgttgggcg gtcagccagg  8580
```

-continued

```
cgggccattt accgtaagtt atgtaacggg cctgctgccg gctctgcggc ctcttccgcg  8640
tcttcgcctt cgccctcaga cgagtcggat ctccctttgg gccgcctccc cgcctgtcta  8700
gcttgactga ctgagataca gcgtaccttc agctcacaga catgataaga tacattgatg  8760
agtttggaca aaccacaact agaatgcagt gaaaaaaatg ctttatttgt gaaatttgtg  8820
atgctattgc tttatttgta accattataa gctgcaataa acaagttaac aacaacaatt  8880
gcattcattt tatgtttcag gttcaggggg aggtgtggga ggttttttaa agcaagtaaa  8940
acctctacaa atgtggtatt ggcccatctc tatcggtatc gtagcataac cccttggggc  9000
ctctaaacgg gtcttgaggg gtttttttgtg cccctcgggc cggattgcta tctaccggca  9060
ttggcgcaga aaaaaatgcc tgatgcgacg ctgcgcgtct tatactccca catatgccag  9120
attcagcaac ggatacggct tccccaactt gcccacttcc atacgtgtcc tccttaccag  9180
aaatttatcc ttaaggtcgt cagctatcct gcaggcgatc tctcgatttc gatcaagaca  9240
ttcctttaat ggtcttttct ggacaccact aggggtcaga agtagttcat caaactttct  9300
tccctcccta atctcattgg ttaccttggg ctatcgaaac ttaattaagc gatctgcatc  9360
tcaattagtc agcaaccata gtcccgcccc taactccgcc catcccgccc ctaactccgc  9420
ccagttccgc ccattctccg ccccatcgct gactaatttt ttttatttat gcagaggccg  9480
aggccgcctc ggcctctgag ctattccaga agtagtgagg aggctttttt ggaggcctag  9540
gcttttgcaa aggaggtagc caacatgatt gaacaagatg gattgcacgc aggttctccc  9600
gccgcttggg tggagaggct attcggctat gactgggcac aacagacaat cggctgctct  9660
gatgccgccg tgttccggct gtcagcgcag gggcgcccgg ttctttttgt caagaccgac  9720
ctgtccggtg ccctgaatga actccaggac gaggcagcgc ggctatcgtg gctggccacg  9780
acgggcgttc cttgcgcagc tgtgctcgac gttgtcactg aagcgggaag ggactggctg  9840
ctattgggcg aagtgccggg gcaggatctc ctgtcatctc accttgctcc tgccgagaaa  9900
gtatccatca tggctgatgc aatgcggcgg ctgcatacgc ttgatccggc tacctgccca  9960
ttcgaccacc aagcgaaaca tcgcatcgag cgagcacgta ctcggatgga agccggtctt  10020
gtcgatcagg atgatctgga cgaagagcat caggggctcg cgccagccga actgttcgcc  10080
aggctcaagg cgcggatgcc cgacggcgag gatctcgtcg tgacccacgg cgatgcctgc  10140
ttgccgaata tcatggtgga aaatggccgc ttttctggat tcatcgactg tggccggctg  10200
ggtgtggcgg accgctatca ggacatagcg ttggctaccc gtgatattgc tgaagagctt  10260
ggcggcgaat gggctgaccg cttcctcgtg ctttacggta tcgccgctcc cgattcgcag  10320
cgcatcgcct tctatcgcct tcttgacgag ttcttctagt atgtaagccc tgtgccttct  10380
agttgccagc catctgttgt ttgcccctcc cccgtgcctt ccttgaccct ggaaggtgcc  10440
actcccactg tcctttccta ataaaatgag gaaattgcat cgcattgtct gagtaggtgt  10500
cattctattc tggggggtgg ggtggggcag gacagcaagg gggaggattg ggaagacaat  10560
agcaggcatg ctggggatgc ggtgggctct atggttaatt aaccagtcaa gtcagctact  10620
tggcgagatc gacttgtctg ggtttcgact acgctcagaa ttgcgtcagt caagttcgat  10680
ctggtccttg ctattgcacc cgttctccga ttacgagttt catttaaatc atgtgagcaa  10740
aaggccagca aaaggccagg aaccgtaaaa aggccgcgtt gctggcgttt ttccataggc  10800
tccgcccccc tgacgagcat cacaaaaatc gacgctcaag tcagaggtgg cgaaacccga  10860
caggactata aagataccag gcgtttcccc ctggaagctc cctcgtgcgc tctcctgttc  10920
cgaccctgcc gcttaccgga tacctgtccg cctttctccc ttcgggaagc gtggcgcttt  10980
ctcatagctc acgctgtagg tatctcagtt cggtgtaggt cgttcgctcc aagctgggct  11040
gtgtgcacga accccccgtt cagcccgacc gctgcgcctt atccggtaac tatcgtcttg  11100
agtccaaccc ggtaagacac gacttatcgc cactggcagc agccactggt aacaggatta  11160
gcagagcgag gtatgtaggc ggtgctacag agttcttgaa gtggtggcct aactacggct  11220
acactagaag aacagtattt ggtatctgcg ctctgctgaa gccagttacc ttcggaaaaa  11280
gagttggtag ctcttgatcc ggcaaacaaa ccaccgctgg tagcggtggt ttttttgttt  11340
gcaagcagca gattacgcgc agaaaaaaag gatctcaaga agatcctttg atcttttcta  11400
cggggtctga cgctcagtgg aacgaaaact cacgttaagg gattttggtc atgagattat  11460
caaaaaggat cttcacctag atccttttaa attaaaaatg aagttttaaa tcaatctaaa  11520
gtatatatga gtaaacttgg tctgacagtt accaatgctt aatcagtgag gcacctatct  11580
cagcgatctg tctatttcgt tcatccatag ttgcatttaa atttccgaac tctccaaggc  11640
cctcgtcgga aaatcttcaa acctttcgtc cgatccatct tgcaggctac ctctcgaacg  11700
aactatcgca agtctcttgg ccggccttgc gccttggcta ttgcttggca gcgcctatcg  11760
ccaggtatta ctccaatccc gaatatccga gatcgggatc acccgagaga agttcaacct  11820
acatcctcaa tcccgatcta tccgagatcc gaggaatatc gaaatcgggg cgcgcctggt  11880
gtaccgagaa cgatcctctc agtgcgagtc tcgacgatcc atatcgttgc ttggcagtca  11940
gccagtcgga atccagcttg ggacccagga agtccaatcg tcagatattg tactcaagcc  12000
tggtcacggc agcgtaccga tctgtttaaa cctagatatt gatagtctga tcggtcaacg  12060
tataatcgag tcctagcttt tgcaaacatc tatcaagaga caggatcagc aggaggcttt  12120
cgcatgagta ttcaacattt ccgtgtcgcc cttattccct tttttgcggc attttgcctt  12180
cctgtttttg ctcacccaga aacgctggtg aaagtaaaag atgctgaaga tcagttgggt  12240
gcgcgagtgg gttacatcga actggatctc aacagcggta agatccttga gagttttcgc  12300
cccgaagaac gttttccaat gatgagcact tttaaagttc tgctatgtgg cgcggtatta  12360
tcccgtattg acgccgggca agagcaactc ggtcgccgca tacactattc tcagaatgac  12420
ttggttgagt attcaccagt cacagaaaag catcttacgg atggcatgac agtaagagaa  12480
ttatgcagtg ctgccataac catgagtgat aacactgcgg ccaacttact tctgacaacg  12540
attggaggac cgaaggagct aaccgctttt ttgcacaaca tgggggatca tgtaactcgc  12600
cttgatcgtt gggaaccgga gctgaatgaa gccataccaa acgacgagcg tgacaccacg  12660
atgcctgtag caatggcaac aaccttgcgt aaactattaa ctggcgaact acttactcta  12720
gcttcccggc aacagttgat agactggatg gaggcggata aagttgcagg accacttctg  12780
cgctcggccc ttccggctgg ctggtttatt gctgataaat ctggagccgg tgagcgtggg  12840
tctcgcggta tcattgcagc actggggcca gatggtaagc cctcccgtat cgtagttatc  12900
tacacgacgg ggagtcaggc aactatggat gaacgaaata gacagatcgc tgagataggt  12960
gcctcactga ttaagcattg gtaaccgatt ctaggtgcat tggcgcagaa aaaaatgcct  13020
gatgcgacgc tgcgcgtctt atactcccac atatgccaga ttcagcaacg gatacggctt  13080
ccccaacttg cccacttcca tacgtgtcct ccttaccaga aatttatcct taagatcgtt  13140
taaactcgac tctggctcta tcgaatctcc gtcgtttcga gcttacgcga acagccgtgg  13200
cgctcatttg ctcgtcgggc atcgaatctc gtcagctatc gtcagcttac ctttttggca  13260
gcgatcgcgg ctcccgacat cttggaccat tagctccaca ggtatcttct tccctctagt  13320
```

```
ggtcataaca gcagcttcag ctacctctca attcaaaaaa cccctcaaga cccgtttaga  13380
ggccccaagg ggttatgcta tcaatcgttg cgttacacac acaaaaaacc aacacacatc  13440
catcttcgat ggatagcgat tttattatct aactgctgat cgagtgtagc cagatctagt  13500
aatcaattac ggggtcatta gttcatagcc catatatgga gttccgcgtt acataactta  13560
cggtaaatgg cccgcctggc tgaccgccca acgacccccg cccattgacg tcaataatga  13620
cgtatgttcc catagtaacg ccaataggga ctttccattg acgtcaatgg gtggagtatt  13680
tacggtaaac tgcccacttg gcagtacatc aagtgtatca tatgccaagt acgcccccta  13740
ttgacgtcaa tgacggtaaa tggcccgcct ggcattatgc ccagtacatg accttatggg  13800
actttcctac ttggcagtac atctacgtat tagtcatcgc tattaccatg ctgatgcggt  13860
tttggcagta catcaatggg cgtggatagc ggtttgactc acggggattt ccaagtctcc  13920
accccattga cgtcaatggg agtttgtttt ggcaccaaaa tcaacgggac tttccaaaat  13980
gtcgtaacaa ctccgcccca ttgacgcaaa tgggcggtag gcgtgtacgg tgggaggtct  14040
atataagcag agctggttta gtgaaccgtc agatcagatc tttgtcgatc ctaccatcca  14100
ctcgacacac ccgccagcgg ccgc                                           14124
```

```
SEQ ID NO: 46          moltype = DNA  length = 13439
FEATURE                Location/Qualifiers
misc_feature           1..13439
                       note = Description of Artificial Sequence: Synthetic
                        polynucleotide
source                 1..13439
                       mol_type = other DNA
                       organism = synthetic construct
SEQUENCE: 46
taatacgact cactataggg agaagtactg ccaccatggg caagaagcaa aatcgcaaga  60
cggggaattc caagacacaa tccgctagcc caccacctaa agagcgttct agctcccctg  120
ctactgagca gtcctggatg gaaaacgact tcgatgaact ccgggaagag ggatttaggc  180
gatccaacta ttcagaactc cgcgaagata tccagacaaa ggggaaggaa gtcgagaatt  240
tcgagaagaa cctcgaggag tgcatcaccc gtatcacaaa cactgagaaa tgtctcaaag  300
aactcatgga acttaagaca aaagccaggg agcttcgaga ggagtgtcgg agtctgagat  360
ccaggtgtga ccagctcgag gagcgcgtga gcgcgatgga agacgagatg aacgagatga  420
aaagagaggg caaattcagg gagaagcgca ttaagaggaa cgaacagagt ctgcaggaga  480
tttgggatta cgtcaagagg cctaacctgc ggttgatcgg cgtccccgag agcgacgtag  540
aaaacgggac taaactggag aatacacttc aagacatcat tcaagaaaat tttccaaacc  600
tggctcggca agctaatgtg caaatccaag agatccaacg cacaccccag cggtatagct  660
ctcggcgtgc cacccctagg catattatcg tgcgctttac taaggtggag atgaaagaga  720
agatgctgcg agccgctcgg gaaaagggaa gggtgacttt gaagggcaaa cctattcggc  780
tgacggttga ccttagcgcc gagacactcc aggcacgccg ggaatggggc cccatcttta  840
atatcctgaa ggagaagaac ttccagccac gaatctctta ccctgcaaag ttgagtttta  900
tctccgaggg tgagattaag tatttcatcg ataaacagat gctgcgagac ttcgtgacaa  960
ctcgcccagc tctcaaggaa ctgctcaaag aggctcttaa tatggagcgc aataatagat  1020
atcaaccctt gcagaaccac gcaaagatgg gaagcggaca gtgtactaat tatgctctct  1080
tgaaattggc tggagatgtt gagagcaacc ctggacctat gaccggctct aactcacata  1140
tcaccatcct tacacttaac attaacggcc tcaactcagc tatcaagcgc catcggctgg  1200
ccagctggat caaatcacag gatccaagcg tttgttgcat ccaagagacc cacctgacct  1260
gtagagatac tcaccgcctc aagatcaagg gatggcgaaa gatttatcag gcgaacggta  1320
agcagaagaa agccggagtc gcaattctgg tctcagacaa gacggatttc aagcccacca  1380
aaattaagcg tgataaggaa ggtcactata ttatggtgaa aggcagcata cagcaggaag  1440
aacttaccat attgaacatc tacgcgccaa acaccggcgc acctcgcttt atcaaacagg  1500
tcctgtccga tctgcagcga gatctggatt ctcatacgtt gattatgggt gatttcaata  1560
caccattgag caccctggat cgcagcacca ggcaaaaggt aaataaagac acgcaagagc  1620
tcaatagcgc actgcatcag gcagatctca ttgatattta tcgcactctt catcctaaga  1680
gtaccgagta cacattcttc agcgccccac atcatacata ctcaaagatc gatcatatcg  1740
tcggctcaaa ggctctgctg tcaaagtgca agcgcacaga gataattaca aattacctgt  1800
cagatcatag cgcgatcaag ctcgagctga gaatcaagaa cctgacccag agccggagta  1860
ccacttggaa gcttaataac ctgctgctca acgattattg ggtccacaat gagatgaagg  1920
cagagattaa aatgttcttc gaaacaaatg agaataagga tactacctat caaaaccttt  1980
gggatgcctt taaggccgtc tgcagaggca agttcatcgc cctcaacgcc tataaaagaa  2040
aacaagagag atctaagatc gatactctca cctctcagct gaaggagttg gagaaacagg  2100
aacagaccca ctccaaggcg tcaagacggc aggagatcac aaagattcgc gccgagttga  2160
aagagatcga aacccaaaag actcttcaga aaattaacga gtctcgtagt tggttcttcg  2220
agcggattaa taagatagac agacctctgg cacgactgat taagaagaag cgcgaaaaga  2280
accagattga taccatcaag aacgacaagg gcgacatcac tactgacccg accgagatcc  2340
agaccactat tcgggagtat tataagcatt tgtatgctaa caagcttgag aacctggaag  2400
agatggacac ttttctggat acctatactc tgccacggct taatcaagag gaagtcgagt  2460
ccctcaaccg cccaattaca ggaagcgaga ttgtggccat aattaactcc ctgccgacaa  2520
agaaatctcc tggtccggac gggtttacag ctgagtttta tcaacggtat atggaagagc  2580
ttgtaccgtt tctgctcaag ctctttcagt ctatagaaaa ggaaggcatc ttgcccaatt  2640
ccttctacga agcttctata atacttattc ccaaaccagg acgcgatacc acaaagaagg  2700
aaaacttccg gcccattagt ctcatgaata tcgacgctaa aatattgaac aagattctcg  2760
ccaacagaat ccaacaacat attaagaaat tgatacatca cgaccaggtg ggtttatac   2820
ctggcatgca gggctggttt aacatccgga agagtattaa cgtcattcaa cacattaata  2880
gagctaagga taagaatcat atgatcatct ctatagacgc ggaaaaggca ttcgataaga  2940
ttcagcagcc atttatgctc aagactctga acaaactcgg catcgacgga acatatttta  3000
agattattcg cgcaatttac gataagccga ctgctaacat tatccttaac ggccaaaagc  3060
tcgaggcctt tccgctcaag actggaaccc gccaaggctg tcccctctcc ccgcttttgt  3120
ttaatattgt actcgaggtg ctggctaggg ctattcgtca agagaaagag attaaaggga  3180
tacagctcgg gaaggaagag gtcaagcttt ccttgttcgc cgatgatatg attgtgtacc  3240
tggagaatcc tattgtgtct gctcagaacc ttcttaaact tatttctaac tttagcaagg  3300
```

-continued

```
tcagcggcta taagattaac gtccagaaat ctcaggcctt tctgtacaca aataatcgac  3360
agaccgaatc ccagataatg ggtgagcttc cgtttgtcat agccagcaaa aggataaagt  3420
atctcggaat ccagctgaca cgagacgtta aagatttgtt taaggaaaat tacaagcctc  3480
tcctgaaaga gattaaggaa gatactaata agtggaagaa tatcccctgt tcatgggttg  3540
gcagaatcaa catagtgaag atggcaatac ttcctaaagt gatatatcgc tttaacgcca  3600
tcccaattaa actgcctatg accttcttta cggagctcga gaaaacaacc cttaaattta  3660
tatggaatca aaagagagca agaatagcga agtccatctt gagccagaag aataaggccg  3720
gtgggattac tttgcctgat tttaagttgt attataaagc cacagtaact aagacagcct  3780
ggtattggta tcagaataga gacatcgacc agtggaatcg gaccgaacca tcagagataa  3840
tgccccacat ctataattac cttatattcg ataagccaga aaagaataaa cagtggggca  3900
aagacagcct cttcaacaag tggtgttggg agaattggct ggccatatgc cggaaactca  3960
agctcgaccc ctttcttaca ccctacacta aatcaacag taggtggatc aaggacttga  4020
atgtcaagcc aaagactata aagacactgg aagagaatct tgggatcaca atacaagata  4080
taggcgtcgg caaagatttt atgtcaaaga cgcccaaggc catggccact aaggataaga  4140
ttgataagtg ggaccttatt aagctcaaaa gcttctgtac tgccaaggag accacgatca  4200
gagttaatag gcagcccact acatgggaaa agattttcgc cacttattca tcagataagg  4260
ggttgataag cagaatatat aacgagctga agcagatcta caagaagaaa acgaataatc  4320
ccatcaagaa gtgggcaaaa gatatgaaca ggcattttag caaagaggat atctacgccg  4380
cgaagaagca tatgaagaag tgtagttcaa gcttggccat tcgtgagatg cagattaaga  4440
cgaccatgcg ataccacctt accccagtga ggatggcaat tatcaagaaa tctggcaata  4500
atagatgttg gcggggctgt ggcgagattg gcaccctgct ccattgctgg tgggattgca  4560
agctggtgca gccgctttgg aaatcagtct ggcgctttct gagggacctc gagcttgaga  4620
ttcccttcga tcccgcaatt cccttgctcg gaatctatcc taacgaatac aagagctgtt  4680
gttacaagga tacgtgtacc cggatgttca tcgcggcctt gtttacgata gctaagacgt  4740
ggaatcagcc taagtgcccc acaatgatcg attggatcaa gaaaatgtgg catatttata  4800
ccatggagta ttacgcagca attaagaatg acgaatttat ttccttcgtt gggacctgga  4860
tgaagctgga gactattatt ctgagcaagc tgtctcagga gcaaaagaca aagcatagaa  4920
tcttctctct cattggtggt aacgactaca aagacgatga cgacaagtaa agcgcttcta  4980
gaagttgtct cctcctgcac tgactgactg atacaatcga tttctggatc cgcaggccta  5040
atcaacctct ggattacaaa atttgtgaaa gattgactgg tattcttaac tatgttgctc  5100
cttttacgct atgtggatac gctgctttaa tgcctttgta tcatgctatt gcttcccgta  5160
tggctttcat tttctcctcc ttgtataaat cctggttgct gtctctttat gaggagttgt  5220
ggcccgttgt caggcaacgt ggcgtggtgt gcactgtgtt tgctgacgca acccccactg  5280
gttggggcat tgccaccacc tgtcagctcc tttccgggac tttcgctttc cccctcccta  5340
ttgccacggc ggaactcatc gccgcctgcc ttgcccgctg ctggacaggg gctcggctgt  5400
tgggcactga caattccgtg gtgttgtcgg ggaagctgac gtcctttcca tggctgctcg  5460
cctgtgttgc cacctggatt ctgcgcggga cgtccttctg ctacgtccct tcggccctca  5520
atccagcgga ccttccttcc cgcgaacaaa cgacccaaca cccgtgcgtt ttattctgtc  5580
tttttattgc cgatcccctc agaagaactc gtcaagaagg cgatagaagg cgatgcgctg  5640
cgaatcggga gcggcgatac cgtaaagcac gaggaagcgg tcagcccatt cgccgccaag  5700
ctcttcagca atatcacggg tagccaacgc tatgtcctga tagcggtcgg ccgctttact  5760
tgtacagctc gtccatgccg agagtgatcc cggcggcggt cacgaactcc agcaggacca  5820
tgtgatcgcg cttctcgttg gggtctttgc tcagggcgga ctgggtgctc aggtagtggt  5880
tgtcgggcag cagcacgggg ccgtcgccga tgggggtgtt ctgctggtag tggtcggcca  5940
ggtgagtcca ggagatgttt cagcactgtt gcctttagtc tcgaggcaac ttagacaact  6000
gagtattgat ctgagcacag cagggtgtga gctgtttgaa gatactgggg ttgggggtga  6060
agaaactgca gaggactaac tgggctgaga cccagtggca atgttttagg gcctaaggaa  6120
tgcctctgaa aatctagatg gacaactttg actttgagaa aagagaggtg gaaatgagga  6180
aaatgacttt tctttattag atttcggtag aaagaacttt catctttccc ctatttttgt  6240
tattcgtttt aaaacatcta tctggaggca ggacaagtat ggtcattaaa aagatgcagg  6300
cagaaggcat atattggctc agtcaaagtg gggaactttg gtggccaaac atacattgct  6360
aaggctattc ctatatcagc tggacacata taaaatgctg ctaatgcttc attacaaact  6420
tatatccttt aattccagat gggggcaaag tatgtccagg ggtgaggaac aattgaaaca  6480
tttgggctgg agtagatttt gaaagtcagc tctgtgtgtg tgtgtgtgtg tgtgtgtgtg  6540
agagcgtgtg tttcttttaa cgttttcagc ctacagcata cagggttcat ggtggcaaga  6600
agataacaag atttaaatta tggccagtga ctagtgctgc aagaagaaca actacctgca  6660
tttaatggga aagcaaaatc tcaggctttg agggaagtta acataggctt gattctgggt  6720
ggaagctggg tgtgtagtta tctggaggcc aggctggagc tctcagctca ctatgggttc  6780
atctttattg tctcctttca tctcaacagc tgcacgctgc cgtcctcgat gttgtggcgg  6840
atcttgaagt tcaccttgat gccgttcttc tgcttgtcgg ccatgatata gacgttgtgg  6900
ctgttgtagt tgtactccag cttgtgcccc aggatgttgc cgtcctcctt gaagtcgatg  6960
cccttcagct cgatgcggtt caccagggtg tcgccctcga acttcacctc ggcgcgggtc  7020
ttgtagttgc cgtcgtcctt gaagaagatg gtgcgctcct ggacgtagcc ttcgggcatg  7080
gcggacttga agaagtcgtg ctgcttcatg tggtcggggt agcggctgaa gcactgcacg  7140
ccgtaggtca gggtggtcac gagggtgggc cagggcacgg gcagcttgcc ggtggtgcag  7200
atgaacttca gggtcagctt gccgtaggtg gcatcgccct cgccctcgcc ggacacgctg  7260
aacttgtggc cgtttacgtc gccgtccagc tcgaccagga tgggcaccac cccggtgaac  7320
agctcctcgc ccttgctcac catggtggcg aattcgaagc ttgagcacga gatctgagtc  7380
cggtaggcct agcggatctg acggttcact aaaccagctc tgcttatata gacctcccac  7440
cgtacacgcc taccgcccat ttgcgtcaat ggggcggagt tgttacgaca ttttggaaag  7500
tcccgttgat tttggtgcca aaacaaactc ccattgacgt caatggggtg gagacttgga  7560
aatccccgtg agtcaaaccg ctatccacgc ccattgatgt actgccaaaa ccgcatcacc  7620
atggtaatag cgatgactaa tacgtagatg tactgccaag taggaaagtc ccataaggtc  7680
atgtactggg cataatgcca ggcgggccat ttaccgtcat tgacgtcaat agggggcgta  7740
cttggcatat gatacacttg atgtactgcc aagtgggcag tttaccgtaa atactccacc  7800
cattgacgtc aatggaaagt ccctattggc gttactatgg gaacatacgt cattattgac  7860
gtcaatgggc gggggtcgtt gggcggtcag ccaggcgggc catttaccgt aagttatgta  7920
acgggcctgc tgccggctct gcggcctctt ccgcgtcttc gccttcgccc tcagacgagt  7980
cggatctccc tttgggccgc ctccccgcct gtctagcttg actgactgag atacagcgta  8040
```

-continued

```
ccttcagctc acagacatga taagatacat tgatgagttt ggacaaacca caactagaat  8100
gcagtgaaaa aaatgcttta tttgtgaaat ttgtgatgct attgctttat ttgtaaccat  8160
tataagctgc aataaacaag ttaacaacaa caattgcatt cattttatgt ttcaggttca  8220
gggggaggtg tgggaggttt tttaaagcaa gtaaaacctc tacaaatgtg gtattggccc  8280
atctctatcg gtatcgtagc ataacccctt ggggcctcta aacgggtctt gaggggtttt  8340
ttgtgcccct cgggccggat tgctatctac cggcattggc gcagaaaaaa atgcctgatg  8400
cgacgctgcg cgtcttatac tcccacatat gccagattca gcaacggata cggcttcccc  8460
aacttgccca cttccatacg tgtcctcctt accagaaatt tatccttaag gtcgtcagct  8520
atcctgcagg cgatctctcg atttcgatca agacattcct ttaatggtct tttctggaca  8580
ccactagggg tcagaagtag ttcatcaaac tttcttccct ccctaatctc attggttacc  8640
ttgggctatc gaaacttaat taagcgatct gcatctcaat tagtcagcaa ccatagtccc  8700
gcccctaact ccgcccatcc cgcccctaac tccgcccagt tccgcccatt ctccgcccca  8760
tcgctgacta attttttta tttatgcaga ggccgaggcc gcctcggcct ctgagctatt  8820
ccagaagtag tgaggaggct tttttggagg cctaggcttt tgcaaaggag gtagccaaca  8880
tgattgaaca agatggattg cacgcaggtt ctcccgccgc ttgggtggag aggctattcg  8940
gctatgactg ggcacaacag acaatcggct gctctgatgc cgccgtgttc cggctgtcag  9000
cgcaggggcg cccggttctt tttgtcaaga ccgacctgtc cggtgccctg aatgaactcc  9060
aggacgaggc agcgcggcta tcgtggctgg ccacgacggg cgttccttgc gcagctgtgc  9120
tcgacgttgt cactgaagcg ggaagggact ggctgctatt gggcgaagtg ccggggcagg  9180
atctcctgtc atctcacctt gctcctgccg agaaagtatc catcatggct gatgcaatgc  9240
ggcggctgca tacgcttgat ccggctacct gcccattcga ccaccaagcg aaacatcgca  9300
tcgagcgagc acgtactcgg atggaagccg gtcttgtcga tcaggatgat ctggacgaag  9360
agcatcaggg gctcgcgcca gccgaactgt tcgccaggct caaggcgcgg atgcccgacg  9420
gcgaggatct cgtcgtgacc cacggcgatg cctgcttgcc gaatatcatg gtggaaaatg  9480
gccgcttttc tggattcatc gactgtggcc ggctgggtgt ggcggaccgc tatcaggaca  9540
tagcgttggc tacccgtgat attgctgaag agcttggcgg cgaatgggct gaccgcttcc  9600
tcgtgcttta cggtatcgcc gctcccgatt cgcagcgcat cgccttctat cgccttcttg  9660
acgagttctt ctagtatgta agccctgtgc cttctagttg ccagccatct gttgtttgcc  9720
cctcccccgt gccttccttg accctggaag gtgccactcc cactgtcctt tcctaataaa  9780
atgaggaaat tgcatcgcat tgtctgagta ggtgtcattc tattctgggg ggtggggtgg  9840
ggcaggacag caagggggag gattgggaag acaatagcag gcatgctggg gatgcggtgg  9900
gctctatggt taattaacca gtcaagtcag ctacttggcg agatcgactt gtctgggttt  9960
cgactacgct cagaattgcg tcagtcaagt tcgatctggt ccttgctatt gcacccgttc  10020
tccgattacg agtttcattt aaatcatgtg agcaaaaggc cagcaaaagg ccaggaaccg  10080
taaaaaggcc gcgttgctgg cgtttttcca taggctccgc ccccctgacg agcatcacaa  10140
aaatcgacgc tcaagtcaga ggtggcgaaa cccgacagga ctataaagat accaggcgtt  10200
tccccctgga agctccctcg tgcgctctcc tgttccgacc ctgccgctta ccggatacct  10260
gtccgccttt ctcccttcgg gaagcgtggc gctttctcat agctcacgct gtaggtatct  10320
cagttcggtg taggtcgttc gctccaagct gggctgtgtg cacgaacccc ccgttcagcc  10380
cgaccgctgc gccttatccg gtaactatcg tcttgagtcc aacccggtaa gacacgactt  10440
atcgccactg gcagcagcca ctggtaacag gattagcaga gcgaggtatg taggcggtgc  10500
tacagagttc ttgaagtggt ggcctaacta cggctacact agaagaacag tatttggtat  10560
ctgcgctctg ctgaagccag ttaccttcgg aaaaagagtt ggtagctctt gatccggcaa  10620
acaaaccacc gctggtagcg gtggtttttt tgtttgcaag cagcagatta cgcgcagaaa  10680
aaaaggatct caagaagatc ctttgatctt ttctacgggg tctgacgctc agtggaacga  10740
aaactcacgt taagggattt tggtcatgag attatcaaaa aggatcttca cctagatcct  10800
tttaaattaa aaatgaagtt ttaaatcaat ctaaagtata tatgagtaaa cttggtctga  10860
cagttaccaa tgcttaatca gtgaggcacc tatctcagcg atctgtctat ttcgttcatc  10920
catagttgca tttaaatttc cgaactctcc aaggccctcg tcggaaaatc ttcaaacctt  10980
tcgtccgatc catcttgcag gctacctctc gaacgaacta tcgcaagtct cttggccggc  11040
cttgcgcctt ggctattgct tggcagcgcc tatcgccagg tattactcca atcccgaata  11100
tccgagatcg ggatcacccg agagaagttc aacctacatc ctcaatcccg atctatccga  11160
gatccgagga atatcgaaat cggggcgcgc ctggtgtacc gagaacgatc ctctcagtgc  11220
gagtctcgac gatccatatc gttgcttggc agtcagccag tcggaatcca gcttgggacc  11280
caggaagtcc aatcgtcaga tattgtactc aagcctggtc acggcagcgt accgatctgt  11340
ttaaacctag atattgatag tctgatcggt caacgtataa tcgagtccta gcttttgcaa  11400
acatctatca agagacagga tcagcaggag gctttcgcat gagtattcaa catttccgtg  11460
tcgcccttat tccctttttt gcggcatttt gccttcctgt ttttgctcac ccagaaacgc  11520
tggtgaaagt aaaagatgct gaagatcagt tgggtgcgcg agtgggttac atcgaactgg  11580
atctcaacag cggtaagatc cttgagagtt ttcgccccga agaacgtttt ccaatgatga  11640
gcacttttaa agttctgcta tgtggcgcgg tattatcccg tattgacgcc gggcaagagc  11700
aactcggtcg ccgcatacac tattctcaga atgacttggt tgagtattca ccagtcacag  11760
aaaagcatct tacggatggc atgacagtaa gagaattatg cagtgctgcc ataaccatga  11820
gtgataacac tgcggccaac ttacttctga caacgattgg aggaccgaag gagctaaccg  11880
cttttttgca caacatgggg gatcatgtaa ctcgccttga tcgttgggaa ccggagctga  11940
atgaagccat accaaacgac gagcgtgaca ccacgatgcc tgtagcaatg gcaacaacct  12000
tgcgtaaact attaactggc gaactactta ctctagcttc ccggcaacag ttgatagact  12060
ggatggaggc ggataaagtt gcaggaccac ttctgcgctc ggcccttccg gctggctggt  12120
ttattgctga taaatctgga gccggtgagc gtgggtctcg cggtatcatt gcagcactgg  12180
ggccagatgg taagccctcc cgtatcgtag ttatctacac gacggggagt caggcaacta  12240
tggatgaacg aaatagacag atcgctgaga taggtgcctc actgattaag cattggtaac  12300
cgattctagg tgcattggcg cagaaaaaaa tgcctgatgc gacgctgcgc gtcttatact  12360
cccacatatg ccagattcag caacggatac ggcttcccca acttgcccac ttccatacgt  12420
gtcctcctta ccagaaattt atccttaaga tcgtttaaac tcgactctgg ctctatcgaa  12480
tctccgtcgt ttcgagctta cgcgaacagc cgtggcgctc atttgctcgt cgggcatcga  12540
atctcgtcag ctatcgtcag cttacctttt tggcagcgat cgcggctccc gacatcttgg  12600
accattagct ccacaggtat cttcttccct ctagtggtca taacagcagc ttcagctacc  12660
tctcaattca aaaaacccct caagacccgt ttagaggccc caaggggtta tgctatcaat  12720
cgttgcgtta cacacacaaa aaaccaacac acatccatct tcgatggata gcgattttat  12780
```

```
tatctaactg ctgatcgagt gtagccagat ctagtaatca attacggggt cattagttca  12840
tagcccatat atggagttcc gcgttacata acttacggta aatggcccgc ctggctgacc  12900
gcccaacgac ccccgcccat tgacgtcaat aatgacgtat gttcccatag taacgccaat  12960
agggactttc cattgacgtc aatgggtgga gtatttacgg taaactgccc acttggcagt  13020
acatcaagtg tatcatatgc caagtacgcc ccctattgac gtcaatgacg gtaaatggcc  13080
cgcctggcat tatgcccagt acatgacctt atgggacttt cctacttggc agtacatcta  13140
cgtattagtc atcgctatta ccatgctgat gcggttttgg cagtacatca atgggcgtgg  13200
atagcggttt gactcacggg gatttccaag tctccacccc attgacgtca atgggagttt  13260
gttttggcac caaaatcaac gggactttcc aaaatgtcgt aacaactccg ccccattgac  13320
gcaaatgggc ggtaggcgtg tacggtggga ggtctatata agcagagctg gtttagtgaa  13380
ccgtcagatc agatctttgt cgatcctacc atccactcga cacacccgcc agcggccgc   13439

SEQ ID NO: 47          moltype = DNA  length = 13436
FEATURE                Location/Qualifiers
misc_feature           1..13436
                       note = Description of Artificial Sequence: Synthetic
                        polynucleotide
source                 1..13436
                       mol_type = other DNA
                       organism = synthetic construct
SEQUENCE: 47
taatacgact cactataggg agaagtactg ccaccatggg caagaagcaa aatcgcaaga  60
cggggaattc caagacacaa tccgctagcc caccacctaa agagcgttct agctcccctg  120
ctactgagca gtcctggatg gaaaacgact tcgatgaact ccgggaagag ggatttaggc  180
gatccaacta ttcagaactc cgcgaagata tccagacaaa ggggaaggaa gtcgagaatt  240
tcgagaagaa cctcgaggag tgcatcaccc gtatcacaaa cactgagaaa tgtctcaaag  300
aactcatgga acttaagaca aaagccaggg agcttcgaga ggagtgtcgg agtctgagat  360
ccaggtgtga ccagctcgag gagcgcgtga gcgcgatgga agacgagatg aacgagatga  420
aaagagaggg caaattcagg gagaagcgca ttaagaggaa cgaacagagt ctgcaggaga  480
tttgggatta cgtcaagagg cctaacctgc ggttgatcgg cgtccccgag agcgacgtag  540
aaaacgggac taaactggag aatacacttc aagacatcat tcaagaaaat tttccaaacc  600
tggctcggca agctaatgtg caaatccaag agatccaacg cacaccccag cggtatagct  660
ctcggcgtgc cacccctagg catattatcg tgcgctttac taaggtggag atgaaagaga  720
agatgctgcg agccgctcgg gaaaagggaa gggtgacttt gaagggcaaa cctattcggc  780
tgacggttga ccttagcgcc gagacactcc aggcacgccg ggaatggggc cccatcttta  840
atatcctgaa ggagaagaac ttccagccac gaatctctta ccctgcaaag ttgagtttta  900
tctccgaggg tgagattaag tatttcatcg ataaacagat gctgcgagac ttcgtgacaa  960
ctcgcccagc tctcaaggaa ctgctcaaag aggctcttaa tatggagcgc aataatagat  1020
atcaaccctt gcagaaccac gcaaagatgg gaagcggagc tactaacttc agcctgctga  1080
agcaggctgg agacgtggag gagaaccctg gacctatgac cggctctaac tcacatatca  1140
ccatccttac acttaacatt aacggcctca actcagctat caagcgccat cggctggcca  1200
gctggatcaa atcacaggat ccaagcgttt gttgcatcca agagacccac ctgacctgta  1260
gagatactca ccgcctcaag atcaagggat ggcgaaagat ttatcaggcg aacggtaagc  1320
agaagaaagc cggagtcgca attctggtct cagacaagac ggatttcaag cccaccaaaa  1380
ttaagcgtga taaggaaggt cactatatta tggtgaaagg cagcatacag caggaagaac  1440
ttaccatatt gaacatctac gcgccaaaca ccggcgcacc tcgctttatc aaacaggtcc  1500
tgtccgatct gcagcgagat ctggattctc atacgttgat tatgggtgat ttcaatacac  1560
cattgagcac cctggatcgc agcaccaggc aaaaggtaaa taaagacacg caagagctca  1620
atagcgcact gcatcaggca gatctcattg atatttatcg cactcttcat cctaagagta  1680
ccgagtacac attcttcagc gccccacatc atacatactc aaagatcgat catatcgtcg  1740
gctcaaaggc tctgctgtca aagtgcaagc gcacagagat aattacaaat tacctgtcag  1800
atcatagcgc gatcaagctc gagctgagaa tcaagaacct gacccagagc cggagtacca  1860
cttggaagct taataacctg ctgctcaacg attattgggt ccacaatgag atgaaggcag  1920
agattaaaat gttcttcgaa acaaatgaga ataaggatac tacctatcaa aacctttggg  1980
atgcctttaa ggccgtctgc agaggcaagt tcatcgccct caacgcctat aaaagaaaac  2040
aagagagatc taagatcgat actctcacct ctcagctgaa ggagttggag aaacaggaac  2100
agacccactc caaggcgtca agacggcagg agatcacaaa gattcgcgcc gagttgaaag  2160
agatcgaaac ccaaaagact cttcagaaaa ttaacgagtc tcgtagttgg ttcttcgagc  2220
ggattaataa gatagacaga cctctggcac gactgattaa gaagaagcgc gaaaagaacc  2280
agattgatac catcaagaac gacaagggcg acatcactac tgacccgacc gagatccaga  2340
ccactattcg ggagtattat aagcatttgt atgctaacaa gcttgagaac ctggaagaga  2400
tggacacttt tctggatacc tatactctgc cacggcttaa tcaagaggaa gtcgagtccc  2460
tcaaccgccc aattacagga agcgagattg tggccataat taactccctg ccgacaaaga  2520
aatctcctgg tccggacggg tttacagctg agttttatca acggtatatg gaagagcttg  2580
taccgtttct gctcaagctc tttcagtcta tagaaaagga aggcatcttg cccaattcct  2640
tctacgaagc ttctataata cttattccca aaccaggacg cgataccaca aagaaggaaa  2700
acttccggcc cattagtctc atgaatatcg acgctaaaat attgaacaag attctcgcca  2760
acagaatcca acaacatatt aagaaattga tacatcacga ccaggtgggg tttatacctg  2820
gcatgcaggg ctggtttaac atccggaaga gtattaacgt cattcaacac attaatagag  2880
ctaaggataa gaatcatatg atcatctcta tagacgcgga aaaggcattc gataagattc  2940
agcagccatt tatgctcaag actctgaaca aactcggcat cgacggaaca tattttaaga  3000
ttattcgcgc aatttacgat aagccgactg ctaacattat ccttaacggc caaaagctcg  3060
aggcctttcc gctcaagact ggaacccgcc aaggctgtcc cctctccccg cttttgttta  3120
atattgtact cgaggtgctg gctagggcta ttcgtcaaga gaaagagatt aaagggatac  3180
agctcgggaa ggaagaggtc aagctttcct tgttcgccga tgatatgatt gtgtacctgg  3240
agaatcctat tgtgtctgct cagaaccttc ttaaacttat ttctaacttt agcaaggtca  3300
gcggctataa gattaacgtc cagaaatctc aggcctttct gtacacaaat aatcgacaga  3360
ccgaatccca gataatgggt gagcttccgt ttgtcatagc cagcaaaagg ataaagtatc  3420
tcggaatcca gctgacacga gacgttaaag atttgtttaa ggaaaattac aagcctctcc  3480
```

-continued

```
tgaaagagat taaggaagat actaataagt ggaagaatat cccctgttca tgggttggca  3540
gaatcaacat agtgaagatg gcaatacttc ctaaagtgat atatcgcttt aacgccatcc  3600
caattaaact gcctatgacc ttctttacgg agctcgagaa aacaaccctt aaatttatat  3660
ggaatcaaaa gagagcaaga atagcgaagt ccatcttgag ccagaagaat aaggccggtg  3720
ggattacttt gcctgatttt aagttgtatt ataaagccac agtaactaag acagcctggt  3780
attggtatca gaatagagac atcgaccagt ggaatcggac cgaaccatca gagataatgc  3840
cccacatcta taattacctt atattcgata agccagaaaa gaataaacag tggggcaaag  3900
acagcctctt caacaagtgg tgttgggaga attggctggc catatgccgg aaactcaagc  3960
tcgacccctt tcttacaccc tacactaaaa tcaacagtag gtggatcaag gacttgaatg  4020
tcaagccaaa gactataaag acactggaag agaatcttgg gatcacaata caagatatag  4080
gcgtcggcaa agattttatg tcaaagacgc ccaaggccat ggccactaag gataagattg  4140
ataagtggga ccttattaag ctcaaaagct tctgtactgc caaggagacc acgatcagag  4200
ttaataggca gcccactaca tgggaaaaga ttttcgccac ttattcatca gataaggggt  4260
tgataagcag aatatataac gagctgaagc agatctacaa gaagaaaacg aataatccca  4320
tcaagaagtg ggcaaaagat atgaacaggc attttagcaa agaggatatc tacgccgcga  4380
agaagcatat gaagaagtgt agttcaagct tggccattcg tgagatgcag attaagacga  4440
ccatgcgata ccaccttacc ccagtgagga tggcaattat caagaaatct ggcaataata  4500
gatgttggcg gggctgtggc gagattggca ccctgctcca ttgctggtgg gattgcaagc  4560
tggtgcagcc gctttggaaa tcagtctggc gctttctgag ggacctcgag cttgagattc  4620
ccttcgatcc cgcaattccc ttgctcggaa tctatcctaa cgaatacaag agctgttgtt  4680
acaaggatac gtgtacccgg atgttcatcg cggccttgtt tacgatagct aagacgtgga  4740
atcagcctaa gtgccccaca atgatcgatt ggatcaagaa aatgtggcat atttatacca  4800
tggagtatta cgcagcaatt aagaatgacg aatttatttc cttcgttggg acctggatga  4860
agctggagac tattattctg agcaagctgt ctcaggagca aaagacaaag catagaatct  4920
tctctctcat tggtggtaac gactacaaag acgatgacga caagtaaagc gcttctagaa  4980
gttgtctcct cctgcactga ctgactgata caatcgattt ctggatccgc aggcctaatc  5040
aacctctgga ttacaaaatt tgtgaaagat tgactggtat tcttaactat gttgctcctt  5100
ttacgctatg tggatacgct gctttaatgc ctttgtatca tgctattgct tcccgtatgg  5160
ctttcatttt ctcctccttg tataaatcct ggttgctgtc tctttatgag gagttgtggc  5220
ccgttgtcag gcaacgtggc gtggtgtgca ctgtgtttgc tgacgcaacc cccactggtt  5280
ggggcattgc caccacctgt cagctccttt ccgggacttt cgctttcccc ctccctattg  5340
ccacggcgga actcatcgcc gcctgccttg cccgctgctg gacaggggct cggctgttgg  5400
gcactgacaa ttccgtggtg ttgtcgggga agctgacgtc ctttccatgg ctgctcgcct  5460
gtgttgccac ctggattctg cgcgggacgt ccttctgcta cgtcccttcg gccctcaatc  5520
cagcggacct tccttcccgc gaacaaacga cccaacaccc gtgcgtttta ttctgtcttt  5580
ttattgccga tcccctcaga agaactcgtc aagaaggcga tagaaggcga tgcgctgcga  5640
atcgggagcg gcgataccgt aaagcacgag gaagcggtca gcccattcgc cgccaagctc  5700
ttcagcaata tcacgggtag ccaacgctat gtcctgatag cggtcggccg ctttacttgt  5760
acagctcgtc catgccgaga gtgatcccgg cggcggtcac gaactccagc aggaccatgt  5820
gatcgcgctt ctcgttgggg tctttgctca gggcggactg ggtgctcagg tagtggttgt  5880
cgggcagcag cacggggccg tcgccgatgg gggtgttctg ctggtagtgg tcggccaggt  5940
gagtccagga gatgtttcag cactgttgcc tttagtctcg aggcaactta gacaactgag  6000
tattgatctg agcacagcag ggtgtgagct gtttgaagat actggggttg gggtgaaga  6060
aactgcagag gactaactgg gctgagaccc agtggcaatg ttttagggcc taaggaatgc  6120
ctctgaaaat ctagatggac aactttgact ttgagaaaag agaggtggaa atgaggaaaa  6180
tgacttttct ttattagatt tcggtagaaa gaactttcat ctttccccta tttttgttat  6240
tcgttttaaa acatctatct ggaggcagga caagtatggt cattaaaaag atgcaggcag  6300
aaggcatata ttggctcagt caaagtgggg aactttggtg gccaaacata cattgctaag  6360
gctattccta tatcagctgg acacatataa aatgctgcta atgcttcatt acaaacttat  6420
atcctttaat tccagatggg ggcaaagtat gtccaggggt gaggaacaat tgaaacattt  6480
gggctggagt agattttgaa agtcagctct gtgtgtgtgt gtgtgtgtgt gtgtgtgaga  6540
gcgtgtgttt cttttaacgt tttcagccta cagcatacag ggttcatggt ggcaagaaga  6600
taacaagatt taaattatgg ccagtgacta gtgctgcaag aagaacaact acctgcattt  6660
aatgggaaag caaaatctca ggctttgagg gaagttaaca taggcttgat tctgggtgga  6720
agctgggtgt gtagttatct ggaggccagg ctggagctct cagctcacta tgggttcatc  6780
tttattgtct cctttcatct caacagctgc acgctgccgt cctcgatgtt gtggcggatc  6840
ttgaagttca ccttgatgcc gttcttctgc ttgtcggcca tgatatagac gttgtggctg  6900
ttgtagttgt actccagctt gtgccccagg atgttgccgt cctccttgaa gtcgatgccc  6960
ttcagctcga tgcggttcac cagggtgtcg ccctcgaact tcacctcggc gcgggtcttg  7020
tagttgccgt cgtccttgaa gaagatggtg cgctcctgga cgtagccttc gggcatggcg  7080
gacttgaaga agtcgtgctg cttcatgtgg tcggggtagc ggctgaagca ctgcacgccg  7140
taggtcaggg tggtcacgag ggtgggccag ggcacgggca gcttgccggt ggtgcagatg  7200
aacttcaggg tcagcttgcc gtaggtggca tcgccctcgc cctcgccgga cacgctgaac  7260
ttgtggccgt ttacgtcgcc gtccagctcg accaggatgg gcaccacccc ggtgaacagc  7320
tcctcgccct tgctcaccat ggtggcgaat tcgaagcttg agcacgagat ctgagtccgg  7380
taggcctagc ggatctgacg gttcactaaa ccagctctgc ttatatagac ctcccaccgt  7440
acacgcctac cgcccatttg cgtcaatggg gcggagttgt tacgacattt tggaaagtcc  7500
cgttgatttt ggtgccaaaa caaactccca ttgacgtcaa tggggtggag acttggaaat  7560
ccccgtgagt caaaccgcta tccacgccca ttgatgtact gccaaaaccg catcaccatg  7620
gtaatagcga tgactaatac gtagatgtac tgccaagtag gaaagtccca taaggtcatg  7680
tactgggcat aatgccaggc gggccattta ccgtcattga cgtcaatagg gggcgtactt  7740
ggcatatgat acacttgatg tactgccaag tgggcagttt accgtaaata ctccacccat  7800
tgacgtcaat ggaaagtccc tattggcgtt actatgggaa catacgtcat tattgacgtc  7860
aatgggcggg ggtcgttggg cggtcagcca ggcgggccat ttaccgtaag ttatgtaacg  7920
ggcctgctgc cggctctgcg gcctcttccg cgtcttcgcc ttcgccctca gacgagtcgg  7980
atctcccttt gggccgcctc cccgcctgtc tagcttgact gactgagata cagcgtacct  8040
tcagctcaca gacatgataa gatacattga tgagtttgga caaaccacaa ctagaatgca  8100
gtgaaaaaaa tgctttattt gtgaaatttg tgatgctatt gctttatttg taaccattat  8160
aagctgcaat aaacaagtta acaacaacaa ttgcattcat tttatgtttc aggttcaggg  8220
```

-continued

```
ggaggtgtgg gaggtttttt aaagcaagta aaacctctac aaatgtggta ttggcccatc  8280
tctatcggta tcgtagcata accccttggg gcctctaaac gggtcttgag gggttttttg  8340
tgcccctcgg gccggattgc tatctaccgg cattggcgca gaaaaaaatg cctgatgcga  8400
cgctgcgcgt cttatactcc cacatatgcc agattcagca acggatacgg cttccccaac  8460
ttgcccactt ccatacgtgt cctccttacc agaaatttat ccttaaggtc gtcagctatc  8520
ctgcaggcga tctctcgatt tcgatcaaga cattccttta atggtctttt ctggacacca  8580
ctaggggtca gaagtagttc atcaaacttt cttccctccc taatctcatt ggttaccttg  8640
ggctatcgaa acttaattaa gcgatctgca tctcaattag tcagcaacca tagtcccgcc  8700
cctaactccg cccatcccgc ccctaactcc gcccagttcc gcccattctc cgccccatcg  8760
ctgactaatt ttttttattt atgcagaggc cgaggccgcc tcggcctctg agctattcca  8820
gaagtagtga ggaggctttt ttggaggcct aggcttttgc aaaggaggta gccaacatga  8880
ttgaacaaga tggattgcac gcaggttctc cgcccgcttg ggtggagagg ctattcggct  8940
atgactgggc acaacagaca atcggctgct ctgatgccgc cgtgttccgg ctgtcagcgc  9000
aggggcgccc ggttcttttt gtcaagaccg acctgtccgg tgccctgaat gaactccagg  9060
acgaggcagc gcggctatcg tggctggcca cgacgggcgt tccttgcgca gctgtgctcg  9120
acgttgtcac tgaagcggga agggactggc tgctattggg cgaagtgccg gggcaggatc  9180
tcctgtcatc tcaccttgct cctgccgaga aagtatccat catggctgat gcaatgcggc  9240
ggctgcatac gcttgatccg gctacctgcc cattcgacca ccaagcgaaa catcgcatcg  9300
agcgagcacg tactcggatg gaagccggtc ttgtcgatca ggatgatctg gacgaagagc  9360
atcaggggct cgcgccagcc gaactgttcg ccaggctcaa ggcgcggatg cccgacggcg  9420
aggatctcgt cgtgacccac ggcgatgcct gcttgccgaa tatcatggtg gaaaatggcc  9480
gcttttctgg attcatcgac tgtggccggc tgggtgtggc ggaccgctat caggacatag  9540
cgttggctac ccgtgatatt gctgaagagc ttggcggcga atgggctgac cgcttcctcg  9600
tgctttacgg tatcgccgct cccgattcgc agcgcatcgc cttctatcgc cttcttgacg  9660
agttcttcta gtatgtaagc cctgtgcctt ctagttgcca gccatctgtt gtttgcccct  9720
cccccgtgcc ttccttgacc ctggaaggtg ccactcccac tgtcctttcc taataaaatg  9780
aggaaattgc atcgcattgt ctgagtaggt gtcattctat tctggggggt ggggtggggc  9840
aggacagcaa gggggaggat tgggaagaca atagcaggca tgctggggat gcggtgggct  9900
ctatggttaa ttaaccagtc aagtcagcta cttggcgaga tcgacttgtc tgggtttcga  9960
ctacgctcag aattgcgtca gtcaagttcg atctggtcct tgctattgca cccgttctcc  10020
gattacgagt ttcatttaaa tcatgtgagc aaaaggccag caaaaggcca ggaaccgtaa  10080
aaaggccgcg ttgctggcgt ttttccatag gctccgcccc cctgacgagc atcacaaaaa  10140
tcgacgctca agtcagaggt ggcgaaaccc gacaggacta taaagatacc aggcgtttcc  10200
ccctggaagc tccctcgtgc gctctcctgt tccgaccctg ccgcttaccg gatacctgtc  10260
cgcctttctc ccttcgggaa gcgtggcgct ttctcatagc tcacgctgta ggtatctcag  10320
ttcggtgtag gtcgttcgct ccaagctggg ctgtgtgcac gaaccccccg ttcagcccga  10380
ccgctgcgcc ttatccggta actatcgtct tgagtccaac ccggtaagac acgacttatc  10440
gccactggca gcagccactg gtaacaggat tagcagagcg aggtatgtag gcggtgctac  10500
agagttcttg aagtggtggc ctaactacgg ctacactaga agaacagtat ttggtatctg  10560
cgctctgctg aagccagtta ccttcggaaa aagagttggt agctcttgat ccggcaaaca  10620
aaccaccgct ggtagcggtg gtttttttgt ttgcaagcag cagattacgc gcagaaaaaa  10680
aggatctcaa gaagatcctt tgatcttttc tacggggtct gacgctcagt ggaacgaaaa  10740
ctcacgttaa gggattttgg tcatgagatt atcaaaaagg atcttcacct agatcctttt  10800
aaattaaaaa tgaagtttta aatcaatcta aagtatatat gagtaaactt ggtctgacag  10860
ttaccaatgc ttaatcagtg aggcacctat ctcagcgatc tgtctatttc gttcatccat  10920
agttgcattt aaatttccga actctccaag gccctcgtcg gaaaatcttc aaacctttcg  10980
tccgatccat cttgcaggct acctctcgaa cgaactatcg caagtctctt ggccggcctt  11040
gcgccttggc tattgcttgg cagcgcctat cgccaggtat tactccaatc ccgaatatcc  11100
gagatcggga tcacccgaga gaagttcaac ctacatcctc aatcccgatc tatccgagat  11160
ccgaggaata tcgaaatcgg ggcgcgcctg gtgtaccgag aacgatcctc tcagtgcgag  11220
tctcgacgat ccatatcgtt gcttggcagt cagccagtcg gaatccagct tgggacccag  11280
gaagtccaat cgtcagatat tgtactcaag cctggtcacg gcagcgtacc gatctgttta  11340
aacctagata ttgatagtct gatcggtcaa cgtataatcg agtcctagct tttgcaaaca  11400
tctatcaaga gacaggatca gcaggaggct ttcgcatgag tattcaacat ttccgtgtcg  11460
cccttattcc cttttttgcg gcattttgcc ttcctgtttt tgctcaccca gaaacgctgg  11520
tgaaagtaaa agatgctgaa gatcagttgg gtgcgcgagt gggttacatc gaactggatc  11580
tcaacagcgg taagatcctt gagagttttc gccccgaaga acgctttcca atgatgagca  11640
cttttaaagt tctgctatgt ggcgcggtat tatcccgtat tgacgccggg caagagcaac  11700
tcggtcgccg catacactat tctcagaatg acttggttga gtattcacca gtcacagaaa  11760
agcatcttac ggatggcatg acagtaagag aattatgcag tgctgccata accatgagtg  11820
ataacactgc ggccaactta cttctgacaa cgattggagg accgaaggag ctaaccgctt  11880
ttttgcacaa catgggggat catgtaactc gccttgatcg ttgggaaccg gagctgaatg  11940
aagccatacc aaacgacgag cgtgacacca cgatgcctgt agcaatggca acaaccttgc  12000
gtaaactatt aactggcgaa ctacttactc tagcttcccg gcaacagttg atagactgga  12060
tggaggcgga taaagttgca ggaccacttc tgcgctcggc ccttccggct ggctggttta  12120
ttgctgataa atctggagcc ggtgagcgtg ggtctcgcgg tatcattgca gcactggggc  12180
cagatggtaa gccctcccgt atcgtagtta tctacacgac ggggagtcag gcaactatgg  12240
atgaacgaaa tagacagatc gctgagatag gtgcctcact gattaagcat tggtaaccga  12300
ttctaggtgc attggcgcag aaaaaaatgc ctgatgcgac gctgcgcgtc ttatactccc  12360
acatatgcca gattcagcaa cggatacggc ttccccaact tgcccacttc catacgtgtc  12420
ctccttacca gaaatttatc cttaagatcg tttaaactcg actctggctc tatcgaatct  12480
ccgtcgtttc gagcttacgc gaacagccgt ggcgctcatt tgctcgtcgg gcatcgaatc  12540
tcgtcagcta tcgtcagctt accttttttgg cagcgatcgc ggctcccgac atcttggacc  12600
attagctcca caggtatctt cttccctcta gtggtcataa cagcagcttc agctacctct  12660
caattcaaaa aacccctcaa gacccgttta gaggccccaa ggggttatgc tatcaatcgt  12720
tgcgttacac acacaaaaaa ccaacacaca tccatcttcg atggatagcg attttattat  12780
ctaactgctg atcgagtgta gccagatcta gtaatcaatt acggggtcat tagttcatag  12840
cccatatatg gagttccgcg ttacataact tacggtaaat ggcccgcctg gctgaccgcc  12900
caacgacccc cgcccattga cgtcaataat gacgtatgtt cccatagtaa cgccaatagg  12960
```

```
gactttccat tgacgtcaat gggtggagta tttacggtaa actgcccact tggcagtaca  13020
tcaagtgtat catatgccaa gtacgccccc tattgacgtc aatgacggta aatggcccgc  13080
ctggcattat gcccagtaca tgaccttatg ggactttcct acttggcagt acatctacgt  13140
attagtcatc gctattacca tgctgatgcg gttttggcag tacatcaatg ggcgtggata  13200
gcggtttgac tcacggggat ttccaagtct ccaccccatt gacgtcaatg ggagtttgtt  13260
ttggcaccaa aatcaacggg actttccaaa atgtcgtaac aactccgccc cattgacgca  13320
aatgggcggt aggcgtgtac ggtgggaggt ctatataagc agagctggtt tagtgaaccg  13380
tcagatcaga tctttgtcga tcctaccatc cactcgacac acccgccagc ggccgc      13436

SEQ ID NO: 48           moltype = DNA  length = 13433
FEATURE                 Location/Qualifiers
misc_feature            1..13433
                        note = Description of Artificial Sequence: Synthetic
                         polynucleotide
source                  1..13433
                        mol_type = other DNA
                        organism = synthetic construct
SEQUENCE: 48
taatacgact cactataggg agaagtactg ccaccatggg caagaagcaa aatcgcaaga  60
cggggaattc caagacacaa tccgctagcc caccacctaa agagcgttct agctcccctg  120
ctactgagca gtcctggatg gaaaacgact tcgatgaact ccgggaagag ggatttaggc  180
gatccaacta ttcagaactc cgcgaagata tccagacaaa ggggaaggaa gtcgagaatt  240
tcgagaagaa cctcgaggag tgcatcaccc gtatcacaaa cactgagaaa tgtctcaaag  300
aactcatgga acttaagaca aaagccaggg agcttcgaga ggagtgtcgg agtctgagat  360
ccaggtgtga ccagctcgag gagcgcgtga gcgcgatgga agacgagatg aacgagatga  420
aaagagaggg caaattcagg gagaagcgca ttaagaggaa cgaacagagt ctgcaggaga  480
tttgggatta cgtcaagagg cctaacctgc ggttgatcgg cgtccccgag agcgacgtag  540
aaaacgggac taaactggag aatacacttc aagacatcat tcaagaaaat tttccaaacc  600
tggctcggca agctaatgtg caaatccaag agatccaacg cacaccccag cggtatagct  660
ctcggcgtgc cacccctagg catattatcg tgcgctttac taaggtggag atgaaagaga  720
agatgctgcg agccgctcgg gaaaagggaa gggtgacttt gaagggcaaa cctattcggc  780
tgacggttga ccttagcgcc gagacactcc aggcacgccg ggaatggggc cccatcttta  840
atatcctgaa ggagaagaac ttccagccac gaatctctta ccctgcaaag ttgagtttta  900
tctccgaggg tgagattaag tatttcatcg ataaacagat gctgcgagac ttcgtgacaa  960
ctcgcccagc tctcaaggaa ctgctcaaag aggctcttaa tatggagcgc aataatagat  1020
atcaaccctt gcagaaccac gcaaagatgg gaagcggaga gggcagagga agtctgctaa  1080
catgcggtga cgtcgaggag aatcctggac ctatgaccgg ctctaactca catatcacca  1140
tccttacact taacattaac ggcctcaact cagctatcaa gcgccatcgg ctggccagct  1200
ggatcaaatc acaggatcca agcgtttgtt gcatccaaga gacccacctg acctgtagag  1260
atactcaccg cctcaagatc aagggatggc gaaagattta tcaggcgaac ggtaagcaga  1320
agaaagccgg agtcgcaatt ctggtctcag acaagacgga tttcaagccc accaaaatta  1380
agcgtgataa ggaaggtcac tatattatgg tgaaaggcag catacagcag gaagaactta  1440
ccatattgaa catctacgcg ccaaacaccg gcgcacctcg ctttatcaaa caggtcctgt  1500
ccgatctgca gcgagatctg gattctcata cgttgattat gggtgatttc aatacaccat  1560
tgagcaccct ggatcgcagc accaggcaaa aggtaaataa agacacgcaa gagctcaata  1620
gcgcactgca tcaggcagat ctcattgata tttatcgcac tcttcatcct aagagtaccg  1680
agtacacatt cttcagcgcc ccacatcata catactcaaa gatcgatcat atcgtcggct  1740
caaaggctct gctgtcaaag tgcaagcgca cagagataat tacaaattac ctgtcagatc  1800
atagcgcgat caagctcgag ctgagaatca agaacctgac ccagagccgg agtaccactt  1860
ggaagcttaa taacctgctg ctcaacgatt attgggtcca caatgagatg aaggcagaga  1920
ttaaaatgtt cttcgaaaca aatgagaata aggatactac ctatcaaaac ctttgggatg  1980
cctttaaggc cgtctgcaga ggcaagttca tcgccctcaa cgcctataaa agaaaacaag  2040
agagatctaa gatcgatact ctcacctctc agctgaagga gttggagaaa caggaacaga  2100
cccactccaa ggcgtcaaga cggcaggaga tcacaaagat tcgcgccgag ttgaaagaga  2160
tcgaaaccca aaagactctt cagaaaatta acgagtctcg tagttggttc ttcgagcgga  2220
ttaataagat agacagacct ctggcacgac tgattaagaa gaagcgcgaa aagaaccaga  2280
ttgataccat caagaacgac aagggcgaca tcactactga cccgaccgag atccagacca  2340
ctattcggga gtattataag catttgtatg ctaacaagct tgagaacctg gaagagatgg  2400
acacttttct ggatacctat actctgccac ggcttaatca agaggaagtc gagtccctca  2460
accgcccaat tacaggaagc gagattgtgg ccataattaa ctccctgccg acaaagaaat  2520
ctcctggtcc ggacgggttt acagctgagt tttatcaacg gtatatggaa gagcttgtac  2580
cgtttctgct caagctcttt cagtctatag aaaaggaagg catcttgccc aattccttct  2640
acgaagcttc tataatactt attcccaaac caggacgcga taccacaaag aaggaaaact  2700
tccggcccat tagtctcatg aatatcgacg ctaaaatatt gaacaagatt ctcgccaaca  2760
gaatccaaca acatattaag aaattgatac atcacgacca ggtggggttt atacctggca  2820
tgcagggctg gtttaacatc cggaagagta ttaacgtcat tcaacacatt aatagagcta  2880
aggataagaa tcatatgatc atctctatag acgcggaaaa ggcattcgat aagattcagc  2940
agccatttat gctcaagact ctgaacaaac tcggcatcga cggaacatat tttaagatta  3000
ttcgcgcaat ttacgataag ccgactgcta acattatcct taacggccaa aagctcgagg  3060
cctttccgct caagactgga acccgccaag gctgtcccct ctccccgctt ttgtttaata  3120
ttgtactcga ggtgctggct agggctattc gtcaagagaa agagattaaa gggatacagc  3180
tcgggaagga agaggtcaag ctttccttgt tcgccgatga tatgattgtg tacctggaga  3240
atcctattgt gtctgctcag aaccttctta aacttatttc taactttagc aaggtcagcg  3300
gctataagat taacgtccag aaatctcagg cctttctgta cacaaataat cgacagaccg  3360
aatcccagat aatgggtgag cttccgtttg tcatagccag caaaaggata aagtatctcg  3420
gaatccagct gacacgagac gttaaagatt tgtttaagga aaattacaag cctctcctga  3480
aagagattaa ggaagatact aataagtgga agaatatccc ctgttcatgg gttggcagaa  3540
tcaacatagt gaagatggca atacttccta aagtgatata tcgctttaac gccatcccaa  3600
ttaaactgcc tatgaccttc tttacggagc tcgagaaaac aacccttaaa tttatatgga  3660
```

-continued

```
atcaaaagag agcaagaata gcgaagtcca tcttgagcca gaagaataag gccggtggga  3720
ttactttgcc tgattttaag ttgtattata aagccacagt aactaagaca gcctggtatt  3780
ggtatcagaa tagagacatc gaccagtgga atcggaccga accatcagag ataatgcccc  3840
acatctataa ttaccttata ttcgataagc cagaaaagaa taaacagtgg ggcaaagaca  3900
gcctcttcaa caagtggtgt tgggagaatt ggctggccat atgccggaaa ctcaagctcg  3960
accccttct tacaccctac actaaaatca acagtaggtg gatcaaggac ttgaatgtca  4020
agccaaagac tataaagaca ctggaagaga atcttgggat cacaatacaa gatataggcg  4080
tcggcaaaga ttttatgtca aagacgccca aggccatggc cactaaggat aagattgata  4140
agtgggacct tattaagctc aaaagcttct gtactgccaa ggagaccacg atcagagtta  4200
ataggcagcc cactacatgg gaaaagattt tcgccactta ttcatcagat aaggggttga  4260
taagcagaat atataacgag ctgaagcaga tctacaagaa gaaaacgaat aatcccatca  4320
agaagtgggc aaaagatatg aacaggcatt ttagcaaaga ggatatctac gccgcgaaga  4380
agcatatgaa gaagtgtagt tcaagcttgg ccattcgtga gatgcagatt aagacgacca  4440
tgcgatacca ccttacccca gtgaggatgg caattatcaa gaaatctggc aataatagat  4500
gttggcgggg ctgtggcgag attggcaccc tgctccattg ctggtgggat tgcaagctgg  4560
tgcagccgct ttggaaatca gtctggcgct ttctgaggga cctcgagctt gagattccct  4620
tcgatcccgc aattcccttg ctcggaatct atcctaacga atacaagagc tgttgttaca  4680
aggatacgtg tacccggatg ttcatcgcgg ccttgtttac gatagctaag acgtggaatc  4740
agcctaagtg ccccacaatg atcgattgga tcaagaaaat gtggcatatt tataccatgg  4800
agtattacgc agcaattaag aatgacgaat ttatttcctt cgttgggacc tggatgaagc  4860
tggagactat tattctgagc aagctgtctc aggagcaaaa gacaaagcat agaatcttct  4920
ctctcattgg tggtaacgac tacaaagacg atgacgacaa gtaaagcgct tctagaagtt  4980
gtctcctcct gcactgactg actgatacaa tcgatttctg gatccgcagg cctaatcaac  5040
ctctggatta caaaatttgt gaaagattga ctggtattct taactatgtt gctcctttta  5100
cgctatgtgg atacgctgct ttaatgcctt tgtatcatgc tattgcttcc cgtatggctt  5160
tcattttctc ctccttgtat aaatcctggt tgctgtctct ttatgaggag ttgtggcccg  5220
ttgtcaggca acgtggcgtg gtgtgcactg tgtttgctga cgcaaccccc actggttggg  5280
gcattgccac cacctgtcag ctcctttccg ggactttcgc tttccccctc cctattgcca  5340
cggcggaact catcgccgcc tgccttgccc gctgctggac aggggctcgg ctgttgggca  5400
ctgacaattc cgtggtgttg tcggggaagc tgacgtcctt tccatggctg ctcgcctgtg  5460
ttgccacctg gattctgcgc gggacgtcct tctgctacgt cccttcggcc ctcaatccag  5520
cggaccttcc ttcccgcgaa caaacgaccc aacacccgtg cgttttattc tgtcttttta  5580
ttgccgatcc cctcagaaga actcgtcaag aaggcgatag aaggcgatgc gctgcgaatc  5640
gggagcggcg ataccgtaaa gcacgaggaa gcggtcagcc cattcgccgc caagctcttc  5700
agcaatatca cgggtagcca acgctatgtc ctgatagcgg tcggccgctt tacttgtaca  5760
gctcgtccat gccgagagtg atcccggcgg cggtcacgaa ctccagcagg accatgtgat  5820
cgcgcttctc gttggggtct ttgctcaggg cggactgggt gctcaggtag tggttgtcgg  5880
gcagcagcac ggggccgtcg ccgatggggg tgttctgctg gtagtggtcg gccaggtgag  5940
tccaggagat gtttcagcac tgttgccttt agtctcgagg caacttagac aactgagtat  6000
tgatctgagc acagcagggt gtgagctgtt tgaagatact ggggttgggg gtgaagaaac  6060
tgcagaggac taactgggct gagacccagt ggcaatgttt tagggcctaa ggaatgcctc  6120
tgaaaatcta gatggacaac tttgactttg agaaaagaga ggtggaaatg aggaaaatga  6180
cttttcttta ttagatttcg gtagaaagaa ctttcatctt tcccctattt ttgttattcg  6240
ttttaaaaca tctatctgga ggcaggacaa gtatggtcat taaaaagatg caggcagaag  6300
gcatatattg gctcagtcaa agtggggaac tttggtggcc aaacatacat tgctaaggct  6360
attcctatat cagctggaca catataaaat gctgctaatg cttcattaca aacttatatc  6420
ctttaattcc agatgggggc aaagtatgtc caggggtgag gaacaattga aacatttggg  6480
ctggagtaga ttttgaaagt cagctctgtg tgtgtgtgtg tgtgtgtgtg tgtgagagcg  6540
tgtgtttctt ttaacgtttt cagcctacag catacagggt tcatggtggc aagaagataa  6600
caagatttaa attatggcca gtgactagtg ctgcaagaag aacaactacc tgcatttaat  6660
gggaaagcaa aatctcaggc tttgagggaa gttaacatag gcttgattct gggtggaagc  6720
tgggtgtgta gttatctgga ggccaggctg gagctctcag ctcactatgg gttcatcttt  6780
attgtctcct ttcatctcaa cagctgcacg ctgccgtcct cgatgttgtg gcggatcttg  6840
aagttcacct tgatgccgtt cttctgcttg tcggccatga tatagacgtt gtggctgttg  6900
tagttgtact ccagcttgtg ccccaggatg ttgccgtcct ccttgaagtc gatgcccttc  6960
agctcgatgc ggttcaccag ggtgtcgccc tcgaacttca cctcggcgcg ggtcttgtag  7020
ttgccgtcgt ccttgaagaa gatggtgcgc tcctggacgt agccttcggg catggcggac  7080
ttgaagaagt cgtgctgctt catgtggtcg gggtagcggc tgaagcactg cacgccgtag  7140
gtcagggtgg tcacgagggt gggccagggc acgggcagct tgccggtggt gcagatgaac  7200
ttcagggtca gcttgccgta ggtggcatcg ccctcgccct cgccggacac gctgaacttg  7260
tggccgttta cgtcgccgtc cagctcgacc aggatgggca ccaccccggt gaacagctcc  7320
tcgcccttgc tcaccatggt ggcgaattcg aagcttgagc acgagatctg agtccggtag  7380
gcctagcgga tctgacggtt cactaaacca gctctgctta tatagacctc ccaccgtaca  7440
cgcctaccgc ccatttgcgt caatggggcg gagttgttac gacattttgg aaagtcccgt  7500
tgattttggt gccaaaacaa actcccattg acgtcaatgg ggtggagact tggaaatccc  7560
cgtgagtcaa accgctatcc acgcccattg atgtactgcc aaaaccgcat caccatggta  7620
atagcgatga ctaatacgta gatgtactgc caagtaggaa agtcccataa ggtcatgtac  7680
tgggcataat gccaggcggg ccatttaccg tcattgacgt caataggggg cgtacttggc  7740
atatgataca cttgatgtac tgccaagtgg gcagtttacc gtaaatactc cacccattga  7800
cgtcaatgga aagtccctat tggcgttact atgggaacat acgtcattat tgacgtcaat  7860
gggcgggggt cgttgggcgg tcagccaggc gggccattta ccgtaagtta tgtaacgggc  7920
ctgctgccgg ctctgcggcc tcttccgcgt cttcgccttc gccctcagac gagtcggatc  7980
tccctttggg ccgcctcccc gcctgtctag cttgactgac tgagatacag cgtaccttca  8040
gctcacagac atgataagat acattgatga gtttggacaa accacaacta gaatgcagtg  8100
aaaaaaatgc tttatttgtg aaatttgtga tgctattgct ttatttgtaa ccattataag  8160
ctgcaataaa caagttaaca acaacaattg cattcatttt atgtttcagg ttcaggggga  8220
ggtgtgggag gtttttttaaa gcaagtaaaa cctctacaaa tgtggtattg gcccatctct  8280
atcggtatcg tagcataacc ccttggggcc tctaaacggg tcttgagggg tttttttgtgc  8340
ccctcgggcc ggattgctat ctaccggcat tggcgcagaa aaaaatgcct gatgcgacgc  8400
```

-continued

```
tgcgcgtctt atactcccac atatgccaga ttcagcaacg gatacggctt ccccaacttg  8460
cccacttcca tacgtgtcct ccttaccaga aatttatcct taaggtcgtc agctatcctg  8520
caggcgatct ctcgatttcg atcaagacat tcctttaatg gtcttttctg gacaccacta  8580
ggggtcagaa gtagttcatc aaactttctt ccctccctaa tctcattggt taccttgggc  8640
tatcgaaact taattaagcg atctgcatct caattagtca gcaaccatag tcccgcccct  8700
aactccgccc atcccgcccc taactccgcc cagttccgcc cattctccgc cccatcgctg  8760
actaattttt tttatttatg cagaggccga ggccgcctcg gcctctgagc tattccagaa  8820
gtagtgagga ggcttttttg gaggcctagg cttttgcaaa ggaggtagcc aacatgattg  8880
aacaagatgg attgcacgca ggttctcccg ccgcttgggt ggagaggcta ttcggctatg  8940
actgggcaca acagacaatc ggctgctctg atgccgccgt gttccggctg tcagcgcagg  9000
ggcgcccggt tctttttgtc aagaccgacc tgtccggtgc cctgaatgaa ctccaggacg  9060
aggcagcgcg gctatcgtgg ctggccacga cgggcgttcc ttgcgcagct gtgctcgacg  9120
ttgtcactga agcgggaagg gactggctgc tattgggcga agtgccgggg caggatctcc  9180
tgtcatctca ccttgctcct gccgagaaag tatccatcat ggctgatgca atgcggcggc  9240
tgcatacgct tgatccggct acctgcccat tcgaccacca agcgaaacat cgcatcgagc  9300
gagcacgtac tcggatggaa gccggtcttg tcgatcagga tgatctggac gaagagcatc  9360
aggggctcgc gccagccgaa ctgttcgcca ggctcaaggc gcggatgccc gacggcgagg  9420
atctcgtcgt gacccacggc gatgcctgct tgccgaatat catggtggaa aatggccgct  9480
tttctggatt catcgactgt ggccggctgg gtgtggcgga ccgctatcag gacatagcgt  9540
tggctacccg tgatattgct gaagagcttg gcggcgaatg ggctgaccgc ttcctcgtgc  9600
tttacggtat cgccgctccc gattcgcagc gcatcgcctt ctatcgcctt cttgacgagt  9660
tcttctagta tgtaagccct gtgccttcta gttgccagcc atctgttgtt tgcccctccc  9720
ccgtgccttc cttgaccctg gaaggtgcca ctcccactgt cctttcctaa taaaatgagg  9780
aaattgcatc gcattgtctg agtaggtgtc attctattct ggggggtggg gtggggcagg  9840
acagcaaggg ggaggattgg gaagacaata gcaggcatgc tggggatgcg gtgggctcta  9900
tggttaatta accagtcaag tcagctactt ggcgagatcg acttgtctgg gtttcgacta  9960
cgctcagaat tgcgtcagtc aagttcgatc tggtccttgc tattgcaccc gttctccgat  10020
tacgagtttc atttaaatca tgtgagcaaa aggccagcaa aaggccagga accgtaaaaa  10080
ggccgcgttg ctggcgtttt tccataggct ccgcccccct gacgagcatc acaaaaatcg  10140
acgctcaagt cagaggtggc gaaacccgac aggactataa agataccagg cgtttccccc  10200
tggaagctcc ctcgtgcgct ctcctgttcc gaccctgccg cttaccggat acctgtccgc  10260
ctttctccct tcgggaagcg tggcgctttc tcatagctca cgctgtaggt atctcagttc  10320
ggtgtaggtc gttcgctcca agctgggctg tgtgcacgaa ccccccgttc agcccgaccg  10380
ctgcgcctta tccggtaact atcgtcttga gtccaacccg gtaagacacg acttatcgcc  10440
actggcagca gccactggta acaggattag cagagcgagg tatgtaggcg gtgctacaga  10500
gttcttgaag tggtggccta actacggcta cactagaaga acagtatttg gtatctgcgc  10560
tctgctgaag ccagttacct tcggaaaaag agttggtagc tcttgatccg gcaaacaaac  10620
caccgctggt agcggtggtt tttttgtttg caagcagcag attacgcgca gaaaaaaagg  10680
atctcaagaa gatcctttga tcttttctac ggggtctgac gctcagtgga acgaaaactc  10740
acgttaaggg attttggtca tgagattatc aaaaaggatc ttcacctaga tccttttaaa  10800
ttaaaaatga agttttaaat caatctaaag tatatatgag taaacttggt ctgacagtta  10860
ccaatgctta atcagtgagg cacctatctc agcgatctgt ctatttcgtt catccatagt  10920
tgcatttaaa tttccgaact ctccaaggcc ctcgtcggaa aatcttcaaa cctttcgtcc  10980
gatccatctt gcaggctacc tctcgaacga actatcgcaa gtctcttggc cggccttgcg  11040
ccttggctat tgcttggcag cgcctatcgc caggtattac tccaatcccg aatatccgag  11100
atcgggatca cccgagagaa gttcaaccta catcctcaat cccgatctat ccgagatccg  11160
aggaatatcg aaatcggggc gcgcctggtg taccgagaac gatcctctca gtgcgagtct  11220
cgacgatcca tatcgttgct tggcagtcag ccagtcggaa tccagcttgg gacccaggaa  11280
gtccaatcgt cagatattgt actcaagcct ggtcacggca gcgtaccgat ctgtttaaac  11340
ctagatattg atagtctgat cggtcaacgt ataatcgagt cctagctttt gcaaacatct  11400
atcaagagac aggatcagca ggaggctttc gcatgagtat tcaacatttc cgtgtcgccc  11460
ttattccctt ttttgcggca ttttgccttc ctgtttttgc tcacccagaa acgctggtga  11520
aagtaaaaga tgctgaagat cagttgggtg cgcgagtggg ttacatcgaa ctggatctca  11580
acagcggtaa gatccttgag agttttcgcc ccgaagaacg ttttccaatg atgagcactt  11640
ttaaagttct gctatgtggc gcggtattat cccgtattga cgccgggcaa gagcaactcg  11700
gtcgccgcat acactattct cagaatgact tggttgagta ttcaccagtc acagaaaagc  11760
atcttacgga tggcatgaca gtaagagaat tatgcagtgc tgccataacc atgagtgata  11820
acactgcggc caacttactt ctgacaacga ttggaggacc gaaggagcta accgcttttt  11880
tgcacaacat gggggatcat gtaactcgcc ttgatcgttg ggaaccggag ctgaatgaag  11940
ccataccaaa cgacgagcgt gacaccacga tgcctgtagc aatggcaaca accttgcgta  12000
aactattaac tggcgaacta cttactctag cttcccggca acagttgata gactggatgg  12060
aggcggataa agttgcagga ccacttctgc gctcggccct tccggctggc tggtttattg  12120
ctgataaatc tggagccggt gagcgtgggt ctcgcggtat cattgcagca ctggggccag  12180
atggtaagcc ctcccgtatc gtagttatct acacgacggg gagtcaggca actatggatg  12240
aacgaaatag acagatcgct gagataggtg cctcactgat taagcattgg taaccgattc  12300
taggtgcatt ggcgcagaaa aaaatgcctg atgcgacgct gcgcgtctta tactcccaca  12360
tatgccagat tcagcaacgg atacggcttc cccaacttgc ccacttccat acgtgtcctc  12420
cttaccagaa atttatcctt aagatcgttt aaactcgact ctggctctat cgaatctccg  12480
tcgtttcgag cttacgcgaa cagccgtggc gctcatttgc tcgtcgggca tcgaatctcg  12540
tcagctatcg tcagcttacc tttttggcag cgatcgcggc tcccgacatc ttggaccatt  12600
agctccacag gtatcttctt ccctctagtg gtcataacag cagcttcagc tacctctcaa  12660
ttcaaaaaac ccctcaagac ccgtttagag gccccaaggg gttatgctat caatcgttgc  12720
gttacacaca caaaaaacca acacacatcc atcttcgatg gatagcgatt ttattatcta  12780
actgctgatc gagtgtagcc agatctagta atcaattacg gggtcattag ttcatagccc  12840
atatatggag ttccgcgtta cataacttac ggtaaatggc ccgcctggct gaccgcccaa  12900
cgacccccgc ccattgacgt caataatgac gtatgttccc atagtaacgc caatagggac  12960
tttccattga cgtcaatggg tggagtattt acggtaaact gcccacttgg cagtacatca  13020
agtgtatcat atgccaagta cgccccctat tgacgtcaat gacggtaaat ggcccgcctg  13080
gcattatgcc cagtacatga ccttatggga ctttcctact tggcagtaca tctacgtatt  13140
```

```
agtcatcgct attaccatgc tgatgcggtt ttggcagtac atcaatgggc gtggatagcg  13200
gtttgactca cggggatttc caagtctcca ccccattgac gtcaatggga gtttgttttg  13260
gcaccaaaat caacgggact ttccaaaatg tcgtaacaac tccgccccat tgacgcaaat  13320
gggcggtagg cgtgtacggt gggaggtcta tataagcaga gctggtttag tgaaccgtca  13380
gatcagatct ttgtcgatcc taccatccac tcgacacacc cgccagcggc cgc         13433

SEQ ID NO: 49          moltype = DNA  length = 9241
FEATURE                Location/Qualifiers
misc_feature           1..9241
                       note = Description of Artificial Sequence: Synthetic
                        polynucleotide
source                 1..9241
                       mol_type = other DNA
                       organism = synthetic construct
SEQUENCE: 49
taatacgact cactataggg agaagtactg ccaccatggg caagaagcaa aatcgcaaga  60
cggggaattc caagacacaa tccgctagcc caccacctaa agagcgttct agctcccctg  120
ctactgagca gtcctggatg gaaaacgact tcgatgaact ccgggaagag ggatttaggc  180
gatccaacta ttcagaactc cgcgaagata tccagacaaa ggggaaggaa gtcgagaatt  240
tcgagaagaa cctcgaggag tgcatcaccc gtatcacaaa cactgagaaa tgtctcaaag  300
aactcatgga acttaagaca aaagccaggg agcttcgaga ggagtgtcgg agtctgagat  360
ccaggtgtga ccagctcgag gagcgcgtga gcgcgatgga agacgagatg aacgagatga  420
aaagagaggg caaattcagg gagaagcgca ttaagaggaa cgaacagagt ctgcaggaga  480
tttgggatta cgtcaagagg cctaacctgc ggttgatcgg cgtccccgag agcgacgtag  540
aaaacgggac taaactggag aatacacttc aagacatcat tcaagaaaat tttccaaacc  600
tggctcggca agctaatgtg caaatccaag agatccaacg cacaccccag cggtatagct  660
ctcggcgtgc cacccctagg catattatcg tgcgctttac taaggtggag atgaaagaga  720
agatgctgcg agccgctcgg gaaaagggaa gggtgacttt gaagggcaaa cctattcggc  780
tgacggttga ccttagcgcc gagacactcc aggcacgccg ggaatggggc cccatcttta  840
atatcctgaa ggagaagaac ttccagccac gaatctctta ccctgcaaag ttgagtttta  900
tctccgaggg tgagattaag tatttcatcg ataaacagat gctgcgagac ttcgtgacaa  960
ctcgcccagc tctcaaggaa ctgctcaaag aggctcttaa tatggagcgc aataatagat  1020
atcaaccctt gcagaaccac gcaaagatgt gagacagccg tcagaccatc aagactagga  1080
agaaactgca tcaactaatg agcaaaatca ccagctaaca tcatagtata catgaccggc  1140
tctaactcac atatcaccat ccttacactt aacattaacg gcctcaactc agctatcaag  1200
cgccatcggc tggccagctg gatcaaatca caggatccaa gcgtttgttg catccaagag  1260
acccacctga cctgtagaga tactcaccgc ctcaagatca agggatggcg aaagatttat  1320
caggcgaacg gtaagcagaa gaaagccgga gtcgcaattc tggtctcaga caagacggat  1380
ttcaagccca ccaaaattaa gcgtgataag gaaggtcact atattatggt gaaaggcagc  1440
atacagcagg aagaacttac catattgaac atctacgcgc caaacaccgg cgcacctcgc  1500
tttatcaaac aggtcctgtc cgatctgcag cgagatctgg attctcatac gttgattatg  1560
ggtgatttca atacaccatt gagcaccctg gatcgcagca ccaggcaaaa ggtaaataaa  1620
gacacgcaag agctcaatag cgcactgcat caggcagatc tcattgatat ttatcgcact  1680
cttcatccta agagtaccga gtacacattc ttcagcgccc cacatcatac atactcaaag  1740
atcgatcata tcgtcggctc aaaggctctg ctgtcaaagt gcaagcgcac agagataatt  1800
acaaattacc tgtcagatca tagcgcgatc aagctcgagc tgagaatcaa gaacctgacc  1860
cagagccgga gtaccacttg gaagcttaat aacctgctgc tcaacgatta ttgggtccac  1920
aatgagatga aggcagagat taaaatgttc ttcgaaacaa atgagaataa ggatactacc  1980
tatcaaaacc tttgggatgc ctttaaggcc gtctgcagag gcaagttcat cgccctcaac  2040
gcctataaaa gaaaacaaga gagatctaag atcgatactc tcacctctca gctgaaggag  2100
ttggagaaac aggaacagac ccactccaag gcgtcaagac ggcaggagat cacaaagatt  2160
cgcgccgagt tgaaagagat cgaaacccaa aagactcttc agaaaattaa cgagtctcgt  2220
agttggttct tcgagcggat taataagata gacagacctc tggcacgact gattaagaag  2280
aagcgcgaaa agaaccagat tgataccatc aagaacgaca agggcgacat cactactgac  2340
ccgaccgaga tccagaccac tattcgggag tattataagc atttgtatgc taacaagctt  2400
gagaacctgg aagagatgga cacttttctg gatacctata ctctgccacg gcttaatcaa  2460
gaggaagtcg agtccctcaa ccgcccaatt acaggaagcg agattgtggc cataattaac  2520
tccctgccga caaagaaatc tcctggtccg gacgggttta cagctgagtt ttatcaacgg  2580
tatatggaag agcttgtacc gtttctgctc aagctctttc agtctataga aaaggaaggc  2640
atcttgccca attccttcta cgaagcttct ataatactta ttcccaaacc aggacgcgat  2700
accacaaaga aggaaaactt ccggcccatt agtctcatga atatcgacgc taaaatattg  2760
aacaagattc tcgccaacag aatccaacaa catattaaga aattgataca tcacgaccag  2820
gtggggttta tacctggcat gcagggctgg tttaacatcc ggaagagtat taacgtcatt  2880
caacacatta atagagctaa ggataagaat catatgatca tctctataga cgcggaaaag  2940
gcattcgata agattcagca gccatttatg ctcaagactc tgaacaaact cggcatcgac  3000
ggaacatatt ttaagattat tcgcgcaatt tacgataagc cgactgctaa cattatcctt  3060
aacggccaaa agctcgaggc ctttccgctc aagactggaa cccgccaagg ctgtcccctc  3120
tccccgcttt tgtttaatat tgtactcgag gtgctggcta gggctattcg tcaagagaaa  3180
gagattaaag ggatacagct cgggaaggaa gaggtcaagc tttccttgtt cgccgatgat  3240
atgattgtgt acctggagaa tcctattgtg tctgctcaga accttcttaa acttatttct  3300
aactttagca aggtcagcgg ctataagatt aacgtccaga aatctcaggc ctttctgtac  3360
acaaataatc gacagaccga atcccagata atgggtgagc ttccgtttgt catagccagc  3420
aaaaggataa agtatctcgg aatccagctg acacgagacg ttaaagattt gtttaaggaa  3480
aattacaagc ctctcctgaa agagattaag gaagatacta ataagtggaa gaatatcccc  3540
tgttcatggg ttggcagaat caacatagtg aagatggcaa tacttcctaa agtgatatat  3600
cgctttaacg ccatcccaat taaactgcct atgaccttct ttacggagct cgagaaaaca  3660
acccttaaat ttatatggaa tcaaaagaga gcaagaatag cgaagtccat cttgagccag  3720
aagaataagg ccggtgggat tactttgcct gattttaagt tgtattataa agccacagta  3780
actaagacag cctggtattg gtatcagaat agagacatcg accagtggaa tcggaccgaa  3840
```

```
ccatcagaga taatgcccca catctataat taccttatat tcgataagcc agaaaagaat  3900
aaacagtggg gcaaagacag cctcttcaac aagtggtgtt gggagaattg gctggccata  3960
tgccggaaac tcaagctcga cccctttctt acaccctaca ctaaaatcaa cagtaggtgg  4020
atcaaggact tgaatgtcaa gccaaagact ataaagacac tggaagagaa tcttgggatc  4080
acaatacaag atataggcgt cggcaaagat tttatgtcaa agacgcccaa ggccatggcc  4140
actaaggata agattgataa gtgggacctt attaagctca aaagcttctg tactgccaag  4200
gagaccacga tcagagttaa taggcagccc actacatggg aaaagatttt cgccacttat  4260
tcatcagata aggggttgat aagcagaata tataacgagc tgaagcagat ctacaagaag  4320
aaaacgaata atcccatcaa gaagtgggca aaagatatga acaggcattt tagcaaagag  4380
gatatctacg ccgcgaagaa gcatatgaag aagtgtagtt caagcttggc cattcgtgag  4440
atgcagatta agacgaccat gcgataccac cttaccccag tgaggatggc aattatcaag  4500
aaatctggca ataatagatg ttggcggggc tgtggcgaga ttggcaccct gctccattgc  4560
tggtgggatt gcaagctggt gcagccgctt tggaaatcag tctggcgctt tctgagggac  4620
ctcgagcttg agattccctt cgatcccgca attcccttgc tcggaatcta tcctaacgaa  4680
tacaagagct gttgttacaa ggatacgtgt acccggatgt tcatcgcggc cttgtttacg  4740
atagctaaga cgtggaatca gcctaagtgc cccacaatga tcgattggat caagaaaatg  4800
tggcatattt ataccatgga gtattacgca gcaattaaga atgacgaatt tatttccttc  4860
gttgggacct ggatgaagct ggagactatt attctgagca agctgtctca ggagcaaaag  4920
acaaagcata gaatcttctc tctcattggt ggtaacgctt ctaactttac tcagttcgtt  4980
ctcgtcgaca atggcggaac tggcgacgtg actgtcgccc caagcaactt cgctaacggg  5040
atcgctgaat ggatcagctc taactcgcgt tcacaggctt acaaagtaac ctgtagcgtt  5100
cgtcagagct ctgcgcagaa tcgcaaatac accatcaaag tcgaggtgcc taaaggcgcc  5160
tggcgttcgt acttaaatat ggaactaacc attccaattt tcgccacgaa ttccgactgc  5220
gagcttattg ttaaggcaat gcaaggtctc ctaaaagatg gaaacccgat tccctcagca  5280
atcgcagcaa actccggcat ctacgccatg gccagcaact tcacccagtt cgtgctggtg  5340
gacaacggcg gcaccggcga cgtgaccgtg gcccccagca acttcgccaa cggcatcgcc  5400
gagtggatca gcagcaacag cagaagccag gcctacaagg tgacctgcag cgtgagacag  5460
agcagcgccc agaacagaaa gtacaccatc aaggtggagg tgcccaaggg cgcctggaga  5520
agctacctga acatggagct gaccatcccc atcttcgcca ccaacagcga ctgcgagctg  5580
atcgtgaagg ccatgcaggg cctgctgaag gacggcaacc ccatccccag cgccatcgcc  5640
gccaacagcg gcatctacga ctacaaagac gatgacgaca agtaaagcaa cctacaaacg  5700
ggtggaggat caccccaccc gacacttcac aatcaagggg tacaatacac aagggtggag  5760
gaacacccca ccctccagac acattacaca gaaatccaat caaacagaag caccatcagg  5820
gcttctgcta ccaaatttat ctcaaaaaac tacaacaagg aatcaccatc agggattccc  5880
tgtgcaatat acgtcaaacg agggccacga cgggaggacg atcacgcctc ccgaatatcg  5940
gcatgtctgg ctttcgaatt cagtgcgtgg agcatcagcc cacgcagcca atcagagtcg  6000
aatacaagtc gactttcgcg aagagcatca gccttcgcgc cattcttaca caaaccacac  6060
tctcccctac aggaacagca tcagcgttcc tgcccagtac ccaactcaag aaaatttatg  6120
tccccatgca gcatcagcgc atgggcccca agaatacatc cccaacaaaa tcacatccga  6180
gcaccaacag ggctcggagt gttgtttctt gtccaactgg acaaaccctc catggaccat  6240
caggccatgg actctcacca acaagacaaa aactactctt ctcgaagcag catcagcgct  6300
tcgaaacact cgagcataca ttgtgcctat ttcttgggtg gacgatcacg ccacccatgc  6360
tctcacgaat ttcaaaacac ggacaaggac gagcaccacc agggctcgtc gttccacgtc  6420
caatacgatt acttaccttt cgggatcacg atcacggatc ccgcagctac atcacttcca  6480
ctcaggacat tcaagcatgc acgatcacgg catgctccac aagtctcaac cacagaaact  6540
accaaatggg ttcagcacca gcgaacccac tcctacctca aacctcttcc cacaaaactg  6600
gcaagcagga tcaccgcttg cccattccaa cataccaaat caaaaacaat tactggtaca  6660
gcatcagcgt accagcccac atctctcact actatcaaaa accaaaccgt tcagcaacag  6720
cgaacggtac acacggaaaa atcaactggt ttacaaatac gaaagacgat cacgctttcg  6780
tccagcgcaa actattacga aaaacatccg acgggaagag caacagcctt cccgcggcgg  6840
aaaacctcac aaaaacacga caaacggatg cacgaacacg gcatccgccg acaacccaca  6900
aacttacaac caggcaaacg gtgcaggatc accgcaccgt acatcaaaca cctcagatct  6960
catgcttcta gaagttgtct cctcctgcac tgactgactg atacaatcga tttctggatc  7020
cgcaggccta atcaacctct ggattacaaa atttgtgaaa gattgactgg tattcttaac  7080
tatgttgctc cttttacgct atgtggatac gctgctttaa tgcctttgta tcatgctatt  7140
gcttcccgta tggctttcat tttctcctcc ttgtataaat cctggttgct gtctctttat  7200
gaggagttgt ggcccgttgt caggcaacgt ggcgtggtgt gcactgtgtt tgctgacgca  7260
acccccactg gttggggcat tgccaccacc tgtcagctcc tttccgggac tttcgctttc  7320
cccctcccta ttgccacggc ggaactcatc gccgcctgcc ttgcccgctg ctggacaggg  7380
gctcggctgt tgggcactga caattccgtg gtgttgtcgg ggaagctgac gtcctttcca  7440
tggctgctcg cctgtgttgc cacctggatt ctgcgcggga cgtccttctg ctacgtccct  7500
tcggccctca atccagcgga ccttccttcc cgctgagaga cacaaaaaat tccaacacac  7560
tattgcaatg aaaataaatt tcctttatta gccagaagtc agatgctcaa ggggcttcat  7620
gatgtcccca taatttttgg cagagggaaa aagatctcag tggtatttgt gagccagggc  7680
attggccttc tgataggcag cctgcacctg aggagtgcgg ccgctttact tgtacagctc  7740
gtccatgccg agagtgatcc cggcggcggt cacgaactcc agcaggacca tgtgatcgcg  7800
cttctcgttg gggtctttgc tcagggcgga ctgggtgctc aggtagtggt tgtcgggcag  7860
cagcacgggg ccgtcgccga tgggggtgtt ctgctggtag tggtcggcga gctgcacgct  7920
gccgtcctcg atgttgtggc ggatcttgaa gttcaccttg atgccgttct tctgcttgtc  7980
ggccatgata tagacgttgt ggctgttgta gttgtactcc agcttgtgcc ccaggatgtt  8040
gccgtcctcc ttgaagtcga tgcccttcag ctcgatgcgg ttcaccaggg tgtcgccctc  8100
gaacttcacc tcggcgcggg tcttgtagtt gccgtcgtcc ttgaagaaga tggtgcgctc  8160
ctggacgtag ccttcgggca tggcggactt gaagaagtcg tgctgcttca tgtggtcggg  8220
gtagcggctg aagcactgca cgccgtaggt cagggtggtc acgagggtgg gccagggcac  8280
gggcagcttg ccggtggtgc agatgaactt cagggtcagc ttgccgtagg tggcatcgcc  8340
ctcgccctcg ccggacacgc tgaacttgtg gccgtttacg tcgccgtcca gctcgaccag  8400
gatgggcacc accccggtga acagctcctc gcccttgctc accatggtgg cgggatctga  8460
cggttcacta aaccagctct gcttatatag acctcccacc gtacacgcct accgcccatt  8520
tgcgtcaatg gggcggagtt gttacgacat tttggaaagt cccgttgatt ttggtgccaa  8580
```

```
aacaaactcc cattgacgtc aatggggtgg agacttggaa atccccgtga gtcaaaccgc  8640
tatccacgcc cattgatgta ctgccaaaac cgcatcacca tggtaatagc gatgactaat  8700
acgtagatgt actgccaagt aggaaagtcc cataaggtca tgtactgggc ataatgccag  8760
gcgggccatt taccgtcatt gacgtcaata gggggcgtac ttggcatatg atacacttga  8820
tgtactgcca agtgggcagt ttaccgtaaa tactccaccc attgacgtca atggaaagtc  8880
cctattggcg ttactatggg aacatacgtc attattgacg tcaatgggcg ggggtcgttg  8940
ggcggtcagc caggcgggcc atttaccgta agttatgtaa cgggcctgct gccggctctg  9000
cggcctcttc cgcgtcttcg ccttcgccct cagacgagtc ggatctccct ttgggccgcc  9060
tccccgcctg tctagcttga ctgactgaga tacagcgtac cttcagctca cagacatgat  9120
aagatacatt gatgagtttg gacaaaccac aactagaatg cagtgaaaaa aatgctttat  9180
ttgtgaaatt tgtgatgcta ttgctttatt tgtaaccatt ataagctgca ataaacaagt  9240
t                                                                 9241

SEQ ID NO: 50          moltype = DNA  length = 7309
FEATURE                Location/Qualifiers
misc_feature           1..7309
                       note = Description of Artificial Sequence: Synthetic
                        polynucleotide
source                 1..7309
                       mol_type = other DNA
                       organism = synthetic construct
SEQUENCE: 50
taatacgact cactataggg agaagtactg ccaccatggg caagaagcaa aatcgcaaga  60
cggggaattc caagacacaa tccgctagcc caccacctaa agagcgttct agctcccctg  120
ctactgagca gtcctggatg gaaaacgact tcgatgaact ccgggaagag ggatttaggc  180
gatccaacta ttcagaactc cgcgaagata tccagacaaa ggggaaggaa gtcgagaatt  240
tcgagaagaa cctcgaggag tgcatcaccc gtatcacaaa cactgagaaa tgtctcaaag  300
aactcatgga acttaagaca aaagccaggg agcttcgaga ggagtgtcgg agtctgagat  360
ccaggtgtga ccagctcgag gagcgcgtga gcgcgatgga agacgagatg aacgagatga  420
aaagagaggg caaattcagg gagaagcgca ttaagaggaa cgaacagagt ctgcaggaga  480
tttgggatta cgtcaagagg cctaacctgc ggttgatcgg cgtccccgag agcgacgtag  540
aaaacgggac taaactggag aatacacttc aagacatcat tcaagaaaat tttccaaacc  600
tggctcggca agctaatgtg caaatccaag agatccaacg cacaccccag cggtatagct  660
ctcggcgtgc cacccctagg catattatcg tgcgctttac taaggtggag atgaaagaga  720
agatgctgcg agccgctcgg gaaaagggaa gggtgacttt gaagggcaaa cctattcggc  780
tgacggttga ccttagcgcc gagacactcc aggcacgccg ggaatggggc cccatcttta  840
atatcctgaa ggagaagaac ttccagccac gaatctctta ccctgcaaag ttgagtttta  900
tctccgaggg tgagattaag tatttcatcg ataaacagat gctgcgagac ttcgtgacaa  960
ctcgcccagc tctcaaggaa ctgctcaaag aggctcttaa tatggagcgc aataatagat  1020
atcaaccctt gcagaaccac gcaaagatgt gagacagccg tcagaccatc aagactagga  1080
agaaactgca tcaactaatg agcaaaatca ccagctaaca tcatagtata catggtcata  1140
ggaacttaca tttcgattat taccttaaac gtgaatgggt taaatgcccc aaccaagaga  1200
catcggctgg ctgaatggat tcagaaacag gacccctata tttgctgtct gcaggagacc  1260
cacttccgtc ctcgcgacac atacagactg aaagtgaggg gctggaaaaa gatcttccat  1320
gccaatggaa atcaaaagaa agctggagtg gctattctca tctcagataa aattgacttc  1380
aaaataaaga atgttactcg agataaggag ggacactaca taatgatcca ggggtccatc  1440
caagaagagg atataactat tattaatatt tatgcaccca acattggcgc ccctcagtac  1500
atcaggcagc tgcttacagc tatcaaggag gaaatcgaca gtaacacgat tatcgtgggg  1560
gactttaaca ccagccttac tccgatggat agatcatcca aaatgaaaat aaataaggaa  1620
acagaggctc ttaatgacac cattgaccag atagatctga ttgatatata taggacattc  1680
catccaaaaa ctgccgatta cactttcttc agcagtgcgc atggaacctt ctccaggata  1740
gatcacatct tgggtcacaa aagtagcctc agtaagttta agaaaattga aatcattagc  1800
agcatctttt ctgaccataa cgctatgcgc ctggagatga atcacaggga gaagaacgta  1860
aagaagacaa acacctggag gctgaacaat acgctgctaa ataaccaaga gatcactgag  1920
gaaatcaaac aggaaataaa aaaatacttg gagacaaatg acaatgaaaa cacgaccacc  1980
cagaacttgt gggatgcagc taaagcggtt ctgagaggga agtttatagc tattcaagcc  2040
taccttaaga aacaggaaaa atctcaagtg aacaatttga ccttacacct aaagaaactg  2100
gagaaggagg agcagaccaa acccaaagtg agcaggagga aagaaatcat caagatcaga  2160
gccgaaatca atgaaataga aactaagaag acaattgcca agatcaataa aactaaatcc  2220
tggttctttg agaagatcaa caaaattgat aagccattag ccagactcat caagaaaaag  2280
agggagagga ctcagatcaa taagatcaga aatgagaaag gggaagttac aaccgacacc  2340
gcggagattc agaacatcct gagagactac tacaagcaac tttatgccaa taaaatggac  2400
aacctggaag aaatggacaa attcctggaa aggtataacc ttccccggct gaaccaggag  2460
gagactgaaa atatcaaccg cccaatcaca agtaatgaga ttgagactgt gattaagaat  2520
cttccaacta acaaaagtcc cggccccgat ggcttcacag gtgaattcta tcagaccttt  2580
cgggaggagt tgacacccat ccttctcaag ctcttccaaa aaattgcaga ggagggcaca  2640
ctcccgaact cattctatga ggccaccatc accctgatcc caaagcccga caaggacact  2700
acaaagaaag aaaattaccg accaatttcc ctgatgaata tcgatgccaa gatcctcaac  2760
aaaatcttgg caaacagaat ccagcagcac attaagagga tcatacacca cgatcaggtg  2820
ggctttatcc cggggatgca aggattcttc aatatccgca aatcaatcaa tgtgatccac  2880
catattaaca agttgaagaa gaagaaccat atgatcatct ccatcgatgc agagaaagct  2940
tttgacaaaa ttcaacaccc atttatgatc aaaactctcc agaaggtggg catcgagggg  3000
acctacctca acataattaa ggccatctat gataagccca cagccaacat cattctcaat  3060
ggtgaaaagc tgaaggcatt tcctctgcgg tccggaacga gacagggatg tcctctctct  3120
cctcttctgt tcaacatcgt tctggaagtc ctagccaccg ctatccgcga ggaaaaggaa  3180
attaaaggca tacagattgg aaaggaagag gtaaaactgt ctctgtttgc ggatgatatg  3240
atactgtaca tagagaatcc taaaactgcc acccggaagc tgttggagct aattaatgag  3300
tatggtaagg tcgccggtta caagattaat gctcagaagt ctcttgcttt cctgtacact  3360
aatgatgaaa agtctgaacg ggaaattatg gagacactcc cctttaccat tgcaaccaaa  3420
```

-continued

```
cgtattaaat accttggcat taacctgcct aaggagacaa aagacctgta tgctgaaaac  3480
tataagacac tgatgaaaga gattaaagat gataccaacc ggtggcggga tatcccatgt  3540
tcttggattg gcagaatcaa cattgtgaag atgagcatcc tgcccaaggc catctacaga  3600
ttcaatgcca tccctatcaa attacctatg gcatttttta cggagctgga acagatcatc  3660
ttaaaatttg tgtggcgcca caagcggccc cgaatcgcca aagcggtctt gaggcagaag  3720
aatggcgctg gggaatccg actccctgac ttcagattgt actacaaagc taccgtcatc  3780
aagacaatct ggtactggca caagaacaga aacatcgatc agtggaacaa gatcgaaagc  3840
cctgagatta acccccgcac ctatggtcaa ctgatctatg acaaaggggg caaggatata  3900
caatggcgca aggacagcct cttcaataag tggtgctggg aaaactggac agccacctgc  3960
aagcgtatga agctggagta ctccctgaca ccatacacaa aaataaactc aaagtggatt  4020
cgagacctca atattcggct ggacactata aaactcctgg aggagaacat tgggcgtaca  4080
ctctttgaca ttaatcatag caagatcttt ttcgatcccc ctcctcgtgt aatggaaata  4140
aaaacaaaaa taaacaagtg ggatctgatg aaacttcaga gcttttgcac cgcaaaggag  4200
accataaaca agacgaagcg ccaaccctca gaatgggaga aaatatttgc gaatgagtct  4260
acggacaaag gcttaatctc caaaatatat aagcagctca ttcagctcaa tatcaaggaa  4320
acaaacaccc cgatccaaaa gtgggcagag gacctaaatc ggcatttctc caaggaagac  4380
atccagacgg ccacgaagca catgaagcga tgctcaactt ccctgattat tcgcgaaatg  4440
cagatcaaga ctactatgcg ctatcacctc actcctgttc ggatgggcat catccggaaa  4500
tctacaaaca acaagtgctg gagagggtgt ggcgaaaagg gaaccctctt gcattgttgg  4560
tgggagtgta agttgatcca gccactatgg cggaccatat ggaggttcct taaaaaactg  4620
aagattgagc tgccatatga cccagcaatc ccactgctgg gcatataccc ggagaaaacc  4680
gtgattcaga aagacacttg cacccgaatg ttcattgcag cattgtttac aatagccagg  4740
tcatggaagc agcctaagtg cccctcgaca gacgagtgga tcaagaagat gtggtacatt  4800
tatactatgg aatattacag cgccatcaaa cgcaacgaaa ttgggtcttt tctggagacg  4860
tggatggatc tagagactgt catccagagt gaggtaagtc agaaagagaa gaacaaatat  4920
cgtattttaa cgcatatttg tggaacctgg aagaatggta cagatgagcc ggtctgccga  4980
accgagattg agacccagat ggactacaaa gacgatgacg acaagtgaag cgcttctaga  5040
agttgtctcc tcctgcactg actgactgat acaatcgatt tctggatccg caggcctaat  5100
caacctctgg attacaaaat ttgtgaaaga ttgactggta ttcttaacta tgttgctcct  5160
tttacgctat gtggatacgc tgctttaatg cctttgtatc atgctattgc ttcccgtatg  5220
gctttcattt tctcctcctt gtataaatcc tggttgctgt ctctttatga ggagttgtgg  5280
cccgttgtca ggcaacgtgg cgtggtgtgc actgtgtttg ctgacgcaac ccccactggt  5340
tggggcattg ccaccacctg tcagctcctt tccgggactt tcgctttccc cctccctatt  5400
gccacggcgg aactcatcgc cgcctgcctt gcccgctgct ggacaggggc tcggctgttg  5460
ggcactgaca attccgtggt gttgtcgggg aagctgacgt cctttccatg gctgctcgcc  5520
tgtgttgcca cctggattct gcgcgggacg tccttctgct acgtcccttc ggccctcaat  5580
ccagcggacc ttccttcccg ctgagagaca caaaaaattc caacacacta ttgcaatgaa  5640
aataaatttc ctttattagc cagaagtcag atgctcaagg ggcttcatga tgtccccata  5700
atttttggca gagggaaaaa gatctcagtg gtatttgtga gccagggcat tggccttctg  5760
ataggcagcc tgcacctgag gagtgcggcc gctttacttg tacagctcgt ccatgccgag  5820
agtgatcccg gcggcggtca cgaactccag caggaccatg tgatcgcgct tctcgttggg  5880
gtctttgctc agggcggact gggtgctcag gtagtggttg tcgggcagca gcacggggcc  5940
gtcgccgatg gggtgttct gctggtagtg gtcggcgagc tgcacgctgc cgtcctcgat  6000
gttgtggcgg atcttgaagt tcaccttgat gccgttcttc tgcttgtcgg ccatgatata  6060
gacgttgtgg ctgttgtagt tgtactccag cttgtgcccc aggatgttgc cgtcctcctt  6120
gaagtcgatg cccttcagct cgatgcggtt caccagggtg tcgccctcga acttcacctc  6180
ggcgcgggtc ttgtagttgc cgtcgtcctt gaagaagatg gtgcgctcct ggacgtagcc  6240
ttcgggcatg gcggacttga agaagtcgtg ctgcttcatg tggtcggggt agcggctgaa  6300
gcactgcacg ccgtaggtca gggtggtcac gagggtgggc cagggcacgg gcagcttgcc  6360
ggtggtgcag atgaacttca gggtcagctt gccgtaggtg gcatcgccct cgccctcgcc  6420
ggacacgctg aacttgtggc cgtttacgtc gccgtccagc tcgaccagga tgggcaccac  6480
cccggtgaac agctcctcgc ccttgctcac catggtggcg ggatctgacg gttcactaaa  6540
ccagctctgc ttatatagac ctcccaccgt acacgcctac cgcccatttg cgtcaatggg  6600
gcggagttgt tacgacattt tggaaagtcc cgttgatttt ggtgccaaaa caaactccca  6660
ttgacgtcaa tggggtggag acttggaaat ccccgtgagt caaaccgcta tccacgccca  6720
ttgatgtact gccaaaaccg catcaccatg gtaatagcga tgactaatac gtagatgtac  6780
tgccaagtag gaaagtccca taaggtcatg tactgggcat aatgccaggc gggccattta  6840
ccgtcattga cgtcaatagg gggcgtactt ggcatatgat acacttgatg tactgccaag  6900
tgggcagttt accgtaaata ctccacccat tgacgtcaat ggaaagtccc tattggcgtt  6960
actatgggaa catacgtcat tattgacgtc aatgggcggg ggtcgttggg cggtcagcca  7020
ggcgggccat ttaccgtaag ttatgtaacg ggcctgctgc cggctctgcg gcctcttccg  7080
cgtcttcgcc ttcgccctca gacgagtcgg atctcccttt gggccgcctc cccgcctgtc  7140
tagcttgact gactgagata cagcgtacct tcagctcaca gacatgataa gatacattga  7200
tgagtttgga caaaccacaa ctagaatgca gtgaaaaaaa tgctttattt gtgaaatttg  7260
tgatgctatt gctttatttg taaccattat aagctgcaat aaacaagtt             7309

SEQ ID NO: 51          moltype = RNA  length = 61
FEATURE                Location/Qualifiers
misc_feature           1..61
                       note = Description of Artificial Sequence: Synthetic
                        oligonucleotide
source                 1..61
                       mol_type = other RNA
                       organism = synthetic construct
SEQUENCE: 51
actcctcccc atcctctccc tctgtccctc tgtccctctg accctgcact gtcccagcac  60
c                                                                  61

SEQ ID NO: 52          moltype = RNA  length = 118
```

```
FEATURE                 Location/Qualifiers
misc_feature            1..118
                        note = Description of Artificial Sequence: Synthetic
                         polynucleotide
source                  1..118
                        mol_type = other RNA
                        organism = synthetic construct
SEQUENCE: 52
caggacacag ccttggatca ggacagagac ttgggggcca tcctgcccct ccaacccgac  60
atgtgtacct cagctttttc cctcacttgc atcaataaag cttctgtgtt tggaacag    118

SEQ ID NO: 53           moltype = RNA  length = 76
FEATURE                 Location/Qualifiers
misc_feature            1..76
                        note = Description of Artificial Sequence: Synthetic
                         oligonucleotide
source                  1..76
                        mol_type = other RNA
                        organism = synthetic construct
SEQUENCE: 53
ggaaggtttt tcttttcctg aggcgaaagt ctcaggtttt gctttttggc ctttcttaaa  60
aaaaaaaaaa gcaaaa                                                  76

SEQ ID NO: 54           moltype = RNA  length = 93
FEATURE                 Location/Qualifiers
misc_feature            1..93
                        note = Description of Artificial Sequence: Synthetic
                         oligonucleotide
source                  1..93
                        mol_type = other RNA
                        organism = synthetic construct
SEQUENCE: 54
gaaggttttt cttttcctga gaaaacaaca cgtattgttt tctcaggttt tgctttttgg  60
cctttttcta gcttaaaaaa aaaaaaagca aaa                               93

SEQ ID NO: 55           moltype = DNA  length = 19
FEATURE                 Location/Qualifiers
source                  1..19
                        mol_type = other DNA
                        organism = unidentified
SEQUENCE: 55
agatgtgtat aagagacag                                               19

SEQ ID NO: 56           moltype = DNA  length = 19
FEATURE                 Location/Qualifiers
misc_feature            1..19
                        note = Description of Unknown: Transposon end sequence
source                  1..19
                        mol_type = other DNA
                        organism = unidentified
SEQUENCE: 56
ctgtctctta tacacatct                                               19

SEQ ID NO: 57           moltype = AA  length = 338
FEATURE                 Location/Qualifiers
REGION                  1..338
                        note = Description of Artificial Sequence: Synthetic
                         polypeptide
source                  1..338
                        mol_type = protein
                        organism = synthetic construct
SEQUENCE: 57
MGKKQNRKTG NSKTQSASPP PKERSSSPAT EQSWMENDFD ELREEGFRRS NYSELREDIQ  60
TKGKEVENFE KNLEECITRI TNTEKCLKEL MELKTKAREL REECRSLRSR CDQLEERVSA  120
MEDEMNEMKR EGKFREKRIK RNEQSLQEIW DYVKRPNLRL IGVPESDVEN GTKLENTLQD  180
IIQENFPNLA RQANVQIQEI QRTPQRYSSR RATPRHIIVR FTKVEMKEKM LRAAREKGRV  240
TLKGKPIRLT VDLSAETLQA RREWGPIFNI LKEKNFQPRI SYPAKLSFIS EGEIKYFIDK  300
QMLRDFVTTR PALKELLKEA LNMERNNRYQ PLQNHAKM                          338

SEQ ID NO: 58           moltype = DNA  length = 1017
FEATURE                 Location/Qualifiers
misc_feature            1..1017
                        note = Description of Artificial Sequence: Synthetic
                         polynucleotide
source                  1..1017
                        mol_type = other DNA
                        organism = synthetic construct
SEQUENCE: 58
atgggcaaga agcaaaatcg caagacgggg aattccaaga cacaatccgc tagcccacca  60
```

-continued

```
cctaaagagc gttctagctc ccctgctact gagcagtcct ggatggaaaa cgacttcgat  120
gaactccggg aagagggatt taggcgatcc aactattcag aactccgcga agatatccag  180
acaaagggga aggaagtcga gaatttcgag aagaacctcg aggagtgcat cacccgtatc  240
acaaacactg agaaatgtct caaagaactc atggaactta agacaaaagc cagggagctt  300
cgagaggagt gtcggagtct gagatccagg tgtgaccagc tcgaggagcg cgtgagcgcg  360
atggaagacg agatgaacga gatgaaaaga gagggcaaat tcagggagaa gcgcattaag  420
aggaacgaac agagtctgca ggagatttgg gattacgtca agaggcctaa cctgcggttg  480
atcggcgtcc ccgagagcga cgtagaaaac gggactaaac tggagaatac acttcaagac  540
atcattcaag aaaatttcc aaacctggct cggcaagcta atgtgcaaat ccaagagatc  600
caacgcacac cccagcggta tagctctcgg cgtgccaccc ctaggcatat tatcgtgcgc  660
tttactaagg tggagatgaa agagaagatg ctgcgagccg ctcgggaaaa gggaagggtg  720
actttgaagg gcaaacctat tcggctgacg gttgacctta gcgccgagac actccaggca  780
cgccgggaat ggggccccat ctttaatatc ctgaaggaga agaacttcca gccacgaatc  840
tcttaccctg caaagttgag ttttatctcc gagggtgaga ttaagtattt catcgataaa  900
cagatgctgc gagacttcgt gacaactcgc ccagctctca aggaactgct caaagaggct  960
cttaatatgg agcgcaataa tagatatcaa cccttgcaga accacgcaaa gatgtga     1017

SEQ ID NO: 59          moltype = AA  length = 1275
FEATURE                Location/Qualifiers
REGION                 1..1275
                       note = Description of Artificial Sequence: Synthetic
                        polypeptide
source                 1..1275
                       mol_type = protein
                       organism = synthetic construct
SEQUENCE: 59
MTGSNSHITI LTLNINGLNS AIKRHRLASW IKSQDPSVCC IQETHLTCRD THRLKIKGWR  60
KIYQANGKQK KAGVAILVSD KTDFKPTKIK RDKEGHYIMV KGSIQQEELT ILNIYAPNTG  120
APRFIKQVLS DLQRDLDSHT LIMGDFNTPL STLDRSTRQK VNKDTQELNS ALHQADLIDI  180
YRTLHPKSTE YTFFSAPHHT YSKIDHIVGS KALLSKCKRT EIITNYLSDH SAIKLELRIK  240
NLTQSRSTTW KLNNLLLNDY WVHNEMKAEI KMFFETNENK DTTYQNLWDA FKAVCRGKFI  300
ALNAYKRKQE RSKIDTLTSQ LKELEKQEQT HSKASRRQEI TKIRAELKEI ETQKTLQKIN  360
ESRSWFFERI NKIDRPLARL IKKKREKNQI DTIKNDKGDI TTDPTEIQTT IREYYKHLYA  420
NKLENLEEMD TFLDTYTLPR LNQEEVESLN RPITGSEIVA IINSLPTKKS PGPDGFTAEF  480
YQRYMEELVP FLLKLFQSIE KEGILPNSFY EASIILIPKP GRDTTKKENF RPISLMNIDA  540
KILNKILANR IQQHIKKLIH HDQVGFIPGM QGWFNIRKSI NVIQHINRAK DKNHMIISID  600
AEKAFDKIQQ PFMLKTLNKL GIDGTYFKII RAIYDKPTAN IILNGQKLEA FPLKTGTRQG  660
CPLSPLLFNI VLEVLARAIR QEKEIKGIQL GKEEVKLSLF ADDMIVYLEN PIVSAQNLLK  720
LISNFSKVSG YKINVQKSQA FLYTNNRQTE SQIMGELPFV IASKRIKYLG IQLTRDVKDL  780
FKENYKPLLK EIKEDTNKWK NIPCSWVGRI NIVKMAILPK VIYRFNAIPI KLPMTFFTEL  840
EKTTLKFIWN QKRARIAKSI LSQKNKAGGI TLPDFKLYYK ATVTKTAWYW YQNRDIDQWN  900
RTEPSEIMPH IYNYLIFDKP EKNKQWGKDS LFNKWCWENW LAICRKLKLD PFLTPYTKIN  960
SRWIKDLNVK PKTIKTLEEN LGITIQDIGV GKDFMSKTPK AMATKDKIDK WDLIKLKSFC  1020
TAKETTIRVN RQPTTWEKIF ATYSSDKGLI SRIYNELKQI YKKKTNNPIK KWAKDMNRHF  1080
SKEDIYAAKK HMKKCSSSLA IREMQIKTTM RYHLTPVRMA IIKKSGNNRC WRGCGEIGTL  1140
LHCWWDCKLV QPLWKSVWRF LRDLELEIPF DPAIPLLGIY PNEYKSCCYK DTCTRMFIAA  1200
LFTIAKTWNQ PKCPTMIDWI KKMWHIYTME YYAAIKNDEF ISFVGTWMKL ETIILSKLSQ  1260
EQKTKHRIFS LIGGN                                                   1275

SEQ ID NO: 60          moltype = DNA  length = 3828
FEATURE                Location/Qualifiers
misc_feature           1..3828
                       note = Description of Artificial Sequence: Synthetic
                        polynucleotide
source                 1..3828
                       mol_type = other DNA
                       organism = synthetic construct
SEQUENCE: 60
atgaccggct ctaactcaca tatcaccatc cttacactta acattaacgg cctcaactca  60
gctatcaagc gccatcggct ggccagctgg atcaaatcac aggatccaag cgtttgttgc  120
atccaagaga cccacctgac ctgtagagat actcaccgcc tcaagatcaa gggatggcga  180
aagatttatc aggcgaacgg taagcagaag aaagccggag tcgcaattct ggtctcagac  240
aagacggatt tcaagcccac caaaattaag cgtgataagg aaggtcacta tattatggtg  300
aaaggcagca tacagcagga agaacttacc atattgaaca tctacgcgcc aaacaccggc  360
gcacctcgct ttatcaaaca ggtcctgtcc gatctgcagc gagatctgga ttctcatacg  420
ttgattatgg gtgatttcaa tacaccattg agcaccctgg atcgcagcac caggcaaaag  480
gtaaataaag acacgcaaga gctcaatagc gcactgcatc aggcagatct cattgatatt  540
tatcgcactc ttcatcctaa gagtaccgag tacacattct tcagcgcccc acatcataca  600
tactcaaaga tcgatcatat cgtcggctca aaggctctgc tgtcaaagtg caagcgcaca  660
gagataatta caaattacct gtcagatcat agcgcgatca agctcgagct gagaatcaag  720
aacctgaccc agagccggag taccacttgg aagcttaata acctgctgct caacgattat  780
tgggtccaca atgagatgaa ggcagagatt aaaatgttct tcgaaacaaa tgagaataag  840
gatactacct atcaaaacct ttgggatgcc tttaaggccg tctgcagagg caagttcatc  900
gccctcaacg cctataaaag aaaacaagag agatctaaga tcgatactct cacctctcag  960
ctgaaggagt tggagaaaca ggaacagacc cactccaagg cgtcaagacg gcaggagatc  1020
acaaagattc gcgccgagtt gaaagagatc gaaacccaaa agactcttca gaaaattaac  1080
gagtctcgta gttggttctt cgagcggatt aataagatag acagacctct ggcacgactg  1140
attaagaaga agcgcgaaaa gaaccagatt gataccatca agaacgacaa gggcgacatc  1200
actactgacc cgaccgagat ccagaccact attcgggagt attataagca tttgtatgct  1260
```

```
aacaagcttg agaacctgga agagatggac acttttctgg atacctatac tctgccacgg  1320
cttaatcaag aggaagtcga gtccctcaac cgcccaatta caggaagcga gattgtggcc  1380
ataattaact ccctgccgac aaagaaatct cctggtccgg acgggtttac agctgagttt  1440
tatcaacggt atatggaaga gcttgtaccg tttctgctca agctctttca gtctatagaa  1500
aaggaaggca tcttgcccaa ttccttctac gaagcttcta taatacttat tcccaaacca  1560
ggacgcgata ccacaaagaa ggaaaacttc cggcccatta gtctcatgaa tatcgacgct  1620
aaaatattga acaagattct cgccaacaga atccaacaac atattaagaa attgatacat  1680
cacgaccagg tggggtttat acctggcatg cagggctggt ttaacatccg gaagagtatt  1740
aacgtcattc aacacattaa tagagctaag gataagaatc atatgatcat ctctatagac  1800
gcggaaaagg cattcgataa gattcagcag ccatttatgc tcaagactct gaacaaactc  1860
ggcatcgacg gaacatattt taagattatt cgcgcaattt acgataagcc gactgctaac  1920
attatcctta acggccaaaa gctcgaggcc tttccgctca agactggaac ccgccaaggc  1980
tgtcccctct ccccgctttt gtttaatatt gtactcgagg tgctggctag ggctattcgt  2040
caagagaaag agattaaagg gatacagctc gggaaggaag aggtcaagct ttccttgttc  2100
gccgatgata tgattgtgta cctggagaat cctattgtgt ctgctcagaa ccttcttaaa  2160
cttatttcta actttagcaa ggtcagcggc tataagatta acgtccagaa atctcaggcc  2220
tttctgtaca caaataatcg acagaccgaa tcccagataa tgggtgagct tccgtttgtc  2280
atagccagca aaaggataaa gtatctcgga atccagctga cacgagacgt taaagatttg  2340
tttaaggaaa attacaagcc tctcctgaaa gagattaagg aagatactaa taagtggaag  2400
aatatcccct gttcatgggt tggcagaatc aacatagtga agatggcaat acttcctaaa  2460
gtgatatatc gctttaacgc catcccaatt aaactgccta tgaccttctt tacggagctc  2520
gagaaaacaa cccttaaatt tatatggaat caaaagagag caagaatagc gaagtccatc  2580
ttgagccaga agaataaggc cggtgggatt actttgcctg attttaagtt gtattataaa  2640
gccacagtaa ctaagacagc ctggtattgg tatcagaata gagacatcga ccagtggaat  2700
cggaccgaac catcagagat aatgccccac atctataatt accttatatt cgataagcca  2760
gaaaagaata aacagtgggg caaagacagc ctcttcaaca agtggtgttg ggagaattgg  2820
ctggccatat gccggaaact caagctcgac ccctttctta caccctacac taaaatcaac  2880
agtaggtgga tcaaggactt gaatgtcaag ccaaagacta taaagacact ggaagagaat  2940
cttgggatca caatacaaga tataggcgtc ggcaaagatt ttatgtcaaa gacgcccaag  3000
gccatggcca ctaaggataa gattgataag tgggacctta ttaagctcaa aagcttctgt  3060
actgccaagg agaccacgat cagagttaat aggcagccca ctacatggga aaagattttc  3120
gccacttatt catcagataa ggggttgata agcagaatat ataacgagct gaagcagatc  3180
tacaagaaga aaacgaataa tcccatcaag aagtgggcaa aagatatgaa caggcatttt  3240
agcaaagagg atatctacgc cgcgaagaag catatgaaga agtgtagttc aagcttggcc  3300
attcgtgaga tgcagattaa gacgaccatg cgataccacc ttaccccagt gaggatggca  3360
attatcaaga aatctggcaa taatagatgt tggcggggct gtggcgagat tggcaccctg  3420
ctccattgct ggtgggattg caagctggtg cagccgcttt ggaaatcagt ctggcgcttt  3480
ctgagggacc tcgagcttga gattcccttc gatcccgcaa ttcccttgct cggaatctat  3540
cctaacgaat acaagagctg ttgttacaag gatacgtgta cccggatgtt catcgcggcc  3600
ttgtttacga tagctaagac gtggaatcag cctaagtgcc ccacaatgat cgattggatc  3660
aagaaaatgt ggcatattta taccatggag tattacgcag caattaagaa tgacgaattt  3720
atttccttcg ttgggacctg gatgaagctg gagactatta ttctgagcaa gctgtctcag  3780
gagcaaaaga caaagcatag aatcttctct ctcattggtg gtaactaa              3828

SEQ ID NO: 61          moltype = AA  length = 1290
FEATURE                Location/Qualifiers
REGION                 1..1290
                       note = Description of Artificial Sequence: Synthetic
                        polypeptide
source                 1..1290
                       mol_type = protein
                       organism = synthetic construct
SEQUENCE: 61
MVIGTYISII TLNVNGLNAP TKRHRLAEWI QKQDPYICCL QETHFRPRDT YRLKVRGWKK  60
IFHANGNQKK AGVAILISDK IDFKIKNVTR DKEGHYIMIQ GSIQEEDITI INIYAPNIGA  120
PQYIRQLLTA IKEEIDSNTI IVGDFNTSLT PMDRSSKMKI NKETEALNDT IDQIDLIDIY  180
RTFHPKTADY TFFSSAHGTF SRIDHILGHK SSLSKFKKIE IISSIFSDHN AMRLEMNHRE  240
KNVKKTNTWR LNNTLLNNQE ITEEIKQEIK KYLETNDNEN TTTQNLWDAA KAVLRGKFIA  300
IQAYLKKQEK SQVNNLTLHL KKLEKEEQTK PKVSRRKEII KIRAEINEIE TKKTIAKINK  360
TKSWFFEKIN KIDKPLARLI KKKRERTQIN KIRNEKGEVT TDTAEIQNIL RDYYKQLYAN  420
KMDNLEEMDK FLERYNLPRL NQEETENINR PITSNEIETV IKNLPTNKSP GPDGFTGEFY  480
QTFREELTPI LLKLFQKIAE EGTLPNSFYE ATITLIPKPD KDTTKKENYR PISLMNIDAK  540
ILNKILANRI QQHIKRIIHH DQVGFIPGMQ GFFNIRKSIN VIHHINKLKK KNHMIISIDA  600
EKAFDKIQHP FMIKTLQKVG IEGTYLNIIK AIYDKPTANI ILNGEKLKAF PLRSGTRQGC  660
PLSPLLFNIV LEVLATAIRE EKEIKGIQIG KEEVKLSLFA DDMILYIENP KTATRKLLEL  720
INEYGKVAGY KINAQKSLAF LYTNDEKSER EIMETLPFTI ATKRIKYLGI NLPKETKDLY  780
AENYKTLMKE IKDDTNRWRD IPCSWIGRIN IVKMSILPKA IYRFNAIPIK LPMAFFTELE  840
QIILKFVWRH KRPRIAKAVL RQKNGAGGIR LPDFRLYYKA TVIKTIWYWH KNRNIDQWNK  900
IESPEINPRT YGQLIYDKGG KDIQWRKDSL FNKWCWENWT ATCKRMKLEY SLTPYTKINS  960
KWIRDLNIRL DTIKLLEENI GRTLFDINHS KIFFDPPPRV MEIKTKINKW DLMKLQSFCT  1020
AKETINKTKR QPSEWEKIFA NESTDKGLIS KIYKQLIQLN IKETNTPIQK WAEDLNRHFS  1080
KEDIQTATKH MKRCSTSLII REMQIKTTMR YHLTPVRMGI IRKSTNNKCW RGCGEKGTLL  1140
HCWWECKLIQ PLWRTIWRFL KKLKIELPYD PAIPLLGIYP EKTVIQKDTC TRMFIAALFT  1200
IARSWKQPKC PSTDEWIKKM WYIYTMEYYS AIKRNEIGSF LETWMDLETV IQSEVSQKEK  1260
NKYRILTHIC GTWKNGTDEP VCRTEIETQM                                  1290

SEQ ID NO: 62          moltype = DNA  length = 3873
FEATURE                Location/Qualifiers
misc_feature           1..3873
```

```
                        note = Description of Artificial Sequence: Synthetic
                         polynucleotide
source                  1..3873
                        mol_type = other DNA
                        organism = synthetic construct
SEQUENCE: 62
atggtcatag gaacatacat atcgataatt accttaaacg tgaatggatt aaatgcccca  60
accaaaagac atagactggc tgaatggata caaaaacaag acccatatat atgctgtcta  120
caagagaccc acttcagacc tagggacaca tacagactga aagtgagggg atggaaaaag  180
atattccatg caaatggaaa tcaaaagaaa gctggagtag ctatactcat atcagataaa  240
atagacttta aaataaagaa tgttacaaga gacaaggaag gacactacat aatgatccag  300
ggatcaatcc aagaagaaga tataacaatt ataaatatat atgcacccaa cataggagca  360
cctcaataca taaggcaact gctaacagct ataaaagagg aaatcgacag taacacaata  420
atagtggggg actttaacac ctcacttaca ccaatggaca gatcatccaa aatgaaaata  480
aataaggaaa cagaagcttt aaatgacaca atagaccaga tagatttaat tgatatatat  540
aggacattcc atccaaaaac agcagattac acgttcttct caagtgcgca cggaacattc  600
tccaggatag atcacatctt gggtcacaaa tcaagcctca gtaaatttaa gaaaattgaa  660
atcatatcaa gcatcttttc tgaccacaac gctatgagat tagaaatgaa tcacagggaa  720
aaaaacgtaa aaaagacaaa cacatggagg ctaaacaata cgttactaaa taaccaagag  780
atcactgaag aaatcaaaca ggaaataaaa aaatacctag agacaaatga caatgaaaac  840
acgacgaccc aaaacctatg ggatgcagca aaagcggttc taagagggaa gtttatagct  900
atacaagcct acctaaagaa acaagaaaaa tctcaagtaa acaatctaac cttacaccta  960
aagaaactag agaaagaaga acaaacaaaa cccaaagtta gcagaaggaa agaaatcata  1020
aagatcagag cagaaataaa tgaaatagaa acaaagaaaa caatagcaaa gatcaataaa  1080
actaaaagtt ggttctttga gaagataaac aaaattgata agccattagc cagactcatc  1140
aagaaaaaga gggagaggac tcaaatcaat aaaatcagaa atgaaaaagg agaagttaca  1200
acagacaccg cagaaataca aaacatccta agagactact acaagcaact ttatgccaat  1260
aaaatggaca acctggaaga aatggacaaa ttcttagaaa ggtataacct tccaagactg  1320
aaccaggaag aaacagaaaa tatcaacaga ccaatcacaa gtaatgaaat tgaaactgtg  1380
attaaaaatc ttccaacaaa caaaagtcca ggaccagatg gcttcacagg tgaattctat  1440
caaacattta gagaagagct aacacccatc cttctcaaac tcttccaaaa aattgcagaa  1500
gaaggaacac tcccaaactc attctatgag gccaccatca ccctgatacc aaaaccagac  1560
aaagacacta caaaaaaaga aaattacaga ccaatatcac tgatgaatat agatgcaaaa  1620
atcctcaaca aaatactagc aaacagaatc caacaacaca ttaaaaggat catacaccac  1680
gatcaagtgg gatttatccc agggatgcaa ggattcttca atatacgcaa atcaatcaat  1740
gtgatacacc atattaacaa attgaagaag aaaaaccata tgatcatctc aatagatgca  1800
gaaaaagctt ttgacaaaat tcaacaccca tttatgataa aaactctcca gaaagtgggc  1860
atagagggaa cctacctcaa cataataaag gccatatatg acaaacccac agcaaacatc  1920
attctcaatg gtgaaaaact gaaagcattt cctctaagat caggaacgag acaaggatgt  1980
ccactctcac cactattatt caacatagtt ctggaagtcc tagccacggc aatcagagaa  2040
gaaaaagaaa taaaaggaat acaaattgga aaagaagaag taaaactgtc actgtttgcg  2100
gatgacatga tactatacat agagaatcct aaaactgcca ccagaaaact gctagagcta  2160
attaatgaat atggtaaagt tgcaggttac aaaattaatg cacagaaatc tcttgcattc  2220
ctatacacta atgatgaaaa atctgaaaga gaaattatgg aaacactccc atttaccatt  2280
gcaacaaaaa gaataaaata cctaggaata aacctaccta aggagacaaa agacctgtat  2340
gcagaaaact ataagacact gatgaaagaa attaaagatg ataccaacag atggagagat  2400
ataccatgtt cttggattgg aagaatcaac attgtgaaaa tgagtatact acccaaagca  2460
atctacagat tcaatgcaat ccctatcaaa ttaccaatgg catttttttac ggagctagaa  2520
caaatcatct taaaatttgt atggagacac aaaagacccc gaatagccaa agcagtcttg  2580
aggcaaaaaa atggagctgg aggaatcaga ctccctgact tcagactata ctacaaagct  2640
acagtaatca agacaatatg gtactggcac aaaaacagaa acatagatca atggaacaag  2700
atagaaagcc cagagattaa ccccacgcacc tatggtcaac taatctatga caaaggaggc  2760
aaagatatac aatggagaaa agacagtctc ttcaataagt ggtgctggga aaactggaca  2820
gccacatgta aaagaatgaa attagaatac tccctaacac catacacaaa aataaactca  2880
aaatggatta gagacctaaa tataagactg gacactataa aactcttaga ggaaaacata  2940
ggaagaacac tctttgacat aaatcacagc aagatctttt tcgatccacc tcctagagta  3000
atggaaataa aaacaaaaat aaacaagtgg gacctaatga aacttcaaag cttttgcaca  3060
gcaaaggaaa ccataaacaa gacgaaaaga caaccctcag aatgggagaa aatatttgca  3120
aatgaatcaa cggacaaagg attaatctcc aaaatatata aacagctcat tcagctcaat  3180
atcaaagaaa caaacacccc aatccaaaaa tgggcagaag acctaaatag acatttctcc  3240
aaagaagaca tacagacggc cacgaagcac atgaaaagat gctcaacatc actaattatt  3300
agagaaatgc aaatcaaaac tacaatgagg tatcacctca ctcctgttag aatgggcatc  3360
atcagaaaat ctacaaacaa caaatgctgg agagggtgtg gagaaaaggg aaccctcttg  3420
cactgttggt gggaatgtaa attgatacag ccactatgga gaacaatatg gaggttcctt  3480
aaaaaactaa aaatagaatt accatatgac ccagcaatcc cactactggg catataccca  3540
gagaaaaccg taattcaaaa agacacatgc acccgaatgt tcattgcagc actatttaca  3600
atagccaggt catggaagca acctaaatgc ccatcgacag acgaatggat aaagaagatg  3660
tggtacatat atacaatgga atattactca gccataaaaa ggaacgaaat tgggtcattt  3720
ttagagacgt ggatggatct agagactgtc atacagagtg aagtaagtca gaaagagaaa  3780
aacaaatatc gtatattaac gcatatatgt ggaacctgga aaaatggtac agatgaaccg  3840
gtctgcagga cagaaattga gacacaaatg taa                               3873

SEQ ID NO: 63           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
```

```
SEQUENCE: 63
PAAKRVKLD                                                  9

SEQ ID NO: 64          moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 64
DYKDDDDK                                                   8

SEQ ID NO: 65          moltype = AA  length = 234
FEATURE                Location/Qualifiers
REGION                 1..234
                       note = Description of Artificial Sequence: Synthetic
                        polypeptide
source                 1..234
                       mol_type = protein
                       organism = synthetic construct
SEQUENCE: 65
ASNFTQFVLV DNGGTGDVTV APSNFANGIA EWISSNSRSQ AYKVTCSVRQ SSAQNRKYTI  60
KVEVPKGAWR SYLNMELTIP IFATNSDCEL IVKAMQGLLK DGNPIPSAIA ANSGIYAMAS  120
NFTQFVLVDN GGTGDVTVAP SNFANGIAEW ISSNSRSQAY KVTCSVRQSS AQNRKYTIKV  180
EVPKGAWRSY LNMELTIPIF ATNSDCELIV KAMQGLLKDG NPIPSAIAAN SGIY        234

SEQ ID NO: 66          moltype = AA  length = 9
FEATURE                Location/Qualifiers
REGION                 1..9
                       note = Description of Unknown: "LAGLIDADG" family peptide
                        motif sequence
source                 1..9
                       mol_type = protein
                       organism = unidentified
SEQUENCE: 66
LAGLIDADG                                                  9

SEQ ID NO: 67          moltype = AA  length = 45
FEATURE                Location/Qualifiers
REGION                 1..45
                       note = Description of Artificial Sequence: Synthetic
                        polypeptide
source                 1..45
                       mol_type = protein
                       organism = synthetic construct
SEQUENCE: 67
LYCRRLKIQV RKAAITSYEK SDGVYTGLST RNQETYETLK HEKPP                  45

SEQ ID NO: 68          moltype = AA  length = 61
FEATURE                Location/Qualifiers
REGION                 1..61
                       note = Description of Artificial Sequence: Synthetic
                        polypeptide
source                 1..61
                       mol_type = protein
                       organism = synthetic construct
SEQUENCE: 68
KVAKKPTNKA PHPKQEPQEI NFPDDLPGSN TAAPVQETLH GCQPVTQEDG KESRISVQER  60
Q                                                                  61

SEQ ID NO: 69          moltype = AA  length = 415
FEATURE                Location/Qualifiers
REGION                 1..415
                       note = Description of Artificial Sequence: Synthetic
                        polypeptide
source                 1..415
                       mol_type = protein
                       organism = synthetic construct
SEQUENCE: 69
EIQLVQSGGG LVKPGGSVRI SCAASGYTFT NYGMNWVRQA PGKGLEWMGW INTHTGEPTY  60
ADSFKGRFTF SLDDSKNTAY LQINSLRAED TAVYFCTRRG YDWYFDVWGQ GTTVTVSSGG  120
GGSGGGGSGG GGSDIQMTQS PSSLSASVGD RVTITCRASQ DINSYLSWFQ QKPGKAPKTL  180
IYRANRLESG VPSRFSGSGS GTDYTLTISS LQYEDFGIYY CQQYDESPWT FGGGTKLEIK  240
SGGGGSGALS NSIMYFSHFV PVFLPAKPTT TPAPRPPTPA PTIASQPLSL RPEACRPAAG  300
GAVHTRGLDI YIWAPLAGTC GVLLLSLVIT LYCRRLKIQV RKAAITSYEK SDGVYTGLST  360
RNQETYETLK HEKPPQGSGS YEDMRGILYA APQLRSIRGQ PGPNHEEDAD SYENM       415

SEQ ID NO: 70          moltype = AA  length = 437
```

```
FEATURE                 Location/Qualifiers
REGION                  1..437
                        note = Description of Artificial Sequence: Synthetic
                         polypeptide
source                  1..437
                        mol_type = protein
                        organism = synthetic construct
SEQUENCE: 70
EIQLVQSGGG LVKPGGSVRI SCAASGYTFT NYGMNWVRQA PGKGLEWMGW INTHTGEPTY  60
ADSFKGRFTF SLDDSKNTAY LQINSLRAED TAVYFCTRRG YDWYFDVWGQ GTTVTVSSGG  120
GGSGGGGSGG GGSDIQMTQS PSSLSASVGD RVTITCRASQ DINSYLSWFQ QKPGKAPKTL  180
IYRANRLESG VPSRFSGSGS GTDYTLTISS LQYEDFGIYY CQQYDESPWT FGGGTKLEIK  240
SGGGGSGALS NSIMYFSHFV PVFLPAKPTT TPAPRPPTPA PTIASQPLSL RPEACRPAAG  300
GAVHTRGLDI YIWAPLAGTC GVLLLSLVIT LYCRLKIQVR KAAITSYEKS DGVYTGLSTR  360
NQETYETLKH EKPPQKKVAK KPTNKAPHPK QEPQEINFPD DLPGSNTAAP VQETLHGCQP  420
VTQEDGKESR ISVQERQ                                                 437

SEQ ID NO: 71           moltype = AA  length = 438
FEATURE                 Location/Qualifiers
REGION                  1..438
                        note = Description of Artificial Sequence: Synthetic
                         polypeptide
source                  1..438
                        mol_type = protein
                        organism = synthetic construct
SEQUENCE: 71
EIQLVQSGGG LVKPGGSVRI SCAASGYTFT NYGMNWVRQA PGKGLEWMGW INTHTGEPTY  60
ADSFKGRFTF SLDDSKNTAY LQINSLRAED TAVYFCTRRG YDWYFDVWGQ GTTVTVSSGG  120
GGSGGGGSGG GGSDIQMTQS PSSLSASVGD RVTITCRASQ DINSYLSWFQ QKPGKAPKTL  180
IYRANRLESG VPSRFSGSGS GTDYTLTISS LQYEDFGIYY CQQYDESPWT FGGGTKLEIK  240
SGGGGSGALS NSIMYFSHFV PVFLPAKPTT TPAPRPPTPA PTIASQPLSL RPEACRPAAG  300
GAVHTRGLDI YIWAPLAGTC GVLLLSLVIT LYCRRLKIQV RKAAITSYEK SDGVYTGLST  360
RNQETYETLK HEKPPQKKVA KKPTNKAPHP KQEPQEINFP DDLPGSNTAA PVQETLHGCQ  420
PVTQEDGKES RISVQERQ                                                438

SEQ ID NO: 72           moltype = AA  length = 44
FEATURE                 Location/Qualifiers
REGION                  1..44
                        note = Description of Artificial Sequence: Synthetic
                         polypeptide
source                  1..44
                        mol_type = protein
                        organism = synthetic construct
SEQUENCE: 72
MRNKKILKED ELLSETQQAA FHQIAMEPFE INVPKPKRRN GVNF                   44

SEQ ID NO: 73           moltype = AA  length = 50
FEATURE                 Location/Qualifiers
REGION                  1..50
                        note = Description of Artificial Sequence: Synthetic
                         polypeptide
source                  1..50
                        mol_type = protein
                        organism = synthetic construct
SEQUENCE: 73
MEQWDHFHNQ QEDTDSCSES VKFDARSMTA LLPPNPKNSP SLQEKLKSFK             50

SEQ ID NO: 74           moltype = RNA  length = 203
FEATURE                 Location/Qualifiers
misc_feature            1..203
                        note = Description of Artificial Sequence: Synthetic
                         polynucleotide
misc_difference         66..185
misc_feature            1..203
                        note = See specification as filed for detailed description
                         of substitutions and preferred embodiments
source                  1..203
                        mol_type = other RNA
                        organism = synthetic construct
SEQUENCE: 74
gctgggtttt tccttgttcg caccggacac ctccagtgac cagacggcaa ggtttttatc  60
ccagtnnnnn nnnnnnnnnn nnnnnnnnnn nnnnnnnnnn nnnnnnnnnn nnnnnnnnnn  120
nnnnnnnnnn nnnnnnnnnn nnnnnnnnnn nnnnnnnnnn nnnnnnnnnn nnnnnnnnnn  180
nnnnnaaaaa aaaaaaaaaa aaa                                          203

SEQ ID NO: 75           moltype = AA  length = 33
FEATURE                 Location/Qualifiers
REGION                  1..33
                        note = Description of Artificial Sequence: Synthetic
```

```
                         polypeptide
source                  1..33
                        mol_type = protein
                        organism = synthetic construct
SEQUENCE: 75
GAAPAAAPAK QEAAAPAPAA KAEAPAAAPA AKA                              33

SEQ ID NO: 76           moltype = AA  length = 20
FEATURE                 Location/Qualifiers
REGION                  1..20
                        note = Description of Artificial Sequence: Synthetic peptide
SITE                    1..20
                        note = This sequence may encompass 1-4 "Gly Gly Gly Gly
                         Ser" repeating units
REGION                  1..20
                        note = See specification as filed for detailed description
                         of substitutions and preferred embodiments
source                  1..20
                        mol_type = protein
                        organism = synthetic construct
SEQUENCE: 76
GGGGSGGGGS GGGGSGGGGS                                             20

SEQ ID NO: 77           moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 77
GGGGGG                                                            6

SEQ ID NO: 78           moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 78
GGGGGGGG                                                          8

SEQ ID NO: 79           moltype = AA  length = 20
FEATURE                 Location/Qualifiers
REGION                  1..20
                        note = Description of Artificial Sequence: Synthetic peptide
SITE                    1..20
                        note = This sequence may encompass 1-4 "Glu Ala Ala Ala
                         Lys" repeating units
REGION                  1..20
                        note = See specification as filed for detailed description
                         of substitutions and preferred embodiments
source                  1..20
                        mol_type = protein
                        organism = synthetic construct
SEQUENCE: 79
EAAAKEAAAK EAAAKEAAAK                                             20

SEQ ID NO: 80           moltype = AA  length = 7
FEATURE                 Location/Qualifiers
source                  1..7
                        mol_type = protein
                        organism = Simian virus 40
SEQUENCE: 80
PKKKRKV                                                           7

SEQ ID NO: 81           moltype = DNA  length = 21
FEATURE                 Location/Qualifiers
source                  1..21
                        mol_type = other DNA
                        organism = Simian virus 40
SEQUENCE: 81
ccaaagaaga agcggaaggt c                                           21

SEQ ID NO: 82           moltype = AA  length = 11
FEATURE                 Location/Qualifiers
REGION                  1..11
                        note = Description of Artificial Sequence: Synthetic peptide
```

-continued

```
source                  1..11
                        mol_type = protein
                        organism = synthetic construct
SEQUENCE: 82
PKKKRKVGGG S                                                       11

SEQ ID NO: 83           moltype = DNA  length = 33
FEATURE                 Location/Qualifiers
misc_feature            1..33
                        note = Description of Artificial Sequence: Synthetic
                         oligonucleotide
source                  1..33
                        mol_type = other DNA
                        organism = synthetic construct
SEQUENCE: 83
ccaaagaaga agcggaaggt cggcggcggc agc                               33

SEQ ID NO: 84           moltype = AA  length = 16
FEATURE                 Location/Qualifiers
REGION                  1..16
                        note = Description of Unknown: Nucleoplasmin bipartite NLS
                         sequence
source                  1..16
                        mol_type = protein
                        organism = unidentified
SEQUENCE: 84
KRPAATKKAG QAKKKK                                                  16

SEQ ID NO: 85           moltype = DNA  length = 48
FEATURE                 Location/Qualifiers
misc_feature            1..48
                        note = Description of Unknown: Nucleoplasmin bipartite NLS
                         sequence
source                  1..48
                        mol_type = other DNA
                        organism = unidentified
SEQUENCE: 85
aaaaggccgg cggccacgaa aaaggccggc caggcaaaaa agaaaaag               48

SEQ ID NO: 86           moltype = AA  length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 86
KRPAATKKAG QAKKKKGGGS                                              20

SEQ ID NO: 87           moltype = DNA  length = 60
FEATURE                 Location/Qualifiers
misc_feature            1..60
                        note = Description of Artificial Sequence: Synthetic
                         oligonucleotide
source                  1..60
                        mol_type = other DNA
                        organism = synthetic construct
SEQUENCE: 87
aaaaggccgg cggccacgaa aaaggccggc caggcaaaaa agaaaaaggg cggcggcagc  60

SEQ ID NO: 88           moltype = AA  length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 88
GGGSKRPAAT KKAGQAKKKK                                              20

SEQ ID NO: 89           moltype = DNA  length = 60
FEATURE                 Location/Qualifiers
misc_feature            1..60
                        note = Description of Artificial Sequence: Synthetic
                         oligonucleotide
source                  1..60
                        mol_type = other DNA
                        organism = synthetic construct
SEQUENCE: 89
```

```
ggcggcggca gcaaaaggcc ggcggccacg aaaaaggccg gccaggcaaa aaagaaaaag  60

SEQ ID NO: 90          moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 90
GGGSPKKKRK V                                                       11

SEQ ID NO: 91          moltype = DNA  length = 33
FEATURE                Location/Qualifiers
misc_feature           1..33
                       note = Description of Artificial Sequence: Synthetic
                        oligonucleotide
source                 1..33
                       mol_type = other DNA
                       organism = synthetic construct
SEQUENCE: 91
ggcggcggca gcccaaagaa gaagcggaag gtc                               33

SEQ ID NO: 92          moltype = DNA  length = 12542
FEATURE                Location/Qualifiers
misc_feature           1..12542
                       note = Description of Artificial Sequence: Synthetic
                        polynucleotide
source                 1..12542
                       mol_type = other DNA
                       organism = synthetic construct
SEQUENCE: 92
ctttcgtccg atccatcttg caggctacct ctcgaacgaa ctatcgcaag tctcttggcc  60
ggccttgcgc cttggctatt gcttggcagc gcctatcgcc aggtattact ccaatcccga  120
atatccgaga tcgggatcac ccgagagaag ttcaacctac atcctcaatc ccgatctatc  180
cgagatccga ggaatatcga aatcggggcg cgcctggtgt accgagaacg atcctctcag  240
tgcgagtctc gacgatccat atcgttgctt ggcagtcagc cagtcggaat ccagcttggg  300
acccaggaag tccaatcgtc agatattgta ctcaagcctg gtcacggcag cgtaccgatc  360
tgtttaaacc tagatattga tagtctgatc ggtcaacgta taatcgagtc ctagcttttg  420
caaacatcta tcaagagaca ggatcagcag gaggctttcg catgagtatt caacatttcc  480
gtgtcgccct tattcccttt tttgcggcat tttgccttcc tgtttttgct cacccagaaa  540
cgctggtgaa agtaaaagat gctgaagatc agttgggtgc gcgagtgggt tacatcgaac  600
tggatctcaa cagcggtaag atccttgaga gttttcgccc cgaagaacgc tttccaatga  660
tgagcacttt taaagttctg ctatgtggcg cggtattatc ccgtattgac gccgggcaag  720
agcaactcgg tcgccgcata cactattctc agaatgactt ggttgagtat tcaccagtca  780
cagaaaagca tcttacggat ggcatgacag taagagaatt atgcagtgct gccataacca  840
tgagtgataa cactgcggcc aacttacttc tgacaacgat tggaggaccg aaggagctaa  900
ccgctttttt gcacaacatg ggggatcatg taactcgcct tgatcgttgg gaaccggagc  960
tgaatgaagc cataccaaac gacgagcgtg acaccacgat gcctgtagca atggcaacaa  1020
ccttgcgtaa actattaact ggcgaactac ttactctagc ttcccggcaa cagttgatag  1080
actggatgga ggcggataaa gttgcaggac cacttctgcg ctcggccctt ccggctggct  1140
ggtttattgc tgataaatct ggagccggtg agcgtgggtc tcgcggtatc attgcagcac  1200
tggggccaga tggtaagccc tcccgtatcg tagttatcta cacgacgggg agtcaggcaa  1260
ctatggatga acgaaataga cagatcgctg agataggtgc ctcactgatt aagcattggt  1320
aaccgattct aggtgcattg gcgcagaaaa aaatgcctga tgcgacgctg cgcgtcttat  1380
actcccacat atgccagatt cagcaacgga tacggcttcc ccaacttgcc cacttccata  1440
cgtgtcctcc ttaccagaaa tttatcctta agatcgttta aactcgactc tggctctatc  1500
gaatctccgt cgtttcgagc ttacgcgaac agccgtggcg ctcatttgct cgtcgggcat  1560
cgaatctcgt cagctatcgt cagcttacct tttggcagc gatcgcggct cccgacatct  1620
tggaccatta gctccacagg tatcttcttc cctctagtgg tcataacagc agcttcagct  1680
acctctcaat tcaaaaaacc cctcaagacc cgtttagagg ccccaagggg ttatgctatc  1740
aatcgttgcg ttacacacac aaaaaaccaa cacacatcca tcttcgatgg atagcgattt  1800
tattatctaa ctgctgatcg agtgtagcca gatctagtaa tcaattacgg ggtcattagt  1860
tcatagccca tatatggagt tccgcgttac ataacttacg gtaaatggcc cgcctggctg  1920
accgcccaac gacccccgcc cattgacgtc aataatgacg tatgttccca tagtaacgcc  1980
aatagggact ttccattgac gtcaatgggt ggagtattta cggtaaactg cccacttggc  2040
agtacatcaa gtgtatcata tgccaagtac gccccctatt gacgtcaatg acggtaaatg  2100
gcccgcctgg cattatgccc agtacatgac cttatgggac tttcctactt ggcagtacat  2160
ctacgtatta gtcatcgcta ttaccatgct gatgcggttt tggcagtaca tcaatgggcg  2220
tggatagcgg tttgactcac ggggatttcc aagtctccac cccattgacg tcaatgggag  2280
tttgttttgg caccaaaatc aacgggactt tccaaaatgt cgtaacaact ccgccccatt  2340
gacgcaaatg ggcggtaggc gtgtacggtg ggaggtctat ataagcagag ctggtttagt  2400
gaaccgtcag atcagatctt tgtcgatcct accatccact cgacacaccc gccagcggcc  2460
gctaatacga ctcactatag ggagaagtac tgccaccatg ggcaagaagc aaaatcgcaa  2520
gacggggaat tccaagacac aatccgctag cccaccacct aaagagcgtt ctagctcccc  2580
tgctactgag cagtcctgga tggaaaacga cttcgatgaa ctccgggaag agggatttag  2640
gcgatccaac tattcagaac tccgcgaaga tatccagaca aaggggaagg aagtcgagaa  2700
tttcgagaag aacctcgagg agtgcatcac ccgtatcaca aacactgaga aatgtctcaa  2760
agaactcatg gaacttaaga caaaagccag ggagcttcga gaggagtgtc ggagtctgag  2820
```

```
atccaggtgt gaccagctcg aggagcgcgt gagcgcgatg gaagacgaga tgaacgagat  2880
gaaaagagag ggcaaattca gggagaagcg cattaagagg aacgaacaga gtctgcagga  2940
gatttgggat tacgtcaaga ggcctaacct gcggttgatc ggcgtccccg agagcgacgt  3000
agaaaacggg actaaactgg agaatacact tcaagacatc attcaagaaa attttccaaa  3060
cctggctcgg caagctaatg tgcaaatcca agagatccaa cgcacacccc agcggtatag  3120
ctctcggcgt gccacccccta ggcatattat cgtgcgcttt actaaggtgg agatgaaaga  3180
gaagatgctg cgagccgctc gggaaaaggg aagggtgact ttgaagggca aacctattcg  3240
gctgacggtt gaccttagcg ccgagacact ccaggcacgc cgggaatggg gccccatctt  3300
taatatcctg aaggagaaga acttccagcc acgaatctct taccctgcaa agttgagttt  3360
tatctccgag ggtgagatta agtatttcat cgataaacag atgctgcgag acttcgtgac  3420
aactcgccca gctctcaagg aactgctcaa agaggctctt aatatggagc gcaataatag  3480
atatcaaccc ttgcagaacc acgcaaagat gccaaagaag aagcggaagg tctgagacag  3540
ccgtcagacc atcaagacta ggaagaaact gcatcaacta atgagcaaaa tcaccagcta  3600
acatcatagt atacatgacc ggctctaact cacatatcac catccttaca cttaacatta  3660
acggcctcaa ctcagctatc aagcgccatc ggctggccag ctggatcaaa tcacaggatc  3720
caagcgtttg ttgcatccaa gagacccacc tgacctgtag agatactcac cgcctcaaga  3780
tcaagggatg gcgaaagatt tatcaggcga acggtaagca gaagaaagcc ggagtcgcaa  3840
ttctggtctc agacaagacg gatttcaagc ccaccaaaat taagcgtgat aaggaaggtc  3900
actatattat ggtgaaaggc agcatacagc aggaagaact taccatattg aacatctacg  3960
cgccaaacac cggcgcacct cgctttatca aacaggtcct gtccgatctg cagcgagatc  4020
tggattctca tacgttgatt atgggtgatt tcaatacacc attgagcacc ctggatcgca  4080
gcaccaggca aaaggtaaat aaagacacgc aagagctcaa tagcgcactg catcaggcag  4140
atctcattga tatttatcgc actcttcatc ctaagagtac cgagtacaca ttcttcagcg  4200
ccccacatca tacatactca aagatcgatc atatcgtcgg ctcaaaggct ctgctgtcaa  4260
agtgcaagcg cacagagata attacaaatt acctgtcaga tcatagcgcg atcaagctcg  4320
agctgagaat caagaacctg acccagagcc ggagtaccac ttggaagctt aataacctgc  4380
tgctcaacga ttattgggtc cacaatgaga tgaaggcaga gattaaaatg ttcttcgaaa  4440
caaatgagaa taaggatact acctatcaaa acctttggga tgcctttaag gccgtctgca  4500
gaggcaagtt catcgccctc aacgcctata aagaaaaaca agagagatct aagatcgata  4560
ctctcacctc tcagctgaag gagttggaga aacaggaaca gacccactcc aaggcgtcaa  4620
gacggcagga gatcacaaag attcgcgccg agttgaaaga gatcgaaacc caaaagactc  4680
ttcagaaaat taacgagtct cgtagttggt tcttcgagcg gattaataag atagacagac  4740
ctctggcacg actgattaag aagaagcgcg aaaagaacca gattgatacc atcaagaacg  4800
acaagggcga catcactact gacccgaccg agatccagac cactattcgg gagtattata  4860
agcatttgta tgctaacaag cttgagaacc tggaagagat ggacactttt ctggatacct  4920
atactctgcc acggcttaat caagaggaag tcgagtccct caaccgccca attacaggaa  4980
gcgagattgt ggccataatt aactccctgc cgacaaagaa atctcctggt ccggacgggt  5040
ttacagctga gttttatcaa cggtatatgg aagagcttgt accgtttctg ctcaagctct  5100
ttcagtctat agaaaaggaa ggcatcttgc ccaattcctt ctacgaagct tctataatac  5160
ttattcccaa accaggacgc gataccacaa agaaggaaaa cttccggccc attagtctca  5220
tgaatatcga cgctaaaata ttgaacaaga ttctcgccaa cagaatccaa caacatatta  5280
agaaattgat acatcacgac caggtggggt ttatacctgg catgcagggc tggtttaaca  5340
tccggaagag tattaacgtc attcaacaca ttaatagagc taaggataag aatcatatga  5400
tcatctctat agacgcggaa aaggcattcg ataagattca gcagccattt atgctcaaga  5460
ctctgaacaa actcggcatc gacggaacat attttaagat tattcgcgca atttacgata  5520
agccgactgc taacattatc cttaacggcc aaaagctcga ggcctttccg ctcaagactg  5580
gaacccgcca aggctgtccc ctctccccgc ttttgtttaa tattgtactc gaggtgctgg  5640
ctagggctat tcgtcaagag aaagagatta aagggataca gctcgggaag gaagaggtca  5700
agctttcctt gttcgccgat gatatgattg tgtacctgga gaatcctatt gtgtctgctc  5760
agaaccttct taaacttatt tctaacttta gcaaggtcag cggctataag attaacgtcc  5820
agaaatctca ggcctttctg tacacaaata atcgacagac cgaatcccag ataatgggtg  5880
agcttccgtt tgtcatagcc agcaaaagga taaagtatct cggaatccag ctgacacgag  5940
acgttaaaga tttgtttaag gaaaattaca agcctctcct gaaagagatt aaggaagata  6000
ctaataagtg gaagaatatc ccctgttcat gggttggcag aatcaacata gtgaagatgg  6060
caatacttcc taaagtgata tatcgcttta acgccatccc aattaaactg cctatgacct  6120
tctttacgga gctcgagaaa acaaccctta aatttatatg gaatcaaaag agagcaagaa  6180
tagcgaagtc catcttgagc cagaagaata aggccggtgg gattactttg cctgatttta  6240
agttgtatta taaagccaca gtaactaaga cagcctggta ttggtatcag aatagagaca  6300
tcgaccagtg gaatcggacc gaaccatcag agataatgcc ccacatctat aattacctta  6360
tattcgataa gccagaaaag aataaacagt ggggcaaaga cagcctcttc aacaagtggt  6420
gttgggagaa ttggctggcc atatgccgga aactcaagct cgaccccttt cttacaccct  6480
acactaaaat caacagtagg tggatcaagg acttgaatgt caagccaaag actataaaga  6540
cactggaaga gaatcttggg atcacaatac aagatatagg cgtcggcaaa gattttatgt  6600
caaagacgcc caaggccatg gccactaagg ataagattga taagtgggac cttattaagc  6660
tcaaaagctt ctgtactgcc aaggagacca cgatcagagt taataggcag cccactacat  6720
gggaaaagat tttcgccact tattcatcag ataaggggtt gataagcaga atatataacg  6780
agctgaagca gatctacaag aagaaaacga ataatcccat caagaagtgg gcaaaagata  6840
tgaacaggca ttttagcaaa gaggatatct acgccgcgaa gaagcatatg aagaagtgta  6900
gttcaagctt ggccattcgt gagatgcaga ttaagacgac catgcgatac caccttaccc  6960
cagtgaggat ggcaattatc aagaaatctg gcaataatag atgttggcgg ggctgtggcg  7020
agattggcac cctgctccat tgctggtggg attgcaagct ggtgcagccg ctttggaaat  7080
cagtctggcg ctttctgagg gacctcgagc ttgagattcc cttcgatccc gcaattccct  7140
tgctcggaat ctatcctaac gaatacaaga gctgttgtta caaggatacg tgtacccgga  7200
tgttcatcgc ggccttgttt acgatagcta agacgtggaa tcagcctaag tgccccacaa  7260
tgatcgattg gatcaagaaa atgtggcata tttataccat ggagtattac gcagcaatta  7320
agaatgacga atttatttcc ttcgttggga cctggatgaa gctggagact attattctga  7380
gcaagctgtc tcaggagcaa aagacaaagc atagaatctt ctctctcatt ggtggtaacg  7440
actacaaaga cgatgacgac aagtaaagcg cttctagaag ttgtctcctc ctgcactgac  7500
tgactgatac aatcgatttc tggatccgca ggcctaatca acctctggat tacaaaattt  7560
```

-continued

```
gtgaaagatt gactggtatt cttaactatg ttgctccttt tacgctatgt ggatacgctg  7620
ctttaatgcc tttgtatcat gctattgctt cccgtatggc tttcattttc tcctccttgt  7680
ataaatcctg gttgctgtct ctttatgagg agttgtggcc cgttgtcagg caacgtggcg  7740
tggtgtgcac tgtgtttgct gacgcaaccc ccactggttg gggcattgcc accacctgtc  7800
agctcctttc cgggactttc gctttccccc tccctattgc cacggcggaa ctcatcgccg  7860
cctgccttgc ccgctgctgg acaggggctc ggctgttggg cactgacaat tccgtggtgt  7920
tgtcggggaa gctgacgtcc tttccatggc tgctcgcctg tgttgccacc tggattctgc  7980
gcgggacgtc cttctgctac gtcccttcgg ccctcaatcc agcggacctt ccttcccgct  8040
gagagacaca aaaaattcca acacactatt gcaatgaaaa taaatttcct ttattagcca  8100
gaagtcagat gctcaagggg cttcatgatg tccccataat ttttggcaga gggaaaaaga  8160
tctcagtggt atttgtgagc cagggcattg gccttctgat aggcagcctg cacctgagga  8220
gtgcggccgc tttacttgta cagctcgtcc atgccgagag tgatcccggc ggcggtcacg  8280
aactccagca ggaccatgtg atcgcgcttc tcgttggggt ctttgctcag ggcggactgg  8340
gtgctcaggt agtggttgtc gggcagcagc acggggccgt cgccgatggg ggtgttctgc  8400
tggtagtggt cggcgagctg cacgctgccg tcctcgatgt tgtggcggat cttgaagttc  8460
accttgatgc cgttcttctg cttgtcggcc atgatataga cgttgtggct gttgtagttg  8520
tactccagct tgtgccccag gatgttgccg tcctccttga agtcgatgcc cttcagctcg  8580
atgcggttca ccagggtgtc gccctcgaac ttcacctcgg cgcgggtctt gtagttgccg  8640
tcgtccttga agaagatggt gcgctcctgg acgtagcctt cgggcatggc ggacttgaag  8700
aagtcgtgct gcttcatgtg gtcggggtag cggctgaagc actgcacgcc gtaggtcagg  8760
gtggtcacga gggtgggcca gggcacgggc agcttgccgg tggtgcagat gaacttcagg  8820
gtcagcttgc cgtaggtggc atcgccctcg ccctcgccgg acacgctgaa cttgtggccg  8880
tttacgtcgc cgtccagctc gaccaggatg ggcaccaccc cggtgaacag ctcctcgccc  8940
ttgctcacca tggtggcggg atctgacggt tcactaaacc agctctgctt atatagacct  9000
cccaccgtac acgcctaccg cccatttgcg tcaatggggc ggagttgtta cgacattttg  9060
gaaagtcccg ttgattttgg tgccaaaaca aactcccatt gacgtcaatg gggtggagac  9120
ttggaaatcc ccgtgagtca aaccgctatc cacgcccatt gatgtactgc caaaaccgca  9180
tcaccatggt aatagcgatg actaatacgt agatgtactg ccaagtagga aagtcccata  9240
aggtcatgta ctgggcataa tgccaggcgg gccatttacc gtcattgacg tcaatagggg  9300
gcgtacttgg catatgatac acttgatgta ctgccaagtg ggcagtttac cgtaaatact  9360
ccacccattg acgtcaatgg aaagtcccta ttggcgttac tatgggaaca tacgtcatta  9420
ttgacgtcaa tgggcggggg tcgttgggcg gtcagccagg cgggccattt accgtaagtt  9480
atgtaacggg cctgctgccg gctctgcggc ctcttccgcg tcttcgcctt cgccctcaga  9540
cgagtcggat ctccctttgg gccgcctccc cgcctgtcta gcttgactga ctgagataca  9600
gcgtaccttc agctcacaga catgataaga tacattgatg agtttggaca aaccacaact  9660
agaatgcagt gaaaaaaatg ctttatttgt gaaatttgtg atgctattgc tttatttgta  9720
accattataa gctgcaataa acaagttaac aacaacaatt gcattcattt tatgtttcag  9780
gttcaggggg aggtgtggga ggttttttaa agcaagtaaa acctctacaa atgtggtatt  9840
ggcccatctc tatcggtatc gtagcataac cccttggggc ctctaaacgg gtcttgaggg  9900
gttttttgtg cccctcgggc cggattgcta tctaccggca ttggcgcaga aaaaaatgcc  9960
tgatgcgacg ctgcgcgtct tatactccca catatgccag attcagcaac ggatacggct  10020
tccccaactt gcccacttcc atacgtgtcc tccttaccag aaatttatcc ttaaggtcgt  10080
cagctatcct gcaggcgatc tctcgatttc gatcaagaca ttcctttaat ggtcttttct  10140
ggacaccact aggggtcaga agtagttcat caaactttct tccctcccta atctcattgg  10200
ttaccttggg ctatcgaaac ttaattaagc gatctgcatc tcaattagtc agcaaccata  10260
gtcccgcccc taactccgcc catcccgccc ctaactccgc ccagttccgc ccattctccg  10320
ccccatcgct gactaatttt ttttatttat gcagaggccg aggccgcctc ggcctctgag  10380
ctattccaga agtagtgagg aggctttttt ggaggcctag gcttttgcaa aggaggtagc  10440
caacatgatt gaacaagatg gattgcacgc aggttctccc gccgcttggg tggagaggct  10500
attcggctat gactgggcac aacagacaat cggctgctct gatgccgccg tgttccggct  10560
gtcagcgcag gggcgcccgg ttctttttgt caagaccgac ctgtccggtg ccctgaatga  10620
actccaggac gaggcagcgc ggctatcgtg gctggccacg acgggcgttc cttgcgcagc  10680
tgtgctcgac gttgtcactg aagcgggaag ggactggctg ctattgggcg aagtgccggg  10740
gcaggatctc ctgtcatctc accttgctcc tgccgagaaa gtatccatca tggctgatgc  10800
aatgcggcgg ctgcatacgc ttgatccggc tacctgccca ttcgaccacc aagcgaaaca  10860
tcgcatcgag cgagcacgta ctcggatgga agccggtctt gtcgatcagg atgatctgga  10920
cgaagagcat caggggctcg cgccagccga actgttcgcc aggctcaagg cgcggatgcc  10980
cgacggcgag gatctcgtcg tgacccacgg cgatgcctgc ttgccgaata tcatggtgga  11040
aaatggccgc ttttctggat tcatcgactg tggccggctg ggtgtggcgg accgctatca  11100
ggacatagcg ttggctaccc gtgatattgc tgaagagctt ggcggcgaat gggctgaccg  11160
cttcctcgtg ctttacggta tcgccgctcc cgattcgcag cgcatcgcct tctatcgcct  11220
tcttgacgag ttcttctagt atgtaagccc tgtgccttct agttgccagc catctgttgt  11280
ttgcccctcc cccgtgcctt ccttgaccct ggaaggtgcc actcccactg tcctttccta  11340
ataaaatgag gaaattgcat cgcattgtct gagtaggtgt cattctattc tggggggtgg  11400
ggtggggcag gacagcaagg gggaggattg ggaagacaat agcaggcatg ctggggatgc  11460
ggtgggctct atggttaatt aaccagtcaa gtcagctact tggcgagatc gacttgtctg  11520
ggtttcgact acgctcagaa ttgcgtcagt caagttcgat ctggtccttg ctattgcacc  11580
cgttctccga ttacgagttt catttaaatc atgtgagcaa aaggccagca aaaggccagg  11640
aaccgtaaaa aggccgcgtt gctggcgttt ttccataggc tccgcccccc tgacgagcat  11700
cacaaaaatc gacgctcaag tcagaggtgg cgaaacccga caggactata aagataccag  11760
gcgtttcccc ctggaagctc cctcgtgcgc tctcctgttc cgaccctgcc gcttaccgga  11820
tacctgtccg cctttctccc ttcgggaagc gtggcgcttt ctcatagctc acgctgtagg  11880
tatctcagtt cggtgtaggt cgttcgctcc aagctgggct gtgtgcacga accccccgtt  11940
cagcccgacc gctgcgcctt atccggtaac tatcgtcttg agtccaaccc ggtaagacac  12000
gacttatcgc cactggcagc agccactggt aacaggatta gcagagcgag gtatgtaggc  12060
ggtgctacag agttcttgaa gtggtggcct aactacggct acactagaag aacagtattt  12120
ggtatctgcg ctctgctgaa gccagttacc ttcggaaaaa gagttggtag ctcttgatcc  12180
ggcaaacaaa ccaccgctgg tagcggtggt ttttttgttt gcaagcagca gattacgcgc  12240
agaaaaaaag gatctcaaga agatcctttg atcttttcta cggggtctga cgctcagtgg  12300
```

```
aacgaaaact cacgttaagg gattttggtc atgagattat caaaaaggat cttcacctag  12360
atccttttaa attaaaaatg aagttttaaa tcaatctaaa gtatatatga gtaaacttgg  12420
tctgacagtt accaatgctt aatcagtgag gcacctatct cagcgatctg tctatttcgt  12480
tcatccatag ttgcatttaa atttccgaac tctccaaggc cctcgtcgga aaatcttcaa  12540
ac                                                                 12542

SEQ ID NO: 93          moltype = DNA  length = 12554
FEATURE                Location/Qualifiers
misc_feature           1..12554
                       note = Description of Artificial Sequence: Synthetic
                        polynucleotide
source                 1..12554
                       mol_type = other DNA
                       organism = synthetic construct
SEQUENCE: 93
cctctcagtg cgagtctcga cgatccatat cgttgcttgg cagtcagcca gtcggaatcc  60
agcttgggac ccaggaagtc caatcgtcag atattgtact caagcctggt cacggcagcg  120
taccgatctg tttaaaccta gatattgata gtctgatcgg tcaacgtata atcgagtcct  180
agcttttgca aacatctatc aagagacagg atcagcagga ggctttcgca tgagtattca  240
acatttccgt gtcgccctta ttcccttttt tgcggcattt tgccttcctg tttttgctca  300
cccagaaacg ctggtgaaag taaaagatgc tgaagatcag ttgggtgcgc gagtgggtta  360
catcgaactg gatctcaaca gcggtaagat ccttgagagt tttcgccccg aagaacgctt  420
tccaatgatg agcactttta aagttctgct atgtggcgcg gtattatccc gtattgacgc  480
cgggcaagag caactcggtc gccgcataca ctattctcag aatgacttgg ttgagtattc  540
accagtcaca gaaaagcatc ttacggatgg catgacagta agagaattat gcagtgctgc  600
cataaccatg agtgataaca ctgcggccaa cttacttctg acaacgattg gaggaccgaa  660
ggagctaacc gcttttttgc acaacatggg ggatcatgta actcgccttg atcgttggga  720
accggagctg aatgaagcca taccaaacga cgagcgtgac accacgatgc ctgtagcaat  780
ggcaacaacc ttgcgtaaac tattaactgg cgaactactt actctagctt cccggcaaca  840
gttgatagac tggatggagg cggataaagt tgcaggacca cttctgcgct cggcccttcc  900
ggctggctgg tttattgctg ataaatctgg agccggtgag cgtgggtctc gcggtatcat  960
tgcagcactg gggccagatg gtaagccctc ccgtatcgta gttatctaca cgacggggag  1020
tcaggcaact atggatgaac gaaatagaca gatcgctgag ataggtgcct cactgattaa  1080
gcattggtaa ccgattctag gtgcattggc gcagaaaaaa atgcctgatg cgacgctgcg  1140
cgtcttatac tcccacatat gccagattca gcaacggata cggcttcccc aacttgccca  1200
cttccatacg tgtcctcctt accagaaatt tatccttaag atcgtttaaa ctcgactctg  1260
gctctatcga atctccgtcg tttcgagctt acgcgaacag ccgtggcgct catttgctcg  1320
tcgggcatcg aatctcgtca gctatcgtca gcttaccttt ttggcagcga tcgcggctcc  1380
cgacatcttg gaccattagc tccacaggta tcttcttccc tctagtggtc ataacagcag  1440
cttcagctac ctctcaattc aaaaaacccc tcaagacccg tttagaggcc ccaaggggtt  1500
atgctatcaa tcgttgcgtt acacacacaa aaaaccaaca cacatccatc ttcgatggat  1560
agcgatttta ttatctaact gctgatcgag tgtagccaga tctagtaatc aattacgggg  1620
tcattagttc atagcccata tatggagttc cgcgttacat aacttacggt aaatggcccg  1680
cctggctgac cgcccaacga cccccgccca ttgacgtcaa taatgacgta tgttcccata  1740
gtaacgccaa tagggacttt ccattgacgt caatgggtgg agtatttacg gtaaactgcc  1800
cacttggcag tacatcaagt gtatcatatg ccaagtacgc cccctattga cgtcaatgac  1860
ggtaaatggc ccgcctggca ttatgcccag tacatgacct tatgggactt tcctacttgg  1920
cagtacatct acgtattagt catcgctatt accatgctga tgcggttttg gcagtacatc  1980
aatgggcgtg gatagcggtt tgactcacgg ggatttccaa gtctccaccc cattgacgtc  2040
aatgggagtt tgttttggca ccaaaatcaa cgggactttc caaaatgtcg taacaactcc  2100
gccccattga cgcaaatggg cggtaggcgt gtacggtggg aggtctatat aagcagagct  2160
ggtttagtga accgtcagat cagatctttg tcgatcctac catccactcg acacacccgc  2220
cagcggccgc taatacgact cactataggg agaagtactg ccaccatggg caagaagcaa  2280
aatcgcaaga cggggaattc caagacacaa tccgctagcc caccacctaa agagcgttct  2340
agctcccctg ctactgagca gtcctggatg gaaaacgact tcgatgaact ccgggaagag  2400
ggatttaggc gatccaacta ttcagaactc cgcgaagata tccagacaaa ggggaaggaa  2460
gtcgagaatt tcgagaagaa cctcgaggag tgcatcaccc gtatcacaaa cactgagaaa  2520
tgtctcaaag aactcatgga acttaagaca aaagccaggg agcttcgaga ggagtgtcgg  2580
agtctgagat ccaggtgtga ccagctcgag gagcgcgtga gcgcgatgga agacgagatg  2640
aacgagatga aaagagaggg caaattcagg gagaagcgca ttaagaggaa cgaacagagt  2700
ctgcaggaga tttgggatta cgtcaagagg cctaacctgc ggttgatcgg cgtccccgag  2760
agcgacgtag aaaacgggac taaactggag aatacacttc aagacatcat tcaagaaaat  2820
tttccaaacc tggctcggca agctaatgtg caaatccaag agatccaacg cacaccccag  2880
cggtatagct ctcggcgtgc caccccctagg catattatcg tgcgctttac taaggtggag  2940
atgaaagaga agatgctgcg agccgctcgg gaaaagggaa gggtgacttt gaagggcaaa  3000
cctattcggc tgacggttga ccttagcgcc gagacactcc aggcacgccg ggaatggggc  3060
cccatcttta atatcctgaa ggagaagaac ttccagccac gaatctctta ccctgcaaag  3120
ttgagtttta tctccgaggg tgagattaag tatttcatcg ataaacagat gctgcgagac  3180
ttcgtgacaa ctcgcccagc tctcaaggaa ctgctcaaag aggctcttaa tatggagcgc  3240
aataatagat atcaacccctt gcagaaccac gcaaagatgg gcggcggcag cccaaagaag  3300
aagcggaagg tctgagacag ccgtcagacc atcaagacta ggaagaaact gcatcaacta  3360
atgagcaaaa tcaccagcta acatcatagt atacatgacc ggctctaact cacatatcac  3420
catccttaca cttaacatta acggcctcaa ctcagctatc aagcgccatc ggctggccag  3480
ctggatcaaa tcacaggatc caagcgtttg ttgcatccaa gagacccacc tgacctgtag  3540
agatactcac cgcctcaaga tcaagggatg gcgaaagatt tatcaggcga acggtaagca  3600
gaagaaagcc ggagtcgcaa ttctggtctc agacaagacg gatttcaagc ccaccaaaat  3660
taagcgtgat aaggaaggtc actatattat ggtgaaaggc agcatacagc aggaagaact  3720
taccatattg aacatctacg cgccaaacac cggcgcacct cgctttatca aacaggtcct  3780
gtccgatctg cagcgagatc tggattctca tacgttgatt atgggtgatt tcaatacacc  3840
```

-continued

```
attgagcacc ctggatcgca gcaccaggca aaaggtaaat aaagacacgc aagagctcaa  3900
tagcgcactg catcaggcag atctcattga tatttatcgc actcttcatc ctaagagtac  3960
cgagtacaca ttcttcagcg ccccacatca tacatactca aagatcgatc atatcgtcgg  4020
ctcaaaggct ctgctgtcaa agtgcaagcg cacagagata attacaaatt acctgtcaga  4080
tcatagcgcg atcaagctcg agctgagaat caagaacctg acccagagcc ggagtaccac  4140
ttggaagctt aataacctgc tgctcaacga ttattgggtc cacaatgaga tgaaggcaga  4200
gattaaaatg ttcttcgaaa caaatgagaa taaggatact acctatcaaa acctttggga  4260
tgcctttaag gccgtctgca gaggcaagtt catcgccctc aacgcctata aaagaaaaca  4320
agagagatct aagatcgata ctctcacctc tcagctgaag gagttggaga aacaggaaca  4380
gacccactcc aaggcgtcaa gacggcagga gatcacaaag attcgcgccg agttgaaaga  4440
gatcgaaacc caaaagactc ttcagaaaat taacgagtct cgtagttggt tcttcgagcg  4500
gattaataag atagacagac ctctggcacg actgattaag aagaagcgcg aaaagaacca  4560
gattgatacc atcaagaacg acaagggcga catcactact gacccgaccg agatccagac  4620
cactattcgg gagtattata agcatttgta tgctaacaag cttgagaacc tggaagagat  4680
ggacactttt ctggatacct atactctgcc acggcttaat caagaggaag tcgagtccct  4740
caaccgccca attacaggaa gcgagattgt ggccataatt aactccctgc cgacaaagaa  4800
atctcctggt ccggacgggt ttacagctga gttttatcaa cggtatatgg aagagcttgt  4860
accgtttctg ctcaagctct ttcagtctat agaaaaggaa ggcatcttgc ccaattcctt  4920
ctacgaagct tctataatac ttattcccaa accaggacgc gataccacaa agaaggaaaa  4980
cttccggccc attagtctca tgaatatcga cgctaaaata ttgaacaaga ttctcgccaa  5040
cagaatccaa caacatatta agaaattgat acatcacgac caggtggggt ttatacctgg  5100
catgcagggc tggtttaaca tccggaagag tattaacgtc attcaacaca ttaatagagc  5160
taaggataag aatcatatga tcatctctat agacgcggaa aaggcattcg ataagattca  5220
gcagccattt atgctcaaga ctctgaacaa actcggcatc gacggaacat attttaagat  5280
tattcgcgca atttacgata agccgactgc taacattatc cttaacggcc aaaagctcga  5340
ggcctttccg ctcaagactg gaacccgcca aggctgtccc ctctccccgc ttttgtttaa  5400
tattgtactc gaggtgctgg ctagggctat tcgtcaagag aaagagatta aagggataca  5460
gctcgggaag gaagaggtca agctttcctt gttcgccgat gatatgattg tgtacctgga  5520
gaatcctatt gtgtctgctc agaaccttct taaacttatt tctaacttta gcaaggtcag  5580
cggctataag attaacgtcc agaaatctca ggcctttctg tacacaaata atcgacagac  5640
cgaatcccag ataatgggtg agcttccgtt tgtcatagcc agcaaaagga taaagtatct  5700
cggaatccag ctgacacgag acgttaaaga tttgtttaag gaaaattaca agcctctcct  5760
gaaagagatt aaggaagata ctaataagtg gaagaatatc cctgttcat gggttggcag  5820
aatcaacata gtgaagatgg caatacttcc taaagtgata tatcgcttta acgccatccc  5880
aattaaactg cctatgacct tctttacgga gctcgagaaa acaaccctta aatttatatg  5940
gaatcaaaag agagcaagaa tagcgaagtc catcttgagc cagaagaata aggccggtgg  6000
gattactttg cctgatttta agttgtatta taaagccaca gtaactaaga cagcctggta  6060
ttggtatcag aatagagaca tcgaccagtg gaatcggacc gaaccatcag agataatgcc  6120
ccacatctat aattacctta tattcgataa gccagaaaag aataaacagt ggggcaaaga  6180
cagcctcttc aacaagtggt gttgggagaa ttggctggcc atatgccgga aactcaagct  6240
cgaccccttt cttacaccct acactaaaat caacagtagg tggatcaagg acttgaatgt  6300
caagccaaag actataaaga cactggaaga gaatcttggg atcacaatac aagatatagg  6360
cgtcggcaaa gattttatgt caaagacgcc caaggccatg gccactaagg ataagattga  6420
taagtgggac cttattaagc tcaaaagctt ctgtactgcc aaggagacca cgatcagagt  6480
taataggcag cccactacat gggaaaagat tttcgccact tattcatcag ataaggggtt  6540
gataagcaga atatataacg agctgaagca gatctacaag aagaaaacga ataatcccat  6600
caagaagtgg gcaaaagata tgaacaggca ttttagcaaa gaggatatct acgccgcgaa  6660
gaagcatatg aagaagtgta gttcaagctt ggccattcgt gagatgcaga ttaagacgac  6720
catgcgatac caccttaccc cagtgaggat ggcaattatc aagaaatctg gcaataatag  6780
atgttggcgg ggctgtggcg agattggcac cctgctccat tgctggtggg attgcaagct  6840
ggtgcagccg ctttggaaat cagtctggcg ctttctgagg gacctcgagc ttgagattcc  6900
cttcgatccc gcaattccct tgctcggaat ctatcctaac gaatacaaga gctgttgtta  6960
caaggatacg tgtacccgga tgttcatcgc ggccttgttt acgatagcta agacgtggaa  7020
tcagcctaag tgccccacaa tgatcgattg gatcaagaaa atgtggcata tttataccat  7080
ggagtattac gcagcaatta agaatgacga atttatttcc ttcgttggga cctggatgaa  7140
gctggagact attattctga gcaagctgtc tcaggagcaa aagacaaagc atagaatctt  7200
ctctctcatt ggtggtaacg actacaaaga cgatgacgac aagtaaagcg cttctagaag  7260
ttgtctcctc ctgcactgac tgactgatac aatcgatttc tggatccgca ggcctaatca  7320
acctctggat tacaaaattt gtgaaagatt gactggtatt cttaactatg ttgctccttt  7380
tacgctatgt ggatacgctg ctttaatgcc tttgtatcat gctattgctt cccgtatggc  7440
tttcattttc tcctccttgt ataaatcctg gttgctgtct ctttatgagg agttgtggcc  7500
cgttgtcagg caacgtggcg tggtgtgcac tgtgtttgct gacgcaaccc ccactggttg  7560
gggcattgcc accacctgtc agctcctttc cgggactttc gctttccccc tccctattgc  7620
cacggcggaa ctcatcgccg cctgccttgc ccgctgctgg acaggggctc ggctgttggg  7680
cactgacaat tccgtggtgt tgtcggggaa gctgacgtcc tttccatggc tgctcgcctg  7740
tgttgccacc tggattctgc gcgggacgtc cttctgctac gtcccttcgg ccctcaatcc  7800
agcggacctt ccttcccgct gagagacaca aaaaattcca acacactatt gcaatgaaaa  7860
taaatttcct ttattagcca gaagtcagat gctcaagggg cttcatgatg tccccataat  7920
ttttggcaga gggaaaaaga tctcagtggt atttgtgagc cagggcattg gccttctgat  7980
aggcagcctg cacctgagga gtgcggccgc tttacttgta cagctcgtcc atgccgagag  8040
tgatcccggc ggcggtcacg aactccagca ggaccatgtg atcgcgcttc tcgttggggt  8100
ctttgctcag ggcggactgg gtgctcaggt agtggttgtc gggcagcagc acggggccgt  8160
cgccgatggg ggtgttctgc tggtagtggt cggcgagctg cacgctgccg tcctcgatgt  8220
tgtggcggat cttgaagttc accttgatgc cgttcttctg cttgtcggcc atgatataga  8280
cgttgtggct gttgtagttg tactccagct tgtgccccag gatgttgccg tcctccttga  8340
agtcgatgcc cttcagctcg atgcggttca ccagggtgtc gccctcgaac ttcacctcgg  8400
cgcgggtctt gtagttgccg tcgtccttga agaagatggt gcgctcctgg acgtagcctt  8460
cgggcatggc ggacttgaag aagtcgtgct gcttcatgtg gtcggggtag cggctgaagc  8520
actgcacgcc gtaggtcagg gtggtcacga gggtgggcca gggcacgggc agcttgccgg  8580
```

-continued

```
tggtgcagat gaacttcagg gtcagcttgc cgtaggtggc atcgccctcg ccctcgccgg  8640
acacgctgaa cttgtggccg tttacgtcgc cgtccagctc gaccaggatg ggcaccaccc  8700
cggtgaacag ctcctcgccc ttgctcacca tggtggcggg atctgacggt tcactaaacc  8760
agctctgctt atatagacct cccaccgtac acgcctaccg cccatttgcg tcaatggggc  8820
ggagttgtta cgacattttg gaaagtcccg ttgattttgg tgccaaaaca aactcccatt  8880
gacgtcaatg ggtggagagc ttggaaatcc ccgtgagtca aaccgctatc cacgcccatt  8940
gatgtactgc caaaaccgca tcaccatggt aatagcgatg actaatacgt agatgtactg  9000
ccaagtagga aagtcccata aggtcatgta ctgggcataa tgccaggcgg gccatttacc  9060
gtcattgacg tcaatagggg gcgtacttgg catatgatac acttgatgta ctgccaagtg  9120
ggcagtttac cgtaaatact ccacccattg acgtcaatgg aaagtcccta ttggcgttac  9180
tatgggaaca tacgtcatta ttgacgtcaa tgggcggggg tcgttgggcg gtcagccagg  9240
cgggccattt accgtaagtt atgtaacggg cctgctgccg gctctgcggc ctcttccgcg  9300
tcttcgcctt cgccctcaga cgagtcggat ctccctttgg gccgcctccc cgcctgtcta  9360
gcttgactga ctgagataca gcgtaccttc agctcacaga catgataaga tacattgatg  9420
agtttggaca aaccacaact agaatgcagt gaaaaaaatg ctttatttgt gaaatttgtg  9480
atgctattgc tttatttgta accattataa gctgcaataa acaagttaac aacaacaatt  9540
gcattcattt tatgtttcag gttcaggggg aggtgtggga ggttttttaa agcaagtaaa  9600
acctctacaa atgtggtatt ggcccatctc tatcggtatc gtagcataac cccttggggc  9660
ctctaaacgg gtcttgaggg gttttttgtg cccctcgggc cggattgcta tctaccggca  9720
ttggcgcaga aaaaaatgcc tgatgcgacg ctgcgcgtct tatactccca catatgccag  9780
attcagcaac ggatacggct tccccaactt gcccacttcc atacgtgtcc tccttaccag  9840
aaatttatcc ttaaggtcgt cagctatcct gcaggcgatc tctcgatttc gatcaagaca  9900
ttcctttaat ggtcttttct ggacaccact aggggtcaga agtagttcat caaactttct  9960
tccctcccta atctcattgg ttaccttggg ctatcgaaac ttaattaagc gatctgcatc  10020
tcaattagtc agcaaccata gtcccgcccc taactccgcc catcccgccc ctaactccgc  10080
ccagttccgc ccattctccg ccccatcgct gactaatttt ttttatttat gcagaggccg  10140
aggccgcctc ggcctctgag ctattccaga agtagtgagg aggctttttt ggaggcctag  10200
gcttttgcaa aggaggtagc caacatgatt gaacaagatg gattgcacgc aggttctccc  10260
gccgcttggg tggagaggct attcggctat gactgggcac aacagacaat cggctgctct  10320
gatgccgccg tgttccggct gtcagcgcag gggcgcccgg ttctttttgt caagaccgac  10380
ctgtccggtg ccctgaatga actccaggac gaggcagcgc ggctatcgtg gctggccacg  10440
acgggcgttc cttgcgcagc tgtgctcgac gttgtcactg aagcgggaag ggactggctg  10500
ctattgggcg aagtgccggg gcaggatctc ctgtcatctc accttgctcc tgccgagaaa  10560
gtatccatca tggctgatgc aatgcggcgg ctgcatacgc ttgatccggc tacctgccca  10620
ttcgaccacc aagcgaaaca tcgcatcgag cgagcacgta ctcggatgga agccggtctt  10680
gtcgatcagg atgatctgga cgaagagcat caggggctcg cgccagccga actgttcgcc  10740
aggctcaagg cgcggatgcc cgacggcgag gatctcgtcg tgacccacgg cgatgcctgc  10800
ttgccgaata tcatggtgga aaatggccgc ttttctggat tcatcgactg tggccggctg  10860
ggtgtggcgg accgctatca ggacatagcg ttggctaccc gtgatattgc tgaagagctt  10920
ggcggcgaat gggctgaccg cttcctcgtg ctttacggta tcgccgctcc cgattcgcag  10980
cgcatcgcct tctatcgcct tcttgacgag ttcttctagt atgtaagccc tgtgccttct  11040
agttgccagc catctgttgt ttgcccctcc cccgtgcctt ccttgaccct ggaaggtgcc  11100
actcccactg tcctttccta ataaaatgag gaaattgcat cgcattgtct gagtaggtgt  11160
cattctattc tggggggtgg ggtggggcag gacagcaagg gggaggattg ggaagacaat  11220
agcaggcatg ctggggatgc ggtgggctct atggttaatt aaccagtcaa gtcagctact  11280
tggcgagatc gacttgtctg ggtttcgact acgctcagaa ttgcgtcagt caagttcgat  11340
ctggtccttg ctattgcacc cgttctccga ttacgagttt catttaaatc atgtgagcaa  11400
aaggccagca aaaggccagg aaccgtaaaa aggccgcgtt gctggcgttt ttccataggc  11460
tccgcccccc tgacgagcat cacaaaaatc gacgctcaag tcagaggtgg cgaaacccga  11520
caggactata aagataccag gcgtttcccc ctggaagctc cctcgtgcgc tctcctgttc  11580
cgaccctgcc gcttaccgga tacctgtccg cctttctccc ttcgggaagc gtggcgcttt  11640
ctcatagctc acgctgtagg tatctcagtt cggtgtaggt cgttcgctcc aagctgggct  11700
gtgtgcacga accccccgtt cagcccgacc gctgcgcctt atccggtaac tatcgtcttg  11760
agtccaaccc ggtaagacac gacttatcgc cactggcagc agccactggt aacaggatta  11820
gcagagcgag gtatgtaggc ggtgctacag agttcttgaa gtggtggcct aactacggct  11880
acactagaag aacagtattt ggtatctgcg ctctgctgaa gccagttacc ttcggaaaaa  11940
gagttggtag ctcttgatcc ggcaaacaaa ccaccgctgg tagcggtggt ttttttgttt  12000
gcaagcagca gattacgcgc agaaaaaaag gatctcaaga agatcctttg atcttttcta  12060
cggggtctga cgctcagtgg aacgaaaact cacgttaagg gattttggtc atgagattat  12120
caaaaaggat cttcacctag atccttttaa attaaaaatg aagttttaaa tcaatctaaa  12180
gtatatatga gtaaacttgg tctgacagtt accaatgctt aatcagtgag gcacctatct  12240
cagcgatctg tctatttcgt tcatccatag ttgcatttaa atttccgaac tctccaaggc  12300
cctcgtcgga aaatcttcaa acctttcgtc cgatccatct tgcaggctac ctctcgaacg  12360
aactatcgca agtctcttgg ccggccttgc gccttggcta ttgcttggca gcgcctatcg  12420
ccaggtatta ctccaatccc gaatatccga gatcgggatc acccgagaga agttcaacct  12480
acatcctcaa tcccgatcta tccgagatcc gaggaatatc gaaatcgggg cgcgcctggt  12540
gtaccgagaa cgat                                                    12554
```

```
SEQ ID NO: 94          moltype = DNA  length = 12569
FEATURE                Location/Qualifiers
misc_feature           1..12569
                       note = Description of Artificial Sequence: Synthetic
                        polynucleotide
source                 1..12569
                       mol_type = other DNA
                       organism = synthetic construct
SEQUENCE: 94
tcgaaatcgg ggcgcgcctg gtgtaccgag aacgatcctc tcagtgcgag tctcgacgat  60
ccatatcgtt gcttggcagt cagccagtcg gaatccagct tgggacccag gaagtccaat  120
```

```
cgtcagatat tgtactcaag cctggtcacg gcagcgtacc gatctgttta aacctagata  180
ttgatagtct gatcggtcaa cgtataatcg agtcctagct tttgcaaaca tctatcaaga  240
gacaggatca gcaggaggct ttcgcatgag tattcaacat ttccgtgtcg cccttattcc  300
ctttttgcg gcattttgcc ttcctgtttt tgctcaccca gaaacgctgg tgaaagtaaa  360
agatgctgaa gatcagttgg gtgcgcgagt gggttacatc gaactggatc tcaacagcgg  420
taagatcctt gagagttttc gccccgaaga acgctttcca atgatgagca cttttaaagt  480
tctgctatgt ggcgcggtat tatcccgtat tgacgccggg caagagcaac tcggtcgccg  540
catacactat tctcagaatg acttggttga gtattcacca gtcacagaaa agcatcttac  600
ggatggcatg acagtaagag aattatgcag tgctgccata accatgagtg ataacactgc  660
ggccaactta cttctgacaa cgattggagg accgaaggag ctaaccgctt ttttgcacaa  720
catgggggat catgtaactc gccttgatcg ttgggaaccg gagctgaatg aagccatacc  780
aaacgacgag cgtgacacca cgatgcctgt agcaatggca acaaccttgc gtaaactatt  840
aactggcgaa ctacttactc tagcttcccg gcaacagttg atagactgga tggaggcgga  900
taaagttgca ggaccacttc tgcgctcggc ccttccggct ggctggttta ttgctgataa  960
atctggagcc ggtgagcgtg ggtctcgcgg tatcattgca gcactggggc cagatggtaa  1020
gccctcccgt atcgtagtta tctacacgac ggggagtcag gcaactatgg atgaacgaaa  1080
tagacagatc gctgagatag gtgcctcact gattaagcat tggtaaccga ttctaggtgc  1140
attggcgcag aaaaaaatgc ctgatgcgac gctgcgcgtc ttatactccc acatatgcca  1200
gattcagcaa cggatacggc ttccccaact tgcccacttc catacgtgtc ctccttacca  1260
gaaatttatc cttaagatcg tttaaactcg actctggctc tatcgaatct ccgtcgtttc  1320
gagcttacgc gaacagccgt ggcgctcatt tgctcgtcgg gcatcgaatc tcgtcagcta  1380
tcgtcagctt accttttgg cagcgatcgc ggctcccgac atcttggacc attagctcca  1440
caggtatctt cttccctcta gtggtcataa cagcagcttc agctacctct caattcaaaa  1500
aacccctcaa gacccgttta gaggccccaa ggggttatgc tatcaatcgt tgcgttacac  1560
acacaaaaaa ccaacacaca tccatcttcg atggatagcg attttattat ctaactgctg  1620
atcgagtgta gccagatcta gtaatcaatt acggggtcat tagttcatag cccatatatg  1680
gagttccgcg ttacataact tacggtaaat ggcccgcctg gctgaccgcc caacgacccc  1740
cgcccattga cgtcaataat gacgtatgtt cccatagtaa cgccaatagg gactttccat  1800
tgacgtcaat gggtggagta tttacggtaa actgcccact tggcagtaca tcaagtgtat  1860
catatgccaa gtacgccccc tattgacgtc aatgacggta aatggcccgc ctggcattat  1920
gcccagtaca tgaccttatg ggactttcct acttggcagt acatctacgt attagtcatc  1980
gctattacca tgctgatgcg gttttggcag tacatcaatg ggcgtggata gcggtttgac  2040
tcacggggat ttccaagtct ccaccccatt gacgtcaatg ggagtttgtt ttggcaccaa  2100
aatcaacggg actttccaaa atgtcgtaac aactccgccc cattgacgca aatgggcggt  2160
aggcgtgtac ggtgggaggt ctatataagc agagctggtt tagtgaaccg tcagatcaga  2220
tctttgtcga tcctaccatc cactcgacac acccgccagc ggccgctaat acgactcact  2280
atagggagaa gtactgccac catgggcaag aagcaaaatc gcaagacggg gaattccaag  2340
acacaatccg ctagcccacc acctaaagag cgttctagct cccctgctac tgagcagtcc  2400
tggatggaaa acgacttcga tgaactccgg gaagagggat ttaggcgatc caactattca  2460
gaactccgcg aagatatcca gacaaagggg aaggaagtcg agaatttcga gaagaacctc  2520
gaggagtgca tcacccgtat cacaaacact gagaaatgtc tcaaagaact catggaactt  2580
aagacaaaag ccagggagct tcgagaggag tgtcggagtc tgagatccag gtgtgaccag  2640
ctcgaggagc gcgtgagcgc gatggaagac gagatgaacg agatgaaaag agagggcaaa  2700
ttcagggaga agcgcattaa gaggaacgaa cagagtctgc aggagatttg ggattacgtc  2760
aagaggccta acctgcggtt gatcggcgtc cccgagagcg acgtagaaaa cgggactaaa  2820
ctggagaata cacttcaaga catcattcaa gaaaattttc caaacctggc tcggcaagct  2880
aatgtgcaaa tccaagagat ccaacgcaca ccccagcggt atagctctcg gcgtgccacc  2940
cctaggcata ttatcgtgcg ctttactaag gtggagatga aagagaagat gctgcgagcc  3000
gctcgggaaa agggaagggt gactttgaag ggcaaaccta ttcggctgac ggttgacctt  3060
agcgccgaga cactccaggc acgccgggaa tggggcccca tctttaatat cctgaaggag  3120
aagaacttcc agccacgaat ctcttaccct gcaaagttga gttttatctc cgagggtgag  3180
attaagtatt tcatcgataa acagatgctg cgagacttcg tgacaactcg cccagctctc  3240
aaggaactgc tcaaagaggc tcttaatatg gagcgcaata atagatatca acccttgcag  3300
aaccacgcaa agatgaaaag gccggcggcc acgaaaaagg ccggccaggc aaaaaagaaa  3360
aagtgagaca gccgtcagac catcaagact aggaagaaac tgcatcaact aatgagcaaa  3420
atcaccagct aacatcatag tatacatgac cggctctaac tcacatatca ccatccttac  3480
acttaacatt aacggcctca actcagctat caagcgccat cggctggcca gctggatcaa  3540
atcacaggat ccaagcgttt gttgcatcca agagacccac ctgacctgta gagatactca  3600
ccgcctcaag atcaagggat ggcgaaagat ttatcaggcg aacggtaagc agaagaaagc  3660
cggagtcgca attctggtct cagacaagac ggatttcaag cccaccaaaa ttaagcgtga  3720
taaggaaggt cactatatta tggtgaaagg cagcatacag caggaagaac ttaccatatt  3780
gaacatctac gcgccaaaca ccggcgcacc tcgctttatc aaacaggtcc tgtccgatct  3840
gcagcgagat ctggattctc atacgttgat tatgggtgat ttcaatacac cattgagcac  3900
cctggatcgc agcaccaggc aaaaggtaaa taaagacacg caagagctca atagcgcact  3960
gcatcaggca gatctcattg atatttatcg cactcttcat cctaagagta ccgagtacac  4020
attcttcagc gccccacatc atacatactc aaagatcgat catatcgtcg gctcaaaggc  4080
tctgctgtca aagtgcaagc gcacagagat aattacaaat tacctgtcag atcatagcgc  4140
gatcaagctc gagctgagaa tcaagaacct gacccagagc cggagtacca cttggaagct  4200
taataacctg ctgctcaacg attattgggt ccacaatgag atgaaggcag agattaaaat  4260
gttcttcgaa acaaatgaga ataaggatac tacctatcaa aacctttggg atgcctttaa  4320
ggccgtctgc agaggcaagt tcatcgccct caacgcctat aaaagaaaac aagagagatc  4380
taagatcgat actctcacct ctcagctgaa ggagttggag aaacaggaac agacccactc  4440
caaggcgtca agacggcagg agatcacaaa gattcgcgcc gagttgaaag agatcgaaac  4500
ccaaaagact cttcagaaaa ttaacgagtc tcgtagttgg ttcttcgagc ggattaataa  4560
gatagacaga cctctggcac gactgattaa gaagaagcgc gaaaagaacc agattgatac  4620
catcaagaac gacaagggcg acatcactac tgacccgacc gagatccaga ccactattcg  4680
ggagtattat aagcatttgt atgctaacaa gcttgagaac ctggaagaga tggacacttt  4740
tctggatacc tatactctgc cacggcttaa tcaagaggaa gtcgagtccc tcaaccgccc  4800
aattacagga agcgagattg tggccataat taactccctg ccgacaaaga aatctcctgg  4860
```

-continued

```
tccggacggg tttacagctg agttttatca acggtatatg gaagagcttg taccgtttct  4920
gctcaagctc tttcagtcta tagaaaagga aggcatcttg cccaattcct tctacgaagc  4980
ttctataata cttattccca aaccaggacg cgataccaca aagaaggaaa acttccggcc  5040
cattagtctc atgaatatcg acgctaaaat attgaacaag attctcgcca acagaatcca  5100
acaacatatt aagaaattga tacatcacga ccaggtgggg tttatacctg gcatgcaggg  5160
ctggtttaac atccggaaga gtattaacgt cattcaacac attaatagag ctaaggataa  5220
gaatcatatg atcatctcta tagacgcgga aaaggcattc gataagattc agcagccatt  5280
tatgctcaag actctgaaca aactcggcat cgacggaaca tattttaaga ttattcgcgc  5340
aatttacgat aagccgactg ctaacattat ccttaacggc caaaagctcg aggcctttcc  5400
gctcaagact ggaacccgcc aaggctgtcc cctctccccg cttttgttta atattgtact  5460
cgaggtgctg gctagggcta ttcgtcaaga gaaagagatt aaagggatac agctcgggaa  5520
ggaagaggtc aagctttcct tgttcgccga tgatatgatt gtgtacctgg agaatcctat  5580
tgtgtctgct cagaaccttc ttaaacttat ttctaacttt agcaaggtca gcggctataa  5640
gattaacgtc cagaaatctc aggcctttct gtacacaaat aatcgacaga ccgaatccca  5700
gataatgggt gagcttccgt ttgtcatagc cagcaaaagg ataaagtatc tcggaatcca  5760
gctgacacga gacgttaaag atttgtttaa ggaaaattac aagcctctcc tgaaagagat  5820
taaggaagat actaataagt ggaagaatat cccctgttca tgggttggca gaatcaacat  5880
agtgaagatg gcaatacttc ctaaagtgat atatcgcttt aacgccatcc caattaaact  5940
gcctatgacc ttctttacgg agctcgagaa aacaaccctt aaatttatat ggaatcaaaa  6000
gagagcaaga atagcgaagt ccatcttgag ccagaagaat aaggccggtg ggattacttt  6060
gcctgatttt aagttgtatt ataaagccac agtaactaag acagcctggt attggtatca  6120
gaatagagac atcgaccagt ggaatcggac cgaaccatca gagataatgc cccacatcta  6180
taattacctt atattcgata agccagaaaa gaataaacag tggggcaaag acagcctctt  6240
caacaagtgg tgttgggaga attggctggc catatgccgg aaactcaagc tcgacccctt  6300
tcttacaccc tacactaaaa tcaacagtag gtggatcaag gacttgaatg tcaagccaaa  6360
gactataaag acactggaag agaatcttgg gatcacaata caagatatag gcgtcggcaa  6420
agattttatg tcaaagacgc ccaaggccat ggccactaag gataagattg ataagtggga  6480
ccttattaag ctcaaaagct tctgtactgc caaggagacc acgatcagag ttaataggca  6540
gcccactaca tgggaaaaga ttttcgccac ttattcatca gataaggggt tgataagcag  6600
aatatataac gagctgaagc agatctacaa gaagaaaacg aataatccca tcaagaagtg  6660
ggcaaaagat atgaacaggc attttagcaa agaggatatc tacgccgcga agaagcatat  6720
gaagaagtgt agttcaagct tggccattcg tgagatgcag attaagacga ccatgcgata  6780
ccaccttacc ccagtgagga tggcaattat caagaaatct ggcaataata gatgttggcg  6840
gggctgtggc gagattggca ccctgctcca ttgctggtgg gattgcaagc tggtgcagcc  6900
gctttggaaa tcagtctggc gctttctgag ggacctcgag cttgagattc ccttcgatcc  6960
cgcaattccc ttgctcggaa tctatcctaa cgaatacaag agctgttgtt acaaggatac  7020
gtgtacccgg atgttcatcg cggccttgtt tacgatagct aagacgtgga atcagcctaa  7080
gtgccccaca atgatcgatt ggatcaagaa aatgtggcat atttatacca tggagtatta  7140
cgcagcaatt aagaatgacg aatttatttc cttcgttggg acctggatga agctggagac  7200
tattattctg agcaagctgt ctcaggagca aaagacaaag catagaatct tctctctcat  7260
tggtggtaac gactacaaag acgatgacga caagtaaagc gcttctagaa gttgtctcct  7320
cctgcactga ctgactgata caatcgattt ctggatccgc aggcctaatc aacctctgga  7380
ttacaaaatt tgtgaaagat tgactggtat tcttaactat gttgctcctt ttacgctatg  7440
tggatacgct gctttaatgc ctttgtatca tgctattgct tcccgtatgg ctttcatttt  7500
ctcctccttg tataaatcct ggttgctgtc tctttatgag gagttgtggc ccgttgtcag  7560
gcaacgtggc gtggtgtgca ctgtgtttgc tgacgcaacc cccactggtt ggggcattgc  7620
caccacctgt cagctccttt ccgggacttt cgctttcccc ctccctattg ccacggcgga  7680
actcatcgcc gcctgccttg cccgctgctg gacaggggct cggctgttgg gcactgacaa  7740
ttccgtggtg ttgtcgggga agctgacgtc ctttccatgg ctgctcgcct gtgttgccac  7800
ctggattctg cgcgggacgt ccttctgcta cgtcccttcg gccctcaatc cagcggacct  7860
tccttcccgc tgagagacac aaaaaattcc aacacactat tgcaatgaaa ataaatttcc  7920
tttattagcc agaagtcaga tgctcaaggg gcttcatgat gtccccataa tttttggcag  7980
agggaaaaag atctcagtgg tatttgtgag ccagggcatt ggccttctga taggcagcct  8040
gcacctgagg agtgcggccg ctttacttgt acagctcgtc catgccgaga gtgatcccgg  8100
cggcggtcac gaactccagc aggaccatgt gatcgcgctt ctcgttgggg tctttgctca  8160
gggcggactg ggtgctcagg tagtggttgt cgggcagcag cacggggccg tcgccgatgg  8220
gggtgttctg ctggtagtgg tcggcgagct gcacgctgcc gtcctcgatg ttgtggcgga  8280
tcttgaagtt caccttgatg ccgttcttct gcttgtcggc catgatatag acgttgtggc  8340
tgttgtagtt gtactccagc ttgtgcccca ggatgttgcc gtcctccttg aagtcgatgc  8400
ccttcagctc gatgcggttc accagggtgt cgccctcgaa cttcacctcg gcgcgggtct  8460
tgtagttgcc gtcgtccttg aagaagatgg tgcgctcctg gacgtagcct tcgggcatgg  8520
cggacttgaa gaagtcgtgc tgcttcatgt ggtcggggta gcggctgaag cactgcacgc  8580
cgtaggtcag ggtggtcacg agggtgggcc agggcacggg cagcttgccg gtggtgcaga  8640
tgaacttcag ggtcagcttg ccgtaggtgg catcgccctc gccctcgccg gacacgctga  8700
acttgtggcc gtttacgtcg ccgtccagct cgaccaggat gggcaccacc ccggtgaaca  8760
gctcctcgcc cttgctcacc atggtggcgg gatctgacgg ttcactaaac cagctctgct  8820
tatatagacc tcccaccgta cacgcctacc gcccatttgc gtcaatgggg cggagttgtt  8880
acgacatttt ggaaagtccc gttgattttg gtgccaaaac aaactcccat tgacgtcaat  8940
ggggtggaga cttggaaatc cccgtgagtc aaaccgctat ccacgcccat tgatgtactg  9000
ccaaaaccgc atcaccatgg taatagcgat gactaatacg tagatgtact gccaagtagg  9060
aaagtcccat aaggtcatgt actgggcata atgccaggcg ggccatttac cgtcattgac  9120
gtcaataggg ggcgtacttg gcatatgata cacttgatgt actgccaagt gggcagttta  9180
ccgtaaatac tccacccatt gacgtcaatg gaaagtccct attggcgtta ctatgggaac  9240
atacgtcatt attgacgtca atgggcgggg gtcgttgggc ggtcagccag gcgggccatt  9300
taccgtaagt tatgtaacgg gcctgctgcc ggctctgcgg cctcttccgc gtcttcgcct  9360
tcgccctcag acgagtcgga tctccctttg ggccgcctcc ccgcctgtct agcttgactg  9420
actgagatac agcgtacctt cagctcacag acatgataag atacattgat gagtttggac  9480
aaaccacaac tagaatgcag tgaaaaaaat gctttatttg tgaaatttgt gatgctattg  9540
ctttatttgt aaccattata agctgcaata aacaagttaa caacaacaat tgcattcatt  9600
```

-continued

```
ttatgtttca ggttcagggg gaggtgtggg aggtttttta aagcaagtaa aacctctaca  9660
aatgtggtat tggcccatct ctatcggtat cgtagcataa ccccttgggg cctctaaacg  9720
ggtcttgagg ggttttttgt gcccctcggg ccggattgct atctaccggc attggcgcag  9780
aaaaaaatgc ctgatgcgac gctgcgcgtc ttatactccc acatatgcca gattcagcaa  9840
cggatacggc ttccccaact tgcccacttc catacgtgtc ctccttacca gaaatttatc  9900
cttaaggtcg tcagctatcc tgcaggcgat ctctcgattt cgatcaagac attcctttaa  9960
tggtcttttc tggacaccac taggggtcag aagtagttca tcaaactttc ttccctccct  10020
aatctcattg gttaccttgg gctatcgaaa cttaattaag cgatctgcat ctcaattagt  10080
cagcaaccat agtcccgccc ctaactccgc ccatcccgcc cctaactccg cccagttccg  10140
cccattctcc gccccatcgc tgactaattt tttttattta tgcagaggcc gaggccgcct  10200
cggcctctga gctattccag aagtagtgag gaggcttttt tggaggccta ggcttttgca  10260
aaggaggtag ccaacatgat tgaacaagat ggattgcacg caggttctcc cgccgcttgg  10320
gtggagaggc tattcggcta tgactgggca caacagacaa tcggctgctc tgatgccgcc  10380
gtgttccggc tgtcagcgca ggggcgcccg gttctttttg tcaagaccga cctgtccggt  10440
gccctgaatg aactccagga cgaggcagcg cggctatcgt ggctggccac gacgggcgtt  10500
ccttgcgcag ctgtgctcga cgttgtcact gaagcgggaa gggactggct gctattgggc  10560
gaagtgccgg ggcaggatct cctgtcatct caccttgctc ctgccgagaa agtatccatc  10620
atggctgatg caatgcggcg gctgcatacg cttgatccgg ctacctgccc attcgaccac  10680
caagcgaaac atcgcatcga gcgagcacgt actcggatgg aagccggtct tgtcgatcag  10740
gatgatctgg acgaagagca tcaggggctc gcgccagccg aactgttcgc caggctcaag  10800
gcgcggatgc ccgacggcga ggatctcgtc gtgacccacg gcgatgcctg cttgccgaat  10860
atcatggtgg aaaatggccg cttttctgga ttcatcgact gtggccggct gggtgtggcg  10920
gaccgctatc aggacatagc gttggctacc cgtgatattg ctgaagagct tggcggcgaa  10980
tgggctgacc gcttcctcgt gctttacggt atcgccgctc ccgattcgca gcgcatcgcc  11040
ttctatcgcc ttcttgacga gttcttctag tatgtaagcc ctgtgccttc tagttgccag  11100
ccatctgttg tttgcccctc ccccgtgcct tccttgaccc tggaaggtgc cactcccact  11160
gtcctttcct aataaaatga ggaaattgca tcgcattgtc tgagtaggtg tcattctatt  11220
ctggggggtg gggtggggca ggacagcaag ggggaggatt gggaagacaa tagcaggcat  11280
gctggggatg cggtgggctc tatggttaat taaccagtca agtcagctac ttggcgagat  11340
cgacttgtct gggtttcgac tacgctcaga attgcgtcag tcaagttcga tctggtcctt  11400
gctattgcac ccgttctccg attacgagtt tcatttaaat catgtgagca aaaggccagc  11460
aaaaggccag gaaccgtaaa aaggccgcgt tgctggcgtt tttccatagg ctccgccccc  11520
ctgacgagca tcacaaaaat cgacgctcaa gtcagaggtg gcgaaacccg acaggactat  11580
aaagatacca ggcgtttccc cctggaagct ccctcgtgcg ctctcctgtt ccgaccctgc  11640
cgcttaccgg atacctgtcc gcctttctcc cttcgggaag cgtggcgctt tctcatagct  11700
cacgctgtag gtatctcagt tcggtgtagg tcgttcgctc caagctgggc tgtgtgcacg  11760
aaccccccgt tcagcccgac cgctgcgcct tatccggtaa ctatcgtctt gagtccaacc  11820
cggtaagaca cgacttatcg ccactggcag cagccactgg taacaggatt agcagagcga  11880
ggtatgtagg cggtgctaca gagttcttga agtggtggcc taactacggc tacactagaa  11940
gaacagtatt tggtatctgc gctctgctga agccagttac cttcggaaaa agagttggta  12000
gctcttgatc cggcaaacaa accaccgctg gtagcggtgg tttttttgtt tgcaagcagc  12060
agattacgcg cagaaaaaaa ggatctcaag aagatccttt gatcttttct acggggtctg  12120
acgctcagtg gaacgaaaac tcacgttaag ggattttggt catgagatta tcaaaaagga  12180
tcttcaccta gatcctttta aattaaaaat gaagttttaa atcaatctaa agtatatatg  12240
agtaaacttg gtctgacagt taccaatgct taatcagtga ggcacctatc tcagcgatct  12300
gtctatttcg ttcatccata gttgcattta aatttccgaa ctctccaagg ccctcgtcgg  12360
aaaatcttca aacctttcgt ccgatccatc ttgcaggcta cctctcgaac gaactatcgc  12420
aagtctcttg gccggccttg cgccttggct attgcttggc agcgcctatc gccaggtatt  12480
actccaatcc cgaatatccg agatcgggat cacccgagag aagttcaacc tacatcctca  12540
atcccgatct atccgagatc cgaggaata                                  12569
```

```
SEQ ID NO: 95          moltype = DNA  length = 12581
FEATURE                Location/Qualifiers
misc_feature           1..12581
                       note = Description of Artificial Sequence: Synthetic
                        polynucleotide
source                 1..12581
                       mol_type = other DNA
                       organism = synthetic construct
SEQUENCE: 95
tatcgaaatc ggggcgcgcc tggtgtaccg agaacgatcc tctcagtgcg agtctcgacg  60
atccatatcg ttgcttggca gtcagccagt cggaatccag cttgggaccc aggaagtcca  120
atcgtcagat attgtactca agcctggtca cggcagcgta ccgatctgtt taaacctaga  180
tattgatagt ctgatcggtc aacgtataat cgagtcctag cttttgcaaa catctatcaa  240
gagacaggat cagcaggagg ctttcgcatg agtattcaac atttccgtgt cgcccttatt  300
ccctttttttg cggcattttg ccttcctgtt tttgctcacc cagaaacgct ggtgaaagta  360
aaagatgctg aagatcagtt gggtgcgcga gtgggttaca tcgaactgga tctcaacagc  420
ggtaagatcc ttgagagttt tcgccccgaa gaacgctttc caatgatgag cacttttaaa  480
gttctgctat gtggcgcggt attatcccgt attgacgccg ggcaagagca actcggtcgc  540
cgcatacact attctcagaa tgacttggtt gagtattcac cagtcacaga aaagcatctt  600
acggatggca tgacagtaag agaattatgc agtgctgcca taaccatgag tgataacact  660
gcggccaact tacttctgac aacgattgga ggaccgaagg agctaaccgc ttttttgcac  720
aacatggggg atcatgtaac tcgccttgat cgttgggaac cggagctgaa tgaagccata  780
ccaaacgacg agcgtgacac cacgatgcct gtagcaatgg caacaacctt gcgtaaacta  840
ttaactggcg aactacttac tctagcttcc cggcaacagt tgatagactg gatggaggcg  900
gataaagttg caggaccact tctgcgctcg gcccttccgg ctggctggtt tattgctgat  960
aaatctggag ccggtgagcg tgggtctcgc ggtatcattg cagcactggg gccagatggt  1020
aagccctccc gtatcgtagt tatctacacg acggggagtc aggcaactat ggatgaacga  1080
aatagacaga tcgctgagat aggtgcctca ctgattaagc attggtaacc gattctaggt  1140
```

-continued

```
gcattggcgc agaaaaaaat gcctgatgcg acgctgcgcg tcttatactc ccacatatgc  1200
cagattcagc aacggatacg gcttccccaa cttgcccact tccatacgtg tcctccttac  1260
cagaaattta tccttaagat cgtttaaact cgactctggc tctatcgaat ctccgtcgtt  1320
tcgagcttac gcgaacagcc gtggcgctca tttgctcgtc gggcatcgaa tctcgtcagc  1380
tatcgtcagc ttaccttttt ggcagcgatc gcggctcccg acatcttgga ccattagctc  1440
cacaggtatc ttcttccctc tagtggtcat aacagcagct tcagctacct ctcaattcaa  1500
aaaacccctc aagacccgtt tagaggcccc aaggggttat gctatcaatc gttgcgttac  1560
acacacaaaa aaccaacaca catccatctt cgatggatag cgattttatt atctaactgc  1620
tgatcgagtg tagccagatc tagtaatcaa ttacggggtc attagttcat agcccatata  1680
tggagttccg cgttacataa cttacggtaa atggcccgcc tggctgaccg cccaacgacc  1740
cccgcccatt gacgtcaata atgacgtatg ttcccatagt aacgccaata gggactttcc  1800
attgacgtca atgggtggag tatttacggt aaactgccca cttggcagta catcaagtgt  1860
atcatatgcc aagtacgccc cctattgacg tcaatgacgg taaatggccc gcctggcatt  1920
atgcccagta catgacctta tgggactttc ctacttggca gtacatctac gtattagtca  1980
tcgctattac catgctgatg cggttttggc agtacatcaa tgggcgtgga tagcggtttg  2040
actcacgggg atttccaagt ctccacccca ttgacgtcaa tgggagtttg ttttggcacc  2100
aaaatcaacg ggactttcca aaatgtcgta acaactccgc cccattgacg caaatgggcg  2160
gtaggcgtgt acggtgggag gtctatataa gcagagctgg tttagtgaac cgtcagatca  2220
gatctttgtc gatcctacca tccactcgac acacccgcca gcggccgcta atacgactca  2280
ctatagggag aagtactgcc accatgggca agaagcaaaa tcgcaagacg gggaattcca  2340
agacacaatc cgctagccca ccacctaaag agcgttctag ctcccctgct actgagcagt  2400
cctggatgga aaacgacttc gatgaactcc gggaagaggg atttaggcga tccaactatt  2460
cagaactccg cgaagatatc cagacaaagg ggaaggaagt cgagaatttc gagaagaacc  2520
tcgaggagtg catcacccgt atcacaaaca ctgagaaatg tctcaaagaa ctcatggaac  2580
ttaagacaaa agccagggag cttcgagagg agtgtcggag tctgagatcc aggtgtgacc  2640
agctcgagga gcgcgtgagc gcgatggaag acgagatgaa cgagatgaaa agagagggca  2700
aattcaggga gaagcgcatt aagaggaacg aacagagtct gcaggagatt tgggattacg  2760
tcaagaggcc taacctgcgg ttgatcggcg tccccgagag cgacgtagaa aacgggacta  2820
aactggagaa tacacttcaa gacatcattc aagaaaattt tccaaacctg gctcggcaag  2880
ctaatgtgca aatccaagag atccaacgca caccccagcg gtatagctct cggcgtgcca  2940
cccctaggca tattatcgtg cgctttacta aggtggagat gaaagagaag atgctgcgag  3000
ccgctcggga aaagggaagg gtgactttga agggcaaacc tattcggctg acggttgacc  3060
ttagcgccga gacactccag gcacgccggg aatggggccc catctttaat atcctgaagg  3120
agaagaactt ccagccacga atctcttacc ctgcaaagtt gagttttatc tccgagggtg  3180
agattaagta tttcatcgat aaacagatgc tgcgagactt cgtgacaact cgcccagctc  3240
tcaaggaact gctcaaagag gctcttaata tggagcgcaa taatagatat caacccttgc  3300
agaaccacgc aaagatgggc ggcggcagca aaaggccggc ggccacgaaa aaggccggcc  3360
aggcaaaaaa gaaaaagtga gacagccgtc agaccatcaa gactaggaag aaactgcatc  3420
aactaatgag caaaatcacc agctaacatc atagtataca tgaccggctc taactcacat  3480
atcaccatcc ttacacttaa cattaacggc ctcaactcag ctatcaagcg ccatcggctg  3540
gccagctgga tcaaatcaca ggatccaagc gtttgttgca tccaagagac ccacctgacc  3600
tgtagagata ctcaccgcct caagatcaag ggatggcgaa agatttatca ggcgaacggt  3660
aagcagaaga aagccggagt cgcaattctg gtctcagaca agacggattt caagcccacc  3720
aaaattaagc gtgataagga aggtcactat attatggtga aaggcagcat acagcaggaa  3780
gaacttacca tattgaacat ctacgcgcca aacaccggcg cacctcgctt tatcaaacag  3840
gtcctgtccg atctgcagcg agatctggat tctcatacgt tgattatggg tgatttcaat  3900
acaccattga gcaccctgga tcgcagcacc aggcaaaagg taaataaaga cacgcaagag  3960
ctcaatagcg cactgcatca ggcagatctc attgatattt atcgcactct tcatcctaag  4020
agtaccgagt acacattctt cagcgcccca catcatacat actcaaagat cgatcatatc  4080
gtcggctcaa aggctctgct gtcaaagtgc aagcgcacag agataattac aaattacctg  4140
tcagatcata gcgcgatcaa gctcgagctg agaatcaaga acctgaccca gagccggagt  4200
accacttgga agcttaataa cctgctgctc aacgattatt gggtccacaa tgagatgaag  4260
gcagagatta aaatgttctt cgaaacaaat gagaataagg atactaccta tcaaaacctt  4320
tgggatgcct ttaaggccgt ctgcagaggc aagttcatcg ccctcaacgc ctataaaaga  4380
aaacaagaga gatctaagat cgatactctc acctctcagc tgaaggagtt ggagaaacag  4440
gaacagaccc actccaaggc gtcaagacgg caggagatca caaagattcg cgccgagttg  4500
aaagagatcg aaacccaaaa gactcttcag aaaattaacg agtctcgtag ttggttcttc  4560
gagcggatta ataagataga cagacctctg gcacgactga ttaagaagaa gcgcgaaaag  4620
aaccagattg ataccatcaa gaacgacaag ggcgacatca ctactgaccc gaccgagatc  4680
cagaccacta ttcgggagta ttataagcat ttgtatgcta acaagcttga gaacctggaa  4740
gagatggaca cttttctgga tacctatact ctgccacggc ttaatcaaga ggaagtcgag  4800
tccctcaacc gcccaattac aggaagcgag attgtggcca taattaactc cctgccgaca  4860
aagaaatctc ctggtccgga cggtttacag gctgagtttt atcaacggta tatggaagag  4920
cttgtaccgt ttctgctcaa gctctttcag tctatagaaa aggaaggcat cttgcccaat  4980
tccttctacg aagcttctat aatacttatt cccaaaccag gacgcgatac cacaaagaag  5040
gaaaacttcc ggcccattag tctcatgaat atcgacgcta aaatattgaa caagattctc  5100
gccaacagaa tccaacaaca tattaagaaa ttgatacatc acgaccaggt ggggtttata  5160
cctggcatgc agggctggtt taacatccgg aagagtatta acgtcattca acacattaat  5220
agagctaagg ataagaatca tatgatcatc tctatagacg cggaaaaggc attcgataag  5280
attcagcagc catttatgct caagactctg aacaaactcg gcatcgacgg aacatatttt  5340
aagattattc gcgcaattta cgataagccg actgctaaca ttatccttaa cggccaaaag  5400
ctcgaggcct ttccgctcaa gactggaacc cgccaaggct gtcccctctc cccgcttttg  5460
tttaatattg tactcgaggt gctggctagg gctattcgtc aagagaaaga gattaaaggg  5520
atacagctcg ggaaggaaga ggtcaagctt tccttgttcg ccgatgatat gattgtgtac  5580
ctggagaatc ctattgtgtc tgctcagaac cttcttaaac ttatttctaa ctttagcaag  5640
gtcagcggct ataagattaa cgtccagaaa tctcaggcct ttctgtacac aaataatcga  5700
cagaccgaat cccagataat gggtgagctt ccgtttgtca tagccagcaa aaggataaag  5760
tatctcggaa tccagctgac acgagacgtt aaagatttgt ttaaggaaaa ttacaagcct  5820
ctcctgaaag agattaagga agatactaat aagtggaaga atatcccctg ttcatgggtt  5880
```

-continued

```
ggcagaatca acatagtgaa gatggcaata cttcctaaag tgatatatcg ctttaacgcc  5940
atcccaatta aactgcctat gaccttcttt acggagctcg agaaaacaac ccttaaattt  6000
atatggaatc aaaagagagc aagaatagcg aagtccatct tgagccagaa gaataaggcc  6060
ggtgggatta ctttgcctga ttttaagttg tattataaag ccacagtaac taagacagcc  6120
tggtattggt atcagaatag agacatcgac cagtggaatc ggaccgaacc atcagagata  6180
atgccccaca tctataatta ccttatattc gataagccag aaaagaataa acagtggggc  6240
aaagacagcc tcttcaacaa gtggtgttgg gagaattggc tggccatatg ccggaaactc  6300
aagctcgacc cctttcttac accctacact aaaatcaaca gtaggtggat caaggacttg  6360
aatgtcaagc caaagactat aaagacactg gaagagaatc ttgggatcac aatacaagat  6420
ataggcgtcg gcaaagattt tatgtcaaag acgcccaagg ccatggccac taaggataag  6480
attgataagt gggaccttat taagctcaaa agcttctgta ctgccaagga gaccacgatc  6540
agagttaata ggcagcccac tacatgggaa aagatttcg ccacttattc atcagataag  6600
gggttgataa gcagaatata taacgagctg aagcagatct acaagaagaa aacgaataat  6660
cccatcaaga agtgggcaaa agatatgaac aggcatttta gcaaagagga tatctacgcc  6720
gcgaagaagc atatgaagaa gtgtagttca agcttggcca ttcgtgagat gcagattaag  6780
acgaccatgc gataccacct taccccagtg aggatggcaa ttatcaagaa atctggcaat  6840
aatagatgtt ggcggggctg tggcgagatt ggcaccctgc tccattgctg gtgggattgc  6900
aagctggtgc agccgctttg gaaatcagtc tggcgctttc tgagggacct cgagcttgag  6960
attcccttcg atcccgcaat tcccttgctc ggaatctatc ctaacgaata caagagctgt  7020
tgttacaagg atacgtgtac ccggatgttc atcgcggcct tgtttacgat agctaagacg  7080
tggaatcagc ctaagtgccc cacaatgatc gattggatca agaaaatgtg gcatatttat  7140
accatggagt attacgcagc aattaagaat gacgaattta tttccttcgt tgggacctgg  7200
atgaagctgg agactattat tctgagcaag ctgtctcagg agcaaaagac aaagcataga  7260
atcttctctc tcattggtgg taacgactac aaagacgatg acgacaagta aagcgcttct  7320
agaagttgtc tcctcctgca ctgactgact gatacaatcg atttctggat ccgcaggcct  7380
aatcaacctc tggattacaa aatttgtgaa agattgactg gtattcttaa ctatgttgct  7440
ccttttacgc tatgtggata cgctgcttta atgcctttgt atcatgctat tgcttcccgt  7500
atggctttca ttttctcctc cttgtataaa tcctggttgc tgtctcttta tgaggagttg  7560
tggcccgttg tcaggcaacg tggcgtggtg tgcactgtgt ttgctgacgc aacccccact  7620
ggttggggca ttgccaccac ctgtcagctc ctttccggga ctttcgcttt ccccctccct  7680
attgccacgg cggaactcat cgccgcctgc cttgcccgct gctggacagg ggctcggctg  7740
ttgggcactg acaattccgt ggtgttgtcg gggaagctga cgtcctttcc atggctgctc  7800
gcctgtgttg ccacctggat tctgcgcggg acgtccttct gctacgtccc ttcggccctc  7860
aatccagcgg accttccttc ccgctgagag acacaaaaaa ttccaacaca ctattgcaat  7920
gaaaataaat ttcctttatt agccagaagt cagatgctca aggggcttca tgatgtcccc  7980
ataattttttg gcagagggaa aaagatctca gtggtatttg tgagccaggg cattggcctt  8040
ctgataggca gcctgcacct gaggagtgcg gccgctttac ttgtacagct cgtccatgcc  8100
gagagtgatc ccggcggcgg tcacgaactc cagcaggacc atgtgatcgc gcttctcgtt  8160
ggggtctttg ctcagggcgg actgggtgct caggtagtgg ttgtcgggca gcagcacggg  8220
gccgtcgccg atgggggtgt tctgctggta gtggtcggcg agctgcacgc tgccgtcctc  8280
gatgttgtgg cggatcttga agttcacctt gatgccgttc ttctgcttgt cggccatgat  8340
atagacgttg tggctgttgt agttgtactc cagcttgtgc cccaggatgt tgccgtcctc  8400
cttgaagtcg atgcccttca gctcgatgcg gttcaccagg gtgtcgccct cgaacttcac  8460
ctcggcgcgg gtcttgtagt tgccgtcgtc cttgaagaag atggtgcgct cctggacgta  8520
gccttcgggc atggcggact tgaagaagtc gtgctgcttc atgtggtcgg ggtagcggct  8580
gaagcactgc acgccgtagg tcagggtggt cacgagggtg ggccagggca cgggcagctt  8640
gccggtggtg cagatgaact tcagggtcag cttgccgtag gtggcatcgc cctcgccctc  8700
gccggacacg ctgaacttgt ggccgtttac gtcgccgtcc agctcgacca ggatgggcac  8760
caccccggtg aacagctcct cgcccttgct caccatggtg gcgggatctg acggttcact  8820
aaaccagctc tgcttatata gacctcccac cgtacacgcc taccgcccat ttgcgtcaat  8880
ggggcggagt tgttacgaca ttttggaaag tcccgttgat tttggtgcca aaacaaactc  8940
ccattgacgt caatggggtg gagacttgga aatccccgtg agtcaaaccg ctatccacgc  9000
ccattgatgt actgccaaaa ccgcatcacc atggtaatag cgatgactaa tacgtagatg  9060
tactgccaag taggaaagtc ccataaggtc atgtactggg cataatgcca ggcgggccat  9120
ttaccgtcat tgacgtcaat agggggcgta cttggcatat gatacacttg atgtactgcc  9180
aagtgggcag tttaccgtaa atactccacc cattgacgtc aatggaaagt ccctattggc  9240
gttactatgg gaacatacgt cattattgac gtcaatgggc gggggtcgtt gggcggtcag  9300
ccaggcgggc catttaccgt aagttatgta acgggcctgc tgccggctct gcggcctctt  9360
ccgcgtcttc gccttcgccc tcagacgagt cggatctccc tttgggccgc ctccccgcct  9420
gtctagcttg actgactgag atacagcgta ccttcagctc acagacatga taagatacat  9480
tgatgagttt ggacaaacca caactagaat gcagtgaaaa aaatgcttta tttgtgaaat  9540
ttgtgatgct attgctttat ttgtaaccat tataagctgc aataaacaag ttaacaacaa  9600
caattgcatt cattttatgt ttcaggttca gggggaggtg tgggaggttt tttaaagcaa  9660
gtaaaacctc tacaaatgtg gtattggccc atctctatcg gtatcgtagc ataacccctt  9720
ggggcctcta aacgggtctt gaggggtttt ttgtgcccct cgggccggat tgctatctac  9780
cggcattggc gcagaaaaaa atgcctgatg cgacgctgcg cgtcttatac tcccacatat  9840
gccagattca gcaacggata cggcttcccc aacttgccca cttccatacg tgtcctcctt  9900
accagaaatt tatccttaag gtcgtcagct atcctgcagg cgatctctcg atttcgatca  9960
agacattcct ttaatggtct tttctggaca ccactagggg tcagaagtag ttcatcaaac  10020
tttcttccct ccctaatctc attggttacc ttgggctatc gaaacttaat taagcgatct  10080
gcatctcaat tagtcagcaa ccatagtccc gcccctaact ccgcccatcc cgcccctaac  10140
tccgcccagt tccgcccatt ctccgcccca tcgctgacta attttttta tttatgcaga  10200
ggccgaggcc gcctcggcct ctgagctatt ccagaagtag tgaggaggct tttttggagg  10260
cctaggcttt tgcaaaggag gtagccaaca tgattgaaca agatggattg cacgcaggtt  10320
ctcccgccgc ttgggtggag aggctattcg gctatgactg ggcacaacag acaatcggct  10380
gctctgatgc cgccgtgttc cggctgtcag cgcaggggcg cccggttctt tttgtcaaga  10440
ccgacctgtc cggtgccctg aatgaactcc aggacgaggc agcgcggcta tcgtggctgg  10500
ccacgacggg cgttccttgc gcagctgtgc tcgacgttgt cactgaagcg ggaagggact  10560
ggctgctatt gggcgaagtg ccggggcagg atctcctgtc atctcacctt gctcctgccg  10620
```

```
agaaagtatc catcatggct gatgcaatgc ggcggctgca tacgcttgat ccggctacct  10680
gcccattcga ccaccaagcg aaacatcgca tcgagcgagc acgtactcgg atggaagccg  10740
gtcttgtcga tcaggatgat ctggacgaag agcatcaggg gctcgcgcca gccgaactgt  10800
tcgccaggct caaggcgcgg atgcccgacg gcgaggatct cgtcgtgacc cacggcgatg  10860
cctgcttgcc gaatatcatg gtggaaaatg gccgcttttc tggattcatc gactgtggcc  10920
ggctgggtgt ggcggaccgc tatcaggaca tagcgttggc tacccgtgat attgctgaag  10980
agcttggcgg cgaatgggct gaccgcttcc tcgtgcttta cggtatcgcc gctcccgatt  11040
cgcagcgcat cgccttctat cgccttcttg acgagttctt ctagtatgta agccctgtgc  11100
cttctagttg ccagccatct gttgtttgcc cctcccccgt gccttccttg accctggaag  11160
gtgccactcc cactgtcctt tcctaataaa atgaggaaat tgcatcgcat tgtctgagta  11220
ggtgtcattc tattctgggg ggtggggtgg ggcaggacag caagggggag gattgggaag  11280
acaatagcag gcatgctggg gatgcggtgg gctctatggt taattaacca gtcaagtcag  11340
ctacttggcg agatcgactt gtctgggttt cgactacgct cagaattgcg tcagtcaagt  11400
tcgatctggt ccttgctatt gcacccgttc tccgattacg agtttcattt aaatcatgtg  11460
agcaaaaggc cagcaaaagg ccaggaaccg taaaaaggcc gcgttgctgg cgtttttcca  11520
taggctccgc ccccctgacg agcatcacaa aaatcgacgc tcaagtcaga ggtggcgaaa  11580
cccgacagga ctataaagat accaggcgtt tccccctgga agctccctcg tgcgctctcc  11640
tgttccgacc ctgccgctta ccggatacct gtccgccttt ctcccttcgg gaagcgtggc  11700
gctttctcat agctcacgct gtaggtatct cagttcggtg taggtcgttc gctccaagct  11760
gggctgtgtg cacgaacccc ccgttcagcc cgaccgctgc gccttatccg gtaactatcg  11820
tcttgagtcc aacccggtaa gacacgactt atcgccactg gcagcagcca ctggtaacag  11880
gattagcaga gcgaggtatg taggcggtgc tacagagttc ttgaagtggt ggcctaacta  11940
cggctacact agaagaacag tatttggtat ctgcgctctg ctgaagccag ttaccttcgg  12000
aaaaagagtt ggtagctctt gatccggcaa acaaaccacc gctggtagcg gtggtttttt  12060
tgtttgcaag cagcagatta cgcgcagaaa aaaaggatct caagaagatc ctttgatctt  12120
ttctacgggg tctgacgctc agtggaacga aaactcacgt taagggattt tggtcatgag  12180
attatcaaaa aggatcttca cctagatcct tttaaattaa aaatgaagtt ttaaatcaat  12240
ctaaagtata tatgagtaaa cttggtctga cagttaccaa tgcttaatca gtgaggcacc  12300
tatctcagcg atctgtctat ttcgttcatc catagttgca tttaaatttc cgaactctcc  12360
aaggccctcg tcggaaaatc ttcaaacctt tcgtccgatc catcttgcag gctacctctc  12420
gaacgaacta tcgcaagtct cttggccggc cttgcgcctt ggctattgct tggcagcgcc  12480
tatcgccagg tattactcca atcccgaata tccgagatcg ggatcacccg agagaagttc  12540
aacctacatc ctcaatcccg atctatccga gatccgagga a                     12581

SEQ ID NO: 96          moltype = DNA  length = 12542
FEATURE                Location/Qualifiers
misc_feature           1..12542
                       note = Description of Artificial Sequence: Synthetic
                        polynucleotide
source                 1..12542
                       mol_type = other DNA
                       organism = synthetic construct
SEQUENCE: 96
gtcggaaaat cttcaaacct ttcgtccgat ccatcttgca ggctacctct cgaacgaact  60
atcgcaagtc tcttggccgg ccttgcgcct tggctattgc ttggcagcgc ctatcgccag  120
gtattactcc aatcccgaat atccgagatc gggatcaccc gagagaagtt caacctacat  180
cctcaatccc gatctatccg agatccgagg aatatcgaaa tcggggcgcg cctggtgtac  240
cgagaacgat cctctcagtg cgagtctcga cgatccatat cgttgcttgg cagtcagcca  300
gtcggaatcc agcttgggac ccaggaagtc caatcgtcag atattgtact caagcctggt  360
cacggcagcg taccgatctg tttaaaccta gatattgata gtctgatcgg tcaacgtata  420
atcgagtcct agcttttgca aacatctatc aagagacagg atcagcagga ggctttcgca  480
tgagtattca acatttccgt gtcgccctta ttcccttttt tgcggcattt tgccttcctg  540
tttttgctca cccagaaacg ctggtgaaag taaaagatgc tgaagatcag ttgggtgcgc  600
gagtgggtta catcgaactg gatctcaaca gcggtaagat ccttgagagt tttcgccccg  660
aagaacgctt tccaatgatg agcactttta aagttctgct atgtggcgcg gtattatccc  720
gtattgacgc cgggcaagag caactcggtc gccgcataca ctattctcag aatgacttgg  780
ttgagtattc accagtcaca gaaaagcatc ttacggatgg catgacagta agagaattat  840
gcagtgctgc cataaccatg agtgataaca ctgcggccaa cttacttctg acaacgattg  900
gaggaccgaa ggagctaacc gcttttttgc acaacatggg ggatcatgta actcgccttg  960
atcgttggga accggagctg aatgaagcca taccaaacga cgagcgtgac accacgatgc  1020
ctgtagcaat ggcaacaacc ttgcgtaaac tattaactgg cgaactactt actctagctt  1080
cccggcaaca gttgatagac tggatggagg cggataaagt tgcaggacca cttctgcgct  1140
cggcccttcc ggctggctgg tttattgctg ataaatctgg agccggtgag cgtgggtctc  1200
gcggtatcat tgcagcactg gggccagatg gtaagccctc ccgtatcgta gttatctaca  1260
cgacggggag tcaggcaact atggatgaac gaaatagaca gatcgctgag ataggtgcct  1320
cactgattaa gcattggtaa ccgattctag gtgcattggc gcagaaaaaa atgcctgatg  1380
cgacgctgcg cgtcttatac tcccacatat gccagattca gcaacggata cggcttcccc  1440
aacttgccca cttccatacg tgtcctcctt accagaaatt tatccttaag atcgtttaaa  1500
ctcgactctg gctctatcga atctccgtcg tttcgagctt acgcgaacag ccgtggcgct  1560
catttgctcg tcgggcatcg aatctcgtca gctatcgtca gcttaccttt ttggcagcga  1620
tcgcggctcc cgacatcttg gaccattagc tccacaggta tcttcttccc tctagtggtc  1680
ataacagcag cttcagctac ctctcaattc aaaaaacccc tcaagacccg tttagaggcc  1740
ccaaggggtt atgctatcaa tcgttgcgtt acacacacaa aaaaccaaca cacatccatc  1800
ttcgatggat agcgatttta ttatctaact gctgatcgag tgtagccaga tctagtaatc  1860
aattacgggg tcattagttc atagcccata tatggagttc cgcgttacat aacttacggt  1920
aaatggcccg cctggctgac cgcccaacga cccccgccca ttgacgtcaa taatgacgta  1980
tgttcccata gtaacgccaa tagggacttt ccattgacgt caatgggtgg agtatttacg  2040
gtaaactgcc cacttggcag tacatcaagt gtatcatatg ccaagtacgc cccctattga  2100
cgtcaatgac ggtaaatggc ccgcctggca ttatgcccag tacatgacct tatgggactt  2160
```

-continued

```
tcctacttgg cagtacatct acgtattagt catcgctatt accatgctga tgcggttttg  2220
gcagtacatc aatgggcgtg gatagcggtt tgactcacgg ggatttccaa gtctccaccc  2280
cattgacgtc aatgggagtt tgttttggca ccaaaatcaa cgggactttc caaaatgtcg  2340
taacaactcc gccccattga cgcaaatggg cggtaggcgt gtacggtggg aggtctatat  2400
aagcagagct ggtttagtga accgtcagat cagatctttg tcgatcctac catccactcg  2460
acacacccgc cagcggccgc taatacgact cactataggg agaagtactg ccaccatgcc  2520
aaagaagaag cggaaggtcg gcaagaagca aaatcgcaag acggggaatt ccaagacaca  2580
atccgctagc ccaccaccta aagagcgttc tagctcccct gctactgagc agtcctggat  2640
ggaaaacgac ttcgatgaac tccgggaaga gggatttagg cgatccaact attcagaact  2700
ccgcgaagat atccagacaa aggggaagga agtcgagaat ttcgagaaga acctcgagga  2760
gtgcatcacc cgtatcacaa acactgagaa atgtctcaaa gaactcatgg aacttaagac  2820
aaaagccagg gagcttcgag aggagtgtcg gagtctgaga tccaggtgtg accagctcga  2880
ggagcgcgtg agcgcgatgg aagacgagat gaacgagatg aaaagagagg gcaaattcag  2940
ggagaagcgc attaagagga acgaacagag tctgcaggag atttgggatt acgtcaagag  3000
gcctaacctg cggttgatcg gcgtccccga gagcgacgta gaaaacggga ctaaactgga  3060
gaatacactt caagacatca ttcaagaaaa ttttccaaac ctggctcggc aagctaatgt  3120
gcaaatccaa gagatccaac gcacacccca gcggtatagc tctcggcgtg ccacccctag  3180
gcatattatc gtgcgcttta ctaaggtgga gatgaaagag aagatgctgc gagccgctcg  3240
ggaaaaggga agggtgactt tgaagggcaa acctattcgg ctgacggttg accttagcgc  3300
cgagacactc caggcacgcc gggaatgggg ccccatcttt aatatcctga aggagaagaa  3360
cttccagcca cgaatctctt accctgcaaa gttgagtttt atctccgagg gtgagattaa  3420
gtatttcatc gataaacaga tgctgcgaga cttcgtgaca actcgcccag ctctcaagga  3480
actgctcaaa gaggctctta atatggagcg caataataga tatcaaccct tgcagaacca  3540
cgcaaagatg tgagacagcc gtcagaccat caagactagg aagaaactgc atcaactaat  3600
gagcaaaatc accagctaac atcatagtat acatgaccgg ctctaactca catatcacca  3660
tccttacact taacattaac ggcctcaact cagctatcaa gcgccatcgg ctggccagct  3720
ggatcaaatc acaggatcca agcgtttgtt gcatccaaga gacccacctg acctgtagag  3780
atactcaccg cctcaagatc aagggatggc gaaagattta tcaggcgaac ggtaagcaga  3840
agaaagccgg agtcgcaatt ctggtctcag acaagacgga tttcaagccc accaaaatta  3900
agcgtgataa ggaaggtcac tatattatgg tgaaaggcag catacagcag gaagaactta  3960
ccatattgaa catctacgcg ccaaacaccg gcgcacctcg ctttatcaaa caggtcctgt  4020
ccgatctgca gcgagatctg gattctcata cgttgattat gggtgatttc aatacaccat  4080
tgagcaccct ggatcgcagc accaggcaaa aggtaaataa agacacgcaa gagctcaata  4140
gcgcactgca tcaggcagat ctcattgata tttatcgcac tcttcatcct aagagtaccg  4200
agtacacatt cttcagcgcc ccacatcata catactcaaa gatcgatcat atcgtcggct  4260
caaaggctct gctgtcaaag tgcaagcgca cagagataat tacaaattac ctgtcagatc  4320
atagcgcgat caagctcgag ctgagaatca agaacctgac ccagagccgg agtaccactt  4380
ggaagcttaa taacctgctg ctcaacgatt attgggtcca caatgagatg aaggcagaga  4440
ttaaaatgtt cttcgaaaca aatgagaata aggatactac ctatcaaaac ctttgggatg  4500
cctttaaggc cgtctgcaga ggcaagttca tcgccctcaa cgcctataaa agaaaacaag  4560
agagatctaa gatcgatact ctcacctctc agctgaagga gttggagaaa caggaacaga  4620
cccactccaa ggcgtcaaga cggcaggaga tcacaaagat tcgcgccgag ttgaaagaga  4680
tcgaaaccca aaagactctt cagaaaatta acgagtctcg tagttggttc ttcgagcgga  4740
ttaataagat agacagacct ctggcacgac tgattaagaa gaagcgcgaa aagaaccaga  4800
ttgataccat caagaacgac aagggcgaca tcactactga cccgaccgag atccagacca  4860
ctattcggga gtattataag catttgtatg ctaacaagct tgagaacctg gaagagatgg  4920
acacttttct ggatacctat actctgccac ggcttaatca agaggaagtc gagtccctca  4980
accgcccaat tacaggaagc gagattgtgg ccataattaa ctccctgccg acaaagaaat  5040
ctcctggtcc ggacgggttt acagctgagt tttatcaacg gtatatggaa gagcttgtac  5100
cgtttctgct caagctcttt cagtctatag aaaaggaagg catcttgccc aattccttct  5160
acgaagcttc tataatactt attcccaaac caggacgcga taccacaaag aaggaaaact  5220
tccggcccat tagtctcatg aatatcgacg ctaaaatatt gaacaagatt ctcgccaaca  5280
gaatccaaca acatattaag aaattgatac atcacgacca ggtggggttt atacctggca  5340
tgcagggctg gtttaacatc cggaagagta ttaacgtcat tcaacacatt aatagagcta  5400
aggataagaa tcatatgatc atctctatag acgcggaaaa ggcattcgat aagattcagc  5460
agccatttat gctcaagact ctgaacaaac tcggcatcga cggaacatat tttaagatta  5520
ttcgcgcaat ttacgataag ccgactgcta acattatcct taacggccaa aagctcgagg  5580
cctttccgct caagactgga acccgccaag gctgtcccct ctccccgctt ttgtttaata  5640
ttgtactcga ggtgctggct agggctattc gtcaagagaa agagattaaa gggatacagc  5700
tcgggaagga agaggtcaag ctttccttgt tcgccgatga tatgattgtg tacctggaga  5760
atcctattgt gtctgctcag aaccttctta aacttatttc taactttagc aaggtcagcg  5820
gctataagat taacgtccag aaatctcagg cctttctgta cacaaataat cgacagaccg  5880
aatcccagat aatgggtgag cttccgtttg tcatagccag caaaaggata aagtatctcg  5940
gaatccagct gacacgagac gttaaagatt tgtttaagga aaattacaag cctctcctga  6000
aagagattaa ggaagatact aataagtgga agaatatccc ctgttcatgg gttggcagaa  6060
tcaacatagt gaagatggca atacttccta aagtgatata tcgctttaac gccatcccaa  6120
ttaaactgcc tatgaccttc tttacggagc tcgagaaaac aaccccttaaa tttatatgga  6180
atcaaaagag agcaagaata gcgaagtcca tcttgagcca gaagaataag gccggtggga  6240
ttactttgcc tgattttaag ttgtattata aagccacagt aactaagaca gcctggtatt  6300
ggtatcagaa tagagacatc gaccagtgga atcggaccga accatcagag ataatgcccc  6360
acatctataa ttaccttata ttcgataagc cagaaaagaa taaacagtgg ggcaaagaca  6420
gcctcttcaa caagtggtgt tgggagaatt ggctggccat atgccggaaa ctcaagctcg  6480
accccttctt tacaccctac actaaaatca acagtaggtg gatcaaggac ttgaatgtca  6540
agccaaagac tataaagaca ctggaagaga atcttgggat cacaatacaa gatataggcg  6600
tcggcaaaga ttttatgtca aagacgccca aggccatggc cactaaggat aagattgata  6660
agtgggacct tattaagctc aaaagcttct gtactgccaa ggagaccacg atcagagtta  6720
ataggcagcc cactacatgg gaaaagattt tcgccactta ttcatcagat aaggggttga  6780
taagcagaat atataacgag ctgaagcaga tctacaagaa gaaaacgaat aatcccatca  6840
agaagtgggc aaaagatatg aacaggcatt ttagcaaaga ggatatctac gccgcgaaga  6900
```

```
agcatatgaa gaagtgtagt tcaagcttgg ccattcgtga gatgcagatt aagacgacca  6960
tgcgatacca ccttacccca gtgaggatgg caattatcaa gaaatctggc aataatagat  7020
gttggcgggg ctgtggcgag attggcaccc tgctccattg ctggtgggat tgcaagctgg  7080
tgcagccgct ttggaaatca gtctggcgct ttctgaggga cctcgagctt gagattccct  7140
tcgatcccgc aattcccttg ctcggaatct atcctaacga atacaagagc tgttgttaca  7200
aggatacgtg tacccggatg ttcatcgcgg ccttgtttac gatagctaag acgtggaatc  7260
agcctaagtg ccccacaatg atcgattgga tcaagaaaat gtggcatatt tataccatgg  7320
agtattacgc agcaattaag aatgacgaat ttatttcctt cgttgggacc tggatgaagc  7380
tggagactat tattctgagc aagctgtctc aggagcaaaa gacaaagcat agaatcttct  7440
ctctcattgg tggtaacgac tacaaagacg atgacgacaa gtaaagcgct tctagaagtt  7500
gtctcctcct gcactgactg actgatacaa tcgatttctg gatccgcagg cctaatcaac  7560
ctctggatta caaaatttgt gaaagattga ctggtattct taactatgtt gctcctttta  7620
cgctatgtgg atacgctgct ttaatgcctt tgtatcatgc tattgcttcc cgtatggctt  7680
tcattttctc ctccttgtat aaatcctggt tgctgtctct ttatgaggag ttgtggcccg  7740
ttgtcaggca acgtggcgtg gtgtgcactg tgtttgctga cgcaaccccc actggttggg  7800
gcattgccac cacctgtcag ctcctttccg ggactttcgc tttccccctc cctattgcca  7860
cggcggaact catcgccgcc tgccttgccc gctgctggac aggggctcgg ctgttgggca  7920
ctgacaattc cgtggtgttg tcggggaagc tgacgtcctt tccatggctg ctcgcctgtg  7980
ttgccacctg gattctgcgc gggacgtcct tctgctacgt cccttcggcc ctcaatccag  8040
cggaccttcc ttcccgctga gagacacaaa aaattccaac acactattgc aatgaaaata  8100
aatttccttt attagccaga agtcagatgc tcaaggggct tcatgatgtc cccataattt  8160
ttggcagagg gaaaaagatc tcagtggtat ttgtgagcca gggcattggc cttctgatag  8220
gcagcctgca cctgaggagt gcggccgctt tacttgtaca gctcgtccat gccgagagtg  8280
atcccggcgg cggtcacgaa ctccagcagg accatgtgat cgcgcttctc gttggggtct  8340
ttgctcaggg cggactgggt gctcaggtag tggttgtcgg gcagcagcac ggggccgtcg  8400
ccgatggggg tgttctgctg gtagtggtcg gcgagctgca cgctgccgtc ctcgatgttg  8460
tggcggatct tgaagttcac cttgatgccg ttcttctgct tgtcggccat gatatagacg  8520
ttgtggctgt tgtagttgta ctccagcttg tgccccagga tgttgccgtc ctccttgaag  8580
tcgatgccct tcagctcgat gcggttcacc agggtgtcgc cctcgaactt cacctcggcg  8640
cgggtcttgt agttgccgtc gtccttgaag aagatggtgc gctcctggac gtagccttcg  8700
ggcatggcgg acttgaagaa gtcgtgctgc ttcatgtggt cggggtagcg gctgaagcac  8760
tgcacgccgt aggtcagggt ggtcacgagg gtgggccagg gcacgggcag cttgccggtg  8820
gtgcagatga acttcagggt cagcttgccg taggtggcat cgccctcgcc ctcgccggac  8880
acgctgaact tgtggccgtt tacgtcgccg tccagctcga ccaggatggg caccaccccg  8940
gtgaacagct cctcgccctt gctcaccatg gtggcgggat ctgacggttc actaaaccag  9000
ctctgcttat atagacctcc caccgtacac gcctaccgcc catttgcgtc aatggggcgg  9060
agttgttacg acattttgga aagtcccgtt gattttggtg ccaaaacaaa ctcccattga  9120
cgtcaatggg gtggagactt ggaaatcccc gtgagtcaaa ccgctatcca cgcccattga  9180
tgtactgcca aaaccgcatc accatggtaa tagcgatgac taatacgtag atgtactgcc  9240
aagtaggaaa gtcccataag gtcatgtact gggcataatg ccaggcgggc catttaccgt  9300
cattgacgtc aataggggc gtacttggca tatgatacac ttgatgtact gccaagtggg  9360
cagtttaccg taaatactcc acccattgac gtcaatggaa agtccctatt ggcgttacta  9420
tgggaacata cgtcattatt gacgtcaatg ggcgggggtc gttgggcggt cagccaggcg  9480
ggccatttac cgtaagttat gtaacgggcc tgctgccggc tctgcggcct cttccgcgtc  9540
ttcgccttcg ccctcagacg agtcggatct ccctttgggc cgcctccccg cctgtctagc  9600
ttgactgact gagatacagc gtaccttcag ctcacagaca tgataagata cattgatgag  9660
tttggacaaa ccacaactag aatgcagtga aaaaaatgct ttatttgtga aatttgtgat  9720
gctattgctt tatttgtaac cattataagc tgcaataaac aagttaacaa caacaattgc  9780
attcatttta tgtttcaggt tcagggggag gtgtgggagg ttttttaaag caagtaaaac  9840
ctctacaaat gtggtattgg cccatctcta tcggtatcgt agcataaccc cttggggcct  9900
ctaaacgggt cttgaggggt tttttgtgcc cctcgggccg gattgctatc taccggcatt  9960
ggcgcagaaa aaaatgcctg atgcgacgct gcgcgtctta tactcccaca tatgccagat  10020
tcagcaacgg atacggcttc cccaacttgc ccacttccat acgtgtcctc cttaccagaa  10080
atttatcctt aaggtcgtca gctatcctgc aggcgatctc tcgatttcga tcaagacatt  10140
cctttaatgg tcttttctgg acaccactag gggtcagaag tagttcatca aactttcttc  10200
cctccctaat ctcattggtt accttgggct atcgaaactt aattaagcga tctgcatctc  10260
aattagtcag caaccatagt cccgccccta actccgccca tcccgcccct aactccgccc  10320
agttccgccc attctccgcc ccatcgctga ctaatttttt ttatttatgc agaggccgag  10380
gccgcctcgg cctctgagct attccagaag tagtgaggag gcttttttgg aggcctaggc  10440
ttttgcaaag gaggtagcca acatgattga acaagatgga ttgcacgcag gttctcccgc  10500
cgcttgggtg gagaggctat tcggctatga ctgggcacaa cagacaatcg gctgctctga  10560
tgccgccgtg ttccggctgt cagcgcaggg gcgcccggtt ctttttgtca agaccgacct  10620
gtccggtgcc ctgaatgaac tccaggacga ggcagcgcgg ctatcgtggc tggccacgac  10680
gggcgttcct tgcgcagctg tgctcgacgt tgtcactgaa gcgggaaggg actggctgct  10740
attgggcgaa gtgccggggc aggatctcct gtcatctcac cttgctcctg ccgagaaagt  10800
atccatcatg gctgatgcaa tgcggcggct gcatacgctt gatccggcta cctgcccatt  10860
cgaccaccaa gcgaaacatc gcatcgagcg agcacgtact cggatggaag ccggtcttgt  10920
cgatcaggat gatctggacg aagagcatca ggggctcgcg ccagccgaac tgttcgccag  10980
gctcaaggcg cggatgcccg acggcgagga tctcgtcgtg acccacggcg atgcctgctt  11040
gccgaatatc atggtggaaa atggccgctt ttctggattc atcgactgtg gccggctggg  11100
tgtggcggac cgctatcagg acatagcgtt ggctacccgt gatattgctg aagagcttgg  11160
cggcgaatgg gctgaccgct tcctcgtgct ttacggtatc gccgctcccg attcgcagcg  11220
catcgccttc tatcgccttc ttgacgagtt cttctagtat gtaagccctg tgccttctag  11280
ttgccagcca tctgttgttt gcccctcccc cgtgccttcc ttgaccctgg aaggtgccac  11340
tcccactgtc ctttcctaat aaaatgagga aattgcatcg cattgtctga gtaggtgtca  11400
ttctattctg gggggtgggg tggggcagga cagcaagggg gaggattggg aagacaatag  11460
caggcatgct ggggatgcgg tgggctctat ggttaattaa ccagtcaagt cagctacttg  11520
gcgagatcga cttgtctggg tttcgactac gctcagaatt gcgtcagtca agttcgatct  11580
ggtccttgct attgcacccg ttctccgatt acgagtttca tttaaatcat gtgagcaaaa  11640
```

```
ggccagcaaa aggccaggaa ccgtaaaaag gccgcgttgc tggcgttttt ccataggctc  11700
cgcccccctg acgagcatca caaaaatcga cgctcaagtc agaggtggcg aaacccgaca  11760
ggactataaa gataccaggc gtttccccct ggaagctccc tcgtgcgctc tcctgttccg  11820
accctgccgc ttaccggata cctgtccgcc tttctccctt cgggaagcgt ggcgctttct  11880
catagctcac gctgtaggta tctcagttcg gtgtaggtcg ttcgctccaa gctgggctgt  11940
gtgcacgaac cccccgttca gcccgaccgc tgcgccttat ccggtaacta tcgtcttgag  12000
tccaacccgg taagacacga cttatcgcca ctggcagcag ccactggtaa caggattagc  12060
agagcgaggt atgtaggcgg tgctacagag ttcttgaagt ggtggcctaa ctacggctac  12120
actagaagaa cagtatttgg tatctgcgct ctgctgaagc cagttacctt cggaaaaaga  12180
gttggtagct cttgatccgg caaacaaacc accgctggta gcggtggttt ttttgtttgc  12240
aagcagcaga ttacgcgcag aaaaaaagga tctcaagaag atcctttgat cttttctacg  12300
gggtctgacg ctcagtggaa cgaaaactca cgttaaggga ttttggtcat gagattatca  12360
aaaaggatct tcacctagat ccttttaaat taaaaatgaa gttttaaatc aatctaaagt  12420
atatatgagt aaacttggtc tgacagttac caatgcttaa tcagtgaggc acctatctca  12480
gcgatctgtc tatttcgttc atccatagtt gcatttaaat ttccgaactc tccaaggccc  12540
tc                                                                 12542
```

```
SEQ ID NO: 97          moltype = DNA  length = 12554
FEATURE                Location/Qualifiers
misc_feature           1..12554
                       note = Description of Artificial Sequence: Synthetic
                        polynucleotide
source                 1..12554
                       mol_type = other DNA
                       organism = synthetic construct
SEQUENCE: 97
ggaaaatctt caaacctttc gtccgatcca tcttgcaggc tacctctcga acgaactatc  60
gcaagtctct tggccggcct tgcgccttgg ctattgcttg gcagcgccta tcgccaggta  120
ttactccaat cccgaatatc cgagatcggg atcacccgag agaagttcaa cctacatcct  180
caatcccgat ctatccgaga tccgaggaat atcgaaatcg gggcgcgcct ggtgtaccga  240
gaacgatcct ctcagtgcga gtctcgacga tccatatcgt tgcttggcag tcagccagtc  300
ggaatccagc ttgggaccca ggaagtccaa tcgtcagata ttgtactcaa gcctggtcac  360
ggcagcgtac cgatctgttt aaacctagat attgatagtc tgatcggtca acgtataatc  420
gagtcctagc ttttgcaaac atctatcaag agacaggatc agcaggaggc tttcgcatga  480
gtattcaaca tttccgtgtc gcccttattc ccttttttgc ggcattttgc cttcctgttt  540
ttgctcaccc agaaacgctg gtgaaagtaa aagatgctga agatcagttg ggtgcgcgag  600
tgggttacat cgaactggat ctcaacagcg gtaagatcct tgagagtttt cgccccgaag  660
aacgctttcc aatgatgagc acttttaaag ttctgctatg tggcgcggta ttatcccgta  720
ttgacgccgg gcaagagcaa ctcggtcgcc gcatacacta ttctcagaat gacttggttg  780
agtattcacc agtcacagaa aagcatctta cggatggcat gacagtaaga gaattatgca  840
gtgctgccat aaccatgagt gataacactg cggccaactt acttctgaca acgattggag  900
gaccgaagga gctaaccgct tttttgcaca acatggggga tcatgtaact cgccttgatc  960
gttgggaacc ggagctgaat gaagccatac caaacgacga gcgtgacacc acgatgcctg  1020
tagcaatggc aacaaccttg cgtaaactat taactggcga actacttact ctagcttccc  1080
ggcaacagtt gatagactgg atggaggcgg ataaagttgc aggaccactt ctgcgctcgg  1140
cccttccggc tggctggttt attgctgata aatctggagc cggtgagcgt gggtctcgcg  1200
gtatcattgc agcactgggg ccagatggta agccctcccg tatcgtagtt atctacacga  1260
cggggagtca ggcaactatg gatgaacgaa atagacagat cgctgagata ggtgcctcac  1320
tgattaagca ttggtaaccg attctaggtg cattggcgca gaaaaaaatg cctgatgcga  1380
cgctgcgcgt cttatactcc cacatatgcc agattcagca acggatacgg cttccccaac  1440
ttgcccactt ccatacgtgt cctccttacc agaaatttat ccttaagatc gtttaaactc  1500
gactctggct ctatcgaatc tccgtcgttt cgagcttacg cgaacagccg tggcgctcat  1560
ttgctcgtcg ggcatcgaat ctcgtcagct atcgtcagct taccttttg gcagcgatcg  1620
cggctcccga catcttggac cattagctcc acaggtatct tcttccctct agtggtcata  1680
acagcagctt cagctacctc tcaattcaaa aaacccctca agacccgttt agaggcccca  1740
aggggttatg ctatcaatcg ttgcgttaca cacacaaaaa accaacacac atccatcttc  1800
gatggatagc gattttatta tctaactgct gatcgagtgt agccagatct agtaatcaat  1860
tacggggtca ttagttcata gcccatatat ggagttccgc gttacataac ttacggtaaa  1920
tggcccgcct ggctgaccgc ccaacgaccc ccgcccattg acgtcaataa tgacgtatgt  1980
tcccatagta acgccaatag ggactttcca ttgacgtcaa tgggtggagt atttacggta  2040
aactgcccac ttggcagtac atcaagtgta tcatatgcca agtacgcccc ctattgacgt  2100
caatgacggt aaatggcccg cctggcatta tgcccagtac atgaccttat gggactttcc  2160
tacttggcag tacatctacg tattagtcat cgctattacc atgctgatgc ggttttggca  2220
gtacatcaat gggcgtggat agcggtttga ctcacgggga tttccaagtc tccaccccat  2280
tgacgtcaat gggagtttgt tttggcacca aaatcaacgg gactttccaa aatgtcgtaa  2340
caactccgcc ccattgacgc aaatgggcgg taggcgtgta cggtgggagg tctatataag  2400
cagagctggt ttagtgaacc gtcagatcag atctttgtcg atcctaccat ccactcgaca  2460
cacccgccag cggccgctaa tacgactcac tatagggaga agtactgcca ccatgccaaa  2520
gaagaagcgg aaggtcggcg gcggcagcgg caagaagcaa aatcgcaaga cggggaattc  2580
caagacacaa tccgctagcc caccacctaa agagcgttct agctcccctg ctactgagca  2640
gtcctggatg gaaaacgact tcgatgaact ccgggaagag ggatttaggc gatccaacta  2700
ttcagaactc cgcgaagata tccagacaaa ggggaaggaa gtcgagaatt tcgagaagaa  2760
cctcgaggag tgcatcaccc gtatcacaaa cactgagaaa tgtctcaaag aactcatgga  2820
acttaagaca aaagccaggg agcttcgaga ggagtgtcgg agtctgagat ccaggtgtga  2880
ccagctcgag gagcgcgtga gcgcgatgga agacgagatg aacgagatga aaagagaggg  2940
caaattcagg gagaagcgca ttaagaggaa cgaacagagt ctgcaggaga tttgggatta  3000
cgtcaagagg cctaacctgc ggttgatcgg cgtccccgag agcgacgtag aaaacgggac  3060
taaactggag aatacacttc aagacatcat tcaagaaaat tttccaaacc tggctcggca  3120
agctaatgtg caaatccaag agatccaacg cacaccccag cggtatagct ctcggcgtgc  3180
```

-continued

```
caccccctagg catattatcg tgcgctttac taaggtggag atgaaagaga agatgctgcg  3240
agccgctcgg gaaaagggaa gggtgacttt gaagggcaaa cctattcggc tgacggttga  3300
ccttagcgcc gagacactcc aggcacgccg ggaatggggc cccatcttta atatcctgaa  3360
ggagaagaac ttccagccac gaatctctta ccctgcaaag ttgagtttta tctccgaggg  3420
tgagattaag tatttcatcg ataaacagat gctgcgagac ttcgtgacaa ctcgcccagc  3480
tctcaaggaa ctgctcaaag aggctcttaa tatggagcgc aataatagat atcaaccctt  3540
gcagaaccac gcaaagatgt gagacagccg tcagaccatc aagactagga agaaactgca  3600
tcaactaatg agcaaaatca ccagctaaca tcatagtata catgaccggc tctaactcac  3660
atatcaccat ccttacactt aacattaacg gcctcaactc agctatcaag cgccatcggc  3720
tggccagctg gatcaaatca caggatccaa gcgtttgttg catccaagag acccacctga  3780
cctgtagaga tactcaccgc ctcaagatca agggatggcg aaagatttat caggcgaacg  3840
gtaagcagaa gaaagccgga gtcgcaattc tggtctcaga caagacggat ttcaagccca  3900
ccaaaattaa gcgtgataag gaaggtcact atattatggt gaaaggcagc atacagcagg  3960
aagaacttac catattgaac atctacgcgc caaacaccgg cgcacctcgc tttatcaaac  4020
aggtcctgtc cgatctgcag cgagatctgg attctcatac gttgattatg ggtgatttca  4080
atacaccatt gagcaccctg gatcgcagca ccaggcaaaa ggtaaataaa gacacgcaag  4140
agctcaatag cgcactgcat caggcagatc tcattgatat ttatcgcact cttcatccta  4200
agagtaccga gtacacattc ttcagcgccc cacatcatac atactcaaag atcgatcata  4260
tcgtcggctc aaaggctctg ctgtcaaagt gcaagcgcac agagataatt acaaattacc  4320
tgtcagatca tagcgcgatc aagctcgagc tgagaatcaa gaacctgacc cagagccgga  4380
gtaccacttg gaagcttaat aacctgctgc tcaacgatta ttgggtccac aatgagatga  4440
aggcagagat taaaatgttc ttcgaaacaa atgagaataa ggatactacc tatcaaaacc  4500
tttgggatgc ctttaaggcc gtctgcagag gcaagttcat cgccctcaac gcctataaaa  4560
gaaaacaaga gagatctaag atcgatactc tcacctctca gctgaaggag ttggagaaac  4620
aggaacagac ccactccaag gcgtcaagac ggcaggagat cacaaagatt cgcgccgagt  4680
tgaaagagat cgaaacccaa aagactcttc agaaaattaa cgagtctcgt agttggttct  4740
tcgagcggat taataagata gacagacctc tggcacgact gattaagaag aagcgcgaaa  4800
agaaccagat tgataccatc aagaacgaca agggcgacat cactactgac ccgaccgaga  4860
tccagaccac tattcgggag tattataagc atttgtatgc taacaagctt gagaacctgg  4920
aagagatgga cacttttctg gatacctata ctctgccacg gcttaatcaa gaggaagtcg  4980
agtccctcaa ccgcccaatt acaggaagcg agattgtggc cataattaac tccctgccga  5040
caaagaaatc tcctggtccg gacgggttta cagctgagtt ttatcaacgg tatatggaag  5100
agcttgtacc gtttctgctc aagctctttc agtctataga aaaggaaggc atcttgccca  5160
attccttcta cgaagcttct ataatactta ttcccaaacc aggacgcgat accacaaaga  5220
aggaaaactt ccggcccatt agtctcatga atatcgacgc taaaatattg aacaagattc  5280
tcgccaacag aatccaacaa catattaaga aattgataca tcacgaccag gtggggttta  5340
tacctggcat gcagggctgg tttaacatcc ggaagagtat taacgtcatt caacacatta  5400
atagagctaa ggataagaat catatgatca tctctataga cgcggaaaag gcattcgata  5460
agattcagca gccatttatg ctcaagactc tgaacaaact cggcatcgac ggaacatatt  5520
ttaagattat tcgcgcaatt tacgataagc cgactgctaa cattatcctt aacggccaaa  5580
agctcgaggc ctttccgctc aagactggaa cccgccaagg ctgtcccctc tccccgcttt  5640
tgtttaatat tgtactcgag gtgctggcta gggctattcg tcaagagaaa gagattaaag  5700
ggatacagct cgggaaggaa gaggtcaagc tttccttgtt cgccgatgat atgattgtgt  5760
acctggagaa tcctattgtg tctgctcaga accttcttaa acttatttct aactttagca  5820
aggtcagcgg ctataagatt aacgtccaga aatctcaggc ctttctgtac acaaataatc  5880
gacagaccga atcccagata atgggtgagc ttccgtttgt catagccagc aaaaggataa  5940
agtatctcgg aatccagctg acacgagacg ttaaagattt gtttaaggaa aattacaagc  6000
ctctcctgaa agagattaag gaagatacta ataagtggaa gaatatcccc tgttcatggg  6060
ttggcagaat caacatagtg aagatggcaa tacttcctaa agtgatatat cgctttaacg  6120
ccatcccaat taaactgcct atgaccttct ttacggagct cgagaaaaca acccttaaat  6180
ttatatggaa tcaaaagaga gcaagaatag cgaagtccat cttgagccag aagaataagg  6240
ccggtgggat tactttgcct gattttaagt tgtattataa agccacagta actaagacag  6300
cctggtattg gtatcagaat agagacatcg accagtggaa tcggaccgaa ccatcagaga  6360
taatgcccca catctataat taccttatat tcgataagcc agaaaagaat aaacagtggg  6420
gcaaagacag cctcttcaac aagtggtgtt gggagaattg gctggccata tgccggaaac  6480
tcaagctcga cccctttctt acaccctaca ctaaaatcaa cagtaggtgg atcaaggact  6540
tgaatgtcaa gccaaagact ataaagacac tggaagagaa tcttgggatc acaatacaag  6600
atataggcgt cggcaaagat tttatgtcaa agacgcccaa ggccatggcc actaaggata  6660
agattgataa gtgggacctt attaagctca aagcttctgt tactgccaag gagaccacga  6720
tcagagttaa taggcagccc actacatggg aaaagatttt cgccacttat tcatcagata  6780
aggggttgat aagcagaata tataacgagc tgaagcagat ctacaagaag aaaacgaata  6840
atcccatcaa gaagtgggca aaagatatga acaggcattt tagcaaagag gatatctacg  6900
ccgcgaagaa gcatatgaag aagtgtagtt caagcttggc cattcgtgag atgcagatta  6960
agacgaccat gcgataccac cttaccccag tgaggatggc aattatcaag aaatctggca  7020
ataatagatg ttggcggggc tgtggcgaga ttggcaccct gctccattgc tggtgggatt  7080
gcaagctggt gcagccgctt tggaaatcag tctggcgctt tctgagggac ctcgagcttg  7140
agattccctt cgatcccgca attcccttgc tcggaatcta tcctaacgaa tacaagagct  7200
gttgttacaa ggatacgtgt acccggatgt tcatcgcggc cttgtttacg atagctaaga  7260
cgtggaatca gcctaagtgc cccacaatga tcgattggat caagaaaatg tggcatattt  7320
ataccatgga gtattacgca gcaattaaga atgacgaatt tatttccttc gttgggacct  7380
ggatgaagct ggagactatt attctgagca agctgtctca ggagcaaaag acaaagcata  7440
gaatcttctc tctcattggt ggtaacgact acaaagacga tgacgacaag taaagcgctt  7500
ctagaagttg tctcctcctg cactgactga ctgatacaat cgatttctgg atccgcaggc  7560
ctaatcaacc tctggattac aaaatttgtg aaagattgac tggtattctt aactatgttg  7620
ctccttttac gctatgtgga tacgctgctt taatgccttt gtatcatgct attgcttccc  7680
gtatggcttt cattttctcc tccttgtata aatcctggtt gctgtctctt tatgaggagt  7740
tgtggcccgt tgtcaggcaa cgtggcgtgg tgtgcactgt gtttgctgac gcaaccccca  7800
ctggttgggg cattgccacc acctgtcagc tcctttccgg gactttcgct ttccccctcc  7860
ctattgccac ggcggaactc atcgccgcct gccttgcccg ctgctggaca ggggctcggc  7920
```

-continued

```
tgttgggcac tgacaattcc gtggtgttgt cggggaagct gacgtccttt ccatggctgc  7980
tcgcctgtgt tgccacctgg attctgcgcg ggacgtcctt ctgctacgtc ccttcggccc  8040
tcaatccagc ggaccttcct tcccgctgag agacacaaaa aattccaaca cactattgca  8100
atgaaaataa atttccttta ttagccagaa gtcagatgct caaggggctt catgatgtcc  8160
ccataatttt tggcagaggg aaaaagatct cagtggtatt tgtgagccag ggcattggcc  8220
ttctgatagg cagcctgcac ctgaggagtg cggccgcttt acttgtacag ctcgtccatg  8280
ccgagagtga tcccggcggc ggtcacgaac tccagcagga ccatgtgatc gcgcttctcg  8340
ttggggtctt tgctcagggc ggactgggtg ctcaggtagt ggttgtcggg cagcagcacg  8400
gggccgtcgc cgatgggggt gttctgctgg tagtggtcgg cgagctgcac gctgccgtcc  8460
tcgatgttgt ggcggatctt gaagttcacc ttgatgccgt tcttctgctt gtcggccatg  8520
atatagacgt tgtggctgtt gtagttgtac tccagcttgt gccccaggat gttgccgtcc  8580
tccttgaagt cgatgccctt cagctcgatg cggttcacca gggtgtcgcc ctcgaacttc  8640
acctcggcgc gggtcttgta gttgccgtcg tccttgaaga agatggtgcg ctcctggacg  8700
tagccttcgg gcatggcgga cttgaagaag tcgtgctgct tcatgtggtc ggggtagcgg  8760
ctgaagcact gcacgccgta ggtcagggtg gtcacgaggg tgggccaggg cacgggcagc  8820
ttgccggtgg tgcagatgaa cttcagggtc agcttgccgt aggtggcatc gccctcgccc  8880
tcgccggaca cgctgaactt gtggccgttt acgtcgccgt ccagctcgac caggatgggc  8940
accaccccgg tgaacagctc ctcgcccttg ctcaccatgg tggcgggatc tgacggttca  9000
ctaaaccagc tctgcttata tagacctccc accgtacacg cctaccgccc atttgcgtca  9060
atggggcgga gttgttacga cattttggaa agtcccgttg attttggtgc caaaacaaac  9120
tcccattgac gtcaatgggg tggagacttg gaaatccccg tgagtcaaac cgctatccac  9180
gcccattgat gtactgccaa aaccgcatca ccatggtaat agcgatgact aatacgtaga  9240
tgtactgcca agtaggaaag tcccataagg tcatgtactg ggcataatgc caggcgggcc  9300
atttaccgtc attgacgtca atagggggcg tacttggcat atgatacact tgatgtactg  9360
ccaagtgggc agtttaccgt aaatactcca cccattgacg tcaatggaaa gtccctattg  9420
gcgttactat gggaacatac gtcattattg acgtcaatgg gcgggggtcg ttgggcggtc  9480
agccaggcgg gccatttacc gtaagttatg taacgggcct gctgccggct ctgcggcctc  9540
ttccgcgtct tcgccttcgc cctcagacga gtcggatctc cctttgggcc gcctccccgc  9600
ctgtctagct tgactgactg agatacagcg taccttcagc tcacagacat gataagatac  9660
attgatgagt ttggacaaac cacaactaga atgcagtgaa aaaaatgctt tatttgtgaa  9720
atttgtgatg ctattgcttt atttgtaacc attataagct gcaataaaca agttaacaac  9780
aacaattgca ttcattttat gtttcaggtt caggggggagg tgtgggaggt tttttaaagc  9840
aagtaaaacc tctacaaatg tggtattggc ccatctctat cggtatcgta gcataacccc  9900
ttggggcctc taaacgggtc ttgaggggtt ttttgtgccc ctcgggccgg attgctatct  9960
accggcattg gcgcagaaaa aaatgcctga tgcgacgctg cgcgtcttat actcccacat  10020
atgccagatt cagcaacgga tacggcttcc ccaacttgcc cacttccata cgtgtcctcc  10080
ttaccagaaa tttatcctta aggtcgtcag ctatcctgca ggcgatctct cgatttcgat  10140
caagacattc ctttaatggt cttttctgga caccactagg ggtcagaagt agttcatcaa  10200
actttcttcc ctccctaatc tcattggtta ccttgggcta tcgaaactta attaagcgat  10260
ctgcatctca attagtcagc aaccatagtc ccgcccctaa ctccgcccat cccgccccta  10320
actccgccca gttccgccca ttctccgccc catcgctgac taattttttt tatttatgca  10380
gaggccgagg ccgcctcggc ctctgagcta ttccagaagt agtgaggagg cttttttgga  10440
ggcctaggct tttgcaaagg aggtagccaa catgattgaa caagatggat tgcacgcagg  10500
ttctcccgcc gcttgggtgg agaggctatt cggctatgac tgggcacaac agacaatcgg  10560
ctgctctgat gccgccgtgt tccggctgtc agcgcagggg cgcccggttc tttttgtcaa  10620
gaccgacctg tccggtgccc tgaatgaact ccaggacgag gcagcgcggc tatcgtggct  10680
ggccacgacg ggcgttcctt gcgcagctgt gctcgacgtt gtcactgaag cgggaaggga  10740
ctggctgcta ttgggcgaag tgccggggca ggatctcctg tcatctcacc ttgctcctgc  10800
cgagaaagta tccatcatgg ctgatgcaat gcggcggctg catacgcttg atccggctac  10860
ctgcccattc gaccaccaag cgaaacatcg catcgagcga gcacgtactc ggatggaagc  10920
cggtcttgtc gatcaggatg atctggacga agagcatcag gggctcgcgc cagccgaact  10980
gttcgccagg ctcaaggcgc ggatgcccga cggcgaggat ctcgtcgtga cccacggcga  11040
tgcctgcttg ccgaatatca tggtggaaaa tggccgcttt tctggattca tcgactgtgg  11100
ccggctgggt gtggcggacc gctatcagga catagcgttg gctacccgtg atattgctga  11160
agagcttggc ggcgaatggg ctgaccgctt cctcgtgctt tacggtatcg ccgctcccga  11220
ttcgcagcgc atcgccttct atcgccttct tgacgagttc ttctagtatg taagccctgt  11280
gccttctagt tgccagccat ctgttgtttg cccctccccc gtgccttcct tgaccctgga  11340
aggtgccact cccactgtcc tttcctaata aaatgaggaa attgcatcgc attgtctgag  11400
taggtgtcat tctattctgg ggggtggggt ggggcaggac agcaaggggg aggattggga  11460
agacaatagc aggcatgctg gggatgcggt gggctctatg gttaattaac cagtcaagtc  11520
agctacttgg cgagatcgac ttgtctgggt ttcgactacg ctcagaattg cgtcagtcaa  11580
gttcgatctg gtccttgcta ttgcacccgt tctccgatta cgagtttcat ttaaatcatg  11640
tgagcaaaag gccagcaaaa ggccaggaac cgtaaaaagg ccgcgttgct ggcgtttttc  11700
cataggctcc gcccccctga cgagcatcac aaaaatcgac gctcaagtca gaggtggcga  11760
aacccgacag gactataaag ataccaggcg tttccccctg gaagctccct cgtgcgctct  11820
cctgttccga ccctgccgct taccggatac ctgtccgcct ttctcccttc gggaagcgtg  11880
gcgctttctc atagctcacg ctgtaggtat ctcagttcgg tgtaggtcgt tcgctccaag  11940
ctgggctgtg tgcacgaacc ccccgttcag cccgaccgct gcgccttatc cggtaactat  12000
cgtcttgagt ccaacccggt aagacacgac ttatcgccac tggcagcagc cactggtaac  12060
aggattagca gagcgaggta tgtaggcggt gctacagagt tcttgaagtg gtggcctaac  12120
tacggctaca ctagaagaac agtatttggt atctgcgctc tgctgaagcc agttaccttc  12180
ggaaaaagag ttggtagctc ttgatccggc aaacaaacca ccgctggtag cggtggtttt  12240
tttgtttgca agcagcagat tacgcgcaga aaaaaaggat ctcaagaaga tcctttgatc  12300
ttttctacgg ggtctgacgc tcagtggaac gaaaactcac gttaagggat tttggtcatg  12360
agattatcaa aaaggatctt cacctagatc cttttaaatt aaaaatgaag ttttaaatca  12420
atctaaagta tatatgagta aacttggtct gacagttacc aatgcttaat cagtgaggca  12480
cctatctcag cgatctgtct atttcgttca tccatagttg catttaaatt tccgaactct  12540
ccaaggccct cgtc                                                   12554
```

-continued

```
SEQ ID NO: 98           moltype = DNA  length = 12569
FEATURE                 Location/Qualifiers
misc_feature            1..12569
                        note = Description of Artificial Sequence: Synthetic
                         polynucleotide
source                  1..12569
                        mol_type = other DNA
                        organism = synthetic construct
SEQUENCE: 98
ggaaaatctt caaacctttc gtccgatcca tcttgcaggc tacctctcga acgaactatc  60
gcaagtctct tggccggcct tgcgccttgg ctattgcttg gcagcgccta tcgccaggta  120
ttactccaat cccgaatatc cgagatcggg atcacccgag agaagttcaa cctacatcct  180
caatcccgat ctatccgaga tccgaggaat atcgaaatcg gggcgcgcct ggtgtaccga  240
gaacgatcct ctcagtgcga gtctcgacga tccatatcgt tgcttggcag tcagccagtc  300
ggaatccagc ttgggaccca ggaagtccaa tcgtcagata ttgtactcaa gcctggtcac  360
ggcagcgtac cgatctgttt aaacctagat attgatagtc tgatcggtca acgtataatc  420
gagtcctagc ttttgcaaac atctatcaag agacaggatc agcaggaggc tttcgcatga  480
gtattcaaca tttccgtgtc gcccttattc ccttttttgc ggcattttgc cttcctgttt  540
ttgctcaccc agaaacgctg gtgaaagtaa aagatgctga agatcagttg ggtgcgcgag  600
tgggttacat cgaactggat ctcaacagcg gtaagatcct tgagagtttt cgccccgaag  660
aacgctttcc aatgatgagc acttttaaag ttctgctatg tggcgcggta ttatcccgta  720
ttgacgccgg gcaagagcaa ctcggtcgcc gcatacacta ttctcagaat gacttggttg  780
agtattcacc agtcacagaa aagcatctta cggatggcat gacagtaaga gaattatgca  840
gtgctgccat aaccatgagt gataacactg cggccaactt acttctgaca acgattggag  900
gaccgaagga gctaaccgct tttttgcaca acatggggga tcatgtaact cgccttgatc  960
gttgggaacc ggagctgaat gaagccatac caaacgacga gcgtgacacc acgatgcctg  1020
tagcaatggc aacaaccttg cgtaaactat taactggcga actacttact ctagcttccc  1080
ggcaacagtt gatagactgg atggaggcgg ataaagttgc aggaccactt ctgcgctcgg  1140
cccttccggc tggctggttt attgctgata aatctggagc cggtgagcgt gggtctcgcg  1200
gtatcattgc agcactgggg ccagatggta agccctcccg tatcgtagtt atctacacga  1260
cggggagtca ggcaactatg gatgaacgaa atagacagat cgctgagata ggtgcctcac  1320
tgattaagca ttggtaaccg attctaggtg cattggcgca gaaaaaaatg cctgatgcga  1380
cgctgcgcgt cttatactcc cacatatgcc agattcagca acggatacgg cttccccaac  1440
ttgcccactt ccatacgtgt cctccttacc agaaatttat ccttaagatc gtttaaactc  1500
gactctggct ctatcgaatc tccgtcgttt cgagcttacg cgaacagccg tggcgctcat  1560
ttgctcgtcg ggcatcgaat ctcgtcagct atcgtcagct taccttttttg gcagcgatcg  1620
cggctcccga catcttggac cattagctcc acaggtatct tcttccctct agtggtcata  1680
acagcagctt cagctacctc tcaattcaaa aaacccctca agacccgttt agaggcccca  1740
aggggttatg ctatcaatcg ttgcgttaca cacacaaaaa accaacacac atccatcttc  1800
gatggatagc gattttatta tctaactgct gatcgagtgt agccagatct agtaatcaat  1860
tacggggtca ttagttcata gcccatatat ggagttccgc gttacataac ttacggtaaa  1920
tggcccgcct ggctgaccgc ccaacgaccc ccgcccattg acgtcaataa tgacgtatgt  1980
tcccatagta acgccaatag ggactttcca ttgacgtcaa tgggtggagt atttacggta  2040
aactgcccac ttggcagtac atcaagtgta tcatatgcca agtacgcccc ctattgacgt  2100
caatgacggt aaatggcccg cctggcatta tgcccagtac atgaccttat gggactttcc  2160
tacttggcag tacatctacg tattagtcat cgctattacc atgctgatgc ggttttggca  2220
gtacatcaat gggcgtggat agcggtttga ctcacgggga tttccaagtc tccaccccat  2280
tgacgtcaat gggagtttgt tttggcacca aaatcaacgg gactttccaa aatgtcgtaa  2340
caactccgcc ccattgacgc aaatgggcgg taggcgtgta cggtgggagg tctatataag  2400
cagagctggt ttagtgaacc gtcagatcag atctttgtcg atcctaccat ccactcgaca  2460
cacccgccag cggccgctaa tacgactcac tatagggaga agtactgcca ccatgaaaag  2520
gccggcggcc acgaaaaagg ccggccaggc aaaaaagaaa aagggcaaga agcaaaatcg  2580
caagacgggg aattccaaga cacaatccgc tagcccacca cctaaagagc gttctagctc  2640
ccctgctact gagcagtcct ggatggaaaa cgacttcgat gaactccggg aagagggatt  2700
taggcgatcc aactattcag aactccgcga agatatccag acaaagggga aggaagtcga  2760
gaatttcgag aagaacctcg aggagtgcat cacccgtatc acaaacactg agaaatgtct  2820
caaagaactc atggaactta agacaaaagc cagggagctt cgagaggagt gtcggagtct  2880
gagatccagg tgtgaccagc tcgaggagcg cgtgagcgcg atggaagacg agatgaacga  2940
gatgaaaaga gagggcaaat tcagggagaa gcgcattaag aggaacgaac agagtctgca  3000
ggagatttgg gattacgtca agaggcctaa cctgcggttg atcggcgtcc ccgagagcga  3060
cgtagaaaac gggactaaac tggagaatac acttcaagac atcattcaag aaaattttcc  3120
aaacctggct cggcaagcta atgtgcaaat ccaagagatc caacgcacac cccagcggta  3180
tagctctcgg cgtgccaccc ctaggcatat tatcgtgcgc tttactaagg tggagatgaa  3240
agagaagatg ctgcgagccg ctcgggaaaa gggaagggtg actttgaagg gcaaacctat  3300
tcggctgacg gttgacctta gcgccgagac actccaggca cgccgggaat ggggccccat  3360
ctttaatatc ctgaaggaga agaacttcca gccacgaatc tcttaccctg caaagttgag  3420
ttttatctcc gagggtgaga ttaagtattt catcgataaa cagatgctgc gagacttcgt  3480
gacaactcgc ccagctctca aggaactgct caaagaggct cttaatatgg agcgcaataa  3540
tagatatcaa cccttgcaga accacgcaaa gatgtgagac agccgtcaga ccatcaagac  3600
taggaagaaa ctgcatcaac taatgagcaa aatcaccagc taacatcata gtatacatga  3660
ccggctctaa ctcacatatc accatcctta cacttaacat taacggcctc aactcagcta  3720
tcaagcgcca tcggctggcc agctggatca aatcacagga tccaagcgtt tgttgcatcc  3780
aagagaccca cctgacctgt agagatactc accgcctcaa gatcaaggga tggcgaaaga  3840
tttatcaggc gaacggtaag cagaagaaag ccggagtcgc aattctggtc tcagacaaga  3900
cggatttcaa gcccaccaaa attaagcgtg ataaggaagg tcactatatt atggtgaaag  3960
gcagcataca gcaggaagaa cttaccatat tgaacatcta cgcgccaaac accggcgcac  4020
ctcgctttat caaacaggtc ctgtccgatc tgcagcgaga tctggattct catacgttga  4080
ttatgggtga tttcaataca ccattgagca ccctggatcg cagcaccagg caaaaggtaa  4140
ataaagacac gcaagagctc aatagcgcac tgcatcaggc agatctcatt gatatttatc  4200
```

-continued

```
gcactcttca tcctaagagt accgagtaca cattcttcag cgccccacat catacatact  4260
caaagatcga tcatatcgtc ggctcaaagg ctctgctgtc aaagtgcaag cgcacagaga  4320
taattacaaa ttacctgtca gatcatagcg cgatcaagct cgagctgaga atcaagaacc  4380
tgacccagag ccggagtacc acttggaagc ttaataacct gctgctcaac gattattggg  4440
tccacaatga gatgaaggca gagattaaaa tgttcttcga aacaaatgag aataaggata  4500
ctacctatca aaacctttgg gatgccttta aggccgtctg cagaggcaag ttcatcgccc  4560
tcaacgccta taaaagaaaa caagagagat ctaagatcga tactctcacc tctcagctga  4620
aggagttgga gaaacaggaa cagacccact ccaaggcgtc aagacggcag gagatcacaa  4680
agattcgcgc cgagttgaaa gagatcgaaa cccaaaagac tcttcagaaa attaacgagt  4740
ctcgtagttg gttcttcgag cggattaata agatagacag acctctggca cgactgatta  4800
agaagaagcg cgaaaagaac cagattgata ccatcaagaa cgacaagggc gacatcacta  4860
ctgacccgac cgagatccag accactattc gggagtatta taagcatttg tatgctaaca  4920
agcttgagaa cctggaagag atggacactt ttctggatac ctatactctg ccacggctta  4980
atcaagagga agtcgagtcc ctcaaccgcc caattacagg aagcgagatt gtggccataa  5040
ttaactccct gccgacaaag aaatctcctg gtccggacgg gtttacagct gagttttatc  5100
aacggtatat ggaagagctt gtaccgtttc tgctcaagct ctttcagtct atagaaaagg  5160
aaggcatctt gcccaattcc ttctacgaag cttctataat acttattccc aaaccaggac  5220
gcgataccac aaagaaggaa aacttccggc ccattagtct catgaatatc gacgctaaaa  5280
tattgaacaa gattctcgcc aacagaatcc aacaacatat taagaaattg atacatcacg  5340
accaggtggg gtttatacct ggcatgcagg gctggtttaa catccggaag agtattaacg  5400
tcattcaaca cattaataga gctaaggata agaatcatat gatcatctct atagacgcgg  5460
aaaaggcatt cgataagatt cagcagccat ttatgctcaa gactctgaac aaactcggca  5520
tcgacggaac atattttaag attattcgcg caatttacga taagccgact gctaacatta  5580
tccttaacgg ccaaaagctc gaggcctttc cgctcaagac tggaacccgc caaggctgtc  5640
ccctctcccc gcttttgttt aatattgtac tcgaggtgct ggctagggct attcgtcaag  5700
agaaagagat taaagggata cagctcggga aggaagaggt caagctttcc ttgttcgccg  5760
atgatatgat tgtgtacctg gagaatccta ttgtgtctgc tcagaacctt cttaaactta  5820
tttctaactt tagcaaggtc agcggctata agattaacgt ccagaaatct caggcctttc  5880
tgtacacaaa taatcgacag accgaatccc agataatggg tgagcttccg tttgtcatag  5940
ccagcaaaag gataaagtat ctcggaatcc agctgacacg agacgttaaa gatttgttta  6000
aggaaaatta caagcctctc ctgaaagaga ttaaggaaga tactaataag tggaagaata  6060
tcccctgttc atgggttggc agaatcaaca tagtgaagat ggcaatactt cctaaagtga  6120
tatatcgctt taacgccatc ccaattaaac tgcctatgac cttctttacg gagctcgaga  6180
aaacaaccct taaatttata tggaatcaaa agagagcaag aatagcgaag tccatcttga  6240
gccagaagaa taaggccggt gggattactt tgcctgattt taagttgtat tataaagcca  6300
cagtaactaa gacagcctgg tattggtatc agaatagaga catcgaccag tggaatcgga  6360
ccgaaccatc agagataatg ccccacatct ataattacct tatattcgat aagccagaaa  6420
agaataaaca gtggggcaaa gacagcctct tcaacaagtg gtgttgggag aattggctgg  6480
ccatatgccg gaaactcaag ctcgacccct ttcttacacc ctacactaaa atcaacagta  6540
ggtggatcaa ggacttgaat gtcaagccaa agactataaa gacactggaa gagaatcttg  6600
ggatcacaat acaagatata ggcgtcggca aagattttat gtcaaagacg cccaaggcca  6660
tggccactaa ggataagatt gataagtggg accttattaa gctcaaaagc ttctgtactg  6720
ccaaggagac cacgatcaga gttaataggc agcccactac atgggaaaag attttcgcca  6780
cttattcatc agataagggg ttgataagca gaatatataa cgagctgaag cagatctaca  6840
agaagaaaac gaataatccc atcaagaagt gggcaaaaga tatgaacagg cattttagca  6900
aagaggatat ctacgccgcg aagaagcata tgaagaagtg tagttcaagc ttggccattc  6960
gtgagatgca gattaagacg accatgcgat accaccttac cccagtgagg atggcaatta  7020
tcaagaaatc tggcaataat agatgttggc ggggctgtgg cgagattggc accctgctcc  7080
attgctggtg ggattgcaag ctggtgcagc cgctttggaa atcagtctgg cgctttctga  7140
gggacctcga gcttgagatt cccttcgatc ccgcaattcc cttgctcgga atctatccta  7200
acgaatacaa gagctgttgt tacaaggata cgtgtacccg gatgttcatc gcggccttgt  7260
ttacgatagc taagacgtgg aatcagccta agtgccccac aatgatcgat tggatcaaga  7320
aaatgtggca tatttatacc atggagtatt acgcagcaat taagaatgac gaatttattt  7380
ccttcgttgg gacctggatg aagctggaga ctattattct gagcaagctg tctcaggagc  7440
aaaagacaaa gcatagaatc ttctctctca ttggtggtaa cgactacaaa gacgatgacg  7500
acaagtaaag cgcttctaga agttgtctcc tcctgcactg actgactgat acaatcgatt  7560
tctggatccg caggcctaat caacctctgg attacaaaat ttgtgaaaga ttgactggta  7620
ttcttaacta tgttgctcct tttacgctat gtggatacgc tgctttaatg cctttgtatc  7680
atgctattgc ttcccgtatg gctttcattt tctcctcctt gtataaatcc tggttgctgt  7740
ctctttatga ggagttgtgg cccgttgtca ggcaacgtgg cgtggtgtgc actgtgtttg  7800
ctgacgcaac ccccactggt tggggcattg ccaccacctg tcagctcctt tccgggactt  7860
tcgctttccc cctccctatt gccacggcgg aactcatcgc cgcctgcctt gcccgctgct  7920
ggacaggggc tcggctgttg ggcactgaca attccgtggt gttgtcgggg aagctgacgt  7980
cctttccatg gctgctcgcc tgtgttgcca cctggattct gcgcgggacg tccttctgct  8040
acgtcccttc ggccctcaat ccagcggacc ttccttcccg ctgagagaca caaaaaattc  8100
caacacacta ttgcaatgaa aataaatttc ctttattagc cagaagtcag atgctcaagg  8160
ggcttcatga tgtccccata atttttggca gagggaaaaa gatctcagtg gtatttgtga  8220
gccagggcat tggccttctg ataggcagcc tgcacctgag gagtgcggcc gctttacttg  8280
tacagctcgt ccatgccgag agtgatcccg gcggcggtca cgaactccag caggaccatg  8340
tgatcgcgct tctcgttggg gtctttgctc agggcggact gggtgctcag gtagtggttg  8400
tcgggcagca gcacggggcc gtcgccgatg ggggtgttct gctggtagtg gtcggcgagc  8460
tgcacgctgc cgtcctcgat gttgtggcgg atcttgaagt tcaccttgat gccgttcttc  8520
tgcttgtcgg ccatgatata gacgttgtgg ctgttgtagt tgtactccag cttgtgcccc  8580
aggatgttgc cgtcctcctt gaagtcgatg cccttcagct cgatgcggtt caccagggtg  8640
tcgccctcga acttcacctc ggcgcgggtc ttgtagttgc cgtcgtcctt gaagaagatg  8700
gtgcgctcct ggacgtagcc ttcgggcatg gcggacttga agaagtcgtg ctgcttcatg  8760
tggtcggggt agcggctgaa gcactgcacg ccgtaggtca gggtggtcac gagggtgggc  8820
cagggcacgg gcagcttgcc ggtggtgcag atgaacttca gggtcagctt gccgtaggtg  8880
gcatcgccct cgccctcgcc ggacacgctg aacttgtggc cgtttacgtc gccgtccagc  8940
```

```
tcgaccagga tgggcaccac cccggtgaac agctcctcgc ccttgctcac catggtggcg  9000
ggatctgacg gttcactaaa ccagctctgc ttatatagac ctcccaccgt acacgcctac  9060
cgcccatttg cgtcaatggg gcggagttgt tacgacattt tggaaagtcc cgttgatttt  9120
ggtgccaaaa caaactccca ttgacgtcaa tggggtggag acttggaaat ccccgtgagt  9180
caaaccgcta tccacgccca ttgatgtact gccaaaaccg catcaccatg gtaatagcga  9240
tgactaatac gtagatgtac tgccaagtag gaaagtccca taaggtcatg tactgggcat  9300
aatgccaggc gggccattta ccgtcattga cgtcaatagg gggcgtactt ggcatatgat  9360
acacttgatg tactgccaag tgggcagttt accgtaaata ctccacccat tgacgtcaat  9420
ggaaagtccc tattggcgtt actatgggaa catacgtcat tattgacgtc aatgggcggg  9480
ggtcgttggg cggtcagcca ggcgggccat ttaccgtaag ttatgtaacg ggcctgctgc  9540
cggctctgcg gcctcttccg cgtcttcgcc ttcgccctca gacgagtcgg atctcccttt  9600
gggccgcctc cccgcctgtc tagcttgact gactgagata cagcgtacct tcagctcaca  9660
gacatgataa gatacattga tgagtttgga caaaccacaa ctagaatgca gtgaaaaaaa  9720
tgctttattt gtgaaatttg tgatgctatt gctttatttg taaccattat aagctgcaat  9780
aaacaagtta acaacaacaa ttgcattcat tttatgtttc aggttcaggg ggaggtgtgg  9840
gaggtttttt aaagcaagta aaacctctac aaatgtggta ttggcccatc tctatcggta  9900
tcgtagcata accccttggg gcctctaaac gggtcttgag gggttttttg tgcccctcgg  9960
gccggattgc tatctaccgg cattggcgca gaaaaaaatg cctgatgcga cgctgcgcgt  10020
cttatactcc cacatatgcc agattcagca acggatacgg cttccccaac ttgcccactt  10080
ccatacgtgt cctccttacc agaaatttat ccttaaggtc gtcagctatc ctgcaggcga  10140
tctctcgatt tcgatcaaga cattccttta atggtctttt ctggacacca ctaggggtca  10200
gaagtagttc atcaaacttt cttccctccc taatctcatt ggttaccttg ggctatcgaa  10260
acttaattaa gcgatctgca tctcaattag tcagcaacca tagtcccgcc cctaactccg  10320
cccatcccgc ccctaactcc gcccagttcc gcccattctc cgccccatcg ctgactaatt  10380
ttttttattt atgcagaggc cgaggccgcc tcggcctctg agctattcca gaagtagtga  10440
ggaggctttt ttggaggcct aggcttttgc aaaggaggta gccaacatga ttgaacaaga  10500
tggattgcac gcaggttctc cggccgcttg ggtggagagg ctattcggct atgactgggc  10560
acaacagaca atcggctgct ctgatgccgc cgtgttccgg ctgtcagcgc aggggcgccc  10620
ggttcttttt gtcaagaccg acctgtccgg tgccctgaat gaactccagg acgaggcagc  10680
gcggctatcg tggctggcca cgacgggcgt tccttgcgca gctgtgctcg acgttgtcac  10740
tgaagcggga agggactggc tgctattggg cgaagtgccg gggcaggatc tcctgtcatc  10800
tcaccttgct cctgccgaga aagtatccat catggctgat gcaatgcggc ggctgcatac  10860
gcttgatccg gctacctgcc cattcgacca ccaagcgaaa catcgcatcg agcgagcacg  10920
tactcggatg gaagccggtc ttgtcgatca ggatgatctg gacgaagagc atcaggggct  10980
cgcgccagcc gaactgttcg ccaggctcaa ggcgcggatg cccgacggcg aggatctcgt  11040
cgtgacccac ggcgatgcct gcttgccgaa tatcatggtg gaaaatggcc gcttttctgg  11100
attcatcgac tgtggccggc tgggtgtggc ggaccgctat caggacatag cgttggctac  11160
ccgtgatatt gctgaagagc ttggcggcga atgggctgac cgcttcctcg tgctttacgg  11220
tatcgccgct cccgattcgc agcgcatcgc cttctatcgc cttcttgacg agttcttcta  11280
gtatgtaagc cctgtgcctt ctagttgcca gccatctgtt gtttgcccct cccccgtgcc  11340
ttccttgacc ctggaaggtg ccactcccac tgtcctttcc taataaaatg aggaaattgc  11400
atcgcattgt ctgagtaggt gtcattctat tctggggggt ggggtggggc aggacagcaa  11460
gggggaggat tgggaagaca atagcaggca tgctggggat gcggtgggct ctatggttaa  11520
ttaaccagtc aagtcagcta cttggcgaga tcgacttgtc tgggtttcga ctacgctcag  11580
aattgcgtca gtcaagttcg atctggtcct tgctattgca cccgttctcc gattacgagt  11640
ttcatttaaa tcatgtgagc aaaaggccag caaaaggcca ggaaccgtaa aaaggccgcg  11700
ttgctggcgt ttttccatag gctccgcccc cctgacgagc atcacaaaaa tcgacgctca  11760
agtcagaggt ggcgaaaccc gacaggacta taaagatacc aggcgtttcc ccctggaagc  11820
tccctcgtgc gctctcctgt tccgaccctg ccgcttaccg gatacctgtc cgcctttctc  11880
ccttcgggaa gcgtggcgct ttctcatagc tcacgctgta ggtatctcag ttcggtgtag  11940
gtcgttcgct ccaagctggg ctgtgtgcac gaaccccccg ttcagcccga ccgctgcgcc  12000
ttatccggta actatcgtct tgagtccaac ccggtaagac acgacttatc gccactggca  12060
gcagccactg gtaacaggat tagcagagcg aggtatgtag gcggtgctac agagttcttg  12120
aagtggtggc ctaactacgg ctacactaga agaacagtat ttggtatctg cgctctgctg  12180
aagccagtta ccttcggaaa aagagttggt agctcttgat ccggcaaaca aaccaccgct  12240
ggtagcggtg gtttttttgt ttgcaagcag cagattacgc gcagaaaaaa aggatctcaa  12300
gaagatcctt tgatcttttc tacggggtct gacgctcagt ggaacgaaaa ctcacgttaa  12360
gggattttgg tcatgagatt atcaaaaagg atcttcacct agatcctttt aaattaaaaa  12420
tgaagtttta aatcaatcta aagtatatat gagtaaactt ggtctgacag ttaccaatgc  12480
ttaatcagtg aggcacctat ctcagcgatc tgtctatttc gttcatccat agttgcattt  12540
aaatttccga actctccaag gccctcgtc                                   12569
```

```
SEQ ID NO: 99          moltype = DNA  length = 12581
FEATURE                Location/Qualifiers
misc_feature           1..12581
                       note = Description of Artificial Sequence: Synthetic
                        polynucleotide
source                 1..12581
                       mol_type = other DNA
                       organism = synthetic construct
SEQUENCE: 99
caaacctttc gtccgatcca tcttgcaggc tacctctcga acgaactatc gcaagtctct  60
tggccggcct tgcgccttgg ctattgcttg gcagcgccta tcgccaggta ttactccaat  120
cccgaatatc cgagatcggg atcacccgag agaagttcaa cctacatcct caatcccgat  180
ctatccgaga tccgaggaat atcgaaatcg gggcgcgcct ggtgtaccga gaacgatcct  240
ctcagtgcga gtctcgacga tccatatcgt tgcttggcag tcagccagtc ggaatccagc  300
ttgggaccca ggaagtccaa tcgtcagata ttgtactcaa gcctggtcac ggcagcgtac  360
cgatctgttt aaacctagat attgatagtc tgatcggtca acgtataatc gagtcctagc  420
ttttgcaaac atctatcaag agacaggatc agcaggaggc tttcgcatga gtattcaaca  480
```

```
tttccgtgtc gcccttattc cctttttttgc ggcattttgc cttcctgttt ttgctcaccc  540
agaaacgctg gtgaaagtaa aagatgctga agatcagttg ggtgcgcgag tgggttacat  600
cgaactggat ctcaacagcg gtaagatcct tgagagtttt cgccccgaag aacgctttcc  660
aatgatgagc acttttaaag ttctgctatg tggcgcggta ttatcccgta ttgacgccgg  720
gcaagagcaa ctcggtcgcc gcatacacta ttctcagaat gacttggttg agtattcacc  780
agtcacagaa aagcatctta cggatggcat gacagtaaga gaattatgca gtgctgccat  840
aaccatgagt gataacactg cggccaactt acttctgaca acgattggag gaccgaagga  900
gctaaccgct tttttgcaca acatggggga tcatgtaact cgccttgatc gttgggaacc  960
ggagctgaat gaagccatac caaacgacga gcgtgacacc acgatgcctg tagcaatggc  1020
aacaaccttg cgtaaactat taactggcga actacttact ctagcttccc ggcaacagtt  1080
gatagactgg atggaggcgg ataaagttgc aggaccactt ctgcgctcgg cccttccggc  1140
tggctggttt attgctgata aatctggagc cggtgagcgt gggtctcgcg gtatcattgc  1200
agcactgggg ccagatggta agccctcccg tatcgtagtt atctacacga cggggagtca  1260
ggcaactatg gatgaacgaa atagacagat cgctgagata ggtgcctcac tgattaagca  1320
ttggtaaccg attctaggtg cattggcgca gaaaaaaatg cctgatgcga cgctgcgcgt  1380
cttatactcc cacatatgcc agattcagca acggatacgg cttccccaac ttgcccactt  1440
ccatacgtgt cctccttacc agaaatttat ccttaagatc gtttaaactc gactctggct  1500
ctatcgaatc tccgtcgttt cgagcttacg cgaacagccg tggcgctcat ttgctcgtcg  1560
ggcatcgaat ctcgtcagct atcgtcagct taccttttttg gcagcgatcg cggctcccga  1620
catcttggac cattagctcc acaggtatct tcttccctct agtggtcata acagcagctt  1680
cagctacctc tcaattcaaa aaacccctca agacccgttt agaggcccca aggggttatg  1740
ctatcaatcg ttgcgttaca cacacaaaaa accaacacac atccatcttc gatggatagc  1800
gattttatta tctaactgct gatcgagtgt agccagatct agtaatcaat tacggggtca  1860
ttagttcata gcccatatat ggagttccgc gttacataac ttacggtaaa tggcccgcct  1920
ggctgaccgc ccaacgaccc ccgcccattg acgtcaataa tgacgtatgt tcccatagta  1980
acgccaatag ggactttcca ttgacgtcaa tgggtggagt atttacggta aactgcccac  2040
ttggcagtac atcaagtgta tcatatgcca agtacgcccc ctattgacgt caatgacggt  2100
aaatggcccg cctggcatta tgcccagtac atgaccttat gggactttcc tacttggcag  2160
tacatctacg tattagtcat cgctattacc atgctgatgc ggttttggca gtacatcaat  2220
gggcgtggat agcggtttga ctcacgggga tttccaagtc tccaccccat tgacgtcaat  2280
gggagtttgt tttggcacca aaatcaacgg gactttccaa aatgtcgtaa caactccgcc  2340
ccattgacgc aaatgggcgg taggcgtgta cggtgggagg tctatataag cagagctggt  2400
ttagtgaacc gtcagatcag atctttgtcg atcctaccat ccactcgaca cacccgccag  2460
cggccgctaa tacgactcac tatagggaga agtactgcca ccatgaaaag gccggcggcc  2520
acgaaaaagg ccggccaggc aaaaaagaaa aagggcggcg gcagcggcaa gaagcaaaat  2580
cgcaagacgg ggaattccaa gacacaatcc gctagcccac cacctaaaga gcgttctagc  2640
tcccctgcta ctgagcagtc ctggatggaa aacgacttcg atgaactccg ggaagaggga  2700
tttaggcgat ccaactattc agaactccgc gaagatatcc agacaaaggg gaaggaagtc  2760
gagaatttcg agaagaacct cgaggagtgc atcacccgta tcacaaacac tgagaaatgt  2820
ctcaaagaac tcatggaact taagacaaaa gccagggagc ttcgagagga gtgtcggagt  2880
ctgagatcca ggtgtgacca gctcgaggag cgcgtgagcg cgatggaaga cgagatgaac  2940
gagatgaaaa gagagggcaa attcagggag aagcgcatta agaggaacga acagagtctg  3000
caggagattt gggattacgt caagaggcct aacctgcggt tgatcggcgt ccccgagagc  3060
gacgtagaaa acgggactaa actggagaat acacttcaag acatcattca agaaaatttt  3120
ccaaacctgg ctcggcaagc taatgtgcaa atccaagaga tccaacgcac accccagcgg  3180
tatagctctc ggcgtgccac ccctaggcat attatcgtgc gctttactaa ggtggagatg  3240
aaagagaaga tgctgcgagc cgctcgggaa aagggaaggg tgactttgaa gggcaaacct  3300
attcggctga cggttgacct tagcgccgag acactccagg cacgccggga atggggcccc  3360
atctttaata tcctgaagga gaagaacttc cagccacgaa tctcttaccc tgcaaagttg  3420
agttttatct ccgagggtga gattaagtat ttcatcgata aacagatgct gcgagacttc  3480
gtgacaactc gcccagctct caaggaactg ctcaaagagg ctcttaatat ggagcgcaat  3540
aatagatatc aacccttgca gaaccacgca aagatgtgag acagccgtca gaccatcaag  3600
actaggaaga aactgcatca actaatgagc aaaatcacca gctaacatca tagtatacat  3660
gaccggctct aactcacata tcaccatcct tacacttaac attaacggcc tcaactcagc  3720
tatcaagcgc catcggctgg ccagctggat caaatcacag gatccaagcg tttgttgcat  3780
ccaagagacc cacctgacct gtagagatac tcaccgcctc aagatcaagg gatggcgaaa  3840
gatttatcag gcgaacggta agcagaagaa agccggagtc gcaattctgg tctcagacaa  3900
gacggatttc aagcccacca aaattaagcg tgataaggaa ggtcactata ttatggtgaa  3960
aggcagcata cagcaggaag aacttaccat attgaacatc tacgcgccaa acaccggcgc  4020
acctcgcttt atcaaacagg tcctgtccga tctgcagcga gatctggatt ctcatacgtt  4080
gattatgggt gatttcaata caccattgag caccctggat cgcagcacca ggcaaaaggt  4140
aaataaagac acgcaagagc tcaatagcgc actgcatcag gcagatctca ttgatattta  4200
tcgcactctt catcctaaga gtaccgagta cacattcttc agcgccccac atcatacata  4260
ctcaaagatc gatcatatcg tcggctcaaa ggctctgctg tcaaagtgca agcgcacaga  4320
gataattaca aattacctgt cagatcatag cgcgatcaag ctcgagctga gaatcaagaa  4380
cctgacccag agccggagta ccacttggaa gcttaataac ctgctgctca acgattattg  4440
ggtccacaat gagatgaagg cagagattaa aatgttcttc gaaacaaatg agaataagga  4500
tactacctat caaaaccttt gggatgcctt taaggccgtc tgcagaggca agttcatcgc  4560
cctcaacgcc tataaaagaa aacaagagag atctaagatc gatactctca cctctcagct  4620
gaaggagttg gagaaacagg aacagaccca ctccaaggcg tcaagacggc aggagatcac  4680
aaagattcgc gccgagttga aagagatcga aacccaaaag actcttcaga aaattaacga  4740
gtctcgtagt tggttcttcg agcggattaa taagatagac agacctctgg cacgactgat  4800
taagaagaag cgcgaaaaga accagattga taccatcaag aacgacaagg gcgacatcac  4860
tactgacccg accgagatcc agaccactat tcgggagtat tataagcatt tgtatgctaa  4920
caagcttgag aacctggaag agatggacac ttttctggat acctatactc tgccacggct  4980
taatcaagag gaagtcgagt ccctcaaccg cccaattaca ggaagcgaga ttgtggccat  5040
aattaactcc ctgccgacaa agaaatctcc tggtccggac gggtttacag ctgagtttta  5100
tcaacggtat atggaagagc ttgtaccgtt tctgctcaag ctctttcagt ctatagaaaa  5160
ggaaggcatc ttgcccaatt ccttctacga agcttctata atacttattc ccaaaccagg  5220
```

-continued

```
acgcgatacc acaaagaagg aaaacttccg gcccattagt ctcatgaata tcgacgctaa  5280
aatattgaac aagattctcg ccaacagaat ccaacaacat attaagaaat tgatacatca  5340
cgaccaggtg gggtttatac ctggcatgca gggctggttt aacatccgga agagtattaa  5400
cgtcattcaa cacattaata gagctaagga taagaatcat atgatcatct ctatagacgc  5460
ggaaaaggca ttcgataaga ttcagcagcc atttatgctc aagactctga acaaactcgg  5520
catcgacgga acatatttta agattattcg cgcaatttac gataagccga ctgctaacat  5580
tatccttaac ggccaaaagc tcgaggcctt tccgctcaag actggaaccc gccaaggctg  5640
tcccctctcc ccgcttttgt ttaatattgt actcgaggtg ctggctaggg ctattcgtca  5700
agagaaagag attaaaggga tacagctcgg gaaggaagag gtcaagcttt ccttgttcgc  5760
cgatgatatg attgtgtacc tggagaatcc tattgtgtct gctcagaacc ttcttaaact  5820
tatttctaac tttagcaagg tcagcggcta taagattaac gtccagaaat ctcaggcctt  5880
tctgtacaca aataatcgac agaccgaatc ccagataatg ggtgagcttc cgtttgtcat  5940
agccagcaaa aggataaagt atctcggaat ccagctgaca cgagacgtta aagatttgtt  6000
taaggaaaat tacaagcctc tcctgaaaga gattaaggaa gatactaata agtggaagaa  6060
tatcccctgt tcatgggttg gcagaatcaa catagtgaag atggcaatac ttcctaaagt  6120
gatatatcgc tttaacgcca tcccaattaa actgcctatg accttcttta cggagctcga  6180
gaaaacaacc cttaaattta tatggaatca aaagagagca agaatagcga agtccatctt  6240
gagccagaag aataaggccg gtgggattac tttgcctgat tttaagttgt attataaagc  6300
cacagtaact aagacagcct ggtattggta tcagaataga gacatcgacc agtggaatcg  6360
gaccgaacca tcagagataa tgccccacat ctataattac cttatattcg ataagccaga  6420
aaagaataaa cagtggggca aagacagcct cttcaacaag tggtgttggg agaattggct  6480
ggccatatgc cggaaactca agctcgaccc ctttcttaca ccctacacta aaatcaacag  6540
taggtggatc aaggacttga atgtcaagcc aaagactata aagacactgg aagagaatct  6600
tgggatcaca atacaagata taggcgtcgg caaagatttt atgtcaaaga cgcccaaggc  6660
catggccact aaggataaga ttgataagtg ggaccttatt aagctcaaaa gcttctgtac  6720
tgccaaggag accacgatca gagttaatag gcagcccact acatgggaaa agattttcgc  6780
cacttattca tcagataagg ggttgataag cagaatatat aacgagctga agcagatcta  6840
caagaagaaa acgaataatc ccatcaagaa gtgggcaaaa gatatgaaca ggcattttag  6900
caaagaggat atctacgccg cgaagaagca tatgaagaag tgtagttcaa gcttggccat  6960
tcgtgagatg cagattaaga cgaccatgcg ataccacctt accccagtga ggatggcaat  7020
tatcaagaaa tctggcaata atagatgttg gcggggctgt ggcgagattg gcaccctgct  7080
ccattgctgg tgggattgca agctggtgca gccgctttgg aaatcagtct ggcgctttct  7140
gagggacctc gagcttgaga ttcccttcga tcccgcaatt cccttgctcg gaatctatcc  7200
taacgaatac aagagctgtt gttacaagga tacgtgtacc cggatgttca tcgcggcctt  7260
gtttacgata gctaagacgt ggaatcagcc taagtgcccc acaatgatcg attggatcaa  7320
gaaaatgtgg catatttata ccatggagta ttacgcagca attaagaatg acgaatttat  7380
ttccttcgtt gggacctgga tgaagctgga gactattatt ctgagcaagc tgtctcagga  7440
gcaaaagaca aagcatagaa tcttctctct cattggtggt aacgactaca aagacgatga  7500
cgacaagtaa agcgcttcta gaagttgtct cctcctgcac tgactgactg atacaatcga  7560
tttctggatc cgcaggccta atcaacctct ggattacaaa atttgtgaaa gattgactgg  7620
tattcttaac tatgttgctc cttttacgct atgtggatac gctgctttaa tgcctttgta  7680
tcatgctatt gcttcccgta tggctttcat tttctcctcc ttgtataaat cctggttgct  7740
gtctctttat gaggagttgt ggcccgttgt caggcaacgt ggcgtggtgt gcactgtgtt  7800
tgctgacgca acccccactg gttggggcat tgccaccacc tgtcagctcc tttccgggac  7860
tttcgctttc cccctcccta ttgccacggc ggaactcatc gccgcctgcc ttgcccgctg  7920
ctggacaggg gctcggctgt tgggcactga caattccgtg gtgttgtcgg ggaagctgac  7980
gtcctttcca tggctgctcg cctgtgttgc cacctggatt ctgcgcggga cgtccttctg  8040
ctacgtccct tcggccctca atccagcgga ccttccttcc cgctgagaga cacaaaaaat  8100
tccaacacac tattgcaatg aaaataaatt tcctttatta gccagaagtc agatgctcaa  8160
ggggcttcat gatgtcccca taatttttgg cagagggaaa aagatctcag tggtatttgt  8220
gagccagggc attggccttc tgataggcag cctgcacctg aggagtgcgg ccgctttact  8280
tgtacagctc gtccatgccg agagtgatcc cggcggcggt cacgaactcc agcaggacca  8340
tgtgatcgcg cttctcgttg gggtctttgc tcagggcgga ctgggtgctc aggtagtggt  8400
tgtcgggcag cagcacgggg ccgtcgccga tgggggtgtt ctgctggtag tggtcggcga  8460
gctgcacgct gccgtcctcg atgttgtggc ggatcttgaa gttcaccttg atgccgttct  8520
tctgcttgtc ggccatgata tagacgttgt ggctgttgta gttgtactcc agcttgtgcc  8580
ccaggatgtt gccgtcctcc ttgaagtcga tgcccttcag ctcgatgcgg ttcaccaggg  8640
tgtcgccctc gaacttcacc tcggcgcggg tcttgtagtt gccgtcgtcc ttgaagaaga  8700
tggtgcgctc ctggacgtag ccttcgggca tggcggactt gaagaagtcg tgctgcttca  8760
tgtggtcggg gtagcggctg aagcactgca cgccgtaggt cagggtggtc acgagggtgg  8820
gccagggcac gggcagcttg ccggtggtgc agatgaactt cagggtcagc ttgccgtagg  8880
tggcatcgcc ctcgccctcg ccggacacgc tgaacttgtg gccgtttacg tcgccgtcca  8940
gctcgaccag gatgggcacc accccggtga acagctcctc gcccttgctc accatggtgg  9000
cgggatctga cggttcacta aaccagctct gcttatatag acctcccacc gtacacgcct  9060
accgcccatt tgcgtcaatg gggcggagtt gttacgacat tttggaaagt cccgttgatt  9120
ttggtgccaa aacaaactcc cattgacgtc aatggggtgg agacttggaa atccccgtga  9180
gtcaaaccgc tatccacgcc cattgatgta ctgccaaaac cgcatcacca tggtaatagc  9240
gatgactaat acgtagatgt actgccaagt aggaaagtcc cataaggtca tgtactgggc  9300
ataatgccag gcgggccatt taccgtcatt gacgtcaata gggggcgtac ttggcatatg  9360
atacacttga tgtactgcca agtgggcagt ttaccgtaaa tactccaccc attgacgtca  9420
atggaaagtc cctattggcg ttactatggg aacatacgtc attattgacg tcaatgggcg  9480
ggggtcgttg ggcggtcagc caggcgggcc atttaccgta agttatgtaa cgggcctgct  9540
gccggctctg cggcctcttc cgcgtcttcg ccttcgccct cagacgagtc ggatctccct  9600
ttgggccgcc tccccgcctg tctagcttga ctgactgaga tacagcgtac cttcagctca  9660
cagacatgat aagatacatt gatgagtttg gacaaaccac aactagaatg cagtgaaaaa  9720
aatgctttat ttgtgaaatt tgtgatgcta ttgctttatt tgtaaccatt ataagctgca  9780
ataaacaagt taacaacaac aattgcattc attttatgtt tcaggttcag ggggaggtgt  9840
gggaggtttt ttaaagcaag taaaacctct acaaatgtgg tattggccca tctctatcgg  9900
tatcgtagca taaccccttg ggcctctaa acgggtcttg aggggttttt tgtgcccctc  9960
```

```
gggccggatt gctatctacc ggcattggcg cagaaaaaaa tgcctgatgc gacgctgcgc  10020
gtcttatact cccacatatg ccagattcag caacggatac ggcttcccca acttgcccac  10080
ttccatacgt gtcctcctta ccagaaattt atccttaagg tcgtcagcta tcctgcaggc  10140
gatctctcga tttcgatcaa gacattcctt taatggtctt ttctggacac cactaggggt  10200
cagaagtagt tcatcaaact ttcttccctc cctaatctca ttggttacct tgggctatcg  10260
aaacttaatt aagcgatctg catctcaatt agtcagcaac catagtcccg cccctaactc  10320
cgcccatccc gcccctaact ccgcccagtt ccgcccattc tccgccccat cgctgactaa  10380
ttttttttat ttatgcagag gccgaggccg cctcggcctc tgagctattc cagaagtagt  10440
gaggaggctt ttttggaggc ctaggctttt gcaaaggagg tagccaacat gattgaacaa  10500
gatggattgc acgcaggttc tcccgccgct tgggtggaga ggctattcgg ctatgactgg  10560
gcacaacaga caatcggctg ctctgatgcc gccgtgttcc ggctgtcagc gcaggggcgc  10620
ccggttcttt ttgtcaagac cgacctgtcc ggtgccctga atgaactcca ggacgaggca  10680
gcgcggctat cgtggctggc cacgacgggc gttccttgcg cagctgtgct cgacgttgtc  10740
actgaagcgg gaagggactg gctgctattg ggcgaagtgc cggggcagga tctcctgtca  10800
tctcaccttg ctcctgccga gaaagtatcc atcatggctg atgcaatgcg gcggctgcat  10860
acgcttgatc cggctacctg cccattcgac caccaagcga aacatcgcat cgagcgagca  10920
cgtactcgga tggaagccgg tcttgtcgat caggatgatc tggacgaaga gcatcagggg  10980
ctcgcgccag ccgaactgtt cgccaggctc aaggcgcgga tgcccgacgg cgaggatctc  11040
gtcgtgaccc acggcgatgc ctgcttgccg aatatcatgg tggaaaatgg ccgcttttct  11100
ggattcatcg actgtggccg gctgggtgtg gcggaccgct atcaggacat agcgttggct  11160
acccgtgata ttgctgaaga gcttggcggc gaatgggctg accgcttcct cgtgctttac  11220
ggtatcgccg ctcccgattc gcagcgcatc gccttctatc gccttcttga cgagttcttc  11280
tagtatgtaa gccctgtgcc ttctagttgc cagccatctg ttgtttgccc ctcccccgtg  11340
ccttccttga ccctggaagg tgccactccc actgtccttt cctaataaaa tgaggaaatt  11400
gcatcgcatt gtctgagtag gtgtcattct attctggggg gtggggtggg gcaggacagc  11460
aagggggagg attgggaaga caatagcagg catgctgggg atgcggtggg ctctatggtt  11520
aattaaccag tcaagtcagc tacttggcga gatcgacttg tctgggtttc gactacgctc  11580
agaattgcgt cagtcaagtt cgatctggtc cttgctattg cacccgttct ccgattacga  11640
gtttcattta aatcatgtga gcaaaaggcc agcaaaaggc caggaaccgt aaaaaggccg  11700
cgttgctggc gtttttccat aggctccgcc cccctgacga gcatcacaaa aatcgacgct  11760
caagtcagag gtggcgaaac ccgacaggac tataaagata ccaggcgttt ccccctggaa  11820
gctccctcgt gcgctctcct gttccgaccc tgccgcttac cggatacctg tccgcctttc  11880
tcccttcggg aagcgtggcg ctttctcata gctcacgctg taggtatctc agttcggtgt  11940
aggtcgttcg ctccaagctg ggctgtgtgc acgaaccccc cgttcagccc gaccgctgcg  12000
ccttatccgg taactatcgt cttgagtcca acccggtaag acacgactta tcgccactgg  12060
cagcagccac tggtaacagg attagcagag cgaggtatgt aggcggtgct acagagttct  12120
tgaagtggtg gcctaactac ggctacacta gaagaacagt atttggtatc tgcgctctgc  12180
tgaagccagt taccttcgga aaaagagttg gtagctcttg atccggcaaa caaaccaccg  12240
ctggtagcgg tggttttttt gtttgcaagc agcagattac gcgcagaaaa aaaggatctc  12300
aagaagatcc tttgatcttt tctacggggt ctgacgctca gtggaacgaa aactcacgtt  12360
aagggatttt ggtcatgaga ttatcaaaaa ggatcttcac ctagatcctt ttaaattaaa  12420
aatgaagttt taaatcaatc taaagtatat atgagtaaac ttggtctgac agttaccaat  12480
gcttaatcag tgaggcacct atctcagcga tctgtctatt tcgttcatcc atagttgcat  12540
ttaaatttcc gaactctcca aggccctcgt cggaaaatct t                    12581

SEQ ID NO: 100          moltype = DNA  length = 12542
FEATURE                 Location/Qualifiers
misc_feature            1..12542
                        note = Description of Artificial Sequence: Synthetic
                         polynucleotide
source                  1..12542
                        mol_type = other DNA
                        organism = synthetic construct
SEQUENCE: 100
ggggcgcgcc tggtgtaccg agaacgatcc tctcagtgcg agtctcgacg atccatatcg  60
ttgcttggca gtcagccagt cggaatccag cttgggaccc aggaagtcca atcgtcagat  120
attgtactca agcctggtca cggcagcgta ccgatctgtt taaacctaga tattgatagt  180
ctgatcggtc aacgtataat cgagtcctag cttttgcaaa catctatcaa gagacaggat  240
cagcaggagg ctttcgcatg agtattcaac atttccgtgt cgcccttatt cccttttttg  300
cggcattttg ccttcctgtt tttgctcacc cagaaacgct ggtgaaagta aaagatgctg  360
aagatcagtt gggtgcgcga gtgggttaca tcgaactgga tctcaacagc ggtaagatcc  420
ttgagagttt tcgccccgaa gaacgctttc caatgatgag cacttttaaa gttctgctat  480
gtggcgcggt attatcccgt attgacgccg ggcaagagca actcggtcgc cgcatacact  540
attctcagaa tgacttggtt gagtattcac cagtcacaga aaagcatctt acggatggca  600
tgacagtaag agaattatgc agtgctgcca taaccatgag tgataacact gcggccaact  660
tacttctgac aacgattgga ggaccgaagg agctaaccgc ttttttgcac aacatggggg  720
atcatgtaac tcgccttgat cgttgggaac cggagctgaa tgaagccata ccaaacgacg  780
agcgtgacac cacgatgcct gtagcaatgg caacaacctt gcgtaaacta ttaactggcg  840
aactacttac tctagcttcc cggcaacagt tgatagactg gatggaggcg gataaagttg  900
caggaccact tctgcgctcg gcccttccgg ctggctggtt tattgctgat aaatctggag  960
ccggtgagcg tgggtctcgc ggtatcattg cagcactggg gccagatggt aagccctccc  1020
gtatcgtagt tatctacacg acggggagtc aggcaactat ggatgaacga aatagacaga  1080
tcgctgagat aggtgcctca ctgattaagc attggtaacc gattctaggt gcattggcgc  1140
agaaaaaaat gcctgatgcg acgctgcgcg tcttatactc ccacatatgc cagattcagc  1200
aacggatacg gcttccccaa cttgcccact tccatacgtg tcctccttac cagaaattta  1260
tccttaagat cgtttaaact cgactctggc tctatcgaat ctccgtcgtt tcgagcttac  1320
gcgaacagcc gtggcgctca tttgctcgtc gggcatcgaa tctcgtcagc tatcgtcagc  1380
ttaccttttt ggcagcgatc gcggctcccg acatcttgga ccattagctc cacaggtatc  1440
ttcttccctc tagtggtcat aacagcagct tcagctacct ctcaattcaa aaaacccctc  1500
```

-continued

```
aagacccgtt tagaggcccc aaggggttat gctatcaatc gttgcgttac acacacaaaa  1560
aaccaacaca catccatctt cgatggatag cgattttatt atctaactgc tgatcgagtg  1620
tagccagatc tagtaatcaa ttacggggtc attagttcat agcccatata tggagttccg  1680
cgttacataa cttacggtaa atggcccgcc tggctgaccg cccaacgacc cccgcccatt  1740
gacgtcaata atgacgtatg ttcccatagt aacgccaata gggactttcc attgacgtca  1800
atgggtggag tatttacggt aaactgccca cttggcagta catcaagtgt atcatatgcc  1860
aagtacgccc cctattgacg tcaatgacgg taaatggccc gcctggcatt atgcccagta  1920
catgacctta tgggactttc ctacttggca gtacatctac gtattagtca tcgctattac  1980
catgctgatg cggttttggc agtacatcaa tgggcgtgga tagcggtttg actcacgggg  2040
atttccaagt ctccacccca ttgacgtcaa tgggagtttg ttttggcacc aaaatcaacg  2100
ggactttcca aaatgtcgta acaactccgc cccattgacg caaatgggcg gtaggcgtgt  2160
acggtgggag gtctatataa gcagagctgg tttagtgaac cgtcagatca gatctttgtc  2220
gatcctacca tccactcgac acacccgcca gcggccgcta atacgactca ctatagggag  2280
aagtactgcc accatgggca agaagcaaaa tcgcaagacg gggaattcca agacacaatc  2340
cgctagccca ccacctaaag agcgttctag ctcccctgct actgagcagt cctggatgga  2400
aaacgacttc gatgaactcc gggaagaggg atttaggcga tccaactatt cagaactccg  2460
cgaagatatc cagacaaagg ggaaggaagt cgagaatttc gagaagaacc tcgaggagtg  2520
catcacccgt atcacaaaca ctgagaaatg tctcaaagaa ctcatggaac ttaagacaaa  2580
agccagggag cttcgagagg agtgtcggag tctgagatcc aggtgtgacc agctcgagga  2640
gcgcgtgagc gcgatggaag acgagatgaa cgagatgaaa agagagggca aattcaggga  2700
gaagcgcatt aagaggaacg aacagagtct gcaggagatt tgggattacg tcaagaggcc  2760
taacctgcgg ttgatcggcg tccccgagag cgacgtagaa aacgggacta aactggagaa  2820
tacacttcaa gacatcattc aagaaaattt tccaaacctg gctcggcaag ctaatgtgca  2880
aatccaagag atccaacgca caccccagcg gtatagctct cggcgtgcca cccctaggca  2940
tattatcgtg cgctttacta aggtggagat gaaagagaag atgctgcgag ccgctcggga  3000
aaagggaagg gtgactttga agggcaaacc tattcggctg acggttgacc ttagcgccga  3060
gacactccag gcacgccggg aatggggccc catctttaat atcctgaagg agaagaactt  3120
ccagccacga atctcttacc ctgcaaagtt gagttttatc tccgagggtg agattaagta  3180
tttcatcgat aaacagatgc tgcgagactt cgtgacaact cgcccagctc tcaaggaact  3240
gctcaaagag gctcttaata tggagcgcaa taatagatat caacccttgc agaaccacgc  3300
aaagatgtga gacagccgtc agaccatcaa gactaggaag aaactgcatc aactaatgag  3360
caaaatcacc agctaacatc atagtataca tgccaaagaa gaagcggaag gtcaccggct  3420
ctaactcaca tatcaccatc cttacactta acattaacgg cctcaactca gctatcaagc  3480
gccatcggct ggccagctgg atcaaatcac aggatccaag cgtttgttgc atccaagaga  3540
cccacctgac ctgtagagat actcaccgcc tcaagatcaa gggatggcga aagatttatc  3600
aggcgaacgg taagcagaag aaagccggag tcgcaattct ggtctcagac aagacggatt  3660
tcaagcccac caaaattaag cgtgataagg aaggtcacta tattatggtg aaaggcagca  3720
tacagcagga agaacttacc atattgaaca tctacgcgcc aaacaccggc gcacctcgct  3780
ttatcaaaca ggtcctgtcc gatctgcagc gagatctgga ttctcatacg ttgattatgg  3840
gtgatttcaa tacaccattg agcaccctgg atcgcagcac caggcaaaag gtaaataaag  3900
acacgcaaga gctcaatagc gcactgcatc aggcagatct cattgatatt tatcgcactc  3960
ttcatcctaa gagtaccgag tacacattct tcagcgcccc acatcataca tactcaaaga  4020
tcgatcatat cgtcggctca aaggctctgc tgtcaaagtg caagcgcaca gagataatta  4080
caaattacct gtcagatcat agcgcgatca agctcgagct gagaatcaag aacctgaccc  4140
agagccggag taccacttgg aagcttaata acctgctgct caacgattat tgggtccaca  4200
atgagatgaa ggcagagatt aaaatgttct tcgaaacaaa tgagaataag gatactacct  4260
atcaaaacct tgggatgcc tttaaggccg tctgcagagg caagttcatc gccctcaacg  4320
cctataaaag aaaacaagag agatctaaga tcgatactct cacctctcag ctgaaggagt  4380
tggagaaaca ggaacagacc cactccaagg cgtcaagacg gcaggagatc acaaagattc  4440
gcgccgagtt gaaagagatc gaaacccaaa agactcttca gaaaattaac gagtctcgta  4500
gttggttctt cgagcggatt aataagatag acagacctct ggcacgactg attaagaaga  4560
agcgcgaaaa gaaccagatt gataccatca agaacgacaa gggcgacatc actactgacc  4620
cgaccgagat ccagaccact attcgggagt attataagca tttgtatgct aacaagcttg  4680
agaacctgga agagatggac acttttctgg atacctatac tctgccacgg cttaatcaag  4740
aggaagtcga gtccctcaac cgcccaatta caggaagcga gattgtggcc ataattaact  4800
ccctgccgac aaagaaatct cctggtccgg acgggtttac agctgagttt tatcaacggt  4860
atatggaaga gcttgtaccg tttctgctca agctctttca gtctatagaa aaggaaggca  4920
tcttgcccaa ttccttctac gaagcttcta taatacttat tcccaaacca ggacgcgata  4980
ccacaaagaa ggaaaacttc cggcccatta gtctcatgaa tatcgacgct aaaatattga  5040
acaagattct cgccaacaga atccaacaac atattaagaa attgatacat cacgaccagg  5100
tggggtttat acctggcatg cagggctggt ttaacatccg gaagagtatt aacgtcattc  5160
aacacattaa tagagctaag gataagaatc atatgatcat ctctatagac gcggaaaagg  5220
cattcgataa gattcagcag ccatttatgc tcaagactct gaacaaactc ggcatcgacg  5280
gaacatattt taagattatt cgcgcaattt acgataagcc gactgctaac attatcctta  5340
acggccaaaa gctcgaggcc tttccgctca agactggaac ccgccaaggc tgtcccctct  5400
ccccgctttt gtttaatatt gtactcgagg tgctggctag ggctattcgt caagagaaag  5460
agattaaagg gatacagctc gggaaggaag aggtcaagct ttccttgttc gccgatgata  5520
tgattgtgta cctggagaat cctattgtgt ctgctcagaa ccttcttaaa cttatttcta  5580
actttagcaa ggtcagcggc tataagatta acgtccagaa atctcaggcc tttctgtaca  5640
caaataatcg acagaccgaa tcccagataa tgggtgagct tccgtttgtc atagccagca  5700
aaaggataaa gtatctcgga atccagctga cacgagacgt taaagatttg tttaaggaaa  5760
attacaagcc tctcctgaaa gagattaagg aagatactaa taagtggaag aatatcccct  5820
gttcatgggt tggcagaatc aacatagtga agatggcaat acttcctaaa gtgatatatc  5880
gctttaacgc catcccaatt aaactgccta tgaccttctt tacggagctc gagaaaacaa  5940
cccttaaatt tatatggaat caaaagagag caagaatagc gaagtccatc ttgagccaga  6000
agaataaggc cggtgggatt actttgcctg attttaagtt gtattataaa gccacagtaa  6060
ctaagacagc ctggtattgg tatcagaata gagacatcga ccagtggaat cggaccgaac  6120
catcagagat aatgccccac atctataatt accttatatt cgataagcca gaaaagaata  6180
aacagtgggg caaagacagc ctcttcaaca agtggtgttg ggagaattgg ctggccatat  6240
```

```
gccggaaact caagctcgac ccctttctta caccctacac taaaatcaac agtaggtgga  6300
tcaaggactt gaatgtcaag ccaaagacta taaagacact ggaagagaat cttgggatca  6360
caatacaaga tataggcgtc ggcaaagatt ttatgtcaaa gacgcccaag gccatggcca  6420
ctaaggataa gattgataag tgggacctta ttaagctcaa aagcttctgt actgccaagg  6480
agaccacgat cagagttaat aggcagccca ctacatggga aaagattttc gccacttatt  6540
catcagataa ggggttgata agcagaatat ataacgagct gaagcagatc tacaagaaga  6600
aaacgaataa tcccatcaag aagtgggcaa aagatatgaa caggcatttt agcaaagagg  6660
atatctacgc cgcgaagaag catatgaaga agtgtagttc aagcttggcc attcgtgaga  6720
tgcagattaa gacgaccatg cgataccacc ttaccccagt gaggatggca attatcaaga  6780
aatctggcaa taatagatgt tggcggggct gtggcgagat tggcaccctg ctccattgct  6840
ggtgggattg caagctggtg cagccgcttt ggaaatcagt ctggcgcttt ctgagggacc  6900
tcgagcttga gattcccttc gatcccgcaa ttcccttgct cggaatctat cctaacgaat  6960
acaagagctg ttgttacaag gatacgtgta cccggatgtt catcgcggcc ttgtttacga  7020
tagctaagac gtggaatcag cctaagtgcc ccacaatgat cgattggatc aagaaaatgt  7080
ggcatattta taccatggag tattacgcag caattaagaa tgacgaattt atttccttcg  7140
ttgggacctg gatgaagctg gagactatta ttctgagcaa gctgtctcag gagcaaaaga  7200
caaagcatag aatcttctct ctcattggtg gtaacgacta caaagacgat gacgacaagt  7260
aaagcgcttc tagaagttgt ctcctcctgc actgactgac tgatacaatc gatttctgga  7320
tccgcaggcc taatcaacct ctggattaca aaatttgtga aagattgact ggtattctta  7380
actatgttgc tccttttacg ctatgtggat acgctgcttt aatgcctttg tatcatgcta  7440
ttgcttcccg tatggctttc attttctcct ccttgtataa atcctggttg ctgtctcttt  7500
atgaggagtt gtggcccgtt gtcaggcaac gtggcgtggt gtgcactgtg tttgctgacg  7560
caacccccac tggttggggc attgccacca cctgtcagct cctttccggg actttcgctt  7620
tccccctccc tattgccacg gcggaactca tcgccgcctg ccttgcccgc tgctggacag  7680
gggctcggct gttgggcact gacaattccg tggtgttgtc ggggaagctg acgtcctttc  7740
catggctgct cgcctgtgtt gccacctgga ttctgcgcgg gacgtccttc tgctacgtcc  7800
cttcggccct caatccagcg gaccttcctt cccgctgaga gacacaaaaa attccaacac  7860
actattgcaa tgaaaataaa tttcctttat tagccagaag tcagatgctc aaggggcttc  7920
atgatgtccc cataattttt ggcagaggga aaaagatctc agtggtattt gtgagccagg  7980
gcattggcct tctgataggc agcctgcacc tgaggagtgc ggccgcttta cttgtacagc  8040
tcgtccatgc cgagagtgat cccggcggcg gtcacgaact ccagcaggac catgtgatcg  8100
cgcttctcgt tggggtcttt gctcagggcg gactgggtgc tcaggtagtg gttgtcgggc  8160
agcagcacgg ggccgtcgcc gatgggggtg ttctgctggt agtggtcggc gagctgcacg  8220
ctgccgtcct cgatgttgtg gcggatcttg aagttcacct tgatgccgtt cttctgcttg  8280
tcggccatga tatagacgtt gtggctgttg tagttgtact ccagcttgtg ccccaggatg  8340
ttgccgtcct ccttgaagtc gatgcccttc agctcgatgc ggttcaccag ggtgtcgccc  8400
tcgaacttca cctcggcgcg ggtcttgtag ttgccgtcgt ccttgaagaa gatggtgcgc  8460
tcctggacgt agccttcggg catggcggac ttgaagaagt cgtgctgctt catgtggtcg  8520
gggtagcggc tgaagcactg cacgccgtag gtcagggtgg tcacgagggt gggccagggc  8580
acgggcagct tgccggtggt gcagatgaac ttcagggtca gcttgccgta ggtggcatcg  8640
ccctcgccct cgccggacac gctgaacttg tggccgttta cgtcgccgtc cagctcgacc  8700
aggatgggca ccaccccggt gaacagctcc tcgcccttgc tcaccatggt ggcgggatct  8760
gacggttcac taaaccagct ctgcttatat agacctccca ccgtacacgc ctaccgccca  8820
tttgcgtcaa tggggcggag ttgttacgac attttggaaa gtcccgttga ttttggtgcc  8880
aaaacaaact cccattgacg tcaatggggt ggagacttgg aaatccccgt gagtcaaacc  8940
gctatccacg cccattgatg tactgccaaa accgcatcac catggtaata gcgatgacta  9000
atacgtagat gtactgccaa gtaggaaagt cccataaggt catgtactgg gcataatgcc  9060
aggcgggcca tttaccgtca ttgacgtcaa tagggggcgt acttggcata tgatacactt  9120
gatgtactgc caagtgggca gtttaccgta aatactccac ccattgacgt caatggaaag  9180
tccctattgg cgttactatg ggaacatacg tcattattga cgtcaatggg cgggggtcgt  9240
tgggcggtca gccaggcggg ccatttaccg taagttatgt aacgggcctg ctgccggctc  9300
tgcggcctct tccgcgtctt cgccttcgcc ctcagacgag tcggatctcc ctttgggccg  9360
cctccccgcc tgtctagctt gactgactga gatacagcgt accttcagct cacagacatg  9420
ataagataca ttgatgagtt tggacaaacc acaactagaa tgcagtgaaa aaaatgcttt  9480
atttgtgaaa tttgtgatgc tattgcttta tttgtaacca ttataagctg caataaacaa  9540
gttaacaaca acaattgcat tcattttatg tttcaggttc agggggaggt gtgggaggtt  9600
ttttaaagca agtaaaacct ctacaaatgt ggtattggcc catctctatc ggtatcgtag  9660
cataacccct tggggcctct aaacgggtct tgaggggttt tttgtgcccc tcgggccgga  9720
ttgctatcta ccggcattgg cgcagaaaaa aatgcctgat gcgacgctgc gcgtcttata  9780
ctcccacata tgccagattc agcaacggat acggcttccc caacttgccc acttccatac  9840
gtgtcctcct taccagaaat ttatccttaa ggtcgtcagc tatcctgcag gcgatctctc  9900
gatttcgatc aagacattcc tttaatggtc ttttctggac accactaggg gtcagaagta  9960
gttcatcaaa ctttcttccc tccctaatct cattggttac cttgggctat cgaaacttaa  10020
ttaagcgatc tgcatctcaa ttagtcagca accatagtcc cgcccctaac tccgcccatc  10080
ccgcccctaa ctccgcccag ttccgcccat tctccgcccc atcgctgact aattttttt  10140
atttatgcag aggccgaggc cgcctcggcc tctgagctat tccagaagta gtgaggaggc  10200
tttttggag gcctaggctt ttgcaaagga ggtagccaac atgattgaac aagatggatt  10260
gcacgcaggt tctcccgccg cttgggtgga gaggctattc ggctatgact gggcacaaca  10320
gacaatcggc tgctctgatg ccgccgtgtt ccggctgtca gcgcaggggc gcccggttct  10380
ttttgtcaag accgacctgt ccggtgccct gaatgaactc caggacgagg cagcgcggct  10440
atcgtggctg gccacgacgg gcgttccttg cgcagctgtg ctcgacgttg tcactgaagc  10500
gggaagggac tggctgctat tgggcgaagt gccggggcag gatctcctgt catctcacct  10560
tgctcctgcc gagaaagtat ccatcatggc tgatgcaatg cggcggctgc atacgcttga  10620
tccggctacc tgcccattcg accaccaagc gaaacatcgc atcgagcgag cacgtactcg  10680
gatggaagcc ggtcttgtcg atcaggatga tctggacgaa gagcatcagg ggctcgcgcc  10740
agccgaactg ttcgccaggc tcaaggcgcg gatgcccgac ggcgaggatc tcgtcgtgac  10800
ccacggcgat gcctgcttgc cgaatatcat ggtggaaaat ggccgctttt ctggattcat  10860
cgactgtggc cggctgggtg tggcggaccg ctatcaggac atagcgttgg ctacccgtga  10920
tattgctgaa gagcttggcg gcgaatgggc tgaccgcttc ctcgtgcttt acggtatcgc  10980
```

```
cgctcccgat tcgcagcgca tcgccttcta tcgccttctt gacgagttct tctagtatgt  11040
aagccctgtg ccttctagtt gccagccatc tgttgtttgc ccctcccccg tgccttcctt  11100
gaccctggaa ggtgccactc ccactgtcct ttcctaataa aatgaggaaa ttgcatcgca  11160
ttgtctgagt aggtgtcatt ctattctggg gggtggggtg gggcaggaca gcaaggggga  11220
ggattgggaa gacaatagca ggcatgctgg ggatgcggtg ggctctatgg ttaattaacc  11280
agtcaagtca gctacttggc gagatcgact tgtctgggtt tcgactacgc tcagaattgc  11340
gtcagtcaag ttcgatctgg tccttgctat tgcacccgtt ctccgattac gagtttcatt  11400
taaatcatgt gagcaaaagg ccagcaaaag gccaggaacc gtaaaaaggc cgcgttgctg  11460
gcgtttttcc ataggctccg cccccctgac gagcatcaca aaaatcgacg ctcaagtcag  11520
aggtggcgaa acccgacagg actataaaga taccaggcgt ttccccctgg aagctccctc  11580
gtgcgctctc ctgttccgac cctgccgctt accggatacc tgtccgcctt tctcccttcg  11640
ggaagcgtgg cgctttctca tagctcacgc tgtaggtatc tcagttcggt gtaggtcgtt  11700
cgctccaagc tgggctgtgt gcacgaaccc cccgttcagc ccgaccgctg cgccttatcc  11760
ggtaactatc gtcttgagtc caacccggta agacacgact tatcgccact ggcagcagcc  11820
actggtaaca ggattagcag agcgaggtat gtaggcggtg ctacagagtt cttgaagtgg  11880
tggcctaact acggctacac tagaagaaca gtatttggta tctgcgctct gctgaagcca  11940
gttaccttcg gaaaaagagt tggtagctct tgatccggca aacaaaccac cgctggtagc  12000
ggtggttttt ttgtttgcaa gcagcagatt acgcgcagaa aaaaaggatc tcaagaagat  12060
cctttgatct tttctacggg gtctgacgct cagtggaacg aaaactcacg ttaagggatt  12120
ttggtcatga gattatcaaa aaggatcttc acctagatcc ttttaaatta aaaatgaagt  12180
tttaaatcaa tctaaagtat atatgagtaa acttggtctg acagttacca atgcttaatc  12240
agtgaggcac ctatctcagc gatctgtcta tttcgttcat ccatagttgc atttaaattt  12300
ccgaactctc caaggccctc gtcggaaaat cttcaaacct ttcgtccgat ccatcttgca  12360
ggctacctct cgaacgaact atcgcaagtc tcttggccgg ccttgcgcct tggctattgc  12420
ttggcagcgc ctatcgccag gtattactcc aatcccgaat atccgagatc gggatcaccc  12480
gagagaagtt caacctacat cctcaatccc gatctatccg agatccgagg aatatcgaaa  12540
tc                                                                 12542

SEQ ID NO: 101         moltype = DNA  length = 12554
FEATURE                Location/Qualifiers
misc_feature           1..12554
                       note = Description of Artificial Sequence: Synthetic
                        polynucleotide
source                 1..12554
                       mol_type = other DNA
                       organism = synthetic construct
SEQUENCE: 101
tggccggcct tgcgccttgg ctattgcttg gcagcgccta tcgccaggta ttactccaat  60
cccgaatatc cgagatcggg atcacccgag agaagttcaa cctacatcct caatcccgat  120
ctatccgaga tccgaggaat atcgaaatcg gggcgcgcct ggtgtaccga gaacgatcct  180
ctcagtgcga gtctcgacga tccatatcgt tgcttggcag tcagccagtc ggaatccagc  240
ttgggaccca ggaagtccaa tcgtcagata ttgtactcaa gcctggtcac ggcagcgtac  300
cgatctgttt aaacctagat attgatagtc tgatcggtca acgtataatc gagtcctagc  360
ttttgcaaac atctatcaag agacaggatc agcaggaggc tttcgcatga gtattcaaca  420
tttccgtgtc gcccttattc ccttttttgc ggcattttgc cttcctgttt ttgctcaccc  480
agaaacgctg gtgaaagtaa aagatgctga agatcagttg ggtgcgcgag tgggttacat  540
cgaactggat ctcaacagcg gtaagatcct tgagagtttt cgccccgaag aacgctttcc  600
aatgatgagc acttttaaag ttctgctatg tggcgcggta ttatcccgta ttgacgccgg  660
gcaagagcaa ctcggtcgcc gcatacacta ttctcagaat gacttggttg agtattcacc  720
agtcacagaa aagcatctta cggatggcat gacagtaaga gaattatgca gtgctgccat  780
aaccatgagt gataacactg cggccaactt acttctgaca acgattggag gaccgaagga  840
gctaaccgct tttttgcaca acatggggga tcatgtaact cgccttgatc gttgggaacc  900
ggagctgaat gaagccatac caaacgacga gcgtgacacc acgatgcctg tagcaatggc  960
aacaacgttg cgtaaactat taactggcga actacttact ctagcttccc ggcaacagtt  1020
gatagactgg atggaggcgg ataaagttgc aggaccactt ctgcgctcgg cccttccggc  1080
tggctggttt attgctgata aatctggagc cggtgagcgt gggtctcgcg gtatcattgc  1140
agcactgggg ccagatggta agccctcccg tatcgtagtt atctacacga cggggagtca  1200
ggcaactatg gatgaacgaa atagacagat cgctgagata ggtgcctcac tgattaagca  1260
ttggtaaccg attctaggtg cattggcgca gaaaaaaatg cctgatgcga cgctgcgcgt  1320
cttatactcc cacatatgcc agattcagca acggatacgg cttcccccaac ttgcccactt  1380
ccatacgtgt cctccttacc agaaatttat ccttaagatc gtttaaactc gactctggct  1440
ctatcgaatc tccgtcgttt cgagcttacg cgaacagccg tggcgctcat ttgctcgtcg  1500
ggcatcgaat ctcgtcagct atcgtcagct tacctttttg gcagcgatcg cggctcccga  1560
catcttggac cattagctcc acaggtatct tcttccctct agtggtcata acagcagctt  1620
cagctacctc tcaattcaaa aaacccctca agacccgttt agaggcccca aggggttatg  1680
ctatcaatcg ttgcgttaca cacacaaaaa accaacacac atccatcttc gatggatagc  1740
gattttatta tctaactgct gatcgagtgt agccagatct agtaatcaat tacggggtca  1800
ttagttcata gcccatatat ggagttccgc gttacataac ttacggtaaa tggcccgcct  1860
ggctgaccgc ccaacgaccc ccgcccattg acgtcaataa tgacgtatgt tcccatagta  1920
acgccaatag ggactttcca ttgacgtcaa tgggtggagt atttacggta aactgcccac  1980
ttggcagtac atcaagtgta tcatatgcca agtacgcccc ctattgacgt caatgacggt  2040
aaatggcccg cctggcatta tgcccagtac atgaccttat gggactttcc tacttggcag  2100
tacatctacg tattagtcat cgctattacc atgctgatgc ggttttggca gtacatcaat  2160
gggcgtggat agcggtttga ctcacgggga tttccaagtc tccaccccat tgacgtcaat  2220
gggagtttgt tttggcacca aaatcaacgg gactttccaa aatgtcgtaa caactccgcc  2280
ccattgacgc aaatgggcgg taggcgtgta cggtgggagg tctatataag cagagctggt  2340
ttagtgaacc gtcagatcag atctttgtcg atcctaccat ccactcgaca cacccgccag  2400
cggccgctaa tacgactcac tatagggaga agtactgcca ccatgggcaa gaagcaaaat  2460
cgcaagacgg ggaattccaa gacacaatcc gctagcccac cacctaaaga gcgttctagc  2520
```

-continued

```
tcccctgcta ctgagcagtc ctggatggaa aacgacttcg atgaactccg ggaagaggga  2580
tttaggcgat ccaactattc agaactccgc gaagatatcc agacaaaggg gaaggaagtc  2640
gagaatttcg agaagaacct cgaggagtgc atcacccgta tcacaaacac tgagaaatgt  2700
ctcaaagaac tcatggaact taagacaaaa gccagggagc ttcgagagga gtgtcggagt  2760
ctgagatcca ggtgtgacca gctcgaggag cgcgtgagcg cgatggaaga cgagatgaac  2820
gagatgaaaa gagagggcaa attcagggag aagcgcatta agaggaacga acagagtctg  2880
caggagattt gggattacgt caagaggcct aacctgcggt tgatcggcgt ccccgagagc  2940
gacgtagaaa acgggactaa actggagaat acacttcaag acatcattca agaaaatttt  3000
ccaaacctgg ctcggcaagc taatgtgcaa atccaagaga tccaacgcac accccagcgg  3060
tatagctctc ggcgtgccac ccctaggcat attatcgtgc gctttactaa ggtggagatg  3120
aaagagaaga tgctgcgagc cgctcgggaa aagggaaggg tgactttgaa gggcaaacct  3180
attcggctga cggttgacct tagcgccgag acactccagg cacgccggga atggggcccc  3240
atctttaata tcctgaagga gaagaacttc cagccacgaa tctcttaccc tgcaaagttg  3300
agttttatct ccgagggtga gattaagtat ttcatcgata aacagatgct gcgagacttc  3360
gtgacaactc gcccagctct caaggaactg ctcaaagagg ctcttaatat ggagcgcaat  3420
aatagatatc aacccttgca gaaccacgca aagatgtgag acagccgtca gaccatcaag  3480
actaggaaga aactgcatca actaatgagc aaaatcacca gctaacatca tagtatacat  3540
gccaaagaag aagcggaagg tcggcggcgg cagcaccggc tctaactcac atatcaccat  3600
ccttacactt aacattaacg gcctcaactc agctatcaag cgccatcggc tggccagctg  3660
gatcaaatca caggatccaa gcgtttgttg catccaagag acccacctga cctgtagaga  3720
tactcaccgc ctcaagatca agggatggcg aaagatttat caggcgaacg gtaagcagaa  3780
gaaagccgga gtcgcaattc tggtctcaga caagacggat ttcaagccca ccaaaattaa  3840
gcgtgataag gaaggtcact atattatggt gaaaggcagc atacagcagg aagaacttac  3900
catattgaac atctacgcgc caaacaccgg cgcacctcgc tttatcaaac aggtcctgtc  3960
cgatctgcag cgagatctgg attctcatac gttgattatg ggtgatttca atacaccatt  4020
gagcaccctg gatcgcagca ccaggcaaaa ggtaaataaa gacacgcaag agctcaatag  4080
cgcactgcat caggcagatc tcattgatat ttatcgcact cttcatccta agagtaccga  4140
gtacacattc ttcagcgccc cacatcatac atactcaaag atcgatcata tcgtcggctc  4200
aaaggctctg ctgtcaaagt gcaagcgcac agagataatt acaaattacc tgtcagatca  4260
tagcgcgatc aagctcgagc tgagaatcaa gaacctgacc cagagccgga gtaccacttg  4320
gaagcttaat aacctgctgc tcaacgatta ttgggtccac aatgagatga aggcagagat  4380
taaaatgttc ttcgaaacaa atgagaataa ggatactacc tatcaaaacc tttgggatgc  4440
ctttaaggcc gtctgcagag gcaagttcat cgccctcaac gcctataaaa gaaaacaaga  4500
gagatctaag atcgatactc tcacctctca gctgaaggag ttggagaaac aggaacagac  4560
ccactccaag gcgtcaagac ggcaggagat cacaaagatt cgcgccgagt tgaaagagat  4620
cgaaacccaa aagactcttc agaaaattaa cgagtctcgt agttggttct tcgagcggat  4680
taataagata gacagacctc tggcacgact gattaagaag aagcgcgaaa agaaccagat  4740
tgataccatc aagaacgaca agggcgacat cactactgac ccgaccgaga tccagaccac  4800
tattcgggag tattataagc atttgtatgc taacaagctt gagaacctgg aagagatgga  4860
cactttctg gatacctata ctctgccacg gcttaatcaa gaggaagtcg agtccctcaa  4920
ccgcccaatt acaggaagcg agattgtggc cataattaac tccctgccga caaagaaatc  4980
tcctggtccg gacgggttta cagctgagtt ttatcaacgg tatatggaag agcttgtacc  5040
gtttctgctc aagctctttc agtctataga aaaggaaggc atcttgccca attccttcta  5100
cgaagcttct ataatactta ttcccaaacc aggacgcgat accacaaaga aggaaaactt  5160
ccggcccatt agtctcatga atatcgacgc taaaatattg aacaagattc tcgccaacag  5220
aatccaacaa catattaaga aattgataca tcacgaccag gtggggttta tacctggcat  5280
gcagggctgg tttaacatcc ggaagagtat taacgtcatt caacacatta atagagctaa  5340
ggataagaat catatgatca tctctataga cgcggaaaag gcattcgata agattcagca  5400
gccatttatg ctcaagactc tgaacaaact cggcatcgac ggaacatatt ttaagattat  5460
tcgcgcaatt tacgataagc cgactgctaa cattatcctt aacggccaaa agctcgaggc  5520
ctttccgctc aagactggaa cccgccaagg ctgtcccctc tccccgcttt tgtttaatat  5580
tgtactcgag gtgctggcta gggctattcg tcaagagaaa gagattaaag ggatacagct  5640
cgggaaggaa gaggtcaagc tttccttgtt cgccgatgat atgattgtgt acctggagaa  5700
tcctattgtg tctgctcaga accttcttaa acttatttct aactttagca aggtcagcgg  5760
ctataagatt aacgtccaga aatctcaggc ctttctgtac acaaataatc gacagaccga  5820
atcccagata atgggtgagc ttccgtttgt catagccagc aaaaggataa agtatctcgg  5880
aatccagctg acacgagacg ttaaagattt gtttaaggaa aattacaagc ctctcctgaa  5940
agagattaag gaagatacta ataagtggaa gaatatcccc tgttcatggg ttggcagaat  6000
caacatagtg aagatggcaa tacttcctaa agtgatatat cgctttaacg ccatcccaat  6060
taaactgcct atgaccttct ttacggagct cgagaaaaca acccttaaat ttatatggaa  6120
tcaaaagaga gcaagaatag cgaagtccat cttgagccag aagaataagg ccggtgggat  6180
tactttgcct gattttaagt tgtattataa agccacagta actaagacag cctggtattg  6240
gtatcagaat agagacatcg accagtggaa tcggaccgaa ccatcagaga taatgcccca  6300
catctataat taccttatat tcgataagcc agaaaagaat aaacagtggg gcaaagacag  6360
cctcttcaac aagtggtgtt gggagaattg gctggccata tgccggaaac tcaagctcga  6420
cccctttctt acaccctaca ctaaaatcaa cagtaggtgg atcaaggact tgaatgtcaa  6480
gccaaagact ataaagacac tggaagagaa tcttgggatc acaatacaag atataggcgt  6540
cggcaaagat tttatgtcaa agacgcccaa ggccatggcc actaaggata agattgataa  6600
gtgggacctt attaagctca aaagcttctg tactgccaag gagaccacga tcagagttaa  6660
taggcagccc actacatggg aaaagatttt cgccacttat tcatcagata aggggttgat  6720
aagcagaata tataacgagc tgaagcagat ctacaagaag aaaacgaata atcccatcaa  6780
gaagtgggca aaagatatga acaggcattt tagcaaagag gatatctacg ccgcgaagaa  6840
gcatatgaag aagtgtagtt caagcttggc cattcgtgag atgcagatta agacgaccat  6900
gcgataccac cttaccccag tgaggatggc aattatcaag aaatctggca ataatagatg  6960
ttggcggggc tgtggcgaga ttggcaccct gctccattgc tggtgggatt gcaagctggt  7020
gcagccgctt tggaaatcag tctggcgctt tctgagggac ctcgagcttg agattccctt  7080
cgatcccgca attccccttgc tcggaatcta tcctaacgaa tacaagagct gttgttacaa  7140
ggatacgtgt acccggatgt tcatcgcggc cttgtttacg atagctaaga cgtggaatca  7200
gcctaagtgc cccacaatga tcgattggat caagaaaatg tggcatattt ataccatgga  7260
```

-continued

```
gtattacgca gcaattaaga atgacgaatt tatttccttc gttgggacct ggatgaagct  7320
ggagactatt attctgagca agctgtctca ggagcaaaag acaaagcata gaatcttctc  7380
tctcattggt ggtaacgact acaaagacga tgacgacaag taaagcgctt ctagaagttg  7440
tctcctcctg cactgactga ctgatacaat cgatttctgg atccgcaggc ctaatcaacc  7500
tctggattac aaaatttgtg aaagattgac tggtattctt aactatgttg ctccttttac  7560
gctatgtgga tacgctgctt taatgccttt gtatcatgct attgcttccc gtatggcttt  7620
cattttctcc tccttgtata aatcctggtt gctgtctctt tatgaggagt tgtggcccgt  7680
tgtcaggcaa cgtggcgtgg tgtgcactgt gtttgctgac gcaaccccca ctggttgggg  7740
cattgccacc acctgtcagc tcctttccgg gactttcgct ttccccctcc ctattgccac  7800
ggcggaactc atcgccgcct gccttgcccg ctgctggaca ggggctcggc tgttgggcac  7860
tgacaattcc gtggtgttgt cggggaagct gacgtccttt ccatggctgc tcgcctgtgt  7920
tgccacctgg attctgcgcg ggacgtcctt ctgctacgtc ccttcggccc tcaatccagc  7980
ggaccttcct tcccgctgag agacacaaaa aattccaaca cactattgca atgaaaataa  8040
atttccttta ttagccagaa gtcagatgct caaggggctt catgatgtcc ccataatttt  8100
tggcagaggg aaaaagatct cagtggtatt tgtgagccag ggcattggcc ttctgatagg  8160
cagcctgcac ctgaggagtg cggccgcttt acttgtacag ctcgtccatg ccgagagtga  8220
tcccggcggc ggtcacgaac tccagcagga ccatgtgatc gcgcttctcg ttggggtctt  8280
tgctcagggc ggactgggtg ctcaggtagt ggttgtcggg cagcagcacg gggccgtcgc  8340
cgatgggggt gttctgctgg tagtggtcgg cgagctgcac gctgccgtcc tcgatgttgt  8400
ggcggatctt gaagttcacc ttgatgccgt tcttctgctt gtcggccatg atatagacgt  8460
tgtggctgtt gtagttgtac tccagcttgt gccccaggat gttgccgtcc tccttgaagt  8520
cgatgccctt cagctcgatg cggttcacca gggtgtcgcc ctcgaacttc acctcggcgc  8580
gggtcttgta gttgccgtcg tccttgaaga agatggtgcg ctcctggacg tagccttcgg  8640
gcatggcgga cttgaagaag tcgtgctgct tcatgtggtc ggggtagcgg ctgaagcact  8700
gcacgccgta ggtcagggtg gtcacgaggg tgggccaggg cacgggcagc ttgccggtgg  8760
tgcagatgaa cttcagggtc agcttgccgt aggtggcatc gccctcgccc tcgccggaca  8820
cgctgaactt gtggccgttt acgtcgccgt ccagctcgac caggatgggc accaccccgg  8880
tgaacagctc ctcgcccttg ctcaccatgg tggcgggatc tgacggttca ctaaaccagc  8940
tctgcttata tagacctccc accgtacacg cctaccgccc atttgcgtca atggggcgga  9000
gttgttacga cattttggaa agtcccgttg attttggtgc caaaacaaac tcccattgac  9060
gtcaatgggg tggagacttg gaaatccccg tgagtcaaac cgctatccac gcccattgat  9120
gtactgccaa aaccgcatca ccatggtaat agcgatgact aatacgtaga tgtactgcca  9180
agtaggaaag tcccataagg tcatgtactg ggcataatgc caggcgggcc atttaccgtc  9240
attgacgtca atagggggcg tacttggcat atgatacact tgatgtactg ccaagtgggc  9300
agtttaccgt aaatactcca cccattgacg tcaatggaaa gtccctattg gcgttactat  9360
gggaacatac gtcattattg acgtcaatgg gcgggggtcg ttgggcggtc agccaggcgg  9420
gccatttacc gtaagttatg taacgggcct gctgccggct ctgcggcctc ttccgcgtct  9480
tcgccttcgc cctcagacga gtcggatctc cctttgggcc gcctccccgc ctgtctagct  9540
tgactgactg agatacagcg taccttcagc tcacagacat gataagatac attgatgagt  9600
ttggacaaac cacaactaga atgcagtgaa aaaaatgctt tatttgtgaa atttgtgatg  9660
ctattgcttt atttgtaacc attataagct gcaataaaca agttaacaac aacaattgca  9720
ttcattttat gtttcaggtt cagggggagg tgtgggaggt tttttaaagc aagtaaaacc  9780
tctacaaatg tggtattggc ccatctctat cggtatcgta gcataacccc ttggggcctc  9840
taaacgggtc ttgagggggt ttttgtgccc ctcgggccgg attgctatct accggcattg  9900
gcgcagaaaa aaatgcctga tgcgacgctg cgcgtcttat actcccacat atgccagatt  9960
cagcaacgga tacggcttcc ccaacttgcc cacttccata cgtgtcctcc ttaccagaaa  10020
tttatcctta aggtcgtcag ctatcctgca ggcgatctct cgatttcgat caagacattc  10080
ctttaatggt cttttctgga caccactagg ggtcagaagt agttcatcaa actttcttcc  10140
ctccctaatc tcattggtta ccttgggcta tcgaaactta attaagcgat ctgcatctca  10200
attagtcagc aaccatagtc ccgcccctaa ctccgcccat cccgccccta actccgccca  10260
gttccgccca ttctccgccc catcgctgac taattttttt tatttatgca gaggccgagg  10320
ccgcctcggc ctctgagcta ttccagaagt agtgaggagg cttttttgga ggcctaggct  10380
tttgcaaagg aggtagccaa catgattgaa caagatggat tgcacgcagg ttctcccgcc  10440
gcttgggtgg agaggctatt cggctatgac tgggcacaac agacaatcgg ctgctctgat  10500
gccgccgtgt tccggctgtc agcgcagggg cgcccggttc tttttgtcaa gaccgacctg  10560
tccggtgccc tgaatgaact ccaggacgag gcagcgcggc tatcgtggct ggccacgacg  10620
ggcgttcctt gcgcagctgt gctcgacgtt gtcactgaag cgggaaggga ctggctgcta  10680
ttgggcgaag tgccggggca ggatctcctg tcatctcacc ttgctcctgc cgagaaagta  10740
tccatcatgg ctgatgcaat gcggcggctg catacgcttg atccggctac ctgcccattc  10800
gaccaccaag cgaaacatcg catcgagcga gcacgtactc ggatggaagc cggtcttgtc  10860
gatcaggatg atctggacga agagcatcag gggctcgcgc cagccgaact gttcgccagg  10920
ctcaaggcgc ggatgcccga cggcgaggat ctcgtcgtga cccacggcga tgcctgcttg  10980
ccgaatatca tggtggaaaa tggccgcttt tctggattca tcgactgtgg ccggctgggt  11040
gtggcggacc gctatcagga catagcgttg gctacccgtg atattgctga agagcttggc  11100
ggcgaatggg ctgaccgctt cctcgtgctt tacggtatcg ccgctcccga ttcgcagcgc  11160
atcgccttct atcgccttct tgacgagttc ttctagtatg taagccctgt gccttctagt  11220
tgccagccat ctgttgtttg cccctccccc gtgccttcct tgaccctgga aggtgccact  11280
cccactgtcc tttcctaata aaatgaggaa attgcatcgc attgtctgag taggtgtcat  11340
tctattctgg ggggtggggt ggggcaggac agcaaggggg aggattggga agacaatagc  11400
aggcatgctg gggatgcggt gggctctatg gttaattaac cagtcaagtc agctacttgg  11460
cgagatcgac ttgtctgggt ttcgactacg ctcagaattg cgtcagtcaa gttcgatctg  11520
gtccttgcta ttgcacccgt tctccgatta cgagtttcat ttaaatcatg tgagcaaaag  11580
gccagcaaaa ggccaggaac cgtaaaaagg ccgcgttgct ggcgtttttc cataggctcc  11640
gcccccctga cgagcatcac aaaaatcgac gctcaagtca gaggtggcga aacccgacag  11700
gactataaag ataccaggcg tttccccctg gaagctccct cgtgcgctct cctgttccga  11760
ccctgccgct taccggatac ctgtccgcct ttctcccttc gggaagcgtg gcgctttctc  11820
atagctcacg ctgtaggtat ctcagttcgg tgtaggtcgt tcgctccaag ctgggctgtg  11880
tgcacgaacc ccccgttcag cccgaccgct gcgccttatc cggtaactat cgtcttgagt  11940
ccaacccggt aagacacgac ttatcgccac tggcagcagc cactggtaac aggattagca  12000
```

gagcgaggta tgtaggcggt gctacagagt tcttgaagtg gtggcctaac tacggctaca 12060
ctagaagaac agtatttggt atctgcgctc tgctgaagcc agttaccttc ggaaaaagag 12120
ttggtagctc ttgatccggc aaacaaacca ccgctggtag cggtggtttt tttgtttgca 12180
agcagcagat tacgcgcaga aaaaaaggat ctcaagaaga tcctttgatc ttttctacgg 12240
ggtctgacgc tcagtggaac gaaaactcac gttaagggat tttggtcatg agattatcaa 12300
aaaggatctt cacctagatc cttttaaatt aaaaatgaag ttttaaatca atctaaagta 12360
tatatgagta aacttggtct gacagttacc aatgcttaat cagtgaggca cctatctcag 12420
cgatctgtct atttcgttca tccatagttg catttaaatt tccgaactct ccaaggccct 12480
cgtcggaaaa tcttcaaacc tttcgtccga tccatcttgc aggctacctc tcgaacgaac 12540
tatcgcaagt ctct 12554

SEQ ID NO: 102 moltype = DNA length = 12569
FEATURE Location/Qualifiers
misc_feature 1..12569
note = Description of Artificial Sequence: Synthetic polynucleotide
source 1..12569
mol_type = other DNA
organism = synthetic construct
SEQUENCE: 102
gacgatccat atcgttgctt ggcagtcagc cagtcggaat ccagcttggg acccaggaag 60
tccaatcgtc agatattgta ctcaagcctg gtcacggcag cgtaccgatc tgtttaaacc 120
tagatattga tagtctgatc ggtcaacgta taatcgagtc ctagcttttg caaacatcta 180
tcaagagaca ggatcagcag gaggctttcg catgagtatt caacatttcc gtgtcgccct 240
tattcccttt tttgcggcat tttgccttcc tgtttttgct cacccagaaa cgctggtgaa 300
agtaaaagat gctgaagatc agttgggtgc gcgagtgggt tacatcgaac tggatctcaa 360
cagcggtaag atccttgaga gttttcgccc cgaagaacgc tttccaatga tgagcacttt 420
taaagttctg ctatgtggcg cggtattatc ccgtattgac gccgggcaag agcaactcgg 480
tcgccgcata cactattctc agaatgactt ggttgagtat tcaccagtca cagaaaagca 540
tcttacggat ggcatgacag taagagaatt atgcagtgct gccataacca tgagtgataa 600
cactgcggcc aacttacttc tgacaacgat tggaggaccg aaggagctaa ccgctttttt 660
gcacaacatg ggggatcatg taactcgcct tgatcgttgg gaaccggagc tgaatgaagc 720
cataccaaac gacgagcgtg acaccacgat gcctgtagca atggcaacaa ccttgcgtaa 780
actattaact ggcgaactac ttactctagc ttcccggcaa cagttgatag actggatgga 840
ggcggataaa gttgcaggac cacttctgcg ctcggccctt ccggctggct ggtttattgc 900
tgataaatct ggagccggtg agcgtgggtc tcgcggtatc attgcagcac tggggccaga 960
tggtaagccc tcccgtatcg tagttatcta cacgacgggg agtcaggcaa ctatggatga 1020
acgaaataga cagatcgctg agataggtgc ctcactgatt aagcattggt aaccgattct 1080
aggtgcattg gcgcagaaaa aaatgcctga tgcgacgctg cgcgtcttat actcccacat 1140
atgccagatt cagcaacgga tacggcttcc ccaacttgcc cacttccata cgtgtcctcc 1200
ttaccagaaa tttatcctta agatcgttta aactcgactc tggctctatc gaatctccgt 1260
cgtttcgagc ttacgcgaac agccgtggcg ctcatttgct cgtcgggcat cgaatctcgt 1320
cagctatcgt cagcttacct ttttggcagc gatcgcggct cccgacatct tggaccatta 1380
gctccacagg tatcttcttc cctctagtgg tcataacagc agcttcagct acctctcaat 1440
tcaaaaaacc cctcaagacc cgtttagagg ccccaagggg ttatgctatc aatcgttgcg 1500
ttacacacac aaaaaaccaa cacacatcca tcttcgatgg atagcgattt tattatctaa 1560
ctgctgatcg agtgtagcca gatctagtaa tcaattacgg ggtcattagt tcatagccca 1620
tatatggagt tccgcgttac ataacttacg gtaaatggcc cgcctggctg accgcccaac 1680
gacccccgcc cattgacgtc aataatgacg tatgttccca tagtaacgcc aatagggact 1740
ttccattgac gtcaatgggt ggagtattta cggtaaactg cccacttggc agtacatcaa 1800
gtgtatcata tgccaagtac gccccctatt gacgtcaatg acggtaaatg gcccgcctgg 1860
cattatgccc agtacatgac cttatgggac tttcctactt ggcagtacat ctacgtatta 1920
gtcatcgcta ttaccatgct gatgcggttt tggcagtaca tcaatgggcg tggatagcgg 1980
tttgactcac ggggatttcc aagtctccac cccattgacg tcaatgggag tttgttttgg 2040
caccaaaatc aacgggactt tccaaaatgt cgtaacaact ccgccccatt gacgcaaatg 2100
ggcggtaggc gtgtacggtg ggaggtctat ataagcagag ctggtttagt gaaccgtcag 2160
atcagatctt tgtcgatcct accatccact cgacacaccc gccagcggcc gctaatacga 2220
ctcactatag ggagaagtac tgccaccatg ggcaagaagc aaaatcgcaa gacggggaat 2280
tccaagacac aatccgctag cccaccacct aaagagcgtt ctagctcccc tgctactgag 2340
cagtcctgga tggaaaacga cttcgatgaa ctccgggaag agggatttag gcgatccaac 2400
tattcagaac tccgcgaaga tatccagaca aaggggaagg aagtcgagaa tttcgagaag 2460
aacctcgagg agtgcatcac ccgtatcaca aacactgaga aatgtctcaa agaactcatg 2520
gaacttaaga caaaagcgag ggagcttcga gaggagtgtc ggagtctgag atccaggtgt 2580
gaccagctcg aggagcgtgt gagcgcgatg gaagacgaga tgaacgagat gaaaagagag 2640
ggcaaattca gggagaagcg cattaagagg aacgaacaga gtctgcagga gatttgggat 2700
tacgtcaaga ggcctaacct gcggttgatc ggcgtccccg agagcgacgt agaaaacggg 2760
actaaactgg agaatacact tcaagacatc attcaagaaa attttccaaa cctggctcgg 2820
caagctaatg tgcaaatcca agagatccaa cgcacacccc agcggtatag ctctcggcgt 2880
gccacccccta ggcatattat cgtgcgcttt actaaggtgg agatgaaaga gaagatgctg 2940
cgagccgctc gggaaaaggg aagggtgact ttgaagggca aacctattcg gctgacggtt 3000
gaccttagcg ccgagacact ccaggcacgc cgggaatggg gccccatctt taatatcctg 3060
aaggagaaga acttccagcc acgaatctct taccctgcaa agttgagttt tatctccgag 3120
ggtgagatta agtatttcat cgataaacag atgctgcgag acttcgtgac aactcgccca 3180
gctctcaagg aactgctcaa agaggctctt aatatggagc gcaataatag atatcaaccc 3240
ttgcagaacc acgcaaagat gtgagacagc cgtcagacca tcaagactag gaagaaactg 3300
catcaactaa tgagcaaaat caccagctaa catcatagta tacatgaaaa ggccggcggc 3360
cacgaaaaag gccggccagg caaaaaagaa aaagaccggc tctaactcac atatcaccat 3420
ccttacactt aacattaacg gcctcaactc agctatcaag cgccatcggc tggccagctg 3480
gatcaaatca caggatccaa gcgtttgttg catccaagag acccacctga cctgtagaga 3540

```
tactcaccgc ctcaagatca agggatggcg aaagatttat caggcgaacg gtaagcagaa  3600
gaaagccgga gtcgcaattc tggtctcaga caagacggat ttcaagccca ccaaaattaa  3660
gcgtgataag gaaggtcact atattatggt gaaaggcagc atacagcagg aagaacttac  3720
catattgaac atctacgcgc caaacaccgg cgcacctcgc tttatcaaac aggtcctgtc  3780
cgatctgcag cgagatctgg attctcatac gttgattatg ggtgatttca atacaccatt  3840
gagcaccctg gatcgcagca ccaggcaaaa ggtaaataaa gacacgcaag agctcaatag  3900
cgcactgcat caggcagatc tcattgatat ttatcgcact cttcatccta agagtaccga  3960
gtacacattc ttcagcgccc cacatcatac atactcaaag atcgatcata tcgtcggctc  4020
aaaggctctg ctgtcaaagt gcaagcgcac agagataatt acaaattacc tgtcagatca  4080
tagcgcgatc aagctcgagc tgagaatcaa gaacctgacc cagagccgga gtaccacttg  4140
gaagcttaat aacctgctgc tcaacgatta ttgggtccac aatgagatga aggcagagat  4200
taaaatgttc ttcgaaacaa atgagaataa ggatactacc tatcaaaacc tttgggatgc  4260
ctttaaggcc gtctgcagag gcaagttcat cgccctcaac gcctataaaa gaaaacaaga  4320
gagatctaag atcgatactc tcacctctca gctgaaggag ttggagaaac aggaacagac  4380
ccactccaag gcgtcaagac ggcaggagat cacaaagatt cgcgccgagt tgaaagagat  4440
cgaaacccaa aagactcttc agaaaattaa cgagtctcgt agttggttct tcgagcggat  4500
taataagata gacagacctc tggcacgact gattaagaag aagcgcgaaa agaaccagat  4560
tgataccatc aagaacgaca agggcgacat cactactgac ccgaccgaga tccagaccac  4620
tattcgggag tattataagc atttgtatgc taacaagctt gagaacctgg aagagatgga  4680
cacttttctg gatacctata ctctgccacg gcttaatcaa gaggaagtcg agtccctcaa  4740
ccgcccaatt acaggaagcg agattgtggc cataattaac tccctgccga caaagaaatc  4800
tcctggtccg gacgggttta cagctgagtt ttatcaacgg tatatggaag agcttgtacc  4860
gtttctgctc aagctctttc agtctataga aaaggaaggc atcttgccca attccttcta  4920
cgaagcttct ataatactta ttcccaaacc aggacgcgat accacaaaga aggaaaactt  4980
ccggcccatt agtctcatga atatcgacgc taaaatattg aacaagattc tcgccaacag  5040
aatccaacaa catattaaga aattgataca tcacgaccag gtggggttta tacctggcat  5100
gcagggctgg tttaacatcc ggaagagtat taacgtcatt caacacatta atagagctaa  5160
ggataagaat catatgatca tctctataga cgcggaaaag gcattcgata agattcagca  5220
gccatttatg ctcaagactc tgaacaaact cggcatcgac ggaacatatt ttaagattat  5280
tcgcgcaatt tacgataagc cgactgctaa cattatcctt aacggccaaa agctcgaggc  5340
ctttccgctc aagactggaa cccgccaagg ctgtcccctc tccccgcttt tgtttaatat  5400
tgtactcgag gtgctggcta gggctattcg tcaagagaaa gagattaaag ggatacagct  5460
cgggaaggaa gaggtcaagc tttccttgtt cgccgatgat atgattgtgt acctggagaa  5520
tcctattgtg tctgctcaga accttcttaa acttatttct aactttagca aggtcagcgg  5580
ctataagatt aacgtccaga aatctcaggc ctttctgtac acaaataatc gacagaccga  5640
atcccagata atgggtgagc ttccgtttgt catagccagc aaaaggataa agtatctcgg  5700
aatccagctg acacgagacg ttaaagattt gtttaaggaa aattacaagc ctctcctgaa  5760
agagattaag gaagatacta ataagtggaa gaatatcccc tgttcatggg ttggcagaat  5820
caacatagtg aagatggcaa tacttcctaa agtgatatat cgctttaacg ccatcccaat  5880
taaactgcct atgaccttct ttacggagct cgagaaaaca acccttaaat ttatatggaa  5940
tcaaaagaga gcaagaatag cgaagtccat cttgagccag aagaataagg ccggtgggat  6000
tactttgcct gattttaagt tgtattataa agccacagta actaagacag cctggtattg  6060
gtatcagaat agagacatcg accagtggaa tcggaccgaa ccatcagaga taatgcccca  6120
catctataat taccttatat tcgataagcc agaaaaagaat aaacagtggg gcaaagacag  6180
cctcttcaac aagtggtgtt gggagaattg gctggccata tgccggaaac tcaagctcga  6240
cccctttctt acaccctaca ctaaaatcaa cagtaggtgg atcaaggact tgaatgtcaa  6300
gccaaagact ataaagacac tggaagagaa tcttgggatc acaatacaag atataggcgt  6360
cggcaaagat tttatgtcaa agacgcccaa ggccatggcc actaaggata agattgataa  6420
gtgggacctt attaagctca aaagcttctg tactgccaag gagaccacga tcagagttaa  6480
taggcagccc actacatggg aaaagatttt cgccacttat tcatcagata aggggttgat  6540
aagcagaata tataacgagc tgaagcagat ctacaagaag aaaacgaata atcccatcaa  6600
gaagtgggca aaagatatga acaggcattt tagcaaagag gatatctacg ccgcgaagaa  6660
gcatatgaag aagtgtagtt caagcttggc cattcgtgag atgcagatta agacgaccat  6720
gcgataccac cttaccccag tgaggatggc aattatcaag aaatctggca ataatagatg  6780
ttggcggggc tgtggcgaga ttggcaccct gctccattgc tggtgggatt gcaagctggt  6840
gcagccgctt tggaaatcag tctggcgctt tctgagggac ctcgagcttg agattccctt  6900
cgatcccgca attcccttgc tcggaatcta tcctaacgaa tacaagagct gttgttacaa  6960
ggatacgtgt acccggatgt tcatcgcggc cttgtttacg atagctaaga cgtggaatca  7020
gcctaagtgc cccacaatga tcgattggat caagaaaatg tggcatattt ataccatgga  7080
gtattacgca gcaattaaga atgacgaatt tatttccttc gttgggacct ggatgaagct  7140
ggagactatt attctgagca agctgtctca ggagcaaaag acaaagcata gaatcttctc  7200
tctcattggt ggtaacgact acaaagacga tgacgacaag taaagcgctt ctagaagttg  7260
tctcctcctg cactgactga ctgatacaat cgatttctgg atccgcaggc ctaatcaacc  7320
tctggattac aaaatttgtg aaagattgac tggtattctt aactatgttg ctccttttac  7380
gctatgtgga tacgctgctt taatgccttt gtatcatgct attgcttccc gtatggcttt  7440
cattttctcc tccttgtata aatcctggtt gctgtctctt tatgaggagt tgtggcccgt  7500
tgtcaggcaa cgtggcgtgg tgtgcactgt gtttgctgac gcaaccccca ctggttgggg  7560
cattgccacc acctgtcagc tcctttccgg gactttcgct ttccccctcc ctattgccac  7620
ggcggaactc atcgccgcct gccttgcccg ctgctggaca ggggctcggc tgttgggcac  7680
tgacaattcc gtggtgttgt cggggaagct gacgtccttt ccatggctgc tcgcctgtgt  7740
tgccacctgg attctgcgcg ggacgtcctt ctgctacgtc ccttcggccc tcaatccagc  7800
ggaccttcct tcccgctgag agacacaaaa aattccaaca cactattgca atgaaaataa  7860
atttccttta ttagccagaa gtcagatgct caaggggctt catgatgtcc ccataatttt  7920
tggcagaggg aaaaagatct cagtggtatt tgtgagccag ggcattggcc ttctgatagg  7980
cagcctgcac ctgaggagtg cggccgcttt acttgtacag ctcgtccatg ccgagagtga  8040
tcccggcggc ggtcacgaac tccagcagga ccatgtgatc gcgcttctcg ttggggtctt  8100
tgctcagggc ggactgggtg ctcaggtagt ggttgtcggg cagcagcacg gggccgtcgc  8160
cgatgggggt gttctgctgg tagtggtcgg cgagctgcac gctgccgtcc tcgatgttgt  8220
ggcggatctt gaagttcacc ttgatgccgt tcttctgctt gtcggccatg atatagacgt  8280
```

```
tgtggctgtt gtagttgtac tccagcttgt gccccaggat gttgccgtcc tccttgaagt  8340
cgatgccctt cagctcgatg cggttcacca gggtgtcgcc ctcgaacttc acctcggcgc  8400
gggtcttgta gttgccgtcg tccttgaaga agatggtgcg ctcctggacg tagccttcgg  8460
gcatggcgga cttgaagaag tcgtgctgct tcatgtggtc ggggtagcgg ctgaagcact  8520
gcacgccgta ggtcagggtg gtcacgaggg tgggccaggg cacgggcagc ttgccggtgg  8580
tgcagatgaa cttcagggtc agcttgccgt aggtggcatc gccctcgccc tcgccggaca  8640
cgctgaactt gtggccgttt acgtcgccgt ccagctcgac caggatgggc accaccccgg  8700
tgaacagctc ctcgcccttg ctcaccatgg tggcgggatc tgacggttca ctaaaccagc  8760
tctgcttata tagacctccc accgtacacg cctaccgccc atttgcgtca atggggcgga  8820
gttgttacga cattttggaa agtcccgttg attttggtgc caaaacaaac tcccattgac  8880
gtcaatgggg tggagacttg gaaatccccg tgagtcaaac cgctatccac gcccattgat  8940
gtactgccaa aaccgcatca ccatggtaat agcgatgact aatacgtaga tgtactgcca  9000
agtaggaaag tcccataagg tcatgtactg ggcataatgc caggcgggcc atttaccgtc  9060
attgacgtca atagggggcg tacttggcat atgatacact tgatgtactg ccaagtgggc  9120
agtttaccgt aaatactcca cccattgacg tcaatggaaa gtccctattg gcgttactat  9180
gggaacatac gtcattattg acgtcaatgg gcgggggtcg ttgggcggtc agccaggcgg  9240
gccatttacc gtaagttatg taacgggcct gctgccggct ctgcggcctc ttccgcgtct  9300
tcgccttcgc cctcagacga gtcggatctc cctttgggcc gcctccccgc ctgtctagct  9360
tgactgactg agatacagcg taccttcagc tcacagacat gataagatac attgatgagt  9420
ttggacaaac cacaactaga atgcagtgaa aaaaatgctt tatttgtgaa atttgtgatg  9480
ctattgcttt atttgtaacc attataagct gcaataaaca agttaacaac aacaattgca  9540
ttcattttat gtttcaggtt caggggggagg tgtgggaggt tttttaaagc aagtaaaacc  9600
tctacaaatg tggtattggc ccatctctat cggtatcgta gcataacccc ttggggcctc  9660
taaacgggtc ttgaggggtt ttttgtgccc ctcgggccgg attgctatct accggcattg  9720
gcgcagaaaa aaatgcctga tgcgacgctg cgcgtcttat actcccacat atgccagatt  9780
cagcaacgga tacggcttcc ccaacttgcc cacttccata cgtgtcctcc ttaccagaaa  9840
tttatcctta aggtcgtcag ctatcctgca ggcgatctct cgatttcgat caagacattc  9900
ctttaatggt cttttctgga caccactagg ggtcagaagt agttcatcaa actttcttcc  9960
ctccctaatc tcattggtta ccttgggcta tcgaaactta attaagcgat ctgcatctca  10020
attagtcagc aaccatagtc ccgcccctaa ctccgcccat cccgccccta actccgccca  10080
gttccgccca ttctccgccc catcgctgac taattttttt tatttatgca gaggccgagg  10140
ccgcctcggc ctctgagcta ttccagaagt agtgaggagg cttttttgga ggcctaggct  10200
tttgcaaagg aggtagccaa catgattgaa caagatggat tgcacgcagg ttctcccgcc  10260
gcttgggtgg agaggctatt cggctatgac tgggcacaac agacaatcgg ctgctctgat  10320
gccgccgtgt tccggctgtc agcgcagggg cgcccggttc tttttgtcaa gaccgacctg  10380
tccggtgccc tgaatgaact ccaggacgag gcagcgcggc tatcgtggct ggccacgacg  10440
ggcgttcctt gcgcagctgt gctcgacgtt gtcactgaag cgggaaggga ctggctgcta  10500
ttgggcgaag tgccggggca ggatctcctg tcatctcacc ttgctcctgc cgagaaagta  10560
tccatcatgg ctgatgcaat gcggcggctg catacgcttg atccggctac ctgcccattc  10620
gaccaccaag cgaaacatcg catcgagcga gcacgtactc ggatggaagc cggtcttgtc  10680
gatcaggatg atctggacga agagcatcag gggctcgcgc cagccgaact gttcgccagg  10740
ctcaaggcgc ggatgcccga cggcgaggat ctcgtcgtga cccacggcga tgcctgcttg  10800
ccgaatatca tggtggaaaa tggccgcttt tctggattca tcgactgtgg ccggctgggt  10860
gtggcggacc gctatcagga catagcgttg gctacccgtg atattgctga agagcttggc  10920
ggcgaatggg ctgaccgctt cctcgtgctt tacggtatcg ccgctcccga ttcgcagcgc  10980
atcgccttct atcgccttct tgacgagttc ttctagtatg taagccctgt gccttctagt  11040
tgccagccat ctgttgtttg cccctccccc gtgccttcct tgaccctgga aggtgccact  11100
cccactgtcc tttcctaata aaatgaggaa attgcatcgc attgtctgag taggtgtcat  11160
tctattctgg ggggtggggt ggggcaggac agcaaggggg aggattggga agacaatagc  11220
aggcatgctg gggatgcggt gggctctatg gttaattaac cagtcaagtc agctacttgg  11280
cgagatcgac ttgtctgggt ttcgactacg ctcagaattg cgtcagtcaa gttcgatctg  11340
gtccttgcta ttgcacccgt tctccgatta cgagtttcat ttaaatcatg tgagcaaaag  11400
gccagcaaaa ggccaggaac cgtaaaaagg ccgcgttgct ggcgtttttc cataggctcc  11460
gcccccctga cgagcatcac aaaaatcgac gctcaagtca gaggtggcga aacccgacag  11520
gactataaag ataccaggcg tttccccctg gaagctccct cgtgcgctct cctgttccga  11580
ccctgccgct taccggatac ctgtccgcct ttctcccttc gggaagcgtg gcgctttctc  11640
atagctcacg ctgtaggtat ctcagttcgg tgtaggtcgt tcgctccaag ctgggctgtg  11700
tgcacgaacc ccccgttcag cccgaccgct gcgccttatc cggtaactat cgtcttgagt  11760
ccaacccggt aagacacgac ttatcgccac tggcagcagc cactggtaac aggattagca  11820
gagcgaggta tgtaggcggt gctacagagt tcttgaagtg gtggcctaac tacggctaca  11880
ctagaagaac agtatttggt atctgcgctc tgctgaagcc agttaccttc ggaaaaagag  11940
ttggtagctc ttgatccggc aaacaaacca ccgctggtag cggtggtttt tttgtttgca  12000
agcagcagat tacgcgcaga aaaaaaggat ctcaagaaga tcctttgatc ttttctacgg  12060
ggtctgacgc tcagtggaac gaaaactcac gttaagggat tttggtcatg agattatcaa  12120
aaaggatctt cacctagatc cttttaaatt aaaaatgaag ttttaaatca atctaaagta  12180
tatatgagta aacttggtct gacagttacc aatgcttaat cagtgaggca cctatctcag  12240
cgatctgtct atttcgttca tccatagttg catttaaatt tccgaactct ccaaggccct  12300
cgtcggaaaa tcttcaaacc tttcgtccga tccatcttgc aggctacctc tcgaacgaac  12360
tatcgcaagt ctcttggccg gccttgcgcc ttggctattg cttggcagcg cctatcgcca  12420
ggtattactc caatcccgaa tatccgagat cgggatcacc cgagagaagt tcaacctaca  12480
tcctcaatcc cgatctatcc gagatccgag gaatatcgaa atcggggcgc gcctggtgta  12540
ccgagaacga tcctctcagt gcgagtctc                                 12569

SEQ ID NO: 103          moltype = DNA  length = 12581
FEATURE                 Location/Qualifiers
misc_feature            1..12581
                        note = Description of Artificial Sequence: Synthetic
                         polynucleotide
source                  1..12581
```

mol_type = other DNA
organism = synthetic construct
SEQUENCE: 103
agatccgagg aatatcgaaa tcggggcgcg cctggtgtac cgagaacgat cctctcagtg 60
cgagtctcga cgatccatat cgttgcttgg cagtcagcca gtcggaatcc agcttgggac 120
ccaggaagtc caatcgtcag atattgtact caagcctggt cacggcagcg taccgatctg 180
tttaaaccta gatattgata gtctgatcgg tcaacgtata atcgagtcct agcttttgca 240
aacatctatc aagagacagg atcagcagga ggctttcgca tgagtattca acatttccgt 300
gtcgccctta ttcccttttt tgcggcattt tgccttcctg tttttgctca cccagaaacg 360
ctggtgaaag taaaagatgc tgaagatcag ttgggtgcgc gagtgggtta catcgaactg 420
gatctcaaca gcggtaagat ccttgagagt tttcgccccg aagaacgctt tccaatgatg 480
agcactttta aagttctgct atgtggcgcg gtattatccc gtattgacgc cgggcaagag 540
caactcggtc gccgcataca ctattctcag aatgacttgg ttgagtattc accagtcaca 600
gaaaagcatc ttacggatgg catgacagta agagaattat gcagtgctgc cataaccatg 660
agtgataaca ctgcggccaa cttacttctg acaacgattg gaggaccgaa ggagctaacc 720
gcttttttgc acaacatggg ggatcatgta actcgccttg atcgttggga accggagctg 780
aatgaagcca taccaaacga cgagcgtgac accacgatgc ctgtagcaat ggcaacaacc 840
ttgcgtaaac tattaactgg cgaactactt actctagctt cccggcaaca gttgatagac 900
tggatggagg cggataaagt tgcaggacca cttctgcgct cggcccttcc ggctggctgg 960
tttattgctg ataaatctgg agccggtgag cgtgggtctc gcggtatcat tgcagcactg 1020
gggccagatg gtaagccctc ccgtatcgta gttatctaca cgacggggag tcaggcaact 1080
atggatgaac gaaatagaca gatcgctgag ataggtgcct cactgattaa gcattggtaa 1140
ccgattctag gtgcattggc gcagaaaaaa atgcctgatg cgacgctgcg cgtcttatac 1200
tcccacatat gccagattca gcaacggata cggcttcccc aacttgccca cttccatacg 1260
tgtcctcctt accagaaatt tatccttaag atcgtttaaa ctcgactctg gctctatcga 1320
atctccgtcg tttcgagctt acgcgaacag ccgtggcgct catttgctcg tcgggcatcg 1380
aatctcgtca gctatcgtca gcttaccttt ttggcagcga tcgcggctcc cgacatcttg 1440
gaccattagc tccacaggta tcttcttccc tctagtggtc ataacagcag cttcagctac 1500
ctctcaattc aaaaaacccc tcaagacccg tttagaggcc ccaaggggtt atgctatcaa 1560
tcgttgcgtt acacacacaa aaaaccaaca cacatccatc ttcgatggat agcgatttta 1620
ttatctaact gctgatcgag tgtagccaga tctagtaatc aattacgggg tcattagttc 1680
atagcccata tatggagttc cgcgttacat aacttacggt aaatggcccg cctggctgac 1740
cgcccaacga cccccgccca ttgacgtcaa taatgacgta tgttcccata gtaacgccaa 1800
tagggacttt ccattgacgt caatgggtgg agtatttacg gtaaactgcc cacttggcag 1860
tacatcaagt gtatcatatg ccaagtacgc cccctattga cgtcaatgac ggtaaatggc 1920
ccgcctggca ttatgcccag tacatgacct tatgggactt tcctacttgg cagtacatct 1980
acgtattagt catcgctatt accatgctga tgcggttttg gcagtacatc aatgggcgtg 2040
gatagcggtt tgactcacgg ggatttccaa gtctccaccc cattgacgtc aatgggagtt 2100
tgttttggca ccaaaatcaa cgggactttc caaaatgtcg taacaactcc gccccattga 2160
cgcaaatggg cggtaggcgt gtacggtggg aggtctatat aagcagagct ggtttagtga 2220
accgtcagat cagatctttg tcgatcctac catccactcg acacacccgc cagcggccgc 2280
taatacgact cactataggg agaagtactg ccaccatggg caagaagcaa aatcgcaaga 2340
cggggaattc caagacacaa tccgctagcc caccacctaa agagcgttct agctcccctg 2400
ctactgagca gtcctggatg gaaaacgact tcgatgaact ccgggaagag ggatttaggc 2460
gatccaacta ttcagaactc cgcgaagata tccagacaaa ggggaaggaa gtcgagaatt 2520
tcgagaagaa cctcgaggag tgcatcaccc gtatcacaaa cactgagaaa tgtctcaaag 2580
aactcatgga acttaagaca aaagccaggg agcttcgaga ggagtgtcgg agtctgagat 2640
ccaggtgtga ccagctcgag gagcgcgtga gcgcgatgga agacgagatg aacgagatga 2700
aaagagaggg caaattcagg gagaagcgca ttaagaggaa cgaacagagt ctgcaggaga 2760
tttgggatta cgtcaagagg cctaacctgc ggttgatcgg cgtccccgag agcgacgtag 2820
aaaacgggac taaactggag aatacacttc aagacatcat tcaagaaaat tttccaaacc 2880
tggctcggca agctaatgtg caaatccaag agatccaacg cacaccccag cggtatagct 2940
ctcggcgtgc cacccctagg catattatcg tgcgctttac taaggtggag atgaaagaga 3000
agatgctgcg agccgctcgg gaaaagggaa gggtgacttt gaagggcaaa cctattcggc 3060
tgacggttga ccttagcgcc gagacactcc aggcacgccg ggaatggggc cccatcttta 3120
atatcctgaa ggagaagaac ttccagccac gaatctctta ccctgcaaag ttgagtttta 3180
tctccgaggg tgagattaag tatttcatcg ataaacagat gctgcgagac ttcgtgacaa 3240
ctcgcccagc tctcaaggaa ctgctcaaag aggctcttaa tatggagcgc aataatagat 3300
atcaaccctt gcagaaccac gcaaagatgt gagacagccg tcagaccatc aagactagga 3360
agaaactgca tcaactaatg agcaaaatca ccagctaaca tcatagtata catgaaaagg 3420
ccggcggcca cgaaaaaggc cggccaggca aaaaagaaaa agggcggcgg cagcaccggc 3480
tctaactcac atatcaccat ccttacactt aacattaacg gcctcaactc agctatcaag 3540
cgccatcggc tggccagctg gatcaaatca caggatccaa gcgtttgttg catccaagag 3600
acccacctga cctgtagaga tactcaccgc ctcaagatca agggatggcg aaagatttat 3660
caggcgaacg gtaagcagaa gaaagccgga gtcgcaattc tggtctcaga caagacggat 3720
ttcaagccca ccaaaattaa gcgtgataag gaaggtcact atattatggt gaaaggcagc 3780
atacagcagg aagaacttac catattgaac atctacgcgc caaacaccgg cgcacctcgc 3840
tttatcaaac aggtcctgtc cgatctgcag cgagatctgg attctcatac gttgattatg 3900
ggtgatttca atacaccatt gagcaccctg gatcgcagca ccaggcaaaa ggtaaataaa 3960
gacacgcaag agctcaatag cgcactgcat caggcagatc tcattgatat ttatcgcact 4020
cttcatccta agagtaccga gtacacattc ttcagcgccc cacatcatac atactcaaag 4080
atcgatcata tcgtcggctc aaaggctctg ctgtcaaagt gcaagcgcac agagataatt 4140
acaaattacc tgtcagatca tagcgcgatc aagctcgagc tgagaatcaa gaacctgacc 4200
cagagccgga gtaccacttg gaagcttaat aacctgctgc tcaacgatta ttgggtccac 4260
aatgagatga aggcagagat taaaatgttc ttcgaaacaa atgagaataa ggatactacc 4320
tatcaaaacc tttgggatgc ctttaaggcc gtctgcagag gcaagttcat cgccctcaac 4380
gcctataaaa gaaaacaaga gagatctaag atcgatactc tcacctctca gctgaaggag 4440
ttggagaaac aggaacagac ccactccaag gcgtcaagac ggcaggagat cacaaagatt 4500
cgcgccgagt tgaaagagat cgaaacccaa aagactcttc agaaaattaa cgagtctcgt 4560

-continued

```
agttggttct tcgagcggat taataagata gacagacctc tggcacgact gattaagaag  4620
aagcgcgaaa agaaccagat tgataccatc aagaacgaca agggcgacat cactactgac  4680
ccgaccgaga tccagaccac tattcgggag tattataagc atttgtatgc taacaagctt  4740
gagaacctgg aagagatgga cacttttctg gatacctata ctctgccacg gcttaatcaa  4800
gaggaagtcg agtccctcaa ccgcccaatt acaggaagcg agattgtggc cataattaac  4860
tccctgccga caaagaaatc tcctggtccg gacgggttta cagctgagtt ttatcaacgg  4920
tatatggaag agcttgtacc gtttctgctc aagctctttc agtctataga aaaggaaggc  4980
atcttgccca attccttcta cgaagcttct ataatactta ttcccaaacc aggacgcgat  5040
accacaaaga aggaaaactt ccggcccatt agtctcatga atatcgacgc taaaatattg  5100
aacaagattc tcgccaacag aatccaacaa catattaaga aattgataca tcacgaccag  5160
gtggggttta tacctggcat gcagggctgg tttaacatcc ggaagagtat taacgtcatt  5220
caacacatta atagagctaa ggataagaat catatgatca tctctataga cgcggaaaag  5280
gcattcgata agattcagca gccatttatg ctcaagactc tgaacaaact cggcatcgac  5340
ggaacatatt ttaagattat tcgcgcaatt tacgataagc cgactgctaa cattatcctt  5400
aacggccaaa agctcgaggc ctttccgctc aagactggaa cccgccaagg ctgtcccctc  5460
tccccgcttt tgtttaatat tgtactcgag gtgctggcta gggctattcg tcaagagaaa  5520
gagattaaag ggatacagct cgggaaggaa gaggtcaagc tttccttgtt cgccgatgat  5580
atgattgtgt acctggagaa tcctattgtg tctgctcaga accttcttaa acttatttct  5640
aactttagca aggtcagcgg ctataagatt aacgtccaga aatctcaggc ctttctgtac  5700
acaaataatc gacagaccga atcccagata atgggtgagc ttccgtttgt catagccagc  5760
aaaaggataa agtatctcgg aatccagctg acacgagacg ttaaagattt gtttaaggaa  5820
aattacaagc ctctcctgaa agagattaag gaagatacta ataagtggaa gaatatcccc  5880
tgttcatggg ttggcagaat caacatagtg aagatggcaa tacttcctaa agtgatatat  5940
cgctttaacg ccatcccaat taaactgcct atgaccttct ttacggagct cgagaaaaca  6000
acccttaaat ttatatggaa tcaaaagaga gcaagaatag cgaagtccat cttgagccag  6060
aagaataagg ccggtgggat tactttgcct gattttaagt tgtattataa agccacagta  6120
actaagacag cctggtattg gtatcagaat agagacatcg accagtggaa tcggaccgaa  6180
ccatcagaga taatgcccca catctataat taccttatat tcgataagcc agaaaagaat  6240
aaacagtggg gcaaagacag cctcttcaac aagtggtgtt gggagaattg gctggccata  6300
tgccggaaac tcaagctcga ccccttttctt acaccctaca ctaaaatcaa cagtaggtgg  6360
atcaaggact tgaatgtcaa gccaaagact ataaagacac tggaagagaa tcttgggatc  6420
acaatacaag atataggcgt cggcaaagat tttatgtcaa agacgcccaa ggccatggcc  6480
actaaggata agattgataa gtgggacctt attaagctca aagcttctg tactgccaag  6540
gagaccacga tcagagttaa taggcagccc actacatggg aaaagatttt cgccacttat  6600
tcatcagata aggggttgat aagcagaata tataacgagc tgaagcagat ctacaagaag  6660
aaaacgaata atcccatcaa gaagtgggca aaagatatga acaggcattt tagcaaagag  6720
gatatctacg ccgcgaagaa gcatatgaag aagtgtagtt caagcttggc cattcgtgag  6780
atgcagatta agacgaccat gcgataccac cttaccccag tgaggatggc aattatcaag  6840
aaatctggca ataatagatg ttggcggggc tgtggcgaga ttggcaccct gctccattgc  6900
tggtgggatt gcaagctggt gcagccgctt tggaaatcag tctggcgctt tctgagggac  6960
ctcgagcttg agattccctt cgatcccgca attcccttgc tcggaatcta tcctaacgaa  7020
tacaagagct gttgttacaa ggatacgtgt acccggatgt tcatcgcggc cttgtttacg  7080
atagctaaga cgtggaatca gcctaagtgc cccacaatga tcgattggat caagaaaatg  7140
tggcatattt ataccatgga gtattacgca gcaattaaga atgacgaatt tatttccttc  7200
gttgggacct ggatgaagct ggagactatt attctgagca agctgtctca ggagcaaaag  7260
acaaagcata gaatcttctc tctcattggt ggtaacgact acaaagacga tgacgacaag  7320
taaagcgctt ctagaagttg tctcctcctg cactgactga ctgatacaat cgatttctgg  7380
atccgcaggc ctaatcaacc tctggattac aaaatttgtg aaagattgac tggtattctt  7440
aactatgttg ctccttttac gctatgtgga tacgctgctt taatgccttt gtatcatgct  7500
attgcttccc gtatggcttt cattttctcc tccttgtata aatcctggtt gctgtctctt  7560
tatgaggagt tgtggcccgt tgtcaggcaa cgtggcgtgg tgtgcactgt gtttgctgac  7620
gcaacccccca ctggttgggg cattgccacc acctgtcagc tcctttccgg gactttcgct  7680
ttccccctcc ctattgccac ggcggaactc atcgccgcct gccttgcccg ctgctggaca  7740
ggggctcggc tgttgggcac tgacaattcc gtggtgttgt cggggaagct gacgtccttt  7800
ccatggctgc tcgcctgtgt tgccacctgg attctgcgcg ggacgtcctt ctgctacgtc  7860
ccttcggccc tcaatccagc ggaccttcct tcccgctgag agacacaaaa aattccaaca  7920
cactattgca atgaaaataa atttccttta ttagccagaa gtcagatgct caaggggctt  7980
catgatgtcc ccataatttt tggcagaggg aaaaagatct cagtggtatt tgtgagccag  8040
ggcattggcc ttctgatagg cagcctgcac ctgaggagtg cggccgcttt acttgtacag  8100
ctcgtccatg ccgagagtga tcccggcggc ggtcacgaac tccagcagga ccatgtgatc  8160
gcgcttctcg ttggggtctt tgctcagggc ggactgggtg ctcaggtagt ggttgtcggg  8220
cagcagcacg gggccgtcgc cgatgggggt gttctgctgg tagtggtcgg cgagctgcac  8280
gctgccgtcc tcgatgttgt ggcggatctt gaagttcacc ttgatgccgt tcttctgctt  8340
gtcggccatg atatagacgt tgtggctgtt gtagttgtac tccagcttgt gccccaggat  8400
gttgccgtcc tccttgaagt cgatgccctt cagctcgatg cggttcacca gggtgtcgcc  8460
ctcgaacttc acctcggcgc gggtcttgta gttgccgtcg tccttgaaga agatggtgcg  8520
ctcctggacg tagccttcgg gcatggcgga cttgaagaag tcgtgctgct tcatgtggtc  8580
ggggtagcgg ctgaagcact gcacgccgta ggtcagggtg gtcacgaggg tgggccaggg  8640
cacgggcagc ttgccggtgg tgcagatgaa cttcagggtc agcttgccgt aggtggcatc  8700
gccctcgccc tcgccggaca cgctgaactt gtggccgttt acgtcgccgt ccagctcgac  8760
caggatgggc accacccccgg tgaacagctc ctcgcccttg ctcaccatgg tggcgggatc  8820
tgacggttca ctaaaccagc tctgcttata tagacctccc accgtacacg cctaccgccc  8880
atttgcgtca atggggcgga gttgttacga cattttggaa agtcccgttg attttggtgc  8940
caaaacaaac tcccattgac gtcaatgggg tggagacttg gaaatccccg tgagtcaaac  9000
cgctatccac gcccattgat gtactgccaa aaccgcatca ccatggtaat agcgatgact  9060
aatacgtaga tgtactgcca agtaggaaag tcccataagg tcatgtactg ggcataatgc  9120
caggcgggcc atttaccgtc attgacgtca atagggggcg tacttggcat atgatacact  9180
tgatgtactg ccaagtgggc agtttaccgt aaatactcca cccattgacg tcaatggaaa  9240
gtccctattg gcgttactat gggaacatac gtcattattg acgtcaatgg gcgggggtcg  9300
```

-continued

```
ttgggcggtc agccaggcgg gccatttacc gtaagttatg taacgggcct gctgccggct  9360
ctgcggcctc ttccgcgtct tcgccttcgc cctcagacga gtcggatctc cctttgggcc  9420
gcctccccgc ctgtctagct tgactgactg agatacagcg taccttcagc tcacagacat  9480
gataagatac attgatgagt ttggacaaac cacaactaga atgcagtgaa aaaaatgctt  9540
tatttgtgaa atttgtgatg ctattgcttt atttgtaacc attataagct gcaataaaca  9600
agttaacaac aacaattgca ttcattttat gtttcaggtt cagggggagg tgtgggaggt  9660
tttttaaagc aagtaaaacc tctacaaatg tggtattggc ccatctctat cggtatcgta  9720
gcataacccc ttggggcctc taaacgggtc ttgaggggtt ttttgtgccc ctcgggccgg  9780
attgctatct accggcattg gcgcagaaaa aaatgcctga tgcgacgctg cgcgtcttat  9840
actcccacat atgccagatt cagcaacgga tacggcttcc ccaacttgcc cacttccata  9900
cgtgtcctcc ttaccagaaa tttatcctta aggtcgtcag ctatcctgca ggcgatctct  9960
cgatttcgat caagacattc ctttaatggt cttttctgga caccactagg ggtcagaagt  10020
agttcatcaa actttcttcc ctccctaatc tcattggtta ccttgggcta tcgaaactta  10080
attaagcgat ctgcatctca attagtcagc aaccatagtc ccgcccctaa ctccgcccat  10140
cccgccccta actccgccca gttccgccca ttctccgccc catcgctgac taattttttt  10200
tatttatgca gaggccgagg ccgcctcggc ctctgagcta ttccagaagt agtgaggagg  10260
cttttttgga ggcctaggct tttgcaaagg aggtagccaa catgattgaa caagatggat  10320
tgcacgcagg ttctcccgcc gcttgggtgg agaggctatt cggctatgac tgggcacaac  10380
agacaatcgg ctgctctgat gccgccgtgt tccggctgtc agcgcagggg cgcccggttc  10440
tttttgtcaa gaccgacctg tccggtgccc tgaatgaact ccaggacgag gcagcgcggc  10500
tatcgtggct ggccacgacg ggcgttcctt gcgcagctgt gctcgacgtt gtcactgaag  10560
cgggaaggga ctggctgcta ttgggcgaag tgccggggca ggatctcctg tcatctcacc  10620
ttgctcctgc cgagaaagta tccatcatgg ctgatgcaat gcggcggctg catacgcttg  10680
atccggctac ctgcccattc gaccaccaag cgaaacatcg catcgagcga gcacgtactc  10740
ggatggaagc cggtcttgtc gatcaggatg atctggacga agagcatcag gggctcgcgc  10800
cagccgaact gttcgccagg ctcaaggcgc ggatgcccga cggcgaggat ctcgtcgtga  10860
cccacggcga tgcctgcttg ccgaatatca tggtggaaaa tggccgcttt tctggattca  10920
tcgactgtgg ccggctgggt gtggcggacc gctatcagga catagcgttg gctacccgtg  10980
atattgctga agagcttggc ggcgaatggg ctgaccgctt cctcgtgctt tacggtatcg  11040
ccgctcccga ttcgcagcgc atcgccttct atcgccttct tgacgagttc ttctagtatg  11100
taagccctgt gccttctagt tgccagccat ctgttgtttg cccctccccc gtgccttcct  11160
tgaccctgga aggtgccact cccactgtcc tttcctaata aaatgaggaa attgcatcgc  11220
attgtctgag taggtgtcat tctattctgg ggggtggggt ggggcaggac agcaaggggg  11280
aggattggga agacaatagc aggcatgctg gggatgcggt gggctctatg gttaattaac  11340
cagtcaagtc agctacttgg cgagatcgac ttgtctgggt ttcgactacg ctcagaattg  11400
cgtcagtcaa gttcgatctg gtccttgcta ttgcacccgt tctccgatta cgagtttcat  11460
ttaaatcatg tgagcaaaag gccagcaaaa ggccaggaac cgtaaaaagg ccgcgttgct  11520
ggcgtttttc cataggctcc gcccccctga cgagcatcac aaaaatcgac gctcaagtca  11580
gaggtggcga aacccgacag gactataaag ataccaggcg tttccccctg gaagctccct  11640
cgtgcgctct cctgttccga ccctgccgct taccggatac ctgtccgcct ttctcccttc  11700
gggaagcgtg gcgctttctc atagctcacg ctgtaggtat ctcagttcgg tgtaggtcgt  11760
tcgctccaag ctgggctgtg tgcacgaacc ccccgttcag cccgaccgct gcgccttatc  11820
cggtaactat cgtcttgagt ccaacccggt aagacacgac ttatcgccac tggcagcagc  11880
cactggtaac aggattagca gagcgaggta tgtaggcggt gctacagagt tcttgaagtg  11940
gtggcctaac tacggctaca ctagaagaac agtatttggt atctgcgctc tgctgaagcc  12000
agttaccttc ggaaaaagag ttggtagctc ttgatccggc aaacaaacca ccgctggtag  12060
cggtggtttt tttgtttgca agcagcagat tacgcgcaga aaaaaaggat ctcaagaaga  12120
tcctttgatc ttttctacgg ggtctgacgc tcagtggaac gaaaactcac gttaagggat  12180
tttggtcatg agattatcaa aaaggatctt cacctagatc cttttaaatt aaaaatgaag  12240
ttttaaatca atctaaagta tatatgagta aacttggtct gacagttacc aatgcttaat  12300
cagtgaggca cctatctcag cgatctgtct atttcgttca tccatagttg catttaaatt  12360
tccgaactct ccaaggccct cgtcggaaaa tcttcaaacc tttcgtccga tccatcttgc  12420
aggctacctc tcgaacgaac tatcgcaagt ctcttggccg gccttgcgcc ttggctattg  12480
cttggcagcg cctatcgcca ggtattactc caatcccgaa tatccgagat cgggatcacc  12540
cgagagaagt tcaacctaca tcctcaatcc cgatctatcc g                    12581
```

```
SEQ ID NO: 104          moltype = DNA  length = 12542
FEATURE                 Location/Qualifiers
misc_feature            1..12542
                        note = Description of Artificial Sequence: Synthetic
                         polynucleotide
source                  1..12542
                        mol_type = other DNA
                        organism = synthetic construct
SEQUENCE: 104
agaacgatcc tctcagtgcg agtctcgacg atccatatcg ttgcttggca gtcagccagt  60
cggaatccag cttgggaccc aggaagtcca atcgtcagat attgtactca agcctggtca  120
cggcagcgta ccgatctgtt taaacctaga tattgatagt ctgatcggtc aacgtataat  180
cgagtcctag cttttgcaaa catctatcaa gagacaggat cagcaggagg ctttcgcatg  240
agtattcaac atttccgtgt cgcccttatt cccttttttg cggcattttg ccttcctgtt  300
tttgctcacc cagaaacgct ggtgaaagta aaagatgctg aagatcagtt gggtgcgcga  360
gtgggttaca tcgaactgga tctcaacagc ggtaagatcc ttgagagttt tcgccccgaa  420
gaacgctttc caatgatgag cacttttaaa gttctgctat gtggcgcggt attatcccgt  480
attgacgccg ggcaagagca actcggtcgc cgcatacact attctcagaa tgacttggtt  540
gagtattcac cagtcacaga aaagcatctt acggatggca tgacagtaag agaattatgc  600
agtgctgcca taaccatgag tgataacact gcggccaact tacttctgac aacgattgga  660
ggaccgaagg agctaaccgc ttttttgcac aacatggggg atcatgtaac tcgccttgat  720
cgttgggaac cggagctgaa tgaagccata ccaaacgacg agcgtgacac cacgatgcct  780
gtagcaatgg caacaacctt gcgtaaacta ttaactggcg aactacttac tctagcttcc  840
```

```
cggcaacagt tgatagactg gatggaggcg gataaagttg caggaccact tctgcgctcg  900
gcccttccgg ctggctggtt tattgctgat aaatctggag ccggtgagcg tgggtctcgc  960
ggtatcattg cagcactggg gccagatggt aagccctccc gtatcgtagt tatctacacg  1020
acggggagtc aggcaactat ggatgaacga aatagacaga tcgctgagat aggtgcctca  1080
ctgattaagc attggtaacc gattctaggt gcattggcgc agaaaaaaat gcctgatgcg  1140
acgctgcgcg tcttatactc ccacatatgc cagattcagc aacggatacg gcttccccaa  1200
cttgcccact tccatacgtg tcctccttac cagaaattta tccttaagat cgtttaaact  1260
cgactctggc tctatcgaat ctccgtcgtt tcgagcttac gcgaacagcc gtggcgctca  1320
tttgctcgtc gggcatcgaa tctcgtcagc tatcgtcagc ttaccttttt ggcagcgatc  1380
gcggctcccg acatcttgga ccattagctc cacaggtatc ttcttccctc tagtggtcat  1440
aacagcagct tcagctacct ctcaattcaa aaaacccctc aagacccgtt tagaggcccc  1500
aaggggttat gctatcaatc gttgcgttac acacacaaaa aaccaacaca catccatctt  1560
cgatggatag cgattttatt atctaactgc tgatcgagtg tagccagatc tagtaatcaa  1620
ttacggggtc attagttcat agcccatata tggagttccg cgttacataa cttacggtaa  1680
atggcccgcc tggctgaccg cccaacgacc cccgcccatt gacgtcaata atgacgtatg  1740
ttcccatagt aacgccaata gggactttcc attgacgtca atgggtggag tatttacggt  1800
aaactgccca cttggcagta catcaagtgt atcatatgcc aagtacgccc cctattgacg  1860
tcaatgacgg taaatggccc gcctggcatt atgcccagta catgacctta tgggactttc  1920
ctacttggca gtacatctac gtattagtca tcgctattac catgctgatg cggttttggc  1980
agtacatcaa tgggcgtgga tagcggtttg actcacgggg atttccaagt ctccacccca  2040
ttgacgtcaa tgggagtttg ttttggcacc aaaatcaacg ggactttcca aaatgtcgta  2100
acaactccgc cccattgacg caaatgggcg gtaggcgtgt acggtgggag gtctatataa  2160
gcagagctgg tttagtgaac cgtcagatca gatctttgtc gatcctacca tccactcgac  2220
acacccgcca gcggccgcta atacgactca ctatagggag aagtactgcc accatgggca  2280
agaagcaaaa tcgcaagacg gggaattcca agacacaatc cgctagccca ccacctaaag  2340
agcgttctag ctcccctgct actgagcagt cctggatgga aaacgacttc gatgaactcc  2400
gggaagaggg atttaggcga tccaactatt cagaactccg cgaagatatc cagacaaagg  2460
ggaaggaagt cgagaatttc gagaagaacc tcgaggagtg catcacccgt atcacaaaca  2520
ctgagaaatg tctcaaagaa ctcatggaac ttaagacaaa agccagggag cttcgagagg  2580
agtgtcggag tctgagatcc aggtgtgacc agctcgagga gcgcgtgagc gcgatggaag  2640
acgagatgaa cgagatgaaa agagagggca aattcaggga gaagcgcatt aagaggaacg  2700
aacagagtct gcaggagatt tgggattacg tcaagaggcc taacctgcgg ttgatcggcg  2760
tccccgagag cgacgtagaa aacgggacta aactggagaa tacacttcaa gacatcattc  2820
aagaaaattt tccaaacctg gctcggcaag ctaatgtgca aatccaagag atccaacgca  2880
caccccagcg gtatagctct cggcgtgcca cccctaggca tattatcgtg cgctttacta  2940
aggtggagat gaaagagaag atgctgcgag ccgctcggga aaagggaagg gtgactttga  3000
agggcaaacc tattcggctg acggttgacc ttagcgccga gacactccag gcacgccggg  3060
aatggggccc catctttaat atcctgaagg agaagaactt ccagccacga atctcttacc  3120
ctgcaaagtt gagttttatc tccgagggtg agattaagta tttcatcgat aaacagatgc  3180
tgcgagactt cgtgacaact cgcccagctc tcaaggaact gctcaaagag gctcttaata  3240
tggagcgcaa taatagatat caacccttgc agaaccacgc aaagatgtga gacagccgtc  3300
agaccatcaa gactaggaag aaactgcatc aactaatgag caaaatcacc agctaacatc  3360
atagtataca tgaccggctc taactcacat atcaccatcc ttacacttaa cattaacggc  3420
ctcaactcag ctatcaagcg ccatcggctg gccagctgga tcaaatcaca ggatccaagc  3480
gtttgttgca tccaagagac ccacctgacc tgtagagata ctcaccgcct caagatcaag  3540
ggatggcgaa agatttatca ggcgaacggt aagcagaaga aagccggagt cgcaattctg  3600
gtctcagaca agacggattt caagcccacc aaaattaagc gtgataagga aggtcactat  3660
attatggtga aaggcagcat acagcaggaa gaacttacca tattgaacat ctacgcgcca  3720
aacaccggcg cacctcgctt tatcaaacag gtcctgtccg atctgcagcg agatctggat  3780
tctcatacgt tgattatggg tgatttcaat acaccattga gcaccctgga tcgcagcacc  3840
aggcaaaagg taaataaaga cacgcaagag ctcaatagcg cactgcatca ggcagatctc  3900
attgatattt atcgcactct tcatcctaag agtaccgagt acacattctt cagcgcccca  3960
catcatacat actcaaagat cgatcatatc gtcggctcaa aggctctgct gtcaaagtgc  4020
aagcgcacag agataattac aaattacctg tcagatcata gcgcgatcaa gctcgagctg  4080
agaatcaaga acctgaccca gagccggagt accacttgga agcttaataa cctgctgctc  4140
aacgattatt gggtccacaa tgagatgaag gcagagatta aaatgttctt cgaaacaaat  4200
gagaataagg atactaccta tcaaaacctt tgggatgcct ttaaggccgt ctgcagaggc  4260
aagttcatcg ccctcaacgc ctataaaaga aaacaagaga gatctaagat cgatactctc  4320
acctctcagc tgaaggagtt ggagaaacag gaacagaccc actccaaggc gtcaagacgg  4380
caggagatca caaagattcg cgccgagttg aaagagatcg aaacccaaaa gactcttcag  4440
aaaattaacg agtctcgtag ttggttcttc gagcggatta ataagataga cagacctctg  4500
gcacgactga ttaagaagaa gcgcgaaaag aaccagattg ataccatcaa gaacgacaag  4560
ggcgacatca ctactgaccc gaccgagatc cagaccacta ttcgggagta ttataagcat  4620
ttgtatgcta acaagcttga gaacctggaa gagatggaca cttttctgga tacctatact  4680
ctgccacggc ttaatcaaga ggaagtcgag tccctcaacc gcccaattac aggaagcgag  4740
attgtggcca taattaactc cctgccgaca aagaaatctc ctggtccgga cgggtttaca  4800
gctgagtttt atcaacggta tatggaagag cttgtaccgt ttctgctcaa gctctttcag  4860
tctatagaaa aggaaggcat cttgcccaat tccttctacg aagcttctat aatacttatt  4920
cccaaaccag gacgcgatac cacaaagaag gaaaacttcc ggcccattag tctcatgaat  4980
atcgacgcta aaatattgaa caagattctc gccaacagaa tccaacaaca tattaagaaa  5040
ttgatacatc acgaccaggt ggggtttata cctggcatgc agggctggtt taacatccgg  5100
aagagtatta acgtcattca acacattaat agagctaagg ataagaatca tatgatcatc  5160
tctatagacg cggaaaaggc attcgataag attcagcagc catttatgct caagactctg  5220
aacaaactcg gcatcgacgg aacatatttt aagattattc gcgcaattta cgataagccg  5280
actgctaaca ttatccttaa cggccaaaag ctcgaggcct ttccgctcaa gactggaacc  5340
cgccaaggct gtcccctctc cccgcttttg tttaatattg tactcgaggt gctggctagg  5400
gctattcgtc aagagaaaga gattaaaggg atacagctcg ggaaggaaga ggtcaagctt  5460
tccttgttcg ccgatgatat gattgtgtac ctggagaatc ctattgtgtc tgctcagaac  5520
cttcttaaac ttatttctaa ctttagcaag gtcagcggct ataagattaa cgtccagaaa  5580
```

```
tctcaggcct ttctgtacac aaataatcga cagaccgaat cccagataat gggtgagctt  5640
ccgtttgtca tagccagcaa aaggataaag tatctcggaa tccagctgac acgagacgtt  5700
aaagatttgt ttaaggaaaa ttacaagcct ctcctgaaag agattaagga agatactaat  5760
aagtggaaga atatcccctg ttcatgggtt ggcagaatca acatagtgaa gatggcaata  5820
cttcctaaag tgatatatcg ctttaacgcc atcccaatta aactgcctat gaccttcttt  5880
acggagctcg agaaaacaac ccttaaattt atatggaatc aaaagagagc aagaatagcg  5940
aagtccatct tgagccagaa gaataaggcc ggtgggatta ctttgcctga ttttaagttg  6000
tattataaag ccacagtaac taagacagcc tggtattggt atcagaatag agacatcgac  6060
cagtggaatc ggaccgaacc atcagagata atgccccaca tctataatta ccttatattc  6120
gataagccag aaaagaataa acagtggggc aaagacagcc tcttcaacaa gtggtgttgg  6180
gagaattggc tggccatatg ccggaaactc aagctcgacc cctttcttac accctacact  6240
aaaatcaaca gtaggtggat caaggacttg aatgtcaagc caaagactat aaagacactg  6300
gaagagaatc ttgggatcac aatacaagat ataggcgtcg gcaaagattt tatgtcaaag  6360
acgcccaagg ccatggccac taaggataag attgataagt gggaccttat taagctcaaa  6420
agcttctgta ctgccaagga gaccacgatc agagttaata ggcagcccac tacatgggaa  6480
aagattttcg ccacttattc atcagataag gggttgataa gcagaatata taacgagctg  6540
aagcagatct acaagaagaa aacgaataat cccatcaaga agtgggcaaa agatatgaac  6600
aggcatttta gcaaagagga tatctacgcc gcgaagaagc atatgaagaa gtgtagttca  6660
agcttggcca ttcgtgagat gcagattaag acgaccatgc gataccacct taccccagtg  6720
aggatggcaa ttatcaagaa atctggcaat aatagatgtt ggcggggctg tggcgagatt  6780
ggcaccctgc tccattgctg gtgggattgc aagctggtgc agccgctttg gaaatcagtc  6840
tggcgctttc tgagggacct cgagcttgag attcccttcg atcccgcaat tcccttgctc  6900
ggaatctatc ctaacgaata caagagctgt tgttacaagg atacgtgtac ccggatgttc  6960
atcgcggcct tgtttacgat agctaagacg tggaatcagc ctaagtgccc cacaatgatc  7020
gattggatca agaaaatgtg gcatatttat accatggagt attacgcagc aattaagaat  7080
gacgaattta tttccttcgt tgggacctgg atgaagctgg agactattat tctgagcaag  7140
ctgtctcagg agcaaaagac aaagcataga atcttctctc tcattggtgg taacgactac  7200
aaagacgatg acgacaagcc aaagaagaag cggaaggtct aaagcgcttc tagaagttgt  7260
ctcctcctgc actgactgac tgatacaatc gatttctgga tccgcaggcc taatcaacct  7320
ctggattaca aaatttgtga aagattgact ggtattctta actatgttgc tccttttacg  7380
ctatgtggat acgctgcttt aatgcctttg tatcatgcta ttgcttcccg tatggctttc  7440
attttctcct ccttgtataa atcctggttg ctgtctcttt atgaggagtt gtggcccgtt  7500
gtcaggcaac gtggcgtggt gtgcactgtg tttgctgacg caacccccac tggttggggc  7560
attgccacca cctgtcagct cctttccggg actttcgctt tccccctccc tattgccacg  7620
gcggaactca tcgccgcctg ccttgcccgc tgctggacag gggctcggct gttgggcact  7680
gacaattccg tggtgttgtc ggggaagctg acgtcctttc catggctgct cgcctgtgtt  7740
gccacctgga ttctgcgcgg gacgtccttc tgctacgtcc cttcggccct caatccagcg  7800
gaccttcctt cccgctgaga gacacaaaaa attccaacac actattgcaa tgaaaataaa  7860
tttcctttat tagccagaag tcagatgctc aaggggcttc atgatgtccc cataattttt  7920
ggcagaggga aaaagatctc agtggtattt gtgagccagg gcattggcct tctgataggc  7980
agcctgcacc tgaggagtgc ggccgcttta cttgtacagc tcgtccatgc cgagagtgat  8040
cccggcggcg gtcacgaact ccagcaggac catgtgatcg cgcttctcgt tggggtcttt  8100
gctcagggcg gactgggtgc tcaggtagtg gttgtcgggc agcagcacgg ggccgtcgcc  8160
gatgggggtg ttctgctggt agtggtcggc gagctgcacg ctgccgtcct cgatgttgtg  8220
gcggatcttg aagttcacct tgatgccgtt cttctgcttg tcggccatga tatagacgtt  8280
gtggctgttg tagttgtact ccagcttgtg ccccaggatg ttgccgtcct ccttgaagtc  8340
gatgcccttc agctcgatgc ggttcaccag ggtgtcgccc tcgaacttca cctcggcgcg  8400
ggtcttgtag ttgccgtcgt ccttgaagaa gatggtgcgc tcctggacgt agccttcggg  8460
catggcggac ttgaagaagt cgtgctgctt catgtggtcg gggtagcggc tgaagcactg  8520
cacgccgtag gtcagggtgg tcacgagggt gggccagggc acgggcagct tgccggtggt  8580
gcagatgaac ttcagggtca gcttgccgta ggtggcatcg ccctcgccct cgccggacac  8640
gctgaacttg tggccgttta cgtcgccgtc cagctcgacc aggatgggca ccaccccggt  8700
gaacagctcc tcgcccttgc tcaccatggt ggcgggatct gacggttcac taaaccagct  8760
ctgcttatat agacctccca ccgtacacgc ctaccgccca tttgcgtcaa tggggcggag  8820
ttgttacgac attttggaaa gtcccgttga ttttggtgcc aaaacaaact cccattgacg  8880
tcaatggggt ggagacttgg aaatccccgt gagtcaaacc gctatccacg cccattgatg  8940
tactgccaaa accgcatcac catggtaata gcgatgacta atacgtagat gtactgccaa  9000
gtaggaaagt cccataaggt catgtactgg gcataatgcc aggcgggcca tttaccgtca  9060
ttgacgtcaa tagggggcgt acttggcata tgatacactt gatgtactgc caagtgggca  9120
gtttaccgta aatactccac ccattgacgt caatggaaag tccctattgg cgttactatg  9180
ggaacatacg tcattattga cgtcaatggg cgggggtcgt tgggcggtca gccaggcggg  9240
ccatttaccg taagttatgt aacgggcctg ctgccggctc tgcggcctct tccgcgtctt  9300
cgccttcgcc ctcagacgag tcggatctcc ctttgggccg cctccccgcc tgtctagctt  9360
gactgactga gatacagcgt accttcagct cacagacatg ataagataca ttgatgagtt  9420
tggacaaacc acaactagaa tgcagtgaaa aaaatgcttt atttgtgaaa tttgtgatgc  9480
tattgcttta tttgtaacca ttataagctg caataaacaa gttaacaaca acaattgcat  9540
tcattttatg tttcaggttc agggggaggt gtgggaggtt ttttaaagca agtaaaacct  9600
ctacaaatgt ggtattggcc catctctatc ggtatcgtag cataacccct tggggcctct  9660
aaacgggtct tgaggggttt tttgtgcccc tcgggccgga ttgctatcta ccggcattgg  9720
cgcagaaaaa aatgcctgat gcgacgctgc gcgtcttata ctcccacata tgccagattc  9780
agcaacggat acggcttccc caacttgccc acttccatac gtgtcctcct taccagaaat  9840
ttatccttaa ggtcgtcagc tatcctgcag gcgatctctc gatttcgatc aagacattcc  9900
tttaatggtc ttttctggac accactaggg gtcagaagta gttcatcaaa ctttcttccc  9960
tccctaatct cattggttac cttgggctat cgaaacttaa ttaagcgatc tgcatctcaa  10020
ttagtcagca accatagtcc cgcccctaac tccgcccatc ccgcccctaa ctccgcccag  10080
ttccgcccat tctccgcccc atcgctgact aatttttttt atttatgcag aggccgaggc  10140
cgcctcggcc tctgagctat tccagaagta gtgaggaggc ttttttggag gcctaggctt  10200
ttgcaaagga ggtagccaac atgattgaac aagatggatt gcacgcaggt tctcccgccg  10260
cttgggtgga gaggctattc ggctatgact gggcacaaca gacaatcggc tgctctgatg  10320
```

```
ccgccgtgtt ccggctgtca gcgcaggggc gcccggttct ttttgtcaag accgacctgt  10380
ccggtgccct gaatgaactc caggacgagg cagcgcggct atcgtggctg gccacgacgg  10440
gcgttccttg cgcagctgtg ctcgacgttg tcactgaagc gggaagggac tggctgctat  10500
tgggcgaagt gccggggcag gatctcctgt catctcacct tgctcctgcc gagaaagtat  10560
ccatcatggc tgatgcaatg cggcggctgc atacgcttga tccggctacc tgcccattcg  10620
accaccaagc gaaacatcgc atcgagcgag cacgtactcg gatggaagcc ggtcttgtcg  10680
atcaggatga tctggacgaa gagcatcagg ggctcgcgcc agccgaactg ttcgccaggc  10740
tcaaggcgcg gatgcccgac ggcgaggatc tcgtcgtgac ccacggcgat gcctgcttgc  10800
cgaatatcat ggtggaaaat ggccgctttt ctggattcat cgactgtggc cggctgggtg  10860
tggcggaccg ctatcaggac atagcgttgg ctacccgtga tattgctgaa gagcttggcg  10920
gcgaatgggc tgaccgcttc ctcgtgcttt acggtatcgc cgctcccgat tcgcagcgca  10980
tcgccttcta tcgccttctt gacgagttct tctagtatgt aagccctgtg ccttctagtt  11040
gccagccatc tgttgtttgc ccctcccccg tgccttcctt gaccctggaa ggtgccactc  11100
ccactgtcct ttcctaataa aatgaggaaa ttgcatcgca ttgtctgagt aggtgtcatt  11160
ctattctggg gggtggggtg gggcaggaca gcaaggggga ggattgggaa gacaatagca  11220
ggcatgctgg ggatgcggtg ggctctatgg ttaattaacc agtcaagtca gctacttggc  11280
gagatcgact tgtctgggtt tcgactacgc tcagaattgc gtcagtcaag ttcgatctgg  11340
tccttgctat tgcacccgtt ctccgattac gagtttcatt taaatcatgt gagcaaaagg  11400
ccagcaaaag gccaggaacc gtaaaaaggc cgcgttgctg gcgtttttcc ataggctccg  11460
cccccctgac gagcatcaca aaaatcgacg ctcaagtcag aggtggcgaa acccgacagg  11520
actataaaga taccaggcgt ttccccctgg aagctccctc gtgcgctctc ctgttccgac  11580
cctgccgctt accggatacc tgtccgcctt tctcccttcg ggaagcgtgg cgctttctca  11640
tagctcacgc tgtaggtatc tcagttcggt gtaggtcgtt cgctccaagc tgggctgtgt  11700
gcacgaaccc cccgttcagc ccgaccgctg cgccttatcc ggtaactatc gtcttgagtc  11760
caacccggta agacacgact tatcgccact ggcagcagcc actggtaaca ggattagcag  11820
agcgaggtat gtaggcggtg ctacagagtt cttgaagtgg tggcctaact acggctacac  11880
tagaagaaca gtatttggta tctgcgctct gctgaagcca gttaccttcg gaaaaagagt  11940
tggtagctct tgatccggca aacaaaccac cgctggtagc ggtggttttt ttgtttgcaa  12000
gcagcagatt acgcgcagaa aaaaaggatc tcaagaagat cctttgatct tttctacggg  12060
gtctgacgct cagtggaacg aaaactcacg ttaagggatt ttggtcatga gattatcaaa  12120
aaggatcttc acctagatcc ttttaaatta aaaatgaagt tttaaatcaa tctaaagtat  12180
atatgagtaa acttggtctg acagttacca atgcttaatc agtgaggcac ctatctcagc  12240
gatctgtcta tttcgttcat ccatagttgc atttaaattt ccgaactctc caaggccctc  12300
gtcggaaaat cttcaaacct ttcgtccgat ccatcttgca ggctacctct cgaacgaact  12360
atcgcaagtc tcttggccgg ccttgcgcct tggctattgc ttggcagcgc ctatcgccag  12420
gtattactcc aatcccgaat atccgagatc gggatcaccc gagagaagtt caacctacat  12480
cctcaatccc gatctatccg agatccgagg aatatcgaaa tcggggcgcg cctggtgtac  12540
cg                                                                 12542
```

```
SEQ ID NO: 105          moltype = DNA  length = 12554
FEATURE                 Location/Qualifiers
misc_feature            1..12554
                        note = Description of Artificial Sequence: Synthetic
                         polynucleotide
source                  1..12554
                        mol_type = other DNA
                        organism = synthetic construct
SEQUENCE: 105
tcgacgatcc atatcgttgc ttggcagtca gccagtcgga atccagcttg ggacccagga  60
agtccaatcg tcagatattg tactcaagcc tggtcacggc agcgtaccga tctgtttaaa  120
cctagatatt gatagtctga tcggtcaacg tataatcgag tcctagcttt tgcaaacatc  180
tatcaagaga caggatcagc aggaggcttt cgcatgagta ttcaacattt ccgtgtcgcc  240
cttattccct tttttgcggc attttgcctt cctgtttttg ctcacccaga aacgctggtg  300
aaagtaaaag atgctgaaga tcagttgggt gcgcgagtgg gttacatcga actggatctc  360
aacagcggta agatccttga gagttttcgc cccgaagaac gctttccaat gatgagcact  420
tttaaagttc tgctatgtgg cgcggtatta tcccgtattg acgccgggca agagcaactc  480
ggtcgccgca tacactattc tcagaatgac ttggttgagt attcaccagt cacagaaaag  540
catcttacgg atggcatgac agtaagagaa ttatgcagtg ctgccataac catgagtgat  600
aacactgcgg ccaacttact tctgacaacg attggaggac cgaaggagct aaccgctttt  660
ttgcacaaca tgggggatca tgtaactcgc cttgatcgtt gggaaccgga gctgaatgaa  720
gccataccaa acgacgagcg tgacaccacg atgcctgtag caatggcaac aaccttgcgt  780
aaactattaa ctggcgaact acttactcta gcttcccggc aacagttgat agactggatg  840
gaggcggata aagttgcagg accacttctg cgctcggccc ttccggctgg ctggtttatt  900
gctgataaat ctggagccgg tgagcgtggg tctcgcggta tcattgcagc actggggcca  960
gatggtaagc cctcccgtat cgtagttatc tacacgacgg ggagtcaggc aactatggat  1020
gaacgaaata gacagatcgc tgagataggt gcctcactga ttaagcattg gtaaccgatt  1080
ctaggtgcat tggcgcagaa aaaaatgcct gatgcgacgc tgcgcgtctt atactcccac  1140
atatgccaga ttcagcaacg gatacggctt ccccaacttg cccacttcca tacgtgtcct  1200
ccttaccaga aatttatcct taagatcgtt taaactcgac tctggctcta tcgaatctcc  1260
gtcgtttcga gcttacgcga acagccgtgg cgctcatttg ctcgtcgggc atcgaatctc  1320
gtcagctatc gtcagcttac ctttttggca gcgatcgcgg ctcccgacat cttggaccat  1380
tagctccaca ggtatcttct tccctctagt ggtcataaca gcagcttcag ctacctctca  1440
attcaaaaaa cccctcaaga cccgtttaga ggccccaagg ggttatgcta tcaatcgttg  1500
cgttacacac acaaaaaacc aacacacatc catcttcgat ggatagcgat tttattatct  1560
aactgctgat cgagtgtagc cagatctagt aatcaattac ggggtcatta gttcatagcc  1620
catatatgga gttccgcgtt acataactta cggtaaatgg cccgcctggc tgaccgccca  1680
acgacccccg cccattgacg tcaataatga cgtatgttcc catagtaacg ccaataggga  1740
ctttccattg acgtcaatgg gtggagtatt tacggtaaac tgcccacttg gcagtacatc  1800
aagtgtatca tatgccaagt acgcccccta ttgacgtcaa tgacggtaaa tggcccgcct  1860
```

-continued

```
ggcattatgc ccagtacatg accttatggg actttcctac ttggcagtac atctacgtat  1920
tagtcatcgc tattaccatg ctgatgcggt tttggcagta catcaatggg cgtggatagc  1980
ggtttgactc acggggattt ccaagtctcc accccattga cgtcaatggg agtttgtttt  2040
ggcaccaaaa tcaacgggac tttccaaaat gtcgtaacaa ctccgcccca ttgacgcaaa  2100
tgggcggtag gcgtgtacgg tgggaggtct atataagcag agctggttta gtgaaccgtc  2160
agatcagatc tttgtcgatc ctaccatcca ctcgacacac ccgccagcgg ccgctaatac  2220
gactcactat agggagaagt actgccacca tgggcaagaa gcaaaatcgc aagacgggga  2280
attccaagac acaatccgct agcccaccac ctaaagagcg ttctagctcc cctgctactg  2340
agcagtcctg gatggaaaac gacttcgatg aactccggga agagggattt aggcgatcca  2400
actattcaga actccgcgaa gatatccaga caaaggggaa ggaagtcgag aatttcgaga  2460
agaacctcga ggagtgcatc acccgtatca caaacactga gaaatgtctc aaagaactca  2520
tggaacttaa gacaaaagcc agggagcttc gagaggagtg tcggagtctg agatccaggt  2580
gtgaccagct cgaggagcgc gtgagcgcga tggaagacga gatgaacgag atgaaaagag  2640
agggcaaatt cagggagaag cgcattaaga ggaacgaaca gagtctgcag gagatttggg  2700
attacgtcaa gaggcctaac ctgcggttga tcggcgtccc cgagagcgac gtagaaaacg  2760
ggactaaact ggagaataca cttcaagaca tcattcaaga aaatttccca aacctggctc  2820
ggcaagctaa tgtgcaaatc caagagatcc aacgcacacc ccagcggtat agctctcggc  2880
gtgccacccc taggcatatt atcgtgcgct ttactaaggt ggagatgaaa gagaagatgc  2940
tgcgagccgc tcgggaaaag ggaagggtga ctttgaaggg caaacctatt cggctgacgg  3000
ttgaccttag cgccgagaca ctccaggcac gccgggaatg ggccccatc tttaatatcc  3060
tgaaggagaa gaacttccag ccacgaatct cttaccctgc aaagttgagt tttatctccg  3120
agggtgagat taagtatttc atcgataaac agatgctgcg agacttcgtg acaactcgcc  3180
cagctctcaa ggaactgctc aaagaggctc ttaatatgga gcgcaataat agatatcaac  3240
ccttgcagaa ccacgcaaag atgtgagaca gccgtcagac catcaagact aggaagaaac  3300
tgcatcaact aatgagcaaa atcaccagct aacatcatag tatacatgac cggctctaac  3360
tcacatatca ccatccttac acttaacatt aacggcctca actcagctat caagcgccat  3420
cggctggcca gctggatcaa atcacaggat ccaagcgttt gttgcatcca agagacccac  3480
ctgacctgta gagatactca ccgcctcaag atcaagggat ggcgaaagat ttatcaggcg  3540
aacggtaagc agaagaaagc cggagtcgca attctggtct cagacaagac ggatttcaag  3600
cccaccaaaa ttaagcgtga taaggaaggt cactatatta tggtgaaagg cagcatacag  3660
caggaagaac ttaccatatt gaacatctac gcgccaaaca ccggcgcacc tcgctttatc  3720
aaacaggtcc tgtccgatct gcagcgagat ctggattctc atacgttgat tatgggtgat  3780
ttcaatacac cattgagcac cctggatcgc agcaccaggc aaaaggtaaa taaagacacg  3840
caagagctca atagcgcact gcatcaggca gatctcattg atatttatcg cactcttcat  3900
cctaagagta ccgagtacac attcttcagc gccccacatc atacatactc aaagatcgat  3960
catatcgtcg gctcaaaggc tctgctgtca aagtgcaagc gcacagagat aattacaaat  4020
tacctgtcag atcatagcgc gatcaagctc gagctgagaa tcaagaacct gacccagagc  4080
cggagtacca cttggaagct taataacctg ctgctcaacg attattgggt ccacaatgag  4140
atgaaggcag agattaaaat gttcttcgaa acaaatgaga ataaggatac tacctatcaa  4200
aacctttggg atgcctttaa ggccgtctgc agaggcaagt tcatcgccct caacgcctat  4260
aaaagaaaac aagagagatc taagatcgat actctcacct ctcagctgaa ggagttggag  4320
aaacaggaac agacccactc caaggcgtca agacggcagg agatcacaaa gattcgcgcc  4380
gagttgaaag agatcgaaac ccaaaagact cttcagaaaa ttaacgagtc tcgtagttgg  4440
ttcttcgagc ggattaataa gatagacaga cctctggcac gactgattaa gaagaagcgc  4500
gaaaagaacc agattgatac catcaagaac gacaagggcg acatcactac tgacccgacc  4560
gagatccaga ccactattcg ggagtattat aagcatttgt atgctaacaa gcttgagaac  4620
ctggaagaga tggacacttt tctggatacc tatactctgc cacggcttaa tcaagaggaa  4680
gtcgagtccc tcaaccgccc aattacagga agcgagattg tggccataat taactccctg  4740
ccgacaaaga aatctcctgg tccggacggg tttacagctg agttttatca acggtatatg  4800
gaagagcttg taccgtttct gctcaagctc tttcagtcta tagaaaagga aggcatcttg  4860
cccaattcct tctacgaagc ttctataata cttattccca aaccaggacg cgataccaca  4920
aagaaggaaa acttccggcc cattagtctc atgaatatcg acgctaaaat attgaacaag  4980
attctcgcca acagaatcca acaacatatt aagaaattga tacatcacga ccaggtgggg  5040
tttatacctg gcatgcaggg ctggtttaac atccggaaga gtattaacgt cattcaacac  5100
attaatagag ctaaggataa gaatcatatg atcatctcta tagacgcgga aaaggcattc  5160
gataagattc agcagccatt tatgctcaag actctgaaca aactcggcat cgacggaaca  5220
tattttaaga ttattcgcgc aatttacgat aagccgactg ctaacattat ccttaacggc  5280
caaaagctcg aggcctttcc gctcaagact ggaacccgcc aaggctgtcc cctctccccg  5340
cttttgttta atattgtact cgaggtgctg gctagggcta ttcgtcaaga gaaagagatt  5400
aaagggatac agctcgggaa ggaagaggtc aagctttcct tgttcgccga tgatatgatt  5460
gtgtacctgg agaatcctat tgtgtctgct cagaaccttc ttaaacttat ttctaacttt  5520
agcaaggtca gcggctataa gattaacgtc cagaaatctc aggcctttct gtacacaaat  5580
aatcgacaga ccgaatccca gataatgggt gagcttccgt ttgtcatagc cagcaaaagg  5640
ataaagtatc tcggaatcca gctgacacga gacgttaaag atttgtttaa ggaaaattac  5700
aagcctctcc tgaaagagat taaggaagat actaataagt ggaagaatat cccctgttca  5760
tgggttggca gaatcaacat agtgaagatg gcaatacttc ctaaagtgat atatcgcttt  5820
aacgccatcc caattaaact gcctatgacc ttctttacgg agctcgagaa aacaaccctt  5880
aaatttatat ggaatcaaaa gagagcaaga atagcgaagt ccatcttgag ccagaagaat  5940
aaggccggtg ggattacttt gcctgatttt aagttgtatt ataaagccac agtaactaag  6000
acagcctggt attggtatca gaatagagac atcgaccagt ggaatcggac cgaaccatca  6060
gagataatgc cccacatcta taattacctt atattcgata agccagaaaa gaataaacag  6120
tggggcaaag acagcctctt caacaagtgg tgttgggaga attggctggc catatgccgg  6180
aaactcaagc tcgacccctt tcttacaccc tacactaaaa tcaacagtag gtggatcaag  6240
gacttgaatg tcaagccaaa gactataaag acactggaag agaatcttgg gatcacaata  6300
caagatatag gcgtcggcaa agattttatg tcaaagacgc ccaaggccat ggccactaag  6360
gataagattg ataagtggga ccttattaag ctcaaaagct tctgtactgc caaggagacc  6420
acgatcagag ttaataggca gcccactaca tgggaaaaga ttttcgccac ttattcatca  6480
gataaggggt tgataagcag aatatataac gagctgaagc agatctacaa gaagaaaacg  6540
aataatccca tcaagaagtg ggcaaaagat atgaacaggc attttagcaa agaggatatc  6600
```

-continued

```
tacgccgcga agaagcatat gaagaagtgt agttcaagct tggccattcg tgagatgcag  6660
attaagacga ccatgcgata ccaccttacc ccagtgagga tggcaattat caagaaatct  6720
ggcaataata gatgttggcg gggctgtggc gagattggca ccctgctcca ttgctggtgg  6780
gattgcaagc tggtgcagcc gctttggaaa tcagtctggc gctttctgag ggacctcgag  6840
cttgagattc ccttcgatcc cgcaattccc ttgctcggaa tctatcctaa cgaatacaag  6900
agctgttgtt acaaggatac gtgtacccgg atgttcatcg cggccttgtt tacgatagct  6960
aagacgtgga atcagcctaa gtgccccaca atgatcgatt ggatcaagaa aatgtggcat  7020
atttatacca tggagtatta cgcagcaatt aagaatgacg aatttatttc cttcgttggg  7080
acctggatga agctggagac tattattctg agcaagctgt ctcaggagca aaagacaaag  7140
catagaatct tctctctcat tggtggtaac gactacaaag acgatgacga caagggcggc  7200
ggcagcccaa agaagaagcg gaaggtctaa agcgcttcta gaagttgtct cctcctgcac  7260
tgactgactg atacaatcga tttctggatc cgcaggccta atcaacctct ggattacaaa  7320
atttgtgaaa gattgactgg tattcttaac tatgttgctc cttttacgct atgtggatac  7380
gctgctttaa tgcctttgta tcatgctatt gcttcccgta tggctttcat tttctcctcc  7440
ttgtataaat cctggttgct gtctctttat gaggagttgt ggcccgttgt caggcaacgt  7500
ggcgtggtgt gcactgtgtt tgctgacgca acccccactg gttggggcat tgccaccacc  7560
tgtcagctcc tttccgggac tttcgctttc cccctcccta ttgccacggc ggaactcatc  7620
gccgcctgcc ttgcccgctg ctggacaggg gctcggctgt tgggcactga caattccgtg  7680
gtgttgtcgg ggaagctgac gtcctttcca tggctgctcg cctgtgttgc cacctggatt  7740
ctgcgcggga cgtccttctg ctacgtccct tcggccctca atccagcgga ccttccttcc  7800
cgctgagaga cacaaaaaat tccaacacac tattgcaatg aaaataaatt tcctttatta  7860
gccagaagtc agatgctcaa ggggcttcat gatgtcccca taatttttgg cagagggaaa  7920
aagatctcag tggtatttgt gagccagggc attggccttc tgataggcag cctgcacctg  7980
aggagtgcgg ccgctttact tgtacagctc gtccatgccg agagtgatcc cggcggcggt  8040
cacgaactcc agcaggacca tgtgatcgcg cttctcgttg gggtctttgc tcagggcgga  8100
ctgggtgctc aggtagtggt tgtcgggcag cagcacgggg ccgtcgccga tgggggtgtt  8160
ctgctggtag tggtcggcga gctgcacgct gccgtcctcg atgttgtggc ggatcttgaa  8220
gttcaccttg atgccgttct tctgcttgtc ggccatgata tagacgttgt ggctgttgta  8280
gttgtactcc agcttgtgcc ccaggatgtt gccgtcctcc ttgaagtcga tgcccttcag  8340
ctcgatgcgg ttcaccaggg tgtcgccctc gaacttcacc tcggcgcggg tcttgtagtt  8400
gccgtcgtcc ttgaagaaga tggtgcgctc ctggacgtag ccttcgggca tggcggactt  8460
gaagaagtcg tgctgcttca tgtggtcggg gtagcggctg aagcactgca cgccgtaggt  8520
cagggtggtc acgagggtgg gccagggcac gggcagcttg ccggtggtgc agatgaactt  8580
cagggtcagc ttgccgtagg tggcatcgcc ctcgccctcg ccggacacgc tgaacttgtg  8640
gccgtttacg tcgccgtcca gctcgaccag gatgggcacc accccggtga acagctcctc  8700
gcccttgctc accatggtgg cgggatctga cggttcacta aaccagctct gcttatatag  8760
acctcccacc gtacacgcct accgcccatt tgcgtcaatg gggcggagtt gttacgacat  8820
tttggaaagt cccgttgatt ttggtgccaa aacaaactcc cattgacgtc aatggggtgg  8880
agacttggaa atccccgtga gtcaaaccgc tatccacgcc cattgatgta ctgccaaaac  8940
cgcatcacca tggtaatagc gatgactaat acgtagatgt actgccaagt aggaaagtcc  9000
cataaggtca tgtactgggc ataatgccag gcgggccatt taccgtcatt gacgtcaata  9060
gggggcgtac ttggcatatg atacacttga tgtactgcca agtgggcagt ttaccgtaaa  9120
tactccaccc attgacgtca atggaaagtc cctattggcg ttactatggg aacatacgtc  9180
attattgacg tcaatgggcg ggggtcgttg ggcggtcagc caggcgggcc atttaccgta  9240
agttatgtaa cgggcctgct gccggctctg cggcctcttc cgcgtcttcg ccttcgccct  9300
cagacgagtc ggatctccct ttgggccgcc tccccgcctg tctagcttga ctgactgaga  9360
tacagcgtac cttcagctca cagacatgat aagatacatt gatgagtttg gacaaaccac  9420
aactagaatg cagtgaaaaa aatgctttat ttgtgaaatt tgtgatgcta ttgctttatt  9480
tgtaaccatt ataagctgca ataaacaagt taacaacaac aattgcattc attttatgtt  9540
tcaggttcag ggggaggtgt gggaggtttt ttaaagcaag taaaacctct acaaatgtgg  9600
tattggccca tctctatcgg tatcgtagca taaccccttg gggcctctaa acgggtcttg  9660
aggggttttt tgtgcccctc gggccggatt gctatctacc ggcattggcg cagaaaaaaa  9720
tgcctgatgc gacgctgcgc gtcttatact cccacatatg ccagattcag caacggatac  9780
ggcttcccca acttgcccac ttccatacgt gtcctcctta ccagaaattt atccttaagg  9840
tcgtcagcta tcctgcaggc gatctctcga tttcgatcaa gacattcctt taatggtctt  9900
ttctggacac cactaggggt cagaagtagt tcatcaaact ttcttccctc cctaatctca  9960
ttggttacct tgggctatcg aaacttaatt aagcgatctg catctcaatt agtcagcaac  10020
catagtcccg cccctaactc cgcccatccc gcccctaact ccgcccagtt ccgcccattc  10080
tccgccccat cgctgactaa ttttttttat ttatgcagag gccgaggccg cctcggcctc  10140
tgagctattc cagaagtagt gaggaggctt ttttggaggc ctaggctttt gcaaaggagg  10200
tagccaacat gattgaacaa gatggattgc acgcaggttc tcccgccgct tgggtggaga  10260
ggctattcgg ctatgactgg gcacaacaga caatcggctg ctctgatgcc gccgtgttcc  10320
ggctgtcagc gcaggggcgc ccggttcttt ttgtcaagac cgacctgtcc ggtgccctga  10380
atgaactcca ggacgaggca gcgcggctat cgtggctggc cacgacgggc gttccttgcg  10440
cagctgtgct cgacgttgtc actgaagcgg gaagggactg gctgctattg ggcgaagtgc  10500
cggggcagga tctcctgtca tctcaccttg ctcctgccga gaaagtatcc atcatggctg  10560
atgcaatgcg gcggctgcat acgcttgatc cggctacctg cccattcgac caccaagcga  10620
aacatcgcat cgagcgagca cgtactcgga tggaagccgg tcttgtcgat caggatgatc  10680
tggacgaaga gcatcagggg ctcgcgccag ccgaactgtt cgccaggctc aaggcgcgga  10740
tgcccgacgg cgaggatctc gtcgtgaccc acggcgatgc ctgcttgccg aatatcatgg  10800
tggaaaatgg ccgcttttct ggattcatcg actgtggccg gctgggtgtg gcggaccgct  10860
atcaggacat agcgttggct acccgtgata ttgctgaaga gcttggcggc gaatgggctg  10920
accgcttcct cgtgctttac ggtatcgccg ctcccgattc gcagcgcatc gccttctatc  10980
gccttcttga cgagttcttc tagtatgtaa gccctgtgcc ttctagttgc cagccatctg  11040
ttgtttgccc ctcccccgtg ccttccttga ccctggaagg tgccactccc actgtccttt  11100
cctaataaaa tgaggaaatt gcatcgcatt gtctgagtag gtgtcattct attctggggg  11160
gtggggtggg gcaggacagc aagggggagg attgggaaga caatagcagg catgctgggg  11220
atgcggtggg ctctatggtt aattaaccag tcaagtcagc tacttggcga gatcgacttg  11280
tctgggtttc gactacgctc agaattgcgt cagtcaagtt cgatctggtc cttgctattg  11340
```

```
cacccgttct ccgattacga gtttcattta aatcatgtga gcaaaaggcc agcaaaaggc  11400
caggaaccgt aaaaaggccg cgttgctggc gtttttccat aggctccgcc cccctgacga  11460
gcatcacaaa aatcgacgct caagtcagag gtggcgaaac ccgacaggac tataaagata  11520
ccaggcgttt ccccctggaa gctccctcgt gcgctctcct gttccgaccc tgccgcttac  11580
cggatacctg tccgcctttc tcccttcggg aagcgtggcg ctttctcata gctcacgctg  11640
taggtatctc agttcggtgt aggtcgttcg ctccaagctg ggctgtgtgc acgaaccccc  11700
cgttcagccc gaccgctgcg ccttatccgg taactatcgt cttgagtcca acccggtaag  11760
acacgactta tcgccactgg cagcagccac tggtaacagg attagcagag cgaggtatgt  11820
aggcggtgct acagagttct tgaagtggtg gcctaactac ggctacacta gaagaacagt  11880
atttggtatc tgcgctctgc tgaagccagt taccttcgga aaaagagttg gtagctcttg  11940
atccggcaaa caaaccaccg ctggtagcgg tggttttttt gtttgcaagc agcagattac  12000
gcgcagaaaa aaaggatctc aagaagatcc tttgatcttt tctacggggt ctgacgctca  12060
gtggaacgaa aactcacgtt aagggatttt ggtcatgaga ttatcaaaaa ggatcttcac  12120
ctagatcctt ttaaattaaa aatgaagttt taaatcaatc taaagtatat atgagtaaac  12180
ttggtctgac agttaccaat gcttaatcag tgaggcacct atctcagcga tctgtctatt  12240
tcgttcatcc atagttgcat ttaaatttcc gaactctcca aggccctcgt cggaaaatct  12300
tcaaaccttt cgtccgatcc atcttgcagg ctacctctcg aacgaactat cgcaagtctc  12360
ttggccggcc ttgcgccttg gctattgctt ggcagcgcct atcgccaggt attactccaa  12420
tcccgaatat ccgagatcgg gatcacccga gagaagttca acctacatcc tcaatcccga  12480
tctatccgag atccgaggaa tatcgaaatc ggggcgcgcc tggtgtaccg agaacgatcc  12540
tctcagtgcg agtc                                                   12554

SEQ ID NO: 106         moltype = DNA  length = 12569
FEATURE                Location/Qualifiers
misc_feature           1..12569
                       note = Description of Artificial Sequence: Synthetic
                        polynucleotide
source                 1..12569
                       mol_type = other DNA
                       organism = synthetic construct
SEQUENCE: 106
accgagaacg atcctctcag tgcgagtctc gacgatccat atcgttgctt ggcagtcagc  60
cagtcggaat ccagcttggg acccaggaag tccaatcgtc agatattgta ctcaagcctg  120
gtcacggcag cgtaccgatc tgtttaaacc tagatattga tagtctgatc ggtcaacgta  180
taatcgagtc ctagcttttg caaacatcta tcaagagaca ggatcagcag gaggctttcg  240
catgagtatt caacatttcc gtgtcgccct tattcccttt tttgcggcat tttgccttcc  300
tgtttttgct cacccagaaa cgctggtgaa agtaaaagat gctgaagatc agttgggtgc  360
gcgagtgggt tacatcgaac tggatctcaa cagcggtaag atccttgaga gttttcgccc  420
cgaagaacgc tttccaatga tgagcacttt taaagttctg ctatgtggcg cggtattatc  480
ccgtattgac gccgggcaag agcaactcgg tcgccgcata cactattctc agaatgactt  540
ggttgagtat tcaccagtca cagaaaagca tcttacggat ggcatgacag taagagaatt  600
atgcagtgct gccataacca tgagtgataa cactgcggcc aacttacttc tgacaacgat  660
tggaggaccg aaggagctaa ccgctttttt gcacaacatg ggggatcatg taactcgcct  720
tgatcgttgg gaaccggagc tgaatgaagc cataccaaac gacgagcgtg acaccacgat  780
gcctgtagca atggcaacaa ccttgcgtaa actattaact ggcgaactac ttactctagc  840
ttcccggcaa cagttgatag actggatgga ggcggataaa gttgcaggac cacttctgcg  900
ctcggccctt ccggctggct ggtttattgc tgataaatct ggagccggtg agcgtgggtc  960
tcgcggtatc attgcagcac tggggccaga tggtaagccc tcccgtatcg tagttatcta  1020
cacgacgggg agtcaggcaa ctatggatga acgaaataga cagatcgctg agataggtgc  1080
ctcactgatt aagcattggt aaccgattct aggtgcattg gcgcagaaaa aaatgcctga  1140
tgcgacgctg cgcgtcttat actcccacat atgccagatt cagcaacgga tacggcttcc  1200
ccaacttgcc cacttccata cgtgtcctcc ttaccagaaa tttatcctta agatcgttta  1260
aactcgactc tggctctatc gaatctccgt cgtttcgagc ttacgcgaac agccgtggcg  1320
ctcatttgct cgtcgggcat cgaatctcgt cagctatcgt cagcttacct ttttggcagc  1380
gatcgcggct cccgacatct tggaccatta gctccacagg tatcttcttc cctctagtgg  1440
tcataacagc agcttcagct acctctcaat tcaaaaaacc cctcaagacc cgtttagagg  1500
ccccaagggg ttatgctatc aatcgttgcg ttacacacac aaaaaaccaa cacacatcca  1560
tcttcgatgg atagcgattt tattatctaa ctgctgatcg agtgtagcca gatctagtaa  1620
tcaattacgg ggtcattagt tcatagccca tatatggagt tccgcgttac ataacttacg  1680
gtaaatggcc cgcctggctg accgcccaac gacccccgcc cattgacgtc aataatgacg  1740
tatgttccca tagtaacgcc aatagggact ttccattgac gtcaatgggt ggagtattta  1800
cggtaaactg cccacttggc agtacatcaa gtgtatcata tgccaagtac gccccctatt  1860
gacgtcaatg acggtaaatg gcccgcctgg cattatgccc agtacatgac cttatgggac  1920
tttcctactt ggcagtacat ctacgtatta gtcatcgcta ttaccatgct gatgcggttt  1980
tggcagtaca tcaatgggcg tggatagcgg tttgactcac ggggatttcc aagtctccac  2040
cccattgacg tcaatgggag tttgttttgg caccaaaatc aacgggactt tccaaaatgt  2100
cgtaacaact ccgccccatt gacgcaaatg ggcggtaggc gtgtacggtg ggaggtctat  2160
ataagcagag ctggtttagt gaaccgtcag atcagatctt tgtcgatcct accatccact  2220
cgacacaccc gccagcggcc gctaatacga ctcactatag ggagaagtac tgccaccatg  2280
ggcaagaagc aaaatcgcaa gacggggaat tccaagacac aatccgctag cccaccacct  2340
aaagagcgtt ctagctcccc tgctactgag cagtcctgga tggaaaacga cttcgatgaa  2400
ctccgggaag agggatttag gcgatccaac tattcagaac tccgcgaaga tatccagaca  2460
aaggggaagg aagtcgagaa tttcgagaag aacctcgagg agtgcatcac ccgtatcaca  2520
aacactgaga aatgtctcaa agaactcatg gaacttaaga caaaagccag ggagcttcga  2580
gaggagtgtc ggagtctgag atccaggtgt gaccagctcg aggagcgcgt gagcgcgatg  2640
gaagacgaga tgaacgagat gaaaagagag ggcaaattca gggagaagcg cattaagagg  2700
aacgaacaga gtctgcagga gatttgggat tacgtcaaga ggcctaacct gcggttgatc  2760
ggcgtccccg agagcgacgt agaaaacggg actaaactgg agaatacact tcaagacatc  2820
attcaagaaa attttccaaa cctggctcgg caagctaatg tgcaaatcca agagatccaa  2880
```

-continued

```
cgcacacccc agcggtatag ctctcggcgt gccaccccta ggcatattat cgtgcgcttt  2940
actaaggtgg agatgaaaga gaagatgctg cgagccgctc gggaaaaggg aagggtgact  3000
ttgaagggca aacctattcg gctgacggtt gaccttagcg ccgagacact ccaggcacgc  3060
cgggaatggg gccccatctt taatatcctg aaggagaaga acttccagcc acgaatctct  3120
taccctgcaa agttgagttt tatctccgag ggtgagatta agtatttcat cgataaacag  3180
atgctgcgag acttcgtgac aactcgccca gctctcaagg aactgctcaa agaggctctt  3240
aatatggagc gcaataatag atatcaaccc ttgcagaacc acgcaaagat gtgagacagc  3300
cgtcagacca tcaagactag gaagaaactg catcaactaa tgagcaaaat caccagctaa  3360
catcatagta tacatgaccg gctctaactc acatatcacc atccttacac ttaacattaa  3420
cggcctcaac tcagctatca agcgccatcg gctggccagc tggatcaaat cacaggatcc  3480
aagcgtttgt tgcatccaag agacccacct gacctgtaga gatactcacc gcctcaagat  3540
caagggatgg cgaaagattt atcaggcgaa cggtaagcag aagaaagccg gagtcgcaat  3600
tctggtctca gacaagacgg atttcaagcc caccaaaatt aagcgtgata aggaaggtca  3660
ctatattatg gtgaaaggca gcatacagca ggaagaactt accatattga acatctacgc  3720
gccaaacacc ggcgcacctc gctttatcaa acaggtcctg tccgatctgc agcgagatct  3780
ggattctcat acgttgatta tgggtgattt caatacacca ttgagcaccc tggatcgcag  3840
caccaggcaa aaggtaaata aagacacgca agagctcaat agcgcactgc atcaggcaga  3900
tctcattgat atttatcgca ctcttcatcc taagagtacc gagtacacat tcttcagcgc  3960
cccacatcat acatactcaa agatcgatca tatcgtcggc tcaaaggctc tgctgtcaaa  4020
gtgcaagcgc acagagataa ttacaaatta cctgtcagat catagcgcga tcaagctcga  4080
gctgagaatc aagaacctga cccagagccg gagtaccact tggaagctta ataacctgct  4140
gctcaacgat tattgggtcc acaatgagat gaaggcagag attaaaatgt tcttcgaaac  4200
aaatgagaat aaggatacta cctatcaaaa cctttgggat gcctttaagg ccgtctgcag  4260
aggcaagttc atcgccctca acgcctataa aagaaaacaa gagagatcta agatcgatac  4320
tctcacctct cagctgaagg agttggagaa acaggaacag acccactcca aggcgtcaag  4380
acggcaggag atcacaaaga ttcgcgccga gttgaaagag atcgaaaccc aaaagactct  4440
tcagaaaatt aacgagtctc gtagttggtt cttcgagcgg attaataaga tagacagacc  4500
tctggcacga ctgattaaga agaagcgcga aaagaaccag attgatacca tcaagaacga  4560
caagggcgac atcactactg acccgaccga gatccagacc actattcggg agtattataa  4620
gcatttgtat gctaacaagc ttgagaacct ggaagagatg gacacttttc tggataccta  4680
tactctgcca cggcttaatc aagaggaagt cgagtccctc aaccgcccaa ttacaggaag  4740
cgagattgtg gccataatta actccctgcc gacaaagaaa tctcctggtc cggacgggtt  4800
tacagctgag ttttatcaac ggtatatgga agagcttgta ccgtttctgc tcaagctctt  4860
tcagtctata gaaaaggaag gcatcttgcc caattccttc tacgaagctt ctataatact  4920
tattcccaaa ccaggacgcg ataccacaaa gaaggaaaac ttccggccca ttagtctcat  4980
gaatatcgac gctaaaatat tgaacaagat tctcgccaac agaatccaac aacatattaa  5040
gaaattgata catcacgacc aggtggggtt tatacctggc atgcagggct ggtttaacat  5100
ccggaagagt attaacgtca ttcaacacat taatagagct aaggataaga atcatatgat  5160
catctctata gacgcggaaa aggcattcga taagattcag cagccattta tgctcaagac  5220
tctgaacaaa ctcggcatcg acggaacata ttttaagatt attcgcgcaa tttacgataa  5280
gccgactgct aacattatcc ttaacggcca aaagctcgag gcctttccgc tcaagactgg  5340
aacccgccaa ggctgtcccc tctccccgct tttgtttaat attgtactcg aggtgctggc  5400
tagggctatt cgtcaagaga aagagattaa agggatacag ctcgggaagg aagaggtcaa  5460
gctttccttg ttcgccgatg atatgattgt gtacctggag aatcctattg tgtctgctca  5520
gaaccttctt aaacttattt ctaactttag caaggtcagc ggctataaga ttaacgtcca  5580
gaaatctcag gcctttctgt acacaaataa tcgacagacc gaatcccaga taatgggtga  5640
gcttccgttt gtcatagcca gcaaaaggat aaagtatctc ggaatccagc tgacacgaga  5700
cgttaaagat ttgtttaagg aaaattacaa gcctctcctg aaagagatta aggaagatac  5760
taataagtgg aagaatatcc cctgttcatg ggttggcaga atcaacatag tgaagatggc  5820
aatacttcct aaagtgatat atcgctttaa cgccatccca attaaactgc ctatgacctt  5880
ctttacggag ctcgagaaaa caacccttaa atttatatgg aatcaaaaga gagcaagaat  5940
agcgaagtcc atcttgagcc agaagaataa ggccggtggg attactttgc ctgattttaa  6000
gttgtattat aaagccacag taactaagac agcctggtat tggtatcaga atagagacat  6060
cgaccagtgg aatcggaccg aaccatcaga gataatgccc cacatctata attaccttat  6120
attcgataag ccagaaaaga ataaacagtg gggcaaagac agcctcttca acaagtggtg  6180
ttgggagaat tggctggcca tatgccggaa actcaagctc gaccccttc ttacacccta  6240
cactaaaatc aacagtaggt ggatcaagga cttgaatgtc aagccaaaga ctataaagac  6300
actggaagag aatcttggga tcacaataca agatataggc gtcggcaaag attttatgtc  6360
aaagacgccc aaggccatgg ccactaagga taagattgat aagtgggacc ttattaagct  6420
caaaagcttc tgtactgcca aggagaccac gatcagagtt aataggcagc ccactacatg  6480
ggaaaagatt ttcgccactt attcatcaga taaggggttg ataagcagaa tatataacga  6540
gctgaagcag atctacaaga agaaaacgaa taatcccatc aagaagtggg caaaagatat  6600
gaacaggcat tttagcaaag aggatatcta cgccgcgaag aagcatatga agaagtgtag  6660
ttcaagcttg gccattcgtg agatgcagat taagacgacc atgcgatacc accttacccc  6720
agtgaggatg gcaattatca agaaatctgg caataataga tgttggcggg gctgtggcga  6780
gattggcacc ctgctccatt gctggtggga ttgcaagctg gtgcagccgc tttggaaatc  6840
agtctggcgc tttctgaggg acctcgagct tgagattccc ttcgatcccg caattccctt  6900
gctcggaatc tatcctaacg aatacaagag ctgttgttac aaggatacgt gtacccggat  6960
gttcatcgcg gccttgttta cgatagctaa gacgtggaat cagcctaagt gccccacaat  7020
gatcgattgg atcaagaaaa tgtggcatat ttataccatg gagtattacg cagcaattaa  7080
gaatgacgaa tttatttcct tcgttgggac ctggatgaag ctggagacta ttattctgag  7140
caagctgtct caggagcaaa agacaaagca tagaatcttc tctctcattg gtggtaacga  7200
ctacaaagac gatgacgaca agaaaaggcc ggcggccacg aaaaaggccg gccaggcaaa  7260
aaagaaaaag taaagcgctt ctagaagttg tctcctcctg cactgactga ctgatacaat  7320
cgatttctgg atccgcaggc ctaatcaacc tctggattac aaaatttgtg aaagattgac  7380
tggtattctt aactatgttg ctccttttac gctatgtgga tacgctgctt taatgccttt  7440
gtatcatgct attgcttccc gtatggcttt cattttctcc tccttgtata aatcctggtt  7500
gctgtctctt tatgaggagt tgtggcccgt tgtcaggcaa cgtggcgtgg tgtgcactgt  7560
gtttgctgac gcaaccccca ctggttgggg cattgccacc acctgtcagc tcctttccgg  7620
```

```
gactttcgct ttccccctcc ctattgccac ggcggaactc atcgccgcct gccttgcccg  7680
ctgctggaca ggggctcggc tgttgggcac tgacaattcc gtggtgttgt cggggaagct  7740
gacgtccttt ccatggctgc tcgcctgtgt tgccacctgg attctgcgcg ggacgtcctt  7800
ctgctacgtc ccttcggccc tcaatccagc ggaccttcct tcccgctgag agacacaaaa  7860
aattccaaca cactattgca atgaaaataa atttccttta ttagccagaa gtcagatgct  7920
caaggggctt catgatgtcc ccataatttt tggcagaggg aaaaagatct cagtggtatt  7980
tgtgagccag ggcattggcc ttctgatagg cagcctgcac ctgaggagtg cggccgcttt  8040
acttgtacag ctcgtccatg ccgagagtga tcccggcggc ggtcacgaac tccagcagga  8100
ccatgtgatc gcgcttctcg ttggggtctt tgctcagggc ggactgggtg ctcaggtagt  8160
ggttgtcggg cagcagcacg gggccgtcgc cgatgggggt gttctgctgg tagtggtcgg  8220
cgagctgcac gctgccgtcc tcgatgttgt ggcggatctt gaagttcacc ttgatgccgt  8280
tcttctgctt gtcggccatg atatagacgt tgtggctgtt gtagttgtac tccagcttgt  8340
gccccaggat gttgccgtcc tccttgaagt cgatgccctt cagctcgatg cggttcacca  8400
gggtgtcgcc ctcgaacttc acctcggcgc gggtcttgta gttgccgtcg tccttgaaga  8460
agatggtgcg ctcctggacg tagccttcgg gcatggcgga cttgaagaag tcgtgctgct  8520
tcatgtggtc ggggtagcgg ctgaagcact gcacgccgta ggtcagggtg gtcacgaggg  8580
tgggccaggg cacgggcagc ttgccggtgg tgcagatgaa cttcagggtc agcttgccgt  8640
aggtggcatc gccctcgccc tcgccggaca cgctgaactt gtggccgttt acgtcgccgt  8700
ccagctcgac caggatgggc accaccccgg tgaacagctc ctcgcccttg ctcaccatgg  8760
tggcgggatc tgacggttca ctaaaccagc tctgcttata tagacctccc accgtacacg  8820
cctaccgccc atttgcgtca atggggcgga gttgttacga cattttggaa agtcccgttg  8880
attttggtgc caaaacaaac tcccattgac gtcaatgggg tggagacttg gaaatccccg  8940
tgagtcaaac cgctatccac gcccattgat gtactgccaa aaccgcatca ccatggtaat  9000
agcgatgact aatacgtaga tgtactgcca agtaggaaag tcccataagg tcatgtactg  9060
ggcataatgc caggcgggcc atttaccgtc attgacgtca atagggggcg tacttggcat  9120
atgatacact tgatgtactg ccaagtgggc agtttaccgt aaatactcca cccattgacg  9180
tcaatggaaa gtccctattg gcgttactat gggaacatac gtcattattg acgtcaatgg  9240
gcgggggtcg ttgggcggtc agccaggcgg gccatttacc gtaagttatg taacggccct  9300
gctgccggct ctgcggcctc ttccgcgtct tcgccttcgc cctcagacga gtcggatctc  9360
cctttgggcc gcctccccgc ctgtctagct tgactgactg agatacagcg taccttcagc  9420
tcacagacat gataagatac attgatgagt ttggacaaac cacaactaga atgcagtgaa  9480
aaaaatgctt tatttgtgaa atttgtgatg ctattgcttt atttgtaacc attataagct  9540
gcaataaaca agttaacaac aacaattgca ttcattttat gtttcaggtt cagggggagg  9600
tgtgggaggt tttttaaagc aagtaaaacc tctacaaatg tggtattggc ccatctctat  9660
cggtatcgta gcataacccc ttggggcctc taaacgggtc ttgaggggtt ttttgtgccc  9720
ctcgggccgg attgctatct accggcattg gcgcagaaaa aaatgcctga tgcgacgctg  9780
cgcgtcttat actcccacat atgccagatt cagcaacgga tacggcttcc ccaacttgcc  9840
cacttccata cgtgtcctcc ttaccagaaa tttatcctta aggtcgtcag ctatcctgca  9900
ggcgatctct cgatttcgat caagacattc ctttaatggt cttttctgga caccactagg  9960
ggtcagaagt agttcatcaa actttcttcc ctccctaatc tcattggtta ccttgggcta  10020
tcgaaactta attaagcgat ctgcatctca attagtcagc aaccatagtc ccgcccctaa  10080
ctccgcccat cccgccccta actccgccca gttccgccca ttctccgccc catcgctgac  10140
taattttttt tatttatgca gaggccgagg ccgcctcggc ctctgagcta ttccagaagt  10200
agtgaggagg cttttttgga ggcctaggct tttgcaaagg aggtagccaa catgattgaa  10260
caagatggat tgcacgcagg ttctcccgcc gcttgggtgg agaggctatt cggctatgac  10320
tgggcacaac agacaatcgg ctgctctgat gccgccgtgt tccggctgtc agcgcagggg  10380
cgcccggttc tttttgtcaa gaccgacctg tccggtgccc tgaatgaact ccaggacgag  10440
gcagcgcggc tatcgtggct ggccacgacg ggcgttcctt gcgcagctgt gctcgacgtt  10500
gtcactgaag cgggaaggga ctggctgcta ttgggcgaag tgccggggca ggatctcctg  10560
tcatctcacc ttgctcctgc cgagaaagta tccatcatgg ctgatgcaat gcggcggctg  10620
catacgcttg atccggctac ctgcccattc gaccaccaag cgaaacatcg catcgagcga  10680
gcacgtactc ggatggaagc cggtcttgtc gatcaggatg atctggacga agagcatcag  10740
gggctcgcgc cagccgaact gttcgccagg ctcaaggcgc ggatgcccga cggcgaggat  10800
ctcgtcgtga cccacggcga tgcctgcttg ccgaatatca tggtggaaaa tggccgcttt  10860
tctggattca tcgactgtgg ccggctgggt gtggcggacc gctatcagga catagcgttg  10920
gctacccgtg atattgctga agagcttggc ggcgaatggg ctgaccgctt cctcgtgctt  10980
tacggtatcg ccgctcccga ttcgcagcgc atcgccttct atcgccttct tgacgagttc  11040
ttctagtatg taagccctgt gccttctagt tgccagccat ctgttgtttg cccctccccc  11100
gtgccttcct tgaccctgga aggtgccact cccactgtcc tttcctaata aaatgaggaa  11160
attgcatcgc attgtctgag taggtgtcat tctattctgg ggggtggggt ggggcaggac  11220
agcaaggggg aggattggga agacaatagc aggcatgctg gggatgcggt gggctctatg  11280
gttaattaac cagtcaagtc agctacttgg cgagatcgac ttgtctgggt ttcgactacg  11340
ctcagaattg cgtcagtcaa gttcgatctg gtccttgcta ttgcacccgt tctccgatta  11400
cgagtttcat ttaaatcatg tgagcaaaag gccagcaaaa ggccaggaac cgtaaaaagg  11460
ccgcgttgct ggcgtttttc cataggctcc gcccccctga cgagcatcac aaaaatcgac  11520
gctcaagtca gaggtggcga aacccgacag gactataaag ataccaggcg tttccccctg  11580
gaagctccct cgtgcgctct cctgttccga ccctgccgct taccggatac ctgtccgcct  11640
ttctcccttc gggaagcgtg gcgctttctc atagctcacg ctgtaggtat ctcagttcgg  11700
tgtaggtcgt tcgctccaag ctgggctgtg tgcacgaacc ccccgttcag cccgaccgct  11760
gcgccttatc cggtaactat cgtcttgagt ccaacccggt aagacacgac ttatcgccac  11820
tggcagcagc cactggtaac aggattagca gagcgaggta tgtaggcggt gctacagagt  11880
tcttgaagtg gtggcctaac tacggctaca ctagaagaac agtatttggt atctgcgctc  11940
tgctgaagcc agttaccttc ggaaaaagag ttggtagctc ttgatccggc aaacaaacca  12000
ccgctggtag cggtggtttt tttgtttgca agcagcagat tacgcgcaga aaaaaaggat  12060
ctcaagaaga tcctttgatc ttttctacgg ggtctgacgc tcagtggaac gaaaactcac  12120
gttaagggat tttggtcatg agattatcaa aaaggatctt cacctagatc cttttaaatt  12180
aaaaatgaag ttttaaatca atctaaagta tatatgagta aacttggtct gacagttacc  12240
aatgcttaat cagtgaggca cctatctcag cgatctgtct atttcgttca tccatagttg  12300
catttaaatt tccgaactct ccaaggccct cgtcggaaaa tcttcaaacc tttcgtccga  12360
```

```
tccatcttgc aggctacctc tcgaacgaac tatcgcaagt ctcttggccg gccttgcgcc  12420
ttggctattg cttggcagcg cctatcgcca ggtattactc caatcccgaa tatccgagat  12480
cgggatcacc cgagagaagt tcaacctaca tcctcaatcc cgatctatcc gagatccgag  12540
gaatatcgaa atcggggcgc gcctggtgt                                   12569

SEQ ID NO: 107         moltype = DNA  length = 12581
FEATURE                Location/Qualifiers
misc_feature           1..12581
                       note = Description of Artificial Sequence: Synthetic
                        polynucleotide
source                 1..12581
                       mol_type = other DNA
                       organism = synthetic construct
SEQUENCE: 107
ccgagaacga tcctctcagt gcgagtctcg acgatccata tcgttgcttg gcagtcagcc  60
agtcggaatc cagcttggga cccaggaagt ccaatcgtca gatattgtac tcaagcctgg  120
tcacggcagc gtaccgatct gtttaaacct agatattgat agtctgatcg gtcaacgtat  180
aatcgagtcc tagcttttgc aaacatctat caagagacag gatcagcagg aggctttcgc  240
atgagtattc aacatttccg tgtcgccctt attccctttt ttgcggcatt ttgccttcct  300
gtttttgctc acccagaaac gctggtgaaa gtaaaagatg ctgaagatca gttgggtgcg  360
cgagtgggtt acatcgaact ggatctcaac agcggtaaga tccttgagag ttttcgcccc  420
gaagaacgct ttccaatgat gagcactttt aaagttctgc tatgtggcgc ggtattatcc  480
cgtattgacg ccgggcaaga gcaactcggt cgccgcatac actattctca gaatgacttg  540
gttgagtatt caccagtcac agaaaagcat cttacggatg gcatgacagt aagagaatta  600
tgcagtgctg ccataaccat gagtgataac actgcggcca acttacttct gacaacgatt  660
ggaggaccga aggagctaac cgcttttttg cacaacatgg gggatcatgt aactcgcctt  720
gatcgttggg aaccggagct gaatgaagcc ataccaaacg acgagcgtga caccacgatg  780
cctgtagcaa tggcaacaac cttgcgtaaa ctattaactg gcgaactact tactctagct  840
tcccggcaac agttgataga ctggatggag gcggataaag ttgcaggacc acttctgcgc  900
tcggcccttc cggctggctg gtttattgct gataaatctg gagccggtga gcgtgggtct  960
cgcggtatca ttgcagcact ggggccagat ggtaagccct cccgtatcgt agttatctac  1020
acgacgggga gtcaggcaac tatggatgaa cgaaatagac agatcgctga gataggtgcc  1080
tcactgatta agcattggta accgattcta ggtgcattgg cgcagaaaaa aatgcctgat  1140
gcgacgctgc gcgtcttata ctcccacata tgccagattc agcaacggat acggcttccc  1200
caacttgccc acttccatac gtgtcctcct taccagaaat ttatccttaa gatcgtttaa  1260
actcgactct ggctctatcg aatctccgtc gtttcgagct tacgcgaaca gccgtggcgc  1320
tcatttgctc gtcgggcatc gaatctcgtc agctatcgtc agcttacctt tttggcagcg  1380
atcgcggctc ccgacatctt ggaccattag ctccacaggt atcttcttcc ctctagtggt  1440
cataacagca gcttcagcta cctctcaatt caaaaaaccc ctcaagaccc gtttagaggc  1500
cccaaggggt tatgctatca atcgttgcgt tacacacaca aaaaaccaac acacatccat  1560
cttcgatgga tagcgatttt attatctaac tgctgatcga gtgtagccag atctagtaat  1620
caattacggg gtcattagtt catagcccat atatggagtt ccgcgttaca taacttacgg  1680
taaatggccc gcctggctga ccgcccaacg acccccgccc attgacgtca ataatgacgt  1740
atgttcccat agtaacgcca atagggactt tccattgacg tcaatgggtg gagtatttac  1800
ggtaaactgc ccacttggca gtacatcaag tgtatcatat gccaagtacg ccccctattg  1860
acgtcaatga cggtaaatgg cccgcctggc attatgccca gtacatgacc ttatgggact  1920
ttcctacttg gcagtacatc tacgtattag tcatcgctat taccatgctg atgcggtttt  1980
ggcagtacat caatgggcgt ggatagcggt ttgactcacg gggatttcca agtctccacc  2040
ccattgacgt caatgggagt ttgttttggc accaaaatca acgggacttt ccaaaatgtc  2100
gtaacaactc cgccccattg acgcaaatgg gcggtaggcg tgtacggtgg gaggtctata  2160
taagcagagc tggtttagtg aaccgtcaga tcagatcttt gtcgatccta ccatccactc  2220
gacacacccg ccagcggccg ctaatacgac tcactatagg gagaagtact gccaccatgg  2280
gcaagaagca aaatcgcaag acggggaatt ccaagacaca atccgctagc ccaccaccta  2340
aagagcgttc tagctcccct gctactgagc agtcctggat ggaaaacgac ttcgatgaac  2400
tccgggaaga gggatttagg cgatccaact attcagaact ccgcgaagat atccagacaa  2460
aggggaagga agtcgagaat ttcgagaaga acctcgagga gtgcatcacc cgtatcacaa  2520
acactgagaa atgtctcaaa gaactcatgg aacttaagac aaaagccagg gagcttcgag  2580
aggagtgtcg gagtctgaga tccaggtgtg accagctcga ggagcgcgtg agcgcgatgg  2640
aagacgagat gaacgagatg aaaagagagg gcaaattcag ggagaagcgc attaagagga  2700
acgaacagag tctgcaggag atttgggatt acgtcaagag gcctaacctg cggttgatcg  2760
gcgtccccga gagcgacgta gaaaacggga ctaaactgga gaatacactt caagacatca  2820
ttcaagaaaa ttttccaaac ctggctcggc aagctaatgt gcaaatccaa gagatccaac  2880
gcacacccca gcggtatagc tctcggcgtg ccacccctag gcatattatc gtgcgcttta  2940
ctaaggtgga gatgaaagag aagatgctgc gagccgctcg ggaaaaggga agggtgactt  3000
tgaagggcaa acctattcgg ctgacggttg accttagcgc cgagacactc caggcacgcc  3060
gggaatgggg ccccatcttt aatatcctga aggagaagaa cttccagcca cgaatctctt  3120
accctgcaaa gttgagtttt atctccgagg gtgagattaa gtatttcatc gataaacaga  3180
tgctgcgaga cttcgtgaca actcgcccag ctctcaagga actgctcaaa gaggctctta  3240
atatggagcg caataataga tatcaaccct tgcagaacca cgcaaagatg tgagacagcc  3300
gtcagaccat caagactagg aagaaactgc atcaactaat gagcaaaatc accagctaac  3360
atcatagtat acatgaccgg ctctaactca catatcacca tccttacact taacattaac  3420
ggcctcaact cagctatcaa gcgccatcgg ctggccagct ggatcaaatc acaggatcca  3480
agcgtttgtt gcatccaaga gacccacctg acctgtagag atactcaccg cctcaagatc  3540
aagggatggc gaaagattta tcaggcgaac ggtaagcaga agaaagccgg agtcgcaatt  3600
ctggtctcag acaagacgga tttcaagccc accaaaatta agcgtgataa ggaaggtcac  3660
tatattatgg tgaaaggcag catacagcag gaagaactta ccatattgaa catctacgcg  3720
ccaaacaccg gcgcacctcg ctttatcaaa caggtcctgt ccgatctgca gcgagatctg  3780
gattctcata cgttgattat gggtgatttc aatacaccat tgagcaccct ggatcgcagc  3840
accaggcaaa aggtaaataa agacacgcaa gagctcaata gcgcactgca tcaggcagat  3900
```

-continued

```
ctcattgata tttatcgcac tcttcatcct aagagtaccg agtacacatt cttcagcgcc  3960
ccacatcata catactcaaa gatcgatcat atcgtcggct caaaggctct gctgtcaaag  4020
tgcaagcgca cagagataat tacaaattac ctgtcagatc atagcgcgat caagctcgag  4080
ctgagaatca agaacctgac ccagagccgg agtaccactt ggaagcttaa taacctgctg  4140
ctcaacgatt attgggtcca caatgagatg aaggcagaga ttaaaatgtt cttcgaaaca  4200
aatgagaata aggatactac ctatcaaaac ctttgggatg cctttaaggc cgtctgcaga  4260
ggcaagttca tcgccctcaa cgcctataaa agaaaacaag agagatctaa gatcgatact  4320
ctcacctctc agctgaagga gttggagaaa caggaacaga cccactccaa ggcgtcaaga  4380
cggcaggaga tcacaaagat tcgcgccgag ttgaaagaga tcgaaaccca aaagactctt  4440
cagaaaatta acgagtctcg tagttggttc ttcgagcgga ttaataagat agacagacct  4500
ctggcacgac tgattaagaa gaagcgcgaa aagaaccaga ttgataccat caagaacgac  4560
aagggcgaca tcactactga cccgaccgag atccagacca ctattcggga gtattataag  4620
catttgtatg ctaacaagct tgagaacctg gaagagatgg acacttttct ggatacctat  4680
actctgccac ggcttaatca agaggaagtc gagtccctca accgcccaat tacaggaagc  4740
gagattgtgg ccataattaa ctccctgccg acaaagaaat ctcctggtcc ggacgggttt  4800
acagctgagt tttatcaacg gtatatggaa gagcttgtac cgtttctgct caagctcttt  4860
cagtctatag aaaaggaagg catcttgccc aattccttct acgaagcttc tataatactt  4920
attcccaaac caggacgcga taccacaaag aaggaaaact tccggcccat tagtctcatg  4980
aatatcgacg ctaaaatatt gaacaagatt ctcgccaaca gaatccaaca acatattaag  5040
aaattgatac atcacgacca ggtggggttt atacctggca tgcagggctg gtttaacatc  5100
cggaagagta ttaacgtcat tcaacacatt aatagagcta aggataagaa tcatatgatc  5160
atctctatag acgcggaaaa ggcattcgat aagattcagc agccatttat gctcaagact  5220
ctgaacaaac tcggcatcga cggaacatat tttaagatta ttcgcgcaat ttacgataag  5280
ccgactgcta acattatcct taacggccaa aagctcgagg cctttccgct caagactgga  5340
acccgccaag gctgtcccct ctccccgctt ttgtttaata ttgtactcga ggtgctggct  5400
agggctattc gtcaagagaa agagattaaa gggatacagc tcgggaagga agaggtcaag  5460
ctttccttgt tcgccgatga tatgattgtg tacctggaga atcctattgt gtctgctcag  5520
aaccttctta aacttatttc taactttagc aaggtcagcg gctataagat taacgtccag  5580
aaatctcagg cctttctgta cacaaataat cgacagaccg aatcccagat aatgggtgag  5640
cttccgtttg tcatagccag caaaaggata aagtatctcg gaatccagct gacacgagac  5700
gttaaagatt tgtttaagga aaattacaag cctctcctga aagagattaa ggaagatact  5760
aataagtgga agaatatccc ctgttcatgg gttggcagaa tcaacatagt gaagatggca  5820
atacttccta aagtgatata tcgctttaac gccatcccaa ttaaactgcc tatgaccttc  5880
tttacggagc tcgagaaaac aaccccttaaa tttatatgga atcaaaagag agcaagaata  5940
gcgaagtcca tcttgagcca gaagaataag gccggtggga ttactttgcc tgattttaag  6000
ttgtattata aagccacagt aactaagaca gcctggtatt ggtatcagaa tagagacatc  6060
gaccagtgga atcggaccga accatcagag ataatgcccc acatctataa ttaccttata  6120
ttcgataagc cagaaaagaa taaacagtgg ggcaaagaca gcctcttcaa caagtggtgt  6180
tgggagaatt ggctggccat atgccggaaa ctcaagctcg acccctttct tacaccctac  6240
actaaaatca acagtaggtg gatcaaggac ttgaatgtca agccaaagac tataaagaca  6300
ctggaagaga atcttgggat cacaatacaa gatataggcg tcggcaaaga ttttatgtca  6360
aagacgccca aggccatggc cactaaggat aagattgata agtgggacct tattaagctc  6420
aaaagcttct gtactgccaa ggagaccacg atcagagtta ataggcagcc cactacatgg  6480
gaaaagattt tcgccactta ttcatcagat aaggggttga taagcagaat atataacgag  6540
ctgaagcaga tctacaagaa gaaaacgaat aatcccatca agaagtgggc aaaagatatg  6600
aacaggcatt ttagcaaaga ggatatctac gccgcgaaga agcatatgaa gaagtgtagt  6660
tcaagcttgg ccattcgtga gatgcagatt aagacgacca tgcgatacca ccttacccca  6720
gtgaggatgg caattatcaa gaaatctggc aataatagat gttggcgggg ctgtggcgag  6780
attggcaccc tgctccattg ctggtgggat tgcaagctgg tgcagccgct ttggaaatca  6840
gtctggcgct ttctgaggga cctcgagctt gagattccct tcgatcccgc aattcccttg  6900
ctcggaatct atcctaacga atacaagagc tgttgttaca aggatacgtg tacccggatg  6960
ttcatcgcgg ccttgtttac gatagctaag acgtggaatc agcctaagtg ccccacaatg  7020
atcgattgga tcaagaaaat gtggcatatt tataccatgg agtattacgc agcaattaag  7080
aatgacgaat ttatttcctt cgttgggacc tggatgaagc tggagactat tattctgagc  7140
aagctgtctc aggagcaaaa gacaaagcat agaatcttct ctctcattgg tggtaacgac  7200
tacaaagacg atgacgacaa gggcggcggc agcaaaaggc cggcggccac gaaaaaggcc  7260
ggccaggcaa aaaagaaaaa gtaaagcgct tctagaagtt gtctcctcct gcactgactg  7320
actgatacaa tcgatttctg gatccgcagg cctaatcaac ctctggatta caaaatttgt  7380
gaaagattga ctggtattct taactatgtt gctcctttta cgctatgtgg atacgctgct  7440
ttaatgcctt tgtatcatgc tattgcttcc cgtatggctt tcattttctc ctccttgtat  7500
aaatcctggt tgctgtctct ttatgaggag ttgtggcccg ttgtcaggca acgtggcgtg  7560
gtgtgcactg tgtttgctga cgcaaccccc actggttggg gcattgccac cacctgtcag  7620
ctcctttccg ggactttcgc tttccccctc cctattgcca cggcggaact catcgccgcc  7680
tgccttgccc gctgctggac aggggctcgg ctgttgggca ctgacaattc cgtggtgttg  7740
tcggggaagc tgacgtcctt tccatggctg ctcgcctgtg ttgccacctg gattctgcgc  7800
gggacgtcct tctgctacgt cccttcggcc ctcaatccag cggaccttcc ttcccgctga  7860
gagacacaaa aaattccaac acactattgc aatgaaaata aatttccttt attagccaga  7920
agtcagatgc tcaaggggct tcatgatgtc cccataattt ttggcagagg gaaaaagatc  7980
tcagtggtat ttgtgagcca gggcattggc cttctgatag gcagcctgca cctgaggagt  8040
gcggccgctt tacttgtaca gctcgtccat gccgagagtg atcccggcgg cggtcacgaa  8100
ctccagcagg accatgtgat cgcgcttctc gttggggtct ttgctcaggg cggactgggt  8160
gctcaggtag tggttgtcgg gcagcagcac ggggccgtcg ccgatggggg tgttctgctg  8220
gtagtggtcg gcgagctgca cgctgccgtc ctcgatgttg tggcggatct tgaagttcac  8280
cttgatgccg ttcttctgct tgtcggccat gatatagacg ttgtggctgt tgtagttgta  8340
ctccagcttg tgccccagga tgttgccgtc ctccttgaag tcgatgccct tcagctcgat  8400
gcggttcacc agggtgtcgc cctcgaactt cacctcggcg cgggtcttgt agttgccgtc  8460
gtccttgaag aagatggtgc gctcctggac gtagccttcg ggcatggcgg acttgaagaa  8520
gtcgtgctgc ttcatgtggt cggggtagcg gctgaagcac tgcacgccgt aggtcagggt  8580
ggtcacgagg gtgggccagg gcacgggcag cttgccggtg gtgcagatga acttcagggt  8640
```

-continued

```
cagcttgccg taggtggcat cgccctcgcc ctcgccggac acgctgaact tgtggccgtt  8700
tacgtcgccg tccagctcga ccaggatggg caccaccccg gtgaacagct cctcgccctt  8760
gctcaccatg gtggcgggat ctgacggttc actaaaccag ctctgcttat atagacctcc  8820
caccgtacac gcctaccgcc catttgcgtc aatggggcgg agttgttacg acattttgga  8880
aagtcccgtt gattttggtg ccaaaacaaa ctcccattga cgtcaatggg gtggagactt  8940
ggaaatcccc gtgagtcaaa ccgctatcca cgcccattga tgtactgcca aaaccgcatc  9000
accatggtaa tagcgatgac taatacgtag atgtactgcc aagtaggaaa gtcccataag  9060
gtcatgtact gggcataatg ccaggcgggc catttaccgt cattgacgtc aatagggggc  9120
gtacttggca tatgatacac ttgatgtact gccaagtggg cagtttaccg taaatactcc  9180
acccattgac gtcaatggaa agtccctatt ggcgttacta tgggaacata cgtcattatt  9240
gacgtcaatg ggcgggggtc gttgggcggt cagccaggcg ggccatttac cgtaagttat  9300
gtaacgggcc tgctgccggc tctgcggcct cttccgcgtc ttcgccttcg ccctcagacg  9360
agtcggatct ccctttgggc cgcctccccg cctgtctagc ttgactgact gagatacagc  9420
gtaccttcag ctcacagaca tgataagata cattgatgag tttggacaaa ccacaactag  9480
aatgcagtga aaaaaatgct ttatttgtga aatttgtgat gctattgctt tatttgtaac  9540
cattataagc tgcaataaac aagttaacaa caacaattgc attcatttta tgtttcaggt  9600
tcagggggag gtgtgggagg ttttttaaag caagtaaaac ctctacaaat gtggtattgg  9660
cccatctcta tcggtatcgt agcataaccc cttggggcct ctaaacgggt cttgaggggt  9720
tttttgtgcc cctcgggccg gattgctatc taccggcatt ggcgcagaaa aaaatgcctg  9780
atgcgacgct gcgcgtctta tactcccaca tatgccagat tcagcaacgg atacggcttc  9840
cccaacttgc ccacttccat acgtgtcctc cttaccagaa atttatcctt aaggtcgtca  9900
gctatcctgc aggcgatctc tcgatttcga tcaagacatt cctttaatgg tcttttctgg  9960
acaccactag ggggtcagaag tagttcatca aactttcttc cctccctaat ctcattggtt  10020
accttgggct atcgaaactt aattaagcga tctgcatctc aattagtcag caaccatagt  10080
cccgccccta actccgccca tcccgcccct aactccgccc agttccgccc attctccgcc  10140
ccatcgctga ctaatttttt ttatttatgc agaggccgag gccgcctcgg cctctgagct  10200
attccagaag tagtgaggag gctttttttgg aggcctaggc ttttgcaaag gaggtagcca  10260
acatgattga acaagatgga ttgcacgcag gttctcccgc cgcttgggtg gagaggctat  10320
tcggctatga ctgggcacaa cagacaatcg gctgctctga tgccgccgtg ttccggctgt  10380
cagcgcaggg gcgcccggtt ctttttgtca agaccgacct gtccggtgcc ctgaatgaac  10440
tccaggacga ggcagcgcgg ctatcgtggc tggccacgac gggcgttcct tgcgcagctg  10500
tgctcgacgt tgtcactgaa gcgggaaggg actggctgct attgggcgaa gtgccggggc  10560
aggatctcct gtcatctcac cttgctcctg ccgagaaagt atccatcatg gctgatgcaa  10620
tgcggcggct gcatacgctt gatccggcta cctgcccatt cgaccaccaa gcgaaacatc  10680
gcatcgagcg agcacgtact cggatggaag ccggtcttgt cgatcaggat gatctggacg  10740
aagagcatca ggggctcgcg ccagccgaac tgttcgccag gctcaaggcg cggatgcccg  10800
acggcgagga tctcgtcgtg acccacggcg atgcctgctt gccgaatatc atggtggaaa  10860
atggccgctt ttctggattc atcgactgtg gccggctggg tgtggcggac cgctatcagg  10920
acatagcgtt ggctacccgt gatattgctg aagagcttgg cggcgaatgg gctgaccgct  10980
tcctcgtgct ttacggtatc gccgctcccg attcgcagcg catcgccttc tatcgccttc  11040
ttgacgagtt cttctagtat gtaagccctg tgccttctag ttgccagcca tctgttgttt  11100
gcccctcccc cgtgccttcc ttgaccctgg aaggtgccac tcccactgtc ctttcctaat  11160
aaaatgagga aattgcatcg cattgtctga gtaggtgtca ttctattctg gggggtgggg  11220
tggggcagga cagcaagggg gaggattggg aagacaatag caggcatgct ggggatgcgg  11280
tgggctctat ggttaattaa ccagtcaagt cagctacttg gcgagatcga cttgtctggg  11340
tttcgactac gctcagaatt gcgtcagtca agttcgatct ggtccttgct attgcacccg  11400
ttctccgatt acgagtttca tttaaatcat gtgagcaaaa ggccagcaaa aggccaggaa  11460
ccgtaaaaag gccgcgttgc tggcgttttt ccataggctc cgcccccctg acgagcatca  11520
caaaaatcga cgctcaagtc agaggtggcg aaacccgaca ggactataaa gataccaggc  11580
gtttccccct ggaagctccc tcgtgcgctc tcctgttccg accctgccgc ttaccggata  11640
cctgtccgcc tttctccctt cgggaagcgt ggcgctttct catagctcac gctgtaggta  11700
tctcagttcg gtgtaggtcg ttcgctccaa gctgggctgt gtgcacgaac cccccgttca  11760
gcccgaccgc tgcgccttat ccggtaacta tcgtcttgag tccaacccgg taagacacga  11820
cttatcgcca ctggcagcag ccactggtaa caggattagc agagcgaggt atgtaggcgg  11880
tgctacagag ttcttgaagt ggtggcctaa ctacggctac actagaagaa cagtatttgg  11940
tatctgcgct ctgctgaagc cagttacctt cggaaaaaga gttggtagct cttgatccgg  12000
caaacaaacc accgctggta gcggtggttt ttttgtttgc aagcagcaga ttacgcgcag  12060
aaaaaaagga tctcaagaag atcctttgat cttttctacg gggtctgacg ctcagtggaa  12120
cgaaaactca cgttaaggga ttttggtcat gagattatca aaaaggatct tcacctagat  12180
ccttttaaat taaaaatgaa gttttaaatc aatctaaagt atatatgagt aaacttggtc  12240
tgacagttac caatgcttaa tcagtgaggc acctatctca gcgatctgtc tatttcgttc  12300
atccatagtt gcatttaaat ttccgaactc tccaaggccc tcgtcggaaa atcttcaaac  12360
ctttcgtccg atccatcttg caggctacct ctcgaacgaa ctatcgcaag tctcttggcc  12420
ggccttgcgc cttggctatt gcttggcagc gcctatcgcc aggtattact ccaatcccga  12480
atatccgaga tcgggatcac ccgagagaag ttcaacctac atcctcaatc ccgatctatc  12540
cgagatccga ggaatatcga aatcggggcg cgcctggtgt a                    12581
```

```
SEQ ID NO: 108          moltype = DNA  length = 12602
FEATURE                 Location/Qualifiers
misc_feature            1..12602
                        note = Description of Artificial Sequence: Synthetic
                         polynucleotide
source                  1..12602
                        mol_type = other DNA
                        organism = synthetic construct
SEQUENCE: 108
tggccggcct tgcgccttgg ctattgcttg gcagcgccta tcgccaggta ttactccaat  60
cccgaatatc cgagatcggg atcacccgag agaagttcaa cctacatcct caatcccgat  120
ctatccgaga tccgaggaat atcgaaatcg gggcgcgcct ggtgtaccga gaacgatcct  180
```

-continued

```
ctcagtgcga gtctcgacga tccatatcgt tgcttggcag tcagccagtc ggaatccagc  240
ttgggaccca ggaagtccaa tcgtcagata ttgtactcaa gcctggtcac ggcagcgtac  300
cgatctgttt aaacctagat attgatagtc tgatcggtca acgtataatc gagtcctagc  360
ttttgcaaac atctatcaag agacaggatc agcaggaggc tttcgcatga gtattcaaca  420
tttccgtgtc gcccttattc ccttttttgc ggcattttgc cttcctgttt ttgctcaccc  480
agaaacgctg gtgaaagtaa aagatgctga agatcagttg ggtgcgcgag tgggttacat  540
cgaactggat ctcaacagcg gtaagatcct tgagagtttt cgccccgaag aacgttttcc  600
aatgatgagc acttttaaag ttctgctatg tggcgcggta ttatcccgta ttgacgccgg  660
gcaagagcaa ctcggtcgcc gcatacacta ttctcagaat gacttggttg agtattcacc  720
agtcacagaa aagcatctta cggatggcat gacagtaaga gaattatgca gtgctgccat  780
aaccatgagt gataacactg cggccaactt acttctgaca acgattggag gaccgaagga  840
gctaaccgct tttttgcaca acatggggga tcatgtaact cgccttgatc gttgggaacc  900
ggagctgaat gaagccatac caaacgacga gcgtgacacc acgatgcctg tagcaatggc  960
aacaaccttg cgtaaactat taactggcga actacttact ctagcttccc ggcaacagtt  1020
gatagactgg atggaggcgg ataaagttgc aggaccactt ctgcgctcgg cccttccggc  1080
tggctggttt attgctgata aatctggagc cggtgagcgt gggtctcgcg gtatcattgc  1140
agcactgggg ccagatggta agccctcccg tatcgtagtt atctacacga cggggagtca  1200
ggcaactatg gatgaacgaa atagacagat cgctgagata ggtgcctcac tgattaagca  1260
ttggtaaccg attctaggtg cattggcgca gaaaaaaatg cctgatgcga cgctgcgcgt  1320
cttatactcc cacatatgcc agattcagca acggatacgg cttccccaac ttgcccactt  1380
ccatacgtgt cctccttacc agaaatttat ccttaagatc gtttaaactc gactctggct  1440
ctatcgaatc tccgtcgttt cgagcttacg cgaacagccg tggcgctcat ttgctcgtcg  1500
ggcatcgaat ctcgtcagct atcgtcagct taccttttg gcagcgatcg cggctcccga  1560
catcttggac cattagctcc acaggtatct tcttccctct agtggtcata acagcagctt  1620
cagctacctc tcaattcaaa aaacccctca agacccgttt agaggcccca aggggttatg  1680
ctatcaatcg ttgcgttaca cacacaaaaa accaacacac atccatcttc gatggatagc  1740
gattttatta tctaactgct gatcgagtgt agccagatct agtaatcaat tacggggtca  1800
ttagttcata gcccatatat ggagttccgc gttacataac ttacggtaaa tggcccgcct  1860
ggctgaccgc ccaacgaccc ccgcccattg acgtcaataa tgacgtatgt tcccatagta  1920
acgccaatag ggactttcca ttgacgtcaa tgggtggagt atttacggta aactgcccac  1980
ttggcagtac atcaagtgta tcatatgcca agtacgcccc ctattgacgt caatgacggt  2040
aaatggcccg cctggcatta tgcccagtac atgaccttat gggactttcc tacttggcag  2100
tacatctacg tattagtcat cgctattacc atgctgatgc ggttttggca gtacatcaat  2160
gggcgtggat agcggtttga ctcacgggga tttccaagtc tccaccccat tgacgtcaat  2220
gggagtttgt tttggcacca aaatcaacgg gactttccaa aatgtcgtaa caactccgcc  2280
ccattgacgc aaatgggcgg taggcgtgta cggtgggagg tctatataag cagagctggt  2340
ttagtgaacc gtcagatcag atctttgtcg atcctaccat ccactcgaca cacccgccag  2400
cggccgctaa tacgactcac tatagggaga agtactgcca ccatgggcaa gaagcaaaat  2460
cgcaagacgg ggaattccaa gacacaatcc gctagcccac cacctaaaga gcgttctagc  2520
tcccctgcta ctgagcagtc ctggatggaa aacgacttcg atgaactccg ggaagaggga  2580
tttaggcgat ccaactattc agaactccgc gaagatatcc agacaaaggg gaaggaagtc  2640
gagaatttcg agaagaacct cgaggagtgc atcacccgta tcacaaacac tgagaaatgt  2700
ctcaaagaac tcatggaact taagacaaaa gccagggagc ttcgagagga gtgtcggagt  2760
ctgagatcca ggtgtgacca gctcgaggag cgcgtgagcg cgatggaaga cgagatgaac  2820
gagatgaaaa gagagggcaa attcagggag aagcgcatta agaggaacga acagagtctg  2880
caggagattt gggattacgt caagaggcct aacctgcggt tgatcggcgt ccccgagagc  2940
gacgtagaaa acgggactaa actggagaat acacttcaag acatcattca agaaaatttt  3000
ccaaacctgg ctcggcaagc taatgtgcaa atccaagaga tccaacgcac accccagcgg  3060
tatagctctc ggcgtgccac ccctaggcat attatcgtgc gctttactaa ggtggagatg  3120
aaagagaaga tgctgcgagc cgctcgggaa aagggaaggg tgactttgaa gggcaaacct  3180
attcggctga cggttgacct tagcgccgag acactccagg cacgccggga atggggcccc  3240
atctttaata tcctgaagga gaagaacttc cagccacgaa tctcttaccc tgcaaagttg  3300
agttttatct ccgagggtga gattaagtat ttcatcgata aacagatgct gcgagacttc  3360
gtgacaactc gcccagctct caaggaactg ctcaaagagg ctcttaatat ggagcgcaat  3420
aatagatatc aacccttgca gaaccacgca aagatgtgag acagccgtca gaccatcaag  3480
actaggaaga aactgcatca actaatgagc aaaatcacca gctaacatca tagtatacat  3540
gccaaagaag aagcggaagg tcggcggcgg cagcaccggc tctaactcac atatcaccat  3600
ccttacactt aacattaacg gcctcaactc agctatcaag cgccatcggc tggccagctg  3660
gatcaaatca caggatccaa gcgtttgttg catccaagag acccacctga cctgtagaga  3720
tactcaccgc ctcaagatca agggatggcg aaagatttat caggcgaacg gtaagcagaa  3780
gaaagccgga gtcgcaattc tggtctcaga caagacggat ttcaagccca ccaaaattaa  3840
gcgtgataag gaaggtcact atattatggt gaaaggcagc atacagcagg aagaacttac  3900
catattgaac atctacgcgc caaacaccgg cgcacctcgc tttatcaaac aggtcctgtc  3960
cgatctgcag cgagatctgg attctcatac gttgattatg ggtgatttca atacaccatt  4020
gagcaccctg gatcgcagca ccaggcaaaa ggtaaataaa gacacgcaag agctcaatag  4080
cgcactgcat caggcagatc tcattgatat ttatcgcact cttcatccta agagtaccga  4140
gtacacattc ttcagcgccc cacatcatac atactcaaag atcgatcata tcgtcggctc  4200
aaaggctctg ctgtcaaagt gcaagcgcac agagataatt acaaattacc tgtcagatca  4260
tagcgcgatc aagctcgagc tgagaatcaa gaacctgacc cagagccgga gtaccacttg  4320
gaagcttaat aacctgctgc tcaacgatta ttgggtccac aatgagatga aggcagagat  4380
taaaatgttc ttcgaaacaa atgagaataa ggatactacc tatcaaaacc tttgggatgc  4440
ctttaaggcc gtctgcagag gcaagttcat cgccctcaac gcctataaaa gaaaacaaga  4500
gagatctaag atcgatactc tcacctctca gctgaaggag ttggagaaac aggaacagac  4560
ccactccaag gcgtcaagac ggcaggagat cacaaagatt cgcgccgagt tgaaagagat  4620
cgaaacccaa aagactcttc agaaaattaa cgagtctcgt agttggttct tcgagcggat  4680
taataagata gacagacctc tggcacgact gattaagaag aagcgcgaaa agaaccagat  4740
tgataccatc aagaacgaca agggcgacat cactactgac ccgaccgaga tccagaccac  4800
tattcgggag tattataagc atttgtatgc taacaagctt gagaacctgg aagagatgga  4860
cacttttctg gatacctata ctctgccacg gcttaatcaa gaggaagtcg agtccctcaa  4920
```

-continued

```
ccgcccaatt acaggaagcg agattgtggc cataattaac tccctgccga caaagaaatc  4980
tcctggtccg gacgggttta cagctgagtt ttatcaacgg tatatggaag agcttgtacc  5040
gtttctgctc aagctctttc agtctataga aaaggaaggc atcttgccca attccttcta  5100
cgaagcttct ataatactta ttcccaaacc aggacgcgat accacaaaga aggaaaactt  5160
ccggcccatt agtctcatga atatcgacgc taaaatattg aacaagattc tcgccaacag  5220
aatccaacaa catattaaga aattgataca tcacgaccag gtggggttta tacctggcat  5280
gcagggctgg tttaacatcc ggaagagtat taacgtcatt caacacatta atagagctaa  5340
ggataagaat catatgatca tctctataga cgcggaaaag gcattcgata agattcagca  5400
gccatttatg ctcaagactc tgaacaaact cggcatcgac ggaacatatt ttaagattat  5460
tcgcgcaatt tacgataagc cgactgctaa cattatcctt aacggccaaa agctcgaggc  5520
ctttccgctc aagactggaa cccgccaagg ctgtcccctc tccccgcttt tgtttaatat  5580
tgtactcgag gtgctggcta gggctattcg tcaagagaaa gagattaaag ggatacagct  5640
cgggaaggaa gaggtcaagc tttccttgtt cgccgatgat atgattgtgt acctggagaa  5700
tcctattgtg tctgctcaga accttcttaa acttatttct aactttagca aggtcagcgg  5760
ctataagatt aacgtccaga aatctcaggc ctttctgtac acaaataatc gacagaccga  5820
atcccagata atgggtgagc ttccgtttgt catagccagc aaaaggataa agtatctcgg  5880
aatccagctg acacgagacg ttaaagattt gtttaaggaa aattacaagc ctctcctgaa  5940
agagattaag gaagatacta ataagtggaa gaatatcccc tgttcatggg ttggcagaat  6000
caacatagtg aagatggcaa tacttcctaa agtgatatat cgctttaacg ccatcccaat  6060
taaactgcct atgaccttct ttacggagct cgagaaaaca accettaaat ttatatggaa  6120
tcaaaagaga gcaagaatag cgaagtccat cttgagccag aagaataagg ccggtgggat  6180
tactttgcct gattttaagt tgtattataa agccacagta actaagacag cctggtattg  6240
gtatcagaat agagacatcg accagtggaa tcggaccgaa ccatcagaga taatgcccca  6300
catctataat taccttatat tcgataagcc agaaaagaat aaacagtggg gcaaagacag  6360
cctcttcaac aagtggtgtt gggagaattg gctggccata tgccggaaac tcaagctcga  6420
cccctttctt acaccctaca ctaaaatcaa cagtaggtgg atcaaggact tgaatgtcaa  6480
gccaaagact ataaagacac tggaagagaa tcttgggatc acaatacaag atataggcgt  6540
cggcaaagat tttatgtcaa agacgcccaa ggccatggcc actaaggata agattgataa  6600
gtgggacctt attaagctca aagcttctg tactgccaag gagaccacga tcagagttaa  6660
taggcagccc actacatggg aaaagatttt cgccacttat tcatcagata aggggttgat  6720
aagcagaata tataacgagc tgaagcagat ctacaagaag aaaacgaata atcccatcaa  6780
gaagtgggca aaagatatga acaggcattt tagcaaagag gatatctacg ccgcgaagaa  6840
gcatatgaag aagtgtagtt caagcttggc cattcgtgag atgcagatta agacgaccat  6900
gcgataccac cttaccccag tgaggatggc aattatcaag aaatctggca ataatagatg  6960
ttggcggggc tgtggcgaga ttggcaccct gctccattgc tggtgggatt gcaagctggt  7020
gcagccgctt tggaaatcag tctggcgctt tctgagggac ctcgagcttg agattccctt  7080
cgatcccgca attcccttgc tcggaatcta tcctaacgaa tacaagagct gttgttacaa  7140
ggatacgtgt acccggatgt tcatcgcggc cttgtttacg atagctaaga cgtggaatca  7200
gcctaagtgc ccacaatga tcgattggat caagaaaatg tggcatattt ataccatgga  7260
gtattacgca gcaattaaga atgacgaatt tatttccttc gttgggacct ggatgaagct  7320
ggagactatt attctgagca agctgtctca ggagcaaaag acaaagcata gaatcttctc  7380
tctcattggt ggtaacgact acaaagacga tgacgacaag aaaaggccgg cggccacgaa  7440
aaaggccggc caggcaaaaa agaaaaagta aagcgcttct agaagttgtc tcctcctgca  7500
ctgactgact gatacaatcg atttctggat ccgcaggcct aatcaacctc tggattacaa  7560
aatttgtgaa agattgactg gtattcttaa ctatgttgct ccttttacgc tatgtggata  7620
cgctgcttta atgcctttgt atcatgctat tgcttcccgt atggctttca ttttctcctc  7680
cttgtataaa tcctggttgc tgtctcttta tgaggagttg tggcccgttg tcaggcaacg  7740
tggcgtggtg tgcactgtgt ttgctgacgc aacccccact ggttggggca ttgccaccac  7800
ctgtcagctc ctttccggga ctttcgcttt ccccctccct attgccacgg cggaactcat  7860
cgccgcctgc cttgcccgct gctggacagg ggctcggctg ttgggcactg acaattccgt  7920
ggtgttgtcg gggaagctga cgtcctttcc atggctgctc gcctgtgttg ccacctggat  7980
tctgcgcggg acgtccttct gctacgtccc ttcggccctc aatccagcgg accttccttc  8040
ccgctgagag acacaaaaaa ttccaacaca ctattgcaat gaaaataaat ttcctttatt  8100
agccagaagt cagatgctca aggggcttca tgatgtcccc ataatttttg gcagagggaa  8160
aaagatctca gtggtatttg tgagccaggg cattggcctt ctgataggca gcctgcacct  8220
gaggagtgcg gccgctttac ttgtacagct cgtccatgcc gagagtgatc ccggcggcgg  8280
tcacgaactc cagcaggacc atgtgatcgc gcttctcgtt ggggtctttg ctcagggcgg  8340
actgggtgct caggtagtgg ttgtcgggca gcagcacggg gccgtcgccg atgggggtgt  8400
tctgctggta gtggtcggcg agctgcacgc tgccgtcctc gatgttgtgg cggatcttga  8460
agttcacctt gatgccgttc ttctgcttgt cggccatgat atagacgttg tggctgttgt  8520
agttgtactc cagcttgtgc cccaggatgt tgccgtcctc cttgaagtcg atgcccttca  8580
gctcgatgcg gttcaccagg gtgtcgccct cgaacttcac ctcggcgcgg gtcttgtagt  8640
tgccgtcgtc cttgaagaag atggtgcgct cctggacgta gccttcgggc atggcggact  8700
tgaagaagtc gtgctgcttc atgtggtcgg ggtagcggct gaagcactgc acgccgtagg  8760
tcagggtggt cacgagggtg ggccagggca cgggcagctt gccggtggtg cagatgaact  8820
tcagggtcag cttgccgtag gtggcatcgc cctcgccctc gccggacacg ctgaacttgt  8880
ggccgtttac gtcgccgtcc agctcgacca ggatgggcac caccccggtg aacagctcct  8940
cgcccttgct caccatggtg gcgggatctg acggttcact aaaccagctc tgcttatata  9000
gacctcccac cgtacacgcc taccgcccat ttgcgtcaat ggggcggagt tgttacgaca  9060
ttttggaaag tcccgttgat tttggtgcca aaacaaactc ccattgacgt caatggggtg  9120
gagacttgga aatccccgtg agtcaaaccg ctatccacgc ccattgatgt actgccaaaa  9180
ccgcatcacc atggtaatag cgatgactaa tacgtagatg tactgccaag taggaaagtc  9240
ccataaggtc atgtactggg cataatgcca ggcgggccat ttaccgtcat tgacgtcaat  9300
agggggcgta cttggcatat gatacacttg atgtactgcc aagtgggcag tttaccgtaa  9360
atactccacc cattgacgtc aatggaaagt ccctattggc gttactatgg gaacatacgt  9420
cattattgac gtcaatgggc gggggtcgtt gggcggtcag ccaggcgggc catttaccgt  9480
aagttatgta acgggcctgc tgccggctct gcggcctctt ccgcgtcttc gccttcgccc  9540
tcagacgagt cggatctccc tttgggccgc ctccccgcct gtctagcttg actgactgag  9600
atacagcgta ccttcagctc acagacatga taagatacat tgatgagttt ggacaaacca  9660
```

```
caactagaat gcagtgaaaa aaatgcttta tttgtgaaat ttgtgatgct attgctttat  9720
ttgtaaccat tataagctgc aataaacaag ttaacaacaa caattgcatt cattttatgt  9780
ttcaggttca gggggaggtg tgggaggttt tttaaagcaa gtaaaacctc tacaaatgtg  9840
gtattggccc atctctatcg gtatcgtagc ataacccctt ggggcctcta aacgggtctt  9900
gaggggtttt ttgtgcccct cgggccggat tgctatctac cggcattggc gcagaaaaaa  9960
atgcctgatg cgacgctgcg cgtcttatac tcccacatat gccagattca gcaacggata  10020
cggcttcccc aacttgccca cttccatacg tgtcctcctt accagaaatt tatccttaag  10080
gtcgtcagct atcctgcagg cgatctctcg atttcgatca agacattcct ttaatggtct  10140
tttctggaca ccactagggg tcagaagtag ttcatcaaac tttcttccct ccctaatctc  10200
attggttacc ttgggctatc gaaacttaat taagcgatct gcatctcaat tagtcagcaa  10260
ccatagtccc gcccctaact ccgcccatcc cgcccctaac tccgcccagt tccgcccatt  10320
ctccgcccca tcgctgacta atttttttta tttatgcaga ggccgaggcc gcctcggcct  10380
ctgagctatt ccagaagtag tgaggaggct tttttggagg cctaggcttt tgcaaaggag  10440
gtagccaaca tgattgaaca agatggattg cacgcaggtt ctcccgccgc ttgggtggag  10500
aggctattcg gctatgactg ggcacaacag acaatcggct gctctgatgc cgccgtgttc  10560
cggctgtcag cgcaggggcg cccggttctt tttgtcaaga ccgacctgtc cggtgccctg  10620
aatgaactcc aggacgaggc agcgcggcta tcgtggctgg ccacgacggg cgttccttgc  10680
gcagctgtgc tcgacgttgt cactgaagcg ggaagggact ggctgctatt gggcgaagtg  10740
ccggggcagg atctcctgtc atctcacctt gctcctgccg agaaagtatc catcatggct  10800
gatgcaatgc ggcggctgca tacgcttgat ccggctacct gcccattcga ccaccaagcg  10860
aaacatcgca tcgagcgagc acgtactcgg atggaagccg gtcttgtcga tcaggatgat  10920
ctggacgaag agcatcaggg gctcgcgcca gccgaactgt tcgccaggct caaggcgcgg  10980
atgcccgacg gcgaggatct cgtcgtgacc cacggcgatg cctgcttgcc gaatatcatg  11040
gtggaaaatg gccgcttttc tggattcatc gactgtggcc ggctgggtgt ggcggaccgc  11100
tatcaggaca tagcgttggc tacccgtgat attgctgaag agcttggcgg cgaatgggct  11160
gaccgcttcc tcgtgcttta cggtatcgcc gctcccgatt cgcagcgcat cgccttctat  11220
cgccttcttg acgagttctt ctagtatgta agccctgtgc cttctagttg ccagccatct  11280
gttgtttgcc cctcccccgt gccttccttg accctggaag gtgccactcc cactgtcctt  11340
tcctaataaa atgaggaaat tgcatcgcat tgtctgagta ggtgtcattc tattctgggg  11400
ggtggggtgg ggcaggacag caagggggag gattgggaag acaatagcag gcatgctggg  11460
gatgcggtgg gctctatggt taattaacca gtcaagtcag ctacttggcg agatcgactt  11520
gtctgggttt cgactacgct cagaattgcg tcagtcaagt tcgatctggt ccttgctatt  11580
gcacccgttc tccgattacg agtttcattt aaatcatgtg agcaaaaggc cagcaaaagg  11640
ccaggaaccg taaaaaggcc gcgttgctgg cgtttttcca taggctccgc ccccctgacg  11700
agcatcacaa aaatcgacgc tcaagtcaga ggtggcgaaa cccgacagga ctataaagat  11760
accaggcgtt tccccctgga agctccctcg tgcgctctcc tgttccgacc ctgccgctta  11820
ccggatacct gtccgccttt ctcccttcgg gaagcgtggc gctttctcat agctcacgct  11880
gtaggtatct cagttcggtg taggtcgttc gctccaagct gggctgtgtg cacgaacccc  11940
ccgttcagcc cgaccgctgc gccttatccg gtaactatcg tcttgagtcc aacccggtaa  12000
gacacgactt atcgccactg gcagcagcca ctggtaacag gattagcaga gcgaggtatg  12060
taggcggtgc tacagagttc ttgaagtggt ggcctaacta cggctacact agaagaacag  12120
tatttggtat ctgcgctctg ctgaagccag ttaccttcgg aaaaagagtt ggtagctctt  12180
gatccggcaa acaaaccacc gctggtagcg gtggtttttt tgtttgcaag cagcagatta  12240
cgcgcagaaa aaaaggatct caagaagatc ctttgatctt ttctacgggg tctgacgctc  12300
agtggaacga aaactcacgt taagggattt tggtcatgag attatcaaaa aggatcttca  12360
cctagatcct tttaaattaa aaatgaagtt ttaaatcaat ctaaagtata tatgagtaaa  12420
cttggtctga cagttaccaa tgcttaatca gtgaggcacc tatctcagcg atctgtctat  12480
ttcgttcatc catagttgca tttaaatttc cgaactctcc aaggccctcg tcggaaaatc  12540
ttcaaacctt tcgtccgatc catcttgcag gctacctctc gaacgaacta tcgcaagtct  12600
ct                                                                 12602

SEQ ID NO: 109          moltype = DNA  length = 12541
FEATURE                 Location/Qualifiers
misc_feature            1..12541
                        note = Description of Artificial Sequence: Synthetic
                         polynucleotide
source                  1..12541
                        mol_type = other DNA
                        organism = synthetic construct
SEQUENCE: 109
tggccggcct tgcgccttgg ctattgcttg gcagcgccta tcgccaggta ttactccaat  60
cccgaatatc cgagatcggg atcacccgag agaagttcaa cctacatcct caatcccgat  120
ctatccgaga tccgaggaat atcgaaatcg gggcgcgcct ggtgtaccga gaacgatcct  180
ctcagtgcga gtctcgacga tccatatcgt tgcttggcag tcagccagtc ggaatccagc  240
ttgggaccca ggaagtccaa tcgtcagata ttgtactcaa gcctggtcac ggcagcgtac  300
cgatctgttt aaacctagat attgatagtc tgatcggtca acgtataatc gagtcctagc  360
ttttgcaaac atctatcaag agacaggatc agcaggaggc tttcgcatga gtattcaaca  420
tttccgtgtc gcccttattc ccttttttgc ggcattttgc cttcctgttt ttgctcaccc  480
agaaacgctg gtgaaagtaa aagatgctga agatcagttg ggtgcgcgag tgggttacat  540
cgaactggat ctcaacagcg gtaagatcct tgagagtttt cgccccgaag aacgctttcc  600
aatgatgagc acttttaaag ttctgctatg tggcgcggta ttatcccgta ttgacgccgg  660
gcaagagcaa ctcggtcgcc gcatacacta ttctcagaat gacttggttg agtattcacc  720
agtcacagaa aagcatctta cggatggcat gacagtaaga gaattatgca gtgctgccat  780
aaccatgagt gataacactg cggccaactt acttctgaca acgattggag gaccgaagga  840
gctaaccgct tttttgcaca acatggggga tcatgtaact cgccttgatc gttgggaacc  900
ggagctgaat gaagccatac caaacgacga gcgtgacacc acgatgcctg tagcaatggc  960
aacaaccttg cgtaaactat taactggcga actacttact ctagcttccc ggcaacagtt  1020
gatagactgg atggaggcgg ataaagttgc aggaccactt ctgcgctcgg cccttccggc  1080
tggctggttt attgctgata aatctggagc cggtgagcgt gggtctcgcg gtatcattgc  1140
```

-continued

```
agcactgggg ccagatggta agccctcccg tatcgtagtt atctacacga cggggagtca  1200
ggcaactatg gatgaacgaa atagacagat cgctgagata ggtgcctcac tgattaagca  1260
ttggtaaccg attctaggtg cattggcgca gaaaaaaatg cctgatgcga cgctgcgcgt  1320
cttatactcc cacatatgcc agattcagca acggatacgg cttccccaac ttgcccactt  1380
ccatacgtgt cctccttacc agaaatttat ccttaagatc gtttaaactc gactctggct  1440
ctatcgaatc tccgtcgttt cgagcttacg cgaacagccg tggcgctcat ttgctcgtcg  1500
ggcatcgaat ctcgtcagct atcgtcagct tacctttttg gcagcgatcg cggctcccga  1560
catcttggac cattagctcc acaggtatct tcttccctct agtggtcata acagcagctt  1620
cagctacctc tcaattcaaa aaacccctca agacccgttt agaggcccca aggggttatg  1680
ctatcaatcg ttgcgttaca cacacaaaaa accaacacac atccatcttc gatggatagc  1740
gattttatta tctaactgct gatcgagtgt agccagatct agtaatcaat tacggggtca  1800
ttagttcata gcccatatat ggagttccgc gttacataac ttacggtaaa tggcccgcct  1860
ggctgaccgc ccaacgaccc ccgcccattg acgtcaataa tgacgtatgt tcccatagta  1920
acgccaatag ggactttcca ttgacgtcaa tgggtggagt atttacggta aactgcccac  1980
ttggcagtac atcaagtgta tcatatgcca agtacgcccc ctattgacgt caatgacggt  2040
aaatggcccg cctggcatta tgcccagtac atgaccttat gggactttcc tacttggcag  2100
tacatctacg tattagtcat cgctattacc atgctgatgc ggttttggca gtacatcaat  2160
gggcgtggat agcggtttga ctcacgggga tttccaagtc tccaccccat tgacgtcaat  2220
gggagtttgt tttggcacca aaatcaacgg gactttccaa aatgtcgtaa caactccgcc  2280
ccattgacgc aaatgggcgg taggcgtgta cggtgggagg tctatataag cagagctggt  2340
ttagtgaacc gtcagatcag atctttgtcg atcctaccat ccactcgaca cacccgccag  2400
cggccgctaa tacgactcac tatagggaga agtactgcca ccatgggcaa gaagcaaaat  2460
cgcaagacgg ggaattccaa gacacaatcc gctagcccac cacctaaaga gcgttctagc  2520
tcccctgcta ctgagcagtc ctggatggaa aacgacttcg atgaactccg ggaagaggga  2580
tttaggcgat ccaactattc agaactccgc gaagatatcc agacaaaggg gaaggaagtc  2640
gagaatttcg agaagaacct cgaggagtgc atcacccgta tcacaaacac tgagaaatgt  2700
ctcaaagaac tcatggaact taagacaaaa gccagggagc ttcgagagga gtgtcggagt  2760
ctgagatcca ggtgtgacca gctcgaggag cgcgtgagcg cgatggaaga cgagatgaac  2820
gagatgaaaa gagagggcaa attcagggag aagcgcatta agaggaacga acagagtctg  2880
caggagattt gggattacgt caagaggcct aacctgcggt tgatcggcgt ccccgagagc  2940
gacgtagaaa acgggactaa actggagaat acacttcaag acatcattca agaaaatttt  3000
ccaaacctgg ctcggcaagc taatgtgcaa atccaagaga tccaacgcac accccagcgg  3060
tatagctctc ggcgtgccac ccctaggcat attatcgtgc gctttactaa ggtggagatg  3120
aaagagaaga tgctgcgagc cgctcgggaa aagggaaggg tgactttgaa gggcaaacct  3180
attcggctga cggttgacct tagcgccgag acactccagg cacgccggga atggggcccc  3240
atctttaata tcctgaagga gaagaacttc cagccacgaa tctcttaccc tgcaaagttg  3300
agttttatct ccgagggtga gattaagtat ttcatcgata aacagatgct gcgagacttc  3360
gtgacaactc gcccagctct caaggaactg ctcaaagagg ctcttaatat ggagcgcaat  3420
aatagatatc aacccttgca gaaccacgca aagatgggct ccggcgaggg caggggaagc  3480
cttctaacat gcggggacgt ggaggaaaat cccggcccag gtagcggccc aaagaagaag  3540
cggaaggtcg gcggcggcag caccggctct aactcacata tcaccatcct tacacttaac  3600
attaacggcc tcaactcagc tatcaagcgc catcggctgg ccagctggat caaatcacag  3660
gatccaagcg tttgttgcat ccaagagacc cacctgacct gtagagatac tcaccgcctc  3720
aagatcaagg gatggcgaaa gatttatcag gcgaacggta agcagaagaa agccggagtc  3780
gcaattctgg tctcagacaa gacggatttc aagcccacca aaattaagcg tgataaggaa  3840
ggtcactata ttatggtgaa aggcagcata cagcaggaag aacttaccat attgaacatc  3900
tacgcgccaa acaccggcgc acctcgcttt atcaaacagg tcctgtccga tctgcagcga  3960
gatctggatt ctcatacgtt gattatgggt gatttcaata caccattgag caccctggat  4020
cgcagcacca ggcaaaaggt aaataaagac acgcaagagc tcaatagcgc actgcatcag  4080
gcagatctca ttgatattta tcgcactctt catcctaaga gtaccgagta cacattcttc  4140
agcgccccac atcatacata ctcaaagatc gatcatatcg tcggctcaaa ggctctgctg  4200
tcaaagtgca agcgcacaga gataattaca aattacctgt cagatcatag cgcgatcaag  4260
ctcgagctga gaatcaagaa cctgacccag agccggagta ccacttggaa gcttaataac  4320
ctgctgctca acgattattg ggtccacaat gagatgaagg cagagattaa aatgttcttc  4380
gaaacaaatg agaataagga tactacctat caaaaccttt gggatgcctt taaggccgtc  4440
tgcagaggca agttcatcgc cctcaacgcc tataaaagaa aacaagagag atctaagatc  4500
gatactctca cctctcagct gaaggagttg gagaaacagg aacagaccca ctccaaggcg  4560
tcaagacggc aggagatcac aaagattcgc gccgagttga aagagatcga aacccaaaag  4620
actcttcaga aaattaacga gtctcgtagt tggttcttcg agcggattaa taagatagac  4680
agacctctgg cacgactgat taagaagaag cgcgaaaaga accagattga taccatcaag  4740
aacgacaagg gcgacatcac tactgacccg accgagatcc agaccactat tcgggagtat  4800
tataagcatt tgtatgctaa caagcttgag aacctggaag agatggacac ttttctggat  4860
acctatactc tgccacggct taatcaagag gaagtcgagt ccctcaaccg cccaattaca  4920
ggaagcgaga ttgtggccat aattaactcc ctgccgacaa agaaatctcc tggtccggac  4980
gggtttacag ctgagtttta tcaacggtat atggaagagc ttgtaccgtt tctgctcaag  5040
ctctttcagt ctatagaaaa ggaaggcatc ttgcccaatt ccttctacga agcttctata  5100
atacttattc ccaaaccagg acgcgatacc acaaagaagg aaaacttccg gcccattagt  5160
ctcatgaata tcgacgctaa aatattgaac aagattctcg ccaacagaat ccaacaacat  5220
attaagaaat tgatacatca cgaccaggtg gggtttatac ctggcatgca gggctggttt  5280
aacatccgga agagtattaa cgtcattcaa cacattaata gagctaagga taagaatcat  5340
atgatcatct ctatagacgc ggaaaaggca ttcgataaga ttcagcagcc atttatgctc  5400
aagactctga acaaactcgg catcgacgga acatatttta agattattcg cgcaatttac  5460
gataagccga ctgctaacat tatccttaac ggccaaaagc tcgaggcctt tccgctcaag  5520
actggaaccc gccaaggctg tcccctctcc ccgcttttgt ttaatattgt actcgaggtg  5580
ctggctaggg ctattcgtca agagaaagag attaaaggga tacagctcgg gaaggaagag  5640
gtcaagcttt ccttgttcgc cgatgatatg attgtgtacc tggagaatcc tattgtgtct  5700
gctcagaacc ttcttaaact tatttctaac tttagcaagg tcagcggcta taagattaac  5760
gtccagaaat ctcaggcctt tctgtacaca aataatcgac agaccgaatc ccagataatg  5820
ggtgagcttc cgtttgtcat agccagcaaa aggataaagt atctcggaat ccagctgaca  5880
```

-continued

```
cgagacgtta aagatttgtt taaggaaaat tacaagcctc tcctgaaaga gattaaggaa  5940
gatactaata agtggaagaa tatcccctgt tcatgggttg gcagaatcaa catagtgaag  6000
atggcaatac ttcctaaagt gatatatcgc tttaacgcca tcccaattaa actgcctatg  6060
accttcttta cggagctcga gaaaacaacc cttaaattta tatggaatca aaagagagca  6120
agaatagcga agtccatctt gagccagaag aataaggccg gtgggattac tttgcctgat  6180
tttaagttgt attataaagc cacagtaact aagacagcct ggtattggta tcagaataga  6240
gacatcgacc agtggaatcg gaccgaacca tcagagataa tgccccacat ctataattac  6300
cttatattcg ataagccaga aaagaataaa cagtggggca aagacagcct cttcaacaag  6360
tggtgttggg agaattggct ggccatatgc cggaaactca agctcgaccc ctttcttaca  6420
ccctacacta aaatcaacag taggtggatc aaggacttga atgtcaagcc aaagactata  6480
aagacactgg aagagaatct tgggatcaca atacaagata taggcgtcgg caaagatttt  6540
atgtcaaaga cgcccaaggc catggccact aaggataaga ttgataagtg ggaccttatt  6600
aagctcaaaa gcttctgtac tgccaaggag accacgatca gagttaatag gcagcccact  6660
acatgggaaa agattttcgc cacttattca tcagataagg ggttgataag cagaatatat  6720
aacgagctga agcagatcta caagaagaaa acgaataatc ccatcaagaa gtgggcaaaa  6780
gatatgaaca ggcattttag caaagaggat atctacgccg cgaagaagca tatgaagaag  6840
tgtagttcaa gcttggccat tcgtgagatg cagattaaga cgaccatgcg ataccacctt  6900
accccagtga ggatggcaat tatcaagaaa tctggcaata atagatgttg gcggggctgt  6960
ggcgagattg gcaccctgct ccattgctgg tgggattgca agctggtgca gccgctttgg  7020
aaatcagtct ggcgctttct gagggacctc gagcttgaga ttcccttcga tcccgcaatt  7080
cccttgctcg gaatctatcc taacgaatac aagagctgtt gttacaagga tacgtgtacc  7140
cggatgttca tcgcggcctt gtttacgata gctaagacgt ggaatcagcc taagtgcccc  7200
acaatgatcg attggatcaa gaaaatgtgg catatttata ccatggagta ttacgcagca  7260
attaagaatg acgaatttat ttccttcgtt gggacctgga tgaagctgga gactattatt  7320
ctgagcaagc tgtctcagga gcaaaagaca aagcatagaa tcttctctct cattggtggt  7380
aacgactaca aagacgatga cgacaagtaa agcgcttcta gaagttgtct cctcctgcac  7440
tgactgactg atacaatcga tttctggatc cgcaggccta atcaacctct ggattacaaa  7500
atttgtgaaa gattgactgg tattcttaac tatgttgctc cttttacgct atgtggatac  7560
gctgctttaa tgcctttgta tcatgctatt gcttcccgta tggctttcat tttctcctcc  7620
ttgtataaat cctggttgct gtctctttat gaggagttgt ggcccgttgt caggcaacgt  7680
ggcgtggtgt gcactgtgtt tgctgacgca acccccactg gttggggcat tgccaccacc  7740
tgtcagctcc tttccgggac tttcgctttc cccctcccta ttgccacggc ggaactcatc  7800
gccgcctgcc ttgcccgctg ctggacaggg gctcggctgt tgggcactga caattccgtg  7860
gtgttgtcgg ggaagctgac gtcctttcca tggctgctcg cctgtgttgc cacctggatt  7920
ctgcgcggga cgtccttctg ctacgtccct tcggccctca atccagcgga ccttccttcc  7980
cgctgagaga cacaaaaaat tccaacacac tattgcaatg aaaataaatt tcctttatta  8040
gccagaagtc agatgctcaa ggggcttcat gatgtcccca taatttttgg cagagggaaa  8100
aagatctcag tggtatttgt gagccagggc attggccttc tgataggcag cctgcacctg  8160
aggagtgcgg ccgctttact tgtacagctc gtccatgccg agagtgatcc cggcggcggt  8220
cacgaactcc agcaggacca tgtgatcgcg cttctcgttg gggtctttgc tcagggcgga  8280
ctgggtgctc aggtagtggt tgtcgggcag cagcacgggg ccgtcgccga tgggggtgtt  8340
ctgctggtag tggtcggcga gctgcacgct gccgtcctcg atgttgtggc ggatcttgaa  8400
gttcaccttg atgccgttct tctgcttgtc ggccatgata tagacgttgt ggctgttgta  8460
gttgtactcc agcttgtgcc ccaggatgtt gccgtcctcc ttgaagtcga tgcccttcag  8520
ctcgatgcgg ttcaccaggg tgtcgccctc gaacttcacc tcggcgcggg tcttgtagtt  8580
gccgtcgtcc ttgaagaaga tggtgcgctc ctggacgtag ccttcgggca tggcggactt  8640
gaagaagtcg tgctgcttca tgtggtcggg gtagcggctg aagcactgca cgccgtaggt  8700
cagggtggtc acgagggtgg gccagggcac gggcagcttg ccggtggtgc agatgaactt  8760
cagggtcagc ttgccgtagg tggcatcgcc ctcgccctcg ccggacacgc tgaacttgtg  8820
gccgtttacg tcgccgtcca gctcgaccag gatgggcacc accccggtga acagctcctc  8880
gcccttgctc accatggtgg cgggatctga cggttcacta aaccagctct gcttatatag  8940
acctcccacc gtacacgcct accgcccatt tgcgtcaatg gggcggagtt gttacgacat  9000
tttggaaagt cccgttgatt ttggtgccaa aacaaactcc cattgacgtc aatggggtgg  9060
agacttggaa atccccgtga gtcaaaccgc tatccacgcc cattgatgta ctgccaaaac  9120
cgcatcacca tggtaatagc gatgactaat acgtagatgt actgccaagt aggaaagtcc  9180
cataaggtca tgtactgggc ataatgccag gcgggccatt taccgtcatt gacgtcaata  9240
gggggcgtac ttggcatatg atacacttga tgtactgcca agtgggcagt ttaccgtaaa  9300
tactccaccc attgacgtca atggaaagtc cctattggcg ttactatggg aacatacgtc  9360
attattgacg tcaatgggcg ggggtcgttg ggcggtcagc caggcgggcc atttaccgta  9420
agttatgtaa cgggcctgct gccggctctg cggcctcttc cgcgtcttcg ccttcgccct  9480
cagacgagtc ggatctccct ttgggccgcc tccccgcctg tctagcttga ctgactgaga  9540
tacagcgtac cttcagctca cagacatgat aagatacatt gatgagtttg gacaaaccac  9600
aactagaatg cagtgaaaaa aatgctttat ttgtgaaatt tgtgatgcta ttgctttatt  9660
tgtaaccatt ataagctgca ataaacaagt taacaacaac aattgcattc attttatgtt  9720
tcaggttcag ggggaggtgt gggaggtttt ttaaagcaag taaaacctct acaaatgtgg  9780
tattggccca tctctatcgg tatcgtagca taacccettg ggcctctaa acgggtcttg  9840
aggggttttt tgtgcccctc gggccggatt gctatctacc ggcattggcg cagaaaaaaa  9900
tgcctgatgc gacgctgcgc gtcttatact cccacatatg ccagattcag caacggatac  9960
ggcttcccca acttgcccac ttccatacgt gtcctcctta ccagaaattt atccttaagg  10020
tcgtcagcta tcctgcaggc gatctctcga tttcgatcaa gacattcctt taatggtctt  10080
ttctggacac cactaggggt cagaagtagt tcatcaaact ttcttccctc cctaatctca  10140
ttggttacct tgggctatcg aaacttaatt aagcgatctg catctcaatt agtcagcaac  10200
catagtcccg cccctaactc cgcccatccc gcccctaact ccgcccagtt ccgcccattc  10260
tccgccccat cgctgactaa ttttttttat ttatgcagag gccgaggccg cctcggcctc  10320
tgagctattc cagaagtagt gaggaggctt ttttggaggc ctaggctttt gcaaaggagg  10380
tagccaacat gattgaacaa gatggattgc acgcaggttc tcccgccgct tgggtggaga  10440
ggctattcgg ctatgactgg gcacaacaga caatcggctg ctctgatgcc gccgtgttcc  10500
ggctgtcagc gcaggggcgc ccggttcttt ttgtcaagac cgacctgtcc ggtgccctga  10560
atgaactcca ggacgaggca gcgcggctat cgtggctggc cacgacgggc gttccttgcg  10620
```

```
cagctgtgct cgacgttgtc actgaagcgg gaagggactg gctgctattg ggcgaagtgc  10680
cggggcagga tctcctgtca tctcaccttg ctcctgccga gaaagtatcc atcatggctg  10740
atgcaatgcg gcggctgcat acgcttgatc cggctacctg cccattcgac caccaagcga  10800
aacatcgcat cgagcgagca cgtactcgga tggaagccgg tcttgtcgat caggatgatc  10860
tggacgaaga gcatcagggg ctcgcgccag ccgaactgtt cgccaggctc aaggcgcgga  10920
tgcccgacgg cgaggatctc gtcgtgaccc acggcgatgc ctgcttgccg aatatcatgg  10980
tggaaaatgg ccgcttttct ggattcatcg actgtggccg gctgggtgtg gcggaccgct  11040
atcaggacat agcgttggct acccgtgata ttgctgaaga gcttggcggc gaatgggctg  11100
accgcttcct cgtgctttac ggtatcgccg ctcccgattc gcagcgcatc gccttctatc  11160
gccttcttga cgagttcttc tagtatgtaa gccctgtgcc ttctagttgc cagccatctg  11220
ttgtttgccc ctcccccgtg ccttccttga ccctggaagg tgccactccc actgtccttt  11280
cctaataaaa tgaggaaatt gcatcgcatt gtctgagtag gtgtcattct attctggggg  11340
gtggggtggg gcaggacagc aagggggagg attgggaaga caatagcagg catgctgggg  11400
atgcggtggg ctctatggtt aattaaccag tcaagtcagc tacttggcga gatcgacttg  11460
tctgggtttc gactacgctc agaattgcgt cagtcaagtt cgatctggtc cttgctattg  11520
caccggttct ccgattacga gtttcattta aatcatgtga gcaaaaggcc agcaaaaggc  11580
caggaaccgt aaaaaggccg cgttgctggc gtttttccat aggctccgcc cccctgacga  11640
gcatcacaaa aatcgacgct caagtcagag gtggcgaaac ccgacaggac tataaagata  11700
ccaggcgttt ccccctggaa gctccctcgt gcgctctcct gttccgaccc tgccgcttac  11760
cggatacctg tccgcctttc tcccttcggg aagcgtggcg ctttctcata gctcacgctg  11820
taggtatctc agttcggtgt aggtcgttcg ctccaagctg ggctgtgtgc acgaaccccc  11880
cgttcagccc gaccgctgcg ccttatccgg taactatcgt cttgagtcca acccggtaag  11940
acacgactta tcgccactgg cagcagccac tggtaacagg attagcagag cgaggtatgt  12000
aggcggtgct acagagttct tgaagtggtg gcctaactac ggctacacta gaagaacagt  12060
atttggtatc tgcgctctgc tgaagccagt taccttcgga aaaagagttg gtagctcttg  12120
atccggcaaa caaaccaccg ctggtagcgg tggttttttt gtttgcaagc agcagattac  12180
gcgcagaaaa aaaggatctc aagaagatcc tttgatcttt tctacggggt ctgacgctca  12240
gtggaacgaa aactcacgtt aagggatttt ggtcatgaga ttatcaaaaa ggatcttcac  12300
ctagatcctt ttaaattaaa aatgaagttt taaatcaatc taaagtatat atgagtaaac  12360
ttggtctgac agttaccaat gcttaatcag tgaggcacct atctcagcga tctgtctatt  12420
tcgttcatcc atagttgcat ttaaatttcc gaactctcca aggccctcgt cggaaaatct  12480
tcaaaccttt cgtccgatcc atcttgcagg ctacctctcg aacgaactat cgcaagtctc  12540
t                                                                 12541

SEQ ID NO: 110         moltype = DNA  length = 12556
FEATURE                Location/Qualifiers
misc_feature           1..12556
                       note = Description of Artificial Sequence: Synthetic
                        polynucleotide
source                 1..12556
                       mol_type = other DNA
                       organism = synthetic construct
SEQUENCE: 110
accgagaacg atcctctcag tgcgagtctc gacgatccat atcgttgctt ggcagtcagc  60
cagtcggaat ccagcttggg acccaggaag tccaatcgtc agatattgta ctcaagcctg  120
gtcacggcag cgtaccgatc tgtttaaacc tagatattga tagtctgatc ggtcaacgta  180
taatcgagtc ctagcttttg caaacatcta tcaagagaca ggatcagcag gaggctttcg  240
catgagtatt caacatttcc gtgtcgccct tattcccttt tttgcggcat tttgccttcc  300
tgtttttgct cacccagaaa cgctggtgaa agtaaaagat gctgaagatc agttgggtgc  360
gcgagtgggt tacatcgaac tggatctcaa cagcggtaag atccttgaga gttttcgccc  420
cgaagaacgc tttccaatga tgagcacttt taaagttctg ctatgtggcg cggtattatc  480
ccgtattgac gccgggcaag agcaactcgg tcgccgcata cactattctc agaatgactt  540
ggttgagtat tcaccagtca cagaaaagca tcttacggat ggcatgacag taagagaatt  600
atgcagtgct gccataacca tgagtgataa cactgcggcc aacttacttc tgacaacgat  660
tggaggaccg aaggagctaa ccgctttttt gcacaacatg ggggatcatg taactcgcct  720
tgatcgttgg gaaccggagc tgaatgaagc cataccaaac gacgagcgtg acaccacgat  780
gcctgtagca atggcaacaa ccttgcgtaa actattaact ggcgaactac ttactctagc  840
ttcccggcaa cagttgatag actggatgga ggcggataaa gttgcaggac cacttctgcg  900
ctcggccctt ccggctggct ggtttattgc tgataaatct ggagccggtg agcgtgggtc  960
tcgcggtatc attgcagcac tggggccaga tggtaagccc tcccgtatcg tagttatcta  1020
cacgacgggg agtcaggcaa ctatggatga acgaaataga cagatcgctg agataggtgc  1080
ctcactgatt aagcattggt aaccgattct aggtgcattg gcgcagaaaa aaatgcctga  1140
tgcgacgctg cgcgtcttat actcccacat atgccagatt cagcaacgga tacggcttcc  1200
ccaacttgcc cacttccata cgtgtcctcc ttaccagaaa tttatcctta agatcgttta  1260
aactcgactc tggctctatc gaatctccgt cgtttcgagc ttacgcgaac agccgtggcg  1320
ctcatttgct cgtcgggcat cgaatctcgt cagctatcgt cagcttacct tttggcagc  1380
gatcgcggct cccgacatct tggaccatta gctccacagg tatcttcttc cctctagtgg  1440
tcataacagc agcttcagct acctctcaat tcaaaaaacc cctcaagacc cgtttagagg  1500
ccccaagggg ttatgctatc aatcgttgcg ttacacacac aaaaaaccaa cacacatcca  1560
tcttcgatgg atagcgattt tattatctaa ctgctgatcg agtgtagcca gatctagtaa  1620
tcaattacgg ggtcattagt tcatagccca tatatggagt tccgcgttac ataacttacg  1680
gtaaatggcc cgcctggctg accgcccaac gacccccgcc cattgacgtc aataatgacg  1740
tatgttccca tagtaacgcc aatagggact ttccattgac gtcaatgggt ggagtattta  1800
cggtaaactg cccacttggc agtacatcaa gtgtatcata tgccaagtac gccccctatt  1860
gacgtcaatg acggtaaatg gcccgcctgg cattatgccc agtacatgac cttatgggac  1920
tttcctactt ggcagtacat ctacgtatta gtcatcgcta ttaccatgct gatgcggttt  1980
tggcagtaca tcaatgggcg tggatagcgg tttgactcac ggggatttcc aagtctccac  2040
cccattgacg tcaatgggag tttgttttgg caccaaaatc aacgggactt tccaaaatgt  2100
cgtaacaact ccgccccatt gacgcaaatg ggcggtaggc gtgtacggtg ggaggtctat  2160
```

-continued

```
ataagcagag ctggtttagt gaaccgtcag atcagatctt tgtcgatcct accatccact  2220
cgacacaccc gccagcggcc gctaatacga ctcactatag ggagaagtac tgccaccatg  2280
ggcaagaagc aaaatcgcaa gacggggaat tccaagacac aatccgctag cccaccacct  2340
aaagagcgtt ctagctcccc tgctactgag cagtcctgga tggaaaacga cttcgatgaa  2400
ctccgggaag agggatttag gcgatccaac tattcagaac tccgcgaaga tatccagaca  2460
aaggggaagg aagtcgagaa tttcgagaag aacctcgagg agtgcatcac ccgtatcaca  2520
aacactgaga aatgtctcaa agaactcatg gaacttaaga caaaagccag ggagcttcga  2580
gaggagtgtc ggagtctgag atccaggtgt gaccagctcg aggagcgcgt gagcgcgatg  2640
gaagacgaga tgaacgagat gaaaagagag ggcaaattca gggagaagcg cattaagagg  2700
aacgaacaga gtctgcagga gatttgggat tacgtcaaga ggcctaacct gcggttgatc  2760
ggcgtccccg agagcgacgt agaaaacggg actaaactgg agaatacact tcaagacatc  2820
attcaagaaa attttccaaa cctggctcgg caagctaatg tgcaaatcca agagatccaa  2880
cgcacacccc agcggtatag ctctcggcgt gccacccccta ggcatattat cgtgcgcttt  2940
actaaggtgg agatgaaaga gaagatgctg cgagccgctc gggaaaaggg aagggtgact  3000
ttgaagggca aacctattcg gctgacggtt gaccttagcg ccgagacact ccaggcacgc  3060
cgggaatggg gccccatctt taatatcctg aaggagaaga acttccagcc acgaatctct  3120
taccctgcaa agttgagttt tatctccgag ggtgagatta agtatttcat cgataaacag  3180
atgctgcgag acttcgtgac aactcgccca gctctcaagg aactgctcaa agaggctctt  3240
aatatggagc gcaataatag atatcaaccc ttgcagaacc acgcaaagat gggctccggc  3300
gagggcaggg gaagccttct aacatgcggg gacgtggagg aaaatcccgg cccaggtagc  3360
ggcaccggct ctaactcaca tatcaccatc cttacactta acattaacgg cctcaactca  3420
gctatcaagc gccatcggct ggccagctgg atcaaatcac aggatccaag cgtttgttgc  3480
atccaagaga cccacctgac ctgtagagat actcaccgcc tcaagatcaa gggatggcga  3540
aagatttatc aggcgaacgg taagcagaag aaagccggag tcgcaattct ggtctcagac  3600
aagacggatt tcaagcccac caaaattaag cgtgataagg aaggtcacta tattatggtg  3660
aaaggcagca tacagcagga agaacttacc atattgaaca tctacgcgcc aaacaccggc  3720
gcacctcgct ttatcaaaca ggtcctgtcc gatctgcagc gagatctgga ttctcatacg  3780
ttgattatgg gtgatttcaa tacaccattg agcaccctgg atcgcagcac caggcaaaag  3840
gtaaataaag acacgcaaga gctcaatagc gcactgcatc aggcagatct cattgatatt  3900
tatcgcactc ttcatcctaa gagtaccgag tacacattct tcagcgcccc acatcataca  3960
tactcaaaga tcgatcatat cgtcggctca aaggctctgc tgtcaaagtg caagcgcaca  4020
gagataatta caaattacct gtcagatcat agcgcgatca agctcgagct gagaatcaag  4080
aacctgaccc agagccggag taccacttgg aagcttaata acctgctgct caacgattat  4140
tgggtccaca atgagatgaa ggcagagatt aaaatgttct tcgaaacaaa tgagaataag  4200
gatactacct atcaaaacct ttgggatgcc tttaaggccg tctgcagagg caagttcatc  4260
gccctcaacg cctataaaag aaaacaagag agatctaaga tcgatactct cacctctcag  4320
ctgaaggagt tggagaaaca ggaacagacc cactccaagg cgtcaagacg gcaggagatc  4380
acaaagattc gcgccgagtt gaaagagatc gaaacccaaa agactcttca gaaaattaac  4440
gagtctcgta gttggttctt cgagcggatt aataagatag acagacctct ggcacgactg  4500
attaagaaga agcgcgaaaa gaaccagatt gataccatca agaacgacaa gggcgacatc  4560
actactgacc cgaccgagat ccagaccact attcgggagt attataagca tttgtatgct  4620
aacaagcttg agaacctgga agagatggac actttttctgg atacctatac tctgccacgg  4680
cttaatcaag aggaagtcga gtccctcaac cgcccaatta caggaagcga gattgtggcc  4740
ataattaact ccctgccgac aaagaaatct cctggtccgg acgggtttac agctgagttt  4800
tatcaacggt atatggaaga gcttgtaccg tttctgctca agctctttca gtctatagaa  4860
aaggaaggca tcttgcccaa ttccttctac gaagcttcta taatacttat tcccaaacca  4920
ggacgcgata ccacaaagaa ggaaaacttc cggcccatta gtctcatgaa tatcgacgct  4980
aaaatattga acaagattct cgccaacaga atccaacaac atattaagaa attgatacat  5040
cacgaccagg tggggtttat acctggcatg cagggctggt ttaacatccg gaagagtatt  5100
aacgtcattc aacacattaa tagagctaag gataagaatc atatgatcat ctctatagac  5160
gcggaaaagg cattcgataa gattcagcag ccatttatgc tcaagactct gaacaaactc  5220
ggcatcgacg gaacatattt taagattatt cgcgcaattt acgataagcc gactgctaac  5280
attatcctta acggccaaaa gctcgaggcc tttccgctca agactggaac ccgccaaggc  5340
tgtcccctct ccccgctttt gtttaatatt gtactcgagg tgctggctag ggctattcgt  5400
caagagaaag agattaaagg gatacagctc gggaaggaag aggtcaagct ttccttgttc  5460
gccgatgata tgattgtgta cctggagaat cctattgtgt ctgctcagaa ccttcttaaa  5520
cttatttcta actttagcaa ggtcagcggc tataagatta acgtccagaa atctcaggcc  5580
tttctgtaca caaataatcg acagaccgaa tcccagataa tgggtgagct tccgtttgtc  5640
atagccagca aaaggataaa gtatctcgga atccagctga cacgagacgt taaagatttg  5700
tttaaggaaa attacaagcc tctcctgaaa gagattaagg aagatactaa taagtggaag  5760
aatatcccct gttcatgggt tggcagaatc aacatagtga agatggcaat acttcctaaa  5820
gtgatatatc gctttaacgc catcccaatt aaactgccta tgaccttctt tacggagctc  5880
gagaaaacaa cccttaaatt tatatggaat caaaagagag caagaatagc gaagtccatc  5940
ttgagccaga agaataaggc cggtgggatt actttgcctg attttaagtt gtattataaa  6000
gccacagtaa ctaagacagc ctggtattgg tatcagaata gagacatcga ccagtggaat  6060
cggaccgaac catcagagat aatgccccac atctataatt accttatatt cgataagcca  6120
gaaaagaata aacagtgggg caaagacagc ctcttcaaca agtggtgttg ggagaattgg  6180
ctggccatat gccggaaact caagctcgac ccctttctta caccctacac taaaatcaac  6240
agtaggtgga tcaaggactt gaatgtcaag ccaaagacta taaagacact ggaagagaat  6300
cttgggatca caatacaaga tataggcgtc ggcaaagatt ttatgtcaaa gacgcccaag  6360
gccatggcca ctaaggataa gattgataag tgggacctta ttaagctcaa aagcttctgt  6420
actgccaagg agaccacgat cagagttaat aggcagccca ctacatggga aaagattttc  6480
gccacttatt catcagataa ggggttgata agcagaatat ataacgagct gaagcagatc  6540
tacaagaaga aaacgaataa tcccatcaag aagtgggcaa aagatatgaa caggcatttt  6600
agcaaagagg atatctacgc cgcgaagaag catatgaaga agtgtagttc aagcttggcc  6660
attcgtgaga tgcagattaa gacgaccatg cgataccacc ttaccccagt gaggatggca  6720
attatcaaga aatctggcaa taatagatgt tggcggggct gtggcgagat tggcaccctg  6780
ctccattgct ggtgggattg caagctggtg cagccgcttt ggaaatcagt ctggcgcttt  6840
ctgagggacc tcgagcttga gattcccttc gatcccgcaa ttcccttgct cggaatctat  6900
```

-continued

```
cctaacgaat acaagagctg ttgttacaag gatacgtgta cccggatgtt catcgcggcc  6960
ttgtttacga tagctaagac gtggaatcag cctaagtgcc ccacaatgat cgattggatc  7020
aagaaaatgt ggcatattta taccatggag tattacgcag caattaagaa tgacgaattt  7080
atttccttcg ttgggacctg gatgaagctg gagactatta ttctgagcaa gctgtctcag  7140
gagcaaaaga caaagcatag aatcttctct ctcattggtg gtaacgacta caaagacgat  7200
gacgacaaga aaaggccggc ggccacgaaa aaggccggcc aggcaaaaaa gaaaaagtaa  7260
agcgcttcta gaagttgtct cctcctgcac tgactgactg atacaatcga tttctggatc  7320
cgcaggccta atcaacctct ggattacaaa atttgtgaaa gattgactgg tattcttaac  7380
tatgttgctc cttttacgct atgtggatac gctgctttaa tgcctttgta tcatgctatt  7440
gcttcccgta tggctttcat tttctcctcc ttgtataaat cctggttgct gtctctttat  7500
gaggagttgt ggcccgttgt caggcaacgt ggcgtggtgt gcactgtgtt tgctgacgca  7560
acccccactg gttggggcat tgccaccacc tgtcagctcc tttccgggac tttcgctttc  7620
cccctcccta ttgccacggc ggaactcatc gccgcctgcc ttgcccgctg ctggacaggg  7680
gctcggctgt tgggcactga caattccgtg gtgttgtcgg ggaagctgac gtcctttcca  7740
tggctgctcg cctgtgttgc cacctggatt ctgcgcggga cgtccttctg ctacgtccct  7800
tcggccctca atccagcgga ccttccttcc cgctgagaga cacaaaaaat tccaacacac  7860
tattgcaatg aaaataaatt tcctttatta gccagaagtc agatgctcaa ggggcttcat  7920
gatgtcccca taatttttgg cagagggaaa aagatctcag tggtatttgt gagccagggc  7980
attggccttc tgataggcag cctgcacctg aggagtgcgg ccgctttact tgtacagctc  8040
gtccatgccg agagtgatcc cggcggcggt cacgaactcc agcaggacca tgtgatcgcg  8100
cttctcgttg gggtctttgc tcagggcgga ctgggtgctc aggtagtggt tgtcgggcag  8160
cagcacgggg ccgtcgccga tgggggtgtt ctgctggtag tggtcggcga gctgcacgct  8220
gccgtcctcg atgttgtggc ggatcttgaa gttcaccttg atgccgttct tctgcttgtc  8280
ggccatgata tagacgttgt ggctgttgta gttgtactcc agcttgtgcc ccaggatgtt  8340
gccgtcctcc ttgaagtcga tgcccttcag ctcgatgcgg ttcaccaggg tgtcgccctc  8400
gaacttcacc tcggcgcggg tcttgtagtt gccgtcgtcc ttgaagaaga tggtgcgctc  8460
ctggacgtag ccttcgggca tggcggactt gaagaagtcg tgctgcttca tgtggtcggg  8520
gtagcggctg aagcactgca cgccgtaggt cagggtggtc acgagggtgg gccagggcac  8580
gggcagcttg ccggtggtgc agatgaactt cagggtcagc ttgccgtagg tggcatcgcc  8640
ctcgccctcg ccggacacgc tgaacttgtg gccgtttacg tcgccgtcca gctcgaccag  8700
gatgggcacc accccggtga acagctcctc gcccttgctc accatggtgg cgggatctga  8760
cggttcacta aaccagctct gcttatatag acctcccacc gtacacgcct accgcccatt  8820
tgcgtcaatg gggcggagtt gttacgacat tttggaaagt cccgttgatt ttggtgccaa  8880
aacaaactcc cattgacgtc aatggggtgg agacttggaa atccccgtga gtcaaaccgc  8940
tatccacgcc cattgatgta ctgccaaaac cgcatcacca tggtaatagc gatgactaat  9000
acgtagatgt actgccaagt aggaaagtcc cataaggtca tgtactgggc ataatgccag  9060
gcgggccatt taccgtcatt gacgtcaata gggggcgtac ttggcatatg atacacttga  9120
tgtactgcca agtgggcagt ttaccgtaaa tactccaccc attgacgtca atggaaagtc  9180
cctattggcg ttactatggg aacatacgtc attattgacg tcaatgggcg ggggtcgttg  9240
ggcggtcagc caggcgggcc atttaccgta agttatgtaa cgggcctgct gccggctctg  9300
cggcctcttc cgcgtcttcg ccttcgccct cagacgagtc ggatctccct ttgggccgcc  9360
tccccgcctg tctagcttga ctgactgaga tacagcgtac cttcagctca cagacatgat  9420
aagatacatt gatgagtttg gacaaaccac aactagaatg cagtgaaaaa aatgctttat  9480
ttgtgaaatt tgtgatgcta ttgctttatt tgtaaccatt ataagctgca ataaacaagt  9540
taacaacaac aattgcattc attttatgtt tcaggttcag ggggaggtgt gggaggtttt  9600
ttaaagcaag taaaacctct acaaatgtgg tattggccca tctctatcgg tatcgtagca  9660
taaccccttg gggcctctaa acgggtcttg aggggttttt tgtgcccctc gggccggatt  9720
gctatctacc ggcattggcg cagaaaaaaa tgcctgatgc gacgctgcgc gtcttatact  9780
cccacatatg ccagattcag caacggatac ggcttcccca acttgcccac ttccatacgt  9840
gtcctcctta ccagaaattt atccttaagg tcgtcagcta tcctgcaggc gatctctcga  9900
tttcgatcaa gacattcctt taatggtctt ttctggacac cactaggggt cagaagtagt  9960
tcatcaaact ttcttccctc cctaatctca ttggttacct tgggctatcg aaacttaatt  10020
aagcgatctg catctcaatt agtcagcaac catagtcccg cccctaactc cgcccatccc  10080
gcccctaact ccgcccagtt ccgcccattc tccgccccat cgctgactaa ttttttttat  10140
ttatgcagag gccgaggccg cctcggcctc tgagctattc cagaagtagt gaggaggctt  10200
ttttggaggc ctaggctttt gcaaaggagg tagccaacat gattgaacaa gatggattgc  10260
acgcaggttc tcccgccgct tgggtggaga ggctattcgg ctatgactgg gcacaacaga  10320
caatcggctg ctctgatgcc gccgtgttcc ggctgtcagc gcaggggcgc ccggttcttt  10380
ttgtcaagac cgacctgtcc ggtgccctga atgaactcca ggacgaggca gcgcggctat  10440
cgtggctggc cacgacgggc gttccttgcg cagctgtgct cgacgttgtc actgaagcgg  10500
gaagggactg gctgctattg ggcgaagtgc cggggcagga tctcctgtca tctcaccttg  10560
ctcctgccga gaaagtatcc atcatggctg atgcaatgcg gcggctgcat acgcttgatc  10620
cggctacctg cccattcgac caccaagcga aacatcgcat cgagcgagca cgtactcgga  10680
tggaagccgg tcttgtcgat caggatgatc tggacgaaga gcatcagggg ctcgcgccag  10740
ccgaactgtt cgccaggctc aaggcgcgga tgcccgacgg cgaggatctc gtcgtgaccc  10800
acggcgatgc ctgcttgccg aatatcatgg tggaaaatgg ccgcttttct ggattcatcg  10860
actgtggccg gctgggtgtg gcggaccgct atcaggacat agcgttggct acccgtgata  10920
ttgctgaaga gcttggcggc gaatgggctg accgcttcct cgtgctttac ggtatcgccg  10980
ctcccgattc gcagcgcatc gccttctatc gccttcttga cgagttcttc tagtatgtaa  11040
gccctgtgcc ttctagttgc cagccatctg ttgtttgccc ctcccccgtg ccttccttga  11100
ccctggaagg tgccactccc actgtccttt cctaataaaa tgaggaaatt gcatcgcatt  11160
gtctgagtag gtgtcattct attctggggg gtggggtggg gcaggacagc aagggggagg  11220
attgggaaga caatagcagg catgctgggg atgcggtggg ctctatggtt aattaaccag  11280
tcaagtcagc tacttggcga gatcgacttg tctgggtttc gactacgctc agaattgcgt  11340
cagtcaagtt cgatctggtc cttgctattg cacccgttct ccgattacga gtttcattta  11400
aatcatgtga gcaaaaggcc agcaaaaggc caggaaccgt aaaaaggccg cgttgctggc  11460
gtttttccat aggctccgcc cccctgacga gcatcacaaa aatcgacgct caagtcagag  11520
gtggcgaaac ccgacaggac tataaagata ccaggcgttt ccccctggaa gctccctcgt  11580
gcgctctcct gttccgaccc tgccgcttac cggatacctg tccgcctttc tcccttcggg  11640
```

-continued

```
aagcgtggcg ctttctcata gctcacgctg taggtatctc agttcggtgt aggtcgttcg  11700
ctccaagctg ggctgtgtgc acgaaccccc cgttcagccc gaccgctgcg ccttatccgg  11760
taactatcgt cttgagtcca acccggtaag acacgactta tcgccactgg cagcagccac  11820
tggtaacagg attagcagag cgaggtatgt aggcggtgct acagagttct tgaagtggtg  11880
gcctaactac ggctacacta gaagaacagt atttggtatc tgcgctctgc tgaagccagt  11940
taccttcgga aaaagagttg gtagctcttg atccggcaaa caaaccaccg ctggtagcgg  12000
tggttttttt gtttgcaagc agcagattac gcgcagaaaa aaaggatctc aagaagatcc  12060
tttgatcttt tctacggggt ctgacgctca gtggaacgaa aactcacgtt aagggatttt  12120
ggtcatgaga ttatcaaaaa ggatcttcac ctagatcctt ttaaattaaa aatgaagttt  12180
taaatcaatc taaagtatat atgagtaaac ttggtctgac agttaccaat gcttaatcag  12240
tgaggcacct atctcagcga tctgtctatt tcgttcatcc atagttgcat ttaaatttcc  12300
gaactctcca aggccctcgt cggaaaatct tcaaaccttt cgtccgatcc atcttgcagg  12360
ctacctctcg aacgaactat cgcaagtctc ttggccggcc ttgcgccttg gctattgctt  12420
ggcagcgcct atcgccaggt attactccaa tcccgaatat ccgagatcgg gatcacccga  12480
gagaagttca acctacatcc tcaatcccga tctatccgag atccgaggaa tatcgaaatc  12540
ggggcgcgcc tggtgt                                                  12556

SEQ ID NO: 111          moltype = RNA  length = 48
FEATURE                 Location/Qualifiers
misc_feature            1..48
                        note = Description of Artificial Sequence: Synthetic
                         oligonucleotide
source                  1..48
                        mol_type = other RNA
                        organism = synthetic construct
SEQUENCE: 111
ctaggaatct ggaagtaccg aggaaactcg gtacttcctg tgtcctag               48

SEQ ID NO: 112          moltype = RNA  length = 37
FEATURE                 Location/Qualifiers
misc_feature            1..37
                        note = Description of Artificial Sequence: Synthetic
                         oligonucleotide
source                  1..37
                        mol_type = other RNA
                        organism = synthetic construct
SEQUENCE: 112
atatggaaga tcctggggaa ctgggatctt cctaagt                           37

SEQ ID NO: 113          moltype = RNA  length = 76
FEATURE                 Location/Qualifiers
source                  1..76
                        mol_type = other RNA
                        organism = synthetic construct
SEQUENCE: 113
gcgcatttag ctcagnnggg agagcgccag actgaananc tggagctcct gtgtncgatc  60
cacagaattc gcacca                                                  76
```

METHODS AND COMPOSITIONS FOR GENOMIC INTEGRATION

CROSS REFERENCE

This application is a continuation application of the international application, PCT/US22/28831, filed on May 11, 2022; which claims the benefit of priority to U.S. Provisional Application No. 63/187,117, filed on May 11, 2021, U.S. Provisional Application No. 63/254,791, filed on Oct. 12, 2021, and U.S. Provisional Application No. 63/274,907, filed on Nov. 2, 2021, each of which is hereby incorporated by reference in its entirety.

SEQUENCE LISTING

The instant application contains a Sequence Listing file named 56371-723-301_SL_1-19-23_rev1-27-23.xml, created on Jan. 19, 2023, revised on Jan. 26, 2023 and is 595,456 bytes in size, and is fully incorporated by reference; an ASCII copy of sequence listing, created on Jun. 17, 2022, named 56371-723_601_SL.txt and was 677,993 bytes in size, was filed in the parent international application, and is fully incorporated by reference.

BACKGROUND

Cell therapy is a rapidly developing field for addressing difficult to treat diseases, such as cancer, persistent infections and certain diseases that are refractory to other forms of treatment. Cell therapy often utilizes cells that are engineered ex vivo and administered to an organism to correct deficiencies within the body. An effective and reliable system for manipulation of a cell's genome is crucial, in the sense that when the engineered cell is administered into an organism, it functions optimally and with prolonged efficacy. Likewise, reliable mechanisms of genetic manipulation form the cornerstone in the success of gene therapy. However, severe deficiencies exist in methods for delivering nucleic acid cargo (e.g., large cargo) in a therapeutically safe and effective manner. Viral delivery mechanisms are frequently used to deliver large nucleic acid cargo in a cell but are tied to safety issues and cannot be used to express the cargo in some cell types. Additionally, subjecting a cell to repeated gene manipulation can affect cell health, induce alterations of cell cycle and render the cell unsuitable for therapeutic use. Advancements are continually sought in the area for efficacious delivery and stabilization of an exogenously introduced genetic material for therapeutic purposes.

SUMMARY

Provided herein is a pharmaceutical composition comprising a therapeutically effective amount of one or more polynucleic acids, or at least one vector encoding the one or more polynucleic acids, the one or more polynucleic acids comprising: a mobile genetic element comprising a sequence encoding a polypeptide; and an insert sequence, wherein the insert sequence comprises a sequence that is a reverse complement of a sequence encoding an exogenous therapeutic polypeptide, wherein the polypeptide encoded by the sequence of the mobile genetic element promotes integration of the insert sequence into a genome of a cell; and wherein the pharmaceutical composition is substantially non-immunogenic to a human subject.

In some embodiments, the polypeptide encoded by the sequence of the mobile genetic element comprises one or more long interspersed nuclear element (LINE) polypeptides, wherein the one or more LINE polypeptides comprises: human ORF1p or a functional fragment thereof, and human ORF2p or a functional fragment thereof.

In some embodiments, the insert sequence stably integrates and/or is retrotransposed into the genome of a human cell.

In some embodiments, the human cell is an immune cell selected from the group consisting of a T cell, a B cell, a myeloid cell, a monocyte, a macrophage and a dendritic cell.

In some embodiments, the insert sequence is integrated into the genome (i) by cleavage of a DNA strand of a target site by an endonuclease encoded by the one or more polynucleic acids, (ii) via target-primed reverse transcription (TPRT) or (iii) via reverse splicing of the insert sequence into a DNA target site of the genome. In some embodiments, the insert sequence is integrated into the genome at a poly T site using specificity of an endonuclease domain of the human ORF2p. In some embodiments, the poly T site comprises the sequence TTTTTA. In some embodiments, the one or more polynucleic acids comprises homology arms complementary to a target site in the genome. In some embodiments, the insert sequence integrates into: (a) the genome at a locus that is not a ribosomal RNA locus; (b) a gene or regulatory region of a gene of the genome, thereby disrupting the gene or downregulating expression of the gene; (c) a gene or regulatory region of a gene of the genome, thereby upregulating expression of the gene; or (d) the genome and replaces a gene of the genome. In some embodiments, the pharmaceutical composition further comprises (i) one or more siRNAs and/or (ii) an RNA guide sequence or a polynucleic acid encoding the RNA guide sequence, and wherein the RNA guide sequence targets a DNA target site of the genome and the insert sequence is integrated into the genome at the DNA target site of the genome. In some embodiments, the one or more polynucleic acids have a total length of from 3 kb to 20 kb. In some embodiments, the one or more polynucleic acids comprises one or more polyribonucleic acids, one or more RNAs or one or more mRNAs. In some embodiments, the exogenous therapeutic polypeptide is selected from the group consisting of a ligand, an antibody, a receptor, an enzyme, a transport protein, a structural protein, a hormone, a contractile protein, a storage protein and a transcription factor. In some embodiments, the exogenous therapeutic polypeptide is a receptor selected from the group consisting of a chimeric antigen receptor (CAR) and a T cell receptor (TCR). In some embodiments, the one or more polynucleic acids comprises a first expression cassette comprising a promoter sequence, a 5' UTR sequence, a 3' UTR sequence and a poly A sequence; wherein: the promoter sequence is upstream of the 5' UTR sequence, the 5' UTR sequence is upstream of the sequence of the mobile genetic element encoding a polypeptide, the 3' UTR sequence is downstream of the insert sequence; and the 3' UTR is upstream of the poly A sequence; and wherein the 5' UTR sequence, the 3' UTR sequence or the poly A sequence comprises a binding site for a human ORF2p or a functional fragment thereof. In some embodiments, the insert sequence comprises a second expression cassette comprising a sequence that is a reverse complement of a promoter sequence, a sequence that is a reverse complement of a 5' UTR sequence, a sequence that is a reverse complement of a 3' UTR sequence and a sequence that is a reverse complement of a poly A sequence; wherein: (i) the sequence that is a reverse complement of a promoter sequence is downstream of the sequence that is a reverse complement of a 5' UTR sequence, (ii) the sequence that is a reverse complement of a 5' UTR sequence is downstream of the sequence that is a reverse complement of a sequence encoding an exogenous therapeutic polypeptide, (iii) the sequence that is a reverse complement of a 3' UTR sequence is upstream of the sequence that is a reverse complement of a sequence encoding an exogenous therapeutic polypeptide, and (iv) the sequence that is a reverse complement of a poly A sequence is upstream of the sequence that is a reverse complement of a 3' UTR sequence and downstream of the sequence of the mobile genetic encoding a polypeptide. In some embodiments, the promoter sequence of the first expression cassette is different from the promoter sequence of the second expression cassette. In some embodiments, the one or more LINE polypeptides comprises a first LINE polypeptide comprising the human ORF1p or functional fragment thereof and a second LINE polypeptide comprising the human ORF2p or functional fragment thereof, wherein the first LINE polypeptide and the second LINE polypeptide are translated from different open reading frames (ORFs). In some embodiments, the one or more polynucleic acids comprises a first polynucleic acid molecule encoding the human ORF1p or functional fragment thereof and a second polynucleic acid molecule encoding the human ORF2p or functional fragment thereof. In some embodiments, the one or more polynucleic acids comprises a 5' UTR sequence and a 3' UTR sequence, wherein the 5' UTR comprises a 5' UTR from LINE-1 or a sequence with at least 80% sequence identity to ACUCCUCCCCAUCCUCUCCCUCUGUCCCUCUGUCCCUCUGACCCUGCACUGUCCCAGC ACC (SEQ ID NO: 51); and/or the 3' UTR comprises a 3' UTR from LINE-1 or a sequence with at least 80% sequence identity to CAGGACACAGCCUUGGAUCAGGACAGAGACUUGGGGGCCAUCCUGCCCCUCCAACCC GACAUGUGUACCUCAGCUUUUUCCCUCACUUGCAUCAAUAAAGCUUCUGUGUUUGGA ACAG (SEQ ID NO: 52). In some embodiments, the sequence encoding the exogenous therapeutic polypeptide does not comprise introns. In some embodiments, the polypeptide encoded by the sequence of the mobile genetic element comprises a C-terminal nuclear localization signal (NLS), an N-terminal NLS or both. In some embodiments, the sequence encoding the exogenous polypeptide is not in frame with a sequence encoding the ORF1p or functional fragment thereof and/or is not in frame with a sequence encoding the ORF2p or functional fragment thereof. In some embodiments, the one or more polynucleic acids comprises a sequence encoding a nuclease domain, a nuclease domain that is not derived from ORF2p, a megaTAL nuclease domain, a TALEN domain, a Cas9 domain, a Cas6 domain, a Cas7 domain, a Cas8 domain, a zinc finger binding domain from an R2 retroelement, or a DNA binding domain that binds to repeat sequences. In some embodiments, the one or more polynucleic acids comprises a sequence encoding the nuclease domain, wherein the nuclease domain does not have nuclease activity or comprises a mutation that reduces activity of the nuclease domain compared to the nuclease domain without the mutation. In some embodiments, the ORF2p or functional fragment thereof lacks endonuclease activity or comprises a mutation selected from the group consisting of S228P and Y1180A, and/or wherein the ORF1p or functional fragment comprises a K3R mutation. In some embodiments, the insert sequence comprises a sequence that is a reverse complement of a sequence encoding two or more exogenous therapeutic polypeptides. In some embodiments, the one or more polynucleic acids comprises one or more polyribonucleic acids, wherein the exogenous therapeutic polypeptide is a receptor selected from the group consisting of a chimeric antigen receptor (CAR) and a T cell receptor (TCR), and wherein the pharmaceutical composition is formulated for systemic administration to a human subject. In some embodiments, the one or more polynucleic acids are formulated in a nanoparticle selected from the group consisting of (i) a lipid nanoparticle and a polymeric nanoparticle; and/or (ii) comprises one or more polynucleic acids selected from the group consisting of glycosylated RNAs, circular RNAs and self-replicating RNAs.

Provided herein is a method, wherein the method is: (i) a method of treating a disease or condition in a human subject in need thereof comprising administering a pharmaceutical composition described herein to the human subject; or (ii) a method of modifying a population of human cells ex vivo comprising contacting a composition to a population of human cell ex vivo, thereby forming an ex vivo modified population of human cells, the composition comprising one or more polynucleic acids, or at least one vector encoding the one or more polynucleic acids, the one or more polynucleic acids comprising: a mobile genetic element comprising a sequence encoding a polypeptide; and an insert sequence, wherein the insert sequence is a reverse complement of a sequence encoding an exogenous therapeutic polypeptide, wherein the ex vivo modified population of human cells is substantially non-immunogenic to a human subject. In some embodiments, the one or more polynucleic acids further comprise (i) a sequence encoding an integrase or a fragment thereof for site directed integration of the insert sequence into the genome and (ii) an integrase genomic landing site sequence that operable by the integrase, wherein the genome landing sequence is greater than 4 consecutive nucleotides long. In some embodiments, the ORF2 and the integrase are on separate polynucleotides. In some embodiments, the ORF2 and the integrase are on a single polynucleotide. In some embodiments, the integrase is not integrated into the genome of the cell. In some embodiments, the integrase is a mutated or truncated recombinant protein. In some embodiments, the integrase genomic landing sequence that is operable by the integrase is greater than 20 nucleotides long, or greater than 30 nucleotides long. In some embodiments, the insert sequence comprises an attachment site operable by the integrase. In some embodiments, the integrase genomic landing site is inserted into the genome using a guide RNA and a Cas system. In some embodiments, the guide RNA, the CAS system and the genomic landing sequence are in a polynucleotide that is separate from the polynucleotide comprising the sequence encoding the LINE1-ORFs and the insert sequence. In some embodiments, one or more ORF polypeptide sequence comprises a mutation. A method for a site-specific integration of a heterologous genomic insert sequence into the genome of a mammalian cell, the method comprising: (i) introducing into the cell (a) a polynucleotide comprising sequences encoding one or more human retrotransposon elements associated with the heterologous insert sequence, and (b) a polynucleotide comprising sequence encoding a guide RNA, an RNA guided integrase or a fragment thereof and a landing sequence operable by the integrase; (ii) verifying the integration of the heterologous insert sequence into the site of the genome.

Provided herein is a method for site-specific integration of a heterologous genomic insert using a LINE retrotransposon system, wherein the LINE retrotransposon system is modified to incorporate a fragment of an integrase protein that can recognize a genomic landing sequence of greater than 10 consecutive nucleotides long, and wherein the LINE retrotransposon system integrates the heterologous genomic insert into the genomic landing sequence recognized by the fragment of the integrase protein. In some embodiments, the method further comprises a step of incorporating into the genome the genomic landing sequence of greater than 4 consecutive nucleotides long. In some embodiments, the step of incorporating into the genome the genomic landing sequence is performed by an RNA-guided CRISPR-Cas system. In some embodiments, the RNA-guided CRISPR-Cas system has an editing function capable of incorporating a sequence of greater than 4 consecutive nucleotides long into a specific genome site. In some embodiments, the RNA-guided CRISPR-Cas system incorporates an ORF-mRNA binding sequence into a specified location within the genome that has sequence homology to the sequence of the guide RNA. In some embodiments, the insert is about 10 kilobases or greater than 10 kilobases. In some embodiments, the polynucleotide is mRNA.

Provided herein is a method of stably integrating an insert sequence into genomic DNA of a target cell, the method comprising: contacting a composition to the target cell, the composition comprising a polynucleic acid, wherein the polynucleic acid comprises: an insert sequence, wherein the insert sequence comprises a sequence that is a reverse complement of a sequence encoding an exogenous polypeptide, and a mobile genetic element comprising a sequence encoding a polypeptide, wherein the polypeptide encoded by the sequence of the mobile genetic element promotes integration of the insert sequence into genomic DNA; stably integrating the insert sequence into the genomic DNA of the target cell; and expressing an exogenous polypeptide in the target cell, wherein the target cell is a human hepatocyte. In some embodiments, the human hepatocyte is a primary cell. In some embodiments, the human hepatocyte is a from a cultured hepatocyte cell line. In some embodiments, incorporating comprises electroporating under conditions optimum for a human hepatocyte. In some embodiments, the method further comprises culturing the human hepatocyte in vitro after incorporating for about 2 hours, about 3 hours, about 4 hours, about 5 hours, about 6 hours, about 8 hours, about 10 hours or about 24 hours. In some embodiments, the method further comprises introducing the human hepatocyte expressing the exogenous polypeptide into a human subject in need thereof. In some embodiments, at least 2% of the human hepatocytes express the exogenous polypeptide at day 10 after incorporating.

Provided herein is a method of stably integrating an insert sequence into genomic DNA of a target cell, the method comprising: contacting a composition to the target cell, the composition comprising a polynucleic acid, wherein the polynucleic acid comprises: an insert sequence, wherein the insert sequence comprises a sequence that is a reverse complement of a sequence encoding an exogenous polypeptide, and a mobile genetic element comprising a sequence encoding a polypeptide, wherein the polypeptide encoded by the sequence of the mobile genetic element promotes integration of the insert sequence into genomic DNA; stably integrating the insert sequence into the genomic DNA of the target cell; and expressing an exogenous polypeptide in the target cell, wherein the target cell is a human cardiomyocyte. In some embodiments, the human cardiomyocyte is a primary cell. In some embodiments, the human cardiomyocyte is a from a cultured cardiomyocyte cell line. In some embodiments, incorporating comprises electroporating under conditions optimum for a human cardiomyocyte. In some embodiments, the method further comprises culturing the cardiomyocyte in vitro after incorporating for about 2 hours, about 3 hours, about 4 hours, about 5 hours, about 6 hours, about 8 hours, about 10 hours or up to 24 hours. In some embodiments, the method further comprises introducing the human cardiomyocyte expressing the exogenous polypeptide into a human subject in need thereof. In some embodiments, at least 2% of the human cardiomyocytes express the exogenous polypeptide at day 10 after incorporating.

Provided herein is a method of stably integrating an insert sequence into genomic DNA of a target cell, the method comprising contacting a composition to the target cell, the composition comprising a polynucleic acid, wherein the polynucleic acid comprises: an insert sequence, wherein the insert sequence comprises a sequence that is a reverse complement of a sequence encoding an exogenous polypeptide, and a mobile genetic element comprising a sequence encoding a polypeptide, wherein the polypeptide encoded by the sequence of the mobile genetic element promotes integration of the insert sequence into genomic DNA; stably integrating the insert sequence into the genomic DNA of the target cell; and expressing an exogenous polypeptide in the target cell, wherein the target cell is a human retinal pigment epithelial cell. In some embodiments, the human retinal pigment epithelial cell is a primary cell. In some embodiments, the human retinal pigment epithelial is a from a cultured retinal pigment epithelial cell line. In some embodiments, incorporating comprises electroporating under conditions optimum for a human retinal pigment epithelial cell. In some embodiments, the method further comprises culturing the retinal pigment epithelial cell in vitro after incorporating for about 2 hours, about 3 hours, about 4 hours, about 5 hours, about 6 hours, about 8 hours, about 10 hours or up to 24 hours. In some embodiments, the method further comprises introducing the human retinal pigment epithelial cell expressing the exogenous polypeptide into a human subject in need thereof. In some embodiments, at least 2% of the human RPE express the exogenous polypeptide at day 10 after incorporating.

Provided herein is a method of stably integrating an insert sequence into genomic DNA of a target cell, the method comprising contacting a composition to the target cell, the composition comprising a polynucleic acid, wherein the polynucleic acid comprises: an insert sequence, wherein the insert sequence comprises a sequence that is a reverse complement of a sequence encoding an exogenous polypeptide, and a mobile genetic element comprising a sequence encoding a polypeptide, wherein the polypeptide encoded by the sequence of the mobile genetic element promotes integration of the insert sequence into genomic DNA: stably integrating the insert sequence into the genomic DNA of the target cell; and expressing an exogenous polypeptide in the target cell, wherein the target cell is a human neuronal cell. In some embodiments, the human neuronal cell is a primary cell. In some embodiments, the human neuronal cell is a from a cultured neuronal cell line. In some embodiments, incorporating comprises electroporating under conditions optimum for a human neuronal cell. In some embodiments, the method further comprises culturing the neuronal cell in vitro after incorporating for about 2 hours, about 3 hours, about 4 hours, about 5 hours, about 6 hours, about 8 hours, about 10 hours or up to 24 hours. In some embodiments, the method further comprises introducing the human neuronal cell expressing the exogenous polypeptide into a human. In some embodiments, at least 2% of the human neuronal cells express the exogenous polypeptide at day 10 after incorporating. In some embodiments, the insert sequence is a human insert sequence. In some embodiments, the exogenous polypeptide is an exogenous therapeutic polypeptide. In some embodiments, the exogenous polypeptide is an exogenous human polypeptide. In some embodiments, the polypeptide encoded by the sequence of the mobile genetic element promotes integration of the insert sequence into genomic DNA via target-primed reverse transcription (TPRT). In some embodiments, the polynucleic acid is an mRNA or an mRNA molecule. In some embodiments, the mobile genetic element comprises a human LINE 1 retrotransposon element. In some embodiments, the ORF2p is selected from a non-human species. In some embodiments, the ORF2p selected from a non-human species is further modified to enhance retrotransposition efficiency and/or translation efficiency. In some embodiments, the cell is an immune cell, a hepatocyte, a cardiomyocyte, a retinal pigment epithelial cell or a neuron. In some embodiments, the ORF2p comprises an nuclear localization sequence (NLS). In some embodiments, the ORF2p comprises at least 2 NLSs that are the same or different. In some embodiments, the NLS is N-terminal to a sequence encoding ORF1p, ORF2p or both. In some embodiments, the NLS is C-terminal to a sequence encoding ORF1p, ORF2p or both. In some embodiments, the NLS is from SV40. In some embodiments, the NLS is from nucleoplasmin. In some embodiments, a first NLS of the at least 2 NLSs is from SV40 and a second NLS of the at least 2 NLSs is from nucleoplasmin. In some embodiments, a first and a second NLS of the at least 2 NLSs are from SV40. In some embodiments, a first and a second NLS of the at least 2 NLSs are from nucleoplasmin. In some embodiments, each of the at least 2 NLSs are the same.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "FIG." herein), of which:

FIG. 3B discloses SEQ ID NOS 111-112, respectively, in order of appearance.

after culturing for 6 days post-electroporation and a graph of the number of GFP integrations per genome according to qPCR (top).

Figure 51:
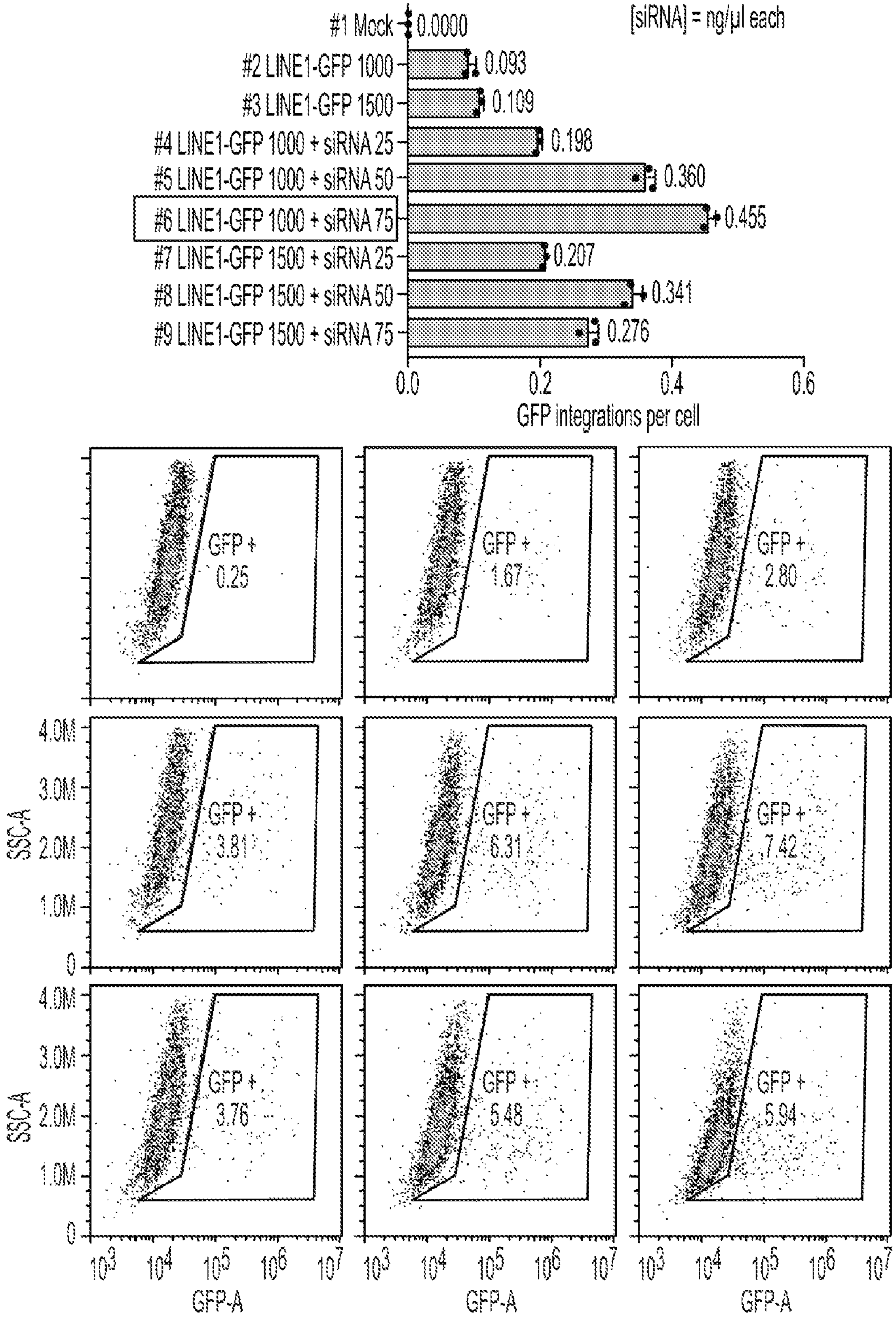

FIG. 51 depicts exemplary flow cytometry data (bottom) showing GFP+ 293T cells electroporated with 1000 ng/μL or 1500 ng/μL LINE 1-GFP mRNA and an siRNA cocktail with 25 ng/μL, 50 ng/μL or 75 ng/μL of each siRNA targeting RNASEL (siRNASEL), ADAR1 (siADAR1), ADAR2 (siADAR2) and BRCA1 (siBRCA1) after culturing for 6 days post-electroporation and a graph of the number of GFP integrations per genome according to qPCR (top).

Figure 52:
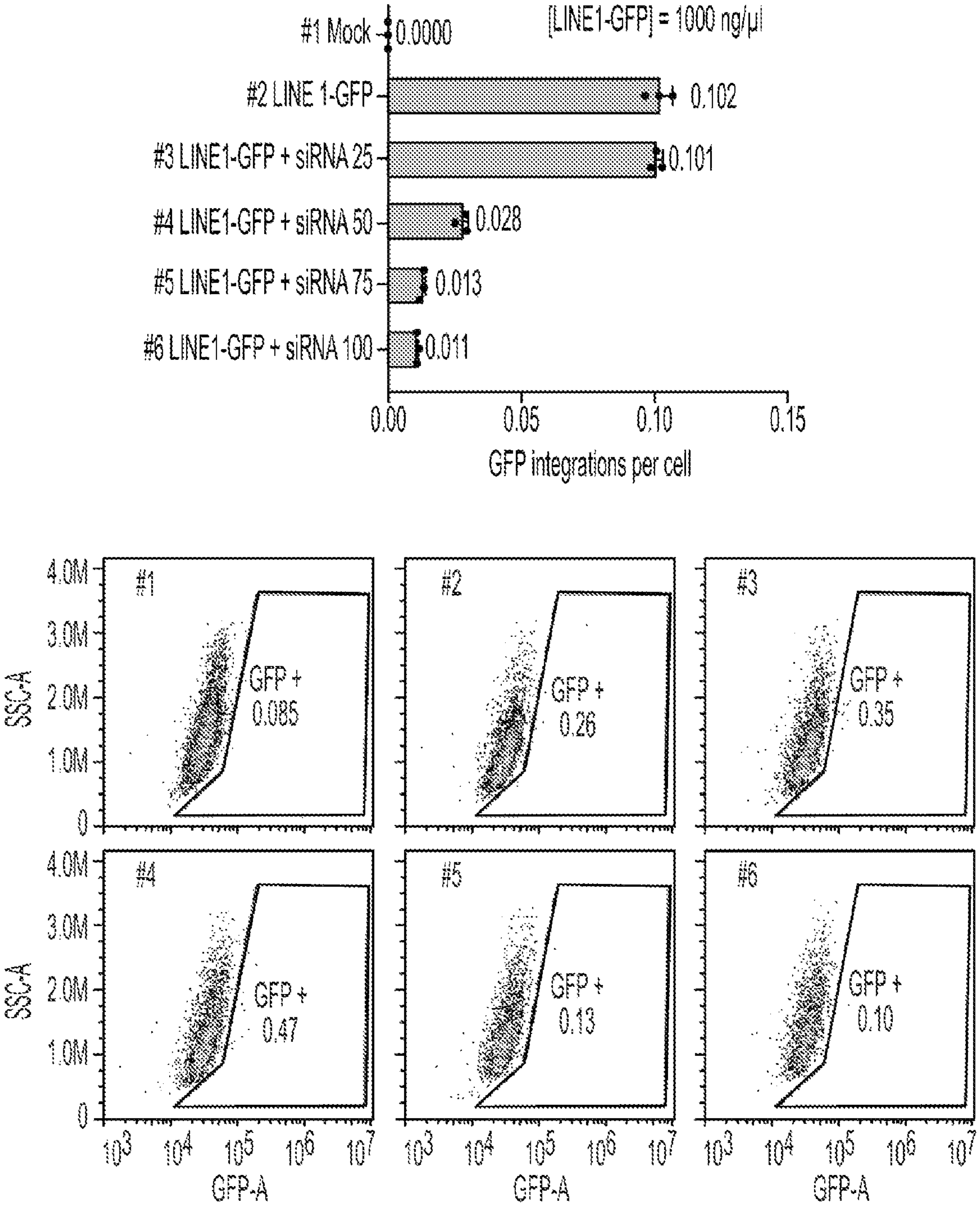

FIG. 52 depicts exemplary flow cytometry data (bottom) showing GFP+ K562 cells electroporated with 1000 ng/μL LINE1-GFP mRNA and an siRNA cocktail with 25 ng/μL, 50 ng/μL or 75 ng/μL of each siRNA targeting RNASEL (siRNASEL), ADAR1 (siADAR1), ADAR2 (siADAR2) and BRCA1 (siBRCA1) after culturing for 5 days post-electroporation and a graph of the number of GFP integrations per cell according to qPCR (top).

Figure 53:
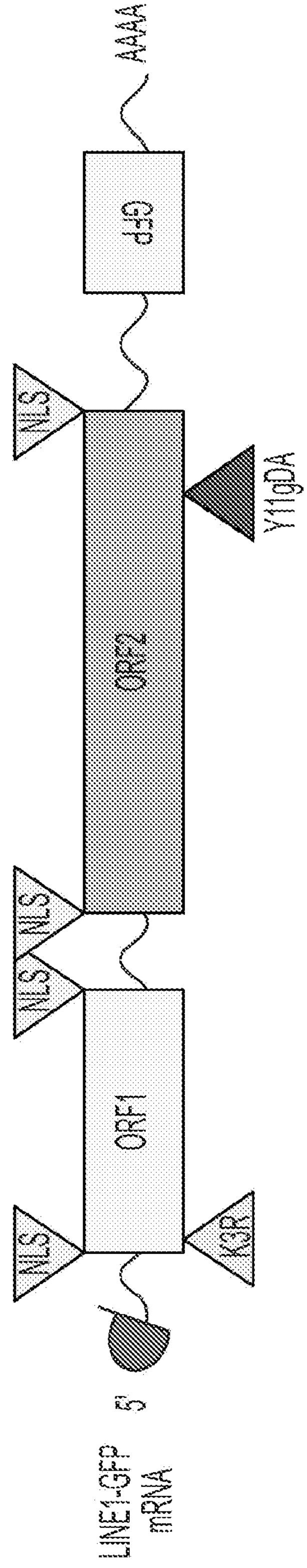

FIG. 53 depicts a schematic showing exemplary locations of extraneous nuclear localization sequences (NLS) and exemplary ORF1p and ORF2p mutations of an exemplary LINE1-GFP mRNA construct.

Figure 54A:
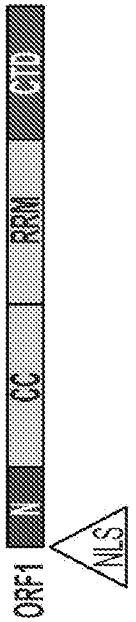

FIG. 54A depicts a schematic showing an exemplary LINE1-GFP construct in which an NLS was inserted at the N-terminal end of the sequence encoding ORF1.

Figure 54B:
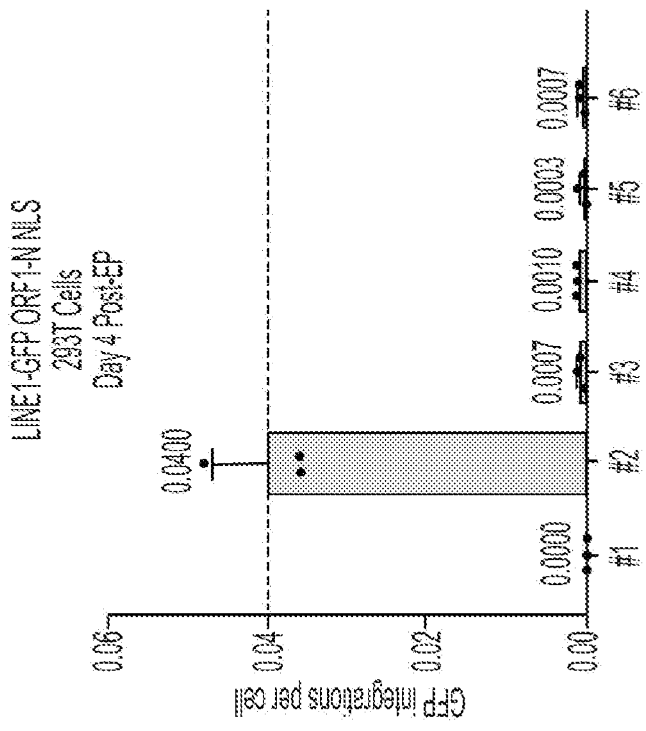

FIG. 54B depicts a bar graph showing GFP integrations per cell on day 4 post electroporation of the indicated constructs into 293T cells.

Figure 54C:
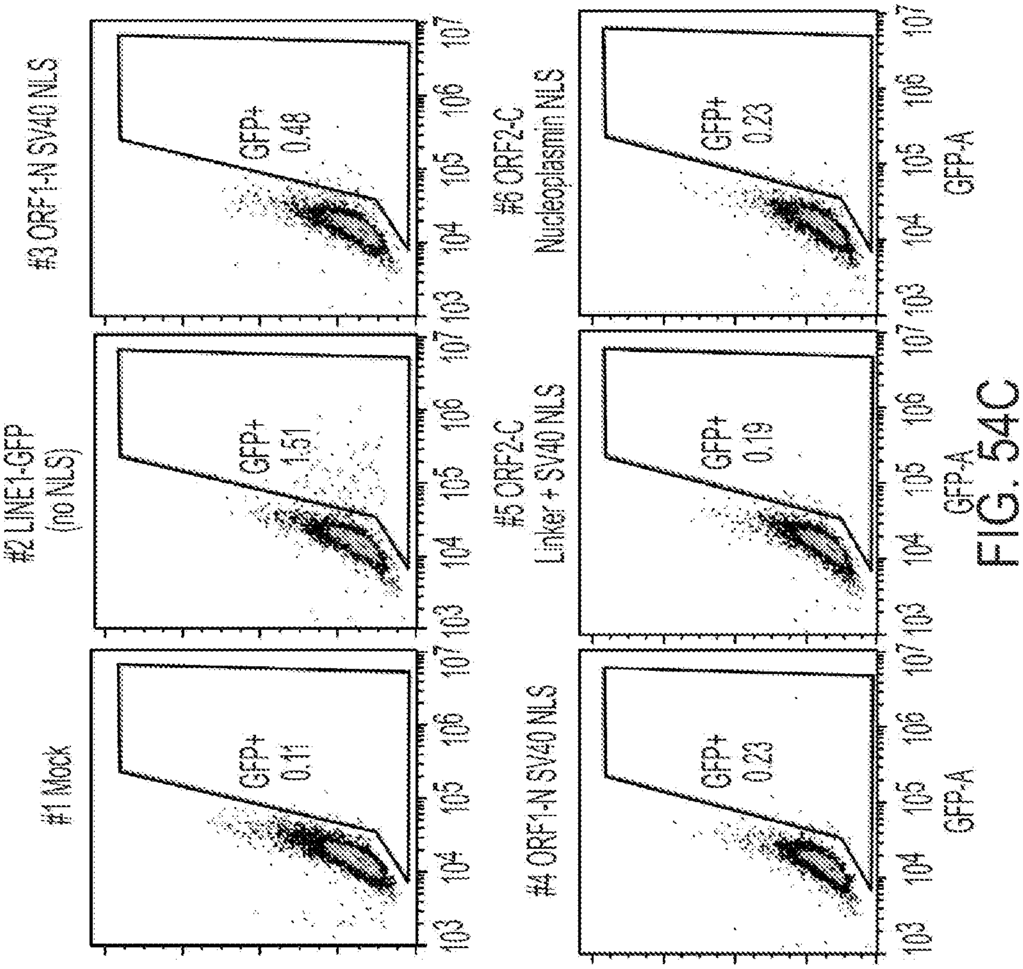

FIG. 54C depicts exemplary flow cytometry showing GFP+ 293T cells on day 4 post electroporation of the indicated constructs.

Figure 55A:
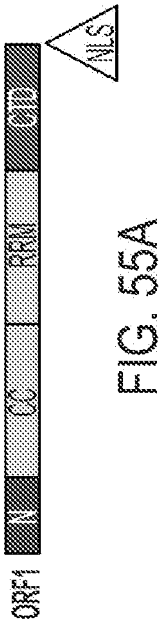

FIG. 55A depicts a schematic showing an exemplary LINE1-GFP construct in which an NLS was inserted at the C-terminal end of the sequence encoding ORF1.

Figure 55B:
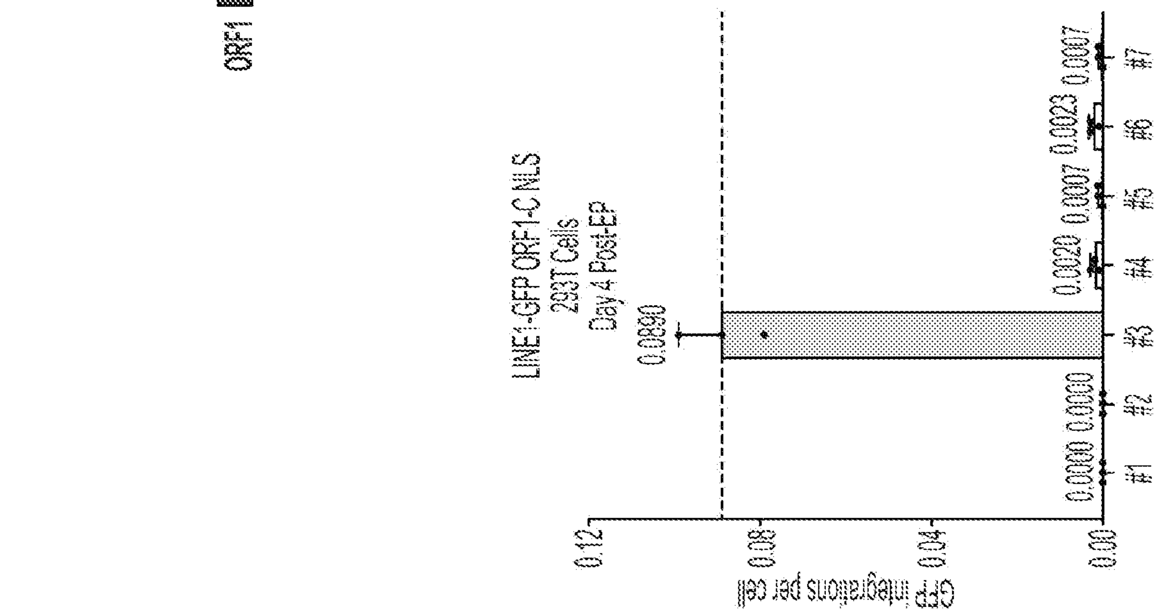

FIG. 55B depicts a bar graph showing GFP integrations per cell on day 4 post electroporation of the indicated constructs into 293T cells.

Figure 55C:
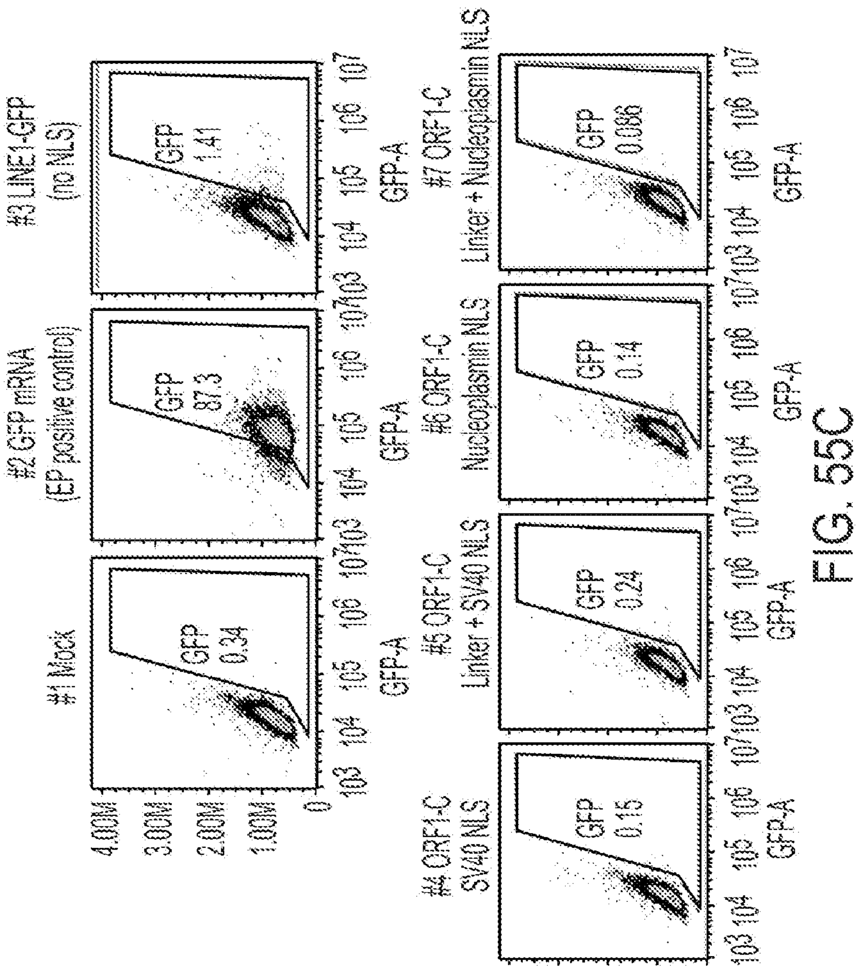

FIG. 55C depicts exemplary flow cytometry showing GFP+ 293T cells on day 4 post electroporation of the indicated constructs.

Figure 56A:
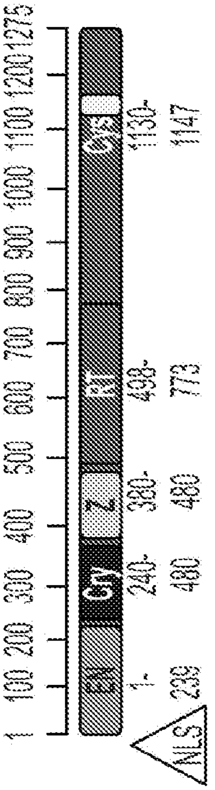

FIG. 56A depicts a schematic showing an exemplary LINE1-GFP construct in which an NLS was inserted at the N-terminal end of the sequence encoding ORF2.

Figure 56B:
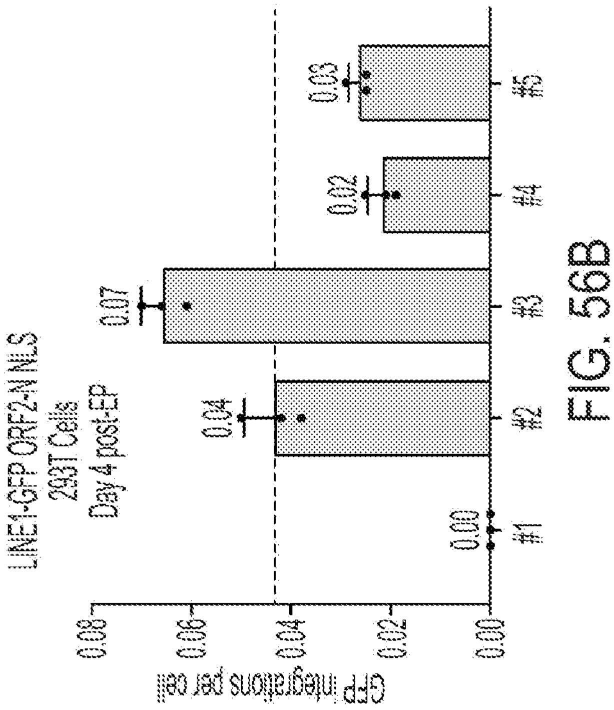

FIG. 56B depicts a bar graph showing GFP integrations per cell on day 4 post electroporation of the indicated constructs into 293T cells.

Figure 56C:
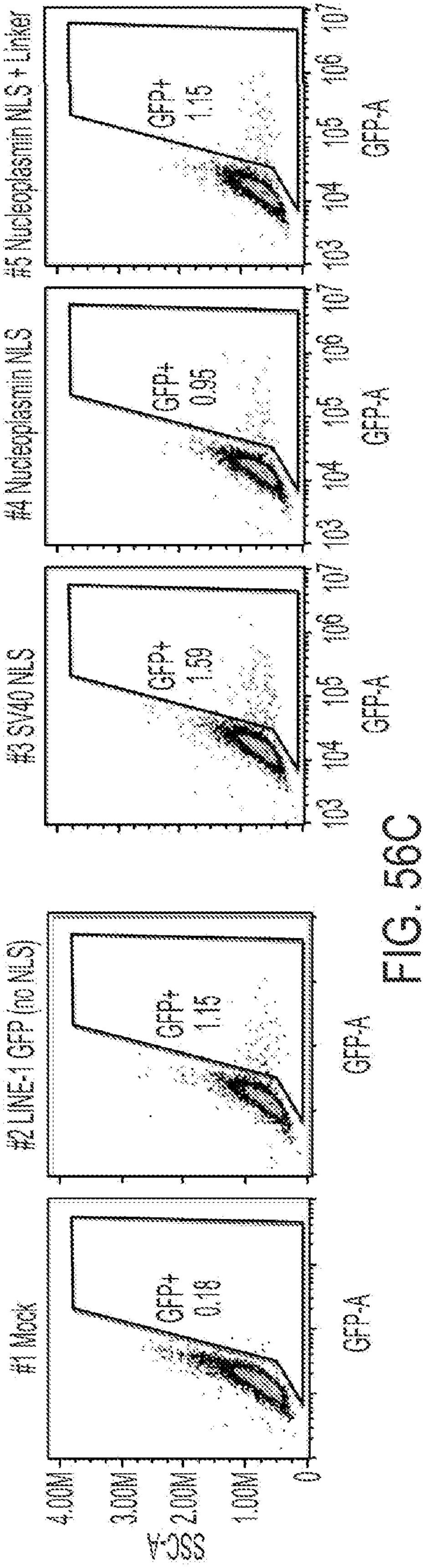

FIG. 56C depicts exemplary flow cytometry showing GFP+ 293T cells on day 4 post electroporation of the indicated constructs.

Figure 57A:
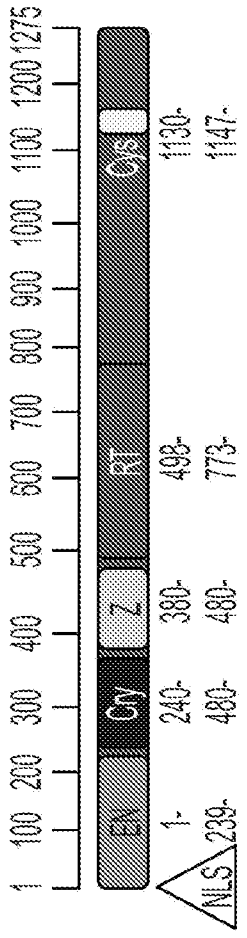

FIG. 57A depicts a schematic showing an exemplary LINE 1-GFP construct in which an NLS and a linker was inserted at the N-terminal end of the sequence encoding ORF2.

Figure 57B:
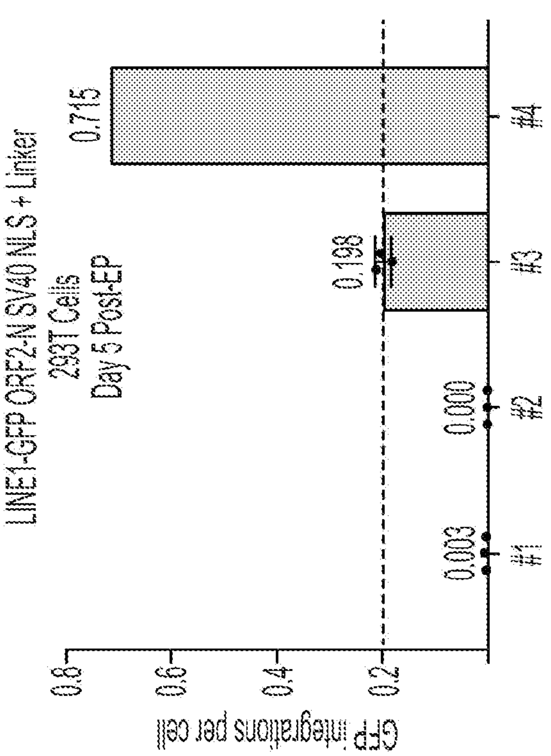

FIG. 57B depicts a bar graph showing GFP integrations per cell on day 5 post electroporation of the indicated constructs into 293T cells.

Figure 57C:
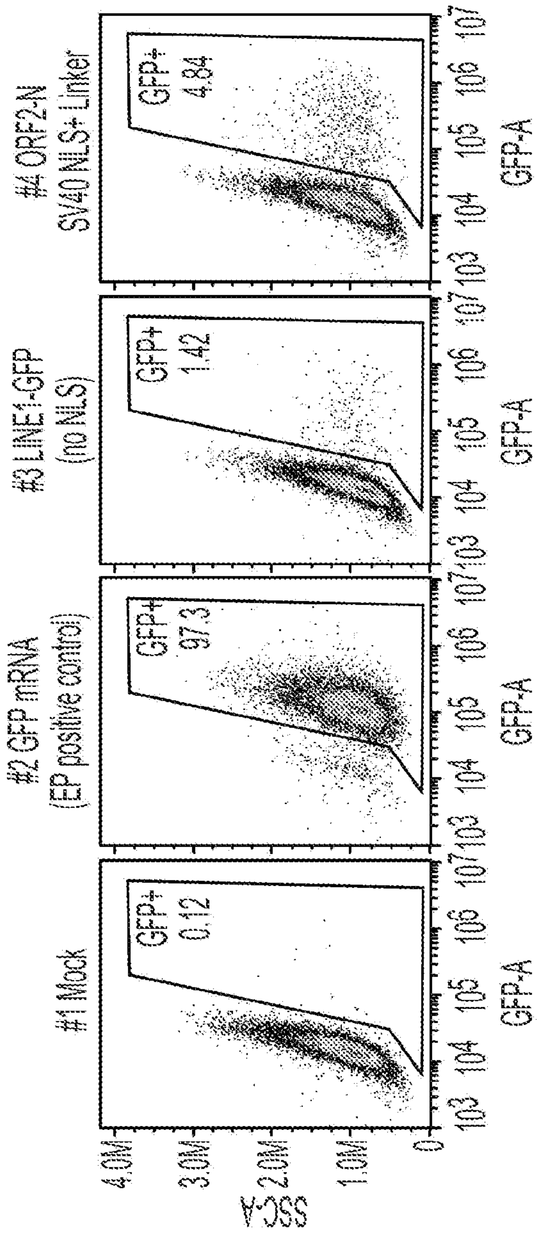

FIG. 57C depicts exemplary flow cytometry showing GFP+ 293T cells on day 5 post electroporation of the indicated constructs.

Figure 58A:
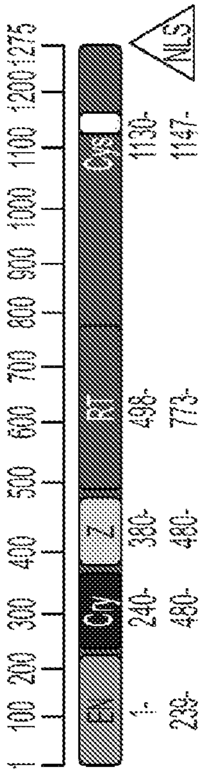

FIG. 58A depicts a schematic showing an exemplary LINE1-GFP construct in which an NLS was inserted at the C-terminal end of the sequence encoding ORF2.

Figure 58B:
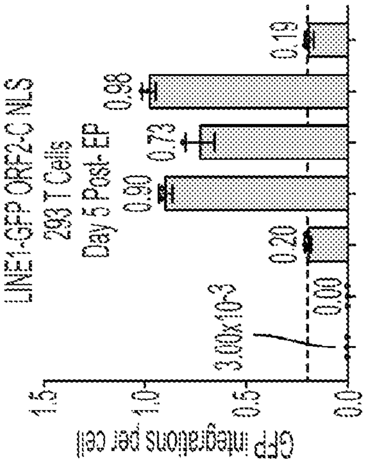

FIG. 58B depicts a bar graph showing GFP integrations per cell on day 5 post electroporation of the indicated constructs into 293T cells.

Figure 58C:
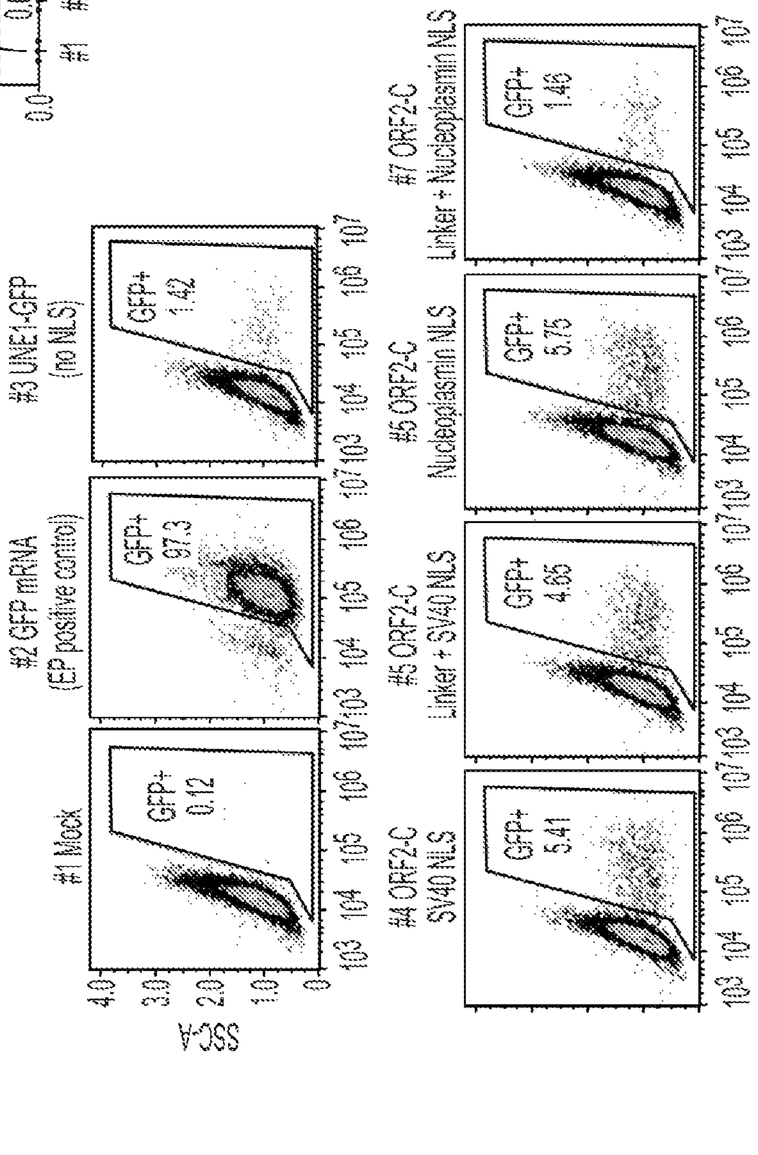

FIG. 58C depicts exemplary flow cytometry showing GFP+ 293T cells on day 5 post electroporation of the indicated constructs.

DETAILED DESCRIPTION

The present invention arises in part from the exciting discovery that a polynucleotide could be designed and developed to accomplish transfer and integration of a genetic cargo (e.g., large genetic cargo) into the genome of a cell. In some embodiments, the polynucleotide comprises (i) a genetic material for stable expression, and (ii) a self-integrating genomic integration machinery that allows stable integration of the genetic material into a cell by non-viral means, that is both safe and efficacious. Moreover, the genetic material may be integrated at a locus other than a ribosomal locus; the genetic material may be integrated site-specifically; and/or the integrated genetic material appear to express without triggering a cell's natural silencing machinery.

Clustered Regularly-Interspaced Short Palindromic Repeats (CRISPR) revolutionized the molecular biology field and has developed into a potent gene editing too. It utilizes homology-directed repair (HDR) and can be directed to a genomic site. CRISPR/Cas9 is a naturally occurring RNA-guided endonuclease. While the CRISPR/Cas9 system has demonstrated great promise for site-specific gene editing and other applications, there are several factors that influence its efficacy which must be addressed, especially if it is to be used for in vivo human gene therapy. These factors include target DNA site selection, sgRNA design, off-target cutting, incidence/efficiency of HDR vs. NHEJ, Cas9 activity, and the method of delivery. Delivery remains the major obstacle for use of CRISPR for in vivo applications. Zinc finger nucleases ZFNs are a fusion protein of Cys2-His2 zinc finger proteins (ZFPs) and a non-specific DNA restriction enzyme derived from FokI endonucleases. Challenges with ZFPs include design and engineering of the ZFP for high-affinity binding of the desired sequence, which is non-trivial. Also, not all sequences are available for ZFP binding, so site selection is limited. Another significant challenge is off-target cutting. Transcription activator-like effector nucleases (TALENs) are a fusion protein comprised of a TALE and a FokI nuclease. While off-target cutting remains a concern, TALENs have been shown in one side-by-side comparison study to be more specific and less cytotoxic than ZFNs. However, TALENs are substantially larger, and the cDNA encoding TALEN only is 3 kb. This makes delivery of a pair of TALENs more challenging than a pair of ZFNs due to delivery vehicle cargo size limitations. Further, packaging and delivery of TALENs in some viral vectors may be problematic due to the high level of repetition in the TALENs sequence. A mutant Cas9 system, a fusion protein of inactive dCas9 and a FokI nuclease dimer increase specificity and reduce off-target cutting, the number of potential target sites is lower due to PAM and other sgRNA design constraints.

The present invention addresses the problems described above by providing new, effective and efficient compositions comprising transposon-based vectors for providing therapy, including gene therapy, to animals and humans. The present invention provides methods of using these compositions for providing therapy to animals and humans. These transposon-based vectors can be used in the preparation of a medicament useful for providing a desired effect to a recipient following administration. Gene therapy includes, but is not limited to, introduction of a gene, such as an exogenous gene, into an animal using a transposon-based vector. These genes may serve a variety of functions in the recipient such as coding for the production of nucleic acids, for example RNA, or coding for the production of proteins and peptides. The present invention can facilitate efficient incorporation of the polynucleotide sequences, including the genes of interest, promoters, insertion sequences, poly A and any regulatory sequences. The invention is based on the finding that human LINE-1 elements are capable of retrotransposition in human cells as well as cells of other animal species and can be manipulated in a versatile manner to achieve efficient delivery and integration of a genetic cargo into the genome of a cell. Such LINE-1 elements have a variety of uses in human and animal genetics including, but not limited to, uses in diagnosis and treatment of genetic disorders and in cancer. The LINE-1 elements of the invention are also useful for the treatment of various phenotypic effects of various diseases. For example, LINE-1 elements may be used for transfer of DNA encoding anti-tumorigenic gene products into cancer cells. Other uses of the LINE-1 elements of the invention will become apparent to the skilled artisan upon a reading of the present specification.

In general, a human LINE-1 element comprises a 5' UTR with an internal promoter, two non-overlapping reading frames (ORF1 and ORF2), a 200 bp 3' UTR and a 3' poly A tail. The LINE-1 retrotransposon can also comprise an endonuclease domain at the LINE-1 ORF2 N-terminus. The finding that LINE-1 encodes an endonuclease demonstrates that the element is capable of autonomous retrotransposition. LINE-1 is a modular protein that contains non-overlapping functional domains which mediate its reverse transcription and integration. In some embodiments, the sequence specificity of the LINE-1 endonuclease itself can be altered or the LINE-1 endonuclease can be replaced with another site-specific endonuclease.

The LINE-1 retrotransposon may be manipulated using recombinant technology to comprise and/or be contiguous with, other nucleic acid elements which render the retrotransposon suitable for insertion of substantial lengths (up to 1 kb, or greater than 1 kb, e.g. greater than 5, 6, 7, 8, 9, or 10 kb) of heterologous or homologous nucleic acid sequence into the genome of a cell. The LINE-1 retrotransposon may also be manipulated using the same type of technology such that insertion of the nucleic acid sequence of heterologous or homologous nucleic acid into the genome of a cell is site-directed (site into which such DNA is inserted is known). Alternatively, the LINE-1 retrotransposon may be manipulated such that the insertion site of the DNA is random. The retrotransposon may also be manipulated to effect insertion of a desired DNA sequence into regions of DNA which are normally transcriptionally silent, wherein the DNA sequence is expressed in a manner such that it does not disrupt the normal expression of genes in the cell. In some embodiments, the integration or retrotransposition is in the trans orientation. In some embodiments, the integration or retrotransposition occurs in the cis orientation.

Since LINE-1 is native to human cells, when the constructs are placed into human cells, they should not be rejected by the immune system as foreign. In addition, the mechanism of LINE-1 retro-integration ensures that only one copy of the gene is integrated at any specific chromosomal location. Accordingly, there is a copy number control built into the system. In contrast, gene transfer procedures using ordinary plasmids offer little or no control regarding copy number and often result in complex arrays of DNA molecules tandemly integrated into the same genomic location.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

As used herein, the singular forms "a", "an" and "the" are intended to include the plural forms as well, unless the context clearly indicates otherwise.

In this application, the use of "or" means "and/or" unless stated otherwise. The terms "and/or" and "any combination thereof" and their grammatical equivalents as used herein, may be used interchangeably. These terms may convey that any combination is specifically contemplated. Solely for illustrative purposes, the following phrases "A, B, and/or C" or "A, B, C, or any combination thereof" may mean "A individually; B individually; C individually; A and B; B and C; A and C; and A, B, and C." The term "or" may be used conjunctively or disjunctively unless the context specifically refers to a disjunctive use.

The term "about" or "approximately" may mean within an acceptable error range for the particular value as determined by one of ordinary skill in the art, which will depend in part on how the value is measured or determined, i.e., the limitations of the measurement system. For example, "about" may mean within 1 or more than 1 standard deviation, per the practice in the art. Alternatively, "about" may mean a range of up to 20%, up to 10%, up to 5%, or up to 1% of a given value. Alternatively, particularly with respect to biological systems or processes, the term may mean within an order of magnitude, within 5-fold, and more preferably within 2-fold, of a value. Where particular values are described in the application and claims, unless otherwise stated the term "about" meaning within an acceptable error range for the particular value should be assumed.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification may be implemented with respect to any method or composition of the present disclosure, and vice versa. Furthermore, compositions of the present disclosure may be used to achieve methods of the present disclosure.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the present disclosures. To facilitate an understanding of the present disclosure, a number of terms and phrases are defined below.

Although various features of the present disclosure can be described in the context of a single embodiment, the features can also be provided separately or in any suitable combination. Conversely, although the present disclosure can be described herein in the context of separate embodiments for clarity, the disclosure can also be implemented in a single embodiment.

Applications of the present disclosure encompasses, but are not limited to methods and compositions related to expression of an exogenous nucleic acid in a cell. In some embodiments, the exogenous nucleic acid is configured for stable integration in the genome of a cell, such as a myeloid cell. In some embodiments, the stable integration of the exogenous nucleic acid may be at specific targets within the genome. In some embodiments, the exogenous nucleic acid comprises one or more coding sequences. In some embodiments, the exogenous nucleic acid may comprise one or more coding comprising a nucleic acid sequence encoding an immune receptor. In some embodiments, the present disclosure provides methods and compositions for a stable incorporation of a nucleic acid encoding a transmembrane receptor implicated in an immune response function (e.g. a phagocytic receptor or synthetic chimeric antigen receptor) into human macrophage or dendritic cell or a suitable myeloid cell or a myeloid precursor cell. An exogenous nucleic acid can refer to a nucleic acid that was not originally in a cell and is added from outside the cell, irrespective of whether it comprises a sequence that may already be present in the cell endogenously. An exogenous nucleic acid may be a DNA or an RNA molecule. An exogenous nucleic acid may comprise a sequence encoding a transgene. An exogenous nucleic acid may encode a recombinant protein, such as a recombinant receptor, or a chimeric antigen receptor (CAR). An exogenous nucleic acid may be referred to as a "genetic cargo" in the context of the exogenous nucleic acid being delivered inside a cell. The genetic cargo may be a DNA or an RNA. Genetic material can generally be delivered inside a cell ex vivo by a few different known techniques using either chemical ($CaCl_2$-medicated transfection), or physical (electroporation), or biological (e.g. viral infection or transduction) means.

Provided herein are compositions and methods for stable, non-viral transfer and integration of genetic material into a cell. In one aspect, the genetic material is a self-integrating polynucleotide. The genetic material can be stably integrated in the genome of the cell. The cell may be a human cell. The method is designed for a safe and reliable integration of a genetic material into the genome of a cell.

Provided herein is pharmaceutical composition comprising a therapeutically effective amount of one or more polynucleic acids, or at least one vector encoding the one or more polynucleic acids, the one or more polynucleic acids comprising: (a) a mobile genetic element comprising a sequence encoding a polypeptide; and (b) an insert sequence, wherein the insert sequence comprises a sequence that is a reverse complement of a sequence encoding an exogenous therapeutic polypeptide, wherein the polypeptide encoded by the sequence of the mobile genetic element promotes integration of the insert sequence into a genome of a cell; and wherein the pharmaceutical composition is substantially non-immunogenic to a human subject.

In some embodiments, the polypeptide encoded by the sequence of the mobile genetic element comprises one or more long interspersed nuclear element (LINE) polypeptides, wherein the one or more LINE polypeptides comprises: (i) human ORF1p or a functional fragment thereof, and (ii) human ORF2p or a functional fragment thereof.

In some embodiments, the insert sequence stably integrates and/or is retrotransposed into the genome of a human cell.

In some embodiments, the human cell is an immune cell selected from the group consisting of a T cell, a B cell, a myeloid cell, a monocyte, a macrophage and a dendritic cell.

In some embodiments, the insert sequence is integrated into the genome (i) by cleavage of a DNA strand of a target site by an endonuclease encoded by the one or more polynucleic acids, (ii) via target-primed reverse transcription (TPRT) or (iii) via reverse splicing of the insert sequence into a DNA target site of the genome.

In some embodiments, the insert sequence is integrated into the genome at a poly T site using specificity of an endonuclease domain of the human ORF2p.

In some embodiments, the poly T site comprises the sequence TTTTTA.

In some embodiments, the one or more polynucleic acids comprises homology arms complementary to a target site in the genome.

In some embodiments, the insert sequence integrates into: (a) the genome at a locus that is not a ribosomal locus; (b) a gene or regulatory region of a gene of the genome, thereby disrupting the gene or downregulating expression of the gene; (c) a gene or regulatory region of a gene of the genome, thereby upregulating expression of the gene; or (d) the genome and replaces a gene of the genome.

In some embodiments, the pharmaceutical composition further comprises (i) one or more siRNAs and/or (ii) an RNA guide sequence or a polynucleic acid encoding the RNA guide sequence, and wherein the RNA guide sequence targets a DNA target site of the genome and the insert sequence is integrated into the genome at the DNA target site of the genome.

In some embodiments, one or more genes are knocked down in the methods provided herein. In some embodiments, one or more siRNAs are employed in the compositions or methods described herein. For example, one or more genes can be knocked down to enhance integration, such as through modulating a pathway that may inhibit LINE-1. In some embodiments, the one or more genes knocked down include ADAR1, ADAR2 (ADAR1B), APOBEC3C, BRCA1, let-7 miRNA, RNase L, TASHOR (HUSH complex) and/or RAD51. For example, knock down of RNase L can be used to enhance integration by inhibiting or preventing degradation of an mRNA, such as an mRNA transcribed from a LINE-1. For example, knock down of ADAR1, ADAR2 (ADAR1B), and/or BRCA1 can be used to enhance integration by inhibiting or preventing ADAR1, ADAR2 (ADAR1B), and/or BRCA1 from inhibiting the cis binding of ORF2p to a poly A tail for L1 RNP assembly. For example, knock down of let-7 miRNA can be used to enhance integration by inhibiting or preventing let-7 miRNA from inhibiting translation, such as translation of ORF2p. let-7 miRNA. For example, knock down of RAD51 and/or BRCA1 can be used to enhance integration by inhibiting or preventing repair of cleaved DNA by RAD51 and/or BRCA1.

In some embodiments, the one or more polynucleic acids have a total length of from 3 kb to 20 kb.

In some embodiments, the one or more polynucleic acids comprises one or more polyribonucleic acids, one or more RNAs or one or more mRNAs.

In some embodiments, the exogenous therapeutic polypeptide is selected from the group consisting of a ligand, an antibody, a receptor, an enzyme, a transport protein, a structural protein, a hormone, a contractile protein, a storage protein and a transcription factor.

In some embodiments, the exogenous therapeutic polypeptide is a receptor selected from the group consisting of a chimeric antigen receptor (CAR) and a T cell receptor (TCR).

In some embodiments, the one or more polynucleic acids comprises a first expression cassette comprising a promoter sequence, a 5' UTR sequence, a 3' UTR sequence and a poly A sequence; wherein: (i) the promoter sequence is upstream of the 5' UTR sequence, (ii) the 5' UTR sequence is upstream of the sequence of the mobile genetic element encoding a polypeptide, (iii) the 3' UTR sequence is downstream of the insert sequence; and (iv) the 3' UTR is upstream of the poly A sequence; and wherein the 5' UTR sequence, the 3' UTR sequence or the poly A sequence comprises a binding site for a human ORF2p or a functional fragment thereof.

In some embodiments, the insert sequence comprises a second expression cassette comprising a sequence that is a reverse complement of a promoter sequence, a sequence that is a reverse complement of a 5' UTR sequence, a sequence that is a reverse complement of a 3' UTR sequence and a sequence that is a reverse complement of a poly A sequence; wherein: (i) the sequence that is a reverse complement of a promoter sequence is downstream of the sequence that is a reverse complement of a 5' UTR sequence, (ii) the sequence that is a reverse complement of a 5' UTR sequence is downstream of the sequence that is a reverse complement of a sequence encoding an exogenous therapeutic polypeptide (iii) the sequence that is a reverse complement of a 3' UTR sequence is upstream of the sequence that is a reverse complement of a sequence encoding an exogenous therapeutic polypeptide, and (iv) the sequence that is a reverse complement of a poly A sequence is upstream of the sequence that is a reverse complement of a 3' UTR sequence and downstream of the sequence of the mobile genetic encoding a polypeptide.

In some embodiments, the promoter sequence of the first expression cassette is different from the promoter sequence of the second expression cassette.

In some embodiments, the one or more LINE polypeptides comprises a first LINE polypeptide comprising the human ORF1p or functional fragment thereof and a second LINE polypeptide comprising the human ORF2p or functional fragment thereof, wherein the first LINE polypeptide and the second LINE polypeptide are translated from different open reading frames (ORFs).

In some embodiments, the one or more polynucleic acids comprises a first polynucleic acid molecule encoding the human ORF1p or functional fragment thereof and a second polynucleic acid molecule encoding the human ORF2p or functional fragment thereof.

In some embodiments, the one or more polynucleic acids comprises a 5' UTR sequence and a 3' UTR sequence, wherein (a) the 5' UTR comprises a 5' UTR from LINE-1 or a sequence with at least 80% sequence identity to ACUCCUCCCCAUCCUCUCCCUCUGUCCCUCUGUCCCUCUGACCCUGCACUGUCCCAGCACC (SEQ ID NO: 51); and/or (b) the 3' UTR comprises a 3' UTR from LINE-1 or a sequence with at least 80% sequence identity to

```
                                          (SEQ ID NO: 52)
CAGGACACAGCCUUGGAUCAGGACAGAGACUUGGG

GGCCAUCCUGCCCCUCCAACCCGACAUGUGUACCU

CAGCUUUUUCCCUCACUUGCAUCAAUAAAGCUUCU

GUGUUUGGAACAG.
```

In some embodiments, the sequence encoding the exogenous therapeutic polypeptide does not comprise introns.

In some embodiments, the polypeptide encoded by the sequence of the mobile genetic element comprises a C-terminal nuclear localization signal (NLS), an N-terminal NLS or both.

In some embodiments, the sequence encoding the exogenous polypeptide is not in frame with a sequence encoding the ORF1p or functional fragment thereof and/or is not in frame with a sequence encoding the ORF2p or functional fragment thereof.

In some embodiments, the one or more polynucleic acids comprises a sequence encoding a nuclease domain, a nuclease domain that is not derived from ORF2p, a megaTAL nuclease domain, a TALEN domain, a Cas9 domain, a Cas6 domain, a Cas7 domain, a Cas8 domain, a zinc finger binding domain from an R2 retroelement, or a DNA binding domain that binds to repeat sequences.

In some embodiments, the one or more polynucleic acids comprises a sequence encoding the nuclease domain, wherein the nuclease domain does not have nuclease activity or comprises a mutation that reduces activity of the nuclease domain compared to the nuclease domain without the mutation.

In some embodiments, the ORF2p or functional fragment thereof lacks endonuclease activity or comprises a mutation selected from the group consisting of S228P and Y1180A, and/or wherein the ORF1p or functional fragment comprises a K3R mutation.

In some embodiments, the insert sequence comprises a sequence that is a reverse complement of a sequence encoding two or more exogenous therapeutic polypeptides.

In some embodiments, the one or more polynucleic acids comprises one or more polyribonucleic acids, wherein the exogenous therapeutic polypeptide is a receptor selected from the group consisting of a chimeric antigen receptor (CAR) and a T cell receptor (TCR), and wherein the pharmaceutical composition is formulated for systemic administration to a human subject.

In some embodiments, the one or more polynucleic acids (i) are formulated in a nanoparticle selected from the group consisting of a lipid nanoparticle and a polymeric nanoparticle; and/or (ii) comprises one or more polynucleic acids selected from the group consisting of glycosylated RNAs, circular RNAs and self-replicating RNAs.

Also provided herein is a method of treating a disease or condition in a human subject in need thereof comprising administering a pharmaceutical composition described herein to the human subject.

Also provided herein is a method of modifying a population of human cells ex vivo comprising contacting a composition to a population of human cell ex vivo, thereby forming an ex vivo modified population of human cells, the composition comprising one or more polynucleic acids, or at least one vector encoding the one or more polynucleic acids, the one or more polynucleic acids comprising: (a) a mobile genetic element comprising a sequence encoding a polypeptide; and (b) an insert sequence, wherein the insert sequence is a reverse complement of a sequence encoding an exogenous therapeutic polypeptide, wherein the ex vivo modified population of human cells is substantially non-immunogenic to a human subject.

In one aspect, provided herein are compositions and methods that allow integration of genetic material into the genome of a cell, wherein the genetic material that can be integrated is not specifically restricted by size. In some aspects, the method described herein provides a one-step, single polynucleotide-mediated delivery and integration of genetic "cargo" in the genome of a cell. The genetic material may comprise a coding sequence, e.g., a sequence encoding a transgene, a peptide, a recombinant protein, or an antibody or fragments thereof, wherein the method and compositions ensure stable expression of the transcribed product encoded by the coding sequence. The genetic material may comprise a non-coding sequence, for example, a regulatory RNA sequences, e.g., a regulatory small inhibitory RNA (siRNA), microRNA (miRNA), long non-coding RNA (lncRNA), or one or more transcription regulators such as a promoter and/or an enhancer, and may also include, but not limited to structural biomolecules such as ribosomal RNA (rRNA), transfer RNA (tRNA) or a fragment thereof or a combination thereof.

In another aspect, provided herein are methods and compositions for site-specific integration of a genetic material that may not be specifically restricted by size, into the genome of a cell via a non-viral delivery that ensures both safety and efficacy of the transfer. Provided methods and compositions may be particularly useful in developing a therapeutic, such as a therapeutic comprising a polynucleotide comprising a genetic material and a machinery that allows transfer into a cell and stable integration into the genome of the cell into which the polynucleotide or an mRNA encoding the polynucleotide is transferred. In some embodiments, the therapeutic may be a cell that comprises a polynucleotide that has been stably integrated into the genome of the cell using the methods and compositions described herein.

In one aspect, the present disclosure provides compositions and methods for stable gene transfer into a cell. In some embodiments, the compositions and methods are for stable gene transfer into an immune cell. In some cases, the immune cell is a myeloid cell. In some cases, the methods described herein relate to development of myeloid cells for immunotherapy.

Provided herein is a method of treating a disease in a subject in need thereof, comprising: administering a pharmaceutical composition to the subject wherein the pharmaceutical composition comprises a polycistronic mRNA sequence encoding a gene or fragment thereof, operably linked to a sequence encoding an L1 retrotransposon; wherein the gene or the fragment thereof is at least 10.1 kb in length.

Provided herein is a method for integrating a nucleic acid sequence into the genome of a cell, comprising contacting the cell with a composition comprising a polycistronic mRNA sequence encoding a gene or fragment thereof, operably linked to a sequence encoding an L1 retrotransposon; wherein the gene or the fragment thereof is at least 10.1 kb in length. In some embodiments, the gene or the fragment thereof (e.g., the payload) is at least about 10.2 kb, 10.3 kb, 10.4 kb, 10.5 kb, 10.6 kb, 10.7 kb, 10.8 kb, 10.9 kb, 11 kb, 12 kb, 13 kb, 14 kb, 15 kb, 16 kb, 17 kb, 18 kb, 19 kb, 20 kb or more in length.

Provided herein is a method for integrating a nucleic acid sequence into the genome of a cell, comprising contacting the cell with a composition comprising a polycistronic mRNA sequence encoding a gene or fragment thereof, operably linked to a sequence encoding an L1 retrotransposon; wherein the gene or the fragment thereof is selected from a group consisting of ABCA4, MY07A, CEP290, CDH23, EYS, USH2a, GPR98, ALMS1, GDE, OTOF, and F8.

Provided herein is a method of expressing a protein encoded by a recombinant nucleic acid in a cell, the method comprising integrating a nucleic acid sequence into the genome of a cell by contacting the cell with a composition comprising a polycistronic mRNA sequence encoding a gene or fragment thereof, operably linked to a sequence encoding an L1 retrotransposon; and expressing a protein encoded by the gene or fragment thereof, wherein expression of the protein is detectable more than 30 days after (a).

In one embodiment of a method described herein, the disease is a genetic disease.

Provided herein is a method of treating Stargardt disease, LCA10, USH1D, DFNB12, retinitis pigmentosa (RP) USH2A, USH2C, Alstrom syndrome, Glycogen storage disease III, Non-syndromic deafness, Hemophilia A, or Leber congenital amaurosis in a subject, the method comprising: (i) introducing into the subject an mRNA encoding a suitable gene or a fragment thereof, operably linked to a human L1 transposon, or (ii) introducing to the subject a population of cells comprising an mRNA encoding a suitable gene or a fragment thereof, operably linked to a human L1 transposon.

In one embodiment of a method described herein, the method comprises treating Stargardt disease in a subject in need thereof, and wherein the mRNA encodes an ABCA4 gene, or a fragment thereof.

In one embodiment of a method described herein, the method comprises treating Usher Syndrome Type 1b (Usher 1b) disease in a subject in need thereof, and wherein the mRNA encodes an MY07A gene, or a fragment thereof.

In one embodiment of a method described herein, the method comprises treating Leber congenital amaurosis (LCA)10 disease in a subject in need thereof, and wherein the mRNA encodes a CEP290 gene, or a fragment thereof.

In one embodiment of a method described herein, the method comprises treating a User Syndrome Type 1D (USH1D) non-syndromic deafness or hearing loss USH1D, DFN12 disease in a subject in need thereof, and wherein the mRNA encodes a CDH23 gene, or a fragment thereof.

In one embodiment of a method described herein, the method comprises treating a retinitis pigmentosa (RP) disease in a subject in need thereof, and wherein the mRNA encodes an EYS gene, or a fragment thereof.

In one embodiment of a method described herein, the method comprises treating a User Syndrome Type 2A (USH2A) and wherein the mRNA encodes an USH2a gene, or a fragment thereof.

In one embodiment of a method described herein, the method comprises treating a User Syndrome Type 2C (USH2C) and wherein the mRNA encodes a GPR98 gene, or a fragment thereof.

In one embodiment of a method described herein, the method comprises treating an Alstrom Syndrome, and wherein the mRNA encodes an ALMS1 gene, or a fragment thereof.

In one embodiment of a method described herein, the method comprises treating a Glycogen Storage Disease III, and wherein the mRNA encodes a GDE gene, or a fragment thereof.

In one embodiment of a method described herein, the method comprises treating a non-syndromic deafness or hearing loss and wherein the mRNA encodes an OTOF gene, or a fragment thereof.

In one embodiment of a method described herein, the method comprises treating Hemophilia A, and the mRNA encodes an Factor VIII (F8) gene, or a fragment thereof.

Provided herein is a method for targeted replacement of a genomic nucleic acid sequence of a cell, the method comprising: (A) introducing to the cell a polynucleotide sequence encoding a first protein complex comprising a targeted excision machinery for excising from the genome of the cell a nucleic acid sequence comprising one or more mutations; and (B) a recombinant mRNA encoding a second protein complex, wherein the recombinant mRNA comprises: (i) a nucleic acid sequence comprising the excised nucleic acid sequence in (A) that does not contain the one or more mutations, and (ii) a sequence encoding an L1 retrotransposon ORF2 protein under the influence of an independent promoter.

In one embodiment of a method described herein, the nucleic acid sequence comprising the one or more mutations comprises a pathogenic variant of a cellular gene.

In one embodiment of a method described herein, the a nucleic acid sequence in (B) comprising the nucleic acid sequence that does not contain the one or more mutations is operably linked to the ORF2 sequence.

In one embodiment of a method described herein, the method further comprising introducing a sequence comprising a plurality of thymidine residues at the excision site.

In some embodiment, introducing the sequence comprises introducing at least four thymidine residues.

In one embodiment of a method described herein, the targeted excision machinery comprises a sequence guided site-specific excision endonuclease.

In one embodiment of a method described herein, the targeted excision machinery comprises a CRISPR-CAS system.

In some embodiments, the targeted excision machinery is a modified recombinant LINE 1 (L1) endonuclease.

In some embodiments, introducing the sequence comprising a plurality of thymidine residues comprises base extension by prime editing at the excision site.

In some embodiments, the mRNA sequence encoding an L1 retrotransposon ORF2 protein further comprises a sequence encoding the L1 retrotransposon ORF1 protein.

In some embodiments, the mRNA comprises a sequence for an inducible promoter.

In one embodiment of a method described herein, the excised sequence is greater than 1000 bases.

In one embodiment of a method described herein, the excised sequence is greater than 6 kb.

In one embodiment of a method described herein, the excised sequence is about 10 kb.

In some embodiments, the cell is a lymphocyte. In some embodiments, the cell is a myeloid cell.

In some embodiments, the cell is an epithelial cell. In some embodiments, the cell is a cancer cell.

In some embodiments, the nucleic acid sequence encodes an ATP-binding cassette (ABC) transporter gene, (ABCA4) gene, or a fragment thereof.

In some embodiments, the nucleic acid sequence encodes an MY07A, CEP290, CDH23, EYS, USH2a, GPR98, ALMS1, GDE, OTOF or an F8 gene or a fragment thereof.

In some embodiments, introducing comprises introducing to the cell ex vivo. In some embodiments, introducing comprises electroporation. In some embodiments, introducing comprises introducing to the cell in vivo. In some embodiments, expression of the nucleic acid sequence comprising the sequence that does not contain the one or more mutations, is detectable at least 35 days after introducing to the cell. In some embodiments, introducing into the subject comprises direct administration of the mRNA systemically.

In some embodiments, introducing into the subject comprises local administration of the mRNA.

In some embodiments, the mRNA sequence comprises a cell targeting moiety.

In some embodiments, the cell targeting moiety is an aptamer.

In some embodiments, introducing into the subject comprises introducing the mRNA in the retina of the subject.

Provided herein is a method of integrating a nucleic acid sequence into a genome of a cell, the method comprising introducing a recombinant mRNA or a vector encoding an mRNA into the cell, wherein the mRNA comprises: (a) an insert sequence, wherein the insert sequence comprises (i) an exogenous sequence, or (ii) a sequence that is a reverse complement of the exogenous sequence; (b) a 5' UTR sequence and a 3' UTR sequence downstream of the 5' UTR sequence; wherein the 5' UTR sequence or the 3' UTR sequence comprises a binding site for a human ORF protein, and wherein the insert sequence is integrated into the genome of the cell, wherein the insert sequence is a gene selected from a group consisting of ABCA4, MY07A, CEP290, CDH23, EYS, USH2a, GPR98, ALMS1, GDE, OTOF, and F8.

In some embodiments, the 5' UTR sequence or the 3' UTR sequence comprises a binding site for human ORF2p.

Provided herein is a method for integrating a nucleic acid sequence into the genome of an immune cell, the method comprising introducing a recombinant mRNA or a vector encoding an mRNA, wherein the mRNA comprises: (a) an insert sequence, wherein the insert sequence comprises (i) an exogenous sequence or (ii) a sequence that is a reverse complement of the exogenous sequence; (b) 5' UTR sequence and a 3' UTR sequence downstream of the 5' UTR sequence, wherein the 5' UTR sequence or the 3' UTR sequence comprises an endonuclease binding site and/or a reverse transcriptase binding site, and wherein the insert sequence is integrated into the genome of the immune cell, wherein the insert sequence is a gene selected from a group consisting of ABCA4, MY07A, CEP290, CDH23, EYS, USH2a, GPR98, ALMS1, GDE, OTOF, and F8.

Provided herein is a method for integrating a nucleic acid sequence into the genome of a cell, the method comprising introducing a recombinant mRNA or a vector encoding an mRNA, wherein the mRNA comprises: (a) an insert sequence, wherein the insert sequence comprises (i) an exogenous sequence or (ii) a sequence that is a reverse complement of the exogenous sequence; (b) a 5' UTR sequence, a sequence of a human retrotransposon downstream of the 5' UTR sequence, and a 3' UTR sequence downstream of the sequence of a human retrotransposon; wherein the 5' UTR sequence or the 3' UTR sequence comprises an endonuclease binding site and/or a reverse transcriptase binding site, and wherein the sequence of a human retrotransposon encodes for two proteins that are translated from a single RNA containing two ORFs, and wherein the insert sequence is integrated into the genome of the cell, wherein the insert sequence is a gene selected from a group consisting of ABCA4, MY07A, CEP290, CDH23, EYS, USH2a, GPR98, ALMS1, GDE, OTOF, and F8.

In some embodiments, the 5' UTR sequence or the 3' UTR sequence comprises an ORF2p binding site. In some embodiments, the ORF2p binding site is a poly A sequence in the 3' UTR sequence.

In some embodiments, the mRNA comprises a sequence of a human retrotransposon. In some embodiments, the sequence of a human retrotransposon is downstream of the 5' UTR sequence.

In some embodiments, the sequence of a human retrotransposon is upstream of the 3' UTR sequence. In some embodiments, the sequence of a human retrotransposon encodes for two proteins that are translated from a single RNA containing two ORFs. In some embodiments, the two ORFs are non-overlapping ORFs.

In some embodiments, the sequence of a human retrotransposon comprises a sequence of a non-LTR retrotransposon. In some embodiments, the sequence of a human retrotransposon encodes comprises a LINE-1 retrotransposon. In some embodiments, the LINE-1 retrotransposon is a human LINE-1 retrotransposon. In some embodiments, the sequence of a human retrotransposon comprises a sequence encoding an endonuclease and/or a reverse transcriptase.

In some embodiments, the endonuclease and/or a reverse transcriptase is ORF2p.

In some embodiments, the reverse transcriptase is a group II intron reverse transcriptase domain.

In some embodiments, the endonuclease and/or a reverse transcriptase is a minke whale endonuclease and/or a reverse transcriptase.

In some embodiments, the sequence of a human retrotransposon comprises a sequence encoding ORF2p. In some embodiments, the insert sequence is integrated into the genome at a poly T site using specificity of an endonuclease domain of the ORF2p. In some embodiments, the poly T site comprises the sequence TTTTTA. In some embodiments, the retrotransposon comprises an ORF1p and/or the ORF2p fused to a nuclear retention sequence. In some embodiments, the nuclear retention sequence is an Alu sequence. In some embodiments, the ORF1p and/or the ORF2p is fused to an MS2 coat protein. In some embodiments, the 5' UTR sequence or the 3' UTR sequence comprises at least one, two, three or more MS2 hairpin sequences.

Provided herein is a composition comprising a recombinant mRNA or vector encoding an mRNA, wherein the mRNA comprises a human LINE-1 transposon sequence comprising: (i) a human LINE-1 transposon 5' UTR sequence, (ii) a sequence encoding ORF1p downstream of the human LINE-1 transposon 5' UTR sequence, (iii) an inter-ORF linker sequence downstream of the sequence encoding ORF1p, (iv) a sequence encoding ORF2p downstream of the inter-ORF linker sequence, and (v) a 3' UTR sequence derived from a human LINE-1 transposon downstream of the sequence encoding ORF2p; wherein the 3' UTR sequence comprises an insert sequence, wherein the insert sequence is a reverse complement of a sequence encoding an exogenous polypeptide or a reverse complement of a sequence encoding an exogenous regulatory element, wherein the insert sequence is a gene selected from a group consisting of ABCA4, MY07A, CEP290, CDH23, EYS, USH2a, GPR98, ALMS1, GDE, OTOF, and F8.

Provided herein is a composition comprising a nucleic acid comprising a nucleotide sequence encoding (a) a long interspersed nuclear element (LINE) polypeptide, wherein the LINE polypeptide includes human ORF1p and human ORF2p; and (b) an insert sequence, wherein the insert sequence is a reverse complement of a sequence encoding an exogenous polypeptide or a reverse complement of a sequence encoding an exogenous regulatory element, wherein the composition is substantially non-immunogenic, wherein the insert sequence is a gene selected from a group consisting of ABCA4, MY07A, CEP290, CDH23, EYS, USH2a, GPR98, ALMS1, GDE, OTOF, and F8.

Immunotherapy using phagocytic cells involves making and using engineered myeloid cells, such as macrophages or other phagocytic cells that attack and kill diseased cells, such as cancer cells, or infected cells. Engineered myeloid cells, such as macrophages and other phagocytic cells are prepared by incorporating in them via recombinant nucleic acid technology, a synthetic, recombinant nucleic acid encoding an engineered protein, such as a chimeric antigen receptor, that comprises a targeted antigen binding extracellular domain that is designed to bind to specific antigens on the surface of a target, such as a target cell, such as a cancer cell. Binding of the engineered chimeric receptor to an antigen on a target, such as cancer antigen (or likewise, a disease target), initiates phagocytosis of the target. This triggers two fold action: one, phagocytic engulfment and lysis of the target destroys the target and eliminates it as a first line of immune defense; two, antigens from the target are digested in the phagolysosome of the myeloid cell, are presented on the surface of the myeloid cell, which then leads to activation of T cells and further activation of the immune response and development of immunological memory. Chimeric receptors are engineered for enhanced phagocytosis and immune activation of the myeloid cell in which it is incorporated and expressed. Chimeric antigen receptors of the disclosure are variously termed herein as a chimeric fusion protein, CFP, phagocytic receptor (PR) fusion protein (PFP), or chimeric antigen receptor for phagocytosis (CAR-P), while each term is directed to the concept of a recombinant chimeric and/or fusion receptor protein. In some embodiments, genes encoding non-receptor proteins are also co-expressed in the myeloid cells, typically for an augmentation of the chimeric antigen receptor function. In summary, contemplated herein are various engineered receptor and non-receptor recombinant proteins that are designed to augment phagocytosis and or immune response of a myeloid cell against a disease target, and methods and compositions for creating and incorporating recombinant nucleic acids that encode the engineered receptors or non-receptor recombinant protein, such that the methods and compositions are suitable for creating an engineered myeloid cell for immunotherapy.

In one aspect, the present disclosure provides compositions and methods for stable gene transfer into a cell, where the cell can be any somatic cell. In some embodiments the compositions and methods are designed for cell-specific or tissue-specific delivery. In some cases, the methods described herein relate to supplying a functional protein or a fragment thereof to compensate for an absent or defective (mutated) protein in vivo, e.g., for a protein replacement therapy.

Incorporation of a recombinant nucleic acid in a cell can be accomplished by one or more gene transfer techniques that are available in the state of the art. However, incorporation of exogenous genetic (e.g., nucleic acid) elements into the genome for therapeutic purposes still faces several challenges. Achieving stable integration in a safe and dependable manner, and efficient and prolonged expression are a few among them. Most of the successful gene transfer systems aimed at genomic integration of the cargo nucleic acid sequence rely on viral delivery mechanisms, which have some inherent safety and efficacy issues. Delivery and integration of long nucleic acid sequences cannot be achieved by current gene editing systems.

Little attention has so far been devoted to making and using engineered myeloid cells for stable long-term gene transfer and expression of the transgene. For example, gene transfer to differentiated mammalian cells ex vivo for cell therapy can be accomplished via viral gene transfer mechanisms. However, there are several strategic disadvantages associated with the use of viral gene-transfer vectors, including an undesired potential for transgene silencing over time, the preferential integration into transcriptionally active sites of the genome with associated undesired activation of other genes (e.g. oncogenes) and genotoxicity. In addition to the safety issues increased expense and cumbersome effort of manufacturing, storing and handling integrating viruses often stand in the way of large-scale use of viral vector mediated of gene-modified cells in therapeutic applications. These persistent concerns associated with viral vectors regarding safety, as well as cost and scale of vector production necessitates alternative methods for effective therapy.

Integration of a transgene into the genome of a cell to be used for an immunotherapy can be advantageous in the sense that it is stable and a lower number of cells is required for delivery during the therapy. On the other hand, integrating a transgene in a non-dividing cell can be challenging in both affecting the health and function of the cell as well as the ultimate lifespan of the cell in vivo, and therefore affects its overall utility as the therapeutic. In some embodiments, the methods described herein for generating a myeloid cell for immunotherapy can be a cumulative product of a number of steps and compositions involving but not limited to, for example, selecting a myeloid cell for modifying; method and compositions for incorporating a recombinant nucleic acid in a myeloid cell; methods and compositions for enhancing expression of the recombinant nucleic acid; methods and compositions for selecting and modifying vectors; methods of preparing a recombinant nucleic acid suitable for in vivo administration for uptake and incorporation of the recombinant nucleic acid by a myeloid cell in vivo and therefore generating a myeloid cell for therapy. In some aspects, one or more embodiments of the various inventions described herein are transferrable among each other, and one of skill in the art is expected to use them in alternatives, combinations or interchangeably without the necessity of undue experimentation. All such variations of the disclosed elements are contemplated and fully encompassed herein.

In one aspect, transposons, or transposable elements (TEs) are considered herein, for means of incorporating a heterologous, synthetic or recombinant nucleic acid encoding a transgene of interest in a myeloid cell. Transposon, or transposable elements are genetic elements that have the capability to transpose fragments of genetic material into the genome by use of an enzyme known as transposase. Mammalian genomes contain a high number of transposable element (TE)-derived sequences, and up to 70% of our genome represents TE-derived sequences (de Koning et al. 2011; Richardson et al. 2015). These elements could be exploited to introduce genetic material into the genome of a cell. The TE elements are capable of mobilization, often termed as “jumping” genetic material within the genome. TEs generally exist in eukaryotic genomes in a reversibly inactive, epigenetically silenced form. In the present disclosure methods and compositions for efficient and stable integration of transgenes into macrophages and other phagocytic cells. The method is based on use of a transposase and transposable elements mRNA-encoded transposase. In some embodiments, Long Interspersed Element-1 (L1) RNAs are used for stable integration and/or retrotransposition of the transgene into a cell (e.g., a macrophage or phagocytic cell.

Contemplated herein are methods for retrotransposon mediated stable integration of an exogenous nucleic acid sequence into the genome of a cell. The method may take advantage of the random genomic integration machinery of the retrotransposon into the cell without creating an adverse effect. Methods described herein can be used for robust and versatile incorporation of an exogenous nucleic acid sequence into a cell, such that the exogenous nucleic acid is incorporated at a safe locus within the genome and is expressed without being silenced by the cell’s inherent defense mechanism. The method described herein can be used to incorporate an exogenous nucleic acid that is about 1 kb, about 2 kb, about 3 kb, about 4 kb, about 5 kb, about 6 kb, about 7 kb about 8 kb, about 9 kb, about 10 kb, or more in size. In some embodiments, the exogenous nucleic acid is not incorporated within a ribosomal locus. In some embodiments, the exogenous nucleic acid is not incorporated within a ROSA26 locus, or another safe harbor locus. In some embodiments, the methods and compositions described herein can incorporate an exogenous nucleic acid sequence anywhere within the genome of the cell. Furthermore, contemplated herein is a retrotransposition system that is developed to incorporate an exogenous nucleic acid sequence into a specific predetermined site within the genome of a cell, without creating an adverse effect. The disclosed methods and compositions incorporate several mechanisms of engineering the retrotransposons for highly specific incorporation of the exogenous nucleic acid into a cell with high fidelity. Retrotransposons chosen for this purpose may be a human retrotransposon.

Methods and compositions described herein represent a salient breakthrough in the molecular systems and mechanisms for manipulating the genome of a cell. Shown here for the first time is a method that exploits a human retrotransposon system into non-virally delivering and stably integrating a large fragment of exogenous nucleic acid sequence (at least greater than 100 nucleobases, at least greater than 1 kb, at least greater than 2 kb, at least greater than 3 kb, etc.) into a non-conserved region of the genome that is not an rDNA or a ribosomal locus or a designated safe-harbor locus such as the ROSA 26 locus.

In some embodiments, a retrotransposable system is used to stably incorporate into the genome and express a non-endogenous nucleic acid, where the non-endogenous nucleic acid comprises retrotransposable elements within the nucleic acid sequence. In some embodiments, a cell’s endogenous retrotransposable system (e.g., proteins and enzymes) is used to stably express a non-endogenous nucleic acid in the cell. In some embodiments, a cell’s endogenous retrotransposable system (e.g., proteins and enzymes, such as a LINE-1 retrotransposition system) is used, but may further express one or more components of the retrotransposable system to stably express a non-endogenous nucleic acid in the cell.

In some embodiments, a synthetic nucleic acid is provided herein, the synthetic nucleic acid encoding a transgene, and encoding one or more components for genomic integration and/or retrotransposition.

In one aspect, provided herein is a method of integrating a nucleic acid sequence into a genome of a cell, the method comprising introducing a recombinant mRNA or a vector encoding an mRNA into the cell, wherein the mRNA comprises: an insert sequence, wherein the insert sequence comprises an exogenous sequence, or a sequence that is a reverse complement of the exogenous sequence; a 5' UTR sequence and a 3' UTR sequence downstream of the 5' UTR sequence; wherein the 5' UTR sequence or the 3' UTR sequence comprises a binding site for a human ORF protein, and wherein the insert sequence is integrated into the genome of the cell. In some embodiments, the 5' UTR sequence or the 3' UTR sequence comprises a binding site for human ORF2p.

In one aspect, provided herein is a method for integrating a nucleic acid sequence into the genome of an immune cell, the method comprising introducing a recombinant mRNA or a vector encoding an mRNA, wherein the mRNA comprises an insert sequence, wherein the insert sequence comprises (i) an exogenous sequence or (ii) a sequence that is a reverse complement of the exogenous sequence; 5' UTR sequence and a 3' UTR sequence downstream of the 5' UTR sequence, wherein the 5' UTR sequence or the 3' UTR sequence comprises an endonuclease binding site and/or a reverse transcriptase binding site, and wherein the transgene sequence is integrated into the genome of the immune cell.

In one aspect, provided herein is a method for integrating a nucleic acid sequence into the genome of a cell, the method comprising introducing a recombinant mRNA or a vector encoding an mRNA, wherein the mRNA comprises an insert sequence, wherein the insert sequence comprises (i) an exogenous sequence or (ii) a sequence that is a reverse complement of the exogenous sequence; a 5' UTR sequence, a sequence of a human retrotransposon downstream of the 5' UTR sequence, and a 3' UTR sequence downstream of the sequence of a human retrotransposon; wherein the 5' UTR sequence or the 3' UTR sequence comprises an endonuclease binding site and/or a reverse transcriptase binding site, and wherein the sequence of a human retrotransposon encodes for two proteins that are translated from a single RNA containing two ORFs, and wherein the insert sequence is integrated into the genome of the cell.

In some embodiments, the 5' UTR sequence or the 3' UTR sequence comprises an ORF2p binding site. In some embodiments, the ORF2p binding site is a poly A sequence in the 3' UTR sequence.

In some embodiments, the mRNA comprises a sequence of a human retrotransposon. In some embodiments, the sequence of a human retrotransposon is downstream of the 5' UTR sequence. In some embodiments, the sequence of a human retrotransposon is upstream of the 3' UTR sequence. In some embodiments, the polynucleotide sequence that is desired to be transferred and incorporated into the genome of a cell (e.g., the insert) is inserted at a site 3' to the sequence encoding ORF1 in a recombinant nucleic acid construct. In some embodiments, the polynucleotide sequence that is desired to be transferred and incorporated into the genome of a cell is inserted at a site 3' to the sequence encoding ORF2 in a recombinant nucleic acid construct. In some embodiments the sequence that is desired to be transferred and incorporated into the genome of a cell is inserted within the 3'-UTR of ORF1 or ORF2, or both. In some embodiments, the polynucleotide sequence that is sequence that is desired to be transferred and incorporated into the genome of a cell is inserted upstream of the poly A tail of ORF2 in a recombinant nucleic acid construct.

In some embodiments, the sequence of a human retrotransposon encodes for two proteins that are translated from a single RNA containing two ORFs. In some embodiments, the two ORFs are non-overlapping ORFs. In some embodiments, the two ORFs are ORF1 and ORF2. In some embodiments, the ORF1 encodes ORF1p and ORF2 encodes ORF2p.

In some embodiments, the sequence of a human retrotransposon comprises a sequence of a non-LTR retrotransposon. In some embodiments, the sequence of a human retrotransposon comprises a LINE-1 retrotransposon. In some embodiments, the LINE-1 retrotransposon is a human LINE-1 retrotransposon. In some embodiments, the sequence of a human retrotransposon comprises a sequence encoding an endonuclease and/or a reverse transcriptase. In some embodiments, the endonuclease and/or a reverse transcriptase is ORF2p. In some embodiments, the reverse transcriptase is a group II intron reverse transcriptase domain. In some embodiments, the endonuclease and/or a reverse transcriptase is a minke whale endonuclease and/or a reverse transcriptase. In some embodiments, the sequence of a human retrotransposon comprises a sequence encoding ORF2p. In some embodiments, the insert sequence is integrated into the genome at a poly T site using specificity of an endonuclease domain of the ORF2p. In some embodiments, the poly T site comprises the sequence TTTTTA.

In some embodiments, provided herein is a polynucleotide construct comprising an mRNA wherein the mRNA comprises a sequence encoding a human retrotransposon, wherein, (i) the sequence of a human retrotransposon comprises a sequence encoding ORF1p, (ii) the mRNA does not comprise a sequence encoding ORF1p, or (iii) the mRNA comprises a replacement of the sequence encoding ORF1p with a 5' UTR sequence from the complement gene. In some embodiments, the mRNA comprises a first mRNA molecule encoding ORF1p, and a second mRNA molecule encoding an endonuclease and/or a reverse transcriptase. In some embodiments, the mRNA is an mRNA molecule comprising a first sequence encoding ORF1p, and a second sequence encoding an endonuclease and/or a reverse transcriptase. In some embodiments, the first sequence encoding ORF1p and the second sequence encoding an endonuclease and/or a reverse transcriptase are separated by a linker sequence.

In some embodiments, the linker sequence comprises an internal ribosome entry sequence (IRES). In some embodiments, the IRES is an IRES from CVB3 or EV71. In some embodiments, the linker sequence encodes a self-cleaving peptide sequence. In some embodiments, the linker sequence encodes a T2A, a E2A or a P2A sequence In some embodiments, the sequence of a human retrotransposon comprises a sequence that encodes ORF1p fused to an additional protein sequence and/or a sequence that encodes ORF2p fused to an additional protein sequence. In some embodiments, the ORF1p and/or the ORF2p is fused to a nuclear retention sequence. In some embodiments, the nuclear retention sequence is an Alu sequence. In some embodiments, the ORF1p and/or the ORF2p is fused to an MS2 coat protein. In some embodiments, the 5' UTR sequence or the 3' UTR sequence comprises at least one, two, three or more MS2 hairpin sequences. In some embodiments, the 5' UTR sequence or the 3' UTR sequence comprises a sequence that promotes or enhances interaction of a poly A tail of the mRNA with the endonuclease and/or a reverse transcriptase. In some embodiments, the 5' UTR sequence or the 3' UTR sequence comprises a sequence that promotes or enhances interaction of a poly-A-binding proteins (e.g., PABP) with the endonuclease and/or a reverse transcriptase. In some embodiments, the 5' UTR sequence or the 3' UTR sequence comprises a sequence that increases specificity of the endonuclease and/or a reverse transcriptase to the mRNA relative to another mRNA expressed by the cell. In some embodiments, the 5' UTR sequence or the 3' UTR sequence comprises an Alu element sequence.

In some embodiments, the first sequence encoding ORF1p and the second sequence encoding an endonuclease and/or a reverse transcriptase have the same promoter. In some embodiments, the insert sequence has a promoter that is different from the promoter of the first sequence encoding ORF1p. In some embodiments, the insert sequence has a promoter that is different from the promoter of the second sequence encoding an endonuclease and/or a reverse transcriptase. In some embodiments, the first sequence encoding ORF1p and/or the second sequence encoding an endonuclease and/or a reverse transcriptase have a promoter or transcription initiation site selected from the group consisting of an inducible promoter, a CMV promoter or transcription initiation site, a T7 promoter or transcription initiation site, an EF1a promoter or transcription initiation site and combinations thereof. In some embodiments, the insert sequence has a promoter or transcription initiation site selected from the group consisting of an inducible promoter, a CMV promoter or transcription initiation site, a T7 promoter or transcription initiation site, an EF1a promoter or transcription initiation site and combinations thereof.

In some embodiments, the first sequence encoding ORF1p and the second sequence encoding an endonuclease and/or a reverse transcriptase are codon optimized for expression in a human cell.

In some embodiments, the mRNA comprises a WPRE element. In some embodiments, the mRNA comprises a selection marker. In some embodiments, the mRNA comprises a sequence encoding an affinity tag. In some embodiments, the affinity tag is linked to the sequence encoding an endonuclease and/or a reverse transcriptase.

In some embodiments, the 3' UTR comprises a poly A sequence or wherein a poly A sequence is added to the mRNA in vitro. In some embodiments, the poly A sequence is downstream of a sequence encoding an endonuclease and/or a reverse transcriptase. In some embodiments, the insert sequence is upstream of the poly A sequence.

In some embodiments, the 3' UTR sequence comprises the insert sequence. In some embodiments, the insert sequence comprises a sequence that is a reverse complement of the sequence encoding the exogenous polypeptide. In some embodiments, the insert sequence comprises a polyadenylation site. In some embodiments, the insert sequence comprises an SV40 polyadenylation site. In some embodiments, the insert sequence comprises a polyadenylation site upstream of the sequence that is a reverse complement of the sequence encoding the exogenous polypeptide. In some embodiments, the insert sequence is integrated into the genome at a locus that is not a ribosomal locus. In some embodiments, the insert sequence is integrated into the genome at a locus that is not a rDNA locus. In some embodiments, the insert sequence integrates into a gene or regulatory region of a gene, thereby disrupting the gene or downregulating expression of the gene. In some embodiments, the insert sequence integrates into a gene or regulatory region of a gene, thereby upregulating expression of the gene. In some embodiments, the insert sequence integrates into the genome and replaces a gene. In some embodiments, the insert sequence is stably integrated into the genome. In some embodiments, the insert sequence is retrotransposed into the genome. In some embodiments, the insert sequence is integrated into the genome by cleavage of a DNA strand of a target site by an endonuclease encoded by the mRNA. In some embodiments, the insert sequence is integrated into the genome via target-primed reverse transcription (TPRT). In some embodiments, the insert sequence is integrated into the genome via reverse splicing of the mRNA into a DNA target site of the genome.

In some embodiments, the cell is an immune cell. In some embodiments, the immune cell is a T cell or a B cell. In some embodiments, the immune cell is a myeloid cell. In some embodiments, the immune cell is selected from a group consisting of a monocyte, a macrophage, a dendritic cell, a dendritic precursor cell, and a macrophage precursor cell.

In some embodiments, the mRNA is a self-integrating mRNA. In some embodiments, the method comprises introducing into the cell the mRNA. In some embodiments, the method comprises introducing into the cell the vector encoding the mRNA. In some embodiments, the method comprises introducing the mRNA or the vector encoding the mRNA into a cell ex vivo. In some embodiments, the method further comprises administering the cell to a human subject. In some embodiments, the method comprises administering the mRNA or the vector encoding the mRNA to a human subject. In some embodiments, an immune response is not elicited in the human subject. In some embodiments, the mRNA or the vector is substantially non-immunogenic.

In some embodiments, the vector is a plasmid or a viral vector. In some embodiments, the vector comprises a non-LTR retrotransposon. In some embodiments, the vector comprises a human L1 element. In some embodiments, the vector comprises a L1 retrotransposon ORF1 gene. In some embodiments, the vector comprises a L1 retrotransposon ORF2 gene. In some embodiments, the vector comprises a L1 retrotransposon. In some embodiments, provided herein is an mRNA comprising sequences encoding human LINE 1 retrotransposition elements, and a payload comprising a nucleic acid sequence which can be retrotransposed and integrated into a genome of a cell comprising the mRNA. In some embodiments, provided herein is an mRNA that can be delivered into a living cell, e.g., a human cell, wherein, the mRNA comprises sequences encoding human LINE 1 retrotransposition elements, and a payload comprising a nucleic acid sequence which can be retrotransposed and integrated into the genome of the cell. In some embodiments, the sequences encoding human LINE 1 retrotransposition elements comprise a L1 retrotransposon ORF1 sequence or a fragment thereof. In some embodiments, the sequences encoding human LINE 1 retrotransposition elements comprise a L1 retrotransposon ORF2 sequence or a fragment thereof. In some embodiments, the sequences encoding human LINE 1 retrotransposition elements comprise a L1 retrotransposon ORF1 sequence or a fragment thereof and a L1 retrotransposon ORF2 sequence or a fragment thereof, and a nucleic acid "payload" sequence which is a heterologous sequence which is integrated into the genome of cell by retrotransposition. (See, for example, FIG. 1B).

In some embodiments, the mRNA is at least about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 kilobases. In some embodiments, the mRNA is a most about 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 or 5 kilobases. In some embodiments, the mRNA is at least about 5.1, 5.2, 5.3, 5.4, 5.5, 5.6, 5.7, 5.8, 5.9 or 6 kilobases. In some embodiments, the mRNA is at least about 6.1, 6.2, 6.3, 6.4, 6.5, 6.6, 6.7, 6.8, 6.9 or 7 kilobases. In some embodiments, the mRNA is at least about 7.1, 7.2, 7.3, 7.4, 7.5, 7.6, 7.7, 7.8, 7.9 or 8 kilobases. In some embodiments, the mRNA is at least about 8.1, 8.2, 8.3, 8.4, 8.5, 8.6, 8.7, 8.8, 8.9 or 9 kilobases. In some embodiments, the mRNA is at least about 9.1, 9.2, 9.3, 9.4, 9.5, 9.6, 9.7, 9.8, 9.9 or 10 kilobases.

In some embodiments, the mRNA comprises a sequence that inhibits or prevents degradation of the mRNA. In some embodiments, the sequence that inhibits or prevents degradation of the mRNA inhibits or prevents degradation of the mRNA by an exonuclease or an RNAse. In some embodiments, the sequence that inhibits or prevents degradation of the mRNA is a G quadruplex, pseudoknot or triplex sequence. In some embodiments, the sequence the sequence that inhibits or prevents degradation of the mRNA is an exoribonuclease-resistant RNA structure from a flavivirus RNA or an ENE element from KSV. In some embodiments, the sequence that inhibits or prevents degradation of the mRNA inhibits or prevents degradation of the mRNA by a deadenylase. In some embodiments, the sequence that inhibits or prevents degradation of the mRNA comprises non-adenosine nucleotides within or at a terminus of a poly A tail of the mRNA. In some embodiments, the sequence that inhibits or prevents degradation of the mRNA increases stability of the mRNA. In some embodiments, the exogenous sequence comprises a sequence encoding an exogenous polypeptide. In some embodiments, the sequence encoding an exogenous polypeptide is not in frame with a sequence encoding an endonuclease and/or a reverse transcriptase. In some embodiments, the sequence encoding an exogenous polypeptide is not in frame with a sequence encoding an endonuclease and/or a reverse transcriptase. In some embodiments, the exogenous sequence does not comprise introns. In some embodiments, the exogenous sequence comprises a sequence encoding an exogenous polypeptide selected from the group consisting of an enzyme, a receptor, a transport protein, a structural protein, a hormone, an antibody, a contractile protein and a storage protein. In some embodiments, the exogenous sequence comprises a sequence encoding an exogenous polypeptide selected from the group consisting of a chimeric antigen receptor (CAR), a ligand, an antibody, a receptor, and an enzyme. In some embodiments, the exogenous sequence comprises a regulatory sequence. In some embodiments, the regulatory sequence comprises a cis-acting regulatory sequence. In some embodiments, the regulatory sequence comprises a cis-acting regulatory sequence selected from the group consisting of an enhancer, a silencer, a promoter or a response element. In some embodiments, the regulatory sequence comprises a trans-acting regulatory sequence. In some embodiments, the regulatory sequence comprises a trans-acting regulatory sequence that encodes a transcription factor.

In some embodiments, integration of the insert sequence does not adversely affect cell health. In some embodiments, the endonuclease, the reverse transcriptase or both are capable of site-specific integration of the insert sequence.

In some embodiments, the retrotransposon system used herein is further engineered for precise site-specific integration. In some embodiments the retrotransposon system used herein is paired with a CRISPR-Cas system to increase specificity. In some embodiments, the ORF polypeptide-binding sequence, e.g., TTTTTA may be engineered site-specifically into a genomic sequence of a cell.

In some embodiments, the mRNA comprises a sequence encoding an additional nuclease domain or a nuclease domain that is not derived from ORF2. In some embodiments, the mRNA comprises a sequence encoding a mega-TAL nuclease domain, a TALEN domain, a Cas9 domain, a zinc finger binding domain from an R2 retroelement, or a DNA binding domain that binds to repetitive sequences such as a Rep78 from AAV. In some embodiments, the endonuclease comprises a mutation that reduces activity of the endonuclease compared to the endonuclease without the mutation. In some embodiments, the endonuclease is an ORF2p endonuclease and the mutation is S228P. In some embodiments, the mRNA comprises a sequence encoding a domain that increases fidelity and/or processivity of the reverse transcriptase. In some embodiments, the reverse transcriptase is a reverse transcriptase from a retroelement other than ORF2 or reverse transcriptase that has higher fidelity and/or processivity compared to a reverse transcriptase of ORF2p. In some embodiments, the reverse transcriptase is a group II intron reverse transcriptase. In some embodiments, the group II intron reverse transcriptase is a group IIA intron reverse transcriptase, a group IIB intron reverse transcriptase, or a group IIC intron reverse transcriptase. In some embodiments, the group II intron reverse transcriptase is TGIRT-II or TGIRT-III.

In some embodiments, the mRNA comprises a sequence comprising an Alu element and/or a ribosome binding aptamer. In some embodiments, the mRNA comprises a sequence encoding a polypeptide comprising a DNA binding domain. In some embodiments, the 3' UTR sequence is derived from a viral 3' UTR or a beta-globin 3' UTR.

In one aspect, provided herein is a composition comprising a recombinant mRNA or vector encoding an mRNA, wherein the mRNA comprises a human LINE-1 transposon sequence comprising a human LINE-1 transposon 5' UTR sequence, a sequence encoding ORF1p downstream of the human LINE-1 transposon 5' UTR sequence, an inter-ORF linker sequence downstream of the sequence encoding ORF1p, a sequence encoding ORF2p downstream of the inter-ORF linker sequence, and a 3' UTR sequence derived from a human LINE-1 transposon downstream of the sequence encoding ORF2p; wherein the 3' UTR sequence comprises an insert sequence, wherein the insert sequence is a reverse complement of a sequence encoding an exogenous polypeptide or a reverse complement of a sequence encoding an exogenous regulatory element.

In some embodiments, the insert sequence integrates into the genome of a cell when introduced into the cell. In some embodiments, the insert sequence integrates into a gene associated a condition or disease, thereby disrupting the gene or downregulating expression of the gene. In some embodiments, the insert sequence integrates into a gene, thereby upregulating expression of the gene. In some embodiments, the recombinant mRNA or vector encoding the mRNA is isolated or purified.

In one aspect, provided herein is a composition comprising a nucleic acid comprising a nucleotide sequence encoding (a) a long interspersed nuclear element (LINE) polypeptide, wherein the LINE polypeptide includes human ORF1p and human ORF2p; and (b) an insert sequence, wherein the insert sequence is a reverse complement of a sequence encoding an exogenous polypeptide or a reverse complement of a sequence encoding an exogenous regulatory element, wherein the composition is substantially non-immunogenic. In some embodiments, integration of the insert sequence does not adversely affect cell health.

In some embodiments, the composition comprises human ORF1p and human ORF2p proteins. In some embodiments, the composition comprises a ribonucleoprotein (RNP) comprising human ORF1p and human ORF2p complexed to the nucleic acid. In some embodiments, the nucleic acid is mRNA.

In one aspect, provided herein is a composition comprising a cell comprising a composition described herein. In some embodiments, the cell is an immune cell. In some embodiments, the immune cell is a T cell or a B cell. In some embodiments, the immune cell is a myeloid cell. In some embodiments, the immune cell is selected from a group consisting of a monocyte, a macrophage, a dendritic cell, a dendritic precursor cell, and a macrophage precursor cell. In some embodiments, the insert sequence is a reverse complement of a sequence encoding an exogenous polypeptide and the exogenous polypeptide is a chimeric antigen receptor (CAR).

In one aspect, provided herein is a pharmaceutical composition comprising a composition described herein, and a pharmaceutically acceptable excipient. In some embodiments, the pharmaceutical composition is for use in gene therapy. In some embodiments, the pharmaceutical composition is for use in the manufacture of a medicament for treating a disease or condition. In some embodiments, the pharmaceutical composition is for use in treating a disease or condition. In one aspect, provided herein is a method of treating a disease in a subject, comprising administering a pharmaceutical composition described herein to a subject with a disease or condition. In some embodiments, the method increases an amount or activity of a protein or functional RNA in the subject. In some embodiments, the subject has a deficient amount or activity of a protein or functional RNA. In some embodiments, the deficient amount or activity of a protein or functional RNA is associated with or causes the disease or condition.

In some embodiments, the method further comprising administering an agent that inhibits human silencing hub (HUSH) complex, an agent that inhibits FAM208A, or an agent that inhibits TRIM28. In some embodiments, the agent that inhibits human silencing hub (HUSH) complex is an agent that inhibits Periphilin, TASOR and/or MPP8. In some embodiments, the agent that inhibits human silencing hub (HUSH) complex inhibits assembly of the HUSH complex. In some embodiments, the agent inhibits the Fanconi anemia complex. In some embodiments, the agent inhibits FANCD2-FANC1 heterodimer monoubiquitylation. In some embodiments, the agent inhibits FANCD2-FANC1 heterodimer formation.

In some embodiments the agent inhibits the Fanconi Anemia (FA) core complex. FA core complex is a component of the Fanconi anemia DNA damage repair pathway, e.g., in chemotherapy induced DNA inter-strand crosslinks. The FA core complex comprises two central diners of the FANCB and FA-associated protein of 100 kDa (FAAP100) subun its, flanked by two copies of the RING finger subunit, FANCL. These two heterotrimers act as a scaffold to assemble the remaining five subunits, resulting in an extended asymmetric structure. Destabilization of the scaffold would disrupt the entire complex, resulting in a non-functional FA pathway. Examples of agents that can inhibit the FA core complex include Bortezomib and curcumin analogs EF24 and 4H-TTD.

Accordingly, it is an object of the present invention to provide novel transposon-based vectors useful in providing gene therapy to an animal. It is an object of the present invention to provide novel transposon-based vectors for use in the preparation of a medicament useful in providing gene therapy to an animal or human. It is another object of the present invention to provide novel transposon-based vectors that encode for the production of desired proteins or peptides in cells. Yet another object of the present invention to provide novel transposon-based vectors that encode for the production of desired nucleic acids in cells. It is a further object of the present invention to provide methods for cell and tissue specific incorporation of transposon-based DNA or RNA constructs comprising targeting a selected gene to a specific cell or tissue of an animal. It is yet another object of the present invention to provide methods for cell and tissue specific expression of transposon-based DNA or RNA constructs comprising designing a DNA or RNA construct with cell specific promoters that enhance stable incorporation of the selected gene by the transposase and expressing the selected gene in the cell. It is an object of the present invention to provide gene therapy for generations through germ line administration of a transposon-based vector. Another object of the present invention is to provide gene therapy in animals through non germ line administration of a transposon-based vector. Another object of the present invention is to provide gene therapy in animals through administration of a transposon-based vector, wherein the animals produce desired proteins, peptides or nucleic acids. Yet another object of the present invention is to provide gene therapy in animals through administration of a transposon-based vector, wherein the animals produce desired proteins or peptides that are recognized by receptors on target cells. Still another object of the present invention is to provide gene therapy in animals through administration of a transposon-based vector, wherein the animals produce desired fusion proteins or fusion peptides, a portion of which are recognized by receptors on target cells, in order to deliver the other protein or peptide component of the fusion protein or fusion peptide to the cell to induce a biological response. Yet another object of the present invention is to provide a method for gene therapy of animals through administration of transposon-based vectors comprising tissue specific promoters and a gene of interest to facilitate tissue specific incorporation and expression of a gene of interest to produce a desired protein, peptide or nucleic acid. Another object of the present invention is to provide a method for gene therapy of animals through administration of transposon-based vectors comprising cell specific promoters and a gene of interest to facilitate cell specific incorporation and expression of a gene of interest to produce a desired protein, peptide or nucleic acid. Still another object of the present invention is to provide a method for gene therapy of animals through administration of transposon-based vectors comprising cell specific promoters and a gene of interest to facilitate cell specific incorporation and expression of a gene of interest to produce a desired protein, peptide or nucleic acid, wherein the desired protein, peptide or nucleic acid has a desired biological effect in the animal.

In one aspect, provided herein are methods and compositions for delivery inside a cell, for example a myeloid cell and stable incorporation of one or more nucleic acids, comprising nucleic acid sequences encoding one or more proteins, wherein the stable incorporation may be via non-viral mechanisms. In some embodiments, the delivery of a nucleic acid composition into a myeloid cell is via a non-viral mechanism. In some embodiments, the delivery of the nucleic acids may further bypass plasmid mediated delivery. A "plasmid," as used herein, refers to a non-viral expression vector, e.g., a nucleic acid molecule that encodes for genes and/or regulatory elements necessary for the expression of genes. A "viral vector," as used herein, refers to a viral-derived nucleic acid that is capable of transporting another nucleic acid into a cell. A viral vector is capable of directing expression of a protein or proteins encoded by one or more genes carried by the vector when it is present in the appropriate environment. Examples for viral vectors include, but are not limited to retroviral, adenoviral, lentiviral and adeno-associated viral vectors.

In some embodiments, provided herein is a method of delivering a composition inside a cell, such as in a myeloid cell, the composition comprising one or more nucleic acid sequences encoding one or more proteins, wherein the one or more nucleic acid sequences is an RNA. In some embodiments, the RNA is mRNA.

In some embodiments, one or more mRNA comprising one or more nucleic acid sequences are delivered. In some embodiments, the one or more mRNA may comprise at least one modified nucleotide. The term "nucleotide," as used herein, refers to a base-sugar-phosphate combination. A nucleotide may comprise a synthetic nucleotide. A nucleotide may comprise a synthetic nucleotide analog. Nucleotides may be monomeric units of a nucleic acid sequence (e.g. deoxyribonucleic acid (DNA) and ribonucleic acid (RNA)). The term nucleotide may include ribonucleoside triphosphates adenosine triphosphate (ATP), uridine triphosphate (UTP), cytosine triphosphate (CTP), guanosine triphosphate (GTP) and deoxyribonucleoside triphosphates such as dATP, dCTP, dITP, dUTP, dGTP, or derivatives thereof. Such derivatives may include, for example, [aS] dATP, 7-deaza-dGTP and 7-deaza-dATP, and nucleotide derivatives that confer nuclease resistance on the nucleic acid molecule containing them. The term nucleotide as used herein may refer to dideoxyribonucleoside triphosphates (ddNTPs) and their derivatives. Illustrative examples of dideoxyribonucleoside triphosphates may include, but are not limited to, ddATP, ddCTP, ddGTP, ddITP, and ddTTP. A nucleotide may be unlabeled or detectably labeled by well-known techniques. Labeling may also be carried out with quantum dots. Detectable labels may include, for example, radioactive isotopes, fluorescent labels, chemiluminescent labels, bioluminescent labels and enzyme labels. Fluorescent labels of nucleotides may include but are not limited fluorescein, 5-carboxyfluorescein (FAM), 2'7'-dimethoxy-4'5-dichloro-6-carboxyfluorescein (JOE), rhodamine, 6-carboxyrhodamine (R6G), N,N,NcN'-tetramethyl-6-carboxyrhodamine (TAMRA), 6-carboxy-X-rhodamine (ROX), 4-(4'dimethylaminophenylazo) benzoic acid (DABCYL), Cascade Blue, Oregon Green, Texas Red, Cyanine and 5-(2'-aminoethyl)aminonaphthalene-1-sulfonic acid (EDANS). Specific examples of fluorescently labeled nucleotides may include [R6G]dUTP, [TAMRA]dUTP, [R110]dCTP, [R6G]dCTP, [TAMRA]dCTP, [JOE]ddATP, [R6G]ddATP, [FAM]ddCTP, [R110]ddCTP, [TAN1RA] ddGTP, [ROX]ddTTP, [dR6G]ddATP, [dR110]ddCTP, [dTAMRA]ddGTP, and [dROX]ddTTP available from Perkin Elmer, Foster City, Calif. FluoroLink DeoxyNucleotides, FluoroLink Cy3-dCTP, FluoroLink Cy5-dCTP, FluoroLink Fluor X-dCTP, FluoroLink Cy3-dUTP, and FluoroLink Cy5-dUTP available from Amersham, Arlington Heights, Ill.; Fluorescein-15-dATP, Fluorescein-12-dUTP, Tetramethyl-rodamine-6-dUTP, TR770-9-dATP, Fluorescein-12-ddUTP, Fluorescein-12-UTP, and Fluorescein-15-2'-dATP available from Boehringer Mannheim, Indianapolis, Ind.; and Chromosome Labeled Nucleotides, BODIPY-FL-1 4-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg. Nucleotides may also be labeled or marked by chemical modification. A chemically-modified single nucleotide can be biotin-dNTP. Some non-limiting examples of biotinylated dNTPs can include, biotin-dATP (e.g., bio-N6-ddATP, biotin-14-dATP), biotin-dCTP (e.g., biotin-11-cICTP, biotin-14-dCTP), and biotin-dUTP (e.g. biotin-II-dUTP, biotin-1,6-dUTP, biotin-20-dUTP).

The terms "polynucleotide," "oligonucleotide," and "nucleic acid" are used interchangeably to refer to a polymeric form of nucleotides of any length, either deoxyribonucleotides or ribonucleotides, or analogs thereof, either in single-, double-, or multi-stranded form. A polynucleotide may be exogenous or endogenous to a cell. A polynucleotide may exist in a cell-free environment. A polynucleotide may be a gene or fragment thereof. A polynucleotide may be DNA. A polynucleotide may be RNA. A polynucleotide may have any three-dimensional structure, and may perform any function, known or unknown. A polynucleotide may comprise one or more analogs (e.g. altered backbone, sugar, or nucleobase). If present, modifications to the nucleotide structure may be imparted before or after assembly of the polymer. Some non-limiting examples of modified nucleotides or analogs include: pseudouridine, 5-bromouracil, 5-methylcytosine, peptide nucleic acid, xeno nucleic acid, morpholinos, locked nucleic acids, glycol nucleic acids, threose nucleic acids, dideoxynucleotides, cordycepin, 7-deaza-GTP, florophores (e.g. rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudourdine, dihydrouridine, queuosine, and wyosine. Non-limiting examples of polynucleotides include coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, eDNA, recombinant polynucleotides, branched polynucleotides, plasmids, vectors, isolated DNA of any sequence, isolated RNA of any sequence, cell-free polynucleotides including cell-free DNA (cfDNA) and cell-free RNA (cfRNA), nucleic acid probes, and primers. The sequence of nucleotides may be interrupted by non-nucleotide components.

In some embodiments, the nucleic acid composition may comprise one or more mRNA, comprising at least one mRNA encoding a transmembrane receptor implicated in an immune response function (e.g. a phagocytic receptor or synthetic chimeric antigen receptor) into human macrophage or dendritic cell or a suitable myeloid cell or a myeloid precursor cell. In some embodiments, the nucleic acid composition comprises one or more mRNA, and one or more lipids for delivery of the nucleic acid into a cell of hematopoietic origin, such as a myeloid cell or a myeloid cell precursor cell. In some embodiments, the one or more lipids may form a liposomal complex.

As used herein, the composition described herein may be used for delivery inside a cell. A cell may originate from any organism having one or more cells. Some non-limiting examples include: a prokaryotic cell, eukaryotic cell, a bacterial cell, an archaeal cell, a cell of a single-cell eukaryotic organism, a protozoa cell, a cell from a plant (e.g. cells from plant crops, fruits, vegetables, grains, soy bean, corn, maize, wheat, seeds, tomatoes, rice, cassava, sugarcane, pumpkin, hay, potatoes, cotton, *cannabis*, tobacco, flowering plants, conifers, gymnosperms, ferns, clubmosses, hornworts, liverworts, mosses), an algal cell, (e.g., *Botryococcus braunii, Chlamydomonas reinhardtii, Nannochloropsis gaditana, Chlorella pyrenoidosa, Sargassum patens* C. Agardh, and the like), seaweeds (e.g. kelp), a fungal cell (e.g., a yeast cell, a cell from a mushroom), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal (e.g., a pig, a cow, a goat, a sheep, a rodent, a rat, a mouse, a non-human primate, a human, etc.), and etcetera. Sometimes a cell may not be originating from a natural organism (e.g. a cell may be a synthetically made, sometimes termed an artificial cell). In some embodiments, the cell referred to herein is a mammalian cell. In some embodiments, the cell is a human cell. The methods and compositions described herein relates to incorporating a genetic material in a cell, more specifically a human cell, wherein the human cell can be any human cell. As used herein, a human cell may be of any origin, for example, a somatic cell, a neuron, a fibroblast, a muscle cell, an epithelial cell, a cardiac cell, or a hematopoietic cell. The methods and compositions described herein can also be applicable to and useful for incorporating exogenous nucleic acid in hard-to-transfect human cell. The methods are simple and universally applicable once a suitable exogenous nucleic acid construct has been designed and developed. The methods and compositions described herein are applicable to incorporate an exogenous nucleic acid in a cell ex vivo. In some embodiments, the compositions may be applicable for systemic administration in an organism, where the nucleic acid material in the composition may be taken up by a cell in vivo, whereupon it is incorporated in cell in vivo.

In some embodiments, the methods and compositions described herein may be directed to incorporating an exogenous nucleic acid in a human hematopoietic cell, for example, a human cell of hematopoietic origin, such as a human myeloid cell or a myeloid cell precursor. However, the methods and compositions described herein can be used or made suitable for use in any biological cell with minimum modifications. Therefore, a cell as may refer to any cell that is a basic structural, functional and/or biological unit of a living organism.

In one aspect, provided herein are methods and compositions for utilizing transposable elements for stable incorporation of one or more nucleic acids into the genome of a cell, where the cell is a member of a hematopoietic cells, for example a myeloid cell. In some embodiments, the one or more nucleic acids comprise at least one nucleic acid sequence encoding a transmembrane receptor protein having a role in immune response. In some embodiments, the methods and compositions are directed to using a retrotransposable element for incorporating one or more nucleic acid sequences into a myeloid cell. The nucleic acid composition may comprise one or more nucleic sequences, such as a gene, where the gene is a transgene. The term "gene," as used herein, refers to a nucleic acid (e.g., DNA such as genomic DNA and cDNA) and its corresponding nucleotide sequence that is involved in encoding an RNA transcript. The term as used herein with reference to genomic DNA includes intervening, non-coding regions as well as regulatory regions and may include 5' and 3' ends. In some uses, the term encompasses the transcribed sequences, including 5' and 3' untranslated regions (5'-UTR and 3'-UTR), exons and introns. In some genes, the transcribed region will contain "open reading frames" that encode polypeptides. In some uses of the term, a "gene" comprises only the coding sequences (e.g., an "open reading frame" or "coding region") necessary for encoding a polypeptide. In some cases, genes do not encode a polypeptide, for example, ribosomal RNA genes (rRNA) and transfer RNA (tRNA) genes. In some cases, the term "gene" includes not only the transcribed sequences, but in addition, also includes non-transcribed regions including upstream and downstream regulatory regions, enhancers and promoters. A gene may refer to an "endogenous gene" or a native gene in its natural location in the genome of an organism. A gene may refer to an "exogenous gene" or a non-native gene. A non-native gene may refer to a gene not normally found in the host organism, but which is introduced into the host organism by gene transfer. A non-native gene may also refer to a gene not in its natural location in the genome of an organism. A non-native gene may also refer to a naturally occurring nucleic acid or polypeptide sequence that comprises mutations, insertions and/or deletions (e.g., non-native sequence).

The term "transgene" refers to any nucleic acid molecule that is introduced into a cell, that may be intermittently termed herein as a recipient cell. The resultant cell after receiving a transgene may be referred to a transgenic cell. A transgene may include a gene that is partly or entirely heterologous (i.e., foreign) to the transgenic organism or cell, or may represent a gene homologous to an endogenous gene of the organism or cell. In some cases, transgenes include any polynucleotide, such as a gene that encodes a polypeptide or protein, a polynucleotide that is transcribed into an inhibitory polynucleotide, or a polynucleotide that is not transcribed (e.g., lacks an expression control element, such as a promoter that drives transcription). Transcripts and encoded polypeptides may be collectively referred to as "gene product." If the polynucleotide is derived from genomic DNA, expression may include splicing of the mRNA in a eukaryotic cell. "Up-regulated," with reference to expression, refers to an increased expression level of a polynucleotide (e.g., RNA such as mRNA) and/or polypeptide sequence relative to its expression level in a wild-type state while "down-regulated" refers to a decreased expression level of a polynucleotide (e.g., RNA such as mRNA) and/or polypeptide sequence relative to its expression in a wild-type state. Expression of a transfected gene may occur transiently or stably in a cell. During "transient expression" the transfected gene is not transferred to the daughter cell during cell division. Since its expression is restricted to the transfected cell, expression of the gene is lost over time. In contrast, stable expression of a transfected gene may occur when the gene is co-transfected with another gene that confers a selection advantage to the transfected cell. Such a selection advantage may be a resistance towards a certain toxin that is presented to the cell. Where a transfected gene is required to be expressed, the application envisages the use of codon-optimized sequences. An example of a codon optimized sequence may be a sequence optimized for expression in a eukaryote, e.g., humans (i.e. being optimized for expression in humans), or for another eukaryote, animal or mammal. Codon optimization for a host species other than human, or for codon optimization for specific organs is known. In some embodiments, the coding sequence encoding a protein may be codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. Codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell may generally reflect the codons used most frequently in peptide synthesis. Accordingly, genes may be tailored for optimal gene expression in a given organism based on codon optimization. Codon usage tables are readily available, for example, at the "Codon Usage Database" available at www.kazusa.orjp/codon/ and these tables may be adapted in a number of ways. Computer algorithms for codon optimizing a particular sequence for expression in a particular host cell are also available, such as Gene Forge (Aptagen; Jacobus, PA), are also available.

A "multicistronic transcript" as used herein refers to an mRNA molecule that contains more than one protein coding region, or cistron. A mRNA comprising two coding regions is denoted a "bicistronic transcript." The "5'-proximal" coding region or cistron is the coding region whose translation initiation codon (usually AUG) is closest to the 5' end of a multicistronic mRNA molecule. A "5'-distal" coding region or cistron is one whose translation initiation codon (usually AUG) is not the closest initiation codon to the 5' end of the mRNA.

The terms "transfection" or "transfected" refer to introduction of a nucleic acid into a cell by non-viral or viral-based methods. The nucleic acid molecules may be gene sequences encoding complete proteins or functional portions thereof. See, e.g., Sambrook et al., 1989, Molecular Cloning: A Laboratory Manual, 18.1-18.88.

The term "promoter," as used herein, refers to a polynucleotide sequence capable of driving transcription of a coding sequence in a cell. Thus, promoters used in the polynucleotide constructs of the disclosure include cis-acting transcriptional control elements and regulatory sequences that are involved in regulating or modulating the timing and/or rate of transcription of a gene. For example, a promoter may be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. A "constitutive promoter" is one that is capable of initiating transcription in nearly all tissue types, whereas a "tissue-specific promoter" initiates transcription only in one or a few particular tissue types. An "inducible promoter" is one that initiates transcription only under particular environmental conditions, developmental conditions, or drug or chemical conditions. Exemplary inducible promoter may be a doxycycline or a tetracycline inducible promoter. Tetracycline regulated promoters may be both tetracycline inducible or tetracycline repressible, called the tet-on and tet-off systems. The tet regulated systems rely on two components, i.e., a tetracycline-controlled regulator (also referred to as transactivator) (tTA or rtTA) and a tTA/rtTA-dependent promoter that controls expression of a downstream cDNA, in a tetracycline-dependent manner. tTA is a fusion protein containing the repressor of the Tn10 tetracycline-resistance operon of *Escherichia coli* and a carboxyl-terminal portion of protein 16 of herpes simplex virus (VP16). The tTA-dependent promoter consists of a minimal RNA polymerase II promoter fused to tet operator (tetO) sequences (an array of seven cognate operator sequences). This fusion converts the tet repressor into a strong transcriptional activator in eukaryotic cells. In the absence of tetracycline or its derivatives (such as doxycycline), tTA binds to the tetO sequences, allowing transcriptional activation of the tTA-dependent promoter. However, in the presence of doxycycline, tTA cannot interact with its target and transcription does not occur. The tet system that uses tTA is termed tet-OFF, because tetracycline or doxycycline allows transcriptional down-regulation. In contrast, in the tet-ON system, a mutant form of tTA, termed rtTA, has been isolated using random mutagenesis. In contrast to tTA, rtTA is not functional in the absence of doxycycline but requires the presence of the ligand for transactivation. The term "exon" refers to a nucleic acid sequence found in genomic DNA that is bioinformatically predicted and/or experimentally confirmed to contribute contiguous sequence to a mature mRNA transcript. The term "intron" refers to a sequence present in genomic DNA that is bioinformatically predicted and/or experimentally confirmed to not encode part of or all of an expressed protein, and which, in endogenous conditions, is transcribed into RNA (e.g. pre-mRNA) molecules, but which is spliced out of the endogenous RNA (e.g. the pre-mRNA) before the RNA is translated into a protein.

The term "splice acceptor site" refers to a sequence present in genomic DNA that is bioinformatically predicted and/or experimentally confirmed to be the acceptor site during splicing of pre-mRNA, which may include identified and unidentified natural and artificially derived or derivable splice acceptor sites.

An "internal ribosome entry site" or "IRES" refers to a nucleotide sequence that allows for 5'-end/cap-independent initiation of translation and thereby raises the possibility to express 2 proteins from a single messenger RNA (mRNA) molecule. IRESs are commonly located in the 5' UTR of positive-stranded RNA viruses with uncapped genomes. Another means to express 2 proteins from a single mRNA molecule is by insertion of a 2A peptide(-like) sequence in between their coding sequence. 2A peptide(-like) sequences mediate self-processing of primary translation products by a process variously referred to as "ribosome skipping", "stop-go" translation and "stop carry-on" translation. 2A peptide (-like) sequences are present in various groups of positive- and double-stranded RNA viruses including Picornaviridae, Flaviviridae, Tetraviridae, Dicistroviridae, Reoviridae and Totiviridae.

The term "2A peptide" refers to a class of 18-22 amino-acid (AA)-long viral oligopeptides that mediate "cleavage" of polypeptides during translation in eukaryotic cells. The designation "2A" refers to a specific region of the viral genome and different viral 2As have generally been named after the virus they were derived from. The first discovered 2A was F2A (foot-and-mouth disease virus), after which E2A (equine rhinitis A virus), P2A (porcine teschovirus-1 2A), and T2A (thosea asigna virus 2A) were also identified. The mechanism of 2A-mediated "self-cleavage" is believed to be ribosome skipping the formation of a glycyl-prolyl peptide bond at the C-terminus of the 2A sequence. 2A peptide(-like) sequences mediate self-processing of primary translation products by a process variously referred to as "ribosome skipping", "stop-go" translation and "stop carry-on" translation. 2A peptide(-like) sequences are present in various groups of positive- and double-stranded RNA viruses including Picornaviridae, Flaviviridae, Tetraviridae, Dicistroviridae, Reoviridae and Totiviridae.

As used herein, the term "operably linked" refers to a functional relationship between two or more segments, such as nucleic acid segments or polypeptide segments. Typically, it refers to the functional relationship of a transcriptional regulatory sequence to a transcribed sequence.

The term "termination sequence" refers to a nucleic acid sequence which is recognized by the polymerase of a host cell and results in the termination of transcription. The termination sequence is a sequence of DNA that, at the 3' end of a natural or synthetic gene, provides for termination of mRNA transcription or both mRNA transcription and ribosomal translation of an upstream open reading frame. Prokaryotic termination sequences commonly comprise a GC-rich region that has a two-fold symmetry followed by an AT-rich sequence. A commonly used termination sequence is the T7 termination sequence. A variety of termination sequences are known in the art and may be employed in the nucleic acid constructs of the present invention, including the TINT3, TL13, TL2, TR1, TR2, and T6S termination signals derived from the bacteriophage lambda, and termination signals derived from bacterial genes, such as the trp gene of *E. coli.*

The terms "polyadenylation sequence" (also referred to as a "poly A site" or "poly A sequence") refers to a DNA sequence which directs both the termination and polyadenylation of the nascent RNA transcript. Efficient polyadenylation of the recombinant transcript is desirable, as transcripts lacking a poly A tail are typically unstable and rapidly degraded. The poly A signal utilized in an expression vector may be "heterologous" or "endogenous". An endogenous poly A signal is one that is found naturally at the 3' end of the coding region of a given gene in the genome. A heterologous poly A signal is one which is isolated from one gene and placed 3' of another gene, e.g., coding sequence for a protein. A commonly used heterologous poly A signal is the SV40 poly A signal. The SV40 poly A signal is contained on a 237 bp BamHI/BclI restriction fragment and directs both termination and polyadenylation; numerous vectors contain the SV40 poly A signal. Another commonly used heterologous poly A signal is derived from the bovine growth hormone (BGH) gene; the BGH poly A signal is also available on a number of commercially available vectors. The poly A signal from the Herpes simplex virus thymidine kinase (HSV tk) gene is also used as a poly A signal on a number of commercial expression vectors. The polyadenylation signal facilitates the transportation of the RNA from within the cell nucleus into the cytosol as well as increases cellular half-life of such an RNA. The polyadenylation signal is present at the 3'-end of an mRNA.

The terms "complement," "complements," "complementary," and "complementarity," as used herein, refer to a sequence that is complementary to and hybridizable to the given sequence. In some cases, a sequence hybridized with a given nucleic acid is referred to as the "complement" or "reverse-complement" of the given molecule if its sequence of bases over a given region is capable of complementarily binding those of its binding partner, such that, for example, A-T, A-U, G-C, and G-U base pairs are formed. In general, a first sequence that is hybridizable to a second sequence is specifically or selectively hybridizable to the second sequence, such that hybridization to the second sequence or set of second sequences is preferred (e.g. thermodynamically more stable under a given set of conditions, such as stringent conditions commonly used in the art) to hybridization with non-target sequences during a hybridization reaction. Typically, hybridizable sequences share a degree of sequence complementarity over all or a portion of their respective lengths, such as between 25%-100% complementarity, including at least 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, and 100% sequence complementarity. Sequence identity, such as for the purpose of assessing percent complementarity, may be measured by any suitable alignment algorithm, including but not limited to the Needleman-Wunsch algorithm (see e.g. the EMBOSS Needle aligner available at www.ebi.ac.uk/Tools/psa/embossneedle/nucleotide.html), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.ukaools/psa/emboss_water/nucleotide.html, optionally with default settings). Optimal alignment can be assessed using any suitable parameters of a chosen algorithm, including default parameters.

Complementarity may be perfect or substantial/sufficient. Perfect complementarity between two nucleic acids may mean that the two nucleic acids may form a duplex in which every base in the duplex is bonded to a complementary base by Watson-Crick pairing. Substantial or sufficient complementary may mean that, a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions may be predicted by using the sequences and standard mathematical calculations to predict the melting temperature ($T_m$) of hybridized strands, or by empirical determination of $T_m$ by using routine methods.

"Transposons" as used herein are segments within the chromosome that can translocate within the genome, also known as "jumping gene". There are two different classes of transposons: class 1, or retrotransposons, that mobilize via an RNA intermediate and a "copy-and-paste" mechanism, and class II, or DNA transposons, that mobilize via excision integration, or a "cut-and-paste" mechanism (Ivics Nat Methods 2009). Bacterial, lower eukaryotic (e.g. yeast) and invertebrate transposons appear to be largely species specific, and cannot be used for efficient transposition of DNA in vertebrate cells. "Sleeping Beauty" (Ivics Cell 1997), was the first active transposon that was artificially reconstructed by sequence shuffling of inactive TEs from fish. This made it possible to successfully achieve DNA integration by transposition into vertebrate cells, including human cells. Sleeping Beauty is a class II DNA transposon belonging to the Tcl/mariner family of transposons (Ni Genomics Proteomics 2008). In the meantime, additional functional transposons have been identified or reconstructed from different species, including *Drosophila*, frog and even human genomes, that all have been shown to allow DNA transposition into vertebrate and also human host cell genomes. Each of these transposons have advantages and disadvantages that are related to transposition efficiency, stability of expression, genetic payload capacity etc. Exemplary class II transposases that have been created include Sleeping Beauty, PiggyBac, Frog Prince, Himarl, Passport, Minos, hAT, Toll, To12, AciDs, PIF, Harbinger, Harbinger3-DR, and Hsmarl.

"Heterologous" as used herein, includes molecules such as DNA and RNA which may not naturally be found in the cell into which it is inserted. For example, when mouse or bacterial DNA is inserted into the genome of a human cell, such DNA is referred to herein as heterologous DNA. In contrast, the term "homologous" as used herein, denotes molecules such as DNA and RNA that are found naturally in the cell into which it is inserted. For example, the insertion of mouse DNA into the genome of a mouse cell constitutes insertion of homologous DNA into that cell. In the latter case, it is not necessary that the homologous DNA be inserted into a site in the cell genome in which it is naturally found; rather, homologous DNA may be inserted at sites other than where it is naturally found, thereby creating a genetic alteration (a mutation) in the inserted site.

A "transposase" is an enzyme that is capable of forming a functional complex with a transposon end-containing composition (e.g., transposons, transposon ends), and catalyze insertion or transposition of the transposon end-containing composition into double stranded DNA which is incubated with an in vitro transposon reaction. The term "transposon end" means a double-stranded DNA that contains the nucleotide sequences (the "transposon end sequences") necessary to form the complex with the transposase or integrase enzyme that is functional in an in vitro transposition reaction.

A transposon end forms a complex or a synaptic complex or a transposon complex or a transposon composition with a transposase or integrase that recognizes and binds to the transposon end, and which complex is capable of inserting or transposing the transposon end into target DNA with which it is incubated in an in vitro transposition reaction. A transposon end exhibits two complementary sequences consisting of a transferred transposon end sequence or transferred strand and a non-transferred transposon end sequence, or non-transferred strand For example, one transposon end that forms a complex with a hyperactive Tn5 transposase that is active in an in vitro transposition reaction comprises a transferred strand that exhibits a transferred transposon end sequence as follows: 5' AGATGTGTATAAGAGACAG 3' (SEQ ID NO: 55), and a non-transferred strand that exhibits a "non-transferred transposon end sequence" as follows: (5' CTGTCTCTTATACACATCT 3' (SEQ ID NO: 56). The 3'-end of a transferred strand is joined or transferred to target DNA in an in vitro transposition reaction. The non-transferred strand, which exhibits a transposon end sequence that is complementary to the transferred transposon end sequence, is not joined or transferred to the target DNA in an in vitro transposition reaction.

In some embodiments, the transferred strand and non-transferred strand are covalently joined. For example, in some embodiments, the transferred and non-transferred strand sequences are provided on a single oligonucleotide, e.g., in a hairpin configuration. As such, although the free end of the non-transferred strand is not joined to the target DNA directly by the transposition reaction, the non-transferred strand becomes attached to the DNA fragment indirectly, because the non-transferred strand is linked to the transferred strand by the loop of the hairpin structure. As used herein an "cleavage domain" refers to a nucleic acid sequence that is susceptible to cleavage by an agent, e.g., an enzyme.

A "restriction site domain" means a tag domain that exhibits a sequence for the purpose of facilitating cleavage using a restriction endonuclease. For example, in some embodiments, the restriction site domain is used to generate di-tagged linear ssDNA fragments. In some embodiments, the restriction site domain is used to generate a compatible double-stranded 5'-end in the tag domain so that this end can be ligated to another DNA molecule using a template-dependent DNA ligase. In some embodiments, the restriction site domain in the tag exhibits the sequence of a restriction site that is present only rarely, if at all, in the target DNA (e.g., a restriction site for a rare-cutting restriction endonuclease such as NotI or AscI).

As used herein, the term "recombinant nucleic acid molecule" refers to a recombinant DNA molecule or a recombinant RNA molecule. A recombinant nucleic acid molecule is any nucleic acid molecule containing joined nucleic acid molecules from different original sources and not naturally attached together. Recombinant RNA molecules include RNA molecules transcribed from recombinant DNA molecules. A recombinant nucleic acid may be synthesized in the laboratory. A recombinant nucleic acid can be prepared by using recombinant DNA technology by using enzymatic modification of DNA, such as enzymatic restriction digestion, ligation, and DNA cloning. A recombinant DNA may be transcribed in vitro, to generate a messenger RNA (mRNA), the recombinant mRNA may be isolated, purified and used to transfect a cell. A recombinant nucleic acid may encode a protein or a polypeptide. A recombinant nucleic acid, under suitable conditions, can be incorporated into a living cell, and can be expressed inside the living cell. As used herein, "expression" of a nucleic acid usually refers to transcription and/or translation of the nucleic acid. The product of a nucleic acid expression is usually a protein but can also be an mRNA. Detection of an mRNA encoded by a recombinant nucleic acid in a cell that has incorporated the recombinant nucleic acid, is considered positive proof that the nucleic acid is "expressed" in the cell. The process of inserting or incorporating a nucleic acid into a cell can be via transformation, transfection or transduction. Transformation is the process of uptake of foreign nucleic acid by a bacterial cell. This process is adapted for propagation of plasmid DNA, protein production, and other applications. Transformation introduces recombinant plasmid DNA into competent bacterial cells that take up extracellular DNA from the environment. Some bacterial species are naturally competent under certain environmental conditions, but competence is artificially induced in a laboratory setting. Transfection is the forced introduction of small molecules such as DNA, RNA, or antibodies into eukaryotic cells. Just to make life confusing, 'transfection' also refers to the introduction of bacteriophage into bacterial cells. 'Transduction' is mostly used to describe the introduction of recombinant viral vector particles into target cells, while 'infection' refers to natural infections of humans or animals with wild-type viruses.

A "stem-loop" sequence refers to a nucleic acid sequence (e.g., RNA sequence) with sufficient self-complementarity to hybridize and form a stem and the regions of non-complementarity that bulges into a loop. The stem may comprise mismatches or bulges.

The term "vector" refers to a nucleic acid molecule capable of transporting or mediating expression of a heterologous nucleic acid. A "vector sequence" as used herein, refers to a sequence of nucleic acid comprising at least one origin of replication and at least one selectable marker gene. Vectors capable of directing the expression of genes and/or nucleic acid sequence to which they are operatively linked are referred to herein as "expression vectors".

A plasmid is a species of the genus encompassed by the term "vector." In general, expression vectors of utility are often in the form of "plasmids" which refer to circular double stranded DNA molecules which, in their vector form are not bound to the chromosome, and typically comprise entities for stable or transient expression of the encoded DNA. Other expression vectors that can be used in the methods as disclosed herein include, but are not limited to plasmids, episomes, bacterial artificial chromosomes, yeast artificial chromosomes, bacteriophages or viral vectors, and such vectors can integrate into the host's genome or replicate autonomously in the cell. A vector can be a DNA or RNA vector. Other forms of expression vectors known by those skilled in the art which serve the equivalent functions can also be used, for example, self-replicating extrachromosomal vectors or vectors capable of integrating into a host genome. Exemplary vectors are those capable of autonomous replication and/or expression of nucleic acids to which they are linked. A safe harbor locus is a region within the genome where additional exogenous or heterologous nucleic acid sequence can be inserted, and the host genome is able to accommodate the inserted genetic material. Exemplary safe harbor sites include but are not limited to: AAVS1 site, GGTA1 site, CMAH site, B4GALNT2 site, B2M site, ROSA26 site, COLA1 site, and TIGRE site. For example, the heterologous nucleic acid described in this disclosure may be integrated at one or more sites in the genome of the cell, wherein the one or more locations is selected from the group consisting of: AAVS1 site, GGTA1 site, CMAH site, B4GALNT2 site, B2M site, ROSA26 site, COLA1 site, and TIGRE site. In some embodiments, the nucleic acid cargo comprising the transgene may be delivered to a R2D locus.

In some embodiments, the nucleic acid cargo comprising the transgene may be delivered to the genome in an intergenic or intragenic region. In some embodiments the nucleic acid cargo comprising the transgene is integrated into the genome 5' or 3' within 0.1 kb, 0.25 kb, 0.5 kb, 0.75, kb, 1 kb, 2 kb, 3 kb, 4 kb, 5 kb, 7.5 kb, 10 kb, 15 kb, 20 kb, 25 kb, 50, 75 kb, or 100 kb of an endogenous active gene. In some embodiments the nucleic acid cargo comprising the transgene is integrated into the genome 5' or 3' within 0.1 kb, 0.25 kb, 0.5 kb, 0.75, kb, 1 kb, 2 kb, 3 kb, 4 kb, 5 kb, 7.5 kb, 10 kb, 15 kb, 20 kb, 25 kb, 50, 75 kb, or 100 kb of an endogenous promoter or enhancer. In some embodiments the nucleic acid cargo comprising the transgene is 50-50,000 base pairs, e.g., between 50-40,000 bp, between 500-30,000 bp between 500-20,000 bp, between 100-15,000 bp, between 500-10,000 bp, between 50-10,000 bp, between 50-5,000 bp. In some embodiments the nucleic acid cargo comprising the transgene is less than 1,000, 1,300, 1500, 2,000, 3,000, 4,000, 5,000, or 7,500 nucleotides in length.

L1 and Non-L1 Retrotransposon Systems

Retrotransposons can contain transposable elements that are active participants in reorganizing their resident genomes. Broadly, retrotransposons can refer to DNA sequences that are transcribed into RNA and translated into protein and have the ability to reverse-transcribe themselves back into DNA. Approximately 45% of the human genome is comprised of sequences that result from transposition events. Retrotransposition occasionally generates target site deletions or adds non-retrotransposon DNA to the genome by processes termed 5'- and 3'-transduction. Recombination between non-homologous retrotransposons causes deletions, duplications or rearrangements of gene sequence. Ongoing retrotransposition can generate novel splice sites, polyadenylation signals and promoters, and so builds new transcription modules.

Generally, retrotransposons may be grouped into two classes, the retrovirus-like LTR retrotransposons, and the non-LTR elements such as human L1 elements, *Neurospora* TAD elements (Kinsey, 1990, Genetics 126:317-326), I factors from *Drosophila* (Bucheton et al., 1984, Cell 38:153-163), and R2Bm from *Bombyx mori* (Luan et al., 1993, Cell 72: 595-605). These two types of retrotransposons are structurally different and also retrotranspose using radically different mechanisms. Exemplary, non-limiting examples of LINE-encoded polypeptides are found in GenBank Accession Nos. AAC51261, AAC51262, AAC51263, AAC51264, AAC51265, AAC51266, AAC51267, AAC51268, AAC51269, AAC51270, AAC51271, AAC51272, AAC51273, AAC51274, AAC51275, AAC51276, AAC51277, AAC51278 and AAC51279.

The decision to focus on LINE-1 to develop into a system as described in the disclosure for a number of reasons at least some of which are exemplified below: (a) LINE-1 (or L1-) elements are autonomous as they encode all of the machinery alone to complete this reverse transcription and integration process; (b) L1 elements are abundant in the human genome, such that these elements may be considered as a naturalized element of the genome; (c) L1 retrotransposon retrotransposes its own mRNA with high degree of specificity, compared to other mRNAs floating around in the cells.

The L1 expresses a 6-kb bicistronic RNA that encodes the 40 kDa Open Reading Frame-1 RNA-binding protein (ORF1p) of essential but uncertain function, and a 150 kDa ORF2 protein with endonuclease and reverse transcriptase (RT) activities. L1 retrotransposition is a complex process involving transcription of the L1, transport of its RNA to the cytoplasm, translation of the bicistronic RNA, formation of a ribonucleoprotein (RNP) particle, its re-import to the nucleus and target-primed reverse transcription at the integration site. A few transcription factors that interact with L Is have been identified. Transcribed L1 RNA forms an RNP in cis with the proteins that are translated from the transcript. L1 integrates into genomic DNA by target-site primer reverse transcription (TPRT) by ORF2p cleavage at the 5'-TTTT-3' where a poly A sequence of L1 RNA anneals and primes reverse transcriptase (RT) activity to make L1 cDNA.

Other mobile elements of the genome can “hijack” the L1 ORF for retrotransposition. For example, Alu elements are such mobile DNA elements that belong to the class of short interspersed elements (SINEs) that are non-autonomous retrotransposons and acquire trans-factors to integrate. Alu elements and SINE-1 elements can associate with the L1 ribonucleoproteins in trans to be also retrotransposed by ORF1p and ORF2p. Somewhat similar to the L1 RNA, the Alu element ends with a long A-run, often referred to as the A-tail, and it also has a smaller A-rich region (indicated by AA) separating the two halves of a diverged dimer structure. Alu elements are likely to have the internal components of an RNA polymerase III promoter (such as, commonly designated as an A box and a B box promoters), but they do not encode a terminator for RNA polymerase III. They may utilize a stretch of T nucleotides at various distances downstream of the Alu element to terminate a transcription. A typical Alu transcript encompasses the entire Alu, including the A-tail, and has a 3' region that is unique for each locus. The Alu RNA folds into separate structures for each monomer unit. The RNA has been shown to bind the 7SL RNA SRP9 and 14 heterodimer, as well as poly A-binding protein (PABP). The poly A tail of Alu primes with T rich (TTTT) region of the genome and attracts ORF2p to bind to the primed region and cleaves at the T rich region via its endonuclease activity. The T-rich region primes reverse transcription by ORF2p on the 3' A-tail region of the Alu element. This creates a cDNA copy of the body of the Alu element. A nick occurs by an unknown mechanism on the second strand and second-strand synthesis is primed. The new Alu element is then flanked by short direct repeats that are duplicates of the DNA sequence between the first and second nicks. Alu elements are extremely prevalent within RNA molecules, owing to their preference for gene-rich regions. A full-length Alu (~300 bp) is derived from the signal recognition particle RNA 7SL and consists of two similar monomers with an A-rich linker in-between, A- and B-boxes present in the 5' monomer, and a poly-A tail lacking the preceding polyadenylation signal resulting in an elongated tail (up to 100 bp in length). Alus can be transcribed by RNA polymerase III using the internal promoters within the A- and B-boxes; however, Alus contain no ORFs and therefore do not encode for protein products.

Other non-L1 transposons include SVAs and HERV-Ks. A full-length SVA (SINE-VNTR-Alu) element (~2-3 kb) is a composite unit that contains a CCCTCT repeat, two Alu-like sequences, a VNTR, a SINE-R region with env (envelope) gene, the 3' LTR of HERV-K10, and a polyadenylation signal followed by a poly-A tail. It is most likely that SVAs are transcribed by RNA polymerase II, although it is unknown whether SVA elements carry an internal promoter.

A full-length HERV-K element (~9-10 kb) is comprised of ancient remnants of endogenous retroviral sequences and includes two flanking LTR regions surrounding three retroviral ORFs: (1) gag encoding the structural proteins of a retroviral capsid; (2) pol-pro encoding the enzymes: protease, RT, and integrase; and (3) env encoding proteins allowing for horizontal transfer. The LTR of HERV-K contains an internal, bidirectional promoter that appears to be under the transcriptional control of RNA polymerase II.

L1 retrotransposition and RNA binding can take place at or near poly-A tail. The 3'-UTR plays a role in the recognition of stringent-type LINE RNA of ORF1 protein (ORF1p). Stringent-type LINEs can contain a stem-loop structure located at the end of the 3'UTR. Branched molecules consisting of junctions between transposon 3'-end cDNA and the target DNA, as well as specific positioning of L1 RNA within ORF2 protein (ORF2p), were detected during initial stages of L1 retrotransposition in vitro. Secondary or tertiary RNA structure shared by L1 and Alu are likely to be responsible for recognition by and binding of ORF2, possibly along with a poly-A tail. In some embodiments, the stem-loop structure located downstream of the poly-A sequence correlates with cleavage intensity.

Mechanisms for restricting or resolving L1 integration have also evolved for the sake of maintaining genetic integrity and stability of the genome. Non-homologous end-joining repair proteins, such as XRCC1, Ku70 and DNA-PK, have been implicated in resolution of the L1 integrate at the time of insertion. In addition, the cell has evolved a number of proteins that stand against unrestricted retrotransposition, including the APOBEC3 family of cytosine deaminases, adenosine deaminase ADAR1, chromatin-remodeling factors and members of the piRNA pathway for post-transcription gene silencing that functions in the male germ line.

I. Compositions Comprising Nucleic Acid Constructs and Methods Involved for Stable Expression of Encoded Protein Provided herein is a recombinant nucleic acid encoding one or more proteins for expression in a cell, such as a myeloid cell. In one embodiment, the recombinant nucleic acid is designed for stable expression of the one or more proteins or polypeptides encoded by the recombinant nucleic acid. In some embodiments, the stable expression is achieved by incorporation of recombinant nucleic acid within the genome of the cell.

It can be easily understood by one of skill in the art that the compositions and methods described herein can be utilized to design products in which the recombinant nucleic acid may comprise one or more sequences that do not translate as a protein or a polypeptide component, but may encode an oligonucleotide that can be a regulatory nucleic acid, such as an inhibitor oligonucleotide product, such as an activator oligonucleotide.

In one aspect, provided herein is a composition comprising a synthetic nucleic acid, comprising a nucleic acid sequence encoding a gene of interest and one or more retrotransposable elements to stably incorporate a non-endogenous nucleic acid into a cell. In some embodiments, the cell is a hematopoietic cell. In some embodiments, the cell is a myeloid cell. In some embodiments, the cell is a precursor cell. In some embodiments, the cell is undifferentiated. In some embodiments, the cell has further differentiation potential. In some embodiments, the cell is not a stem cell.

A. LINE/Alu Retrotransposon Construct

In some embodiments, the present disclosure may utilize a retrotransposable system to stably incorporate into the genome and express a non-endogenous nucleic acid, where the non-endogenous nucleic acid comprises retrotransposable elements within the nucleic acid sequence. In some embodiments, the present disclosure may utilize a cell's endogenous retrotransposable system (e.g., proteins and enzymes), to stably express a non-endogenous nucleic acid in the cell. In some embodiments, the present disclosure may utilize a cell's endogenous retrotransposable system (e.g., proteins and enzymes, such as a LINE1 retrotransposition system), but may further express one or more components of the retrotransposable system to stably express a non-endogenous nucleic acid in the cell.

In some embodiments, a synthetic nucleic acid is provided herein, the synthetic nucleic acid encoding a transgene, and encoding one or more components for retrotransposition. The synthetic nucleic acid described herein is interchangeably termed as a nucleic acid construct, transgene or the exogenous nucleic acid.

In one aspect, provided herein is a method of integrating a nucleic acid sequence into a genome of a cell, the method comprising introducing a recombinant mRNA or a vector encoding an mRNA into the cell, wherein the mRNA comprises: an insert sequence, wherein the insert sequence comprises an exogenous sequence, or a sequence that is a reverse complement of the exogenous sequence; a 5' UTR sequence and a 3' UTR sequence downstream of the 5' UTR sequence; wherein the 5' UTR sequence or the 3' UTR sequence comprises a binding site for a human ORF protein, and wherein the insert sequence is integrated into the genome of the cell.

In some embodiments, the 5' UTR sequence or the 3' UTR sequence comprises a binding site for human ORF2p.

In one aspect, provided herein is a method for integrating a nucleic acid sequence into the genome of an immune cell, the method comprising introducing a recombinant mRNA or a vector encoding an mRNA, wherein the mRNA comprises an insert sequence, wherein the insert sequence comprises (i) an exogenous sequence or (ii) a sequence that is a reverse complement of the exogenous sequence; 5' UTR sequence and a 3' UTR sequence downstream of the 5' UTR sequence, wherein the 5' UTR sequence or the 3' UTR sequence comprises an endonuclease binding site and/or a reverse transcriptase binding site, and wherein the transgene sequence is integrated into the genome of the immune cell.

In one aspect, provided herein is a method for integrating a nucleic acid sequence into the genome of a cell, the method comprising introducing a recombinant mRNA or a vector encoding an mRNA, wherein the mRNA comprises an insert sequence, wherein the insert sequence comprises (i) an exogenous sequence or (ii) a sequence that is a reverse complement of the exogenous sequence; a 5' UTR sequence, a sequence of a human retrotransposon downstream of the 5' UTR sequence, and a 3' UTR sequence downstream of the sequence of a human retrotransposon; wherein the 5' UTR sequence or the 3' UTR sequence comprises an endonuclease binding site and/or a reverse transcriptase binding site, and wherein the sequence of a human retrotransposon encodes for two proteins that are translated from a single RNA containing two ORFs, and wherein the insert sequence is integrated into the genome of the cell.

In some embodiments, the 5' UTR sequence or the 3' UTR sequence comprises an ORF2p binding site. In some embodiments, the ORF2p binding site is a poly A sequence in the 3' UTR sequence.

In some embodiments, the mRNA comprises a sequence of a human retrotransposon. In some embodiments, the sequence of a human retrotransposon is downstream of the 5' UTR sequence. In some embodiments, the sequence of a human retrotransposon is upstream of the 3' UTR sequence.

In some embodiments, the sequence of a human retrotransposon encodes for two proteins that are translated from a single RNA containing two ORFs. In some embodiments, the two ORFs are non-overlapping ORFs. In some embodiments, the two ORFs are ORF1 and ORF2. In some embodiments, the ORF1 encodes ORF1p and ORF2 encodes ORF2p.

In some embodiments, the sequence of a human retrotransposon comprises a sequence of a non-LTR retrotransposon. In some embodiments, the sequence of a human retrotransposon encodes comprises a LINE-1 retrotransposon. In some embodiments, the LINE-1 retrotransposon is a human LINE-1 retrotransposon. In some embodiments, the sequence of a human retrotransposon comprises a sequence encoding an endonuclease and/or a reverse transcriptase. In some embodiments, the endonuclease and/or a reverse transcriptase is ORF2p. In some embodiments, the reverse transcriptase is a group II intron reverse transcriptase domain. In some embodiments, the endonuclease and/or a reverse transcriptase is a minke whale endonuclease and/or a reverse transcriptase. In some embodiments, the sequence of a human retrotransposon comprises a sequence encoding ORF2p. In some embodiments, the insert sequence is integrated into the genome at a poly T site using specificity of an endonuclease domain of the ORF2p. In some embodiments, the poly T site comprises the sequence TTTTTA.

In some embodiments, (i) the sequence of a human retrotransposon comprises a sequence encoding ORF1p, (ii) the mRNA does not comprise a sequence encoding ORF1p, or (iii) the mRNA comprises a replacement of the sequence encoding ORF1p with a 5' UTR sequence from the complement gene. In some embodiments, the mRNA comprises a first mRNA molecule encoding ORF1p, and a second mRNA molecule encoding an endonuclease and/or a reverse transcriptase. In some embodiments, the mRNA is an mRNA molecule comprising a first sequence encoding ORF1p, and a second sequence encoding an endonuclease and/or a reverse transcriptase. In some embodiments, the first sequence encoding ORF1p and the second sequence encoding an endonuclease and/or a reverse transcriptase are separated by a linker sequence.

In some embodiments, the linker sequence comprises an internal ribosome entry sequence (IRES). In some embodiments, the IRES is an IRES from CVB3 or EV71. In some embodiments, the linker sequence encodes a self-cleaving peptide sequence. In some embodiments, the linker sequence encodes a T2A, a E2A or a P2A sequence In some embodiments, the sequence of a human retrotransposon comprises a sequence that encodes ORF1p fused to an additional protein sequence and/or a sequence that encodes ORF2p fused to an additional protein sequence. In some embodiments, the ORF1p and/or the ORF2p is fused to a nuclear retention sequence. In some embodiments, the nuclear retention sequence is an Alu sequence. In some embodiments, the ORF1p and/or the ORF2p is fused to an MS2 coat protein. In some embodiments, the 5' UTR sequence or the 3' UTR sequence comprises at least one, two, three or more MS2 hairpin sequences. In some embodiments, the 5' UTR sequence or the 3' UTR sequence comprises a sequence that promotes or enhances interaction of a poly A tail of the mRNA with the endonuclease and/or a reverse transcriptase. In some embodiments, the 5' UTR sequence or the 3' UTR sequence comprises a sequence that promotes or enhances interaction of a poly-A-binding protein (PABP) with the endonuclease and/or a reverse transcriptase. In some embodiments, the 5' UTR sequence or the 3' UTR sequence comprises a sequence that increases specificity of the endonuclease and/or a reverse transcriptase to the mRNA relative to another mRNA expressed by the cell. In some embodiments, the 5' UTR sequence or the 3' UTR sequence comprises an Alu element sequence.

In some embodiments, the first sequence encoding ORF1p and the second sequence encoding an endonuclease and/or a reverse transcriptase have the same promoter. In some embodiments, the insert sequence has a promoter that is different from the promoter of the first sequence encoding ORF1p. In some embodiments, the insert sequence has a promoter that is different from the promoter of the second sequence encoding an endonuclease and/or a reverse transcriptase. In some embodiments, the first sequence encoding ORF1p and/or the second sequence encoding an endonuclease and/or a reverse transcriptase have a promoter or transcription initiation site selected from the group consisting of an inducible promoter, a CMV promoter or transcription initiation site, a T7 promoter or transcription initiation site, an EF1a promoter or transcription initiation site and combinations thereof. In some embodiments, the insert sequence has a promoter or transcription initiation site selected from the group consisting of an inducible promoter, a CMV promoter or transcription initiation site, a T7 promoter or transcription initiation site, an EF1a promoter or transcription initiation site and combinations thereof.

In some embodiments, the first sequence encoding ORF1p and the second sequence encoding an endonuclease and/or a reverse transcriptase are codon optimized for expression in a human cell.

In some embodiments, the mRNA comprises a WPRE element. In some embodiments, the mRNA comprises a selection marker. In some embodiments, the mRNA comprises a sequence encoding an affinity tag. In some embodiments, the affinity tag is linked to the sequence encoding an endonuclease and/or a reverse transcriptase.

In some embodiments, the 3' UTR comprises a poly A sequence or wherein a poly A sequence is added to the mRNA in vitro. In some embodiments, the poly A sequence is downstream of a sequence encoding an endonuclease and/or a reverse transcriptase. In some embodiments, the insert sequence is upstream of the poly A sequence.

In some embodiments, the 3' UTR sequence comprises the insert sequence. In some embodiments, the insert sequence comprises a sequence that is a reverse complement of the sequence encoding the exogenous polypeptide. In some embodiments, the insert sequence comprises a polyadenylation site. In some embodiments, the insert sequence comprises an SV40 polyadenylation site. In some embodiments, the insert sequence comprises a polyadenylation site upstream of the sequence that is a reverse complement of the sequence encoding the exogenous polypeptide. In some embodiments, the insert sequence is integrated into the genome at a locus that is not a ribosomal locus. In some embodiments, the insert sequence integrates into a gene or regulatory region of a gene, thereby disrupting the gene or downregulating expression of the gene. In some embodiments, the insert sequence integrates into a gene or regulatory region of a gene, thereby upregulating expression of the gene. In some embodiments, the insert sequence integrates into the genome and replaces a gene. In some embodiments, the insert sequence is stably integrated into the genome. In some embodiments, the insert sequence is retrotransposed into the genome. In some embodiments, the insert sequence is integrated into the genome by cleavage of a DNA strand of a target site by an endonuclease encoded by the mRNA. In some embodiments, the insert sequence is integrated into the genome via target-primed reverse transcription (TPRT). In some embodiments, the insert sequence is integrated into the genome via reverse splicing of the mRNA into a DNA target site of the genome.

In some embodiments, the cell is an immune cell. In some embodiments, the immune cell is a T cell or a B cell. In some embodiments, the immune cell is a myeloid cell. In some embodiments, the immune cell is selected from a group consisting of a monocyte, a macrophage, a dendritic cell, a dendritic precursor cell, and a macrophage precursor cell.

In some embodiments, the mRNA is a self-integrating mRNA. In some embodiments, the method comprises introducing into the cell the mRNA. In some embodiments, the method comprises introducing into the cell the vector encoding the mRNA. In some embodiments, the method comprises introducing the mRNA or the vector encoding the mRNA into a cell ex vivo. In some embodiments, the method further comprises administering the cell to a human subject. In some embodiments, the method comprises administering the mRNA or the vector encoding the mRNA to a human subject. In some embodiments, an immune response is not elicited in the human subject. In some embodiments, the mRNA or the vector is substantially non-immunogenic.

In some embodiments, the vector is a plasmid or a viral vector. In some embodiments, the vector comprises a non-LTR retrotransposon. In some embodiments, the vector comprises a human L1 element. In some embodiments, the vector comprises a L1 retrotransposon ORF1 gene. In some embodiments, the vector comprises a L1 retrotransposon ORF2 gene. In some embodiments, the vector comprises a L1 retrotransposon.

In some embodiments, the mRNA is at least about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 kilobases. In some embodiments, the mRNA is a most about 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 or 5 kilobases.

In some embodiments, the mRNA comprises a payload that is at least about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 kilobases. In some embodiments, the mRNA is a most about 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 or 5 kilobases. In some embodiments, the mRNA is at least about 5.1, 5.2, 5.3, 5.4, 5.5, 5.6, 5.7, 5.8, 5.9 or 6 kilobases. In some embodiments, the mRNA is at least about 6.1, 6.2, 6.3, 6.4, 6.5, 6.6, 6.7, 6.8, 6.9 or 7 kilobases. In some embodiments, the mRNA is at least about 7.1, 7.2, 7.3, 7.4, 7.5, 7.6, 7.7, 7.8, 7.9 or 8 kilobases. In some embodiments, the mRNA is at least about 8.1, 8.2, 8.3, 8.4, 8.5, 8.6, 8.7, 8.8, 8.9 or 9 kilobases. In some embodiments, the mRNA is at least about 9.1, 9.2, 9.3, 9.4, 9.5, 9.6, 9.7, 9.8, 9.9 or 10 kilobases. In some embodiments, the mRNA is at least about 10.1, 10.2, 10.3, 10.4, 10.5, 10.6, 10.7, 10.8, 10.9 or 11 kilobases. In some embodiments, the mRNA is at least about 11.1, 11.2, 11.3, 11.4, 11.5, 11.6, 11.7, 11.8, 11.9 or 12 kilobases. In some embodiments, the mRNA comprises a payload of about 6.8 kB, e.g., a sequence encoding a ABCA4 gene product. In some embodiments, the mRNA comprises a payload of about 6.7 kB, e.g., a sequence encoding a MY07A gene product. In some embodiments, the mRNA comprises a payload of about 7.5 kB, e.g., a sequence encoding a CEP290 gene product. In some embodiments, the mRNA comprises a payload of about 10.1 kB, e.g., a sequence encoding a CDH23 gene product. In some embodiments, the mRNA comprises a payload of about 9.4 kB, e.g., a sequence encoding a EYS gene product. In some embodiments, the mRNA comprises a payload of about 15.6 kB, e.g., a sequence encoding a USH2a gene product. In some embodiments, the mRNA comprises a payload of about 12.5 kB, e.g., a sequence encoding a ALMS1 gene product. In some embodiments, the mRNA comprises a payload of about 4.6 kB, e.g., a sequence encoding a GDE gene product. In some embodiments, the mRNA comprises a payload of about 6 kB, e.g., a sequence encoding the OTOF gene product. In some embodiments, the mRNA comprises a payload of about 7.1 kB, e.g., a sequence encoding a F8 gene product.

One of the advantages of using the method of integration of a nucleic acid into the genome using retrotransposition is that it can be designed as described herein to deliver a nucleic acid cargo that is much larger than that using any other existing methods. For example, lentiviral and adeno-associated viral (AAV) gene delivery method are not expected to deliver a nucleic acid cargo of greater than 4 kB. In addition, lentiviral delivery entails risk of insertional mutagenesis and other toxicities. AAV mediated delivery entails unresolved liver and CNS toxicity. On the other hand, retrotransposition mediated method (Retro-T) using mRNA as described herein is rapid, safer and less complex than these viral methods.

In some embodiments, the mRNA comprises a sequence that inhibits or prevents degradation of the mRNA. In some embodiments, the sequence that inhibits or prevents degradation of the mRNA inhibits or prevents degradation of the mRNA by an exonuclease or an RNAse. In some embodiments, the sequence that inhibits or prevents degradation of the mRNA is a G quadruplex, pseudoknot or triplex sequence. In some embodiments, the sequence the sequence that inhibits or prevents degradation of the mRNA is an exoribonuclease-resistant RNA structure from a flavivirus RNA or an ENE element from KSV. In some embodiments, the sequence that inhibits or prevents degradation of the mRNA inhibits or prevents degradation of the mRNA by a deadenylase. In some embodiments, the sequence that inhibits or prevents degradation of the mRNA comprises non-adenosine nucleotides within or at a terminus of a poly A tail of the mRNA. In some embodiments, the sequence that inhibits or prevents degradation of the mRNA increases stability of the mRNA. In some embodiments, the exogenous sequence comprises a sequence encoding an exogenous polypeptide. In some embodiments, the sequence encoding an exogenous polypeptide is not in frame with a sequence encoding an endonuclease and/or a reverse transcriptase. In some embodiments, the sequence encoding an exogenous polypeptide is not in frame with a sequence encoding an endonuclease and/or a reverse transcriptase. In some embodiments, the exogenous sequence does not comprise introns. In some embodiments, the exogenous sequence comprises a sequence encoding an exogenous polypeptide selected from the group consisting of an enzyme, a receptor, a transport protein, a structural protein, a hormone, an antibody, a contractile protein and a storage protein. In some embodiments, the exogenous sequence comprises a sequence encoding an exogenous polypeptide selected from the group consisting of a chimeric antigen receptor (CAR), a ligand, an antibody, a receptor, and an enzyme. In some embodiments, the exogenous sequence comprises a regulatory sequence. In some embodiments, the regulatory sequence comprises a cis-acting regulatory sequence. In some embodiments, the regulatory sequence comprises a cis-acting regulatory sequence selected from the group consisting of an enhancer, a silencer, a promoter or a response element. In some embodiments, the regulatory sequence comprises a trans-acting regulatory sequence. In some embodiments, the regulatory sequence comprises a trans-acting regulatory sequence that encodes a transcription factor.

In some embodiments, integration of the insert sequence does not adversely affect cell health. In some embodiments, the endonuclease, the reverse transcriptase or both are capable of site-specific integration of the insert sequence.

In some embodiments, the mRNA comprises a sequence encoding an additional nuclease domain or a nuclease domain that is not derived from ORF2. In some embodiments, the mRNA comprises a sequence encoding a megaTAL nuclease domain, a TALEN domain, a Cas9 domain, a zinc finger binding domain from an R2 retroelement, or a DNA binding domain that binds to repetitive sequences such as a Rep78 from AAV. In some embodiments, the endonuclease comprises a mutation that reduces activity of the endonuclease compared to the endonuclease without the mutation. In some embodiments, the endonuclease is an ORF2p endonuclease and the mutation is S228P. In some embodiments, the mRNA comprises a sequence encoding a domain that increases fidelity and/or processivity of the reverse transcriptase. In some embodiments, the reverse transcriptase is a reverse transcriptase from a retroelement other than ORF2 or reverse transcriptase that has higher fidelity and/or processivity compared to a reverse transcriptase of ORF2p. In some embodiments, the reverse transcriptase is a group II intron reverse transcriptase. In some embodiments, the group II intron reverse transcriptase is a group IIA intron reverse transcriptase, a group IIB intron reverse transcriptase, or a group IIC intron reverse transcriptase. In some embodiments, the group II intron reverse transcriptase is TGIRT-II or TGIRT-III.

In some embodiments, the mRNA comprises a sequence comprising an Alu element and/or a ribosome binding aptamer. In some embodiments, the mRNA comprises a sequence encoding a polypeptide comprising a DNA binding domain. In some embodiments, the 3' UTR sequence is derived from a viral 3' UTR or a beta-globin 3' UTR.

In one aspect, provided herein is a composition comprising a recombinant mRNA or vector encoding an mRNA, wherein the mRNA comprises a human LINE-1 transposon sequence comprising a human LINE-1 transposon 5' UTR sequence, a sequence encoding ORF1p downstream of the human LINE-1 transposon 5' UTR sequence, an inter-ORF linker sequence downstream of the sequence encoding ORF1p,a sequence encoding ORF2p downstream of the inter-ORF linker sequence, and a 3' UTR sequence derived from a human LINE-1 transposon downstream of the sequence encoding ORF2p; wherein the 3' UTR sequence comprises an insert sequence, wherein the insert sequence is a reverse complement of a sequence encoding an exogenous polypeptide or a reverse complement of a sequence encoding an exogenous regulatory element.

In some embodiments, the insert sequence integrates into the genome of a cell when introduced into the cell. In some embodiments, the insert sequence integrates into a gene associated a condition or disease, thereby disrupting the gene or downregulating expression of the gene. In some embodiments, the insert sequence integrates into a gene, thereby upregulating expression of the gene. In some embodiments, the recombinant mRNA or vector encoding the mRNA is isolated or purified.

In one aspect, provided herein is a composition comprising a nucleic acid comprising a nucleotide sequence encoding (a) a long interspersed nuclear element (LINE) polypeptide, wherein the LINE polypeptide includes human ORF1p and human ORF2p; and (b) an insert sequence, wherein the insert sequence is a reverse complement of a sequence encoding an exogenous polypeptide or a reverse complement of a sequence encoding an exogenous regulatory element, wherein the composition is substantially non-immunogenic.

In some embodiments, the composition comprises human ORF1p and human ORF2p proteins. In some embodiments, the composition comprises a ribonucleoprotein (RNP) comprising human ORF1p and human ORF2p complexed to the nucleic acid. In some embodiments, the nucleic acid is mRNA.

In one aspect, provided herein is a composition comprising a cell comprising a composition described herein. In some embodiments, the cell is an immune cell. In some embodiments, the immune cell is a T cell or a B cell. In some embodiments, the immune cell is a myeloid cell. In some embodiments, the immune cell is selected from a group consisting of a monocyte, a macrophage, a dendritic cell, a dendritic precursor cell, and a macrophage precursor cell. In some embodiments, the insert sequence is a reverse complement of a sequence encoding an exogenous polypeptide and the exogenous polypeptide is a chimeric antigen receptor (CAR).

In one aspect, provided herein is a pharmaceutical composition comprising a composition described herein, and a pharmaceutically acceptable excipient. In some embodiments, the pharmaceutical composition is for use in gene therapy. In some embodiments, the pharmaceutical composition is for use in the manufacture of a medicament for treating a disease or condition. In some embodiments, the pharmaceutical composition is for use in treating a disease or condition. In one aspect, provided herein is a method of treating a disease in a subject, comprising administering a pharmaceutical composition described herein to a subject with a disease or condition. In some embodiments, the method increases an amount or activity of a protein or functional RNA in the subject. In some embodiments, the subject has a deficient amount or activity of a protein or functional RNA. In some embodiments, the deficient amount or activity of a protein or functional RNA is associated with or causes the disease or condition.

In some embodiments, the method further comprising administering an agent that inhibits human silencing hub (HUSH) complex, an agent that inhibits FAM208A, or an agent that inhibits TRIM28. In some embodiments, the agent that inhibits human silencing hub (HUSH) complex is an agent that inhibits Periphilin, TASOR and/or MPP8. In some embodiments, the agent that inhibits human silencing hub (HUSH) complex inhibits assembly of the HUSH complex.

In some embodiments, the agent inhibits the Fanconi anemia complex. In some embodiments, the agent inhibits FANCD2-FANC1 heterodimer monoubiquitylation. In some embodiments, the agent inhibits FANCD2-FANC1 heterodimer formation. In some embodiments the agent inhibits the Fanconi Anemia (FA) core complex. FA core complex is a component of the Fanconi anemia DNA damage repair pathway, e.g., in chemotherapy induced DNA inter-strand crosslinks. The FA core complex comprises two central dimers of the FANCB and FA-associated protein of 100 kDa (FAAP100) subunits, flanked by two copies of the RUNG finger subunit, FANCL. These two heterotrimers act as a scaffold to assemble the remaining five subunits, resulting in an extended asymmetric structure. Destabilization of the scaffold would disrupt the entire complex, resulting in a non-functional FA pathway. Examples of agents that can inhibit the FA core complex include Bortezomib and curcumin analogs EF24 and 4H-TTD.

In some embodiments, the sequences to be inserted may be placed under the control of tissue-specific elements, such that the entire inserted DNA is only functional in those cells in which the tissue-specific element is active.

In one aspect, provided herein are method and compositions for stable gene transfer to a cell by introducing to the cell a heterologous nucleic acid or gene of interest (e.g., a transgene, a regulatory sequence, for example, a sequence for an inhibitory nucleic acid, an siRNA, a miRNA), flanked by sequences that cause retrotransposition of the heterologous nucleic acid sequence into the genome of the cell. In some embodiments, the heterologous nucleic acid is termed insert for the purpose of the description in this document, where the insert is the nucleic acid sequence that will be reverse transcribed and inserted into the genome of the cell by the intended design of the constructs described herein. In some embodiments, the heterologous nucleic acid is also termed the cargo, or cargo sequence for the purpose of the description in this document. The cargo can comprise the sequence of the heterologous nucleic acid that that is inserted in the genome. In some embodiments, the cell may be a cell mammalian cell. The mammalian cell may be of epithelial, mesothelial or endothelial origin. In some embodiments, the cell may be a stem cell. In some embodiments, the cell may be a precursor cell. In some embodiments, the cell may be a cell that is terminally differentiated. In some embodiments, the cell may be a muscle cell, a cardiac cell, an epithelial cell, a hematopoietic cell, a mucous cell, an epidermal cell, a squamous cell, a cartilage cell, a bone cell, or any cell of mammalian origin. In some embodiments, the cell is of hematopoietic lineage. In some embodiments, he cell is of myeloid lineage, or a phagocytic cell, for example a monocyte, macrophage, a dendritic cell or a myeloid precursor cell. In some embodiments, the nucleic acid encoding the transgene is an mRNA.

In some embodiments, the retrotransposable elements may be derived from a non-LTR retrotransposon.

Provided herein is a method of integrating a nucleic acid sequence into a genome of a cell, the method comprising introducing a recombinant mRNA or a vector encoding an mRNA into the cell, wherein the mRNA comprises an insert sequence and wherein the insert sequence is integrated into the genome of the cell. In some embodiments, the insert sequence comprises (i) an exogenous sequence, or (ii) a sequence that is a reverse complement of the exogenous sequence; a 5' UTR sequence and a 3' UTR sequence downstream of the 5' UTR sequence; wherein the 5' UTR sequence or the 3' UTR sequence comprises a binding site for a human ORF protein. In some embodiments, the ORF protein is a human LINE 1 ORF2 protein. In some embodiments, the ORF protein is a non-human ORF protein. In some embodiments, the ORF protein is a chimeric protein, a recombinant protein or an engineered protein.

Provided herein is a method for integrating a nucleic acid sequence into the genome of an immune cell, the method comprising introducing a recombinant mRNA or a vector encoding an mRNA, wherein the mRNA comprises, (a) an insert sequence, wherein the insert sequence comprises (i) an exogenous sequence or (ii) a sequence that is a reverse complement of the exogenous sequence; (b) 5' UTR sequence and a 3' UTR sequence downstream of the 5' UTR sequence, wherein the 5' UTR sequence or the 3' UTR sequence comprises an endonuclease binding site and a reverse transcriptase binding site, and wherein the transgene sequence is integrated into the genome of the immune cell.

In some embodiments, the structural elements that mediate RNA integration or transposition may be encoded in a synthetic construct and are relied upon to deliver a heterologous gene of interest to the cell. In some embodiments, the synthetic construct may comprise a nucleic acid encoding the heterologous gene of interest and the structural elements that cause integration or retrotransposition of a heterologous gene of interest into the genome. In some embodiments, the structural elements that cause integration or retrotransposition may include a 5' L1 RNA region, and a 3'-L1 region, the latter comprising a poly A 3' region for priming. In some embodiments, the 5' L1 RNA region may comprise one or more stem loop regions. In some embodiments, the L1-3' region may comprise one or more stem loop regions. In some embodiments, the 5'- and 3' L1 regions are constructed as flanking the nucleic acid sequence encoding the heterologous gene of interest (the transgene). In some embodiments, the structural elements may include a region from an L1 or an Alu RNA comprising the hairpin loop structure that includes the A-Box and the B-Box elements that are ribosomal binding sites In some embodiments, the synthetic nucleic acid may comprise a L1-Ta promoter.

There may be two types of LINE RNA recognition by ORF2p—the stringent and the relaxed. In the stringent type RT recognizes its own 3'UTR tail, and in the relaxed type RT does not require any specific recognition except for the poly-A tail. Division into the stringent and the relaxed type came from the observation that some LINE/SINE pairs share the same 3'-end. For the stringent type, the experimental studies showed that a 3'UTR stem-loop promotes retrotransposition. The 5'-UTR of the LINE retrotransposition sequences have been shown to contain three conserved stem loop regions.

In some embodiments, the transgene, or transcript of interest may be flanked by transposable elements from a L1 or an Alu sequence at the 5' and the 3' end. In some embodiments, the 5' region of a retrotransposon comprises an Alu sequence. In some embodiments, the 3' region of a retrotransposon comprises an Alu sequence. In some embodiments, the 5' region of a retrotransposon comprises an L1 sequence. In some embodiments, the 3' region of a retrotransposon comprises an L1 sequence. In some embodiments, the transgene or transcript of interest is flanked by an SVA transposon sequence.

In some embodiments, the transcript of interest may comprise an L1 or an Alu sequence, encoding the binding regions for ORF2p and the 3'-poly A priming regions. In some embodiments, the heterologous nucleic acid encoding the transgene of interest may be flanked by an L1 or an Alu sequence, encoding the binding regions for ORF1p and the 3'-poly A priming regions. The 3'-region may comprise one or more stem loop structures. In some embodiments, the transcript of interest is structured for cis integration or retrotransposition. In some embodiments, the transcript of interest is structured for trans integration or retrotransposition.

In some embodiments, the retrotransposon is a human retrotransposon. The sequence of a human retrotransposon can comprise a sequence encoding an endonuclease and/or a reverse transcriptase. The sequence of a human retrotransposon can encode for two proteins that are translated from a single RNA containing two non-overlapping ORFs. In some embodiments, the two ORFs are ORF1 and ORF2.

Accordingly, provided herein is a method for stably integrating a heterologous nucleic acid encoding a transgene into the genome of a cell, such as a myeloid cell, the method comprising introducing to the cell a nucleic acid encoding: the transgene; one or more 5' nucleic acid sequences flanking the region encoding the transgene, comprising a 5' region of a retrotransposon; and one or more 3' nucleic acid sequence flanking the region encoding the transgene, comprising a 3' region of a retrotransposon, wherein the 3' region of the retrotransposon comprises a genomic DNA priming sequence and a LINE transposase binding sequence, having the respective endonuclease and reverse transcriptase (RT) activity.

Provided herein is a method for integrating a nucleic acid sequence into the genome of a cell, the method comprising introducing a recombinant mRNA or a vector encoding an mRNA, wherein the mRNA comprises an insert sequence, wherein the insert sequence comprises (i) an exogenous sequence or (ii) a sequence that is a reverse complement of the exogenous sequence; (b) a 5' UTR sequence, a sequence of a human retrotransposon downstream of the 5' UTR sequence, and a 3' UTR sequence downstream of the sequence of a human retrotransposon; wherein the 5' UTR sequence or the 3' UTR sequence comprises an endonuclease binding site and a reverse transcriptase binding site, and wherein the sequence of a human retrotransposon encodes for two proteins that are translated from a single RNA containing two ORFs, and wherein the insert sequence is integrated into the genome of the cell.

In some embodiments, the method comprising using a single nucleic acid molecule for delivering and integrating the insert sequence into the genome of a cell. The single nucleic acid molecule may be a plasmid vector. The single nucleic acid may be DNA or an RNA molecule. The single nucleic acid may be an mRNA.

In some embodiments, the method comprises introducing into a cell one or more polynucleotides comprising the human retrotransposon and a heterologous nucleic acid sequence. In some embodiments, the one or more polynucleotides comprises (i) a first nucleic acid molecule encoding an ORF1p; (ii) a second nucleic acid molecule encoding an ORF2p and a sequence encoding a cargo. In some embodiments, the first nucleic acid and the second nucleic acid are mRNA. In some embodiments, the first nucleic acid and the second nucleic acid are DNA, e.g., encoded in separate plasmid vectors.

Provided herein is a self-integrating polynucleotide that comprises a sequence which is inserted into the genome of a cell, and insert is stably integrated into the genome by the self-integrating naked polynucleotide. In some embodiments, the polynucleotide is an RNA. In some embodiments, the polynucleotide is an mRNA. In some embodiments, the polynucleotide is an mRNA that has modifications. In some embodiments, the modifications ensure protection against RNases in the intracellular milieu. In some embodiments, the modifications include substituted modified nucleotides, e.g., 5-methylcytidine, pseudouridine or 2-thiouridine.

In some embodiments, a single polynucleotide is used for delivery and genomic integration of the insert (or cargo) nucleic acid. In some embodiments, the single polynucleotide is bicistronic. In some embodiments, the single polynucleotide is tricistronic. In some embodiments, the single polynucleotide is multi-cistronic. In some embodiments, a two or more polynucleotide molecules are used for delivery and genomic integration of the insert (or cargo) nucleic acid.

In some embodiments, a retrotransposable genetic element may be generated, the retrotransposable genetic element comprising (i) a heterologous nucleic acid encoding a transgene or a non-coding sequence to be inserted into the genome of a cell (the insert); (ii) a nucleic sequence encoding one or more retrotransposon ORF-encoding sequences; (iii) one or more UTR regions of the ORF-coding sequences, such that the heterologous nucleic acid encoding a transgene or a non-coding sequence to be inserted is comprised within the UTR sequences; wherein the 3' region of the retrotransposon ORF-encoding sequences comprises a genomic DNA priming sequence.

In some embodiments, the retrotransposable genetic element may be introduced into a cell for stably integrating the transgene into the genomic DNA. In some embodiments, the retrotransposable genetic element comprises (a) a retrotransposon protein coding sequence, and a 3' UTR; and (b) a sequence comprising a heterologous nucleic acid that is to be inserted (e.g., integrated) within the genome of a cell. The retrotransposon protein coding sequence, and the 3' UTR may be a complete and sufficient unit for delivering the heterologous nucleic acid sequence within the genome of the cell, and comprise the retrotransposable elements, such as an endonuclease, a reverse transcriptase, a sequence in the 3' UTR for binding to and priming the genomic DNA at the region cleaved by the endonuclease to start reverse transcribing and incorporating the heterologous nucleic acid.

In some embodiments, the coding sequence of the insert is in forward orientation with respect to the coding sequence of the one or more ORFs. In some embodiments, the coding sequence of the insert is in reverse orientation with respect to the coding sequence of the one or more ORFs. The coding sequence of the insert and the coding sequence of the one or more ORFs may comprise distinct regulatory elements, including 5' UTR, 3' UTR, promoter, enhancer, etc. In some embodiments, the 3' UTR or the 5'-UTR of the insert may comprise the coding sequence of the one or more ORFs, and likewise, the coding sequence of the insert may be situated within in the 3' UTR of the coding sequence of the one or more ORFs.

In some embodiments, a retrotransposable genetic element may be generated, the retrotransposable genetic element comprising: (a) an insert sequence, comprising (i) an exogenous sequence, a sequence that is a reverse complement of the exogenous sequence; a 5' UTR sequence and a 3' UTR sequence downstream of the 5' UTR sequence; wherein the 5' UTR sequence or the 3' UTR sequence comprises a binding site for a human ORF protein.

In some embodiments, the retrotransposon may comprise a SINE or LINE element. In some embodiments, the retrotransposon comprises a SINE or LINE stem loop structure, such as an Alu element.

In some embodiments, the retrotransposon is a LINE-1 (L1) retrotransposon. In some embodiments, the retrotransposon is human LINE-1. Human LINE-1 sequences are abundant in the human genome. There are approximately 13,224 total human L1s, of which 480 are active, which make up about 3.6%. Therefore, human L1 proteins are well tolerated and non-immunogenic in humans. Moreover, a tight regulation of random transposition in human ensures that random transposase activity will not be triggered by introduction of the L1 system as described herein. In addition, the retrotransposable constructs designed herein may comprise targeted and specific incorporation of the insert sequence. In some embodiments, the retrotransposable genetic element may comprise designs intended to overcome the silencing machinery actively prevalent in human cells, while being careful that random integration resulting in genomic instability is not initiated.

Accordingly, the retrotransposable constructs may comprise a sequence encoding a human LINE-1 ORF1 protein; and a human LINE-1 ORF2 protein. In some embodiments, the construct comprises a nucleic acid sequence encoding an ORF1p protein with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to MGKKQNRKTGNSKTQSASPPPK-ERSSSPATEQSWMENDFDELREEGFRRSNYSEL-REDIQTKGK EVENFEKNLEEC-ITRITNTEKCLKELMELKTKARELREECRSLRSRCD-QLEERVSAMEDEMNEM KREGKFREKRIKR-NEQSLQEIWDYVKRPNLRLIGVPESD-VENGTKLENTLQDIIQENFPNLARQA NVQIQEIQRTPQRYSSRRAT-PRHIIVRFTKVEMKEKMLRAAREKGRVTLKGK-PIRLTVDLSAETL QARREWGPIFNILKEKNFQPRI-SYPAKLSFISEGEIKYFIDKQMLRDFVTTRPALKEL-LKEALNME RNNRYQPLQNHAKM (SEQ ID NO: 57). In some embodiments, the construct comprises a nucleic acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to (SEQ ID NO: 58)

```
atgggcaagaagcaaaatcgcaagacggggaattc

caagacacaatccgctagcccaccacctaaagagc

gttctagctcccctgctactgagcagtcctggatg

gaaaacgacttcgatgaactccgggaagagggatt

taggcgatccaactattcagaactccgcgaagata

tccagacaaaggggaaggaagtcgagaatttcgag

aagaacctcgaggagtgcatcacccgtatcacaaa

cactgagaaatgtctcaaagaactcatggaactta

agacaaaagccagggagcttcgagaggagtgtcgg

agtctgagatccaggtgtgaccagctcgaggagcg

cgtgagcgcgatggaagacgagatgaacgagatga

aaagagagggcaaattcagggagaagcgcattaag

aggaacgaacagagtctgcaggagatttgggatta

cgtcaagaggcctaacctgcggttgatcggcgtcc

ccgagagcgacgtagaaaacgggactaaactggag

aatacacttcaagacatcattcaagaaaattttcc

aaacctggctcggcaagctaatgtgcaaatccaag

agatccaacgcacaccccagcggtatagctctcgg

cgtgccacccctaggcatattatcgtgcgctttac

taaggtggagatgaaagagaagatgctgcgagccg

ctcgggaaaagggaagggtgactttgaagggcaaa
```

-continued

```
cctattcggctgacggttgaccttagcgccgagac

actccaggcacgccgggaatggggccccatcttta

atatcctgaaggagaagaacttccagccacgaatc

tcttaccctgcaaagttgagttttatctccgaggg

tgagattaagtatttcatcgataaacagatgctgc

gagacttcgtgacaactcgcccagctctcaaggaa

ctgctcaaagaggctcttaatatggagcgcaataa

tagatatcaaccccttgcagaaccacgcaaagatg

tga.
```

In some embodiments, the construct comprises a nucleic acid sequence encoding an ORF2p protein with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to MTGSNSHIT-ILTLNINGLNSAIKRHRLASWIKSQDPSVCCIQETHLT-CRDTHRLKIKGWRKIYQAN GKQKKAGVAIL-VSDKTDFKPTKIKRDKEGHYIMVKGSIQQEELTIL-NIYAPNTGAPRFIKQVLSDL QRDLD-SHTLIMGDFNTPLSTLDRSTRQKVNKDTQELN-SALHQADLIDIYRTLHPKSTEYTFFSAP HHTYSKI-DHIVGSKALLSKCKRTEIITNYLSDHSAIKLELRI-KNLTQSRSTTWKLNNLLLN-DYWV HNEMKAEIKMFFETNENKDT-TYQNLWDAFKAVCRGKFIALNAYKRKQERSKIDTLT-SQLKELE KQEQTHSKASRRQEITKIRAELKEI-ETQKTLQKINESRSWFFERINKIDRPLARLIKKKRE-KNQIDTI KNDKGDITTDPTEIQTTIREYYKHLYAN-KLENLEEMDTFLDTYTLPRLNQEEVESLNRPITGSEIV AIINSLPTKKSPGPDGFTAEFYQRYMEELVP-FLLKLFQSIEKEGILPNSFYEASIILIPKPGRDTTKKE NFRPISLMNIDAKILNKILANRIQQHIKKLIHHDQVG-FIPGMQGWFNIRKSINVIQHINRAKDKNH MIISI-DAEKAFDKIQQPFMLKTLNKLGIDGTYFKII-RAIYDKPTANIILNGQKLEAFPLKTGTRQGC PLSPLLFNIVLEVLARAIRQEKEIKGIQLGKEEVKLSL-FADDMIVYLENPIVSAQNLLKLISNFSKV SGYK-INVQKSQAFLYTNNRQTESQIMGELPFVIASKRI-KYLGIQLTRDVKDLFKENYKPLLKEIKE DTNKWKNIPCSWVGRINIVKMAILPKVIYRFNAIP-IKLPMTFFTELEKTTLKFIWNQKRARIAKSIL SQKNK-AGGITLPDFKLYYKATVTKTAWYWYQNR-DIDQWNRTEPSEIMPHIYNYLIFDKPEKNK QWGKDSLFNKWCWENWLAICRKLKLDPFLTPYT-KINSRWIKDLNVKPKTIKTLEENLGITIQDIG VGKDFMSKTPKAMATKDKIDKWDLIKLKSFCTA-KETTIRVNRQPTTWEKIFATYSSDKGLISRIY NELKQIYKKKTNNPIKKWAKDMNRHFSKEDI-YAAKKHMKKCSSSLAIREMQIKTTMRYHLTPV RMAIIKKSGNNRCWRGCGEIGTLLHCWWDCK-LVQPLWKSVWRFLRDLELEIPFDPAIPLLGIYP NEYKSCCYKDTCTRMFIAALFTIAKTWNQPKCPT-MIDWIKKMWHIYTMEYYAAIKNDEFISFVG TWMKLETIILSKLSQEQKTKHRIFSLIGGN (SEQ ID NO: 59). In some embodiments, the construct comprises a nucleic acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to (SEQ ID NO: 60)

atgaccggctctaactcacatatcaccatccttac acttaacattaacggcctcaactcagctatcaagc gccatcggctggccagctggatcaaatcacaggat ccaagcgtttgttgcatccaagagacccacctgac ctgtagagatactcaccgcctcaagatcaagggat ggcgaaagatttatcaggcgaacggtaagcagaag aaagccggagtcgcaattctggtctcagacaagac ggatttcaagcccaccaaaattaagcgtgataagg aaggtcactatattatggtgaaaggcagcatacag caggaagaacttaccatattgaacatctacgcgcc aaacaccggcgcacctcgctttatcaaacaggtcc tgtccgatctgcagcgagatctggattctcatacg ttgattatgggtgatttcaatacaccattgagcac cctggatcgcagcaccaggcaaaaggtaaataaag acacgcaagagctcaatagcgcactgcatcaggca gatctcattgatatttatcgcactcttcatcctaa gagtaccgagtacacattcttcagcgccccacatc atacatactcaaagatcgatcatatcgtcggctca aaggctctgctgtcaaagtgcaagcgcacagagat aattacaaattacctgtcagatcatagcgcgatca agctcgagctgagaatcaagaacctgacccagagc cggagtaccacttggaagcttaataacctgctgct caacgattattgggtccacaatgagatgaaggcag agattaaaatgttcttcgaaacaaatgagaataag gatactacctatcaaaacctttgggatgcctttaa ggccgtctgcagaggcaagttcatcgccctcaacg cctataaaagaaaacaagagagatctaagatcgat actctcacctctcagctgaaggagttggagaaaca ggaacagacccactccaaggcgtcaagacggcagg agatcacaaagattcgcgccgagttgaaagagatc gaaacccaaaagactcttcagaaaattaacgagtc tcgtagttggttcttcgagcggattaataagatag acagacctctggcacgactgattaagaagaagcgc gaaaagaaccagattgataccatcaagaacgacaa gggcgacatcactactgacccgaccgagatccaga ccactattcgggagtattataagcatttgtatgct aacaagcttgagaacctggaagagatggacacttt tctggatacctatactctgccacggcttaatcaag -continued aggaagtcgagtccctcaaccgcccaattacagga agcgagattgtggccataattaactccctgccgac aaagaaatctcctggtccggacgggtttacagctg agtttatcaacggtatatggaagagcttgtaccg tttctgctcaagctctttcagtctatagaaaagga aggcatcttgcccaattccttctacgaagcttcta taatacttattcccaaaccaggacgcgataccaca aagaaggaaaacttccggcccattagtctcatgaa tatcgacgctaaaatattgaacaagattctcgcca acagaatccaacaacatattaagaaattgatacat cacgaccaggtggggtttatacctggcatgcaggg ctggtttaacatccggaagagtattaacgtcattc aacacattaatagagctaaggataagaatcatatg atcatctctatagacgcggaaaaggcattcgataa gattcagcagccatttatgctcaagactctgaaca aactcggcatcgacggaacatattttaagattatt cgcgcaatttacgataagccgactgctaacattat ccttaacggccaaaagctcgaggcctttccgctca agactggaacccgccaaggctgtcccctctccccg cttttgtttaatattgtactcgaggtgctggctag ggctattcgtcaagagaaagagattaaagggatac agctcgggaaggaagaggtcaagctttccttgttc gccgatgatatgattgtgtacctggagaatcctat tgtgtctgctcagaaccttcttaaacttatttcta actttagcaaggtcagcggctataagattaacgtc cagaaatctcaggcctttctgtacacaaataatcg acagaccgaatcccagataatgggtgagcttccgt ttgtcatagccagcaaaaggataaagtatctcgga atccagctgacacgagacgttaaagatttgtttaa ggaaaattacaagcctctcctgaaagagattaagg aagatactaataagtggaagaatatcccctgttca tgggttggcagaatcaacatagtgaagatggcaat acttcctaaagtgatatatcgctttaacgccatcc caattaaactgcctatgaccttctttacggagctc gagaaaacaacccttaaatttatatggaatcaaaa gagagcaagaatagcgaagtccatcttgagccaga agaataaggccggtgggattactttgcctgatttt aagttgtattataaagccacagtaactaagacagc ctggtattggtatcagaatagagacatcgaccagt ggaatcggaccgaaccatcagagataatgccccac -continued

```
atctataattaccttatattcgataagccagaaaa
gaataaacagtggggcaaagacagcctcttcaaca
agtggtgttgggagaattggctggccatatgccgg
aaactcaagctcgacccctttcttacaccctacac
taaaatcaacagtaggtggatcaaggacttgaatg
tcaagccaaagactataaagacactggaagagaat
cttgggatcacaatacaagatataggcgtcggcaa
agattttatgtcaaagacgcccaaggccatggcca
ctaaggataagattgataagtgggaccttattaag
ctcaaaagcttctgtactgccaaggagaccacgat
cagagttaataggcagcccactacatgggaaaaga
ttttcgccacttattcatcagataaggggttgata
agcagaatatataacgagctgaagcagatctacaa
gaagaaaacgaataatcccatcaagaagtgggcaa
aagatatgaacaggcattttagcaaagaggatatc
tacgccgcgaagaagcatatgaagaagtgtagttc
aagcttggccattcgtgagatgcagattaagacga
ccatgcgataccaccttaccccagtgaggatggca
attatcaagaaatctggcaataatagatgttggcg
gggctgtggcgagattggcaccctgctccattgct
ggtgggattgcaagctggtgcagccgctttggaaa
tcagtctggcgctttctgagggacctcgagcttga
gattcccttcgatcccgcaattcccttgctcggaa
tctatcctaacgaatacaagagctgttgttacaag
gatacgtgtacccggatgttcatcgcggccttgtt
tacgatagctaagacgtggaatcagcctaagtgcc
ccacaatgatcgattggatcaagaaaatgtggcat
atttataccatggagtattacgcagcaattaagaa
tgacgaatttatttccttcgttgggacctggatga
agctggagactattattctgagcaagctgtctcag
gagcaaaagacaaagcatagaatcttctctctcat
tggtggtaactaa.
```

In some embodiments, the construct comprises a nucleic acid sequence encoding an ORF2p protein with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to MVIGTY-
ISIITLNVNGLNAPTKRHRLAEWIQKQDPYIC-
CLQETHFRPRDTYRLKVRGWKKIFHAN GNQKK-
AGVAILISDKIDFKIKNVTRDKEGHYIMIQGSIQEEDITI-
INIYAPNIGAPQYIRQLLTAIKE
EIDSNTIIVGDFNTSLTPMDRSSKMKINKETEAL-
NDTIDQIDLIDIYRTFHPKTADYTFFSSAHGTFS
RIDHILGHKSSLSKFKKIEIISSIFSDHNAMR-
LEMNHREKNVKKTNTWRLNNTLLNNQEITEEIKQ
EIKKYLETNDNENTTTQNLWDAAKAVLRGKFIAI-
QAYLKKQEKSQVNNLTLHLKKLEKEEQTK
PKVSRRKEIIKIRAEINEIETKK-
TIAKINKTKSWFFEKINKIDKPLARLIKKKR-
ERTQINKIRNEKGE VTTDTAEIQNILRDYYKQLY-
ANKMDNLEEMDKFLERYNLPRLNQEETENINRPI-
TSNEIETVIKNL PTNKSPGPDGFTGEFYQTFREELT-
PILLKLFQKIAEEGTLPNSFYEATI-
TLIPKPDKDTTKKENYRPI SLMNIDAKILNKILAN-
RIQQHIKRIIHHDQVGFIPGMQGFFNIRKSINVIHHI-
NKLKKKNHMIISIDA EKAFD-
KIQHPFMIKTLQKVGIEGTYLNIIKAIYDKP-
TANIILNGEKLKAFPLRSGTRQGCPLSPLLF NIVLEV-
LATAIREEKEIKGIQIGKEEVKLSLFADDMILYIENP-
KTATRKLLELINEYGKVAGYKINA QKSLAFLY-
TNDEKSEREIMETLPFTIATKRIKYLGINLPKETKDLY-
AENYKTLMKEIKDDTNRWR DIPCSWIGRINIVKM-
SILPKAIYRFNAIPIKLPMAFFTELEQIILKFVWRHKRPRI-
AKAVLRQKNGA
GGIRLPDFRLYYKATVIKTIWYWHKNRNIDQWNK-
IESPEINPRTYGQLIYDKGGKDIQWRKDSLF NKWC-
WENWTATCKRMKLEYSLTPYTKINSKWIRDLNIRLD-
TIKLLEENIGRTLFDINHSKIFFDPP
PRVMEIKTKINKWDLMKLQSFCTA-
KETINKTKRQPSEWEKIFANESTDKGLIS-
KIYKQLIQLNIKE TNTPIQKWAE-
DLNRHFSKEDIQTATKHMKRCSTSLIIREMQIKTT-
MRYHLTPVRMGIIRKSTNNK
CWRGCGEKGTLLHCWWECK-
LIQPLWRTIWRFLKKLKIELPYDPAIPLLGIYPEKT-
VIQKDTCTR MFIAALFTIARSWKQPKCPSTDEWIK-
KMWYIYTMEYYSAIKRNEIGSFLETWMDLETVIQ-
SEVSQ KEKNKYRILTHICGTWKNGTDEPVCRTEI-
ETQM (SEQ ID NO: 61). In some embodiments, the construct comprises a nucleic acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to

```
                                   (SEQ ID NO: 62)
atggtcataggaacatacatatcgataattacctt
aaacgtgaatggattaaatgccccaaccaaaagac
atagactggctgaatggatacaaaaacaagaccca
tatatatgctgtctacaagagacccacttcagacc
tagggacacatacagactgaaagtgaggggatgga
aaaagatattccatgcaaatggaaatcaaaagaaa
gctggagtagctatactcatatcagataaaataga
ctttaaaataaagaatgttacaagagacaaggaag
gacactacataatgatccagggatcaatccaagaa
gaagatataacaattataaatatatatgcacccaa
cataggagcacctcaatacataaggcaactgctaa
cagctataaaagaggaaatcgacagtaacacaata
atagtgggggactttaacacctcacttacaccaat
ggacagatcatccaaaatgaaaataaataaggaaa
cagaagctttaaatgacacaatagaccagatagat
```

-continued ttaattgatatatataggacattccatccaaaaac
agcagattacacgttcttctcaagtgcgcacggaa
cattctccaggatagatcacatcttgggtcacaaa
tcaagcctcagtaaatttaagaaaattgaaatcat
atcaagcatcttttctgaccacaacgctatgagat
tagaaatgaatcacagggaaaaaaacgtaaaaaag
acaaacacatggaggctaaacaatacgttactaaa
taaccaagagatcactgaagaaatcaaacaggaaa
taaaaaaatacctagagacaaatgacaatgaaaac
acgacgacccaaaacctatgggatgcagcaaaagc
ggttctaagagggaagtttatagctatacaagcct
acctaaagaaacaagaaaaatctcaagtaaacaat
ctaaccttacacctaaagaaactagagaaagaaga
acaaacaaaacccaaagttagcagaaggaaagaaa
tcataaagatcagagcagaaataaatgaaatagaa
acaaagaaaacaatagcaaagatcaataaaactaa
aagttggttctttgagaagataaacaaaattgata
agccattagccagactcatcaagaaaaagagggag
aggactcaaatcaataaaatcagaaatgaaaaagg
agaagttacaacagacaccgcagaaatacaaaaca
tcctaagagactactacaagcaactttatgccaat
aaaatggacaacctggaagaaatggacaaattctt
agaaaggtataaccttccaagactgaaccaggaag
aaacagaaaatatcaacagaccaatcacaagtaat
gaaattgaaactgtgattaaaaatcttccaacaaa
caaaagtccaggaccagatggcttcacaggtgaat
tctatcaaacatttagagaagagctaacacccatc
cttctcaaactcttccaaaaaattgcagaagaagg
aacactcccaaactcattctatgaggccaccatca
ccctgataccaaaaccagacaaagacactacaaaa
aaagaaaattacagaccaatatcactgatgaatat
agatgcaaaaatcctcaacaaaatactagcaaaca
gaatccaacaacacattaaaaggatcatacaccac
gatcaagtgggatttatcccagggatgcaaggatt
cttcaatatacgcaaatcaatcaatgtgatacacc
atattaacaaattgaagaagaaaaaccatatgatc
atctcaatagatgcagaaaaagcttttgacaaaat
tcaacacccatttatgataaaaactctccagaaag
tgggcatagagggaacctacctcaacataataaag
gccatatatgacaaacccacagcaaacatcattct -continued caatggtgaaaaactgaaagcatttcctctaagat
caggaacgagacaaggatgtccactctcaccacta
ttattcaacatagttctggaagtcctagccacggc
aatcagagaagaaaaagaaataaaaggaatacaaa
ttggaaaagaagaagtaaaactgtcactgtttgcg
gatgacatgatactatacatagagaatcctaaaac
tgccaccagaaaactgctagagctaattaatgaat
atggtaaagttgcaggttacaaaattaatgcacag
aaatctcttgcattcctatacactaatgatgaaaa
atctgaaagagaaattatggaaacactcccattta
ccattgcaacaaaaagaataaaatacctaggaata
aacctacctaaggagacaaaagacctgtatgcaga
aaactataagacactgatgaaagaaattaaagatg
ataccaacagatggagagatataccatgttcttgg
attggaagaatcaacattgtgaaaatgagtatact
acccaaagcaatctacagattcaatgcaatcccta
tcaaattaccaatggcatttttttacggagctagaa
caaatcatcttaaaatttgtatggagacacaaaag
accccgaatagccaaagcagtcttgaggcaaaaaa
atggagctggaggaatcagactccctgacttcaga
ctatactacaaagctacagtaatcaagacaatatg
gtactggcacaaaaacagaaacatagatcaatgga
acaagatagaaagcccagagattaacccacgcacc
tatggtcaactaatctatgacaaaggaggcaaaga
tatacaatggagaaaagacagtctcttcaataagt
ggtgctgggaaaactggacagccacatgtaaaaga
atgaaattagaatactccctaacaccatacacaaa
aataaactcaaaatggattagagacctaaatataa
gactggacactataaaactcttagaggaaaacata
ggaagaacactctttgacataaatcacagcaagat
ctttttcgatccacctcctagagtaatggaaataa
aaacaaaaataaacaagtgggacctaatgaaactt
caaagcttttgcacagcaaaggaaaccataaacaa
gacgaaaagacaaccctcagaatgggagaaaatat
ttgcaaatgaatcaacggacaaaggattaatctcc
aaaatatataaacagctcattcagctcaatatcaa
agaaacaaacaccccaatccaaaaatgggcagaag
acctaaatagacatttctccaaagaagacatacag
acggccacgaagcacatgaaaagatgctcaacatc
actaattattagagaaatgcaaatcaaaactacaa
tgaggtatcacctcactcctgttagaatgggcatc -continued

```
atcagaaaatctacaaacaacaaatgctggagagg

gtgtggagaaaagggaaccctcttgcactgttggt

gggaatgtaaattgatacagccactatggagaaca

atatggaggttccttaaaaaactaaaaatagaatt

accatatgacccagcaatcccactactgggcatat

acccagagaaaaccgtaattcaaaaagacacatgc

acccgaatgttcattgcagcactatttacaatagc

caggtcatggaagcaacctaaatgcccatcgacag

acgaatggataaagaagatgtggtacatatataca

atggaatattactcagccataaaaaggaacgaaat

tgggtcatttttagagacgtggatggatctagaga

ctgtcatacagagtgaagtaagtcagaaagagaaa

aacaaatatcgtatattaacgcatatatgtggaac

ctggaaaaatggtacagatgaaccggtctgcagga

cagaaattgagacacaaatgtaa.
```

In some embodiments, the construct comprises a nucleic acid sequence encoding a nuclear localization sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to PAAKRVKLD (SEQ ID NO: 63). In some embodiments, the nuclear localization sequence is fused to the ORF2p sequence. In some embodiments, the construct comprises a nucleic acid sequence encoding a flag tag having the sequence DYKDDDDK (SEQ ID NO: 64). In some embodiments, the flag tag is fused to the ORF2p sequence. In some embodiments, the flag tag is fused to the nuclear localization sequence.

In some embodiments, the construct comprises a nucleic acid sequence encoding an MS2 coat protein with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to ASNFTQFVLVDNGGTGDVTVAPSNFANGIAEWISSN-SRSQAYKVTCSVRQSSAQNRKYTIKVEV PKGAWR-SYLNMELTIPIFATNSDCELIVKAMQGLLKDGNPIP-SAIAANSGIYAMASNFTQFVLVD NGGTGDVTVAPSNFANGIAEWISSNSR-SQAYKVTCSVRQSSAQNRKYTIKVEVPKGAWRSYLN MELTIPIFATNSDCELIVKAMQGLLKDGNPIPSA-IAANSGIY (SEQ ID NO: 65). In some embodiments, the MS2 coat protein sequence is fused to the ORF2p sequence.

In some embodiments, the transgene may comprise a flanking sequence which comprises an Alu ORF2p recognition sequence.

In some embodiments, additional elements may be introduced into the mRNA. In some embodiments, the additional elements may be an IRES element or a T2A element. In some embodiments, the mRNA transcript comprises one, two, three or more stop codons at the 3'-end.

In some embodiments, the one, two, three or more stop codons are designed to be in tandem. In some embodiments, the one, two, three or more stop codons are designed to be in all three reading frames. In some embodiments, the one, two, three or more stop codons may be designed to be both in multiple reading frames and in tandem.

In some embodiments, one or more target specific nucleotides may be added at the priming end of the L1 or the Alu RNA priming region.

In some embodiments, the 5' UTR sequence or the 3' UTR sequence in addition to be able to bind the ORF protein may also be capable of binding to one or more endogenous proteins that regulate gene retrotransposition and/or stable integration. In some embodiments, the flanking sequence is capable of binding to a PABP protein.

In some embodiments, the 5' region flanking the transcript may comprise a strong promoter. In some embodiments, the promoter is a CMV promoter.

In some embodiments, an additional nucleic encoding L1 ORF2p is introduced into the cell. In some embodiments, the sequence encoding L1 ORF1 is omitted, and only L1-ORF2 is included. In some embodiments, the nucleic acid encoding the transgene with the flanking elements is mRNA. In some embodiments, the endogenous L1-ORF1p function may be suppressed or inhibited.

In some embodiments, the nucleic acid encoding the transgene with the retrotransposition flanking elements comprise one or more nucleic acid modifications. In some embodiments, the nucleic acid encoding the transgene with the retrotransposition flanking elements comprises one or more nucleic acid modifications in the transgene. In some embodiments, the modifications comprise codon optimization of the transgene sequence. In some embodiments, the codon optimization is for more efficient recognition by the human translational machinery, leading to more efficient expression in a human cell. In some embodiments, the one or more nucleic acid modification is performed in the 5'-flanking sequence or the 3'-flanking sequence including one or more stem-loop regions. the nucleic acid encoding the transgene with the retrotransposition flanking elements comprise one, two, three, four, five, six, seven eight, nine, ten or more nucleic acid modifications.

In some embodiments, the retrotransposed transgene is stably expressed for the life of the cell. In some embodiments, the cell is a myeloid cell. In some embodiments, the myeloid cell is a monocyte precursor cell. In some embodiments, the myeloid cell is an immature monocyte. In some embodiments, the monocyte is an undifferentiated monocyte. In some embodiments, the myeloid cell is a CD14+ cell. In some embodiments, the myeloid cell does not express CD16 marker. In some embodiments, the myeloid cell is capable of remaining functionally active for a desired period of greater than 3 days, greater than 4 days, greater than 5 days, greater than 6 days, greater than 7 days, greater than 8 days, greater than 9 days, greater than 10 days, greater than 11 days, greater than 12 days, greater than 13 days, greater than 14 days or more under suitable conditions. A suitable condition may denote an in vitro condition, or an in vivo condition or a combination of both.

In some embodiments, the retrotransposed transgene may be stably expressed in the cell for about 2 days, about 3 days, about 4 days, about 5 days, about 6 days, about 7 days, about 8 days, about 9 days or about 10 days. In some embodiments, the retrotransposed transgene is stably expressed in the cell for more than 10 days. In some embodiments, the retrotransposed transgene is stably expressed in the cell for more than 2 weeks. In some embodiments, the retrotransposed transgene is stably expressed in the cell for about 1 month.

In some embodiments, the retrotransposed transgene may be modified for stable expression. In some embodiments, the retrotransposed transgene may be modified for resistant to in vivo silencing.

In some embodiments, the expression of the retrotransposed transgene may be controlled by a strong promoter. In some embodiments, the expression of the retrotransposed transgene may be controlled by a moderately strong promoter. In some embodiments, the expression of the retrotransposed transgene may be controlled by a strong promoter that can be regulated in an in vivo environment. In some embodiments, the promoter is a CMV promoter. In some embodiments, the promoter is a L1-Ta promoter.

In some embodiments, the ORF1p may be overexpressed. In some embodiments, the ORF2 may be overexpressed. In some embodiments, the ORF1p or ORF2p or both are overexpressed. In some embodiments, upon overexpression of an ORF1, ORF1p is at least 1.1 fold, 1.5 fold, 2 fold, 3 fold, 4 fold, 5 fold, 6 fold, 7 fold, 8 fold, 9 fold, 10 fold, 12 fold, 14 fold, 16 fold, 18 fold, 20 fold, 30 fold, 40 fold, 50 fold, 60 fold, 70 fold, 80 fold, 90 fold, or at least 100 fold higher than a cell not overexpressing and ORF1.

In some embodiments, upon overexpression of an ORF2 sequence, ORF2p is at least 1.1 fold, 1.5 fold, 2 fold, 3 fold, 4 fold, 5 fold, 6 fold, 7 fold, 8 fold, 9 fold, 10 fold, 12 fold, 14 fold, 16 fold, 18 fold, 20 fold, 30 fold, 40 fold, 50 fold, 60 fold, 70 fold, 80 fold, 90 fold, or at least 100 fold higher than a cell not overexpressing and ORF2p.

Retrotransposition Fidelity and Target Specificity

The LINE-1 elements can bind to their own mRNA poly A tail to initiate retrotransposition. LINE-1 elements preferably retrotranspose their own mRNA over random mRNAs (Dewannieux et al., 2013, 3,000-fold higher LINE-1 retrotransposition as compared to random mRNAs). In addition, LINE-1 elements can also integrate non-specific poly-A sequences within a genome.

In one aspect, provided herein are retrotransposition compositions and methods of using the same with increased retrotransposition specificity. For example, retrotransposition compositions with high specificity may be used for highly specific and efficient reverse transcription and subsequently, integration into genome of a target cell, e.g., a myeloid cell. In some embodiments, a retrotransposition composition provided herein comprises a retrotransposition cassette that comprises one or more additional components that increases integration or retrotransposing specificity. For example, the retrotransposon cassette may encode one or more additional elements that allows for high affinity RNA-protein interaction to out compete non-specific binding between poly-A sequences and ORF2.

Accordingly, several measures are disclosed herein for enhancing integration or retrotransposition efficiency.

One exemplary measure for enhancing integration or retrotransposition efficiency is external manipulation of the cells. The endonuclease function of the retrotransposition machinery delivered in a cell may likely be subject to inhibition by the cell's transposition silencing machinery, such as DNA repair pathways. For example, small molecules can be used to modulate or inhibit DNA repair pathways in the cells prior to introducing the nucleic acid. For example, cell sorting and/or synchronization can be used prior to introducing the nucleic acid, such as by electroporation, as cell cycle synchronized cell populations were shown to increase gene transfer to the cells. Cell sorting may be utilized to synchronize or homogenize the cell types and increase uniform transfer and expression of the exogenous nucleic acid. Uniformity may be achieved sorting stem cells from non-stem cells. Another exemplary measure for enhancing integration or retrotransposition efficiency is to enhance biochemical activity. For example, this may be achieved by increasing reverse-transcriptase processivity or DNA cleavage (endonuclease) activity. Another exemplary measure for enhancing integration or retrotransposition efficiency is to subvert endogenous silencing mechanisms. For example, this may be achieved by replacing entire LINE-1 sequence with a different organisms' LINE-1. Another exemplary measure for enhancing integration or retrotransposition efficiency is to enhance translation and ribosome binding. For example, this may be achieved by increasing expression of LINE-1 proteins, increasing LINE protein binding LINE-1 mRNA, or increasing LINE-1 complex binding to ribosomes. Another exemplary measure for enhancing integration or retrotransposition efficiency is to increase nuclear import or retention. For example, this may be achieved by fusing the LINE-1 sequence to a nuclear retention signal sequence. Another exemplary measure for enhancing integration or retrotransposition efficiency is to enhance sequence-specific insertion. For example, this may be achieved by fusing a targeting domain to ORF2 to increase sequence specific retrotransposition.

In one embodiment, the method encompasses enhancing the retrotransposon for increasing specificity and robustness of expression of the cargo by modifying the UTR sequence of the LINE-1 ORFs. In some embodiments, the 5'UTR upstream of ORF1 or ORF2 encoding sequence may be further modified to comprise a sequence that is complementary to the sequence of a target region within the genome that helps in homologous recombination at the specific site where the ORF nuclease can act and the retrotransposition can take place. In some embodiments, the sequence that can bind to a target sequence by homology is between 2-15 nucleotides long. In some embodiments, the sequence having homology to a genomic target that is included in the 5'UTR of an ORF1 mRNA may be about 3 nucleotides, about 4 nucleotides, about 5 nucleotides, about 6 nucleotides, about 7 nucleotides, about 8 nucleotides, about 9 nucleotides or about 10 nucleotides long. In some embodiments, the sequence having homology to a genomic target is about 12 or about 15 nucleotides long. In some embodiments, the sequence having homology to a genomic target is at least about 10, 15, 20, 25, 30, 35, 40, 45, 50, 55, 60, 65, 70, 75, 80, 85, 90, 95, 100, 105, 110, 115, 1120 or 125 nucleotides in length. In some embodiments, the sequence having homology to a genomic target comprises about 2-5, about 2-6, about 2-8 or about 2-10, or about 2-12 contiguous nucleotides that share complementarity with the respective target region within the genome. In some embodiments, the sequence having homology to a genomic target is at least about or about 10, 15, 20, 25, 30, 35, 40, 45, 50, 55, 60, 65, 70, 75, 80, 85, 90, 95, 100, 105, 110, 115, 1120 or 125 contiguous nucleotides that share complementarity with the respective target region within the genome.

In some embodiments, an ORF2 is associated with or fused to an additional protein domain that comprises RNA binding activity. In some embodiments, the retrotransposon cassette comprises a cognate RNA sequence that comprises affinity with the additional protein domain associated with or fused to the ORF2. In some embodiments, the ORF2 is associated with or fused to a MS2-MCP coat protein. In some embodiments, the retrotransposon cassette further comprises a MS2 hairpin RNA sequence in the 3' or 5' UTR sequence that interacts with the MS2-MCP coat protein. In some embodiments, the ORF2 is associated with or fused to a PP7 coat protein. In some embodiments, the retrotransposon cassette further comprises a PP7 hairpin RNA sequence in the 3' or 5' UTR sequence that interacts with the MS2-MCP coat protein. In some embodiments, the one or more additional elements increases retrotransposition specificity by at least 1.5 fold, at least 2 fold, at least 3 fold, at least 4 fold, at least 5 fold, at least 10 fold, at least 20 fold, at least 30 fold, at least 50 fold, at least 100 fold, at least 200 fold, at least 300 fold, at least 500 fold, at least 1000 fold, at least 1500 fold, at least 2000 fold, at least 3000 fold, at least 5000 fold or more as compared to a retrotransposon cassette without the one or more additional elements.

The DNA endonuclease domain appears to have specificity for a series of purines 3' of the target site followed by a series of pyrimidines $(Py)_n \downarrow (Pu)_n$. An exemplary sequence may be $(Adenosine)_n \downarrow (Thymidine)_n$.

In one aspect, provided herein are methods of using retrotransposition having high target specificity. In some embodiments, a CRISPR-Cas guide RNA system is combined with the LINE-retrotransposon system used here to increase the precision of site directed retrotransposition. In some embodiments, the system incorporates a prime editing guide RNA (pegRNA) to incorporate one or more ORF-binding sequence into a specific genomic locus. In some embodiments, the pegRNA incorporates the sequence that binds human ORF, e.g. TTTTTA in a site-specific manner. In some embodiments, the CRISPR-Cas system comprises a Cas9 enzyme. In some embodiments the CRISPR-Cas comprises a Cfp1 enzyme. In some embodiments, the Cas9 is a dCas9, paired with a nickase system.

Consequently, provided herein is a method and compositions for stable incorporation of a transgene into the genome of a myeloid cell, such as a monocyte or macrophage, wherein the method comprises incorporating the transgene using a non-LTR retrotransposon system, wherein the retrotransposition occurs at a specific genomic locus with a target specificity, high precision and fidelity. Therefore, in some embodiments, the method comprises administration to the cell a composition comprising a system having at least one transgene, flanked with one or more retrotransposable elements, and one or more nucleic acids encoding one or more proteins for increasing the transposition specificity, and/or further comprising modifying one or more genes associated with the retrotransposition.

The nucleic acid comprising the transgene, situated in 3' UTR region of the retrotransposable elements is often referred to as a retrotransposition cassette. Accordingly, in some embodiments, the retrotransposition cassette comprises the nucleic acid encoding the transgene and flanking Alu transposable elements. The retrotransposable elements comprise a sequence for binding the retrotransposons, for example, L1-transposons, such as L1-ORF proteins, ORF1p and ORF2p. ORF proteins are known to bind to their own mRNA sequence for retrotransposition. Therefore, the retrotransposition cassette comprises the nucleic acid encoding the transgene; a flanking L1-ORF2p binding sequence, and/or a L1-ORF1p binding sequence, comprising a sequence encoding a L1-ORF1p encoding sequence and a L1-ORF2p encoding sequence outside the transgene sequence. In some embodiments, the L1-ORF1 and L1-ORF2 are interspersed by a spacer region, also termed as an ORF1-ORF2 inter-region. In some embodiments, the L1-ORF1 and L1-ORF2 coding sequences are in an opposite orientation with respect to the coding region of the transgene. The retrotransposition cassette can comprise a poly A region downstream of the L1-ORF2-coding sequence and the transgene sequence is placed downstream of the poly A sequence. The L1-ORF2 comprises a nucleic acid sequence that encodes an endonuclease (EN) and a reverse transcriptase (RT) followed by the poly A sequence. In some embodiments, the L1-ORF2 sequence in the retrotransposition cassette described herein is a complete (intact) sequence, that is, encodes the full length native (WT) L1-ORF2 sequence. In some embodiments, the L1-ORF2 sequence in the retrotransposition cassette described herein comprises a partial or modified sequence.

The system described herein can comprise a promoter for expressing the L1-ORF1p and L1-ORF2p. In some embodiments, the transgene expression is driven by a separate promoter. In some embodiments, the transgene and the ORFs are in tandem orientation. In some embodiments, the transgene and the ORFs are in opposite orientation.

In some embodiments, the method comprises incorporating one or more elements in addition to the retrotransposon cassette. In some embodiments, the one or more additional elements comprise a nucleic acid sequence encoding one or more domains of a heterologous protein. The heterologous protein may be a sequence specific nucleic acid binding protein, for example, a sequence specific DNA binding protein domain (DBD). In some embodiments, the heterologous protein is a nuclease or a fragment thereof. In some embodiments, the additional elements comprise a nucleic acid sequence encoding one or more nuclease domains or fragments thereof from a heterologous protein. In some embodiments, the heterologous nuclease domain has reduced nuclease activity. In some embodiments, the heterologous nuclease domain is rendered inactive. In some embodiments, the ORF2 nuclease is rendered inactive; whereas one or more nuclease domains from the heterologous protein is configured to render specificity to the retrotransposition. In some embodiments, one or more nuclease domains or fragments thereof from the heterologous protein targets a specific desired polynucleotide within the genome where retrotransposition and incorporation of the polynucleotide of interest is to be incorporated. In some embodiments, the one or more nuclease domains from the heterologous protein comprise a mega-TAL nuclease domain, TALENs, or a zinc finger nuclease domain, for example, a mega-TAL, a TALE, or a zinc finger domain fused to or associated with a nuclease domain, e.g., a FokI nuclease domain. In some embodiments, the one or more nuclease domains from the heterologous protein comprise a CRISPR-Cas protein domain loaded with a specific guide nucleic acid, e.g., a guide RNA (gRNA) for a specific target locus. In some embodiments, the CRISPR-Cas protein is a Cas9, a Cas12a, a Cas12b, a Cas13, a CasX, or a CasY protein domain. In some embodiments, the one or more nuclease domains from the heterologous protein has target specificity.

In some embodiments, the additional nuclease domain may be incorporated into the ORF2 domain. In some embodiments, the additional nuclease may be fused with the ORF2p domain. In some embodiments, the additional nuclease domain may be fused to an ORF2p, wherein the ORF2p includes a mutation in the ORF2p endonuclease domain. In some embodiments, the mutation inactivates the ORF2p endonuclease domain. In some embodiments, the mutation is a point mutation. In some embodiments, the mutation is a deletion. In some embodiments, the mutation is an insertion. In some embodiments, the mutation abrogates the ORF2 endonuclease (nickase) activity. In some embodiments, a mutation inactivates the DNA target recognition of ORF2p endonuclease. In some embodiments, the mutation covers a region associated with ORF2p nuclease-DNA recognition. In some embodiments, a mutation reduces the DNA target recognition of ORF2p endonuclease. In some embodiments, the ORF2p endonuclease domain mutation is in the N-terminal region of the protein. In some embodiments, the ORF2p endonuclease domain mutation is in a conserved region of the protein. In some embodiments, the ORF2p endonuclease domain mutation is in the conserved N-terminal region of the protein. In some embodiments, the mutation comprises the N14 amino acid within L1 endonuclease domain. In some embodiments, the mutation comprises 2, 3, 4, 5, 6, 7, 8, 9, 10, 11, 12, 13, 14, 15, 16, 17, 18, 19, 20 or more consecutive amino acids including the N14 amino acid within L1 endonuclease domain. In some embodiments, the mutation comprises the comprises the E43 amino acid within L1 endonuclease. In some embodiments, the mutation comprises 2, 3, 4, 5, 6, 7, 8, 9, 10, 11, 12, 13, 14, 15, 16, 17, 18, 19, 20 or more consecutive amino acids including the E43 amino acid within L1 endonuclease domain. In some embodiments, the mutation comprises 2 or more amino acids in the L1 endonuclease domain including N14, or E43 or a combination thereof. In some embodiments, the mutation comprises D145 of the L1 endonuclease domain. In some embodiments, the mutation may be D145A. In some embodiments, the may be a comprise D205 of the L1 endonuclease domain. In some embodiments, the mutation may be D205G. In some embodiments, the mutation may comprise H230 of L1 endonuclease domain. In some embodiments, the may be a comprise S228 of the L1 endonuclease domain. In some embodiments, the mutation may be S228P.

In some embodiments, a mutation reduces the DNA target recognition of ORF2p endonuclease by at least 50%. In some embodiments, a mutation reduces the DNA target recognition of ORF2p endonuclease by at least 60%. In some embodiments, a mutation reduces the DNA target recognition of ORF2p endonuclease by at least 70%. In some embodiments, a mutation reduces the DNA target recognition of ORF2p endonuclease 80%. In some embodiments, a mutation reduces the DNA target recognition of ORF2p endonuclease 90%. In some embodiments, a mutation reduces the DNA target recognition of ORF2p by 95%. In some embodiments, a mutation reduces the DNA target recognition of ORF2p by 100%.

In some embodiments, the mutation is a deletion. In some embodiments, the deletion is complete, i.e., 100% of the L1 endonuclease domain is deleted. In some embodiments, the deletion is partial. In some embodiments, the about 98%, about 95%, about 94%, about 93%, about 92% about 91%, about 90%, about 85%, about 80%, about 75%, about 70%, about 65%, about 60%, or about 50% of the ORF2 endonuclease domain is deleted.

In some embodiments, an additional nuclease domain is inserted into the ORF2 protein sequence. In some embodiments, ORF2 endonuclease domain is deleted, and is replaced with an endonuclease domain from a heterologous protein. In some embodiments, the ORF2 endonuclease is partially deleted and replaced with an endonuclease domain from a heterologous protein. The endonuclease domain from a heterologous protein may be a mega-TAL nuclease domain. The endonuclease domain from a heterologous protein may be a TALENs. The endonuclease domain from a heterologous protein may be a Cas9 loaded with a specific gRNA for a locus.

In some embodiments, the endonuclease is an endonuclease that has (i) a specific target on the genome and (ii) it creates a 5'-P and a 3'-OH terminus at the cleavage site.

In some embodiments, the additional endonuclease domain from a heterologous protein is an endonuclease domain from a related retrotransposon.

In some embodiments, the endonuclease domain from a heterologous protein may comprise a bacterial endonuclease engineered for targeting a specific site. In some embodiments, the endonuclease domain from a heterologous protein may comprise a domain of a homing endonuclease or a fragment thereof. In some embodiments, the endonuclease is a homing endonuclease. In some embodiments, the homing endonuclease is an engineered LAGLIDADG homing endonucleases (LHEs) ("LAGLIDADG" disclosed as SEQ ID NO: 66) or a fragment thereof. In some embodiments, additional endonucleases may be a restriction endonuclease, Cre, Cas TAL or fragments thereof. In some embodiments, the endonuclease may comprise a Group II intron encoded protein (ribozyme) or a fragment thereof.

An engineered or modified L1-ORF2p as discussed in the preceding paragraphs, that is endowed with specific DNA targeting capability due to the additional/heterologous endonuclease is expected to be highly advantageous in driving targeted stable integration of a transgene into the genome. The engineered L1-ORF2p can generate much reduced off-target effects when expressed in a cell than using a native, non-engineered L1-ORF2p. In some embodiments, the engineered L1-ORF2p generates no off-target effect.

In some embodiments, the engineered or modified L1-ORF2p targets a recognition site that is other than the usual $(Py)_n{\downarrow}(Pu)_n$ site. In some embodiments, engineered L1-ORF2p targets a recognition site that comprises the $(Py)_n{\downarrow}(Pu)_n$ site, for example, TTTT/AA site, such as a hybrid target site. In some embodiments, the engineered L1-ORF2p targets a recognition site having at least one nucleotide in addition to the conventional L1-ORF2 $(Py)_n{\downarrow}(Pu)_m$ site, for example TTTT/AAG, or TTTT/AAC, or TTTT/AAT, TTTT/AAA, GTTTT/AA, CTTTT/AA, ATTTT/AA, or TTTTT/AA. In some embodiments, the engineered L1-ORF2p targets a recognition site that is in addition to the conventional L1-ORF2p $(Py)_n{\downarrow}(Pu)_n$ site. In some embodiments, the engineered L1-ORF2p targets a recognition site that is other than to the conventional L1-ORF2p $(Py)_n{\downarrow}(Pu)_n$ site. In some embodiments, the engineered L1-ORF2p targets a recognition site that is 4, 5, 6, 7, 8, 9, 10 or more nucleotides long. In some embodiments, the engineered or modified L1-ORF2p recognition site may be 11, 12, 13, 14, 15, 16, 17, 18, 19, 20 or more nucleotides.

The engineered L1-ORF2p can be engineered to retain its ability to bind to its own mRNA after translation and reverse transcribe with high efficiency. In some embodiments, the engineered L1-ORF2p has enhanced efficiency of reverse transcription compared to a native (WT) L1-ORF2p.

In some embodiments, the system comprising a retrotransposable element further comprises a gene modification that reduces non-specific retrotransposition. In some embodiments, the gene modification may comprise a sequence encoding the L1-ORF2p. In some embodiments, the modification may comprise mutation of one or more amino acids that are essential for binding to a protein that helps ORF2p binding to the target genomic DNA. A protein that helps ORF2p binding to the target genomic DNA may be part of the chromatin-ORF interactome. In some embodiments, the modification may comprise one or more amino acids that are essential for binding to a protein that helps ORF2p DNA endonuclease activity. In some embodiments, the modification may comprise one or more amino acids that are essential for binding to a protein that helps ORF2p RT activity. In some embodiments, the modification may comprise at a protein binding site on ORF2p such that the association of a protein with ORF2p is altered, wherein binding of the protein to ORF2p is required for binding to chromatin. In some embodiments, the modification may comprise at a protein binding site on ORF2p such that the association of the protein with ORF2p is more stringent and/or specific than in absence of the modification. In some embodiments, as a consequence of altered association of ORF2p with the protein owing to the modification of ORF2p coding sequence at the protein binding site, the binding of ORF2p to the target DNA has increased specificity. In some embodiments, the modification may reduce binding of ORF2 to one or more proteins that are part of the ORF2p chromatin interactome.

In some embodiments, the gene modification may be in the PIP domain of ORF2p.

In some embodiments, the gene modification may be in one or more genes encoding a protein that binds to an ORF2p and helps in the recognition, binding, endonuclease or RT activity of ORF2p. In some embodiments, the gene modification may be in one or more genes encoding PCNA, PARP1, PABP, MCM, TOP1, RPA, PURA, PURB, RUVBL2, NAP1, ZCCHC3, UPF1 or MOV10 proteins at an ORF2p interacting site for each protein or at a site that affects the protein's interaction with ORF2p or the interaction of ORF2p with target DNA. In some embodiments, the modification may be on an ORF2p binding domain of PCNA at an ORF2p interacting site or at a site that affects the protein's interaction with ORF2p or the interaction of ORF2p with target DNA. In some embodiments, the modification may be on an ORF2p binding domain of TOP1. In some embodiments, the modification may be on an ORF2p binding domain of RPA. In some embodiments, the modification may be on an ORF2p binding domain of PARP1 at an ORF2p interacting site or at a site that affects the protein's interaction with ORF2p or the interaction of ORF2p with target DNA. In some embodiments, the modification may be on an ORF2p binding domain of PABP (e.g., PABPC1) at an ORF2p interacting site or at a site that affects the protein's interaction with ORF2p or the interaction of ORF2p with target DNA. In some embodiments, the gene modification may be on an MCM gene. In some embodiments, the gene modification may be on a gene encoding MCM3 protein at an ORF2p interacting site or at a site that affects the protein's interaction with ORF2p or the interaction of ORF2p with target DNA. In some embodiments, the gene modification may be on a gene encoding MCM5 protein at an ORF2p interacting site or at a site that affects the protein's interaction with ORF2p or the interaction of ORF2p with target DNA. In some embodiments, the gene modification may be on a gene encoding MCM6 protein at an ORF2p interacting site or at a site that affects the protein's interaction with ORF2p or the interaction of ORF2p with target DNA. In some embodiments, the gene modification may be on a gene encoding MEPCE protein at an ORF2p interacting site or at a site that affects the protein's interaction with ORF2p or the interaction of ORF2p with target DNA. In some embodiments, the gene modification may be on a gene encoding on a gene encoding RUVBL1 or RUVBL2 protein at an ORF2p interacting site or at a site that affects the protein's interaction with ORF2p or the interaction of ORF2p with target DNA. In some embodiments, the gene modification may be on a gene encoding on a gene encoding TROVE protein at an ORF2p interacting site or at a site that affects the protein's interaction with ORF2p or the interaction of ORF2p with target DNA.

In some embodiments, the retrotransposition system disclosed herein comprises one or more elements that increase the fidelity of reverse transcription.

In some embodiments, the L1-ORF2 RT domain is modified. In some embodiments, the modification includes one or more of: increasing fidelity, increasing processivity, increasing DNA-RNA substrate affinity; or inactivating RNase H activity.

In some embodiments, the modification comprises introducing one or more mutations in the RT domain of the L1-ORF2, such that the fidelity of the RT is increased. In some embodiments, the mutation comprises a point mutation. In some embodiments, the mutation comprises alteration, such as substitution of one, two three, four, five, six or more amino acids in the L1-ORF2p RT domain. In some embodiments, the mutation comprises deletion of one or more amino acids, for example, one, two, three, four, five, six, seven, eight, nine, ten or more amino acids in the L1-ORF2p RT domain. In some embodiments, the mutation may comprise an in-del mutation. In some embodiments, the mutation may comprise a frame-shift mutation.

In some embodiments, the modification may comprise inclusion of an additional RT domain or fragment thereof from a second protein. In some embodiments, the second protein is a viral reverse transcriptase. In some embodiments, the second protein is a non-viral reverse transcriptase. In some embodiments, the second protein is a retrotransposable element. In some embodiments, the second protein is a non-LTR retrotransposable element. In some embodiments, the second protein is a group II intron protein. In some embodiments, the group II intron is as TGIRTII. In some embodiments, the second protein is a Cas nickase, wherein the retrotransposable system further comprises introducing a guide RNA. In some embodiments, the second protein is a Cas9 endonuclease, wherein the retrotransposable system further comprises introducing a guide RNA. In some embodiments, the second protein or fragment thereof is fused to the N-terminus of the L1-ORF2 RT domain or the modified L1-ORF2 RT domain. In some embodiments, the second protein or fragment thereof is fused to the C-terminus of the L1-ORF2 RT domain or the modified L1-ORF2 RT domain.

In some embodiments, the additional RT domain or fragment thereof from the second protein is incorporated in the retrotransposition system in addition to the full-length WT L1-ORF2p RT domain. In some embodiments, the additional RT domain or fragment thereof from the second protein is incorporated in presence of a modified (engineered) L1-ORF2p RT domain or a fragment thereof, where the modification (or engineering) may comprise a mutation for enhancement of the L1-ORF2p RT processivity, stability and/or fidelity of the modified L1-ORF2p RT compared to the native or WT ORF2p.

In some embodiments, the reverse transcriptase domain could be replaced with other more highly processive and high-fidelity RT domains from other retroelements or group II introns, such as TGIRTII.

In some embodiments, the modification may comprise a fusion with an additional RT domain or fragment thereof from a second protein. In some embodiments, the second protein may comprise a retroelement. The additional RT domain or fragment thereof from a second protein is configured to increase the fidelity of reverse transcription of the fused L1-ORF2p RT domain. In some embodiments, the nucleic acid encoding the additional RT domain or fragment thereof is fused to a native or WT L1-ORF2 encoding sequence. In some embodiments, the nucleic acid encoding the additional RT domain or fragment thereof from a second protein is fused to a modified L1-ORF2 encoding sequence. In some embodiments, the modification comprises introducing one or more mutations in the RT domain of the L1-ORF2 or fragment thereof, such that the fidelity of the fused RT is increased. In some embodiments, the mutation in the RT domain of the L1-ORF2 or fragment thereof comprises a point mutation. In some embodiments, the mutation comprises alteration, such as substitution of one, two three, four, five, six or more amino acids in the L1-ORF2p RT domain. In some embodiments, the mutation comprises deletion of one or more amino acids, for example, one, two, three, four, five, six, seven, eight, nine, ten or more amino acids in the L1-ORF2p RT domain. In some embodiments, the mutation may comprise an in-del mutation. In some embodiments, the mutation may comprise a frame-shift mutation.

In some embodiments, the modified L1-ORF2p RT domain has increased processivity than the WT L1-ORF2p RT domain.

In some embodiments, the modified L1-ORF2p RT domain has at least 10% higher processivity and/or fidelity over the WT L1-ORF2p RT domain. In some embodiments, the modified L1-ORF2p RT domain has at least 20%, 30%, 40%, 50%, 60%, 70%, 80%, 90%, 100%, 110%, 120%, 150%, 200%, 300%, 400%, 500%, 1000% or higher processivity and/or fidelity over the WT L1-ORF2p RT domain. In some embodiments, the modified RT can process greater than 6 kb nucleic acid stretch. In some embodiments, the modified RT can process greater than 7 kb nucleic acid stretch. In some embodiments, the modified RT can process greater than 8 kb nucleic acid stretch. In some embodiments, the modified RT can process greater than 9 kb nucleic acid stretch. In some embodiments, the modified RT can process greater than 10 kb nucleic acid stretch.

B. Group II Introns and Ribozymes

Group II enzymes are mobile ribozymes that self-splice precursor RNAs, yielding excised intron lariat RNAs. The introns encode a reverse transcriptase. The reverse transcriptase may stabilize the RNA for forward and reverse splicing, and later in converting the integrated intron RNA to DNA.

Group II RNAs are characterized by a conserved secondary structure spanning 400-800 nucleotides. The secondary structure is formed by six domains DI-VI, and is organized in a structure resembling a wheel, where the domains radiate from a central point. The domains interact to form a conserved tertiary structure that brings together distant sequences to form an active site. The active site binds the splice sites and branch point residue nucleotide and in association of Mg2+ cations, activate catalysis of splicing. The DV domain is within the active site, which has the conserved catalytic AGC and an AY bulge and both these regions bind Mg2+ ions necessary for the catalysis. DI is the largest domain with upper and lower halves separated by kappa and zeta motifs. The lower half contains the ε' motif, which is associated with an active site. The upper half contains sequence elements that bind to the 5' and 3' exons at the active sites. DIV encodes the intron-encoded protein (IEP) with subdomain IVa near the 5'-end containing the high affinity binding site for IEP. Group II introns have conserved 5'- and 3'-end sequences, GUGYG and AY respectively.

Group II RNA introns can be utilized to retrotranspose a sequence of interest into DNA via target primed reverse transcription. This process of transposition by Group II RNA introns is often referred to as retrohoming. Group II introns recognize DNA target sites by base pairing of the intron RNA to the DNA target sequence, they can be modified to retarget a specific sequence carried within the intron to a desired DNA site.

In some embodiments, the method and compositions for retrotransposition described herein may comprise a Group II intron sequence, a modified Group II intron sequence or a fragment thereof. Exemplary Group II IEPs (maturase) include but are not limited to bacterial, fungal, yeast IEPs, that are functional in human cells. In particular, the nuclease leaves a 3'-OH at the cleavage site of the DNA which can be utilized by another RT for priming and reverse transcription. An exemplary Group II maturase may be TGIRT (thermally stable group II intron maturase).

In one or more embodiments of several aspects described herein, the nucleic acid construct comprises an RNA. In one or more embodiments of several aspects of the disclosure, the nucleic acid construct is an RNA. In one or more embodiments of several aspects of the disclosure, the nucleic acid construct is an mRNA. In one aspect, the mRNA comprises a sequence of a heterologous gene or portion thereof, wherein the heterologous gene or portion thereof encodes a polypeptide or protein. In some embodiments, the mRNA comprises a sequence encoding a fusion protein. In some embodiments, the mRNA comprises a sequence encoding a recombinant protein. In some embodiments, the mRNA comprises a sequence encoding a synthetic protein. In some embodiments, the nucleic acid comprises one or more sequences, wherein the one or more sequences encode on or more heterologous proteins, one or more recombinant proteins, or one or more synthetic proteins or a combination thereof. In some embodiments, the nucleic acid comprises one or more sequences, wherein the one or more sequences encode on or more heterologous proteins comprising a synthetic protein or a recombinant protein. In some embodiments, the synthetic or recombinant protein is a recombinant fusion protein.

C. Retrotransposon Systems Comprising an Site Directed Editing and/or Integrase

In one aspect, provided herein are methods of using retrotransposition having high target specificity following modification over the pegRNA mediated incorporation of LINE binding sequences site-specifically into the genome, with the help of guide RNA and a Cas protein. In some embodiments, a CRISPR-Cas guide RNA system is combined with the LINE-retrotransposon system used here to increase the precision of site directed retrotransposition; for example, the system incorporates a prime editing guide RNA (pegRNA) to incorporate one or more ORF-binding sequence into a specific genomic locus. In some embodiments, the pegRNA incorporates the sequence that binds human ORF, e.g. TTTTTA in a site-specific manner. In some embodiments, the CRISPR-Cas system comprises a Cas9 enzyme. In some embodiments the CRISPR-Cas comprises a Cfp1 enzyme. In some embodiments, the Cas9 is a dCas9, paired with a nickase system.

In some embodiments, the retrotransposon systems described herein comprise (i) a LINE1 retrotransposon element, and (ii) an integrase system or parts thereof. Some integrase systems are capable of site-specific integration—of double stranded DNA. In order to bypass the double stranded DNA delivery and/or integration into a genome, provided herein is a recombinant hybrid system wherein the integrase or a fragment thereof incorporated within a recombinant ORF protein, or delivered separately as a separate nucleic acid (e.g. mRNA) encoding an integrase or fragment thereof that recognizes a specific genomic site; and couples with the LINE 1 reverse transcription and insertion of a cargo sequence within the genome of a cell or an organism at the precise location led by the specificity of the integrase. This could be achieved in a few alternative ways. In some embodiments, the cargo sequence comprises an attachment site that is recognized and utilized by the integrase to draw the cargo to the landing site within the genome, also recognized by the same integrase. The integrase is capable of a single strand cut. The integrase DNA recognition site, i.e., the genomic landing sequence, can be 10 nucleotides long, e.g., 12, 14, 16, 18, 20, 22, 24, 26, 28, 30 or more nucleotides long, thereby conferring greater specificity than any other system. The integrase may be truncated or otherwise mutated to allow the ORF to reverse transcribe and integrate the cargo sequence at the integrase specified genomic site. Conversely, the ORF protein may also be mutated at the RNA recognition site to allow the integrase recognize the genomic integration sequence preferentially recognized by the integrase (also termed the "genomic landing sequence or site". In alternative embodiments, the integrase is encoded by a separate polynucleotide, and may be driven by a CRISPR Cas system and a guide RNA to a site that can be nicked and an integrase landing sequence further comprising an ORF binding site comprising the 4 nucleotides may be introduced, thereafter the integrase draws in the cargo sequence that comprises the attachment sequence to the landing sequence, followed by the LINE1 activity leading to genomic integration at the site specified by the integrase system. Any catalytic activity of the integrase leading to double-stranded DNA incorporation in the genome is mutated or truncated, otherwise, silenced.

In one or more of embodiments of several aspects of the disclosure, the nucleic acid construct is developed for expressing in a eukaryotic cell. In some embodiments, the nucleic acid construct is developed for expressing in a human cell. In some embodiments, the nucleic acid construct is developed for expressing in a hematopoietic cell. In some embodiments, the nucleic acid construct is developed for expressing in a myeloid cell. In some embodiments, the myeloid cell is a human cell.

II. Modifications in Nucleic Acid Constructs for Methods of Enhancement of Expression of Encoded Protein In some aspects of the disclosure, the recombinant nucleic acid is modified for enhanced expression of the protein encoded by a sequence of the nucleic acid. Enhanced expression of the protein encoded therein can be a function of the nucleic acid stability, translation efficiency and the stability of the translated protein. A number of modifications are contemplated herein for incorporation in the design of the nucleic acid construct that can confer nucleic acid stability, such as stability of the messenger RNA encoding the exogenous or heterologous protein, which may be a synthetic recombinant protein or a fragment thereof.

In some embodiments, the nucleic acid is mRNA, comprising one or more sequences, wherein the one or more sequences encode one or more heterologous proteins comprising a synthetic or a recombinant fusion protein.

In some embodiments, one or more modifications are made in the mRNA comprising a sequence encoding a recombinant or fusion protein to increase the mRNA half-life.

Structural Elements to Block 5'- and 3'-Degradations by Exonucleases: 5'-Cap and 3' UTR Modifications A proper 5'-cap structure is important in the synthesis of functional messenger RNA. In some embodiments, the 5'-cap comprises a guanosine triphosphate arranged as GpppG at the 5' terminus of the nucleic acid. In some embodiments, the mRNA comprises a 5' 7-methylguanosine cap, m7-GpppG. A 5' 7-methylguanosine cap increases mRNA translational efficiency and prevents degradation of mRNA 5'-3' exonucleases. In some embodiments, the mRNA comprises "anti-reverse" cap analog (ARCA, $m^{7,3'-O}$GpppG). Translational efficiency, however, can be markedly increased by usage of the ARCA. In some embodiments, the guanosine cap is a Cap 0 structure. In some embodiments, the guanosine cap is a Cap 1 structure. In addition to its essential role of cap-dependent initiation of protein synthesis, the mRNA cap also functions as a protective group from 5' to 3' exonuclease cleavage and a unique identifier for recruiting protein factors for pre-mRNA splicing, polyadenylation and nuclear export. It acts as the anchor for the recruitment of initiation factors that initiate protein synthesis and the 5' to 3' looping of mRNA during translation. Three enzymatic activities are required to generate the Cap 0 structure, namely, RNA triphosphatase (TPase), RNA guanylyltransferase (GTase) and guanine-N7 methyltransferase (guanine-N7 MTase). Each of these enzyme activities carries out an essential step in the conversion of the 5' triphosphate of nascent RNA to the Cap 0 structure. RNA TPase removes the γ-phosphate from the 5' triphosphate to generate 5' diphosphate RNA. GTase transfers a GMP group from GTP to the 5' diphosphate via a lysine-GMP covalent intermediate. The guanine-N7 MTase then adds a methyl group to the N7 amine of the guanine cap to form the cap 0 structure. For Cap 1 structure, m7G-specific 2'O methyltransferase (2'O MTase) methylates the +1 ribonucleotide at the 2'O position of the ribose to generate the cap 1 structure. The nuclear RNA capping enzyme interacts with the polymerase subunit of RNA polymerase II complex at phosphorylated Ser5 of the C-terminal heptad repeats. RNA guanine-N7 methyltransferase also interacts with the RNA polymerase II phosphorylated heptad repeats. In some embodiments, the cap is a G-quadruplex cap.

In some embodiments, the mRNA is synthesized by in vitro transcription (IVT). In some embodiments, mRNA synthesis and capping may be performed in one step. Capping may occur in the same reaction mixture as IVT. In some embodiments, mRNA synthesis and capping may be performed in separate steps. mRNA thus formed by IVT is purified and then capped.

In some embodiments, the nucleic acid construct, e.g., the mRNA construct, comprises one or more sequences encoding a protein or a polypeptide of interest can be designed to comprise elements that protect, prevent, inhibit or reduce degradation of the mRNA by endogenous 5'-3' exoribonucleases, for example, Xrn1. Xrn1 is a cellular enzyme in the normal RNA decay pathways that degrades 5' monophosphorylated RNAs. However, some viral RNA structural elements are found to be particularly resistant to such RNases, for example, the Xrn1-resistant structure in flavivirus sfRNAs, called the 'xrRNA'. For example, the mosquito-borne flaviviruses (MBFV) genomes contain discrete RNA structures in their 3'-untranslated region (UTR) that block the progression of Xrn1. These RNA elements are sufficient to block Xrn1 without the use of accessory proteins. xrRNAs halt the enzyme at a defined location such that the viral RNA located downstream of the xrRNAs is protected from degradation. The xrRNAs from Zika virus or Murray Valley encephalitis virus, for example, comprise three-way junction and multiple pseudoknot interactions that create an unusual and complex fold that requires a set of nucleotides conserved across the MBFVs structure. xrRNAs halt the enzyme at a defined location such that the viral RNA located downstream of the xrRNAs is protected from degradation. The 5'-end of the RNA passes through a ringlike structure of the fold and is believed to remain protected from the Xrn1-like exonuclease.

In some embodiments, the nucleic acid construct comprising the one or more sequences that encode a protein of interest may comprise one or more xrRNA structures incorporated therein. In some embodiments, the xrRNA is a stretch of nucleotides having the conserved regions of the 3' UTR of one or more viral xrRNA sequences. In some embodiments, 1, 2, 3, 4, 5, 6, 7, 8, 9, 10 or more xrRNA elements are incorporated within the nucleic acid construct. In some embodiments, 2 or more xrRNA elements are incorporated in tandem within the nucleic acid construct. In some embodiments, the xrRNA comprise one or more regions comprising conserved sequences or fragments thereof or modifications thereof. In some embodiments, the xrRNA is placed at the 3'UTR of a retrotransposon element. In some embodiments, the xrRNA is placed at upstream of the sequences encoding the one or more proteins or polypeptides. In some embodiments, the xrRNA is placed in the 3'UTR of a retrotransposon element, such as an ORF2 sequence, and upstream of the sequences encoding the one or more proteins or polypeptides.

In some embodiments, the xrRNA structure comprises a MBFV xrRNA sequence, or a sequence that is at least 90% identical thereof. In some embodiments, the xrRNA structure comprises a tick-borne flaviviruses (TBFVs) xrRNA sequence, or a sequence that is at least 90% identical thereof. In some embodiments, the xrRNA structure comprises a tick-borne flaviviruses (TBFVs) xrRNA sequence, or a sequence that is at least 90% identical thereof. In some embodiments, the xrRNA structure comprises a tick-borne flaviviruses (TBFVs) xrRNA sequence, or a sequence that is at least 90% identical thereof. In some embodiments, the xrRNA structure comprises a xrRNA sequence from a member of no known arthropod vector flaviviruses (NKVFVs), or a sequence that is at least 90% identical thereof. In some embodiments, the xrRNA structure comprises a xrRNA sequence from a member of insect-specific flaviviruses (ISFVs), or a sequence that is at least 90% identical thereof. In some embodiments, the xrRNA structure comprises a Zikavirus xrRNA sequence, or a sequence that is at least 90% identical thereof. It is hereby contemplated that any known xrRNA structural elements or conceivable non-obvious variations thereof may be used for the purpose described herein.

Several messenger RNAs from different organisms exhibit one or more pseudoknot structures that exhibits resistance from 5'-3' exonuclease. A pseudoknot is a RNA structure that is minimally composed of two helical segments connected by single-stranded regions or loops. Although several distinct folding topologies of pseudoknots exist.

Poly A Tail Modifications

The poly A structure in the 3'UTR of an mRNA is an important regulator of mRNA half-life. Deadenylation of the 3' end of the poly A tail is the first step of the intracellular mRNA degradation. In some embodiments, the length of the poly A tail of the mRNA construct is taken into critical consideration and designed for maximizing the expression of the protein encoded by the mRNA coding region, and the mRNA stability. In some embodiments, the nucleic acid construct comprises one or more poly A sequences. In some embodiments, the poly A sequence at the 3'UTR of the sequences encoding the one or more proteins or polypeptides comprise 20-200 adenosine nucleobases. In some embodiments, the poly A sequence comprises 30-200 adenosine nucleobases. In some embodiments, the poly A sequence comprises 50-200 adenosine nucleobases. In some embodiments, the poly A sequence comprises 80-200 adenosine nucleobases. In some embodiments, the mRNA segment comprising the sequences that encode one or more proteins or polypeptides comprises a 3'-UTR having a poly-A tail comprising about 180 adenosine nucleobases, or about 140 adenosine nucleobases, or about 120 adenosine nucleobases. In some embodiments, the poly A tail comprises about 122 adenosine nucleobases. In some embodiments, the poly A sequence comprises 50 adenosine nucleobases. In some embodiments, the poly A sequence comprises 30 adenosine nucleobases. In some embodiments, the adenosine nucleobases in the poly A tail are placed in tandem, with or without intervening non-adenosine bases. In some embodiments, one or more non-adenosine nucleobases are incorporated in the poly A tail, which confer further resistance to certain exonucleases.

In some embodiments, the stretch of adenosines in poly A tail of the construct comprises one or more non-adenosine (A) nucleobase. In some embodiments, the non-A nucleobase is present at −3, −2, −1, and/or +1 position at the poly A 3'-terminal region. In some embodiments, the non-A bases comprise a guanosine (G) or a cytosine (C) or an uracil base (U). In some embodiments, the non-A base is a G. In some embodiments, the non-A base more than one, in tandem, for example, GG. In some embodiments, the modification at the 3' end of the poly A tail with one or more non-A base is directed at disrupting the A base stacking at the poly A tail. The poly A base stacking promotes deadenylation by various deadenylating enzymes, and therefore 3' end of poly A tail ending in -AAAG, -AAAGA, or -AAAGGA are effective in conferring stability against deadenylation. In some organisms, a GC sequence intervening a poly A sequence is shown to effectively show down 3'-5' exonuclease mediated decay. A modification contemplated herein comprises an intervening non-A residue, or a non-A residue duplex intervening a poly A stretch at the 3' end.

In some embodiments, a triplex structure is introduced in the 3' UTR which effectively stalls or slows down exonuclease activity involving the 3' end.

In some embodiments, the mRNA with the modifications described above has an extended half-life and demonstrates stable expression over a longer period than the unmodified mRNA. In some embodiments, the mRNA stably expresses for greater than 2 days, 3 days, 4 days, 5 days, 6 days, 7 days, 8 days 9 days or 10 days or more, and the mRNA or its protein product is detectable in vivo. In some embodiments, the mRNA is detected up to 3 days, 4 days, 5 days, 6 days, 7 days, 8 days, 9 days, 10 days, 11 days, 12 days, 13 days, 14 days or 15 days in vivo. In some embodiments, a protein product of the mRNA is detected up to 3 days, 4 days, 5 days, 6 days, 7 days, 8 days, 9 days, 10 days, 11 days, 12 days, 13 days, 14 days, 15 days, 16 days, 17 days, 18 days, 20 days, 25 days or 30 days in vivo.

CircRNA and tectoRNA

Figure 3A:
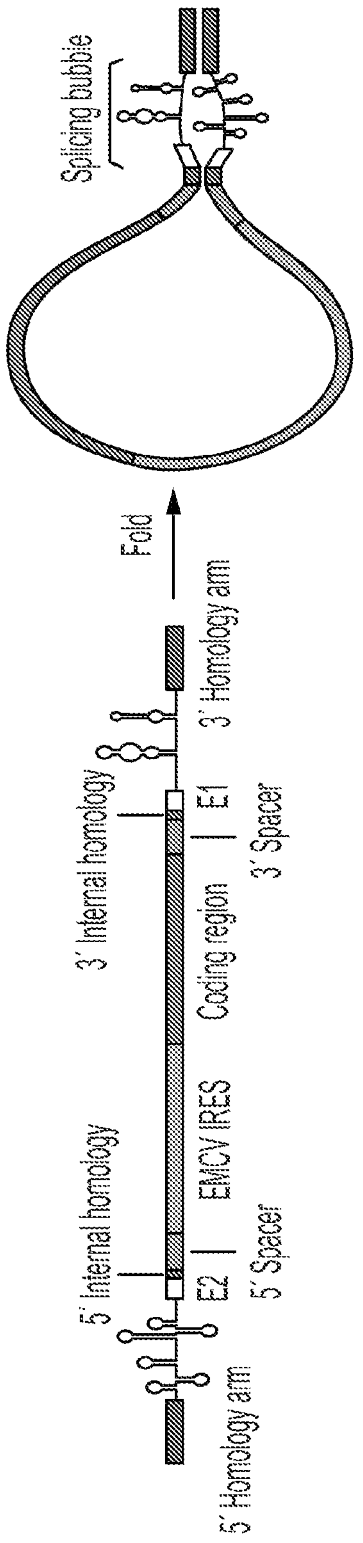
FIG. 3A illustrates an exemplary diagram of conventional circRNA structure and formation.

Circular RNA is useful in the design and production of stable form of RNA used as a messenger RNA to direct synthesis protein chains, such as long, multiply repeating protein chains. There are few methods to make circular RNA (circRNA). They include protein-mediated ligation of RNA ends using RNA ligase and using a split self-splicing intron, such that if the two halves of the intron are located and the ends of a transcribed mRNA, the intron will splice itself out and leave a ligated product (FIG. 3A). Another technique relies on the ability of T4 DNA ligase to act as an RNA ligase when the RNA ends to be ligated are held together by an oligonucleotide. Both these techniques suffer from inefficiency and require a large amount of enzyme. A third technique uses the cyclization or circularization activity of group I introns where most of the intron sequences that carry out the reaction must remain a part of the circle. Group I introns share a complex set of secondary and tertiary structures containing a series of conserved RNA stem loops which form the catalytic core. Many of these introns are self-splicing in vitro and can splice and form two ligated exons as RNA with no accessory protein factors. The products created by the group I autocatalytic reaction are (1) an upstream exon ligated at the 5' splice site to the 3' splice site of a downstream exon and (2) a linear intron that can undergo further reversible auto-catalysis to form a circular intron. The presence of such a large highly structured nucleic acid sequence severely limits the types of RNA sequences that can be made circular by that technique. In addition, the catalytic activity of the intron may remain and interfere with structure and function of the circular RNA.

It is useful to increase the rate of the reaction, and thus the overall efficiency, by bringing the ends of the RNA in closer proximity. Previous work has achieved this by including complementary RNA sequences 3' and 5' to the ends of the mRNA such that upon hybridization of these sequences, the ends of the mRNA are in closer proximity such that it can undergo the ligation or self-splicing reaction with an overall faster rate compared to without the complementary sequences. These are called homology arms (FIG. 3A) of the self-splicing version of the circularization reaction. A major issue with such hybridization strategy is that if there are complementary sequences within the coding region to either of the homology arms, hybridization would actually inhibit the splicing reaction and the arms would need to be optimized for each new coding region. An alternative to this strategy described herein is the use of RNA sequences that fold a three-dimensional structure to form a stable binding interaction that is independent of sequence.

Non-Watson-Crick RNA tertiary interactions can be exploited to construct 'tectoRNA' molecular units, defined as RNA molecules capable of self-assembly. The use of such type of tertiary interactions allows one to control and modulate the assembly process by manipulating cation concentration (e.g. $Mg^{2+}$), and/or suitable temperature and employing modularly designed 'selector' RNA molecules. For the self-assembly of one-dimensional arrays, a basic modular unit was designed that comprises a 4-way junction with an interacting module on each helical arm. In some embodiments, the interacting module is a GAAA loop or a specific GAAA loop receptor. Each tectoRNA can interact with two other tectoRNAs via the formation of four loop-receptor interactions, two with each partner molecule.

In some embodiments, the tectoRNA structures are suitably selected, and integrated in the RNA comprising the exon and intron to form a circRNA. In some embodiments, the integration is done by well-known molecular biology techniques such as ligation. In some embodiments, the tectoRNA forms a stable structure at high temperatures. The tectoRNA structure do not compete with internal RNA sequences, thereby creating high efficiency circularization and splicing.

The circRNA can comprise a coding sequence described in any of the preceding sections. For example, it can comprise a sequence encoding fusion protein comprising a tethering or a receptor molecule. The receptor can be a phagocytic receptor fusion protein.

In some embodiments, the intron is a self-splicing intron.

In some embodiments, the terminal regions having the tertiary structures, also termed scaffolding regions for the circRNA, are about 30 nucleotides to about 100 nucleotides long. In some embodiments, the tertiary structure motif is about 45 nucleotides, about 50 nucleotides, about 55 nucleotides, about 60 nucleotides, about 65 nucleotides, about 70 nucleotides or about 75 nucleotides long. In some embodiments, the tertiary motifs are formed at high temperatures. In some embodiments, the tertiary motifs are stable.

In some embodiments, the nucleic acid construct having the one or more modifications as described herein and comprising one or more sequences encoding one or more proteins or polypeptides, is stable when administered in vivo. In some embodiments, the nucleic acid is an mRNA. In some embodiments, the mRNA comprising one or more sequences encoding one or more proteins or polypeptides is stable in vivo for more than 2 days, for more than 3 days, more than 4 days, more than 5 days, more than 6 days, more than 7 days, more than 8 days, more than 9 days, more than 10 days, more than 11 days, more than 12 days, more than 13 days, more than 14 days, more than 15 days, more than 16 days, more than 17 days, more than 18 days, more than 19 days, or more than 20 days. In some embodiments, the protein encoded by the sequences in the mRNA can be detected in vivo at greater than 3 days, 4 days, 5 days, 6 days, 7 days, 8 days, 9 days, 10 days, 11 days, 12 days, 13 days, 14 days, 15 days, 16 days, 17 days, 18 days, 19 days, or 20 days. In some embodiments, the protein encoded by the sequences in the mRNA can be detected in vivo for about 7 days after the mRNA is administered. In some embodiments, the protein encoded by the sequences in the mRNA can be detected in vivo for about 14 days after the mRNA is administered. In some embodiments, the protein encoded by the sequences in the mRNA can be detected in vivo for about 21 days after the mRNA is administered. In some embodiments, the protein encoded by the sequences in the mRNA can be detected in vivo for about 30 days after the mRNA is administered. In some embodiments, the protein encoded by the sequences in the mRNA can be detected in vivo for more than about 30 days after the mRNA is administered.

In some aspects, enhancing nucleic acid uptake or incorporation within the cell is contemplated for enhancing expression of the retrotransposition. One of the methods include obtaining a homogenous population of cells to initiate incorporation of the nucleic acid, e.g. via transfection, in case of plasmid vector constructs, or via electroporation or any other means that may be used suitably to deliver a nucleic acid molecule into the cell. In some embodiments, cell cycle synchronization may be sought. Cell cycle synchronization may be accomplished by sorting cells for a certain common phenotype. In some embodiments, the cell population may be subjected to a treatment with a reagent that can stall cell cycle progression of all cells at a certain stage. Exemplary reagents can be found in commercial databases, such as www.tocris.com/cell-biology/cell-cycle-inhibitors, or www.scbt.com/browse/chemicals-Other-Chemicals-cell-cycle-arresting-compounds. For example, itraconazole or nocodazole inhibits cell cycle at G1 phase, or reagents that arrest cell cycle at G0/G1 phase, for example, 5-[(4-Ethylphenyl)methylene]-2-thioxo-4-thiazolidinone (compound 10058-F4) (Tocris Bioscience); or a G2M cell cycle blocker, such as AZD 5438 (chemical name, 4-[2-Methyl-1-(1-methylethyl)-1H-imidazol-5-yl]-N-[4-(methylsulfonyl)phenyl]-2-pyrimidinamine) which blocks cell cycle at G2M, G1 or S phases, to name a few. Cyclosporin, hydroxyurea, thymidine, are well known reagents that can cause cell cycle arrests. Some reagents may irreversibly alter a cell state or may be toxic for the cells.

Serum deprivation of cells for about 2-16 hours prior to electroporation or transfection, depending on the cell type, may also be an easy and reversible strategy for cell synchronization.

In some embodiments, retrotransposition efficiency may be increased by encouraging generation of DNA double stranded breaks to a cell that has been transfected with or electroporated with the retrotransposition constructs as described herein and/or modulating the DNA repair machinery.

Application of these techniques may be limited depending on end uses of the cell that would undergo the genetic manipulation ex vivo for stable incorporation of a nucleic acid sequence by this method. In some cases, use of such techniques may be contemplated where robust expression of the protein or transcript encoded by the incorporated nucleic acid is expected as an outcome for a determined period of time. Method of introducing double stranded breaks in a cell include subjecting the cell to controlled ionizing radiation of about 0.1 Gy or less for a short period.

In some embodiments, efficiency of LINE-1 mediated retrotransposition may be increased by treating the cell with small molecule inhibitors of DNA repair proteins to increase the window for the reverse transcriptase to act. Exemplary small molecule inhibitors of DNA repair proteins may be Benzamide (CAS 55-21-0), Olaparib (Lynparza) (CAS 763113-22-0), Rucaparib (Clovis-AG014699, PF-01367338 Pfizer), Niraparib (MK-827 Tesaro) CAS 1038915-60-4); Veliparib (ABT-888 Abbvie) (CAS 912444-00-9); Camptothecin (CPT) (CAS 7689-03-4); Irinotecan (CAS 100286-90-6); Topotecan (Hycamtin® GlaxoSmithKline) (CAS 123948-87-8); NSC 19630 (CAS 72835-26-8); NSC 617145 (CAS 203115-63-3); ML216 (CAS 1430213-30-1); 6-hydroxyDL-dopa (CAS 21373-30-8); D-103; D-G23; DIDS (CAS 67483-13-0); B02 (CAS 1290541-46-6); RI-1 (CAS 415713-60-9); RI-2 (CAS 1417162-36-7); Streptonigrin (SN) (CAS 3930-19-6).

III. Nucleic Acid Carzo:

A. Transgene

In one aspect the transgene or noncoding sequence that is the heterologous nucleic acid sequence to be inserted within the genome of a cell is delivered as an mRNA. The mRNA may comprise greater than about 100, 200, 300, 400, 500, 600, 700, 800, 900, 1000, 1100, 1200, 1300, 1400, 1500, 1600, 1700, 1800, 1900, 2000, 3000, 4000, 5000, 6000, 7000, 8000, 9000, 10,000 bases. In some embodiments, the mRNA may be more than 10,000 bases long. In some embodiments, the mRNA may be about 11,000 bases long.

In some embodiments, the mRNA may be about 12,000 bases long. In some embodiments, the mRNA comprises a transgene sequence that encodes a fusion protein. In some embodiments, the nucleic acid is delivered as a plasmid.

In some embodiments, the nucleic acid is delivered in the cell by transfection. In some embodiments, the nucleic acid is delivered in the cell by electroporation. In some embodiments, the transfection or electroporation is repeated more than once to enhance incorporation of the nucleic acid into the cell.

Contemplated herein are retrotransposon mediated stable integration of a recombinant nucleic acid encoding a phagocytic or tethering receptor (PR) fusion protein (CFP). In some embodiments, the CFPs comprise: a PR subunit comprising: a transmembrane domain, and an intracellular domain comprising an intracellular signaling domain; and an extracellular domain comprising an antigen binding domain specific to an antigen of a target cell; wherein the transmembrane domain and the extracellular domain are operatively linked.

In some embodiments, the nucleic acid comprises a sequence encoding a chimeric fusion protein (CFP), the CFP comprising an extracellular domain comprising a CD5 binding domain, and a transmembrane domain operatively linked to the extracellular domain. In some embodiments, the CD5 binding domain is a CD5 binding protein, such as an antigen binding fragment of an antibody, a Fab fragment, an scFv domain or an sdAb domain. In some embodiments, wherein the CD5 binding domain comprises an scFv comprising (i) a variable heavy chain (VH) sequence with at least 90% sequence identity to EIQLVQSGG-GLVKPGGSVRISCAASGYTFTNYGMNWVRQAPGK-GLEWMGWINTHTGEPTYAD SFKGRFTFSLDDSKN-TAYLQINSLRAEDTAVYFCTRRGYDWYFDVWGQG-TTVTV (SEQ ID NO: 1); and (ii) a variable light chain (VL) sequence with at least 90% sequence identity to DIQMTQSPSSLSASVGDRVTITCRASQDIN-SYLSWFQQKPGKAPKTLIYRANRLESGVPSRFSGSG SGTDYTLTISSLQYEDFGIYYCQQYDESPWTFGGGT-KLEIK (SEQ ID NO: 2). In some embodiments, the CFP further comprises an intracellular domain, wherein the intracellular domain comprises one or more intracellular signaling domains, and wherein a wild-type protein comprising the intracellular domain does not comprise the extracellular domain. In some embodiments, the one or more intracellular signaling domains comprises a phagocytic signaling domain. In some embodiments, the phagocytosis signaling domain comprises an intracellular signaling domain derived from a receptor other than Megf10, MerTk, FcαR, and Bai1. In some embodiments, the phagocytosis signaling domain comprises an intracellular signaling domain derived from FcγR, FcαR or FcεR. In some embodiments, the phagocytosis signaling domain comprises an intracellular signaling domain with at least 90% sequence identity to LYCRRLKIQVRKAAITSYEKSDGVYTGLSTRNQETY-ETLKHEKPP (SEQ ID NO: 67). In some embodiments, the one or more intracellular signaling domains further comprises a proinflammatory signaling domain. In some embodiments, the proinflammatory signaling domain comprises a PI3-kinase (PI3K) recruitment domain. In some embodiments, the proinflammatory signaling domain comprises a sequence with at least 90% sequence identity to YEDMRGILYAAPQLRSIRGQPGPNHEEDADSYENM (SEQ ID NO: 4). In some embodiments, the proinflammatory signaling domain is derived from an intracellular signaling domain of CD40. In some embodiments, the proinflammatory signaling domain comprises a sequence with at least 90% sequence identity to KVAKKPTNKAPHPKQEPQEINFPDDLPGSN-TAAPVQETLHGCQPVTQEDGKESRISVQERQ (SEQ ID NO: 68). In some embodiments, the transmembrane domain comprises a CD8 transmembrane domain. In some embodiments, the transmembrane domain comprises a sequence with at least 90% sequence identity to IYI-WAPLAGTCGVLLLSLVIT (SEQ ID NO: 6). In some embodiments, the extracellular domain further comprises a hinge domain derived from CD8, wherein the hinge domain is operatively linked to the transmembrane domain and the CD5 binding domain. In some embodiments, the extracellular domain comprises a sequence with at least 90% sequence identity to ALSNSIMYFSHFVPVFLPAKPTTT-PAPRPPTPAPTIASQPLSLRPEACRPAAGGAVHTRGLD (SEQ ID NO: 7). In some embodiments, the CFP comprises an extracellular domain comprising a scFv that specifically binds CD5, and a hinge domain derived from CD8; a hinge domain derived from CD28 or at least a portion of an extracellular domain from CD68; a CD8 transmembrane domain, a CD28 transmembrane domain or a CD68 transmembrane domain; and an intracellular domain comprising at least two intracellular signaling domains, wherein the at least two intracellular signaling domains comprise: a first intracellular signaling domain derived from FcγR or FcεR, and a second intracellular signaling domain comprising a PI3K recruitment domain, or derived from CD40. In some embodiments, the recombinant polynucleic acid is an mRNA or circRNA. In some embodiments, the nucleic acid is delivered into a myeloid cell. In some embodiments, the nucleic acid is delivered into a CD14+ cell, a CD14+CD16− cell, an M0 macrophage, an M2 macrophage, an M1 macrophage or a mosaic myeloid cell/macrophage. In some embodiments, the fusion protein comprises a sequence with at least 90% sequence identity to EIQLVQSGGGLVKPGGSVRISCAASGYTFTNYGMNWVRQAPGKGLEWMGWINTHTGEPTYAD SFKGRFTFSLDDSKNTAYLQINSLRAEDTAVYFCTRRGYDWYFDVWGQGTTVTVSSGGGGSGG GGSGGGGSDIQMTQSPSSLSASVGDRVTITCRASQDINSYLSWFQQKPGKAPKTLIYRANRLESG VPSRFSGSGSGTDYTLTISSLQYEDFGIYYCQQYDESPWTFGGGTKLEIKSGGGGSGALSNSIMYF SHFVPVFLPAKPTTTPAPRPPTPAPTIASQPLSLRPEACRPAAGGAVHTRGLDIYIWAPLAGTCGV LLLSLVITLYCRRLKIQVRKAAITSYEKSDGVYTGLSTRNQETYETLKHEKPPQGSGSYEDMRGI LYAAPQLRSIRGQPGPNHEEDADSYENM (SEQ ID NO: 69). In some embodiments, the fusion protein comprises a sequence with at least 90% sequence identity to (SEQ ID NO: 70)

```
EIQLVQSGGGLVKPGGSVRISCAASGYTFTNYGMN
WVRQAPGKGLEWMGWINTHTGEPTYADSFKGRFTF
SLDDSKNTAYLQINSLRAEDTAVYFCTRRGYDWYF
DVWGQGTTVTVSSGGGGSGGGGSGGGGSDIQMTQS
PSSLSASVGDRVTITCRASQDINSYLSWFQQKPGK
APKTLIYRANRLESGVPSRFSGSGSGTDYTLTISS
LQYEDFGIYYCQQYDESPWTFGGGTKLEIKSGGGG
SGALSNSIMYFSHFVPVFLPAKPTTTPAPRPPTPA
PTIASQPLSLRPEACRPAAGGAVHTRGLDIYIWAP
LAGTCGVLLLSLVITLYCRLKIQVRKAAITSYEKS
DGVYTGLSTRNQETYETLKHEKPPQKKVAKKPTNK
APHPKQEPQEINFPDDLPGSNTAAPVQETLHGCQP
VTQEDGKESRISVQERQ
```

or (SEQ ID NO: 71)

```
EIQLVQSGGGLVKPGGSVRISCAASGYTFTNYGMN
WVRQAPGKGLEWMGWINTHTGEPTYADSFKGRFTF
SLDDSKNTAYLQINSLRAEDTAVYFCTRRGYDWYF
DVWGQGTTVTVSSGGGGSGGGGSGGGGSDIQMTQS
```

-continued

```
PSSLSASVGDRVTITCRASQDINSYLSWFQQKPGK
APKTLIYRANRLESGVPSRFSGSGSGTDYTLTISS
LQYEDFGIYYCQQYDESPWTFGGGTKLEIKSGGGG
SGALSNSIMYFSHFVPVFLPAKPTTTPAPRPPTPA
PTIASQPLSLRPEACRPAAGGAVHTRGLDIYIWAP
LAGTCGVLLLSLVITLYCRRLKIQVRKAAITSYEK
SDGVYTGLSTRNQETYETLKHEKPPQKKVAKKPTN
KAPHPKQEPQEINFPDDLPGSNTAAPVQETLHGCQ
PVTQEDGKESRISVQERQ.
```

In some embodiments, the fusion protein is a transmembrane protein, an intracellular protein or an intracellular protein. In one embodiment the fusion protein is directed to enhancing the function of an immune cell, e.g., a myeloid cell, selected from monocyte, macrophages dendritic cells or precursors thereof. In one embodiment the fusion protein augments a cellular function of an immune cell, such as phagocytosis. The disclosure is not limited by the transgenes that can be expressed using the methods and compositions described. The transgenes indicated in this section are exemplary.

Provided herein are exemplary transgene candidates, for stable integration into the genome of a phagocytic cell. In one embodiment the transgene is a recombinant nucleic acid encoding a phagocytic receptor (PR) fusion protein (CFP). The recombinant nucleic acid has a PR subunit comprising: (i) a transmembrane domain, and (ii) an intracellular domain comprising a phagocytic receptor intracellular signaling domain; and an extracellular antigen binding domain specific to an antigen of a target cell; wherein the transmembrane domain and the extracellular antigen binding domain are operatively linked such that antigen binding to the target by the extracellular antigen binding domain of the fused receptor activated in the intracellular signaling domain of the phagocytic receptor. In some embodiments, the recombinant nucleic acid encodes a chimeric antigen receptor. In some embodiments, the chimeric antigen receptor is a chimeric antigen receptor (phagocytosis) (CAR-P). In some embodiments, the fusion protein is a recombinant protein for locking anti-phagocytic signals. In some embodiments, the fusion protein is a phagocytosis enhancing chimeric protein. In some embodiments, the chimeric protein has intracellular domains comprising active phagocytosis signal transduction domains. In some embodiments, the chimeric protein enhances the phagocytic potential by enhancing the inflammatory potential of the phagocytic cell in which it expresses. In some embodiments, the transgene is designed to express a chimeric protein which is activated by contact with an antigen in a target cell, whereupon the phagocytic cell phagocytoses the target cell and kills the target cell.

The terms "spacer" or "linker" as used in reference to a fusion protein refers to a peptide sequence that joins the protein domains of a fusion protein. Generally, a spacer has no specific biological activity other than to join or to preserve some minimum distance or other spatial relationship between the proteins or RNA sequences. However, in some embodiments, the constituent amino acids of a spacer can be selected to influence some property of the molecule such as the folding, net charge, or hydrophobicity of the molecule. Suitable linkers for use in an embodiment of the present disclosure are well known to those of skill in the art and include, but are not limited to, straight or branched-chain carbon linkers, heterocyclic carbon linkers, or peptide linkers. The linker is used to separate two antigenic peptides by a distance sufficient to ensure that, in some embodiments, each antigenic peptide properly folds. Exemplary peptide linker sequences adopt a flexible extended conformation and do not exhibit a propensity for developing an ordered secondary structure. Typical amino acids in flexible protein regions include Gly, Asn and Ser. Virtually any permutation of amino acid sequences containing Gly, Asn and Ser would be expected to satisfy the above criteria for a linker sequence. Other near neutral amino acids, such as Thr and Ala, also can be used in the linker sequence.

The various exemplary proteins encoded by a transgene that can be expressed for enhancing the immune potential of a phagocytic cell are described below. This is not an exhaustive list but serves as an exemplary list for transgene design within the scope of the present disclosure.

In some embodiments, the PSP subunit comprises a transmembrane (TM) domain of a phagocytic receptor.

In some embodiments, the PSP subunit comprises an ICD domain of a phagocytic receptor.

In some embodiments, the ICD encoded by the recombinant nucleic acid comprises a domain selected from the group consisting of lectin, dectin 1, mannose receptor (CD206), scavenger receptor A1 (SRA1), MARCO, CD36, CD163, MSR1, SCARA3, COLEC12, SCARA5, SCARB1, SCARB2, CD68, OLR1, SCARF1, SCARF2, CXCL16, STAB1, STAB2, SRCRB4D, SSC5D, CD205, CD207, CD209, RAGE, CD14, CD64, F4/80, CCR2, CX3CR1, CSF1R, Tie2, HuCRIg(L), and CD169 receptor.

In some embodiments, the ICD comprises the signaling domain derived from any one or more of: lectin, dectin 1, mannose receptor (CD206), scavenger receptor A1 (SRA1), MARCO (Macrophage Receptor with Collagenous Structure, aliases: SRA6, SCARA2), CD36 (Thrombospondin receptor, aliases: Scavenger Receptor class B, member 3), CD163 (Scavenger receptor, cysteine rich-type 1), MSR1, SCARA3, COLEC12 (aliases: Scavenger Receptor With C-Type Lectin, SCARA4, or Collectin 12), SCARA5, SCARB1, SCARB2, CD68 (SCARD, microsialin), OLR1 (Oxidized Low Density Lipoprotein Receptor 1, LOX1, or C-Type Lectin Domain Family 8 Member A), SCARF1, SCARF2, SRCRB4D, SSC5D, and CD169 (aliases, Sialoadhesin receptor, SIGLEC1).

In some embodiments, the recombinant nucleic acid encodes, for example, an intracellular domain of human MARCO. The PSR subunit comprises an intracellular domain having a 44 amino acid ICD of human MARCO having an amino acid sequence: MRNKKILKEDELL-SETQQAAFHQIAMEPFEINVPKPKRRNGVNF (SEQ ID NO: 72). In some embodiments, the PSR subunit comprises a variant which is at least 70%, 75%, 80%, 85%, 90% or 95% identical to the intracellular domain of MARCO.

In some embodiments, for example, the PSR (phagocytic scavenger receptor) comprises a transmembrane region of human MARCO.

In some embodiments, the recombinant nucleic acid encodes an intracellular domain of human SRA1. The PSR subunit comprises an intracellular domain having a 50 amino acid ICD of human SRA1 having an amino acid sequence: MEQWDHFHNQQEDTDSCSESVKF-DARSMTA LLPPNPKNSPSLQEKLKSFK (SEQ ID NO: 73). In some embodiments, the PSR subunit comprises a variant which is at least 70%, 75%, 80%, 85%, 90% or 95% identical to the intracellular domain of human SRA1. The intracellular region of SRA has a phosphorylation site.

In some embodiments, the PSR comprises a transmembrane region of human SRA1.

In some embodiments, for example, the recombinant nucleic acid comprises an intracellular domain of CD36. In some embodiments, the recombinant nucleic acid comprises a TM domain of CD36. Naturally occurring full length CD36 has two TM domains and two short intracellular domains, and an extracellular domain of CD36 binds to oxidized LDL. Both of the intracellular domains contain pairs of cysteines that are fatty acid acylated. It lacks known signaling domains (e.g. kinase, phosphatase, g-protein binding, or scaffolding domains). N-terminal cytoplasmic domain is extremely short (5-7 amino acid residues) and is closely associated with the internal leaflet of the plasma membrane. The carboxy-terminal domain contains 13 amino acids, containing a CXCX5K motif homologous to a region in the intracellular domain of CD4 and CD8 that is known to interact with signaling molecules. The intracellular domain of CD36 is capable of assembling a signaling complex that activates lyn kinases, MAP kinases and Focal Adhesion Kinases (FAK), and inactivation of src homology 2-containing phosphotyrosine phosphatase (SHP-2). Members of the guanine nucleotide exchange factors (GEFs) have been identified as potential key signaling intermediates.

In some embodiments, the recombinant nucleic acid encodes for example, an intracellular domain of human SCARA3. In some embodiments, the PSR subunit comprises a variant which is at least 70%, 75%, 80%, 85%, 90% or 95% identical to the intracellular domain of human SCARA3. In some embodiments, the PSR comprises the TM domain of SCARA3. In some embodiments, the TM domains are about 20-30 amino acids long.

Scavenger receptors may occur as homo or hetero dimers. MARCO, for example occurs as a homo trimer.

In some embodiments, the TM domain or the ICD domain of the PSP is not derived from FcR, Megf10, Bai1 or MerTK. In some embodiments, the ICD of the PSR does not comprise a CD3 zeta intracellular domain.

In some embodiments, the intracellular domain and transmembrane domains are derived from FcR beta.

In one aspect the recombinant nucleic acid encodes a chimeric antigenic receptor for enhanced phagocytosis (CAR-P), which is a phagocytic scavenger receptor (PSR) fusion protein (CFP) comprising: (a) an extracellular domain comprising an extracellular antigen binding domain specific to an antigen of a target cell, (b) a transmembrane domain, and (c) a recombinant PSR intracellular signaling domain, wherein the recombinant PSR intracellular signaling domain comprises a first portion derived from a phagocytic and a second portion derived from non-phagocytic receptor.

In some embodiments, the second portion is not a PI3K recruitment domain. In some embodiments, the second portion is a PI3K recruitment domain.

The second portion derived from non-phagocytic receptor may comprise an intracellular signaling domain that enhances phagocytosis, and/or inflammatory potential of the engineered phagocytic cells expressing the recombinant nucleic acid. In some embodiments, the second portion derived from non-phagocytic receptor comprises more than one intracellular domain (ICD). In some embodiments, the second portion derived from non-phagocytic receptor comprises a second ICD. In some embodiments, the second portion derived from non-phagocytic receptor comprises a second and a third ICD. In some embodiments, the second portion derived from non-phagocytic receptor comprises a second, a third and a fourth ICD, wherein the second portion is encoded by the recombinant nucleic acid. The respective second portions comprising a second, or third or fourth ICD derived from non-phagocytic receptor are described as follows.

Chimeric Antigen Receptors for Enhancing Intracellular Signaling and Inflammation Activation In one aspect, the recombinant nucleic acid encodes a second intracellular domain in addition to the phagocytic ICD, which confers capability of potent pro-inflammatory immune activation, such as when macrophages engage in fighting infection. The second intracellular domain (second ICD) is fused to the cytoplasmic terminus of the first phagocytic ICD. The second intracellular domain provides a second signal is necessary to trigger inflammasomes and pro-inflammatory signals. Nod-like receptors (NLRs) are a subset of receptors that are activated in innate immune response, and oligomerize to form multi-protein complexes that serve as platforms to recruit proinflammatory caspases and induce their cleavage and activation. This leads to direct activation of ROS, and often result in a violent cell death known as pyroptosis. There are four inflammasome complexes, NLRP1m, NLRP3, IPAF and AIM2.

The tumor microenvironment (TME) constitutes an immunosuppressive environment. Influence of IL-10, glucocorticoid hormones, apoptotic cells, and immune complexes can interfere with innate immune cell function. Immune cells, including phagocytic cells settle into a tolerogenic phenotype. In macrophages, this phenotype, commonly known as the M2 phenotype is distinct from the M1 phenotype, where the macrophages are potent and capable of killing pathogens. Macrophages exposed to LPS or IFN-gamma, for example, can polarize towards an M1 phenotype, whereas macrophages exposed to IL-4 or IL-13 will polarize towards an M2 phenotype. LPS or IFN-gamma can interact with Toll-like receptor 4 (TLR4) on the surface of macrophages inducing the Trif and MyD88 pathways, inducing the activation of transcription factors IRF3, AP-1, and NFKB and thus activating TNFs genes, interferon genes, CXCL10, NOS2, IL-12, etc., which are necessary in a pro-inflammatory M1 macrophage response. Similarly, IL-4 and IL-13 bind to IL-4R, activation the Jak/Stat6 pathway, which regulates the expression of CCL17, ARG1, IRF4, IL-10, SOCS3, etc., which are genes associated with an anti-inflammatory response (M2 response). Expression of CD14, CD80, D206 and low expression of CD163 are indicators of macrophage polarization towards the M1 phenotype.

In some embodiments, the recombinant nucleic acid encodes one or more additional intracellular domains, comprising a cytoplasmic domain for inflammatory response. In some embodiments, expression of the recombinant nucleic acid encoding the phagocytic receptor (PR) fusion protein (CFP) comprising the cytoplasmic domain for inflammatory response in the engineered macrophages confers potent pro-inflammatory response similar to the M1 phenotype.

In some embodiments, the cytoplasmic domain for inflammatory response can be the signal transducing domains or regions of TLR3, 4, 9, MYD88, TRIF, RIG-1, MDA5, CD40, IFN receptor, NLRP-1-14, NOD1, NOD2, Pyrin, AIM2, NLRC4, CD40.

In some embodiments, the expression of the recombinant nucleic acid encoding the phagocytic scavenger receptor (PSR) fusion protein (CFP) comprises a pro-inflammatory cytoplasmic domain for activation of IL-1 signaling cascade.

In some embodiments, the cytoplasmic portion of the chimeric receptor (for example, phagocytic receptor (PR) fusion protein (CFP)) comprises a cytoplasmic domain from a toll-like receptor, such as the intracellular signaling domains of toll-like receptor 3 (TLR3), toll-like receptor 4 (TLR4), toll-like receptor 7 (TLR7), toll-like receptor 8 (TLR8), toll-like receptor 9 (TLR9). In some embodiments, the cytoplasmic portion of the chimeric receptor comprises a suitable region from interleukin-1 receptor-associated kinase 1 (IRAK1). In some embodiments, the cytoplasmic portion of the chimeric receptor comprises a suitable region from differentiation primary response protein (MYD88)._In some embodiments, the cytoplasmic portion of the chimeric receptor comprises a suitable region from myelin and lymphocyte protein (MAL). In some embodiments, the cytoplasmic portion of the chimeric receptor comprises a suitable region from retinoic acid inducible gene (RIG-1).

In some embodiments, the transmembrane domain of the PSR comprises the transmembrane domain of any one of MYD88, TLR3, TLR4, TLR7, TLR8, TLR9, MAL, IRAK1, proteins.

In some embodiments, the recombinant PSR intracellular signaling domain comprises a first portion derived from a phagocytic and a second portion derived from non-phagocytic receptor wherein the second portion derived from non-phagocytic receptor comprises a phosphorylation site. In some embodiments, the phosphorylation site comprises amino acid sequences suitable for an autophosphorylation site. In some embodiments, the phosphorylation site comprises amino acid sequences suitable phosphorylation by Src family kinases. In some embodiments, the phosphorylation site comprises amino acid sequences, which upon phosphorylation are capable of binding to SH2 domains in a kinase. In some embodiments, a receptor tyrosine kinase domain is fused at the cytoplasmic end of the CFP in addition to the first cytoplasmic portion. In some embodiments, the phosphorylation is a tyrosine phosphorylation.

In some embodiments, the second intracellular domain is an Immune receptor Tyrosine Activation Motif (ITAM). The ITAM motif is present in mammalian a and 3 immunoglobulin proteins, TCR γ receptors, FCR γ receptors subunits, CD3 chains receptors and NFAT activation molecule.

In some embodiments, the CFP intracellular domain comprises one ITAM motif. In some embodiments, the CFP intracellular domain comprises more than one ITAM motifs. In some embodiments, the CFP intracellular domain comprises two or more ITAM motifs. In some embodiments, the CFP intracellular domain comprises three or more ITAM motifs. In some embodiments, the CFP intracellular domain comprises four or more ITAM motifs. In some embodiments, the CFP intracellular domain comprises five or more ITAM motifs. In some embodiments, the CFP intracellular domain comprises six or more ITAM motifs. In some embodiments, the CFP intracellular domain comprises seven or more ITAM motifs. In some embodiments, the CFP intracellular domain comprises eight or more ITAM motifs. In some embodiments, the CFP intracellular domain comprises nine or more ITAM motifs. In some embodiments, the CFP intracellular domain comprises ten or more ITAM motifs.

In some embodiments, one or more domains in the first phagocytic ICD comprises a mutation.

In some embodiments, one or more domains in the second ICD comprises a mutation to enhance a kinase binding domain, to generate a phosphorylation site, to generate an SH2 docking site or a combination thereof.

Co-Expression of an Inflammatory Gene

In one aspect, the recombinant nucleic acid comprises a coding sequence for a pro-inflammatory gene, which is co-expressed with the CFP in the engineered cell. In some embodiments, the pro-inflammatory gene is a cytokine.

Examples include but not limited to TNF-α, IL-1a, IL-1P, IL-6, CSF, GMCSF, or IL-12 or interferons.

The recombinant nucleic acid encoding the proinflammatory gene can be monocistronic, wherein the two coding sequences for (a) the PSP and (b) the proinflammatory gene are post-transcriptionally or post-translationally cleaved for independent expression.

In some embodiments, the two coding sequences comprise a self-cleavage domain, encoding a P2A sequence, for example.

In some embodiments, the two coding regions are separated by an IRES site.

In some embodiments, the two coding sequences are encoded by a bicistronic genetic element.

The coding regions for (a) the PSP and (b) the proinflammatory gene can be unidirectional, where each is under a separate regulatory control. In some embodiments, the coding regions for both are bidirectional and drive in opposite directions. Each coding sequence is under a separate regulatory control.

Co-expression of the proinflammatory gene is designed to confer strong inflammatory stimulation of the macrophage and activate the surrounding tissue for inflammation.

Integrin Activation Domains

Cell-cell and cell-substratum adhesion is mediated by the binding of integrin extracellular domains to diverse protein ligands; however, cellular control of these adhesive interactions and their translation into dynamic cellular responses, such as cell spreading or migration, requires the integrin cytoplasmic tails. These short tails bind to intracellular ligands that connect the receptors to signaling pathways and cytoskeletal networks (Calderwood DA, 2004, Integrin Activation, Journal of Cell Science 117, 657-666). Integrins are heterodimeric adhesion receptors formed by the non-covalent association of α and β subunits. Each subunit is a type I transmembrane glycoprotein that has relatively large extracellular domains and, with the exception of the β4 subunit, a short cytoplasmic tail. Individual integrin family members have the ability to recognize multiple ligands. Integrins can bind to a large number of extracellular matrix proteins (bone matrix proteins, collagens, fibronectins, fibrinogen, laminins, thrombospondins, vitronectin, and von Willebrand factor), reflecting the primary function of integrins in cell adhesion to extracellular matrices. Many "counter-receptors" are ligands, reflecting the role of integrins in mediating cell-cell interactions. Integrins undergo conformational changes to increase ligand affinity.

The Integrin $\beta_2$ subfamily consists of four different integrin receptors, $\alpha_M\beta_2$ (CD11b/CD18, Mac-1, CR3, Mo-1), $\alpha_L\beta_2$ (CD11a/CD18, LFA-1), $\alpha_X\beta_2$ (CD11c/CD18), and $\alpha_D\beta_2$ (CD11d/CD18). These leukocyte integrins are involved in virtually every aspect of leukocyte function, including the immune response, adhesion to and transmigration through the endothelium, phagocytosis of pathogens, and leukocyte activation.

The a subunits of all $\beta_2$ integrins contain an inserted region of ~200 amino acids, termed the I or A domain. Highly conserved I domains are found in several other integrin a subunits and other proteins, such as certain coagulation and complement proteins. I domains mediate protein-protein interactions, and in integrins, they are integrally involved in the binding of protein ligands. Although the I domains dominate the ligand binding functions of their integrins, other regions of the a subunits do influence ligand recognition. As examples, in $\alpha_M\beta_2$ a mAb (OKM1) recognizing an epitope outside the I domain but in the $\alpha_M$ subunit inhibits ligand binding; and the EF-hand regions in $\alpha_L\beta_2$ and $\alpha_2\beta_1$, integrins with I domains in their a subunits, contribute to ligand recognition. The $\alpha_M$ subunit, and perhaps other a subunits, contains a lectin-like domain, which is involved in engagement of non-protein ligands, and occupancy may modulate the function of the I domain.

As integrins lack enzymatic activity, signaling is instead induced by the assembly of signaling complexes on the cytoplasmic face of the plasma membrane. Formation of these complexes is achieved in two ways; first, by receptor clustering, which increases the avidity of molecular interactions thereby increasing the on-rate of binding of effector molecules, and second, by induction of conformational changes in receptors that creates or exposes effector binding sites. Within the ECM, integrins have the ability to bind fibronectin, laminins, collagens, tenascin, vitronectin and thrombospondin. Clusters of integrin/ECM interactions form focal adhesions, concentrating cytoskeletal components and signaling molecules within the cell. The cytoplasmic tail of integrins serve as a binding site for α-actinin and talin which then recruit vinculin, a protein involved in anchoring F-actin to the membrane. Talin is activated by kinases such as protein kinase C (PKCα).

Integrins are activated by selectins. Leucocytes express L-selectin, activated platelets express P-selectin, and activated endothelial cells express E- and P-selectin. P-selectin-mediated adhesion enables chemokine- or platelet-activating factor-triggered activation of β2 integrins, which stabilizes adhesion. It also facilitates release of chemokines from adherent leucocytes. The cytoplasmic domain of P-selectin glycoprotein ligand 1 formed a constitutive complex with Nef-associated factor 1. After binding of P-selectin, Src kinases phosphorylated Nef-associated factor 1, which recruit the phosphoinositide-3-OH kinase p85-p110 heterodimer and result in activation of leukocyte integrins. E-selectin ligands transduce signals that also affect P2 integrin function. Selectins trigger activation of Src family kinases. SFKs activated by selectin engagement phosphorylate the immunoreceptor tyrosine-based activation motifs (ITAMs) in the cytoplasmic domains of DAP12 and FcRγ. In some respects, CD44 is sufficient to transduce signals from E-selectin. CD44 triggers the inside-out signaling of integrins. A final common step in integrin activation is binding of talin to the cytoplasmic tail of the β subunit. Kindlins, another group of cytoplasmic adaptors, bind to a different region of integrin 3 tails. Kindlins increase the clustering of talin-activated integrins. Kindlins are responsive to selectin signaling, however, kindlins are found mostly in hematopoietic cells, such as neutrophils. Selectin signaling as well as signaling upon integrin activation by chemokines components have shared components, including SFKs, Syk, and SLP-76.

In some embodiments, the intracellular domain of the recombinant PSR fusion protein comprises an integrin activation domain. The integrin activation domain comprises an intracellular domain of a selectin, for example, a P-selectin, L-selectin or E-selectin.

In some embodiments, the intracellular domain of the recombinant PSR fusion protein comprises an integrin activation domain of laminin.

In some embodiments, the intracellular domain of the recombinant PSR fusion protein comprises an integrin activation domain for activation of Talin.

In some embodiments, the intracellular domain of the recombinant PSR fusion protein comprises an integrin activation domain fused to the cytoplasmic end of the phagocytic receptor ICD domain.

Chimeric Receptor for Enhancing Antigen Cross Presentation

In some embodiments, the recombinant nucleic acid encodes a domain capable of enabling cross presentation of antigens. In general, MHC class I molecules present self- or pathogen-derived antigens that are synthesized within the cell, whereas exogenous antigens derived via endocytic uptake are loaded onto MHC class II molecules for presentation to CD4+ T cells. MHC I-restricted presentation of endogenous antigens, in which peptides are generated by the proteasome. However, in some cases, DC can process exogenous antigens into the MHC-1 pathway for presentation to CD8+ T cells. This is referred to as cross presentation of antigens. Soluble or exogenous antigenic components may get degraded by lysosomal proteases in the vacuoles and cross presented by DCs, instead of following the endocytic pathway. In some instances, chaperones, such as heat shock protein 90 (Hsp90) have shown to help cross present antigens by certain APCs. HSP-peptide complexes are known to be internalized by a distinct group of receptors compared to free polypeptides. These receptors are from the scavenger receptor families and included LOX-1, SREC-I/SCARF-I, and FEEL1/Stabilin-1. Both SREC-I and LOX-1 have been shown to mediate the cross presentation of molecular chaperone bound antigens and lead to activation of $CD8^+$ T lymphocytes.

SREC-1 (scavenger receptor expressed by endothelial cells) has no significant homology to other types of scavenger receptors but has unique domain structures. It contains 10 repeats of EGF-like cysteine-rich motifs in the extracellular domain. Recently, the structure of SREC-I was shown to be similar to that of a transmembrane protein with 16 EGF-like repeats encoded by the *Caenorhabditis elegans* gene ced-I, which functions as a cell surface phagocytic receptor that recognizes apoptotic cells.

Cross presentation of cancer antigens through the Class-I MHC pathway results in enhanced CD8+ T cell response, which is associated with cytotoxicity and therefore beneficial in tumor regression.

In some embodiments, the intracellular domain of the CFP comprises a SREC1 intracellular domain. In some embodiments, the intracellular domain of the CFP comprises a SRECII intracellular domain.

In some embodiments, the PSR subunit comprises: an intracellular domain comprising a PSR intracellular signaling domain from SREC1 or SRECII.

In some embodiments, the PSR subunit comprises: (i) a transmembrane domain, and (ii) an intracellular domain comprising a PSR intracellular signaling domain from SREC1 or SRECII.

In some embodiments, the PSR subunit comprises: (i) a transmembrane domain, (ii) an intracellular domain comprising a PSR intracellular signaling domain, and (iii) an extracellular domain from SREC1 or SRECII.

Transmembrane Domain of a CFP Fusion Protein

In some embodiments, the TM encoded by the recombinant nucleic acid comprises a domain of a scavenger receptor (SR). In some embodiments, the TM can be the TM domain of or derived from any one or more of: lectin, dectin 1, mannose receptor (CD206), SRA1, MARCO, CD36, CD163, MSR1, SCARA3, COLEC12, SCARA5, SCARB1, SCARB2, CD68, OLR1, SCARF1, SCARF2, SRCRB4D, SSC5D, and CD169.

In some embodiments, the TM domains are about 20-30 amino acids long. TM domains of SRs are about 20-30 amino acids long.

The TM domain or the ICD domain of the PSP is not derived from Megf10, Bai1 or MerTK. The ICD of the PSR does not comprise a CD3 zeta intracellular domain.

In some embodiments, the TM is derived from the same phagocytic receptor as the ICD.

In some embodiments, the TM region is derived from a plasma membrane protein. The TM can be selected from an Fc receptor (FcR). In some embodiments, nucleic acid sequence encoding domains from specific FcRs are used for cell-specific expression of a recombinant construct. An FCR-alpha region comprising the TM domain may be used for macrophage specific expression of the construct. FcRβ recombinant protein expresses in mast cells.

In some embodiments, the CFP comprises the TM of an FCR-beta (FcRβ).

In some embodiments, the CFP comprises both the FcRβTM and ICD domains.

In some embodiments, the TM domain is derived from CD8.

In some embodiments, the TM is derived from CD2.

In some embodiments, the TM is derived from FCR alpha.

Extracellular Domain of a CFP Fusion Protein

The extracellular domain comprises an antigen binding domain that binds to one or more target antigens on a target cell. The target binding domain is specific for the target. The extracellular domain can include an antibody or an antigen-binding domain selected from intrabodies, peptibodies, nanobodies, single domain antibodies. SMIPs, and multispecific antibodies.

In some embodiments, the extracellular domain includes a Fab binding domain. In yet other such embodiments, the extracellular domain includes a scFv.

In some embodiments, the chimeric antigen receptor comprises an extracellular antigen binding domain is derived from the group consisting of an antigen-binding fragment (Fab), a single-chain variable fragment (scFv), a nanobody, a VH domain, a VL domain, a single domain antibody (sdAb), a VNAR domain, and a VHH domain, a bispecific antibody, a diabody, or a functional fragment of any thereof. In some embodiments, the antigen-binding fragment (Fab), a single-chain variable fragment (scFv), a nanobody, a VH domain, a VL domain, a single domain antibody (sdAb), a VNAR domain, and a VHH domain, a bispecific antibody, a diabody, or a functional fragment of any thereof specifically bind to one or more antigens.

In some embodiments, the antigens are cancer antigens, and the target cell is a target cancer cell. In some embodiments, the antigen for a target cancer cell is selected from the group consisting of CD3, CD4, CD5, CD7, CD19, CCR2, CCR4, CD30, CD37, TCRB1/2, TCR □□, TCR □□. CD22, HER2 (ERBB2/neu), Mesothelin, PSCA, CD123, CD30, CD171, CD138, CS-1, CLECLI, CD33, CD79b, EGFRvIII, GD2, GD3, BCMA, PSMA, RORI, FLT3, TAG72, CD38, CD44v6, CEA, EPCAM, B7H3 (CD276), KIT (CD 117), CD213A2, IL-1 IRa, PRSS21, VEGFR2, CD24, MUC-16, PDGFR-beta, SSEA-4, CD20, MUC1, EGFR, NCAM, Prostase, PAP, ELF2M, Ephrin B2, FAP, EphA2, GM3, TEM1/CD248, TEM7R, CLDN6, TSHR, GPRC5D, CD97, CD179a, ALK, and IGLL1.

Various cancer antigen targets can be selected from cancer antigens known to one of skill in the art. Depending on the cancer and the cell type involved cancer antigens are mutated native proteins. The antigen binding domains are screened for specificity towards mutated/cancer antigens and not the native antigens.

In some embodiments, for example, the cancer antigen for a target cancer cell can be one or more of the mutated/cancer antigens: MUC16, CCAT2, CTAG1A, CTAG1B, MAGE A1, MAGEA2, MAGEA3, MAGE A4, MAGEA6, PRAME, PCA3, MAGE C1, MAGEC2, MAGED2, AFP, MAGEA8, MAGE9, MAGEA11, MAGEA12, IL13RA2, PLAC1, SDCCAG8, LSP1, CT45A1, CT45A2, CT45A3, CT45A5, CT45A6, CT45A8, CT45A10, CT47A1, CT47A2, CT47A3, CT47A4, CT47A5, CT47A6, CT47A8, CT47A9, CT47A10, CT47A11, CT47A12, CT47B1, SAGE1, and CT55.

In some embodiments, for example, the cancer antigen for a target cancer cell can be one or more of the mutated/cancer antigens: CD2, CD3, CD4, CD5, CD7, CD8, CD20, CD30, CD45, CD56, where the cancer is a T cell lymphoma.

In some embodiments, for example, the cancer antigen for a target cancer cell can be one or more of the mutated/cancer antigens: IDH1, ATRX, PRL3, or ETBR, where the cancer is a glioblastoma.

In some embodiments, for example, the cancer antigen for a target cancer cell can be one or more of the mutated/cancer antigens: CA125, beta-hCG, urinary gonadotropin fragment, AFP, CEA, SCC, inhibin or extradiol, where the cancer is ovarian cancer.

In some embodiments, the cancer antigen for a target cancer cell may be HER2.

In some embodiments, the cancer antigen for a target cancer cell may be EGFR Variant III.

In some embodiments, the cancer antigen for a target cancer cell may be CD19.

In some embodiments, the SR subunit region comprises an extracellular domain (ECD) of the scavenger receptor. In some embodiments, the ECD of the scavenger receptor comprises an ECD domain of the SR comprising the ICD and the TM domains. In some embodiments, the SR-ECD contributes to the binding of the phagocyte to the target cell, and in turn is activated, and activates the phagocytosis of the target cell.

In some embodiments, the PSR domain optionally comprises the ECD domain or portion thereof of the respective scavenger receptor the ICD and TM domains of which is incorporated in the PSR.

Therefore, in some embodiments, In some embodiments, the ECD encoded by the recombinant nucleic acid comprises a domain selected from the group consisting of lectin, dectin 1, mannose receptor (CD206), scavenger receptor A1 (SRA1), MARCO, CD36, CD163, MSR1, SCARA3, COLEC12, SCARA5, SCARB1, SCARB2, CD68, OLR1, SCARF1, SCARF2, CXCL16, STAB1, STAB2, SRCRB4D, SSC5D, CD205, CD207, CD209, RAGE, CD14, CD64, F4/80, CCR2, CX3CR1, CSF1R, Tie2, HuCRIg(L), and CD169 receptor. The extracellular domains of most macrophage scavenger receptors contain scavenger receptors with a broad binding specificity that may be used to discriminate between self and non-self in the nonspecific antibody-independent recognition of foreign substances. The type I and II class A scavenger receptors (SR-AII and SR-AII) are trimeric membrane glycoproteins with a small NH2-terminal intracellular domain, and an extracellular portion containing a short spacer domain, an α-helical coiled-coil domain, and a triple-helical collagenous domain. The type I receptor additionally contains a cysteine-rich COOH-terminal (SRCR) domain. These receptors are present in macrophages in diverse tissues throughout the body and exhibit an unusually broad ligand binding specificity. They bind a wide variety of polyanions, including chemically modified proteins, such as modified LDL, and they have been implicated in cholesterol deposition during atherogenesis. They may also play a role in cell adhesion processes in macrophage-associated host defense and inflammatory conditions.

In some embodiments, the SR ECD is designed to bind to pro-apoptotic cells. In some embodiments, the scavenger receptor ECD comprises a binding domain for a cell surface molecule of a cancer cell or an infected cell.

In some embodiments, the extracellular domain of the PR subunit is linked by a linker to a target cell binding domain, such as an antibody or part thereof, specific for a cancer antigen.

In some embodiments, the extracellular antigen binding domain comprises one antigen binding domain. In some embodiments, the extracellular antigen binding domain comprises more than one binding domain. In some embodiments, the binding domain is an scFv. In some embodiments, the binding domain is an single domain antibody (sdAb). In some embodiments, the binding domain is fused to the recombinant PR at the extracellular domain. In some embodiments, the binding domain (e.g., scFv) and the extracellular domain of the PR are linked via a linker.

In some embodiments, the ECD antigen binding domain can bind to an intracellular antigen. In some embodiments, the intracellular antigen is a cancer antigen.

In some embodiments, the extracellular antigen binding domain binds to the target ligand with an affinity of less than 1000 nM. In some embodiments, the extracellular antigen binding domain binds to the target ligand with an affinity of less than 500 nM. In some embodiments, the extracellular antigen binding domain binds to the target ligand with an affinity of less than 450 nM. In some embodiments, the extracellular antigen binding domain binds to the target ligand with an affinity of less than 400 nM. In some embodiments, the extracellular antigen binding domain binds to the target ligand with an affinity of less than 350 nM. In some embodiments, the extracellular antigen binding domain binds to the target ligand with an affinity of less than 250 nM. In some embodiments, the extracellular antigen binding domain binds to the target ligand with an affinity of less than 200 nM. In some embodiments, the extracellular antigen binding domain binds to the target ligand with an affinity of less than 100 nM. In some embodiments, the extracellular antigen binding domain binds to the target ligand with an affinity ranging between than 200 nM to 1000 nM. In some embodiments, the extracellular antigen binding domain binds to the target ligand with an affinity ranging between than 300 nM to 1.5 mM. In some embodiments, the antigen binding domain binds to the target ligand with an affinity >200 nM, >300 nM or >500 nM.

Peptide Linker

In some embodiments, the extracellular antigen binding domains, scFvs are linked to the TM domain or other extracellular domains by a linker. In some embodiments, where there are more than one scfv at the extracellular antigen binding domain the more than scfvs are linked with each other by linkers.

In some embodiments, the linkers are flexible. In some embodiments, the linkers comprise a hinge region. Linkers are usually short peptide sequences. In some embodiments, the linkers are stretches of Glycine and one or more Serine residues. Other amino acids preferred for short peptide linkers include but are not limited to threonine (Thr), serine (Ser), proline (Pro), glycine (Gly), aspartic acid (Asp), lysine (Lys), glutamine (Gln), asparagine (Asn), and alanine (Ala) arginine (Arg), phenylalanine (Phe), glutamic acid (Glu). Of these Pro, Thr, and Gln are frequently used amino acids for natural linkers. Pro is a unique amino acid with a cyclic side chain which causes a very restricted conformation. Pro-rich sequences are used as interdomain linkers, including the linker between the lipoyl and E3 binding domain in pyruvate dehydrogenase ($GA_2PA_3PAKQEA_3PAPA_2KAEAPA_3PA_2KA$ (SEQ ID NO: 75)). For the purpose of the disclosure, the empirical linkers may be flexible linkers, rigid linkers, and cleavable linkers. Sequences such as (G4S)x (where x is multiple copies of the moiety, designated as 1, 2, 3, 4, and so on) (SEQ ID NO: 76) comprise a flexible linker sequence. Other flexible sequences used herein include several repeats of glycine, e.g., (Gly)6 (SEQ ID NO: 77) or (Gly)8 (SEQ ID NO: 78). On the other hand, a rigid linker may be used, for example, a linker (EAAAK)x, where x is an integer, 1, 2, 3, 4 etc. (SEQ ID NO: 79) gives rise to a rigid linker.

In some embodiments, the linker comprises at least 2, or at least 3 amino acids. In some embodiments, the linker comprises 4 amino acids. In some embodiments, the linker comprises 5 amino acids. In some embodiments, the linker comprises 6 amino acids. In some embodiments, the linker comprises 7 amino acids. In some embodiments, the linker comprises 8 amino acids. In some embodiments, the linker comprises 9 amino acids. In some embodiments, the linker comprises 8 amino acids. In some embodiments, the linker comprises 10 amino acids. In some embodiments, the linker comprises 11 amino acids. In some embodiments, the linker comprises 12 amino acids. In some embodiments, the linker comprises 13 amino acids. In some embodiments, the linker comprises 14 amino acids. In some embodiments, the linker comprises 15 amino acids. In some embodiments, the linker comprises 16 amino acids. In some embodiments, the linker comprises 17 amino acids. In some embodiments, the linker comprises 18 amino acids. In some embodiments, the linker comprises 19 amino acids. In some embodiments, the linker comprises 20 amino acids.

As contemplated herein, any suitable ECD, TM or ICD domain can be cloned interchangeably in the suitable portion of any one of the CARP receptors described in the disclosure to obtain a protein with enhanced phagocytosis compared to an endogenous receptor.

Characteristics of the Fusion Proteins:

The CFP can structurally incorporate into the cell membrane of the cell in which it is expressed. Specific leader sequences in the nucleic acid construct, such as the signal peptide can be used to direct plasma membrane expression of the encoded protein. The transmembrane domain encoded by the construct can incorporate the expressed protein in the plasma membrane of the cell.

In some embodiments, the transmembrane domain comprises a TM domain of an FcRalpha receptor, which dimerizes with endogenous FcR-gamma receptors in the macrophages, ensuring macrophage specific expression.

The CFP can render the cell that expresses it as potently phagocytic. When the recombinant nucleic acid encoding the CFP is expressed in a cell, the cell can exhibit an increased phagocytosis of a target cell having the antigen of a target cell, compared to a cell not expressing the recombinant nucleic acid. When the recombinant nucleic acid is expressed in a cell, the cell can exhibit an increased phagocytosis of a target cell having the antigen of a target cell, compared to a cell not expressing the recombinant nucleic acid. In some embodiments, the recombinant nucleic acid when expressed in a cell, the cell exhibits at least 2-fold increased phagocytosis of a target cell having the antigen of a target cell, compared to a cell not expressing the recombinant nucleic acid. In some embodiments, the recombinant nucleic acid when expressed in a cell, the cell exhibits at least 3-fold, 4-fold, 5-fold, 6-fold, 7-fold, 8-fold, 9-fold, 10-fold, 20-fold 30-fold or at least 5-fold increased phagocytosis of a target cell having the antigen of a target cell, compared to a cell not expressing the recombinant nucleic acid.

In some embodiments, expression of SIRP-ΔICD enhances phagocytosis of the cell expressing it by 1.1 fold or more, 1.2 fold or more, 1.3 fold or more, q.4 fold or more, 1.5 fold or more, by 1.6 fold or more, 1.7 fold or more, 1.8 fold or more, 1.9 fold or more, 2 fold or more, 3 fold or more, 4 fold or more, 5 fold or more, 8 fold or more, 10 fold or more, 15 fold or more, 20 fold or more, 30 fold or more, 40 fold or more, 50 fold or more, 60 fold or more, 70 fold or more 80 fold or more, 90 fold or more, 100 fold or more, compared to a cell not expressing SIRP-ΔICD.

In some embodiments, the cells co-expressing SIRP-ΔICD and a CFP encoding a phagocytic receptor as described herein exhibits an augmented phagocytosis compared to a cell that does not express either of the proteins. In some embodiments, co-expressing SIRP-ΔICD and a CFP encoding a phagocytic receptor as described herein exhibits more than 2-fold, more than 3-fold, more than 4-fold, more than 5-fold, more than 6-fold, more than 7-fold, more than 8-fold, more than 9-fold, more than 10-fold, more than 20-fold, more than 30-fold, more than 40-fold, more than 50-fold, more than 60-fold, more than 70-fold, more than 80-fold, more than 90-fold, more than 100-fold, or more than 150-fold or more than 200-fold increase in phagocytic potential (measured in fold change of phagocytic index) compared to a cell that does not express either the SIRP-ΔICD or the CFP encoding a phagocytic receptor.

In some embodiments, expression of the any one of a CFP expressing a CD47 blocking extracellular domain of SIRPα and an intracellular domain of a phagocytic receptor augments phagocytic activity of a cell expressing it by at least 1.5 fold or more, 1.6 fold or more, 1.7 fold or more, 1.8 fold or more, 1.9 fold or more, 2 fold or more, 3 fold or more, 4 fold or more, 5 fold or more, 8 fold or more, 10 fold or more, 15 fold or more, 20 fold or more, 30 fold or more, 40 fold or more, 50 fold or more, 60 fold or more, 70 fold or more 80 fold or more, 90 fold or more, 100 fold or more, compared to a cell not expressing the CFP, or compared to a cell expressing SIRP-ΔICD.

In some embodiments, the enhancement in phagocytosis of target cells by a cell expressing either SIRP-ΔICD is highly increased compared to a phagocytic cell not expressing SIRP-ΔICD.

In some embodiments, the enhancement in phagocytosis of target cells by a cell expressing a CFP comprising a CD47 blocking extracellular domain of SIRPα and an intracellular domain of a phagocytic receptor is highly increased compared to a control phagocytic cell not expressing the fusion protein or a control phagocytic cell expressing the SIRP-ΔICD.

In some embodiments, when the recombinant nucleic acid described herein is expressed in a cell, the cell exhibits an increased cytokine production. The cytokine can comprise any one of: IL-1, IL-6, IL-12, IL-23, TNF, CXCL9, CXCL10, CXCL11, IL-18, IL-23, IL-27 and interferons.

In some embodiments, when the recombinant nucleic acid described herein is expressed in a cell, the cell exhibits an increased cell migration.

In some embodiments, when the recombinant nucleic acid described herein is expressed in a cell, the cell exhibits an increased immune activity. In some embodiments, when the recombinant nucleic acid is expressed in a cell, the cell exhibits an increased expression of MHC II. In some embodiments, when the recombinant nucleic acid is expressed in a cell, the cell exhibits an increased expression of CD80. In some embodiments, when the recombinant nucleic acid is expressed in a cell, the cell exhibits an increased expression of CD86. In some embodiments, when the recombinant nucleic acid is expressed in a cell, the cell exhibits an increased iNOS production.

In some embodiments, when the recombinant nucleic acid is expressed in a cell, the cell exhibits decreased trogocytosis of a target cell expressing the antigen of a target cell compared to a cell not expressing the recombinant nucleic acid.

In embodiments, the chimeric receptors may be glycosylated, pegylated, and/or otherwise post-translationally modified. In further embodiments, glycosylation, pegylation, and/or other posttranslational modifications may occur in vivo or in vitro and/or may be performed using chemical techniques. In additional embodiments, any glycosylation, pegylation and/or other posttranslational modifications may be N-linked or O-linked. In embodiments any one of the chimeric receptors may be enzymatically or functionally active such that, when the extracellular domain is bound by a ligand, a signal is transduced to polarize a macrophage.

In some embodiments, the chimeric fusion protein (CFP) comprises an extracellular domain (ECD) targeted to bind to CD5 (CD5 binding domain), for example, comprising a heavy chain variable region (VH) having an amino acid sequence as set forth in SEQ ID NO: 1. In some embodiments, the chimeric CFP comprises a CD5 binding heavy chain variable domain comprising an amino acid sequence that has at least 80%, 85%, 90%, 95%, 96%, 97%, 98%, 99% sequence identity to SEQ ID NO: 1. In some embodiments, the extracellular domain (ECD) targeted to bind to CD5 (CD5 binding domain) comprises a light chain variable domain ($V_L$) having an amino acid sequence as set forth in SEQ ID NO: 2. In some embodiments, the chimeric CFP comprises a CD5 binding light chain variable domain comprising an amino acid sequence that has at least 80%, 85%, 90%, 95%, 96%, 97%, 98%, 99% sequence identity to SEQ ID NO: 2.

In some embodiments, the CFP comprises an extracellular domain targeted to bind to HER2 (HER2 binding domain) having for example a heavy chain variable domain amino acid sequence as set forth in SEQ ID NO: 8 and a light chain variable domain amino acid sequence as set forth in SEQ ID NO: 9. In some embodiments, the CFP comprises a HER2 binding heavy chain variable domain comprising an amino acid sequence that has at least 80%, 85%, 90%, 95%, 96%, 97%, 98%, 99% sequence identity to SEQ ID NO: 8. In some embodiments, the CFP comprises a HER2 binding light chain variable domain comprising an amino acid sequence that has at least 80%, 85%, 90%, 95%, 96%, 97%, 98%, 99% sequence identity to SEQ ID NO: 9.

In some embodiments, the CFP comprises a hinge connecting the ECD to the transmembrane (TM). In some embodiments the hinge comprises the amino acid sequence of the hinge region of a CD8 receptor. In some embodiments, the CFP may comprise a hinge having the amino acid sequence set forth in SEQ ID NO: 7 (CD8a chain hinge domain). In some embodiments, the PFP hinge region comprises an amino acid sequence that is at least 80%, 85%, 90%, 95%, 96%, 97%, 98%, 99% sequence identity to SEQ ID NO: 7.

In some embodiments, the CFP comprises a CD8 transmembrane region, for example having an amino acid sequence set forth in SEQ ID NO: 6. In some embodiments, the CFP TM region comprises an amino acid sequence that is at least 80%, 85%, 90%, 95%, 96%, 97%, 98%, 99% sequence identity to SEQ ID NO: 6.

In some embodiments, the CFP comprises an intracellular domain having an FcR domain. In some embodiments, the CFP comprises an FcR domain intracellular domain comprises an amino acid sequence set forth in SEQ ID NO: 3, or at least a sequence having 80%, 85%, 90%, 95%, 96%, 97%, 98%, 99% sequence identity to SEQ ID NO: 3.

In some embodiments, the CFP comprises an intracellular domain having a PI3K recruitment domain. In some embodiments the PI3K recruitment domain comprises an amino sequence set forth in SEQ ID NO: 4. In some embodiments the PI3K recruitment domain comprises an amino acid sequence that has at least 80%, 85%, 90%, 95%, 96%, 97%, 98%, 99% sequence identity to SEQ ID NO: 4.

In some embodiments, the CFP comprises an intracellular domain having a CD40 intracellular domain. In some embodiments the CD40 ICD comprises an amino sequence set forth in SEQ ID NO: 5. In some embodiments the CD40 ICD comprises an amino acid sequence that has at least 80%, 85%, 90%, 95%, 96%, 97%, 98%, 99% sequence identity to SEQ ID NO: 5.

In some embodiments, the CD5 binding domain comprises an scFv comprising: (i) a variable heavy chain ($V_H$) sequence of SEQ ID NO: 1 or with at least 90% sequence identity to SEQ ID NO: 1; and (ii) a variable light chain ($V_L$) sequence of SEQ ID NO: 2 or with at least 70%, 75%, 80%, 85%, 90%, 91%, 92%, 93%, 94%, 95%, 96%, 97%, 98% or 99% sequence identity to SEQ ID NO: 2. In some embodiments, the CD5 binding domain comprises an scFv comprising SEQ ID NO: 33 or with at least 70%, 75%, 80%, 85%, 90%, 91%, 92%, 93%, 94%, 95%, 96%, 97%, 98% or 99% sequence identity to SEQ ID NO: 33. In some embodiments, the HER2 binding domain comprises an scFv comprising: (i) a variable heavy chain ($V_H$) sequence of SEQ ID NO: 8 or with at least 70%, 75%, 80%, 85%, 90%, 91%, 92%, 93%, 94%, 95%, 96%, 97%, 98% or 99% sequence identity to SEQ ID NO: 8; and (ii) a variable light chain ($V_L$) sequence of SEQ ID NO: 9 or with at least 70%, 75%, 80%, 85%, 90%, 91%, 92%, 93%, 94%, 95%, 96%, 97%, 98% or 99% sequence identity to SEQ ID NO: 9. In some embodiments, the CD5 binding domain comprises an scFv comprising SEQ ID NO: 32 or with at least 70%, 75%, 80%, 85%, 90%, 91%, 92%, 93%, 94%, 95%, 96%, 97%, 98% or 99% sequence identity to SEQ ID NO: 32. In some embodiments, the CFP further comprises an intracellular domain, wherein the intracellular domain comprises one or more intracellular signaling domains, and wherein a wild-type protein comprising the intracellular domain does not comprise the extracellular domain.

In some embodiments, the extracellular domain further comprises a hinge domain derived from CD8, wherein the hinge domain is operatively linked to the transmembrane domain and the anti-CD5 binding domain. In some embodiments, the extracellular hinge domain comprises a sequence of SEQ ID NO: 7 or with at least 70%, 75%, 80%, 85%, 90%, 91%, 92%, 93%, 94%, 95%, 96%, 97%, 98% or 99% sequence identity to SEQ ID NO: 7.

In some embodiments, the CFP comprises an extracellular domain fused to a transmembrane domain of SEQ ID NO: 30 or with at least 70%, 75%, 80%, 85%, 90%, 91%, 92%, 93%, 94%, 95%, 96%, 97%, 98% or 99% sequence identity to SEQ ID NO: 30. In some embodiments, the CFP comprises an extracellular domain fused to a transmembrane domain of SEQ ID NO: 31 or with at least 70%, 75%, 80%, 85%, 90%, 91%, 92%, 93%, 94%, 95%, 96%, 97%, 98% or 99% sequence identity to SEQ ID NO: 31.

In some embodiments, the transmembrane domain comprises a CD8 transmembrane domain. In some embodiments, the transmembrane domain comprises a sequence of SEQ ID NO: 6 or 29 or with at least 70%, 75%, 80%, 85%, 90%, 91%, 92%, 93%, 94%, 95%, 96%, 97%, 98% or 99% sequence identity to SEQ ID NO: 6 or 29. In some embodiments, the transmembrane domain comprises a sequence of SEQ ID NO: 18 or with at least 70%, 75%, 80%, 85%, 90%, 91%, 92%, 93%, 94%, 95%, 96%, 97%, 98% or 99% sequence identity to SEQ ID NO: 18. In some embodiments, the transmembrane domain comprises a sequence of SEQ ID NO: 34 or with at least 70%, 75%, 80%, 85%, 90%, 91%, 92%, 93%, 94%, 95%, 96%, 97%, 98% or 99% sequence identity to SEQ ID NO: 34. In some embodiments, the transmembrane domain comprises a sequence of SEQ ID NO: 19 or with at least 70%, 75%, 80%, 85%, 90%, 91%, 92%, 93%, 94%, 95%, 96%, 97%, 98% or 99% sequence identity to SEQ ID NO: 19.

In some embodiments, the CFP comprises one or more intracellular signaling domains that comprise a phagocytic signaling domain. In some embodiments, the phagocytosis signaling domain comprises an intracellular signaling domain derived from a receptor other than Megf10, MerTk, FcRα, and Bai1. In some embodiments, the phagocytosis signaling domain comprises an intracellular signaling domain derived from a receptor other than Megf10, MerTk, an FcR, and Bai1. In some embodiments, the phagocytosis signaling domain comprises an intracellular signaling domain derived from a receptor other than CD3ζ. In some embodiments, the phagocytosis signaling domain comprises an intracellular signaling domain derived from FcRγ, FcRα or FcRε. In some embodiments, the phagocytosis signaling domain comprises an intracellular signaling domain derived from CD3ζ. In some embodiments, the CFP comprises an intracellular signaling domain of any one of SEQ ID NOs: 3, 20, 27 and 28 or with at least 70%, 75%, 80%, 85%, 90%, 91%, 92%, 93%, 94%, 95%, 96%, 97%, 98% or 99% sequence identity to any one of SEQ ID NOs: 3, 20, 27 and 28. In some embodiments, the one or more intracellular signaling domains further comprises a proinflammatory signaling domain. In some embodiments, the proinflammatory signaling domain comprises a PI3-kinase (PI3K) recruitment domain. In some embodiments, the proinflammatory signaling domain comprises a sequence of SEQ ID NO: 4 or with at least 70%, 75%, 80%, 85%, 90%, 91%, 92%, 93%, 94%, 95%, 96%, 97%, 98% or 99% sequence identity to SEQ ID NO: 4. In some embodiments, the proinflammatory signaling domain is derived from an intracellular signaling domain of CD40. In some embodiments, the proinflammatory signaling domain comprises a sequence of SEQ ID NO: 5 or with at least 70%, 75%, 80%, 85%, 90%, 91%, 92%, 93%, 94%, 95%, 96%, 97%, 98% or 99% sequence identity to SEQ ID NO: 5. In some embodiments, the CFP comprises an intracellular signaling domain of SEQ ID NO: 21 or with at least 70%, 75%, 80%, 85%, 90%, 91%, 92%, 93%, 94%, 95%, 96%, 97%, 98% or 99% sequence identity to SEQ ID NO: 21. In some embodiments, the CFP comprises an intracellular signaling domain of SEQ ID NO: 23 or with at least 70%, 75%, 80%, 85%, 90%, 91%, 92%, 93%, 94%, 95%, 96%, 97%, 98% or 99% sequence identity to SEQ ID NO: 23.

In some embodiments, the CFP comprises a sequence of SEQ ID NO: 14 or with at least 70%, 75%, 80%, 85%, 90%, 91%, 92%, 93%, 94%, 95%, 96%, 97%, 98% or 99% sequence identity to SEQ ID NO: 14. In some embodiments, the CFP comprises a sequence of SEQ ID NO: 15 or with at least 70%, 75%, 80%, 85%, 90%, 91%, 92%, 93%, 94%, 95%, 96%, 97%, 98% or 99% sequence identity to SEQ ID NO: 15. In some embodiments, the CFP comprises a sequence of SEQ ID NO: 16 or with at least 70%, 75%, 80%, 85%, 90%, 91%, 92%, 93%, 94%, 95%, 96%, 97%, 98% or 99% sequence identity to SEQ ID NO: 16. In some embodiments, the CFP comprises a sequence of SEQ ID NO: 24 or with at least 70%, 75%, 80%, 85%, 90%, 91%, 92%, 93%, 94%, 95%, 96%, 97%, 98% or 99% sequence identity to SEQ ID NO: 24. In some embodiments, the CFP comprises a sequence of SEQ ID NO:25 or with at least 70%, 75%, 80%, 85%, 70%, 75%, 80%, 85%, 90%, 91%, 92%, 93%, 94%, 95%, 96%, 97%, 98% or 99%, 91%, 92%, 93%, 94%, 95%, 96%, 97%, 98% or 99% sequence identity to SEQ ID NO: 25.

In some embodiments, the CFP comprises: (a) an extracellular domain comprising: (i) a scFv that specifically binds CD5, and (ii) a hinge domain derived from CD8; a hinge domain derived from CD28 or at least a portion of an extracellular domain from CD68; (b) a CD8 transmembrane domain, a CD28 transmembrane domain, a CD2 transmembrane domain or a CD68 transmembrane domain; and (c) an intracellular domain comprising at least two intracellular signaling domains, wherein the at least two intracellular signaling domains comprise: (i) a first intracellular signaling domain derived from FcRα, FcRγ or FcRε, and (ii) a second intracellular signaling domain: (A) comprising a PI3K recruitment domain, or (B) derived from CD40. In some embodiments, the CFP comprises as an alternative (c) to the above: an intracellular domain comprising at least two intracellular signaling domains, wherein the at least two intracellular signaling domains comprise: (i) a first intracellular signaling domain derived from a phagocytic receptor intracellular domain, and (ii) a second intracellular signaling domain derived from a scavenger receptor phagocytic receptor intracellular domain comprising: (A) comprising a PI3K recruitment domain, or (B) derived from CD40. Exemplary scavenger receptors from which an intracellular signaling domain may be derived may be found in Table 2. In some embodiments, the CFP comprises and intracellular signaling domain derived from an intracellular signaling domain of an innate immune receptor.

In some embodiments, the recombinant polynucleic acid is an mRNA. In some embodiments, the recombinant polynucleic acid is a circRNA. In some embodiments, the recombinant polynucleic acid is a viral vector. In some embodiments, the recombinant polynucleic acid is delivered via a viral vector.

In some embodiments, the myeloid cell is a CD14+ cell, a CD14+/CD16− cell, a CD14+/CD16+ cell, a CD14−/CD16+ cell, CD14−/CD16− cell, a dendritic cell, an M0 macrophage, an M2 macrophage, an M1 macrophage or a mosaic myeloid cell/macrophage/dendritic cell.

In one aspect, provided herein is a method of treating cancer in a human subject in need thereof comprising administering a pharmaceutical composition to the human subject, the pharmaceutical composition comprising: (a) a myeloid cell comprising a recombinant polynucleic acid sequence, wherein the polynucleic acid sequence comprises a sequence encoding a chimeric fusion protein (CFP), the CFP comprising: (i) an extracellular domain comprising an anti-CD5 binding domain, and (ii) a transmembrane domain operatively linked to the extracellular domain; and (b) a pharmaceutically acceptable carrier; wherein the myeloid cell expresses the CFP.

In some embodiments, upon binding of the CFP to CD5 expressed by a target cancer cell of the subject killing or phagocytosis activity of the myeloid cell is increased by greater than 20% compared to a myeloid cell not expressing the CFP. In some embodiments, growth of a tumor is inhibited in the human subject.

In some embodiments, the cancer is a CD5+ cancer. In some embodiments, the cancer is leukemia, T cell lymphoma, or B cell lymphoma. In some embodiments, the CFP comprises one or more sequences shown in Table A and/or Table B below.

TABLE A

Exemplary sequences of CFPs and domains thereof

| SEQ ID NO | PFP/Domain | Sequence |
|---|---|---|
| 1 | Anti-CD5 heavy chain variable domain | EIQLVQSGGGLVKPGGSVRISCAASGYTFTNYGMNWV RQAPGKGLEWMGWINTHTGEPTYADSFKGRFTFSLDD SKNTAYLQINSLRAEDTAVYFCTRRGYDWYFDVWGQ GTTVTV |
| 2 | Anti-CD5 light chain variable domain | DIQMTQSPSSLSASVGDRVTITCRASQDINSYLSWFQQK PGKAPKTLIYRANRLESGVPSRFSGSGSGTDYTLTISSLQ YEDFGIYYCQQYDESPWTFGGGTKLEIK |
| 33 | Anti-CD5 scFv | EIQLVQSGGGLVKPGGSVRISCAASGYTFTNYGMNWV RQAPGKGLEWMGWINTHTGEPTYADSFKGRFTFSLDD SKNTAYLQINSLRAEDTAVYFCTRRGYDWYFDVWGQ GTTVTV*SSGGGGSGGGGSGGGGS*DIQMTQSPSSLSASV GDRVTITCRASQDINSYLSWFQQKPGKAPKTLIYRANR LESGVPSRFSGSGSGTDYTLTISSLQYEDFGIYYCQQYD ESPWTFGGGTKLEIK |
| 3 | FcRγ-chain intracellular signaling domain | LYCRRLKIQVRKAAITSYEKSDGVYTGLSTRNQETYET LKHEKPPQ |
| 20 | FcRγ-chain intracellular signaling domain | LYCRLKIQVRKAAITSYEKSDGVYTGLSTRNQETYETL KHEKPPQ |
| 27 | FcRγ-chain intracellular signaling domain | RLKIQVRKAAITSYEKSDGVYTGLSTRNQETYETLKHE KPPQ |
| 28 | FcRγ-chain intracellular signaling domain | RLKIQVRKAAITSYEKSDGVYTGLSTRNQETYETLKHE KPPQ |
| 4 | PI3K recruitment domain | YEDMRGILYAAPQLRSIRGQPGPNHEEDADSYENM |
| 5 | CD40 intracellular domain | KKVAKKPTNKAPHPKQEPQEINFPDDLPGSNTAAPVQE TLHGCQPVTQEDGKESRISVQERQ |
| 6 | CD8α chain transmembrane domain | IYIWAPLAGTCGVLLLSLVIT |
| 29 | CD8α chain transmembrane domain | IYIWAPLAGTCGVLLLSLVITLYC |
| 7 | CD8α chain hinge domain | ALSNSIMYFSHFVPVFLPAKPTTTPAPRPPTPAPTIASQP LSLRPEACRPAAGGAVHTRGLD |
| 8 | Anti-HER2 heavy chain variable domain | DIQMTQSPSSLSASVGDRVTITCRASQDVNTAVAWYQQ KPGKAPKLLIYSASFLYSGVPSRFSGSRSGTDFTLTISSL QPEDFATYYCQQHYTTPPTFGQGTKVEIKRTGSTSGSG KPGSGEGSEVQLVE |
| 9 | Anti-HER2 light chain variable domain | LVQPGGSLRLSCAASGFNIKDTYIHWVRQAPGKGLEW VARIYPTNGYTRYADSVKGRFTISADTSKNTAYLQMNS LRAEDTAVYYCSRWGGDGFYAMDVWGQGTLVTV |
| 32 | Anti-HER2 scFv | DIQMTQSPSSLSASVGDRVTITCRASQDVNTAVAWYQQ KPGKAPKLLIYSASFLYSGVPSRFSGSRSGTDFTLTISSL QPEDFATYYCQQHYTTPPTFGQGTKVEIKRTGSTSGSG KPGSGEGSEVQLVESSGGGGSGGGGSGGGGSLVQPGGS LRLSCAASGFNIKDTYIHWVRQAPGKGLEWVARIYPTN GYTRYADSVKGRFTISADTSKNTAYLQMNSLRAEDTA VYYCSRWGGDGFYAMDVWGQGTLVTV |
| 17 | GMCSF Signal peptide | MWLQSLLLLGTVACSIS |
| 18 | CD28 transmembrane domain | FWVLVVVGGVLACYSLLVTVAFIIFWV |

TABLE A-continued

Exemplary sequences of CFPs and domains thereof

| SEQ ID NO | PFP/Domain | Sequence |
|---|---|---|
| 34 | CD2 Transmembrane domain | IYLIIGICGGGSLLMVFVALLVFYIT |
| 19 | CD 68 transmembrane domain | ILLPLIIGLILLGLLALVLIAFCII |
| 21 | TNFR1 intracellular domain | QRWKSKLYSIVCGKSTPEKEGELEGTTTKPLAPNPSFSP TPGFTPTLGFSPVPSSTFTSSSTYTPGDCPNFAAPRREVA PPYQGADPILATALASDPIPNPLQKWEDSAHKPQSLDTD DPATLYAVVENVPPLRWKEFVRRLGLSDHEIDRLELQN GRCLREAQYSMLATWRRRTPRREATLELLGRVLRDMD LLGCLEDIEEALCGPAALPPAPSLLR |
| 22 | TNFR2 intracellular domain | PLCLQREAKVPHLPADKARGTQGPEQQHLLITAPSSSSS SLESSASALDRRAPTRNQPQAPGVEASGAGEARASTGS SDSSPGGHGTQVNVTCIVNVCSSSDHSSQCSSQASSTM GDTDSSPSESPKDEQVPFSKEECAFRSQLETPETLLGSTE EKPLPLGVPDAGMKPS |
| 23 | MDA5 intracellular domain | MSNGYSTDENFRYLISCFRARVKMYIQVEPVLDYLTFL PAEVKEQIQRTVATSGNMQAVELLLSTLEKGVWHLGW TREFVEALRRTGSPLAARYMNPELTDLPSPSFENAHDE YLQLLNLLQPTLVDKLLVRDVLDKCMEEELLTIEDRNR IAAAENNGNESGVRELLKRIVQKENWFSAFLNVLRQTG NNELVQELTGSDCSESNAEIEN |
| 30 | CD8α chain hinge domain + transmembrane domain | ALSNSIMYFSHFVPVFLPAKPTTTPAPRPPTPAPTIASQP LSLRPEACRPAAGGAVHTRGLDIYIWAPLAGTCGVLLL SLVITLYC |
| 31 | CD8α chain hinge domain + transmembrane domain | ALSNSIMYFSHFVPVFLPAKPTTTPAPRPPTPAPTIASQP LSLRPEACRPAAGGAVHTRGLDIYIWAPLAGTCGVLLL SLVIT |
| 14 | CD5-FcRγ-PI3K | MWLQSLLLLGTVACSISEIQLVQSGGGLVKPGGSVRISC AASGYTFTNYGMNWVRQAPGKGLEWMGWINTHTGEP TYADSFKGRFTFSLDDSKNTAYLQINSLRAEDTAVYFC TRRGYDWYFDVWGQGTTVTV*SSGGGGSGGGGSGGGG* *S*DIQMTQSPSSLSASVGDRVTITCRASQDINSYLSWFQQ KPGKAPKTLIYRANRLESGVPSRFSGSGSGTDYTLTISSL QYEDFGIYYCQQYDESPWTFGGGTKLEIKSGGGGSGAL SNSIMYFSHFVPVFLPAKPTTTPAPRPPTPAPTIASQPLSL RPEACRPAAGGAVHTRGLDIYIWAPLAGTCGVLLLSLV ITLYCRRLKIQVRKAAITSYEKSDGVYTGLSTRNQETYE TLKHEKPPQGSGSYEDMRGILYAAPQLRSIRGQPGPNHE EDADSYENM |
| 15 | HER2-FcRγ-PD3K | MWLQSLLLLGTVACSISDIQMTQSPSSLSASVGDRVTIT CRASQDVNTAVAWYQQKPGKAPKLLIYSASFLYSGVP SRFSGSRSGTDFTLTISSLQPEDFATYYCQQHYTTPPTFG QGTKVEIKRTGSTSGSGKPGSGEGSEVQLVESGGGLVQ PGGSLRLSCAASGFNIKDTYIHWVRQAPGKGLEWVARI YPTNGYTRYADSVKGRFTISADTSKNTAYLQMNSLRAE DTAVYYCSRWGGDGFYAMDVWGQGTLVTVSSSGGGG SGALSNSIMYFSHFVPVFLPAKPTTTPAPRPPTPAPTIAS QPLSLRPEACRPAAGGAVHTRGLDIYIWAPLAGTCGVL LLSLVITLYCRRLKIQVRKAAITSYEKSDGVYTGLSTRN QETYETLKHEKPPQGSGSYEDMRGILYAAPQLRSIRGQP GPNHEEDADSYENM |
| 16 | CD5-FcRγ-CD40 | MWLQSLLLLGTVACSISEIQLVQSGGGLVKPGGSVRISC AASGYTFTNYGMNWVRQAPGKGLEWMGWINTHTGEP TYADSFKGRFTFSLDDSKNTAYLQINSLRAEDTAVYFC TRRGYDWYFDVWGQGTTVTVSSGGGGSGGGGSGGGG SDIQMTQSPSSLSASVGDRVTITCRASQDINSYLSWFQQ KPGKAPKTLIYRANRLESGVPSRFSGSGSGTDYTLTISSL QYEDFGIYYCQQYDESPWTFGGGTKLEIKSGGGGSGAL SNSIMYFSHFVPVFLPAKPTTTPAPRPPTPAPTIASQPLSL RPEACRPAAGGAVHTRGLDIYIWAPLAGTCGVLLLSLV ITLYCRLKIQVRKAAITSYEKSDGVYTGLSTRNQETYET LKHEKPPQKKVAKKPTNKAPHPKQEPQEINFPDDLPGS NTAAPVQETLHGCQPVTQEDGKESRISVQERQ |

TABLE A-continued

| SEQ ID NO | PFP/Domain | Sequence |
|---|---|---|
| | Exemplary sequences of CFPs and domains thereof | |
| 24 | CD5-FcRγ-MDA5 | MWLQSLLLLGTVACSISEIQLVQSGGGLVKPGGSVRISC AASGYTFTNYGMNWVRQAPGKGLEWMGWINTHTGEP TYADSFKGRFTFSLDDSKNTAYLQINSLRAEDTAVYFC TRRGYDWYFDVWGQGTTVTVSSGGGGSGGGGSGGGG SDIQMTQSPSSLSASVGDRVTITCRASQDINSYLSWFQQ KPGKAPKTLIYRANRLESGVPSRFSGSGSGTDYTLTISSL QYEDFGIYYCQQYDESPWTFGGGTKLEIKSGGGGSGAL SNSIMYFSHFVPVFLPAKPTTTPAPRPPTPAPTIASQPLSL RPEACRPAAGGAVHTRGLDIYIWAPLAGTCGVLLLSLV ITLYCRLKIQVRKAAITSYEKSDGVYTGLSTRNQETYET LKHEKPPQGSGSMSNGYSTDENFRYLISCFRARVKMYI QVEPVLDYLTFLPAEVKEQIQRTVATSGNMQAVELLLS TLEKGVWHLGWTREFVEALRRTGSPLAARYMNPELTD LPSPSFENAHDEYLQLLNLLQPTLVDKLLVRDVLDKCM EEELLTIEDRNRIAAAENNGNESGVRELLKRIVQKENW FSAFLNVLRQTGNNELVQELTGSDCSESNAEIEN |
| 25 | CD5-FcRγ-TNFR1 | MWLQSLLLLGTVACSISEIQLVQSGGGLVKPGGSVRISC AASGYTFTNYGMNWVRQAPGKGLEWMGWINTHTGEP TYADSFKGRFTFSLDDSKNTAYLQINSLRAEDTAVYFC TRRGYDWYFDVWGQGTTVTVSSGGGGSGGGGSGGGG SDIQMTQSPSSLSASVGDRVTITCRASQDINSYLSWFQQ KPGKAPKTLIYRANRLESGVPSRFSGSGSGTDYTLTISSL QYEDFGIYYCQQYDESPWTFGGGTKLEIKSGGGGSGAL SNSIMYFSHFVPVFLPAKPTTTPAPRPPTPAPTIASQPLSL RPEACRPAAGGAVHTRGLDIYIWAPLAGTCGVLLLSLV ITLYCRLKIQVRKAAITSYEKSDGVYTGLSTRNQETYET LKHEKPPQGSGSQRWKSKLYSIVCGKSTPEKEGELEGT TTKPLAPNPSFSPTPGFTPTLGFSPVPSSTFTSSSTYTPGD CPNFAAPRREVAPPYQGADPILATALASDPIPNPLQKWE DSAHKPQSLDTDDPATLYAVVENVPPLRWKEFVRRLG LSDHEIDRLELQNGRCLREAQYSMLATWRRRTPRREAT LELLGRVLRDMDLLGCLEDIEEALCGPAALPPAPSLLR |
| 26 | CD5-FcRγ-TNFR2 | MWLQSLLLLGTVACSISEIQLVQSGGGLVKPGGSVRISC AASGYTFTNYGMNWVRQAPGKGLEWMGWINTHTGEP TYADSFKGRFTFSLDDSKNTAYLQINSLRAEDTAVYFC TRRGYDWYFDVWGQGTTVTVSSGGGGSGGGGSGGGG SDIQMTQSPSSLSASVGDRVTITCRASQDINSYLSWFQQ KPGKAPKTLIYRANRLESGVPSRFSGSGSGTDYTLTISSL QYEDFGIYYCQQYDESPWTFGGGTKLEIKSGGGGSGAL SNSIMYFSHFVPVFLPAKPTTTPAPRPPTPAPTIASQPLSL RPEACRPAAGGAVHTRGLDIYIWAPLAGTCGVLLLSLV ITLYCRLKIQVRKAAITSYEKSDGVYTGLSTRNQETYET LKHEKPPQGSGSPLCLQREAKVPHLPADKARGTQGPEQ QHLLITAPSSSSSSLESSASALDRRAPTRNQPQAPGVEAS GAGEARASTGSSDSSPGGHGTQVNVTCIVNVCSSSDHS SQCSSQASSTMGDTDSSPSESPKDEQVPFSKEECAFRSQ LETPETLLGSTEEKPLPLGVPDAGMKPS |

TABLE B

| SEQ ID | Sequence |
|---|---|
| | Linker sequences |
| 10 | SSGGGGSGGGGSGGGGS |
| 11 | SGGGGSG |
| 12 | SGGG |
| 13 | GSGS |

IV. Noncoding Exogenous Sequence for Delivery and Incorporation into the Genome of a Cell.

A noncoding sequence may be delivered into the cell and designed to be incorporated in the genome of the cell. The noncoding sequence as used herein, is a sequence that does not result in a translated protein product, but may have regulatory elements, such as transcribed products, such as inhibitory RNA.

In some embodiments, such a sequence may be a miRNA sequence. In some embodiments, the sequence may be a sequence for siRNA generation. In some embodiments, the sequence may comprise an intronic sequence, or a binding site created such that one or more DNA binding proteins can dock on the site and influence the nature and behavior of the adjoining regions. In some embodiments, the sequence may be a transcription factor binding site. In some embodiments, the sequence may comprise an enhancer binding site. In some embodiments, the sequence may comprise a binding site for topoisomerase, gyrase, reverse transcriptase, polymerase, poly A binding protein, guanylyl cyclase, ligase, restriction enzymes, DNA methylase, HDAC enzymes, and many others. In some embodiments, the noncoding sequence may be directed to manipulating heterochromatin. A noncoding insert sequence, as it may also be referred to here, may be a few nucleotides to 5 kB in length.

V. Plasmid Design and Recombinant Nucleic Acid Design Comprising an Insert Sequence The nucleic acid construct comprising one or more sequences encoding one or more proteins or polypeptides is incorporated in a plasmid for transcription and generating an mRNA. mRNA can be transcribed in an in vitro system using synthetic system of cell extracts. Alternatively, mRNA can be generated in a cell and harvested. The cell can be a prokaryotic cell, such as a bacterial cell. In some embodiments, the cell is a eukaryotic cell. In some embodiments, the transcription occurs in a synthetic system. Provided herein are exemplary plasmid design.

In some embodiments, of the various aspects of the disclosure, a plasmid is designed for expression of the mRNA molecule comprising a heterologous sequence of interest that encodes a protein or a polypeptide. The plasmid comprises, inter alia, the sequences for genomic integration elements for integration of the heterologous sequence of interest that encodes a protein or a polypeptide; the sequence comprising the transgene or fragment thereof, operably linked to its separate promoter and regulatory elements that are required for its expression in the host following integration in the host genome, (such as, the subject who is administered the mRNA); one or more regulatory elements for transcription and generation of the mRNA including a promoter for expression of the mRNA, e.g. in a bacterial cell or cell extract, and 3' stabilizing elements; sequences for one or more detection marker and/or selection markers.

As is known to one of skill in the art, a plasmid backbone can be an available vector, such as an in-house or commercially developed vector, that can be improved in various ways for best expression of the transcribed sequences, for example, (but not limited to), by introducing one or more desirable restriction digestion sites in the MCS (multiple cloning site), introducing a desired promoter for overall mRNA transcription, such as the T7 promoter, exchanging an existing sequence within the plasmid vector for one or more desired sequences, or introducing one or more desired segments, such as a selection marker sequence.

The plasmid comprises transcription regulatory elements, such as a promoter at the 5' region, and a 3'-stabilizing element. In some embodiments, the promoter is chosen for enhanced mRNA transcription in the desired cell, such as an *E. coli* bacterial cell. In some embodiments, the promoter for transcription of the plasmid is selected from a T7 promoter, a Sp6 promoter, pL (lambda) promoter, T3 promoter, trp promoter, araBad promoter, lac promoter or a Ptac promoter. In some embodiments, the promoter is a T7 promoter. T7 or Sp6 promoters are constitutive promoters and are useful for high level transcription or in vitro transcription. In some embodiments, the 3' stabilizing element is a sequence from BGH 3' element, WPRE 3' element, SV40 element, hGH element and other elements. The 3' element comprises the necessary poly A and transcription termination sequences.

Exemplary selection markers include antibiotic selection marker and/or expression detection marker. Antibiotic selection markers include but are not limited to ampicillin resistance gene sequence (beta lactamase gene or fragment thereof) conferring resistance to ampicillin, for example G418 selection marker, tetracycline resistance gene sequence conferring resistance to tetracycline, kanamycin resistance gene sequence conferring resistance to kanamycin, erythromycin resistance gene sequence conferring resistance to erythromycin, chloramphenicol resistance gene sequence conferring resistance to chloramphenicol, neomycin resistant gene sequence conferring resistance to neomycin, and others. Exemplary expression detection marker include FLAG, HA, GFP and others.

In some embodiments, the and other tags that can be fused to one or more coding sequences to function as a surrogate for the expression of the desired protein or peptide to which it is fused.

In some embodiments, the plasmid is less than 20 kb in length. In some embodiments, the plasmid is less than 19 kb in length. In some embodiments, the plasmid is less than 20 kb in length. In some embodiments, the plasmid is less than 18 kb in length. In some embodiments, the plasmid is less than 20 kb in length. In some embodiments, the plasmid is less than 17 kb in length. In some embodiments, the plasmid is less than 20 kb in length. In some embodiments, the plasmid is less than 16 kb in length. In some embodiments, the plasmid is less than 15 kb in length. In some embodiments, the plasmid is less than 14 kb in length. In some embodiments, the plasmid is less than 13 kb in length. In some embodiments, the plasmid is less than 12 kb in length. In some embodiments, the plasmid is about 15 kb, about 14 kb, about 13 kb, about 12 kb or about 10 kb in length.

In some embodiments, the codon is optimized for maximized transcription suitable for the transcription system.

VI. Features Related to the Expression of the Transgene In Vivo

Transcription Regulatory Elements in the Recombinant Nucleic Acid Construct (Transgene)

In some embodiments, the recombinant nucleic comprises one or more regulatory elements within the noncoding regions that can be manipulated for desired expression profiles of the encoded proteins. In some embodiments, the noncoding region may comprise suitable enhancer. In some embodiments, the enhancer comprises a binding region for a regulator protein or peptide may be added to the cell or the system comprising the cell, for commencement of expression of the protein encoded under the influence of the enhancer. Conversely, a regulatory element may comprise a protein binding domain that remains bound with the cognate protein and continue to inhibit transcription and/or translation of recombinant protein until an extracellular signal is provided for the protein to decouple from the bound position to allow commencement of the protein synthesis. Examples include but are not limited to Tetracycline-inducible (Tet-Inducible or Tet-on) and Tetracycline repressible (Tet-off) systems known to one of skill in the art.

Construct comprising metabolic switch: In some embodiments, the 5' and 3' untranslated regions flanking the coding regions of the construct may be manipulated for regulation of expression of the recombinant protein encoded by the nucleic acid constructs described above. For instance, the 3'UTR may comprise one or more elements that are inserted for stabilizing the mRNA. In some embodiments, AU-Rich Elements (ARE) sequences are inserted in the 3' UTR that result in binding of RNA binding proteins that stabilize or destabilize the mRNA, allowing control of the mRNA half-life.

In some embodiments, the 3'UTR may comprise a conserved region for RNA binding proteins (e.g. GAPDH) binding to mature mRNA strand preventing translation. In some embodiments, glycolysis results in the uncoupling of the RNA binding proteins (e.g. GAPDH) allowing for mRNA strand translation. The principle of the metabolic switch is to trigger expression of target genes when a cell enters a certain metabolic state. In resting cells, for example, GAPDH is an RNA binding protein (RBP). It binds to ARE sequences in the 3'UTR, preventing translation of mRNA. When the cell enters glycolysis, GAPDH is required to convert glucose into ATP, coming off the mRNA allowing for translation of the protein to occur. In some embodiments, the environment in which the cell comprising the recombinant nucleic acid is present, provides the metabolic switch to the gene expression. For example, hypoxic condition can trigger the metabolic switch inducing the disengaging of GAPDH from the mRNA. The expression of the mRNA therefore can be induced only when the macrophage leaves the circulation and enters into a tumor environment, which is hypoxic. This allows for systemic administration of the nucleic acid or a cell comprising the nucleic acid, but ensures a local expression, specifically targeting the tumor environment.

In some embodiments, the nucleic acid construct can be a split construct, for example, allowing a portion of the construct to be expressed under the control of a constitutive expression system whereas another portion of the nucleic acid is expressed under control of a metabolic switch, as described above. In some embodiments, the nucleic acid may be under bicistronic control. In some embodiments, the bicistronic vector comprises a first coding sequence under a first regulatory control, comprising the coding sequence of a target recognition moiety which may be under constitutive control; and a second coding sequence encoding an inflammatory gene expression which may be under the metabolic switch. In some embodiments, the bicistronic vector may be unidirectional. In some embodiments, the bicistronic vector may be bidirectional.

In some embodiments, the ARE sequences comprise protein binding motifs for binding ARE sequence that bind to ADK, ALDH18A1, ALDH6A1, ALDOA, ASS1, CCBL2, CS, DUT, ENO1, FASN, FDPS, GOT2, HADHB, HK2, HSD17B10, MDH2, NME1, NQ01, PKM2, PPP1CC, SUCLG1, TP11, GAPDH, or LDH.

Pharmaceutical Compositions and Immunotherapy

In one aspect provided herein is a pharmaceutical composition comprising (i) the nucleic acid encoding the transgene is incorporated in a transpositioning or retrotranspositioning system comprising the transgene, the 5'- and 3'-flanking transposition or retrotranspositioning elements, the expression regulation elements, such as promoters, introns; and a nucleic acid encoding the transposase or retrotransposase, (ii) a nucleic acid delivery vehicle and a pharmaceutically acceptable salt or excipient.

In some embodiments, the pharmaceutical composition comprises cells comprising the nucleic acid encoding the transgene that is stably integrated in the genome of the cell and a pharmaceutically acceptable excipient. Nucleic acid constructs can be delivered with cationic lipids (Goddard, et al, Gene Therapy, 4:1231-1236, 1997; Gorman, et al, Gene Therapy 4:983-992, 1997; Chadwick, et al, Gene Therapy 4:937-942, 1997; Gokhale, et al, Gene Therapy 4:1289-1299, 1997; Gao, and Huang, Gene Therapy 2:710-722, 1995), using viral vectors (Monahan, et al, Gene Therapy 4:40-49, 1997; Onodera, et al, Blood 91:30-36, 1998), by uptake of "naked DNA", and the like. Techniques well known in the art for the transformation of cells (see discussion above) can be used for the ex vivo administration of nucleic acid constructs. The exact formulation, route of administration and dosage can be chosen empirically. (See e.g. Fingl et al., 1975, in "The Pharmacological Basis of Therapeutics", Ch. 1 pl).

In some embodiments, the nucleic acid comprising the transgene and the transposable elements is introduced or incorporated in the cell by known methods of nucleic acid transfer inside a cell, such as using lipofectamine, or calcium phosphate, or via physical means such as electroporation or nucleofection.

In some embodiments, the nucleic acid is encapsulated in liposomes or lipid nanoparticles. LNPs are 100-300 nm in diameter provide efficient means of mRNA delivery to various cell types, including macrophages. In some embodiments, the nucleic acid is transferred by other nanoparticles. In some embodiments, the vector for expression of the CFP is of a viral origin, namely a lentiviral vector or an adenoviral vector. In some embodiments, the nucleic acid encoding the recombinant nucleic acid is encoded by a lentiviral vector. In some embodiments, the lentiviral vector is prepared in-house and manufactured in large scale for the purpose. In some embodiments, commercially available lentiviral vectors are utilized, as is known to one of skill in the art.

In some embodiments, the viral vector is an Adeno-Associated Virus (AAV) vector.

The methods find use in a variety of applications in which it is desired to introduce an exogenous nucleic acid into a target cell and are particularly of interest where it is desired to express a protein encoded by an expression cassette in a target cell, where the target cell or cells are part of a multicellular organism. The transposase system may be administered to the organism or host in a manner such that the targeting construct is able to enter the target cell(s), e.g., via an in vivo or ex vivo protocol. Such cells or organs are typically returned to a living body.

In some embodiments, the transgene encoding a fusion protein related to immune function is stably integrated in a living cell of a subject ex vivo, following which the cell comprising the transgene is returned to the subject. Of exemplary importance, the CFP transgene (phagocytic receptor fusion protein) is intended for expression in an immune cell, such as a myeloid cell, a phagocytic cell, a macrophage, a monocyte or a cell of dendritic cell lineage is contacted ex vivo with the recombinant nucleic acids for stable transfer of the transgene and re-introduced in the same subject for combating a disease of the subject. The diseases contemplated comprises infectious diseases, cancer and autoimmune diseases. The nucleic acid encoding the PSR subunit comprising fusion protein (CFP) described herein is used to generate engineered phagocytic cells for treating cancer.

Cancers include, but are not limited to T cell lymphoma, cutaneous lymphoma, B cell cancer (e.g., multiple myeloma, Waldenstrom's macroglobulinemia), the heavy chain diseases (such as, for example, alpha chain disease, gamma chain disease, and mu chain disease), benign monoclonal gammopathy, and immunocytic amyloidosis, melanomas, breast cancer, lung cancer, bronchus cancer, colorectal cancer, prostate cancer (e.g., metastatic, hormone refractory prostate cancer), pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. Other non-limiting examples of types of cancers applicable to the methods encompassed by the present disclosure include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, the cancer is an epithelial cancer such as, but not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers can be characterized in various other ways including, but not limited to, serous, endometrioid, mucinous, clear cell, or undifferentiated. In some embodiments, the present disclosure is used in the treatment, diagnosis, and/or prognosis of lymphoma or its subtypes, including, but not limited to, mantle cell lymphoma. Lymphoproliferative disorders are also considered to be proliferative diseases.

In general, cellular immunotherapy comprises providing the patient a medicament comprising live cells, which should be HLA matched for compatibility with the subject, and such that the cells do not lead to graft versus Host Disease, GVHD. A subject arriving at the clinic for personalized medicine and immunotherapy as described above, is routinely HLA typed for determining the HLA antigens expressed by the subject.

Therapeutic Advantages of mRNA Driven Delivery

In one embodiment, provided herein is a method of introducing a nucleic acid sequence into a cell for sustained gene expression in the cell without adverse effects. In some embodiments, the cell is within a living system, e.g., a host organism such as a human. The nucleic acid sequence is an mRNA.

In particular, delivery via retrotransposon poses to be a highly lucrative mode. mRNA driven delivery simplifies gene delivery. While other technologies require expensive and sophisticated design and manufacturing, and a solution for delivery of the nucleic acid into the cell, and gene editing technologies to assist in integration, retrotransposon mediated delivery itself encodes for the editing machinery, encodes for new genes to be delivered. In addition, a single mRNA may be sufficient for gene delivery and editing.

In one embodiment, mRNA delivery is advantageous in that it can ensure introduction of a nucleic acid cargo without size restraint.

Table 9 summarizes some of the advantages over the other existing methods of nucleic acid deliveries.

TABLE 9

Advantages of retrotransposon mediated gene delivery

| | Lentiviral delivery | AAV-delivery | Retrotransposon delivery |
|---|---|---|---|
| Payload | ~4 kb | ~4 kb | >10 kb |
| Toxicity | Insertional mutagenesis | Unresolved liver & CNS toxicity | Unknown, pending clinical development |
| Manufacturing | Complex, expensive | Complex, expensive | Inexpensive, rapid |

Retrotransposons are advantageous for applications across multiple modalities. Gene manipulation using this method is easily attained both in vivo and ex vivo. In one embodiment, the application of retrotransposon may be in vivo, a piece of genetic material encoded in an mRNA can be directly introduced into a patient by systemic or local introduction. In contrast, cells can be taken out from a subject, and manipulated ex vivo and then introduced either to the same subject (autologous) or to another human (heterologous).

In one embodiment, retrotransposons and the related methods described herein may be instrumental in gene therapy. With the advantage of capacity to introduce large payloads, large sections of DNA carrying a gene encoding an entire protein may be introduced in one shot without requiring multiple introductions and multiple editing events. In one embodiment, for example, a gene that encodes a defective protein may be excised, the correct gene may be introduced in the correct site in one integration event using a retrotransposon mediated delivery. In one example, CRISPR editing may be used to excise a gene from precise locus and retrotransposition may be used to replace the correct genes. In some embodiments, a preferred retrotransposon integration site may be introduced at the excision site.

In one embodiment, retrotransposons and the related methods described herein may be instrumental in gene editing.

In one embodiment, retrotransposons and the related methods described herein may be instrumental in transcriptional regulation.

In one embodiment, retrotransposons and the related methods described herein may be instrumental in genome engineering.

In one embodiment, provided herein is a composition for incorporating a heterologous nucleic acid sequence in the genome comprising one or more polynucleic acids further comprise (i) a sequence encoding an integrase or a fragment thereof for site directed integration of the insert sequence into the genome and (ii) a genome landing site sequence that operable by the integrase, wherein the genome landing sequence is greater than 4, 5, 6, 7, 8, 9, or 10 consecutive nucleotides long. In some embodiments the integrase is a bacterial integrase. In some embodiments, the integrase is a serine integrase.

In some embodiments, the composition comprises an ORF2 and an integrase or a fragment thereof, wherein the integrase and the ORF2 are on separate polynucleotides. In some embodiments, the integrase has a capability of integrating nucleic acid sequence into a genomic site that has a genomic landing sequence that is about 10 nucleotides long, about 20 nucleotides long, about 30 nucleotides long, about 40 nucleotides long.

In some embodiments, the ORF2 and the integrase are on a single polynucleotide. In some embodiments, the ORF2 is modified to incorporate a fragment of an integrase protein that can recognize a genomic landing sequence of greater than 10 consecutive nucleotides long, and wherein the LINE retrotransposon system integrates the heterologous genomic insert into the genomic landing sequence recognized by the fragment of an integrase protein that has been incorporated into the genome.

In some embodiments, the integrase is not integrated into the genome of the cell. In some embodiments, the integrase is a recombinant protein. In some embodiments the ORF protein, e.g., the ORF2 protein is a recombinant (e.g., chimeric) protein, which comprises at least a fragment of a bacterial serine integrase that is capable of recognizing a genomic landing sequence of an integrase, e.g., a bacterial integrase, e.g., a bacterial serine integrase, wherein the genome landing sequence that is operable by the integrase and is greater than 20 nucleotides long, or greater than 30 nucleotides long. In some embodiments, the one or more of the ORF protein sequence comprise a mutation. In some embodiments, the recombinant (e.g., chimeric) ORF protein comprises a deletion of the target recognition sequence. In some embodiments, the recombinant (e.g., chimeric) ORF protein comprises a fragment of the integrase, e.g., a bacterial integrase, e.g., a bacterial serine integrase, which comprises a catalytic domain or a fragment thereof, a site-specific genomic integration recognition domain.

Provided herein is a pharmaceutical composition, wherein the insert sequence comprises an attachment site operable by the integrase.

In some embodiments, the genomic landing site is inserted into the genome using a guide RNA and a Cas system. In some embodiments, the guide RNA, the CAS system and the genomic landing sequence are in a polynucleotide that is separate from the polynucleotide comprising the sequence encoding the LINE1-ORFs and the insert sequence.

Provided herein is a method for a site-specific integration of a heterologous genomic insert sequence into the genome of a mammalian cell, the method comprising: (i) introducing into the cell (a) a polynucleotide comprising sequences encoding one or more human retrotransposon elements associated with the heterologous insert sequence, and (b) a polynucleotide comprising sequence encoding a guide RNA, an RNA guided integrase or a fragment thereof and a landing sequence operable by the integrase; (ii) verifying the integration of the heterologous insert sequence into the site of the genome.

Provided herein is a method for site-specific integration of a heterologous genomic insert using a LINE retrotransposon system, wherein the LINE retrotransposon system is modified to incorporate a fragment of an integrase protein that can recognize a genomic landing sequence of greater than 10 consecutive nucleotides long, and wherein the LINE retrotransposon system integrates the heterologous genomic insert into the genomic landing sequence recognized by the fragment of the integrase protein that has been incorporated into the genome. In some embodiments, the integrase recognizes and contacts the genomic landing sequence, and the reverse transcriptase elements of the LINE (L1) retrotransposon system reverse transcribes and incorporates the insert sequence (e.g., the cargo sequence) at the specific site of the genome landing sequence. In some embodiments, the method comprises a step of incorporating into the genome the genomic landing sequence of greater than 10 consecutive nucleotides long. In some embodiments, the step of incorporating into the genome the genomic landing sequence is performed by an RNA-guided CRISPR-Cas system. In some embodiments, the RNA-guided CRISPR-Cas system has an editing function capable of incorporating a sequence of greater than 10 consecutive nucleotides long into a specific genome site.

Therefore, provided herein is a modified L1 retrotransposition system comprising a site specific integrase DNA recognition moiety; wherein the integrase DNA recognition moiety recognizes the genomic sequence for site-specific integration, and wherein the L1 retrotransposition system reverse transcribes and integrates the sequence comprising the heterologous insert into the genomic site at or near the site recognized by the integrase. Existing systems incorporating an integrase, such as a serine integrase may comprise a DNA integration system, using for example a plasmid, a viral delivery system, each of which can be bypassed for the safer and sure mRNA system as used herein, and without the limitation of cargo size.

In one embodiment, retrotransposons and the related methods described herein may be instrumental in developing cell therapy, for example chimeric antigen receptor (CAR)T cells, in NK cell therapy or in myeloid cell therapy. In one embodiment, retrotransposons and the related methods described herein may be instrumental in delivery of genes into neurons, which are difficult to access by existing technologies.

In one aspect, provided herein is a method for targeted replacement of a genomic nucleic acid sequence of a cell, the method comprising: (A) introducing to the cell a polynucleotide sequence encoding a first protein complex comprising a targeted excision machinery for excising from the genome of the cell a nucleic acid sequence comprising one or more mutations; and (B) a recombinant mRNA encoding a second protein complex, wherein the recombinant mRNA comprises: (i) a nucleic acid sequence comprising the excised nucleic acid sequence in (A) that does not contain the one or more mutations, and (ii) a sequence encoding an L1 retrotransposon ORF2 protein under the influence of an independent promoter.

In one embodiment, the first protein complex may be an endonuclease complex independent of the second protein complex. In one embodiment, the first protein complex comprises a CRISPR-CAS system that uses sequence guided genomic DNA excision. In one embodiment, the methods described herein couples a CRISPR CAS system or any other gene editing system with a L1 transposon machinery (e.g., the second protein complex) that delivers a replacement gene with a payload capacity of greater than 4 kb, or 5 kb, or 6 kb, or 7 kb, or 8 kb or 9 kb or 10 kb. This coupling can be utilized in precisely excising a large fragment (a mutated gene causing a disease) from the genomic locus and integrating a large fragment of a gene or an entire gene that encodes a correct, non-mutated sequence.

A large number of genetic diseases may require delivery of gene delivery of large payloads, often exceeding the functional capacity of existing methods. Contemplated herein are methods and compositions disclosed herein that can be instrumental in further designing therapy for such diseases using retrotransposons. An exemplary list of genetic diseases include but are not limited to the ones listed in Table 10.

TABLE 10

List of potential gene therapy applications

| Disease | Gene | CDS | Expression | Prevalence |
|---|---|---|---|---|
| Stargardt | ABCA4 | 6.8 kb | Rod and Cone PRs | 1:8000 |
| Usher 1B | MY07A | 6.7 kb | RPE and PRs | 3.2:100,000 |
| LCA10 | CEP290 | 7.4 kb | PR (pan retinal) | 1:50,000 |
| USH1D, DFNB12 | CDH23 | 10.1 kb | PR | 3:100,000 |
| RP | EYS | 9.4 kb | PR ECM | 1:50,000 |
| USH2A | USH2a | 15.6 kb | Rod and Cone PRs | 4:100,000 |
| USH2C | GPR98 | 18.0 kb | Mainly PRs | 1:100,000 |
| Alstrom syndrome | ALMS1 | 12.5 kb | Rod and Cone PRs | 1:1,000,000 |
| Glycogen storage disease III | GDE | 4.6 kb | Muscle, Liver | 1:8000 |
| Non-syndromic deafness | OTOF | 6.0 kb | Ear | 14:100,000 |
| Hemophilia A | F8 | 7.1 kb | Liver | 1:10,000 |
| Leber congenital aumaurosis | CEP290 | 7.5 kb | Retina | 5:100,000 |

Provided herein is a method for targeted replacement of a genomic nucleic acid sequence in a cell. In one embodiment, the method comprises: (A) excising from the genome of the cell a nucleic acid sequence comprising one or more mutations and (B) introducing into the cell a recombinant mRNA encoding: (i) a nucleic acid sequence comprising a wild type sequence relative to the sequence excised in (A) that does not contain the one or more mutation, (ii) a sequence encoding an L1 retrotransposon ORF2 protein under the influence of an independent promoter. In one embodiment, Step (A) further comprises introducing a short sequence comprising at least a plurality of adenylate residues at the excision site. In one embodiment, the In one embodiment, the nucleic acid sequence comprising a wild type sequence is operably linked with the ORF2 encoding sequence in a way such that the ORF2 reverse transcriptase integrates the sequence comprising the wild type non-mutated sequence into the genome.

In one embodiment, the cell is a lymphocyte.

In one embodiment, the cell is an epithelial cell. In some embodiments the cell is a retinal pigmented epithelial cell (RPE).

In one embodiment, the cell is a neuron.

In one embodiment, the cell is a myeloid cell.

In one embodiment, the cell is a stem cell.

In one embodiment, the cell is a cancer cell.

In one embodiment, the gene is selected from a group consisting of ABCA4, MY07A, CEP290, CDH23, EYS, USH2a, GPR98, ALMS1, GDE, OTOF and F8.

In one embodiment, the mRNA comprises a sequence for an inducible promoter.

In one embodiment, the expression of the nucleic acid sequence comprising a non-mutated sequence is detectable at least 20, 21, 22, 23, 24, 25, 26, 27, 28, 29, 30, 31, 32, 33, 34 or 35 days post infection.

In one embodiment, the method comprises introducing into the cell a recombinant mRNA in vivo.

In one embodiment, the method comprises introducing into the cell a recombinant mRNA ex vivo.

Provided herein is a method of treating a genetic disease in a subject in need thereof, comprising: introducing into the subject a composition comprising a polycistronic mRNA encoding a gene or fragment thereof, operably linked to a sequence encoding an L1 retrotransposon; wherein the gene or the fragment thereof is at least 10.1 kb in length.

In one embodiment, the method comprises directly introducing the mRNA systemically.

In one embodiment, the method comprises directly introducing the mRNA locally.

In one embodiment, the genetic disease is a retinal disease. For example, the disease is macular dystrophy. In one embodiment, the disease is Stargardt disease, also known as juvenile macular degeneration, or fundus flavimaculatus. The disease causes progressive degeneration and damage of the macula. The condition has a genetic basis due to mutation in the ATP-binding cassette (ABC) transporter gene, (ABCA4) gene, and arises from the deposition of lipofuscin-like substance in the retinal pigmented epithelium (RPE) with secondary photoreceptor cell death. In some embodiments, the method comprises direct delivery of the mRNA to the retina.

In one embodiment, the method comprises treating a nonsyndromic autosomal recessive deafness (DFNB12) and deafness associated with retinitis pigmentosa and vestibular dysfunction (USHID). In one embodiment, provided herein is a method of treating non-syndromic deafness (DFNB12) or Usher syndrome (USH1D), the method comprises introducing an mRNA comprising a copy of CDH23 or a fragment thereof operably linked to a sequence encoding an L1 retrotransposon.

Cell Specific Expression of Exogenous Polypeptide

Stable expression of an exogenous polypeptide may be accomplished in a variety of cell types (e.g. target cell types) using a mobile genetic element to target integration of a polynucleotide sequence (e.g. often referred to herein as an insert sequence in a construct) in the genome of the cell (e.g. a target cell). In some embodiments, the target cell is a post-mitotic cell, e.g., a mammalian cardiomyocyte, or an RPE cell. In some embodiments, the mobile genetic element comprises a human LINE 1 sequence. In some embodiments, the mobile genetic element is a human LINE1 sequence. In some embodiments, the mobile genetic element comprises a sequence encoding a human L1 ORFp1 protein. In some embodiments, the mobile genetic element comprises a sequence encoding a human L1-ORFp2 protein. In some embodiments, the mobile genetic element comprises a sequence encoding a human ORFp1 and human ORFp2 polypeptides. In some embodiments, a polynucleotide sequence is introduced in a target cell, the polynucleotide comprises of a sequence encoding a mobile genetic element, and an insert sequence. In some embodiments, the mobile genetic element comprises a polypeptide that post-translationally promotes a stable integration of an insert sequence into the genome of the target cell. In some embodiments, the mobile genetic element comprises a polypeptide further configured for site-specific integration of a given insert sequence into the genome of the target cell, for example but not limited to the embodiments as is described elsewhere in the specification.

In some embodiments, the polynucleotide described herein is an mRNA. The mRNA may be bicistronic or polycistronic. As is exemplified by the working embodiments, the insert sequence and the sequence encoding the mobile genetic element can be in reverse orientation with respect to each other. The mobile genetic element may integrate the insert sequence via target-primed reverse transcription (TPRT).

In some embodiments, the mobile genetic element comprises the human L1 retrotransposon, or fragments thereof.

In some embodiments, the polynucleotide can be specifically targeted to a cell type. In some embodiments, the polynucleotide may be composed in a nanoparticle, wherein the nanoparticle comprises one or more targeting moieties known to one of skill in the art.

Provided herein is a method of stably integrating an insert sequence into genomic DNA of a target cell, the method comprising contacting a composition to the target cell, the composition comprising a polynucleic acid, wherein the polynucleic acid comprises: an insert sequence, wherein the insert sequence comprises a sequence that is a reverse complement of a sequence encoding an exogenous polypeptide, and a mobile genetic element comprising a sequence encoding a polypeptide, wherein the polypeptide encoded by the sequence of the mobile genetic element promotes integration of the insert sequence into genomic DNA; stably integrating the insert sequence into the genomic DNA of the target cell; and expressing an exogenous polypeptide in the target cell, wherein the target cell is a human hepatocyte. In some embodiments polynucleic acid is mRNA. In some embodiments, the mRNA is encapsulated in a nanoparticle for intracellular delivery. In some embodiments, the nanoparticle comprises a lipid. In some embodiments, the polynucleic acid is introduced into the hepatocyte by contacting a composition, comprising, for example, the polynucleic acid and a delivery vehicle (e.g., a nanoparticle comprises a lipid) to the hepatocyte such that it results in the successful uptake of the polynucleic acid by the hepatocyte. In some embodiments, the incorporation is via electroporation. In some embodiments, the polynucleic acid composition is electroporated in the hepatocyte. In some embodiments, the hepatocyte is electroporated under conditions suitable for expression of the polynucleic acid-encoded polypeptides and conducive to the viability of the hepatocyte. In some embodiments the integration of the insert into the genome of the hepatocyte is verified after incorporation the polynucleic acid by methods known to one of skill in the art, e.g., by genome sequencing. In some embodiments, the expression of the polypeptide from integrated insert sequence is verified at a suitable interval following incorporation of the polynucleic acid in the hepatocyte, wherein the suitable interval is about 4, 6, 8, 10, 12, 24 or 48 hours. In some embodiments, following electroporation of a population of cells comprising hepatocytes, the population of cells comprising the hepatocytes that have been subjected to the electroporation is cultured under conditions suitable for a hepatocyte for at least about 2 hours, about 3 hours, about 4 hours, about 5 hours, about 6 hours, about 8 hours, about 10 hours or about 24 hours. In some embodiments, the hepatocyte is cultured for about 48 hours, 72 hours, 96 hours or more under conditions suitable for a hepatocyte for growth. In some embodiments, the expression of a polypeptide encoded by the polynucleotide (e.g., the insert) is verified after 48, 72, or 96 hours, or after 4 days, 5 days, 6 days, 7 days, 8 days, 9 days, 10 days or more in culture. In some embodiments, at least 2% of the human hepatocytes express the exogenous polypeptide at day 10 after incorporating. In some embodiments, about 2%, or about 5%, or about 10% or more of the human hepatocytes in the population of cells subjected to the electroporation express the exogenous polypeptide at day 10 after incorporating.

Provided herein is a method of stably integrating an insert sequence into genomic DNA of a target cell, the method comprising contacting a composition to the target cell, the composition comprising a polynucleic acid, wherein the polynucleic acid comprises: an insert sequence, wherein the insert sequence comprises a sequence that is a reverse complement of a sequence encoding an exogenous polypeptide, and a mobile genetic element comprising a sequence encoding a polypeptide, wherein the polypeptide encoded by the sequence of the mobile genetic element promotes integration of the insert sequence into genomic DNA; stably integrating the insert sequence into the genomic DNA of the target cell; and expressing an exogenous polypeptide in the target cell, wherein the target cell is a human cardiomyocyte. In some embodiments polynucleic acid is mRNA. In some embodiments, the mRNA is encapsulated in a nanoparticle for intracellular delivery. In some embodiments, the nanoparticle comprises a lipid. In some embodiments, the polynucleic acid is introduced into the cardiomyocyte by contacting a composition, comprising, for example, the polynucleic acid and a delivery vehicle (e.g., a nanoparticle comprises a lipid) to the cardiomyocyte such that it results in the successful uptake of the polynucleic acid by the cardiomyocyte. In some embodiments, the incorporation is via electroporation. In some embodiments, the polynucleic acid composition is electroporated in the cardiomyocyte. In some embodiments, the cardiomyocyte is electroporated under conditions suitable for expression of the polynucleic acid-encoded polypeptides and conducive to the viability of the cardiomyocyte. In some embodiments the integration of the insert into the genome of the cardiomyocyte is verified after incorporation the polynucleic acid by methods known to one of skill in the art, e.g., by genome sequencing. In some embodiments, the expression of the polypeptide from integrated insert sequence is verified at a suitable interval following incorporation of the polynucleic acid in the cardiomyocyte, wherein the suitable interval is about 4, 6, 8, 10, 12, 24 or 48 hours. In some embodiments, following electroporation of a population of cells comprising cardiomyocytes, the population of cells comprising the cardiomyocytes that have been subjected to the electroporation is cultured under conditions suitable for a cardiomyocyte for at least about 2 hours, about 3 hours, about 4 hours, about 5 hours, about 6 hours, about 8 hours, about 10 hours or about 24 hours. In some embodiments, the cardiomyocyte is cultured for about 48 hours, 72 hours, 96 hours or more under conditions suitable for a cardiomyocyte for growth. In some embodiments, the expression of a polypeptide encoded by the polynucleotide (e.g., the insert) is verified after 48, 72, or 96 hours, or after 4 days, 5 days, 6 days, 7 days, 8 days, 9 days, 10 days or more in culture. In some embodiments, at least 2% of the human cardiomyocytes express the exogenous polypeptide at day 10 after incorporating. In some embodiments, about 2%, or about 5%, or about 10% or more of the human cardiomyocytes in the population of cells subjected to the electroporation express the exogenous polypeptide at day 10 after incorporating. Provided herein is a method of stably integrating an insert sequence into genomic DNA of a target cell, the method comprising contacting a composition to the target cell, the composition comprising a polynucleic acid, wherein the polynucleic acid comprises: an insert sequence, wherein the insert sequence comprises a sequence that is a reverse complement of a sequence encoding an exogenous polypeptide, and a mobile genetic element comprising a sequence encoding a polypeptide, wherein the polypeptide encoded by the sequence of the mobile genetic element promotes integration of the insert sequence into genomic DNA; stably integrating the insert sequence into the genomic DNA of the target cell; and expressing an exogenous polypeptide in the target cell, wherein the target cell is a human retinal pigment epithelial cell (RPE). In some embodiments polynucleic acid is mRNA. In some embodiments, the mRNA is encapsulated in a nanoparticle for intracellular delivery. In some embodiments, the nanoparticle comprises a lipid. In some embodiments, the polynucleic acid is introduced into the RPE by contacting a composition, comprising, for example, the polynucleic acid and a delivery vehicle (e.g., a nanoparticle comprises a lipid) to the RPE such that it results in the successful uptake of the polynucleic acid by the RPE. In some embodiments, the incorporation is via electroporation. In some embodiments, the polynucleic acid composition is electroporated in the RPE. In some embodiments, the RPE is electroporated under conditions suitable for expression of the polynucleic acid-encoded polypeptides and conducive to the viability of the RPE. In some embodiments the integration of the insert into the genome of the RPE is verified after incorporation the polynucleic acid by methods known to one of skill in the art, e.g., by genome sequencing. In some embodiments, the expression of the polypeptide from integrated insert sequence is verified at a suitable interval following incorporation of the polynucleic acid in the RPE, wherein the suitable interval is about 4, 6, 8, 10, 12, 24 or 48 hours. In some embodiments, following electroporation of a population of cells comprising RPEs, the population of cells comprising the RPEs that have been subjected to the electroporation is cultured under conditions suitable for a RPE for at least about 2 hours, about 3 hours, about 4 hours, about 5 hours, about 6 hours, about 8 hours, about 10 hours or about 24 hours. In some embodiments, the RPE is cultured for about 48 hours, 72 hours, 96 hours or more under conditions suitable for a RPE for growth. In some embodiments, the expression of a polypeptide encoded by the polynucleotide (e.g., the insert) is verified after 48, 72, or 96 hours, or after 4 days, 5 days, 6 days, 7 days, 8 days, 9 days, 10 days or more in culture. In some embodiments, at least 2% of the human RPEs express the exogenous polypeptide at day 10 after incorporating. In some embodiments, about 2%, or about 5%, or about 10% or more of the human RPEs in the population of cells subjected to the electroporation express the exogenous polypeptide at day 10 after incorporating.

Provided herein is a method of stably integrating an insert sequence into genomic DNA of a target cell, the method comprising contacting a composition to the target cell, the composition comprising a polynucleic acid, wherein the polynucleic acid comprises: an insert sequence, wherein the insert sequence comprises a sequence that is a reverse complement of a sequence encoding an exogenous polypeptide, and a mobile genetic element comprising a sequence encoding a polypeptide, wherein the polypeptide encoded by the sequence of the mobile genetic element promotes integration of the insert sequence into genomic DNA; stably integrating the insert sequence into the genomic DNA of the target cell; and expressing an exogenous polypeptide in the target cell, wherein the target cell is a human neuronal cell. In some embodiments polynucleic acid is mRNA. In some embodiments, the mRNA is encapsulated in a nanoparticle for intracellular delivery. In some embodiments, the nanoparticle comprises a lipid. In some embodiments, the polynucleic acid is introduced into the neuronal cell by contacting a composition, comprising, for example, the polynucleic acid and a delivery vehicle (e.g., a nanoparticle comprises a lipid) to the neuronal cell such that it results in the successful uptake of the polynucleic acid by the neuronal cell. In some embodiments, the incorporation is via electroporation. In some embodiments, the polynucleic acid composition is electroporated in the neuronal cell. In some embodiments, the neuronal cell is electroporated under conditions suitable for expression of the polynucleic acid-encoded polypeptides and conducive to the viability of the neuronal cell. In some embodiments the integration of the insert into the genome of the neuronal cell is verified after incorporation the polynucleic acid by methods known to one of skill in the art, e.g., by genome sequencing. In some embodiments, the expression of the polypeptide from integrated insert sequence is verified at a suitable interval following incorporation of the polynucleic acid in the neuronal cell, wherein the suitable interval is about 4, 6, 8, 10, 12, 24 or 48 hours. In some embodiments, following electroporation of a population of cells comprising neuronal cells, the population of cells comprising the neuronal cells that have been subjected to the electroporation is cultured under conditions suitable for a neuronal cell for at least about 2 hours, about 3 hours, about 4 hours, about 5 hours, about 6 hours, about 8 hours, about 10 hours or about 24 hours. In some embodiments, the neuronal cell is cultured for about 48 hours, 72 hours, 96 hours or more under conditions suitable for a neuronal cell for growth. In some embodiments, the expression of a polypeptide encoded by the polynucleotide (e.g., the insert) is verified after 48, 72, or 96 hours, or after 4 days, 5 days, 6 days, 7 days, 8 days, 9 days, 10 days or more in culture. In some embodiments, at least 2% of the human neuronal cells express the exogenous polypeptide at day 10 after incorporating. In some embodiments, about 2%, or about 5%, or about 10% or more of the human neuronal cells in the population of cells subjected to the electroporation express the exogenous polypeptide at day 10 after incorporating.

EXAMPLES

It should be appreciated that the invention should not be construed to be limited to the examples which are now described; rather, the invention should be construed to include any and all applications provided herein and all equivalent variations within the skill of the ordinary artisan.

Example 1. Exemplary Retrotransposon Designs Constructs

Figure 1A:
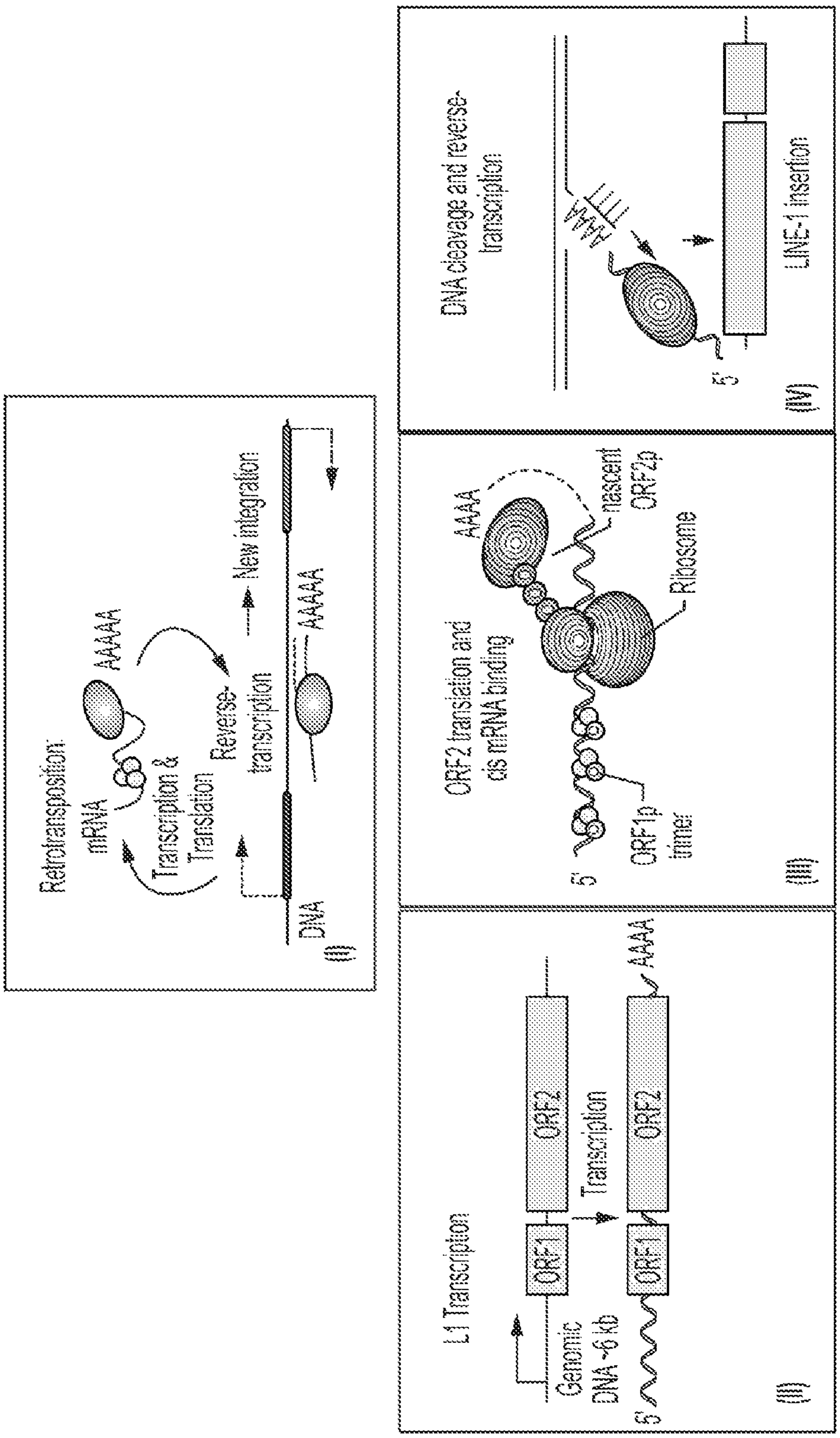
FIG. 1A illustrates a general mechanism of action of retrotransposons. (I) is a schematic representing the overall lifecycle of an autonomous retrotransposon. (II) LINE-1 retrotransposon comprises LINE-1 elements, which encode two proteins ORF1p and ORF2p that are expressed as mRNAs. The bicistronic mRNA is translated into the two proteins, and when ORF2p is translated by a read-through event by the ribosome, it binds the 3' end of its own mRNA through the poly A tail (III). ORF2p cleaves at a consensus sequence TAAAA, where the poly A at the 3' end of the mRNA hybridizes and primes the reverse transcriptase activity of the ORF2 protein. The protein reverse-transcribes the mRNA back into DNA leading to an insertion of the LINE-1 sequence back into a new location in the genome (IV).
Figure 1B:
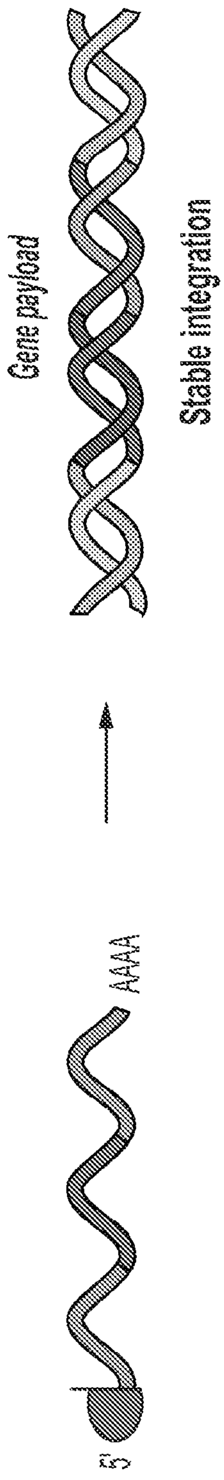
FIG. 1B is an illustration of a schematic diagram of an mRNA construct that comprises a genetic payload (left) that can be designed for integration into the genome (right).
Figure 1C:
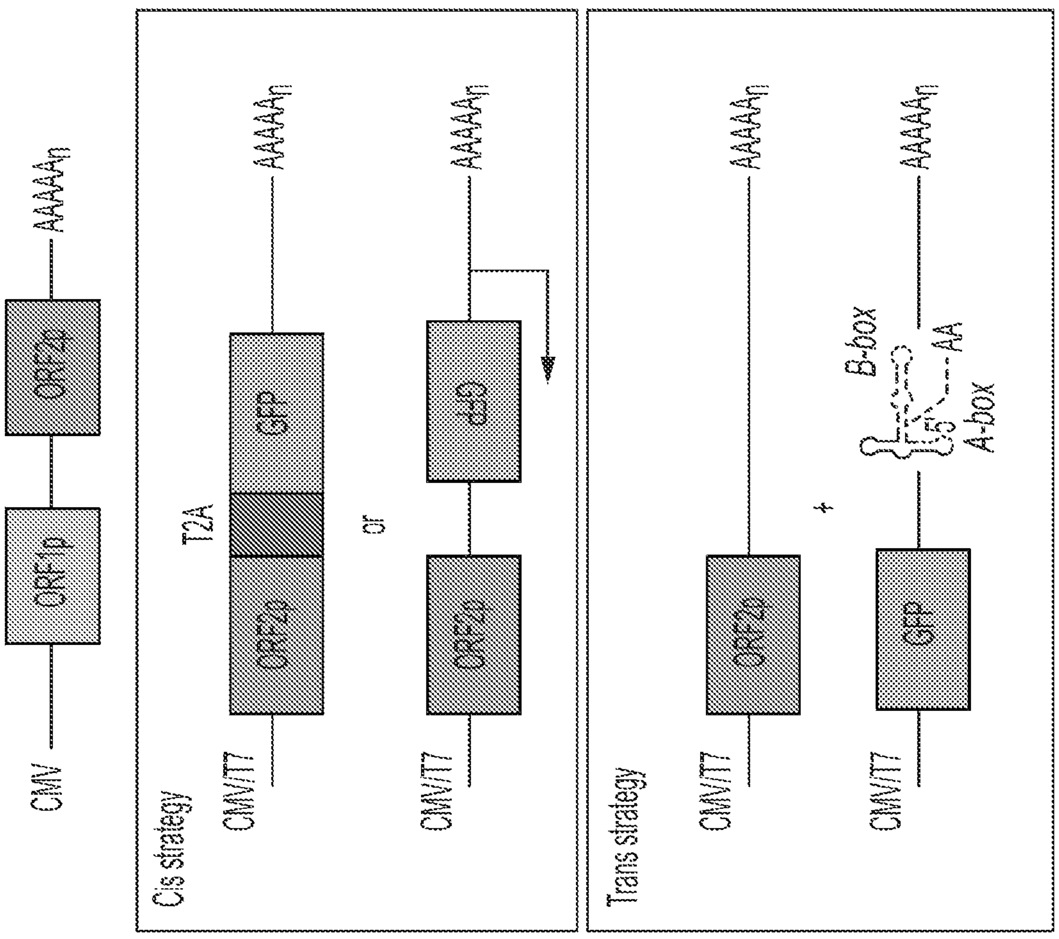
FIG. 1C illustrates various exemplary designs for integrating an mRNA encoding a transgene into the genome of a cell. GFP shown here in a box is an exemplary transgene.
Figure 1D:
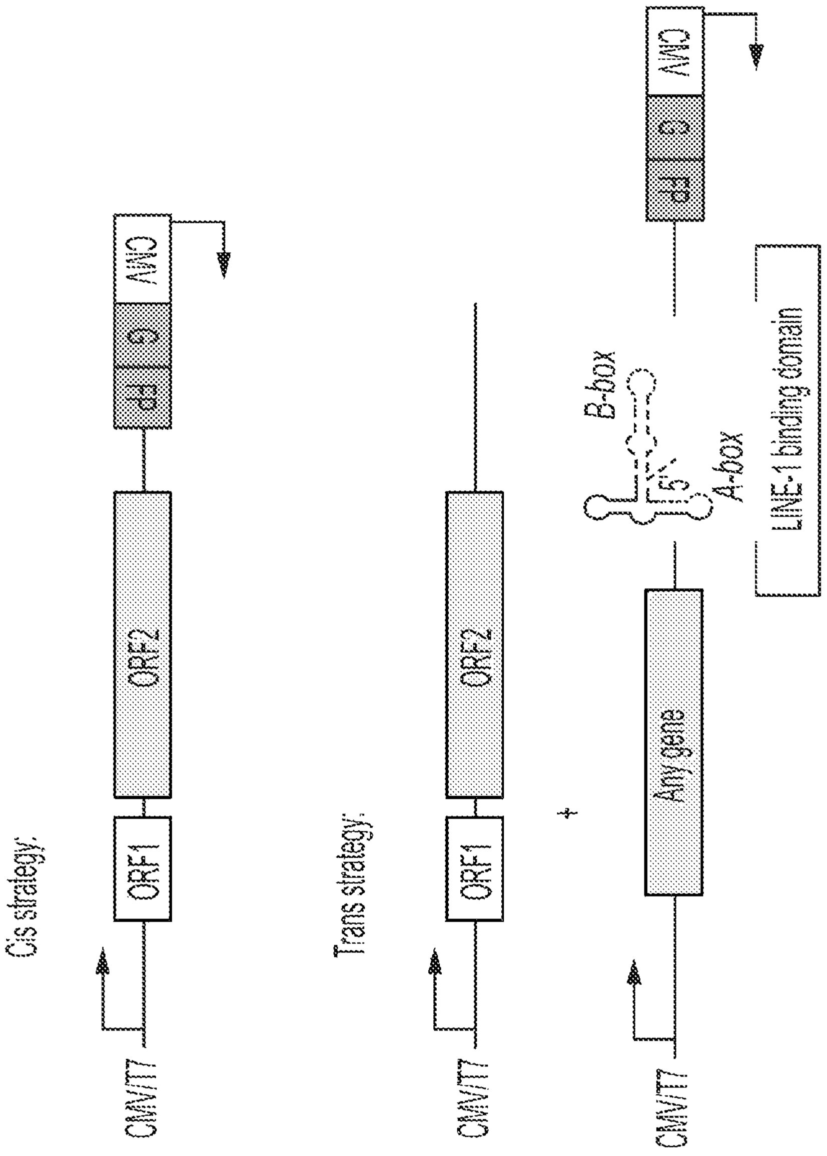
FIG. 1D illustrates various exemplary designs for integrating an mRNA encoding a transgene into the genome of a cell. GFP shown here in a box is an exemplary transgene.
Figure 1E:
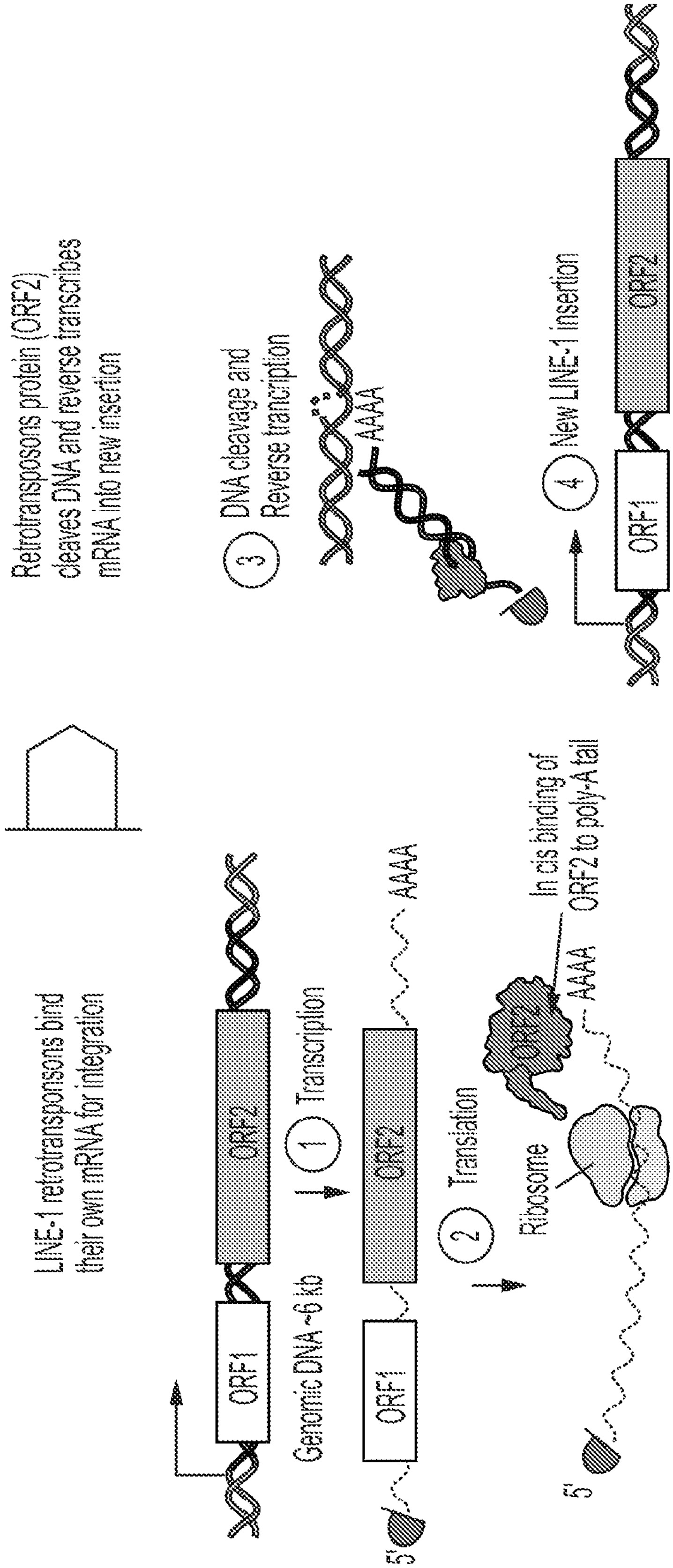
FIG. 1E is an illustration a schematic of the LINE-1 retrotransposition cycle showing the mechanism of action of the LINE transposons and introduction of a transgene cargo into a retrotransposon cite. LINE-1 retrotransposons are genomic sequences that encode for two proteins, ORF1 and ORF2. These elements are transcribed and translated into proteins that form an RNA-protein complex with the LINE-1 mRNA, ORF1 trimers, and ORF2, a reverse-transcriptase endonuclease. This complex translocates back into the nuclease where it cleaves DNA at a 5'-TTTT N-3' motif and is primed for reverse-transcription of the LINE-1 RNA by the ORF2 protein by making an RNA-DNA hybrid with the poly A tail of the mRNA and the resected cleaved DNA. Reverse-transcription of the LINE-1 into cDNA leads to a new LINE-1 integration event.

Provided here are exemplary strategies of designing retrotransposon constructs for incorporating into the genome of a cell and expressing an exemplary transgene. FIG. 1B and FIG. 1C illustrates various strategic designs for integrating an mRNA encoding transgene into the genome of a cell. GFP shown here in a box is an exemplary transgene. The mRNA encoding the transgene (e.g., GFP) can be co-expressed with a nucleic acid sequence encoding an ORF2p protein, in either sense or antisense orientation; the respective coding sequences may be in a monocistronic or bicistronic construct shown under exemplary Cis-strategies (FIG. 1B and FIG. 1C). CMV/T7 are promoters.

Figure 2A:
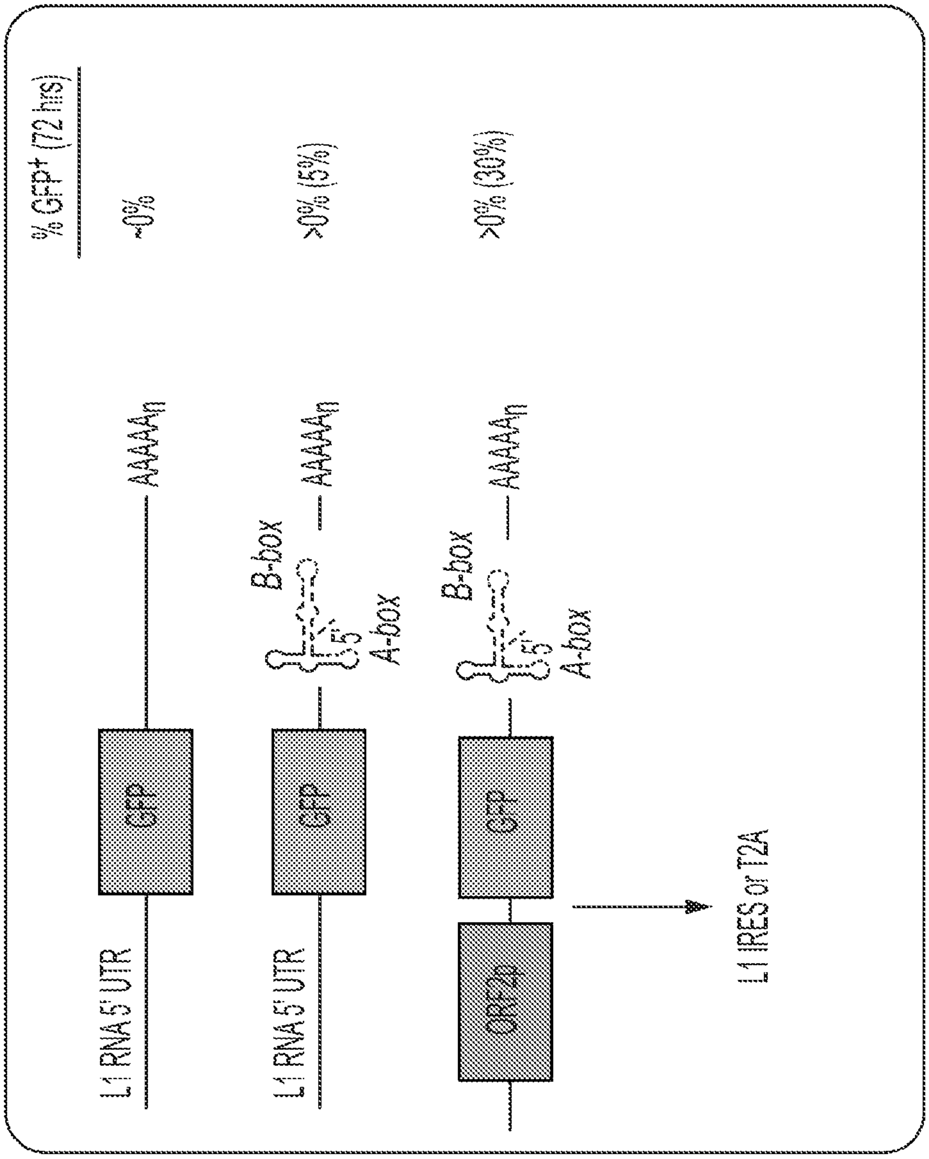
FIG. 2A illustrates three exemplary designs for expressing an exemplary transgene GFP by stably incorporating the sequence encoding GFP using the constructs. Expected GFP expression levels at 72 hours are shown on the right side.
Figure 2B:
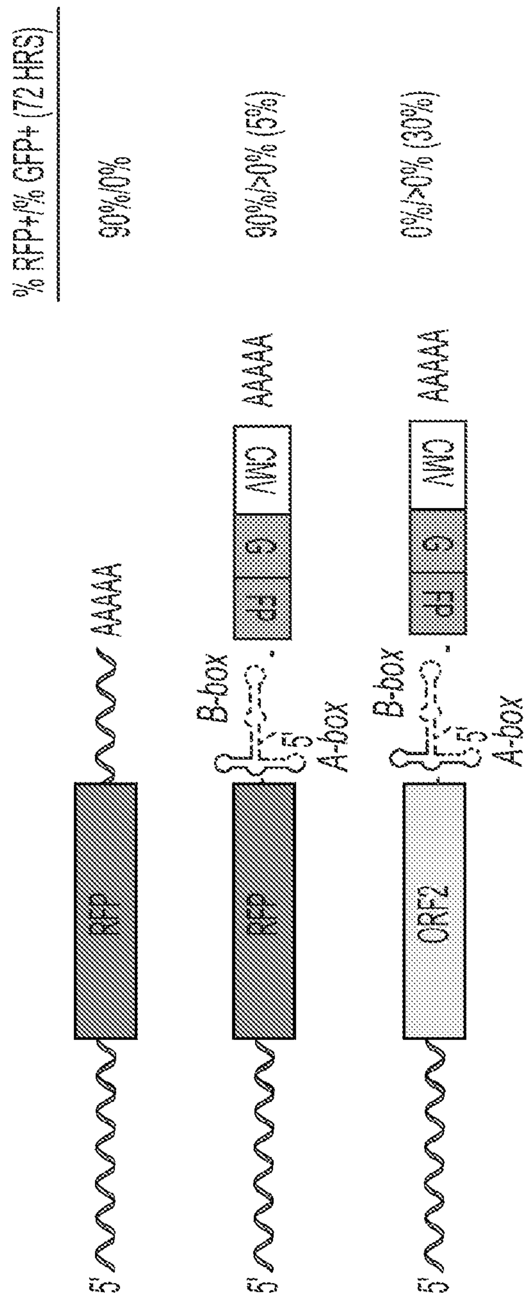
FIG. 2B illustrates three exemplary designs for expressing an exemplary transgene GFP by stably incorporating the sequence encoding RFP, RFP and GFP or ORF2p and GFP using the constructs. Expected GFP and RFP expression levels at 72 hours are shown on the right side.

On the other hand, the same could be directed to be expressed in a trans manner. The trans-strategy can include a sequence encoding an ORF2p protein or both ORF1p and ORF2p proteins from a bicistronic sequence and an mRNA encoding a GFP in a sense or antisense direction in the 3'UTR of any gene. The transgene is flanked by a retrotransposing sequence comprising transposase binding sequences, an A-box and B-box, and a poly A tail. FIG. 2A illustrates three exemplary designs for expressing an exemplary transgene GFP by stably incorporating the sequence encoding GFP using the constructs. The first construct comprises a sequence encoding GFP, flanked by L1 5'-UTR; and a poly A sequence at the 3' UTR, in absence of any transposase binding elements. The second and the third constructs comprise a sequence encoding GFP, a 3'UTR an A Box and a B-box, and a poly A sequence at the 3' UTR. The third construct comprises an additional sequence encoding ORF2p. Expected GFP expression levels at 72 hours are shown on the right side. FIG. 2B illustrates three exemplary designs for expressing an exemplary transgene GFP in an mRNA that either encodes RFP or ORF2p by stably incorporating the sequence encoding GFP using the constructs. The first construct comprises a sequence encoding RFP, and a poly A sequence at the 3' UTR, in absence of any L1 elements. The second and the third constructs comprise a 3'UTR comprising an A Box and a B-box, and a poly A sequence at the 3' UTR. The second construct comprises a sequence encoding RFP and the third construct comprises a sequence encoding ORF2p. Expected RFP and GFP expression levels at 72 hours are shown on the right side.

Example 2. Exemplary circRNA Designs Constructs

In this example, modular designs for circRNA are demonstrated, which incorporate a stretch of about 50 nucleotide long RNA having naturally occurring tertiary structures in order to prepare a circRNA. Use of the tertiary-structure forming RNA makes the circRNA formation process independent of sequence mediated hybridization for circularization. These RNA motifs having tertiary structures can be incorporated in the desired RNA having an exon and an intron in place of the 5' and 3' homology arms, thereby forming the terminal RNA scaffolds for circularization.

Figure 3C:
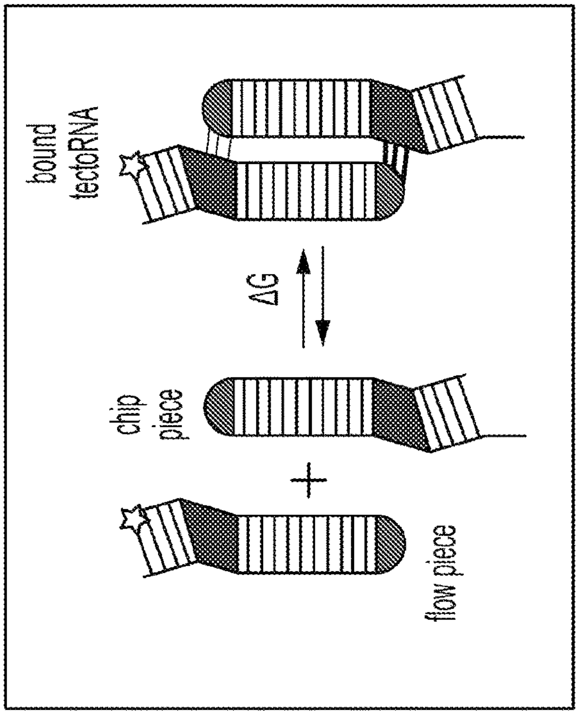
FIG. 3C illustrates exemplary structures of chip-flow piece RNAs as platforms for testing potential tectoRNA.
Figure 3B:
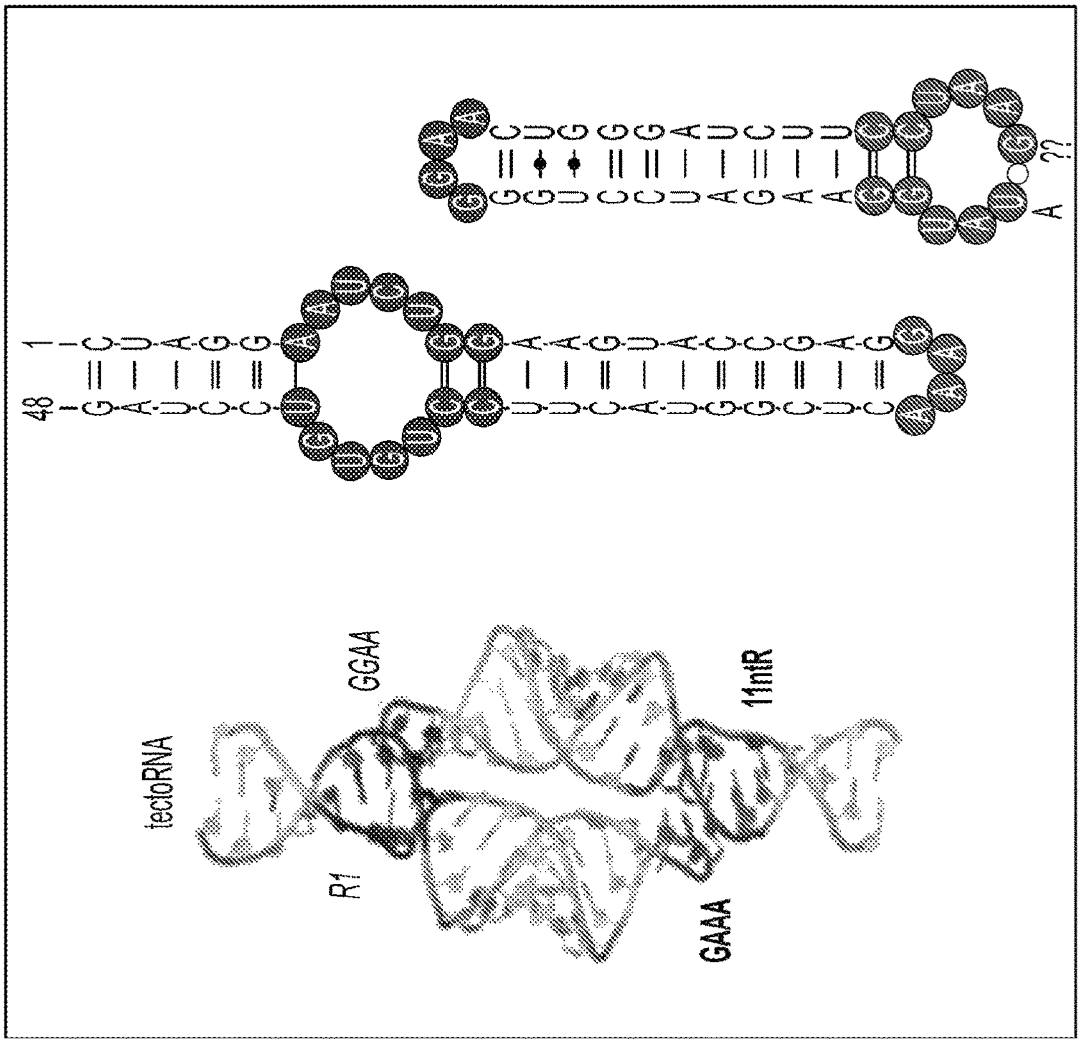
FIG. 3B illustrates two views of an exemplary RL-GAAA tectoRNA motif designs.

TectoRNA: RNA-RNA binding interfaces are constructed by combining pairs of GNRA loop/loop-receptor interaction motifs, yielding high affinity, high specificity tertiary structures. (FIG. 3B). Pairs of GNRA loop/loop-receptor interaction motifs are fused using the four-way junction from the hairpin ribozyme to create divalent, self-assembling scaffolding units ('tectoRNA') which help form a closed cooperatively assembling ring-shaped complexes. Using two orthogonal loop/loop-receptor interaction motifs, RNA monomers are designed that are capable of directional assembly in either the parallel ('up-up') or anti-parallel ('up-down') assembly modes. In anti-parallel assembly of interacting molecules, each incorporated monomer switches the directionality of the growing chain and thus compensates for its intrinsic bending, producing long, relatively straight multi-unit chains. For selecting a tectoRNA scaffolds having minimum occurrences of alternative secondary structures, sequences are checked by submitting them to the RNA folding program Mfold (bioinfo.math.rpi.edu/~zukerm/rna/mfold) which predicts the thermodynamically favored secondary structure of a given RNA sequence. A thermodynamically favored structure is selected for scaffolding that has minimum alternative secondary structures (typically but not exclusively, no other secondary structure is closer than 15% in energy to the lowest energy structure). RNA molecule is prepared by conventional methods, such as in vitro run-off transcription using T7 RNA polymerase. FIG. 3B shows a RL-GAAA loop structure. In order to profile tectoRNA heterodimers a fluorescence-based chip-flow piece testing method is utilized. In this method, a library of potential variants of the structured RNA (chip piece) is synthesized as DNA templates and amplified to include sequencing adapters and regions for RNAP initiation. Each DNA variant is transcribed in situ into RNA, enabling display of sequence-identified clusters of RNA on the surface of the sequencing chip. The fluorescently-labeled tectoRNA binding partner, the "flow piece", is introduced to the sequencing chip flow cell at increasing concentrations, allowing quantification of bound fluorescence to each cluster of RNA after equilibration. These fluorescence values are used to derive the affinity of the flow piece to each chip piece variant (FIG. 3C), in terms of the dissociation constant ($K_d$) and binding free energy, ($\Delta G=RT \log(K_d)$).

The selected terminal RNA scaffold segments comprising the tertiary structures are incorporated using T7 transcription or ligated at the 5' and 3' ends of the desired RNA to be circularized; or are incorporated in the desired RNA by any known molecular biology techniques.

Example 3: Exemplary Retrotransposon Designs with Enhanced Specificity

In this example, designs for a nucleic acid construct for L1-mediated retrotransposon for enhanced target specificity is demonstrated. An mRNA is designed comprising ORF2 encoding sequence and a sequence encoding a gene of interest, to incorporate the gene of interest into the genome of a cell using ORF2. In one exemplary design, the construct comprises an ORF2 that is further modified.

Figure 4A:
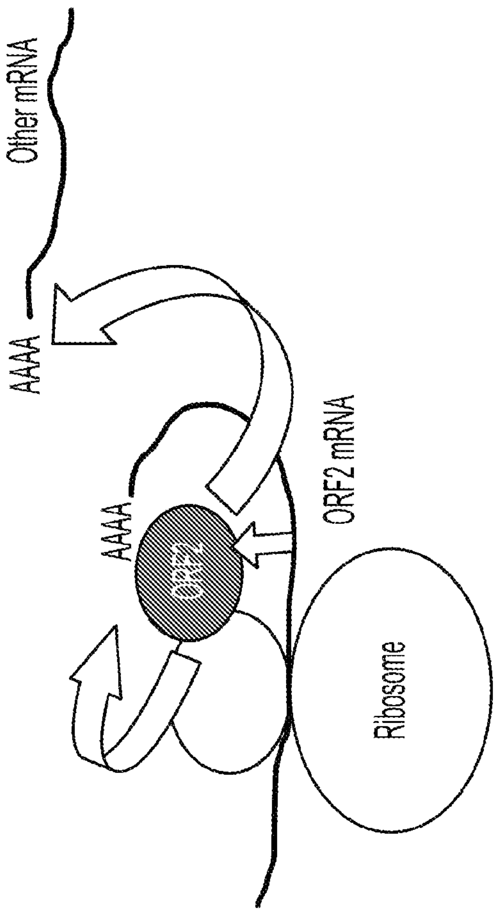
FIG. 4A illustrates an exemplary schematic showing ORF2p binding to an ORF2 poly A region.

As shown in FIG. 4A, ORF2 protein initiates retrotransposition by binding to its own poly A sequence. However, because poly A is abundantly present in mRNAs, a non-specific binding and integration becomes a possibility. To increase the specificity, a recombinant ORF2 is designed comprising an mRNA-binding domain of a heterologous protein, and the cognate mRNA sequence for the heterologous mRNA-binding domain is inserted near the poly A sequence in the 3'-UTR and the ORF2 poly A binding site.

Figure 4B:
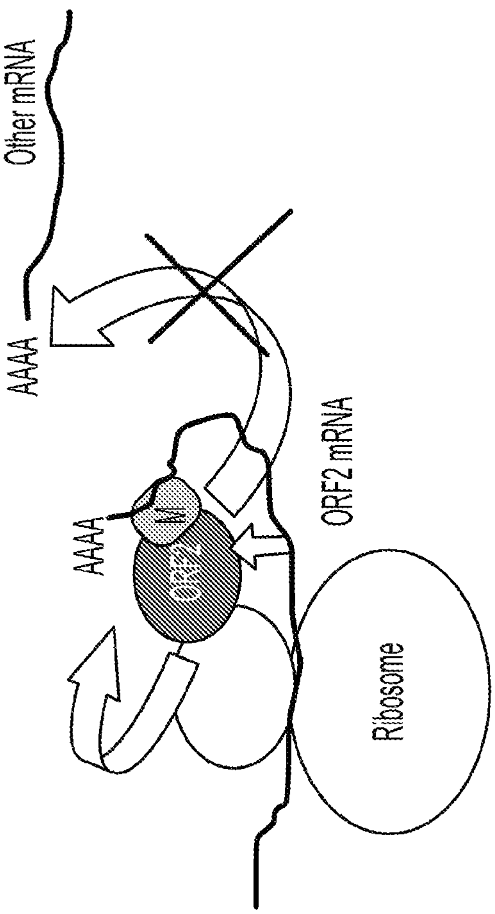
FIG. 4B illustrates an exemplary schematic showing how a fusion of ORF2p with an MS2 RNA binding domain binds to an MS2 binding RNA sequence in the 3'UTR of an mRNA encoding the ORF2 an increase specificity.

A chimeric ORF2 is thereby generated as shown in (FIG. 4B), in which a high affinity RNA-binding domain of a heterologous protein encoding sequence is incorporated or fused to the ORF2 sequence and cognate RNA sequences corresponding to the high affinity RNA-binding protein is incorporated in the 3'UTR region of the mRNA, proximal to the poly A region. In this example the heterologous high affinity RNA-binding domain is derived from MCP coat protein MS2 (shown as M in the figure), is incorporated within the ORF2 sequence and the cognate sequence, the MS2 hairpin, is included in the 3' UTR sequence of the mRNA (FIG. 4B). The MS2 binds to the cognate sequence, increasing the specificity of the chimeric ORF2 to its own mRNA for reverse transcribing and incorporating the respective sequence associated with the ORF2 mRNA in the mammalian cell genome (FIG. 4B).

Figure 4C:
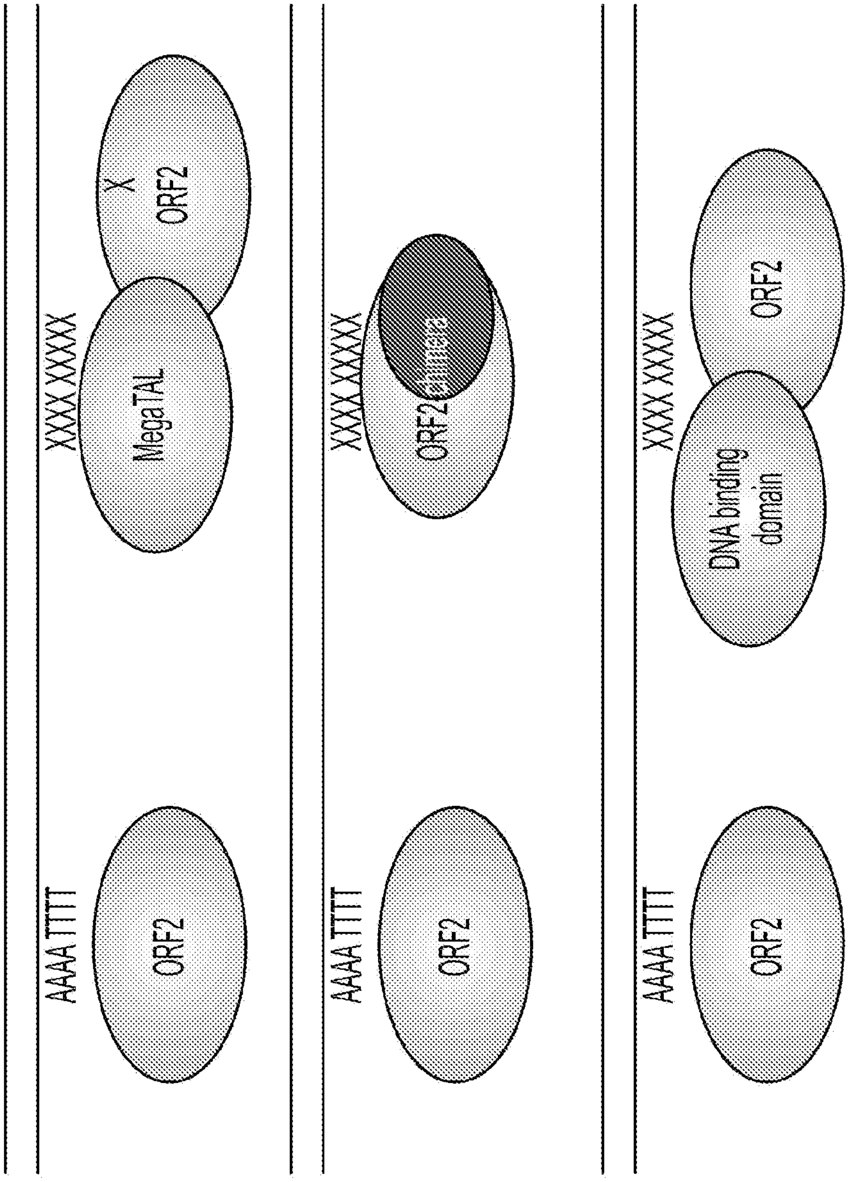
FIG. 4C illustrates exemplary designs of retrotransposon systems for stably integrating a nucleic acid into the genome of a cell at specific sites. The upper panel shows a design using an ORFp2-MegaTAL DNA binding domain fusion where the DNA binding and endonuclease activity of ORF2p is mutated to be inactive. The middle panel shows a chimeric ORF2p where the endonuclease domain has been replaced with a high specificity and high-fidelity nuclease domain of another protein. The lower panel shows a fusion of a DNA binding domain of a heterologous protein with ORF2p such that the fusion protein binds to ORF2 binding site as well additional DNA sequences in the vicinity of the ORF2 site.

In other exemplary designs, attempts to increase specificity of integration of the transgene by the ORF2 within the genome of a target cell is undertaken. In one exemplary design, Mega TAL encoding sequence fused to an ORF2 as shown in FIG. 4C (upper panel). Along with that, the ORF2 is mutated to remove its ability to recognize and bind to RNA sequence that has less specificity. The fused protein is directed to the TAL binding sequence incorporated within the 3'UTR and perform endonuclease function. The Mega TAL DNA binding sequence is targeted by the fusion protein. Likewise, other chimera (FIG. 4C (middle panel)) and fusion protein with a specific DNA binding domain FIG. 4C (lower panel) are designed.

Example 4. Exemplary Plasmid Design and Developments for LINE-1 Mediated Retrotransposition of an Exogenous Nucleic Acid Sequence In this example plasmid vectors are generated for delivery and incorporation of a recombinant LINE-1 construct comprising an ORF2 transposon element operably linked to a transgene transposable into a mammalian cell, and regulatory elements for mRNA transcription and stabilization. The mRNA can be transcribed in a bacterial host cell, which can be further processed and/or purified for introduction into a mammalian cell in vitro or administration in an organism, such as a mammal, a rodent, sheep, pig or a human.

Any suitable vector backbone is used for incorporating the recombinant nucleic acid sequence as insert and transcribing in a bacterial system for mRNA generation; or in vitro transcription system may be utilized to generate an mRNA comprising the recombinant nucleic acid sequence. Several features are added to the plasmid. Upon successful scalable mRNA production, and purification, the mRNA may be introduced in a mammalian cell of interest, such as a myeloid cell.

Figure 5:
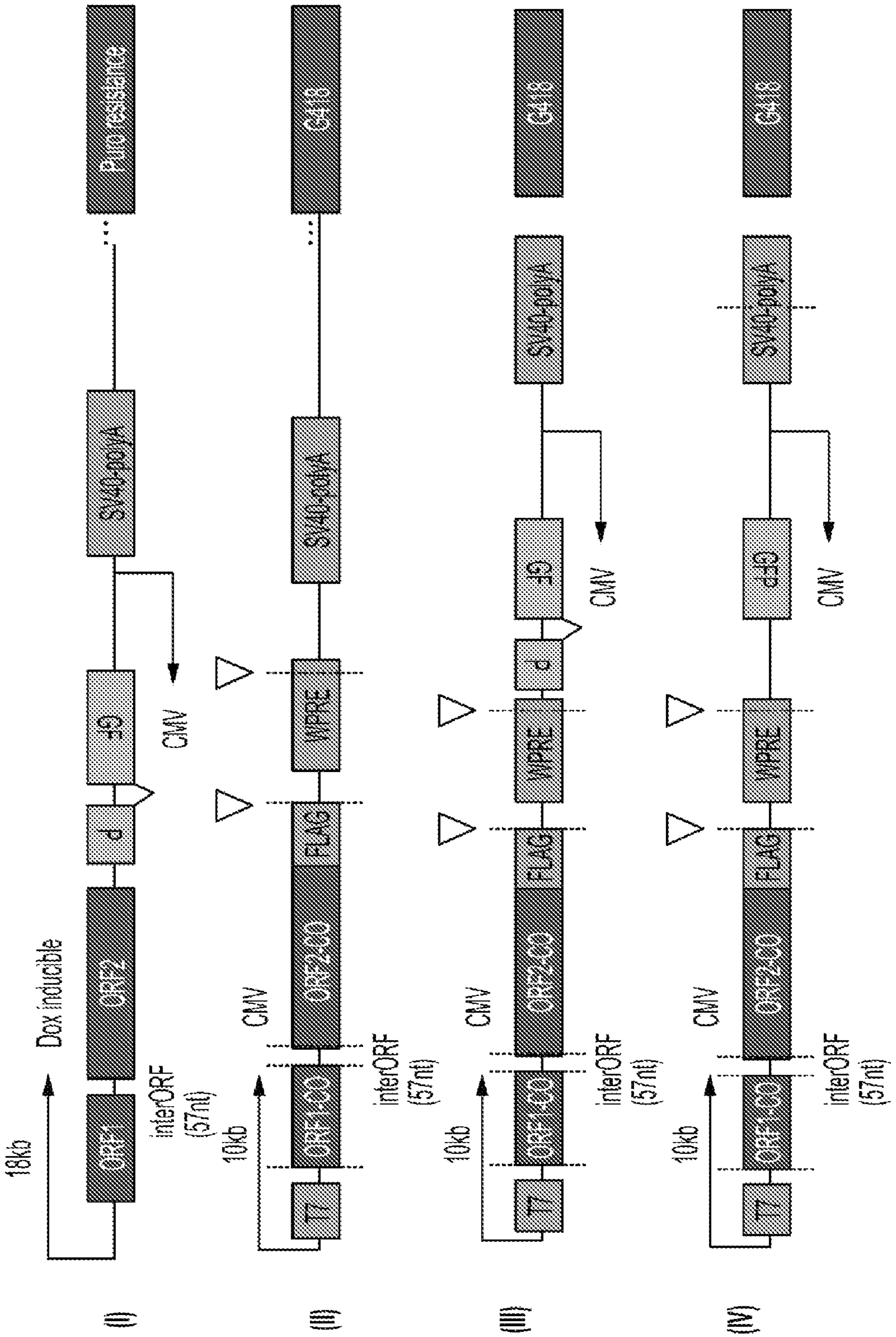
FIG. 5 illustrates exemplary constructs (I)-(X) for integrating an mRNA encoding a transgene into the genome of a cell.
Figure 5:
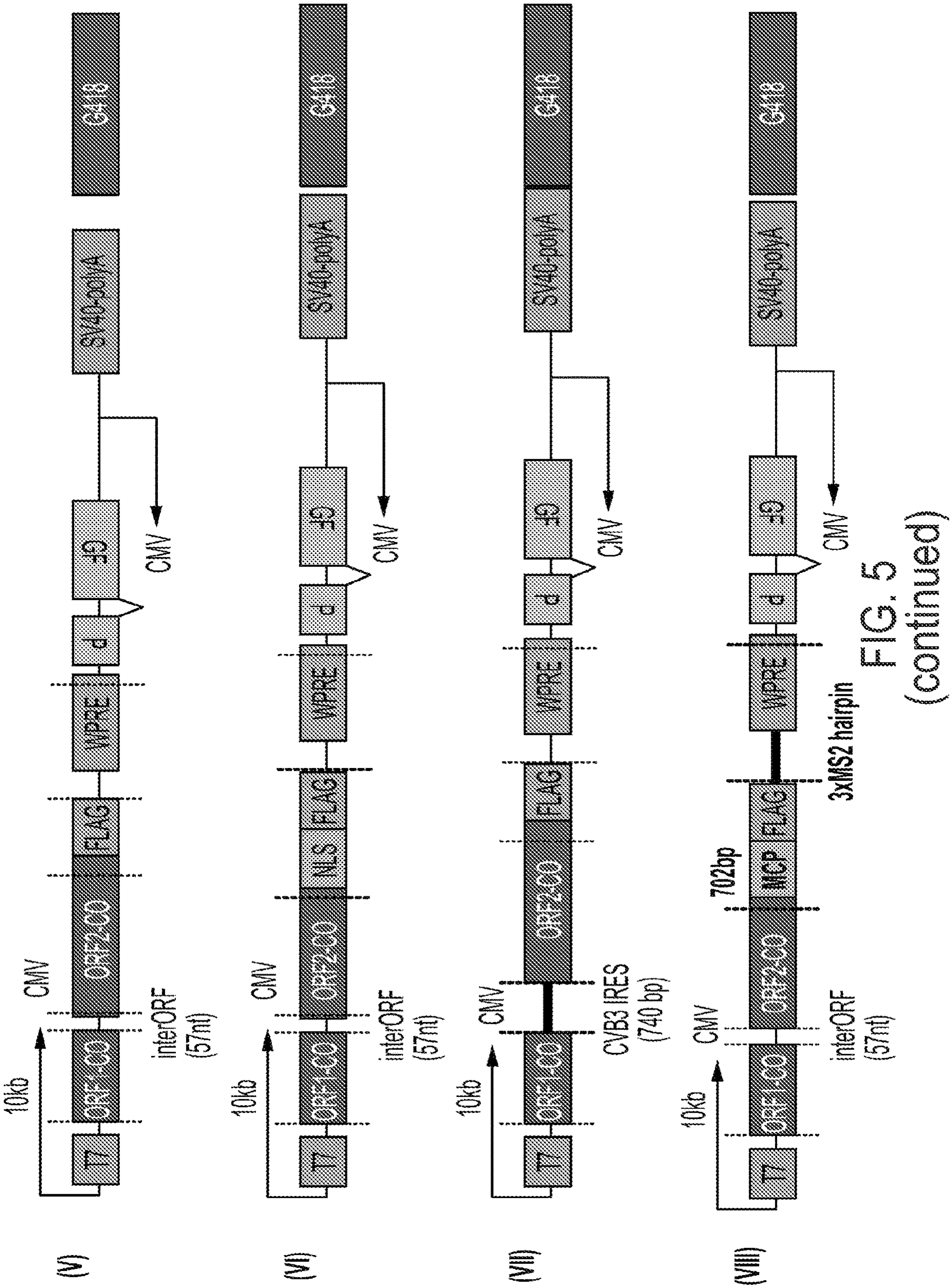
Figure 5:
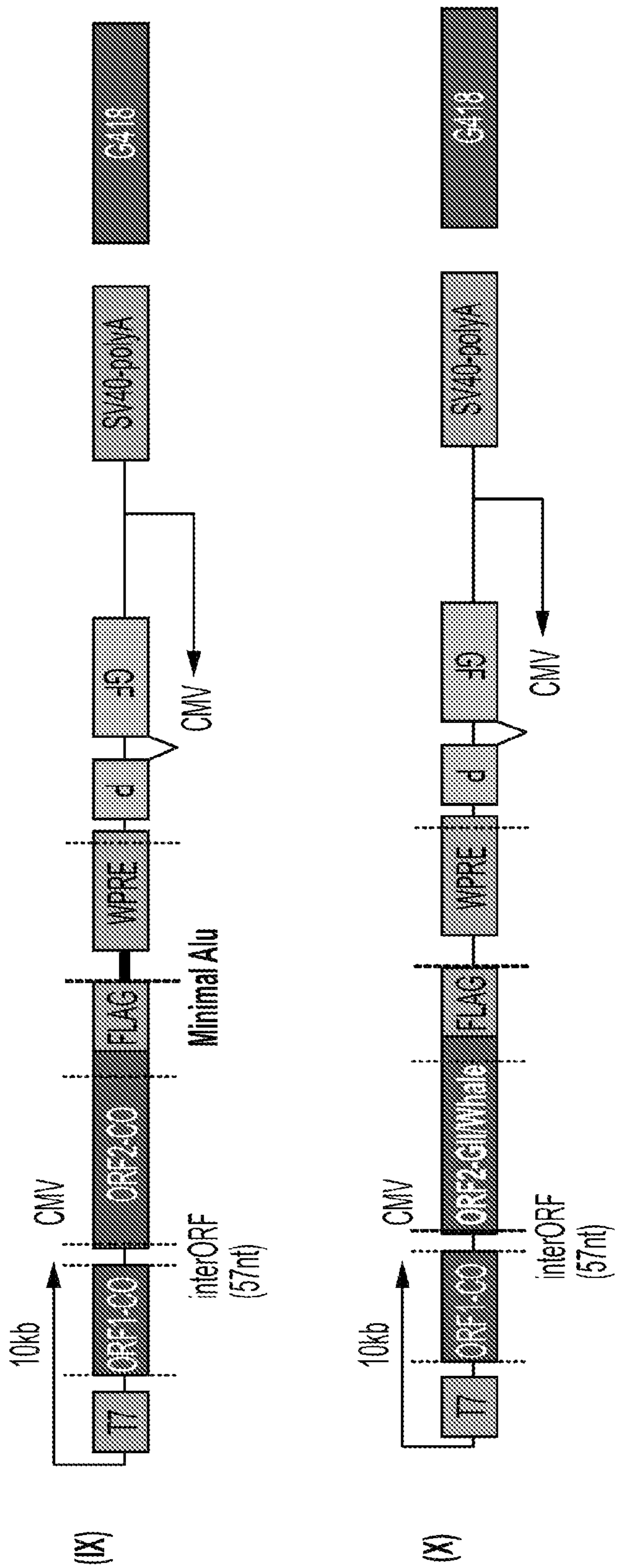

Plasmids traditionally used in the field of study for retrotransposition lack designer genes, gene blocks, and Gibson assembly methods were used regularly to insert different features. A new vector that takes features from the old vectors but has flexibility to insert new features can be beneficial both for the study and optimization of LINE-1 elements as a gene delivery system. Below is an outline of base features and additional features that can increase retrotransposition frequency, both using the plasmid alone or the mRNA transcribed from the plasmid. In an exemplary plasmid design shown graphically in FIG. 5(I), which contains the natural LINE-1 sequence with the original 5'UTR, 3'UTR and interORF sequence with no restriction sites to swap out any of these features. New optimized plasmid:

- Removed Dox inducible promoter, replaced with CMV or EIF1a or EF1a promoter
- Added a T7 site to make mRNA
- Codon optimized ORF1 and ORF2
- Added a WPRE element to stabilize mRNA
- Added FLAG tag to ORF2 to help with protein detection
- Decreased size from 18 kb to 14 kb
- Added blunt restriction sites (dotted lines with blunt arrows) at each feature to facilitate insertions
- Includes a G418 selection marker
- The plasmid is shown in FIG. 5 (II).

With Gibson a reverse split GFP is inserted for plasmid reporter gene as shown in FIG. 5 (III). A complete reverse GFP for the mRNA reporter is inserted as in FIG. 5 (IV).

Using the plasmid construct in FIG. 5 (V) as parent, a nuclear localization sequence (NLS) is inserted at the N terminus of ORF2 to help with nuclear import (FIG. 5 (VI)). An IRES or another termination/promoter sequence is inserted to increase expression of ORF2 (FIG. 5 (VII)). To facilitate stronger interactions between ORF2 and the mRNA, MS2 hairpins are inserted in the 3'UTR and a MS2 coat protein sequence in the N terminus of the ORF2 protein (FIG. 5 (VIII)). A corresponding exemplary ORF2 with enhanced specificity and its mechanism of action is disclosed in the preceding example and in FIG. 4B. To facilitate stronger interactions of the mRNA with the translating ribosome and to stall translation so that nascent ORF2 will more likely bind the mRNA, an Alu element is inserted in the 3'UTR of the mRNA (FIG. 5 (IX)). To potentially use a more active ORF2 protein, the ORF2's RT domain is replaced with the Group II intron's reverse transcriptase domain (FIG. 5 (X)). Additionally, the minke whale genome has the highest number and percentage of active LINE elements (~5,000 with 60% active compared to humans that have 480 with 3.6% active). The two sequences are 67% identical and the whale sequence has the active endonuclease and reverse-transcriptase residues. The respective minke whale domains can be used to replace native ORF2 endonuclease and/or RT domains or design a chimera domain.

Figure 6A:
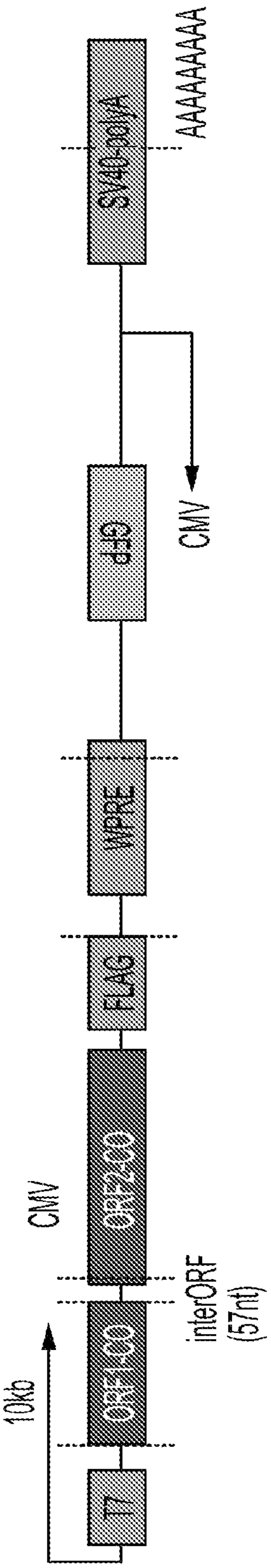
FIG. 6A illustrates an exemplary construct with a sequence encoding ORF1p for integrating an mRNA encoding a transgene into the genome of a cell.
Figure 6B:
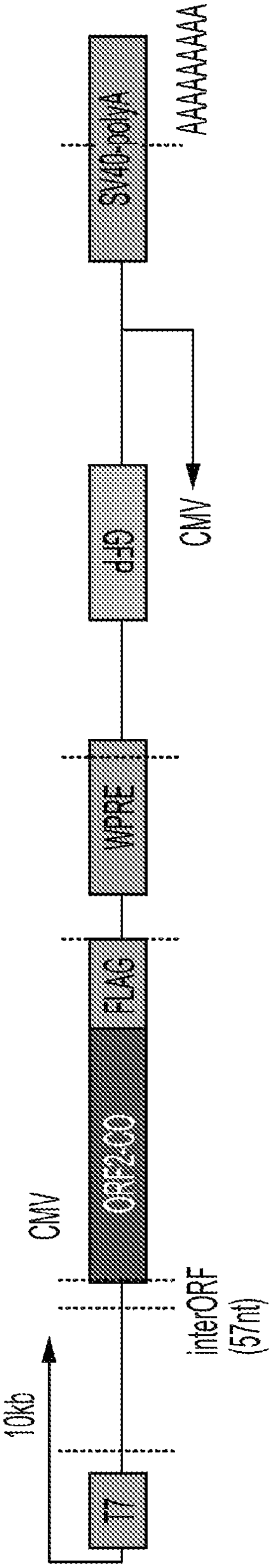
FIG. 6B illustrates an exemplary construct without a sequence encoding ORF1p for integrating an mRNA encoding a transgene into the genome of a cell.

Example 5. mRNA Design Synthetic mRNA Generation mRNA can be strategically designed for synthetic production by oligosynthesis and or ligation of oligonucleotides. Additionally, such designs are useful for in vitro transcription (IVT) mediated mRNA generation. The mRNA strategy can include the same variants as the plasmid strategy discussed in the previous example. The main differences are that the reporter GFP sequence does not include an intron (FIG. 6A) and that the constructs can be delivered without the ORF1 coding region (FIG. 6B).

Example 6. Structural Features for Increased mRNA Half-Life

In this example, structural features are introduced in the mRNA comprising the retrotransposition elements and/or the transgene for increasing the mRNA half-life. The goal is to increase the duration of protein expression from the mRNA in primary monocytes from three days to at least 5 days with an ultimate goal of 10 days.

Figure 7A:
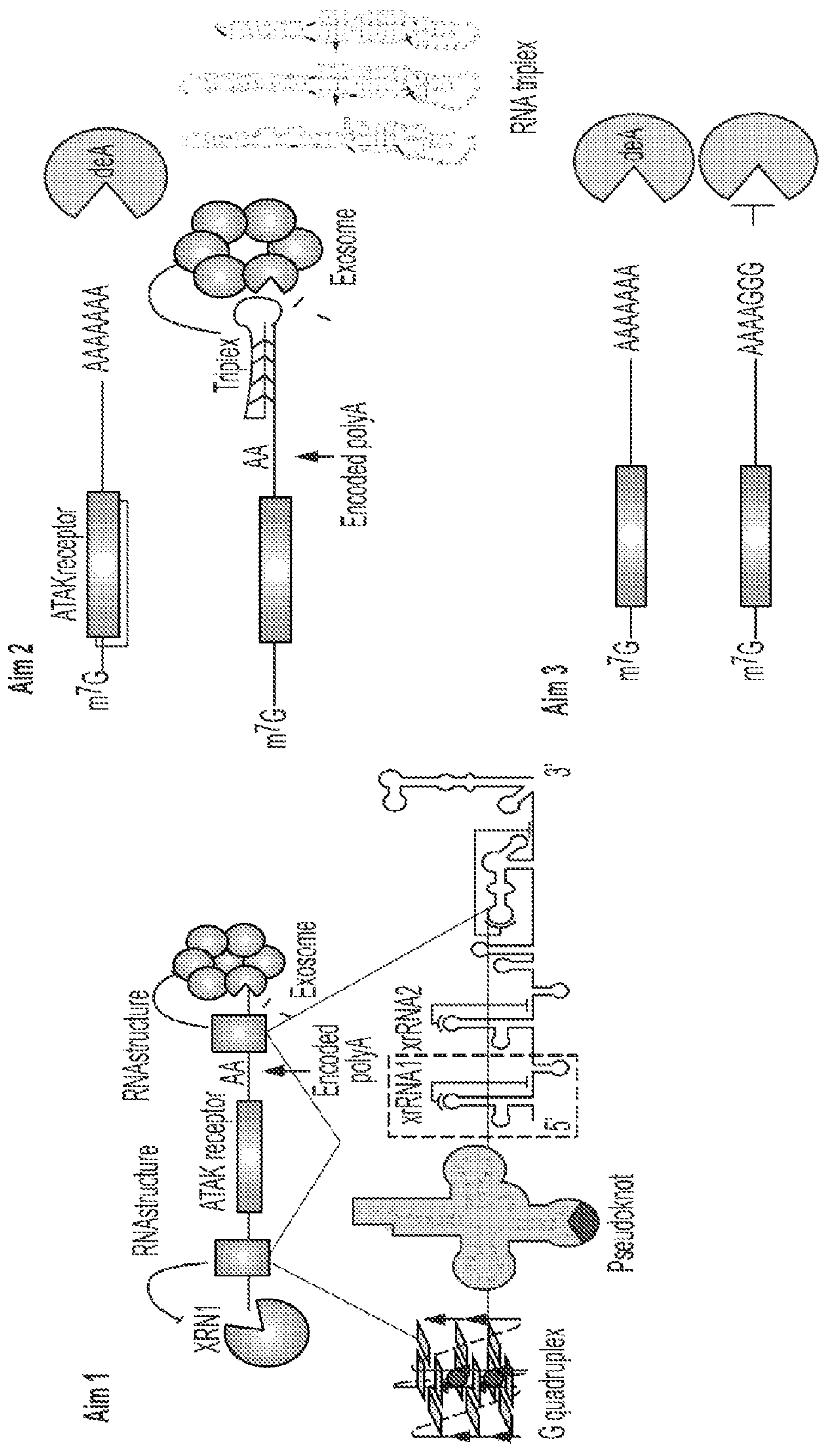
FIG. 7A illustrates exemplary methods of improving mRNA half-life by inhibiting degradation by 5'-3' exonucleases, such as XRN1, or 3'-5' exosomal degradation, by introducing structures corresponding to a G-quadruplex, or, a pseudoknot (SEQ ID NO: 113) in the 5'UTR; and/or xrRNAs, a triplex motifs (SEQ ID NOS: 74, 54, and 53, respectively, in order of appearance) and/or a non-A nucleotide residues in the 3'UTR.
Figure 7C:
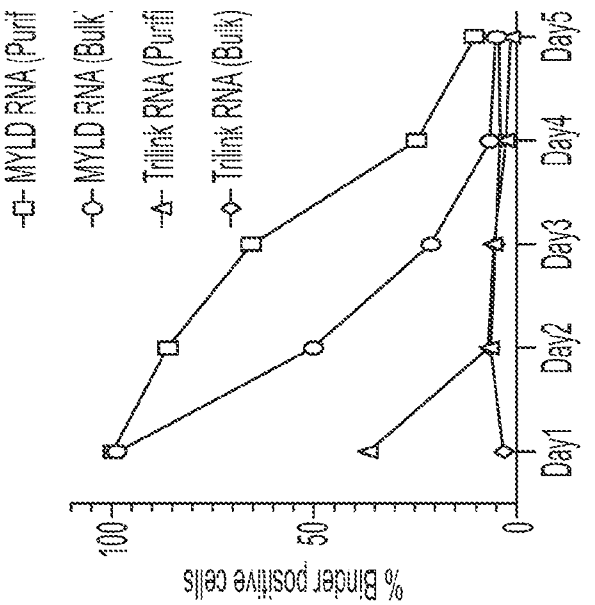
FIG. 7C shows expected results of introducing bulk or purified RNA encoding a chimeric receptor that binds a cancer cell as described in FIG. 7B on increased and prolonged expression of the chimeric receptors.
Figure 7B:
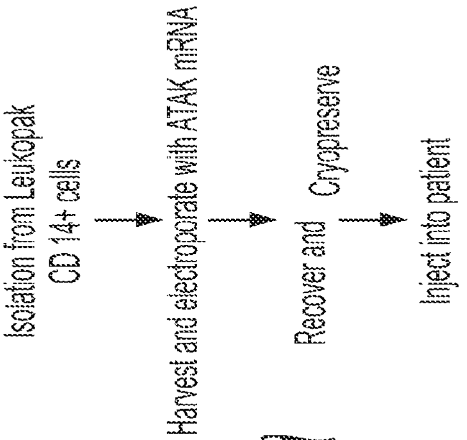
FIG. 7B illustrates an exemplary schematic of a myeloid cell expressing a transgene encoding a chimeric receptor that binds a cancer cell and induces anti-cancer activity.
Figure 7B:
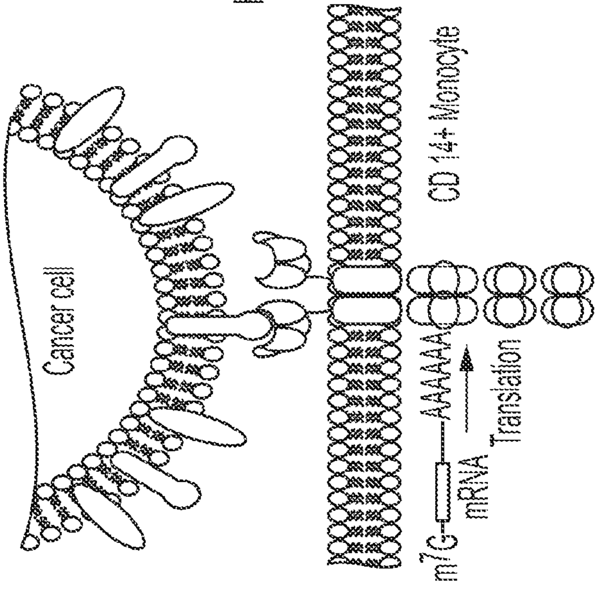

As shown in FIG. 7B (left), the mRNA comprising a sequence encoding the transgene when introduced into a CD14+ myeloid cell (monocyte), is translated and expresses a chimeric receptor (an ATAK construct) capable of binding to an antigen on a cancer cell.

A number of mRNA designs are generated by synthesizing various gene blocks comprising singly, or combinations of one or more of: (i) a G-quadruplex, (ii) a viral pseudoknot structure in the 5' UTR; and/or (iii) one or (iv) more xrRNA loop structures in the 3' UTR (v) a triplex RNA structure as shown in FIG. 7A; and cloned into the transcription vector at the respective UTRs adjoining the coding sequence of the transgene. These constructs are individually prepared by an off-site vendor and tested in-house for determining stability of the mRNA, as measured by the expression of the chimeric receptor (An exemplary receptor and its function is depicted graphically in FIG. 7B (left). The process flow chart is shown on FIG. 7B (right). In short, constructs are cloned into plasmids, with encoded or modified poly A tails. The mRNA was transcribed and purified. Meanwhile, frozen monocytes are thawed and harvested. Harvested cells were electroporated with the purified mRNA (5-10 ug), and cultured for 1, 2, 3, 5 days. Cells positive for the chimeric receptor (binder positive cells), are detected by means of their ability to bind to a target cell or a substrate coated with the target antigen. The expected results are shown in FIG. 7C. Bulk or purified mRNA expressing one or more of the structural features outlined in (i)-(v) (data denoted by solid squares) or a combination thereof outperforms the commercially available counterparts that do not contain any of the features outlined in (i)-(v) (data denoted by triangles).

Example 7. LINE-1 Retrotransposon Plasmid Mediated Delivery of GFP Gene

Figure 8A:
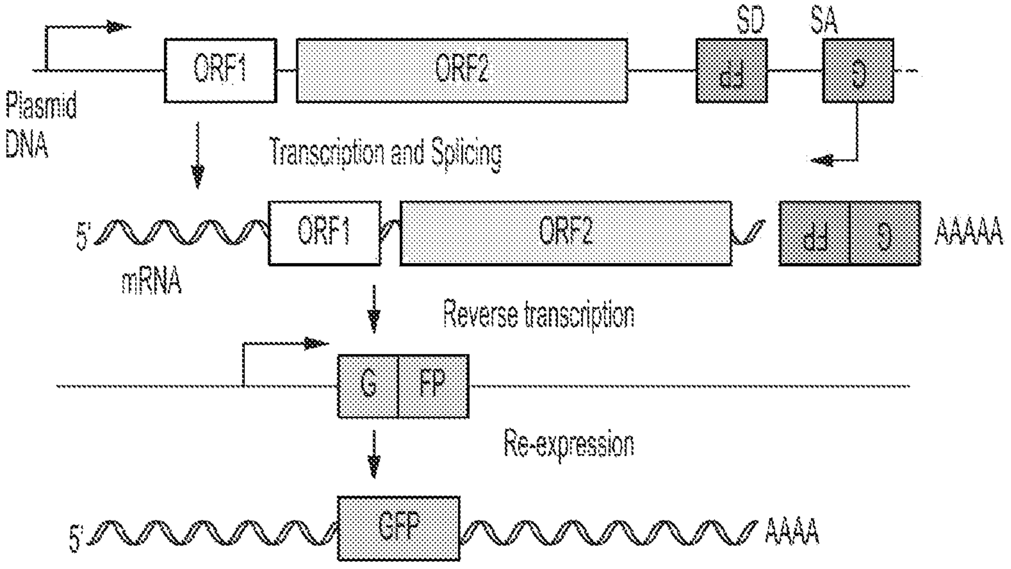
FIG. 8A shows an exemplary plasmid design and expected LINE-1 mRNA transcript with a cargo nucleic acid sequence. The plasmid has a LINE-1 sequence (comprising ORF1 and ORF2 protein encoding sequences) and a cargo sequence which is a nucleic acid sequence encoding GFP, where the coding sequence of GFP is interrupted with an intron. The GFP is not expressed until the sequence is integrated in the genome and the intron is spliced.
Figure 8B:
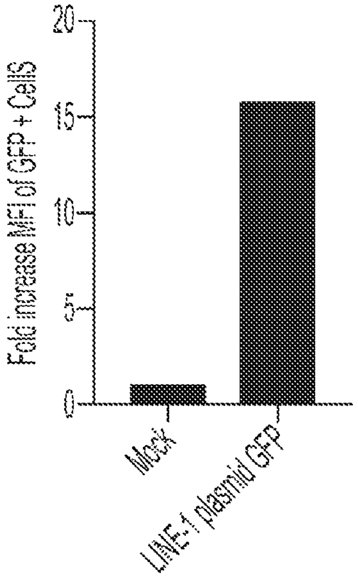
FIG. 8B shows exemplary results showing successful integration of the mRNA transcript encoded by the plasmid shown in FIG. 8A and expression of GFP relative to mock-transfected cells (fold increase in mean fluorescence intensity of GFP positive cells is shown). Mock transfected cells were transfected by the vector lacking the GFP cargo sequence.
Figure 8C:
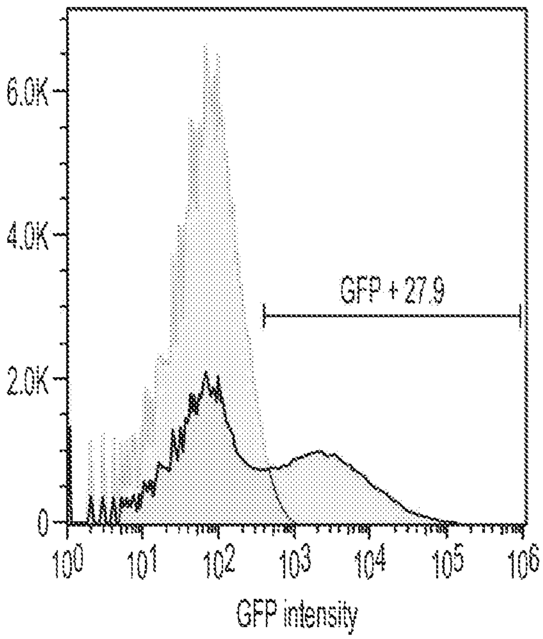
FIG. 8C shows exemplary flow cytometry results from the results shown in FIG. 8B.

In this test run, genomic integration of a GFP cargo and expression the GFP protein using a LINE-1 retrotransposon system was verified. The LINE-I-GFP construct (LINE-1 plasmid GFP) is exemplified in FIG. 8A: A plasmid construct having a LINE-1 sequence encoding ORF1p (ORF1), a sequence encoding ORF2p (ORF2), and a CMV promoter driven split GFP gene situated in the 3'UTR of the LINE-1 in reverse orientation with respect to the ORFs. The split GFP is designed to have an intronic sequence inserted in between a splice donor and acceptor sites, which ensures that the GFP is expressed only after integration and splicing mediated removal of the noncoding sequence in the middle of the coding sequence. In this case the cargo is 2.1 kb. HEK293T cells were transfected with the plasmid using Fugene reagent, and plasmid positive cells were selected by puromycin. The mRNA generated from a genome integrated GFP successfully translates and is measured by flow cytometry, as indicated as change in mean fluorescence intensity (MFI) (FIG. 8B) and fraction of cells with GFP fluorescence intensity compared to mock transfected cells (FIG. 8C). Mock transfected cells received the plasmid that lack the GFP sequence.

Figure 9A:
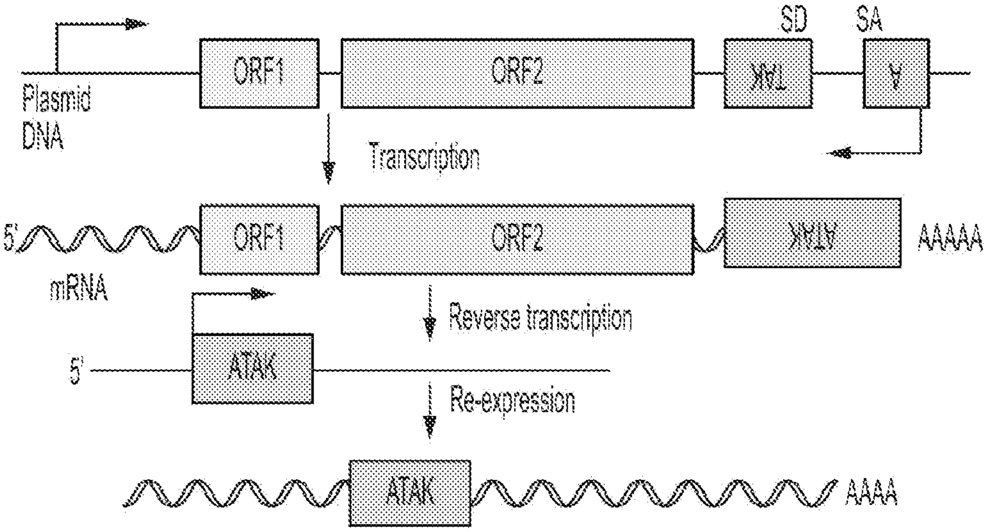
FIG. 9A shows an exemplary plasmid design and expected LINE-1 mRNA transcript with a cargo nucleic acid sequence. The plasmid has a LINE-1 sequence (comprising ORF1 and ORF2 protein encoding sequences) and a cargo sequence which is a nucleic acid sequence encoding a recombinant chimeric fusion receptor protein (ATAK receptor) that has extracellular region capable of binding to CD5 and an intracellular region comprising an FCR intracellular domain and a PI3 kinase recruitment domain. The coding sequence of the ATAK receptor is interrupted with an intron.
Figure 9B:
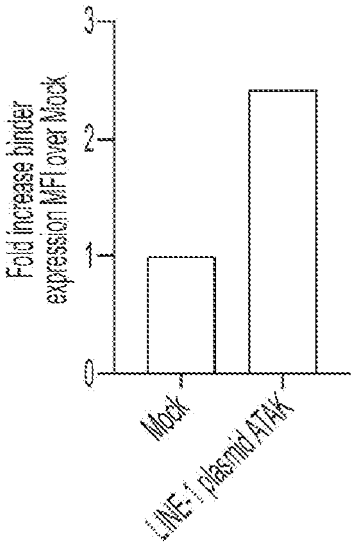
FIG. 9B shows exemplary results showing successful integration of the mRNA transcript encoded by the plasmid shown in FIG. 9A and expression of ATAK relative to mock-transfected cells (fold increase in mean fluorescence intensity of ATAK positive cells is shown). Mock transfected cells were transfected by the vector lacking the ATAK cargo sequence. Expression of ATAK receptor protein was detected by binding with a labeled CD5 antibody.
Figure 9C:
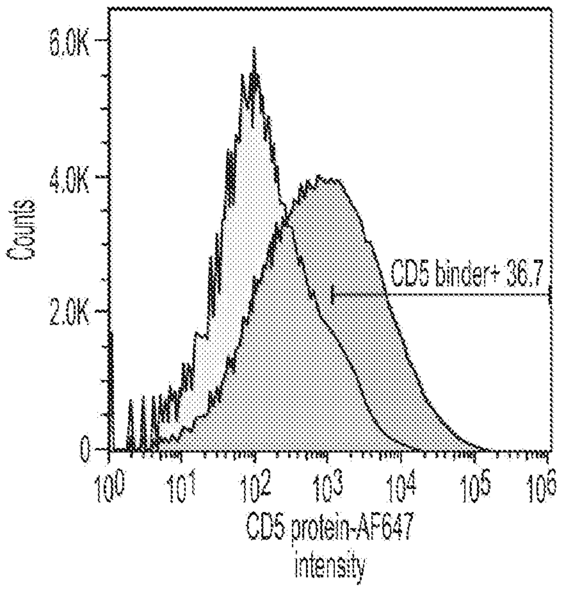
FIG. 9C shows exemplary flow cytometry results from the results shown in FIG. 9B.

Example 8. LINE-1 Retrotransposon Plasmid Mediated Delivery of a Chimeric Receptor Gene This example demonstrates that a recombinant gene can be successfully expressed using the LINE-1 sequence in a cell. HEK 293 cells were transfected with a plasmid having the LINE-1 elements, with a 3 kb cargo sequence encoding recombinant receptor protein CD5-intron-fcr-PI3K (ATAK) that is interrupted by an intron sequence in the CD5 binding domain. The cargo is a chimeric receptor that has a CD5 binding extracellular domain, a FCRγ transmembrane domain, and an intracellular domain having a PI3-kinase recruitment domain. The schematic representation of the retrotransposon plasmid is shown in FIG. 9A. As in the design of the experiment above, the ATAK receptor cannot express unless it is integrated in the genome and the intron is spliced off. Following transfection in HEK293T cells, the receptor expression is detected using labeled CD5 as bait for the CD5 binding extracellular domain. Results shown in FIGS. 9B and 9C show successful integration and expression of the receptor. 36.5% cells were ATAK (CD5 binder) positive (FIG. 9C).

Figure 10A:
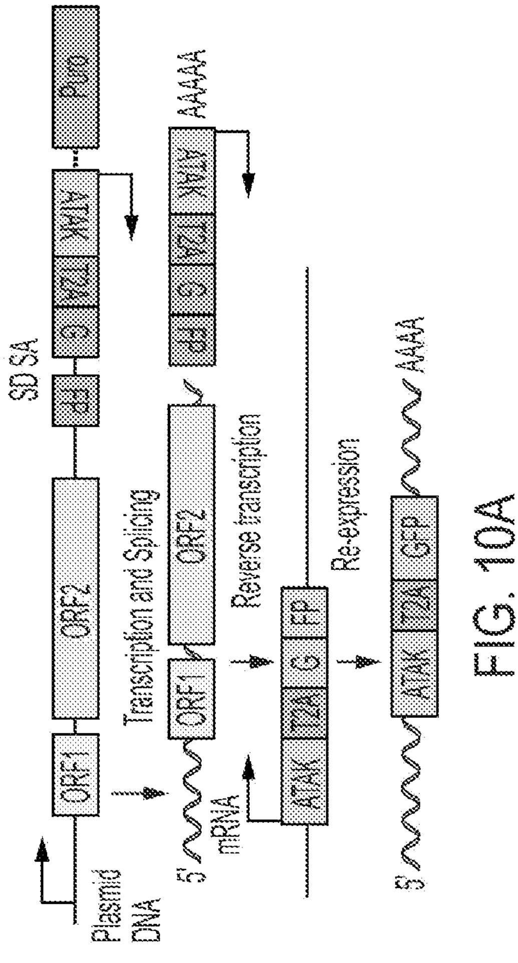
FIG. 10A shows an exemplary plasmid design and expected LINE-1 mRNA transcript with a cargo nucleic acid sequence. The plasmid has a LINE-1 sequence (comprising ORF1 and ORF2 protein encoding sequences) and a cargo sequence which is a nucleic acid sequence encoding a recombinant chimeric fusion receptor protein (ATAK receptor) followed by a T2A self-cleavage sequence followed by a split GFP sequence (all in a reverse orientation relative to the LINE-1 sequence). The coding sequence of the GFP is interrupted with an intron. Expected mRNA after reverse transcription and integration of the cargo are depicted.
Figure 10B:
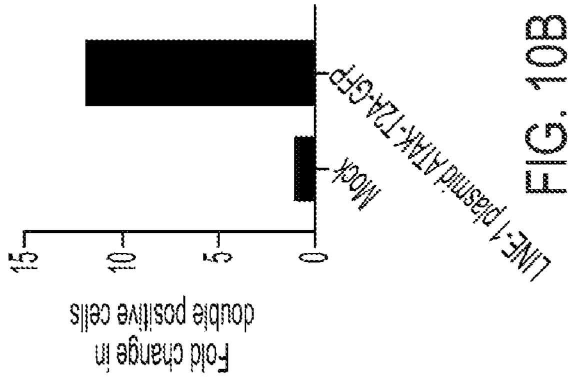
FIG. 10B shows exemplary results showing successful integration of the mRNA transcript encoded by the plasmid shown in FIG. 10A and expression of ATAK-T2A-GFP relative to mock-transfected cells (fold change in GFP and ATAK double positive cells is shown). Mock transfected cells were transfected by the vector lacking the ATAK cargo sequence. Expression of ATAK receptor protein was detected by binding with a labeled CD5 antibody.
Figure 10C:
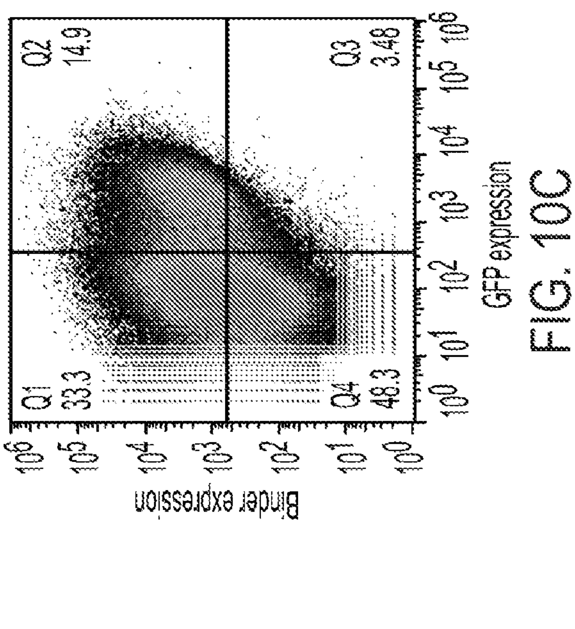
FIG. 10C shows representative flow cytometry data from two separate experimental runs for expression of both GFP and CD5 binder (ATAK) using the experimental setup shown in FIG. 10A.
Figure 10D:
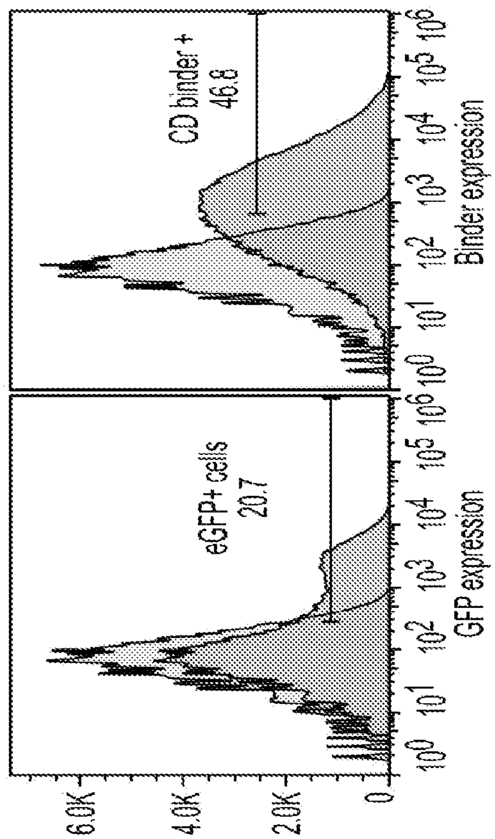
FIG. 10D shows representative flow cytometry data from two separate experimental runs for expression of both GFP and CD5 binder (ATAK) using the experimental setup shown in FIG. 10A.

In a further modification, a LINE-1 construct (LINE-1plasmid-cd5_fcr-pi3k_t2a_GFPintron) with a longer 3.7 kb cargo sequence encoding a non-interrupted recombinant receptor protein CD5-intron-fcr-PI3K and an interrupted GFP sequence with a T2A sequence between receptor and the GFP sequences (FIG. 10A). Normalized against mock-transfected cells, there was a greater than 10-fold increase of the ATAK receptor and GFP double-positive cells was noted (FIG. 10B). Exemplary fluorescence identification of GFP and fluorescent tagged CD5 binding and gating quantitation for experimental runs are shown in FIG. 10C and FIG. 10D.

Figure 11A:
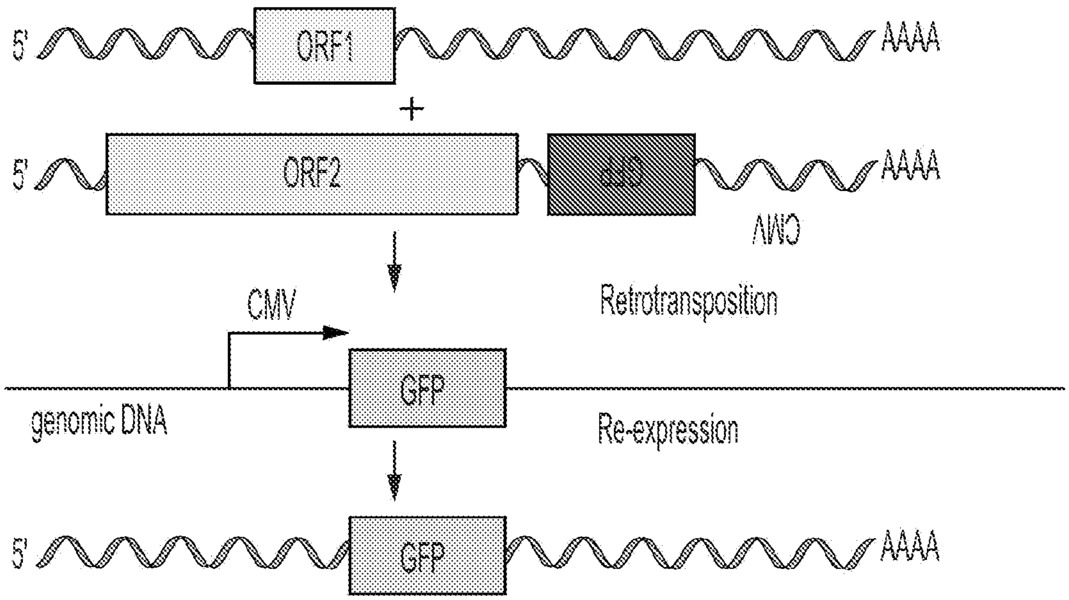
FIG. 11A shows exemplary mRNA constructs for retrotransposition-based gene delivery. The ORF1 and ORF2 sequences are in two difference mRNA molecules. The ORF2p (ORF2) coding mRNA comprises and inverted GFP coding sequence.
Figure 11B:
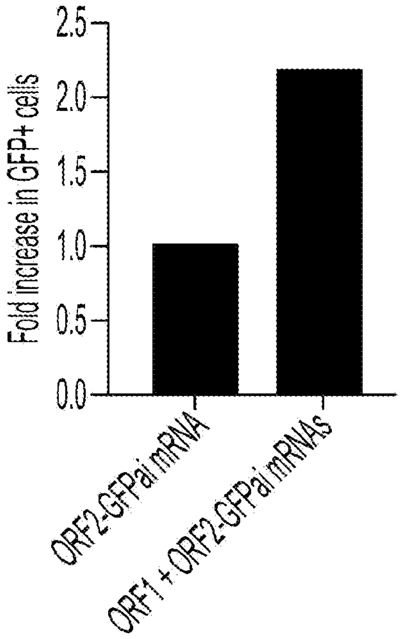
FIG. 11B depicts exemplary data showing expression of GFP (fold increase in mean fluorescence intensity of GFP positive cells is shown) upon electroporating both ORF1-mRNA and ORF2-FLAG-GFPai mRNA normalized to electroporation of ORF2-FLAG-GFPai mRNA only.

Example 9. mRNA Encoding LINE-1 Retrotransposon for Delivery of a Cargo Gene In this assay, capability of delivering and expressing a LINE-1 retrotransposable gene sequence as an mRNA was tested. An mRNA encoding an ORF1 (ORF1-FLAG-mRNA), and an mRNA encoding ORF2 and GFP in the antisense direction with a CMV promoter sequence (ORF2-FLAG-GFPai) are designed as shown in FIG. 1A. The cargo size in this assay was 2.4 kb, and GFP is in antisense orientation with respect to ORF2 sequence. The mRNAs were electroporated in 293T cells and the reporter genes expression was demonstrated as shown in FIG. 11B. This experimental set up demonstrated that no ORF1-read-through is necessary for the expression of the ORF2p, and expression of ORF2p from a different mRNA molecule can allow higher expression of ORF2p and GFP. With these results, a successful delivery of the LINE-1 and cargo in the form of mRNA was achieved.

Figure 12A:
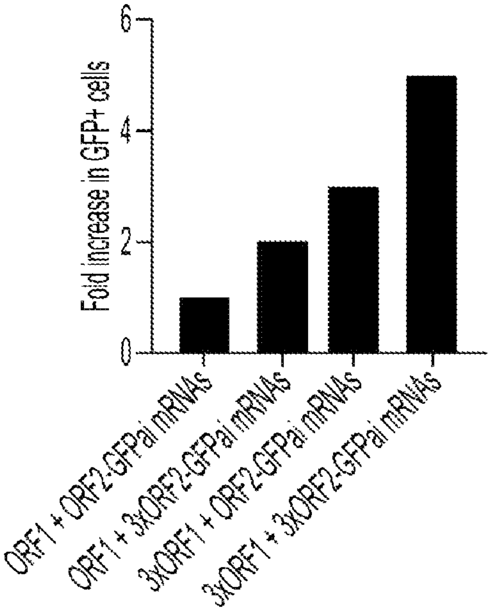
FIG. 12A depicts exemplary data showing expression of GFP (fold increase in mean fluorescence intensity of GFP positive cells is shown) upon electroporating ORF1-mRNA and ORF2-FLAG-GFPai mRNA at different amounts. Fold increase is relative to 1×ORF2-GFPao and 1×ORF1 mRNA.
Figure 12B:
FIG. 12B shows an exemplary fluorescent microscopy image of GFP+ cells following electroporation of the mRNA depicted in FIG. 11A.

In order to determine whether the relative levels of ORF1 and ORF2 mRNA affected GFP expression an experiment was set up to test the varying amounts of ORF1 and ORF2 mRNAs (FIG. 11A). 3× the amount of each and together is tested for increases in GFP+ cells and results are shown in FIG. 12A. Fold increase is relative to 1×ORF2-GFP and 1×ORF1 mRNA. GFP expression was higher when 3×ORF1 was used with 1×ORF2, but not the reverse; whereas having both 3×ORF1 and 3×ORF2 showed the maximum level of GFP expression in the sets compared. The cargo size here is 2.4 kb. FIG. 12B shows fluorescent microscopy image of GFP+ cells following retrotransposon mRNA electroporation.

Figure 13A:
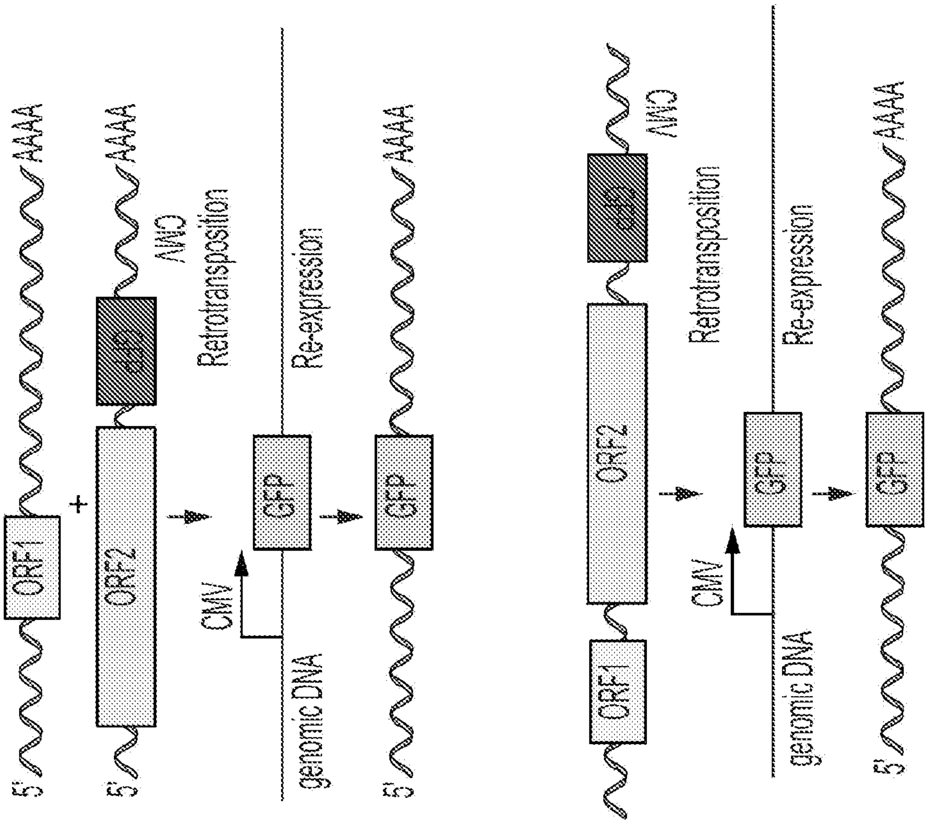
FIG. 13A shows exemplary mRNA constructs where the ORF1 and ORF2 sequences are in two difference mRNA molecules (top panel) and a LINE-1 mRNA transcript comprising ORF1 and ORF2 protein encoding sequences on a single mRNA molecule (bottom panel) for gene delivery. mRNA contains the bicistronic ORF1 and ORF2 sequence with a CMV-GFP sequence in the 3'UTR going from 3'-5'. Upon retrotransposition of the delivered ORF2-cmv-GFP antisense (LINE-1 mRNA), cells are expected to express GFP.
Figure 13B:
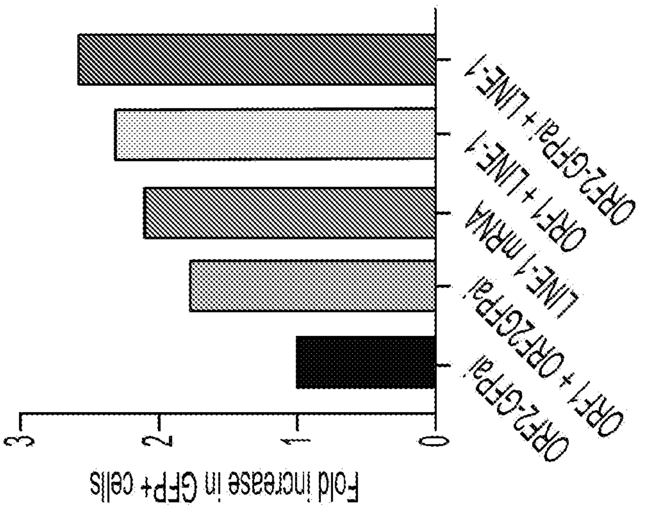
FIG. 13B depicts exemplary data showing expression of GFP (fold increase in mean fluorescence intensity of GFP positive cells is shown) upon electroporating the constructs depicted in FIG. 13A.

A complete LINE-1 mRNA encoding both ORF1 and ORF2 and GFP transgene in antisense orientation in a single mRNA molecule (LINE 1-GFP mRNA construct) was tested for delivery and genomic integration in a cell. mRNA contains the bicistronic ORF1 and ORF2 sequence with a CMV-GFP sequence in the 3'UTR going from 3'-5' (FIG. 13A). In this study the cargo size is 2.4 kb. As shown in FIG. 13B, upon retrotransposition of the delivered ORF2-cmv-GFP antisense (LINE-1 mRNA), third bar from left, cells expressed higher GFP compared to ORF1 and ORF2 being on separate mRNA molecules (graph bar 1, 2). Inclusion of ORF1 in a separate mRNA in addition to LINE-1 complete mRNA increased GFP expression over LINE-1 alone. Inclusion of ORF2+GFP expectantly showed higher GFP which could be the contribution of the additional ORF2 with the GFP cargo encoding mRNA.

Figure 14B:
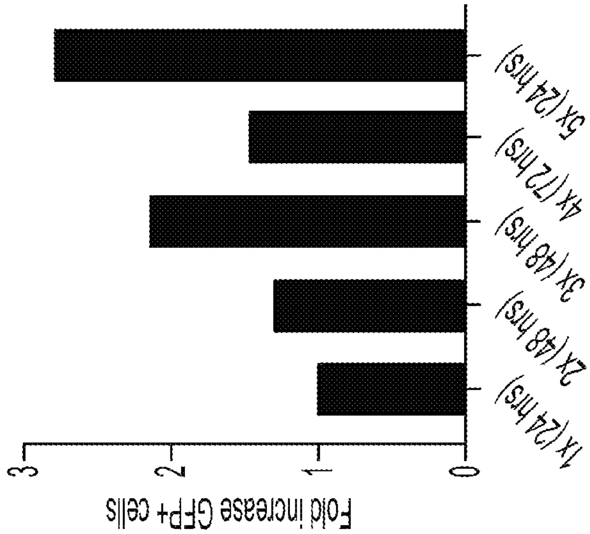
FIG. 14B depicts exemplary data showing expression of GFP at the indicated times (fold increase in mean fluorescence intensity of GFP positive cells is shown) upon electroporating 1-5 times according to FIG. 14A.
Figure 14A:
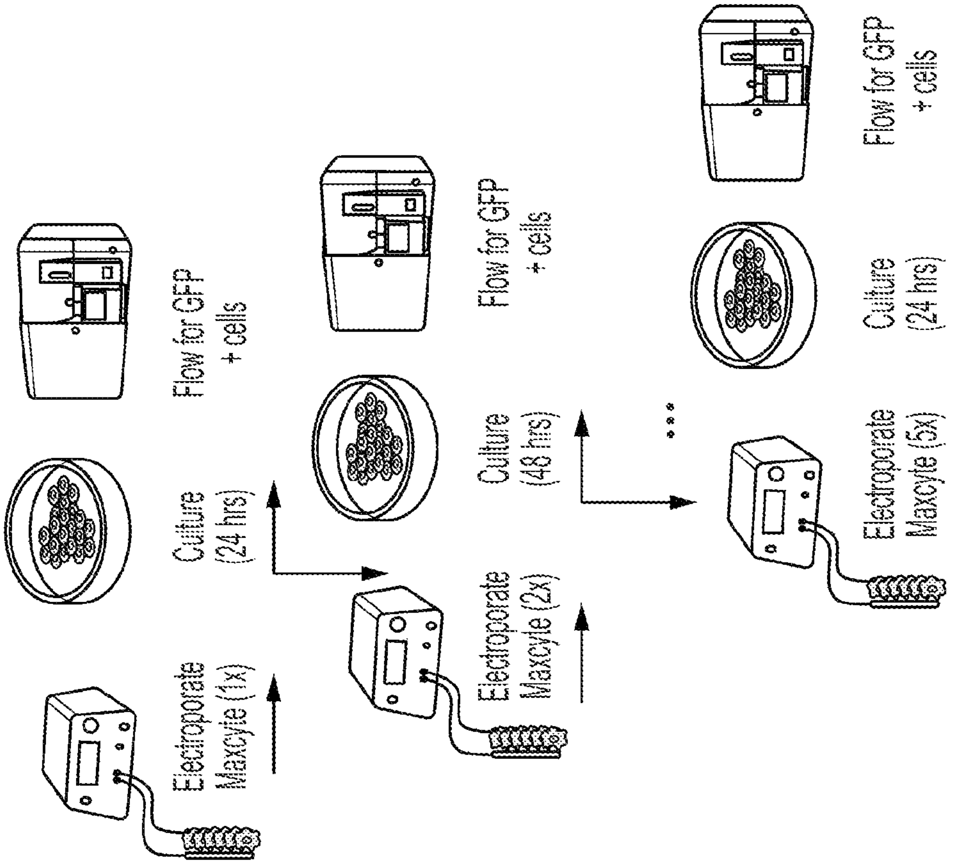
FIG. 14A shows an exemplary experimental design for testing whether multiple electroporations increases retrotransposition efficiency. HEK293T cells were electroporated every 48 hours with the Maxcyte system and assessed for GFP positive cells using flow after culturing for 24-72 hrs.

To test whether subsequent electroporation increases retrotransposition efficiency, cells were electroporation every 48 hours. GFP positive cells were assessed using flow after culturing for 24-72 hrs. The fluorescence data were normalized to the values in the set with a single electroporation event. As shown in FIGS. 14A and 14B, multiple electroporation led to an upward trend in the expression of the transposed gene, but the changes were modest.

Figure 15A:
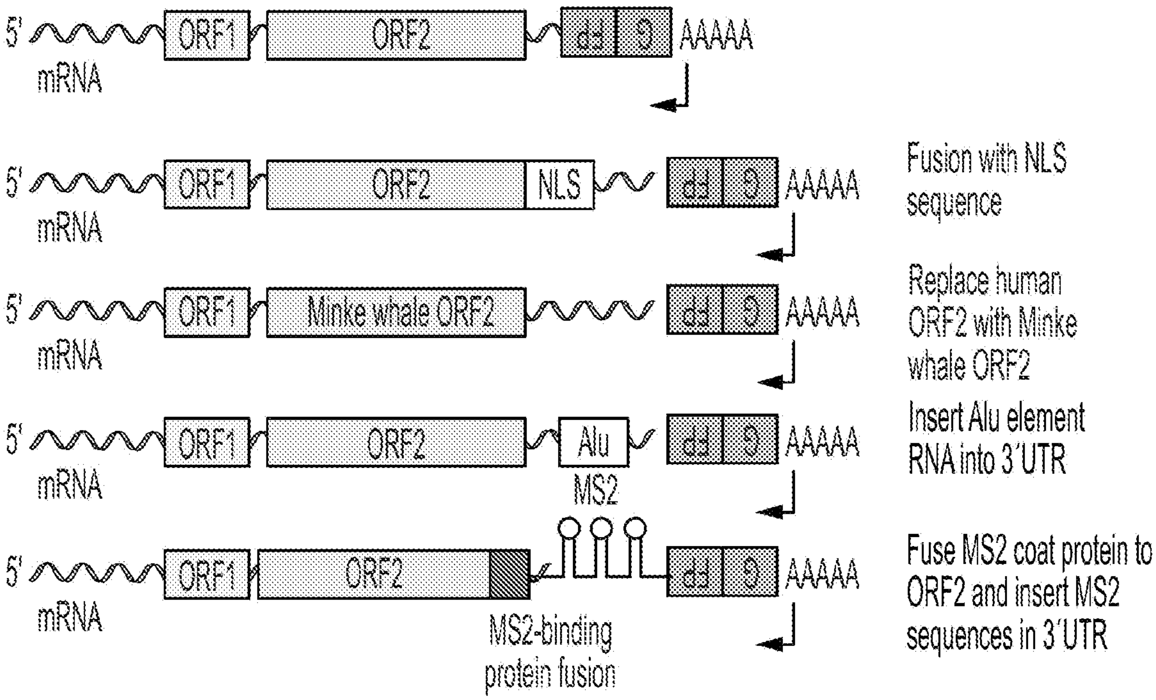
FIG. 15A depicts exemplary constructs to enhance retrotransposition via mRNA delivery. In one construct a nuclear localization signal (NLS) sequence is fused to the C terminus of the ORF2 sequence (ORF2-NLS fusion). In one construct a Minke whale ORF2 sequence was used in place of the human ORF2. In one construct a minimal sequence of the Alu element (AJL-H33delta) is inserted in the 3'UTR of the LINE-1 sequence. In one construct MS2 hairpins are inserted in the 3'UTR of the LINE-1 sequence and an MS2 hairpin binding protein (MCP) sequence is fused to the ORF2 sequence.

Example 10. Modifications to the ORF2 Protein Sequence to Enhance Retrotransposition by mRNA Modification of the LINE-1 sequence to enhance retrotransposition via mRNA delivery were tested using GFP reporter as readout. The experiment was performed as follows. All modifications were in the context of the bicistronic ORF1 and ORF2 sequence. (i) ORF2-NLS fusion was created by inserting C-terminal NLS sequence to the ORF2 sequence. (ii) Human ORF2 was replaced with Minke whale ORF2; (Ivancevic et al., 2016). (iii) Incorporation of an Alu element in the 3'UTR: Using a minimal sequence of the Alu element (AJL-H33Δ; Ahl et al., 2015) in the 3'UTR of the LINE-1. (iv) MS2-hairpin in the 3'UTR+ORF2-MCP fusion: MS2 hairpins in the 3'UTR of the LINE-1 sequence and a MS2 hairpin binding protein (MCP) fused to the ORF2 sequence (FIG. 15A). The mock construct had the wild-type human ORF2 sequence.

Figure 15B:
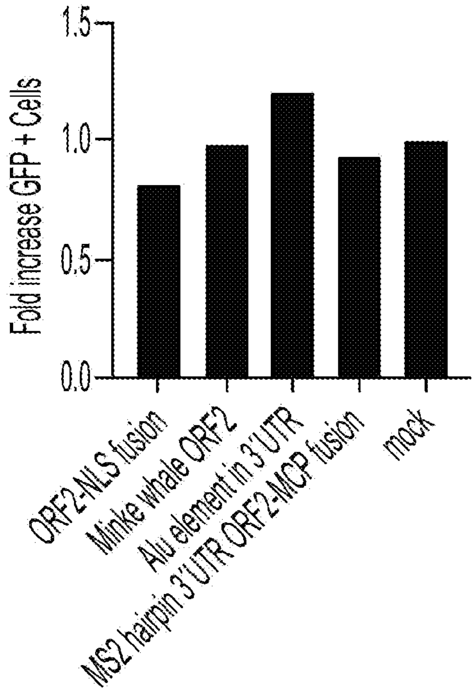
FIG. 15B depicts exemplary data showing expression of GFP (fold increase in mean fluorescence intensity of GFP positive cells is shown) using the constructs depicted in FIG. 15A.

Quantification of the fold increase in the fraction of GFP positive cells relative to mock construct electroporated cells are shown in FIG. 15B.

Example 11. Retrotransposition in an Immune Cell

Figure 16B:
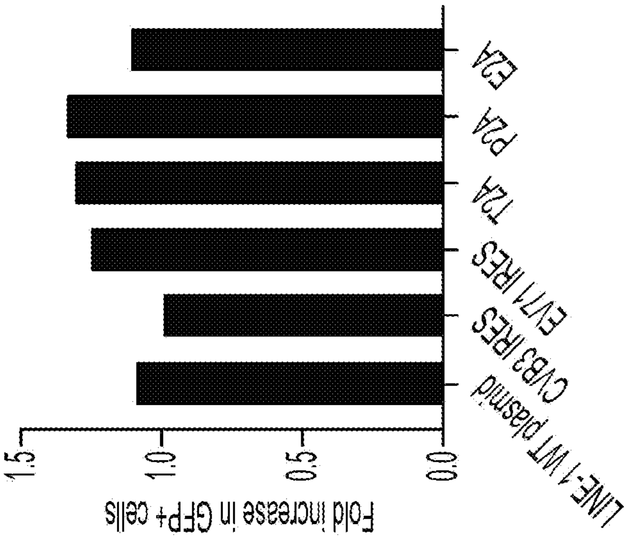
FIG. 16B depicts exemplary data showing expression of GFP (fold increase in mean fluorescence intensity of GFP positive cells is shown) using the constructs depicted in FIG. 16A.
Figure 16A:
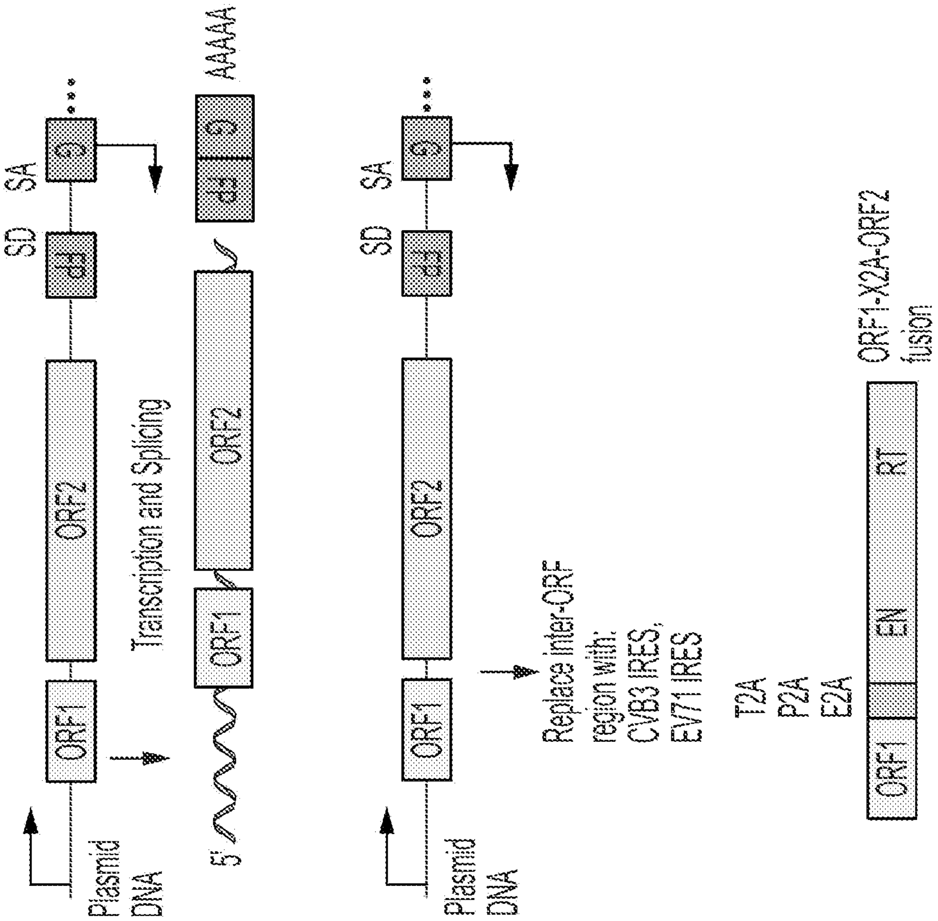
FIG. 16A shows exemplary plasmid constructs where the ORF1 and ORF2 sequences are in two difference plasmid molecules (top panel) and a plasmid encoding a LINE-1 mRNA transcript comprising ORF1 and ORF2 protein encoding sequences on a single mRNA molecule with various replacements of the inter-ORF sequence between ORF1 and ORF2 (bottom panel) for gene delivery.

In this experiment, the inter-ORF region is further manipulated to determine if any of the changes improve GFP expression after transfection of the HEK cells. Taking LINE-1plasmid GFP, the inter-ORF region is manipulated as follows: (a) In one construct the inter-ORF region is replaced with an IRES from CVB3; (b) In another construct, the inter-ORF region is replaced with an IRES from EV71; (c) In three separate constructs, an E2A or P2A or T2A self-cleavage sequence is intercalated in the inter-ORF region. Result are as shown in FIG. 16. Compared to the LINE-1 plasmid GFP (LINE-1 wild type plasmid) led to only modest changes in the GFP readout, especially with T2A sequence insertion. Insertion of EV71 IRES sequence improved GFP expression, while CVB3 IRES did not show any improvement.

Example 12. Retrotransposition in an Immune Cell

Figure 17B:
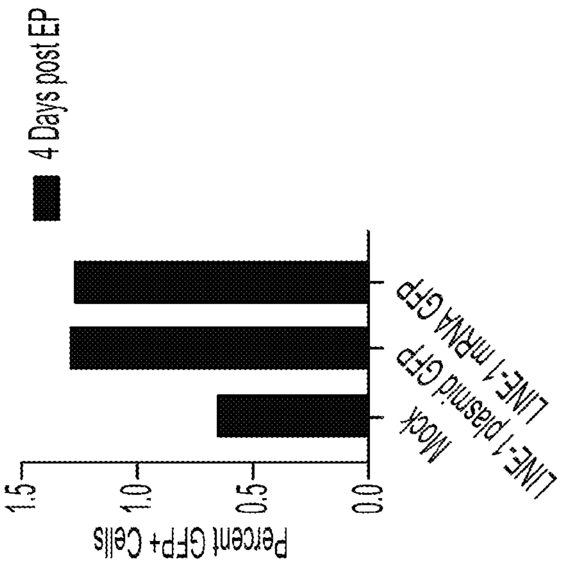
FIG. 17B depicts exemplary data showing expression of GFP (fold increase in mean fluorescence intensity of GFP positive cells is shown) in Jurkat cells using the constructs depicted in FIG. 17A. The plasmid construct was transfected, and the mRNA construct was electroporated.
Figure 17A:
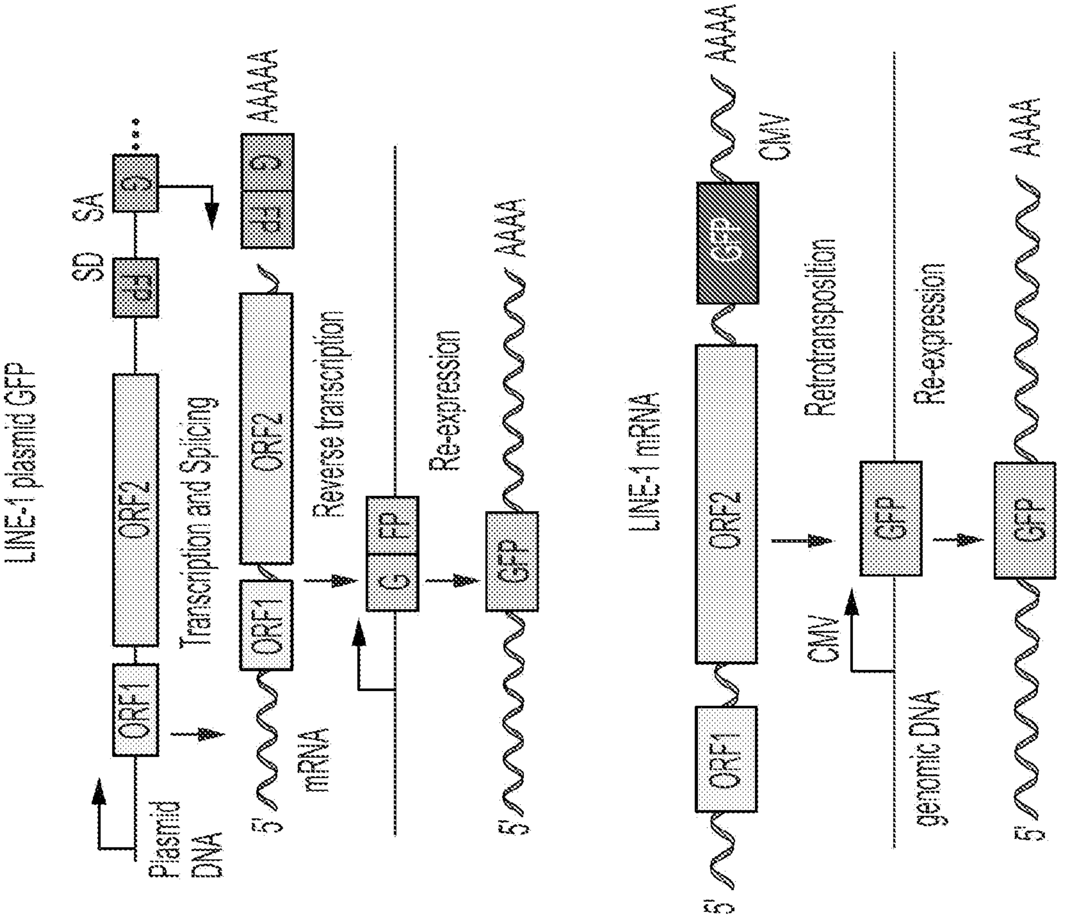
FIG. 17A depicts an exemplary plasmid construct encoding a LINE-1 mRNA transcript comprising ORF1 and ORF2 protein encoding sequences on a single mRNA molecule with a GFP sequence (top panel) and an exemplary LINE-1 mRNA transcript comprising ORF1 and ORF2 protein encoding sequences on a single mRNA molecule with a GFP sequence.

To test retrotransposition in immune cells, LINE-1 plasmid and mRNA were tested with the CMV-GFP antisense reporter cargo by electroporating into Jurkat cells, which is a T cell lymphoma line (FIG. 17A-FIG. 17B). Mock set were electroporated with a plasmid with no GFP sequence. GFP expression in the transfected cells was assessed, representative data at 4 days post electroporation is shown in FIG. 17B. Fold increase is reported relative to mock transfected cells. Both plasmid and mRNA delivery modes resulted in successful GFP expression.

Figure 18A:
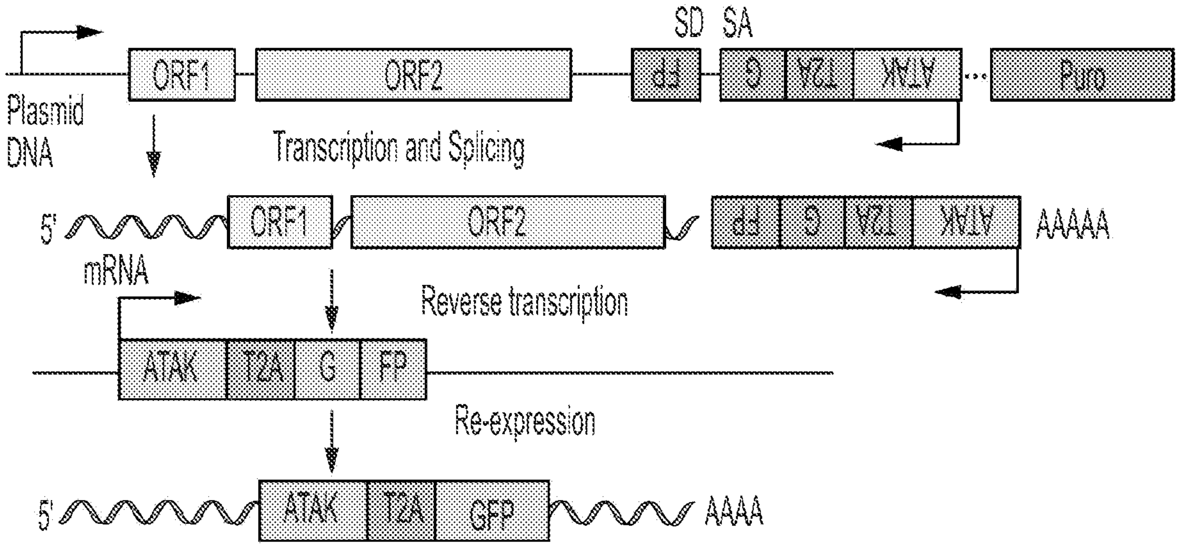
FIG. 18A shows an exemplary plasmid design and expected LINE-1 mRNA transcript with a cargo nucleic acid sequence. The plasmid has a LINE-1 sequence (comprising ORF1 and ORF2 protein encoding sequences) and a cargo sequence which is a nucleic acid sequence encoding a recombinant chimeric fusion receptor protein (ATAK receptor) followed by a T2A self-cleavage sequence followed by a split GFP sequence (all in a reverse orientation relative to the LINE-1 sequence). The coding sequence of the GFP is interrupted with an intron. Expected mRNA after reverse transcription and integration of the cargo are depicted.
Figure 18B:
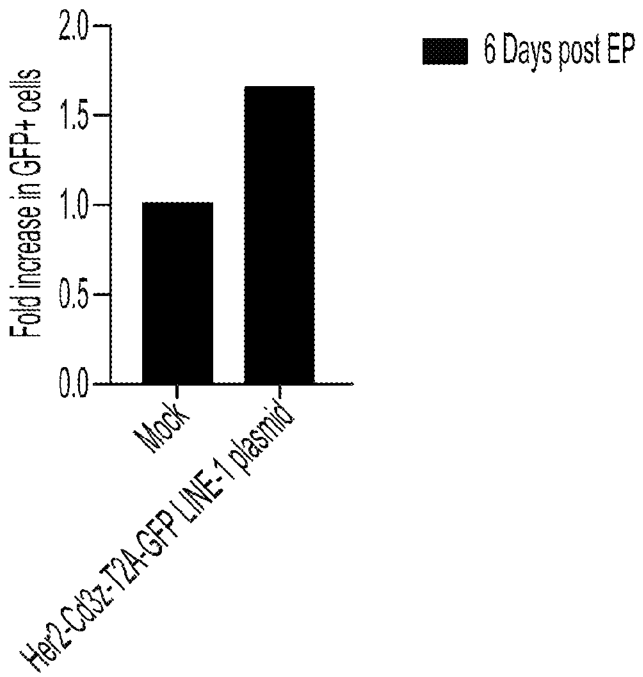
FIG. 18B shows exemplary results showing successful integration of the mRNA transcript encoded by the plasmid shown in FIG. 10A and expression of ATAK-T2A-GFP relative to mock-transfected cells (fold change in GFP and ATAK double positive cells is shown) in a myeloid cell line (THP-1). Data represents expression at 6 days post transfection, normalized over mock plasmid transfected cells wherein the mock plasmid does not have GFP coding sequence.

Next, THP-1 cells (a myeloid, monocytic cell line) were electroporated with a plasmid having LINE-1 sequences and a 3.7 kb cargo encoding a chimeric HER-2 binding receptor, and a split GFP (LINE-1 plasmid Her2-Cd3z-T2A-GFPintron) (FIG. 18A). The cargo is a chimeric receptor that comprises a HER2 binding extracellular domain, a CD3z transmembrane domain, and split GFP reporter. The plasmid was successfully integrated into the genome and showed prolonged expression, as demonstrated in FIG. 18B. Representative expression at day 6 post transfection is shown in the figure. From these studies, it was demonstrated that LINE-1 mediated gene delivery can result in successful stable genomic integration in various cell types, including epithelial cell types (HEK-293T cells); T cells (e.g., Jurkat cells); and cells of myeloid lineage (e.g., THP-1 cells) and results in prolonged expression. Moreover, unlike CRISPR dependent technologies such as Prime editing, retrotransposition can result in integration of large genetic cargo, and, these can be delivered as a single nucleic acid construct.

Example 13. External Methods for Further Enhancing Efficiency of LINE-1 Mediated Retrotransposition of the Cargo Sequences In this section, methods for further enhancing the efficiency of retrotransposition of cargo sequences into the genome of cells are detailed.

Figure 19:
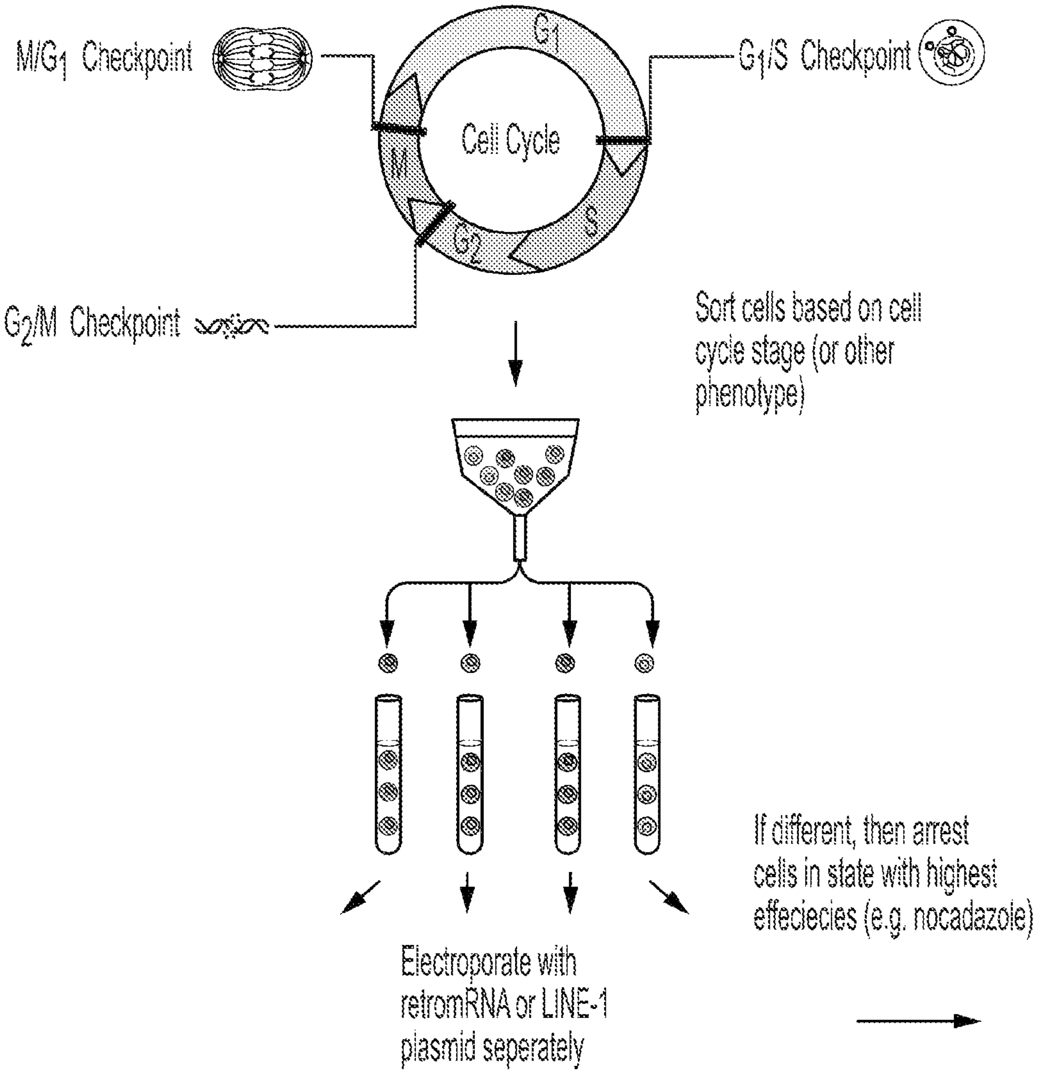
FIG. 19 illustrates an exemplary experimental set up for cell synchronization. A heterogenous cell population is sorted based on cell cycle stage, prior to delivery of an exogenous nucleic acid. Cell cycle synchronization is expected to result in higher expression and stabilization of the exogenous nucleic acid delivered. If cells are not homogeneous after cell sorting, then cells can be further incubated with a suitable agent that arrests cell cycle at a stage.

Cell cycle synchronization by selection of cells in a population that are in a certain stage of cell cycle or G1 arrest by a suitable agent can lead to higher nucleic acid uptake efficiency, e.g., plasmid vector transfection efficiency or electroporation efficiency. In this assay, cells are presorted and each group is separately electroporated to ensure uniform electroporation. The efficiencies of electroporation are compared between these groups and a cell cycle stage that results in highest efficiency as determined by the expression of the GFP test plasmid or mRNA is selected (FIG. 19).

In another variation of this experiment, cells are synchronized with or without sorting by treating the cells, with a cell cycle arrest reagent for a few hours prior to electroporation. An exemplary list of cell cycle arrest reagents is provided in Table 1. The list is non-exhaustive, and is inclusive of reagents that can be proapoptotic, and hence careful selection suitable for the purpose and dose and time of incubation is optimized for use in the particular context.

TABLE 1

Exemplary non-exhaustive list of small molecule reagents that are used for inhibiting cell cycle

| Agent | Cell cycle | Mechanism |
|---|---|---|
| 5-[(4-Ethylphenyl)methylene]-2-thioxo-4-thiazolidinone | Arrests cell cycle at G0-G1 | Inhibits c-Myc-Max dimerization |
| Itraconazole | Inhibits cell cycle at G1 | SMO antagonist |
| ABT 751 (Tocris Bioscience, cat #4138) | Blocks cell cycle at G2M | Inhibits microtubule proliferation |
| Artesunate | Arrests cell cycle at G2M | Suppresses ROS-induced NLRP3 |
| AZD 5438 | Blocks cell cycle at G2M, M, S and G1 phases | Inhibits Cdk |
| Baicalein | Arrests cell cycle at G1 and G2 phases | Inhibits lipoxygenases |
| CPI 203 (alternative name: TEN 101) | Arrests cell cycle at G1 phase | BET bromodomain inhibitor |
| Diadzein | Arrests cell cycle at G1 | Estrogen receptor agonist |
| DIM | Blocks cell cycle at G2M | Induces EGFR activation |
| Epothilone B | Arrests cell cycle at G2M | Inhibits tubulin proliferation |
| Indirubin-3'-oxime | Antiproliferative | Inhibits GSK3b |
| MPC 6827 hydrochloride | Cell cycle arrest | Inhibits microtubule proliferation |
| Pladienolide | Inhibits G1 and G2/M | Decreases mRNA splicing |
| Plumbagin | Induces G2/M arrest | Inhibits TOR signaling and others |
| Temsirolimus | Induces G1/S | mTOR inhibitor |
| Toceranib | Cell cycle arrest | Inhibits PDGFR and VEGFR |
| WYE 687 dihydrochloride | Induces G1 arrest | mTOR inhibitor |
| YC1 | Induces G1 arrest | Guanylyl cyclase activator |

Figure 20:
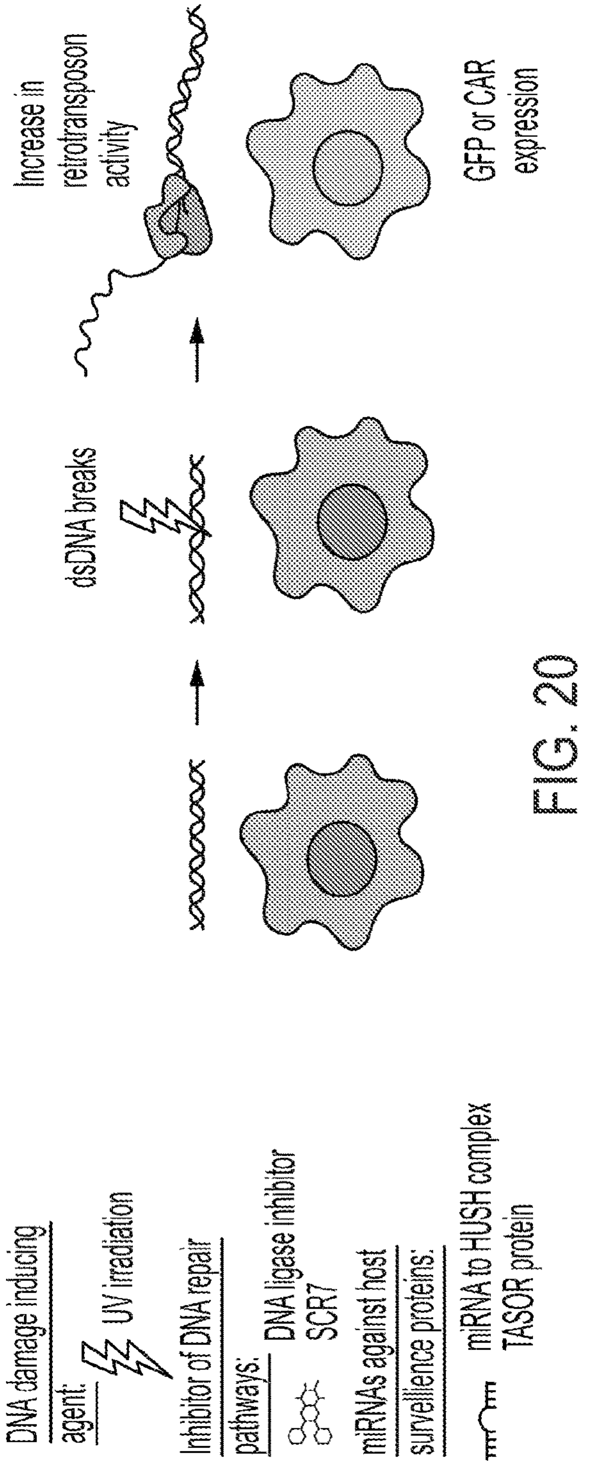
FIG. 20 illustrates an exemplary method for increasing retrotransposon efficiency by inducing DNA double stranded breaks, with or without inhibiting DNA repair pathways, such as by inducing DNA ligase inhibitor SCR7 or inhibiting host surveillance proteins, for example, using miRNA to HUSH complex TASOR protein.

For certain ex vivo usages, retrotransposition is enhanced by inducing DNA double stranded breaks (DSB) in a cell that expresses a retrotransposition machinery as described in any of the examples above by controlled irradiation, which create opportunities for the homologous recombination and priming for the reverse transcriptase (FIG. 20). In another example, cells transfected with LINE-1 plasmid GFP construct and subjected to an irradiation pulse. GFP expression is monitored. The intensity and time of irradiation is optimized for obtaining the maximum benefit, as indicated by higher GFP expression.

In another example, cells transfected with LINE-1 plasmid GFP were divided into experimental sets that are treated as follows (i) irradiation in order to induce DSB (as described above); (ii) treat cells in this set with a small molecule, such as SCR7, that blocks DNA ligase and therefore inhibits the DNA damage repair machinery. Preventing protective repair mechanism from inhibiting the progress of the retrotransposition is expected to enhance GFP expression: (iii) irradiate the cells then treat the cells with SCR7, combination of the two is expected to show a more robust effect. GFP expression is monitored over a period of 6 days, and the set that shows maximum GFP fluorescence over the longest period indicates a condition that is adopted in further studies.

Figure 21:
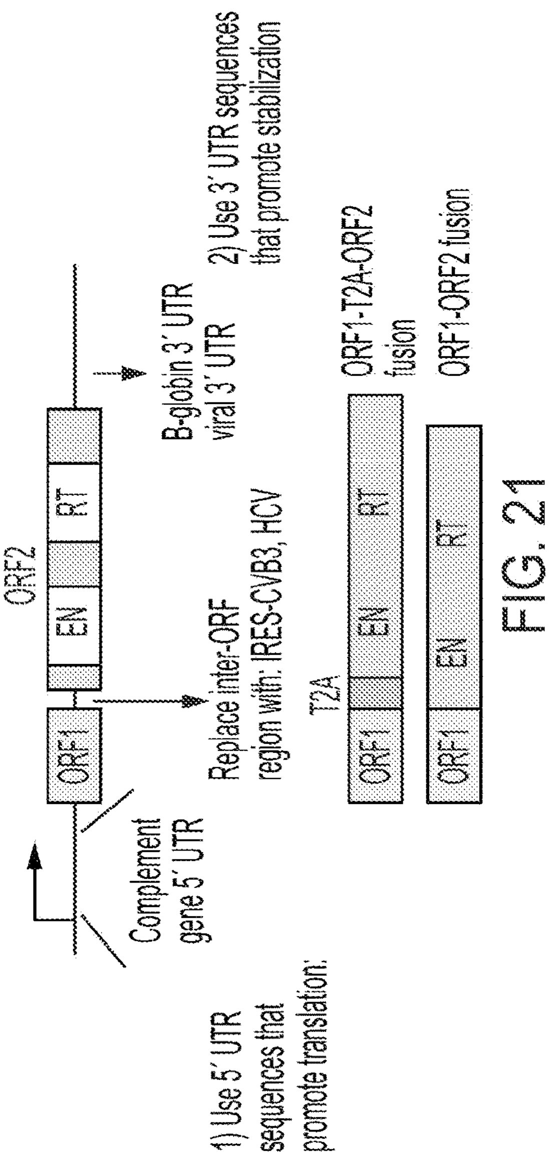
FIG. 21 illustrates exemplary constructs for integrating an mRNA encoding a transgene into the genome of a cell.

Example 14. Enhancing Efficiency of LINE-1 Mediated Retrotransposition of the Cargo Sequences by Further Modification of the Construct Enhancing non-coding regions of the construct to offer stability and higher expression. In this example a LINE-1 plasmid-GFP is further modified to test for increased GFP expression as follows: (a) In one construct, the 5'UTR is replaced with an UTR of a complement gene; (b) In another construct, the 3' UTR is replaced with the UTR sequence of B-globin gene for increased stability; (c) In another construct the inter-ORF region is replaced with an IRES from CVB3; (d) In another construct, the inter-ORF region is replaced with an IRES from EV71 (e) In three separate constructs, an E2A or P2A or T2A self-cleavage sequence is intercalated in the inter-ORF region as shown in a diagrammatic representation in FIG. 21. In addition to the above, various combinations of (a)-(e) and additional combinations listed in Table 2 are tested using the same set-up as above. GFP expressions are monitored after transfection of the constructs in parallel test sets into HEK293T cells to see if any of these constructs increased GFP expression compared to the LINE-1 plasmid GFP alone. The combinations that show improvement are adopted.

TABLE 2

Exemplary combinations of 5' and 3' UTR and inter-ORF insertion elements for inclusion in the LINE-1 construct for increase in retrotransposition efficiency.

| 5'-UTR sequences selected from sequences | 3'-UTR sequences | Inter-ORF sequences |
|---|---|---|
| Complement 5'UTR | WPRE | T2A, E2A, P2A |
| Covid-19 5' leader sequence | B-globin 3'UTR | CVB3 IRES |
| CYBA 5'UTR | RSV RSE | EV71 IRES |
| CYP2E1 5' UTR | AREs | EMCV IRES |
| | RNA zipcodes for the ER | PV IRES |
| | | CSFV IRES |
| | mtRNR1-AES | HRV2 IRES |
| | | AAA (tri alanine fusion or any fusion-linker sequence) |

Figure 22:
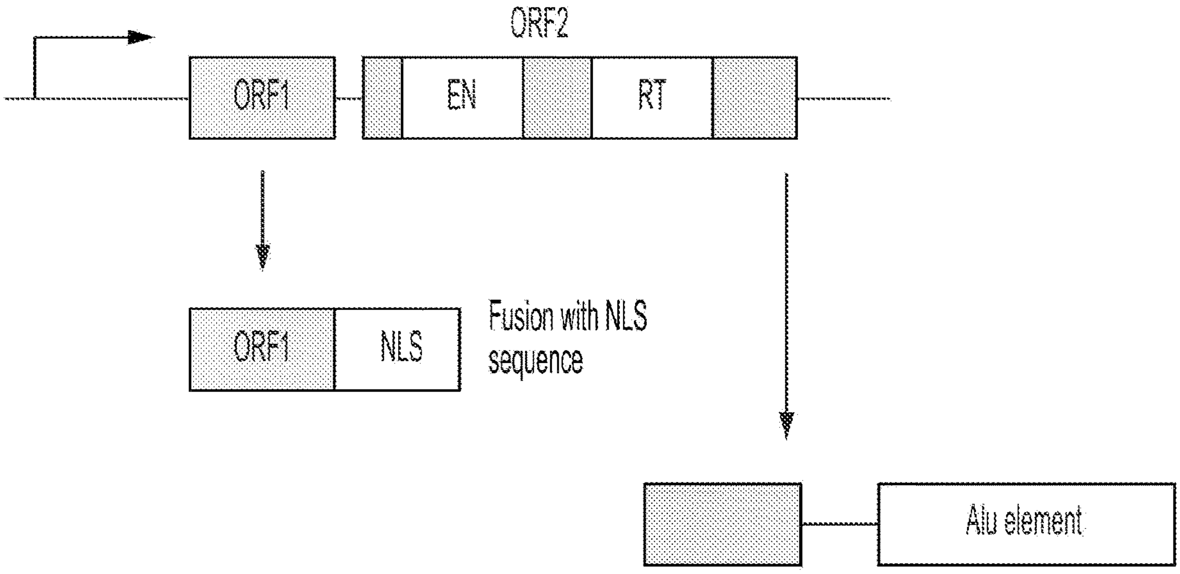
FIG. 22 illustrates exemplary constructs for integrating an mRNA encoding a transgene into the genome of a cell.

II. Enhancing localization and retention of the ORFs in the nucleus. In this example, LINE-1 plasmid-GFP is further modified to test for increased GFP expression as follows: (a) the ORF2 encoding sequence is fused with a nuclear localization sequence (NLS) (graphically represented in FIG. 15A second construct from top). (b) the ORF1 encoding sequence is fused with a nuclear localization sequence (NLS), graphically represented in FIG. 22; and (c) An Alu binding sequence is inserted 3' of the sequence encoding ORF2 reverse transcriptase (graphically represented in FIG. 15A, fourth construct from the top; (d) Both (a) and (c) together (not shown); (e) Both (b) and (c) together, the NLS sequence is fused to the ORF1 N-terminus, and an Alu binding sequence is inserted 3' of the sequence encoding ORF2 reverse transcriptase (FIG. 22) and (f) Integrating a SINE-derived nuclear RNA LOcalizatIoN (SIRLOIN) sequence in LINE-1 3' UTR. HEK-293T cells were transfected with constructs (a)-(f) and the LINE-plasmid GFP construct in parallel. GFP expression is monitored after transfection into HEK293T cells. The set that shows maximum GFP fluorescence over the longest period is adopted.

Figure 23:
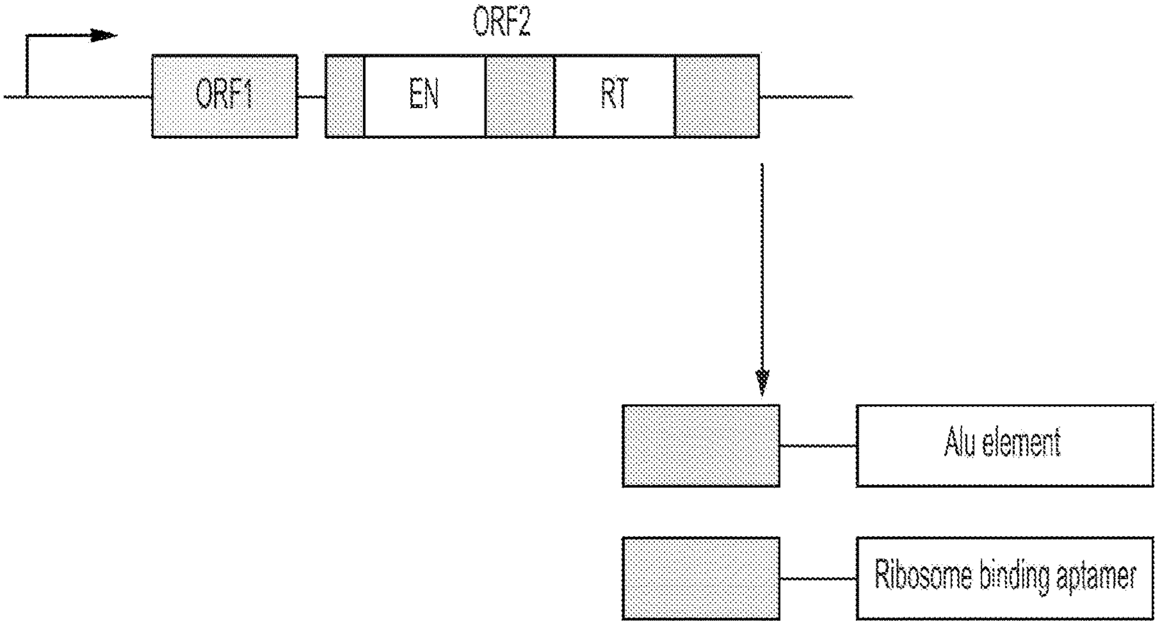
FIG. 23 illustrates exemplary constructs for integrating an mRNA encoding a transgene into the genome of a cell.

III. Modifying construct to increase LINE-1-protein-RNA complex binding to the ribosome. In this example, an additional sequence is inserted in the 3'UTR of the LINE-1 construct to increase association of the LINE-1 protein RNA construct to the ribosomes, the sequence is an Alu element, or a ribosome binding aptamer (FIG. 23).

For enhancing LINE-1 protein-RNA complex binding to the ribosome, insertion of the following elements in the 3' UTR of the mRNA is done and tested similar to the experiments above. Insertion of Alu elements is described above. In separate constructs, Alu element truncations, Ribosome binding aptamers (109.2-3) and Ribosome expansion segments (ES9S) binding sequence are inserted and each tested for increase in GFP expression.

Figure 24:
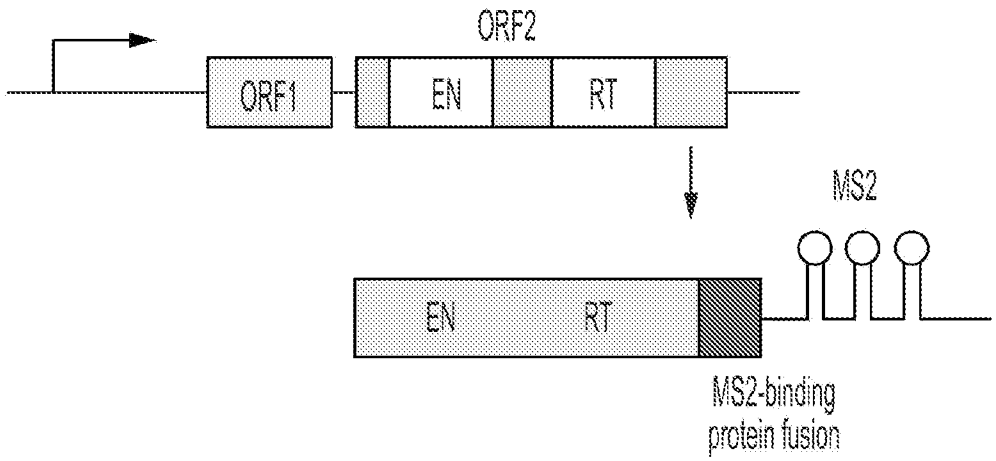
FIG. 24 illustrates exemplary constructs for integrating an mRNA encoding a transgene into the genome of a cell.

IV. Enhancing binding of ORF2 to its own mRNA for retrotransposition. In this example, a sequence containing MS2 binding loop structure is introduced into the 3'UTR of the LINE-1, and a sequence encoding MS2 RNA binding domain is fused to the RNA binding domain of the ORF2p-RT (graphically represented in FIGS. 4A and 4B, and FIG. 24, construct SEQ ID NO: 15). The fused protein will specifically attach to the MS2-binding structural motif in the 3' UTR, and therefore any non-specific binding and retrotransposition is minimized (FIG. 24). GFP expression is monitored after transfection into HEK293T cells. Following a similar design, the ORF is fused with the protein binding sequences shown in left column of Table 3 below, combined with a cognate sequence inserted in the 3'UTR region of the ORF2 shown in the corresponding right column in the same row.

TABLE 3

Exemplary list of elements to enhance translation efficiency and stability of the LINE-1 proteins and increased expression of LINE-1 proteins.

| Elements to be fused with the LINE-1 ORF2 | 3' UTR sequence recognizable by the element |
|---|---|
| PP7 coat protein | PP7 |
| Streptavidin | S1m aptamer |
| Tobramycin | Tobramycin aptamer |

Figure 25:
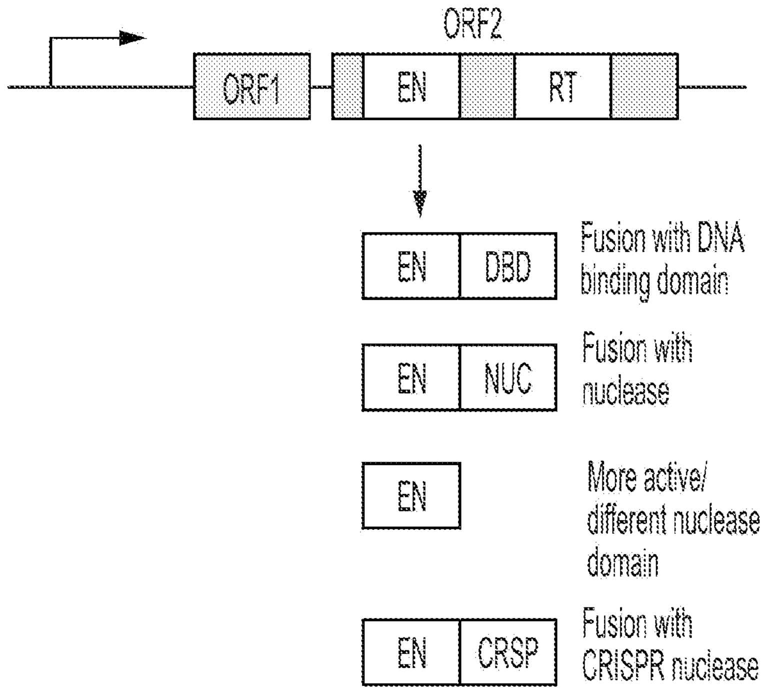
FIG. 25 illustrates exemplary constructs for integrating an mRNA encoding a transgene into the genome of a cell.

V. Modifying the endonuclease function of the retrotransposon. In this example, the constructs are modified to test increase in GFP expression as follows. In a first experimental set, the LINE-1 plasmid GFP is cut at the 3'end of the endonuclease coding sequence of ORF2, and a sequence encoding the DNA binding domain (DBD) of a heterologous zinc finger protein (ZFP) is inserted. In another experimental set, the endonuclease domain is fused with a CRISPR nuclease. A variety of nucleases can be tested by modifying the LINE-1 plasmid GFP ORF by creating a fusion protein using DNA binding domains and cleavage domain as shown in a non-exhaustive list in Table 4, In addition, two ORF-2 domains are encoded in one set to facilitate dimerization. The construct that has higher GFP expression than the ORF2 endonuclease can be further selected. The plasmid designs are graphically represented in FIG. 25. GFP expression is monitored after transfection of the plasmids into HEK293T cells, and the set that yielded best.

TABLE 4

| Exemplary non-exhaustive list of additional DNA cleavage domains/enzymes that can be fused to or inserted in place of LINE-1 endonuclease. | |
|---|---|
| Gene/Enzyme | Description |
| FokI | Class II endonuclease from Flavobacterium okeanokoites, recognition and cleavage sequence are separated by a few nucleotides; recognizes DNA sequence 5-GGATG-3' |
| Restriction enzymes, | e.g., HindII, EcoR1, BamH1 |
| LAGLIDADG family nuclease A ("LAGLIDADG" disclosed as SEQ ID NO: 66) | Intron encoded homing proteins found in various genera including bacteria |
| GIY-YIG | This domain is found in the amino terminal region of excinuclease abc subunit c (uvrC), bacteriophage T4, endonuclease segA, segB, seg C, seg D, and seg E and group I introns of fungi and phage. |
| His-Cys box | Homing endonucleases containing two clusters of conserved histidine and cysteine residues over a 100 amino acid region. |
| H—N—H | Widely present nuclease in phage DNA. Crucial component of the terminase packaging reaction of *E. coli* phage HK97. |
| PD-(D/E)xK | Phosphodiesterases, present in a large number of proteins, e.g., DUF4420, DUF3883, DUF4263, COG5482, COG1395, Tsp45I, HaeII, Eco47II, ScaI, HpaII. |
| Vsr-like/EDxHD | C-terminal nuclease domain that displays recognizable homology to bacterial Very short repair (Vsr) endonucleases |

Figure 26:
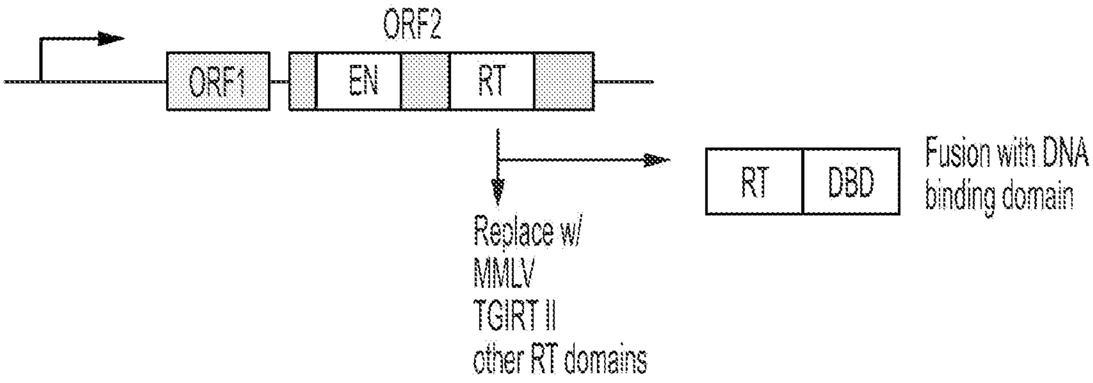
FIG. 26 illustrates exemplary constructs for integrating an mRNA encoding a transgene into the genome of a cell.

VI. Modifying the reverse transcriptase function of the retrotransposon. In this example, the reverse transcriptase domain of ORF2 is modified for increasing its efficiency. In one experimental set, the sequence encoding the human ORF2 in LINE-1plasmid GFP is excised and replaced with a sequence encoding MMLV or TGIRTII In another experimental set, the ORF2 reverse transcriptase domain is fused with a DNA binding domain of a heterologous protein. The reverse transcriptase domains and/or the DNA binding domains can be selected from a non-exhaustive list provided in Table 5A-Table 5B. The constructs are graphically exemplified in FIG. 26. GFP expression is monitored after transfection into HEK293T cells.

TABLE 5A

| Selected non-exhaustive list of reverse transcriptase for replacing the LINE-1 RT for higher efficiency | |
|---|---|
| Reverse Transcriptase | Description |
| M-MLV-RT | Murine leukemia virus |
| TGIRT-II | Thermostable group II intron reverse transcriptase with high fidelity and processivity |
| AMV-RT | Avian Myeloblastosis Virus reverse transcriptase |
| Group II intron maturase RT | Derived from *Eubacterium rectale* |
| HIV-RT | Efficient RT derived from HIV |
| TERT | Catalyzes the RNA-dependent extension of 3'-chromosomal termini with the 6-nucleotide telomeric repeat unit, 5'-TTAGGG-3'. |

TABLE 5B

| Selected non-exhaustive list of DNA-binding domains for fusing to a RT for higher efficiency DNA binding domains (DBD) |
|---|
| Zinc finger domains |
| Leucine zipper (bZip) |
| Helix-turn-helix domain |
| HMG-box |
| R2 retroelement DBD |
| Sso7d |
| Protein A (ssDNA) |
| OB-fold (ssDNA) |

Figure 27:
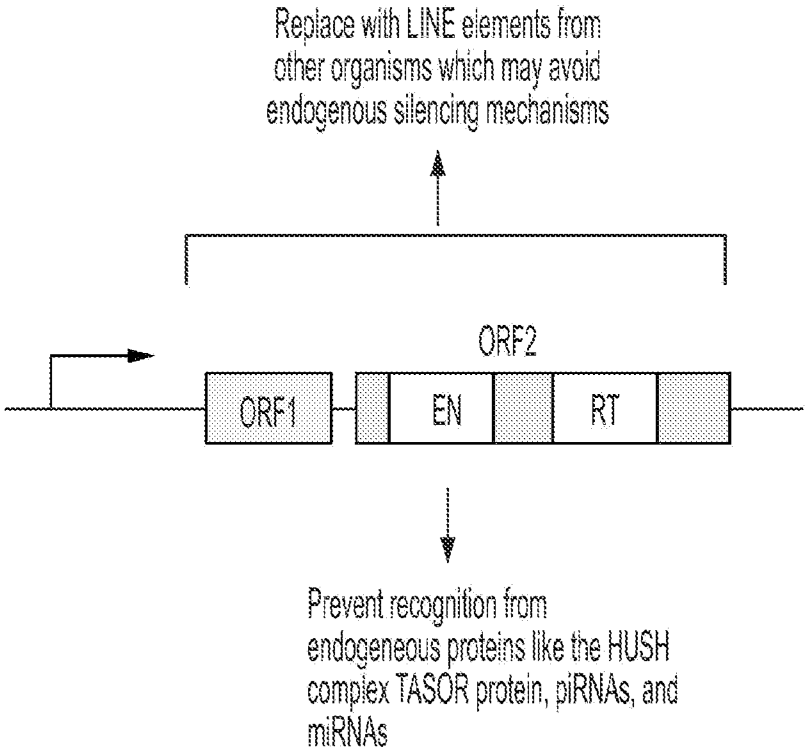
FIG. 27 illustrates exemplary constructs for integrating an mRNA encoding a transgene into the genome of a cell.

VII. Replacing human LINE-1 with LINE-1 from other organisms. In this example, the sequence encoding human LINE-1 is replaced by a LINE-1 from a different organism. In one example, the human LINE-1 construct is compared with a construct where the human LINE-1 is replaced by a minke whale LINE-1 sequence (FIG. 27). Using the same experimental framework, a number of ORFs are tested. An exemplary non-exhaustive list is provided in Table 6 below. A further comprehensive list is available in Ivancevic A. et al., Genome Biol Evol 8(11):3301-3322.

TABLE 6

| Exemplary LINE-1 elements from organism for use in replacement of the human LINE-1 | |
|---|---|
| Species Name | No of total LINE-1/ No active/percent active |
| *Balaenoptera acutorostrata scammoni* | 8,012/5,006/62.4% |
| *Rhinopithecus roxellana* | 11,115/2,954/26.5% |
| *Mus musculus* | 18,280/4,143/22.66% |
| *Aedes aegypti* | 519/184/35.4% |
| *Zea mays* | 744/165/22.17% |
| *Brassica napus* | 1,929/565/29.2% |
| *Brassica rapa* | 543/228/41.9% |
| *Danio rerio* | 590/268/45.4% |

In another set, human LINE-1 is retained as in the GFP plasmid, but an inhibitor of human LINE-1 silencer is utilized to prevent recognition by endogenous proteins like HUSH complex TASOR protein. In this case, the TASOR inhibitor is an inhibitory RNA, such as a miRNA.

Figure 28:
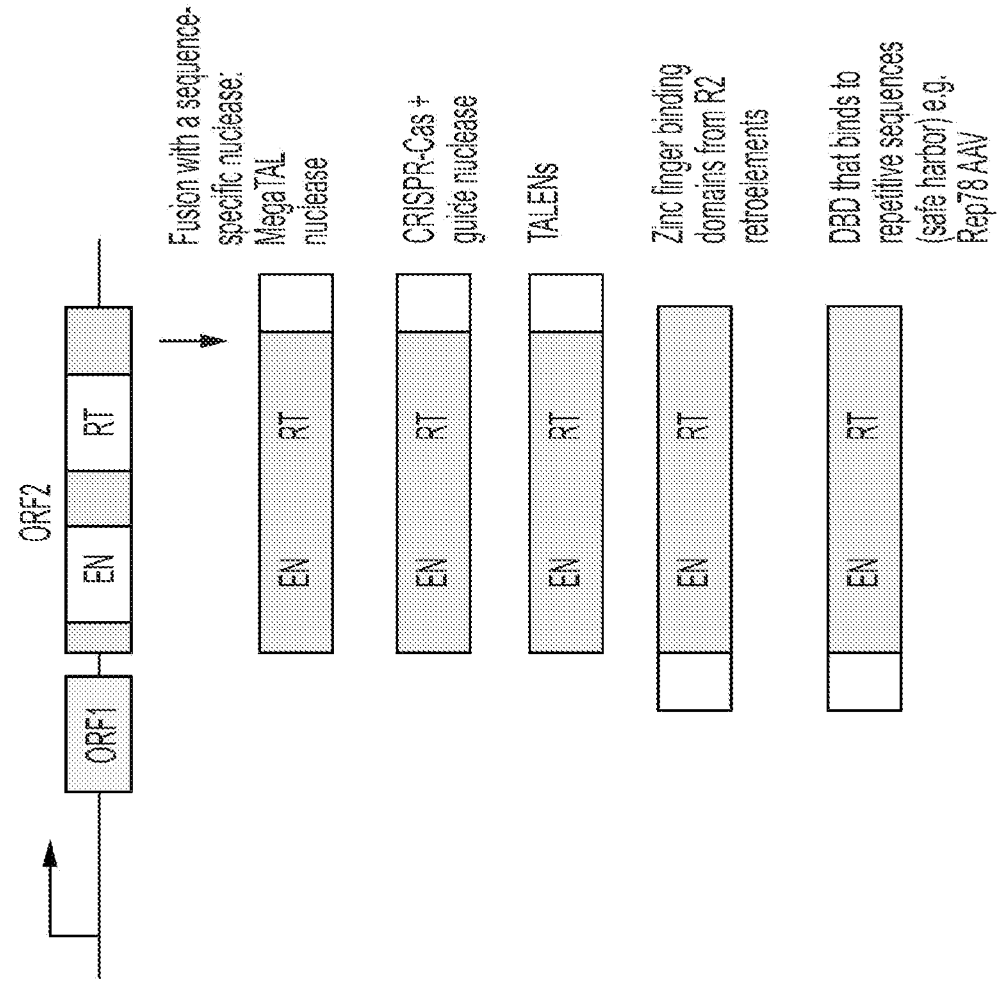
FIG. 28 illustrates exemplary constructs for integrating an mRNA encoding a transgene into the genome of a cell.

VIII. LINE-1 fusion proteins for target specificity. In this example, the LINE-1 plasmid GFP ORF2 is fused with a domain of a MegaTAL nuclease, a CRISPR-CAS nuclease, a TALEN, R2 retroelement binding zinc finger binding domain, or a DNA binding domain that can bind to repetitive elements such as Rep78 AAV. FIG. 28 exemplifies the deigns. Table 7 provides a list of the different elements that can be fused to increase sequence specific retrotransposition.

TABLE 7

| Exemplary proteins with DNA binding domains to be fused to ORF2 for increasing retrotransposition specificity Elements |
|---|
| Transcription Factors |
| MegaTAL nucleases |
| TALENs |
| Zinc finger binding domains from other retroelements |
| Safe harbor binding proteins |
| Cfp1 |

Each plasmid is transfected into HEK293 cells and GFP expression is monitored.

The modifications described in this section under (I)-(VIII) are designed to test for increase in retrotransposition efficiency, using GFP as readout. Following this, a number of useful modifications from (I)-(VIII) are incorporated into a single retrotransposition construct, tested with GFP as insert for the outcome, and the GFP sequence is replaced by the desired insert sequence.

Example 15. Delivering a Large Payload for Prolonged Expression Using Retrotransposon Technology Provided here are exemplary demonstrations of retrotransposon constructs are versatile for incorporating nucleic acid payloads into the genome of a cell and expressing an exemplary transgene. Retrotransposon constructs were designed as elaborated elsewhere in the disclosure.

Figure 29:
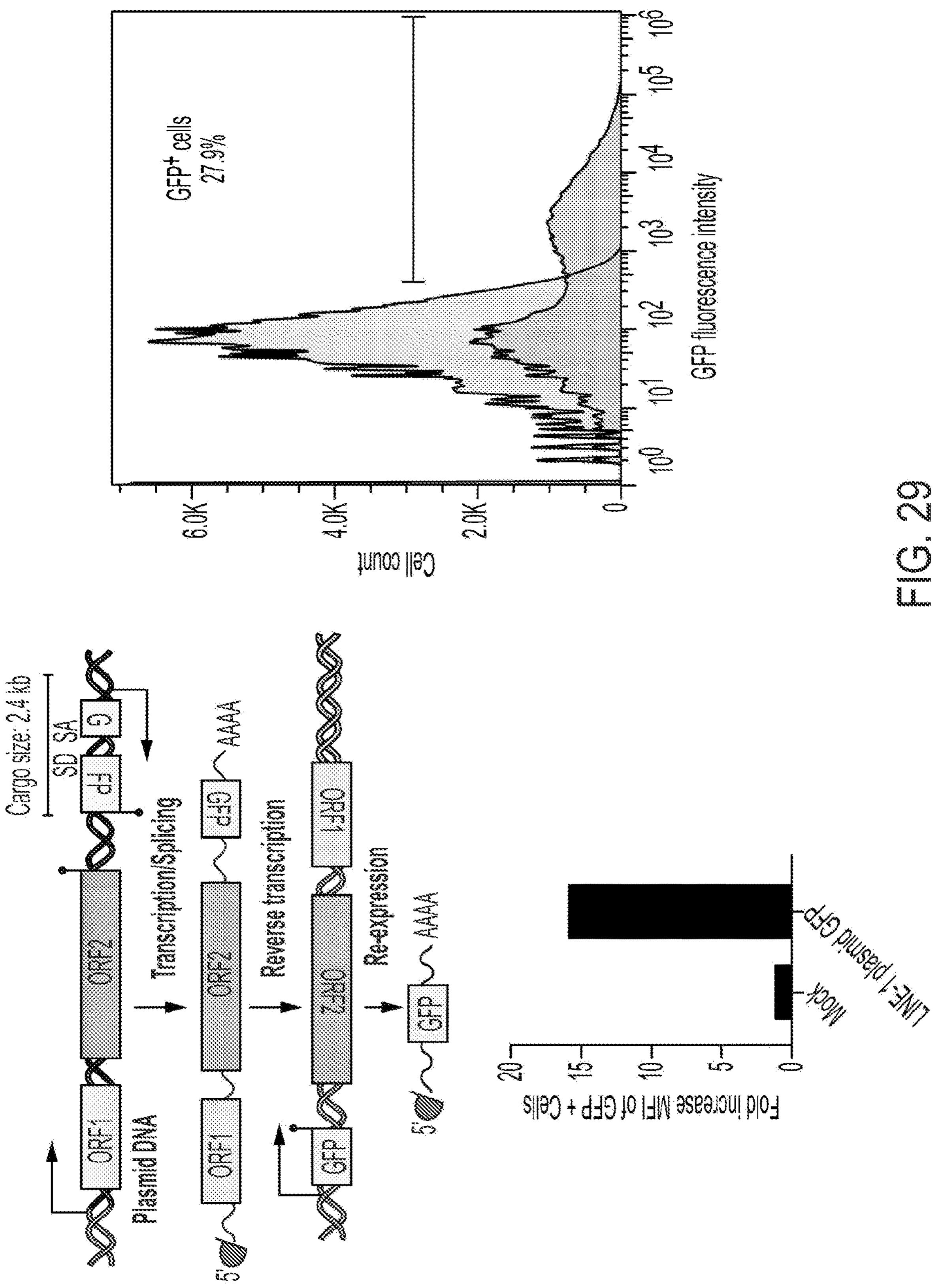
FIG. 29 illustrates exemplary retrotransposon constructs (left) with a 2.4 kb cargo with a general mechanism of action of the retrotransposon, and a representative data (right) for expression of a fluorescent GFP marker encoded by the cargo from a nucleic acid sequence integrated into the genome in HEK293 cells. Placement of an antisense GFP gene split with an intron in the sense direction and a promoter sequence in the 3'UTR of the LINE-1 leads to reconstitution and retrotransposition of the GFP cargo. GFP expression in 293T cells transfected with the construct shown on the left, as measured by flow cytometry (right) and quantitated bar graphs (bottom left). Data collected 35 days after doxycycline induction of the ORF.

Briefly, in one set of validation experiments, GFP encoding payloads were constructed as follows: an antisense promoter sequence under doxycycline inducible control followed by antisense GFP gene split with an intron in the sense direction was placed downstream of the LINE-1 ORFs (FIG. 29). Splicing donor (SD) and splicing acceptor (SA) sequences are recognized and spliced out only when the mRNA is produced from the promoter in the top strand, therefore only the GFP gene integrated into genome from spliced mRNA generates fluorescent signal. As shown in the representative flow cytometry data in FIG. 2, the GFP expression was measured 35 days post doxycycline induction of the ORF expression using flow cytometry (green histogram) compared to a negative control plasmid (grey histogram). In this case, the cargo size was 2.4 kb.

Figure 30:
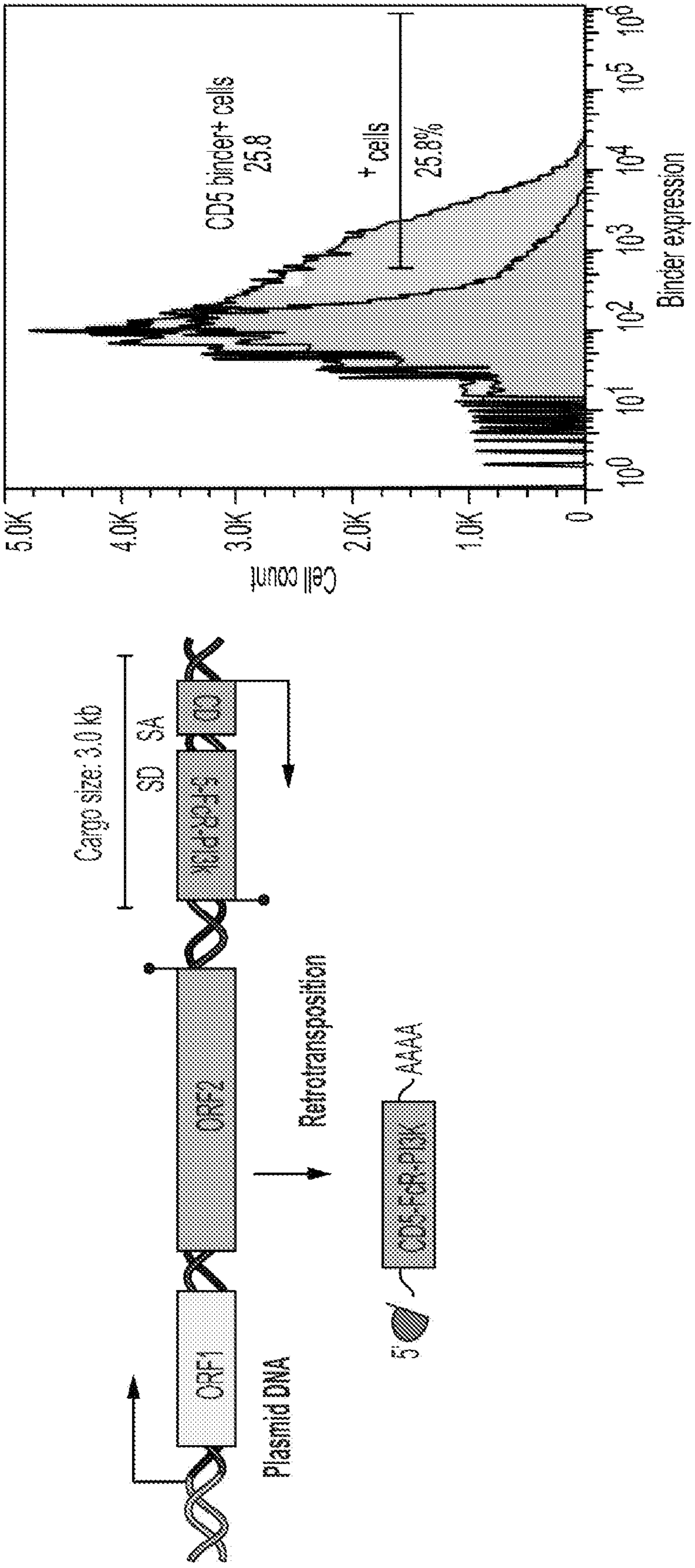
FIG. 30 illustrates exemplary retrotransposon constructs (left) with a 3.0 kb cargo comprising a membrane protein (CD5 binder chimeric antigen receptor, CD5-CAR), and a representative flow cytometry data for expression of the CD5 binder (right) from the nucleic acid sequence integrated into the genome in HEK293 cells. % of CD5 binder positive (+) cells is indicated in the inset.

The cargo GFP gene in the previous construct was replaced with intron interrupted CD5-FcR-P13K CAR-M sequence (Morrissey et al., 2018). The CD5 binder expression was measured by flow cytometry using a Alexa647-conjugated CD5 protein such that retrotransposed cells are CD5-AF647 positive (red histogram) compared with a plasmid transfected negative control cell population (grey histogram) (FIG. 30). Successful expression of the 3.0 kb construct was demonstrated as shown in the figure.

Figure 31:
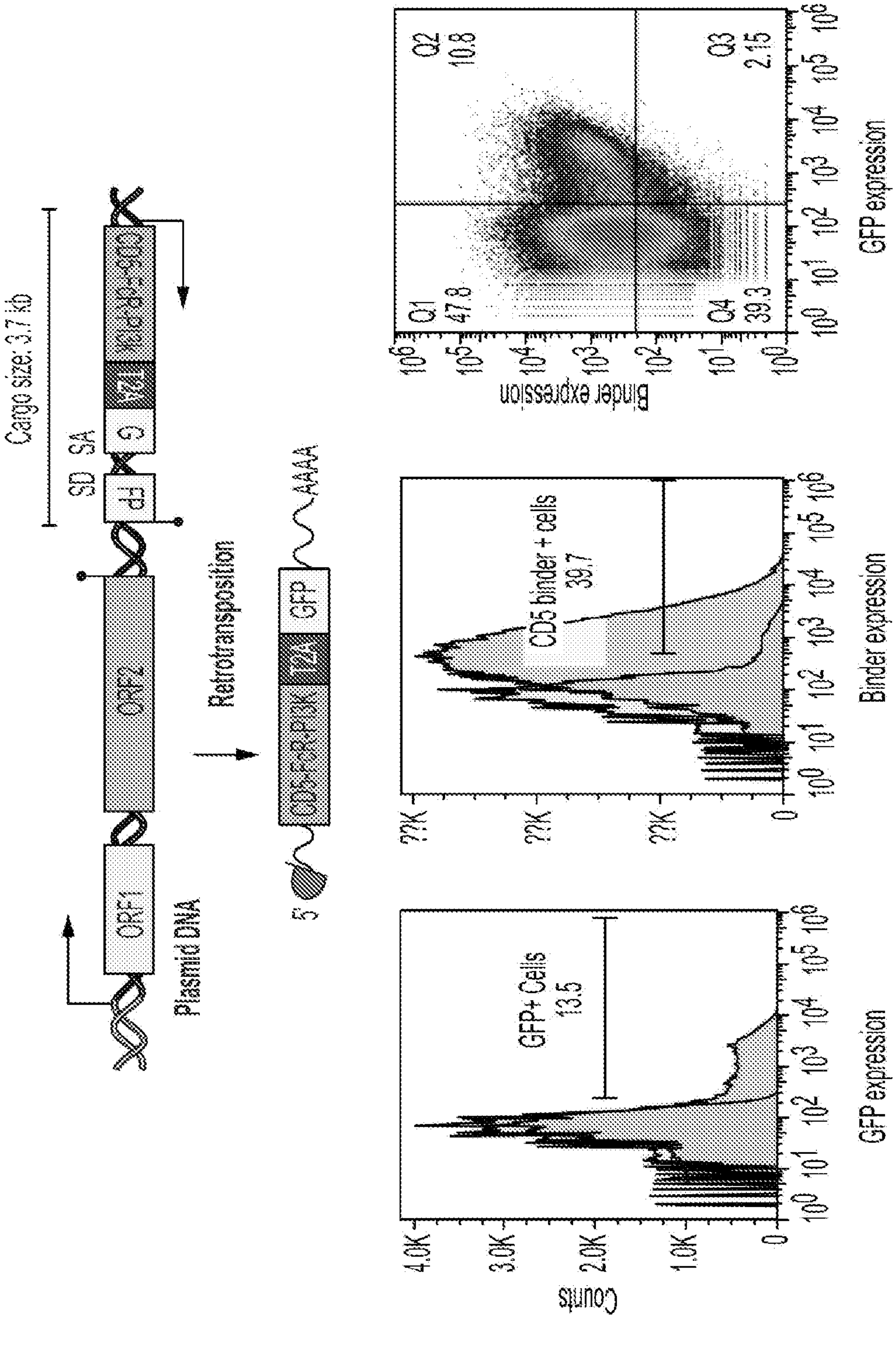
FIG. 31 illustrates an exemplary retrotransposon construct (top) with a 3.7 kb cargo comprising a membrane protein (CD5 binder chimeric antigen receptor, CD5-CAR and a GFP separated by an auto-cleavable T2A element), and a representative flow cytometry data (bottom) demonstrating the expression of the CD5 binder and GFP.

The cargo gene length was extended by adding the intron-interrupted GFP gene after the T2A sequence downstream of the CD5-FcR-PI3K CAR-M sequence (FIG. 31). The CD5 binder expression was measured by flow cytometry using a Alexa647-conjugated CD5 protein. The CD5 binder positive cells shown by red histogram, in comparison with a negative control (grey histogram). The GFP expression is measured using flow cytometry (green histogram) compared to a negative control plasmid transfected cells (grey histogram). The flow cytometry signal in the Q2 showed that 10.8% cells express both CAR-M and GFP proteins.

Figure 32:
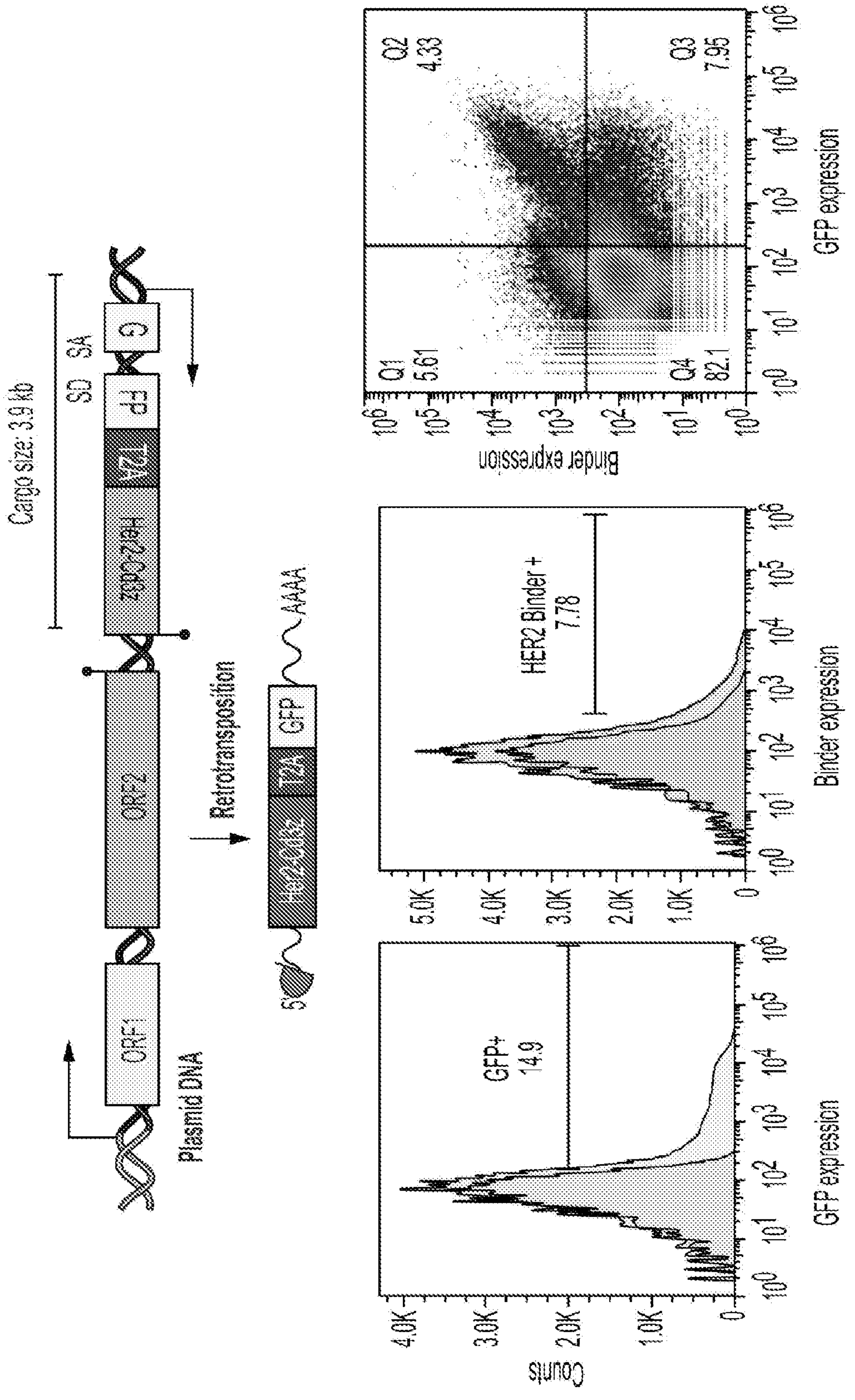
FIG. 32 illustrates an exemplary retrotransposon construct (top) with a 3.9 kb cargo comprising a membrane protein (HER2 binder chimeric antigen receptor, and a GFP separated by an auto-cleavable T2A element), and a representative flow cytometry data (bottom) demonstrating the expression of the HER2 binder and GFP.
Figure 33A:
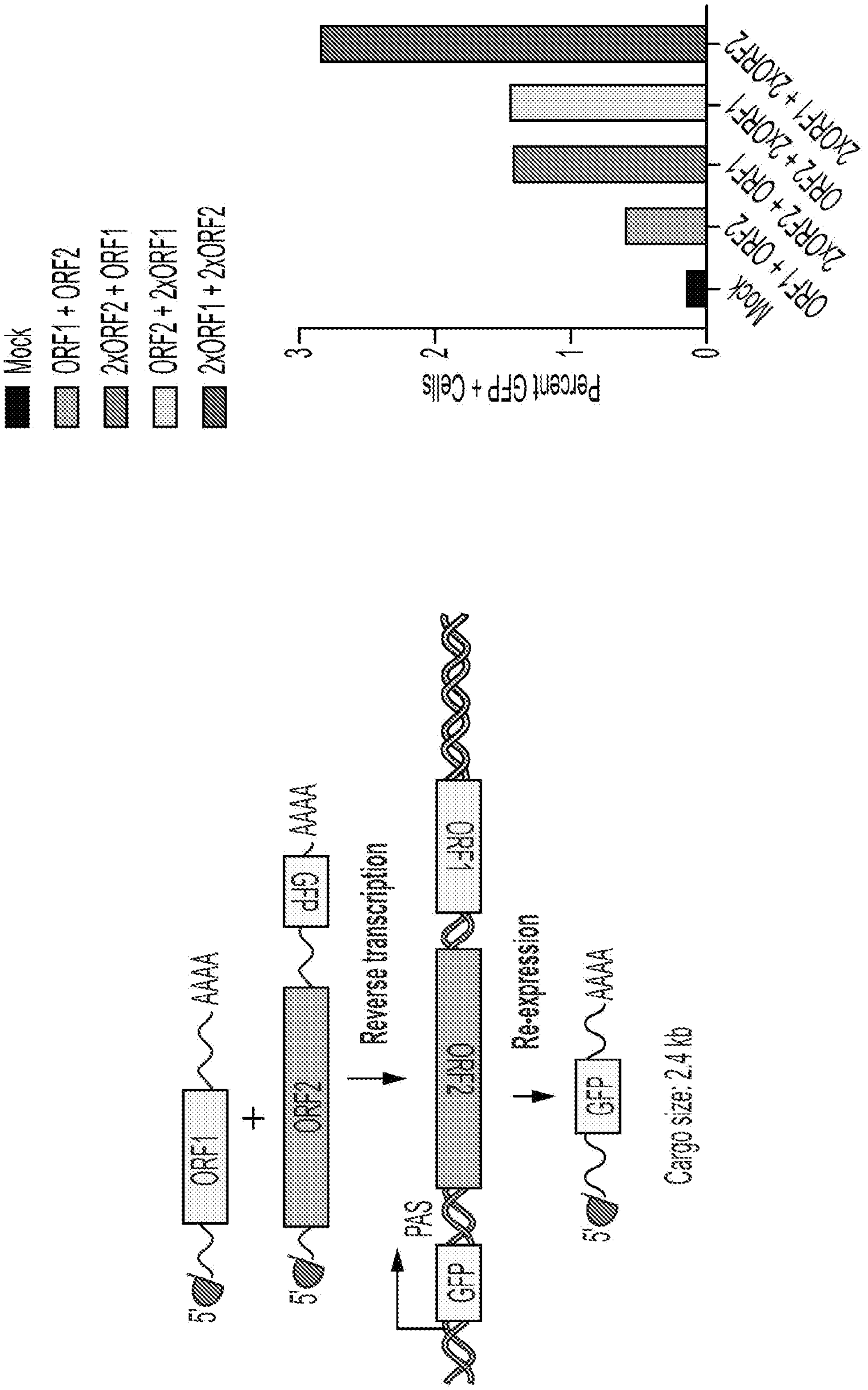
FIG. 33A shows exemplary data for delivery of retrotransposon elements delivered as mRNA.
Figure 33B:
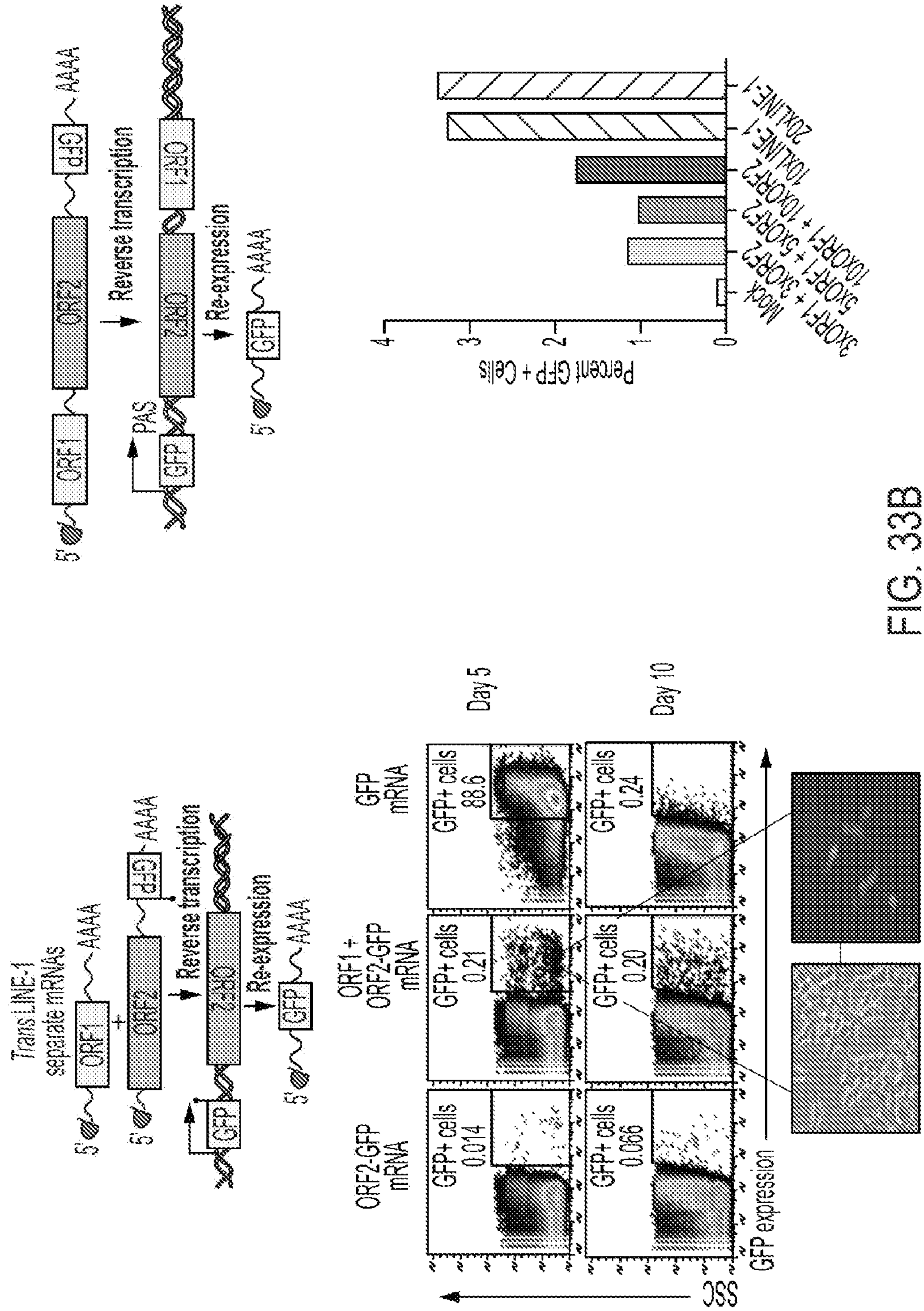
FIG. 33B shows schematic diagram showing a trans and a cis mRNA design for delivery of LINE1 mRNA with GFP cargo (top panel). Representative results of electroporation of 293T cells with trans mRNAs with separate ORF1 and ORF2 mRNAs. 293T cells were electroporated with 100 ug/mL of mRNA either with ORF2 alone, ORF1+ORF2 mRNAs, each at 100 ug/mL, or a GFP-encoding mRNA with the same 5' and 3'UTRs as the ORF1 mRNA (left panel of data plots). Retrotransposition events result in GFP-positive cells. Cells were assayed for GFP fluorescence by flow cytometry 4 days and 10 days post-electroporation. Mock electroporated cells serve as the negative control population for gating. Bar graph on the right shows results from a representative experiment indicating titration of trans mRNAs and cis ORF1 and ORF2 containing mRNA concentration during electroporation. Trans mRNAs solid bars and cis mRNA stripes. 20× is 2000 ug/mL in the electroporation reaction.
Figure 33C:
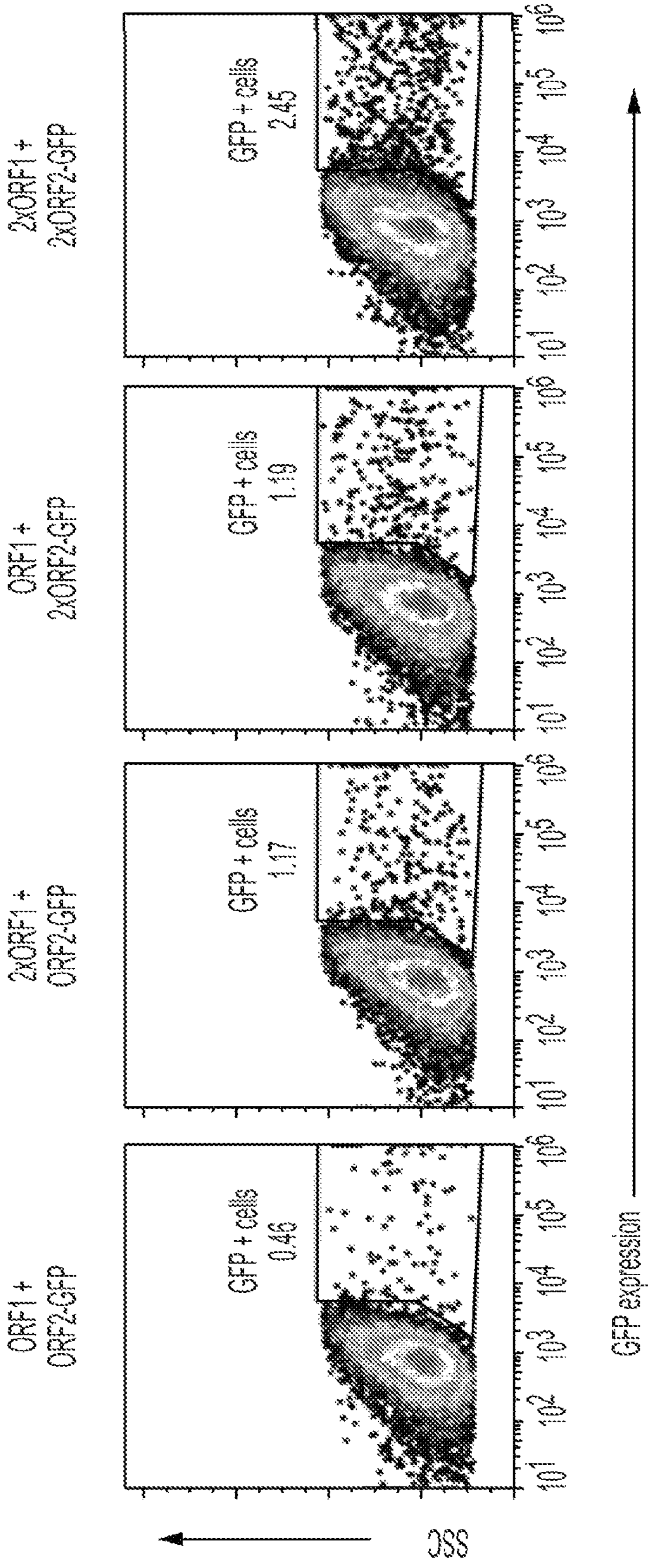
FIG. 33C shows titration of the ORF1 and ORF2-GFPai trans mRNAs. Increasing the concentration separately and together during the electroporation to 200 ug/mL increases retrotransposition of the GFP gene cargo.
Figure 33D:
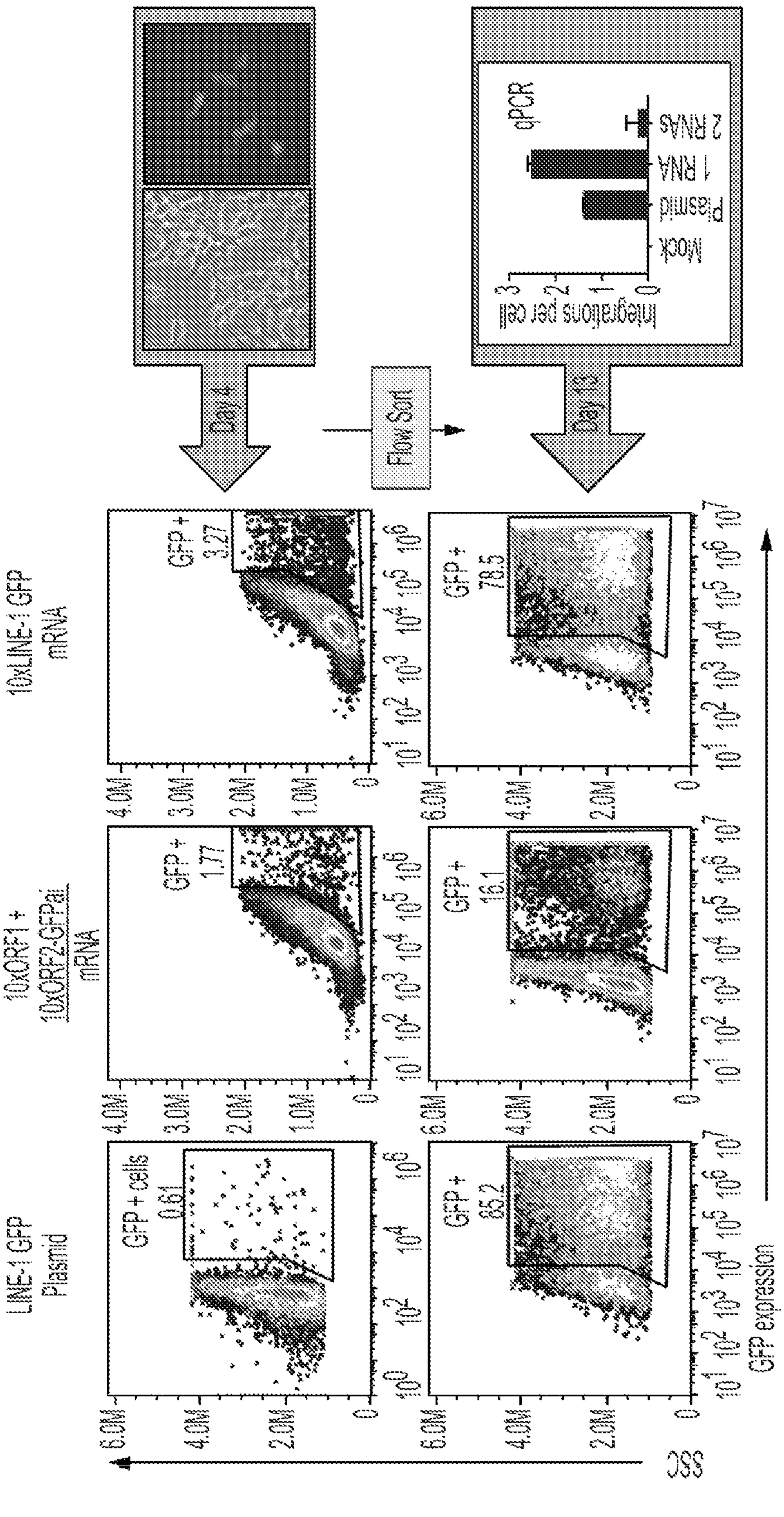
FIG. 33D illustrates an exemplary data for the different constructs indicated above each flow cytometry data plot in the figure, the top panel on day 4, and the bottom panel on day 13. Right hand figures illustrate light and fluorescent microscopic images of a the GFP expressing cells in culture. Copies of integrated cargo per construct is demonstrated in the bottom right at day 13. qPCR assay for genomic DNA integration from different LINE-1 plasmid transfected, LINE-1 mRNA (retro-mRNA), and ORF1 and ORF2-GFP mRNA electroporated cells is shown. Two qPCR primer-probe sets were used, one for the housekeeping gene RPS30 and the other for the GFP gene. Plasmid-transfected cells use a plasmid that does not contain and SV40 maintenance sequence. Integration per cell is calculated from determining copy numbers per samples through interpolation of a standard curve of plasmid and genomic DNA, and normalizing for the two copies of RPS30 per 293T cell. Error bars denote standard deviation of three technical replicate measurements.
Figure 34:
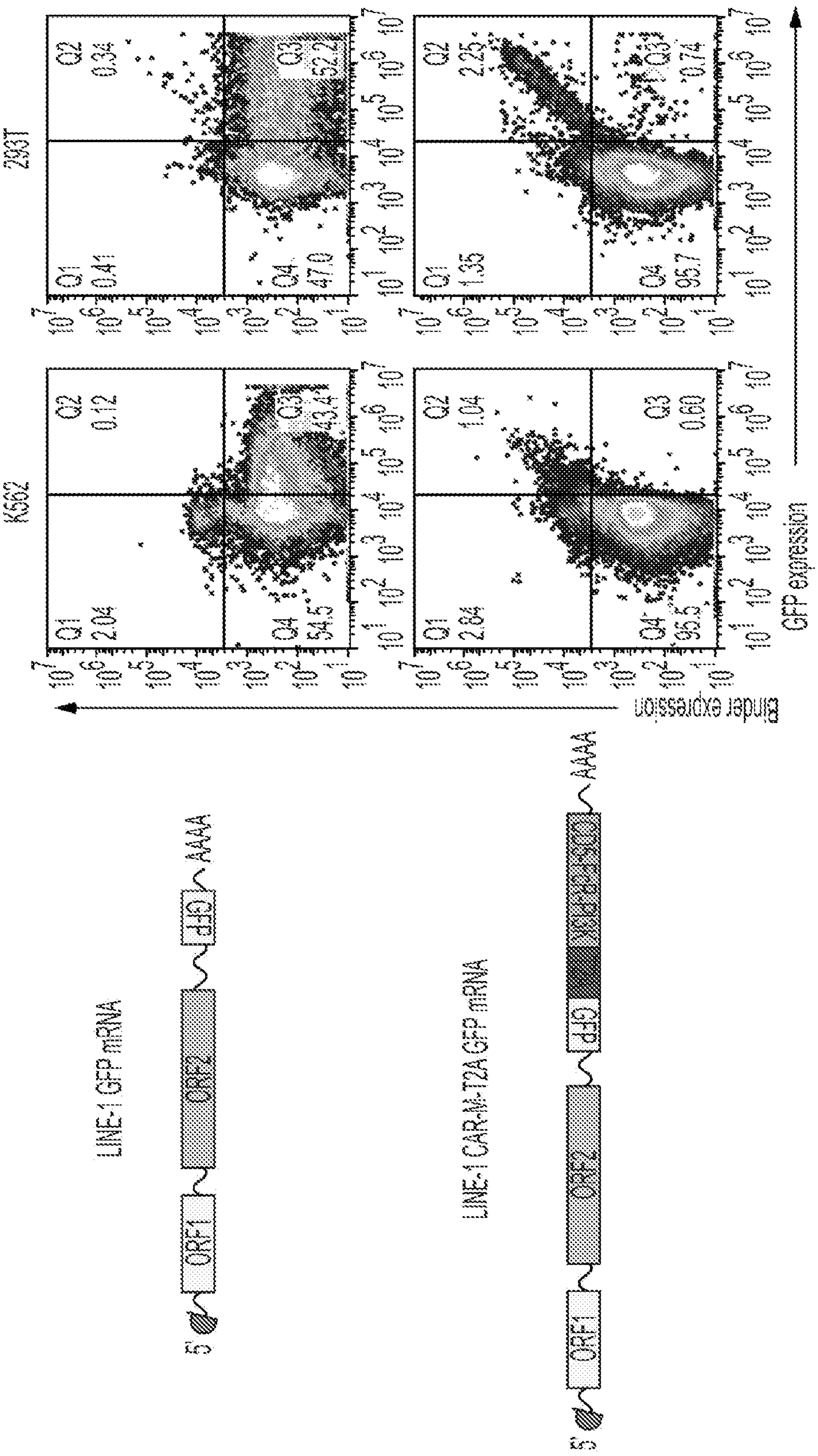
FIG. 34 illustrates exemplary retrotransposon construct (left) and expression data (right) in the indicated cell lines.
Figure 35:
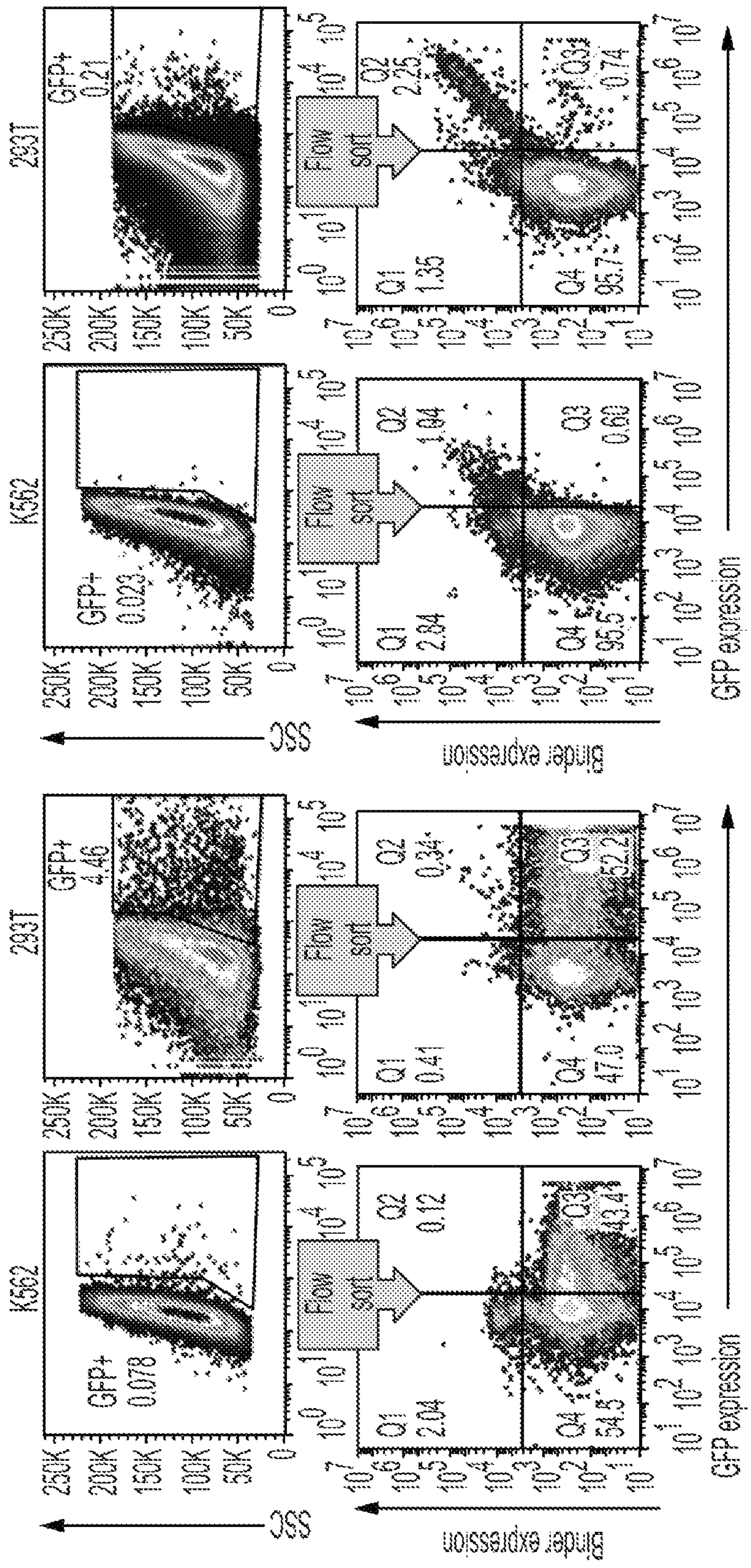
FIG. 35 illustrates flow cytometry data showing expression of LINE 1 GFP constructs in K562, 293T and THP1 cells (upper panel); and number of integrations of LINE-2-GFP mRNA per cell in K562 and THP-1 cell lines (lower panel).
Figure 35:
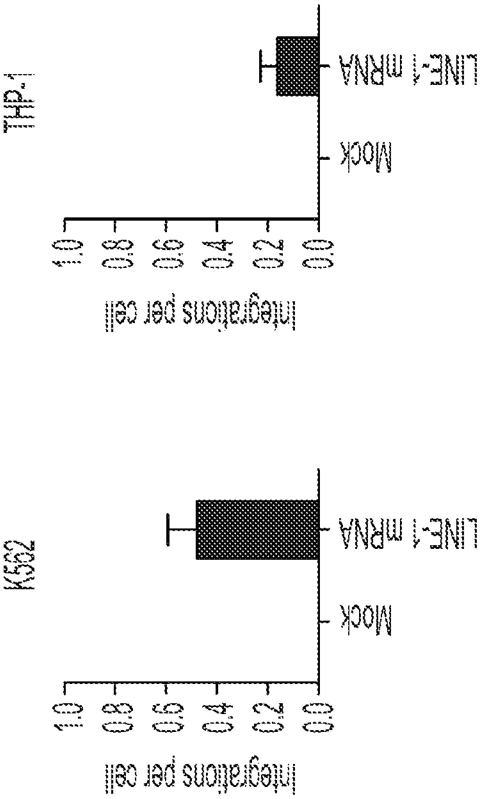

As shown in FIG. 32, the payload size limit has not been reached with retrotransposon delivery and integration (Retro-T delivery) with a 3.9 kb payload. The delivery mechanism described here was successful for expression of the first generation CART construct and GFP (separated by T2A site). In this example, different constructs were tested for retrotransposition efficiency of the insert sequence. FIG. 33A shows gene delivery as mRNA results in successful integration. This data is the first to show that Retro T can be delivered as mRNA. A trans strategy of using separate mRNAs encoding for ORF1 and ORF2 with antisense promoter and GFP cargo (ORF2-GFPai) in the 3' UTR for gene delivery was explored, as exemplified graphically in FIG. 33B (top panel). FIGS. 33B-33D demonstrate experimental results from multiple representative assays. Separate mRNAs that expression the LINE-1 proteins could reconstitute the RNA-protein complex required for retrotransposition. The cis strategy uses a single bicistronic LINE-1 mRNA with the antisense promoter and GFP gene cargo in the 3'UTR. Constructs comprising variable amounts and proportions of ORF2 and ORF1 were compared as shown in FIG. 33B and FIG. 33C with GFP encoding sequence as payload. FIG. 33D shows that introducing a single mRNA yields higher number of integrations per cell. Sorting of 293T GFP cells to enrich for retrotransposed cells for biochemical and integration assays. Cells are the same as in FIG. 33B and show GFP expression 4 days post-sort in bottom panels. The graph shows qPCR assay for genomic DNA integration from different LINE-1 plasmid transfected, LINE-1 mRNA (retro-mRNA), and ORF1 and ORF2-GFP mRNA electroporated cells. Two qPCR primer-probe sets were used, one for the housekeeping gene RPS30 and the other for the GFP gene. Plasmid-transfected cells use a plasmid that does not contain and SV40 maintenance sequence. Integration per cell is calculated from determining copy numbers per samples through interpolation of a standard curve of plasmid and genomic DNA and normalizing for the two copies of RPS30 per 293T cell. Error bars denote standard deviation of three technical replicate measurements.

Example 16. Delivery to Diverse Cell Types

Figure 36:
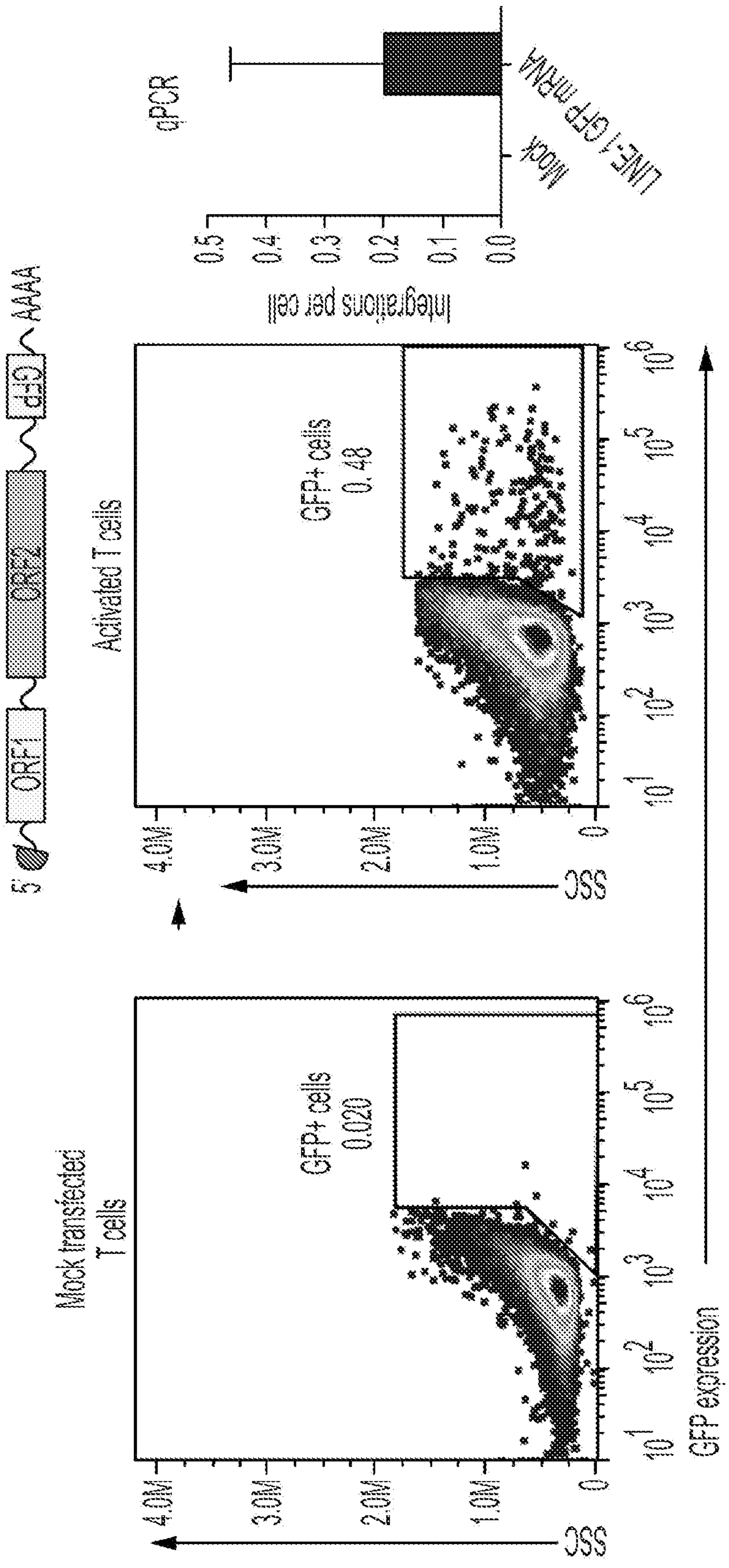
FIG. 36 illustrates flow cytometry data showing expression of LINE 1 GFP constructs in primary T cells (left). Integrations per cell are indicated in the graph on the right. Data was collected on day 6 after electroporation.
Figure 37A:
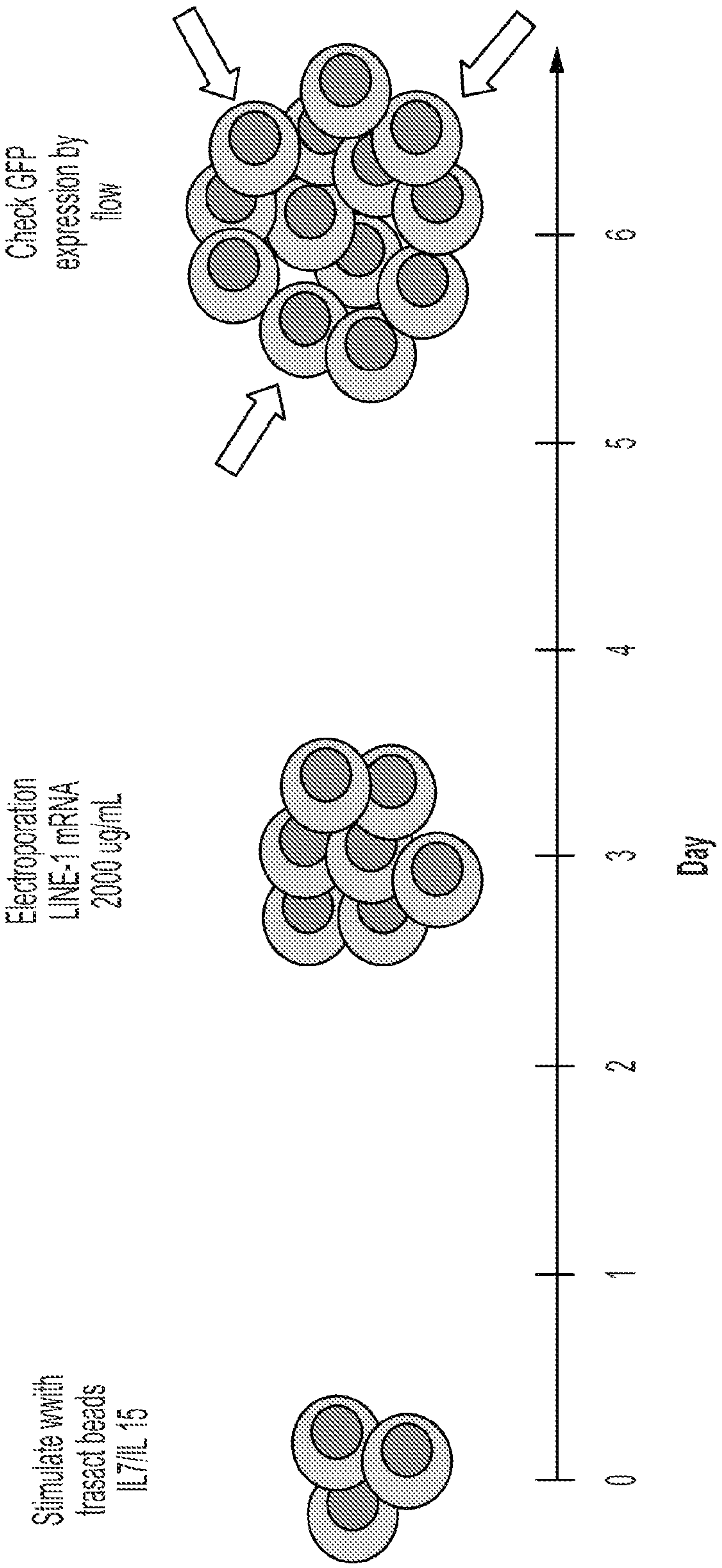
FIG. 37A shows a schematic of activation, culture times, electroporation, and GFP expression assay of isolated primary T cells.
Figure 37B:
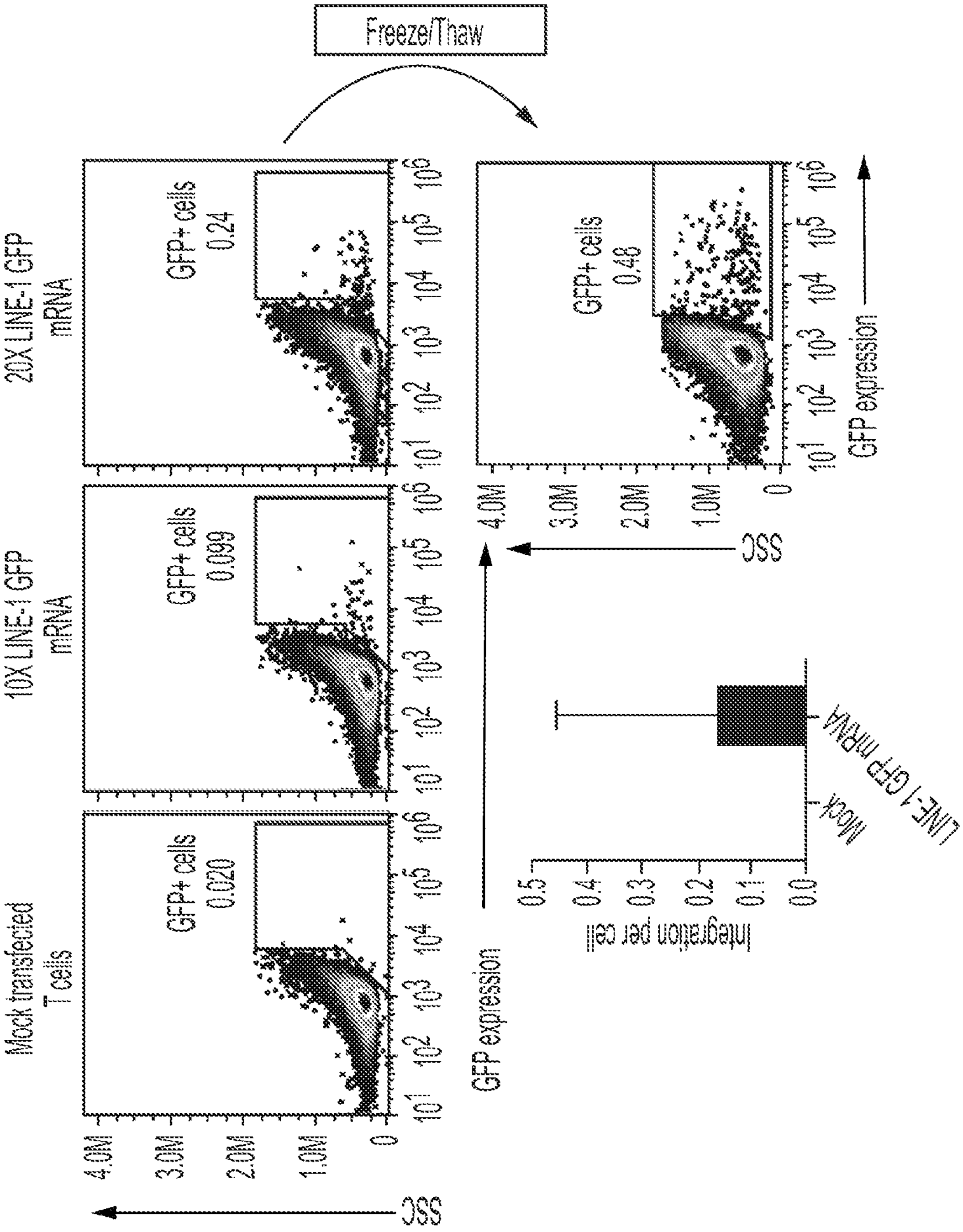
FIG. 37B illustrates flow cytometry data showing expression of LINE 1 GFP mRNA constructs in primary T cells at the indicated concentrations and before and after freeze-thaw as indicated in the figure. Integrations per cell is shown in the bar diagram. GFP expression using a retro-mRNA electroporation with a GFP cargo. GFP expression was assayed 4 days post electroporation and 15 days of culturing post electroporation. Primary T cells were cryo-preserved and thawed during this time. qPCR integration assay for GFP integration. Genomic DNA from the 20× sample was isolated and assayed for copies of GFP.
Figure 38:
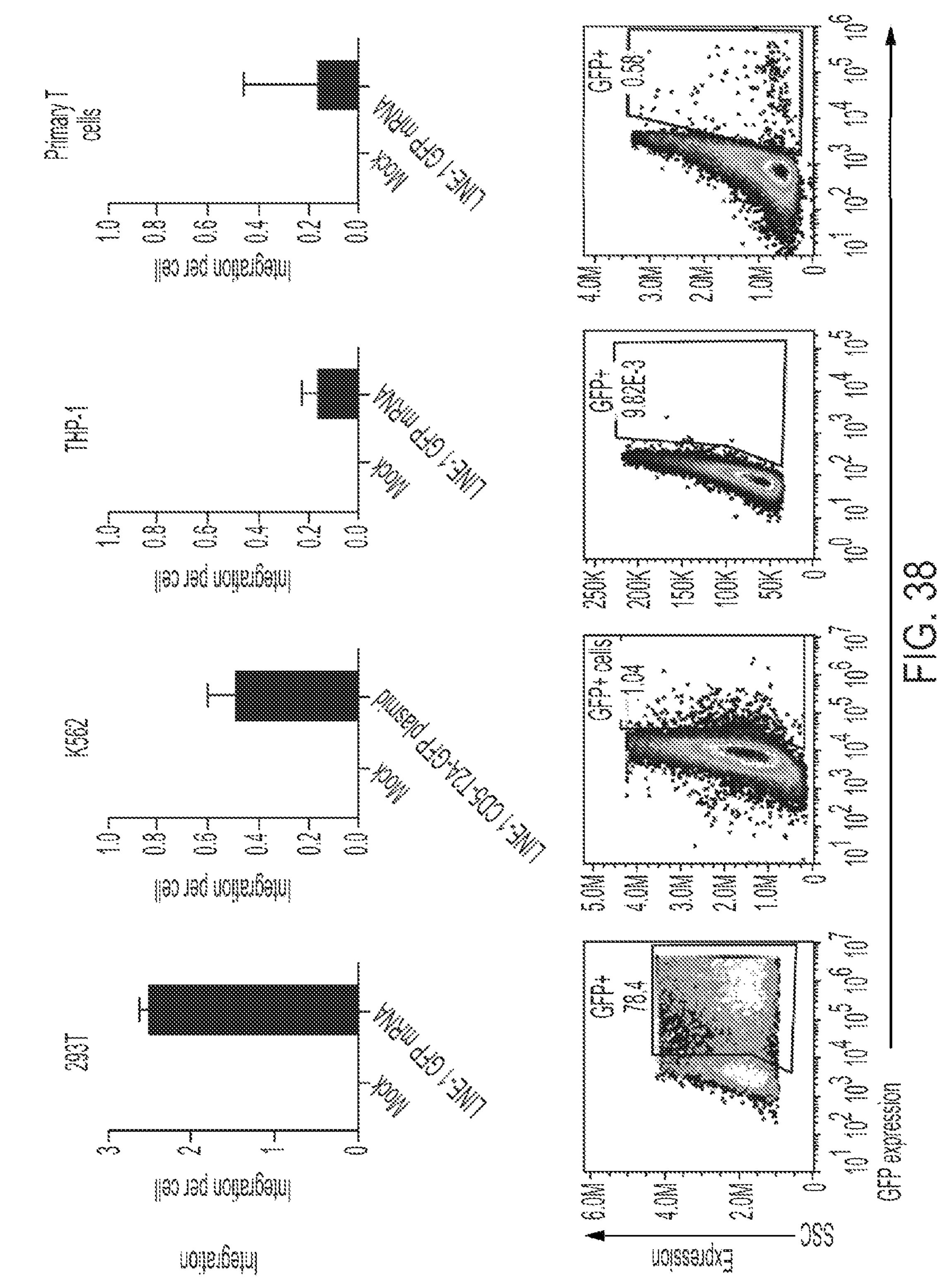
FIG. 38 demonstrates a summary of results of retrotransposon integration and expression across cell types.
Figure 39:
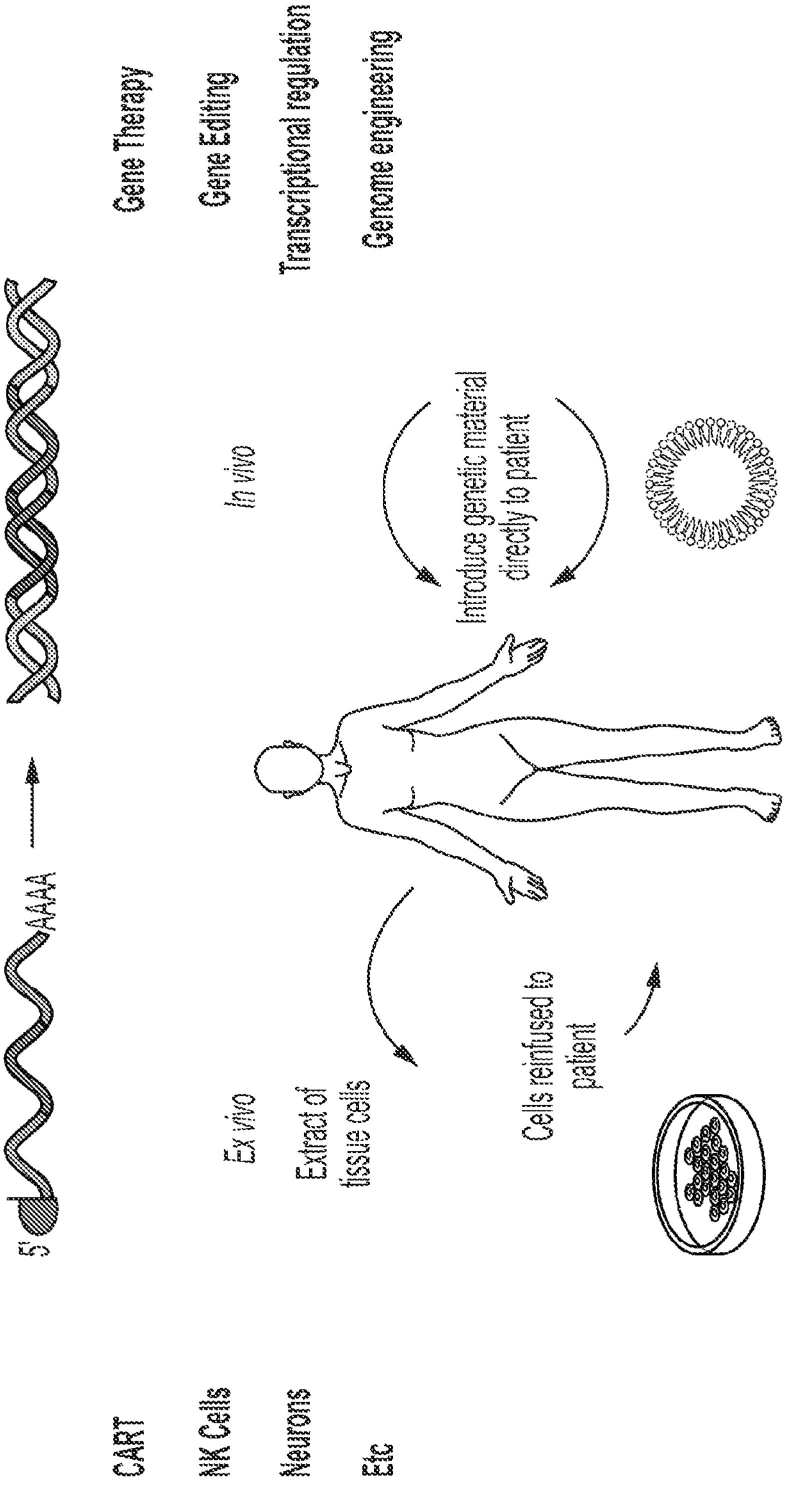
FIG. 39 shows various applications of the technology described herein, including but not limited to use of CART cells, NK cells, neurons and other cells for cell therapy, and use of in vivo applications in including but not limited to gene therapy, gene editing, transcription regulation, and genome engineering.

As shown in FIGS. 34-38, the mRNA constructs comprising a gene of interest, e.g. encoding a CAR protein, or for example, a GFP protein can be efficiently expressed in diverse cell types, such as epithelial cells (e.g., HEK 293 cells), monocytic cells lines (e.g., THP-1 cells), lymphoblastic cell lines (e.g., K562 cells), and primary lymphocytes (T cells). Activated primary T cells were also successfully transfected with mRNA with genomic integration and expression of GFP (FIG. 36). Primary T cells were isolated and expanded using IL7/IL15; and a 1 Gen CAR construct was delivered on day 2 post activation. Cells sorted and frozen. GFP expression was detectable after a freeze-thaw cycle (FIG. 37A-B). This indicates the versatile nature of mRNA mediated delivery and L1-transposon mediated integration. FIG. 38 shows a representative assay of GFP mRNA integration and expression in 293T cells, K562 cells, THP-1 cells and Primary T cells.

Example 17. Modifying the Retrotransposition System, Exchanging for Site-Specificity of an Integrase for Genomic Integration In this prophetic example, large mRNA constructs are stably incorporated and expressed in non-dividing mammalian cell using the retrotransposon integration system into the genome of the cell with a high degree of location specificity using serine integrases. Retrotransposon constructs are designed as elaborated elsewhere in the disclosure.

In this example a first construct, an mRNA construct is designed to include Cas endonuclease fused with a serine integrase comprising a mutation in the catalytic domain that eliminates a possibility of double stranded polynucleotide integration by the integrase, and prime editing guide RNA (pegRNA) oligonucleotides directed to a specific genomic locus, e.g., a histone gene locus, an actin gene locus etc, depending on which the guide RNA is specifically designed. One or more T2A cleavage sites separate the coding sequence of the individual proteins, e.g. Cas9, and the serine integrase of the fragment thereof. The pegRNAs are designed to insert a 41 bp AttB landing site. In one or more alternative designs, a LINE 1 ORF2 binding site is incorporated that is located conveniently and in proximity (e.g., juxtaposed) for binding of an ORF2 protein in relation to the integrase binding site.

A second mRNA construct is designed to include a LINE1 mRNA fused with a cargo sequence that is greater than 5, 6, 7, 8, 9, 10 kilobases, and encoding a protein; a mutated endonuclease, and an AttP attachment site fused to the cargo sequence for the integrase to attract and bring the cargo sequence to the landing sequence. The AttP attachment site is complementary to the AttB landing site.

The mRNA constructs are prepared through in vitro transcription and then purified. Each of resulting purified mRNA constructs are incorporated separately into lipid nanoparticles (LNP). Using electroporation, the two mRNA constructs are co-delivered using LNPs into cell. The Cas9 endonuclease fused to the pegRNAs is guided to insert the genomic landing sequence into the specific gene locus. The AttB landing site acts like a beacon that attracts for the AttP attachment site, which by design is comprised within the cargo sequence that is associated with the LINE1 mRNA. Co-translation of the proteins lead to generation of the ORF polypeptides, and led by the integrase and tethered by the attachment site, the ORF contacts with the associated ORF binding site at the proximity, and integrates the cargo at the specific site.

In yet another alternative design system, the integrase system is altogether bypassed and the PEG-RNA incorporates only a ORF binding site at a specific genomic locus directed by the guide RNA.

Site-specific integration is confirmed by Sanger sequencing. Flow cytometry is performed to demonstrate the expression of the insert sequence in the cell. Cell survival and genomic integration is found to be higher than often found in plasmid- or vector-based systems, as the mRNA has less of a detrimental impact on the cells.

Example 18. Exemplary Sequences

Following are exemplary sequences of the constructs used in the examples. These sequences are for reference exemplary purposes and sequence variations and optimizations that are conceivable by one of skill in the art without undue experimentation are contemplated and encompassed by the disclosure. Where mRNA sequences are referred in the sequence title, the construct recites nucleotides of a DNA template and one of skill in the art can easily derive the corresponding mRNA sequence.

TABLE 8

| Plasmid and mRNA construct sequences |
|---|
| ORF1-FLAG-mRNA (Codon Optimized human ORF1 coding sequence-FLAG) (SEQ ID NO: 35): TAATACGACTCACTATAGGGAGAAAGACGCCACCATGGGCAAGAA GCAAAATCGCAAGACGGGGAATTCCAAGACACAATCCGCTAGCCC ACCACCTAAAGAGCGTTCTAGCTCCCCTGCTACTGAGCAGTCCTG GATGGAAAACGACTTCGATGAACTCCGGGAAGAGGGATTTAGGCG ATCCAACTATTCAGAACTCCGCGAAGATATCCAGACAAAGGGGAA GGAAGTCGAGAATTTCGAGAAGAACCTCGAGGAGTGCATCACCCG TATCACAAACACTGAGAAATGTCTCAAAGAACTCATGGAACTTAA GACAAAAGCCAGGGAGCTTCGAGAGGAGTGTCGGAGTCTGAGATC CAGGTGTGACCAGCTCGAGGAGCGCGTGAGCGCGATGGAAGACGA GATGAACGAGATGAAAAGAGAGGGCAAATTCAGGGAGAAGCGCAT TAAGAGGAACGAACAGAGTCTGCAGGAGATTTGGGATTACGTCAA |

TABLE 8-continued

| Plasmid and mRNA construct sequences |
|---|
| GAGGCCTAACCTGCGGTTGATCGGCGTCCCCGAGAGCGACGTAGA AAACGGGACTAAACTGGAGAATACACTTCAAGACATCATTCAAGA AAATTTTCCAAACCTGGCTCGGCAAGCTAATGTGCAAATCCAAGA GATCCAACGCACACCCCAGCGGTATAGCTCTCGGCGTGCCACCCC TAGGCATATTATCGTGCGCTTTACTAAGGTGGAGATGAAAGAGAA GATGCTGCGAGCCGCTCGGGAAAAGGGAAGGGTGACTTTGAAGGG CAAACCTATTCGGCTGACGGTTGACCTTAGCGCCGAGACACTCCA GGCACGCCGGGAATGGGGCCCCATCTTTAATATCCTGAAGGAGAA GAACTTCCAGCCACGAATCTCTTACCCTGCAAAGTTGAGTTTTAT CTCCGAGGGTGAGATTAAGTATTTCATCGATAAACAGATGCTGCG AGACTTCGTGACAACTCGCCCAGCTCTCAAGGAACTGCTCAAAGA GGCTCTTAATATGGAGCGCAATAATAGATATCAACCCTTGCAGAA CCACGCAAAGATGGATTATAAGGATGACGATGATAAATGA (SEQ ID NO: 35) |
| ORF2-FLAG-GFP aim RNA (Codon Optimized human ORF2 coding sequence) (SEQ ID NO: 36) TAATACGACTCACTATAGGGAGAAAGACGCCACCATGACAGGTTC AAATAGTCACATTACGATTCTCACTCTGAATATAAATGGGCTGAA TTCTGCAATTAAACGGCACAGGCTTGCTTCCTGGATAAAGTCTCA AGACCCCTCAGTGTGCTGTATTCAGGAAACGCATCTCACGTGCAG GGACACCCATCGGCTGAAAATAAAAGGCTGGCGGAAGATCTACCA AGCCAATGGAAAACAAAAGAAGGCTGGGGTGGCGATACTTGTAAG CGATAAAACAGACTTTAAACCAACTAAGATCAAACGGGACAAAGA GGGCCATTACATCATGGTAAAGGGTAGTATTCAACAAGAGGAGCT GACTATCCTGAATATTTATGCACCTAATACTGGAGCCCCCAGATT CATAAAGCAAGTGTTGAGTGACCTTCAACGCGACCTCGACTCCCA CACTCTGATCATGGGAGACTTTAACACCCCGCTGTCCACTCTCGA CAGATCTACTAGACAGAAAGTCAACAAGGATACACAGGAACTGAA CAGTGCTCTCCACCAAGCGGACCTTATCGACATCTACAGAACACT CCACCCCAAAAGCACAGAATATACCTTCTTTTCAGCCCCTCACCA CACCTATTCCAAAATTGACCACATTGTGGGGAGTAAAGCCCTTCT CTCCAAATGTAAACGGACCGAAATTATCACTAACTATCTCTCCGA CCACAGTGCAATAAAACTTGAATTGCGAATTAAGAATCTCACTCA AAGTAGATCCACGACATGGAAACTGAACAATCTCCTCTTGAATGA CTACTGGGTGCATAACGAAATGAAGGCTGAAATAAAGATGTTCTT TGAGACCAACGAAAACAAAGACACCACGTACCAGAATCTCTGGGA CGCTTTCAAAGCAGTGTGTCGAGGAAAATTTATTGCACTGAATGC TTACAAGCGGAAGCAGGAAAGATCCAAAATAGACACCCTGACTAG CCAACTTAAAGAACTGGAAAAGCAAGAGCAAACTCATAGCAAAGC TAGCCGTCGCCAAGAAATTACGAAAATCAGAGCTGAACTGAAGGA AATTGAGACACAGAAAACCCTGCAAAAGATAAATGAAAGCCGCAG CTGGTTCTTTGAACGCATCAACAAAATCGATAGGCCACTTGCTCG CCTTATCAAGAAGAAAAGGGAGAAGAATCAAATCGACACTATAAA GAATGATAAAGGCGATATAACCACCGATCCCACAGAAATTCAAAC AACCATACGCGAATACTACAAACACCTCTACGCCAATAAACTCGA AAATCTCGAGGAAATGGATACATTCCTCGACACGTACACCCTTCC CAGGCTGAACCAGGAAGAAGTTGAATCACTGAATCGGCCTATCAC GGGGAGTGAAATAGTAGCTATCATCAATTCACTCCCTACCAAGAA GTCACCCGGACCTGATGGATTCACCGCCGAATTCTACCAGAGATA CATGGAAGAACTGGTGCCCTTCTTGCTGAAACTTTTCCAAAGTAT TGAGAAAGAGGGAATACTTCCAAACTCATTTTATGAGGCATCCAT CATTCTGATCCCGAAGCCCGGCAGGGACACGACCAAGAAAGAGAA TTTTCGACCAATCTCATTGATGAACATTGATGCAAAGATCCTCAA TAAAATACTGGCAAATCGGATTCAGCAGCACATAAAGAAGCTGAT CCACCATGATCAAGTAGGCTTCATCCCCGGTATGCAAGGTTGGTT CAATATACGAAAATCAATCAATGTTATCCAGCATATAAACCGGGC CAAAGACAAGAACCACATGATTATTAGTATCGATGCTGAGAAAGC CTTTGACAAAATACAACAACCCTTCATGCTGAAAACATTGAATAA GCTGGGAATTGATGGCACCTACTTCAAAATCATCAGAGCCATATA TGACAAACCAACAGCAAATATCATTCTGAATGGTCAGAAATTGGA AGCATTCCCCTTGAAAACCGGCACACGGCAGGGTTGCCCTCTGTC ACCACTCCTCTTCAACATCGTGTTGGAAGTTCTTGCCCGCGCAAT CCGGCAGGAAAAGGAAATCAAGGGCATTCAACTGGGCAAAGAGGA AGTTAAATTGAGCCTGTTTGCAGACGACATGATCGTCTATTTGGA AAACCCCATAGTTAGTGCACAAAATCTGCTGAAGTTGATCAGTAA TTTCTCCAAAGTGAGTGGGTACAAAATCAATGTGCAAAAGAGCCA AGCTTTCTTGTACACCAACAACAGGCAAACTGAGTCTCAAATCAT GGGCGAACTCCCCTTCGTGATTGCATCCAAGCGGATCAAATACCT GGGGATTCAATTGACTCGTGATGTGAAGGACCTCTTCAAGGAGAA CTACAAACCCCTGCTCAAGGAAATCAAAGAGGACACAAACAAATG GAAGAACATTCCATGCTCTTGGGTGGGAAGGATCAATATCGTCAA AATGGCCATCCTGCCCAAGGTAATTTACAGGTTCAATGCTATACC CATCAAGCTCCCCATGACATTCTTCACAGAACTTGAAAAGACGAC GCTGAAGTTCATTTGGAACCAGAAACGTGCCAGGATTGCTAAATC TATTCTCTCCCAAAAGAACAAAGCTGGCGGAATCACACTCCCAGA CTTCAAACTTTACTACAAGGCGACCGTGACGAAAACGGCTTGGTA CTGGTACCAAAACAGGGATATAGATCAATGGAACCGAACGGAGCC |

TABLE 8-continued

| Plasmid and mRNA construct sequences |
|---|
| CAGCGAAATTATGCCTCATATATACAACTATCTGATCTTTGACAA<br>ACCGGAGAAGAACAAGCAATGGGGAAAGGATAGTCTGTTTAATAA<br>ATGGTGCTGGGAAAACTGGCTCGCAATCTGTAGGAAGCTGAAACT<br>GGATCCATTCTTGACGCCTTATACAAAGATAAATTCCCGATGGAT<br>TAAAGATCTCAACGTGAAACCCAAAACAATTAAAACCCTCGAGGA<br>AAACCTGGGTATTACGATTCAGGACATTGGGGTGGAAAGGACTT<br>CATGTCCAAAACCCCAAAAGCGATGGCAACCAAAGACAAAATCGA<br>CAAATGGGATCTCATAAAACTTAAGTCATTTTGCACAGCTAAAGA<br>AACGACAATTAGGGTGAACCGACAACCGACCACTTGGGAGAAAAT<br>CTTCGCAACATACAGTTCTGACAAAGGCCTGATTTCCAGGATCTA<br>CAATGAATTGAAACAAATTTACAAGAAGAAGACGAACAACCCTAT<br>AAAGAAATGGGCCAAGGACATGAACAGACACTTCTCTAAGGAAGA<br>CATTTATGCAGCCAAGAAACACATGAAGAAATGCAGCTCTTCACT<br>GGCAATCAGGGAAATGCAAATCAAAACAACAATGAGATATCATCT<br>CACACCCGTCAGAATGGCCATCATTAAGAAGAGCGGAAACAACCG<br>GTGCTGGCGTGGTTGCGGAGAAATCGGTACTCTCCTTCACTGTTG<br>GTGGGACTGTAAACTCGTTCAACCACTGTGGAAGTCTGTGTGGCG<br>GTTCCTCAGAGATCTGGAACTCGAAATCCCATTTGACCCAGCCAT<br>CCCTCTCCTGGGTATATACCCGAATGAGTATAAATCCTGCTGCTA<br>TAAAGACACCTGCACAAGGATGTTTATTGCAGCTCTCTTCACAAT<br>CGCGAAGACGTGGAACCAACCCAAATGTCCGACTATGATTGACTG<br>GATTAAGAAGATGTGGCACATATACACTATGGAATACTATGCTGC<br>GATCAAGAACGATGAGTTCATATCATTTGTGGGCACATGGATGAA<br>ACTCGAAACCATCATACTCTCTAAATTGAGTCAAGAACAGAAAAC<br>TAAACACCGTATATTTTCCCTGATCGGTGGGAATTAGCTACAAAG<br>ACGATGACGACAAGGACCATGGAGACGGTGAGAGACACAAAAAAT<br>TCCAACACACTATTGCAATGAAAATAAATTTCCTTTATTAGCCAG<br>AAGTCAGATGCTCAAGGGGCTTCATGATGTCCCCATAATTTTTGG<br>CAGAGGGAAAAAGATCTCAGTGGTATTTGTGAGCCAGGGCATTGG<br>CCTTCTGATAGGCAGCCTGCACCTGAGGAGTGCGGCCGCTTTACT<br>TGTACAGCTCGTCCATGCCGAGAGTGATCCCGGCGGCGGTCACGA<br>ACTCCAGCAGGACCATGTGATCGCGCTTCTCGTTGGGGTCTTTGC<br>TCAGGGCGGACTGGGTGCTCAGGTAGTGGTTGTCGGGCAGCAGCA<br>CGGGGCCGTCGCCGATGGGGGTGTTCTGCTGGTAGTGGTCGGCGA<br>GCTGCACGCTGCCGTCCTCGATGTTGTGGCGGATCTTGAAGTTCA<br>CCTTGATGCCGTTCTTCTGCTTGTCGGCCATGATATAGACGTTGT<br>GGCTGTTGTAGTTGTACTCCAGCTTGTGCCCCAGGATGTTGCCGT<br>CCTCCTTGAAGTCGATGCCCTTCAGCTCGATGCGGTTCACCAGGG<br>TGTCGCCCTCGAACTTCACCTCGGCGCGGGTCTTGTAGTTGCCGT<br>CGTCCTTGAAGAAGATGGTGCGCTCCTGGACGTAGCCTTCGGGCA<br>TGGCGGACTTGAAGAAGTCGTGCTGCTTCATGTGGTCGGGGTAGC<br>GGCTGAAGCACTGCACGCCGTAGGTCAGGGTGGTCACGAGGGTGG<br>GCCAGGGCACGGGCAGCTTGCCGGTGGTGCAGATGAACTTCAGGG<br>TCAGCTTGCCGTAGGTGGCATCGCCCTCGCCCTCGCCGGACACGC<br>TGAACTTGTGGCCGTTTACGTCGCCGTCCAGCTCGACCAGGATGG<br>GCACCACCCCGGTGAACAGCTCCTCGCCCTTGCTCACCATGGTGG<br>CGGGATCTGACGGTTCACTAAACCAGCTCTGCTTATATAGACCTC<br>CCACCGTACACGCCTACCGCCCATTTGCGTCAATGGGGCGGAGTT<br>GTTACGACATTTTGGAAAGTCCCGTTGATTTTGGTGCCAAAACAA<br>ACTCCCATTGACGTCAATGGGGTGGAGACTTGGAAATCCCCGTGA<br>GTCAAACCGCTATCCACGCCCATTGATGTACTGCCAAAACCGCAT<br>CACCATGGTAATAGCGATGACTAATACGTAGATGTACTGCCAAGT<br>AGGAAAGTCCCATAAGGTCATGTACTGGGCATAATGCCAGGCGGG<br>CCATTTACCGTCATTGACGTCAATAGGGGGCGTACTTGGCATATG<br>ATACACTTGATGTACTGCCAAGTGGGCAGTTTACCGTAAATACTC<br>CACCCATTGACGTCAATGGAAAGTCCCTATTGGCGTTACTATGGG<br>AACATACGTCATTATTGACGTCAATGGGCGGGGGTCGTTGGGCGG<br>TCAGCCAGGCGGGCCATTTACCGTAAGTTATGTAACGACGTCTCA<br>GCTGACAATGAGATCACATGGACACAGGAAGGGGAATATCACACT<br>CTGGGGACTGTGGTGGGGTCGGGGGAGGGGGAGGGATAGCATTG<br>GGAGATATACCTAATGCTAGATGACACATTAGTGGGTGCAGCGCA<br>CCAGCATGGCACATGTATACATATGTAACTAACCTGCACAATGTG<br>CACATGTACCCTAAAACTTAGAGTATAATGGATCCGCAGGCCTCT<br>GCTAGCTTGACTGACTGAGATACAGCGTACCTTCAGCTCACAGAC<br>ATGATAAGATACATTGATGAGTTTGGACAAACCACAACTAGAATG<br>CAGTGAAAAAAATGCTTTATTTGTGAAATTTGTGATGCTATTGCT<br>TTATTTGTAACCATTATAAGCTGCAATAAACAAGTT<br>(SEQ ID NO: 36) |
| LINE-1 plasmid GFP (SEQ ID NO: 37)<br>CGGCCGCGGGGGGAGGAGCCAAGATGGCCGAATAGGAACAGCTCC<br>GGTCTACAGCTCCCAGCGTGAGCGACGCAGAAGACGGTGATTTCT<br>GCATTTCCATCTGAGGTACCGGGTTCATCTCACTAGGGAGTGCCA<br>GACAGTGGGCGCAGGCCAGTGTGTGTGCGCACCGTGCGCGAGCCG<br>AAGCAGGGCGAGGCATTGCCTCACCTGGGAAGCGCAAGGGGTCAG<br>GGAGTTCCCTTTCCGAGTCAAAGAAAGGGGTGACGGACGCACCTG<br>GAAAATCGGGTCACTCCCACCCGAATATTGCGCTTTTCAGACCGG<br>CTTAAGAAACGGCGCACCACGAGACTATATCCCACACCTGGCTCG<br>GAGGGTCCTACGCCCACGGAATCTCGCTGATTGCTAGCACAGCAG<br>TCTGAGATCAAACTGCAAGGCGGCAACGAGGCTGGGGGAGGGGCG<br>CCCGCCATTGCCCAGGCTTGCTTAGGTAAACAAAGCAGCAGGGAA<br>GCTCGAACTGGGTGGAGCCCACCACAGCTCAAGGAGGCCTGCCTG<br>CCTCTGTAGGCTCCACCTCTGGGGGCAGGGCACAGACAAACAAAA<br>AGACAGCAGTAACCTCTGCAGACTTAAGTGTCCCTGTCTGACAGC<br>TTTGAAGAGAGCAGTGGTTCTCCCAGCACGCAGCTGGAGATCTGA<br>GAACGGGCAGACTGCCTCCTCAAGTGGGTCCCTGACCCCTGACCC<br>CCGAGCAGCCTAACTGGGAGGCACCCCCCAGCAGGGGCACACTGA<br>CACCTCACACGGCAGGGTATTCCAACAGACCTGCAGCTGAGGGTC<br>CTGTCTGTTAGAAGGAAAACTAACAACCAGAAAGGACATCTACAC<br>CGAAAACCCATCTGTACATCACCATCATCAAAGACCAAAAGTAGA<br>TAAAACCACAAAGATGGGGAAAAAACAGAACAGAAAAACTGGAAA<br>CTCTAAAACGCAGAGCGCCTCTCCTCCTCCAAAGGAACGCAGTTC<br>CTCACCAGCAACAGAACAAAGCTGGATGGAGAATGATTTTGATGA<br>GCTGAGAGAAGAAGGCTTCAGACGATCAAATTACTCTGAGCTACG<br>GGAGGACATTCAAACCAAAGGCAAAGAAGTTGAAAACTTTGAAAA<br>AAATTTAGAAGAATGTATAACTAGAATAACCAATACAGAGAAGTG<br>CTTAAAGGAGCTGATGGAGCTGAAAACCAAGGCTCGAGAACTACG<br>TGAAGAATGCAGAAGCCTCAGGAGCCGATGCGATCAACTGGAAGA<br>AAGGGTATCAGCAATGGAAGATGAAATGAATGAAATGAAGCGAGA<br>AGGGAAGTTTAGAGAAAAAAGAATAAAAAGAAATGAGCAAAGCCT<br>CCAAGAAATATGGGACTATGTGAAAAGACCAAATCTACGTCTGAT<br>TGGTGTACCTGAAAGTGATGTGGAGAATGGAACCAAGTTGGAAAA<br>CACTCTGCAGGATATTATCCAGGAGAACTTCCCCAATCTAGCAAG<br>GCAGGCCAACGTTCAGATTCAGGAAATACAGAGAACGCCACAAAG<br>ATACTCCTCGAGAAGAGCAACTCCAAGACACATAATTGTCAGATT<br>CACCAAAGTTGAAATGAAGGAAAAAATGTTAAGGGCAGCCAGAGA<br>GAAAGGTCGGGTTACCCTCAAAGGAAAGCCCATCAGACTAACAGC<br>GGATCTCTCGGCAGAAACCCTACAAGCCAGAAGAGAGTGGGGGCC<br>AATATTCAACATTCTTAAAGAAAAGAATTTTCAACCCAGAATTTC<br>ATATCCAGCCAAACTAAGCTTCATAAGTGAAGGAGAAATAAAATA<br>CTTTATAGACAAGCAAATGTTGAGAGATTTTGTCACCACCAGGCC<br>TGCCCTAAAAGAGCTCCTGAAGGAAGCGCTAAACATGGAAAGGAA<br>CAACCGGTACCAGCCGCTGCAAAATCATGCCAAAATGTAAAGACC<br>ATCAAGACTAGGAAGAAACTGCATCAACTAATGAGCAAAATCACC<br>AGCTAACATCATAATGACAGGATCAACTTCACACATAACAATATT<br>AACTTTAAATATAAATGGACTAAATTCTGCAATTAAAAGACACAG<br>ACTGGCAAGTTGGATAAAGAGTCAAGACCCATCAGTGTGCTGTAT<br>TCAGGAAACCCATCTCACGTGCAGAGACACACATAGGCTCAAAAT<br>AAAAGGATGGAGGAAGATCTACCAAGCCAATGGAAAACAAAAAAA<br>GGCAGGGGTTGCAATCCTAGTCTCTGATAAAACAGACTTTAAACC<br>AACAAAGATCAAAAGAGACAAAGAAGGCCATTACATAATGGTAAA<br>GGGATCAATTCAACAAGAGGAGCTAACTATCCTAAATATTTATGC<br>ACCCAATACAGGAGCACCCAGATTCATAAAGCAAGTCCTCAGTGA<br>CCTACAAAGAGACTTAGACTCCCACACATTAATAATGGGAGACTT<br>TAACACCCCACTGTCAACATTAGACAGATCAACGAGACAGAAAGT<br>CAACAAGGATACCCAGGAATTGAACTCAGCTCTGCACCAAGCAGA<br>CCTAATAGACATCTACAGAACTCTCCACCCCAAATCAACAGAATA<br>TACATTTTTTTCAGCACCACACCACACCTATTCCAAAATTGACCA<br>CATAGTTGGAAGTAAAGCTCTCCTCAGCAAATGTAAAAGAACAGA<br>AATTATAACAAACTATCTCTCAGACCACAGTGCAATCAAACTAGA<br>ACTCAGGATTAAGAATCTCACTCAAAGCCGCTCAACTACATGGAA<br>ACTGAACAACCTGCTCCTGAATGACTACTGGGTACATAACGAAAT<br>GAAGGCAGAAATAAAGATGTTCTTTGAAACCAACGAGAACAAAGA<br>CACCACATACCAGAATCTCTGGGACGCATTCAAAGCAGTGTGTAG<br>AGGGAAATTTATAGCACTAAATGCCTACAAGAGAAAGCAGGAAAG<br>ATCCAAAATTGACACCCTAACATCACAATTAAAAGAACTAGAAAA<br>GCAAGAGCAAACACATTCAAAAGCTAGCAGAAGGCAAGAAATAAC<br>TAAAATCAGAGCAGAACTGAAGGAAATAGAGACACAAAAAACCCT<br>TCAAAAAATCAATGAATCCAGGAGCTGGTTTTTTGAAAGGATCAA<br>CAAAATTGATAGACCGCTAGCAAGACTAATAAAGAAAAAAAGAGA<br>GAAGAATCAAATAGACACAATAAAAAATGATAAAGGGGATATCAC<br>CACCGATCCCACAGAAATACAAACTACCATCAGAGAATACTACAA<br>ACACCTCTACGCAAATAAACTAGAAAATCTAGAAGAAATGGATAC<br>ATTCCTCGACACATACACTCTCCCAAGACTAAACCAGGAAGAAGT<br>TGAATCTCTGAATCGACCAATAACAGGCTCTGAAATTGTGGCAAT<br>AATCAATAGTTTACCAACCAAAAAGAGTCCAGGACCAGATGGATT<br>CACAGCCGAATTCTACCAGAGGTACAAGGAGGAACTGGTACCATT<br>CCTTCTGAAACTATTCCAATCAATAGAAAAAGAGGGAATCCTCCC<br>TAACTCATTTTATGAGGCCAGCATCATTCTGATACCAAAGCCGGG<br>CAGAGACACAACCAAAAAAGAGAATTTTAGACCAATATCCTTGAT<br>GAACATTGATGCAAAAATCCTCAATAAAATACTGGCAAACCGAAT<br>CCAGCAGCACATCAAAAAGCTTATCCACCATGATCAAGTGGGCTT<br>CATCCCTGGGATGCAAGGCTGGTTCAATATACGCAAATCAATAAA<br>TGTAATCCAGCATATAAACAGAGCCAAAGACAAAAACCACATGAT<br>TATCTCAATAGATGCAGAAAAAGCCTTTGACAAAATTCAACAACC<br>CTTCATGCTAAAAACTCTCAATAAATTAGGTATTGATGGGACGTA |

TABLE 8-continued

| Plasmid and mRNA construct sequences |
|---|
| TTTCAAAATAATAAGAGCTATCTATGACAAACCCACAGCCAATAT |
| CATACTGAATGGGCAAAAACTGGAAGCATTCCCTTTGAAAACCGG |
| CACAAGACAGGGATGCCCTCTCTCACCGCTCCTATTCAACATAGT |
| GTTGGAAGTTCTGGCCAGGGCAATCAGGCAGGAGAAGGAAATAAA |
| GGGTATTCAATTAGGAAAAGAGGAAGTCAAATTGTCCCTGTTTGC |
| AGACGACATGATTGTTTATCTAGAAAACCCCATCGTCTCAGCCCA |
| AAATCTCCTTAAGCTGATAAGCAACTTCAGCAAAGTCTCAGGATA |
| CAAAATCAATGTACAAAAATCACAAGCATTCTTATACACCAACAA |
| CAGACAAACAGAGAGCCAAATCATGGGTGAACTCCCATTCACAAT |
| TGCTTCAAAGAGAATAAAATACCTAGGAATCCAACTTACAAGGGA |
| TGTGAAGGACCTCTTCAAGGAGAACTACAAACCACTGCTCAAGGA |
| AATAAAAGAGGAGACAAACAAATGGAAGAACATTCCATGCTCATG |
| GGTAGGAAGAATCAATATCGTGAAAATGGCCATACTGCCCAAGGT |
| AATTTACAGATTCAATGCCATCCCCATCAAGCTACCAATGACTTT |
| CTTCACAGAATTGGAAAAAACTACTTTAAAGTTCATATGGAACCA |
| AAAAAGAGCCCGCATTGCCAAGTCAATCCTAAGCCAAAAGAACAA |
| AGCTGGAGGCATCACACTACCTGACTTCAAACTATACTACAAGGC |
| TACAGTAACCAAAACAGCATGGTACTGGTACCAAAACAGAGATAT |
| AGATCAATGGAACAGAACAGAGCCCTCAGAAATAATGCCGCATAT |
| CTACAACTATCTGATCTTTGACAAACCTGAGAAAAACAAGCAATG |
| GGGAAAGGATTCCCTATTTAATAAATGGTGCTGGGAAAACTGGCT |
| AGCCATATGTAGAAAGCTGAAACTGGATCCCTTCCTTACACCTTA |
| TACAAAAATCAATTCAAGATGGATTAAAGATTTAAACGTTAAACC |
| TAAAACCATAAAAACCCTAGAAGAAAACCTAGGCATTACCATTCA |
| GGACATAGGCGTGGGCAAGGACTTCATGTCCAAAACACCAAAAGC |
| AATGGCAACAAAAGACAAAATTGACAAATGGGATCTAATTAAACT |
| AAAGAGCTTCTGCACAGCAAAAGAAACTACCATCAGAGTGAACAG |
| GCAACCTACAACATGGGAGAAAATTTTTGCAACCTACTCATCTGA |
| CAAAGGGCTAATATCCAGAATCTACAATGAACTCAAACAAATTTA |
| CAAGAAAAAAACAAACAACCCCATCAAAAAGTGGGCGAAGGACAT |
| GAACAGACACTTCTCAAAAGAAGACATTTATGCAGCCAAAAAACA |
| CATGAAGAAATGCTCATCATCACTGGCCATCAGAGAAATGCAAAT |
| CAAAACCACTATGAGATATCATCTCACACCAGTTAGAATGGCAAT |
| CATTAAAAAGTCAGGAAACAACAGGTGCTGGAGAGGATGCGGAGA |
| AATAGGAACACTTTTACACTGTTGGTGGGACTGTAAACTAGTTCA |
| ACCATTGTGGAAGTCAGTGTGGCGATTCCTCAGGGATCTAGAACT |
| AGAAATACCATTTGACCCAGCCATCCCATTACTGGGTATATACCC |
| AAATGAGTATAAATCATGCTGCTATAAAGACACATGCACACGTAT |
| GTTTATTGCGGCACTATTCACAATAGCAAAGACTTGGAACCAACC |
| CAAATGTCCAACAATGATAGACTGGATTAAGAAAATGTGGCACAT |
| ATACACCATGGAATACTATGCAGCCATAAAAAATGATGAGTTCAT |
| ATCCTTTGTAGGGACATGGATGAAATTGGAAACCATCATTCTCAG |
| TAAACTATCGCAAGAACAAAAAACCAAACACCGCATATTCTCACT |
| CATAGGTGGGAATTGAACAATGAGATCACATGGACACAGGAAGGG |
| GAATATCACACTCTGGGGACTGTGGTGGGGTCGGGGGAGGGGGGA |
| GGGATAGCATTGGGAGATATACCTAATGCTAGATGACACATTAGT |
| GGGTGCAGCGCACCAGCATGGCACATGTATACGGATCCGAATTCT |
| CGACGGATCGATCCGAACAAACGACCCAACACCCGTGCGTTTTAT |
| TCTGTCTTTTTATTGCCGATCCCCTCAGAAGAACTCGTCAAGAAG |
| GCGATAGAAGGCGATGCGCTGCGAATCGGGAGCGGCGATACCGTA |
| AAGCACGAGGAAGCGGTCAGCCCATTCGCCGCCAAGCTCTTCAGC |
| AATATCACGGGTAGCCAACGCTATGTCCTGATAGCGGTCGGCCGC |
| TTTACTTGTACAGCTCGTCCATGCCGAGAGTGATCCCGGCGGCGG |
| TCACGAACTCCAGCAGGACCATGTGATCGCGCTTCTCGTTGGGGT |
| CTTTGCTCAGGGCGGACTGGGTGCTCAGGTAGTGGTTGTCGGGCA |
| GCAGCACGGGGCCGTCGCCGATGGGGGTGTTCTGCTGGTAGTGGT |
| CGGCCAGGTGAGTCCAGGAGATGTTTCAGCACTGTTGCCTTTAGT |
| CTCGAGGCAACTTAGACAACTGAGTATTGATCTGAGCACAGCAGG |
| GTGTGAGCTGTTTGAAGATACTGGGGTTGGGGGTGAAGAAACTGC |
| AGAGGACTAACTGGGCTGAGACCCAGTGGCAATGTTTTAGGGCCT |
| AAGGAATGCCTCTGAAAATCTAGATGGACAACTTTGACTTTGAGA |
| AAAGAGAGGTGGAAATGAGGAAAATGACTTTTCTTTATTAGATTT |
| CGGTAGAAAGAACTTTCATCTTTCCCCTATTTTTGTTATTCGTTT |
| TAAAACATCTATCTGGAGGCAGGACAAGTATGGTCATTAAAAAGA |
| TGCAGGCAGAAGGCATATATTGGCTCAGTCAAAGTGGGGAACTTT |
| GGTGGCCAAACATACATTGCTAAGGCTATTCCTATATCAGCTGGA |
| CACATATAAAATGCTGCTAATGCTTCATTACAAACTTATATCCTT |
| TAATTCCAGATGGGGGCAAAGTATGTCCAGGGGTGAGGAACAATT |
| GAAACATTTGGGCTGGAGTAGATTTTGAAAGTCAGCTCTGTGTGT |
| GTGTGTGTGTGTGTGTGTGTGAGAGCGTGTGTTTCTTTTAACGTT |
| TTCAGCCTACAGCATACAGGGTTCATGGTGGCAAGAAGATAACAA |
| GATTTAAATTATGGCCAGTGACTAGTGCTGCAAGAAGAACAACTA |
| CCTGCATTTAATGGGAAAGCAAAATCTCAGGCTTTGAGGGAAGTT |
| AACATAGGCTTGATTCTGGGTGGAAGCTGGGTGTGTAGTTATCTG |
| GAGGCCAGGCTGGAGCTCTCAGCTCACTATGGGTTCATCTTTATT |
| GTCTCCTTTCATCTCAACAGCTGCACGCTGCCGTCCTCGATGTTG |
| TGGCGGATCTTGAAGTTCACCTTGATGCCGTTCTTCTGCTTGTCG |
| GCCATGATATAGACGTTGTGGCTGTTGTAGTTGTACTCCAGCTTG |

TABLE 8-continued

| Plasmid and mRNA construct sequences |
|---|
| TGCCCCAGGATGTTGCCGTCCTCCTTGAAGTCGATGCCCTTCAGC |
| TCGATGCGGTTCACCAGGGTGTCGCCCTCGAACTTCACCTCGGCG |
| CGGGTCTTGTAGTTGCCGTCGTCCTTGAAGAAGATGGTGCGCTCC |
| TGGACGTAGCCTTCGGGCATGGCGGACTTGAAGAAGTCGTGCTGC |
| TTCATGTGGTCGGGGTAGCGGCTGAAGCACTGCACGCCGTAGGTC |
| AGGGTGGTCACGAGGGTGGGCCAGGGCACGGGCAGCTTGCCGGTG |
| GTGCAGATGAACTTCAGGGTCAGCTTGCCGTAGGTGGCATCGCCC |
| TCGCCCTCGCCGGACACGCTGAACTTGTGGCCGTTTACGTCGCCG |
| TCCAGCTCGACCAGGATGGGCACCACCCCGGTGAACAGCTCCTCG |
| CCCTTGCTCACCATGGTGGCGAATTCGAAGCTTGAGCTCGAGATC |
| TGAGTCCGGTAGCGCTAGCGGATCTGACGGTTCACTAAACCAGCT |
| CTGCTTATATAGACCTCCCACCGTACACGCCTACCGCCCATTTGC |
| GTCAATGGGGCGGAGTTGTTACGACATTTTGGAAAGTCCCGTTGA |
| TTTTGGTGCCAAAACAAACTCCCATTGACGTCAATGGGGTGGAGA |
| CTTGGAAATCCCCGTGAGTCAAACCGCTATCCACGCCCATTGATG |
| TACTGCCAAAACCGCATCACCATGGTAATAGCGATGACTAATACG |
| TAGATGTACTGCCAAGTAGGAAAGTCCCATAAGGTCATGTACTGG |
| GCATAATGCCAGGCGGGCCATTTACCGTCATTGACGTCAATAGGG |
| GGCGTACTTGGCATATGATACACTTGATGTACTGCCAAGTGGGCA |
| GTTTACCGTAAATACTCCACCCATTGACGTCAATGGAAAGTCCCT |
| ATTGGCGTTACTATGGGAACATACGTCATTATTGACGTCAATGGG |
| CGGGGGTCGTTGGGCGGTCAGCCAGGCGGGCCATTTACCGTAAGT |
| TATGTAACGCGGAACTCCATATATGGGCTATGAACTAATGACCCC |
| GTAATTGATTACTATTAGCCCGGGGGATCCAGACATGATAAGATA |
| CATTGATGAGTTTGGACAAACCACAACTAGAATGCAGTGAAAAAA |
| ATGCTTTATTTGTGAAATTTGTGATGCTATTGCTTTATTTGTAAC |
| CATTATAAGCTGCAATAAACAAGTTAACAACAACAATTGCATTCA |
| TTTTATGTTTCAGGTTCAGGGGGAGGTGTGGGAGGTTTTTTAAAG |
| CAAGTAAAACCTCTACAAATGTGGTATGGCTGATTATGATCCGGC |
| TGCCTCGCGCGTTTCGGTGATGACGGTGAAAACCTCTGACACATG |
| CAGCTCCCGGAGACGGTCACAGCTTGTCTGTAAGCGGATGCCGGG |
| AGCAGACAAGCCCGTCAGGGCGCGTCAGCGGGTGTTGGCGGGTGT |
| CGGGGCGCAGCCATGAGGTCGATCGACTCTAGAGGATCGATCCCC |
| GCCCCGGACGAACTAAACCTGACTACGACATCTCTGCCCCTTCTT |
| CGCGGGGCAGTGCATGTAATCCCTTCAGTTGGTTGGTACAACTTG |
| CCAACTGGGCCCTGTTCCACATGTGACACGGGGGGGGACCAAACA |
| CAAAGGGAGGCCTATATAAGCAGAGCTCGTTTAGTGAACCGTCAG |
| ATCGCCGGGGTTCTCTGACTGTAGTTGACATCCTTATAAATGGAT |
| GTGCACATTTGCCAACACTGAGTGGCTTTCATCCTGGAGCAGACT |
| TTGCAGTCTGTGGACTGCAACACAACATTGCCTTTATGTGTAACT |
| CTTGGCTGAAGCTCTTACACCAATGCTGGGGGACATGTACCTCCC |
| AGGGGCCCAGGAAGACTACGGGAGGCTACACCAACGTCAATCAGA |
| GGGGCCTGTGTAGCTACCGATAAGCGGACCCTCAAGAGGGCATTA |
| GCAATAGTGTTTATAAGGCCCCCTTGTTAACCCTAAACGGGTAGC |
| ATATGCTTCCCGGGTAGTAGTATATACTATCCAGACTAACCCTAA |
| TTCAATAGCATATGTTACCCAACGGGAAGCATATGCTATCGAATT |
| AGGGTTAGTAAAAGGGTCCTAAGGAACAGCGATATCTCCCACCCC |
| ATGAGCTGTCACGGTTTTATTTACATGGGGTCAGGATTCCACGAG |
| GGTAGTGAACCATTTTAGTCACAAGGGCAGTGGCTGAAGATCAAG |
| GAGCGGGCAGTGAACTCTCCTGAATCTTCGCCTGCTTCTTCATTC |
| TCCTTCGTTTAGCTAATAGAATAACTGCTGAGTTGTGAACAGTAA |
| GGTGTATGTGAGGTGCTCGAAAACAAGGTTTCAGGTGACGCCCCC |
| AGAATAAAATTTGGACGGGGGGTTCAGTGGTGGCATTGTGCTATG |
| ACACCAATATAACCCTCACAAACCCCTTGGGCAATAAATACTAGT |
| GTAGGAATGAAACATTCTGAATATCTTTAACAATAGAAATCCATG |
| GGGTGGGGACAAGCCGTAAAGACTGGATGTCCATCTCACACGAAT |
| TTATGGCTATGGGCAACACATAATCCTAGTGCAATATGATACTGG |
| GGTTATTAAGATGTGTCCCAGGCAGGGACCAAGACAGGTGAACCA |
| TGTTGTTACACTCTATTTGTAACAAGGGGAAAGAGAGTGGACGCC |
| GACAGCAGCGGACTCCACTGGTTGTCTCTAACACCCCCGAAAATT |
| AAACGGGGCTCCACGCCAATGGGGCCCATAAACAAAGACAAGTGG |
| CCACTCTTTTTTTTGAAATTGTGGAGTGGGGGCACGCGTCAGCCC |
| CCACACGCCGCCCTGCGGTTTTGGACTGTAAAATAAGGGTGTAAT |
| AACTTGGCTGATTGTAACCCCGCTAACCACTGCGGTCAAACCACT |
| TGCCCACAAAACCACTAATGGCACCCCGGGGAATACCTGCATAAG |
| TAGGTGGGCGGGCCAAGATAGGGGCGCGATTGCTGCGATCTGGAG |
| GACAAATTACACACACTTGCGCCTGAGCGCCAAGCACAGGGTTGT |
| TGGTCCTCATATTCACGAGGTCGCTGAGAGCACGGTGGGCTAATG |
| TTGCCATGGGTAGCATATACTACCCAAATATCTGGATAGCATATG |
| CTATCCTAATCTATATCTGGGTAGCATAGGCTATCCTAATCTATA |
| TCTGGGTAGCATATGCTATCCTAATCTATATCTGGGTAGTATATG |
| CTATCCTAATTTATATCTGGGTAGCATAGGCTATCCTAATCTATA |
| TCTGGGTAGCATATGCTATCCTAATCTATATCTGGGTAGTATATG |
| CTATCCTAATCTGTATCCGGGTAGCATATGCTATCCTAATAGAGA |
| TTAGGGTAGTATATGCTATCCTAATTTATATCTGGGTAGCATATA |
| CTACCCAAATATCTGGATAGCATATGCTATCCTAATCTATATCTG |
| GGTAGCATATGCTATCCTAATCTATATCTGGGTAGCATAGGCTAT |
| CCTAATCTATATCTGGGTAGCATATGCTATCCTAATCTATATCTG |

TABLE 8-continued

Plasmid and mRNA construct sequences

GGTAGTATATGCTATCCTAATTTATATCTGGGTAGCATAGGCTAT
CCTAATCTATATCTGGGTAGCATATGCTATCCTAATCTATATCTG
GGTAGTATATGCTATCCTAATCTGTATCCGGGTAGCATATGCTAT
CCTCATGCATATACAGTCAGCATATGATACCCAGTAGTAGAGTGG
GAGTGCTATCCTTTGCATATGCCGCCACCTCCCAAGGGGGCGTGA
ATTTTCGCTGCTTGTCCTTTTCCTGCATGCTGGTTGCTCCCATTC
TTAGGTGAATTTAAGGAGGCCAGGCTAAAGCCGTCGCATGTCTGA
TTGCTCACCAGGTAAATGTCGCTAATGTTTTCCAACGCGAGAAGG
TGTTGAGCGCGGAGCTGAGTGACGTGACAACATGGGTATGCCCAA
TTGCCCCATGTTGGGAGGACGAAAATGGTGACAAGACAGATGGCC
AGAAATACACCAACAGCACGCATGATGTCTACTGGGGATTTATTC
TTTAGTGCGGGGGAATACACGGCTTTTAATACGATTGAGGGCGTC
TCCTAACAAGTTACATCACTCCTGCCCTTCCTCACCCTCATCTCC
ATCACCTCCTTCATCTCCGTCATCTCCGTCATCACCCTCCGCGGC
AGCCCCTTCCACCATAGGTGGAAACCAGGGAGGCAAATCTACTCC
ATCGTCAAAGCTGCACACAGTCACCCTGATATTGCAGGTAGGAGC
GGGCTTTGTCATAACAAGGTCCTTAATCGCATCCTTCAAAACCTC
AGCAAATATATGAGTTTGTAAAAAGACCATGAAATAACAGACAAT
GGACTCCCTTAGCGGGCCAGGTTGTGGGCCGGGTCCAGGGGCCAT
TCCAAAGGGGAGACGACTCAATGGTGTAAGACGACATTGTGGAAT
AGCAAGGGCAGTTCCTCGCCTTAGGTTGTAAAGGGAGGTCTTACT
ACCTCCATATACGAACACACCGGCGACCCAAGTTCCTTCGTCGGT
AGTCCTTTCTACGTGACTCCTAGCCAGGAGAGCTCTTAAACCTTC
TGCAATGTTCTCAAATTTCGGGTTGGAACCTCCTTGACCACGATG
CTTTCCAAACCACCCTCCTTTTTTGCGCCTGCCTCCATCACCCTG
ACCCCGGGGTCCAGTGCTTGGGCCTTCTCCTGGGTCATCTGCGGG
GCCCTGCTCTATCGCTCCCGGGGGCACGTCAGGCTCACCATCTGG
GCCACCTTCTTGGTGGTATTCAAAATAATCGGCTTCCCCTACAGG
GTGGAAAAATGGCCTTCTACCTGGAGGGGGCCTGCGCGGTGGAGA
CCCGGATGATGATGACTGACTACTGGGACTCCTGGGCCTCTTTTC
TCCACGTCCACGACCTCTCCCCCTGGCTCTTTCACGACTTCCCCC
CCTGGCTCTTTCACGTCCTCTACCCCGGCGGCCTCCACTACCTCC
TCGACCCCGGCCTCCACTACCTCCTCGACCCCGGCCTCCACTGCC
TCCTCGACCCCGGCCTCCACCTCCTGCTCCTGCCCCTCCTGCTCC
TGCCCCTCCTCCTGCTCCTGCCCCTCCTGCCCCTCCTGCTCCTGC
CCCTCCTGCCCCTCCTGCTCCTGCCCCTCCTGCCCCTCCTGCTCC
TGCCCCTCCTGCCCCTCCTCCTGCTCCTGCCCCTCCTGCCCCTCC
TCCTGCTCCTGCCCCTCCTGCCCCTCCTGCTCCTGCCCCTCCTGC
CCCTCCTGCTCCTGCCCCTCCTGCCCCTCCTGCTCCTGCCCCTCC
TGCTCCTGCCCCTCCTGCTCCTGCCCCTCCTGCTCCTGCCCCTCC
TGCCCCTCCTGCCCCTCCTCCTGCTCCTGCCCCTCCTGCTCCTGC
CCCTCCTGCCCCTCCTGCCCCTCCTGCTCCTGCCCCTCCTCCTGC
TCCTGCCCCTCCTGCCCCTCCTGCCCCTCCTCCTGCTCCTGCCCC
TCCTGCCCCTCCTCCTGCTCCTGCCCCTCCTCCTGCTCCTGCCCC
TCCTGCCCCTCCTGCCCCTCCTCCTGCTCCTGCCCCTCCTGCCCC
TCCTCCTGCTCCTGCCCCTCCTCCTGCTCCTGCCCCTCCTGCCCC
TCCTGCCCCTCCTCCTGCTCCTGCCCCTCCTCCTGCTCCTGCCCC
TCCTGCCCCTCCTGCCCCTCCTGCCCCTCCTCCTGCTCCTGCCCC
TCCTCCTGCTCCTGCCCCTCCTGCTCCTGCCCCTCCCGCTCCTGC
TCCTGCTCCTGTTCCACCGTGGGTCCCTTTGCAGCCAATGCAACT
TGGACGTTTTTGGGGTCTCCGGACACCATCTCTATGTCTTGGCCC
TGATCCTGAGCCGCCCGGGGCTCCTGGTCTTCCGCCTCCTCGTCC
TCGTCCTCTTCCCCGTCCTCGTCCATGGTTATCACCCCCTCTTCT
TTGAGGTCCACTGCCGCCGGAGCCTTCTGGTCCAGATGTGTCTCC
CTTCTCTCCTAGGCCATTTCCAGGTCCTGTACCTGGCCCCTCGTC
AGACATGATTCACACTAAAAGAGATCAATAGACATCTTTATTAGA
CGACGCTCAGTGAATACAGGGAGTGCAGACTCCTGCCCCCTCCAA
CAGCCCCCCCACCCTCATCCCCTTCATGGTCGCTGTCAGACAGAT
CCAGGTCTGAAAATTCCCCATCCTCCGAACCATCCTCGTCCTCAT
CACCAATTACTCGCAGCCCGGAAAACTCCCGCTGAACATCCTCAA
GATTTGCGTCCTGAGCCTCAAGCCAGGCCTCAAATTCCTCGTCCC
CCTTTTTGCTGGACGGTAGGGATGGGGATTCTCGGGACCCCTCCT
CTTCCTCTTCAAGGTCACCAGACAGAGATGCTACTGGGGCAACGG
AAGAAAAGCTGGGTGCGGCCTGTGAGGATCAGCTTATCGATGATA
AGCTGTCAAACATGAGAATTCTTGAAGACGAAAGGGCCTCGTGAT
ACGCCTATTTTTATAGGTTAATGTCATGATAATAATGGTTTCTTA
GACGTCAGGTGGCACTTTTCGGGGAAATGTGCGCGGAACCCCTAT
TTGTTTATTTTTCTAAATACATTCAAATATGTATCCGCTCATGAG
ACAATAACCCTGATAAATGCTTCAATAATATTGAAAAAGGAAGAG
TATGAGTATTCAACATTTCCGTGTCGCCCTTATTCCCTTTTTTGC
GGCATTTTGCCTTCCTGTTTTTGCTCACCCAGAAACGCTGGTGAA
AGTAAAAGATGCTGAAGATCAGTTGGGTGCACGAGTGGGTTACAT
CGAACTGGATCTCAACAGCGGTAAGATCCTTGAGAGTTTTCGCCC
CGAAGAACGTTTTCCAATGATGAGCACTTTTAAAGTTCTGCTATG
TGGCGCGGTATTATCCCGTGTTGACGCCGGGCAAGAGCAACTCGG
TCGCCGCATACACTATTCTCAGAATGACTTGGTTGAGTACTCACC
AGTCACAGAAAAGCATCTTACGGATGGCATGACAGTAAGAGAATT
ATGCAGTGCTGCCATAACCATGAGTGATAACACTGCGGCCAACTT

TABLE 8-continued

Plasmid and mRNA construct sequences

ACTTCTGACAACGATCGGAGGACCGAAGGAGCTAACCGCTTTTTT
GCACAACATGGGGGATCATGTAACTCGCCTTGATCGTTGGGAACC
GGAGCTGAATGAAGCCATACCAAACGACGAGCGTGACACCACGAT
GCCTGCAGCAATGGCAACAACGTTGCGCAAACTATTAACTGGCGA
ACTACTTACTCTAGCTTCCCGGCAACAATTAATAGACTGGATGGA
GGCGGATAAAGTTGCAGGACCACTTCTGCGCTCGGCCCTTCCGGC
TGGCTGGTTTATTGCTGATAAATCTGGAGCCGGTGAGCGTGGGTC
TCGCGGTATCATTGCAGCACTGGGGCCAGATGGTAAGCCCTCCCG
TATCGTAGTTATCTACACGACGGGGAGTCAGGCAACTATGGATGA
ACGAAATAGACAGATCGCTGAGATAGGTGCCTCACTGATTAAGCA
TTGGTAACTGTCAGACCAAGTTTACTCATATATACTTTAGATTGA
TTTAAAACTTCATTTTTAATTTAAAAGGATCTAGGTGAAGATCCT
TTTTGATAATCTCATGACCAAAATCCCTTAACGTGAGTTTTCGTT
CCACTGAGCGTCAGACCCCGTAGAAAAGATCAAAGGATCTTCTTG
AGATCCTTTTTTTCTGCGCGTAATCTGCTGCTTGCAAACAAAAAA
ACCACCGCTACCAGCGGTGGTTTGTTTGCCGGATCAAGAGCTACC
AACTCTTTTTCCGAAGGTAACTGGCTTCAGCAGAGCGCAGATACC
AAATACTGTCCTTCTAGTGTAGCCGTAGTTAGGCCACCACTTCAA
GAACTCTGTAGCACCGCCTACATACCTCGCTCTGCTAATCCTGTT
ACCAGTGGCTGCTGCCAGTGGCGATAAGTCGTGTCTTACCGGGTT
GGACTCAAGACGATAGTTACCGGATAAGGCGCAGCGGTCGGGCTG
AACGGGGGGTTCGTGCACACAGCCCAGCTTGGAGCGAACGACCTA
CACCGAACTGAGATACCTACAGCGTGAGCTATGAGAAAGCGCCAC
GCTTCCCGAAGGGAGAAAGGCGGACAGGTATCCGGTAAGCGGCAG
GGTCGGAACAGGAGAGCGCACGAGGGAGCTTCCAGGGGGAAACGC
CTGGTATCTTTATAGTCCTGTCGGGTTTCGCCACCTCTGACTTGA
GCGTCGATTTTTGTGATGCTCGTCAGGGGGGCGGAGCCTATGGAA
AAACGCCAGCAACGCGGCCTTTTTACGGTTCCTGGCCTTTTGCTG
GCCTTTTGCTCACATGTTCTTTCCTGCGTTATCCCCTGATTCTGT
GGATAACCGTATTACCGCCTTTGAGTGAGCTGATACCGCTCGCCG
CAGCCGAACGACCGAGCGCAGCGAGTCAGTGAGCGAGGAAGCGGA
AGAGCGCCTGATGCGGTATTTTCTCCTTACGCATCTGTGCGGTAT
TTCACACCGCATATGGTGCACTCTCAGTACAATCTGCTCTGATGC
CGCATAGTTAAGCCAGCTGTGGAATGTGTGTCAGTTAGGGTGTGG
AAAGTCCCCAGGCTCCCCAGCAGGCAGAAGTATGCAAAGCATGCA
TCTCAATTAGTCAGCAACCAGGTGTGGAAAGTCCCCAGGCTCCCC
AGCAGGCAGAAGTATGCAAAGCATGCATCTCAATTAGTCAGCAAC
CATAGTCCCGCCCCTAACTCCGCCCATCCCGCCCCTAACTCCGCC
CAGTTCCGCCCATTCTCCGCCCCATGGCTGACTAATTTTTTTTAT
TTATGCAGAGGCCGAGGCCGCCTCGGCCTCTGAGCTATTCCAGAA
GTAGTGAGGAGGCTTTTTTGGAGGCCTAGGCTTTTGCAAAAAGCT
TGCATGCCTGCAGGTCGGCCGCCACGACCGGTGCCGCCACCATCC
CCTGACCCACGCCCCTGACCCCTCACAAGGAGACGACCTTCCATG
ACCGAGTACAAGCCCACGGTGCGCCTCGCCACCCGCGACGACGTC
CCCCGGGCCGTACGCACCCTCGCCGCCGCGTTCGCCGACTACCCC
GCCACGCGCCACACCGTCGACCCGGACCGCCACATCGAGCGGGTC
ACCGAGCTGCAAGAACTCTTCCTCACGCGCGTCGGGCTCGACATC
GGCAAGGTGTGGGTCGCGGACGACGGCGCCGCGGTGGCGGTCTGG
ACCACGCCGGAGAGCGTCGAAGCGGGGGCGGTGTTCGCCGAGATC
GGCCCGCGCATGGCCGAGTTGAGCGGTTCCCGGCTGGCCGCGCAG
CAACAGATGGAAGGCCTCCTGGCGCCGCACCGGCCCAAGGAGCCC
GCGTGGTTCCTGGCCACCGTCGGCGTCTCGCCCGACCACCAGGGC
AAGGGTCTGGGCAGCGCCGTCGTGCTCCCCGGAGTGGAGGCGGCC
GAGCGCGCCGGGGTGCCCGCCTTCCTGGAGACCTCCGCGCCCCGC
AACCTCCCCTTCTACGAGCGGCTCGGCTTCACCGTCACCGCCGAC
GTCGAGGTGCCCGAAGGACCGCGCACCTGGTGCATGACCCGCAAG
CCCGGTGCCTGACGCCCGCCCCACGACCCGCAGCGCCCGACCGAA
AGGAGCGCACGACCCCATGGCTCCGACCGAAGCCGACCCGGGCGG
CCCCGCCGACCCCGCACCCGCCCCCGAGGCCCACCGACTCTAGAG
GATCATAATCAGCCATACCACATTTGTAGAGGTTTTACTTGCTTT
AAAAAACCTCCCACACCTCCCCCTGAACCTGAAACATAAAATGAA
TGCAATTGTTGTTGTTAACTTGTTTATTGCAGCTTATAATGGTTA
CAAATAAAGCAATAGCATCACAAATTTCACAAATAAAGCATTTTT
TTCACTGCATTCTAGTTGTGGTTTGTCCAAACTCATCAATGTATC
TTATCATGTCTGGATCACTCGCCGATAGTGGAAACCGACGCCCCA
GCACTCGTCCGAGGGCAAAGGAATAGGGGAGATGGGGGAGGCTAA
CTGAAACACGGAAGGAGACAATACCGGAAGGAACCCGCGCTATGA
CGGCAATAAAAGACAGAATAAAACGCACGGGTGTTGGGTCGTTT
GTTCATAAACGCGGGGTTCGGTCCCAGGGCTGGCACTCTGTCGAT
ACCCCACCGAGACCCCATTGGGGCCAATACGCCCGCGTTTCTTCC
TTTTCCCCACCCCACCCCCCAAGTTCGGGTGAAGGCCCAGGGCTC
GCAGCCAACGTCGGGGCGGCAGGCCCTGCCATAGCCACTGGCCCC
GTGGGTTAGGGACGGGGTCCCCCATGGGGAATGGTTTATGGTTCG
TGGGGGTTATTATTTTGGGCGTTGCGTGGGGTCTGGTCCACGACT
GGACTGAGCAGACAGACCCATGGTTTTTGGATGGCCTGGGCATGG
ACCGCATGTACTGGCGCGACACGAACACCGGGCGTCTGTGGCTGC
CAAACACCCCCGACCCCCAAAAACCACCGCGCGGATTTCTGGCGT
GCCAAGCTAGTCGACCAATTCTCATGTTTGACAGCTTATCATCGC

TABLE 8-continued

Plasmid and mRNA construct sequences

AGATCCGGGCAACGTTGTTGCATTGCTGCAGGCGCAGAACTGGTA
GGTATGGAAGATCTCTAGAAGCTGGGTACCAGCTGCTAGCAAGCT
TGCTAGCGGCCGGCTCGAGTTTACTCCCTATCAGTGATAGAGAAC
GTATGTCGAGTTTACTCCCTATCAGTGATAGAGAACGATGTCGAG
TTTACTCCCTATCAGTGATAGAGAACGTATGTCGAGTTTACTCCC
TATCAGTGATAGAGAACGTATGTCGAGTTTACTCCCTATCAGTGA
TAGAGAACGTATGTCGAGTTTATCCCTATCAGTGATAGAGAACGT
ATGTCGAGTTTACTCCCTATCAGTGATAGAGAACGTATGTCGAGG
TAGGCGTGTACGGTG
(SEQ ID NO: 37)

LINE1-GFP mRNA (SEQ ID NO: 38)
TAATACGACTCACTATAGGGAGAAGTACTGCCACCATGGGCAAGA
AGCAAAATCGCAAGACGGGGAATTCCAAGACACAATCCGCTAGCC
CACCACCTAAAGAGCGTTCTAGCTCCCCTGCTACTGAGCAGTCCT
GGATGGAAAACGACTTCGATGAACTCCGGGAAGAGGGATTTAGGC
GATCCAACTATTCAGAACTCCGCGAAGATATCCAGACAAAGGGGA
AGGAAGTCGAGAATTTCGAGAAGAACCTCGAGGAGTGCATCACCC
GTATCACAAACACTGAGAAATGTCTCAAAGAACTCATGGAACTTA
AGACAAAAGCCAGGGAGCTTCGAGAGGAGTGTCGGAGTCTGAGAT
CCAGGTGTGACCAGCTCGAGGAGCGCGTGAGCGCGATGGAAGACG
AGATGAACGAGATGAAAAGAGAGGGCAAATTCAGGGAGAAGCGCA
TTAAGAGGAACGAACAGAGTCTGCAGGAGATTTGGGATTACGTCA
AGAGGCCTAACCTGCGGTTGATCGGCGTCCCCGAGAGCGACGTAG
AAAACGGGACTAAACTGGAGAATACACTTCAAGACATCATTCAAG
AAAATTTTCCAAACCTGGCTCGGCAAGCTAATGTGCAAATCCAAG
AGATCCAACGCACACCCCAGCGGTATAGCTCTCGGCGTGCCACCC
CTAGGCATATTATCGTGCGCTTTACTAAGGTGGAGATGAAAGAGA
AGATGCTGCGAGCCGCTCGGGAAAAGGGAAGGGTGACTTTGAAGG
GCAAACCTATTCGGCTGACGGTTGACCTTAGCGCCGAGACACTCC
AGGCACGCCGGGAATGGGGCCCCATCTTTAATATCCTGAAGGAGA
AGAACTTCCAGCCACGAATCTCTTACCCTGCAAAGTTGAGTTTTA
TCTCCGAGGGTGAGATTAAGTATTTCATCGATAAACAGATGCTGC
GAGACTTCGTGACAACTCGCCCAGCTCTCAAGGAACTGCTCAAAG
AGGCTCTTAATATGGAGCGCAATAATAGATATCAACCCTTGCAGA
ACCACGCAAAGATGTGAGACAGCCGTCAGACCATCAAGACTAGGA
AGAAACTGCATCAACTAATGAGCAAATCACCAGCTAACATCATA
GTATACATGACCGGCTCTAACTCACATATCACCATCCTTACACTT
AACATTAACGGCCTCAACTCAGCTATCAAGCGCCATCGGCTGGCC
AGCTGGATCAAATCACAGGATCCAAGCGTTTGTTGCATCCAAGAG
ACCCACCTGACCTGTAGAGATACTCACCGCCTCAAGATCAAGGGA
TGGCGAAAGATTTATCAGGCGAACGGTAAGCAGAAGAAAGCCGGA
GTCGCAATTCTGGTCTCAGACAAGACGGATTTCAAGCCCACCAAA
ATTAAGCGTGATAAGGAAGGTCACTATATTATGGTGAAAGGCAGC
ATACAGCAGGAAGAACTTACCATATTGAACATCTACGCGCCAAAC
ACCGGCGCACCTCGCTTTATCAAACAGGTCCTGTCCGATCTGCAG
CGAGATCTGGATTCTCATACGTTGATTATGGGTGATTTCAATACA
CCATTGAGCACCCTGGATCGCAGCACCAGGCAAAAGGTAAATAAA
GACACGCAAGAGCTCAATAGCGCACTGCATCAGGCAGATCTCATT
GATATTTATCGCACTCTTCATCCTAAGAGTACCGAGTACACATTC
TTCAGCGCCCCACATCATACATACTCAAAGATCGATCATATCGTC
GGCTCAAAGGCTCTGCTGTCAAAGTGCAAGCGCACAGAGATAATT
ACAAATTACCTGTCAGATCATAGCGCGATCAAGCTCGAGCTGAGA
ATCAAGAACCTGACCCAGAGCCGGAGTACCACTTGGAAGCTTAAT
AACCTGCTGCTCAACGATTATTGGGTCCACAATGAGATGAAGGCA
GAGATTAAAATGTTCTTCGAAACAAATGAGAATAAGGATACTACC
TATCAAAACCTTTGGGATGCCTTTAAGGCCGTCTGCAGAGGCAAG
TTCATCGCCCTCAACGCCTATAAAAGAAAACAAGAGAGATCTAAG
ATCGATACTCTCACCTCTCAGCTGAAGGAGTTGGAGAAACAGGAA
CAGACCCACTCCAAGGCGTCAAGACGGCAGGAGATCACAAAGATT
CGCGCCGAGTTGAAAGAGATCGAAACCCAAAAGACTCTTCAGAAA
ATTAACGAGTCTCGTAGTTGGTTCTTCGAGCGGATTAATAAGATA
GACAGACCTCTGGCACGACTGATTAAGAAGAAGCGCGAAAAGAAC
CAGATTGATACCATCAAGAACGACAAGGGCGACATCACTACTGAC
CCGACCGAGATCCAGACCACTATTCGGGAGTATTATAAGCATTTG
TATGCTAACAAGCTTGAGAACCTGGAAGAGATGGACACTTTTCTG
GATACCTATACTCTGCCACGGCTTAATCAAGAGGAAGTCGAGTCC
CTCAACCGCCCAATTACAGGAAGCGAGATTGTGGCCATAATTAAC
TCCCTGCCGACAAAGAAATCTCCTGGTCCGGACGGGTTTACAGCT
GAGTTTTATCAACGGTATATGGAAGAGCTTGTACCGTTTCTGCTC
AAGCTCTTTCAGTCTATAGAAAAGGAAGGCATCTTGCCCAATTCC
TTCTACGAAGCTTCTATAATACTTATTCCCAAACCAGGACGCGAT
ACCACAAAGAAGGAAAACTTCCGGCCCATTAGTCTCATGAATATC
GACGCTAAAATATTGAACAAGATTCTCGCCAACAGAATCCAACAA
CATATTAAGAAATTGATACATCACGACCAGGTGGGGTTTATACCT
GGCATGCAGGGCTGGTTTAACATCCGGAAGAGTATTAACGTCATT
CAACACATTAATAGAGCTAAGGATAAGAATCATATGATCATCTCT
ATAGACGCGGAAAAGGCATTCGATAAGATTCAGCAGCCATTTATG
CTCAAGACTCTGAACAAACTCGGCATCGACGGAACATATTTTAAG
ATTATTCGCGCAATTTACGATAAGCCGACTGCTAACATTATCCTT
AACGGCCAAAAGCTCGAGGCCTTTCCGCTCAAGACTGGAACCCGC
CAAGGCTGTCCCCTCTCCCCGCTTTTGTTTAATATTGTACTCGAG
GTGCTGGCTAGGGCTATTCGTCAAGAGAAAGAGATTAAAGGGATA
CAGCTCGGGAAGGAAGAGGTCAAGCTTTCCTTGTTCGCCGATGAT
ATGATTGTGTACCTGGAGAATCCTATTGTGTCTGCTCAGAACCTT
CTTAAACTTATTTCTAACTTTAGCAAGGTCAGCGGCTATAAGATT
AACGTCCAGAAATCTCAGGCCTTTCTGTACACAAATAATCGACAG
ACCGAATCCCAGATAATGGGTGAGCTTCCGTTTGTCATAGCCAGC
AAAAGGATAAAGTATCTCGGAATCCAGCTGACACGAGACGTTAAA
GATTTGTTTAAGGAAAATTACAAGCCTCTCCTGAAAGAGATTAAG
GAAGATACTAATAAGTGGAAGAATATCCCCTGTTCATGGGTTGGC
AGAATCAACATAGTGAAGATGGCAATACTTCCTAAAGTGATATAT
CGCTTTAACGCCATCCCAATTAAACTGCCTATGACCTTCTTTACG
GAGCTCGAGAAAACAACCCTTAAATTTATATGGAATCAAAAGAGA
GCAAGAATAGCGAAGTCCATCTTGAGCCAGAAGAATAAGGCCGGT
GGGATTACTTTGCCTGATTTTAAGTTGTATTATAAAGCCACAGTA
ACTAAGACAGCCTGGTATTGGTATCAGAATAGAGACATCGACCAG
TGGAATCGGACCGAACCATCAGAGATAATGCCCCACATCTATAAT
TACCTTATATTCGATAAGCCAGAAAAGAATAAACAGTGGGGCAAA
GACAGCCTCTTCAACAAGTGGTGTTGGGAGAATTGGCTGGCCATA
TGCCGGAAACTCAAGCTCGACCCCTTTCTTACACCCTACACTAAA
ATCAACAGTAGGTGGATCAAGGACTTGAATGTCAAGCCAAAGACT
ATAAAGACACTGGAAGAGAATCTTGGGATCACAATACAAGATATA
GGCGTCGGCAAAGATTTTATGTCAAAGACGCCCAAGGCCATGGCC
ACTAAGGATAAGATTGATAAGTGGGACCTTATTAAGCTCAAAAGC
TTCTGTACTGCCAAGGAGACCACGATCAGAGTTAATAGGCAGCCC
ACTACATGGGAAAAGATTTTCGCCACTTATTCATCAGATAAGGGG
TTGATAAGCAGAATATATAACGAGCTGAAGCAGATCTACAAGAAG
AAAACGAATAATCCCATCAAGAAGTGGGCAAAAGATATGAACAGG
CATTTTAGCAAAGAGGATATCTACGCCGCGAAGAAGCATATGAAG
AAGTGTAGTTCAAGCTTGGCCATTCGTGAGATGCAGATTAAGACG
ACCATGCGATACCACCTTACCCCAGTGAGGATGGCAATTATCAAG
AAATCTGGCAATAATAGATGTTGGCGGGGCTGTGGCGAGATTGGC
ACCCTGCTCCATTGCTGGTGGGATTGCAAGCTGGTGCAGCCGCTT
TGGAAATCAGTCTGGCGCTTTCTGAGGGACCTCGAGCTTGAGATT
CCCTTCGATCCCGCAATTCCCTTGCTCGGAATCTATCCTAACGAA
TACAAGAGCTGTTGTTACAAGGATACGTGTACCCGGATGTTCATC
GCGGCCTTGTTTACGATAGCTAAGACGTGGAATCAGCCTAAGTGC
CCCACAATGATCGATTGGATCAAGAAAATGTGGCATATTTATACC
ATGGAGTATTACGCAGCAATTAAGAATGACGAATTTATTTCCTTC
GTTGGGACCTGGATGAAGCTGGAGACTATTATTCTGAGCAAGCTG
TCTCAGGAGCAAAAGACAAAGCATAGAATCTTCTCTCTCATTGGT
GGTAACGACTACAAAGACGATGACGACAAGTAAAGCGCTTCTAGA
AGTTGTCTCCTCCTGCACTGACTGACTGATACAATCGATTTCTGG
ATCCGCAGGCCTAATCAACCTCTGGATTACAAAATTTGTGAAAGA
TTGACTGGTATTCTTAACTATGTTGCTCCTTTTACGCTATGTGGA
TACGCTGCTTTAATGCCTTTGTATCATGCTATTGCTTCCCGTATG
GCTTTCATTTTCTCCTCCTTGTATAAATCCTGGTTGCTGTCTCTT
TATGAGGAGTTGTGGCCCGTTGTCAGGCAACGTGGCGTGGTGTGC
ACTGTGTTTGCTGACGCAACCCCCACTGGTTGGGGCATTGCCACC
ACCTGTCAGCTCCTTTCCGGGACTTTCGCTTTCCCCCTCCCTATT
GCCACGGCGGAACTCATCGCCGCCTGCCTTGCCCGCTGCTGGACA
GGGGCTCGGCTGTTGGGCACTGACAATTCCGTGGTGTTGTCGGGG
AAGCTGACGTCCTTTCCATGGCTGCTCGCCTGTGTTGCCACCTGG
ATTCTGCGCGGGACGTCCTTCTGCTACGTCCCTTCGGCCCTCAAT
CCAGCGGACCTTCCTTCCCGCTGAGAGACACAAAAAATTCCAACA
CACTATTGCAATGAAAATAAATTTCCTTTATTAGCCAGAAGTCAG
ATGCTCAAGGGGCTTCATGATGTCCCCATAATTTTTGGCAGAGGG
AAAAAGATCTCAGTGGTATTTGTGAGCCAGGGCATTGGCCTTCTG
ATAGGCAGCCTGCACCTGAGGAGTGCGGCCGCTTTACTTGTACAG
CTCGTCCATGCCGAGAGTGATCCCGGCGGCGGTCACGAACTCCAG
CAGGACCATGTGATCGCGCTTCTCGTTGGGGTCTTTGCTCAGGGC
GGACTGGGTGCTCAGGTAGTGGTTGTCGGGCAGCAGCACGGGGCC
GTCGCCGATGGGGGTGTTCTGCTGGTAGTGGTCGGCGAGCTGCAC
GCTGCCGTCCTCGATGTTGTGGCGGATCTTGAAGTTCACCTTGAT
GCCGTTCTTCTGCTTGTCGGCCATGATATAGACGTTGTGGCTGTT
GTAGTTGTACTCCAGCTTGTGCCCCAGGATGTTGCCGTCCTCCTT
GAAGTCGATGCCCTTCAGCTCGATGCGGTTCACCAGGGTGTCGCC
CTCGAACTTCACCTCGGCGCGGGTCTTGTAGTTGCCGTCGTCCTT
GAAGAAGATGGTGCGCTCCTGGACGTAGCCTTCGGGCATGGCGGA
CTTGAAGAAGTCGTGCTGCTTCATGTGGTCGGGGTAGCGGCTGAA
GCACTGCACGCCGTAGGTCAGGGTGGTCACGAGGGTGGGCCAGGG
CACGGGCAGCTTGCCGGTGGTGCAGATGAACTTCAGGGTCAGCTT
GCCGTAGGTGGCATCGCCCTCGCCCTCGCCGGACACGCTGAACTT
GTGGCCGTTTACGTCGCCGTCCAGCTCGACCAGGATGGGCACCAC
CCCGGTGAACAGCTCCTCGCCCTTGCTCACCATGGTGGCGGGATC

TABLE 8-continued

Plasmid and mRNA construct sequences

TGACGGTTCACTAAACCAGCTCTGCTTATATAGACCTCCCACCGT
ACACGCCTACCGCCCATTTGCGTCAATGGGGCGGAGTTGTTACGA
CATTTTGGAAAGTCCCGTTGATTTTGGTGCCAAAACAAACTCCCA
TTGACGTCAATGGGGTGGAGACTTGGAAATCCCCGTGAGTCAAAC
CGCTATCCACGCCCATTGATGTACTGCCAAAACCGCATCACCATG
GTAATAGCGATGACTAATACGTAGATGTACTGCCAAGTAGGAAAG
TCCCATAAGGTCATGTACTGGGCATAATGCCAGGCGGGCCATTTA
CCGTCATTGACGTCAATAGGGGGCGTACTTGGCATATGATACACT
TGATGTACTGCCAAGTGGGCAGTTTACCGTAAATACTCCACCCAT
TGACGTCAATGGAAAGTCCCTATTGGCGTTACTATGGGAACATAC
GTCATTATTGACGTCAATGGGCGGGGGTCGTTGGGCGGTCAGCCA
GGCGGGCCATTTACCGTAAGTTATGTAACGGGCCTGCTGCCGGCT
CTGCGGCCTCTTCCGCGTCTTCGCCTTCGCCCTCAGACGAGTCGG
ATCTCCCTTTGGGCCGCCTCCCCGCCTGTCTAGCTTGACTGACTG
AGATACAGCGTACCTTCAGCTCACAGACATGATAAGATACATTGA
TGAGTTTGGACAAACCACAACTAGAATGCAGTGAAAAAAATGCTT
TATTTGTGAAATTTGTGATGCTATTGCTTTATTTGTAACCATTAT
AAGCTGCAATAAACAAGTT
(SEQ ID NO: 38)

LINE-1-plasmid CD5-intron-FCR-PI3K
(SEQ ID NO: 39)
CGGCCGCGGGGGGAGGAGCCAAGATGGCCGAATAGGAACAGCTCC
GGTCTACAGCTCCCAGCGTGAGCGACGCAGAAGACGGTGATTTCT
GCATTTCCATCTGAGGTACCGGGTTCATCTCACTAGGGAGTGCCA
GACAGTGGGCGCAGGCCAGTGTGTGTGCGCACCGTGCGCGAGCCG
AAGCAGGGCGAGGCATTGCCTCACCTGGGAAGCGCAAGGGGTCAG
GGAGTTCCCTTTCCGAGTCAAAGAAAGGGGTGACGGACGCACCTG
GAAAATCGGGTCACTCCCACCCGAATATTGCGCTTTTCAGACCGG
CTTAAGAAACGGCGCACCACGAGACTATATCCCACACCTGGCTCG
GAGGGTCCTACGCCCACGGAATCTCGCTGATTGCTAGCACAGCAG
TCTGAGATCAAACTGCAAGGCGGCAACGAGGCTGGGGGAGGGGCG
CCCGCCATTGCCCAGGCTTGCTTAGGTAAACAAAGCAGCAGGGAA
GCTCGAACTGGGTGGAGCCCACCACAGCTCAAGGAGGCCTGCCTG
CCTCTGTAGGCTCCACCTCTGGGGGCAGGGCACAGACAAACAAAA
AGACAGCAGTAACCTCTGCAGACTTAAGTGTCCCTGTCTGACAGC
TTTGAAGAGAGCAGTGGTTCTCCCAGCACGCAGCTGGAGATCTGA
GAACGGGCAGACTGCCTCCTCAAGTGGGTCCCTGACCCCTGACCC
CCGAGCAGCCTAACTGGGAGGCACCCCCCAGCAGGGGCACACTGA
CACCTCACACGGCAGGGTATTCCAACAGACCTGCAGCTGAGGGTC
CTGTCTGTTAGAAGGAAAACTAACAACCAGAAAGGACATCTACAC
CGAAAACCCATCTGTACATCACCATCATCAAAGACCAAAAGTAGA
TAAAACCACAAAGATGGGGAAAAAACAGAACAGAAAAACTGGAAA
CTCTAAAACGCAGAGCGCCTCTCCTCCTCCAAAGGAACGCAGTTC
CTCACCAGCAACAGAACAAAGCTGGATGGAGAATGATTTTGATGA
GCTGAGAGAAGAAGGCTTCAGACGATCAAATTACTCTGAGCTACG
GGAGGACATTCAAACCAAAGGCAAAGAAGTTGAAAACTTTGAAAA
AAATTTAGAAGAATGTATAACTAGAATAACCAATACAGAGAAGTG
CTTAAAGGAGCTGATGGAGCTGAAAACCAAGGCTCGAGAACTACG
TGAAGAATGCAGAAGCCTCAGGAGCCGATGCGATCAACTGGAAGA
AAGGGTATCAGCAATGGAAGATGAAATGAATGAAATGAAGCGAGA
AGGGAAGTTTAGAGAAAAAAGAATAAAAAGAAATGAGCAAAGCCT
CCAAGAAATATGGGACTATGTGAAAAGACCAAATCTACGTCTGAT
TGGTGTACCTGAAAGTGATGTGGAGAATGGAACCAAGTTGGAAAA
CACTCTGCAGGATATTATCCAGGAGAACTTCCCCAATCTAGCAAG
GCAGGCCAACGTTCAGATTCAGGAAATACAGAGAACGCCACAAAG
ATACTCCTCGAGAAGAGCAACTCCAAGACACATAATTGTCAGATT
CACCAAAGTTGAAATGAAGGAAAAAATGTTAAGGGCAGCCAGAGA
GAAAGGTCGGGTTACCCTCAAAGGAAAGCCCATCAGACTAACAGC
GGATCTCTCGGCAGAAACCCTACAAGCCAGAAGAGAGTGGGGGCC
AATATTCAACATTCTTAAAGAAAAGAATTTTCAACCCAGAATTTC
ATATCCAGCCAAACTAAGCTTCATAAGTGAAGGAGAAATAAAATA
CTTTATAGACAAGCAAATGTTGAGAGATTTTGTCACCACCAGGCC
TGCCCTAAAAGAGCTCCTGAAGGAAGCGCTAAACATGGAAAGGAA
CAACCGGTACCAGCCGCTGCAAAATCATGCCAAAATGTAAAGACC
ATCAAGACTAGGAAGAAACTGCATCAACTAATGAGCAAAATCACC
AGCTAACATCATAATGACAGGATCAACTTCACACATAACAATATT
AACTTTAAATATAAATGGACTAAATTCTGCAATTAAAAGACACAG
ACTGGCAAGTTGGATAAAGAGTCAAGACCCATCAGTGTGCTGTAT
TCAGGAAACCCATCTCACGTGCAGAGACACACATAGGCTCAAAAT
AAAAGGATGGAGGAAGATCTACCAAGCCAATGGAAAACAAAAAAA
GGCAGGGGTTGCAATCCTAGTCTCTGATAAAACAGACTTTAAACC
AACAAAGATCAAAAGAGACAAAGAAGGCCATTACATAATGGTAAA
GGGATCAATTCAACAAGAGGAGCTAACTATCCTAAATATTTATGC
ACCCAATACAGGAGCACCCAGATTCATAAAGCAAGTCCTCAGTGA
CCTACAAAGAGACTTAGACTCCCACACATTAATAATGGGAGACTT
TAACACCCCACTGTCAACATTAGACAGATCAACGAGACAGAAAGT
CAACAAGGATACCCAGGAATTGAACTCAGCTCTGCACCAAGCAGA
CCTAATAGACATCTACAGAACTCTCCACCCCAAATCAACAGAATA
TACATTTTTTCAGCACCACACCACACCTATTCCAAAATTGACCA
CATAGTTGGAAGTAAAGCTCTCCTCAGCAAATGTAAAAGAACAGA
AATTATAACAAACTATCTCTCAGACCACAGTGCAATCAAACTAGA
ACTCAGGATTAAGAATCTCACTCAAAGCCGCTCAACTACATGGAA
ACTGAACAACCTGCTCCTGAATGACTACTGGGTACATAACGAAAT
GAAGGCAGAAATAAAGATGTTCTTTGAAACCAACGAGAACAAAGA
CACCACATACCAGAATCTCTGGGACGCATTCAAAGCAGTGTGTAG
AGGGAAATTTATAGCACTAAATGCCTACAAGAGAAAGCAGGAAAG
ATCCAAAATTGACACCCTAACATCACAATTAAAAGAACTAGAAAA
GCAAGAGCAAACACATTCAAAAGCTAGCAGAAGGCAAGAAATAAC
TAAAATCAGAGCAGAACTGAAGGAAATAGAGACACAAAAAACCCT
TCAAAAAATCAATGAATCCAGGAGCTGGTTTTTTGAAAGGATCAA
CAAAATTGATAGACCGCTAGCAAGACTAATAAAGAAAAAAAGAGA
GAAGAATCAAATAGACACAATAAAAAATGATAAAGGGGATATCAC
CACCGATCCCACAGAAATACAAACTACCATCAGAGAATACTACAA
ACACCTCTACGCAAATAAACTAGAAAATCTAGAAGAAATGGATAC
ATTCCTCGACACATACACTCTCCCAAGACTAAACCAGGAAGAAGT
TGAATCTCTGAATCGACCAATAACAGGCTCTGAAATTGTGGCAAT
AATCAATAGTTTACCAACCAAAAAGAGTCCAGGACCAGATGGATT
CACAGCCGAATTCTACCAGAGGTACAAGGAGGAACTGGTACCATT
CCTTCTGAAACTATTCCAATCAATAGAAAAAGAGGGAATCCTCCC
TAACTCATTTTATGAGGCCAGCATCATTCTGATACCAAAGCCGGG
CAGAGACACAACCAAAAAAGAGAATTTTAGACCAATATCCTTGAT
GAACATTGATGCAAAAATCCTCAATAAAATACTGGCAAACCGAAT
CCAGCAGCACATCAAAAAGCTTATCCACCATGATCAAGTGGGCTT
CATCCCTGGGATGCAAGGCTGGTTCAATATACGCAAATCAATAAA
TGTAATCCAGCATATAAACAGAGCCAAAGACAAAAACCACATGAT
TATCTCAATAGATGCAGAAAAAGCCTTTGACAAAATTCAACAACC
CTTCATGCTAAAAACTCTCAATAAATTAGGTATTGATGGGACGTA
TTTCAAAATAATAAGAGCTATCTATGACAAACCCACAGCCAATAT
CATACTGAATGGGCAAAAACTGGAAGCATTCCCTTTGAAAACCGG
CACAAGACAGGGATGCCCTCTCTCACCGCTCCTATTCAACATAGT
GTTGGAAGTTCTGGCCAGGGCAATCAGGCAGGAGAAGGAAATAAA
GGGTATTCAATTAGGAAAAGAGGAAGTCAAATTGTCCCTGTTTGC
AGACGACATGATTGTTTATCTAGAAAACCCCATCGTCTCAGCCCA
AAATCTCCTTAAGCTGATAAGCAACTTCAGCAAAGTCTCAGGATA
CAAAATCAATGTACAAAAATCACAAGCATTCTTATACACCAACAA
CAGACAAACAGAGAGCCAAATCATGGGTGAACTCCCATTCACAAT
TGCTTCAAAGAGAATAAAATACCTAGGAATCCAACTTACAAGGGA
TGTGAAGGACCTCTTCAAGGAGAACTACAAACCACTGCTCAAGGA
AATAAAAGAGGAGACAAACAAATGGAAGAACATTCCATGCTCATG
GGTAGGAAGAATCAATATCGTGAAAATGGCCATACTGCCCAAGGT
AATTTACAGATTCAATGCCATCCCCATCAAGCTACCAATGACTTT
CTTCACAGAATTGGAAAAAACTACTTTAAAGTTCATATGGAACCA
AAAAAGAGCCCGCATTGCCAAGTCAATCCTAAGCCAAAAGAACAA
AGCTGGAGGCATCACACTACCTGACTTCAAACTATACTACAAGGC
TACAGTAACCAAAACAGCATGGTACTGGTACCAAAACAGAGATAT
AGATCAATGGAACAGAACAGAGCCCTCAGAAATAATGCCGCATAT
CTACAACTATCTGATCTTTGACAAACCTGAGAAAAACAAGCAATG
GGGAAAGGATTCCCTATTTAATAAATGGTGCTGGGAAAACTGGCT
AGCCATATGTAGAAAGCTGAAACTGGATCCCTTCCTTACACCTTA
TACAAAAATCAATTCAAGATGGATTAAAGATTTAAACGTTAAACC
TAAAACCATAAAAACCCTAGAAGAAAACCTAGGCATTACCATTCA
GGACATAGGCGTGGGCAAGGACTTCATGTCCAAAACACCAAAAGC
AATGGCAACAAAAGACAAAATTGACAAATGGGATCTAATTAAACT
AAAGAGCTTCTGCACAGCAAAAGAAACTACCATCAGAGTGAACAG
GCAACCTACAACATGGGAGAAAATTTTTGCAACCTACTCATCTGA
CAAAGGGCTAATATCCAGAATCTACAATGAACTCAAACAAATTTA
CAAGAAAAAAACAAACAACCCCATCAAAAAGTGGGCGAAGGACAT
GAACAGACACTTCTCAAAAGAAGACATTTATGCAGCCAAAAAACA
CATGAAGAAATGCTCATCATCACTGGCCATCAGAGAAATGCAAAT
CAAAACCACTATGAGATATCATCTCACACCAGTTAGAATGGCAAT
CATTAAAAAGTCAGGAAACAACAGGTGCTGGAGAGGATGCGGAGA
AATAGGAACACTTTTACACTGTTGGTGGGACTGTAAACTAGTTCA
ACCATTGTGGAAGTCAGTGTGGCGATTCCTCAGGGATCTAGAACT
AGAAATACCATTTGACCCAGCCATCCCATTACTGGGTATATACCC
AAATGAGTATAAATCATGCTGCTATAAAGACACATGCACACGTAT
GTTTATTGCGGCACTATTCACAATAGCAAAGACTTGGAACCAACC
CAAATGTCCAACAATGATAGACTGGATTAAGAAAATGTGGCACAT
ATACACCATGGAATACTATGCAGCCATAAAAAATGATGAGTTCAT
ATCCTTTGTAGGGACATGGATGAAATTGGAAACCATCATTCTCAG
TAAACTATCGCAAGAACAAAAAACCAAACACCGCATATTCTCACT
CATAGGTGGGAATTGAACAATGAGATCACATGGACACAGGAAGGG
GAATATCACACTCTGGGGACTGTGGTGGGGTCGGGGGAGGGGGGA
GGGATAGCATTGGGAGATATACCTAATGCTAGATGACACATTAGT
GGGTGCAGCGCACCAGCATGGCACATGTATACGGATCCGAATTCT
CGACGGATCGATCCGAACAAACGACCCAACACCCGTGCGTTTTAT TABLE 8-continued

| Plasmid and mRNA construct sequences |
|---|
| TCTGTCTTTTTATTGCCGATCCCCTCAGAAGAACTCGTCAAGAAG<br>GCGATAGAAGGCGATGCGCTGCGAATCGGGAGCGGCGATACCGTA<br>AAGCACGAGGAAGCGGTCAGCCCATTCGCCGCCAAGCTCTTCAGC<br>AATATCACGGGTAGCCAACGCTATGTCCTGATAGCGGTCGGCCGC<br>TCATGTTCTCGTAGGAGTCGGCGTCCTCTTCGTGGTTAGGTCCAG<br>GTTGGCCTCTGATAGACCGCAGCTGAGGAGCGGCGTACAGAATGC<br>CTCTCATGTCCTCATAGCTGCCGCTGCCTTGTGGAGGCTTCTCGT<br>GCTTCAGTGTCTCGTATGTCTCTTGATTCCGGGTGCTCAGGCCGG<br>TGTACACGCCATCAGATTTCTCGTAGCTGGTGATGGCGGCCTTCC<br>GCACTTGGATCTTCAGCCGTCTGCAGTACAGGGTGATGACCAGAG<br>ACAGCAGCAGGACACCACATGTGCCAGCCAGAGGGGCCCAAATGT<br>AGATATCCAGGCCTCTGGTATGCACAGCTCCGCCTGCAGCAGGTC<br>TACAGGCTTCAGGTCTGAGAGACAGAGGCTGGCTGGCGATTGTAG<br>GAGCTGGTGTAGGTGGTCTAGGAGCGGGTGTTGTTGTAGGCTTGG<br>CGGGCAGAAACACGGGCACGAAGTGGCTGAAGTACATGATGCTAT<br>TGCTCAGGGCTCCGCTTCCTCCGCCGCCTGATTTGATTTCCAGCT<br>TGGTGCCTCCGCCAAATGTCCAAGGGCTCTCGTCGTACTGCTGGC<br>AGTAGTAGATGCCGAAGTCCTCGTACTGCAGGCTGCTGATTGTCA<br>GGGTGTAGTCGGTGCCAGAGCCGCTGCCAGAAAATCTGCTTGGCA<br>CGCCGCTTTCCAGTCTGTTGGCCCGGTAGATCAGTGTCTTAGGGG<br>CCTTGCCAGGCTTCTGCTGGAACCAGCTCAGGTAGCTGTTGATGT<br>CCTGGCTGGCTCTACAGGTGATGGTCACTCTATCGCCCACAGAGG<br>CAGACAGGCTGCTAGGGCTCTGTGTCATCTGGATATCAGAGCCAC<br>CACCGCCAGATCCACCGCCACCTGATCCTCCGCCTCCGCTAGAAA<br>CTGTCACTGTGGTGCCCTGGCCCCACACATCGAAGTACCAGTCGT<br>AGCCTCTTCTGGTGCAGAAGTACACGGCGGTATCCTCGGCTCTCA<br>GGCTGTTGATCTGCAGGTAGGCGGTGTTCTTGCTGTCGTCCAGGC<br>TGAAGGTGAATCTGCCCTTAAAGCTATCGGCGTAGGTTGGCTCGC<br>CGGTGTGGGTATTGATCCAGCCCATCCACTCAAGGCCAGGTGAGT<br>CCAGGAGATGTTTCAGCACTGTTGCCTTTAGTCTCGAGGCAACTT<br>AGACAACTGAGTATTGATCTGAGCACAGCAGGGTGTGAGCTGTTT<br>GAAGATACTGGGGTTGGGGGTGAAGAAACTGCAGAGGACTAACTG<br>GGCTGAGACCCAGTGGCAATGTTTTAGGGCCTAAGGAATGCCTCT<br>GAAAATCTAGATGGACAACTTTGACTTTGAGAAAAGAGAGGTGGA<br>AATGAGGAAAATGACTTTTCTTTATTAGATTTCGGTAGAAAGAAC<br>TTTCATCTTTCCCCTATTTTTGTTATTCGTTTTAAAACATCTATC<br>TGGAGGCAGGACAAGTATGGTCATTAAAAAGATGCAGGCAGAAGG<br>CATATATTGGCTCAGTCAAAGTGGGGAACTTTGGTGGCCAAACAT<br>ACATTGCTAAGGCTATTCCTATATCAGCTGGACACATATAAAATG<br>CTGCTAATGCTTCATTACAAACTTATATCCTTTAATTCCAGATGG<br>GGGCAAAGTATGTCCAGGGGTGAGGAACAATTGAAACATTTGGGC<br>TGGAGTAGATTTTGAAAGTCAGCTCTGTGTGTGTGTGTGTGTGTG<br>TGTGTGTGAGAGCGTGTGTTTCTTTTAACGTTTTCAGCCTACAGC<br>ATACAGGGTTCATGGTGGCAAGAAGATAACAAGATTTAAATTATG<br>GCCAGTGACTAGTGCTGCAAGAAGAACAACTACCTGCATTTAATG<br>GGAAAGCAAAATCTCAGGCTTTGAGGGAAGTTAACATAGGCTTGA<br>TTCTGGGTGGAAGCTGGGTGTGTAGTTATCTGGAGGCCAGGCTGG<br>AGCTCTCAGCTCACTATGGGTTCATCTTTATTGTCTCCTTTTTCC<br>AGGGGCCTGTCGGACCCAGTTCATGCCGTAGTTGGTGAAGGTGTA<br>GCCGCTGGCGGCACAGCTGATTCTGACAGATCCGCCAGGTTTCAC<br>AAGTCCGCCGCCAGACTGAACCAGCTGGATCTCAGAGATGCTACA<br>GGCCACTGTTCCCAGCAGCAGCAGAGACTGCAGCCACATCTGGTG<br>GCGAATTCGAAGCTTGAGCTCGAGATCTGAGTCCGGTAGCTGAAC<br>CGTCAGATCGCCGGCTAGCGGATCTGACGGTTCACTAAACCAGCT<br>CTGCTTATATAGACCTCCCACCGTACACGCCTACCGCCCATTTGC<br>GTCAATGGGGCGGAGTTGTTACGACATTTTGGAAAGTCCCGTTGA<br>TTTTGGTGCCAAAACAAACTCCCATTGACGTCAATGGGGTGGAGA<br>CTTGGAAATCCCCGTGAGTCAAACCGCTATCCACGCCCATTGATG<br>TACTGCCAAAACCGCATCACCATGGTAATAGCGATGACTAATACG<br>TAGATGTACTGCCAAGTAGGAAAGTCCCATAAGGTCATGTACTGG<br>GCATAATGCCAGGCGGGCCATTTACCGTCATTGACGTCAATAGGG<br>GGCGTACTTGGCATATGATACACTTGATGTACTGCCAAGTGGGCA<br>GTTTACCGTAAATACTCCACCCATTGACGTCAATGGAAAGTCCCT<br>ATTGGCGTTACTATGGGAACATACGTCATTATTGACGTCAATGGG<br>CGGGGGTCGTTGGGCGGTCAGCCAGGCGGGCCATTTACCGTAAGT<br>TATGTAACGCGGAACTCCATATATGGGCTATGAACTAATGACCCC<br>GTAATTGATTACTATTAGCCCGGGGGATCCAGACATGATAAGATA<br>CATTGATGAGTTTGGACAAACCACAACTAGAATGCAGTGAAAAAA<br>ATGCTTTATTTGTGAAATTTGTGATGCTATTGCTTTATTTGTAAC<br>CATTATAAGCTGCAATAAACAAGTTAACAACAACAATTGCATTCA<br>TTTTATGTTTCAGGTTCAGGGGGAGGTGTGGGAGGTTTTTTAAAG<br>CAAGTAAAACCTCTACAAATGTGGTATGGCTGATTATGATCCGGC<br>TGCCTCGCGCGTTTCGGTGATGACGGTGAAAACCTCTGACACATG<br>CAGCTCCCGGAGACGGTCACAGCTTGTCTGTAAGCGGATGCCGGG<br>AGCAGACAAGCCCGTCAGGGCGCGTCAGCGGGTGTTGGCGGGTGT<br>CGGGGCGCAGCCATGAGGTCGATCGACTCTAGAGGATCGATCCCC<br>GCCCCGGACGAACTAAACCTGACTACGACATCTCTGCCCCTTCTT<br>CGCGGGGCAGTGCATGTAATCCCTTCAGTTGGTTGGTACAACTTG |

TABLE 8-continued

| Plasmid and mRNA construct sequences |
|---|
| CCAACTGGGCCCTGTTCCACATGTGACACGGGGGGGGACCAAACA<br>CAAAGGGGTTCTCTGACTGTAGTTGACATCCTTATAAATGGATGT<br>GCACATTTGCCAACACTGAGTGGCTTTCATCCTGGAGCAGACTTT<br>GCAGTCTGTGGACTGCAACACAACATTGCCTTTATGTGTAACTCT<br>TGGCTGAAGCTCTTACACCAATGCTGGGGGACATGTACCTCCCAG<br>GGGCCCAGGAAGACTACGGGAGGCTACACCAACGTCAATCAGAGG<br>GGCCTGTGTAGCTACCGATAAGCGGACCCTCAAGAGGGCATTAGC<br>AATAGTGTTTATAAGGCCCCCTTGTTAACCCTAAACGGGTAGCAT<br>ATGCTTCCCGGGTAGTAGTATATACTATCCAGACTAACCCTAATT<br>CAATAGCATATGTTACCCAACGGGAAGCATATGCTATCGAATTAG<br>GGTTAGTAAAAGGGTCCTAAGGAACAGCGATATCTCCCACCCCAT<br>GAGCTGTCACGGTTTTATTTACATGGGGTCAGGATTCCACGAGGG<br>TAGTGAACCATTTTAGTCACAAGGGCAGTGGCTGAAGATCAAGGA<br>GCGGGCAGTGAACTCTCCTGAATCTTCGCCTGCTTCTTCATTCTC<br>CTTCGTTTAGCTAATAGAATAACTGCTGAGTTGTGAACAGTAAGG<br>TGTATGTGAGGTGCTCGAAAACAAGGTTTCAGGTGACGCCCCCAG<br>AATAAAATTTGGACGGGGGGTTCAGTGGTGGCATTGTGCTATGAC<br>ACCAATATAACCCTCACAAACCCCTTGGGCAATAAATACTAGTGT<br>AGGAATGAAACATTCTGAATATCTTTAACAATAGAAATCCATGGG<br>GTGGGGACAAGCCGTAAAGACTGGATGTCCATCTCACACGAATTT<br>ATGGCTATGGGCAACACATAATCCTAGTGCAATATGATACTGGGG<br>TTATTAAGATGTGTCCCAGGCAGGGACCAAGACAGGTGAACCATG<br>TTGTTACACTCTATTTGTAACAAGGGGAAAGAGAGTGGACGCCGA<br>CAGCAGCGGACTCCACTGGTTGTCTCTAACACCCCCGAAAATTAA<br>ACGGGGCTCCACGCCAATGGGGCCCATAAACAAAGACAAGTGGCC<br>ACTCTTTTTTTTGAAATTGTGGAGTGGGGGCACGCGTCAGCCCCC<br>ACACGCCGCCCTGCGGTTTTGGACTGTAAAATAAGGGTGTAATAA<br>CTTGGCTGATTGTAACCCCGCTAACCACTGCGGTCAAACCACTTG<br>CCCACAAAACCACTAATGGCACCCCGGGGAATACCTGCATAAGTA<br>GGTGGGCGGGCCAAGATAGGGGCGCGATTGCTGCGATCTGGAGGA<br>CAAATTACACACACTTGCGCCTGAGCGCCAAGCACAGGGTTGTTG<br>GTCCTCATATTCACGAGGTCGCTGAGAGCACGGTGGGCTAATGTT<br>GCCATGGGTAGCATATACTACCCAAATATCTGGATAGCATATGCT<br>ATCCTAATCTATATCTGGGTAGCATAGGCTATCCTAATCTATATC<br>TGGGTAGCATATGCTATCCTAATCTATATCTGGGTAGTATATGCT<br>ATCCTAATTTATATCTGGGTAGCATAGGCTATCCTAATCTATATC<br>TGGGTAGCATATGCTATCCTAATCTATATCTGGGTAGTATATGCT<br>ATCCTAATCTGTATCCGGGTAGCATATGCTATCCTAATAGAGATT<br>AGGGTAGTATATGCTATCCTAATTTATATCTGGGTAGCATATACT<br>ACCCAAATATCTGGATAGCATATGCTATCCTAATCTATATCTGGG<br>TAGCATATGCTATCCTAATCTATATCTGGGTAGCATAGGCTATCC<br>TAATCTATATCTGGGTAGCATATGCTATCCTAATCTATATCTGGG<br>TAGTATATGCTATCCTAATTTATATCTGGGTAGCATAGGCTATCC<br>TAATCTATATCTGGGTAGCATATGCTATCCTAATCTATATCTGGG<br>TAGTATATGCTATCCTAATCTGTATCCGGGTAGCATATGCTATCC<br>TCATGCATATACAGTCAGCATATGATACCCAGTAGTAGAGTGGGA<br>GTGCTATCCTTTGCATATGCCGCCACCTCCCAAGGGGGCGTGAAT<br>TTTCGCTGCTTGTCCTTTTCCTGCATGCTGGTTGCTCCCATTCTT<br>AGGTGAATTTAAGGAGGCCAGGCTAAAGCCGTCGCATGTCTGATT<br>GCTCACCAGGTAAATGTCGCTAATGTTTTCCAACGCGAGAAGGTG<br>TTGAGCGCGGAGCTGAGTGACGTGACAACATGGGTATGCCCAATT<br>GCCCCATGTTGGGAGGACGAAAATGGTGACAAGACAGATGGCCAG<br>AAATACACCAACAGCACGCATGATGTCTACTGGGGATTTATTCTT<br>TAGTGCGGGGGAATACACGGCTTTTAATACGATTGAGGGCGTCTC<br>CTAACAAGTTACATCACTCCTGCCCTTCCTCACCCTCATCTCCAT<br>CACCTCCTTCATCTCCGTCATCTCCGTCATCACCCTCCGCGGCAG<br>CCCCTTCCACCATAGGTGGAAACCAGGGAGGCAAATCTACTCCAT<br>CGTCAAAGCTGCACACAGTCACCCTGATATTGCAGGTAGGAGCGG<br>GCTTTGTCATAACAAGGTCCTTAATCGCATCCTTCAAAACCTCAG<br>CAAATATATGAGTTTGTAAAAAGACCATGAAATAACAGACAATGG<br>ACTCCCTTAGCGGGCCAGGTTGTGGGCCGGGTCCAGGGGCCATTC<br>CAAAGGGGAGACGACTCAATGGTGTAAGACGACATTGTGGAATAG<br>CAAGGGCAGTTCCTCGCCTTAGGTTGTAAAGGGAGGTCTTACTAC<br>CTCCATATACGAACACACCGGCGACCCAAGTTCCTTCGTCGGTAG<br>TCCTTTCTACGTGACTCCTAGCCAGGAGAGCTCTTAAACCTTCTG<br>CAATGTTCTCAAATTTCGGGTTGGAACCTCCTTGACCACGATGCT<br>TTCCAAACCACCCTCCTTTTTTGCGCCTGCCTCCATCACCCTGAC<br>CCCGGGGTCCAGTGCTTGGGCCTTCTCCTGGGTCATCTGCGGGGC<br>CCTGCTCTATCGCTCCCGGGGGCACGTCAGGCTCACCATCTGGGC<br>CACCTTCTTGGTGGTATTCAAAATAATCGGCTTCCCCTACAGGGT<br>GGAAAAATGGCCTTCTACCTGGAGGGGGCCTGCGCGGTGGAGACC<br>CGGATGATGATGACTGACTACTGGGACTCCTGGGCCTCTTTTCTC<br>CACGTCCACGACCTCTCCCCCTGGCTCTTTCACGACTTCCCCCCC<br>TGGCTCTTTCACGTCCTCTACCCCGGCGGCCTCCACTACCTCCTC<br>GACCCCGGCCTCCACTACCTCCTCGACCCCGGCCTCCACTGCCTC<br>CTCGACCCCGGCCTCCACCTCCTGCTCCTGCCCCTCCTGCTCCTG<br>CCCCTCCTCCTGCTCCTGCCCCTCCTGCCCCTCCTGCTCCTGCCC<br>CTCCTGCCCCTCCTGCTCCTGCCCCTCCTGCCCCTCCTGCTCCTG |

TABLE 8-continued

| Plasmid and mRNA construct sequences |
|---|
| CCCCTCCTGCCCCTCCTCCTGCTCCTGCCCCTCCTGCCCCTCCTC CTGCTCCTGCCCCTCCTGCCCCTCCTGCTCCTGCCCCTCCTGCCC CTCCTGCTCCTGCCCCTCCTGCCCCTCCTGCTCCTGCCCCTCCTG CTCCTGCCCCTCCTGCTCCTGCCCCTCCTGCTCCTGCCCCTCCTG CCCCTCCTGCCCCTCCTCCTGCTCCTGCCCCTCCTGCTCCTGCCC CTCCTGCCCCTCCTGCCCCTCCTGCTCCTGCCCCTCCTCCTGCTC CTGCCCCTCCTGCCCCTCCTGCCCCTCCTCCTGCTCCTGCCCCTC CTGCCCCTCCTCCTGCTCCTGCCCCTCCTCCTGCTCCTGCCCCTC CTGCCCCTCCTGCCCCTCCTCCTGCTCCTGCCCCTCCTGCCCCTC CTCCTGCTCCTGCCCCTCCTCCTGCTCCTGCCCCTCCTGCCCCTC CTGCCCCTCCTCCTGCTCCTGCCCCTCCTCCTGCTCCTGCCCCTC CTGCCCCTCCTGCCCCTCCTGCCCCTCCTCCTGCTCCTGCCCCTC CTCCTGCTCCTGCCCCTCCTGCTCCTGCCCCTCCCGCTCCTGCTC CTGCTCCTGTTCCACCGTGGGTCCCTTTGCAGCCAATGCAACTTG GACGTTTTTGGGGTCTCCGGACACCATCTCTATGTCTTGGCCCTG ATCCTGAGCCGCCCGGGGCTCCTGGTCTTCCGCCTCCTCGTCCTC GTCCTCTTCCCCGTCCTCGTCCATGGTTATCACCCCCTCTTCTTT GAGGTCCACTGCCGCCGGAGCCTTCTGGTCCAGATGTGTCTCCCT TCTCTCCTAGGCCATTTCCAGGTCCTGTACCTGGCCCCTCGTCAG ACATGATTCACACTAAAAGAGATCAATAGACATCTTTATTAGACG ACGCTCAGTGAATACAGGGAGTGCAGACTCCTGCCCCCTCCAACA GCCCCCCCACCCTCATCCCCTTCATGGTCGCTGTCAGACAGATCC AGGTCTGAAAATTCCCCATCCTCCGAACCATCCTCGTCCTCATCA CCAATTACTCGCAGCCCGGAAAACTCCCGCTGAACATCCTCAAGA TTTGCGTCCTGAGCCTCAAGCCAGGCCTCAAATTCCTCGTCCCCC TTTTTGCTGGACGGTAGGGATGGGGATTCTCGGGACCCCTCCTCT TCCTCTTCAAGGTCACCAGACAGAGATGCTACTGGGGCAACGGAA GAAAAGCTGGGTGCGGCCTGTGAGGATCAGCTTATCGATGATAAG CTGTCAAACATGAGAATTCTTGAAGACGAAAGGGCCTCGTGATAC GCCTATTTTTATAGGTTAATGTCATGATAATAATGGTTTCTTAGA CGTCAGGTGGCACTTTTCGGGGAAATGTGCGCGGAACCCCTATTT GTTTATTTTTCTAAATACATTCAAATATGTATCCGCTCATGAGAC AATAACCCTGATAAATGCTTCAATAATATTGAAAAAGGAAGAGTA TGAGTATTCAACATTTCCGTGTCGCCCTTATTCCCTTTTTTGCGG CATTTTGCCTTCCTGTTTTTGCTCACCCAGAAACGCTGGTGAAAG TAAAAGATGCTGAAGATCAGTTGGGTGCACGAGTGGGTTACATCG AACTGGATCTCAACAGCGGTAAGATCCTTGAGAGTTTTCGCCCCG AAGAACGTTTTCCAATGATGAGCACTTTTAAAGTTCTGCTATGTG GCGCGGTATTATCCCGTGTTGACGCCGGGCAAGAGCAACTCGGTC GCCGCATACACTATTCTCAGAATGACTTGGTTGAGTACTCACCAG TCACAGAAAAGCATCTTACGGATGGCATGACAGTAAGAGAATTAT GCAGTGCTGCCATAACCATGAGTGATAACACTGCGGCCAACTTAC TTCTGACAACGATCGGAGGACCGAAGGAGCTAACCGCTTTTTTGC ACAACATGGGGGATCATGTAACTCGCCTTGATCGTTGGGAACCGG AGCTGAATGAAGCCATACCAAACGACGAGCGTGACACCACGATGC CTGCAGCAATGGCAACAACGTTGCGCAAACTATTAACTGGCGAAC TACTTACTCTAGCTTCCCGGCAACAATTAATAGACTGGATGGAGG CGGATAAAGTTGCAGGACCACTTCTGCGCTCGGCCCTTCCGGCTG GCTGGTTTATTGCTGATAAATCTGGAGCCGGTGAGCGTGGGTCTC GCGGTATCATTGCAGCACTGGGGCCAGATGGTAAGCCCTCCCGTA TCGTAGTTATCTACACGACGGGGAGTCAGGCAACTATGGATGAAC GAAATAGACAGATCGCTGAGATAGGTGCCTCACTGATTAAGCATT GGTAACTGTCAGACCAAGTTTACTCATATATACTTTAGATTGATT TAAAACTTCATTTTTAATTTAAAAGGATCTAGGTGAAGATCCTTT TTGATAATCTCATGACCAAAATCCCTTAACGTGAGTTTTCGTTCC ACTGAGCGTCAGACCCCGTAGAAAAGATCAAAGGATCTTCTTGAG ATCCTTTTTTTCTGCGCGTAATCTGCTGCTTGCAAACAAAAAAAC CACCGCTACCAGCGGTGGTTTGTTTGCCGGATCAAGAGCTACCAA CTCTTTTTCCGAAGGTAACTGGCTTCAGCAGAGCGCAGATACCAA ATACTGTCCTTCTAGTGTAGCCGTAGTTAGGCCACCACTTCAAGA ACTCTGTAGCACCGCCTACATACCTCGCTCTGCTAATCCTGTTAC CAGTGGCTGCTGCCAGTGGCGATAAGTCGTGTCTTACCGGGTTGG ACTCAAGACGATAGTTACCGGATAAGGCGCAGCGGTCGGGCTGAA CGGGGGGTTCGTGCACACAGCCCAGCTTGGAGCGAACGACCTACA CCGAACTGAGATACCTACAGCGTGAGCTATGAGAAAGCGCCACGC TTCCCGAAGGGAGAAAGGCGGACAGGTATCCGGTAAGCGGCAGGG TCGGAACAGGAGAGCGCACGAGGGAGCTTCCAGGGGGAAACGCCT GGTATCTTTATAGTCCTGTCGGGTTTCGCCACCTCTGACTTGAGC GTCGATTTTTGTGATGCTCGTCAGGGGGGCGGAGCCTATGGAAAA ACGCCAGCAACGCGGCCTTTTTACGGTTCCTGGCCTTTTGCTGGC CTTTTGCTCACATGTTCTTTCCTGCGTTATCCCCTGATTCTGTGG ATAACCGTATTACCGCCTTTGAGTGAGCTGATACCGCTCGCCGCA GCCGAACGACCGAGCGCAGCGAGTCAGTGAGCGAGGAAGCGGAAG AGCGCCTGATGCGGTATTTTCTCCTTACGCATCTGTGCGGTATTT CACACCGCATATGGTGCACTCTCAGTACAATCTGCTCTGATGCCG CATAGTTAAGCCAGCTGTGGAATGTGTGTCAGTTAGGGTGTGGAA AGTCCCCAGGCTCCCCAGCAGGCAGAAGTATGCAAAGCATGCATC TCAATTAGTCAGCAACCAGGTGTGGAAAGTCCCCAGGCTCCCCAG CAGGCAGAAGTATGCAAAGCATGCATCTCAATTAGTCAGCAACCA TAGTCCCGCCCCTAACTCCGCCCATCCCGCCCCTAACTCCGCCCA GTTCCGCCCATTCTCCGCCCCATGGCTGACTAATTTTTTTTATTT ATGCAGAGGCCGAGGCCGCCTCGGCCTCTGAGCTATTCCAGAAGT AGTGAGGAGGCTTTTTTGGAGGCCTAGGCTTTTGCAAAAAGCTTG CATGCCTGCAGGTCGGCCGCCACGACCGGTGCCGCCACCATCCCC TGACCCACGCCCCTGACCCCTCACAAGGAGACGACCTTCCATGAC CGAGTACAAGCCCACGGTGCGCCTCGCCACCCGCGACGACGTCCC CCGGGCCGTACGCACCCTCGCCGCCGCGTTCGCCGACTACCCCGC CACGCGCCACACCGTCGACCCGGACCGCCACATCGAGCGGGTCAC CGAGCTGCAAGAACTCTTCCTCACGCGCGTCGGGCTCGACATCGG CAAGGTGTGGGTCGCGGACGACGGCGCCGCGGTGGCGGTCTGGAC CACGCCGGAGAGCGTCGAAGCGGGGGCGGTGTTCGCCGAGATCGG CCCGCGCATGGCCGAGTTGAGCGGTTCCCGGCTGGCCGCGCAGCA ACAGATGGAAGGCCTCCTGGCGCCGCACCGGCCCAAGGAGCCCGC GTGGTTCCTGGCCACCGTCGGCGTCTCGCCCGACCACCAGGGCAA GGGTCTGGGCAGCGCCGTCGTGCTCCCCGGAGTGGAGGCGGCCGA GCGCGCCGGGGTGCCCGCCTTCCTGGAGACCTCCGCGCCCCGCAA CCTCCCCTTCTACGAGCGGCTCGGCTTCACCGTCACCGCCGACGT CGAGGTGCCCGAAGGACCGCGCACCTGGTGCATGACCCGCAAGCC CGGTGCCTGACGCCCGCCCCACGACCCGCAGCGCCCGACCGAAAG GAGCGCACGACCCCATGGCTCCGACCGAAGCCGACCCGGGCGGCC CCGCCGACCCCGCACCCGCCCCCGAGGCCCACCGACTCTAGAGGA TCATAATCAGCCATACCACATTTGTAGAGGTTTTACTTGCTTTAA AAAACCTCCCACACCTCCCCCTGAACCTGAAACATAAAATGAATG CAATTGTTGTTGTTAACTTGTTTATTGCAGCTTATAATGGTTACA AATAAAGCAATAGCATCACAAATTTCACAAATAAAGCATTTTTTT CACTGCATTCTAGTTGTGGTTTGTCCAAACTCATCAATGTATCTT ATCATGTCTGGATCACTCGCCGATAGTGGAAACCGACGCCCCAGC ACTCGTCCGAGGGCAAAGGAATAGGGGAGATGGGGGAGGCTAACT GAAACACGGAAGGAGACAATACCGGAAGGAACCCGCGCTATGACG GCAATAAAAAGACAGAATAAAACGCACGGGTGTTGGGTCGTTTGT TCATAAACGCGGGGTTCGGTCCCAGGGCTGGCACTCTGTCGATAC CCCACCGAGACCCCATTGGGGCCAATACGCCCGCGTTTCTTCCTT TTCCCCACCCCACCCCCCAAGTTCGGGTGAAGGCCCAGGGCTCGC AGCCAACGTCGGGGCGGCAGGCCCTGCCATAGCCACTGGCCCCGT GGGTTAGGGACGGGGTCCCCCATGGGGAATGGTTTATGGTTCGTG GGGGTTATTATTTTGGGCGTTGCGTGGGGTCTGGTCCACGACTGG ACTGAGCAGACAGACCCATGGTTTTTGGATGGCCTGGGCATGGAC CGCATGTACTGGCGCGACACGAACACCGGGCGTCTGTGGCTGCCA AACACCCCCGACCCCCAAAAACCACCGCGCGGATTTCTGGCGTGC CAAGCTAGTCGACCAATTCTCATGTTTGACAGCTTATCATCGCAG ATCCGGGCAACGTTGTTGCATTGCTGCAGGCGCAGAACTGGTAGG TATGGAAGATCTCTAGAAGCTGGGTACCAGCTGCTAGCAAGCTTG CTAGCGGCCGGCTCGAGTTTACTCCCTATCAGTGATAGAGAACGT ATGTCGAGTTTACTCCCTATCAGTGATAGAGAACGATGTCGAGTT TACTCCCTATCAGTGATAGAGAACGTATGTCGAGTTTACTCCCTA TCAGTGATAGAGAACGTATGTCGAGTTTACTCCCTATCAGTGATA GAGAACGTATGTCGAGTTTATCCCTATCAGTGATAGAGAACGTAT GTCGAGTTTACTCCCTATCAGTGATAGAGAACGTATGTCGAGGTA GGCGTGTACGGTGGGAGGCCTATATAAGCAGAGCTCGTTTAG (SEQ ID NO: 39) |
| LINE-1 plasmid-CD5_FCR-PI3K_T2A-GFP intron (SEQ ID NO: 40) CGGCCGCGGGGGGAGGAGCCAAGATGGCCGAATAGGAACAGCTCC GGTCTACAGCTCCCAGCGTGAGCGACGCAGAAGACGGTGATTTCT GCATTTCCATCTGAGGTACCGGGTTCATCTCACTAGGGAGTGCCA GACAGTGGGCGCAGGCCAGTGTGTGTGCGCACCGTGCGCGAGCCG AAGCAGGGCGAGGCATTGCCTCACCTGGGAAGCGCAAGGGGTCAG GGAGTTCCCTTTCCGAGTCAAAGAAAGGGGTGACGGACGCACCTG GAAAATCGGGTCACTCCCACCCGAATATTGCGCTTTTCAGACCGG CTTAAGAAACGGCGCACCACGAGACTATATCCCACACCTGGCTCG GAGGGTCCTACGCCCACGGAATCTCGCTGATTGCTAGCACAGCAG TCTGAGATCAAACTGCAAGGCGGCAACGAGGCTGGGGGAGGGGCG CCCGCCATTGCCCAGGCTTGCTTAGGTAAACAAAGCAGCAGGGAA GCTCGAACTGGGTGGAGCCCACCACAGCTCAAGGAGGCCTGCCTG CCTCTGTAGGCTCCACCTCTGGGGGCAGGGCACAGACAAACAAAA AGACAGCAGTAACCTCTGCAGACTTAAGTGTCCCTGTCTGACAGC TTTGAAGAGAGCAGTGGTTCTCCCAGCACGCAGCTGGAGATCTGA GAACGGGCAGACTGCCTCCTCAAGTGGGTCCCTGACCCCTGACCC CCGAGCAGCCTAACTGGGAGGCACCCCCCAGCAGGGGCACACTGA CACCTCACACGGCAGGGTATTCCAACAGACCTGCAGCTGAGGGTC CTGTCTGTTAGAAGGAAAACTAACAACCAGAAAGGACATCTACAC CGAAAACCCATCTGTACATCACCATCATCAAAGACCAAAAGTAGA TAAAACCACAAAGATGGGGAAAAAACAGAACAGAAAAACTGGAAA CTCTAAAACGCAGAGCGCCTCTCCTCCTCCAAAGGAACGCAGTTC CTCACCAGCAACAGAACAAAGCTGGATGGAGAATGATTTTGATGA |

TABLE 8-continued

| Plasmid and mRNA construct sequences |
|---|
| GCTGAGAGAAGAAGGCTTCAGACGATCAAATTACTCTGAGCTACG |
| GGAGGACATTCAAACCAAAGGCAAAGAAGTTGAAAACTTTGAAAA |
| AAATTTAGAAGAATGTATAACTAGAATAACCAATACAGAGAAGTG |
| CTTAAAGGAGCTGATGGAGCTGAAAACCAAGGCTCGAGAACTACG |
| TGAAGAATGCAGAAGCCTCAGGAGCCGATGCGATCAACTGGAAGA |
| AAGGGTATCAGCAATGGAAGATGAAATGAATGAAATGAAGCGAGA |
| AGGGAAGTTTAGAGAAAAAGAATAAAAAGAAATGAGCAAAGCCT |
| CCAAGAAATATGGGACTATGTGAAAAGACCAAATCTACGTCTGAT |
| TGGTGTACCTGAAAGTGATGTGGAGAATGGAACCAAGTTGGAAAA |
| CACTCTGCAGGATATTATCCAGGAGAACTTCCCCAATCTAGCAAG |
| GCAGGCCAACGTTCAGATTCAGGAAATACAGAGAACGCCACAAAG |
| ATACTCCTCGAGAAGAGCAACTCCAAGACACATAATTGTCAGATT |
| CACCAAAGTTGAAATGAAGGAAAAAATGTTAAGGGCAGCCAGAGA |
| GAAAGGTCGGGTTACCCTCAAAGGAAAGCCCATCAGACTAACAGC |
| GGATCTCTCGGCAGAAACCCTACAAGCCAGAAGAGAGTGGGGGCC |
| AATATTCAACATTCTTAAAGAAAAGAATTTTCAACCCAGAATTTC |
| ATATCCAGCCAAACTAAGCTTCATAAGTGAAGGAGAAATAAAATA |
| CTTTATAGACAAGCAAATGTTGAGAGATTTTGTCACCACCAGGCC |
| TGCCCTAAAAGAGCTCCTGAAGGAAGCGCTAAACATGGAAAGGAA |
| CAACCGGTACCAGCCGCTGCAAAATCATGCCAAAATGTAAAGACC |
| ATCAAGACTAGGAAGAAACTGCATCAACTAATGAGCAAAATCACC |
| AGCTAACATCATAATGACAGGATCAACTTCACACATAACAATATT |
| AACTTTAAATATAAATGGACTAAATTCTGCAATTAAAAGACACAG |
| ACTGGCAAGTTGGATAAAGAGTCAAGACCCATCAGTGTGCTGTAT |
| TCAGGAAACCCATCTCACGTGCAGAGACACACATAGGCTCAAAAT |
| AAAAGGATGGAGGAAGATCTACCAAGCCAATGGAAAACAAAAAAA |
| GGCAGGGGTTGCAATCCTAGTCTCTGATAAAACAGACTTTAAACC |
| AACAAAGATCAAAAGAGACAAAGAAGGCCATTACATAATGGTAAA |
| GGGATCAATTCAACAAGAGGAGCTAACTATCCTAAATATTTATGC |
| ACCCAATACAGGAGCACCCAGATTCATAAAGCAAGTCCTCAGTGA |
| CCTACAAAGAGACTTAGACTCCCACACATTAATAATGGGAGACTT |
| TAACACCCCACTGTCAACATTAGACAGATCAACGAGACAGAAAGT |
| CAACAAGGATACCCAGGAATTGAACTCAGCTCTGCACCAAGCAGA |
| CCTAATAGACATCTACAGAACTCTCCACCCCAAATCAACAGAATA |
| TACATTTTTTTCAGCACCACACCACACCTATTCCAAAATTGACCA |
| CATAGTTGGAAGTAAAGCTCTCCTCAGCAAATGTAAAAGAACAGA |
| AATTATAACAAACTATCTCTCAGACCACAGTGCAATCAAACTAGA |
| ACTCAGGATTAAGAATCTCACTCAAAGCCGCTCAACTACATGGAA |
| ACTGAACAACCTGCTCCTGAATGACTACTGGGTACATAACGAAAT |
| GAAGGCAGAAATAAAGATGTTCTTTGAAACCAACGAGAACAAAGA |
| CACCACATACCAGAATCTCTGGGACGCATTCAAAGCAGTGTGTAG |
| AGGGAAATTTATAGCACTAAATGCCTACAAGAGAAAGCAGGAAAG |
| ATCCAAAATTGACACCCTAACATCACAATTAAAAGAACTAGAAAA |
| GCAAGAGCAAACACATTCAAAAGCTAGCAGAAGGCAAGAAATAAC |
| TAAAATCAGAGCAGAACTGAAGGAAATAGAGACACAAAAAACCCT |
| TCAAAAAATCAATGAATCCAGGAGCTGGTTTTTTGAAAGGATCAA |
| CAAAATTGATAGACCGCTAGCAAGACTAATAAAGAAAAAAAGAGA |
| GAAGAATCAAATAGACACAATAAAAAATGATAAAGGGGATATCAC |
| CACCGATCCCACAGAAATACAAACTACCATCAGAGAATACTACAA |
| ACACCTCTACGCAAATAAACTAGAAAATCTAGAAGAAATGGATAC |
| ATTCCTCGACACATACACTCTCCCAAGACTAAACCAGGAAGAAGT |
| TGAATCTCTGAATCGACCAATAACAGGCTCTGAAATTGTGGCAAT |
| AATCAATAGTTTACCAACCAAAAAGAGTCCAGGACCAGATGGATT |
| CACAGCCGAATTCTACCAGAGGTACAAGGAGGAACTGGTACCATT |
| CCTTCTGAAACTATTCCAATCAATAGAAAAAGAGGGAATCCTCCC |
| TAACTCATTTTATGAGGCCAGCATCATTCTGATACCAAAGCCGGG |
| CAGAGACACAACCAAAAAAGAGAATTTTAGACCAATATCCTTGAT |
| GAACATTGATGCAAAAATCCTCAATAAAATACTGGCAAACCGAAT |
| CCAGCAGCACATCAAAAAGCTTATCCACCATGATCAAGTGGGCTT |
| CATCCCTGGGATGCAAGGCTGGTTCAATATACGCAAATCAATAAA |
| TGTAATCCAGCATATAAACAGAGCCAAAGACAAAAACCACATGAT |
| TATCTCAATAGATGCAGAAAAAGCCTTTGACAAAATTCAACAACC |
| CTTCATGCTAAAAACTCTCAATAAATTAGGTATTGATGGGACGTA |
| TTTCAAAATAATAAGAGCTATCTATGACAAACCCACAGCCAATAT |
| CATACTGAATGGGCAAAAACTGGAAGCATTCCCTTTGAAAACCGG |
| CACAAGACAGGGATGCCCTCTCTCACCGCTCCTATTCAACATAGT |
| GTTGGAAGTTCTGGCCAGGGCAATCAGGCAGGAGAAGGAAATAAA |
| GGGTATTCAATTAGGAAAAGAGGAAGTCAAATTGTCCCTGTTTGC |
| AGACGACATGATTGTTTATCTAGAAAACCCCATCGTCTCAGCCCA |
| AAATCTCCTTAAGCTGATAAGCAACTTCAGCAAAGTCTCAGGATA |
| CAAAATCAATGTACAAAAATCACAAGCATTCTTATACACCAACAA |
| CAGACAAACAGAGAGCCAAATCATGGGTGAACTCCCATTCACAAT |
| TGCTTCAAAGAGAATAAAATACCTAGGAATCCAACTTACAAGGGA |
| TGTGAAGGACCTCTTCAAGGAGAACTACAAACCACTGCTCAAGGA |
| AATAAAAGAGGAGACAAACAAATGGAAGAACATTCCATGCTCATG |
| GGTAGGAAGAATCAATATCGTGAAAATGGCCATACTGCCCAAGGT |
| AATTTACAGATTCAATGCCATCCCCATCAAGCTACCAATGACTTT |
| CTTCACAGAATTGGAAAAAACTACTTTAAAGTTCATATGGAACCA |

TABLE 8-continued

| Plasmid and mRNA construct sequences |
|---|
| AAAAAGAGCCCGCATTGCCAAGTCAATCCTAAGCCAAAAGAACAA |
| AGCTGGAGGCATCACACTACCTGACTTCAAACTATACTACAAGGC |
| TACAGTAACCAAAACAGCATGGTACTGGTACCAAAACAGAGATAT |
| AGATCAATGGAACAGAACAGAGCCCTCAGAAATAATGCCGCATAT |
| CTACAACTATCTGATCTTTGACAAACCTGAGAAAAACAAGCAATG |
| GGGAAAGGATTCCCTATTTAATAAATGGTGCTGGGAAAACTGGCT |
| AGCCATATGTAGAAAGCTGAAACTGGATCCCTTCCTTACACCTTA |
| TACAAAAATCAATTCAAGATGGATTAAAGATTTAAACGTTAAACC |
| TAAAACCATAAAAACCCTAGAAGAAAACCTAGGCATTACCATTCA |
| GGACATAGGCGTGGGCAAGGACTTCATGTCCAAAACACCAAAAGC |
| AATGGCAACAAAAGACAAAATTGACAAATGGGATCTAATTAAACT |
| AAAGAGCTTCTGCACAGCAAAAGAAACTACCATCAGAGTGAACAG |
| GCAACCTACAACATGGGAGAAAATTTTTGCAACCTACTCATCTGA |
| CAAAGGGCTAATATCCAGAATCTACAATGAACTCAAACAAATTTA |
| CAAGAAAAAAACAAACAACCCCATCAAAAAGTGGGCGAAGGACAT |
| GAACAGACACTTCTCAAAAGAAGACATTTATGCAGCCAAAAAACA |
| CATGAAGAAATGCTCATCATCACTGGCCATCAGAGAAATGCAAAT |
| CAAAACCACTATGAGATATCATCTCACACCAGTTAGAATGGCAAT |
| CATTAAAAAGTCAGGAAACAACAGGTGCTGGAGAGGATGCGGAGA |
| AATAGGAACACTTTTACACTGTTGGTGGGACTGTAAACTAGTTCA |
| ACCATTGTGGAAGTCAGTGTGGCGATTCCTCAGGGATCTAGAACT |
| AGAAATACCATTTGACCCAGCCATCCCATTACTGGGTATATACCC |
| AAATGAGTATAAATCATGCTGCTATAAAGACACATGCACACGTAT |
| GTTTATTGCGGCACTATTCACAATAGCAAAGACTTGGAACCAACC |
| CAAATGTCCAACAATGATAGACTGGATTAAGAAAATGTGGCACAT |
| ATACACCATGGAATACTATGCAGCCATAAAAAATGATGAGTTCAT |
| ATCCTTTGTAGGGACATGGATGAAATTGGAAACCATCATTCTCAG |
| TAAACTATCGCAAGAACAAAAAACCAAACACCGCATATTCTCACT |
| CATAGGTGGGAATTGAACAATGAGATCACATGGACACAGGAAGGG |
| GAATATCACACTCTGGGGACTGTGGTGGGGTCGGGGGAGGGGGGA |
| GGGATAGCATTGGGAGATATACCTAATGCTAGATGACACATTAGT |
| GGGTGCAGCGCACCAGCATGGCACATGTATACGGATCCGAATTCT |
| CGACGGATCGATCCGAACAAACGACCCAACACCCGTGCGTTTTAT |
| TCTGTCTTTTTATTGCCGATCCCCTCAGAAGAACTCGTCAAGAAG |
| GCGATAGAAGGCGATGCGCTGCGAATCGGGAGCGGCGATACCGTA |
| AAGCACGAGGAAGCGGTCAGCCCATTCGCCGCCAAGCTCTTCAGC |
| AATATCACGGGTAGCCAACGCTATGTCCTGATAGCGGTCGGCCGC |
| TTTACTTGTACAGCTCGTCCATGCCGAGAGTGATCCCGGCGGCGG |
| TCACGAACTCCAGCAGGACCATGTGATCGCGCTTCTCGTTGGGGT |
| CTTTGCTCAGGGCGGACTGGGTGCTCAGGTAGTGGTTGTCGGGCA |
| GCAGCACGGGGCCGTCGCCGATGGGGGTGTTCTGCTGGTAGTGGT |
| CGGCCAGGTGAGTCCAGGAGATGTTTCAGCACTGTTGCCTTTAGT |
| CTCGAGGCAACTTAGACAACTGAGTATTGATCTGAGCACAGCAGG |
| GTGTGAGCTGTTTGAAGATACTGGGGTTGGGGGTGAAGAAACTGC |
| AGAGGACTAACTGGGCTGAGACCCAGTGGCAATGTTTTAGGGCCT |
| AAGGAATGCCTCTGAAAATCTAGATGGACAACTTTGACTTTGAGA |
| AAAGAGAGGTGGAAATGAGGAAAATGACTTTTCTTTATTAGATTT |
| CGGTAGAAAGAACTTTCATCTTTCCCCTATTTTTGTTATTCGTTT |
| TAAAACATCTATCTGGAGGCAGGACAAGTATGGTCATTAAAAAGA |
| TGCAGGCAGAAGGCATATATTGGCTCAGTCAAAGTGGGGAACTTT |
| GGTGGCCAAACATACATTGCTAAGGCTATTCCTATATCAGCTGGA |
| CACATATAAAATGCTGCTAATGCTTCATTACAAACTTATATCCTT |
| TAATTCCAGATGGGGGCAAAGTATGTCCAGGGGTGAGGAACAATT |
| GAAACATTTGGGCTGGAGTAGATTTTGAAAGTCAGCTCTGTGTGT |
| GTGTGTGTGTGTGTGTGTGTGAGAGCGTGTGTTTCTTTTAACGTT |
| TTCAGCCTACAGCATACAGGGTTCATGGTGGCAAGAAGATAACAA |
| GATTTAAATTATGGCCAGTGACTAGTGCTGCAAGAAGAACAACTA |
| CCTGCATTTAATGGGAAAGCAAAATCTCAGGCTTTGAGGGAAGTT |
| AACATAGGCTTGATTCTGGGTGGAAGCTGGGTGTGTAGTTATCTG |
| GAGGCCAGGCTGGAGCTCTCAGCTCACTATGGGTTCATCTTTATT |
| GTCTCCTTTCATCTCAACAGCTGCACGCTGCCGTCCTCGATGTTG |
| TGGCGGATCTTGAAGTTCACCTTGATGCCGTTCTTCTGCTTGTCG |
| GCCATGATATAGACGTTGTGGCTGTTGTAGTTGTACTCCAGCTTG |
| TGCCCCAGGATGTTGCCGTCCTCCTTGAAGTCGATGCCCTTCAGC |
| TCGATGCGGTTCACCAGGGTGTCGCCCTCGAACTTCACCTCGGCG |
| CGGGTCTTGTAGTTGCCGTCGTCCTTGAAGAAGATGGTGCGCTCC |
| TGGACGTAGCCTTCGGGCATGGCGGACTTGAAGAAGTCGTGCTGC |
| TTCATGTGGTCGGGGTAGCGGCTGAAGCACTGCACGCCGTAGGTC |
| AGGGTGGTCACGAGGGTGGGCCAGGGCACGGGCAGCTTGCCGGTG |
| GTGCAGATGAACTTCAGGGTCAGCTTGCCGTAGGTGGCATCGCCC |
| TCGCCCTCGCCGGACACGCTGAACTTGTGGCCGTTTACGTCGCCG |
| TCCAGCTCGACCAGGATGGGCACCACCCCGGTGAACAGCTCCTCG |
| CCCTTGCTCACCATAGGGCCGGGATTCTCCTCCACGTCACCGCAT |
| GTTAGAAGACTTCCTCTGCCCTCCATGTTCTCGTAGGAGTCGGCG |
| TCCTCTTCGTGGTTAGGTCCAGGTTGGCCTCTGATAGACCGCAGC |
| TGAGGAGCGGCGTACAGAATGCCTCTCATGTCCTCATAGCTGCCG |
| CTGCCTTGTGGAGGCTTCTCGTGCTTCAGTGTCTCGTATGTCTCT |
| TGATTCCGGGTGCTCAGGCCGGTGTACACGCCATCAGATTTCTCG |

TABLE 8-continued

Plasmid and mRNA construct sequences

TAGCTGGTGATGGCGGCCTTCCGCACTTGGATCTTCAGCCGTCTG
CAGTACAGGGTGATGACCAGAGACAGCAGCAGGACACCACATGTG
CCAGCCAGAGGGGCCCAAATGTAGATATCCAGGCCTCTGGTATGC
ACAGCTCCGCCTGCAGCAGGTCTACAGGCTTCAGGTCTGAGAGAC
AGAGGCTGGCTGGCGATTGTAGGAGCTGGTGTAGGTGGTCTAGGA
GCGGGTGTTGTTGTAGGCTTGGCGGGCAGAAACACGGGCACGAAG
TGGCTGAAGTACATGATGCTATTGCTCAGGGCTCCGCTTCCTCCG
CCGCCTGATTTGATTTCCAGCTTGGTGCCTCCGCCAAATGTCCAA
GGGCTCTCGTCGTACTGCTGGCAGTAGTAGATGCCGAAGTCCTCG
TACTGCAGGCTGCTGATTGTCAGGGTGTAGTCGGTGCCAGAGCCG
CTGCCAGAAAATCTGCTTGGCACGCGCGCTTTCCAGTCTGTTGGCC
CGGTAGATCAGTGTCTTAGGGGCCTTGCCAGGCTTCTGCTGGAAC
CAGCTCAGGTAGCTGTTGATGTCCTGGCTGGCTCTACAGGTGATG
GTCACTCTATCGCCCACAGAGGCAGACAGGCTGCTAGGGCTCTGT
GTCATCTGGATATCAGAGCCACCACCGCCAGATCCACCGCCACCT
GATCCTCCGCCTCCGCTAGAAACTGTCACTGTGGTGCCCTGGCCC
CACACATCGAAGTACCAGTCGTAGCCTCTTCTGGTGCAGAAGTAC
ACGGCGGTATCCTCGGCTCTCAGGCTGTTGATCTGCAGGTAGGCG
GTGTTCTTGCTGTCGTCCAGGCTGAAGGTGAATCTGCCCTTAAAG
CTATCGGCGTAGGTTGGCTCGCCGGTGTGGGTATTGATCCAGCCC
ATCCACTCAAGGCCTTTTCCAGGGGCCTGTCGGACCCAGTTCATG
CCGTAGTTGGTGAAGGTGTAGCCGCTGGCGGCACAGCTGATTCTG
ACAGATCCGCCAGGTTTCACAAGTCCGCCGCCAGCTGAACCAGC
TGGATCTCAGAGATGCTACAGGCCACTGTTCCCAGCAGCAGCAGA
GACTGCAGCCACATTCGAAGCTTGAGCTCGAGATCTGAGTCCGGT
AGCGCTAGCGGATCTGACGGTTCACTAAACCAGCTCTGCTTATAT
AGACCTCCCACCGTACACGCCTACCGCCCATTTGCGTCAATGAGG
CGGAGTTGTTACGACATTTTGGAAAGTCCCGTTGATTTTGGTGCC
AAAACAAACTCCCATTGACGTCAATGGGGTGGAGACTTGGAAATC
CCCGTGAGTCAAACCGCTATCCACGCCCATTGATGTACTGCCAAA
ACCGCATCACCATGGTAATAGCGATGACTAATACGTAGATGTACT
GCCAAGTAGGAAAGTCCCATAAGGTCATGTACTGGGCATAATGCC
AGGCGGGCCATTTACCGTCATTGACGTCAATAGGGGGCGTACTTG
GCATATGATACACTTGATGTACTGCCAAGTGGGCAGTTTACCGTA
AATACTCCACCCATTGACGTCAATGGAAAGTCCCTATTGGCGTTA
CTATGGGAACATACGTCATTATTGACGTCAATGGGCGGGGGTCGT
TGGGCCGGTCAGCCAGGCGGGCCATTTACCGTAAGTTATGTAACGC
GGAACTCCATATATGGGCTATGAACTAATGACCCCGTAATTGATT
ACTATTAGCCCGGGGGATCCAGACATGATAAGATACATTGATGAG
TTTGGACAAACCACAACTAGAATGCAGTGAAAAAAATGCTTTATT
TGTGAAATTTGTGATGCTATTGCTTTATTTGTAACCATTATAAGC
TGCAATAAACAAGTTAACAACAACAATTGCATTCATTTTATGTTT
CAGGTTCAGGGGGAGGTGTGGGAGGTTTTTTAAAGCAAGTAAAAC
CTCTACAAATGTGGTATGCTGATTATGATCCGGCTGCCTGCGG
GTTTCGGTGATGACGGTGAAAACCTCTGACACATGCAGCTCCCGG
AGACGGTCACAGCTTGTCGTAAGCGGATGCCGGGAGCAGACAAG
CCCGTCAGGGCGCGTCAGCGGGTGTTGGCGGGTGTCGGGGCGCAG
CCATGAGGTCGATCGACTCTAGAGGATCGATCCCCGCCCCGGACG
AACTAAACCTGACTACGACATCTCTGCCCCTTCTTCGCGGGACG
TGCATGTAATCCTTCAGTTGGTTGGTACAACTTGCCAACTGGGC
CCTGTTCCACATGTGACACGGGGGGGACCAAACACAAAGGGGTT
CTCTGACTGTAGTTGACATCCTTATAAATGGATGTGCACATTTGC
CAACACTGAGTGGCTTTCATCCTGGAGCAGATTTGCAGTCTGTG
GACTGCAACACAACATTGCCTTTATGTGTAACTCTTGGCTGAAGC
TCTTACACCAATGCTGGGGGACATGTACCTCCCAGGGGCCCAGGA
AGACTACGGGAGGCTACACCAACGTCAATCAGAGGGGCCTGTGTA
GCTACCGATAAGCGGACCCTCAAGAGGGCATTAGCAATAGTGTTT
ATAAGGCCCCCTTGTTAACCCTAAACGGGTAGCATATGCTTCCCG
GGTAGTAGTATATACTATCCAGACTAACCCTAATTCAATAGCATA
TGTTACCCAACGGGAAGCATATGCTATCGAATTAGGGTTAGTAAA
AGGGTCCTAAGGAACAGCAGATATCTCCCACCCATGAGCTGTCAC
GGTTTTATTTACATGGGGTCAGGATTCCATGAGGGTAGTGAACCA
TTTTAGTCACAAGGGCAGTGGCTGAAGATCAAGGAGCGGGCAGTG
AACTCTCCTGAATCTTCGCCTGCTTCTTCATTCTCCTTCGTTTAG
CTAATAGAATAACTGCTGAGTTGTGAACAGTAAGCTAAGGTGAGC
GTGCTCGAAAACAAGGTTTCAGGTGACGCCCCAGAATAAAATTT
GGACGGGGGGTTCAGTGGTGGCATTGTGCTATGACACCAATATAA
CCCTCACAAACCCCTTGGGCAATAAATACTAGTGTAGGAATGAAA
CATTCTGAATATCTTTAACAATAGAATCATGGGGTGGGGACAA
GCCGTAAAGACTGGATGTCCATCTCACACGAATTTATGGCTATGG
GCAACACATAATCCTAGTGCAATATGATACTGGGGTTATTAAGAT
GTGTCCCAGGCAGGGACCAAGACAGGTGAACCATGTTGTTACACT
CTATTTGTAACAGGATAAGTAGGATGGACGCCGACAGCAGCGGA
CTCCACTGGTTGTCTCTAACACCCCCGAAAATTAAACGGGGCTCC
ACGCCAATGGGCCCATAAACAAAGACAAGTGGCCACTCTTTTTT
TTGAAATTGTGGAGTGGGGCACGCGTCAGCCCCCACACGCCGCC
CTGCGGTTTTGGACTGTAAAATAAGGGTGTAATAACTTGGCTGAT
TGTAACCCCGCTAACCACTGCGGTCAAACCACTTGCCCACAAAAC

TABLE 8-continued

Plasmid and mRNA construct sequences

CACTAATGGCACCCCGGGGAATACCTGCATAAGTAGGTGGGCGGG
CCAAGATAGGGGCGCGATTGCTGCGATCTGGAGGACAAATTACAC
ACACTTGCGCCTGAGCGCCAAGCACAGGGTTGTTGGTCCTCATAT
TCACGAGGTCGCTGAGAGCACGGTGGGCTAATGTTGCCATGGGTA
GCATATACTACCCAAATATCTGGATAGCATATGCTATCCTAATCT
ATATCTGGGTAGCATAGGCTATCTAATCTATATCTGGGTAGCAT
ATGCTATCCTAATCTATATCTGGGTAGTATATGCTATCCTAATTT
ATATCTGGGTAGCATAGGCTATCCTAATCTATATCTGGGTAGCAT
ATGCTATCCTAATCTATATCTGGGTAGTATATGCTATCCTAATCT
GTATCCGGGTAGCATATGCTATCCTAATAGAGATTAGGGTAGTAT
ATGCTATCCTAATTTATATCTGGGTAGCATATACTACCCAAATAT
CTGGATAGCATATGCTATCCTAATCTATATCTGGGTAGCATATGC
TATCCTAATCTATATCTGGGTAGCATAGGCTATCCTAATCTATAT
CTGGGTAGCATATGCTATCCTAATCTATATCTGGGTAGTATATGC
TATCCTAATTTATATCTGGGTAGCATAGGCTATCCTAATCTATAT
CTGGGTAGCATATGCTATCCTAATCTATATCTGGGTAGTATATGC
TATCCTAATCTGTATCCGGGTAGCATATGCTATCCTCATGCATAT
ACAGTCAGCATATGATACCCAGTAGTAGAGTGGGAGTGCTATCCT
TTGCATATGCCGCACCTCCCAAGGGGCGTGAATTTTCGCTGCT
TGTCCTTTTCCTGCATGCTGGTTGCTCCCATTCTTAGGTGAATTT
AAGGAGGCCAGGCTAAAGCCGTCGCATGTCTGATTGCTCACCAGG
TAAATGTCGCTAATGTTTTCCAACGCGAGAAGGTGTTGAGCGCGG
AGCTGAGTGACGTGACAACATGGGTATGCCCAATTGCCCCATGTT
GGGAGGACGAAAATGGTGACAAGACAGATGGCCAGAAATACACCA
ACAGCACGCATGATGTCTACTGGGGATTATTCTTTAGTGCGGGG
GAATACACGGCTTTTAATACGATTGAGGGCGTCTCCTAACAAGTT
ACATCACTCCTGCCCTTCCTCACCCTCATCTCCATCACCTCCTTC
ATCTCCGTCATCTCCGTCATCACCCTCCGCGGCAGCCCCTTCCAC
CATAGGTGGAAAACAGGGAGGCAAATCTACTCCATCGTCAAAGCT
GCACACAGTCACCCTGATATTGCAGGTAGGAGCGGGCTTTGTCAT
AACAAGGTCCTTAATCGCATCCTTCAAAACCTCAGCAAATATATG
AGTTTGTAAAAAGACCATGAAATAACAGACAATGGACTCCCTTAG
CGGGCAGGTTGTGGCGGGTCCAGGGGCATTCCAAAGGGGAG
ACGACTCAATGGTGTAAGACGACATTGTGGAATAGCAAGGGCAGT
TCCTCGCCTTAGGTTGTAAAGGGAGGTCTTACTACCTCCATATAC
GAACACACCGCCAAGTTCCTTCGTCGGTAGTCCTTTCTAC
GTGACTCCTAGCCAGGAGAGCTCTTAAACCTTCTGCAATGTTCTC
AAATTTCGGGTTGGAACCTCCTTGACCACGATGCTTTCCAAACCA
CCCTCCTTTTTTGCGCCTGCCTCCATCACCCTGACCCCGGGGTCC
AGTGCTTGGGCCTTCTCCTGGGTCATCTGCGGGGCCTGCTCTAT
CGCTCCCGGGGCACGTCAGGCTCACCATCTGGGCCACCTTCTTG
GTGGTATTCAAAATAATCGGCTTCCCCTACAGGGTGGAAAAATGG
CCTTCTACCTGGAGGGGCCTGCGCGGTGGAGACCCGGATGATGA
TGACTGACTACTGGGACTCTCTGGGCCTCTTTTCTCACGTCCACG
ACCTCTCCCCTGGCTCTTTACGACTTCCCCCCTGGCTCTTTC
ACGTCCTCTACCCCGGCGGCCTCCACTACCTCCTGACCCCGGCC
TCCACTACCTCCTCGACCCCGGCCTCCACTGCCTCCTCGACCCCG
GCCTCCACTGCCTCCTGCCCCTCCTGCTCCTGCCCCTCCTCC
TGCTCCTGCCCCTCCTGCCCCTCCTGCTCCTGCCCCTCCTGC
CCCTCCTCCTGCTCCTGCCCCTCCTGCCCCTCCTCCTGCTCCTGC
CCCTCCTGCCCCTCCTGCTCCTGCCCCTCCTGCTCCTGCTGCCCC
TCCTGCTCCTGCCCCTCCTGCTCCTGCCCCTCCTGCCCCTCCTGC
CCCTCCTCCTGCTCCTGCCCCTCCTGCTCCTGCCCCTCCTGCCCC
TCCTGCCCCTCCTGCTCCTGCCCCTCCTGCTCCTGCCCCTCCTGC
CCCTCCTGCCCCTCCTGCTCCTGCCCCTCCTGCTCCTGCCCCTCC
TGCCCCTCCTGCCCCTCCTGCTCCTGCCCCTCCTGCCCCTCCTGC
TCCTGCCCCTCCTGCTCCTGCCCCTCCTGCCCCTCCTCCTGCTCC
TGCCCCTCCTCCTGCTCCTGCCCCTCCTGCCCCTCCTGCCCCTCC
TCCTGCTCCTGCCCCTCCTGCTCCTGCCCCTCCTGCCCCTCCTGC
TCCTGCCCCTCCTGCCCCTCCCGCTCCTGCTCCTGCTCCTGT
TCCACCGTGGGTCCCTTTGCAGCCAATGCAACTTGGACGTTTTTG
GGGTCTCCGGACACATCTCTATGTCTTGGCCCTGATCCTGAGCC
GCCCGGGGCTCCTGGTCTTCCGCTCCTGCGTCCTCGTCCTCTTCC
CCGTCCTCGTCCATGGTTATCACCCCCTCTTCTTTGAGGTCCACT
GCCGCCGGAGCCTTCTGGTCCAGATGTGTCTCCCTTCTCTCCTAG
GCCATTTCAGGTCCTGACTTCTGCCCCCTCGTCAGACATGATTCA
CACTAAAAGAGATCAATAGACATCTTTATTAGACAGACGCTCAGTG
AATACAGGGAGTGCAGACTCCTGCCCCCTCCAACAGCCCCCCAC
CCTCATCCCCTTCATGGTCGCTGTCAGACAGATCCAGGTCTGAAA
ATTCCCATCCTCCGAACCTGCTCCTGCCTCCATCACCAATTACTG
GCAGCCCGGAAAATCCCGCTGAACATCTCAAGATTTGCTTCCT
GAGCCTCAAGCCAGGCCTCAAATTCCTCGTCCCCCTTTTTGCTGG
ACGGTAGGATGGGGATTCTCGGGACCCCTCCTCTTCCTCTTCAA
GGTCACCAGACAGAGATGCTACTGGGGCAACGGAAGAAAGCTGG
GTGCGGCCTGTGAGGATCAGCTTATCGATGATAAGCTGTCAAACA

TABLE 8-continued

Plasmid and mRNA construct sequences

TGAGAATTCTTGAAGACGAAAGGGCCTCGTGATACGCCTATTTTT
ATAGGTTAATGTCATGATAATAATGGTTTCTTAGACGTCAGGTGG
CACTTTTCGGGGAAATGTGCGCGGAACCCCTATTTGTTTATTTTT
CTAAATACATTCAAATATGTATCCGCTCATGAGACAATAACCCTG
ATAAATGCTTCAATAATATTGAAAAAGGAAGAGTATGAGTATTCA
ACATTTCCGTGTCGCCCTTATTCCCTTTTTTGCGGCATTTTGCCT
TCCTGTTTTTGCTCACCCAGAAACGCTGGTGAAAGTAAAAGATGC
TGAAGATCAGTTGGGTGCACGAGTGGGTTACATCGAACTGGATCT
CAACAGCGGTAAGATCCTTGAGAGTTTTCGCCCCGAAGAACGTTT
TCCAATGATGAGCACTTTTAAAGTTCTGCTATGTGGCGCGGTATT
ATCCCGTGTTGACGCCGGGCAAGAGCAACTCGGTCGCCGCATACA
CTATTCTCAGAATGACTTGGTTGAGTACTCACCAGTCACAGAAAA
GCATCTTACGGATGGCATGACAGTAAGAGAATTATGCAGTGCTGC
CATAACCATGAGTGATAACACTGCGGCCAACTTACTTCTGACAAC
GATCGGAGGACCGAAGGAGCTAACCGCTTTTTTGCACAACATGGG
GGATCATGTAACTCGCCTTGATCGTTGGGAACCGGAGCTGAATGA
AGCCATACCAAACGACGAGCGTGACACCACGATGCCTGCAGCAAT
GGCAACAACGTTGCGCAAACTATTAACTGGCGAACTACTTACTCT
AGCTTCCCGGCAACAATTAATAGACTGGATGGAGGCGGATAAAGT
TGCAGGACCACTTCTGCGCTCGGCCCTTCCGGCTGGCTGGTTTAT
TGCTGATAAATCTGGAGCCGGTGAGCGTGGGTCTCGCGGTATCAT
TGCAGCACTGGGGCCAGATGGTAAGCCCTCCCGTATCGTAGTTAT
CTACACGACGGGGAGTCAGGCAACTATGGATGAACGAAATAGACA
GATCGCTGAGATAGGTGCCTCACTGATTAAGCATTGGTAACTGTC
AGACCAAGTTTACTCATATATACTTTAGATTGATTTAAAACTTCA
TTTTTAATTTAAAAGGATCTAGGTGAAGATCCTTTTTGATAATCT
CATGACCAAAATCCCTTAACGTGAGTTTTCGTTCCACTGAGCGTC
AGACCCCGTAGAAAAGATCAAAGGATCTTCTTGAGATCCTTTTTT
TCTGCGCGTAATCTGCTGCTTGCAAACAAAAAAACCACCGCTACC
AGCGGTGGTTTGTTTGCCGGATCAAGAGCTACCAACTCTTTTTCC
GAAGGTAACTGGCTTCAGCAGAGCGCAGATACCAAATACTGTCCT
TCTAGTGTAGCCGTAGTTAGGCCACCACTTCAAGAACTCTGTAGC
ACCGCCTACATACCTCGCTCTGCTAATCCTGTTACCAGTGGCTGC
TGCCAGTGGCGATAAGTCGTGTCTTACCGGGTTGGACTCAAGACG
ATAGTTACCGGATAAGGCGCAGCGGTCGGGCTGAACGGGGGGTTC
GTGCACACAGCCCAGCTTGGAGCGAACGACCTACACCGAACTGAG
ATACCTACAGCGTGAGCTATGAGAAAGCGCCACGCTTCCCGAAGG
GAGAAAGGCGGACAGGTATCCGGTAAGCGGCAGGGTCGGAACAGG
AGAGCGCACGAGGGAGCTTCCAGGGGGAAACGCCTGGTATCTTTA
TAGTCCTGTCGGGTTTCGCCACCTCTGACTTGAGCGTCGATTTTT
GTGATGCTCGTCAGGGGGGCGGAGCCTATGGAAAAACGCCAGCAA
CGCGGCCTTTTTACGGTTCCTGGCCTTTTGCTGGCCTTTTGCTCA
CATGTTCTTTCCTGCGTTATCCCCTGATTCTGTGGATAACCGTAT
TACCGCCTTTGAGTGAGCTGATACCGCTCGCCGCAGCCGAACGAC
CGAGCGCAGCGAGTCAGTGAGCGAGGAAGCGGAAGAGCGCCTGAT
GCGGTATTTTCTCCTTACGCATCTGTGCGGTATTTCACACCGCAT
ATGGTGCACTCTCAGTACAATCTGCTCTGATGCCGCATAGTTAAG
CCAGCTGTGGAATGTGTGTCAGTTAGGGTGTGGAAAGTCCCCAGG
CTCCCCAGCAGGCAGAAGTATGCAAAGCATGCATCTCAATTAGTC
AGCAACCAGGTGTGGAAAGTCCCCAGGCTCCCCAGCAGGCAGAAG
TATGCAAAGCATGCATCTCAATTAGTCAGCAACCATAGTCCCGCC
CCTAACTCCGCCCATCCCGCCCCTAACTCCGCCCAGTTCCGCCCA
TTCTCCGCCCCATGGCTGACTAATTTTTTTTATTTATGCAGAGGC
CGAGGCCGCCTCGGCCTCTGAGCTATTCCAGAAGTAGTGAGGAGG
CTTTTTTGGAGGCCTAGGCTTTTGCAAAAAGCTTGCATGCCTGCA
GGTCGGCCGCCACGACCGGTGCCGCCACCATCCCCTGACCCACGC
CCCTGACCCCTCACAAGGAGACGACCTTCCATGACCGAGTACAAG
CCCACGGTGCGCCTCGCCACCCGCGACGACGTCCCCCGGGCCGTA
CGCACCCTCGCCGCCGCGTTCGCCGACTACCCCGCCACGCGCCAC
ACCGTCGACCCGGACCGCCACATCGAGCGGGTCACCGAGCTGCAA
GAACTCTTCCTCACGCGCGTCGGGCTCGACATCGGCAAGGTGTGG
GTCGCGGACGACGGCGCCGCGGTGGCGGTCTGGACCACGCCGGAG
AGCGTCGAAGCGGGGGCGGTGTTCGCCGAGATCGGCCCGCGCATG
GCCGAGTTGAGCGGTTCCCGGCTGGCCGCGCAGCAACAGATGGAA
GGCCTCCTGGCGCCGCACCGGCCCAAGGAGCCCGCGTGGTTCCTG
GCCACCGTCGGCGTCTCGCCCGACCACCAGGGCAAGGGTCTGGGC
AGCGCCGTCGTGCTCCCCGGAGTGGAGGCGGCCGAGCGCGCCGGG
GTGCCCGCCTTCCTGGAGACCTCCGCGCCCCGCAACCTCCCCTTC
TACGAGCGGCTCGGCTTCACCGTCACCGCCGACGTCGAGGTGCCC
GAAGGACCGCGCACCTGGTGCATGACCCGCAAGCCCGGTGCCTGA
CGCCCGCCCCACGACCCGCAGCGCCCGACCGAAAGGAGCGCACGA
CCCCATGGCTCCGACCGAAGCCGACCCGGGCGGCCCCGCCGACCC
CGCACCCGCCCCCGAGGCCCACCGACTCTAGAGGATCATAATCAG
CCATACCACATTTGTAGAGGTTTTACTTGCTTTAAAAAACCTCCC
ACACCTCCCCCTGAACCTGAAACATAAAATGAATGCAATTGTTGT
TGTTAACTTGTTTATTGCAGCTTATAATGGTTACAAATAAAGCAA
TAGCATCACAAATTTCACAAATAAAGCATTTTTTTCACTGCATTC
TAGTTGTGGTTTGTCCAAACTCATCAATGTATCTTATCATGTCTG

TABLE 8-continued

Plasmid and mRNA construct sequences

GATCACTCGCCGATAGTGGAAACCGACGCCCCAGCACTCGTCCGA
GGGCAAAGGAATAGGGGAGATGGGGGAGGCTAACTGAAACACGGA
AGGAGACAATACCGGAAGGAACCCGCGCTATGACGGCAATAAAAA
GACAGAATAAAACGCACGGGTGTTGGGTCGTTTGTTCATAAACGC
GGGGTTCGGTCCCAGGGCTGGCACTCTGTCGATACCCCACCGAGA
CCCCATTGGGGCCAATACGCCCGCGTTTCTTCCTTTTCCCCACCC
CACCCCCCAAGTTCGGGTGAAGGCCCAGGGCTCGCAGCCAACGTC
GGGGCGGCAGGCCCTGCCATAGCCACTGGCCCCGTGGGTTAGGGA
CGGGGTCCCCCATGGGGAATGGTTTATGGTTCGTGGGGGTTATTA
TTTTGGGCGTTGCGTGGGGTCTGGTCCACGACTGGACTGAGCAGA
CAGACCCATGGTTTTTGGATGGCCTGGGCATGGACCGCATGTACT
GGCGCGACACGAACACCGGGCGTCTGTGGCTGCCAAACACCCCCG
ACCCCCAAAAACCACCGCGCGGATTTCTGGCGTGCCAAGCTAGTC
GACCAATTCTCATGTTTGACAGCTTATCATCGCAGATCCGGGCAA
CGTTGTTGCATTGCTGCAGGCGCAGAACTGGTAGGTATGGAAGAT
CTCTAGAAGCTGGGTACCAGCTGCTAGCAAGCTTGCTAGCGGCCG
GCTCGAGTTTACTCCCTATCAGTGATAGAGAACGTATGTCGAGTT
TACTCCCTATCAGTGATAGAGAACGATGTCGAGTTTACTCCCTAT
CAGTGATAGAGAACGTATGTCGAGTTTACTCCCTATCAGTGATAG
AGAACGTATGTCGAGTTTACTCCCTATCAGTGATAGAGAACGTAT
GTCGAGTTTATCCCTATCAGTGATAGAGAACGTATGTCGAGTTTA
CTCCCTATCAGTGATAGAGAACGTATGTCGAGGTAGGCGTGTACG
GTGGGAGGCCTATATAAGCAGAGCTCGTTTAGTGAACCGTCAGAT
CGCCG
(SEQ ID NO: 40)

LINE-1 plasmid Her2-Cd3z-T2A GFP intron
(SEQ ID NO: 41)
CGGCCGCGGGGGGAGGAGCCAAGATGGCCGAATAGGAACAGCTCC
GGTCTACAGCTCCCAGCGTGAGCGACGCAGAAGACGGTGATTTCT
GCATTTCCATCTGAGGTACCGGGTTCATCTCACTAGGGAGTGCCA
GACAGTGGGCGCAGGCCAGTGTGTGTGCGCACCGTGCGCGAGCCG
AAGCAGGGCGAGGCATTGCCTCACCTGGGAAGCGCAAGGGGTCAG
GGAGTTCCCTTTCCGAGTCAAAGAAAGGGGTGACGGACGCACCTG
GAAAATCGGGTCACTCCCACCCGAATATTGCGCTTTTCAGACCGG
CTTAAGAAACGGCGCACCACGAGACTATATCCCACACCTGGCTCG
GAGGGTCCTACGCCCACGGAATCTCGCTGATTGCTAGCACAGCAG
TCTGAGATCAAACTGCAAGGCGGCAACGAGGCTGGGGGAGGGGCG
CCCGCCATTGCCCAGGCTTGCTTAGGTAAACAAAGCAGCAGGGAA
GCTCGAACTGGGTGGAGCCCACCACAGCTCAAGGAGGCCTGCCTG
CCTCTGTAGGCTCCACCTCTGGGGGCAGGGCACAGACAAACAAAA
AGACAGCAGTAACCTCTGCAGACTTAAGTGTCCCTGTCTGACAGC
TTTGAAGAGAGCAGTGGTTCTCCCAGCACGCAGCTGGAGATCTGA
GAACGGGCAGACTGCCTCCTCAAGTGGGTCCCTGACCCCTGACCC
CCGAGCAGCCTAACTGGGAGGCACCCCCCAGCAGGGGCACACTGA
CACCTCACACGGCAGGGTATTCCAACAGACCTGCAGCTGAGGGTC
CTGTCTGTTAGAAGGAAAACTAACAACCAGAAAGGACATCTACAC
CGAAAACCCATCTGTACATCACCATCATCAAAGACCAAAAGTAGA
TAAAACCACAAAGATGGGGAAAAAACAGAACAGAAAAACTGGAAA
CTCTAAAACGCAGAGCGCCTCTCCTCCTCCAAAGGAACGCAGTTC
CTCACCAGCAACAGAACAAAGCTGGATGGAGAATGATTTTGATGA
GCTGAGAGAAGAAGGCTTCAGACGATCAAATTACTCTGAGCTACG
GGAGGACATTCAAACCAAAGGCAAAGAAGTTGAAAACTTTGAAAA
AAATTTAGAAGAATGTATAACTAGAATAACCAATACAGAGAAGTG
CTTAAAGGAGCTGATGGAGCTGAAAACCAAGGCTCGAGAACTACG
TGAAGAATGCAGAAGCCTCAGGAGCCGATGCGATCAACTGGAAGA
AAGGGTATCAGCAATGGAAGATGAAATGAATGAAATGAAGCGAGA
AGGGAAGTTTAGAGAAAAAAGAATAAAAAGAAATGAGCAAAGCCT
CCAAGAAATATGGGACTATGTGAAAAGACCAAATCTACGTCTGAT
TGGTGTACCTGAAAGTGATGTGGAGAATGGAACCAAGTTGGAAAA
CACTCTGCAGGATATTATCCAGGAGAACTTCCCCAATCTAGCAAG
GCAGGCCAACGTTCAGATTCAGGAAATACAGAGAACGCCACAAAG
ATACTCCTCGAGAAGAGCAACTCCAAGACACATAATTGTCAGATT
CACCAAAGTTGAAATGAAGGAAAAAATGTTAAGGGCAGCCAGAGA
GAAAGGTCGGGTTACCCTCAAAGGAAAGCCCATCAGACTAACAGC
GGATCTCTCGGCAGAAACCCTACAAGCCAGAAGAGAGTGGGGGCC
AATATTCAACATTCTTAAAGAAAAGAATTTTCAACCCAGAATTTC
ATATCCAGCCAAACTAAGCTTCATAAGTGAAGGAGAAATAAAATA
CTTTATAGACAAGCAAATGTTGAGAGATTTTGTCACCACCAGGCC
TGCCCTAAAAGAGCTCCTGAAGGAAGCGCTAAACATGGAAAGGAA
CAACCGGTACCAGCCGCTGCAAAATCATGCCAAAATGTAAAGACC
ATCAAGACTAGGAAGAAACTGCATCAACTAATGAGCAAAATCACC
AGCTAACATCATAATGACAGGATCAACTTCACACATAACAATATT
AACTTTAAATATAAATGGACTAAATTCTGCAATTAAAAGACACAG
ACTGGCAAGTTGGATAAAGAGTCAAGACCCATCAGTGTGCTGTAT
TCAGGAAACCCATCTCACGTGCAGAGACACACATAGGCTCAAAAT
AAAAGGATGGAGGAAGATCTACCAAGCCAATGGAAAACAAAAAAA
GGCAGGGGTTGCAATCCTAGTCTCTGATAAAACAGACTTTAAACC TABLE 8-continued

| Plasmid and mRNA construct sequences |
|---|
| AACAAAGATCAAAAGAGACAAAGAAGGCCATTACATAATGGTAAA |
| GGGATCAATTCAACAAGAGGAGCTAACTATCCTAAATATTTATGC |
| ACCCAATACAGGAGCACCCAGATTCATAAAGCAAGTCCTCAGTGA |
| CCTACAAAGAGACTTAGACTCCCACACATTAATAATGGGAGACTT |
| TAACACCCCACTGTCAACATTAGACAGATCAACGAGACAGAAAGT |
| CAACAAGGATACCCAGGAATTGAACTCAGCTCTGCACCAAGCAGA |
| CCTAATAGACATCTACAGAACTCTCCACCCCAAATCAACAGAATA |
| TACATTTTTTTCAGCACCACACCACACCTATTCCAAAATTGACCA |
| CATAGTTGGAAGTAAAGCTCTCCTCAGCAAATGTAAAAGAACAGA |
| AATTATAACAAACTATCTCTCAGACCACAGTGCAATCAAACTAGA |
| ACTCAGGATTAAGAATCTCACTCAAAGCCGCTCAACTACATGGAA |
| ACTGAACAACCTGCTCCTGAATGACTACTGGGTACATAACGAAAT |
| GAAGGCAGAAATAAAGATGTTCTTTGAAACCAACGAGAACAAAGA |
| CACCACATACCAGAATCTCTGGGACGCATTCAAAGCAGTGTGTAG |
| AGGGAAATTTATAGCACTAAATGCCTACAAGAGAAAGCAGGAAAG |
| ATCCAAAATTGACACCCTAACATCACAATTAAAAGAACTAGAAAA |
| GCAAGAGCAAACACATTCAAAAGCTAGCAGAAGGCAAGAAATAAC |
| TAAAATCAGAGCAGAACTGAAGGAAATAGAGACACAAAAAACCCT |
| TCAAAAAATCAATGAATCCAGGAGCTGGTTTTTTGAAAGGATCAA |
| CAAAATTGATAGACCGCTAGCAAGACTAATAAAGAAAAAAAGAGA |
| GAAGAATCAAATAGACACAATAAAAAATGATAAAGGGGATATCAC |
| CACCGATCCCACAGAAATACAAACTACCATCAGAGAATACTACAA |
| ACACCTCTACGCAAATAAACTAGAAAATCTAGAGAAATGGATAC |
| ATTCCTCGACACATACACTCTCCCAAGACTAAACCAGGAAGAAGT |
| TGAATCTCTGAATCGACCAATAACAGGCTCTGAAATTGTGGCAAT |
| AATCAATAGTTTACCAACCAAAAAGAGTCCAGGACCAGATGGATT |
| CACAGCCGAATTCTACCAGAGGTACAAGGAGGAACTGGTACCATT |
| CCTTCTGAAACTATTCCAATCAATAGAAAAAGAGGGAATCCTCCC |
| TAACTCATTTTATGAGGCCAGCATCATTCTGATACCAAAGCCGGG |
| CAGAGACACAACCAAAAAAGAGAATTTTAGACCAATATCCTTGAT |
| GAACATTGATGCAAAAATCCTCAATAAAATACTGGCAAACCGAAT |
| CCAGCAGCACATCAAAAAGCTTATCCACCATGATCAAGTGGGCTT |
| CATCCCTGGGATGCAAGGCTGGTTCAATATACGCAAATCAATAAA |
| TGTAATCCAGCATATAAACAGAGCCAAAGACAAAAACCACATGAT |
| TATCTCAATAGATGCAGAAAAAGCCTTTGACAAAATTCAACAACC |
| CTTCATGCTAAAAACTCTCAATAAATTAGGTATTGATGGGACGTA |
| TTTCAAAATAATAAGAGCTATCTATGACAAACCCACAGCCAATAT |
| CATACTGAATGGGCAAAAACTGGAAGCATTCCCTTTGAAAACCGG |
| CACAAGACAGGGATGCCCTCTCTCACCGCTCCTATTCAACATAGT |
| GTTGGAAGTTCTGGCCAGGGCAATCAGGCAGGAGAAGGAAATAAA |
| GGGTATTCAATTAGGAAAAGAGGAAGTCAAATTGTCCCTGTTTGC |
| AGACGACATGATTGTTTATCTAGAAAACCCCATCGTCTCAGCCCA |
| AAATCTCCTTAAGCTGATAAGCAACTTCAGCAAAGTCTCAGGATA |
| CAAAATCAATGTACAAAAATCACAAGCATTCTTATACACCAACAA |
| CAGACAAACAGAGAGCCAAATCATGGGTGAACTCCCATTCACAAT |
| TGCTTCAAAGAGAATAAAATACCTAGGAATCCAACTTACAAGGGA |
| TGTGAAGGACCTCTTCAAGGAGAACTACAAACCACTGCTCAAGGA |
| AATAAAAGAGGAGACAAACAAATGGAAGAACATTCCATGCTCATG |
| GGTAGGAAGAATCAATATCGTGAAAATGGCCATACTGCCCAAGGT |
| AATTTACAGATTCAATGCCATCCCCATCAAGCTACCAATGACTTT |
| CTTCACAGAATTGGAAAAAACTACTTTAAAGTTCATATGGAACCA |
| AAAAAGAGCCCGCATTGCCAAGTCAATCCTAAGCCAAAAGAACAA |
| AGCTGGAGGCATCACACTACCTGACTTCAAACTATACTACAAGGC |
| TACAGTAACCAAAACAGCATGGTACTGGTACCAAAACAGAGATAT |
| AGATCAATGGAACAGAACAGAGCCCTCAGAAATAATGCCGCATAT |
| CTACAACTATCTGATCTTTGACAAACCTGAGAAAAACAAGCAATG |
| GGGAAAGGATTCCCTATTTAATAAATGGTGCTGGGAAAACTGGCT |
| AGCCATATGTAGAAAGCTGAAACTGGATCCCTTCCTTACACCTTA |
| TACAAAAATCAATTCAAGATGGATTAAAGATTTAAACGTTAAACC |
| TAAAACCATAAAAACCCTAGAAGAAAACCTAGGCATTACCATTCA |
| GGACATAGGCGTGGGCAAGGACTTCATGTCCAAAACACCAAAAGC |
| AATGGCAACAAAAGACAAAATTGACAAATGGGATCTAATTAAACT |
| AAAGAGCTTCTGCACAGCAAAAGAAACTACCATCAGAGTGAACAG |
| GCAACCTACAACATGGGAGAAAATTTTTGCAACCTACTCATCTGA |
| CAAAGGGCTAATATCCAGAATCTACAATGAACTCAAACAAATTTA |
| CAAGAAAAAAACAAACAACCCCATCAAAAAGTGGGCGAAGGACAT |
| GAACAGACACTTCTCAAAAGAAGACATTTATGCAGCCAAAAAACA |
| CATGAAGAAATGCTCATCATCACTGGCCATCAGAGAAATGCAAAT |
| CAAAACCACTATGAGATATCATCTCACACCAGTTAGAATGGCAAT |
| CATTAAAAAGTCAGGAAACAACAGGTGCTGGAGAGGATGCGGAGA |
| AATAGGAACACTTTTACACTGTTGGTGGGACTGTAAACTAGTTCA |
| ACCATTGTGGAAGTCAGTGTGGCGATTCCTCAGGGATCTAGAACT |
| AGAAATACCATTTGACCCAGCCATCCCATTACTGGGTATATACCC |
| AAATGAGTATAAATCATGCTGCTATAAAGACACATGCACACGTAT |
| GTTTATTGCGGCACTATTCACAATAGCAAAGACTTGGAACCAACC |
| CAAATGTCCAACAATGATAGACTGGATTAAGAAAATGTGGCACAT |
| ATACACCATGGAATACTATGCAGCCATAAAAAATGATGAGTTCAT |
| ATCCTTTGTAGGGACATGGATGAAATTGGAAACCATCATTCTCAG |

TABLE 8-continued

| Plasmid and mRNA construct sequences |
|---|
| TAAACTATCGCAAGAACAAAAAACCAAACACCGCATATTCTCACT |
| CATAGGTGGGAATTGAACAATGAGATCACATGGACACAGGAAGGG |
| GAATATCACACTCTGGGGACTGTGGTGGGGTCGGGGGAGGGGGGA |
| GGGATAGCATTGGGAGATATACCTAATGCTAGATGACACATTAGT |
| GGGTGCAGCGCACCAGCATGGCACATGTATACGGATCCGAATTCT |
| CGACGGATCGATCCGAACAAACGACCCAACACCCGTGCGTTTTAT |
| TCTGTCTTTTTATTGCCGATCCCCTCAGAAGAACTCGTCAAGAAG |
| GCGATAGAAGGCGATGCGCTGCGAATCGGGAGCGGCGATACCGTA |
| AAGCACGAGGAAGCGGTCAGCCCATTCGCCGCCAAGCTCTTCAGC |
| AATATCACGGGTAGCCAACGCTATGTCCTGATAGCGGTCGGCCGC |
| TTTACTTGTACAGCTCGTCCATGCCGAGAGTGATCCCGGCGGCGG |
| TCACGAACTCCAGCAGGACCATGTGATCGCGCTTCTCGTTGGGGT |
| CTTTGCTCAGGGCGGACTGGGTGCTCAGGTAGTGGTTGTCGGGCA |
| GCAGCACGGGGCCGTCGCCGATGGGGGTGTTCTGCTGGTAGTGGT |
| CGGCCAGGTGAGTCCAGGAGATGTTTCAGCACTGTTGCCTTTAGT |
| CTCGAGGCAACTTAGACAACTGAGTATTGATCTGAGCACAGCAGG |
| GTGTGAGCTGTTTGAAGATACTGGGGTTGGGGGTGAAGAAACTGC |
| AGAGGACTAACTGGGCTGAGACCCAGTGGCAATGTTTTAGGGCCT |
| AAGGAATGCCTCTGAAAATCTAGATGGACAACTTTGACTTTGAGA |
| AAAGAGAGGTGGAAATGAGGAAAATGACTTTTCTTTATTAGATTT |
| CGGTAGAAAGAACTTTCATCTTTCCCCTATTTTTGTTATTCGTTT |
| TAAAACATCTATCTGGAGGCAGGACAAGTATGGTCATTAAAAAGA |
| TGCAGGCAGAAGGCATATATTGGCTCAGTCAAAGTGGGGAACTTT |
| GGTGGCCAAACATACATTGCTAAGGCTATTCCTATATCAGCTGGA |
| CACATATAAAATGCTGCTAATGCTTCATTACAAACTTATATCCTT |
| TAATTCCAGATGGGGGCAAAGTATGTCCAGGGGTGAGGAACAATT |
| GAAACATTTGGGCTGGAGTAGATTTTGAAAGTCAGCTCTGTGTGT |
| GTGTGTGTGTGTGTGTGTGAGAGCGTGTGTTTCTTTTAACGTT |
| TTCAGCCTACAGCATACAGGGTTCATGGTGGCAAGAAGATAACAA |
| GATTTAAATTATGGCCAGTGACTAGTGCTGCAAGAAGAACAACTA |
| CCTGCATTTAATGGGAAAGCAAAATCTCAGGCTTTGAGGGAAGTT |
| AACATAGGCTTGATTCTGGGTGGAAGCTGGGTGTGTAGTTATCTG |
| GAGGCCAGGCTGGAGCTCTCAGCTCACTATGGGTTCATCTTTATT |
| GTCTCCTTTCATCTCAACAGCTGCACGCTGCCGTCCTCGATGTTG |
| TGGCGGATCTTGAAGTTCACCTTGATGCCGTTCTTCTGCTTGTCG |
| GCCATGATATAGACGTTGTGGCTGTTGTAGTTGTACTCCAGCTTG |
| TGCCCCAGGATGTTGCCGTCCTCCTTGAAGTCGATGCCCTTCAGC |
| TCGATGCGGTTCACCAGGGTGTCGCCCTCGAACTTCACCTCGGCG |
| CGGGTCTTGTAGTTGCCGTCGTCCTTGAAGAAGATGGTGCGCTCC |
| TGGACGTAGCCTTCGGGCATGGCGGACTTGAAGAATAGTGAACCG |
| TCAGATCGCCGGTCGTGCTGCTTCATGTGGTCGGGGTAGCGGCTG |
| AAGCACTGCACGCCGTAGGTCAGGGTGGTCACGAGGGTGGGCCAG |
| GGCACGGGCAGCTTGCCGGTGGTGCAGATGAACTTCAGGGTCAGC |
| TTGCCGTAGGTGGCATCGCCCTCGCCCTCGCCGGACACGCTGAAC |
| TTGTGGCCGTTTACGTCGCCGTCCAGCTCGACCAGGATGGGCACC |
| ACCCCGGTGAACAGCTCCTCGCCCTTGCTCACCATAGGGCCGGGA |
| TTCTCCTCCACGTCACCGCATGTTAGAAGACTTCCTCTGCCCTCT |
| CTTGGAGGCAGGGCCTGCATGTGCAGGGCATCGTAGGTATCCTTG |
| GTGGCTGTGCTCAGTCCCTGGTACAGTCCATCGTGGCCCTTGCCT |
| CTTCTTCTCTCGCCCTTCATGCCGATCTCGCTGTAGGCCTCGGCC |
| ATCTTGTCTTTCTGCAGCTCATTATACAGGCCCTCTTGAGGATTC |
| TTTCTCCGCTGGGGCTTGCCGCCCATCTCAGGATCTCTGCCTCTC |
| CGCTTATCCAGCACGTCGTACTCTTCTCTTCTCCCCAGGTTCAGC |
| TCGTTGTACAGCTGATTCTGGCCCTGCTGGTAAGCAGGAGCGTCG |
| GCGGATCTGCTGAACTTCACTCTGCAGTACAGGGTGATGACCAGA |
| GAGAGCAGCAGAACGCCACATGTCAGCCAGAGGGGCCCAAATG |
| TAGATATCCAGGCCTCTGGTATGCACAGCTCCGCCAGCTGCAGGT |
| CTACAGGCTTCAGGTCTGAGAGACAGAGGCTGGCTGGCGATTGTA |
| GGAGCTGGTGTAGGTGGTCTAGGAGCGGGTGTTGTTGTAGGCTTG |
| GCGGGCAGAAACACGGGCACGAAGTGGCTGAAGTACATGATGCTA |
| TTGCTCAGGGCTCCGCTTCCTCCGCCTCCGCTAGAAGAAACTGTG |
| ACCAGGGTGCCCTGTCCCCAAACATCCATGGCGTAGAAGCCGTCG |
| CCTCCCCATCTAGAACAGTAGTACACGGCGGTGTCCTCGGCTCTC |
| AGGCTGTTCATCTGCAGGTAGGCGGTGTTCTTGCTGGTGTCGGCG |
| CTGATGGTGAATCTGCCCTTCACGCTATCGGCGTATCTGGTGTAG |
| CCGTTGGTGGGGTAGATTCTGGCGACCCATTCAAGTCCCTTTCCA |
| GGGGCCTGTCGGACCCAGTGGATGTAGGTGTCCTTGATGTTGAAG |
| CCGCTGGCGGCACAAGACAGTCTCAGAGAGCCGCCAGGCTGAACA |
| AGTCCTCCGCCAGATTCAACCAGCTGCACCTCAGATCCTTCGCCA |
| GATCCAGGCTTTCCAGAGCCGCTGGTGCTGCCTGTTCTCTTGATT |
| TCCACCTTGGTGCCCTGGCCAAAGGTTGGAGGTGTGGTGTAGTGC |
| TGCTGGCAGTAGTAGGTGGCGAAGTCCTCAGGCTGCAGGCTAGAG |
| ATGGTCAGGGTGAAGTCGGTGCCAGATCTGCTGCCGCTGAATCTG |
| CTTGGCACGCCGCTGTACAGAAAGCTGGCGCTGTAGATCAGCAGC |
| TTAGGGGCTTTTCCAGGCTTCTGCTGATACCAGGCCACGGCGGTA |
| TTCACATCCTGGCTGGCTCTACAGGTGATGGTCACTCTATCGCCC |
| ACAGAGGCAGACAGGCTGCTAGGGCTCTGTGTCATCTGGATGTCG |
| CTGATGCTGCAGGCCACTGTTCCCAGCAGCAGCAGAGACTGCAGC |

TABLE 8-continued

Plasmid and mRNA construct sequences

CACATTCGAAGCTTGAGCTCGAGATCTGAGTCCGGTAGCGCTAGC
GGATCTGACGGTTCACTAAACCAGCTCTGCTTATATAGACCTCCC
ACCGTACACGCCTACCGCCCATTTGCGTCAATGGGGCGGAGTTGT
TACGACATTTTGGAAAGTCCCGTTGATTTTGGTGCCAAAACAAAC
TCCCATTGACGTCAATGGGGTGGAGACTTGGAAATCCCCGTGAGT
CAAACCGCTATCCACGCCCATTGATGTACTGCCAAAACCGCATCA
CCATGGTAATAGCGATGACTAATACGTAGATGTACTGCCAAGTAG
GAAAGTCCCATAAGGTCATGTACTGGGCATAATGCCAGGCGGGCC
ATTTACCGTCATTGACGTCAATAGGGGGCGTACTTGGCATATGAT
ACACTTGATGTACTGCCAAGTGGGCAGTTTACCGTAAATACTCCA
CCCATTGACGTCAATGGAAAGTCCCTATTGGCGTTACTATGGGAA
CATACGTCATTATTGACGTCAATGGGCGGGGGTCGTTGGGCGGTC
AGCCAGGCGGGCCATTTACCGTAAGTTATGTAACGCGGAACTCCA
TATATGGGCTATGAACTAATGACCCCGTAATTGATTACTATTAGC
CCGGGGGATCCAGACATGATAAGATACATTGATGAGTTTGGACAA
ACCACAACTAGAATGCAGTGAAAAAAATGCTTTATTTGTGAAATT
TGTGATGCTATTGCTTTATTTGTAACCATTATAAGCTGCAATAAA
CAAGTTAACAACAACAATTGCATTCATTTTATGTTTCAGGTTCAG
GGGGAGGTGTGGGAGGTTTTTTAAAGCAAGTAAAACCTCTACAAA
TGTGGTATGGCTGATTATGATCCGGCTGCCTCGCGCGTTTCGGTG
ATGACGGTGAAAACCTCTGACACATGCAGCTCCCGGAGACGGTCA
CAGCTTGTCTGTAAGCGGATGCCGGGAGCAGACAAGCCCGTCAGG
GCGCGTCAGCGGGTGTTGGCGGGTGTCGGGGCGCAGCCATGAGGT
CGATCGACTCTAGAGGATCGATCCCCGCCCCGGACGAACTAAACC
TGACTACGACATCTCTGCCCCTTCTTCGCGGGGCAGTGCATGTAA
TCCCTTCAGTTGGTTGGTACAACTTGCCAACTGGGCCCTGTTCCA
CATGTGACACGGGGGGGGACCAAACACAAAGGGGTTCTCTGACTG
TAGTTGACATCCTTATAAATGGATGTGCACATTTGCCAACACTGA
GTGGCTTTCATCCTGGAGCAGACTTTGCAGTCTGTGGACTGCAAC
ACAACATTGCCTTTATGTGTAACTCTTGGCTGAAGCTCTTACACC
AATGCTGGGGGACATGTACCTCCCAGGGGCCCAGGAAGACTACGG
GAGGCTACACCAACGTCAATCAGAGGGGCCTGTGTAGCTACCGAT
AAGCGGACCCTCAAGAGGGCATTAGCAATAGTGTTTATAAGGCCC
CCTTGTTAACCCTAAACGGGTAGCATATGCTTCCCGGGTAGTAGT
ATATACTATCCAGACTAACCCTAATTCAATAGCATATGTTACCCA
ACGGGAAGCATATGCTATCGAATTAGGGTTAGTAAAAGGGTCCTA
AGGAACAGCGATATCTCCCACCCCATGAGCTGTCACGGTTTTATT
TACATGGGGTCAGGATTCCACGAGGGTAGTGAACCATTTTAGTCA
CAAGGGCAGTGGCTGAAGATCAAGGAGCGGGCAGTGAACTCTCCT
GAATCTTCGCCTGCTTCTTCATTCTCCTTCGTTTAGCTAATAGAA
TAACTGCTGAGTTGTGAACAGTAAGGTGTATGTGAGGTGCTCGAA
AACAAGGTTTCAGGTGACGCCCCCAGAATAAAATTTGGACGGGGG
GTTCAGTGGTGGCATTGTGCTATGACACCAATATAACCCTCACAA
ACCCCTTGGGCAATAAATACTAGTGTAGGAATGAAACATTCTGAA
TATCTTTAACAATAGAAATCCATGGGGTGGGGACAAGCCGTAAAG
ACTGGATGTCCATCTCACACGAATTTATGGCTATGGGCAACACAT
AATCCTAGTGCAATATGATACTGGGGTTATTAAGATGTGTCCCAG
GCAGGGACCAAGACAGGTGAACCATGTTGTTACACTCTATTTGTA
ACAAGGGGAAAGAGAGTGGACGCCGACAGCAGCGGACTCCACTGG
TTGTCTCTAACACCCCCGAAAATTAAACGGGGCTCCACGCCAATG
GGGCCCATAAACAAAGACAAGTGGCCACTCTTTTTTTTGAAATTG
TGGAGTGGGGGCACGCGTCAGCCCCCACACGCCGCCCTGCGGTTT
TGGACTGTAAAATAAGGGTGTAATAACTTGGCTGATTGTAACCCC
GCTAACCACTGCGGTCAAACCACTTGCCCACAAAACCACTAATGG
CACCCCGGGGAATACCTGCATAAGTAGGTGGGCGGGCCAAGATAG
GGGCGCGATTGCTGCGATCTGGAGGACAAATTACACACACTTGCG
CCTGAGCGCCAAGCACAGGGTTGTTGGTCCTCATATTCACGAGGT
CGCTGAGAGCACGGTGGGCTAATGTTGCCATGGGTAGCATATACT
ACCCAAATATCTGGATAGCATATGCTATCCTAATCTATATCTGGG
TAGCATAGGCTATCCTAATCTATATCTGGGTAGCATATGCTATCC
TAATCTATATCTGGGTAGTATATGCTATCCTAATTTATATCTGGG
TAGCATAGGCTATCCTAATCTATATCTGGGTAGCATATGCTATCC
TAATCTATATCTGGGTAGTATATGCTATCCTAATCTGTATCCGGG
TAGCATATGCTATCCTAATAGAGATTAGGGTAGTATATGCTATCC
TAATTTATATCTGGGTAGCATATACTACCCAAATATCTGGATAGC
ATATGCTATCCTAATCTATATCTGGGTAGCATATGCTATCCTAAT
CTATATCTGGGTAGCATAGGCTATCCTAATCTATATCTGGGTAGC
ATATGCTATCCTAATCTATATCTGGGTAGTATATGCTATCCTAAT
TTATATCTGGGTAGCATAGGCTATCCTAATCTATATCTGGGTAGC
ATATGCTATCCTAATCTATATCTGGGTAGTATATGCTATCCTAAT
CTGTATCCGGGTAGCATATGCTATCCTCATGCATATACAGTCAGC
ATATGATACCCAGTAGTAGAGTGGGAGTGCTATCCTTTGCATATG
CCGCCACCTCCCAAGGGGGCGTGAATTTTCGCTGCTTGTCCTTTT
CCTGCATGCTGGTTGCTCCCATTCTTAGGTGAATTTAAGGAGGGGCC
AGGCTAAAGCCGTCGCATGTCTGATTGCTCACCAGGTAAATGTCG
CTAATGTTTTCCAACGCGAGAAGGTGTTGAGCGCGGAGCTGAGTG
ACGTGACAACATGGGTATGCCCAATTGCCCCATGTTGGGAGGACG
AAAATGGTGACAAGACAGATGGCCAGAAATACACCAACAGCACGC

TABLE 8-continued

Plasmid and mRNA construct sequences

ATGATGTCTACTGGGGATTTATTCTTTAGTGCGGGGGAATACACG
GCTTTTAATACGATTGAGGGCGTCTCCTAACAAGTTACATCACTC
CTGCCCTTCCTCACCCTCATCTCCATCACCTCCTTCATCTCCGTC
ATCTCCGTCATCACCCTCCGCGGCAGCCCCTTCCACCATAGGTGG
AAACCAGGGAGGCAAATCTACTCCATCGTCAAAGCTGCACACAGT
CACCCTGATATTGCAGGTAGGAGCGGGCTTTGTCATAACAAGGTC
CTTAATCGCATCCTTCAAAACCTCAGCAAATATATGAGTTTGTAA
AAAGACCATGAAATAACAGACAATGGACTCCCTTAGCGGGCCAGG
TTGTGGGCCGGGTCCAGGGGCCATTCCAAAGGGGAGACGACTCAA
TGGTGTAAGACGACATTGTGGAATAGCAAGGGCAGTTCCTCGCCT
TAGGTTGTAAAGGGAGGTCTTACTACCTCCATATACGAACACACC
GGCGACCCAAGTTCCTTCGTCGGTAGTCCTTTCTACGTGACTCCT
AGCCAGGAGAGCTCTTAAACCTTCTGCAATGTTCTCAAATTTCGG
GTTGGAACCTCCTTGACCACGATGCTTTCCAAACCACCCTCCTTT
TTTGCGCCTGCCTCCATCACCCTGACCCCGGGGTCCAGTGCTTGG
GCCTTCTCCTGGGTCATCTGCGGGGCCCTGCTCTATCGCTCCCGG
GGGCACGTCAGGCTCACCATCTGGGCCACCTTCTTGGTGGTATTC
AAAATAATCGGCTTCCCCTACAGGGTGGAAAAATGGCCTTCTACC
TGGAGGGGGCCTGCGCGGTGGAGACCCGGATGATGATGACTGACT
ACTGGGACTCCTGGGCCTCTTTTCTCCACGTCCACGACCTCTCCC
CCTGGCTCTTTCACGACTTCCCCCCCTGGCTCTTTCACGTCCTCT
ACCCCGGCGGCCTCCACTACCTCCTCGACCCCGGCCTCCACTACC
TCCTCGACCCCGGCCTCCACTGCCTCCTCGACCCCGGCCTCCACC
TCCTGCTCCTGCCCCTCCTGCTCCTGCCCCTCCTCCTGCTCCTGC
CCCTCCTGCCCCTCCTGCTCCTGCCCCTCCTGCCCCTCCTGCTCC
TGCCCCTCCTGCCCCTCCTGCTCCTGCCCCTCCTGCCCCTCCTCC
TGCTCCTGCCCCTCCTGCCCCTCCTCCTGCTCCTGCCCCTCCTGC
CCCTCCTGCTCCTGCCCCTCCTGCCCCTCCTGCTCCTGCCCCTCC
TGCCCCTCCTGCTCCTGCCCCTCCTGCTCCTGCCCCTCCTGCTCC
TGCCCCTCCTGCTCCTGCCCCTCCTGCCCCTCCTGCCCCTCCTCC
TGCTCCTGCCCCTCCTGCTCCTGCCCCTCCTGCCCCTCCTGCCCC
TCCTGCTCCTGCCCCTCCTCCTGCTCCTGCCCCTCCTGCCCCTCC
TGCCCCTCCTCCTGCTCCTGCCCCTCCTGCCCCTCCTCCTGCTCC
TGCCCCTCCTCCTGCTCCTGCCCCTCCTGCCCCTCCTGCCCCTCC
TCCTGCTCCTGCCCCTCCTGCCCCTCCTCCTGCTCCTGCCCCTCC
TCCTGCTCCTGCCCCTCCTGCCCCTCCTGCCCCTCCTCCTGCTCC
TGCCCCTCCTCCTGCTCCTGCCCCTCCTGCCCCTCCTGCCCCTCC
TGCCCCTCCTCCTGCTCCTGCCCCTCCTCCTGCTCCTGCCCCTCC
TGCTCCTGCCCCTCCCGCTCCTGCTCCTGCTCCTGTTCCACCGTG
GGTCCCTTTGCAGCCAATGCAACTTGGACGTTTTTGGGGTCTCCG
GACACCATCTCTATGTCTTGGCCCTGATCCTGAGCCGCCCGGGGC
TCCTGGTCTTCCGCCTCCTCGTCCTCGTCCTCTTCCCCGTCCTCG
TCCATGGTTATCACCCCCCTCTTCTTTGAGGTCCACTGCCGCCGGA
GCCTTCTGGTCCAGATGTGTCTCCCTTCTCTCCTAGGCCATTTCC
AGGTCCTGTACCTGGCCCCTCGTCAGACATGATTCACACTAAAAG
AGATCAATAGACATCTTTATTAGACGACGCTCAGTGAATACAGGG
AGTGCAGACTCCTGCCCCCTCCAACAGCCCCCCCACCCTCATCCC
CTTCATGGTCGCTGTCAGACAGATCCAGGTCTGAAAATTCCCCAT
CCTCCGAACCATCCTCGTCCTCATCACCAATTACTCGCAGCCCGG
AAAACTCCCGCTGAACATCCTCAAGATTTGCGTCCTGAGCCTCAA
GCCAGGCCTCAAATTCCTCGTCCCCCTTTTTGCTGGACGGTAGGG
ATGGGGATTCTCGGGACCCCTCCTCTTCCTCTTCAAGGTCACCAG
ACAGAGATGCTACTGGGGCAACGGAAGAAAAGCTGGGTGCGGCCT
GTGAGGATCAGCTTATCGATGATAAGCTGTCAAACATGAGAATTC
TTGAAGACGAAAGGGCCTCGTGATACGCCTATTTTTATAGGTTAA
TGTCATGATAATAATGGTTTCTTAGACGTCAGGTGGCACTTTTCG
GGGAAATGTGCGCGGAACCCCTATTTGTTTATTTTTCTAAATACA
TTCAAATATGTATCCGCTCATGAGACAATAACCCTGATAAATGCT
TCAATAATATTGAAAAAGGAAGAGTATGAGTATTCAACATTTCCG
TGTCGCCCTTATTCCCTTTTTTGCGGCATTTTGCCTTCCTGTTTT
TGCTCACCCAGAAACGCTGGTGAAAGTAAAAGATGCTGAAGATCA
GTTGGGTGCACGAGTGGGTTACATCGAACTGGATCTCAACAGCGG
TAAGATCCTTGAGAGTTTTCGCCCCGAAGAACGTTTTCCAATGAT
GAGCACTTTTAAAGTTCTGCTATGTGGCGCGGTATTATCCCGTGT
TGACGCCGGGCAAGAGCAACTCGGTCGCCGCATACACTATTCTCA
GAATGACTTGGTTGAGTACTCACCAGTCACAGAAAAGCATCTTAC
GGATGGCATGACAGTAAGAGAATTATGCAGTGCTGCCATAACCAT
GAGTGATAACACTGCGGCCAACTTACTTCTGACAACGATCGGAGG
ACCGAAGGAGCTAACCGCTTTTTTGCACAACATGGGGGATCATGT
AACTCGCCTTGATCGTTGGGAACCGGAGCTGAATGAAGCCATACC
AAACGACGAGCGTGACACCACGATGCCTGCAGCAATGGCAACAAC
GTTGCGCAAACTATTAACTGGCGAACTACTTACTCTAGCTTCCCG
GCAACAATTAATAGACTGGATGGAGGCGGATAAAGTTGCAGGACC
ACTTCTGCGCTCGGCCCTTCCGGCTGGCTGGTTTATTGCTGATAA
ATCTGGAGCCGGTGAGCGTGGGTCTCGCGGTATCATTGCAGCACT
GGGGCCAGATGGTAAGCCCTCCCGTATCGTAGTTATCTACACGAC
GGGGAGTCAGGCAACTATGGATGAACGAAATAGACAGATCGCTGA
GATAGGTGCCTCACTGATTAAGCATTGGTAACTGTCAGACCAAGT

TABLE 8-continued

Plasmid and mRNA construct sequences

TTACTCATATATACTTTAGATTGATTTAAAACTTCATTTTTAATT
TAAAAGGATCTAGGTGAAGATCCTTTTTGATAATCTCATGACCAA
AATCCCTTAACGTGAGTTTTCGTTCCACTGAGCGTCAGACCCCGT
AGAAAAGATCAAAGGATCTTCTTGAGATCCTTTTTTTCTGCGCGT
AATCTGCTGCTTGCAAACAAAAAAACCACCGCTACCAGCGGTGGT
TTGTTTGCCGGATCAAGAGCTACCAACTCTTTTTCCGAAGGTAAC
TGGCTTCAGCAGAGCGCAGATACCAAATACTGTCCTTCTAGTGTA
GCCGTAGTTAGGCCACCACTTCAAGAACTCTGTAGCACCGCCTAC
ATACCTCGCTCTGCTAATCCTGTTACCAGTGGCTGCTGCCAGTGG
CGATAAGTCGTGTCTTACCGGGTTGGACTCAAGACGATAGTTACC
GGATAAGGCGCAGCGGTCGGGCTGAACGGGGGGTTCGTGCACACA
GCCCAGCTTGGAGCGAACGACCTACACCGAACTGAGATACCTACA
GCGTGAGCTATGAGAAAGCGCCACGCTTCCCGAAGGGAGAAAGGC
GGACAGGTATCCGGTAAGCGGCAGGGTCGGAACAGGAGAGCGCAC
GAGGGAGCTTCCAGGGGGAAACGCCTGGTATCTTTATAGTCCTGT
CGGGTTTCGCCACCTCTGACTTGAGCGTCGATTTTTGTGATGCTC
GTCAGGGGGGCGGAGCCTATGGAAAAACGCCAGCAACGCGGCCTT
TTTACGGTTCCTGGCCTTTTGCTGGCCTTTTGCTCACATGTTCTT
TCCTGCGTTATCCCCTGATTCTGTGGATAACCGTATTACCGCCTT
TGAGTGAGCTGATACCGCTCGCCGCAGCCGAACGACCGAGCGCAG
CGAGTCAGTGAGCGAGGAAGCGGAAGAGCGCCTGATGCGGTATTT
TCTCCTTACGCATCTGTGCGGTATTTCACACCGCATATGGTGCAC
TCTCAGTACAATCTGCTCTGATGCCGCATAGTTAAGCCAGCTGTG
GAATGTGTGTCAGTTAGGGTGTGGAAAGTCCCCAGGCTCCCCAGC
AGGCAGAAGTATGCAAAGCATGCATCTCAATTAGTCAGCAACCAG
GTGTGGAAAGTCCCCAGGCTCCCCAGCAGGCAGAAGTATGCAAAG
CATGCATCTCAATTAGTCAGCAACCATAGTCCCGCCCCTAACTCC
GCCCATCCCGCCCCTAACTCCGCCCAGTTCCGCCCATTCTCCGCC
CCATGGCTGACTAATTTTTTTTATTTATGCAGAGGCCGAGGCCGC
CTCGGCCTCTGAGCTATTCCAGAAGTAGTGAGGAGGCTTTTTTGG
AGGCCTAGGCTTTTGCAAAAAGCTTGCATGCCTGCAGGTCGGCCG
CCACGACCGGTGCCGCCACCATCCCCTGACCCACGCCCCTGACCC
CTCACAAGGAGACGACCTTCCATGACCGAGTACAAGCCCACGGTG
CGCCTCGCCACCCGCGACGACGTCCCCCGGGCCGTACGCACCCTC
GCCGCCGCGTTCGCCGACTACCCCGCCACGCGCCACACCGTCGAC
CCGGACCGCCACATCGAGCGGGTCACCGAGCTGCAAGAACTCTTC
CTCACGCGCGTCGGGCTCGACATCGGCAAGGTGTGGGTCGCGGAC
GACGGCGCCGCGGTGGCGGTCTGGACCACGCCGGAGAGCGTCGAA
GCGGGGGCGGTGTTCGCCGAGATCGGCCCGCGCATGGCCGAGTTG
AGCGGTTCCCGGCTGGCCGCGCAGCAACAGATGGAAGGCCTCCTG
GCGCCGCACCGGCCCAAGGAGCCCGCGTGGTTCCTGGCCACCGTC
GGCGTCTCGCCCGACCACCAGGGCAAGGGTCTGGGCAGCGCCGTC
GTGCTCCCCGGAGTGGAGGCGGCCGAGCGCGCCGGGGTGCCCGCC
TTCCTGGAGACCTCCGCGCCCCGCAACCTCCCCTTCTACGAGCGG
CTCGGCTTCACCGTCACCGCCGACGTCGAGGTGCCCGAAGGACCG
CGCACCTGGTGCATGACCCGCAAGCCCGGTGCCTGACGCCCGCCC
CACGACCCGCAGCGCCCGACCGAAAGGAGCGCACGACCCCATGGC
TCCGACCGAAGCCGACCCGGGCGGCCCCGCCGACCCCGCACCCGC
CCCCGAGGCCCACCGACTCTAGAGGATCATAATCAGCCATACCAC
ATTTGTAGAGGTTTTACTTGCTTTAAAAAACCTCCCACACCTCCC
CCTGAACCTGAAACATAAAATGAATGCAATTGTTGTTGTTAACTT
GTTTATTGCAGCTTATAATGGTTACAAATAAAGCAATAGCATCAC
AAATTTCACAAATAAAGCATTTTTTTCACTGCATTCTAGTTGTGG
TTTGTCCAAACTCATCAATGTATCTTATCATGTCTGGATCACTCG
CCGATAGTGGAAACCGACGCCCCAGCACTCGTCCGAGGGCAAAGG
AATAGGGGAGATGGGGGAGGCTAACTGAAACACGGAAGGAGACAA
TACCGGAAGGAACCCGCGCTATGACGGCAATAAAAAGACAGAATA
AAACGCACGGGTGTTGGGTCGTTTGTTCATAAACGCGGGGTTCGG
TCCCAGGGCTGGCACTCTGTCGATACCCCACCGAGACCCCATTGG
GGCCAATACGCCCGCGTTTCTTCCTTTTCCCCACCCCACCCCCCA
AGTTCGGGTGAAGGCCCAGGGCTCGCAGCCAACGTCGGGGCGGCA
GGCCCTGCCATAGCCACTGGCCCCGTGGGTTAGGGACGGGGTCCC
CCATGGGGAATGGTTTATGGTTCGTGGGGGTTATTATTTTGGGCG
TTGCGTGGGGTCTGGTCCACGACTGGACTGAGCAGACAGACCCAT
GGTTTTTGGATGGCCTGGGCATGGACCGCATGTACTGGCGCGACA
CGAACACCGGGCGTCTGTGGCTGCCAAACACCCCCGACCCCCAAA
AACCACCGCGCGGATTTCTGGCGTGCCAAGCTAGTCGACCAATTC
TCATGTTTGACAGCTTATCATCGCAGATCCGGGCAACGTTGTTGC
ATTGCTGCAGGCGCAGAACTGGTAGGTATGGAAGATCTCTAGAAG
CTGGGTACCAGCTGCTAGCAAGCTTGCTAGCGGCCGGCTCGAGTT
TACTCCCTATCAGTGATAGAGAACGTATGTCGAGTTTACTCCCTA
TCAGTGATAGAGAACGATGTCGAGTTTACTCCCTATCAGTGATAG
AGAACGTATGTCGAGTTTACTCCCTATCAGTGATAGAGAACGTAT
GTCGAGTTTACTCCCTATCAGTGATAGAGAACGTATGTCGAGTTT
ATCCCTATCAGTGATAGAGAACGTATGTCGAGTTTACTCCCTATC
AGTGATAGAGAACGTATGTCGAGGTAGGCGTGTACGGTGGGAGGC
CTATATAAGCAGAGCTCGTT
(SEQ ID NO: 41)

LINE-1 ORF2-NLS mRNA (SEQ ID NO: 42)
TAATACGACTCACTATAGGGAGAAGTACTGCCACCATGGGCAAGA
AGCAAAATCGCAAGACGGGGAATTCCAAGACACAATCCGCTAGCC
CACCACCTAAAGAGCGTTCTAGCTCCCCTGCTACTGAGCAGTCCT
GGATGGAAAACGACTTCGATGAACTCCGGGAAGAGGGATTTAGGC
GATCCAACTATTCAGAACTCCGCGAAGATATCCAGACAAAGGGGA
AGGAAGTCGAGAATTTCGAGAAGAACCTCGAGGAGTGCATCACCC
GTATCACAAACACTGAGAAATGTCTCAAAGAACTCATGGAACTTA
AGACAAAAGCCAGGGAGCTTCGAGAGGAGTGTCGGAGTCTGAGAT
CCAGGTGTGACCAGCTCGAGGAGCGCGTGAGCGCGATGGAAGACG
AGATGAACGAGATGAAAAGAGAGGGCAAATTCAGGGAGAAGCGCA
TTAAGAGGAACGAACAGAGTCTGCAGGAGATTTGGGATTACGTCA
AGAGGCCTAACCTGCGGTTGATCGGCGTCCCCGAGAGCGACGTAG
AAAACGGGACTAAACTGGAGAATACACTTCAAGACATCATTCAAG
AAAATTTTCCAAACCTGGCTCGGCAAGCTAATGTGCAAATCCAAG
AGATCCAACGCACACCCCAGCGGTATAGCTCTCGGCGTGCCACCC
CTAGGCATATTATCGTGCGCTTTACTAAGGTGGAGATGAAAGAGA
AGATGCTGCGAGCCGCTCGGGAAAAGGGAAGGGTGACTTTGAAGG
GCAAACCTATTCGGCTGACGGTTGACCTTAGCGCCGAGACACTCC
AGGCACGCCGGGAATGGGGCCCCATCTTTAATATCCTGAAGGAGA
AGAACTTCCAGCCACGAATCTCTTACCCTGCAAAGTTGAGTTTTA
TCTCCGAGGGTGAGATTAAGTATTTCATCGATAAACAGATGCTGC
GAGACTTCGTGACAACTCGCCCAGCTCTCAAGGAACTGCTCAAAG
AGGCTCTTAATATGGAGCGCAATAATAGATATCAACCCTTGCAGA
ACCACGCAAAGATGTGAGACAGCCGTCAGACCATCAAGACTAGGA
AGAAACTGCATCAACTAATGAGCAAAATCACCAGCTAACATCATA
GTATACATGACCGGCTCTAACTCACATATCACCATCCTTACACTT
AACATTAACGGCCTCAACTCAGCTATCAAGCGCCATCGGCTGGCC
AGCTGGATCAAATCACAGGATCCAAGCGTTTGTTGCATCCAAGAG
ACCCACCTGACCTGTAGAGATACTCACCGCCTCAAGATCAAGGGA
TGGCGAAAGATTTATCAGGCGAACGGTAAGCAGAAGAAAGCCGGA
GTCGCAATTCTGGTCTCAGACAAGACGGATTTCAAGCCCACCAAA
ATTAAGCGTGATAAGGAAGGTCACTATATTATGGTGAAAGGCAGC
ATACAGCAGGAAGAACTTACCATATTGAACATCTACGCGCCAAAC
ACCGGCGCACCTCGCTTTATCAAACAGGTCCTGTCCGATCTGCAG
CGAGATCTGGATTCTCATACGTTGATTATGGGTGATTTCAATACA
CCATTGAGCACCCTGGATCGCAGCACCAGGCAAAAGGTAAATAAA
GACACGCAAGAGCTCAATAGCGCACTGCATCAGGCAGATCTCATT
GATATTTATCGCACTCTTCATCCTAAGAGTACCGAGTACACATTC
TTCAGCGCCCCACATCATACATACTCAAAGATCGATCATATCGTC
GGCTCAAAGGCTCTGCTGTCAAAGTGCAAGCGCACAGAGATAATT
ACAAATTACCTGTCAGATCATAGCGCGATCAAGCTCGAGCTGAGA
ATCAAGAACCTGACCCAGAGCCGGAGTACCACTTGGAAGCTTAAT
AACCTGCTGCTCAACGATTATTGGGTCCACAATGAGATGAAGGCA
GAGATTAAAATGTTCTTCGAAACAAATGAGAATAAGGATACTACC
TATCAAAACCTTTGGGATGCCTTTAAGGCCGTCTGCAGAGGCAAG
TTCATCGCCCTCAACGCCTATAAAAGAAAACAAGAGAGATCTAAG
ATCGATACTCTCACCTCTCAGCTGAAGGAGTTGGAGAAACAGGAA
CAGACCCACTCCAAGGCGTCAAGACGGCAGGAGATCACAAAGATT
CGCGCCGAGTTGAAAGAGATCGAAACCCAAAAGACTCTTCAGAAA
ATTAACGAGTCTCGTAGTTGGTTCTTCGAGCGGATTAATAAGATA
GACAGACCTCTGGCACGACTGATTAAGAAGAAGCGCGAAAAGAAC
CAGATTGATACCATCAAGAACGACAAGGGCGACATCACTACTGAC
CCGACCGAGATCCAGACCACTATTCGGGAGTATTATAAGCATTTG
TATGCTAACAAGCTTGAGAACCTGGAAGAGATGGACACTTTTCTG
GATACCTATACTCTGCCACGGCTTAATCAAGAGGAAGTCGAGTCC
CTCAACCGCCCAATTACAGGAAGCGAGATTGTGGCCATAATTAAC
TCCCTGCCGACAAAGAAATCTCCTGGTCCGGACGGGTTTACAGCT
GAGTTTTATCAACGGTATATGGAAGAGCTTGTACCGTTTCTGCTC
AAGCTCTTTCAGTCTATAGAAAAGGAAGGCATCTTGCCCAATTCC
TTCTACGAAGCTTCTATAATACTTATTCCCAAACCAGGACGCGAT
ACCACAAAGAAGGAAAACTTCCGGCCCATTAGTCTCATGAATATC
GACGCTAAAATATTGAACAAGATTCTCGCCAACAGAATCCAACAA
CATATTAAGAAATTGATACATCACGACCAGGTGGGGTTTATACCT
GGCATGCAGGGCTGGTTTAACATCCGGAAGAGTATTAACGTCATT
CAACACATTAATAGAGCTAAGGATAAGAATCATATGATCATCTCT
ATAGACGCGGAAAAGGCATTCGATAAGATTCAGCAGCCATTTATG
CTCAAGACTCTGAACAAACTCGGCATCGACGGAACATATTTTAAG
ATTATTCGCGCAATTTACGATAAGCCGACTGCTAACATTATCCTT
AACGGCCAAAAGCTCGAGGCCTTTCCGCTCAAGACTGGAACCCGC
CAAGGCTGTCCCCTCTCCCCGCTTTTGTTTAATATTGTACTCGAG
GTGCTGGCTAGGGCTATTCGTCAAGAGAAAGAGATTAAAGGGATA
CAGCTCGGGAAGGAAGAGGTCAAGCTTTCCTTGTTCGCCGATGAT
ATGATTGTGTACCTGGAGAATCCTATTGTGTCTGCTCAGAACCTT
CTTAAACTTATTTCTAACTTTAGCAAGGTCAGCGGCTATAAGATT
AACGTCCAGAAATCTCAGGCCTTTCTGTACACAAATAATCGACAG
ACCGAATCCCAGATAATGGGTGAGCTTCCGTTTGTCATAGCCAGC

TABLE 8-continued

Plasmid and mRNA construct sequences

AAAAGGATAAAGTATCTCGGAATCCAGCTGACACGAGACGTTAAA
GATTTGTTTAAGGAAAATTACAAGCCTCTCCTGAAAGAGATTAAG
GAAGATACTAATAAGTGGAAGAATATCCCCTGTTCATGGGTTGGC
AGAATCAACATAGTGAAGATGGCAATACTTCCTAAAGTGATATAT
CGCTTTAACGCCATCCCAATTAAACTGCCTATGACCTTCTTTACG
GAGCTCGAGAAAACAACCCTTAAATTTATATGGAATCAAAAGAGA
GCAAGAATAGCGAAGTCCATCTTGAGCCAGAAGAATAAGGCCGGT
GGGATTACTTTGCCTGATTTTAAGTTGTATTATAAAGCCACAGTA
ACTAAGACAGCCTGGTATTGGTATCAGAATAGAGACATCGACCAG
TGGAATCGGACCGAACCATCAGAGATAATGCCCCACATCTATAAT
TACCTTATATTCGATAAGCCAGAAAAGAATAAACAGTGGGGCAAA
GACAGCCTCTTCAACAAGTGGTGTTGGGAGAATTGGCTGGCCATA
TGCCGGAAACTCAAGCTCGACCCCTTTCTTACACCCTACACTAAA
ATCAACAGTAGGTGGATCAAGGACTTGAATGTCAAGCCAAAGACT
ATAAAGACACTGGAAGAGAATCTTGGGATCACAATACAAGATATA
GGCGTCGGCAAAGATTTTATGTCAAAGACGCCCAAGGCCATGGCC
ACTAAGGATAAGATTGATAAGTGGGACCTTATTAAGCTCAAAAGC
TTCTGTACTGCCAAGGAGACCACGATCAGAGTTAATAGGCAGCCC
ACTACATGGGAAAAGATTTCGCCACTTATTCATCAGATAAGGGG
TTGATAAGCAGAATATATAACGAGCTGAAGCAGATCTACAAGAAG
AAAACGAATAATCCCATCAAGAAGTGGGCAAAAGATATGAACAGG
CATTTTAGCAAAGAGGATATCTACGCCGCGAAGAAGCATATGAAG
AAGTGTAGTTCAAGCTTGGCCATTCGTGAGATGCAGATTAAGACG
ACCATGCGATACCACCTTACCCCAGTGAGGATGGCAATTATCAAG
AAATCTGGCAATAATAGATGTTGGCGGGGCTGTGGCGAGATTGGC
ACCCTGCTCCATTGCTGGTGGGATTGCAAGCTGGTGCAGCCGCTT
TGGAAATCAGTCTGGCGCTTTCTGAGGGACCTCGAGCTTGAGATT
CCCTTCGATCCCGCAATTCCCTTGCTCGGAATCTATCCTAACGAA
TACAAGAGCTGTTGTTACAAGGATACGTGTACCCGGATGTTCATC
GCGGCCTTGTTTACGATAGCTAAGACGTGGAATCAGCCTAAGTGC
CCCACAATGATCGATTGGATCAAGAAAATGTGGCATATTTATACC
ATGGAGTATTACGCAGCAATTAAGAATGACGAATTTATTTCCTTC
GTTGGGACCTGGATGAAGCTGGAGACTATTATTCTGAGCAAGCTG
TCTCAGGAGCAAAAGACAAAGCATAGAATCTTCTCTCTCATTGGT
GGTAACGACTACAAAGACGATGACGACAAGCCCGCCGCCAAGAGG
GTGAAGCTGGACTAAAGCGCTTCTAGAAGTTGTCTCCTCCTGCAC
TGACTGACTGATACAATCGATTTCTGGATCCGCAGGCCTAATCAA
CCTCTGGATTACAAAATTTGTGAAAGATTGACTGGTATTCTTAAC
TATGTTGCTCCTTTTACGCTATGTGGATACGCTGCTTTAATGCCT
TTGTATCATGCTATTGCTTCCCGTATGGCTTTCATTTTCTCCTCC
TTGTATAAATCCTGGTTGCTGTCTCTTTATGAGGAGTTGTGGCCC
GTTGTCAGGCAACGTGGCGTGGTGTGCACTGTGTTTGCTGACGCA
ACCCCCACTGGTTGGGGCATTGCCACCACCTGTCAGCTCCTTTCC
GGGACTTTCGCTTTCCCCCTCCCTATTGCCACGGCGGAACTCATC
GCCGCCTGCCTTGCCCGCTGCTGGACAGGGGCTCGGCTGTTGGGC
ACTGACAATTCCGTGGTGTTGTCGGGGAAGCTGACGTCCTTTCCA
TGGCTGCTCGCCTGTGTTGCCACCTGGATTCTGCGCGGGACGTCC
TTCTGCTACGTCCCTTCGGCCCTCAATCCAGCGGACCTTCCTTCC
CGCTGAGAGACACAAAAAATTCCAACACACTATTGCAATGAAAAT
AAATTTCCTTTATTAGCCAGAAGTCAGATGCTCAAGGGGCTTCAT
GATGTCCCCATAATTTTTGGCAGAGGGAAAAAGATCTCAGTGGTA
TTTGTGAGCCAGGGCATTGGCCTTCTGATAGGCAGCCTGCACCTG
AGGAGTGCGGCCGCTTTACTTGTACAGCTCGTCCATGCCGAGAGT
GATCCCGGCGGCGGTCACGAACTCCAGCAGGACCATGTGATCGCG
CTTCTCGTTGGGGTCTTTGCTCAGGGCGGACTGGGTGCTCAGGTA
GTGGTTGTCGGGCAGCAGCACGGGGCCGTCGCCGATGGGGGTGTT
CTGCTGGTAGTGGTCGGCGAGCTGCACGCTGCCGTCCTCGATGTT
GTGGCGGATCTTGAAGTTCACCTTGATGCCGTTCTTCTGCTTGTC
GGCCATGATATAGACGTTGTGGCTGTTGTAGTTGTACTCCAGCTT
GTGCCCCAGGATGTTGCCGTCCTCCTTGAAGTCGATGCCCTTCAG
CTCGATGCGGTTCACCAGGGTGTCGCCCTCGAACTTCACCTCGGC
GCGGGTCTTGTAGTTGCCGTCGTCCTTGAAGAAGATGGTGCGCTC
CTGGACGTAGCCTTCGGGCATGGCGGACTTGAAGAAGTCGTGCTG
CTTCATGTGGTCGGGGTAGCGGCTGAAGCACTGCACGCCGTAGGT
CAGGGTGGTCACGAGGGTGGGCCAGGGCACGGGCAGCTTGCCGGT
GGTGCAGATGAACTTCAGGGTCAGCTTGCCGTAGGTGGCATCGCC
CTCGCCCTCGCCGGACACGCTGAACTTGTGGCCGTTTACGTCGCC
GTCCAGCTCGACCAGGATGGGCACCACCCCGGTGAACAGCTCCTC
GCCCTTGCTCACCATGGTGGCGGGATCTGACGGTTCACTAAACCA
GCTCTGCTTATATAGACCTCCCACCGTACACGCCTACCGCCCATT
TGCGTCAATGGGGCGGAGTTGTTACGACATTTTGGAAAGTCCCGT
TGATTTTGGTGCCAAAACAAACTCCCATTGACGTCAATGGGGTGG
AGACTTGGAAATCCCCGTGAGTCAAACCGCTATCCACGCCCATTG
ATGTACTGCCAAAACCGCATCACCATGGTAATAGCGATGACTAAT
ACGTAGATGTACTGCCAAGTAGGAAAGTCCCATAAGGTCATGTAC
TGGGCATAATGCCAGGCGGGCCATTTACCGTCATTGACGTCAATA
GGGGGCGTACTTGGCATATGATACACTTGATGTACTGCCAAGTGG
GCAGTTTACCGTAAATACTCCACCCATTGACGTCAATGGAAAGTC
CCTATTGGCGTTACTATGGGAACATACGTCATTATTGACGTCAAT
GGGCGGGGGTCGTTGGGCGGTCAGCCAGGCGGGCCATTTACCGTA
AGTTATGTAACGGGCCTGCTGCCGGCTCTGCGGCCTCTTCCGCGT
CTTCGCCTTCGCCCTCAGACGAGTCGGATCTCCCTTTGGGCCGCC
TCCCCGCCTGTCTAGCTTGACTGACTGAGATACAGCGTACCTTCA
GCTCACAGACATGATAAGATACATTGATGAGTTTGGACAAACCAC
AACTAGAATGCAGTGAAAAAAATGCTTTATTTGTGAAATTTGTGA
TGCTATTGCTTTATTTGTAACCATTATAAGCTGCAATAAACAAGT
T
(SEQ ID NO: 42)

LINE-1 alu mRNA GFP (SEQ ID NO: 43)
TAATACGACTCACTATAGGGAGAAGTACTGCCACCATGGGCAAGA
AGCAAAATCGCAAGACGGGGAATTCCAAGACACAATCCGCTAGCC
CACCACCTAAAGAGCGTTCTAGCTCCCCTGCTACTGAGCAGTCCT
GGATGGAAAACGACTTCGATGAACTCCGGGAAGAGGGATTTAGGC
GATCCAACTATTCAGAACTCCGCGAAGATATCCAGACAAAGGGGA
AGGAAGTCGAGAATTTCGAGAAGAACCTCGAGGAGTGCATCACCC
GTATCACAAACACTGAGAAATGTCTCAAAGAACTCATGGAACTTA
AGACAAAAGCCAGGGAGCTTCGAGAGGAGTGTCGGAGTCTGAGAT
CCAGGTGTGACCAGCTCGAGGAGCGCGTGAGCGCGATGGAAGACG
AGATGAACGAGATGAAAAGAGAGGGCAAATTCAGGGAGAAGCGCA
TTAAGAGGAACGAACAGAGTCTGCAGGAGATTTGGGATTACGTCA
AGAGGCCTAACCTGCGGTTGATCGGCGTCCCCGAGAGCGACGTAG
AAAACGGGACTAAACTGGAGAATACACTTCAAGACATCATTCAAG
AAAATTTTCCAAACCTGGCTCGGCAAGCTAATGTGCAAATCCAAG
AGATCCAACGCACACCCCAGCGGTATAGCTCTCGGCGTGCCACCC
CTAGGCATATTATCGTGCGCTTTACTAAGGTGGAGATGAAAGAGA
AGATGCTGCGAGCCGCTCGGGAAAAGGGAAGGGTGACTTTGAAGG
GCAAACCTATTCGGCTGACGGTTGACCTTAGCGCCGAGACACTCC
AGGCACGCCGGGAATGGGGCCCCATCTTTAATATCCTGAAGGAGA
AGAACTTCCAGCCACGAATCTCTTACCCTGCAAAGTTGAGTTTTA
TCTCCGAGGGTGAGATTAAGTATTTCATCGATAAACAGATGCTGC
GAGACTTCGTGACAACTCGCCCAGCTCTCAAGGAACTGCTCAAAG
AGGCTCTTAATATGGAGCGCAATAATAGATATCAACCCTTGCAGA
ACCACGCAAAGATGTGAGACAGCCGTCAGACCATCAAGACTAGGA
AGAAACTGCATCAACTAATGAGCAAAATCACCAGCTAACATCATA
GTATACATGACCGGCTCTAACTCACATATCACCATCCTTACACTT
AACATTAACGGCCTCAACTCAGCTATCAAGCGCCATCGGCTGGCC
AGCTGGATCAAATCACAGGATCCAAGCGTTTGTTGCATCCAAGAG
ACCCACCTGACCTGTAGAGATACTCACCGCCTCAAGATCAAGGGA
TGGCGAAAGATTTATCAGGCGAACGGTAAGCAGAAGAAAGCCGGA
GTCGCAATTCTGGTCTCAGACAAGACGGATTTCAAGCCCACCAAA
ATTAAGCGTGATAAGGAAGGTCACTATATTATGGTGAAAGGCAGC
ATACAGCAGGAAGAACTTACCATATTGAACATCTACGCGCCAAAC
ACCGGCGCACCTCGCTTTATCAAACAGGTCCTGTCCGATCTGCAG
CGAGATCTGGATTCTCATACGTTGATTATGGGTGATTTCAATACA
CCATTGAGCACCCTGGATCGCAGCACCAGGCAAAAGGTAAATAAA
GACACGCAAGAGCTCAATAGCGCACTGCATCAGGCAGATCTCATT
GATATTTATCGCACTCTTCATCCTAAGAGTACCGAGTACACATTC
TTCAGCGCCCCACATCATACATACTCAAAGATCGATCATATCGTC
GGCTCAAAGGCTCTGCTGTCAAAGTGCAAGCGCACAGAGATAATT
ACAAATTACCTGTCAGATCATAGCGCGATCAAGCTCGAGCTGAGA
ATCAAGAACCTGACCCAGAGCCGGAGTACCACTTGGAAGCTTAAT
AACCTGCTGCTCAACGATTATTGGGTCCACAATGAGATGAAGGCA
GAGATTAAAATGTTCTTCGAAACAAATGAGAATAAGGATACTACC
TATCAAAACCTTTGGGATGCCTTTAAGGCCGTCTGCAGAGGCAAG
TTCATCGCCCTCAACGCCTATAAAAGAAAACAAGAGAGATCTAAG
ATCGATACTCTCACCTCTCAGCTGAAGGAGTTGGAGAAACAGGAA
CAGACCCACTCCAAGGCGTCAAGACGGCAGGAGATCACAAAGATT
CGCGCCGAGTTGAAAGAGATCGAAACCCAAAAGACTCTTCAGAAA
ATTAACGAGTCTCGTAGTTGGTTCTTCGAGCGGATTAATAAGATA
GACAGACCTCTGGCACGACTGATTAAGAAGAAGCGCGAAAAGAAC
CAGATTGATACCATCAAGAACGACAAGGGCGACATCACTACTGAC
CCGACCGAGATCCAGACCACTATTCGGGAGTATTATAAGCATTTG
TATGCTAACAAGCTTGAGAACCTGGAAGAGATGGACACTTTTCTG
GATACCTATACTCTGCCACGGCTTAATCAAGAGGAAGTCGAGTCC
CTCAACCGCCCAATTACAGGAAGCGAGATTGTGGCCATAATTAAC
TCCCTGCCGACAAAGAAATCTCCTGGTCCGGACGGGTTTACAGCT
GAGTTTTATCAACGGTATATGGAAGAGCTTGTACCGTTTCTGCTC
AAGCTCTTTCAGTCTATAGAAAAGGAAGGCATCTTGCCCAATTCC
TTCTACGAAGCTTCTATAATACTTATTCCCAAACCAGGACGCGAT
ACCACAAAGAAGGAAAACTTCCGGCCCATTAGTCTCATGAATATC
GACGCTAAAATATTGAACAAGATTCTCGCCAACAGAATCCAACAA
CATATTAAGAAATTGATACATCACGACCAGGTGGGGTTTATACCT
GGCATGCAGGGCTGGTTTAACATCCGGAAGAGTATTAACGTCATT
CAACACATTAATAGAGCTAAGGATAAGAATCATATGATCATCTCT
ATAGACGCGGAAAAGGCATTCGATAAGATTCAGCAGCCATTTATG TABLE 8-continued Plasmid and mRNA construct sequences CTCAAGACTCTGAACAAACTCGGCATCGACGGAACATATTTTAAG
ATTATTCGCGCAATTTACGATAAGCCGACTGCTAACATTATCCTT
AACGGCCAAAAGCTCGAGGCCTTTCCGCTCAAGACTGGAACCCGC
CAAGGCTGTCCCCTCTCCCCGCTTTTGTTTAATATTGTACTCGAG
GTGCTGGCTAGGGCTATTCGTCAAGAGAAAGAGATTAAAGGGATA
CAGCTCGGGAAGGAAGAGGTCAAGCTTTCCTTGTTCGCCGATGAT
ATGATTGTGTACCTGGAGAATCCTATTGTGTCTGCTCAGAACCTT
CTTAAACTTATTTCTAACTTTAGCAAGGTCAGCGGCTATAAGATT
AACGTCCAGAAATCTCAGGCCTTTCTGTACACAAATAATCGACAG
ACCGAATCCCAGATAATGGGTGAGCTTCCGTTTGTCATAGCCAGC
AAAAGGATAAAGTATCTCGGAATCCAGCTGACACGAGACGTTAAA
GATTTGTTTAAGGAAAATTACAAGCCTCTCCTGAAAGAGATTAAG
GAAGATACTAATAAGTGGAAGAATATCCCCTGTTCATGGGTTGGC
AGAATCAACATAGTGAAGATGGCAATACTTCCTAAAGTGATATAT
CGCTTTAACGCCATCCCAATTAAACTGCCTATGACCTTCTTTACG
GAGCTCGAGAAAACAACCCTTAAATTTATATGGAATCAAAAGAGA
GCAAGAATAGCGAAGTCCATCTTGAGCCAGAAGAATAAGGCCGGT
GGGATTACTTTGCCTGATTTTAAGTTGTATTATAAAGCCACAGTA
ACTAAGACAGCCTGGTATTGGTATCAGAATAGAGACATCGACCAG
TGGAATCGGACCGAACCATCAGAGATAATGCCCCACATCTATAAT
TACCTTATATTCGATAAGCCAGAAAAGAATAAACAGTGGGGCAAA
GACAGCCTCTTCAACAAGTGGTGTTGGGAGAATTGGCTGGCCATA
TGCCGGAAACTCAAGCTCGACCCCTTTCTTACACCCTACACTAAA
ATCAACAGTAGGTGGATCAAGGACTTGAATGTCAAGCCAAAGACT
ATAAAGACACTGGAAGAGAATCTTGGGATCACAATACAAGATATA
GGCGTCGGCAAAGATTTTATGTCAAAGACGCCCAAGGCCATGGCC
ACTAAGGATAAGATTGATAAGTGGGACCTTATTAAGCTCAAAAGC
TTCTGTACTGCCAAGGAGACCACGATCAGAGTTAATAGGCAGCCC
ACTACATGGGAAAAGATTTTCGCCACTTATTCATCAGATAAGGGG
TTGATAAGCAGAATATATAACGAGCTGAAGCAGATCTACAAGAAG
AAAACGAATAATCCCATCAAGAAGTGGGCAAAAGATATGAACAGG
CATTTTAGCAAAGAGGATATCTACGCCGCGAAGAAGCATATGAAG
AAGTGTAGTTCAAGCTTGGCCATTCGTGAGATGCAGATTAAGACG
ACCATGCGATACCACCTTACCCCAGTGAGGATGGCAATTATCAAG
AAATCTGGCAATAATAGATGTTGGCGGGGCTGTGGCGAGATTGGC
ACCCTGCTCCATTGCTGGTGGGATTGCAAGCTGGTGCAGCCGCTT
TGGAAATCAGTCTGGCGCTTTCTGAGGGACCTCGAGCTTGAGATT
CCCTTCGATCCCGCAATTCCCTTGCTCGGAATCTATCCTAACGAA
TACAAGAGCTGTTGTTACAAGGATACGTGTACCCGGATGTTCATC
GCGGCCTTGTTTACGATAGCTAAGACGTGGAATCAGCCTAAGTGC
CCCACAATGATCGATTGGATCAAGAAAATGTGGCATATTTATACC
ATGGAGTATTACGCAGCAATTAAGAATGACGAATTTATTTCCTTC
GTTGGGACCTGGATGAAGCTGGAGACTATTATTCTGAGCAAGCTG
TCTCAGGAGCAAAAGACAAAGCATAGAATCTTCTCTCTCATTGGT
GGTAACGACTACAAAGACGATGACGACAAGTAAAGCGGCCGGGCG
CGGTGGCTCACGCCTGTAATCCCAGCACTTTGGGAGGCCGAGGCG
GGAGGATCGCAGTTCGAGACCAGCGCGAGACCCCGTCTCTACAAA
AATACAAAAATTAGCTTCTAGAAGTTGTCTCCTCCTGCACTGACT
GACTGATACAATCGATTTCTGGATCCGCAGGCCTAATCAACCTCT
GGATTACAAAATTTGTGAAAGATTGACTGGTATTCTTAACTATGT
TGCTCCTTTTACGCTATGTGGATACGCTGCTTTAATGCCTTTGTA
TCATGCTATTGCTTCCCGTATGGCTTTCATTTTCTCCTCCTTGTA
TAAATCCTGGTTGCTGTCTCTTTATGAGGAGTTGTGGCCCGTTGT
CAGGCAACGTGGCGTGGTGTGCACTGTGTTTGCTGACGCAACCCC
CACTGGTTGGGGCATTGCCACCACCTGTCAGCTCCTTTCCGGGAC
TTTCGCTTTCCCCCTCCCTATTGCCACGGCGGAACTCATCGCCGC
CTGCCTTGCCCGCTGCTGGACAGGGGCTCGGCTGTTGGGCACTGA
CAATTCCGTGGTGTTGTCGGGGAAGCTGACGTCCTTTCCATGGCT
GCTCGCCTGTGTTGCCACCTGGATTCTGCGCGGGACGTCCTTCTG
CTACGTCCCTTCGGCCCTCAATCCAGCGGACCTTCCTTCCCGCTG
AGAGACACAAAAAATTCCAACACACTATTGCAATGAAAATAAATT
TCCTTTATTAGCCAGAAGTCAGATGCTCAAGGGGCTTCATGATGT
CCCCATAATTTTTGGCAGAGGGAAAAAGATCTCAGTGGTATTTGT
GAGCCAGGGCATTGGCCTTCTGATAGGCAGCCTGCACCTGAGGAG
TGCGGCCGCTTTACTTGTACAGCTCGTCCATGCCGAGAGTGATCC
CGGCGGCGGTCACGAACTCCAGCAGGACCATGTGATCGCGCTTCT
CGTTGGGGTCTTTGCTCAGGGCGGACTGGGTGCTCAGGTAGTGGT
TGTCGGGCAGCAGCACGGGGCCGTCGCCGATGGGGGTGTTCTGCT
GGTAGTGGTCGGCGAGCTGCACGCTGCCGTCCTCGATGTTGTGGC
GGATCTTGAAGTTCACCTTGATGCCGTTCTTCTGCTTGTCGGCCA
TGATATAGACGTTGTGGCTGTTGTAGTTGTACTCCAGCTTGTGCC
CCAGGATGTTGCCGTCCTCCTTGAAGTCGATGCCCTTCAGCTCGA
TGCGGTTCACCAGGGTGTCGCCCTCGAACTTCACCTCGGCGCGGG
TCTTGTAGTTGCCGTCGTCCTTGAAGAAGATGGTGCGCTCCTGGA
CGTAGCCTTCGGGCATGGCGGACTTGAAGAAGTCGTGCTGCTTCA
TGTGGTCGGGGTAGCGGCTGAAGCACTGCACGCCGTAGGTCAGGG
TGGTCACGAGGGTGGGCCAGGGCACGGGCAGCTTGCCGGTGGTGC
AGATGAACTTCAGGGTCAGCTTGCCGTAGGTGGCATCGCCCTCGC
CCTCGCCGGACACGCTGAACTTGTGGCCGTTTACGTCGCCGTCCA
GCTCGACCAGGATGGGCACCACCCCGGTGAACAGCTCCTCGCCCT
TGCTCACCATGGTGGCGGGATCTGACGGTTCACTAAACCAGCTCT
GCTTATATAGACCTCCCACCGTACACGCCTACCGCCCATTTGCGT
CAATGGGGCGGAGTTGTTACGACATTTTGGAAAGTCCCGTTGATT
TTGGTGCCAAAACAAACTCCCATTGACGTCAATGGGGTGGAGACT
TGGAAATCCCCGTGAGTCAAACCGCTATCCACGCCCATTGATGTA
CTGCCAAAACCGCATCACCATGGTAATAGCGATGACTAATACGTA
GATGTACTGCCAAGTAGGAAAGTCCCATAAGGTCATGTACTGGGC
ATAATGCCAGGCGGGCCATTTACCGTCATTGACGTCAATAGGGGG
CGTACTTGGCATATGATACACTTGATGTACTGCCAAGTGGGCAGT
TTACCGTAAATACTCCACCCATTGACGTCAATGGAAAGTCCCTAT
TGGCGTTACTATGGGAACATACGTCATTATTGACGTCAATGGGCG
GGGGTCGTTGGGCGGTCAGCCAGGCGGGCCATTTACCGTAAGTTA
TGTAACGGGCCTGCTGCCGGCTCTGCGGCCTCTTCCGCGTCTTCG
CCTTCGCCCTCAGACGAGTCGGATCTCCCTTTGGGCCGCCTCCCC
GCCTGTCTAGCTTGACTGACTGAGATACAGCGTACCTTCAGCTCA
CAGACATGATAAGATACATTGATGAGTTTGGACAAACCACAACTA
GAATGCAGTGAAAAAAATGCTTTATTTGTGAAATTTGTGATGCTA
TTGCTTTATTTGTAACCATTATAAGCTGCAATAAACAAGTT
(SEQ ID NO: 43)

LINE-1 plasmid CVBE IRES GFP (SEQ ID NO: 44)
TAATACGACTCACTATAGGGAGAAGTACTGCCACCATGGGCAAGA
AGCAAAATCGCAAGACGGGGAATTCCAAGACACAATCCGCTAGCC
CACCACCTAAAGAGCGTTCTAGCTCCCCTGCTACTGAGCAGTCCT
GGATGGAAAACGACTTCGATGAACTCCGGGAAGAGGGATTTAGGC
GATCCAACTATTCAGAACTCCGCGAAGATATCCAGACAAAGGGGA
AGGAAGTCGAGAATTTCGAGAAGAACCTCGAGGAGTGCATCACCC
GTATCACAAACACTGAGAAATGTCTCAAAGAACTCATGGAACTTA
AGACAAAAGCCAGGGAGCTTCGAGAGGAGTGTCGGAGTCTGAGAT
CCAGGTGTGACCAGCTCGAGGAGCGCGTGAGCGCGATGGAAGACG
AGATGAACGAGATGAAAAGAGAGGGCAAATTCAGGGAGAAGCGCA
TTAAGAGGAACGAACAGAGTCTGCAGGAGATTTGGGATTACGTCA
AGAGGCCTAACCTGCGGTTGATCGGCGTCCCCGAGAGCGACGTAG
AAAACGGGACTAAACTGGAGAATACACTTCAAGACATCATTCAAG
AAAATTTTCCAAACCTGGCTCGGCAAGCTAATGTGCAAATCCAAG
AGATCCAACGCACACCCCAGCGGTATAGCTCTCGGCGTGCCACCC
CTAGGCATATTATCGTGCGCTTTACTAAGGTGGAGATGAAAGAGA
AGATGCTGCGAGCCGCTCGGGAAAAGGGAAGGGTGACTTTGAAGG
GCAAACCTATTCGGCTGACGGTTGACCTTAGCGCCGAGACACTCC
AGGCACGCCGGGAATGGGGCCCCATCTTTAATATCCTGAAGGAGA
AGAACTTCCAGCCACGAATCTCTTACCCTGCAAAGTTGAGTTTTA
TCTCCGAGGGTGAGATTAAGTATTTCATCGATAAACAGATGCTGC
GAGACTTCGTGACAACTCGCCCAGCTCTCAAGGAACTGCTCAAAG
AGGCTCTTAATATGGAGCGCAATAATAGATATCAACCCTTGCAGA
ACCACGCAAAGATGTGAGACAGTTAAAACAGCCTGTGGGTTGATC
CCACCCACAGGCCCATTGGGCGCTAGCACTCTGGTATCACGGTAC
CTTTGTGCGCCTGTTTTATACCCCCTCCCCCAACTGTAACTTAGA
AGTAACACACACCGATCAACAGTCAGCGTGGCACACCAGCCACGT
TTTGATCAAGCACTTCTGTTACCCCGGACTGAGTATCAATAGACT
GCTCACGCGGTTGAAGGAGAAAGCGTTCGTTATCCGGCCAACTAC
TTCGAAAAACCTAGTAACACCGTGGAAGTTGCAGAGTGTTTCGCT
CAGCACTACCCCAGTGTAGATCAGGTCGATGAGTCACCGCATTCC
CCACGGGCGACCGTGGCGGTGGCTGCGTTGGCGGCCTGCCCATGG
GGAAACCCATGGGACGCTCTAATACAGACATGGTGCGAAGAGTCT
ATTGAGCTAGTTGGTAGTCCTCCGGCCCCTGAATGCGGCTAATCC
TAACTGCGGAGCACACACCCTCAAGCCAGAGGGCAGTGTGTCGTA
ACGGGCAACTCTGCAGCGGAACCGACTACTTTGGGTGTCCGTGTT
TCATTTTATTCCTATACTGGCTGCTTATGGTGACAATTGAGAGAT
CGTTACCATATAGCTATTGGATTGGCCATCCGGTGACTAATAGAG
CTATTATATATCCCTTTGTTGGGTTTATACCACTTAGCTTGAAAG
AGGTTAAAACATTACAATTCATTGTTAAGTTGAATACAGCAAATA
CATGACCGGCTCTAACTCACATATCACCATCCTTACACTTAACAT
TAACGGCCTCAACTCAGCTATCAAGCGCCATCGGCTGGCCAGCTG
GATCAAATCACAGGATCCAAGCGTTTGTTGCATCCAAGAGACCCA
CCTGACCTGTAGAGATACTCACCGCCTCAAGATCAAGGGATGGCG
AAAGATTTATCAGGCGAACGGTAAGCAGAAGAAAGCCGGAGTCGC
AATTCTGGTCTCAGACAAGACGGATTTCAAGCCCACCAAAATTAA
GCGTGATAAGGAAGGTCACTATATTATGGTGAAAGGCAGCATACA
GCAGGAAGAACTTACCATATTGAACATCTACGCGCCAAACACCGG
CGCACCTCGCTTTATCAAACAGGTCCTGTCCGATCTGCAGCGAGA
TCTGGATTCTCATACGTTGATTATGGGTGATTTCAATACACCATT
GAGCACCCTGGATCGCAGCACCAGGCAAAAGGTAAATAAAGACAC
GCAAGAGCTCAATAGCGCACTGCATCAGGCAGATCTCATTGATAT
TTATCGCACTCTTCATCCTAAGAGTACCGAGTACACATTCTTCAG
CGCCCCACATCATACATACTCAAAGATCGATCATATCGTCGGCTC
AAAGGCTCTGCTGTCAAAGTGCAAGCGCACAGAGATAATTACAAA TABLE 8-continued

| Plasmid and mRNA construct sequences |
|---|
| TTACCTGTCAGATCATAGCGCGATCAAGCTCGAGCTGAGAATCAA |
| GAACCTGACCCAGAGCCGGAGTACCACTTGGAAGCTTAATAACCT |
| GCTGCTCAACGATTATTGGGTCCACAATGAGATGAAGGCAGAGAT |
| TAAAATGTTCTTCGAAACAAATGAGAATAAGGATACTACCTATCA |
| AAACCTTTGGGATGCCTTTAAGGCCGTCTGCAGAGGCAAGTTCAT |
| CGCCCTCAACGCCTATAAAAGAAAACAAGAGAGATCTAAGATCGA |
| TACTCTCACCTCTCAGCTGAAGGAGTTGGAGAAACAGGAACAGAC |
| CCACTCCAAGGCGTCAAGACGGCAGGAGATCACAAAGATTCGCGC |
| CGAGTTGAAAGAGATCGAAACCCAAAAGACTCTTCAGAAAATTAA |
| CGAGTCTCGTAGTTGGTTCTTCGAGCGGATTAATAAGATAGACAG |
| ACCTCTGGCACGACTGATTAAGAAGAAGCGCGAAAAGAACCAGAT |
| TGATACCATCAAGAACGACAAGGGCGACATCACTACTGACCCGAC |
| CGAGATCCAGACCACTATTCGGGAGTATTATAAGCATTTGTATGC |
| TAACAAGCTTGAGAACCTGGAAGAGATGGACACTTTTCTGGATAC |
| CTATACTCTGCCACGGCTTAATCAAGAGGAAGTCGAGTCCCTCAA |
| CCGCCCAATTACAGGAAGCGAGATTGTGGCCATAATTAACTCCCT |
| GCCGACAAAGAAATCTCCTGGTCCGGACGGGTTTACAGCTGAGTT |
| TTATCAACGGTATATGGAAGAGCTTGTACCGTTTCTGCTCAAGCT |
| CTTTCAGTCTATAGAAAAGGAAGGCATCTTGCCCAATTCCTTCTA |
| CGAAGCTTCTATAATACTTATTCCCAAACCAGGACGCGATACCAC |
| AAAGAAGGAAAACTTCCGGCCCATTAGTCTCATGAATATCGACGC |
| TAAAATATTGAACAAGATTCTCGCCAACAGAATCCAACAACATAT |
| TAAGAAATTGATACATCACGACCAGGTGGGGTTTATACCTGGCAT |
| GCAGGGCTGGTTTAACATCCGGAAGAGTATTAACGTCATTCAACA |
| CATTAATAGAGCTAAGGATAAGAATCATATGATCATCTCTATAGA |
| CGCGGAAAAGGCATTCGATAAGATTCAGCAGCCATTTATGCTCAA |
| GACTCTGAACAAACTCGGCATCGACGGAACATATTTTAAGATTAT |
| TCGCGCAATTTACGATAAGCCGACTGCTAACATTATCCTTAACGG |
| CCAAAAGCTCGAGGCCTTTCCGCTCAAGACTGGAACCCGCCAAGG |
| CTGTCCCCTCTCCCCGCTTTTGTTTAATATTGTACTCGAGGTGCT |
| GGCTAGGGCTATTCGTCAAGAGAAAGAGATTAAAGGGATACAGCT |
| CGGGAAGGAAGAGGTCAAGCTTTCCTTGTTCGCCGATGATATGAT |
| TGTGTACCTGGAGAATCCTATTGTGTCTGCTCAGAACCTTCTTAA |
| ACTTATTTCTAACTTTAGCAAGGTCAGCGGCTATAAGATTAACGT |
| CCAGAAATCTCAGGCCTTTCTGTACACAAATAATCGACAGACCGA |
| ATCCCAGATAATGGGTGAGCTTCCGTTTGTCATAGCCAGCAAAAG |
| GATAAAGTATCTCGGAATCCAGCTGACACGAGACGTTAAAGATTT |
| GTTTAAGGAAAATTACAAGCCTCTCCTGAAAGAGATTAAGGAAGA |
| TACTAATAAGTGGAAGAATATCCCCTGTTCATGGGTTGGCAGAAT |
| CAACATAGTGAAGATGGCAATACTTCCTAAAGTGATATATCGCTT |
| TAACGCCATCCCAATTAAACTGCCTATGACCTTCTTTACGGAGCT |
| CGAGAAAACAACCCTTAAATTTATATGGAATCAAAAGAGAGCAG |
| AATAGCGAAGTCCATCTTGAGCCAGAAGAATAAGGCCGGTGGGAT |
| TACTTTGCCTGATTTTAAGTTGTATTATAAAGCCACAGTAACTAA |
| GACAGCCTGGTATTGGTATCAGAATAGAGACATCGACCAGTGGAA |
| TCGGACCGAACCATCAGAGATAATGCCCCACATCTATAATTACCT |
| TATATTCGATAAGCCAGAAAAGAATAAACAGTGGGGCAAAGACAG |
| CCTCTTCAACAAGTGGTGTTGGGAGAATTGGCTGGCCATATGCCG |
| GAAACTCAAGCTCGACCCCTTTCTTACACCCTACACTAAAATCAA |
| CAGTAGGTGGATCAAGGACTTGAATGTCAAGCCAAAGACTATAAA |
| GACACTGGAAGAGAATCTTGGGATCACAATACAAGATATAGGCGT |
| CGGCAAAGATTTTATGTCAAAGACGCCCAAGGCCATGGCCACTAA |
| GGATAAGATTGATAAGTGGGACCTTATTAAGCTCAAAAGCTTCTG |
| TACTGCCAAGGAGACCACGATCAGAGTTAATAGGCAGCCCACTAC |
| ATGGGAAAAGATTTTCGCCACTTATTCATCAGATAAGGGGTTGAT |
| AAGCAGAATATATAACGAGCTGAAGCAGATCTACAAGAAGAAAAC |
| GAATAATCCCATCAAGAAGTGGGCAAAAGATATGAACAGGCATTT |
| TAGCAAAGAGGATATCTACGCCGCGAAGAAGCATATGAAGAAGTG |
| TAGTTCAAGCTTGGCCATTCGTGAGATGCAGATTAAGACGACCAT |
| GCGATACCACCTTACCCCAGTGAGGATGGCAATTATCAAGAAATC |
| TGGCAATAATAGATGTTGGCGGGGCTGTGGCGAGATTGGCACCCT |
| GCTCCATTGCTGGTGGGATTGCAAGCTGGTGCAGCCGCTTTGGAA |
| ATCAGTCTGGCGCTTTCTGAGGGACCTCGAGCTTGAGATTCCCTT |
| CGATCCCGCAATTCCCTTGCTCGGAATCTATCCTAACGAATACAA |
| GAGCTGTTGTTACAAGGATACGTGTACCCGGATGTTCATCGCGGC |
| CTTGTTTACGATAGCTAAGACGTGGAATCACCTAAGTGCCCCAC |
| AATGATCGATTGGATCAAGAAAATGTGGCATATTTATACCATGGA |
| GTATTACGCAGCAATTAAGAATGACGAATTTATTTCCTTCGTTGG |
| GACCTGGATGAAGCTGGAGACTATTATTCTGAGCAAGCTGTCTCA |
| GGAGCAAAAGACAAAGCATAGAATCTTCTCTCTCATTGGTGGTAA |
| CGACTACAAAGACGATGACGACAAGTAAAGCGCTTCTAGAAGTTG |
| TCTCCTCCTGCACTGACTGACTGATACAATCGATTTCTGGATCCG |
| CAGGCCTAATCAACCTCTGGATTACAAAATTTGTGAAAGATTGAC |
| TGGTATTCTTAACTATGTTGCTCCTTTTACGCTATGTGGATACGC |
| TGCTTTAATGCCTTTGTATCATGCTATTGCTTCCCGTATGGCTTT |
| CATTTTCTCCTCCTTGTATAAATCCTGGTTGCTGTCTCTTTATGA |
| GGAGTTGTGGCCCGTTGTCAGGCAACGTGGCGTGGTGTGCACTGT |
| GTTTGCTGACGCAACCCCCACTGGTTGGGGCATTGCCACCACCTG |

TABLE 8-continued

| Plasmid and mRNA construct sequences |
|---|
| TCAGCTCCTTTCCGGGACTTTCGCTTTCCCCCTCCCTATTGCCAC |
| GGCGGAACTCATCGCCGCCTGCCTTGCCCGCTGCTGGACAGGGGC |
| TCGGCTGTTGGGCACTGACAATTCCGTGGTGTTGTCGGGGAAGCT |
| GACGTCCTTTCCATGGCTGCTCGCCTGTGTTGCCACCTGGATTCT |
| GCGCGGGACGTCCTTCTGCTACGTCCCTTCGGCCCTCAATCCAGC |
| GGACCTTCCTTCCCGCGAACAAACGACCCAACACCCGTGCGTTTT |
| ATTCTGTCTTTTTATTGCCGATCCCCTCAGAAGAACTCGTCAAGA |
| AGGCGATAGAAGGCGATGCGCTGCGAATCGGGAGCGGCGATACCG |
| TAAAGCACGAGGAAGCGGTCAGCCCATTCGCCGCCAAGCTCTTCA |
| GCAATATCACGGGTAGCCAACGCTATGTCCTGATAGCGGTCGGCC |
| GCTTTACTTGTACAGCTCGTCCATGCCGAGAGTGATCCCGGCGGC |
| GGTCACGAACTCCAGCAGGACCATGTGATCGCGCTTCTCGTTGGG |
| GTCTTTGCTCAGGGCGGACTGGGTGCTCAGGTAGTGGTTGTCGGG |
| CAGCAGCACGGGGCCGTCGCCGATGGGGGTGTTCTGCTGGTAGTG |
| GTCGGCCAGGTGAGTCCAGGAGATGTTTCAGCACTGTTGCCTTTA |
| GTCTCGAGGCAACTTAGACAACTGAGTATTGATCTGAGCACAGCA |
| GGGTGTGAGCTGTTTGAAGATACTGGGGTTGGGGGTGAAGAAACT |
| GCGAGGACTAACTGGGCTGAGACCCAGTGGCAATGTTTTAGGGC |
| CTAAGGAATGCCTCTGAAAATCTAGATGGACAACTTTGACTTTGA |
| GAAAAGAGAGGTGGAAATGAGGAAAATGACTTTTCTTTATTAGAT |
| TTCGGTAGAAAGAACTTTCATCTTTCCCCTATTTTTGTTATTCGT |
| TTTAAAACATCTATCTGGAGGCAGGACAAGTATGGTCATTAAAAA |
| GATGCAGGCAGAAGGCATATATTGGCTCAGTCAAAGTGGGGAACT |
| TTGGTGGCCAAACATACATTGCTAAGGCTATTCCTATATCAGCTG |
| GACACATATAAAATGCTGCTAATGCTTCATTACAAACTTATATCC |
| TTTAATTCCAGATGGGGGCAAAGTATGTCCAGGGGTGAGGAACAA |
| TTGAAACATTTGGGCTGGAGTAGATTTTGAAAGTCAGCTCTGTGT |
| GTGTGTGTGTGTGTGTGTGTGAGAGCGTGTGTTTCTTTTAACG |
| TTTTCAGCCTACAGCATACAGGGTTCATGGTGGCAAGAAGATAAC |
| AAGATTTAAATTATGGCCAGTGACTAGTGCTGCAAGAAGAACAAC |
| TACCTGCATTTAATGGGAAAGCAAAATCTCAGGCTTTGAGGGAAG |
| TTAACATAGGCTTGATTCTGGGTGGAAGCTGGGTGTGTAGTTATC |
| TGGAGGCCAGGCTGGAGCTCTCAGCTCACTATGGGTTCATCTTTA |
| TTGTCTCCTTTCATCTCAACAGCTGCACGCTGCCGTCCTCGATGT |
| TGTGGCGGATCTTGAAGTTCACCTTGATGCCGTTCTTCTGCTTGT |
| CGGCCATGATATAGACGTTGTGGCTGTTGTAGTTGTACTCCAGCT |
| TGTGCCCCAGGATGTTGCCGTCCTCCTTGAAGTCGATGCCCTTCA |
| GCTCGATGCGGTTCACCAGGGTGTCGCCCTCGAACTTCACCTCGG |
| CGCGGGTCTTGTAGTTGCCGTCGTCCTTGAAGAAGATGGTGCGCT |
| CCTGGACGTAGCCTTCGGGCATGGCGGACTTGAAGAAGTCGTGCT |
| GCTTCATGTGGTCGGGGTAGCGGCTGAAGCACTGCACGCCGTAGG |
| TCAGGGTGGTCACGAGGGTGGGCCAGGGCACGGGCAGCTTGCCGG |
| TGGTGCAGATGAACTTCAGGGTCAGCTTGCCGTAGGTGGCATCGC |
| CCTCGCCCTCGCCGGACACGCTGAACTTGTGGCCGTTTACGTCGC |
| CGTCCAGCTCGACCAGGATGGGCACCACCCCGGTGAACAGCTCCT |
| CGCCCTTGCTCACCATGGTGGCGAATTCGAAGCTTGAGCACGAGA |
| TCTGAGTCCGGTAGGCCTAGCGGATCTGACGGTTCACTAAACCAG |
| CTCTGCTTATATAGACCTCCCACCGTACACGCCTACCGCCCATTT |
| GCGTCAATGGGGCGGAGTTGTTACGACATTTTGGAAAGTCCCGTT |
| GATTTTGGTGCCAAAACAAACTCCCATTGACGTCAATGGGGTGGA |
| GACTTGGAAATCCCCGTGAGTCAAACCGCTATCCACGCCCATTGA |
| TGTACTGCCAAAACCGCATCACCATGGTAATAGCGATGACTAATA |
| CGTAGATGTACTGCCAAGTAGGAAAGTCCCATAAGGTCATGTACT |
| GGGCATAATGCCAGGCGGGCCATTTACCGTCATTGACGTCAATAG |
| GGGGCGTACTTGGCATATGATACACTTGATGTACTGCCAAGTGGG |
| CAGTTTACCGTAAATACTCCACCCATTGACGTCAATGGAAAGTCC |
| CTATTGGCGTTACTATGGGAACATACGTCATTATTGACGTCAATG |
| GGCGGGGGTCGTTGGGCGGTCAGCCAGGCGGGCCATTTACCGTAA |
| GTTATGTAACGGGCCTGCTGCCGGCTCTGCGGCCTCTTCCGCGTC |
| TTCGCCTTCGCCCTCAGACGAGTCGGATCTCCCTTTGGGCCGCCT |
| CCCCGCCTGTCTAGCTTGACTGACTGAGATACAGCGTACCTTCAG |
| CTCACAGACATGATAAGATACATTGATGAGTTTGGACAAACCACA |
| ACTAGAATGCAGTGAAAAAAATGCTTTATTTGTGAAATTTGTGAT |
| GCTATTGCTTTATTTGTAACCATTATAAGCTGCAATAAACAAGTT |
| AACAACAACAATTGCATTCATTTTATGTTTCAGGTTCAGGGGGAG |
| GTGTGGGAGGTTTTTTAAAGCAAGTAAAACCTCTACAAATGTGGT |
| ATTGGCCCATCTCTATCGGTATCGTAGCATAACCCCTTGGGGCCT |
| CTAAACGGGTCTTGAGGGGTTTTTTGTGCCCCTCGGGCCGGATTG |
| CTATCTACCGGCATTGGCGCAGAAAAAAATGCCTGATGCGACGCT |
| GCGCGTCTTATACTCCCACATATGCCAGATTCAGCAACGGATACG |
| GCTTCCCCAACTTGCCCACTTCCATACGTGTCCTCCTTACCAGAA |
| ATTTATCCTTAAGGTCGTCAGCTATCCTGCAGGCGATCTCTCGAT |
| TTCGATCAAGACATTCCTTTAATGGTCTTTTCTGGACACCACTAG |
| GGGTCAGAAGTAGTTCATCAAACTTTCTTCCCTCCCTAATCTCAT |
| TGGTTACCTTGGGCTATCGAAACTTAATTAAGCGATCTGCATCTC |
| AATTAGTCAGCAACCATAGTCCCGCCCCTAACTCCGCCCATCCCG |
| CCCCTAACTCCGCCCAGTTCCGCCCATTCTCCGCCCCATCGCTGA |
| CTAATTTTTTTTATTTATGCAGAGGCCGAGGCCGCCTCGGCCTCT |

TABLE 8-continued

Plasmid and mRNA construct sequences

GAGCTATTCCAGAAGTAGTGAGGAGGCTTTTTTGGAGGCCTAGGC
TTTTGCAAAGGAGGTAGCCAACATGATTGAACAAGATGGATTGCA
CGCAGGTTCTCCGCCGCTTGGGTGGAGAGGCTATTCGGCTATGA
CTGGGCACAACAGACAATCGGCTGCTCTGATGCCGCCGTGTTCCG
GCTGTCAGCGCAGGGGCGCCCGGTTCTTTTTGTCAAGACCGACCT
GTCCGGTGCCCTGAATGAACTCCAGGACGAGGCAGCGCGGCTATC
GTGGCTGGCCACGACGGGCGTTCCTTGCGCAGCTGTGCTCGACGT
TGTCACTGAAGCGGGAAGGGACTGGCTGCTATTGGGCGAAGTGCC
GGGGCAGGATCTCCTGTCATCTCACCTTGCTCCTGCCGAGAAAGT
ATCCATCATGGCTGATGCAATGCGGCGGCTGCATACGCTTGATCC
GGCTACCTGCCCATTCGACCACCAAGCGAAACATCGCATCGAGCG
AGCACGTACTCGGATGGAAGCCGGTCTTGTCGATCAGGATGATCT
GGACGAAGAGCATCAGGGGCTCGCGCCAGCCGAACTGTTCGCCAG
GCTCAAGGCGCGGATGCCCGACGGCGAGGATCTCGTCGTGACCCA
CGGCGATGCCTGCTTGCCGAATATCATGGTGGAAAATGGCCGCTT
TTCTGGATTCATCGACTGTGGCCGGCTGGGTGTGGCGGACCGCTA
TCAGGACATAGCGTTGGCTACCCGTGATATTGCTGAAGAGCTTGG
CGGCGAATGGGCTGACCGCTTCCTCGTGCTTTACGGTATCGCCGC
TCCCGATTCGCAGCGCATCGCCTTCTATCGCCTTCTTGACGAGTT
CTTCTAGTATGTAAGCCCTGTGCCTTCTAGTTGCCAGCCATCTGT
TGTTTGCCCCTCCCCCGTGCCTTCCTTGACCCTGGAAGGTGCCAC
TCCCACTGTCCTTTCCTAATAAAATGAGGAAATTGCATCGCATTG
TCTGAGTAGGTGTCATTCTATTCTGGGGGGTGGGGTGGGGCAGGA
CAGCAAGGGGGAGGATTGGGAAGACAATAGCAGGCATGCTGGGGA
TGCGGTGGGCTCTATGGTTAATTAACCAGTCAAGTCAGCTACTTG
GCGAGATCGACTTGTCTGGGTTTCGACTACGCTCAGAATTGCGTC
AGTCAAGTTCGATCTGGTCCTTGCTATTGCACCCGTTCTCCGATT
ACGAGTTTCATTTAAATCATGTGAGCAAAAGGCCAGCAAAAGGCC
AGGAACCGTAAAAAGGCCGCGTTGCTGGCGTTTTTCCATAGGCTC
CGCCCCCCTGACGAGCATCACAAAAATCGACGCTCAAGTCAGAGG
TGGCGAAACCCGACAGGACTATAAAGATACCAGGCGTTTCCCCCT
GGAAGCTCCCTCGTGCGCTCTCCTGTTCCGACCCTGCCGCTTACC
GGATACCTGTCCGCCTTTCTCCCTTCGGGAAGCGTGGCGCTTTCT
CATAGCTCACGCTGTAGGTATCTCAGTTCGGTGTAGGTCGTTCGC
TCCAAGCTGGGCTGTGTGCACGAACCCCCCGTTCAGCCCGACCGC
TGCGCCTTATCCGGTAACTATCGTCTTGAGTCCAACCCGGTAAGA
CACGACTTATCGCCACTGGCAGCAGCCACTGGTAACAGGATTAGC
AGAGCGAGGTATGTAGGCGGTGCTACAGAGTTCTTGAAGTGGTGG
CCTAACTACGGCTACACTAGAAGAACAGTATTTGGTATCTGCGCT
CTGCTGAAGCCAGTTACCTTCGGAAAAAGAGTTGGTAGCTCTTGA
TCCGGCAAACAAACCACCGCTGGTAGCGGTGGTTTTTTTGTTTGC
AAGCAGCAGATTACGCGCAGAAAAAAAGGATCTCAAGAAGATCCT
TTGATCTTTTCTACGGGGTCTGACGCTCAGTGGAACGAAAACTCA
CGTTAAGGGATTTTGGTCATGAGATTATCAAAAAGGATCTTCACC
TAGATCCTTTTAAATTAAAAATGAAGTTTTAAATCAATCTAAAGT
ATATATGAGTAAACTTGGTCTGACAGTTACCAATGCTTAATCAGT
GAGGCACCTATCTCAGCGATCTGTCTATTTCGTTCATCCATAGTT
GCATTTAAATTTCCGAACTCTCCAAGGCCCTCGTCGGAAAATCTT
CAAACCTTTCGTCCGATCCATCTTGCAGGCTACCTCTCGAACGAA
CTATCGCAAGTCTCTTGGCCGGCCTTGCGCCTTGGCTATTGCTTG
GCAGCGCCTATCGCCAGGTATTACTCCAATCCCGAATATCCGAGA
TCGGGATCACCCGAGAGAAGTTCAACCTACATCCTCAATCCCGAT
CTATCCGAGATCCGAGGAATATCGAAATCGGGGCGCGCCTGGTGT
ACCGAGAACGATCCTCTCAGTGCGAGTCTCGACGATCCATATCGT
TGCTTGGCAGTCAGCCAGTCGGAATCCAGCTTGGGACCCAGGAAG
TCCAATCGTCAGATATTGTACTCAAGCCTGGTCACGGCAGCGTAC
CGATCTGTTTAAACCTAGATATTGATAGTCTGATCGGTCAACGTA
TAATCGAGTCCTAGCTTTTGCAAACATCTATCAAGAGACAGGATC
AGCAGGAGGCTTTCGCATGAGTATTCAACATTTCCGTGTCGCCCT
TATTCCCTTTTTTGCGGCATTTTGCCTTCCTGTTTTTGCTCACCC
AGAAACGCTGGTGAAAGTAAAAGATGCTGAAGATCAGTTGGGTGC
GCGAGTGGGTTACATCGAACTGGATCTCAACAGCGGTAAGATCCT
TGAGAGTTTTCGCCCCGAAGAACGCTTTCCAATGATGAGCACTTT
TAAAGTTCTGCTATGTGGCGCGGTATTATCCCGTATTGACGCCGG
GCAAGAGCAACTCGGTCGCCGCATACACTATTCTCAGAATGACTT
GGTTGAGTATTCACCAGTCACAGAAAAGCATCTTACGGATGGCAT
GACAGTAAGAGAATTATGCAGTGCTGCCATAACCATGAGTGATAA
CACTGCGGCCCGGCCGCAACTTACTTCTGACAACGATTGGAGGAC
CGAAGGAGCTAACCGCTTTTTTGCACAACATGGGGGATCATGTAA
CTCGCCTTGATCGTTGGGAACCGGAGCTGAATGAAGCCATACCAA
ACGACGAGCGTGACACCACGATGCCTGTAGCAATGGCAACAACCT
TGCGTAAACTATTAACTGGCGAACTACTTACTCTAGCTTCCCGGC
AACAGTTGATAGACTGGATGGAGGCGGATAAAGTTGCAGGACCAC
TTCTGCGCTCGGCCCTTCCGGCTGGCTGGTTTATTGCTGATAAAT
CTGGAGCCGGTGAGCGTGGGTCTCGCGGTATCATTGCAGCACTGG
GGCCAGATGGTAAGCCCTCCCGTATCGTAGTTATCTACACGACGG
GGAGTCAGGCAACTATGGATGAACGAAATAGACAGATCGCTGAGA
TAGGTGCCTCACTGATTAAGCATTGGTAACCGATTCTAGGTGCAT
TGGCGCAGAAAAAAATGCCTGATGCGACGCTGCGCGTCTTATACT
CCCACATATGCCAGATTCAGCAACGGATACGGCTTCCCCAACTTG
CCCACTTCCATACGTGTCCTCCTTACCAGAAATTTATCCTTAAGA
TCGTTTAAACTCGACTCTGGCTCTATCGAATCTCCGTCGTTTCGA
GCTTACGCGAACAGCCGTGGCGCTCATTTGCTCGTCGGGCATCGA
ATCTCGTCAGCTATCGTCAGCTTACCTTTTTGGCAGCGATCGCGG
CTCCCGACATCTTGGACCATTAGCTCCACAGGTATCTTCTTCCCT
CTAGTGGTCATAACAGCAGCTTCAGCTACCTCTCAATTCAAAAAA
CCCCTCAAGACCCGTTTAGAGGCCCCAAGGGGTTATGCTATCAAT
CGTTGCGTTACACACACAAAAAACCAACACACATCCATCTTCGAT
GGATAGCGATTTTATTATCTAACTGCTGATCGAGTGTAGCCAGAT
CTAGTAATCAATTACGGGGTCATTAGTTCATAGCCCATATATGGA
GTTCCGCGTTACATAACTTACGGTAAATGGCCCGCCTGGCTGACC
GCCCAACGACCCCCGCCCATTGACGTCAATAATGACGTATGTTCC
CATAGTAACGCCAATAGGGACTTTCCATTGACGTCAATGGGTGGA
GTATTTACGGTAAACTGCCCACTTGGCAGTACATCAAGTGTATCA
TATGCCAAGTACGCCCCCTATTGACGTCAATGACGGTAAATGGCC
CGCCTGGCATTATGCCCAGTACATGACCTTATGGGACTTTCCTAC
TTGGCAGTACATCTACGTATTAGTCATCGCTATTACCATGCTGAT
GCGGTTTTGGCAGTACATCAATGGGCGTGGATAGCGGTTTGACTC
ACGGGGATTTCCAAGTCTCCACCCCATTGACGTCAATGGGAGTTT
GTTTTGGCACCAAAATCAACGGGACTTTCCAAAATGTCGTAACAA
CTCCGCCCCATTGACGCAAATGGGCGGTAGGCGTGTACGGTGGGA
GGTCTATATAAGCAGAGCTGGTTTAGTGAACCGTCAGATCAGATC
TTTGTCGATCCTACCATCCACTCGACACACCCGCCAG
(SEQ ID NO: 44)

LINE-1 Plasmid EV71 IRES (SEQ ID NO: 45)
TAATACGACTCACTATAGGGAGAAGTACTGCCACCATGGGCAAGA
AGCAAAATCGCAAGACGGGGAATTCCAAGACACAATCCGCTAGCC
CACCACCTAAAGAGCGTTCTAGCTCCCCTGCTACTGAGCAGTCCT
GGATGGAAAACGACTTCGATGAACTCCGGGAAGAGGGATTTAGGC
GATCCAACTATTCAGAACTCCGCGAAGATATCCAGACAAAGGGGA
AGGAAGTCGAGAATTTCGAGAAGAACCTCGAGGAGTGCATCACCC
GTATCACAAACACTGAGAAATGTCTCAAAGAACTCATGGAACTTA
AGACAAAAGCCAGGGAGCTTCGAGAGGAGTGTCGGAGTCTGAGAT
CCAGGTGTGACCAGCTCGAGGAGCGCGTGAGCGCGATGGAAGACG
AGATGAACGAGATGAAAAGAGAGGGCAAATTCAGGGAGAAGCGCA
TTAAGAGGAACGAACAGAGTCTGCAGGAGATTTGGGATTACGTCA
AGAGGCCTAACCTGCGGTTGATCGGCGTCCCCGAGAGCGACGTAG
AAAACGGGACTAAACTGGAGAATACACTTCAAGACATCATTCAAG
AAAATTTTCCAAACCTGGCTCGGCAAGCTAATGTGCAAATCCAAG
AGATCCAACGCACACCCCAGCGGTATAGCTCTCGGCGTGCCACCC
CTAGGCATATTATCGTGCGCTTTACTAAGGTGGAGATGAAAGAGA
AGATGCTGCGAGCCGCTCGGGAAAAGGGAAGGGTGACTTTGAAGG
GCAAACCTATTCGGCTGACGGTTGACCTTAGCGCCGAGACACTCC
AGGCACGCCGGGAATGGGGCCCCATCTTTAATATCCTGAAGGAGA
AGAACTTCCAGCCACGAATCTCTTACCCTGCAAAGTTGAGTTTTA
TCTCCGAGGGTGAGATTAAGTATTTCATCGATAAACAGATGCTGC
GAGACTTCGTGACAACTCGCCCAGCTCTCAAGGAACTGCTCAAAG
AGGCTCTTAATATGGAGCGCAATAATAGATATCAACCCTTGCAGA
ACCACGCAAAGATGTGAGACAGTTAAAACAGCTGTGGGTTGTCAC
CCACCCACAGGGTCCACTGGGCGCTAGTACACTGGTATCTCGGTA
CCTTTGTACGCCTGTTTTATACCCCCTCCCTGATTTGCAACTTAG
AAGCAACGCAAACCAGATCAATAGTAGGTGTGACATACCAGTCGC
ATCTTGATCAAGCACTTCTGTATCCCCGGACCGAGTATCAATAGA
CTGTGCACACGGTTGAAGGAGAAAACGTCCGTTACCCGGCTAACT
ACTTCGAGAAGCCTAGTAACGCCATTGAAGTTGCAGAGTGTTTCG
CTCAGCACTCCCCCCGTGTAGATCAGGTCGATGAGTCACCGCATT
CCCCACGGGCGACCGTGGCGGTGGCTGCGTTGGCGGCCTGCCTAT
GGGGTAACCCATAGGACGCTCTAATACGGACATGGCGTGAAGAGT
CTATTGAGCTAGTTAGTAGTCCTCCGGCCCCTGAATGCGGCTAAT
CCTAACTGCGGAGCACATACCCTTAATCCAAAGGGCAGTGTGTCG
TAACGGGCAACTCTGCAGCGGAACCGACTACTTTGGGTGTCCGTG
TTTCTTTTTATTCTTGTATTGGCTGCTTATGGTGACAATTAAAGA
ATTGTTACCATATAGCTATTGGATTGGCCATCCAGTGTCAAACAG
AGCTATTGTATATCTCTTTGTTGGATTCACACCTCTCACTCTTGA
AACGTTACACACCCTCAATTACATTATACTGCTGAACACGAAGCG
TACATGACCGGCTCTAACTCACATATCACCATCCTTACACTTAAC
ATTAACGGCCTCAACTCAGCTATCAAGCGCCATCGGCTGGCCAGC
TGGATCAAATCACAGGATCCAAGCGTTTGTTGCATCCAAGAGACC
CACCTGACCTGTAGAGATACTCACCGCCTCAAGATCAAGGGATGG
CGAAAGATTTATCAGGCGAACGGTAAGCAGAAGAAAGCCGGAGTC
GCAATTCTGGTCTCAGACAAGACGGATTTCAAGCCCACCAAAATT
AAGCGTGATAAGGAAGGTCACTATATTATGGTGAAAGGCAGCATA
CAGCAGGAAGAACTTACCATATTGAACATCTACGCGCCAAACACC
GGCGCACCTCGCTTTATCAAACAGGTCCTGTCCGATCTGCAGCGA
GATCTGGATTCTCATACGTTGATTATGGGTGATTTCAATACACCA TABLE 8-continued

| Plasmid and mRNA construct sequences |
| --- |
| TTGAGCACCCTGGATCGCAGCACCAGGCAAAAGGTAAATAAAGAC |
| ACGCAAGAGCTCAATAGCGCACTGCATCAGGCAGATCTCATTGAT |
| ATTTATCGCACTCTTCATCCTAAGAGTACCGAGTACACATTCTTC |
| AGCGCCCCACATCATACATACTCAAAGATCGATCATATCGTCGGC |
| TCAAAGGCTCTGCTGTCAAAGTGCAAGCGCACAGAGATAATTACA |
| AATTACCTGTCAGATCATAGCGCGATCAAGCTCGAGCTGAGAATC |
| AAGAACCTGACCCAGAGCCGGAGTACCACTTGGAAGCTTAATAAC |
| CTGCTGCTCAACGATTATTGGGTCCACAATGAGATGAAGGCAGAG |
| ATTAAAATGTTCTTCGAAACAAATGAGAATAAGGATACTACCTAT |
| CAAAACCTTTGGGATGCCTTTAAGGCCGTCTGCAGAGGCAAGTTC |
| ATCGCCCTCAACGCCTATAAAAGAAAACAAGAGAGATCTAAGATC |
| GATACTCTCACCTCTCAGCTGAAGGAGTTGGAGAAACAGGAACAG |
| ACCCACTCCAAGGCGTCAAGACGGCAGGAGATCACAAAGATTCGC |
| GCCGAGTTGAAAGAGATCGAAACCCAAAGACTCTTCAGAAAATT |
| AACGAGTCTCGTAGTTGGTTCTTCGAGCGGATTAATAAGATAGAC |
| AGACCTCTGGCACGACTGATTAAGAAGAAGCGCGAAAAGAACCAG |
| ATTGATACCATCAAGAACGACAAGGGCGACATCACTACTGACCCG |
| ACCGAGATCCAGACCACTATTCGGGAGTATTATAAGCATTTGTAT |
| GCTAACAAGCTTGAGAACCTGGAAGAGATGGACACTTTTCTGGAT |
| ACCTATACTCTGCCACGGCTTAATCAAGAGGAAGTCGAGTCCCTC |
| AACCGCCCAATTACAGGAAGCGAGATTGTGGCCATAATTAACTCC |
| CTGCCGACAAAGAAATCTCCTGGTCCGGACGGGTTTACAGCTGAG |
| TTTTATCAACGGTATATGGAAGAGCTTGTACCGTTTCTGCTCAAG |
| CTCTTTCAGTCTATAGAAAAGGAAGGCATCTTGCCCAATTCCTTC |
| TACGAAGCTTCTATAATACTTATTCCCAAACCAGGACGCGATACC |
| ACAAAGAAGGAAAACTTCCGGCCCATTAGTCTCATGAATATCGAC |
| GCTAAAATATTGAACAAGATTCTCGCCAACAGAATCCAACAACAT |
| ATTAAGAAATTGATACATCACGACCAGGTGGGGTTTATACCTGGC |
| ATGCAGGGCTGGTTTAACATCCGGAAGAGTATTAACGTCATTCAA |
| CACATTAATAGAGCTAAGGATAAGAATCATATGATCATCTCTATA |
| GACGCGGAAAAGGCATTCGATAAGATTCAGCAGCCATTTATGCTC |
| AAGACTCTGAACAAACTCGGCATCGACGGAACATATTTTAAGATT |
| ATTCGCGCAATTTACGATAAGCCGACTGCTAACATTATCCTTAAC |
| GGCCAAAAGCTCGAGGCCTTTCCGCTCAAGACTGGAACCCGCCAA |
| GGCTGTCCCCTCTCCCCGCTTTTGTTTAATATTGTACTCGAGGTG |
| CTGGCTAGGGCTATTCGTCAAGAGAAAGAGATTAAAGGGATACAG |
| CTCGGGAAGGAAGAGGTCAAGCTTTCCTTGTTCGCCGATGATATG |
| ATTGTGTACCTGGAGAATCCTATTGTGTCTGCTCAGAACCTTCTT |
| AAACTTATTTCTAACTTTAGCAAGGTCAGCGGCTATAAGATTAAC |
| GTCCAGAAATCTCAGGCCTTTCTGTACACAAATAATCGACAGACC |
| GAATCCCAGATAATGGGTGAGCTTCCGTTTGTCATAGCCAGCAAA |
| AGGATAAAGTATCTCGGAATCCAGCTGACACGAGACGTTAAAGAT |
| TTGTTTAAGGAAAATTACAAGCCTCTCCTGAAAGAGATTAAGGAA |
| GATACTAATAAGTGGAAGAATATCCCCTGTTCATGGGTTGGCAGA |
| ATCAACATAGTGAAGATGGCAATACTTCCTAAAGTGATATATCGC |
| TTTAACGCCATCCCAATTAAACTGCCTATGACCTTCTTTACGGAG |
| CTCGAGAAAACAACCCTTAAATTTATATGGAATCAAAAGAGAGCA |
| AGAATAGCGAAGTCCATCTTGAGCCAGAAGAATAAGGCCGGTGGG |
| ATTACTTTGCCTGATTTTAAGTTGTATTATAAAGCCACAGTAACT |
| AAGACAGCCTGGTATTGGTATCAGAATAGAGACATCGACCAGTGG |
| AATCGGACCGAACCATCAGAGATAATGCCCCACATCTATAATTAC |
| CTTATATTCGATAAGCCAGAAAAGAATAAACAGTGGGGCAAAGAC |
| AGCCTCTTCAACAAGTGGTGTTGGGAGAATTGGCTGGCCATATGC |
| CGGAAACTCAAGCTCGACCCCTTTCTTACACCCTACACTAAAATC |
| AACAGTAGGTGGATCAAGGACTTGAATGTCAAGCCAAAGACTATA |
| AAGACACTGGAAGAGAATCTTGGGATCACAATACAAGATATAGGC |
| GTCGGCAAAGATTTTATGTCAAAGACGCCCAAGGCCATGGCCACT |
| AAGGATAAGATTGATAAGTGGGACCTTATTAAGCTCAAAAGCTTC |
| TGTACTGCCAAGGAGACCACGATCAGAGTTAATAGGCAGCCCACT |
| ACATGGGAAAAGATTTTCGCCACTTATTCATCAGATAAGGGGTTG |
| ATAAGCAGAATATATAACGAGCTGAAGCAGATCTACAAGAAGAAA |
| ACGAATAATCCCATCAAGAAGTGGGCAAAAGATATGAACAGGCAT |
| TTTAGCAAAGAGGATATCTACGCCGCGAAGAAGCATATGAAGAAG |
| TGTAGTTCAAGCTTGGCCATTCGTGAGATGCAGATTAAGACGACC |
| ATGCGATACCACCTTACCCCAGTGAGGATGGCAATTATCAAGAAA |
| TCTGGCAATAATAGATGTTGGCGGGGCTGTGGCGAGATTGGCACC |
| CTGCTCCATTGCTGGTGGGATTGCAAGCTGGTGCAGCCGCTTTGG |
| AAATCAGTCTGGCGCTTTCTGAGGGACCTCGAGCTTGAGATTCCC |
| TTCGATCCCGCAATTCCCTTGCTCGGAATCTATCCTAACGAATAC |
| AAGAGCTGTTGTTACAAGGATACGTGTACCCGGATGTTCATCGCG |
| GCCTTGTTTACGATAGCTAAGACGTGGAATCAGCCTAAGTGCCCC |
| ACAATGATCGATTGGATCAAGAAAATGTGGCATATTTATACCATG |
| GAGTATTACGCAGCAATTAAGAATGACGAATTTATTTCCTTCGTT |
| GGGACCTGGATGAAGCTGGAGACTATTATTCTGAGCAAGCTGTCT |
| CAGGAGCAAAAGACAAAGCATAGAATCTTCTCTCTCATTGGTGGT |
| AACGACTACAAAGACGATGACGACAAGTAAAGCGCTTCTAGAAGT |
| TGTCTCCTCCTGCACTGACTGACTGATACAATCGATTTCTGGATC |
| CGCAGGCCTAATCAACCTCTGGATTACAAAATTTGTGAAAGATTG |

TABLE 8-continued

| Plasmid and mRNA construct sequences |
| --- |
| ACTGGTATTCTTAACTATGTTGCTCCTTTTACGCTATGTGGATAC |
| GCTGCTTTAATGCCTTTGTATCATGCTATTGCTTCCCGTATGGCT |
| TTCATTTTCTCCTCCTTGTATAAATCCTGGTTGCTGTCTCTTTAT |
| GAGGAGTTGTGGCCCGTTGTCAGGCAACGTGGCGTGGTGTGCACT |
| GTGTTTGCTGACGCAACCCCCACTGGTTGGGGCATTGCCACCACC |
| TGTCAGCTCCTTTCCGGGACTTTCGCTTTCCCCCTCCCTATTGCC |
| ACGGCGGAACTCATCGCCGCCTGCCTTGCCCGCTGCTGGACAGGG |
| GCTCGGCTGTTGGGCACTGACAATTCCGTGGTGTTGTCGGGGAAG |
| CTGACGTCCTTTCCATGGCTGCTCGCCTGTGTTGCCACCTGGATT |
| CTGCGCGGGACGTCCTTCTGCTACGTCCCTTCGGCCCTCAATCCA |
| GCGGACCTTCCTTCCCGCGAACAAACGACCCAACACCCGTGCGTT |
| TTATTCTGTCTTTTTATTGCCGATCCCCTCAGAAGAACTCGTCAA |
| GAAGGCGATAGAAGGCGATGCGCTGCGAATCGGGAGCGGCGATAC |
| CGTAAAGCACGAGGAAGCGGTCAGCCCATTCGCCGCCAAGCTCTT |
| CAGCAATATCACGGGTAGCCAACGCTATGTCCTGATAGCGGTCGG |
| CCGCTTTACTTGTACAGCTCGTCCATGCCGAGAGTGATCCCGGCG |
| GCGGTCACGAACTCCAGCAGGACCATGTGATCGCGCTTCTCGTTG |
| GGGTCTTTGCTCAGGGCGGACTGGGTGCTCAGGTAGTGGTTGTCG |
| GGCAGCAGCACGGGGCCGTCGCCGATGGGGGTGTTCTGCTGGTAG |
| TGGTCGGCCAGGTGAGTCCAGGAGATGTTTCAGCACTGTTGCCTT |
| TAGTCTCGAGGCAACTTAGACAACTGAGTATTGATCTGAGCACAG |
| CAGGGTGTGAGCTGTTTGAAGATACTGGGGTTGGGGGTGAAGAAA |
| CTGCAGAGGACTAACTGGGCTGAGACCCAGTGGCAATGTTTTAGG |
| GCCTAAGGAATGCCTCTGAAAATCTAGATGGACAACTTTGACTTT |
| GAGAAAAGAGAGGTGGAAATGAGGAAAATGACTTTTCTTTATTAG |
| ATTTCGGTAGAAAGAACTTTCATCTTTCCCCTATTTTTGTTATTC |
| GTTTTAAAACATCTATCTGGAGGCAGGACAAGTATGGTCATTAAA |
| AAGATGCAGGCAGAAGGCATATATTGGCTCAGTCAAAGTGGGGAA |
| CTTTGGTGGCCAAACATACATTGCTAAGGCTATTCCTATATCAGC |
| TGGACACATATAAAATGCTGCTAATGCTTCATTACAAACTTATAT |
| CCTTTAATTCCAGATGGGGGCAAAGTATGTCCAGGGGTGAGGAAC |
| AATTGAAACATTTGGGCTGGAGTAGATTTTGAAAGTCAGCTCTGT |
| GTGTGTGTGTGTGTGTGTGTGTGTGTGAGAGCGTGTGTTTCTTTTAA |
| CGTTTTCAGCCTACAGCATACAGGGTTCATGGTGGCAAGAAGATA |
| ACAAGATTTAAATTATGGCCAGTGACTAGTGCTGCAAGAAGAACA |
| ACTACCTGCATTTAATGGGAAAGCAAAATCTCAGGCTTTGAGGGA |
| AGTTAACATAGGCTTGATTCTGGGTGGAAGCTGGGTGTGTAGTTA |
| TCTGGAGGCCAGGCTGGAGCTCTCAGCTCACTATGGGTTCATCTT |
| TATTGTCTCCTTTCATCTCAACAGCTGCACGCTGCCGTCCTCGAT |
| GTTGTGGCGGATCTTGAAGTTCACCTTGATGCCGTTCTTCTGCTT |
| GTCGGCCATGATATAGACGTTGTGGCTGTTGTAGTTGTACTCCAG |
| CTTGTGCCCCAGGATGTTGCCGTCCTCCTTGAAGTCGATGCCCTT |
| CAGCTCGATGCGGTTCACCAGGGTGTCGCCCTCGAACTTCACCTC |
| GGCGCGGGTCTTGTAGTTGCCGTCGTCCTTGAAGAAGATGGTGCG |
| CTCCTGGACGTAGCCTTCGGGCATGGCGGACTTGAAGAAGTCGTG |
| CTGCTTCATGTGGTCGGGGTAGCGGCTGAAGCACTGCACGCCGTA |
| GGTCAGGGTGGTCACGAGGGTGGGCCAGGGCACGGGCAGCTTGCC |
| GGTGGTGCAGATGAACTTCAGGGTCAGCTTGCCGTAGGTGGCATC |
| GCCCTCGCCCTCGCCGGACACGCTGAACTTGTGGCCGTTTACGTC |
| GCCGTCCAGCTCGACCAGGATGGGCACCACCCCGGTGAACAGCTC |
| CTCGCCCTTGCTCACCATGGTGGCGAATTCGAAGCTTGAGCACGA |
| GATCTGAGTCCGGTAGGCCTAGCGGATCTGACGGTTCACTAAACC |
| AGCTCTGCTTATATAGACCTCCCACCGTACACGCCTACCGCCCAT |
| TTGCGTCAATGGGGCGGAGTTGTTACGACATTTTGGAAAGTCCCG |
| TTGATTTTGGTGCCAAAACAAACTCCCATTGACGTCAATGGGGTG |
| GAGACTTGGAAATCCCCGTGAGTCAAACCGCTATCCACGCCCATT |
| GATGTACTGCCAAAACCGCATCACCATGGTAATAGCGATGACTAA |
| TACGTAGATGTACTGCCAAGTAGGAAAGTCCCATAAGGTCATGTA |
| CTGGGCATAATGCCAGGCGGGCCATTTACCGTCATTGACGTCAAT |
| AGGGGGCGTACTTGGCATATGATACACTTGATGTACTGCCAAGTG |
| GGCAGTTTACCGTAAATACTCCACCCATTGACGTCAATGGAAAGT |
| CCCTATTGGCGTTACTATGGGAACATACGTCATTATTGACGTCAA |
| TGGGCGGGGGTCGTTGGGCGGTCAGCCAGGCGGGCCATTTACCGT |
| AAGTTATGTAACGGGCCTGCTGCCGGCTCTGCGGCCTCTTCCGCG |
| TCTTCGCCTTCGCCCTCAGACGAGTCGGATCTCCCTTTGGGCCGC |
| CTCCCCGCCTGTCTAGCTTGACTGACTGAGATACAGCGTACCTTC |
| AGCTCACAGACATGATAAGATACATTGATGAGTTTGGACAAACCA |
| CAACTAGAATGCAGTGAAAAAAATGCTTTATTTGTGAAATTTGTG |
| ATGCTATTGCTTTATTTGTAACCATTATAAGCTGCAATAAACAAG |
| TTAACAACAACAATTGCATTCATTTTATGTTTCAGGTTCAGGGGG |
| AGGTGTGGGAGGTTTTTTAAAGCAAGTAAAACCTCTACAAATGTG |
| GTATTGGCCCATCTCTATCGGTATCGTAGCATAACCCCTTGGGGC |
| CTCTAAACGGGTCTTGAGGGGTTTTTTGTGCCCCTCGGGCCGGAT |
| TGCTATCTACCGGCATTGGCGCAGAAAAAAATGCCTGATGCGACG |
| CTGCGCGTCTTATACTCCCACATATGCCAGATTCAGCAACGGATA |
| CGGCTTCCCCAACTTGCCCACTTCCATACGTGTCCTCCTTACCAG |
| AAATTTATCCTTAAGGTCGTCAGCTATCCTGCAGGCGATCTCTCG |
| ATTTCGATCAAGACATTCCTTTAATGGTCTTTTCTGGACACCACT |

TABLE 8-continued

Plasmid and mRNA construct sequences

AGGGGTCAGAAGTAGTTCATCAAACTTTCTTCCCTCCCTAATCTC
ATTGGTTACCTTGGGCTATCGAAACTTAATTAAGCGATCTGCATC
TCAATTAGTCAGCAACCATAGTCCCGCCCCTAACTCCGCCCATCC
CGCCCCTAACTCCGCCCAGTTCCGCCCATTCTCCGCCCCATCGCT
GACTAATTTTTTTTATTTATGCAGAGGCCGAGGCCGCCTCGGCCT
CTGAGCTATTCCAGAAGTAGTGAGGAGGCTTTTTTGGAGGCCTAG
GCTTTTGCAAAGGAGGTAGCCAACATGATTGAACAAGATGGATTG
CACGCAGGTTCTCCCGCCGCTTGGGTGGAGAGGCTATTCGGCTAT
GACTGGGCACAACAGACAATCGGCTGCTCTGATGCCGCCGTGTTC
CGGCTGTCAGCGCAGGGGCGCCCGGTTCTTTTTGTCAAGACCGAC
CTGTCCGGTGCCCTGAATGAACTCCAGGACGAGGCAGCGCGGCTA
TCGTGGCTGGCCACGACGGGCGTTCCTTGCGCAGCTGTGCTCGAC
GTTGTCACTGAAGCGGGAAGGGACTGGCTGCTATTGGGCGAAGTG
CCGGGGCAGGATCTCCTGTCATCTCACCTTGCTCCTGCCGAGAAA
GTATCCATCATGGCTGATGCAATGCGGCGGCTGCATACGCTTGAT
CCGGCTACCTGCCCATTCGACCACCAAGCGAAACATCGCATCGAG
CGAGCACGTACTCGGATGGAAGCCGGTCTTGTCGATCAGGATGAT
CTGGACGAAGAGCATCAGGGGCTCGCGCCAGCCGAACTGTTCGCC
AGGCTCAAGGCGCGGATGCCCGACGGCGAGGATCTCGTCGTGACC
CACGGCGATGCCTGCTTGCCGAATATCATGGTGGAAAATGGCCGC
TTTTCTGGATTCATCGACTGTGGCCGGCTGGGTGTGGCGGACCGC
TATCAGGACATAGCGTTGGCTACCCGTGATATTGCTGAAGAGCTT
GGCGGCGAATGGGCTGACCGCTTCCTCGTGCTTTACGGTATCGCC
GCTCCCGATTCGCAGCGCATCGCCTTCTATCGCCTTCTTGACGAG
TTCTTCTAGTATGTAAGCCCTGTGCCTTCTAGTTGCCAGCCATCT
GTTGTTTGCCCCTCCCCCGTGCCTTCCTTGACCCTGGAAGGTGCC
ACTCCCACTGTCCTTTCCTAATAAAATGAGGAAATTGCATCGCAT
TGTCTGAGTAGGTGTCATTCTATTCTGGGGGGTGGGGTGGGGCAG
GACAGCAAGGGGGAGGATTGGGAAGACAATAGCAGGCATGCTGGG
GATGCGGTGGGCTCTATGGTTAATTAACCAGTCAAGTCAGCTACT
TGGCGAGATCGACTTGTCTGGGTTTCGACTACGCTCAGAATTGCG
TCAGTCAAGTTCGATCTGGTCCTTGCTATTGCACCCGTTCTCCGA
TTACGAGTTTCATTTAAATCATGTGAGCAAAAGGCCAGCAAAAGG
CCAGGAACCGTAAAAAGGCCGCGTTGCTGGCGTTTTTCCATAGGC
TCCGCCCCCCTGACGAGCATCACAAAAATCGACGCTCAAGTCAGA
GGTGGCGAAACCCGACAGGACTATAAAGATACCAGGCGTTTCCCC
CTGGAAGCTCCCTCGTGCGCTCTCCTGTTCCGACCCTGCCGCTTA
CCGGATACCTGTCCGCCTTTCTCCCTTCGGGAAGCGTGGCGCTTT
CTCATAGCTCACGCTGTAGGTATCTCAGTTCGGTGTAGGTCGTTC
GCTCCAAGCTGGGCTGTGTGCACGAACCCCCCGTTCAGCCCGACC
GCTGCGCCTTATCCGGTAACTATCGTCTTGAGTCCAACCCGGTAA
GACACGACTTATCGCCACTGGCAGCAGCCACTGGTAACAGGATTA
GCAGAGCGAGGTATGTAGGCGGTGCTACAGAGTTCTTGAAGTGGT
GGCCTAACTACGGCTACACTAGAAGAACAGTATTTGGTATCTGCG
CTCTGCTGAAGCCAGTTACCTTCGGAAAAAGAGTTGGTAGCTCTT
GATCCGGCAAACAAACCACCGCTGGTAGCGGTGGTTTTTTTGTTT
GCAAGCAGCAGATTACGCGCAGAAAAAAAGGATCTCAAGAAGATC
CTTTGATCTTTTCTACGGGGTCTGACGCTCAGTGGAACGAAAACT
CACGTTAAGGGATTTTGGTCATGAGATTATCAAAAAGGATCTTCA
CCTAGATCCTTTTAAATTAAAAATGAAGTTTTAAATCAATCTAAA
GTATATATGAGTAAACTTGGTCTGACAGTTACCAATGCTTAATCA
GTGAGGCACCTATCTCAGCGATCTGTCTATTTCGTTCATCCATAG
TTGCATTTAAATTTCCGAACTCTCCAAGGCCCTCGTCGGAAAATC
TTCAAACCTTTCGTCCGATCCATCTTGCAGGCTACCTCTCGAACG
AACTATCGCAAGTCTCTTGGCCGGCCTTGCGCCTTGGCTATTGCT
TGGCAGCGCCTATCGCCAGGTATTACTCCAATCCCGAATATCCGA
GATCGGGATCACCCGAGAGAAGTTCAACCTACATCCTCAATCCCG
ATCTATCCGAGATCCGAGGAATATCGAAATCGGGGCGCGCCTGGT
GTACCGAGAACGATCCTCTCAGTGCGAGTCTCGACGATCCATATC
GTTGCTTGGCAGTCAGCCAGTCGGAATCCAGCTTGGGACCCAGGA
AGTCCAATCGTCAGATATTGTACTCAAGCCTGGTCACGGCAGCGT
ACCGATCTGTTTAAACCTAGATATTGATAGTCTGATCGGTCAACG
TATAATCGAGTCCTAGCTTTTGCAAACATCTATCAAGAGACAGGA
TCAGCAGGAGGCTTTCGCATGAGTATTCAACATTTCCGTGTCGCC
CTTATTCCCTTTTTTGCGGCATTTTGCCTTCCTGTTTTTGCTCAC
CCAGAAACGCTGGTGAAAGTAAAAGATGCTGAAGATCAGTTGGGT
GCGCGAGTGGGTTACATCGAACTGGATCTCAACAGCGGTAAGATC
CTTGAGAGTTTTCGCCCCGAAGAACGCTTTCCAATGATGAGCACT
TTTAAAGTTCTGCTATGTGGCGCGGTATTATCCCGTATTGACGCC
GGGCAAGAGCAACTCGGTCGCCGCATACACTATTCTCAGAATGAC
TTGGTTGAGTATTCACCAGTCACAGAAAAGCATCTTACGGATGGC
ATGACAGTAAGAGAATTATGCAGTGCTGCCATAACCATGAGTGAT
AACACTGCGGCCCGGCCGCAACTTACTTCTGACAACGATTGGAGG
ACCGAAGGAGCTAACCGCTTTTTTGCACAACATGGGGGATCATGT
AACTCGCCTTGATCGTTGGGAACCGGAGCTGAATGAAGCCATACC
AAACGACGAGCGTGACACCACGATGCCTGTAGCAATGGCAACAAC
CTTGCGTAAACTATTAACTGGCGAACTACTTACTCTAGCTTCCCG
GCAACAGTTGATAGACTGGATGGAGGCGGATAAAGTTGCAGGACC

TABLE 8-continued

Plasmid and mRNA construct sequences

ACTTCTGCGCTCGGCCCTTCCGGCTGGCTGGTTTATTGCTGATAA
ATCTGGAGCCGGTGAGCGTGGGTCTCGCGGTATCATTGCAGCACT
GGGGCCAGATGGTAAGCCCTCCCGTATCGTAGTTATCTACACGAC
GGGGAGTCAGGCAACTATGGATGAACGAAATAGACAGATCGCTGA
GATAGGTGCCTCACTGATTAAGCATTGGTAACCGATTCTAGGTGC
ATTGGCGCAGAAAAAAATGCCTGATGCGACGCTGCGCGTCTTATA
CTCCCACATATGCCAGATTCAGCAACGGATACGGCTTCCCCAACT
TGCCCACTTCCATACGTGTCCTCCTTACCAGAAATTTATCCTTAA
GATCGTTTAAACTCGACTCTGGCTCTATCGAATCTCCGTCGTTTC
GAGCTTACGCGAACAGCCGTGGCGCTCATTTGCTCGTCGGGCATC
GAATCTCGTCAGCTATCGTCAGCTTACCTTTTTGGCAGCGATCGC
GGCTCCCGACATCTTGGACCATTAGCTCCACAGGTATCTTCTTCC
CTCTAGTGGTCATAACAGCAGCTTCAGCTACCTCTCAATTCAAAA
AACCCCTCAAGACCCGTTTAGAGGCCCCAAGGGGTTATGCTATCA
ATCGTTGCGTTACACACACAAAAAACCAACACACATCCATCTTCG
ATGGATAGCGATTTTATTATCTAACTGCTGATCGAGTGTAGCCAG
ATCTAGTAATCAATTACGGGGTCATTAGTTCATAGCCCATATATG
GAGTTCCGCGTTACATAACTTACGGTAAATGGCCCGCCTGGCTGA
CCGCCCAACGACCCCCGCCCATTGACGTCAATAATGACGTATGTT
CCCATAGTAACGCCAATAGGGACTTTCCATTGACGTCAATGGGTG
GAGTATTTACGGTAAACTGCCCACTTGGCAGTACATCAAGTGTAT
CATATGCCAAGTACGCCCCCTATTGACGTCAATGACGGTAAATGG
CCCGCCTGGCATTATGCCCAGTACATGACCTTATGGGACTTTCCT
ACTTGGCAGTACATCTACGTATTAGTCATCGCTATTACCATGCTG
ATGCGGTTTTGGCAGTACATCAATGGGCGTGGATAGCGGTTTGAC
TCACGGGGATTTCCAAGTCTCCACCCCATTGACGTCAATGGGAGT
TTGTTTTGGCACCAAAATCAACGGGACTTTCCAAAATGTCGTAAC
AACTCCGCCCCATTGACGCAAATGGGCGGTAGGCGTGTACGGTGG
GAGGTCTATATAAGCAGAGCTGGTTTAGTGAACCGTCAGATCAGA
TCTTTGTCGATCCTACCATCCACTCGACACACCCGCCAG
(SEQ ID NO: 45)

LINE-1 plasmid ORF1-E2A-ORF2 GFP
(SEQ ID NO: 46)
TAATACGACTCACTATAGGGAGAAGTACTGCCACCATGGGCAAGA
AGCAAAATCGCAAGACGGGGAATTCCAAGACACAATCCGCTAGCC
CACCACCTAAAGAGCGTTCTAGCTCCCCTGCTACTGAGCAGTCCT
GGATGGAAAACGACTTCGATGAACTCCGGGAAGAGGGATTTAGGC
GATCCAACTATTCAGAACTCCGCGAAGATATCCAGACAAAGGGGA
AGGAAGTCGAGAATTTCGAGAAGAACCTCGAGGAGTGCATCACCC
GTATCACAAACACTGAGAAATGTCTCAAAGAACTCATGGAACTTA
AGACAAAAGCCAGGGAGCTTCGAGAGGAGTGTCGGAGTCTGAGAT
CCAGGTGTGACCAGCTCGAGGAGCGCGTGAGCGCGATGGAAGACG
AGATGAACGAGATGAAAAGAGAGGGCAAATTCAGGGAGAAGCGCA
TTAAGAGGAACGAACAGAGTCTGCAGGAGATTTGGGATTACGTCA
AGAGGCCTAACCTGCGGTTGATCGGCGTCCCCGAGAGCGACGTAG
AAAACGGGACTAAACTGGAGAATACACTTCAAGACATCATTCAAG
AAAATTTTCCAAACCTGGCTCGGCAAGCTAATGTGCAAATCCAAG
AGATCCAACGCACACCCCAGCGGTATAGCTCTCGGCGTGCCACCC
CTAGGCATATTATCGTGCGCTTTACTAAGGTGGAGATGAAAGAGA
AGATGCTGCGAGCCGCTCGGGAAAAGGGAAGGGTGACTTTGAAGG
GCAAACCTATTCGGCTGACGGTTGACCTTAGCGCCGAGACACTCC
AGGCACGCCGGGAATGGGGCCCCATCTTTAATATCCTGAAGGAGA
AGAACTTCCAGCCACGAATCTCTTACCCTGCAAAGTTGAGTTTTA
TCTCCGAGGGTGAGATTAAGTATTTCATCGATAAACAGATGCTGC
GAGACTTCGTGACAACTCGCCCAGCTCTCAAGGAACTGCTCAAAG
AGGCTCTTAATATGGAGCGCAATAATAGATATCAACCCTTGCAGA
ACCACGCAAAGATGGGAAGCGGACAGTGTACTAATTATGCTCTCT
TGAAATTGGCTGGAGATGTTGAGAGCAACCCTGGACCTATGACCG
GCTCTAACTCACATATCACCATCCTTACACTTAACATTAACGGCC
TCAACTCAGCTATCAAGCGCCATCGGCTGGCCAGCTGGATCAAAT
CACAGGATCCAAGCGTTTGTTGCATCCAAGAGACCCACCTGACCT
GTAGAGATACTCACCGCCTCAAGATCAAGGGATGGCGAAAGATTT
ATCAGGCGAACGGTAAGCAGAAGAAAGCCGGAGTCGCAATTCTGG
TCTCAGACAAGACGGATTTCAAGCCCACCAAAATTAAGCGTGATA
AGGAAGGTCACTATATTATGGTGAAAGGCAGCATACAGCAGGAAG
AACTTACCATATTGAACATCTACGCGCCAAACACCGGCGCACCTC
GCTTTATCAAACAGGTCCTGTCCGATCTGCAGCGAGATCTGGATT
CTCATACGTTGATTATGGGTGATTTCAATACACCATTGAGCACCC
TGGATCGCAGCACCAGGCAAAAGGTAAATAAAGACACGCAAGAGC
TCAATAGCGCACTGCATCAGGCAGATCTCATTGATATTTATCGCA
CTCTTCATCCTAAGAGTACCGAGTACACATTCTTCAGCGCCCCAC
ATCATACATACTCAAAGATCGATCATATCGTCGGCTCAAAGGCTC
TGCTGTCAAAGTGCAAGCGCACAGAGATAATTACAAATTACCTGT
CAGATCATAGCGCGATCAAGCTCGAGCTGAGAATCAAGAACCTGA
CCCAGAGCCGGAGTACCACTTGGAAGCTTAATAACCTGCTGCTCA
ACGATTATTGGGTCCACAATGAGATGAAGGCAGAGATTAAAATGT
TCTTCGAAACAAATGAGAATAAGGATACTACCTATCAAAACCTTT TABLE 8-continued

| Plasmid and mRNA construct sequences |
| --- |
| GGGATGCCTTTAAGGCCGTCTGCAGAGGCAAGTTCATCGCCCTCA |
| ACGCCTATAAAAGAAAACAAGAGAGATCTAAGATCGATACTCTCA |
| CCTCTCAGCTGAAGGAGTTGGAGAAACAGGAACAGACCCACTCCA |
| AGGCGTCAAGACGGCAGGAGATCACAAAGATTCGCGCCGAGTTGA |
| AAGAGATCGAAACCCAAAAGACTCTTCAGAAAATTAACGAGTCTC |
| GTAGTTGGTTCTTCGAGCGGATTAATAAGATAGACAGACCTCTGG |
| CACGACTGATTAAGAAGAAGCGCGAAAAGAACCAGATTGATACCA |
| TCAAGAACGACAAGGGCGACATCACTACTGACCCGACCGAGATCC |
| AGACCACTATTCGGGAGTATTATAAGCATTTGTATGCTAACAAGC |
| TTGAGAACCTGGAAGAGATGGACACTTTTCTGGATACCTATACTC |
| TGCCACGGCTTAATCAAGAGGAAGTCGAGTCCCTCAACCGCCCAA |
| TTACAGGAAGCGAGATTGTGGCCATAATTAACTCCCTGCCGACAA |
| AGAAATCTCCTGGTCCGGACGGGTTTACAGCTGAGTTTTATCAAC |
| GGTATATGGAAGAGCTTGTACCGTTTCTGCTCAAGCTCTTTCAGT |
| CTATAGAAAAGGAAGGCATCTTGCCCAATTCCTTCTACGAAGCTT |
| CTATAATACTTATTCCCAAACCAGGACGCGATACCACAAAGAAGG |
| AAAACTTCCGGCCCATTAGTCTCATGAATATCGACGCTAAAATAT |
| TGAACAAGATTCTCGCCAACAGAATCCAACAACATATTAAGAAAT |
| TGATACATCACGACCAGGTGGGGTTTATACCTGGCATGCAGGGCT |
| GGTTTAACATCCGGAAGAGTATTAACGTCATTCAACACATTAATA |
| GAGCTAAGGATAAGAATCATATGATCATCTCTATAGACGCGGAAA |
| AGGCATTCGATAAGATTCAGCAGCCATTTATGCTCAAGACTCTGA |
| ACAAACTCGGCATCGACGGAACATATTTTAAGATTATTCGCGCAA |
| TTTACGATAAGCCGACTGCTAACATTATCCTTAACGGCCAAAAGC |
| TCGAGGCCTTTCCGCTCAAGACTGGAACCCGCCAAGGCTGTCCCC |
| TCTCCCCGCTTTTGTTTAATATTGTACTCGAGGTGCTGGCTAGGG |
| CTATTCGTCAAGAGAAAGAGATTAAAGGGATACAGCTCGGGAAGG |
| AAGAGGTCAAGCTTTCCTTGTTCGCCGATGATATGATTGTGTACC |
| TGGAGAATCCTATTGTGTCTGCTCAGAACCTTCTTAAACTTATTT |
| CTAACTTTAGCAAGGTCAGCGGCTATAAGATTAACGTCCAGAAAT |
| CTCAGGCCTTTCTGTACACAAATAATCGACAGACCGAATCCCAGA |
| TAATGGGTGAGCTTCCGTTTGTCATAGCCAGCAAAAGGATAAAGT |
| ATCTCGGAATCCAGCTGACACGAGACGTTAAAGATTTGTTTAAGG |
| AAAATTACAAGCCTCTCCTGAAAGAGATTAAGGAAGATACTAATA |
| AGTGGAAGAATATCCCCTGTTCATGGGTTGGCAGAATCAACATAG |
| TGAAGATGGCAATACTTCCTAAAGTGATATATCGCTTTAACGCCA |
| TCCCAATTAAACTGCCTATGACCTTCTTTACGGAGCTCGAGAAAA |
| CAACCCTTAAATTTATATGGAATCAAAAGAGAGCAAGAATAGCGA |
| AGTCCATCTTGAGCCAGAAGAATAAGGCCGGTGGGATTACTTTGC |
| CTGATTTTAAGTTGTATTATAAAGCCACAGTAACTAAGACAGCCT |
| GGTATTGGTATCAGAATAGAGACATCGACCAGTGGAATCGGACCG |
| AACCATCAGAGATAATGCCCCACATCTATAATTACCTTATATTCG |
| ATAAGCCAGAAAAGAATAAACAGTGGGGCAAAGACAGCCTCTTCA |
| ACAAGTGGTGTTGGGAGAATTGGCTGGCCATATGCCGGAAACTCA |
| AGCTCGACCCCTTTCTTACACCCTACACTAAAATCAACAGTAGGT |
| GGATCAAGGACTTGAATGTCAAGCCAAAGACTATAAAGACACTGG |
| AAGAGAATCTTGGGATCACAATACAAGATATAGGCGTCGGCAAAG |
| ATTTTATGTCAAAGACGCCCAAGGCCATGGCCACTAAGGATAAGA |
| TTGATAAGTGGGACCTTATTAAGCTCAAAAGCTTCTGTACTGCCA |
| AGGAGACCACGATCAGAGTTAATAGGCAGCCCACTACATGGGAAA |
| AGATTTTCGCCACTTATTCATCAGATAAGGGGTTGATAAGCAGAA |
| TATATAACGAGCTGAAGCAGATCTACAAGAAGAAAACGAATAATC |
| CCATCAAGAAGTGGGCAAAAGATATGAACAGGCATTTTAGCAAAG |
| AGGATATCTACGCCGCGAAGAAGCATATGAAGAAGTGTAGTTCAA |
| GCTTGGCCATTCGTGAGATGCAGATTAAGACGACCATGCGATACC |
| ACCTTACCCCAGTGAGGATGGCAATTATCAAGAAATCTGGCAATA |
| ATAGATGTTGGCGGGGCTGTGGCGAGATTGGCACCCTGCTCCATT |
| GCTGGTGGGATTGCAAGCTGGTGCAGCCGCTTTGGAAATCAGTCT |
| GGCGCTTTCTGAGGGACCTCGAGCTTGAGATTCCCTTCGATCCCG |
| CAATTCCCTTGCTCGGAATCTATCCTAACGAATACAAGAGCTGTT |
| GTTACAAGGATACGTGTACCCGGATGTTCATCGCGGCCTTGTTTA |
| CGATAGCTAAGACGTGGAATCAGCCTAAGTGCCCCACAATGATCG |
| ATTGGATCAAGAAAATGTGGCATATTTATACCATGGAGTATTACG |
| CAGCAATTAAGAATGACGAATTTATTTCCTTCGTTGGGACCTGGA |
| TGAAGCTGGAGACTATTATTCTGAGCAAGCTGTCTCAGGAGCAAA |
| AGACAAAGCATAGAATCTTCTCTCTCATTGGTGGTAACGACTACA |
| AAGACGATGACGACAAGTAAAGCGCTTCTAGAAGTTGTCTCCTCC |
| TGCACTGACTGACTGATACAATCGATTTCTGGATCCGCAGGCCTA |
| ATCAACCTCTGGATTACAAAATTTGTGAAAGATTGACTGGTATTC |
| TTAACTATGTTGCTCCTTTTACGCTATGTGGATACGCTGCTTTAA |
| TGCCTTTGTATCATGCTATTGCTTCCCGTATGGCTTTCATTTTCT |
| CCTCCTTGTATAAATCCTGGTTGCTGTCTCTTTATGAGGAGTTGT |
| GGCCCGTTGTCAGGCAACGTGGCGTGGTGTGCACTGTGTTTGCTG |
| ACGCAACCCCCACTGGTTGGGGCATTGCCACCACCTGTCAGCTCC |
| TTTCCGGGACTTTCGCTTTCCCCCTCCCTATTGCCACGGCGGAAC |
| TCATCGCCGCCTGCCTTGCCCGCTGCTGGACAGGGGCTCGGCTGT |
| TGGGCACTGACAATTCCGTGGTGTTGTCGGGGAAGCTGACGTCCT |
| TTCCATGGCTGCTCGCCTGTGTTGCCACCTGGATTCTGCGCGGGA |

TABLE 8-continued

| Plasmid and mRNA construct sequences |
| --- |
| CGTCCTTCTGCTACGTCCCTTCGGCCCTCAATCCAGCGGACCTTC |
| CTTCCCGCGAACAAACGACCCAACACCCGTGCGTTTTATTCTGTC |
| TTTTTATTGCCGATCCCCTCAGAAGAACTCGTCAAGAAGGCGATA |
| GAAGGCGATGCGCTGCGAATCGGGAGCGGCGATACCGTAAAGCAC |
| GAGGAAGCGGTCAGCCCATTCGCCGCCAAGCTCTTCAGCAATATC |
| ACGGGTAGCCAACGCTATGTCCTGATAGCGGTCGGCCGCTTTACT |
| TGTACAGCTCGTCCATGCCGAGAGTGATCCCGGCGGCGGTCACGA |
| ACTCCAGCAGGACCATGTGATCGCGCTTCTCGTTGGGGTCTTTGC |
| TCAGGGCGGACTGGGTGCTCAGGTAGTGGTTGTCGGGCAGCAGCA |
| CGGGGCCGTCGCCGATGGGGGTGTTCTGCTGGTAGTGGTCGGCCA |
| GGTGAGTCCAGGAGATGTTTCAGCACTGTTGCCTTTAGTCTCGAG |
| GCAACTTAGACAACTGAGTATTGATCTGAGCACAGCAGGGTGTGA |
| GCTGTTTGAAGATACTGGGGTTGGGGGTGAAGAAACTGCAGAGGA |
| CTAACTGGGCTGAGACCCAGTGGCAATGTTTTAGGGCCTAAGGAA |
| TGCCTCTGAAAATCTAGATGGACAACTTTGACTTTGAGAAAAGAG |
| AGGTGGAAATGAGGAAAATGACTTTTCTTTATTAGATTTCGGTAG |
| AAAGAACTTTCATCTTTCCCCTATTTTTGTTATTCGTTTTAAAAC |
| ATCTATCTGGAGGCAGGACAAGTATGGTCATTAAAAAGATGCAGG |
| CAGAAGGCATATATTGGCTCAGTCAAAGTGGGGAACTTTGGTGGC |
| CAAACATACATTGCTAAGGCTATTCCTATATCAGCTGGACACATA |
| TAAAATGCTGCTAATGCTTCATTACAAACTTATATCCTTTAATTC |
| CAGATGGGGGCAAAGTATGTCCAGGGGTGAGGAACAATTGAAACA |
| TTTGGGCTGGAGTAGATTTTGAAAGTCAGCTCTGTGTGTGTGTGT |
| GTGTGTGTGTGTGTGAGAGCGTGTGTTTCTTTTAACGTTTTCAGC |
| CTACAGCATACAGGGTTCATGGTGGCAAGAAGATAACAAGATTTA |
| AATTATGGCCAGTGACTAGTGCTGCAAGAAGAACAACTACCTGCA |
| TTTAATGGGAAAGCAAAATCTCAGGCTTTGAGGGAAGTTAACATA |
| GGCTTGATTCTGGGTGGAAGCTGGGTGTGTAGTTATCTGGAGGCC |
| AGGCTGGAGCTCTCAGCTCACTATGGGTTCATCTTTATTGTCTCC |
| TTTCATCTCAACAGCTGCACGCTGCCGTCCTCGATGTTGTGGCGG |
| ATCTTGAAGTTCACCTTGATGCCGTTCTTCTGCTTGTCGGCCATG |
| ATATAGACGTTGTGGCTGTTGTAGTTGTACTCCAGCTTGTGCCCC |
| AGGATGTTGCCGTCCTCCTTGAAGTCGATGCCCTTCAGCTCGATG |
| CGGTTCACCAGGGTGTCGCCCTCGAACTTCACCTCGGCGCGGGTC |
| TTGTAGTTGCCGTCGTCCTTGAAGAAGATGGTGCGCTCCTGGACG |
| TAGCCTTCGGGCATGGCGGACTTGAAGAAGTCGTGCTGCTTCATG |
| TGGTCGGGGTAGCGGCTGAAGCACTGCACGCCGTAGGTCAGGGTG |
| GTCACGAGGGTGGGCCAGGGCACGGGCAGCTTGCCGGTGGTGCAG |
| ATGAACTTCAGGGTCAGCTTGCCGTAGGTGGCATCGCCCTCGCCC |
| TCGCCGGACACGCTGAACTTGTGGCCGTTTACGTCGCCGTCCAGC |
| TCGACCAGGATGGGCACCACCCCGGTGAACAGCTCCTCGCCCTTG |
| CTCACCATGGTGGCGAATTCGAAGCTTGAGCACGAGATCTGAGTC |
| CGGTAGGCCTAGCGGATCTGACGGTTCACTAAACCAGCTCTGCTT |
| ATATAGACCTCCCACCGTACACGCCTACCGCCCATTTGCGTCAAT |
| GGGGCGGAGTTGTTACGACATTTTGGAAAGTCCCGTTGATTTTGG |
| TGCCAAAACAAACTCCCATTGACGTCAATGGGGTGGAGACTTGGA |
| AATCCCCGTGAGTCAAACCGCTATCCACGCCCATTGATGTACTGC |
| CAAAACCGCATCACCATGGTAATAGCGATGACTAATACGTAGATG |
| TACTGCCAAGTAGGAAAGTCCCATAAGGTCATGTACTGGGCATAA |
| TGCCAGGCGGGCCATTTACCGTCATTGACGTCAATAGGGGGCGTA |
| CTTGGCATATGATACACTTGATGTACTGCCAAGTGGGCAGTTTAC |
| CGTAAATACTCCACCCATTGACGTCAATGGAAAGTCCCTATTGGC |
| GTTACTATGGGAACATACGTCATTATTGACGTCAATGGGCGGGGG |
| TCGTTGGGCGGTCAGCCAGGCGGGCCATTTACCGTAAGTTATGTA |
| ACGGGCCTGCTGCCGGCTCTGCGGCCTCTTCCGCGTCTTCGCCTT |
| CGCCCTCAGACGAGTCGGATCTCCCTTTGGGCCGCCTCCCCGCCT |
| GTCTAGCTTGACTGACTGAGATACAGCGTACCTTCAGCTCACAGA |
| CATGATAAGATACATTGATGAGTTTGGACAAACCACAACTAGAAT |
| GCAGTGAAAAAAATGCTTTATTTGTGAAATTTGTGATGCTATTGC |
| TTTATTTGTAACCATTATAAGCTGCAATAAACAAGTTAACAACAA |
| CAATTGCATTCATTTTATGTTTCAGGTTCAGGGGGAGGTGTGGGA |
| GGTTTTTTAAAGCAAGTAAAACCTCTACAAATGTGGTATTGGCCC |
| ATCTCTATCGGTATCGTAGCATAACCCCTTGGGGCCTCTAAACGG |
| GTCTTGAGGGGTTTTTTGTGCCCCTCGGGCCGGATTGCTATCTAC |
| CGGCATTGGCGCAGAAAAAATGCCTGATGCGACGCTGCGCGTCT |
| TATACTCCCACATATGCCAGATTCAGCAACGGATACGGCTTCCCC |
| AACTTGCCCACTTCCATACGTGTCCTCCTTACCAGAAATTTATCC |
| TTAAGGTCGTCAGCTATCCTGCAGGCGATCTCTCGATTTCGATCA |
| AGACATTCCTTTAATGGTCTTTTCTGGACACCACTAGGGGTCAGA |
| AGTAGTTCATCAAACTTTCTTCCCTCCCTAATCTCATTGGTTACC |
| TTGGGCTATCGAAACTTAATTAAGCGATCTGCATCTCAATTAGTC |
| AGCAACCATAGTCCCGCCCCTAACTCCGCCCATCCCGCCCCTAAC |
| TCCGCCCAGTTCCGCCCATTCTCCGCCCCATCGCTGACTAATTTT |
| TTTTATTTATGCAGAGGCCGAGGCCGCCTCGGCCTCTGAGCTATT |
| CCAGAAGTAGTGAGGAGGCTTTTTTGGAGGCCTAGGCTTTTGCAA |
| AGGAGGTAGCCAACATGATTGAACAAGATGGATTGCACGCAGGTT |
| CTCCCGCCGCTTGGGTGGAGAGGCTATTCGGCTATGACTGGGCAC |
| AACAGACAATCGGCTGCTCTGATGCCGCCGTGTTCCGGCTGTCAG |

TABLE 8-continued

| Plasmid and mRNA construct sequences |
|---|

CGCAGGGGCGCCCGGTTCTTTTTGTCAAGACCGACCTGTCCGGTG
CCCTGAATGAACTCCAGGACGAGGCAGCGCGGCTATCGTGGCTGG
CCACGACGGGCGTTCCTTGCGCAGCTGTGCTCGACGTTGTCACTG
AAGCGGGAAGGGACTGGCTGCTATTGGGCGAAGTGCCGGGGCAGG
ATCTCCTGTCATCTCACCTTGCTCCTGCCGAGAAAGTATCCATCA
TGGCTGATGCAATGCGGCGGCTGCATACGCTTGATCCGGCTACCT
GCCCATTCGACCACCAAGCGAAACATCGCATCGAGCGAGCACGTA
CTCGGATGGAAGCCGGTCTTGTCGATCAGGATGATCTGGACGAAG
AGCATCAGGGGCTCGCGCCAGCCGAACTGTTCGCCAGGCTCAAGG
CGCGGATGCCCGACGGCGAGGATCTCGTCGTGACCCACGGCGATG
CCTGCTTGCCGAATATCATGGTGGAAAATGGCCGCTTTTCTGGAT
TCATCGACTGTGGCCGGCTGGGTGTGGCGGACCGCTATCAGGACA
TAGCGTTGGCTACCCGTGATATTGCTGAAGAGCTTGGCGGCGAAT
GGGCTGACCGCTTCCTCGTGCTTTACGGTATCGCCGCTCCCGATT
CGCAGCGCATCGCCTTCTATCGCCTTCTTGACGAGTTCTTCTAGT
ATGTAAGCCCTGTGCCTTCTAGTTGCCAGCCATCTGTTGTTTGCC
CCTCCCCCGTGCCTTCCTTGACCCTGGAAGGTGCCACTCCCACTG
TCCTTTCCTAATAAAATGAGGAAATTGCATCGCATTGTCTGAGTA
GGTGTCATTCTATTCTGGGGGGTGGGGTGGGGCAGGACAGCAAGG
GGGAGGATTGGGAAGACAATAGCAGGCATGCTGGGGATGCGGTGG
GCTCTATGGTTAATTAACCAGTCAAGTCAGCTACTTGGCGAGATC
GACTTGTCTGGGTTTCGACTACGCTCAGAATTGCGTCAGTCAAGT
TCGATCTGGTCCTTGCTATTGCACCCGTTCTCCGATTACGAGTTT
CATTTAAATCATGTGAGCAAAAGGCCAGCAAAAGGCCAGGAACCG
TAAAAAGGCCGCGTTGCTGGCGTTTTTCCATAGGCTCCGCCCCCC
TGACGAGCATCACAAAAATCGACGCTCAAGTCAGAGGTGGCGAAA
CCCGACAGGACTATAAAGATACCAGGCGTTTCCCCCTGGAAGCTC
CCTCGTGCGCTCTCCTGTTCCGACCCTGCCGCTTACCGGATACCT
GTCCGCCTTTCTCCCTTCGGGAAGCGTGGCGCTTTCTCATAGCTC
ACGCTGTAGGTATCTCAGTTCGGTGTAGGTCGTTCGCTCCAAGCT
GGGCTGTGTGCACGAACCCCCCGTTCAGCCCGACCGCTGCGCCTT
ATCCGGTAACTATCGTCTTGAGTCCAACCCGGTAAGACACGACTT
ATCGCCACTGGCAGCAGCCACTGGTAACAGGATTAGCAGAGCGAG
GTATGTAGGCGGTGCTACAGAGTTCTTGAAGTGGTGGCCTAACTA
CGGCTACACTAGAAGAACAGTATTTGGTATCTGCGCTCTGCTGAA
GCCAGTTACCTTCGGAAAAAGAGTTGGTAGCTCTTGATCCGGCAA
ACAAACCACCGCTGGTAGCGGTGGTTTTTTTGTTTGCAAGCAGCA
GATTACGCGCAGAAAAAAAGGATCTCAAGAAGATCCTTTGATCTT
TTCTACGGGGTCTGACGCTCAGTGGAACGAAAACTCACGTTAAGG
GATTTTGGTCATGAGATTATCAAAAAGGATCTTCACCTAGATCCT
TTTAAATTAAAAATGAAGTTTTAAATCAATCTAAAGTATATATGA
GTAAACTTGGTCTGACAGTTACCAATGCTTAATCAGTGAGGCACC
TATCTCAGCGATCTGTCTATTTCGTTCATCCATAGTTGCATTTAA
ATTTCCGAACTCTCCAAGGCCCTCGTCGGAAAATCTTCAAACCTT
TCGTCCGATCCATCTTGCAGGCTACCTCTCGAACGAACTATCGCA
AGTCTCTTGGCCGGCCTTGCGCCTTGGCTATTGCTTGGCAGCGCC
TATCGCCAGGTATTACTCCAATCCCGAATATCCGAGATCGGGATC
ACCCGAGAGAAGTTCAACCTACATCCTCAATCCCGATCTATCCGA
GATCCGAGGAATATCGAAATCGGGGCGCGCCTGGTGTACCGAGAA
CGATCCTCTCAGTGCGAGTCTCGACGATCCATATCGTTGCTTGGC
AGTCAGCCAGTCGGAATCCAGCTTGGGACCCAGGAAGTCCAATCG
TCAGATATTGTACTCAAGCCTGGTCACGGCAGCGTACCGATCTGT
TTAAACCTAGATATTGATAGTCTGATCGGTCAACGTATAATCGAG
TCCTAGCTTTTGCAAACATCTATCAAGAGACAGGATCAGCAGGAG
GCTTTCGCATGAGTATTCAACATTTCCGTGTCGCCCTTATTCCCT
TTTTTGCGGCATTTTGCCTTCCTGTTTTTGCTCACCCAGAAACGC
TGGTGAAAGTAAAAGATGCTGAAGATCAGTTGGGTGCGCGAGTGG
GTTACATCGAACTGGATCTCAACAGCGGTAAGATCCTTGAGAGTT
TTCGCCCCGAAGAACGCTTTCCAATGATGAGCACTTTTAAAGTTC
TGCTATGTGGCGCGGTATTATCCCGTATTGACGCCGGGCAAGAGC
AACTCGGTCGCCGCATACACTATTCTCAGAATGACTTGGTTGAGT
ATTCACCAGTCACAGAAAAGCATCTTACGGATGGCATGACAGTAA
GAGAATTATGCAGTGCTGCCATAACCATGAGTGATAACACTGCGG
CCAACTTACTTCTGACAACGATTGGAGGACCGAAGGAGCTAACCG
CTTTTTTGCACAACATGGGGGATCATGTAACTCGCCTTGATCGTT
GGGAACCGGAGCTGAATGAAGCCATACCAAACGACGAGCGTGACA
CCACGATGCCTGTAGCAATGGCAACAACCTTGCGTAAACTATTAA
CTGGCGAACTACTTACTCTAGCTTCCCGGCAACAGTTGATAGACT
GGATGGAGGCGGATAAAGTTGCAGGACCACTTCTGCGCTCGGCCC
TTCCGGCTGGCTGGTTTATTGCTGATAAATCTGGAGCCGGTGAGC
GTGGGTCTCGCGGTATCATTGCAGCACTGGGGCCAGATGGTAAGC
CCTCCCGTATCGTAGTTATCTACACGACGGGGAGTCAGGCAACTA
TGGATGAACGAAATAGACAGATCGCTGAGATAGGTGCCTCACTGA
TTAAGCATTGGTAACCGATTCTAGGTGCATTGGCGCAGAAAAAAA
TGCCTGATGCGACGCTGCGCGTCTTATACTCCCACATATGCCAGA
TTCAGCAACGGATACGGCTTCCCCAACTTGCCCACTTCCATACGT
GTCCTCCTTACCAGAAATTTATCCTTAAGATCGTTTAAACTCGAC
TCTGGCTCTATCGAATCTCCGTCGTTTCGAGCTTACGCGAACAGC
CGTGGCGCTCATTTGCTCGTCGGGCATCGAATCTCGTCAGCTATC
GTCAGCTTACCTTTTTGGCAGCGATCGCGGCTCCCGACATCTTGG
ACCATTAGCTCCACAGGTATCTTCTTCCCTCTAGTGGTCATAACA
GCAGCTTCAGCTACCTCTCAATTCAAAAAACCCCTCAAGACCCGT
TTAGAGGCCCCAAGGGGTTATGCTATCAATCGTTGCGTTACACAC
ACAAAAAACCAACACACATCCATCTTCGATGGATAGCGATTTTAT
TATCTAACTGCTGATCGAGTGTAGCCAGATCTAGTAATCAATTAC
GGGGTCATTAGTTCATAGCCCATATATGGAGTTCCGCGTTACATA
ACTTACGGTAAATGGCCCGCCTGGCTGACCGCCCAACGACCCCCG
CCCATTGACGTCAATAATGACGTATGTTCCCATAGTAACGCCAAT
AGGGACTTTCCATTGACGTCAATGGGTGGAGTATTTACGGTAAAC
TGCCCACTTGGCAGTACATCAAGTGTATCATATGCCAAGTACGCC
CCCTATTGACGTCAATGACGGTAAATGGCCCGCCTGGCATTATGC
CCAGTACATGACCTTATGGGACTTTCCTACTTGGCAGTACATCTA
CGTATTAGTCATCGCTATTACCATGCTGATGCGGTTTTGGCAGTA
CATCAATGGGCGTGGATAGCGGTTTGACTCACGGGGATTTCCAAG
TCTCCACCCCATTGACGTCAATGGGAGTTTGTTTTGGCACCAAAA
TCAACGGGACTTTCCAAAATGTCGTAACAACTCCGCCCCATTGAC
GCAAATGGGCGGTAGGCGTGTACGGTGGGAGGTCTATATAAGCAG
AGCTGGTTTAGTGAACCGTCAGATCAGATCTTTGTCGATCCTACC
ATCCACTCGACACACCCGCCAGCGGCCGC
(SEQID NO: 46)

LINE-1 plasmid ORF1-P2A-ORF2 GFP
(SEQ ID NO: 47)
TAATACGACTCACTATAGGGAGAAGTACTGCCACCATGGGCAAGA
AGCAAAATCGCAAGACGGGGAATTCCAAGACACAATCCGCTAGCC
CACCACCTAAAGAGCGTTCTAGCTCCCCTGCTACTGAGCAGTCCT
GGATGGAAAACGACTTCGATGAACTCCGGGAAGAGGGATTTAGGC
GATCCAACTATTCAGAACTCCGCGAAGATATCCAGACAAAGGGGA
AGGAAGTCGAGAATTTCGAGAAGAACCTCGAGGAGTGCATCACCC
GTATCACAAACACTGAGAAATGTCTCAAAGAACTCATGGAACTTA
AGACAAAAGCCAGGGAGCTTCGAGAGGAGTGTCGGAGTCTGAGAT
CCAGGTGTGACCAGCTCGAGGAGCGCGTGAGCGCGATGGAAGACG
AGATGAACGAGATGAAAAGAGAGGGCAAATTCAGGGAGAAGCGCA
TTAAGAGGAACGAACAGAGTCTGCAGGAGATTTGGGATTACGTCA
AGAGGCCTAACCTGCGGTTGATCGGCGTCCCCGAGAGCGACGTAG
AAAACGGGACTAAACTGGAGAATACACTTCAAGACATCATTCAAG
AAAATTTTCCAAACCTGGCTCGGCAAGCTAATGTGCAAATCCAAG
AGATCCAACGCACACCCCAGCGGTATAGCTCTCGGCGTGCCACCC
CTAGGCATATTATCGTGCGCTTTACTAAGGTGGAGATGAAAGAGA
AGATGCTGCGAGCCGCTCGGGAAAAGGGAAGGGTGACTTTGAAGG
GCAAACCTATTCGGCTGACGGTTGACCTTAGCGCCGAGACACTCC
AGGCACGCCGGGAATGGGGCCCCATCTTTAATATCCTGAAGGAGA
AGAACTTCCAGCCACGAATCTCTTACCCTGCAAAGTTGAGTTTTA
TCTCCGAGGGTGAGATTAAGTATTTCATCGATAAACAGATGCTGC
GAGACTTCGTGACAACTCGCCCAGCTCTCAAGGAACTGCTCAAAG
AGGCTCTTAATATGGAGCGCAATAATAGATATCAACCCTTGCAGA
ACCACGCAAAGATGGGAAGCGGAGCTACTAACTTCAGCCTGCTGA
AGCAGGCTGGAGACGTGGAGGAGAACCCTGGACCTATGACCGGCT
CTAACTCACATATCACCATCCTTACACTTAACATTAACGGCCTCA
ACTCAGCTATCAAGCGCCATCGGCTGGCCAGCTGGATCAAATCAC
AGGATCCAAGCGTTTGTTGCATCCAAGAGACCCACCTGACCTGTA
GAGATACTCACCGCCTCAAGATCAAGGGATGGCGAAAGATTTATC
AGGCGAACGGTAAGCAGAAGAAAGCCGGAGTCGCAATTCTGGTCT
CAGACAAGACGGATTTCAAGCCCACCAAAATTAAGCGTGATAAGG
AAGGTCACTATATTATGGTGAAAGGCAGCATACAGCAGGAAGAAC
TTACCATATTGAACATCTACGCGCCAAACACCGGCGCACCTCGCT
TTATCAAACAGGTCCTGTCCGATCTGCAGCGAGATCTGGATTCTC
ATACGTTGATTATGGGTGATTTCAATACACCATTGAGCACCCTGG
ATCGCAGCACCAGGCAAAAGGTAAATAAAGACACGCAAGAGCTCA
ATAGCGCACTGCATCAGGCAGATCTCATTGATATTTATCGCACTC
TTCATCCTAAGAGTACCGAGTACACATTCTTCAGCGCCCCACATC
ATACATACTCAAAGATCGATCATATCGTCGGCTCAAAGGCTCTGC
TGTCAAAGTGCAAGCGCACAGAGATAATTACAAATTACCTGTCAG
ATCATAGCGCGATCAAGCTCGAGCTGAGAATCAAGAACCTGACCC
AGAGCCGGAGTACCACTTGGAAGCTTAATAACCTGCTGCTCAACG
ATTATTGGGTCCACAATGAGATGAAGGCAGAGATTAAAATGTTCT
TCGAAACAAATGAGAATAAGGATACTACCTATCAAAACCTTTGGG
ATGCCTTTAAGGCCGTCTGCAGAGGCAAGTTCATCGCCCTCAACG
CCTATAAAAGAAAACAAGAGAGATCTAAGATCGATACTCTCACCT
CTCAGCTGAAGGAGTTGGAGAAACAGGAACAGACCCACTCCAAGG
CGTCAAGACGGCAGGAGATCACAAAGATTCGCGCCGAGTTGAAAG
AGATCGAAACCCAAAAGACTCTTCAGAAAATTAACGAGTCTCGTA
GTTGGTTCTTCGAGCGGATTAATAAGATAGACAGACCTCTGGCAC
GACTGATTAAGAAGAAGCGCGAAAAGAACCAGATTGATACCATCA
AGAACGACAAGGGCGACATCACTACTGACCCGACCGAGATCCAGA
CCACTATTCGGGAGTATTATAAGCATTTGTATGCTAACAAGCTTG TABLE 8-continued

| Plasmid and mRNA construct sequences |
| --- |
| AGAACCTGGAAGAGATGGACACTTTTCTGGATACCTATACTCTGC |
| CACGGCTTAATCAAGAGGAAGTCGAGTCCCTCAACCGCCCAATTA |
| CAGGAAGCGAGATTGTGGCCATAATTAACTCCCTGCCGACAAAGA |
| AATCTCCTGGTCCGGACGGGTTTACAGCTGAGTTTTATCAACGGT |
| ATATGGAAGAGCTTGTACCGTTTCTGCTCAAGCTCTTTCAGTCTA |
| TAGAAAAGGAAGGCATCTTGCCCAATTCCTTCTACGAAGCTTCTA |
| TAATACTTATTCCCAAACCAGGACGCGATACCACAAAGAAGGAAA |
| ACTTCCGGCCCATTAGTCTCATGAATATCGACGCTAAAATATTGA |
| ACAAGATTCTCGCCAACAGAATCCAACAACATATTAAGAAATTGA |
| TACATCACGACCAGGTGGGGTTTATACCTGGCATGCAGGGCTGGT |
| TTAACATCCGGAAGAGTATTAACGTCATTCAACACATTAATAGAG |
| CTAAGGATAAGAATCATATGATCATCTCTATAGACGCGGAAAAGG |
| CATTCGATAAGATTCAGCAGCCATTTATGCTCAAGACTCTGAACA |
| AACTCGGCATCGACGGAACATATTTAAGATTATTCGCGCAATTT |
| ACGATAAGCCGACTGCTAACATTATCCTTAACGGCCAAAAGCTCG |
| AGGCCTTTCCGCTCAAGACTGGAACCCGCCAAGGCTGTCCCCTCT |
| CCCCGCTTTTGTTTAATATTGTACTCGAGGTGCTGGCTAGGGCTA |
| TTCGTCAAGAGAAAGAGATTAAAGGGATACAGCTCGGGAAGGAAG |
| AGGTCAAGCTTTCCTTGTTCGCCGATGATATGATTGTGTACCTGG |
| AGAATCCTATTGTGTCTGCTCAGAACCTTCTTAAACTTATTTCTA |
| ACTTTAGCAAGGTCAGCGGCTATAAGATTAACGTCCAGAAATCTC |
| AGGCCTTTCTGTACACAAATAATCGACAGACCGAATCCCAGATAA |
| TGGGTGAGCTTCCGTTTGTCATAGCCAGCAAAAGGATAAAGTATC |
| TCGGAATCCAGCTGACACGAGACGTTAAAGATTTGTTTAAGGAAA |
| ATTACAAGCCTCTCCTGAAAGAGATTAAGGAAGATACTAATAAGT |
| GGAAGAATATCCCCTGTTCATGGGTTGGCAGAATCAACATAGTGA |
| AGATGGCAATACTTCCTAAAGTGATATATCGCTTTAACGCCATCC |
| CAATTAAACTGCCTATGACCTTCTTTACGGAGCTCGAGAAAACAA |
| CCCTTAAATTTATATGGAATCAAAAGAGAGCAAGAATAGCGAAGT |
| CCATCTTGAGCCAGAAGAATAAGGCCGGTGGGATTACTTTGCCTG |
| ATTTTAAGTTGTATTATAAAGCCACAGTAACTAAGACAGCCTGGT |
| ATTGGTATCAGAATAGAGACATCGACCAGTGGAATCGGACCGAAC |
| CATCAGAGATAATGCCCCACATCTATAATTACCTTATATTCGATA |
| AGCCAGAAAAGAATAAACAGTGGGGCAAAGACAGCCTCTTCAACA |
| AGTGGTGTTGGGAGAATTGGCTGGCCATATGCCGGAAACTCAAGC |
| TCGACCCCTTTCTTACACCCTACACTAAAATCAACAGTAGGTGGA |
| TCAAGGACTTGAATGTCAAGCCAAAGACTATAAAGACACTGGAAG |
| AGAATCTTGGGATCACAATACAAGATATAGGCGTCGGCAAAGATT |
| TTATGTCAAAGACGCCCAAGGCCATGGCCACTAAGGATAAGATTG |
| ATAAGTGGGACCTTATTAAGCTCAAAAGCTTCTGTACTGCCAAGG |
| AGACCACGATCAGAGTTAATAGGCAGCCCACTACATGGGAAAAGA |
| TTTTCGCCACTTATTCATCAGATAAGGGGTTGATAAGCAGAATAT |
| ATAACGAGCTGAAGCAGATCTACAAGAAGAAAACGAATAATCCCA |
| TCAAGAAGTGGGCAAAAGATATGAACAGGCATTTTAGCAAAGAGG |
| ATATCTACGCCGCGAAGAAGCATATGAAGAAGTGTAGTTCAAGCT |
| TGGCCATTCGTGAGATGCAGATTAAGACGACCATGCGATACCACC |
| TTACCCCAGTGAGGATGGCAATTATCAAGAAATCTGGCAATAATA |
| GATGTTGGCGGGGCTGTGGCGAGATTGGCACCCTGCTCCATTGCT |
| GGTGGGATTGCAAGCTGGTGCAGCCGCTTTGGAAATCAGTCTGGC |
| GCTTTCTGAGGGACCTCGAGCTTGAGATTCCCTTCGATCCCGCAA |
| TTCCCTTGCTCGGAATCTATCCTAACGAATACAAGAGCTGTTGTT |
| ACAAGGATACGTGTACCCGGATGTTCATCGCGGCCTTGTTTACGA |
| TAGCTAAGACGTGGAATCAGCCTAAGTGCCCCACAATGATCGATT |
| GGATCAAGAAAATGTGGCATATTTATACCATGGAGTATTACGCAG |
| CAATTAAGAATGACGAATTTATTTCCTTCGTTGGGACCTGGATGA |
| AGCTGGAGACTATTATTCTGAGCAAGCTGTCTCAGGAGCAAAAGA |
| CAAAGCATAGAATCTTCTCTCTCATTGGTGGTAACGACTACAAAG |
| ACGATGACGACAAGTAAAGCGCTTCTAGAAGTTGTCTCCTCCTGC |
| ACTGACTGACTGATACAATCGATTTCTGGATCCGCAGGCCTAATC |
| AACCTCTGGATTACAAAATTTGTGAAAGATTGACTGGTATTCTTA |
| ACTATGTTGCTCCTTTTACGCTATGTGGATACGCTGCTTTAATGC |
| CTTTGTATCATGCTATTGCTTCCCGTATGGCTTTCATTTTCTCCT |
| CCTTGTATAAATCCTGGTTGCTGTCTCTTTATGAGGAGTTGTGGC |
| CCGTTGTCAGGCAACGTGGCGTGGTGTGCACTGTGTTTGCTGACG |
| CAACCCCCACTGGTTGGGGCATTGCCACCACCTGTCAGCTCCTTT |
| CCGGGACTTTCGCTTTCCCCCTCCCTATTGCCACGGCGGAACTCA |
| TCGCCGCCTGCCTTGCCCGCTGCTGGACAGGGGCTCGGCTGTTGG |
| GCACTGACAATTCCGTGGTGTTGTCGGGGAAGCTGACGTCCTTTC |
| CATGGCTGCTCGCCTGTGTTGCCACCTGGATTCTGCGCGGGACGT |
| CCTTCTGCTACGTCCCTTCGGCCCTCAATCCAGCGGACCTTCCTT |
| CCCGCGAACAAACGACCCAACACCCGTGCGTTTTATTCTGTCTTT |
| TTATTGCCGATCCCCTCAGAAGAACTCGTCAAGAAGGCGATAGAA |
| GGCGATGCGCTGCGAATCGGGAGCGGCGATACCGTAAAGCACGAG |
| GAAGCGGTCAGCCCATTCGCCGCCAAGCTCTTCAGCAATATCACG |
| GGTAGCCAACGCTATGTCCTGATAGCGGTCGGCCGCTTTACTTGT |
| ACAGCTCGTCCATGCCGAGAGTGATCCCGGCGGCGGTCACGAACT |
| CCAGCAGGACCATGTGATCGCGCTTCTCGTTGGGGTCTTTGCTCA |
| GGGCGGACTGGGTGCTCAGGTAGTGGTTGTCGGGCAGCAGCACGG |

TABLE 8-continued

| Plasmid and mRNA construct sequences |
| --- |
| GGCCGTCGCCGATGGGGGTGTTCTGCTGGTAGTGGTCGGCCAGGT |
| GAGTCCAGGAGATGTTTCAGCACTGTTGCCTTTAGTCTCGAGGCA |
| ACTTAGACAACTGAGTATTGATCTGAGCACAGCAGGGTGTGAGCT |
| GTTTGAAGATACTGGGGTTGGGGGTGAAGAAACTGCAGAGGACTA |
| ACTGGGCTGAGACCCAGTGGCAATGTTTTAGGGCCTAAGGAATGC |
| CTCTGAAAATCTAGATGGACAACTTTGACTTTGAGAAAAGAGAGG |
| TGGAAATGAGGAAAATGACTTTTCTTTATTAGATTTCGGTAGAAA |
| GAACTTTCATCTTTCCCCTATTTTTGTTATTCGTTTTAAAACATC |
| TATCTGGAGGCAGGACAAGTATGGTCATTAAAAAGATGCAGGCAG |
| AAGGCATATATTGGCTCAGTCAAAGTGGGGAACTTTGGTGGCCAA |
| ACATACATTGCTAAGGCTATTCCTATATCAGCTGGACACATATAA |
| AATGCTGCTAATGCTTCATTACAAACTTATATCCTTTAATTCCAG |
| ATGGGGGCAAAGTATGTCCAGGGGTGAGGAACAATTGAAACATTT |
| GGGCTGGAGTAGATTTTGAAAGTCAGCTCTGTGTGTGTGTGTGTG |
| TGTGTGTGTGTGAGAGCGTGTGTTTCTTTTAACGTTTTCAGCCTA |
| CAGCATACAGGGTTCATGGTGGCAAGAAGATAACAAGATTTAAAT |
| TATGGCCAGTGACTAGTGCTGCAAGAAGAACAACTACCTGCATTT |
| AATGGGAAAGCAAAATCTCAGGCTTTGAGGGAAGTTAACATAGGC |
| TTGATTCTGGGTGGAAGCTGGGTGTGTAGTTATCTGGAGGCCAGG |
| CTGGAGCTCTCAGCTCACTATGGGTTCATCTTTATTGTCTCCTTT |
| CATCTCAACAGCTGCACGCTGCCGTCCTCGATGTTGTGGCGGATC |
| TTGAAGTTCACCTTGATGCCGTTCTTCTGCTTGTCGGCCATGATA |
| TAGACGTTGTGGCTGTTGTAGTTGTACTCCAGCTTGTGCCCCAGG |
| ATGTTGCCGTCCTCCTTGAAGTCGATGCCCTTCAGCTCGATGCGG |
| TTCACCAGGGTGTCGCCCTCGAACTTCACCTCGGCGCGGGTCTTG |
| TAGTTGCCGTCGTCCTTGAAGAAGATGGTGCGCTCCTGGACGTAG |
| CCTTCGGGCATGGCGGACTTGAAGAAGTCGTGCTGCTTCATGTGG |
| TCGGGGTAGCGGCTGAAGCACTGCACGCCGTAGGTCAGGGTGGTC |
| ACGAGGGTGGGCCAGGGCACGGGCAGCTTGCCGGTGGTGCAGATG |
| AACTTCAGGGTCAGCTTGCCGTAGGTGGCATCGCCCTCGCCCTCG |
| CCGGACACGCTGAACTTGTGGCCGTTTACGTCGCCGTCCAGCTCG |
| ACCAGGATGGGCACCACCCCGGTGAACAGCTCCTCGCCCTTGCTC |
| ACCATGGTGGCGAATTCGAAGCTTGAGCACGAGATCTGAGTCCGG |
| TAGGCCTAGCGGATCTGACGGTTCACTAAACCAGCTCTGCTTATA |
| TAGACCTCCCACCGTACACGCCTACCGCCCATTTGCGTCAATGGG |
| GCGGAGTTGTTACGACATTTTGGAAAGTCCCGTTGATTTTGGTGC |
| CAAAACAAACTCCCATTGACGTCAATGGGGTGGAGACTTGGAAAT |
| CCCCGTGAGTCAAACCGCTATCCACGCCCATTGATGTACTGCCAA |
| AACCGCATCACCATGGTAATAGCGATGACTAATACGTAGATGTAC |
| TGCCAAGTAGGAAAGTCCCATAAGGTCATGTACTGGGCATAATGC |
| CAGGCGGGCCATTTACCGTCATTGACGTCAATAGGGGGCGTACTT |
| GGCATATGATACACTTGATGTACTGCCAAGTGGGCAGTTTACCGT |
| AAATACTCCACCCATTGACGTCAATGGAAAGTCCCTATTGGCGTT |
| ACTATGGGAACATACGTCATTATTGACGTCAATGGGCGGGGGTCG |
| TTGGGCGGTCAGCCAGGCGGGCCATTTACCGTAAGTTATGTAACG |
| GGCCTGCTGCCGGCTCTGCGGCCTCTTCCGCGTCTTCGCCTTCGC |
| CCTCAGACGAGTCGGATCTCCCTTTGGGCCGCCTCCCCGCCTGTC |
| TAGCTTGACTGACTGAGATACAGCGTACCTTCAGCTCACAGACAT |
| GATAAGATACATTGATGAGTTTGGACAAACCACAACTAGAATGCA |
| GTGAAAAAAATGCTTTATTTGTGAAATTTGTGATGCTATTGCTTT |
| ATTTGTAACCATTATAAGCTGCAATAAACAAGTTAACAACAACAA |
| TTGCATTCATTTTATGTTTCAGGTTCAGGGGGAGGTGTGGGAGGT |
| TTTTTAAAGCAAGTAAAACCTCTACAAATGTGGTATTGGCCCATC |
| TCTATCGGTATCGTAGCATAACCCCTTGGGGCCTCTAAACGGGTC |
| TTGAGGGGTTTTTTGTGCCCCTCGGGCCGGATTGCTATCTACCGG |
| CATTGGCGCAGAAAAAAATGCCTGATGCGACGCTGCGCGTCTTAT |
| ACTCCCACATATGCCAGATTCAGCAACGGATACGGCTTCCCCAAC |
| TTGCCCACTTCCATACGTGTCCTCCTTACCAGAAATTTATCCTTA |
| AGGTCGTCAGCTATCCTGCAGGCGATCTCTCGATTTCGATCAAGA |
| CATTCCTTTAATGGTCTTTTCTGGACACCACTAGGGGTCAGAAGT |
| AGTTCATCAAACTTTCTTCCCTCCCTAATCTCATTGGTTACCTTG |
| GGCTATCGAAACTTAATTAAGCGATCTGCATCTCAATTAGTCAGC |
| AACCATAGTCCCGCCCCTAACTCCGCCCATCCCGCCCCTAACTCC |
| GCCCAGTTCCGCCCATTCTCCGCCCCATCGCTGACTAATTTTTTT |
| TATTTATGCAGAGGCCGAGGCCGCCTCGGCCTCTGAGCTATTCCA |
| GAAGTAGTGAGGAGGCTTTTTTGGAGGCCTAGGCTTTTGCAAAGG |
| AGGTAGCCAACATGATTGAACAAGATGGATTGCACGCAGGTTCTC |
| CCGCCGCTTGGGTGGAGAGGCTATTCGGCTATGACTGGGCACAAC |
| AGACAATCGGCTGCTCTGATGCCGCCGTGTTCCGGCTGTCAGCGC |
| AGGGGCGCCCGGTTCTTTTTGTCAAGACCGACCTGTCCGGTGCCC |
| TGAATGAACTCCAGGACGAGGCAGCGCGGCTATCGTGGCTGGCCA |
| CGACGGGCGTTCCTTGCGCAGCTGTGCTCGACGTTGTCACTGAAG |
| CGGGAAGGGACTGGCTGCTATTGGGCGAAGTGCCGGGGCAGGATC |
| TCCTGTCATCTCACCTTGCTCCTGCCGAGAAAGTATCCATCATGG |
| CTGATGCAATGCGGCGGCTGCATACGCTTGATCCGGCTACCTGCC |
| CATTCGACCACCAAGCGAAACATCGCATCGAGCGAGCACGTACTC |
| GGATGGAAGCCGGTCTTGTCGATCAGGATGATCTGGACGAAGAGC |
| ATCAGGGGCTCGCGCCAGCCGAACTGTTCGCCAGGCTCAAGGCGC |

TABLE 8-continued

| Plasmid and mRNA construct sequences |
|---|
| GGATGCCCGACGGCGAGGATCTCGTCGTGACCCACGGCGATGCCT<br>GCTTGCCGAATATCATGGTGGAAAATGGCCGCTTTTCTGGATTCA<br>TCGACTGTGGCCGGCTGGGTGTGGCGGACCGCTATCAGGACATAG<br>CGTTGGCTACCCGTGATATTGCTGAAGAGCTTGGCGGCGAATGGG<br>CTGACCGCTTCCTCGTGCTTTACGGTATCGCCGCTCCCGATTCGC<br>AGCGCATCGCCTTCTATCGCCTTCTTGACGAGTTCTTCTAGTATG<br>TAAGCCCTGTGCCTTCTAGTTGCCAGCCATCTGTTGTTTGCCCCT<br>CCCCCGTGCCTTCCTTGACCCTGGAAGGTGCCACTCCCACTGTCC<br>TTTCCTAATAAAATGAGGAAATTGCATCGCATTGTCTGAGTAGGT<br>GTCATTCTATTCTGGGGGGTGGGGTGGGGCAGGACAGCAAGGGGG<br>AGGATTGGGAAGACAATAGCAGGCATGCTGGGGATGCGGTGGGCT<br>CTATGGTTAATTAACCAGTCAAGTCAGCTACTTGGCGAGATCGAC<br>TTGTCTGGGTTTCGACTACGCTCAGAATTGCGTCAGTCAAGTTCG<br>ATCTGGTCCTTGCTATTGCACCCGTTCTCCGATTACGAGTTTCAT<br>TTAAATCATGTGAGCAAAAGGCCAGCAAAAGGCCAGGAACCGTAA<br>AAAGGCCGCGTTGCTGGCGTTTTTCCATAGGCTCCGCCCCCCTGA<br>CGAGCATCACAAAAATCGACGCTCAAGTCAGAGGTGGCGAAACCC<br>GACAGGACTATAAAGATACCAGGCGTTTCCCCCTGGAAGCTCCCT<br>CGTGCGCTCTCCTGTTCCGACCCTGCCGCTTACCGGATACCTGTC<br>CGCCTTTCTCCCTTCGGGAAGCGTGGCGCTTTCTCATAGCTCACG<br>CTGTAGGTATCTCAGTTCGGTGTAGGTCGTTCGCTCCAAGCTGGG<br>CTGTGTGCACGAACCCCCCGTTCAGCCCGACCGCTGCGCCTTATC<br>CGGTAACTATCGTCTTGAGTCCAACCCGGTAAGACACGACTTATC<br>GCCACTGGCAGCAGCCACTGGTAACAGGATTAGCAGAGCGAGGTA<br>TGTAGGCGGTGCTACAGAGTTCTTGAAGTGGTGGCCTAACTACGG<br>CTACACTAGAAGAACAGTATTTGGTATCTGCGCTCTGCTGAAGCC<br>AGTTACCTTCGGAAAAAGAGTTGGTAGCTCTTGATCCGGCAAACA<br>AACCACCGCTGGTAGCGGTGGTTTTTTTGTTTGCAAGCAGCAGAT<br>TACGCGCAGAAAAAAAGGATCTCAAGAAGATCCTTTGATCTTTTC<br>TACGGGGTCTGACGCTCAGTGGAACGAAAACTCACGTTAAGGGAT<br>TTTGGTCATGAGATTATCAAAAAGGATCTTCACCTAGATCCTTTT<br>AAATTAAAAATGAAGTTTTAAATCAATCTAAAGTATATATGAGTA<br>AACTTGGTCTGACAGTTACCAATGCTTAATCAGTGAGGCACCTAT<br>CTCAGCGATCTGTCTATTTCGTTCATCCATAGTTGCATTTAAATT<br>TCCGAACTCTCCAAGGCCCTCGTCGGAAAATCTTCAAACCTTTCG<br>TCCGATCCATCTTGCAGGCTACCTCTCGAACGAACTATCGCAAGT<br>CTCTTGGCCGGCCTTGCGCCTTGGCTATTGCTTGGCAGCGCCTAT<br>CGCCAGGTATTACTCCAATCCCGAATATCCGAGATCGGGATCACC<br>CGAGAGAAGTTCAACCTACATCCTCAATCCCGATCTATCCGAGAT<br>CCGAGGAATATCGAAATCGGGGCGCGCCTGGTGTACCGAGAACGA<br>TCCTCTCAGTGCGAGTCTCGACGATCCATATCGTTGCTTGGCAGT<br>CAGCCAGTCGGAATCCAGCTTGGGACCCAGGAAGTCCAATCGTCA<br>GATATTGTACTCAAGCCTGGTCACGGCAGCGTACCGATCTGTTTA<br>AACCTAGATATTGATAGTCTGATCGGTCAACGTATAATCGAGTCC<br>TAGCTTTTGCAAACATCTATCAAGAGACAGGATCAGCAGGAGGCT<br>TTCGCATGAGTATTCAACATTTCCGTGTCGCCCTTATTCCCTTTT<br>TTGCGGCATTTTGCCTTCCTGTTTTTGCTCACCCAGAAACGCTGG<br>TGAAAGTAAAAGATGCTGAAGATCAGTTGGGTGCGCGAGTGGGTT<br>ACATCGAACTGGATCTCAACAGCGGTAAGATCCTTGAGAGTTTTC<br>GCCCCGAAGAACGCTTTCCAATGATGAGCACTTTTAAAGTTCTGC<br>TATGTGGCGCGGTATTATCCCGTATTGACGCCGGGCAAGAGCAAC<br>TCGGTCGCCGCATACACTATTCTCAGAATGACTTGGTTGAGTATT<br>CACCAGTCACAGAAAAGCATCTTACGGATGGCATGACAGTAAGAG<br>AATTATGCAGTGCTGCCATAACCATGAGTGATAACACTGCGGCCA<br>ACTTACTTCTGACAACGATTGGAGGACCGAAGGAGCTAACCGCTT<br>TTTTGCACAACATGGGGGATCATGTAACTCGCCTTGATCGTTGGG<br>AACCGGAGCTGAATGAAGCCATACCAAACGACGAGCGTGACACCA<br>CGATGCCTGTAGCAATGGCAACAACCTTGCGTAAACTATTAACTG<br>GCGAACTACTTACTCTAGCTTCCCGGCAACAGTTGATAGACTGGA<br>TGGAGGCGGATAAAGTTGCAGGACCACTTCTGCGCTCGGCCCTTC<br>CGGCTGGCTGGTTTATTGCTGATAAATCTGGAGCCGGTGAGCGTG<br>GGTCTCGCGGTATCATTGCAGCACTGGGGCCAGATGGTAAGCCCT<br>CCCGTATCGTAGTTATCTACACGACGGGGAGTCAGGCAACTATGG<br>ATGAACGAAATAGACAGATCGCTGAGATAGGTGCCTCACTGATTA<br>AGCATTGGTAACCGATTCTAGGTGCATTGGCGCAGAAAAAATGC<br>CTGATGCGACGCTGCGCGTCTTATACTCCCACATATGCCAGATTC<br>AGCAACGGATACGGCTTCCCCAACTTGCCCACTTCCATACGTGTC<br>CTCCTTACCAGAAATTTATCCTTAAGATCGTTTAAACTCGACTCT<br>GGCTCTATCGAATCTCCGTCGTTTCGAGCTTACGCGAACAGCCGT<br>GGCGCTCATTTGCTCGTCGGGCATCGAATCTCGTCAGCTATCGTC<br>AGCTTACCTTTTTGGCAGCGATCGCGGCTCCCGACATCTTGGACC<br>ATTAGCTCCACAGGTATCTTCTTCCCTCTAGTGGTCATAACAGCA<br>GCTTCAGCTACCTCTCAATTCAAAAAACCCCTCAAGACCCGTTTA<br>GAGGCCCCAAGGGGTTATGCTATCAATCGTTGCGTTACACACACA<br>AAAAACCAACACACATCCATCTTCGATGGATAGCGATTTTATTAT<br>CTAACTGCTGATCGAGTGTAGCCAGATCTAGTAATCAATTACGGG<br>GTCATTAGTTCATAGCCCATATATGGAGTTCCGCGTTACATAACT<br>TACGGTAAATGGCCCGCCTGGCTGACCGCCCAACGACCCCCGCCC |

TABLE 8-continued

| Plasmid and mRNA construct sequences |
|---|
| ATTGACGTCAATAATGACGTATGTTCCCATAGTAACGCCAATAGG<br>GACTTTCCATTGACGTCAATGGGTGGAGTATTTACGGTAAACTGC<br>CCACTTGGCAGTACATCAAGTGTATCATATGCCAAGTACGCCCCC<br>TATTGACGTCAATGACGGTAAATGGCCCGCCTGGCATTATGCCCA<br>GTACATGACCTTATGGGACTTTCCTACTTGGCAGTACATCTACGT<br>ATTAGTCATCGCTATTACCATGCTGATGCGGTTTTGGCAGTACAT<br>CAATGGGCGTGGATAGCGGTTTGACTCACGGGGATTTCCAAGTCT<br>CCACCCCATTGACGTCAATGGGAGTTTGTTTTGGCACCAAAATCA<br>ACGGGACTTTCCAAAATGTCGTAACAACTCCGCCCCATTGACGCA<br>AATGGGCGGTAGGCGTGTACGGTGGGAGGTCTATATAAGCAGAGC<br>TGGTTTAGTGAACCGTCAGATCAGATCTTTGTCGATCCTACCATC<br>CACTCGACACACCCGCCAGCGGCCGC<br>(SEQ ID NO: 47) |
| LINE-1 plasmid ORF1-T2A ORF2 GFP<br>(SEQ ID NO: 48)<br>TAATACGACTCACTATAGGGAGAAGTACTGCCACCATGGGCAAGA<br>AGCAAAATCGCAAGACGGGGAATTCCAAGACACAATCCGCTAGCC<br>CACCACCTAAAGAGCGTTCTAGCTCCCCTGCTACTGAGCAGTCCT<br>GGATGGAAAACGACTTCGATGAACTCCGGGAAGAGGGATTTAGGC<br>GATCCAACTATTCAGAACTCCGCGAAGATATCCAGACAAAGGGGA<br>AGGAAGTCGAGAATTTCGAGAAGAACCTCGAGGAGTGCATCACCC<br>GTATCACAAACACTGAGAAATGTCTCAAAGAACTCATGGAACTTA<br>AGACAAAAGCCAGGGAGCTTCGAGAGGAGTGTCGGAGTCTGAGAT<br>CCAGGTGTGACCAGCTCGAGGAGCGCGTGAGCGCGATGGAAGACG<br>AGATGAACGAGATGAAAAGAGAGGGCAAATTCAGGGAGAAGCGCA<br>TTAAGAGGAACGAACAGAGTCTGCAGGAGATTTGGGATTACGTCA<br>AGAGGCCTAACCTGCGGTTGATCGGCGTCCCCGAGAGCGACGTAG<br>AAAACGGGACTAAACTGGAGAATACACTTCAAGACATCATTCAAG<br>AAAATTTTCCAAACCTGGCTCGGCAAGCTAATGTGCAAATCCAAG<br>AGATCCAACGCACACCCCAGCGGTATAGCTCTCGGCGTGCCACCC<br>CTAGGCATATTATCGTGCGCTTTACTAAGGTGGAGATGAAAGAGA<br>AGATGCTGCGAGCCGCTCGGGAAAAGGGAAGGGTGACTTTGAAGG<br>GCAAACCTATTCGGCTGACGGTTGACCTTAGCGCCGAGACACTCC<br>AGGCACGCCGGGAATGGGGCCCCATCTTTAATATCCTGAAGGAGA<br>AGAACTTCCAGCCACGAATCTCTTACCCTGCAAAGTTGAGTTTTA<br>TCTCCGAGGGTGAGATTAAGTATTTCATCGATAAACAGATGCTGC<br>GAGACTTCGTGACAACTCGCCCAGCTCTCAAGGAACTGCTCAAAG<br>AGGCTCTTAATATGGAGCGCAATAATAGATATCAACCCTTGCAGA<br>ACCACGCAAAGATGGGAAGCGGAGAGGGCAGAGGAAGTCTGCTAA<br>CATGCGGTGACGTCGAGGAGAATCCTGGACCTATGACCGGCTCTA<br>ACTCACATATCACCATCCTTACACTTAACATTAACGGCCTCAACT<br>CAGCTATCAAGCGCCATCGGCTGGCCAGCTGGATCAAATCACAGG<br>ATCCAAGCGTTTGTTGCATCCAAGAGACCCACCTGACCTGTAGAG<br>ATACTCACCGCCTCAAGATCAAGGGATGGCGAAAGATTTATCAGG<br>CGAACGGTAAGCAGAAGAAAGCCGGAGTCGCAATTCTGGTCTCAG<br>ACAAGACGGATTTCAAGCCCACCAAAATTAAGCGTGATAAGGAAG<br>GTCACTATATTATGGTGAAAGGCAGCATACAGCAGGAAGAACTTA<br>CCATATTGAACATCTACGCGCCAAACACCGGCGCACCTCGCTTTA<br>TCAAACAGGTCCTGTCCGATCTGCAGCGAGATCTGGATTCTCATA<br>CGTTGATTATGGGTGATTTCAATACACCATTGAGCACCCTGGATC<br>GCAGCACCAGGCAAAAGGTAAATAAAGACACGCAAGAGCTCAATA<br>GCGCACTGCATCAGGCAGATCTCATTGATATTTATCGCACTCTTC<br>ATCCTAAGAGTACCGAGTACACATTCTTCAGCGCCCCACATCATA<br>CATACTCAAAGATCGATCATATCGTCGGCTCAAAGGCTCTGCTGT<br>CAAAGTGCAAGCGCACAGAGATAATTACAAATTACCTGTCAGATC<br>ATAGCGCGATCAAGCTCGAGCTGAGAATCAAGAACCTGACCCAGA<br>GCCGGAGTACCACTTGGAAGCTTAATAACCTGCTGCTCAACGATT<br>ATTGGGTCCACAATGAGATGAAGGCAGAGATTAAAATGTTCTTCG<br>AAACAAATGAGAATAAGGATACTACCTATCAAAACCTTTGGGATG<br>CCTTTAAGGCCGTCTGCAGAGGCAAGTTCATCGCCCTCAACGCCT<br>ATAAAAGAAAACAAGAGAGATCTAAGATCGATACTCTCACCTCTC<br>AGCTGAAGGAGTTGGAGAAACAGGAACAGACCCACTCCAAGGCGT<br>CAAGACGGCAGGAGATCACAAAGATTCGCGCCGAGTTGAAAGAGA<br>TCGAAACCCAAAAGACTCTTCAGAAAATTAACGAGTCTCGTAGTT<br>GGTTCTTCGAGCGGATTAATAAGATAGACAGACCTCTGGCACGAC<br>TGATTAAGAAGAAGCGCGAAAAGAACCAGATTGATACCATCAAGA<br>ACGACAAGGGCGACATCACTACTGACCCGACCGAGATCCAGACCA<br>CTATTCGGGAGTATTATAAGCATTTGTATGCTAACAAGCTTGAGA<br>ACCTGGAAGAGATGGACACTTTTCTGGATACCTATACTCTGCCAC<br>GGCTTAATCAAGAGGAAGTCGAGTCCCTCAACCGCCCAATTACAG<br>GAAGCGAGATTGTGGCCATAATTAACTCCCTGCCGACAAAGAAAT<br>CTCCTGGTCCGGACGGGTTTACAGCTGAGTTTTATCAACGGTATA<br>TGGAAGAGCTTGTACCGTTTCTGCTCAAGCTCTTTCAGTCTATAG<br>AAAAGGAAGGCATCTTGCCCAATTCCTTCTACGAAGCTTCTATAA<br>TACTTATTCCCAAACCAGGACGCGATACCACAAAGAAGGAAAACT<br>TCCGGCCCATTAGTCTCATGAATATCGACGCTAAAATATTGAACA<br>AGATTCTCGCCAACAGAATCCAACAACATATTAAGAAATTGATAC |

TABLE 8-continued

| Plasmid and mRNA construct sequences |
| --- |
| ATCACGACCAGGTGGGGTTTATACCTGGCATGCAGGGCTGGTTTA |
| ACATCCGGAAGAGTATTAACGTCATTCAACACATTAATAGAGCTA |
| AGGATAAGAATCATATGATCATCTCTATAGACGCGGAAAAGGCAT |
| TCGATAAGATTCAGCAGCCATTTATGCTCAAGACTCTGAACAAAC |
| TCGGCATCGACGGAACATATTTTAAGATTATTCGCGCAATTTACG |
| ATAAGCCGACTGCTAACATTATCCTTAACGGCCAAAAGCTCGAGG |
| CCTTTCCGCTCAAGACTGGAACCCGCCAAGGCTGTCCCCTCTCCC |
| CGCTTTTGTTTAATATTGTACTCGAGGTGCTGGCTAGGGCTATTC |
| GTCAAGAGAAAGAGATTAAAGGGATACAGCTCGGGAAGGAAGAGG |
| TCAAGCTTTCCTTGTTCGCCGATGATATGATTGTGTACCTGGAGA |
| ATCCTATTGTGTCTGCTCAGAACCTTCTTAAACTTATTTCTAACT |
| TTAGCAAGGTCAGCGGCTATAAGATTAACGTCCAGAAATCTCAGG |
| CCTTTCTGTACACAAATAATCGACAGACCGAATCCCAGATAATGG |
| GTGAGCTTCCGTTTGTCATAGCCAGCAAAAGGATAAAGTATCTCG |
| GAATCCAGCTGACACGAGACGTTAAAGATTTGTTTAAGGAAAATT |
| ACAAGCCTCTCCTGAAAGAGATTAAGGAAGATACTAATAAGTGGA |
| AGAATATCCCCTGTTCATGGGTTGGCAGAATCAACATAGTGAAGA |
| TGGCAATACTTCCTAAAGTGATATATCGCTTTAACGCCATCCCAA |
| TTAAACTGCCTATGACCTTCTTTACGGAGCTCGAGAAAACAACCC |
| TTAAATTTATATGGAATCAAAAGAGAGCAAGAATAGCGAAGTCCA |
| TCTTGAGCCAGAAGAATAAGGCCGGTGGGATTACTTTGCCTGATT |
| TTAAGTTGTATTATAAAGCCACAGTAACTAAGACAGCCTGGTATT |
| GGTATCAGAATAGAGACATCGACCAGTGGATCGGACCGAACCAT |
| CAGAGATAATGCCCCACATCTATAATTACCTTATATTCGATAAGC |
| CAGAAAAGAATAAACAGTGGGGCAAAGACAGCCTCTTCAACAAGT |
| GGTGTTGGGAGAATTGGCTGGCCATATGCCGGAAACTCAAGCTCG |
| ACCCCTTTCTTACACCCTACACTAAAATCAACAGTAGGTGGATCA |
| AGGACTTGAATGTCAAGCCAAAGACTATAAAGACACTGGAAGAGA |
| ATCTTGGGATCACAATACAAGATATAGGCGTCGCAAAGATTTTA |
| TGTCAAAGACGCCCAAGGCCATGGCCACTAAGGATAAGATTGATA |
| AGTGGGACCTTATTAAGCTCAAAAGCTTCTGTACTGCCAAGGAGA |
| CCACGATCAGAGTTAATAGGCAGCCCACTACATGGGAAAAGATTT |
| TCGCCACTTATTCATCAGATAAGGGGTTGATAAGCAGAATATATA |
| ACGAGCTGAAGCAGATCTACAAGAAGAAAACGAATAATCCCATCA |
| AGAAGTGGGCAAAAGATATGAACAGGCATTTTAGCAAAGAGGATA |
| TCTACGCCGCGAAGAAGCATATGAAGAAGTGTAGTTCAAGCTTGG |
| CCATTCGTGAGATGCAGATTAAGACGACCATGCGATACCACCTTA |
| CCCCAGTGAGGATGGCAATTATCAAGAAATCTGGCAATAATAGAT |
| GTTGGCGGGGCTGTGGCGAGATTGGCACCCTGCTCCATTGCTGGT |
| GGGATTGCAAGCTGGTGCAGCCGCTTTGGAAATCAGTCTGGCGCT |
| TTCTGAGGGACCTCGAGCTTGAGATTCCCTTCGATCCCGCAATTC |
| CCTTGCTCGGAATCTATCCTAACGAATACAAGAGCTGTTGTTACA |
| AGGATACGTGTACCCGGATGTTCATCGCGGCCTTGTTTACGATAG |
| CTAAGACGTGGAATCAGCCTAAGTGCCCCACAATGATCGATTGGA |
| TCAAGAAAATGTGGCATATTTATACCATGGAGTATTACGCAGCAA |
| TTAAGAATGACGAATTATTTCCTTCGTTGGGACCTGGATGAAGC |
| TGGAGACTATTATTCTGAGCAAGCTGTCTCAGGAGCAAAAGACAA |
| AGCATAGAATCTTCTCTCTCATTGGTGGTAACGACTACAAAGACG |
| ATGACGACAAGTAAAGCGCTTCTAGAAGTTGTCTCCTCCTGCACT |
| GACTGACTGATACAATCGATTTCTGGATCCGCAGGCCTAATCAAC |
| CTCTGGATTACAAAATTTGTGAAAGATTGACTGGTATTCTTAACT |
| ATGTTGCTCCTTTTACGCTATGTGGATACGCTGCTTTAATGCCTT |
| TGTATCATGCTATTGCTTCCCGTATGGCTTTCATTTTCTCCTCCT |
| TGTATAAATCCTGGTTGCTGTCTCTTTATGAGGAGTTGTGGCCCG |
| TTGTCAGGCAACGTGGCGTGGTGTGCACTGTGTTTGCTGACGCAA |
| CCCCCACTGGTTGGGGCATTGCCACCACCTGTCAGCTCCTTTCCG |
| GGACTTTCGCTTTCCCCCTCCCTATTGCCACGGCGGAACTCATCG |
| CCGCCTGCCTTGCCCGCTGCTGGACAGGGGCTCGGCTGTTGGGCA |
| CTGACAATTCCGTGGTGTTGTCGGGGAAGCTGACGTCCTTTCCAT |
| GGCTGCTCGCCTGTGTTGCCACCTGGATTCTGCGCGGGACGTCCT |
| TCTGCTACGTCCCTTCGGCCCTCAATCCAGCGGACCTTCCTTCCC |
| GCGAACAAACGACCCAACACCCGTGCGTTTTATTCTGTCTTTTTA |
| TTGCCGATCCCCTCAGAAGAACTCGTCAAGAAGGCGATAGAAGGC |
| GATGCGCTGCGAATCGGGAGCGGCGATACCGTAAAGCACGAGGAA |
| GCGGTCAGCCCATTCGCCGCCAAGCTCTTCAGCAATATCACGGGT |
| AGCCAACGCTATGTCCTGATAGCGGTCGGCCGCTTTACTTGTACA |
| GCTCGTCCATGCCGAGAGTGATCCCGGCGGCGGTCACGAACTCCA |
| GCAGGACCATGTGATCGCGCTTCTCGTTGGGGTCTTTGCTCAGGG |
| CGGACTGGGTGCTCAGGTAGTGGTTGTCGGGCAGCAGCACGGGGC |
| CGTCGCCGATGGGGGTGTTCTGCTGGTAGTGGTCGGCCAGGTGAG |
| TCCAGGAGATGTTTCAGCACTGTTGCCTTTAGTCTCGAGGCAACT |
| TAGACAACTGAGTATTGATCTGAGCACAGCAGGGTGTGAGCTGTT |
| TGAAGATACTGGGGTTGGGGGTGAAGAAACTGCAGAGGACTAACT |
| GGGCTGAGACCCAGTGGCAATGTTTTAGGGCCTAAGGAATGCCTC |
| TGAAAATCTAGATGGACAACTTTGACTTTGAGAAAAGAGAGGTGG |
| AAATGAGGAAAATGACTTTTCTTTATTAGATTTCGGTAGAAAGAA |
| CTTTCATCTTTCCCCTATTTTTGTTATTCGTTTTAAAACATCTAT |
| CTGGAGGCAGGACAAGTATGGTCATTAAAAAGATGCAGGCAGAAG |

TABLE 8-continued

| Plasmid and mRNA construct sequences |
| --- |
| GCATATATTGGCTCAGTCAAAGTGGGGAACTTTGGTGGCCAAACA |
| TACATTGCTAAGGCTATTCCTATATCAGCTGGACACATATAAAAT |
| GCTGCTAATGCTTCATTACAAACTTATATCCTTTAATTCCAGATG |
| GGGGCAAAGTATGTCCAGGGGTGAGGAACAATTGAAACATTTGGG |
| CTGGAGTAGATTTTGAAAGTCAGCTCTGTGTGTGTGTGTGTGTGT |
| GTGTGTGTGAGAGCGTGTGTTTCTTTTAACGTTTTCAGCCTACAG |
| CATACAGGGTTCATGGTGGCAAGAAGATAACAAGATTTAAATTAT |
| GGCCAGTGACTAGTGCTGCAAGAAGAACAACTACCTGCATTTAAT |
| GGGAAAGCAAAATCTCAGGCTTTGAGGGAAGTTAACATAGGCTTG |
| ATTCTGGGTGGAAGCTGGGTGTGTAGTTATCTGGAGGCCAGGCTG |
| GAGCTCTCAGCTCACTATGGGTTCATCTTTATTGTCTCCTTTCAT |
| CTCAACAGCTGCACGCTGCCGTCCTCGATGTTGTGGCGGATCTTG |
| AAGTTCACCTTGATGCCGTTCTTCTGCTTGTCGGCCATGATATAG |
| ACGTTGTGGCTGTTGTAGTTGTACTCCAGCTTGTGCCCCAGGATG |
| TTGCCGTCCTCCTTGAAGTCGATGCCCTTCAGCTCGATGCGGTTC |
| ACCAGGGTGTCGCCCTCGAACTTCACCTCGGCGCGGGTCTTGTAG |
| TTGCCGTCGTCCTTGAAGAAGATGGTGCGCTCCTGGACGTAGCCT |
| TCGGGCATGGCGGACTTGAAGAAGTCGTGCTGCTTCATGTGGTCG |
| GGGTAGCGGCTGAAGCACTGCACGCCGTAGGTCAGGGTGGTCACG |
| AGGGTGGGCCAGGGCACGGGCAGCTTGCCGGTGGTGCAGATGAAC |
| TTCAGGGTCAGCTTGCCGTAGGTGGCATCGCCCTCGCCCTCGCCG |
| GACACGCTGAACTTGTGGCCGTTTACGTCGCCGTCCAGCTCGACC |
| AGGATGGGCACCACCCCGGTGAACAGCTCCTCGCCCTTGCTCACC |
| ATGGTGGCGAATTCGAAGCTTGAGCACGAGATCTGAGTCCGGTAG |
| GCCTAGCGGATCTGACGGTTCACTAAACCAGCTCTGCTTATATAG |
| ACCTCCCACCGTACACGCCTACCGCCCATTTGCGTCAATGGGGCG |
| GAGTTGTTACGACATTTTGGAAAGTCCCGTTGATTTTGGTGCCAA |
| AACAAACTCCCATTGACGTCAATGGGGTGGAGACTTGGAAATCCC |
| CGTGAGTCAAACCGCTATCCACGCCCATTGATGTACTGCCAAAAC |
| CGCATCACCATGGTAATAGCGATGACTAATACGTAGATGTACTGC |
| CAAGTAGGAAAGTCCCATAAGGTCATGTACTGGGCATAATGCCAG |
| GCGGGCCATTTACCGTCATTGACGTCAATAGGGGGCGTACTTGGC |
| ATATGATACACTTGATGTACTGCCAAGTGGGCAGTTTACCGTAAA |
| TACTCCACCCATTGACGTCAATGGAAAGTCCCTATTGGCGTTACT |
| ATGGGAACATACGTCATTATTGACGTCAATGGGCGGGGGTCGTTG |
| GGCGGTCAGCCAGGCGGGCCATTTACCGTAAGTTATGTAACGGGC |
| CTGCTGCCGGCTCTGCGGCCTCTTCCGCGTCTTCGCCTTCGCCCT |
| CAGACGAGTCGGATCTCCCTTTGGGCCGCCTCCCCGCCTGTCTAG |
| CTTGACTGACTGAGATACAGCGTACCTTCAGCTCACAGACATGAT |
| AAGATACATTGATGAGTTTGGACAAACCACAACTAGAATGCAGTG |
| AAAAAAATGCTTTATTTGTGAAATTTGTGATGCTATTGCTTTATT |
| TGTAACCATTATAAGCTGCAATAAACAAGTTAACAACAACAATTG |
| CATTCATTTTATGTTTCAGGTTCAGGGGGAGGTGTGGGAGGTTTT |
| TTAAAGCAAGTAAAACCTCTACAAATGTGGTATTGGCCCATCTCT |
| ATCGGTATCGTAGCATAACCCCTTGGGGCCTCTAAACGGGTCTTG |
| AGGGGTTTTTTGTGCCCCTCGGGCCGGATTGCTATCTACCGGCAT |
| TGGCGCAGAAAAAAATGCCTGATGCGACGCTGCGCGTCTTATACT |
| CCCACATATGCCAGATTCAGCAACGGATACGGCTTCCCCAACTTG |
| CCCACTTCCATACGTGTCCTCCTTACCAGAAATTTATCCTTAAGG |
| TCGTCAGCTATCCTGCAGGCGATCTCTCGATTTCGATCAAGACAT |
| TCCTTTAATGGTCTTTTCTGGACACCACTAGGGGTCAGAAGTAGT |
| TCATCAAACTTTCTTCCCTCCCTAATCTCATTGGTTACCTTGGGC |
| TATCGAAACTTAATTAAGCGATCTGCATCTCAATTAGTCAGCAAC |
| CATAGTCCCGCCCCTAACTCCGCCCATCCCGCCCCTAACTCCGCC |
| CAGTTCCGCCCATTCTCCGCCCCATCGCTGACTAATTTTTTTTAT |
| TTATGCAGAGGCCGAGGCCGCCTCGGCCTCTGAGCTATTCCAGAA |
| GTAGTGAGGAGGCTTTTTTGGAGGCCTAGGCTTTTGCAAAGGAGG |
| TAGCCAACATGATTGAACAAGATGGATTGCACGCAGGTTCTCCCG |
| CCGCTTGGGTGGAGAGGCTATTCGGCTATGACTGGGCACAACAGA |
| CAATCGGCTGCTCTGATGCCGCCGTGTTCCGGCTGTCAGCGCAGG |
| GGCGCCCGGTTCTTTTTGTCAAGACCGACCTGTCCGGTGCCCTGA |
| ATGAACTCCAGGACGAGGCAGCGCGGCTATCGTGGCTGGCCACGA |
| CGGGCGTTCCTTGCGCAGCTGTGCTCGACGTTGTCACTGAAGCGG |
| GAAGGGACTGGCTGCTATTGGGCGAAGTGCCGGGGCAGGATCTCC |
| TGTCATCTCACCTTGCTCCTGCCGAGAAAGTATCCATCATGGCTG |
| ATGCAATGCGGCGGCTGCATACGCTTGATCCGGCTACCTGCCCAT |
| TCGACCACCAAGCGAAACATCGCATCGAGCGAGCACGTACTCGGA |
| TGGAAGCCGGTCTTGTCGATCAGGATGATCTGGACGAAGAGCATC |
| AGGGGCTCGCGCCAGCCGAACTGTTCGCCAGGCTCAAGGCGCGGA |
| TGCCCGACGGCGAGGATCTCGTCGTGACCCACGGCGATGCCTGCT |
| TGCCGAATATCATGGTGGAAAATGGCCGCTTTTCTGGATTCATCG |
| ACTGTGGCCGGCTGGGTGTGGCGGACCGCTATCAGGACATAGCGT |
| TGGCTACCCGTGATATTGCTGAAGAGCTTGGCGGCGAATGGGCTG |
| ACCGCTTCCTCGTGCTTTACGGTATCGCCGCTCCCGATTCGCAGC |
| GCATCGCCTTCTATCGCCTTCTTGACGAGTTCTTCTAGTATGTAA |
| GCCCTGTGCCTTCTAGTTGCCAGCCATCTGTTGTTTGCCCCTCCC |
| CCGTGCCTTCCTTGACCCTGGAAGGTGCCACTCCCACTGTCCTTT |
| CCTAATAAAATGAGGAAATTGCATCGCATTGTCTGAGTAGGTGTC |

TABLE 8-continued

Plasmid and mRNA construct sequences

ATTCTATTCTGGGGGGTGGGGTGGGGCAGGACAGCAAGGGGGAGG
ATTGGGAAGACAATAGCAGGCATGCTGGGGATGCGGTGGGCTCTA
TGGTTAATTAACCAGTCAAGTCAGCTACTTGGCGAGATCGACTTG
TCTGGGTTTCGACTACGCTCAGAATTGCGTCAGTCAAGTTCGATC
TGGTCCTTGCTATTGCACCCGTTCTCCGATTACGAGTTTCATTTA
AATCATGTGAGCAAAAGGCCAGCAAAAGGCCAGGAACCGTAAAAA
GGCCGCGTTGCTGGCGTTTTTCCATAGGCTCCGCCCCCCTGACGA
GCATCACAAAAATCGACGCTCAAGTCAGAGGTGGCGAAACCCGAC
AGGACTATAAAGATACCAGGCGTTTCCCCCTGGAAGCTCCCTCGT
GCGCTCTCCTGTTCCGACCCTGCCGCTTACCGGATACCTGTCCGC
CTTTCTCCCTTCGGGAAGCGTGGCGCTTTCTCATAGCTCACGCTG
TAGGTATCTCAGTTCGGTGTAGGTCGTTCGCTCCAAGCTGGGCTG
TGTGCACGAACCCCCCGTTCAGCCCGACCGCTGCGCCTTATCCGG
TAACTATCGTCTTGAGTCCAACCCGGTAAGACACGACTTATCGCC
ACTGGCAGCAGCCACTGGTAACAGGATTAGCAGAGCGAGGTATGT
AGGCGGTGCTACAGAGTTCTTGAAGTGGTGGCCTAACTACGGCTA
CACTAGAAGAACAGTATTTGGTATCTGCGCTCTGCTGAAGCCAGT
TACCTTCGGAAAAAGAGTTGGTAGCTCTTGATCCGGCAAACAAAC
CACCGCTGGTAGCGGTGGTTTTTTTGTTTGCAAGCAGCAGATTAC
GCGCAGAAAAAAAGGATCTCAAGAAGATCCTTTGATCTTTTCTAC
GGGGTCTGACGCTCAGTGGAACGAAAACTCACGTTAAGGGATTTT
GGTCATGAGATTATCAAAAAGGATCTTCACCTAGATCCTTTTAAA
TTAAAAATGAAGTTTTAAATCAATCTAAAGTATATATGAGTAAAC
TTGGTCTGACAGTTACCAATGCTTAATCAGTGAGGCACCTATCTC
AGCGATCTGTCTATTTCGTTCATCCATAGTTGCATTTAAATTTCC
GAACTCTCCAAGGCCCTCGTCGGAAAATCTTCAAACCTTTCGTCC
GATCCATCTTGCAGGCTACCTCTCGAACGAACTATCGCAAGTCTC
TTGGCCGGCCTTGCGCCTTGGCTATTGCTTGGCAGCGCCTATCGC
CAGGTATTACTCCAATCCCGAATATCCGAGATCGGGATCACCCGA
GAGAAGTTCAACCTACATCCTCAATCCCGATCTATCCGAGATCCG
AGGAATATCGAAATCGGGGCGCGCCTGGTGTACCGAGAACGATCC
TCTCAGTGCGAGTCTCGACGATCCATATCGTTGCTTGGCAGTCAG
CCAGTCGGAATCCAGCTTGGGACCCAGGAAGTCCAATCGTCAGAT
ATTGTACTCAAGCCTGGTCACGGCAGCGTACCGATCTGTTTAAAC
CTAGATATTGATAGTCTGATCGGTCAACGTATAATCGAGTCCTAG
CTTTTGCAAACATCTATCAAGAGACAGGATCAGCAGGAGGCTTTC
GCATGAGTATTCAACATTTCCGTGTCGCCCTTATTCCCTTTTTTG
CGGCATTTTGCCTTCCTGTTTTTGCTCACCCAGAAACGCTGGTGA
AAGTAAAAGATGCTGAAGATCAGTTGGGTGCGCGAGTGGGTTACA
TCGAACTGGATCTCAACAGCGGTAAGATCCTTGAGAGTTTTCGCC
CCGAAGAACGCTTTCCAATGATGAGCACTTTTAAAGTTCTGCTAT
GTGGCGCGGTATTATCCCGTATTGACGCCGGGCAAGAGCAACTCG
GTCGCCGCATACACTATTCTCAGAATGACTTGGTTGAGTATTCAC
CAGTCACAGAAAAGCATCTTACGGATGGCATGACAGTAAGAGAAT
TATGCAGTGCTGCCATAACCATGAGTGATAACACTGCGGCCAACT
TACTTCTGACAACGATTGGAGGACCGAAGGAGCTAACCGCTTTTT
TGCACAACATGGGGGATCATGTAACTCGCCTTGATCGTTGGGAAC
CGGAGCTGAATGAAGCCATACCAAACGACGAGCGTGACACCACGA
TGCCTGTAGCAATGGCAACAACCTTGCGTAAACTATTAACTGGCG
AACTACTTACTCTAGCTTCCCGGCAACAGTTGATAGACTGGATGG
AGGCGGATAAAGTTGCAGGACCACTTCTGCGCTCGGCCCTTCCGG
CTGGCTGGTTTATTGCTGATAAATCTGGAGCCGGTGAGCGTGGGT
CTCGCGGTATCATTGCAGCACTGGGGCCAGATGGTAAGCCCTCCC
GTATCGTAGTTATCTACACGACGGGGAGTCAGGCAACTATGGATG
AACGAAATAGACAGATCGCTGAGATAGGTGCCTCACTGATTAAGC
ATTGGTAACCGATTCTAGGTGCATTGGCGCAGAAAAAAATGCCTG
ATGCGACGCTGCGCGTCTTATACTCCCACATATGCCAGATTCAGC
AACGGATACGGCTTCCCCAACTTGCCCACTTCCATACGTGTCCTC
CTTACCAGAAATTTATCCTTAAGATCGTTTAAACTCGACTCTGGC
TCTATCGAATCTCCGTCGTTTCGAGCTTACGCGAACAGCCGTGGC
GCTCATTTGCTCGTCGGGCATCGAATCTCGTCAGCTATCGTCAGC
TTACCTTTTTGGCAGCGATCGCGGCTCCCGACATCTTGGACCATT
AGCTCCACAGGTATCTTCTTCCCTCTAGTGGTCATAACAGCAGCT
TCAGCTACCTCTCAATTCAAAAAACCCCTCAAGACCCGTTTAGAG
GCCCCAAGGGGTTATGCTATCAATCGTTGCGTTACACACACAAAA
AACCAACACACATCCATCTTCGATGGATAGCGATTTTATTATCTA
ACTGCTGATCGAGTGTAGCCAGATCTAGTAATCAATTACGGGGTC
ATTAGTTCATAGCCCATATATGGAGTTCCGCGTTACATAACTTAC
GGTAAATGGCCCGCCTGGCTGACCGCCCAACGACCCCCGCCCATT
GACGTCAATAATGACGTATGTTCCCATAGTAACGCCAATAGGGAC
TTTCCATTGACGTCAATGGGTGGAGTATTTACGGTAAACTGCCCA
CTTGGCAGTACATCAAGTGTATCATATGCCAAGTACGCCCCCTAT
TGACGTCAATGACGGTAAATGGCCCGCCTGGCATTATGCCCAGTA
CATGACCTTATGGGACTTTCCTACTTGGCAGTACATCTACGTATT
AGTCATCGCTATTACCATGCTGATGCGGTTTTGGCAGTACATCAA
TGGGCGTGGATAGCGGTTTGACTCACGGGGATTTCCAAGTCTCCA
CCCCATTGACGTCAATGGGAGTTTGTTTTGGCACCAAAATCAACG
GGACTTTCCAAAATGTCGTAACAACTCCGCCCCATTGACGCAAAT

TABLE 8-continued

Plasmid and mRNA construct sequences

GGGCGGTAGGCGTGTACGGTGGGAGGTCTATATAAGCAGAGCTGG
TTTAGTGAACCGTCAGATCAGATCTTTGTCGATCCTACCATCCAC
TCGACACACCCGCCAGCGGCCGC
(SEQ ID NO: 48)

LINE-1 ORF2-MCP MS2 mRNA (SEQ ID NO: 49)
TAATACGACTCACTATAGGGAGAAGTACTGCCACCATGGGCAAGA
AGCAAAATCGCAAGACGGGGAATTCCAAGACACAATCCGCTAGCC
CACCACCTAAAGAGCGTTCTAGCTCCCCTGCTACTGAGCAGTCCT
GGATGGAAAACGACTTCGATGAACTCCGGGAAGAGGGATTTAGGC
GATCCAACTATTCAGAACTCCGCGAAGATATCCAGACAAAGGGGA
AGGAAGTCGAGAATTTCGAGAAGAACCTCGAGGAGTGCATCACCC
GTATCACAAACACTGAGAAATGTCTCAAAGAACTCATGGAACTTA
AGACAAAAGCCAGGGAGCTTCGAGAGGAGTGTCGGAGTCTGAGAT
CCAGGTGTGACCAGCTCGAGGAGCGCGTGAGCGCGATGGAAGACG
AGATGAACGAGATGAAAAGAGAGGGCAAATTCAGGGAGAAGCGCA
TTAAGAGGAACGAACAGAGTCTGCAGGAGATTTGGGATTACGTCA
AGAGGCCTAACCTGCGGTTGATCGGCGTCCCCGAGAGCGACGTAG
AAAACGGGACTAAACTGGAGAATACACTTCAAGACATCATTCAAG
AAAATTTTCCAAACCTGGCTCGGCAAGCTAATGTGCAAATCCAAG
AGATCCAACGCACACCCCAGCGGTATAGCTCTCGGCGTGCCACCC
CTAGGCATATTATCGTGCGCTTTACTAAGGTGGAGATGAAAGAGA
AGATGCTGCGAGCCGCTCGGGAAAAGGGAAGGGTGACTTTGAAGG
GCAAACCTATTCGGCTGACGGTTGACCTTAGCGCCGAGACACTCC
AGGCACGCCGGGAATGGGGCCCCATCTTTAATATCCTGAAGGAGA
AGAACTTCCAGCCACGAATCTCTTACCCTGCAAAGTTGAGTTTTA
TCTCCGAGGGTGAGATTAAGTATTTCATCGATAAACAGATGCTGC
GAGACTTCGTGACAACTCGCCCAGCTCTCAAGGAACTGCTCAAAG
AGGCTCTTAATATGGAGCGCAATAATAGATATCAACCCTTGCAGA
ACCACGCAAAGATGTGAGACAGCCGTCAGACCATCAAGACTAGGA
AGAAACTGCATCAACTAATGAGCAAAATCACCAGCTAACATCATA
GTATACATGACCGGCTCTAACTCACATATCACCATCCTTACACTT
AACATTAACGGCCTCAACTCAGCTATCAAGCGCCATCGGCTGGCC
AGCTGGATCAAATCACAGGATCCAAGCGTTTGTTGCATCCAAGAG
ACCCACCTGACCTGTAGAGATACTCACCGCCTCAAGATCAAGGGA
TGGCGAAAGATTTATCAGGCGAACGGTAAGCAGAAGAAAGCCGGA
GTCGCAATTCTGGTCTCAGACAAGACGGATTTCAAGCCCACCAAA
ATTAAGCGTGATAAGGAAGGTCACTATATTATGGTGAAAGGCAGC
ATACAGCAGGAAGAACTTACCATATTGAACATCTACGCGCCAAAC
ACCGGCGCACCTCGCTTTATCAAACAGGTCCTGTCCGATCTGCAG
CGAGATCTGGATTCTCATACGTTGATTATGGGTGATTTCAATACA
CCATTGAGCACCCTGGATCGCAGCACCAGGCAAAAGGTAAATAAA
GACACGCAAGAGCTCAATAGCGCACTGCATCAGGCAGATCTCATT
GATATTTATCGCACTCTTCATCCTAAGAGTACCGAGTACACATTC
TTCAGCGCCCCACATCATACATACTCAAAGATCGATCATATCGTC
GGCTCAAAGGCTCTGCTGTCAAAGTGCAAGCGCACAGAGATAATT
ACAAATTACCTGTCAGATCATAGCGCGATCAAGCTCGAGCTGAGA
ATCAAGAACCTGACCCAGAGCCGGAGTACCACTTGGAAGCTTAAT
AACCTGCTGCTCAACGATTATTGGGTCCACAATGAGATGAAGGCA
GAGATTAAAATGTTCTTCGAAACAAATGAGAATAAGGATACTACC
TATCAAAACCTTTGGGATGCCTTTAAGGCCGTCTGCAGAGGCAAG
TTCATCGCCCTCAACGCCTATAAAAGAAAACAAGAGAGATCTAAG
ATCGATACTCTCACCTCTCAGCTGAAGGAGTTGGAGAAACAGGAA
CAGACCCACTCCAAGGCGTCAAGACGGCAGGAGATCACAAAGATT
CGCGCCGAGTTGAAAGAGATCGAAACCCAAAAGACTCTTCAGAAA
ATTAACGAGTCTCGTAGTTGGTTCTTCGAGCGGATTAATAAGATA
GACAGACCTCTGGCACGACTGATTAAGAAGAAGCGCGAAAAGAAC
CAGATTGATACCATCAAGAACGACAAGGGCGACATCACTACTGAC
CCGACCGAGATCCAGACCACTATTCGGGAGTATTATAAGCATTTG
TATGCTAACAAGCTTGAGAACCTGGAAGAGATGGACACTTTTCTG
GATACCTATACTCTGCCACGGCTTAATCAAGAGGAAGTCGAGTCC
CTCAACCGCCCAATTACAGGAAGCGAGATTGTGGCCATAATTAAC
TCCCTGCCGACAAAGAAATCTCCTGGTCCGGACGGGTTTACAGCT
GAGTTTTATCAACGGTATATGGAAGAGCTTGTACCGTTTCTGCTC
AAGCTCTTTCAGTCTATAGAAAAGGAAGGCATCTTGCCCAATTCC
TTCTACGAAGCTTCTATAATACTTATTCCCAAACCAGGACGCGAT
ACCACAAAGAAGGAAAACTTCCGGCCCATTAGTCTCATGAATATC
GACGCTAAAATATTGAACAAGATTCTCGCCAACAGAATCCAACAA
CATATTAAGAAATTGATACATCACGACCAGGTGGGGTTTATACCT
GGCATGCAGGGCTGGTTTAACATCCGGAAGAGTATTAACGTCATT
CAACACATTAATAGAGCTAAGGATAAGAATCATATGATCATCTCT
ATAGACGCGGAAAAGGCATTCGATAAGATTCAGCAGCCATTTATG
CTCAAGACTCTGAACAAACTCGGCATCGACGGAACATATTTTAAG
ATTATTCGCGCAATTTACGATAAGCCGACTGCTAACATTATCCTT
AACGGCCAAAAGCTCGAGGCCTTTCCGCTCAAGACTGGAACCCGC
CAAGGCTGTCCCCTCTCCCCGCTTTTGTTTAATATTGTACTCGAG
GTGCTGGCTAGGGCTATTCGTCAAGAGAAAGAGATTAAAGGGATA
CAGCTCGGGAAGGAAGAGGTCAAGCTTTCCTTGTTCGCCGATGAT

TABLE 8-continued

| Plasmid and mRNA construct sequences |
|---|
| ATGATTGTGTACCTGGAGAATCCTATTGTGTCTGCTCAGAACCTT<br>CTTAAACTTATTTCTAACTTTAGCAAGGTCAGCGGCTATAAGATT<br>AACGTCCAGAAATCTCAGGCCTTTCTGTACACAAATAATCGACAG<br>ACCGAATCCCAGATAATGGGTGAGCTTCCGTTTGTCATAGCCAGC<br>AAAAGGATAAAGTATCTCGGAATCCAGCTGACACGAGACGTTAAA<br>GATTTGTTTAAGGAAAATTACAAGCCTCTCCTGAAAGAGATTAAG<br>GAAGATACTAATAAGTGGAAGAATATCCCCTGTTCATGGGTTGGC<br>AGAATCAACATAGTGAAGATGGCAATACTTCCTAAAGTGATATAT<br>CGCTTTAACGCCATCCCAATTAAACTGCCTATGACCTTCTTTACG<br>GAGCTCGAGAAAACAACCCTTAAATTTATATGGAATCAAAAGAGA<br>GCAAGAATAGCGAAGTCCATCTTGAGCCAGAAGAATAAGGCCGGT<br>GGGATTACTTTGCCTGATTTTAAGTTGTATTATAAAGCCACAGTA<br>ACTAAGACAGCCTGGTATTGGTATCAGAATAGAGACATCGACCAG<br>TGGAATCGGACCGAACCATCAGAGATAATGCCCCACATCTATAAT<br>TACCTTATATTCGATAAGCCAGAAAAGAATAAACAGTGGGGCAAA<br>GACAGCCTCTTCAACAAGTGGTGTTGGGAGAATTGGCTGGCCATA<br>TGCCGGAAACTCAAGCTCGACCCCTTTCTTACACCCTACACTAAA<br>ATCAACAGTAGGTGGATCAAGGACTTGAATGTCAAGCCAAAGACT<br>ATAAAGACACTGGAAGAGAATCTTGGGATCACAATACAAGATATA<br>GGCGTCGGCAAAGATTTTATGTCAAAGACGCCCAAGGCCATGGCC<br>ACTAAGGATAAGATTGATAAGTGGGACCTTATTAAGCTCAAAAGC<br>TTCTGTACTGCCAAGGAGACCACGATCAGAGTTAATAGGCAGCCC<br>ACTACATGGGAAAAGATTTTCGCCACTTATTCATCAGATAAGGGG<br>TTGATAAGCAGAATATATAACGAGCTGAAGCAGATCTACAAGAAG<br>AAAACGAATAATCCCATCAAGAAGTGGGCAAAAGATATGAACAGG<br>CATTTTAGCAAAGAGGATATCTACGCCGCGAAGAAGCATATGAAG<br>AAGTGTAGTTCAAGCTTGGCCATTCGTGAGATGCAGATTAAGACG<br>ACCATGCGATACCACCTTACCCCAGTGAGGATGGCAATTATCAAG<br>AAATCTGGCAATAATAGATGTTGGCGGGGCTGTGGCGAGATTGGC<br>ACCCTGCTCCATTGCTGGTGGGATTGCAAGCTGGTGCAGCCGCTT<br>TGGAAATCAGTCTGGCGCTTTCTGAGGGACCTCGAGCTTGAGATT<br>CCCTTCGATCCCGCAATTCCCTTGCTCGGAATCTATCCTAACGAA<br>TACAAGAGCTGTTGTTACAAGGATACGTGTACCCGGATGTTCATC<br>GCGGCCTTGTTTACGATAGCTAAGACGTGGAATCAGCCTAAGTGC<br>CCCACAATGATCGATTGGATCAAGAAAATGTGGCATATTTATACC<br>ATGGAGTATTACGCAGCAATTAAGAATGACGAATTTATTTCCTTC<br>GTTGGGACCTGGATGAAGCTGGAGACTATTATTCTGAGCAAGCTG<br>TCTCAGGAGCAAAAGACAAAGCATAGAATCTTCTCTCTCATTGGT<br>GGTAACGCTTCTAACTTTACTCAGTTCGTTCTCGTCGACAATGGC<br>GGAACTGGCGACGTGACTGTCGCCCCAAGCAACTTCGCTAACGGG<br>ATCGCTGAATGGATCAGCTCTAACTCGCGTTCACAGGCTTACAAA<br>GTAACCTGTAGCGTTCGTCAGAGCTCTGCGCAGAATCGCAAATAC<br>ACCATCAAAGTCGAGGTGCCTAAAGGCGCCTGGCGTTCGTACTTA<br>AATATGGAACTAACCATTCCAATTTTCGCCACGAATTCCGACTGC<br>GAGCTTATTGTTAAGGCAATGCAAGGTCTCCTAAAAGATGGAAAC<br>CCGATTCCCTCAGCAATCGCAGCAAACTCCGGCATCTACGCCATG<br>GCCAGCAACTTCACCCAGTTCGTGCTGGTGGACAACGGCGGCACC<br>GGCGACGTGACCGTGGCCCCCAGCAACTTCGCCAACGGCATCGCC<br>GAGTGGATCAGCAGCAACAGCAGAAGCCAGGCCTACAAGGTGACC<br>TGCAGCGTGAGACAGAGCAGCGCCCAGAACAGAAAGTACACCATC<br>AAGGTGGAGGTGCCCAAGGGCGCCTGGAGAAGCTACCTGAACATG<br>GAGCTGACCATCCCCATCTTCGCCACCAACAGCGACTGCGAGCTG<br>ATCGTGAAGGCCATGCAGGGCCTGCTGAAGGACGGCAACCCCATC<br>CCCAGCGCCATCGCCGCCAACAGCGGCATCTACGACTACAAAGAC<br>GATGACGACAAGTAAAGCAACCTACAAACGGGTGGAGGATCACCC<br>CACCCGACACTTCACAATCAAGGGGTACAATACACAGGGTGGAG<br>GAACACCCCACCCTCCAGACACATTACACAGAAATCCAATCAAAC<br>AGAAGCACCATCAGGGCTTCTGCTACCAAATTTATCTCAAAAAAC<br>TACAACAAGGAATCACCATCAGGGATTCCCTGTGCAATATACGTC<br>AAACGAGGGCCACGACGGGAGGACGATCACGCCTCCCGAATATCG<br>GCATGTCTGGCTTTCGAATTCAGTGCGTGGAGCATCAGCCCACGC<br>AGCCAATCAGAGTCGAATACAAGTCGACTTTCGCGAAGAGCATCA<br>GCCTTCGCGCCATTCTTACACAAACCACACTCTCCCCTACAGGAA<br>CAGCATCAGCGTTCCTGCCCAGTACCCAACTCAAGAAAATTTATG<br>TCCCCATGCAGCATCAGCGCATGGGCCCAAGAATACATCCCCAA<br>CAAAATCACATCCGAGCACCAACAGGGCTCGGAGTGTTGTTTCTT<br>GTCCAACTGGACAAACCCTCCATGGACCATCAGGCCATGGACTCT<br>CACCAACAAGACAAAAACTACTCTTCTCGAAGCAGCATCAGCGCT<br>TCGAAACACTCGAGCATACATTGTGCCTATTTCTTGGGTGGACGA<br>TCACGCCACCCATGCTCTCACGAATTTCAAAACACGGACAAGGAC<br>GAGCACCACCAGGGCTCGTCGTTCCACGTCCAATACGATTACTTA<br>CCTTTCGGGATCACGATCACGGATCCCGCAGCTACATCACTTCCA<br>CTCAGGACATTCAAGCATGCACGATCACGGCATGCTCCACAAGTC<br>TCAACCACAGAAACTACCAAATGGGTTCAGCACCAGCGAACCCAC<br>TCCTACCTCAAACCTCTTCCCACAAAACTGGCAAGCAGGATCACC<br>GCTTGCCCATTCCAACATACCAAATCAAAAACAATTACTGGTACA<br>GCATCAGCGTACCAGCCCACATCTCTCACTACTATCAAAAACCAA<br>ACCGTTCAGCAACAGCGAACGGTACACACGGAAAAATCAACTGGT |

TABLE 8-continued

| Plasmid and mRNA construct sequences |
|---|
| TTACAAATACGAAAGACGATCACGCTTTCGTCCAGCGCAAACTAT<br>TACGAAAAACATCCGACGGGAAGAGCAACAGCCTTCCCGCGGCGG<br>AAAACCTCACAAAAACACGACAAACGGATGCACGAACACGGCATC<br>CGCCGACAACCCACAAACTTACAACCAGGCAAACGGTGCAGGATC<br>ACCGCACCGTACATCAAACACCTCAGATCTCATGCTTCTAGAAGT<br>TGTCTCCTCCTGCACTGACTGACTGATACAATCGATTTCTGGATC<br>CGCAGGCCTAATCAACCTCTGGATTACAAAATTTGTGAAAGATTG<br>ACTGGTATTCTTAACTATGTTGCTCCTTTTACGCTATGTGGATAC<br>GCTGCTTTAATGCCTTTGTATCATGCTATTGCTTCCCGTATGGCT<br>TTCATTTTCTCCTCCTTGTATAAATCCTGGTTGCTGTCTCTTTAT<br>GAGGAGTTGTGGCCCGTTGTCAGGCAACGTGGCGTGGTGTGCACT<br>GTGTTTGCTGACGCAACCCCCACTGGTTGGGGCATTGCCACCACC<br>TGTCAGCTCCTTTCCGGGACTTTCGCTTTCCCCCTCCCTATTGCC<br>ACGGCGGAACTCATCGCCGCCTGCCTTGCCCGCTGCTGGACAGGG<br>GCTCGGCTGTTGGGCACTGACAATTCCGTGGTGTTGTCGGGGAAG<br>CTGACGTCCTTTCCATGGCTGCTCGCCTGTGTTGCCACCTGGATT<br>CTGCGCGGGACGTCCTTCTGCTACGTCCCTTCGGCCCTCAATCCA<br>GCGGACCTTCCTTCCCGCTGAGAGACACAAAAAATTCCAACACAC<br>TATTGCAATGAAAATAAATTTCCTTTATTAGCCAGAAGTCAGATG<br>CTCAAGGGGCTTCATGATGTCCCCATAATTTTTGGCAGAGGGAAA<br>AAGATCTCAGTGGTATTTGTGAGCCAGGGCATTGGCCTTCTGATA<br>GGCAGCCTGCACCTGAGGAGTGCGGCCGCTTTACTTGTACAGCTC<br>GTCCATGCCGAGAGTGATCCCGGCGGCGGTCACGAACTCCAGCAG<br>GACCATGTGATCGCGCTTCTCGTTGGGGTCTTTGCTCAGGGCGGA<br>CTGGGTGCTCAGGTAGTGGTTGTCGGGCAGCAGCACGGGGCCGTC<br>GCCGATGGGGGTGTTCTGCTGGTAGTGGTCGGCGAGCTGCACGCT<br>GCCGTCCTCGATGTTGTGGCGGATCTTGAAGTTCACCTTGATGCC<br>GTTCTTCTGCTTGTCGGCCATGATATAGACGTTGTGGCTGTTGTA<br>GTTGTACTCCAGCTTGTGCCCCAGGATGTTGCCGTCCTCCTTGAA<br>GTCGATGCCCTTCAGCTCGATGCGGTTCACCAGGGTGTCGCCCTC<br>GAACTTCACCTCGGCGCGGGTCTTGTAGTTGCCGTCGTCCTTGAA<br>GAAGATGGTGCGCTCCTGGACGTAGCCTTCGGGCATGGCGGACTT<br>GAAGAAGTCGTGCTGCTTCATGTGGTCGGGGTAGCGGCTGAAGCA<br>CTGCACGCCGTAGGTCAGGGTGGTCACGAGGGTGGGCCAGGGCAC<br>GGGCAGCTTGCCGGTGGTGCAGATGAACTTCAGGGTCAGCTTGCC<br>GTAGGTGGCATCGCCCTCGCCCTCGCCGGACACGCTGAACTTGTG<br>GCCGTTTACGTCGCCGTCCAGCTCGACCAGGATGGGCACCACCCC<br>GGTGAACAGCTCCTCGCCCTTGCTCACCATGGTGGCGGGATCTGA<br>CGGTTCACTAAACCAGCTCTGCTTATATAGACCTCCCACCGTACA<br>CGCCTACCGCCCATTTGCGTCAATGGGGCGGAGTTGTTACGACAT<br>TTTGGAAAGTCCCGTTGATTTTGGTGCCAAAACAAACTCCCATTG<br>ACGTCAATGGGGTGGAGACTTGGAAATCCCCGTGAGTCAAACCGC<br>TATCCACGCCCATTGATGTACTGCCAAAACCGCATCACCATGGTA<br>ATAGCGATGACTAATACGTAGATGTACTGCCAAGTAGGAAAGTCC<br>CATAAGGTCATGTACTGGGCATAATGCCAGGCGGGCCATTTACCG<br>TCATTGACGTCAATAGGGGGCGTACTTGGCATATGATACACTTGA<br>TGTACTGCCAAGTGGGCAGTTTACCGTAAATACTCCACCCATTGA<br>CGTCAATGGAAAGTCCCTATTGGCGTTACTATGGGAACATACGTC<br>ATTATTGACGTCAATGGGCGGGGGTCGTTGGGCGGTCAGCCAGGC<br>GGGCCATTTACCGTAAGTTATGTAACGGGCCTGCTGCCGGCTCTG<br>CGGCCTCTTCCGCGTCTTCGCCTTCGCCCTCAGACGAGTCGGATC<br>TCCCTTTGGGCCGCCTCCCCGCCTGTCTAGCTTGACTGACTGAGA<br>TACAGCGTACCTTCAGCTCACAGACATGATAAGATACATTGATGA<br>GTTTGGACAAACCACAACTAGAATGCAGTGAAAAAAATGCTTTAT<br>TTGTGAAATTTGTGATGCTATTGCTTTATTTGTAACCATTATAAG<br>CTGCAATAAACAAGTT<br>(SEQ ID NO: 49)<br><br>LINEI ORF2-minke mRNA GFP (SEQ ID NO: 50)<br>TAATACGACTCACTATAGGGAGAAGTACTGCCACCATGGGCAAGA<br>AGCAAAATCGCAAGACGGGGAATTCCAAGACACAATCCGCTAGCC<br>CACCACCTAAAGAGCGTTCTAGCTCCCCTGCTACTGAGCAGTCCT<br>GGATGGAAAACGACTTCGATGAACTCCGGGAAGAGGGATTTAGGC<br>GATCCAACTATTCAGAACTCCGCGAAGATATCCAGACAAAGGGGA<br>AGGAAGTCGAGAATTTCGAGAAGAACCTCGAGGAGTGCATCACCC<br>GTATCACAAACACTGAGAAATGTCTCAAAGAACTCATGGAACTTA<br>AGACAAAAGCCAGGGAGCTTCGAGAGGAGTGTCGGAGTCTGAGAT<br>CCAGGTGTGACCAGCTCGAGGAGCGCGTGAGCGCGATGGAAGACG<br>AGATGAACGAGATGAAAAGAGAGGGCAAATTCAGGGAGAAGCGCA<br>TTAAGAGGAACGAACAGAGTCTGCAGGAGATTTGGGATTACGTCA<br>AGAGGCCTAACCTGCGGTTGATCGGCGTCCCCGAGAGCGACGTAG<br>AAAACGGGACTAAACTGGAGAATACACTTCAAGACATCATTCAAG<br>AAAATTTTCCAAACCTGGCTCGGCAAGCTAATGTGCAAATCCAAG<br>AGATCCAACGCACACCCCAGCGGTATAGCTCTCGGCGTGCCACCC<br>CTAGGCATATTATCGTGCGCTTTACTAAGGTGGAGATGAAAGAGA<br>AGATGCTGCGAGCCGCTCGGGAAAAGGGAAGGGTGACTTTGAAGG<br>GCAAACCTATTCGGCTGACGGTTGACCTTAGCGCCGAGACACTCC<br>AGGCACGCCGGGAATGGGGCCCCATCTTTAATATCCTGAAGGAGA |

TABLE 8-continued

| Plasmid and mRNA construct sequences |
|---|
| AGAACTTCCAGCCACGAATCTCTTACCCTGCAAAGTTGAGTTTTA |
| TCTCCGAGGGTGAGATTAAGTATTTCATCGATAAACAGATGCTGC |
| GAGACTTCGTGACAACTCGCCCAGCTCTCAAGGAACTGCTCAAAG |
| AGGCTCTTAATATGGAGCGCAATAATAGATATCAACCCTTGCAGA |
| ACCACGCAAAGATGTGAGACAGCCGTCAGACCATCAAGACTAGGA |
| AGAAACTGCATCAACTAATGAGCAAAATCACCAGCTAACATCATA |
| GTATACATGGTCATAGGAACTTACATTTCGATTATTACCTTAAAC |
| GTGAATGGGTTAAATGCCCCAACCAAGAGACATCGGCTGGCTGAA |
| TGGATTCAGAAACAGGACCCCTATATTTGCTGTCTGCAGGAGACC |
| CACTTCCGTCCTCGCGACACATACAGACTGAAAGTGAGGGGCTGG |
| AAAAAGATCTTCCATGCCAATGGAAATCAAAAGAAAGCTGGAGTG |
| GCTATTCTCATCTCAGATAAAATTGACTTCAAAATAAAGAATGTT |
| ACTCGAGATAAGGAGGGACACTACATAATGATCCAGGGGTCCATC |
| CAAGAAGAGGATATAACTATTATTAATATTTATGCACCCAACATT |
| GGCGCCCCTCAGTACATCAGGCAGCTGCTTACAGCTATCAAGGAG |
| GAAATCGACAGTAACACGATTATCGTGGGGGACTTTAACACCAGC |
| CTTACTCCGATGGATAGATCATCCAAAATGAAAATAAATAAGGAA |
| ACAGAGGCTCTTAATGACACCATTGACCAGATAGATCTGATTGAT |
| ATATATAGGACATTCCATCCAAAAACTGCCGATTACACTTTCTTC |
| AGCAGTGCGCATGGAACCTTCTCCAGGATAGATCACATCTTGGGT |
| CACAAAAGTAGCCTCAGTAAGTTTAAGAAAATTGAAATCATTAGC |
| AGCATCTTTTCTGACCATAACGCTATGCGCCTGGAGATGAATCAC |
| AGGGAGAAGAACGTAAAGAAGACAAACACCTGGAGGCTGAACAAT |
| ACGCTGCTAAATAACCAAGAGATCACTGAGGAAATCAAACAGGAA |
| ATAAAAAAATACTTGGAGACAAATGACAATGAAAACACGACCACC |
| CAGAACTTGTGGGATGCAGCTAAAGCGGTTCTGAGAGGGAAGTTT |
| ATAGCTATTCAAGCCTACCTTAAGAAACAGGAAAAATCTCAAGTG |
| AACAATTTGACCTTACACCTAAAGAAACTGGAGAAGGAGGAGCAG |
| ACCAAACCCAAAGTGAGCAGGAGGAAAGAAATCATCAAGATCAGA |
| GCCGAAATCAATGAAATAGAAACTAAGAAGACAATTGCCAAGATC |
| AATAAAACTAAATCCTGGTTCTTTGAGAAGATCAACAAAATTGAT |
| AAGCCATTAGCCAGACTCATCAAGAAAAAGAGGGAGAGGACTCAG |
| ATCAATAAGATCAGAAATGAGAAAGGGGAAGTTACAACCGACACC |
| GCGGAGATTCAGAACATCCTGAGAGACTACTACAAGCAACTTTAT |
| GCCAATAAAATGGACAACCTGGAAGAAATGGACAAATTCCTGGAA |
| AGGTATAACCTTCCCCGGCTGAACCAGGAGGAGACTGAAAATATC |
| AACCGCCCAATCACAAGTAATGAGATTGAGACTGTGATTAAGAAT |
| CTTCCAACTAACAAAAGTCCCGGCCCCGATGGCTTCACAGGTGAA |
| TTCTATCAGACCTTTCGGGAGGAGTTGACACCCATCCTTCTCAAG |
| CTCTTCCAAAAAATTGCAGAGGAGGGCACACTCCCGAACTCATTC |
| TATGAGGCCACCATCACCCTGATCCCAAAGCCCGACAAGGACACT |
| ACAAAGAAAGAAAATTACCGACCAATTTCCCTGATGAATATCGAT |
| GCCAAGATCCTCAACAAAATCTTGGCAAACAGAATCCAGCAGCAC |
| ATTAAGAGGATCATACACCACGATCAGGTGGGCTTTATCCCGGGG |
| ATGCAAGGATTCTTCAATATCCGCAAATCAATCAATGTGATCCAC |
| CATATTAACAAGTTGAAGAAGAAGAACCATATGATCATCTCCATC |
| GATGCAGAGAAAGCTTTTGACAAAATTCAACACCCATTTATGATC |
| AAAACTCTCCAGAAGGTGGGCATCGAGGGGACCTACCTCAACATA |
| ATTAAGGCCATCTATGATAAGCCCACAGCCAACATCATTCTCAAT |
| GGTGAAAAGCTGAAGGCATTTCCTCTGCGGTCCGGAACGAGACAG |
| GGATGTCCTCTCTCTCCTCTTCTGTTCAACATCGTTCTGGAAGTC |
| CTAGCCACCGCTATCCGCGAGGAAAAGGAAATTAAAGGCATACAG |
| ATTGGAAAGGAAGAGGTAAAACTGTCTCTGTTTGCGGATGATATG |
| ATACTGTACATAGAGAATCCTAAAACTGCCACCCGGAAGCTGTTG |
| GAGCTAATTAATGAGTATGGTAAGGTCGCCGGTTACAAGATTAAT |
| GCTCAGAAGTCTCTTGCTTTCCTGTACACTAATGATGAAAAGTCT |
| GAACGGGAAATTATGGAGACACTCCCCTTTACCATTGCAACCAAA |
| CGTATTAAATACCTTGGCATTAACCTGCCTAAGGAGACAAAAGAC |
| CTGTATGCTGAAAACTATAAGACACTGATGAAAGAGATTAAAGAT |
| GATACCAACCGGTGGCGGGATATCCCATGTTCTTGGATTGGCAGA |
| ATCAACATTGTGAAGATGAGCATCCTGCCCAAGGCCATCTACAGA |
| TTCAATGCCATCCCTATCAAATTACCTATGGCATTTTTTACGGAG |
| CTGGAACAGATCATCTTAAAATTTGTGTGGCGCCACAAGCGGCCC |
| CGAATCGCCAAAGCGGTCTTGAGGCAGAAGAATGGCGCTGGGGGA |
| ATCCGACTCCCTGACTTCAGATTGTACTACAAAGCTACCGTCATC |
| AAGACAATCTGGTACTGGCACAAGAACAGAAACATCGATCAGTGG |
| AACAAGATCGAAAGCCCTGAGATTAACCCCCGCACCTATGGTCAA |
| CTGATCTATGACAAAGGGGGCAAGGATATACAATGGCGCAAGGAC |
| AGCCTCTTCAATAAGTGGTGCTGGGAAAACTGGACAGCCACCTGC |
| AAGCGTATGAAGCTGGAGTACTCCCTGACACCATACACAAAAATA |
| AACTCAAAGTGGATTCGAGACCTCAATATTCGGCTGGACACTATA |
| AAACTCCTGGAGGAGAACATTGGGCGTACACTCTTTGACATTAAT |
| CATAGCAAGATCTTTTTCGATCCCCCTCCTCGTGTAATGGAAATA |
| AAAACAAAAATAAACAAGTGGGATCTGATGAAACTTCAGAGCTTT |
| TGCACCGCAAAGGAGACCATAAACAAGACGAAGCGCCAACCCTCA |
| GAATGGGAGAAAATATTTGCGAATGAGTCTACGGACAAAGGCTTA |
| ATCTCCAAAATATATAAGCAGCTCATTCAGCTCAATATCAAGGAA |
| ACAAACACCCCGATCCAAAAGTGGGCAGAGGACCTAAATCGGCAT |
| TTCTCCAAGGAAGACATCCAGACGGCCACGAAGCACATGAAGCGA |
| TGCTCAACTTCCCTGATTATTCGCGAAATGCAGATCAAGACTACT |
| ATGCGCTATCACCTCACTCCTGTTCGGATGGGCATCATCCGGAAA |
| TCTACAAACAACAAGTGCTGGAGAGGGTGTGGCGAAAAGGGAACC |
| CTCTTGCATTGTTGGTGGGAGTGTAAGTTGATCCAGCCACTATGG |
| CGGACCATATGGAGGTTCCTTAAAAAACTGAAGATTGAGCTGCCA |
| TATGACCCAGCAATCCCACTGCTGGGCATATACCCGGAGAAAACC |
| GTGATTCAGAAAGACACTTGCACCCGAATGTTCATTGCAGCATTG |
| TTTACAATAGCCAGGTCATGGAAGCAGCCTAAGTGCCCCTCGACA |
| GACGAGTGGATCAAGAAGATGTGGTACATTTATACTATGGAATAT |
| TACAGCGCCATCAAACGCAACGAAATTGGGTCTTTTCTGGAGACG |
| TGGATGGATCTAGAGACTGTCATCCAGAGTGAGGTAAGTCAGAAA |
| GAGAAGAACAAATATCGTATTTTAACGCATATTTGTGGAACCTGG |
| AAGAATGGTACAGATGAGCCGGTCTGCCGAACCGAGATTGAGACC |
| CAGATGGACTACAAAGACGATGACGACAAGTGAAGCGCTTCTAGA |
| AGTTGTCTCCTCCTGCACTGACTGACTGATACAATCGATTTCTGG |
| ATCCGCAGGCCTAATCAACCTCTGGATTACAAAATTTGTGAAAGA |
| TTGACTGGTATTCTTAACTATGTTGCTCCTTTTACGCTATGTGGA |
| TACGCTGCTTTAATGCCTTTGTATCATGCTATTGCTTCCCGTATG |
| GCTTTCATTTTCTCCTCCTTGTATAAATCCTGGTTGCTGTCTCTT |
| TATGAGGAGTTGTGGCCCGTTGTCAGGCAACGTGGCGTGGTGTGC |
| ACTGTGTTTGCTGACGCAACCCCCACTGGTTGGGGCATTGCCACC |
| ACCTGTCAGCTCCTTTCCGGGACTTTCGCTTTCCCCCTCCCTATT |
| GCCACGGCGGAACTCATCGCCGCCTGCCTTGCCCGCTGCTGGACA |
| GGGGCTCGGCTGTTGGGCACTGACAATTCCGTGGTGTTGTCGGGG |
| AAGCTGACGTCCTTTCCATGGCTGCTCGCCTGTGTTGCCACCTGG |
| ATTCTGCGCGGGACGTCCTTCTGCTACGTCCCTTCGGCCCTCAAT |
| CCAGCGGACCTTCCTTCCCGCTGAGAGACACAAAAAATTCCAACA |
| CACTATTGCAATGAAAATAAATTTCCTTTATTAGCCAGAAGTCAG |
| ATGCTCAAGGGGCTTCATGATGTCCCCATAATTTTTGGCAGAGGG |
| AAAAAGATCTCAGTGGTATTTGTGAGCCAGGGCATTGGCCTTCTG |
| ATAGGCAGCCTGCACCTGAGGAGTGCGGCCGCTTTACTTGTACAG |
| CTCGTCCATGCCGAGAGTGATCCCGGCGGCGGTCACGAACTCCAG |
| CAGGACCATGTGATCGCGCTTCTCGTTGGGGTCTTTGCTCAGGGC |
| GGACTGGGTGCTCAGGTAGTGGTTGTCGGGCAGCAGCACGGGGCC |
| GTCGCCGATGGGGGTGTTCTGCTGGTAGTGGTCGGCGAGCTGCAC |
| GCTGCCGTCCTCGATGTTGTGGCGGATCTTGAAGTTCACCTTGAT |
| GCCGTTCTTCTGCTTGTCGGCCATGATATAGACGTTGTGGCTGTT |
| GTAGTTGTACTCCAGCTTGTGCCCCAGGATGTTGCCGTCCTCCTT |
| GAAGTCGATGCCCTTCAGCTCGATGCGGTTCACCAGGGTGTCGCC |
| CTCGAACTTCACCTCGGCGCGGGTCTTGTAGTTGCCGTCGTCCTT |
| GAAGAAGATGGTGCGCTCCTGGACGTAGCCTTCGGGCATGGCGGA |
| CTTGAAGAAGTCGTGCTGCTTCATGTGGTCGGGGTAGCGGCTGAA |
| GCACTGCACGCCGTAGGTCAGGGTGGTCACGAGGGTGGGCCAGGG |
| CACGGGCAGCTTGCCGGTGGTGCAGATGAACTTCAGGGTCAGCTT |
| GCCGTAGGTGGCATCGCCCTCGCCCTCGCCGGACACGCTGAACTT |
| GTGGCCGTTTACGTCGCCGTCCAGCTCGACCAGGATGGGCACCAC |
| CCCGGTGAACAGCTCCTCGCCCTTGCTCACCATGGTGGCGGGATC |
| TGACGGTTCACTAAACCAGCTCTGCTTATATAGACCTCCCACCGT |
| ACACGCCTACCGCCCATTTGCGTCAATGGGGCGGAGTTGTTACGA |
| CATTTTGGAAAGTCCCGTTGATTTTGGTGCCAAAACAAACTCCCA |
| TTGACGTCAATGGGGTGGAGACTTGGAAATCCCCGTGAGTCAAAC |
| CGCTATCCACGCCCATTGATGTACTGCCAAAACCGCATCACCATG |
| GTAATAGCGATGACTAATACGTAGATGTACTGCCAAGTAGGAAAG |
| TCCCATAAGGTCATGTACTGGGCATAATGCCAGGCGGGCCATTTA |
| CCGTCATTGACGTCAATAGGGGGCGTACTTGGCATATGATACACT |
| TGATGTACTGCCAAGTGGGCAGTTTACCGTAAATACTCCACCCAT |
| TGACGTCAATGGAAAGTCCCTATTGGCGTTACTATGGGAACATAC |
| GTCATTATTGACGTCAATGGGCGGGGGTCGTTGGGCGGTCAGCCA |
| GGCGGGCCATTTACCGTAAGTTATGTAACGGGCCTGCTGCCGGCT |
| CTGCGGCCTCTTCCGCGTCTTCGCCTTCGCCCTCAGACGAGTCGG |
| ATCTCCCTTTGGGCCGCCTCCCCGCCTGTCTAGCTTGACTGACTG |
| AGATACAGCGTACCTTCAGCTCACAGACATGATAAGATACATTGA |
| TGAGTTTGGACAAACCACAACTAGAATGCAGTGAAAAAAATGCTT |
| TATTTGTGAAATTTGTGATGCTATTGCTTTATTTGTAACCATTAT |
| AAGCTGCAATAAACAAGTT |
| (SEQ ID NO: 50) |

Example 19. Enriching Stably Retrotransposed Cells

Figure 40:
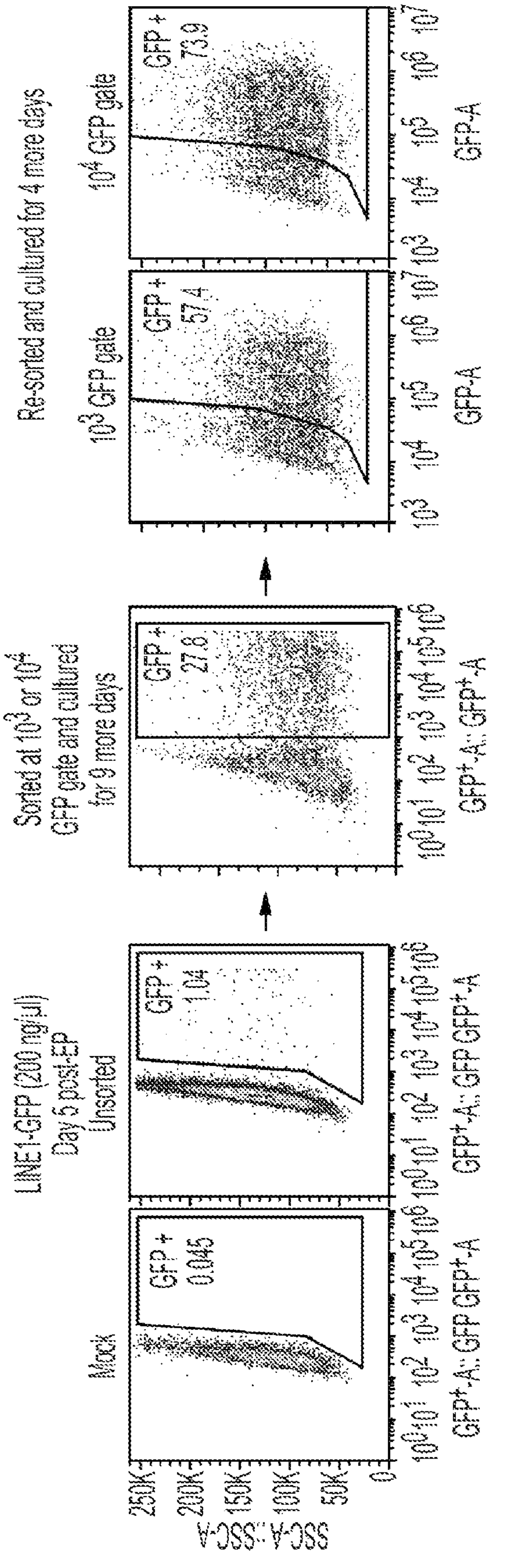
FIG. 40 depicts exemplary flow cytometry data showing sorting and enriching GFP+ 293T cells electroporated with 2000 ng/μL LINE1-GFP mRNA. The first panel shows flow cytometry data for mock electroporated cells in the absence of LINE1-GFP mRNA. The second panel shows flow cytometry data collected 5 days post electroporation for unsorted cells electroporated with LINE 1-GFP mRNA. The GFP+ cells from the second panel were sorted and the flow cytometry data are shown in the third panel. The GFP+ cells from the third panel were cultured for 9 days post sorting and resorted using 10^3 or 10^4 GFP fluorescence intensity gate. The fourth panel shows flow cytometry data for cells resorted using GFP+ at 10^3 GFP gate collected 4 days after resorting. The fifth panel shows flow cytometry data for cells resorted using GFP+ at 10^3 GFP gate collected 4 days after resorting.

In an effort to increase the cell yield having stably integrated nucleic acid sequence a method of sorting and culturing was attempted, as described in this example. 293T cells were electroporated with LINE1-GFP mRNA produced by IVT and cultured in vitro for at least 3 days. Expression of GFP was determined periodically using flow cytometry, as shown in FIG. 40. Genomic integration per genome was evaluated using quantitative PCR. Interpolations of nucleic acid encoding GFP in the genome per genome were evaluated using standard curves for GFP and a housekeeping gene (FAU). In a sorting and enrichment culture of GFP positive cells, shown in FIG. 40, it was evident that integration was stable for multiple cell passages (at least 18 days post EP), and considerable enrichment was possible. GFP expression was detectable in ~1% of 293T cells 5 days post-EP. GFP+ cells were enriched to ~28% after first sorting and was further enriched up to ~74% of cells after 2nd sorting. (FIG. 40, FIG. 41C).

Figure 41A:
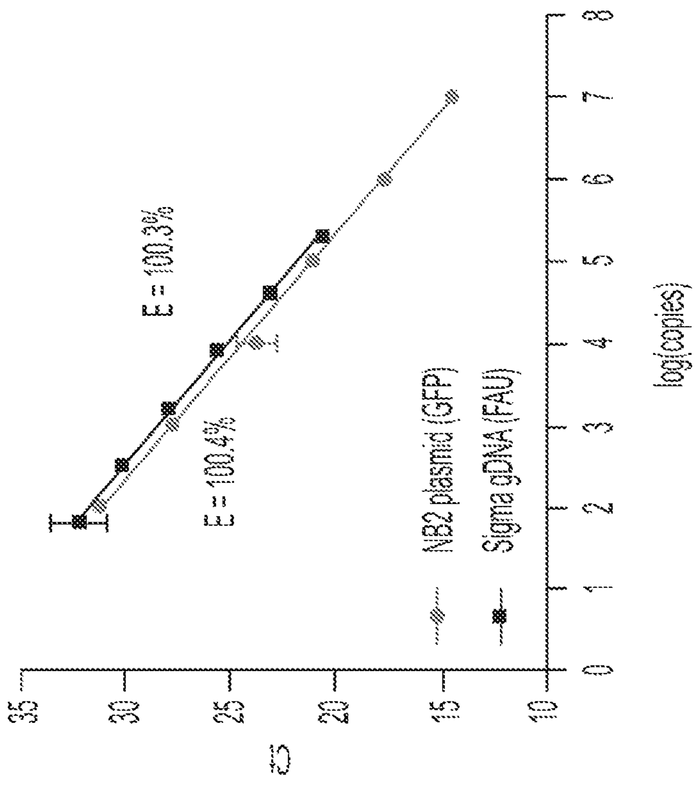
FIG. 41A shows a standard curve for GFP (NB2 plasmid) and a housekeeping gene (FAU) for evaluating genomic integration of GFP-encoding nucleic acid per cell using quantitative PCR.
Figure 41B:
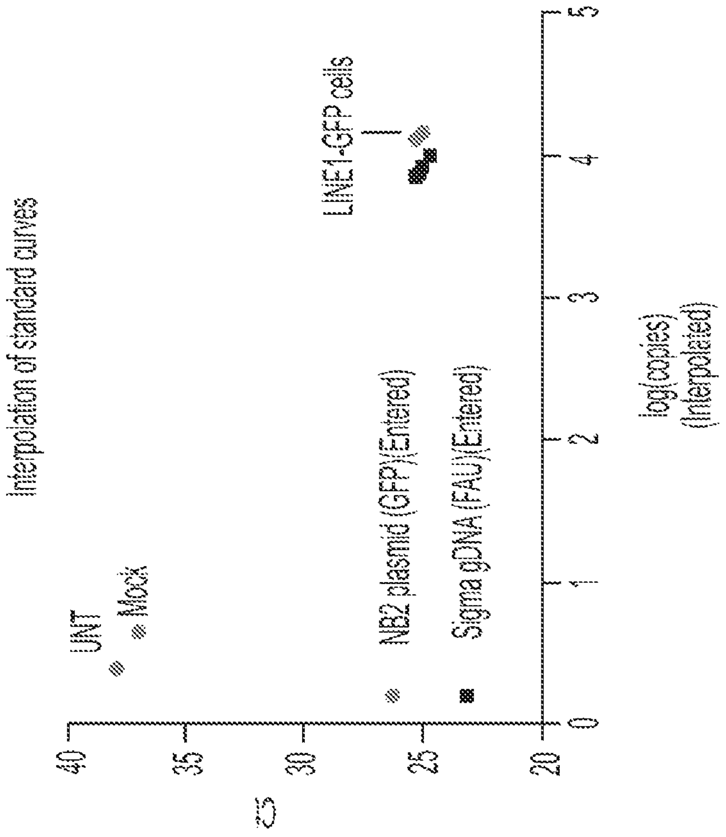
FIG. 41B shows results of an exemplary graph depicting interpolation of the standard curves of FIG. 41A for quantitation of genomic integration.
Figure 41C:
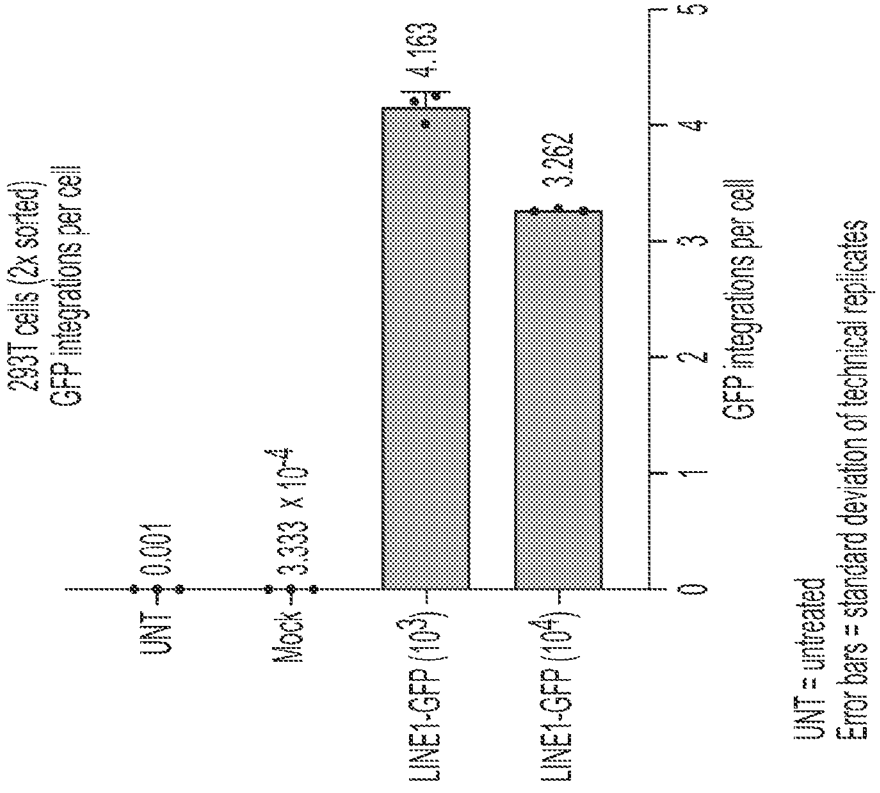
FIG. 41C shows the number of the GFP gene integrated into genome of 293T cells following LINE 1-GFP mRNA electroporation and double sorting as shown in FIG. 40. The average number of GFP integrations per cell when gated at 10^3 GFP+ cells and at 10^4 GFP+ cells according to qPCR are shown.

Standard curves and exemplary quantitation of genomic integrations are shown in FIGS. 41A and 41B respectively. FIG. 41C shows average number of GFP integrations per genome when gated at 10^3 units of GFP fluorescence intensity and at 10^4 units of GFP fluorescence intensity.

Figure 42:
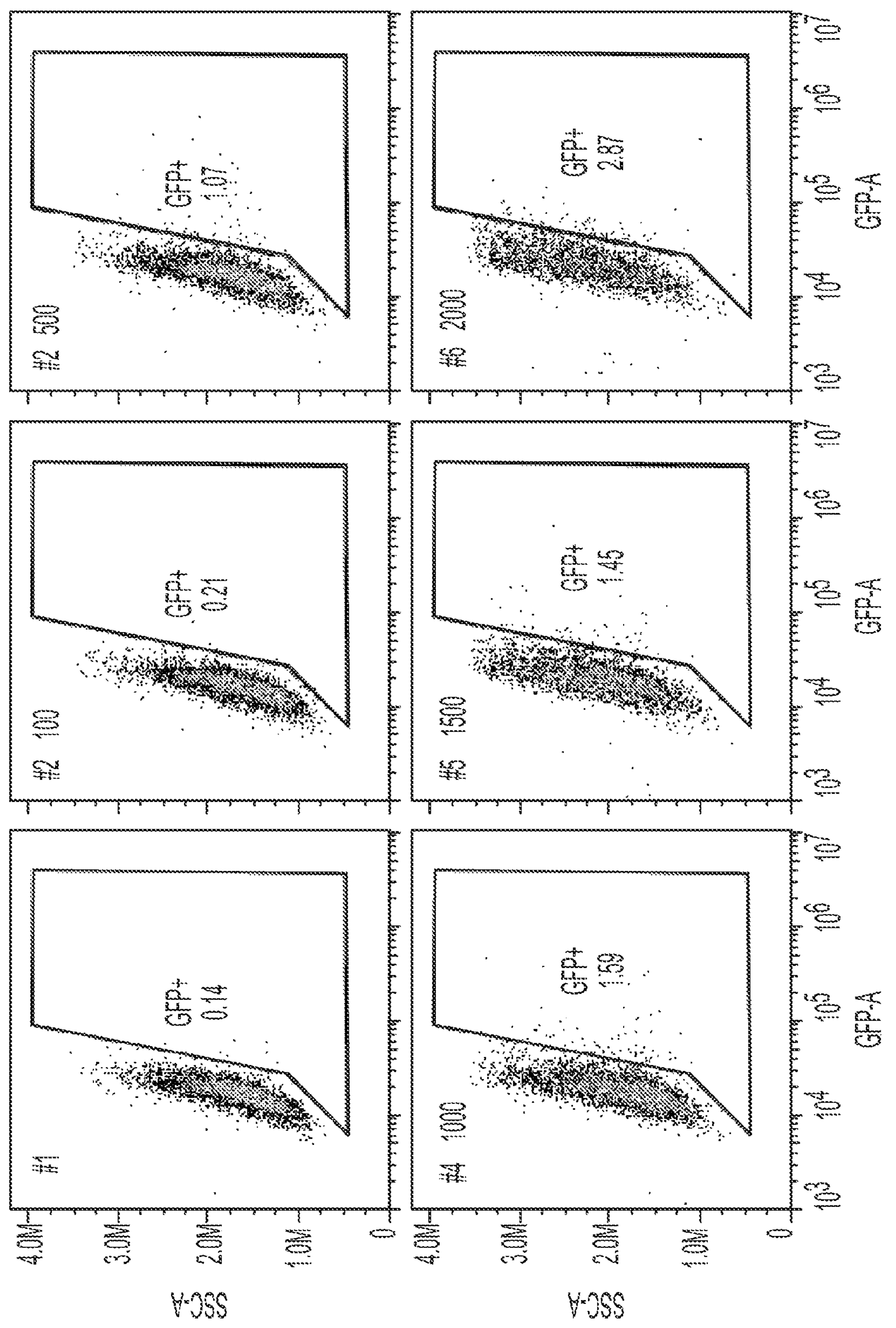
FIG. 42 depicts exemplary flow cytometry data showing GFP+ 293T cells electroporated with the indicated titrated amounts of LINE 1-GFP mRNA, in ng/μL in electroporation solution, after culturing for 3 days post-electroporation.
Figure 43:
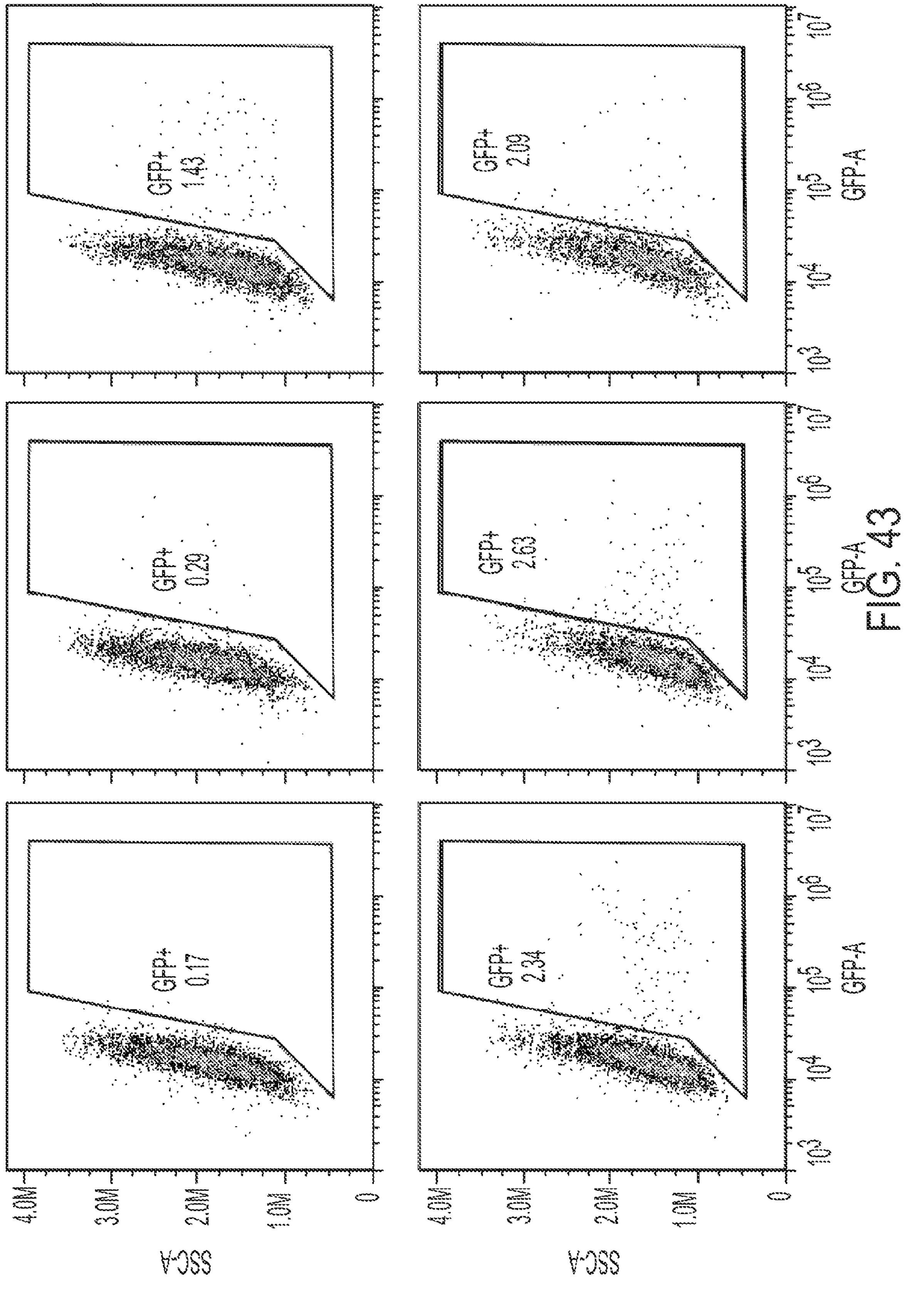
FIG. 43 depicts exemplary flow cytometry data showing GFP+ 293T cells electroporated with the indicated titrated amounts of LINE 1-GFP mRNA, in ng/μL in electroporation solution, after culturing for 5 days post-electroporation.
Figure 44:
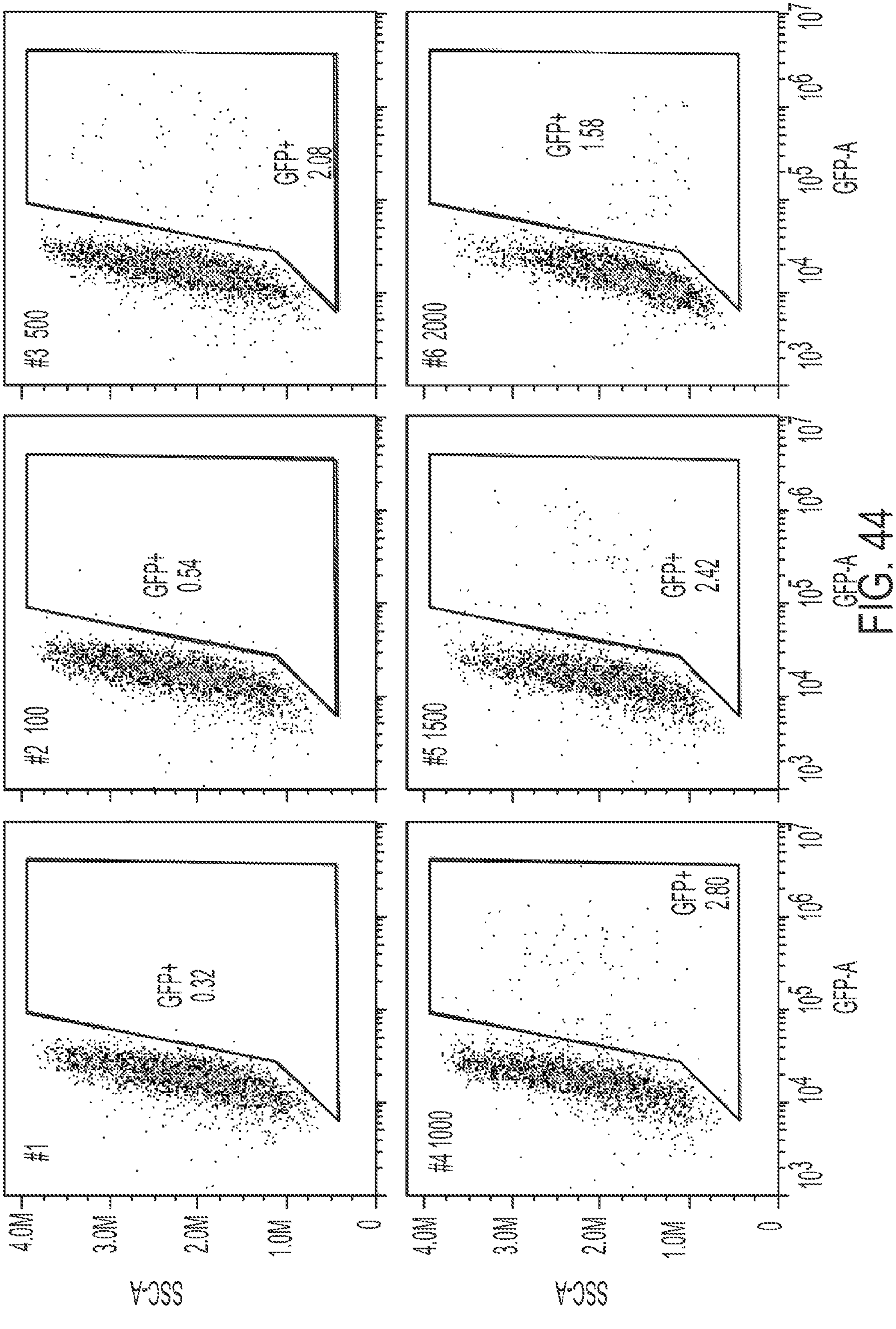
FIG. 44 depicts exemplary flow cytometry data showing GFP+ 293T cells electroporated with the indicated titrated amounts of LINE 1-GFP mRNA, in ng/μL in electroporation solution, after culturing for 7 days post-electroporation.
Figure 45:
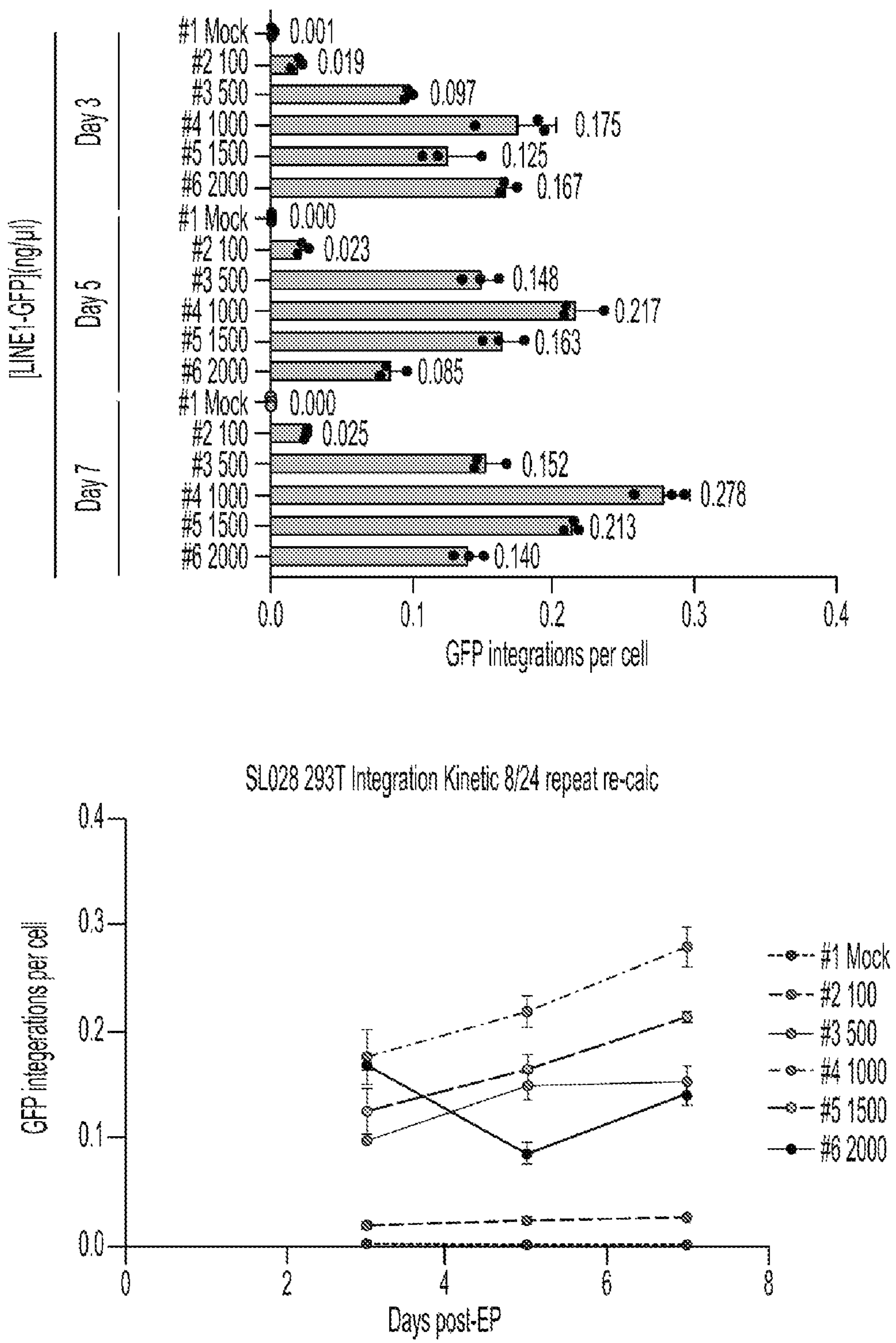
FIG. 45 shows a graph of the number of GFP integrations per genome of 293T cells electroporated with the indicated titrated amounts of LINE1-GFP mRNA, in ng/μL in electroporation solution, according to qPCR after culturing for 3, 5 or 7 days post-electroporation according to FIGS. 42-44 (top) and a graph of the integration kinetics (bottom) according to the data from FIGS. 42-44.
Figure 46:
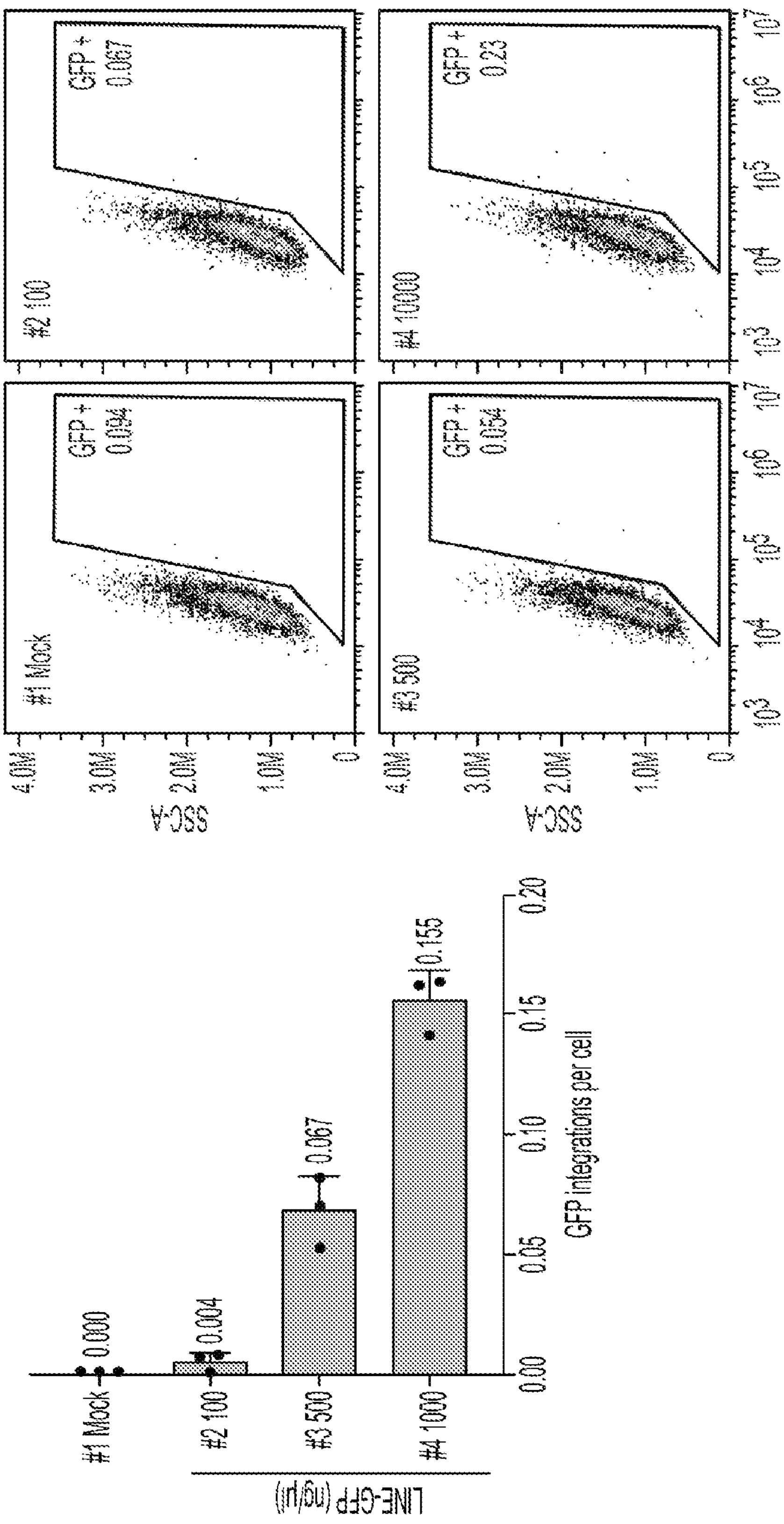
FIG. 46 depicts exemplary flow cytometry data (right) showing GFP+ K562 cells electroporated with the indicated titrated amounts of LINE1-GFP mRNA, in ng/μL in electroporation solution, after culturing for 6 days post-electroporation, and a graph of the number of GFP integrations per genome according to qPCR (left).
Figure 47:
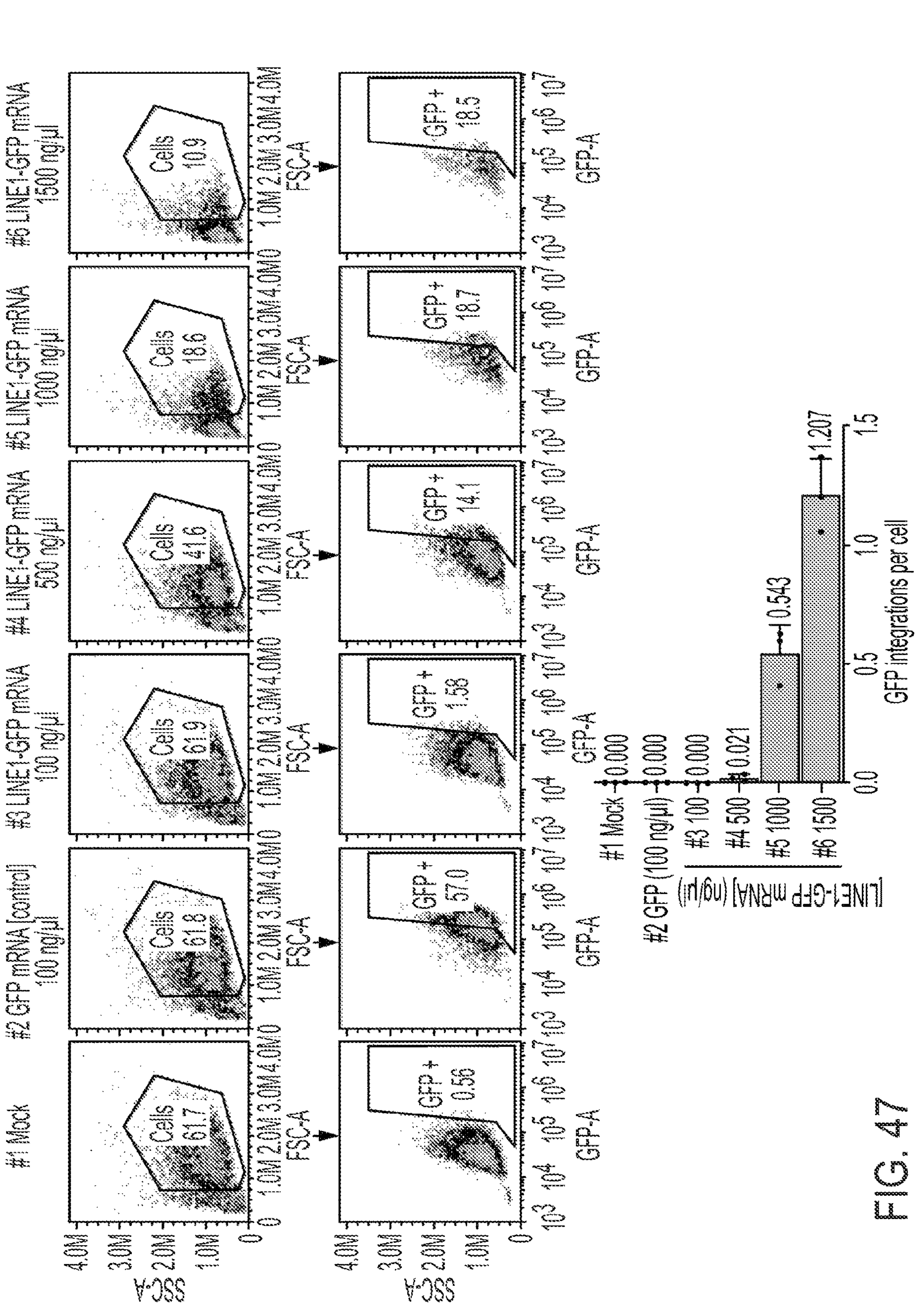
FIG. 47 depicts exemplary flow cytometry data (top) showing GFP+ human primary monocytes electroporated with the indicated titrated amounts of LINE1-GFP mRNA after culturing for 3 days post-electroporation, and a graph of the number of GFP integrations per genome according to qPCR (bottom).
Figure 48:
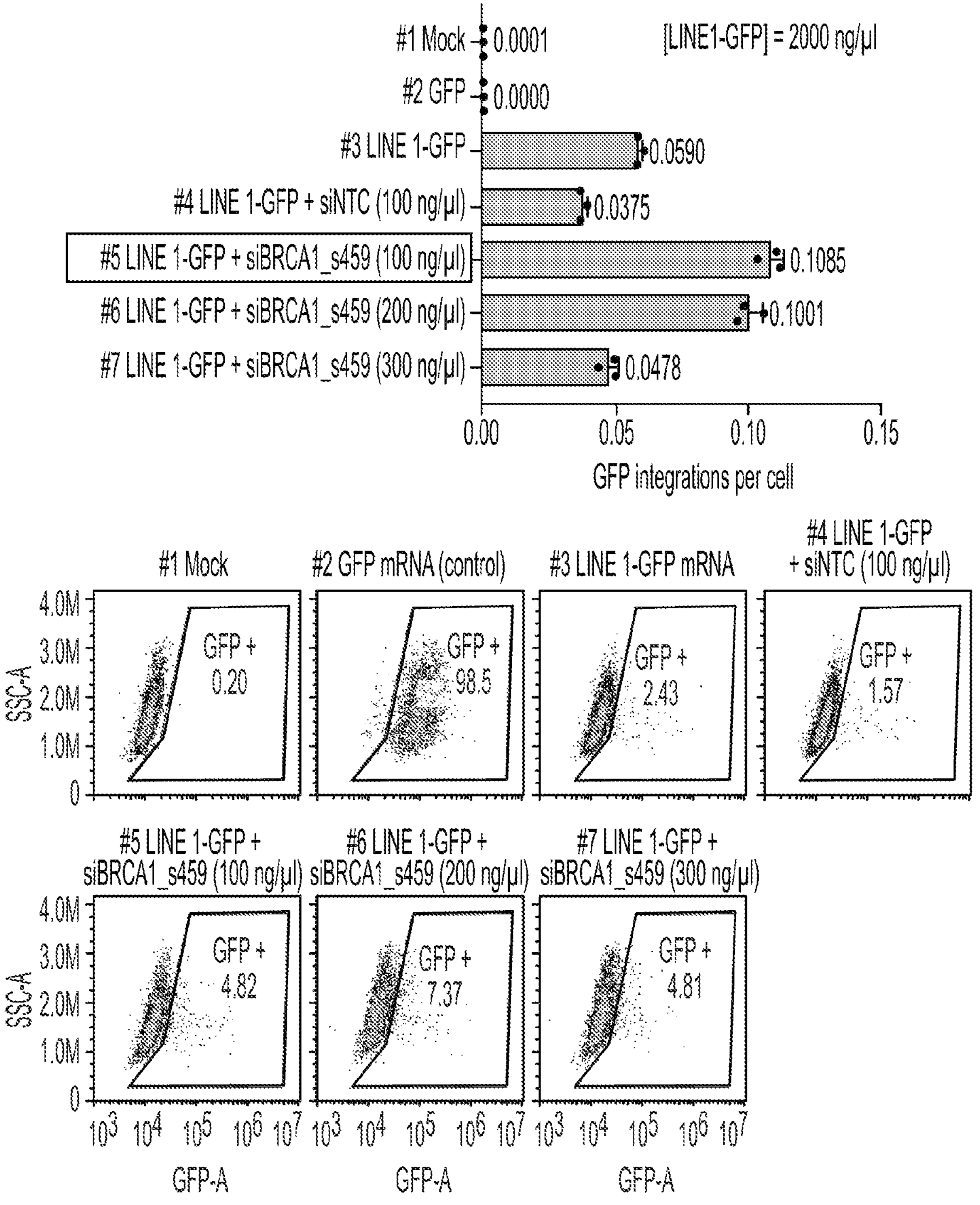
FIG. 48 depicts exemplary flow cytometry data (bottom) showing GFP+ 293T cells electroporated with 2000 ng/μL LINE1-GFP mRNA and 100 ng/μL, 200 ng/μL or 300 ng/μL of an siRNA targeting BRCA1 (siBRCA1) after culturing for 4 days post-electroporation and a graph of the number of GFP integrations per genome according to qPCR (top).
Figure 49:
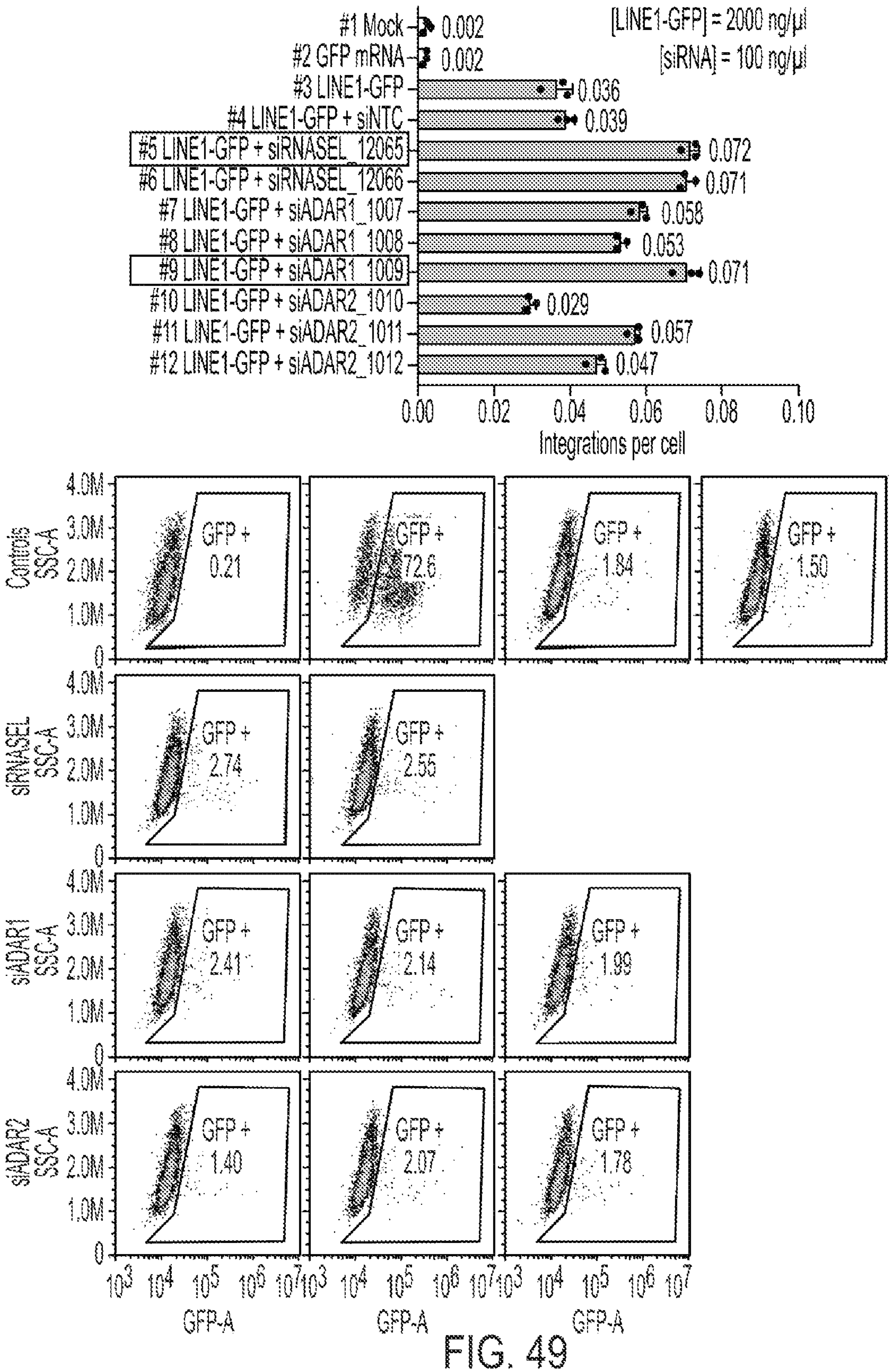
FIG. 49 depicts exemplary flow cytometry data (bottom) showing GFP+ 293T cells electroporated with 2000 ng/μL LINE1-GFP mRNA and 100 ng/μL of an siRNA targeting RNASEL (siRNASEL), ADAR1 (siADAR1), or ADAR2 (siADAR2) after culturing for 6 days post-electroporation and a graph of the number of GFP integrations per genome according to qPCR (top).
Figure 50:
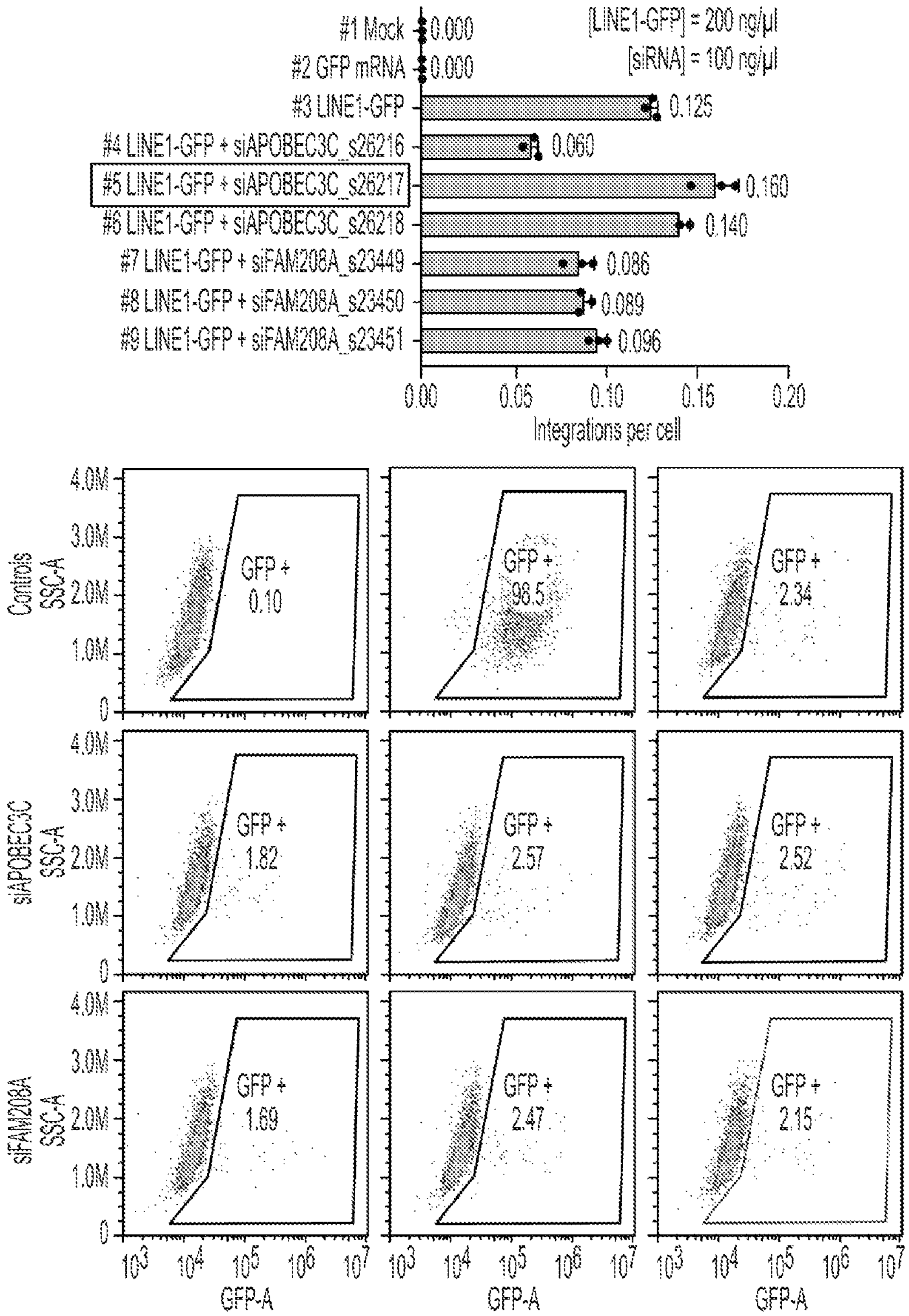
FIG. 50 depicts exemplary flow cytometry data (bottom) showing GFP+ 293T cells electroporated with 2000 ng/μL LINE1-GFP mRNA and 100 ng/μL of an siRNA targeting APOBEC3C (siAPOBEC3C) or FAM208A (siFAM208A)

Example 20. Titration of mRNA Concentration for Increased Transposon Mediated Integration The concentration of LINE1-GFP mRNA used for electroporation was titrated for optimum genomic integration per cell in different cell types, 293T cells, K562 and THP-1 cells (FIGS. 42-46). 100, 500, 1000, 1500 and 2000 ng/μL of mRNA were tested for GFP expression and number of integrations per cell. Concentrations higher than 1000 ng/μl cause cell death. From the results shown in FIGS. 42, 43 and 44 that 1000 ng/μl causes a higher and long-term expression of GFP encoded by the retrotransposed integrated nucleic acid. Integrated DNA encoded protein expression starts to be detectable at day 3 and peaks around day 6-7 (FIG. 45). However, genomic integration and expression of the LINE-1 GFP mRNA in K562 and THP-1 was quite low; integration was detected at about 0.067-0.155 per cell in K562 cells (FIG. 46). (THP-1 data not shown). Higher LINE1-GFP mRNA concentrations (1500 and 2000 ng/μl) caused cell death in these cells. GFP mRNA expression in PD-0015 monocytes was detected at day 3 post electroporation, with detectable integration per cell. (FIG. 47). Steps were to be taken for more extensive DNase 1 treatment, and test mRNA batches were to be evaluated for residual plasmid before electroporation. Accuracy in determination of integration levels in the genome could be improved by first enriching for integrated DNA sequence by PCR followed by paired end sequencing leading to mapping the integration sites within the genome. Next generation sequencing is considered the gold standard in this respect, which involves gDNA extraction→shearing by sonication→DNA linkers ligated onto DNA ends→nested PCR (1: one primer for linker, second to integrated DNA, 2: Illumina sequencing adapters added)→paired-end sequencing.

Example 21. Improvement of Integration Efficiency by Knockdown of Candidates that Prevent Transposon Mediated Integration In this example, a number of endogenous candidates were knocked down using siRNA to determine if the knockdown could result in higher integration of test nucleic acid encoding GFP. Candidates included inhibitors of LINE1 retrotransposition: ADAR1, ADAR2 (ADAR1B), APOBEC3C, BRCA1, let-7 miRNA, RNase L, TASOR (HUSH complex), RAD51. siRNAs (3 per target candidate) were made, electroporated in test cells along with LINE 1-GFP mRNA and tested for alteration of the LINE-1 GFP expression by flow cytometry and its genome integration by qPCR and a cocktail of the siRNA that help increase LINE-1 GFP integration and expression was selected for further titration. Results from the different siRNAs tested are shown in FIGS. 48-51. Knockdown of ADAR1, BRCA and RNASEL tested individually induced about 2-fold increase in integration of LINE1-GFP. ADAR2, RAD51 and APOEBEC3C each led to less than 1.5-fold increase, and let7 miRNA and TASOR each led to no increase. In the study shown in FIG. 48, LINE-1 GFP (2000 ng/μL) was electroporated with an siBRCA at 100, 200 and 300 ng/μL in 293 cells, data shown at 4 days post electroporation. With 100 ng/μL, the integration rate was approximately ~0.06 GFP copies per cell, and siBRCA1_s459 (100 ng/μl) increases integration by ~2-fold. Data shown in FIG. 49 demonstrates that at day 6 post electroporation, each of siRNASEL and siADAR1 siRNAs separately increased integration about 2-fold. On the other hand, siAPOBEC3C_s2617 increases GFP integration <1.5-fold (FIG. 50) at 6 days post electroporation.

TABLE 11

Effect of specific knockdowns on genomic integration rate.

| Target | GFP integration fold change in 293T cells |
|---|---|
| ADAR1 | ~2 fold increase |
| ADAR2 | <1.5-fold increase |
| APOEBEC3C | <1.5-fold increase |
| BRCA | ~2 fold increase |
| Let7 miRNA | No increase |
| RNASEL | ~2 fold increase |
| TASOR (Hush complex) | No increase |
| RAD51 | <1.5-fold increase |

siRNA against ADAR, APOEBEC3C, BRCA and RNASEL were chosen for the siRNA cocktail. Using 1000 ng/μL and 1500 ng/μL LINE1-GFP mRNA in two sets of experiments, the concentration of the siRNAs for electroporation was titrated next. It was observed that LINE1-GFP mRNA at 1500 ng/μL was slightly toxic (FIG. 51). With 1000 ng/μL, 75 ng/uL of each siRNA resulted in ~5-fold improvement of integration of GFP in 293T cells. These results were highly encouraging and support further development. Results from a similar experiment in K562 cells are shown in FIG. 52.

Example 20. Improvement of Retrotransposition Efficiency

Efficiency of retrotransposition can be impacted by numerous variables, such as the level of retrotransposon gene integration and subsequent transcription and translation efficiency of an integrated gene. In this example, variables such as LINE-1 mutations, mRNA sequence alterations/additions, and alterations in mRNA chemistry, are tested for their impact on increasing retrotransposition efficiency and expression of the construct in a cell. To improve the cargo gene integration, the following exemplary experiments will be conducted to test their impact on increasing retrotransposition efficiency and expression of the construct in a cell: (1) mRNA modifications, such as those that increase mRNA stability and protein expression; (2) sequence modifications, such as addition of nuclear localization sequences (NLSs) and introducing mutations in LINE-1 proteins to enhance localization and integration; (3) methods to improve cargo expression and; (4) bioinformatic analysis on various retroelements from different organisms.

The learnings from these experiments are adapted across a number of human cell types, including myeloid cells, T cells, hepatocytes, cardiomyocytes, neurons and retinal pigment epithelial cells, to determine the specificity and versatility of these approaches to different cell types. In vivo delivery of the retrotransposon will also be conducted in mice.

Exemplary cells included in these experiments include hepatocytes, cardiomyocytes, retinal pigment epithelial cells and neurons. Primary cells and cell lines will be used and can be cultured in conditions optimal for each cell type/cell line. Test constructs include plasmid constructs and mRNA constructs comprising a sequence encoding GFP along with a promoter and a poly A sequence that is inserted in reverse orientation relative to the ORF1/2 genes in the retrotransposon complex as described elsewhere in the specification. For plasmid constructs, test constructs include constructs that contain the GFP gene in an antisense orientation interrupted by an intron in sense orientation. For mRNA constructs, test constructs include constructs without an intron. Retrotransposition conditions can include reagents to enhance integration, with the GFP-retrotransposon delivered to the cells in vitro via electroporation and/or a transfection reagent. Electroporation conditions optimized for each specific cell type are used.

Efficiency of integration is determined by flow cytometry, for example using gates set up based on SSC and FSC. GFP is measured in negative control and positive control to set gates for flow cytometry. An exemplary negative control used will be set at <0.1% GFP+. An exemplary positive control used will be set at >90% GFP+. GFP is measured in negative control and positive control to set gates for flow cytometry. An exemplary negative control used will be set at <0.1% GFP+. An exemplary positive control used will be set at >90% GFP+. An exemplary measurement indicative of successful integration is measurement of GFP expression, as determined by flow cytometry, in >2% of cells by day 10 post retrotransposition. Another exemplary measurement indicative of successful integration is measurement of GFP expression, as determined by flow cytometry, in >10% of cells by day 10 post retrotransposition.

Additional assays such as PCR and next generation sequencing (NGS) are performed, for example, to confirm integration. Next generation sequencing can be performed on the transfected/electroporated cells.

Exemplary mRNA structures that may directly impact mRNA stability and translation efficiency to which modifications will be tested to increase stability and protein expression include the 5' CAP, the poly(A) tail, and the untranslated regions (UTRs). For example, enzymatic incorporation of the 5'CAP and use of CAP analogies, such as 7-methylguanosine, will be tested. Enzymatic incorporation of the 5'CAP may be efficient than using CAP analogs. For example, variation of the poly(A) tail length will be also be tested to determine whether the poly(A) tail length impacts translation efficiency. For example, variation of the percent GC content of mRNA will be tested to determine whether the GC content impacts translation efficiency. High GC content may increase mRNA secondary structure stability. Low GC content may reduce translatability of the mRNA. Sequence-specific mRNA variations can be tested to arrive at an optimum GC content. In another exemplary method, substituting certain codons with rare codons and inserting modified nucleotides will be undertaken in order to determine if it can affect translation efficiency. Other exemplary nucleotide modifications that will be tested to increase stability and protein expression include use of 5-methylcytidine (m5C) and pseudouridine (Ψ) nucleotides. An exemplary measurement indicative of successful integration is measurement of GFP expression, as determined by flow cytometry, in >2% of cells by day 10 post retrotransposition. Another exemplary measurement indicative of successful integration is measurement of GFP expression, as determined by flow cytometry, in >10% of cells by day 10 post retrotransposition.

Different mRNA production processes will also be tested for increased transcription of full-length mRNAs.

Exemplary NLS sequence modifications will be tested, such as for enhanced localization and integration, include various NLS sequences, placement of the NLS sequences upstream or downstream of LINE-1 elements and the number of NLS sequences used. As above, GFP is measured in negative control and positive control to set gates for flow cytometry. As above, an exemplary negative control used will be set at <0.1% GFP+. As above, an exemplary positive control used will be set at >90% GFP+. An exemplary measurement indicative of successful cargo gene expression is measurement of increased GFP expression, as determined by flow cytometry, in >10% of cells by day 10 post retrotransposition.

Exemplary sequence modifications that encode mutations in LINE-1 proteins that will be tested, such as for enhanced localization and integration, include K3R of ORF1 protein and Y1180A of ORF2. As above, GFP is measured in negative control and positive control to set gates for flow cytometry. As above, an exemplary negative control used will be set at <0.1% GFP+. As above, an exemplary positive control used will be set at >90% GFP+. An exemplary measurement indicative of successful cargo gene expression is measurement of increased GFP expression, as determined by flow cytometry, in >10% of cells by day 10 post retrotransposition.

Example 21. Effect of Introducing a Nuclear Localization Signal in Retrotransposition by Human LINE1 Constructs In this example, several constructs were generated and tested in which a nuclear localization signal was inserted in different locations as described below, and retrotransposition activity was tested in HEK293T cells. mRNA constructs containing one or more various NLSs and different numbers of total NLSs comprising the retrotransposon sequences described herein were electroporated in the 293T cells, and the number of insertions of a test gene in the genome of a cell was investigated. NLSs were individually tested at the following positions in LINE1-GFP mRNA as summarized in FIG. 53: (i) ORF1-N, in which an NLS was inserted at the N-terminal end of the sequence encoding ORF1 of a LINE 1-GFP construct (FIG. 54A); (ii) ORF1-C, in which an NLS was inserted at the C-terminal end of the sequence encoding ORF1 of a LINE 1-GFP construct (FIG. 55A), (iii) ORF2-N, in which an NLS was inserted at the N-terminal end of the sequence encoding ORF2 of a LINE1-GFP construct (FIG. 56A); (iv) ORF2-N, in which an V40 NLS and a linker was inserted at the N-terminal end of the sequence encoding ORF2 of a LINE1-GFP construct (FIG. 57A); and (v) ORF2-C in which an NLS was inserted at the C-terminal end of the sequence encoding ORF2 of a LINE 1-GFP construct (FIG. 58A). In each case, retrotransposition using the LINE GFP NLS constructs was measured in number of GFP insertions per cell (genome).

Table 12A details sequences relevant to the constructs in tests described for FIGS. 54A-55C.

TABLE 12A

| NLS | Amino acid sequence and nucleic acid sequence |
| --- | --- |
| (#3) SV40 NLS | PKKKRKV (SEQ ID NO: 80) ccaaagaagaagcggaaggtc (SEQ ID NO: 81) |
| (#4) SV40 NLS + Linker (linker sequence underlined) | PKKKRKVGGGS (SEQ ID NO: 82) ccaaagaagaagcggaaggtcggcggcggcagc (SEQ ID NO: 83) |
| (#5) Nucleoplasmin NLS | KRPAATKKAGQAKKKK (SEQ ID NO: 84) aaaaggccggcggccacgaaaaaggccggccaggcaaaaaagaaaaag (SEQ ID NO: 85) |
| (#6) Nucleoplasmin NLS + Linker (linker sequence underlined) | KRPAATKKAGQAKKKKGGGS (SEQ ID NO: 86) aaaaggccggcggccacgaaaaaggccggccaggcaaaaaagaaaaagggcggcggcagc (SEQ ID NO: 87) |

As shown in FIGS. 54B-54C and FIGS. 55B-55C, NLS insertions at N-terminal and C-terminal of ORF1 sequence abolishes retrotransposition activity of the LINE-1 constructs. On the other hand, each of the constructs shown in FIGS. 56A-58C showed some improvement in retrotransposition, with insertion of the NLS in either ORF2 N or C terminal.

Table 12B details sequences relevant to the constructs in tests described for FIGS. 56-56C.

TABLE 12B

| NLS | Amino acid sequence and nucleic acid sequence |
| --- | --- |
| (#3) SV40 NLS | PKKKRKV (SEQ ID NO: 80)<br>ccaaagaagaagcggaaggtc (SEQ ID NO: 81) |
| (#4) Nucleoplasmin NLS | KRPAATKKAGQAKKKK (SEQ ID NO: 84)<br>aaaaggccggcggccacgaaaaaggccggccaggcaaaaaagaaaaag (SEQ ID NO: 85) |
| (#5) Linker + Nucleoplasmin NLS (linker sequence underlined) | GGGSKRPAATKKAGQAKKKK (SEQ ID NO: 88)<br>ggcggcggcagcaaaaggccggcggccacgaaaaaggccggccaggcaaaaaagaaaaag (SEQ ID NO: 89) |

With insertion of an NLS at the N terminal end of ORF2 sequence, about 2-fold increase in number of insertions per cell. (FIGS. 56B, and 56C). However, using the SV40 NLS with the addition of a linker sequence shown in Table 12C, increases the number of GFP integrations by about 3.5 folds (FIGS. 57B and 57C).

Table 12C details sequences relevant to the constructs in tests described for FIGS. 57-57C.

TABLE 12C

| NLS | Amino acid sequence and nucleic acid sequence |
| --- | --- |
| (#4a) SV40 NLS + Linker (linker sequence underlined) | PKKKRKVGGGS (SEQ ID NO: 82)<br>ccaaagaagaagcggaaggtcggcggcggcagc (SEQ ID NO: 83) |

However, surprisingly, insertion of the NLS at the ORF2 C terminus increases the retrotransposition by about 5 fold (FIG. 58B-58C).

Table 12D details sequences relevant to the constructs in tests described for FIGS. 58A-58C.

TABLE 12D

| NLS | Amino acid sequence and nucleic acid sequence |
|---|---|
| (#3) SV40 NLS | PKKKRKV (SEQ ID NO: 80)<br>ccaaagaagaagcggaaggtc (SEQ ID NO: 81) |
| (#4) Linker + SV40 NLS | GGGSPKKKRKV (SEQ ID NO: 90)<br>ggcggcggcagcccaaagaagaagcggaaggtc (SEQ ID NO: 91) |
| (#5) Nucleoplasmin NLS | KRPAATKKAGQAKKKK (SEQ ID NO: 84)<br>aaaaggccggcggccacgaaaaaggccggccaggcaaaaaagaaaaag (SEQ ID NO: 85) |
| (#6) Linker + Nucleoplasmin NLS | GGGSKRPAATKKAGQAKKKK (SEQ ID NO: 88)<br>ggcggcggcagcaaaaggccggcggccacgaaaaaggccggccaggcaaaaaagaaaaag (SEQ ID NO: 89) |

Insertion of both the SV40 NLS and Nucleoplasmin NLS C-terminal to ORF2 leads to >5% GFP positive cells compared to less than 2% in cells that were electroporated with a LINE1-GFP mRNA construct without an NLS sequence. These results indicate that the ORF2 modifications with NLS increases retrotransposition efficiency. Most significantly, insertion at the C-terminal provides higher increase in retrotransposition of LINE1 elements.

Exemplary plasmids used for these experiments are shown in Table 13.

TABLE 13

Exemplary plasmid sequences

| Name | Sequence |
|---|---|
| >RET-002 LINE1-GFP ORF1-CSV40-NLS | CTTTCGTCCGATCCATCTTGCAGGCTACCTCTCGAACGAACTATCGCAAGTCTCTTGGCCGGCCTTG<br>CGCCTTGGCTATTGCTTGGCAGCGCCTATCGCCAGGTATTACTCCAATCCCGAATATCCGAGATCGG<br>GATCACCCGAGAGAAGTTCAACCTACATCCTCAATCCCGATCTATCCGAGATCCGAGGAATATCGAA<br>ATCGGGGCGCGCCTGGTGTACCGAGAACGATCCTCTCAGTGCGAGTCTCGACGATCCATATCGTTGC<br>TTGGCAGTCAGCCAGTCGGAATCCAGCTTGGGACCCAGGAAGTCCAATCGTCAGATATTGTACTCAA<br>GCCTGGTCACGGCAGCGTACCGATCTGTTTAAACCTAGATATTGATAGTCTGATCGGTCAACGTATA<br>ATCGAGTCCTAGCTTTTGCAAACATCTATCAAGAGACAGGATCAGCAGGAGGCTTTCGCATGAGTAT<br>TCAACATTTCCGTGTCGCCCTTATTCCCTTTTTTGCGGCATTTTGCCTTCCTGTTTTTGCTCACCCA<br>GAAACGCTGGTGAAAGTAAAAGATGCTGAAGATCAGTTGGGTGCGCGAGTGGGTTACATCGAACTGG<br>ATCTCAACAGCGGTAAGATCCTTGAGAGTTTTCGCCCCGAAGAACGCTTTCCAATGATGAGCACTTT<br>TAAAGTTCTGCTATGTGGCGCGGTATTATCCCGTATTGACGCCGGGCAAGAGCAACTCGGTCGCCGC<br>ATACACTATTCTCAGAATGACTTGGTTGAGTATTCACCAGTCACAGAAAAGCATCTTACGGATGGCA<br>TGACAGTAAGAGAATTATGCAGTGCTGCCATAACCATGAGTGATAACACTGCGGCCAACTTACTTCT<br>GACAACGATTGGAGGACCGAAGGAGCTAACCGCTTTTTTGCACAACATGGGGGATCATGTAACTCGC<br>CTTGATCGTTGGGAACCGGAGCTGAATGAAGCCATACCAAACGACGAGCGTGACACCACGATGCCTG<br>TAGCAATGGCAACAACCTTGCGTAAACTATTAACTGGCGAACTACTTACTCTAGCTTCCCGGCAACA<br>GTTGATAGACTGGATGGAGGCGGATAAAGTTGCAGGACCACTTCTGCGCTCGGCCCTTCCGGCTGGC<br>TGGTTTATTGCTGATAAATCTGGAGCCGGTGAGCGTGGGTCTCGCGGTATCATTGCAGCACTGGGGC<br>CAGATGGTAAGCCCTCCCGTATCGTAGTTATCTACACGACGGGGAGTCAGGCAACTATGGATGAACG<br>AAATAGACAGATCGCTGAGATAGGTGCCTCACTGATTAAGCATTGGTAACCGATTCTAGGTGCATTG<br>GCGCAGAAAAAAATGCCTGATGCGACGCTGCGCGTCTTATACTCCCACATATGCCAGATTCAGCAAC<br>GGATACGGCTTCCCCAACTTGCCCACTTCCATACGTGTCCTCCTTACCAGAAATTTATCCTTAAGAT<br>CGTTTAAACTCGACTCTGGCTCTATCGAATCTCCGTCGTTTCGAGCTTACGCGAACAGCCGTGGCGC<br>TCATTTGCTCGTCGGGCATCGAATCTCGTCAGCTATCGTCAGCTTACCTTTTTGGCAGCGATCGCGG<br>CTCCCGACATCTTGGACCATTAGCTCCACAGGTATCTTCTTCCCTCTAGTGGTCATAACAGCAGCTT<br>CAGCTACCTCTCAATTCAAAAAACCCCTCAAGACCCGTTTAGAGGCCCCAAGGGGTTATGCTATCAA<br>TCGTTGCGTTACACACACAAAAAACCAACACACATCCATCTTCGATGGATAGCGATTTTATTATCTA<br>ACTGCTGATCGAGTGTAGCCAGATCTAGTAATCAATTACGGGGTCATTAGTTCATAGCCCATATATG<br>GAGTTCCGCGTTACATAACTTACGGTAAATGGCCCGCCTGGCTGACCGCCCAACGACCCCCGCCCAT<br>TGACGTCAATAATGACGTATGTTCCCATAGTAACGCCAATAGGGACTTTCCATTGACGTCAATGGGT<br>GGAGTATTTACGGTAAACTGCCCACTTGGCAGTACATCAAGTGTATCATATGCCAAGTACGCCCCCT<br>ATTGACGTCAATGACGGTAAATGGCCCGCCTGGCATTATGCCCAGTACATGACCTTATGGGACTTTC<br>CTACTTGGCAGTACATCTACGTATTAGTCATCGCTATTACCATGCTGATGCGGTTTTGGCAGTACAT<br>CAATGGGCGTGGATAGCGGTTTGACTCACGGGGATTTCCAAGTCTCCACCCCATTGACGTCAATGGG<br>AGTTTGTTTTGGCACCAAAATCAACGGGACTTTCCAAAATGTCGTAACAACTCCGCCCCATTGACGC<br>AAATGGGCGGTAGGCGTGTACGGTGGGAGGTCTATATAAGCAGAGCTGGTTTAGTGAACCGTCAGAT<br>CAGATCTTTGTCGATCCTACCATCCACTCGACACACCCGCCAGCGGCCGCTAATACGACTCACTATA<br>GGGAGAAGTACTGCCACCATGGGCAAGAAGCAAAATCGCAAGACGGGGAATTCCAAGACACAATCCG<br>CTAGCCCACCACCTAAAGAGCGTTCTAGCTCCCCTGCTACTGAGCAGTCCTGGATGGAAAACGACTT<br>CGATGAACTCCGGGAAGAGGGATTTAGGCGATCCAACTATTCAGAACTCCGCGAAGATATCCAGACA<br>AAGGGGAAGGAAGTCGAGAATTTCGAGAAGAACCTCGAGGAGTGCATCACCCGTATCACAAACACTG<br>AGAAATGTCTCAAAGAACTCATGGAACTTAAGACAAAAGCCAGGGAGCTTCGAGAGGAGTGTCGGAG<br>TCTGAGATCCAGGTGTGACCAGCTCGAGGAGCGCGTGAGCGCGATGGAAGACGAGATGAACGAGATG<br>AAAAGAGAGGGCAAATTCAGGGAGAAGCGCATTAAGAGGAACGAACAGAGTCTGCAGGAGATTTGGG<br>ATTACGTCAAGAGGCCTAACCTGCGGTTGATCGGCGTCCCCGAGAGCGACGTAGAAAACGGGACTAA<br>ACTGGAGAATACACTTCAAGACATCATTCAAGAAAATTTTCCAAACCTGGCTCGGCAAGCTAATGTG<br>CAAATCCAAGAGATCCAACGCACACCCCAGCGGTATAGCTCTCGGCGTGCCACCCCTAGGCATATTA<br>TCGTGCGCTTTACTAAGGTGGAGATGAAAGAGAAGATGCTGCGAGCCGCTCGGGAAAAGGGAAGGGT<br>GACTTTGAAGGGCAAACCTATTCGGCTGACGGTTGACCTTAGCGCCGAGACACTCCAGGCACGCCGG<br>GAATGGGGCCCCATCTTTAATATCCTGAAGGAGAAGAACTTCCAGCCACGAATCTCTTACCCTGCAA<br>AGTTGAGTTTTATCTCCGAGGGTGAGATTAAGTATTTCATCGATAAACAGATGCTGCGAGACTTCGT |

TABLE 13-continued

Exemplary plasmid sequences

| Name | Sequence |
|---|---|
| | GACAACTCGCCCAGCTCTCAAGGAACTGCTCAAAGAGGCTCTTAATATGGAGCGCAATAATAGATAT |
| | CAACCCTTGCAGAACCACGCAAAGATGccaaagaagaagcggaaggtcTGAGACAGCCGTCAGACCA |
| | TCAAGACTAGGAAGAAACTGCATCAACTAATGAGCAAAATCACCAGCTAACATCATAGTATACATGA |
| | CCGGCTCTAACTCACATATCACCATCCTTACACTTAACATTAACGGCCTCAACTCAGCTATCAAGCG |
| | CCATCGGCTGGCCAGCTGGATCAAATCACAGGATCCAAGCGTTTGTTGCATCCAAGAGACCCACCTG |
| | ACCTGTAGAGATACTCACCGCCTCAAGATCAAGGGATGGCGAAAGATTTATCAGGCGAACGGTAAGC |
| | AGAAGAAAGCCGGAGTCGCAATTCTGGTCTCAGACAAGACGGATTTCAAGCCCACCAAAATTAAGCG |
| | TGATAAGGAAGGTCACTATATTATGGTGAAAGGCAGCATACAGCAGGAAGAACTTACCATATTGAAC |
| | ATCTACGCGCCAAACACCGGCGCACCTCGCTTTATCAAACAGGTCCTGTCCGATCTGCAGCGAGATC |
| | TGGATTCTCATACGTTGATTATGGGTGATTTCAATACACCATTGAGCACCCTGGATCGCAGCACCAG |
| | GCAAAAGGTAAATAAAGACACGCAAGAGCTCAATAGCGCACTGCATCAGGCAGATCTCATTGATATT |
| | TATCGCACTCTTCATCCTAAGAGTACCGAGTACACATTCTTCAGCGCCCCACATCATACATACTCAA |
| | AGATCGATCATATCGTCGGCTCAAAGGCTCTGCTGTCAAAGTGCAAGCGCACAGAGATAATTACAAA |
| | TTACCTGTCAGATCATAGCGCGATCAAGCTCGAGCTGAGAATCAAGAACCTGACCCAGAGCCGGAGT |
| | ACCACTTGGAAGCTTAATAACCTGCTGCTCAACGATTATTGGGTCCACAATGAGATGAAGGCAGAGA |
| | TTAAAATGTTCTTCGAAACAAATGAGAATAAGGATACTACCTATCAAAACCTTTGGGATGCCTTTAA |
| | GGCCGTCTGCAGAGGCAAGTTCATCGCCCTCAACGCCTATAAAAGAAAACAAGAGAGATCTAAGATC |
| | GATACTCTCACCTCTCAGCTGAAGGAGTTGGAGAAACAGGAACAGACCCACTCCAAGGCGTCAAGAC |
| | GGCAGGAGATCACAAAGATTCGCGCCGAGTTGAAAGAGATCGAAACCCAAAAGACTCTTCAGAAAAT |
| | TAACGAGTCTCGTAGTTGGTTCTTCGAGCGGATTAATAAGATAGACAGACCTCTGGCACGACTGATT |
| | AAGAAGAAGCGCGAAAAGAACCAGATTGATACCATCAAGAACGACAAGGGCGACATCACTACTGACC |
| | CGACCGAGATCCAGACCACTATTCGGGAGTATTATAAGCATTTGTATGCTAACAAGCTTGAGAACCT |
| | GGAAGAGATGGACACTTTTCTGGATACCTATACTCTGCCACGGCTTAATCAAGAGGAAGTCGAGTCC |
| | CTCAACCGCCCAATTACAGGAAGCGAGATTGTGGCCATAATTAACTCCCTGCCGACAAAGAAATCTC |
| | CTGGTCCGGACGGGTTTACAGCTGAGTTTTATCAACGGTATATGGAAGAGCTTGTACCGTTTCTGCT |
| | CAAGCTCTTTCAGTCTATAGAAAAGGAAGGCATCTTGCCCAATTCCTTCTACGAAGCTTCTATAATA |
| | CTTATTCCCAAACCAGGACGCGATACCACAAAGAAGGAAAACTTCCGGCCCATTAGTCTCATGAATA |
| | TCGACGCTAAAATATTGAACAAGATTCTCGCCAACAGAATCCAACAACATATTAAGAAATTGATACA |
| | TCACGACCAGGTGGGGTTTATACCTGGCATGCAGGGCTGGTTTAACATCCGGAAGAGTATTAACGTC |
| | ATTCAACACATTAATAGAGCTAAGGATAAGAATCATATGATCATCTCTATAGACGCGGAAAAGGCAT |
| | TCGATAAGATTCAGCAGCCATTTATGCTCAAGACTCTGAACAAACTCGGCATCGACGGAACATATTT |
| | TAAGATTATTCGCGCAATTTACGATAAGCCGACTGCTAACATTATCCTTAACGGCCAAAAGCTCGAG |
| | GCCTTTCCGCTCAAGACTGGAACCCGCCAAGGCTGTCCCCTCTCCCCGCTTTTGTTTAATATTGTAC |
| | TCGAGGTGCTGGCTAGGGCTATTCGTCAAGAGAAAGAGATTAAAGGGATACAGCTCGGGAAGGAAGA |
| | GGTCAAGCTTTCCTTGTTCGCCGATGATATGATTGTGTACCTGGAGAATCCTATTGTGTCTGCTCAG |
| | AACCTTCTTAAACTTATTTCTAACTTTAGCAAGGTCAGCGGCTATAAGATTAACGTCCAGAAATCTC |
| | AGGCCTTTCTGTACACAAATAATCGACAGACCGAATCCCAGATAATGGGTGAGCTTCCGTTTGTCAT |
| | AGCCAGCAAAAGGATAAAGTATCTCGGAATCCAGCTGACACGAGACGTTAAAGATTTGTTTAAGGAA |
| | AATTACAAGCCTCTCCTGAAAGAGATTAAGGAAGATACTAATAAGTGGAAGAATATCCCCTGTTCAT |
| | GGGTTGGCAGAATCAACATAGTGAAGATGGCAATACTTCCTAAAGTGATATATCGCTTTAACGCCAT |
| | CCCAATTAAACTGCCTATGACCTTCTTTACGGAGCTCGAGAAAACAACCCTTAAATTTATATGGAAT |
| | CAAAAGAGAGCAAGAATAGCGAAGTCCATCTTGAGCCAGAAGAATAAGGCCGGTGGGATTACTTTGC |
| | CTGATTTTAAGTTGTATTATAAAGCCACAGTAACTAAGACAGCCTGGTATTGGTATCAGAATAGAGA |
| | CATCGACCAGTGGAATCGGACCGAACCATCAGAGATAATGCCCCACATCTATAATTACCTTATATTC |
| | GATAAGCCAGAAAAGAATAAACAGTGGGGCAAAGACAGCCTCTTCAACAAGTGGTGTTGGGAGAATT |
| | GGCTGGCCATATGCCGGAAACTCAAGCTCGACCCCTTTCTTACACCCTACACTAAAATCAACAGTAG |
| | GTGGATCAAGGACTTGAATGTCAAGCCAAAGACTATAAAGACACTGGAAGAGAATCTTGGGATCACA |
| | ATACAAGATATAGGCGTCGGCAAAGATTTTATGTCAAAGACGCCCAAGGCCATGGCCACTAAGGATA |
| | AGATTGATAAGTGGGACCTTATTAAGCTCAAAAGCTTCTGTACTGCCAAGGAGACCACGATCAGAGT |
| | TAATAGGCAGCCCACTACATGGGAAAAGATTTTCGCCACTTATTCATCAGATAAGGGGTTGATAAGC |
| | AGAATATATAACGAGCTGAAGCAGATCTACAAGAAGAAAACGAATAATCCCATCAAGAAGTGGGCAA |
| | AAGATATGAACAGGCATTTTAGCAAAGAGGATATCTACGCCGCGAAGAAGCATATGAAGAAGTGTAG |
| | TTCAAGCTTGGCCATTCGTGAGATGCAGATTAAGACGACCATGCGATACCACCTTACCCCAGTGAGG |
| | ATGGCAATTATCAAGAAATCTGGCAATAATAGATGTTGGCGGGGCTGTGGCGAGATTGGCACCCTGC |
| | TCCATTGCTGGTGGGATTGCAAGCTGGTGCAGCCGCTTTGGAAATCAGTCTGGCGCTTTCTGAGGGA |
| | CCTCGAGCTTGAGATTCCCTTCGATCCCGCAATTCCCTTGCTCGGAATCTATCCTAACGAATACAAG |
| | AGCTGTTGTTACAAGGATACGTGTACCCGGATGTTCATCGCGGCCTTGTTTACGATAGCTAAGACGT |
| | GGAATCAGCCTAAGTGCCCCACAATGATCGATTGGATCAAGAAAATGTGGCATATTTATACCATGGA |
| | GTATTACGCAGCAATTAAGAATGACGAATTTATTTCCTTCGTTGGGACCTGGATGAAGCTGGAGACT |
| | ATTATTCTGAGCAAGCTGTCTCAGGAGCAAAAGACAAAGCATAGAATCTTCTCTCTCATTGGTGGTA |
| | ACGACTACAAAGACGATGACGACAAGTAAAGCGCTTCTAGAAGTTGTCTCCTCCTGCACTGACTGAC |
| | TGATACAATCGATTTCTGGATCCGCAGGCCTAATCAACCTCTGGATTACAAAATTTGTGAAAGATTG |
| | ACTGGTATTCTTAACTATGTTGCTCCTTTTACGCTATGTGGATACGCTGCTTTAATGCCTTTGTATC |
| | ATGCTATTGCTTCCCGTATGGCTTTCATTTTCTCCTCCTTGTATAAATCCTGGTTGCTGTCTCTTTA |
| | TGAGGAGTTGTGGCCCGTTGTCAGGCAACGTGGCGTGGTGTGCACTGTGTTTGCTGACGCAACCCCC |
| | ACTGGTTGGGGCATTGCCACCACCTGTCAGCTCCTTTCCGGGACTTTCGCTTTCCCCCTCCCTATTG |
| | CCACGGCGGAACTCATCGCCGCCTGCCTTGCCCGCTGCTGGACAGGGGCTCGGCTGTTGGGCACTGA |
| | CAATTCCGTGGTGTTGTCGGGGAAGCTGACGTCCTTTCCATGGCTGCTCGCCTGTGTTGCCACCTGG |
| | ATTCTGCGCGGGACGTCCTTCTGCTACGTCCCTTCGGCCCTCAATCCAGCGGACCTTCCTTCCCGCt |
| | gagagacacaaaaaattccaacacactattgcaatgaaaataaatttcctttattagccagaagtca |
| | gatgctcaaggggcttcatgatgtccccataatttttggcagagggaaaaagatctcagtggtattt |
| | gtgagccagggcattggccttctgataggcagcctgcacctgaggagtgcggccgctttacttgtac |
| | agctcgtccatgccgagagtgatcccggcggcggtcacgaactccagcaggaccatgtgatcgcgct |
| | tctcgttggggtctttgctcagggcggactgggtgctcaggtagtggttgtcgggcagcagcacggg |
| | gccgtcgccgatgggggtgttctgctggtagtggtcggcgagctgcacgctgccgtcctcgatgttg |
| | tggcggatcttgaagttcaccttgatgccgttcttctgcttgtcggccatgatatagacgttgtggc |

TABLE 13-continued

Exemplary plasmid sequences

| Name | Sequence |
|---|---|
| | tgttgtagttgtactccagcttgtgccccaggatgttgccgtcctccttgaagtcgatgcccttcag |
| | ctcgatgcggttcaccagggtgtcgccctcgaacttcacctcggcgcgggtcttgtagttgccgtcg |
| | tccttgaagaagatggtgcgctcctggacgtagccttcgggcatggcggacttgaagaagtcgtgct |
| | gcttcatgtggtcggggtagcggctgaagcactgcacgccgtaggtcagggtggtcacgagggtggg |
| | ccagggcacgggcagcttgccggtggtgcagatgaacttcagggtcagcttgccgtaggtggcatcg |
| | ccctcgccctcgccggacacgctgaacttgtggccgtttacgtcgccgtccagctcgaccaggatgg |
| | gcaccaccccggtgaacagctcctcgcccttgctcaccatggtggcgggatctgacggttcactaaa |
| | ccagctctgcttatatagacctcccaccgtacacgcctaccgcccatttgcgtcaatggggcggagt |
| | tgttacgacattttggaaagtcccgttgattttggtgccaaaacaaactcccattgacgtcaatggg |
| | gtggagacttggaaatccccgtgagtcaaaccgctatccacgcccattgatgtactgccaaaaccgc |
| | atcaccatggtaatagcgatgactaatacgtagatgtactgccaagtaggaaagtcccataaggtca |
| | tgtactgggcataatgccaggcgggccatttaccgtcattgacgtcaatagggggcgtacttggcat |
| | atgatacacttgatgtactgccaagtgggcagtttaccgtaaatactccacccattgacgtcaatgg |
| | aaagtccctattggcgttactatgggaacatacgtcattattgacgtcaatgggcgggggtcgttgg |
| | gcggtcagccaggcgggccatttaccgtaagttatgtaacgGGCCTGCTGCCGGCTCTGCGGCCTCT |
| | TCCGCGTCTTCGCCTTCGCCCTCAGACGAGTCGGATCTCCCTTTGGGCCGCCTCCCCGCCTGTCTAG |
| | CTTGACTGACTGAGATACAGCGTACCTTCAGCTCACAGACATGATAAGATACATTGATGAGTTTGGA |
| | CAAACCACAACTAGAATGCAGTGAAAAAAATGCTTTATTTGTGAAATTTGTGATGCTATTGCTTTAT |
| | TTGTAACCATTATAAGCTGCAATAAACAAGTTAACAACAACAATTGCATTCATTTTATGTTTCAGGT |
| | TCAGGGGGAGGTGTGGGAGGTTTTTTAAAGCAAGTAAAACCTCTACAAATGTGGTATTGGCCCATCT |
| | CTATCGGTATCGTAGCATAACCCCTTGGGGCCTCTAAACGGGTCTTGAGGGGTTTTTTGTGCCCCTC |
| | GGGCCGGATTGCTATCTACCGGCATTGGCGCAGAAAAAAATGCCTGATGCGACGCTGCGCGTCTTAT |
| | ACTCCCACATATGCCAGATTCAGCAACGGATACGGCTTCCCCAACTTGCCCACTTCCATACGTGTCC |
| | TCCTTACCAGAAATTTATCCTTAAGGTCGTCAGCTATCCTGCAGGCGATCTCTCGATTTCGATCAAG |
| | ACATTCCTTTAATGGTCTTTTCTGGACACCACTAGGGGTCAGAAGTAGTTCATCAAACTTTCTTCCC |
| | TCCCTAATCTCATTGGTTACCTTGGGCTATCGAAACTTAATTAAGCGATCTGCATCTCAATTAGTCA |
| | GCAACCATAGTCCCGCCCCTAACTCCGCCCATCCCGCCCCTAACTCCGCCCAGTTCCGCCCATTCTC |
| | CGCCCCATCGCTGACTAATTTTTTTTATTTATGCAGAGGCCGAGGCCGCCTCGGCCTCTGAGCTATT |
| | CCAGAAGTAGTGAGGAGGCTTTTTTGGAGGCCTAGGCTTTTGCAAAGGAGGTAGCCAACATGATTGA |
| | ACAAGATGGATTGCACGCAGGTTCTCCCGCCGCTTGGGTGGAGAGGCTATTCGGCTATGACTGGGCA |
| | CAACAGACAATCGGCTGCTCTGATGCCGCCGTGTTCCGGCTGTCAGCGCAGGGGCGCCCGGTTCTTT |
| | TTGTCAAGACCGACCTGTCCGGTGCCCTGAATGAACTCCAGGACGAGGCAGCGCGGCTATCGTGGCT |
| | GGCCACGACGGGCGTTCCTTGCGCAGCTGTGCTCGACGTTGTCACTGAAGCGGGAAGGGACTGGCTG |
| | CTATTGGGCGAAGTGCCGGGGCAGGATCTCCTGTCATCTCACCTTGCTCCTGCCGAGAAAGTATCCA |
| | TCATGGCTGATGCAATGCGGCGGCTGCATACGCTTGATCCGGCTACCTGCCCATTCGACCACCAAGC |
| | GAAACATCGCATCGAGCGAGCACGTACTCGGATGGAAGCCGGTCTTGTCGATCAGGATGATCTGGAC |
| | GAAGAGCATCAGGGGCTCGCGCCAGCCGAACTGTTCGCCAGGCTCAAGGCGCGGATGCCCGACGGCG |
| | AGGATCTCGTCGTGACCCACGGCGATGCCTGCTTGCCGAATATCATGGTGGAAAATGGCCGCTTTTC |
| | TGGATTCATCGACTGTGGCCGGCTGGGTGTGGCGGACCGCTATCAGGACATAGCGTTGGCTACCCGT |
| | GATATTGCTGAAGAGCTTGGCGGCGAATGGGCTGACCGCTTCCTCGTGCTTTACGGTATCGCCGCTC |
| | CCGATTCGCAGCGCATCGCCTTCTATCGCCTTCTTGACGAGTTCTTCTAGTATGTAAGCCCTGTGCC |
| | TTCTAGTTGCCAGCCATCTGTTGTTTGCCCCTCCCCCGTGCCTTCCTTGACCCTGGAAGGTGCCACT |
| | CCCACTGTCCTTTCCTAATAAAATGAGGAAATTGCATCGCATTGTCTGAGTAGGTGTCATTCTATTC |
| | TGGGGGGTGGGGTGGGGCAGGACAGCAAGGGGGAGGATTGGGAAGACAATAGCAGGCATGCTGGGGA |
| | TGCGGTGGGCTCTATGGTTAATTAACCAGTCAAGTCAGCTACTTGGCGAGATCGACTTGTCTGGGTT |
| | TCGACTACGCTCAGAATTGCGTCAGTCAAGTTCGATCTGGTCCTTGCTATTGCACCCGTTCTCCGAT |
| | TACGAGTTTCATTTAAATCATGTGAGCAAAAGGCCAGCAAAAGGCCAGGAACCGTAAAAAGGCCGCG |
| | TTGCTGGCGTTTTTCCATAGGCTCCGCCCCCCTGACGAGCATCACAAAAATCGACGCTCAAGTCAGA |
| | GGTGGCGAAACCCGACAGGACTATAAAGATACCAGGCGTTTCCCCCTGGAAGCTCCCTCGTGCGCTC |
| | TCCTGTTCCGACCCTGCCGCTTACCGGATACCTGTCCGCCTTTCTCCCTTCGGGAAGCGTGGCGCTT |
| | TCTCATAGCTCACGCTGTAGGTATCTCAGTTCGGTGTAGGTCGTTCGCTCCAAGCTGGGCTGTGTGC |
| | ACGAACCCCCCGTTCAGCCCGACCGCTGCGCCTTATCCGGTAACTATCGTCTTGAGTCCAACCCGGT |
| | AAGACACGACTTATCGCCACTGGCAGCAGCCACTGGTAACAGGATTAGCAGAGCGAGGTATGTAGGC |
| | GGTGCTACAGAGTTCTTGAAGTGGTGGCCTAACTACGGCTACACTAGAAGAACAGTATTTGGTATCT |
| | GCGCTCTGCTGAAGCCAGTTACCTTCGGAAAAAGAGTTGGTAGCTCTTGATCCGGCAAACAAACCAC |
| | CGCTGGTAGCGGTGGTTTTTTTGTTTGCAAGCAGCAGATTACGCGCAGAAAAAAAGGATCTCAAGAA |
| | GATCCTTTGATCTTTTCTACGGGGTCTGACGCTCAGTGGAACGAAAACTCACGTTAAGGGATTTTGG |
| | TCATGAGATTATCAAAAAGGATCTTCACCTAGATCCTTTTAAATTAAAAATGAAGTTTTAAATCAAT |
| | CTAAAGTATATATGAGTAAACTTGGTCTGACAGTTACCAATGCTTAATCAGTGAGGCACCTATCTCA |
| | GCGATCTGTCTATTTCGTTCATCCATAGTTGCATTTAAATTTCCGAACTCTCCAAGGCCCTCGTCGG |
| | AAAATCTTCAAAC (SEQ ID NO: 92) |
| >ret- | CCTCTCAGTGCGAGTCTCGACGATCCATATCGTTGCTTGGCAGTCAGCCAGTCGGAATCCAGCTTGG |
| 003- | GACCCAGGAAGTCCAATCGTCAGATATTGTACTCAAGCCTGGTCACGGCAGCGTACCGATCTGTTTA |
| line1- | AACCTAGATATTGATAGTCTGATCGGTCAACGTATAATCGAGTCCTAGCTTTTGCAAACATCTATCA |
| gfp- | AGAGACAGGATCAGCAGGAGGCTTTCGCATGAGTATTCAACATTTCCGTGTCGCCCTTATTCCCTTT |
| orf1-c- | TTTGCGGCATTTTGCCTTCCTGTTTTTGCTCACCCAGAAACGCTGGTGAAAGTAAAAGATGCTGAAG |
| linker_ | ATCAGTTGGGTGCGCGAGTGGGTTACATCGAACTGGATCTCAACAGCGGTAAGATCCTTGAGAGTTT |
| sv40-nls | TCGCCCCGAAGAACGCTTTCCAATGATGAGCACTTTTAAAGTTCTGCTATGTGGCGCGGTATTATCC |
| | CGTATTGACGCCGGGCAAGAGCAACTCGGTCGCCGCATACACTATTCTCAGAATGACTTGGTTGAGT |
| | ATTCACCAGTCACAGAAAAGCATCTTACGGATGGCATGACAGTAAGAGAATTATGCAGTGCTGCCAT |
| | AACCATGAGTGATAACACTGCGGCCAACTTACTTCTGACAACGATTGGAGGACCGAAGGAGCTAACC |
| | GCTTTTTTGCACAACATGGGGGATCATGTAACTCGCCTTGATCGTTGGGAACCGGAGCTGAATGAAG |
| | CCATACCAAACGACGAGCGTGACACCACGATGCCTGTAGCAATGGCAACAACCTTGCGTAAACTATT |
| | AACTGGCGAACTACTTACTCTAGCTTCCCGGCAACAGTTGATAGACTGGATGGAGGCGGATAAAGTT |
| | GCAGGACCACTTCTGCGCTCGGCCCTTCCGGCTGGCTGGTTTATTGCTGATAAATCTGGAGCCGGTG |

TABLE 13-continued

Exemplary plasmid sequences

| Name | Sequence |
| --- | --- |
| | AGCGTGGGTCTCGCGGTATCATTGCAGCACTGGGGCCAGATGGTAAGCCCTCCCGTATCGTAGTTAT |
| | CTACACGACGGGGAGTCAGGCAACTATGGATGAACGAAATAGACAGATCGCTGAGATAGGTGCCTCA |
| | CTGATTAAGCATTGGTAACCGATTCTAGGTGCATTGGCGCAGAAAAAAATGCCTGATGCGACGCTGC |
| | GCGTCTTATACTCCCACATATGCCAGATTCAGCAACGGATACGGCTTCCCCAACTTGCCCACTTCCA |
| | TACGTGTCCTCCTTACCAGAAATTTATCCTTAAGATCGTTTAAACTCGACTCTGGCTCTATCGAATC |
| | TCCGTCGTTTCGAGCTTACGCGAACAGCCGTGGCGCTCATTTGCTCGTCGGGCATCGAATCTCGTCA |
| | GCTATCGTCAGCTTACCTTTTTGGCAGCGATCGCGGCTCCCGACATCTTGGACCATTAGCTCCACAG |
| | GTATCTTCTTCCCTCTAGTGGTCATAACAGCAGCTTCAGCTACCTCTCAATTCAAAAAACCCCTCAA |
| | GACCCGTTTAGAGGCCCCAAGGGGTTATGCTATCAATCGTTGCGTTACACACACAAAAAACCAACAC |
| | ACATCCATCTTCGATGGATAGCGATTTTATTATCTAACTGCTGATCGAGTGTAGCCAGATCTAGTAA |
| | TCAATTACGGGGTCATTAGTTCATAGCCCATATATGGAGTTCCGCGTTACATAACTTACGGTAAATG |
| | GCCCGCCTGGCTGACCGCCCAACGACCCCCGCCCATTGACGTCAATAATGACGTATGTTCCCATAGT |
| | AACGCCAATAGGGACTTTCCATTGACGTCAATGGGTGGAGTATTTACGGTAAACTGCCCACTTGGCA |
| | GTACATCAAGTGTATCATATGCCAAGTACGCCCCCTATTGACGTCAATGACGGTAAATGGCCCGCCT |
| | GGCATTATGCCCAGTACATGACCTTATGGGACTTTCCTACTTGGCAGTACATCTACGTATTAGTCAT |
| | CGCTATTACCATGCTGATGCGGTTTTGGCAGTACATCAATGGGCGTGGATAGCGGTTTGACTCACGG |
| | GGATTTCCAAGTCTCCACCCCATTGACGTCAATGGGAGTTTGTTTTGGCACCAAAATCAACGGGACT |
| | TTCCAAAATGTCGTAACAACTCCGCCCCATTGACGCAAATGGGCGGTAGGCGTGTACGGTGGGAGGT |
| | CTATATAAGCAGAGCTGGTTTAGTGAACCGTCAGATCAGATCTTTGTCGATCCTACCATCCACTCGA |
| | CACACCCGCCAGCGGCCGCTAATACGACTCACTATAGGGAGAAGTACTGCCACCATGGGCAAGAAGC |
| | AAAATCGCAAGACGGGGAATTCCAAGACACAATCCGCTAGCCCACCACCTAAAGAGCGTTCTAGCTC |
| | CCCTGCTACTGAGCAGTCCTGGATGGAAAACGACTTCGATGAACTCCGGGAAGAGGGATTTAGGCGA |
| | TCCAACTATTCAGAACTCCGCGAAGATATCCAGACAAAGGGGAAGGAAGTCGAGAATTTCGAGAAGA |
| | ACCTCGAGGAGTGCATCACCCGTATCACAAACACTGAGAAATGTCTCAAAGAACTCATGGAACTTAA |
| | GACAAAAGCCAGGGAGCTTCGAGAGGAGTGTCGGAGTCTGAGATCCAGGTGTGACCAGCTCGAGGAG |
| | CGCGTGAGCGCGATGGAAGACGAGATGAACGAGATGAAAAGAGAGGGCAAATTCAGGGAGAAGCGCA |
| | TTAAGAGGAACGAACAGAGTCTGCAGGAGATTTGGGATTACGTCAAGAGGCCTAACCTGCGGTTGAT |
| | CGGCGTCCCCGAGAGCGACGTAGAAAACGGGACTAAACTGGAGAATACACTTCAAGACATCATTCAA |
| | GAAAATTTTCCAAACCTGGCTCGGCAAGCTAATGTGCAAATCCAAGAGATCCAACGCACACCCCAGC |
| | GGTATAGCTCTCGGCGTGCCACCCCTAGGCATATTATCGTGCGCTTTACTAAGGTGGAGATGAAAGA |
| | GAAGATGCTGCGAGCCGCTCGGGAAAAGGGAAGGGTGACTTTGAAGGGCAAACCTATTCGGCTGACG |
| | GTTGACCTTAGCGCCGAGACACTCCAGGCACGCCGGGAATGGGGCCCCATCTTTAATATCCTGAAGG |
| | AGAAGAACTTCCAGCCACGAATCTCTTACCCTGCAAAGTTGAGTTTTATCTCCGAGGGTGAGATTAA |
| | GTATTTCATCGATAAACAGATGCTGCGAGACTTCGTGACAACTCGCCCAGCTCTCAAGGAACTGCTC |
| | AAAGAGGCTCTTAATATGGAGCGCAATAATAGATATCAACCCTTGCAGAACCACGCAAAGATGggcg |
| | gcggcagcccaaagaagaagcggaaggtcTGAGACAGCCGTCAGACCATCAAGACTAGGAAGAAACT |
| | GCATCAACTAATGAGCAAAATCACCAGCTAACATCATAGTATACATGACCGGCTCTAACTCACATAT |
| | CACCATCCTTACACTTAACATTAACGGCCTCAACTCAGCTATCAAGCGCCATCGGCTGGCCAGCTGG |
| | ATCAAATCACAGGATCCAAGCGTTTGTTGCATCCAAGAGACCCACCTGACCTGTAGAGATACTCACC |
| | GCCTCAAGATCAAGGGATGGCGAAAGATTTATCAGGCGAACGGTAAGCAGAAGAAAGCCGGAGTCGC |
| | AATTCTGGTCTCAGACAAGACGGATTTCAAGCCCACCAAAATTAAGCGTGATAAGGAAGGTCACTAT |
| | ATTATGGTGAAAGGCAGCATACAGCAGGAAGAACTTACCATATTGAACATCTACGCGCCAAACACCG |
| | GCGCACCTCGCTTTATCAAACAGGTCCTGTCCGATCTGCAGCGAGATCTGGATTCTCATACGTTGAT |
| | TATGGGTGATTTCAATACACCATTGAGCACCCTGGATCGCAGCACCAGGCAAAAGGTAAATAAAGAC |
| | ACGCAAGAGCTCAATAGCGCACTGCATCAGGCAGATCTCATTGATATTTATCGCACTCTTCATCCTA |
| | AGAGTACCGAGTACACATTCTTCAGCGCCCCACATCATACATACTCAAAGATCGATCATATCGTCGG |
| | CTCAAAGGCTCTGCTGTCAAAGTGCAAGCGCACAGAGATAATTACAAATTACCTGTCAGATCATAGC |
| | GCGATCAAGCTCGAGCTGAGAATCAAGAACCTGACCCAGAGCCGGAGTACCACTTGGAAGCTTAATA |
| | ACCTGCTGCTCAACGATTATTGGGTCCACAATGAGATGAAGGCAGAGATTAAAATGTTCTTCGAAAC |
| | AAATGAGAATAAGGATACTACCTATCAAAACCTTTGGGATGCCTTTAAGGCCGTCTGCAGAGGCAAG |
| | TTCATCGCCCTCAACGCCTATAAAAGAAAACAAGAGAGATCTAAGATCGATACTCTCACCTCTCAGC |
| | TGAAGGAGTTGGAGAAACAGGAACAGACCCACTCCAAGGCGTCAAGACGGCAGGAGATCACAAAGAT |
| | TCGCGCCGAGTTGAAAGAGATCGAAACCCAAAAGACTCTTCAGAAAATTAACGAGTCTCGTAGTTGG |
| | TTCTTCGAGCGGATTAATAAGATAGACAGACCTCTGGCACGACTGATTAAGAAGAAGCGCGAAAAGA |
| | ACCAGATTGATACCATCAAGAACGACAAGGGCGACATCACTACTGACCCGACCGAGATCCAGACCAC |
| | TATTCGGGAGTATTATAAGCATTTGTATGCTAACAAGCTTGAGAACCTGGAAGAGATGGACACTTTT |
| | CTGGATACCTATACTCTGCCACGGCTTAATCAAGAGGAAGTCGAGTCCCTCAACCGCCCAATTACAG |
| | GAAGCGAGATTGTGGCCATAATTAACTCCCTGCCGACAAAGAAATCTCCTGGTCCGGACGGGTTTAC |
| | AGCTGAGTTTTATCAACGGTATATGGAAGAGCTTGTACCGTTTCTGCTCAAGCTCTTTCAGTCTATA |
| | GAAAAGGAAGGCATCTTGCCCAATTCCTTCTACGAAGCTTCTATAATACTTATTCCCAAACCAGGAC |
| | GCGATACCACAAAGAAGGAAAACTTCCGGCCCATTAGTCTCATGAATATCGACGCTAAAATATTGAA |
| | CAAGATTCTCGCCAACAGAATCCAACAACATATTAAGAAATTGATACATCACGACCAGGTGGGGTTT |
| | ATACCTGGCATGCAGGGCTGGTTTAACATCCGGAAGAGTATTAACGTCATTCAACACATTAATAGAG |
| | CTAAGGATAAGAATCATATGATCATCTCTATAGACGCGGAAAAGGCATTCGATAAGATTCAGCAGCC |
| | ATTTATGCTCAAGACTCTGAACAAACTCGGCATCGACGGAACATATTTTAAGATTATTCGCGCAATT |
| | TACGATAAGCCGACTGCTAACATTATCCTTAACGGCCAAAAGCTCGAGGCCTTTCCGCTCAAGACTG |
| | GAACCCGCCAAGGCTGTCCCCTCTCCCCGCTTTTGTTTAATATTGTACTCGAGGTGCTGGCTAGGGC |
| | TATTCGTCAAGAGAAAGAGATTAAAGGGATACAGCTCGGGAAGGAAGAGGTCAAGCTTTCCTTGTTC |
| | GCCGATGATATGATTGTGTACCTGGAGAATCCTATTGTGTCTGCTCAGAACCTTCTTAAACTTATTT |
| | CTAACTTTAGCAAGGTCAGCGGCTATAAGATTAACGTCCAGAAATCTCAGGCCTTTCTGTACACAAA |
| | TAATCGACAGACCGAATCCCAGATAATGGGTGAGCTTCCGTTTGTCATAGCCAGCAAAAGGATAAAG |
| | TATCTCGGAATCCAGCTGACACGAGACGTTAAAGATTTGTTTAAGGAAAATTACAAGCCTCTCCTGA |
| | AAGAGATTAAGGAAGATACTAATAAGTGGAAGAATATCCCCTGTTCATGGGTTGGCAGAATCAACAT |
| | AGTGAAGATGGCAATACTTCCTAAAGTGATATATCGCTTTAACGCCATCCCAATTAAACTGCCTATG |
| | ACCTTCTTTACGGAGCTCGAGAAAACAACCCTTAAATTTATATGGAATCAAAAGAGAGCAAGAATAG |
| | CGAAGTCCATCTTGAGCCAGAAGAATAAGGCCGGTGGGATTACTTTGCCTGATTTTAAGTTGTATTA |

TABLE 13-continued

Exemplary plasmid sequences

| Name | Sequence |
| --- | --- |
| | TAAAGCCACAGTAACTAAGACAGCCTGGTATTGGTATCAGAATAGAGACATCGACCAGTGGAATCGG |
| | ACCGAACCATCAGAGATAATGCCCCACATCTATAATTACCTTATATTCGATAAGCCAGAAAAGAATA |
| | AACAGTGGGGCAAAGACAGCCTCTTCAACAAGTGGTGTTGGGAGAATTGGCTGGCCATATGCCGGAA |
| | ACTCAAGCTCGACCCCTTTCTTACACCCTACACTAAAATCAACAGTAGGTGGATCAAGGACTTGAAT |
| | GTCAAGCCAAAGACTATAAAGACACTGGAAGAGAATCTTGGGATCACAATACAAGATATAGGCGTCG |
| | GCAAAGATTTTATGTCAAAGACGCCCAAGGCCATGGCCACTAAGGATAAGATTGATAAGTGGGACCT |
| | TATTAAGCTCAAAAGCTTCTGTACTGCCAAGGAGACCACGATCAGAGTTAATAGGCAGCCCACTACA |
| | TGGGAAAAGATTTTCGCCACTTATTCATCAGATAAGGGGTTGATAAGCAGAATATATAACGAGCTGA |
| | AGCAGATCTACAAGAAGAAAACGAATAATCCCATCAAGAAGTGGGCAAAAGATATGAACAGGCATTT |
| | TAGCAAAGAGGATATCTACGCCGCGAAGAAGCATATGAAGAAGTGTAGTTCAAGCTTGGCCATTCGT |
| | GAGATGCAGATTAAGACGACCATGCGATACCACCTTACCCCAGTGAGGATGGCAATTATCAAGAAAT |
| | CTGGCAATAATAGATGTTGGCGGGGCTGTGGCGAGATTGGCACCCTGCTCCATTGCTGGTGGGATTG |
| | CAAGCTGGTGCAGCCGCTTTGGAAATCAGTCTGGCGCTTTCTGAGGGACCTCGAGCTTGAGATTCCC |
| | TTCGATCCCGCAATTCCCTTGCTCGGAATCTATCCTAACGAATACAAGAGCTGTTGTTACAAGGATA |
| | CGTGTACCCGGATGTTCATCGCGGCCTTGTTTACGATAGCTAAGACGTGGAATCAGCCTAAGTGCCC |
| | CACAATGATCGATTGGATCAAGAAAATGTGGCATATTTATACCATGGAGTATTACGCAGCAATTAAG |
| | AATGACGAATTTATTTCCTTCGTTGGGACCTGGATGAAGCTGGAGACTATTATTCTGAGCAAGCTGT |
| | CTCAGGAGCAAAAGACAAAGCATAGAATCTTCTCTCTCATTGGTGGTAACGACTACAAAGACGATGA |
| | CGACAAGTAAAGCGCTTCTAGAAGTTGTCTCCTCCTGCACTGACTGACTGATACAATCGATTTCTGG |
| | ATCCGCAGGCCTAATCAACCTCTGGATTACAAAATTTGTGAAAGATTGACTGGTATTCTTAACTATG |
| | TTGCTCCTTTTACGCTATGTGGATACGCTGCTTTAATGCCTTTGTATCATGCTATTGCTTCCCGTAT |
| | GGCTTTCATTTTCTCCTCCTTGTATAAATCCTGGTTGCTGTCTCTTTATGAGGAGTTGTGGCCCGTT |
| | GTCAGGCAACGTGGCGTGGTGTGCACTGTGTTTGCTGACGCAACCCCCACTGGTTGGGGCATTGCCA |
| | CCACCTGTCAGCTCCTTTCCGGGACTTTCGCTTTCCCCCTCCCTATTGCCACGGCGGAACTCATCGC |
| | CGCCTGCCTTGCCCGCTGCTGGACAGGGGCTCGGCTGTTGGGCACTGACAATTCCGTGGTGTTGTCG |
| | GGGAAGCTGACGTCCTTTCCATGGCTGCTCGCCTGTGTTGCCACCTGGATTCTGCGCGGGACGTCCT |
| | TCTGCTACGTCCCTTCGGCCCTCAATCCAGCGGACCTTCCTTCCCGCtgagagacacaaaaaattcc |
| | aacacactattgcaatgaaaataaatttcctttattagccagaagtcagatgctcaaggggcttcat |
| | gatgtccccataattttttggcagagggaaaaagatctcagtggtatttgtgagccagggcattggcc |
| | ttctgataggcagcctgcacctgaggagtgcggccgctttacttgtacagctcgtccatgccgagag |
| | tgatcccggcggcggtcacgaactccagcaggaccatgtgatcgcgcttctcgttggggtctttgct |
| | cagggcggactgggtgctcaggtagtggttgtcgggcagcagcacggggccgtcgccgatgggggtg |
| | ttctgctggtagtggtcggcgagctgcacgctgccgtcctcgatgttgtggcggatcttgaagttca |
| | ccttgatgccgttcttctgcttgtcggccatgatatagacgttgtggctgttgtagttgtactccag |
| | cttgtgccccaggatgttgccgtcctccttgaagtcgatgcccttcagctcgatgcggttcaccagg |
| | gtgtcgccctcgaacttcacctcggcgcgggtcttgtagttgccgtcgtccttgaagaagatggtgc |
| | gctcctggacgtagccttcgggcatggcggacttgaagaagtcgtgctgcttcatgtggtcggggta |
| | gcggctgaagcactgcacgccgtaggtcagggtggtcacgagggtgggccagggcacgggcagcttg |
| | ccggtggtgcagatgaacttcagggtcagcttgccgtaggtggcatcgccctcgccctcgccggaca |
| | cgctgaacttgtggccgtttacgtcgccgtccagctcgaccaggatgggcaccaccccggtgaacag |
| | ctcctcgcccttgctcaccatggtggcgggatctgacggttcactaaaccagctctgcttatataga |
| | cctcccaccgtacacgcctaccgcccatttgcgtcaatggggcggagttgttacgacattttggaaa |
| | gtcccgttgattttggtgccaaaacaaactcccattgacgtcaatggggtggagacttggaaatccc |
| | cgtgagtcaaaccgctatccacgcccattgatgtactgccaaaaccgcatcaccatggtaatagcga |
| | tgactaatacgtagatgtactgccaagtaggaaagtcccataaggtcatgtactgggcataatgcca |
| | ggcgggccatttaccgtcattgacgtcaatagggggcgtacttggcatatgatacacttgatgtact |
| | gccaagtgggcagtttaccgtaaatactccacccattgacgtcaatggaaagtccctattggcgtta |
| | ctatgggaacatacgtcattattgacgtcaatgggcgggggtcgttgggcggtcagccaggcgggcc |
| | atttaccgtaagttatgtaacgGGCCTGCTGCCGGCTCTGCGGCCTCTTCCGCGTCTTCGCCTTCGC |
| | CCTCAGACGAGTCGGATCTCCCTTTGGGCCGCCTCCCCGCCTGTCTAGCTTGACTGACTGAGATACA |
| | GCGTACCTTCAGCTCACAGACATGATAAGATACATTGATGAGTTTGGACAAACCACAACTAGAATGC |
| | AGTGAAAAAAATGCTTTATTTGTGAAATTTGTGATGCTATTGCTTTATTTGTAACCATTATAAGCTG |
| | CAATAAACAAGTTAACAACAACAATTGCATTCATTTTATGTTTCAGGTTCAGGGGGAGGTGTGGGAG |
| | GTTTTTTAAAGCAAGTAAAACCTCTACAAATGTGGTATTGGCCCATCTCTATCGGTATCGTAGCATA |
| | ACCCCTTGGGGCCTCTAAACGGGTCTTGAGGGGTTTTTTGTGCCCCTCGGGCCGGATTGCTATCTAC |
| | CGGCATTGGCGCAGAAAAAAATGCCTGATGCGACGCTGCGCGTCTTATACTCCCACATATGCCAGAT |
| | TCAGCAACGGATACGGCTTCCCCAACTTGCCCACTTCCATACGTGTCCTCCTTACCAGAAATTTATC |
| | CTTAAGGTCGTCAGCTATCCTGCAGGCGATCTCTCGATTTCGATCAAGACATTCCTTTAATGGTCTT |
| | TTCTGGACACCACTAGGGGTCAGAAGTAGTTCATCAAACTTTCTTCCCTCCCTAATCTCATTGGTTA |
| | CCTTGGGCTATCGAAACTTAATTAAGCGATCTGCATCTCAATTAGTCAGCAACCATAGTCCCGCCCC |
| | TAACTCCGCCCATCCCGCCCCTAACTCCGCCCAGTTCCGCCCATTCTCCGCCCCATCGCTGACTAAT |
| | TTTTTTTATTTATGCAGAGGCCGAGGCCGCCTCGGCCTCTGAGCTATTCCAGAAGTAGTGAGGAGGC |
| | TTTTTTGGAGGCCTAGGCTTTTGCAAAGGAGGTAGCCAACATGATTGAACAAGATGGATTGCACGCA |
| | GGTTCTCCCGCCGCTTGGGTGGAGAGGCTATTCGGCTATGACTGGGCACAACAGACAATCGGCTGCT |
| | CTGATGCCGCCGTGTTCCGGCTGTCAGCGCAGGGGCGCCCGGTTCTTTTTGTCAAGACCGACCTGTC |
| | CGGTGCCCTGAATGAACTCCAGGACGAGGCAGCGCGGCTATCGTGGCTGGCCACGACGGGCGTTCCT |
| | TGCGCAGCTGTGCTCGACGTTGTCACTGAAGCGGGAAGGGACTGGCTGCTATTGGGCGAAGTGCCGG |
| | GGCAGGATCTCCTGTCATCTCACCTTGCTCCTGCCGAGAAAGTATCCATCATGGCTGATGCAATGCG |
| | GCGGCTGCATACGCTTGATCCGGCTACCTGCCCATTCGACCACCAAGCGAAACATCGCATCGAGCGA |
| | GCACGTACTCGGATGGAAGCCGGTCTTGTCGATCAGGATGATCTGGACGAAGAGCATCAGGGGCTCG |
| | CGCCAGCCGAACTGTTCGCCAGGCTCAAGGCGCGGATGCCCGACGGCGAGGATCTCGTCGTGACCCA |
| | CGGCGATGCCTGCTTGCCGAATATCATGGTGGAAAATGGCCGCTTTTCTGGATTCATCGACTGTGGC |
| | CGGCTGGGTGTGGCGGACCGCTATCAGGACATAGCGTTGGCTACCCGTGATATTGCTGAAGAGCTTG |
| | GCGGCGAATGGGCTGACCGCTTCCTCGTGCTTTACGGTATCGCCGCTCCCGATTCGCAGCGCATCGC |
| | CTTCTATCGCCTTCTTGACGAGTTCTTCTAGTATGTAAGCCCTGTGCCTTCTAGTTGCCAGCCATCT |
| | GTTGTTTGCCCCTCCCCCGTGCCTTCCTTGACCCTGGAAGGTGCCACTCCCACTGTCCTTTCCTAAT |

TABLE 13-continued

| Exemplary plasmid sequences | |
|---|---|
| Name | Sequence |
| | AAAATGAGGAAATTGCATCGCATTGTCTGAGTAGGTGTCATTCTATTCTGGGGGGTGGGGTGGGGCA<br>GGACAGCAAGGGGGAGGATTGGGAAGACAATAGCAGGCATGCTGGGGATGCGGTGGGCTCTATGGTT<br>AATTAACCAGTCAAGTCAGCTACTTGGCGAGATCGACTTGTCTGGGTTTCGACTACGCTCAGAATTG<br>CGTCAGTCAAGTTCGATCTGGTCCTTGCTATTGCACCCGTTCTCCGATTACGAGTTTCATTTAAATC<br>ATGTGAGCAAAAGGCCAGCAAAAGGCCAGGAACCGTAAAAAGGCCGCGTTGCTGGCGTTTTTCCATA<br>GGCTCCGCCCCCCTGACGAGCATCACAAAAATCGACGCTCAAGTCAGAGGTGGCGAAACCCGACAGG<br>ACTATAAAGATACCAGGCGTTTCCCCCTGGAAGCTCCCTCGTGCGCTCTCCTGTTCCGACCCTGCCG<br>CTTACCGGATACCTGTCCGCCTTTCTCCCTTCGGGAAGCGTGGCGCTTTCTCATAGCTCACGCTGTA<br>GGTATCTCAGTTCGGTGTAGGTCGTTCGCTCCAAGCTGGGCTGTGTGCACGAACCCCCCGTTCAGCC<br>CGACCGCTGCGCCTTATCCGGTAACTATCGTCTTGAGTCCAACCCGGTAAGACACGACTTATCGCCA<br>CTGGCAGCAGCCACTGGTAACAGGATTAGCAGAGCGAGGTATGTAGGCGGTGCTACAGAGTTCTTGA<br>AGTGGTGGCCTAACTACGGCTACACTAGAAGAACAGTATTTGGTATCTGCGCTCTGCTGAAGCCAGT<br>TACCTTCGGAAAAAGAGTTGGTAGCTCTTGATCCGGCAAACAAACCACCGCTGGTAGCGGTGGTTTT<br>TTTGTTTGCAAGCAGCAGATTACGCGCAGAAAAAAAGGATCTCAAGAAGATCCTTTGATCTTTTCTA<br>CGGGGTCTGACGCTCAGTGGAACGAAAACTCACGTTAAGGGATTTTGGTCATGAGATTATCAAAAAG<br>GATCTTCACCTAGATCCTTTTAAATTAAAAATGAAGTTTTAAATCAATCTAAAGTATATATGAGTAA<br>ACTTGGTCTGACAGTTACCAATGCTTAATCAGTGAGGCACCTATCTCAGCGATCTGTCTATTTCGTT<br>CATCCATAGTTGCATTTAAATTTCCGAACTCTCCAAGGCCCTCGTCGGAAAATCTTCAAACCTTTCG<br>TCCGATCCATCTTGCAGGCTACCTCTCGAACGAACTATCGCAAGTCTCTTGGCCGGCCTTGCGCCTT<br>GGCTATTGCTTGGCAGCGCCTATCGCCAGGTATTACTCCAATCCCGAATATCCGAGATCGGGATCAC<br>CCGAGAGAAGTTCAACCTACATCCTCAATCCCGATCTATCCGAGATCCGAGGAATATCGAAATCGGG<br>GCGCGCCTGGTGTACCGAGAACGAT (SEQ ID NO: 93) |
| >RET-<br>004<br>LINE1-<br>GFP<br>ORF1-C<br>Nucleo-<br>plasmin-<br>NLS | TCGAAATCGGGGCGCGCCTGGTGTACCGAGAACGATCCTCTCAGTGCGAGTCTCGACGATCCATATC<br>GTTGCTTGGCAGTCAGCCAGTCGGAATCCAGCTTGGGACCCAGGAAGTCCAATCGTCAGATATTGTA<br>CTCAAGCCTGGTCACGGCAGCGTACCGATCTGTTTAAACCTAGATATTGATAGTCTGATCGGTCAAC<br>GTATAATCGAGTCCTAGCTTTTGCAAACATCTATCAAGAGACAGGATCAGCAGGAGGCTTTCGCATG<br>AGTATTCAACATTTCCGTGTCGCCCTTATTCCCTTTTTTGCGGCATTTTGCCTTCCTGTTTTTGCTC<br>ACCCAGAAACGCTGGTGAAAGTAAAAGATGCTGAAGATCAGTTGGGTGCGCGAGTGGGTTACATCGA<br>ACTGGATCTCAACAGCGGTAAGATCCTTGAGAGTTTTCGCCCCGAAGAACGCTTTCCAATGATGAGC<br>ACTTTTAAAGTTCTGCTATGTGGCGCGGTATTATCCCGTATTGACGCCGGGCAAGAGCAACTCGGTC<br>GCCGCATACACTATTCTCAGAATGACTTGGTTGAGTATTCACCAGTCACAGAAAAGCATCTTACGGA<br>TGGCATGACAGTAAGAGAATTATGCAGTGCTGCCATAACCATGAGTGATAACACTGCGGCCAACTTA<br>CTTCTGACAACGATTGGAGGACCGAAGGAGCTAACCGCTTTTTTGCACAACATGGGGGATCATGTAA<br>CTCGCCTTGATCGTTGGGAACCGGAGCTGAATGAAGCCATACCAAACGACGAGCGTGACACCACGAT<br>GCCTGTAGCAATGGCAACAACCTTGCGTAAACTATTAACTGGCGAACTACTTACTCTAGCTTCCCGG<br>CAACAGTTGATAGACTGGATGGAGGCGGATAAAGTTGCAGGACCACTTCTGCGCTCGGCCCTTCCGG<br>CTGGCTGGTTTATTGCTGATAAATCTGGAGCCGGTGAGCGTGGGTCTCGCGGTATCATTGCAGCACT<br>GGGGCCAGATGGTAAGCCCTCCCGTATCGTAGTTATCTACACGACGGGGAGTCAGGCAACTATGGAT<br>GAACGAAATAGACAGATCGCTGAGATAGGTGCCTCACTGATTAAGCATTGGTAACCGATTCTAGGTG<br>CATTGGCGCAGAAAAAAATGCCTGATGCGACGCTGCGCGTCTTATACTCCCACATATGCCAGATTCA<br>GCAACGGATACGGCTTCCCCAACTTGCCCACTTCCATACGTGTCCTCCTTACCAGAAATTTATCCTT<br>AAGATCGTTTAAACTCGACTCTGGCTCTATCGAATCTCCGTCGTTTCGAGCTTACGCGAACAGCCGT<br>GGCGCTCATTTGCTCGTCGGGCATCGAATCTCGTCAGCTATCGTCAGCTTACCTTTTTGGCAGCGAT<br>CGCGGCTCCCGACATCTTGGACCATTAGCTCCACAGGTATCTTCTTCCCTCTAGTGGTCATAACAGC<br>AGCTTCAGCTACCTCTCAATTCAAAAAACCCCTCAAGACCCGTTTAGAGGCCCCAAGGGGTTATGCT<br>ATCAATCGTTGCGTTACACACACAAAAAACCAACACACATCCATCTTCGATGGATAGCGATTTTATT<br>ATCTAACTGCTGATCGAGTGTAGCCAGATCTAGTAATCAATTACGGGGTCATTAGTTCATAGCCCAT<br>ATATGGAGTTCCGCGTTACATAACTTACGGTAAATGGCCCGCCTGGCTGACCGCCCAACGACCCCCG<br>CCCATTGACGTCAATAATGACGTATGTTCCCATAGTAACGCCAATAGGGACTTTCCATTGACGTCAA<br>TGGGTGGAGTATTTACGGTAAACTGCCCACTTGGCAGTACATCAAGTGTATCATATGCCAAGTACGC<br>CCCCTATTGACGTCAATGACGGTAAATGGCCCGCCTGGCATTATGCCCAGTACATGACCTTATGGGA<br>CTTTCCTACTTGGCAGTACATCTACGTATTAGTCATCGCTATTACCATGCTGATGCGGTTTTGGCAG<br>TACATCAATGGGCGTGGATAGCGGTTTGACTCACGGGGATTTCCAAGTCTCCACCCCATTGACGTCA<br>ATGGGAGTTTGTTTTGGCACCAAAATCAACGGGACTTTCCAAAATGTCGTAACAACTCCGCCCCATT<br>GACGCAAATGGGCGGTAGGCGTGTACGGTGGGAGGTCTATATAAGCAGAGCTGGTTTAGTGAACCGT<br>CAGATCAGATCTTTGTCGATCCTACCATCCACTCGACACACCCGCCAGCGGCCGCTAATACGACTCA<br>CTATAGGGAGAAGTACTGCCACCATGGGCAAGAAGCAAAATCGCAAGACGGGGAATTCCAAGACACA<br>ATCCGCTAGCCCACCACCTAAAGAGCGTTCTAGCTCCCCTGCTACTGAGCAGTCCTGGATGGAAAAC<br>GACTTCGATGAACTCCGGGAAGAGGGATTTAGGCGATCCAACTATTCAGAACTCCGCGAAGATATCC<br>AGACAAAGGGGAAGGAAGTCGAGAATTTCGAGAAGAACCTCGAGGAGTGCATCACCCGTATCACAAA<br>CACTGAGAAATGTCTCAAAGAACTCATGGAACTTAAGACAAAAGCCAGGGAGCTTCGAGAGGAGTGT<br>CGGAGTCTGAGATCCAGGTGTGACCAGCTCGAGGAGCGCGTGAGCGCGATGGAAGACGAGATGAACG<br>AGATGAAAAGAGAGGGCAAATTCAGGGAGAAGCGCATTAAGAGGAACGAACAGAGTCTGCAGGAGAT<br>TTGGGATTACGTCAAGAGGCCTAACCTGCGGTTGATCGGCGTCCCCGAGAGCGACGTAGAAAACGGG<br>ACTAAACTGGAGAATACACTTCAAGACATCATTCAAGAAAATTTTCCAAACCTGGCTCGGCAAGCTA<br>ATGTGCAAATCCAAGAGATCCAACGCACACCCCAGCGGTATAGCTCTCGGCGTGCCACCCCTAGGCA<br>TATTATCGTGCGCTTTACTAAGGTGGAGATGAAAGAGAAGATGCTGCGAGCCGCTCGGGAAAAGGGA<br>AGGGTGACTTTGAAGGGCAAACCTATTCGGCTGACGGTTGACCTTAGCGCCGAGACACTCCAGGCAC<br>GCCGGGAATGGGGCCCCATCTTTAATATCCTGAAGGAGAAGAACTTCCAGCCACGAATCTCTTACCC<br>TGCAAAGTTGAGTTTTATCTCCGAGGGTGAGATTAAGTATTTCATCGATAAACAGATGCTGCGAGAC<br>TTCGTGACAACTCGCCCAGCTCTCAAGGAACTGCTCAAAGAGGCTCTTAATATGGAGCGCAATAATA<br>GATATCAACCCTTGCAGAACCACGCAAAGATGaaaaggccggcggccacgaaaaaggccggccaggc<br>aaaaaagaaaaagTGAGACAGCCGTCAGACCATCAAGACTAGGAAGAAACTGCATCAACTAATGAGC<br>AAAATCACCAGCTAACATCATAGTATACATGACCGGCTCTAACTCACATATCACCATCCTTACACTT<br>AACATTAACGGCCTCAACTCAGCTATCAAGCGCCATCGGCTGGCCAGCTGGATCAAATCACAGGATC |

TABLE 13-continued

Exemplary plasmid sequences

| Name | Sequence |
|---|---|
| | CAAGCGTTTGTTGCATCCAAGAGACCCACCTGACCTGTAGAGATACTCACCGCCTCAAGATCAAGGG<br>ATGGCGAAAGATTTATCAGGCGAACGGTAAGCAGAAGAAAGCCGGAGTCGCAATTCTGGTCTCAGAC<br>AAGACGGATTTCAAGCCCACCAAAATTAAGCGTGATAAGGAAGGTCACTATATTATGGTGAAAGGCA<br>GCATACAGCAGGAAGAACTTACCATATTGAACATCTACGCGCCAAACACCGGCGCACCTCGCTTTAT<br>CAAACAGGTCCTGTCCGATCTGCAGCGAGATCTGGATTCTCATACGTTGATTATGGGTGATTTCAAT<br>ACACCATTGAGCACCCTGGATCGCAGCACCAGGCAAAAGGTAAATAAAGACACGCAAGAGCTCAATA<br>GCGCACTGCATCAGGCAGATCTCATTGATATTTATCGCACTCTTCATCCTAAGAGTACCGAGTACAC<br>ATTCTTCAGCGCCCCACATCATACATACTCAAAGATCGATCATATCGTCGGCTCAAAGGCTCTGCTG<br>TCAAAGTGCAAGCGCACAGAGATAATTACAAATTACCTGTCAGATCATAGCGCGATCAAGCTCGAGC<br>TGAGAATCAAGAACCTGACCCAGAGCCGGAGTACCACTTGGAAGCTTAATAACCTGCTGCTCAACGA<br>TTATTGGGTCCACAATGAGATGAAGGCAGAGATTAAAATGTTCTTCGAAACAAATGAGAATAAGGAT<br>ACTACCTATCAAAACCTTTGGGATGCCTTTAAGGCCGTCTGCAGAGGCAAGTTCATCGCCCTCAACG<br>CCTATAAAAGAAAACAAGAGAGATCTAAGATCGATACTCTCACCTCTCAGCTGAAGGAGTTGGAGAA<br>ACAGGAACAGACCCACTCCAAGGCGTCAAGACGGCAGGAGATCACAAAGATTCGCGCCGAGTTGAAA<br>GAGATCGAAACCCAAAAGACTCTTCAGAAAATTAACGAGTCTCGTAGTTGGTTCTTCGAGCGGATTA<br>ATAAGATAGACAGACCTCTGGCACGACTGATTAAGAAGAAGCGCGAAAAGAACCAGATTGATACCAT<br>CAAGAACGACAAGGGCGACATCACTACTGACCCGACCGAGATCCAGACCACTATTCGGGAGTATTAT<br>AAGCATTTGTATGCTAACAAGCTTGAGAACCTGGAAGAGATGGACACTTTTCTGGATACCTATACTC<br>TGCCACGGCTTAATCAAGAGGAAGTCGAGTCCCTCAACCGCCCAATTACAGGAAGCGAGATTGTGGC<br>CATAATTAACTCCCTGCCGACAAAGAAATCTCCTGGTCCGGACGGGTTTACAGCTGAGTTTTATCAA<br>CGGTATATGGAAGAGCTTGTACCGTTTCTGCTCAAGCTCTTTCAGTCTATAGAAAAGGAAGGCATCT<br>TGCCCAATTCCTTCTACGAAGCTTCTATAATACTTATTCCCAAACCAGGACGCGATACCACAAAGAA<br>GGAAAACTTCCGGCCCATTAGTCTCATGAATATCGACGCTAAAATATTGAACAAGATTCTCGCCAAC<br>AGAATCCAACAACATATTAAGAAATTGATACATCACGACCAGGTGGGGTTTATACCTGGCATGCAGG<br>GCTGGTTTAACATCCGGAAGAGTATTAACGTCATTCAACACATTAATAGAGCTAAGGATAAGAATCA<br>TATGATCATCTCTATAGACGCGGAAAAGGCATTCGATAAGATTCAGCAGCCATTTATGCTCAAGACT<br>CTGAACAAACTCGGCATCGACGGAACATATTTTAAGATTATTCGCGCAATTTACGATAAGCCGACTG<br>CTAACATTATCCTTAACGGCCAAAAGCTCGAGGCCTTTCCGCTCAAGACTGGAACCCGCCAAGGCTG<br>TCCCCTCTCCCCGCTTTTGTTTAATATTGTACTCGAGGTGCTGGCTAGGGCTATTCGTCAAGAGAAA<br>GAGATTAAAGGGATACAGCTCGGGAAGGAAGAGGTCAAGCTTTCCTTGTTCGCCGATGATATGATTG<br>TGTACCTGGAGAATCCTATTGTGTCTGCTCAGAACCTTCTTAAACTTATTTCTAACTTTAGCAAGGT<br>CAGCGGCTATAAGATTAACGTCCAGAAATCTCAGGCCTTTCTGTACACAAATAATCGACAGACCGAA<br>TCCCAGATAATGGGTGAGCTTCCGTTTGTCATAGCCAGCAAAAGGATAAAGTATCTCGGAATCCAGC<br>TGACACGAGACGTTAAAGATTTGTTTAAGGAAAATTACAAGCCTCTCCTGAAAGAGATTAAGGAAGA<br>TACTAATAAGTGGAAGAATATCCCCTGTTCATGGGTTGGCAGAATCAACATAGTGAAGATGGCAATA<br>CTTCCTAAAGTGATATATCGCTTTAACGCCATCCCAATTAAACTGCCTATGACCTTCTTTACGGAGC<br>TCGAGAAAACAACCCTTAAATTTATATGGAATCAAAAGAGAGCAAGAATAGCGAAGTCCATCTTGAG<br>CCAGAAGAATAAGGCCGGTGGGATTACTTTGCCTGATTTTAAGTTGTATTATAAAGCCACAGTAACT<br>AAGACAGCCTGGTATTGGTATCAGAATAGAGACATCGACCAGTGGAATCGGACCGAACCATCAGAGA<br>TAATGCCCCACATCTATAATTACCTTATATTCGATAAGCCAGAAAAGAATAAACAGTGGGGCAAAGA<br>CAGCCTCTTCAACAAGTGGTGTTGGGAGAATTGGCTGGCCATATGCCGGAAACTCAAGCTCGACCCC<br>TTTCTTACACCCTACACTAAAATCAACAGTAGGTGGATCAAGGACTTGAATGTCAAGCCAAAGACTA<br>TAAAGACACTGGAAGAGAATCTTGGGATCACAATACAAGATATAGGCGTCGGCAAAGATTTTATGTC<br>AAAGACGCCCAAGGCCATGGCCACTAAGGATAAGATTGATAAGTGGGACCTTATTAAGCTCAAAAGC<br>TTCTGTACTGCCAAGGAGACCACGATCAGAGTTAATAGGCAGCCCACTACATGGGAAAAGATTTTCG<br>CCACTTATTCATCAGATAAGGGGTTGATAAGCAGAATATATAACGAGCTGAAGCAGATCTACAAGAA<br>GAAAACGAATAATCCCATCAAGAAGTGGGCAAAAGATATGAACAGGCATTTTAGCAAAGAGGATATC<br>TACGCCGCGAAGAAGCATATGAAGAAGTGTAGTTCAAGCTTGGCCATTCGTGAGATGCAGATTAAGA<br>CGACCATGCGATACCACCTTACCCAGTGAGGATGGCAATTATCAAGAAATCTGGCAATAATAGATG<br>TTGGCGGGGCTGTGGCGAGATTGGCACCCTGCTCCATTGCTGGTGGGATTGCAAGCTGGTGCAGCCG<br>CTTTGGAAATCAGTCTGGCGCTTTCTGAGGGACCTCGAGCTTGAGATTCCCTTCGATCCCGCAATTC<br>CCTTGCTCGGAATCTATCCTAACGAATACAAGAGCTGTTGTTACAAGGATACGTGTACCCGGATGTT<br>CATCGCGGCCTTGTTTACGATAGCTAAGACGTGGAATCAGCCTAAGTGCCCCACAATGATCGATTGG<br>ATCAAGAAAATGTGGCATATTTATACCATGGAGTATTACGCAGCAATTAAGAATGACGAATTTATTT<br>CCTTCGTTGGGACCTGGATGAAGCTGGAGACTATTATTCTGAGCAAGCTGTCTCAGGAGCAAAAGAC<br>AAAGCATAGAATCTTCTCTCTCATTGGTGGTAACGACTACAAAGACGATGACGACAAGTAAAGCGCT<br>TCTAGAAGTTGTCTCCTCCTGCACTGACTGACTGATACAATCGATTTCTGGATCCGCAGGCCTAATC<br>AACCTCTGGATTACAAAATTTGTGAAAGATTGACTGGTATTCTTAACTATGTTGCTCCTTTTACGCT<br>ATGTGGATACGCTGCTTTAATGCCTTTGTATCATGCTATTGCTTCCCGTATGGCTTTCATTTTCTCC<br>TCCTTGTATAAATCCTGGTTGCTGTCTCTTTATGAGGAGTTGTGGCCCGTTGTCAGGCAACGTGGCG<br>TGGTGTGCACTGTGTTTGCTGACGCAACCCCCACTGGTTGGGGCATTGCCACCACCTGTCAGCTCCT<br>TTCCGGGACTTTCGCTTTCCCCCTCCCTATTGCCACGGCGGAACTCATCGCCGCCTGCCTTGCCCGC<br>TGCTGGACAGGGGCTCGGCTGTTGGGCACTGACAATTCCGTGGTGTTGTCGGGGAAGCTGACGTCCT<br>TTCCATGGCTGCTCGCCTGTGTTGCCACCTGGATTCTGCGCGGGACGTCCTTCTGCTACGTCCCTTC<br>GGCCCTCAATCCAGCGGACCTTCCTTCCCGCtgagagacacaaaaaattccaacacactattgcaat<br>gaaaataaatttcctttattagccagaagtcagatgctcaaggggcttcatgatgtccccataattt<br>ttggcagagggaaaaagatctcagtggtatttgtgagccagggcattggccttctgataggcagcct<br>gcacctgaggagtgcggccgctttacttgtacagctcgtccatgccgagagtgatcccggcggcggt<br>cacgaactccagcaggaccatgtgatcgcgcttctcgttggggtctttgctcagggcggactgggtg<br>ctcaggtagtggttgtcgggcagcagcacggggccgtcgccgatgggggtgttctgctggtagtggt<br>cggcgagctgcacgctgccgtcctcgatgttgtggcggatcttgaagttcaccttgatgccgttctt<br>ctgcttgtcggccatgatatagacgttgtggctgttgtagttgtactccagcttgtgccccaggatg<br>ttgccgtcctccttgaagtcgatgcccttcagctcgatgcggttcaccagggtgtcgccctcgaact<br>tcacctcggcgcgggtcttgtagttgccgtcgtccttgaagaagatggtgcgctcctggacgtagcc<br>ttcgggcatggcggacttgaagaagtcgtgctgcttcatgtggtcggggtagcggctgaagcactgc<br>acgccgtaggtcagggtggtcacgagggtgggccagggcacgggcagcttgccggtggtgcagatga |

TABLE 13-continued

| Exemplary plasmid sequences | |
|---|---|
| Name | Sequence |
| | acttcagggtcagcttgccgtaggtggcatcgccctcgccctcgccggacacgctgaacttgtggcc<br>gtttacgtcgccgtccagctcgaccaggatgggcaccaccccggtgaacagctcctcgcccttgctc<br>accatggtggcgggatctgacggttcactaaaccagctctgcttatatagacctcccaccgtacacg<br>cctaccgcccatttgcgtcaatggggcggagttgttacgacattttggaaagtcccgttgattttgg<br>tgccaaaacaaactcccattgacgtcaatggggtggagacttggaaatccccgtgagtcaaaccgct<br>atccacgcccattgatgtactgccaaaaccgcatcaccatggtaatagcgatgactaatacgtagat<br>gtactgccaagtaggaaagtcccataaggtcatgtactgggcataatgccaggcgggccatttaccg<br>tcattgacgtcaataggggggcgtacttggcatatgatacacttgatgtactgccaagtgggcagttt<br>accgtaaatactccacccattgacgtcaatggaaagtccctattggcgttactatgggaacatacgt<br>cattattgacgtcaatgggcgggggtcgttgggcggtcagccaggcgggccatttaccgtaagttat<br>gtaacgGGCCTGCTGCCGGCTCTGCGGCCTCTTCCGCGTCTTCGCCTTCGCCCTCAGACGAGTCGGA<br>TCTCCCTTTGGGCCGCCTCCCCGCCTGTCTAGCTTGACTGACTGAGATACAGCGTACCTTCAGCTCA<br>CAGACATGATAAGATACATTGATGAGTTTGGACAAACCACAACTAGAATGCAGTGAAAAAAATGCTT<br>TATTTGTGAAATTTGTGATGCTATTGCTTTATTTGTAACCATTATAAGCTGCAATAAACAAGTTAAC<br>AACAACAATTGCATTCATTTTATGTTTCAGGTTCAGGGGGAGGTGTGGGAGGTTTTTTAAAGCAAGT<br>AAAACCTCTACAAATGTGGTATTGGCCCATCTCTATCGGTATCGTAGCATAACCCCTTGGGGCCTCT<br>AAACGGGTCTTGAGGGGTTTTTTGTGCCCCTCGGGCCGGATTGCTATCTACCGGCATTGGCGCAGAA<br>AAAAATGCCTGATGCGACGCTGCGCGTCTTATACTCCCACATATGCCAGATTCAGCAACGGATACGG<br>CTTCCCCAACTTGCCCACTTCCATACGTGTCCTCCTTACCAGAAATTTATCCTTAAGGTCGTCAGCT<br>ATCCTGCAGGCGATCTCTCGATTTCGATCAAGACATTCCTTTAATGGTCTTTTCTGGACACCACTAG<br>GGGTCAGAAGTAGTTCATCAAACTTTCTTCCCTCCCTAATCTCATTGGTTACCTTGGGCTATCGAAA<br>CTTAATTAAGCGATCTGCATCTCAATTAGTCAGCAACCATAGTCCCGCCCCTAACTCCGCCCATCCC<br>GCCCCTAACTCCGCCCAGTTCCGCCCATTCTCCGCCCCATCGCTGACTAATTTTTTTTATTTATGCA<br>GAGGCCGAGGCCGCCTCGGCCTCTGAGCTATTCCAGAAGTAGTGAGGAGGCTTTTTTGGAGGCCTAG<br>GCTTTTGCAAAGGAGGTAGCCAACATGATTGAACAAGATGGATTGCACGCAGGTTCTCCCGCCGCTT<br>GGGTGGAGAGGCTATTCGGCTATGACTGGGCACAACAGACAATCGGCTGCTCTGATGCCGCCGTGTT<br>CCGGCTGTCAGCGCAGGGGCGCCCGGTTCTTTTTGTCAAGACCGACCTGTCCGGTGCCCTGAATGAA<br>CTCCAGGACGAGGCAGCGCGGCTATCGTGGCTGGCCACGACGGGCGTTCCTTGCGCAGCTGTGCTCG<br>ACGTTGTCACTGAAGCGGGAAGGGACTGGCTGCTATTGGGCGAAGTGCCGGGGCAGGATCTCCTGTC<br>ATCTCACCTTGCTCCTGCCGAGAAAGTATCCATCATGGCTGATGCAATGCGGCGGCTGCATACGCTT<br>GATCCGGCTACCTGCCCATTCGACCACCAAGCGAAACATCGCATCGAGCGAGCACGTACTCGGATGG<br>AAGCCGGTCTTGTCGATCAGGATGATCTGGACGAAGAGCATCAGGGGCTCGCGCCAGCCGAACTGTT<br>CGCCAGGCTCAAGGCGCGGATGCCCGACGGCGAGGATCTCGTCGTGACCCACGGCGATGCCTGCTTG<br>CCGAATATCATGGTGGAAAATGGCCGCTTTTCTGGATTCATCGACTGTGGCCGGCTGGGTGTGGCGG<br>ACCGCTATCAGGACATAGCGTTGGCTACCCGTGATATTGCTGAAGAGCTTGGCGGCGAATGGGCTGA<br>CCGCTTCCTCGTGCTTTACGGTATCGCCGCTCCCGATTCGCAGCGCATCGCCTTCTATCGCCTTCTT<br>GACGAGTTCTTCTAGTATGTAAGCCCTGTGCCTTCTAGTTGCCAGCCATCTGTTGTTTGCCCCTCCC<br>CCGTGCCTTCCTTGACCCTGGAAGGTGCCACTCCCACTGTCCTTTCCTAATAAAATGAGGAAATTGC<br>ATCGCATTGTCTGAGTAGGTGTCATTCTATTCTGGGGGGTGGGGTGGGGCAGGACAGCAAGGGGGAG<br>GATTGGGAAGACAATAGCAGGCATGCTGGGGATGCGGTGGGCTCTATGGTTAATTAACCAGTCAAGT<br>CAGCTACTTGGCGAGATCGACTTGTCTGGGTTTCGACTACGCTCAGAATTGCGTCAGTCAAGTTCGA<br>TCTGGTCCTTGCTATTGCACCCGTTCTCCGATTACGAGTTTCATTTAAATCATGTGAGCAAAAGGCC<br>AGCAAAAGGCCAGGAACCGTAAAAAGGCCGCGTTGCTGGCGTTTTTCCATAGGCTCCGCCCCCCTGA<br>CGAGCATCACAAAAATCGACGCTCAAGTCAGAGGTGGCGAAACCCGACAGGACTATAAAGATACCAG<br>GCGTTTCCCCCTGGAAGCTCCCTCGTGCGCTCTCCTGTTCCGACCCTGCCGCTTACCGGATACCTGT<br>CCGCCTTTCTCCCTTCGGGAAGCGTGGCGCTTTCTCATAGCTCACGCTGTAGGTATCTCAGTTCGGT<br>GTAGGTCGTTCGCTCCAAGCTGGGCTGTGTGCACGAACCCCCCGTTCAGCCCGACCGCTGCGCCTTA<br>TCCGGTAACTATCGTCTTGAGTCCAACCCGGTAAGACACGACTTATCGCCACTGGCAGCAGCCACTG<br>GTAACAGGATTAGCAGAGCGAGGTATGTAGGCGGTGCTACAGAGTTCTTGAAGTGGTGGCCTAACTA<br>CGGCTACACTAGAAGAACAGTATTTGGTATCTGCGCTCTGCTGAAGCCAGTTACCTTCGGAAAAAGA<br>GTTGGTAGCTCTTGATCCGGCAAACAAACCACCGCTGGTAGCGGTGGTTTTTTTGTTTGCAAGCAGC<br>AGATTACGCGCAGAAAAAAAGGATCTCAAGAAGATCCTTTGATCTTTTCTACGGGGTCTGACGCTCA<br>GTGGAACGAAAACTCACGTTAAGGGATTTTGGTCATGAGATTATCAAAAAGGATCTTCACCTAGATC<br>CTTTTAAATTAAAAATGAAGTTTTAAATCAATCTAAAGTATATATGAGTAAACTTGGTCTGACAGTT<br>ACCAATGCTTAATCAGTGAGGCACCTATCTCAGCGATCTGTCTATTTCGTTCATCCATAGTTGCATT<br>TAAATTTCCGAACTCTCCAAGGCCCTCGTCGGAAAATCTTCAAACCTTTCGTCCGATCCATCTTGCA<br>GGCTACCTCTCGAACGAACTATCGCAAGTCTCTTGGCCGGCCTTGCGCCTTGGCTATTGCTTGGCAG<br>CGCCTATCGCCAGGTATTACTCCAATCCCGAATATCCGAGATCGGGATCACCCGAGAGAAGTTCAAC<br>CTACATCCTCAATCCCGATCTATCCGAGATCCGAGGAATA (SEQ ID NO: 94) |
| RET-<br>005<br>LINE1-<br>GFP<br>ORF1-C<br>Linker_<br>Nucleo-<br>plasmin-<br>NLS | TATCGAAATCGGGGCGCGCCTGGTGTACCGAGAACGATCCTCTCAGTGCGAGTCTCGACGATCCATA<br>TCGTTGCTTGGCAGTCAGCCAGTCGGAATCCAGCTTGGGACCCAGGAAGTCCAATCGTCAGATATTG<br>TACTCAAGCCTGGTCACGGCAGCGTACCGATCTGTTTAAACCTAGATATTGATAGTCTGATCGGTCA<br>ACGTATAATCGAGTCCTAGCTTTTGCAAACATCTATCAAGAGACAGGATCAGCAGGAGGCTTTCGCA<br>TGAGTATTCAACATTTCCGTGTCGCCCTTATTCCCTTTTTTGCGGCATTTTGCCTTCCTGTTTTTGC<br>TCACCCAGAAACGCTGGTGAAAGTAAAAGATGCTGAAGATCAGTTGGGTGCGCGAGTGGGTTACATC<br>GAACTGGATCTCAACAGCGGTAAGATCCTTGAGAGTTTTCGCCCCGAAGAACGCTTTCCAATGATGA<br>GCACTTTTAAAGTTCTGCTATGTGGCGCGGTATTATCCCGTATTGACGCCGGGCAAGAGCAACTCGG<br>TCGCCGCATACACTATTCTCAGAATGACTTGGTTGAGTATTCACCAGTCACAGAAAAGCATCTTACG<br>GATGGCATGACAGTAAGAGAATTATGCAGTGCTGCCATAACCATGAGTGATAACACTGCGGCCAACT<br>TACTTCTGACAACGATTGGAGGACCGAAGGAGCTAACCGCTTTTTTGCACAACATGGGGGATCATGT<br>AACTCGCCTTGATCGTTGGGAACCGGAGCTGAATGAAGCCATACCAAACGACGAGCGTGACACCACG<br>ATGCCTGTAGCAATGGCAACAACCTTGCGTAAACTATTAACTGGCGAACTACTTACTCTAGCTTCCC<br>GGCAACAGTTGATAGACTGGATGGAGGCGGATAAAGTTGCAGGACCACTTCTGCGCTCGGCCCTTCC<br>GGCTGGCTGGTTTATTGCTGATAAATCTGGAGCCGGTGAGCGTGGGTCTCGCGGTATCATTGCAGCA<br>CTGGGGCCAGATGGTAAGCCCTCCCGTATCGTAGTTATCTACACGACGGGGAGTCAGGCAACTATGG |

TABLE 13-continued

Exemplary plasmid sequences

| Name | Sequence |
|---|---|
| | ATGAACGAAATAGACAGATCGCTGAGATAGGTGCCTCACTGATTAAGCATTGGTAACCGATTCTAGG |
| | TGCATTGGCGCAGAAAAAAATGCCTGATGCGACGCTGCGCGTCTTATACTCCCACATATGCCAGATT |
| | CAGCAACGGATACGGCTTCCCCAACTTGCCCACTTCCATACGTGTCCTCCTTACCAGAAATTTATCC |
| | TTAAGATCGTTTAAACTCGACTCTGGCTCTATCGAATCTCCGTCGTTTCGAGCTTACGCGAACAGCC |
| | GTGGCGCTCATTTGCTCGTCGGGCATCGAATCTCGTCAGCTATCGTCAGCTTACCTTTTTGGCAGCG |
| | ATCGCGGCTCCCGACATCTTGGACCATTAGCTCCACAGGTATCTTCTTCCCTCTAGTGGTCATAACA |
| | GCAGCTTCAGCTACCTCTCAATTCAAAAAACCCCTCAAGACCCGTTTAGAGGCCCCAAGGGGTTATG |
| | CTATCAATCGTTGCGTTACACACACAAAAAACCAACACACATCCATCTTCGATGGATAGCGATTTTA |
| | TTATCTAACTGCTGATCGAGTGTAGCCAGATCTAGTAATCAATTACGGGGTCATTAGTTCATAGCCC |
| | ATATATGGAGTTCCGCGTTACATAACTTACGGTAAATGGCCCGCCTGGCTGACCGCCCAACGACCCC |
| | CGCCCATTGACGTCAATAATGACGTATGTTCCCATAGTAACGCCAATAGGGACTTTCCATTGACGTC |
| | AATGGGTGGAGTATTTACGGTAAACTGCCCACTTGGCAGTACATCAAGTGTATCATATGCCAAGTAC |
| | GCCCCCTATTGACGTCAATGACGGTAAATGGCCCGCCTGGCATTATGCCCAGTACATGACCTTATGG |
| | GACTTTCCTACTTGGCAGTACATCTACGTATTAGTCATCGCTATTACCATGCTGATGCGGTTTTGGC |
| | AGTACATCAATGGGCGTGGATAGCGGTTTGACTCACGGGGATTTCCAAGTCTCCACCCCATTGACGT |
| | CAATGGGAGTTTGTTTTGGCACCAAAATCAACGGGACTTTCCAAAATGTCGTAACAACTCCGCCCCA |
| | TTGACGCAAATGGGCGGTAGGCGTGTACGGTGGGAGGTCTATATAAGCAGAGCTGGTTTAGTGAACC |
| | GTCAGATCAGATCTTTGTCGATCCTACCATCCACTCGACACACCCGCCAGCGGCCGCTAATACGACT |
| | CACTATAGGGAGAAGTACTGCCACCATGGGCAAGAAGCAAAATCGCAAGACGGGGAATTCCAAGACA |
| | CAATCCGCTAGCCCACCACCTAAAGAGCGTTCTAGCTCCCCTGCTACTGAGCAGTCCTGGATGGAAA |
| | ACGACTTCGATGAACTCCGGGAAGAGGGATTTAGGCGATCCAACTATTCAGAACTCCGCGAAGATAT |
| | CCAGACAAAGGGGAAGGAAGTCGAGAATTTCGAGAAGAACCTCGAGGAGTGCATCACCCGTATCACA |
| | AACACTGAGAAATGTCTCAAAGAACTCATGGAACTTAAGACAAAAGCCAGGGAGCTTCGAGAGGAGT |
| | GTCGGAGTCTGAGATCCAGGTGTGACCAGCTCGAGGAGCGCGTGAGCGCGATGGAAGACGAGATGAA |
| | CGAGATGAAAAGAGAGGGCAAATTCAGGGAGAAGCGCATTAAGAGGAACGAACAGAGTCTGCAGGAG |
| | ATTTGGGATTACGTCAAGAGGCCTAACCTGCGGTTGATCGGCGTCCCCGAGAGCGACGTAGAAAACG |
| | GGACTAAACTGGAGAATACACTTCAAGACATCATTCAAGAAAATTTTCCAAACCTGGCTCGGCAAGC |
| | TAATGTGCAAATCCAAGAGATCCAACGCACACCCCAGCGGTATAGCTCTCGGCGTGCCACCCCTAGG |
| | CATATTATCGTGCGCTTTACTAAGGTGGAGATGAAAGAGAAGATGCTGCGAGCCGCTCGGGAAAAGG |
| | GAAGGGTGACTTTGAAGGGCAAACCTATTCGGCTGACGGTTGACCTTAGCGCCGAGACACTCCAGGC |
| | ACGCCGGGAATGGGGCCCCATCTTTAATATCCTGAAGGAGAAGAACTTCCAGCCACGAATCTCTTAC |
| | CCTGCAAAGTTGAGTTTTATCTCCGAGGGTGAGATTAAGTATTTCATCGATAAACAGATGCTGCGAG |
| | ACTTCGTGACAACTCGCCCAGCTCTCAAGGAACTGCTCAAAGAGGCTCTTAATATGGAGCGCAATAA |
| | TAGATATCAACCCTTGCAGAACCACGCAAAGATGggcggcggcagcaaaaggccggcggccacgaaa |
| | aaggccggccaggcaaaaaagaaaaagTGAGACAGCCGTCAGACCATCAAGACTAGGAAGAAACTGC |
| | ATCAACTAATGAGCAAAATCACCAGCTAACATCATAGTATACATGACCGGCTCTAACTCACATATCA |
| | CCATCCTTACACTTAACATTAACGGCCTCAACTCAGCTATCAAGCGCCATCGGCTGGCCAGCTGGAT |
| | CAAATCACAGGATCCAAGCGTTTGTTGCATCCAAGAGACCCACCTGACCTGTAGAGATACTCACCGC |
| | CTCAAGATCAAGGGATGGCGAAAGATTTATCAGGCGAACGGTAAGCAGAAGAAAGCCGGAGTCGCAA |
| | TTCTGGTCTCAGACAAGACGGATTTCAAGCCCACCAAAATTAAGCGTGATAAGGAAGGTCACTATAT |
| | TATGGTGAAAGGCAGCATACAGCAGGAAGAACTTACCATATTGAACATCTACGCGCCAAACACCGGC |
| | GCACCTCGCTTTATCAAACAGGTCCTGTCCGATCTGCAGCGAGATCTGGATTCTCATACGTTGATTA |
| | TGGGTGATTTCAATACACCATTGAGCACCCTGGATCGCAGCACCAGGCAAAAGGTAAATAAAGACAC |
| | GCAAGAGCTCAATAGCGCACTGCATCAGGCAGATCTCATTGATATTTATCGCACTCTTCATCCTAAG |
| | AGTACCGAGTACACATTCTTCAGCGCCCCACATCATACATACTCAAAGATCGATCATATCGTCGGCT |
| | CAAAGGCTCTGCTGTCAAAGTGCAAGCGCACAGAGATAATTACAAATTACCTGTCAGATCATAGCGC |
| | GATCAAGCTCGAGCTGAGAATCAAGAACCTGACCCAGAGCCGGAGTACCACTTGGAAGCTTAATAAC |
| | CTGCTGCTCAACGATTATTGGGTCCACAATGAGATGAAGGCAGAGATTAAAATGTTCTTCGAAACAA |
| | ATGAGAATAAGGATACTACCTATCAAAACCTTTGGGATGCCTTTAAGGCCGTCTGCAGAGGCAAGTT |
| | CATCGCCCTCAACGCCTATAAAAGAAAACAAGAGAGATCTAAGATCGATACTCTCACCTCTCAGCTG |
| | AAGGAGTTGGAGAAACAGGAACAGACCCACTCCAAGGCGTCAAGACGGCAGGAGATCACAAAGATTC |
| | GCGCCGAGTTGAAAGAGATCGAAACCCAAAAGACTCTTCAGAAAATTAACGAGTCTCGTAGTTGGTT |
| | CTTCGAGCGGATTAATAAGATAGACAGACCTCTGGCACGACTGATTAAGAAGAAGCGCGAAAAGAAC |
| | CAGATTGATACCATCAAGAACGACAAGGGCGACATCACTACTGACCCGACCGAGATCCAGACCACTA |
| | TTCGGGAGTATTATAAGCATTTGTATGCTAACAAGCTTGAGAACCTGGAAGAGATGGACACTTTTCT |
| | GGATACCTATACTCTGCCACGGCTTAATCAAGAGGAAGTCGAGTCCCTCAACCGCCCAATTACAGGA |
| | AGCGAGATTGTGGCCATAATTAACTCCCTGCCGACAAAGAAATCTCCTGGTCCGGACGGGTTTACAG |
| | CTGAGTTTTATCAACGGTATATGGAAGAGCTTGTACCGTTTCTGCTCAAGCTCTTTCAGTCTATAGA |
| | AAAGGAAGGCATCTTGCCCAATTCCTTCTACGAAGCTTCTATAATACTTATTCCCAAACCAGGACGC |
| | GATACCACAAAGAAGGAAAACTTCCGGCCCATTAGTCTCATGAATATCGACGCTAAAATATTGAACA |
| | AGATTCTCGCCAACAGAATCCAACAACATATTAAGAAATTGATACATCACGACCAGGTGGGGTTTAT |
| | ACCTGGCATGCAGGGCTGGTTTAACATCCGGAAGAGTATTAACGTCATTCAACACATTAATAGAGCT |
| | AAGGATAAGAATCATATGATCATCTCTATAGACGCGGAAAAGGCATTCGATAAGATTCAGCAGCCAT |
| | TTATGCTCAAGACTCTGAACAAACTCGGCATCGACGGAACATATTTTAAGATTATTCGCGCAATTTA |
| | CGATAAGCCGACTGCTAACATTATCCTTAACGGCCAAAAGCTCGAGGCCTTTCCGCTCAAGACTGGA |
| | ACCCGCCAAGGCTGTCCCCTCTCCCCGCTTTTGTTTAATATTGTACTCGAGGTGCTGGCTAGGGCTA |
| | TTCGTCAAGAGAAAGAGATTAAAGGGATACAGCTCGGGAAGGAAGAGGTCAAGCTTTCCTTGTTCGC |
| | CGATGATATGATTGTGTACCTGGAGAATCCTATTGTGTCTGCTCAGAACCTTCTTAAACTTATTTCT |
| | AACTTTAGCAAGGTCAGCGGCTATAAGATTAACGTCCAGAAATCTCAGGCCTTTCTGTACACAAATA |
| | ATCGACAGACCGAATCCCAGATAATGGGTGAGCTTCCGTTTGTCATAGCCAGCAAAAGGATAAAGTA |
| | TCTCGGAATCCAGCTGACACGAGACGTTAAAGATTTGTTTAAGGAAAATTACAAGCCTCTCCTGAAA |
| | GAGATTAAGGAAGATACTAATAAGTGGAAGAATATCCCCTGTTCATGGGTTGGCAGAATCAACATAG |
| | TGAAGATGGCAATACTTCCTAAAGTGATATATCGCTTTAACGCCATCCCAATTAAACTGCCTATGAC |
| | CTTCTTTACGGAGCTCGAGAAAACAACCCTTAAATTTATATGGAATCAAAAGAGAGCAAGAATAGCG |
| | AAGTCCATCTTGAGCCAGAAGAATAAGGCCGGTGGATTACTTTGCCTGATTTTAAGTTGTATTATA |
| | AAGCCACAGTAACTAAGACAGCCTGGTATTGGTATCAGAATAGAGACATCGACCAGTGGAATCGGAC |

TABLE 13-continued

| Exemplary plasmid sequences | |
|---|---|
| Name | Sequence |
| | CGAACCATCAGAGATAATGCCCCACATCTATAATTACCTTATATTCGATAAGCCAGAAAAGAATAAA<br>CAGTGGGGCAAAGACAGCCTCTTCAACAAGTGGTGTTGGGAGAATTGGCTGGCCATATGCCGGAAAC<br>TCAAGCTCGACCCCTTTCTTACACCCTACACTAAAATCAACAGTAGGTGGATCAAGGACTTGAATGT<br>CAAGCCAAAGACTATAAAGACACTGGAAGAGAATCTTGGGATCACAATACAAGATATAGGCGTCGGC<br>AAAGATTTTATGTCAAAGACGCCCAAGGCCATGGCCACTAAGGATAAGATTGATAAGTGGGACCTTA<br>TTAAGCTCAAAAGCTTCTGTACTGCCAAGGAGACCACGATCAGAGTTAATAGGCAGCCCACTACATG<br>GGAAAAGATTTTCGCCACTTATTCATCAGATAAGGGGTTGATAAGCAGAATATATAACGAGCTGAAG<br>CAGATCTACAAGAAGAAAACGAATAATCCCATCAAGAAGTGGGCAAAAGATATGAACAGGCATTTTA<br>GCAAAGAGGATATCTACGCCGCGAAGAAGCATATGAAGAAGTGTAGTTCAAGCTTGGCCATTCGTGA<br>GATGCAGATTAAGACGACCATGCGATACCACCTTACCCCAGTGAGGATGGCAATTATCAAGAAATCT<br>GGCAATAATAGATGTTGGCGGGGCTGTGGCGAGATTGGCACCCTGCTCCATTGCTGGTGGGATTGCA<br>AGCTGGTGCAGCCGCTTTGGAAATCAGTCTGGCGCTTTCTGAGGGACCTCGAGCTTGAGATTCCCTT<br>CGATCCCGCAATTCCCTTGCTCGGAATCTATCCTAACGAATACAAGAGCTGTTGTTACAAGGATACG<br>TGTACCCGGATGTTCATCGCGGCCTTGTTTACGATAGCTAAGACGTGGAATCAGCCTAAGTGCCCCA<br>CAATGATCGATTGGATCAAGAAAATGTGGCATATTTATACCATGGAGTATTACGCAGCAATTAAGAA<br>TGACGAATTTATTTCCTTCGTTGGGACCTGGATGAAGCTGGAGACTATTATTCTGAGCAAGCTGTCT<br>CAGGAGCAAAAGACAAAGCATAGAATCTTCTCTCTCATTGGTGGTAACGACTACAAAGACGATGACG<br>ACAAGTAAAGCGCTTCTAGAAGTTGTCTCCTCCTGCACTGACTGACTGATACAATCGATTTCTGGAT<br>CCGCAGGCCTAATCAACCTCTGGATTACAAAATTTGTGAAAGATTGACTGGTATTCTTAACTATGTT<br>GCTCCTTTTACGCTATGTGGATACGCTGCTTTAATGCCTTTGTATCATGCTATTGCTTCCCGTATGG<br>CTTTCATTTTCTCCTCCTTGTATAAATCCTGGTTGCTGTCTCTTTATGAGGAGTTGTGGCCCGTTGT<br>CAGGCAACGTGGCGTGGTGTGCACTGTGTTTGCTGACGCAACCCCCACTGGTTGGGGCATTGCCACC<br>ACCTGTCAGCTCCTTTCCGGGACTTTCGCTTTCCCCCTCCCTATTGCCACGGCGGAACTCATCGCCG<br>CCTGCCTTGCCCGCTGCTGGACAGGGGCTCGGCTGTTGGGCACTGACAATTCCGTGGTGTTGTCGGG<br>GAAGCTGACGTCCTTTCCATGGCTGCTCGCCTGTGTTGCCACCTGGATTCTGCGCGGGACGTCCTTC<br>TGCTACGTCCCTTCGGCCCTCAATCCAGCGGACCTTCCTTCCCGCtgagagacacaaaaaattccaa<br>cacactattgcaatgaaaataaatttcctttattagccagaagtcagatgctcaaggggcttcatga<br>tgtccccataatttttggcagagggaaaaagatctcagtggtatttgtgagccagggcattggcctt<br>ctgataggcagcctgcacctgaggagtgcggccgctttacttgtacagctcgtccatgccgagagtg<br>atcccggcggcggtcacgaactccagcaggaccatgtgatcgcgcttctcgttggggtctttgctca<br>gggcggactgggtgctcaggtagtggttgtcgggcagcagcacggggccgtcgccgatgggggtgtt<br>ctgctggtagtggtcggcgagctgcacgctgccgtcctcgatgttgtggcggatcttgaagttcacc<br>ttgatgccgttcttctgcttgtcggccatgatatagacgttgtggctgttgtagttgtactccagct<br>tgtgccccaggatgttgccgtcctccttgaagtcgatgcccttcagctcgatgcggttcaccagggt<br>gtcgccctcgaacttcacctcggcgcgggtcttgtagttgccgtcgtccttgaagaagatggtgcgc<br>tcctggacgtagccttcgggcatggcggacttgaagaagtcgtgctgcttcatgtggtcggggtagc<br>ggctgaagcactgcacgccgtaggtcagggtggtcacgagggtgggccagggcacgggcagcttgcc<br>ggtggtgcagatgaacttcagggtcagcttgccgtaggtggcatcgccctcgccctcgccggacacg<br>ctgaacttgtggccgtttacgtcgccgtccagctcgaccaggatgggcaccaccccggtgaacagct<br>cctcgcccttgctcaccatggtggcgggatctgacggttcactaaaccagctctgcttatatagacc<br>tcccaccgtacacgcctaccgcccatttgcgtcaatggggcggagttgttacgacattttggaaagt<br>cccgttgattttggtgccaaaacaaactcccattgacgtcaatggggtggagacttggaaatccccg<br>tgagtcaaaccgctatccacgcccattgatgtactgccaaaaccgcatcaccatggtaatagcgatg<br>actaatacgtagatgtactgccaagtaggaaagtcccataaggtcatgtactgggcataatgccagg<br>cgggccatttaccgtcattgacgtcaatagggggcgtacttggcatatgatacacttgatgtactgc<br>caagtgggcagtttaccgtaaatactccacccattgacgtcaatggaaagtccctattggcgttact<br>atgggaacatacgtcattattgacgtcaatgggcgggggtcgttgggcggtcagccaggcgggccat<br>ttaccgtaagttatgtaacgGGCCTGCTGCCGGCTCTGCGGCCTCTTCCGCGTCTTCGCCTTCGCCC<br>TCAGACGAGTCGGATCTCCCTTTGGGCCGCCTCCCCGCCTGTCTAGCTTGACTGACTGAGATACAGC<br>GTACCTTCAGCTCACAGACATGATAAGATACATTGATGAGTTTGGACAAACCACAACTAGAATGCAG<br>TGAAAAAAATGCTTTATTTGTGAAATTTGTGATGCTATTGCTTTATTTGTAACCATTATAAGCTGCA<br>ATAAACAAGTTAACAACAACAATTGCATTCATTTTATGTTTCAGGTTCAGGGGGAGGTGTGGGAGGT<br>TTTTTAAAGCAAGTAAAACCTCTACAAATGTGGTATTGGCCCATCTCTATCGGTATCGTAGCATAAC<br>CCCTTGGGGCCTCTAAACGGGTCTTGAGGGGTTTTTTGTGCCCCTCGGGCCGGATTGCTATCTACCG<br>GCATTGGCGCAGAAAAAAATGCCTGATGCGACGCTGCGCGTCTTATACTCCCACATATGCCAGATTC<br>AGCAACGGATACGGCTTCCCCAACTTGCCCACTTCCATACGTGTCCTCCTTACCAGAAATTTATCCT<br>TAAGGTCGTCAGCTATCCTGCAGGCGATCTCTCGATTTCGATCAAGACATTCCTTTAATGGTCTTTT<br>CTGGACACCACTAGGGGTCAGAAGTAGTTCATCAAACTTTCTTCCCTCCCTAATCTCATTGGTTACC<br>TTGGGCTATCGAAACTTAATTAAGCGATCTGCATCTCAATTAGTCAGCAACCATAGTCCCGCCCCTA<br>ACTCCGCCCATCCCGCCCCTAACTCCGCCCAGTTCCGCCCATTCTCCGCCCCATCGCTGACTAATTT<br>TTTTTATTTATGCAGAGGCCGAGGCCGCCTCGGCCTCTGAGCTATTCCAGAAGTAGTGAGGAGGCTT<br>TTTTGGAGGCCTAGGCTTTTGCAAAGGAGGTAGCCAACATGATTGAACAAGATGGATTGCACGCAGG<br>TTCTCCCGCCGCTTGGGTGGAGAGGCTATTCGGCTATGACTGGGCACAACAGACAATCGGCTGCTCT<br>GATGCCGCCGTGTTCCGGCTGTCAGCGCAGGGGCGCCCGGTTCTTTTTGTCAAGACCGACCTGTCCG<br>GTGCCCTGAATGAACTCCAGGACGAGGCAGCGCGGCTATCGTGGCTGGCCACGACGGGCGTTCCTTG<br>CGCAGCTGTGCTCGACGTTGTCACTGAAGCGGGAAGGGACTGGCTGCTATTGGGCGAAGTGCCGGGG<br>CAGGATCTCCTGTCATCTCACCTTGCTCCTGCCGAGAAAGTATCCATCATGGCTGATGCAATGCGGC<br>GGCTGCATACGCTTGATCCGGCTACCTGCCCATTCGACCACCAAGCGAAACATCGCATCGAGCGAGC<br>ACGTACTCGGATGGAAGCCGGTCTTGTCGATCAGGATGATCTGGACGAAGAGCATCAGGGGCTCGCG<br>CCAGCCGAACTGTTCGCCAGGCTCAAGGCGCGGATGCCCGACGGCGAGGATCTCGTCGTGACCCACG<br>GCGATGCCTGCTTGCCGAATATCATGGTGGAAAATGGCCGCTTTTCTGGATTCATCGACTGTGGCCG<br>GCTGGGTGTGGCGGACCGCTATCAGGACATAGCGTTGGCTACCCGTGATATTGCTGAAGAGCTTGGC<br>GGCGAATGGGCTGACCGCTTCCTCGTGCTTTACGGTATCGCCGCTCCCGATTCGCAGCGCATCGCCT<br>TCTATCGCCTTCTTGACGAGTTCTTCTAGTATGTAAGCCCTGTGCCTTCTAGTTGCCAGCCATCTGT<br>TGTTTGCCCCTCCCCCGTGCCTTCCTTGACCCTGGAAGGTGCCACTCCCACTGTCCTTTCCTAATAA<br>AATGAGGAAATTGCATCGCATTGTCTGAGTAGGTGTCATTCTATTCTGGGGGGTGGGGTGGGGCAGG |

TABLE 13-continued

Exemplary plasmid sequences

| Name | Sequence |
| --- | --- |
| | ACAGCAAGGGGGAGGATTGGGAAGACAATAGCAGGCATGCTGGGGATGCGGTGGGCTCTATGGTTAA<br>TTAACCAGTCAAGTCAGCTACTTGGCGAGATCGACTTGTCTGGGTTTCGACTACGCTCAGAATTGCG<br>TCAGTCAAGTTCGATCTGGTCCTTGCTATTGCACCCGTTCTCCGATTACGAGTTTCATTTAAATCAT<br>GTGAGCAAAAGGCCAGCAAAAGGCCAGGAACCGTAAAAAGGCCGCGTTGCTGGCGTTTTTCCATAGG<br>CTCCGCCCCCCTGACGAGCATCACAAAAATCGACGCTCAAGTCAGAGGTGGCGAAACCCGACAGGAC<br>TATAAAGATACCAGGCGTTTCCCCCTGGAAGCTCCCTCGTGCGCTCTCCTGTTCCGACCCTGCCGCT<br>TACCGGATACCTGTCCGCCTTTCTCCCTTCGGGAAGCGTGGCGCTTTCTCATAGCTCACGCTGTAGG<br>TATCTCAGTTCGGTGTAGGTCGTTCGCTCCAAGCTGGGCTGTGTGCACGAACCCCCCGTTCAGCCCG<br>ACCGCTGCGCCTTATCCGGTAACTATCGTCTTGAGTCCAACCCGGTAAGACACGACTTATCGCCACT<br>GGCAGCAGCCACTGGTAACAGGATTAGCAGAGCGAGGTATGTAGGCGGTGCTACAGAGTTCTTGAAG<br>TGGTGGCCTAACTACGGCTACACTAGAAGAACAGTATTTGGTATCTGCGCTCTGCTGAAGCCAGTTA<br>CCTTCGGAAAAAGAGTTGGTAGCTCTTGATCCGGCAAACAAACCACCGCTGGTAGCGGTGGTTTTTT<br>TGTTTGCAAGCAGCAGATTACGCGCAGAAAAAAAGGATCTCAAGAAGATCCTTTGATCTTTTCTACG<br>GGGTCTGACGCTCAGTGGAACGAAAACTCACGTTAAGGGATTTTGGTCATGAGATTATCAAAAAGGA<br>TCTTCACCTAGATCCTTTTAAATTAAAAATGAAGTTTTAAATCAATCTAAAGTATATATGAGTAAAC<br>TTGGTCTGACAGTTACCAATGCTTAATCAGTGAGGCACCTATCTCAGCGATCTGTCTATTTCGTTCA<br>TCCATAGTTGCATTTAAATTTCCGAACTCTCCAAGGCCCTCGTCGGAAAATCTTCAAACCTTTCGTC<br>CGATCCATCTTGCAGGCTACCTCTCGAACGAACTATCGCAAGTCTCTTGGCCGGCCTTGCGCCTTGG<br>CTATTGCTTGGCAGCGCCTATCGCCAGGTATTACTCCAATCCCGAATATCCGAGATCGGGATCACCC<br>GAGAGAAGTTCAACCTACATCCTCAATCCCGATCTATCCGAGATCCGAGGAA (SEQ ID NO:<br>95) |
| RET-<br>006<br>LINE1-<br>GFP<br>ORF1-<br>NSV40<br>NLS | GTCGGAAAATCTTCAAACCTTTCGTCCGATCCATCTTGCAGGCTACCTCTCGAACGAACTATCGCAA<br>GTCTCTTGGCCGGCCTTGCGCCTTGGCTATTGCTTGGCAGCGCCTATCGCCAGGTATTACTCCAATC<br>CCGAATATCCGAGATCGGGATCACCCGAGAGAAGTTCAACCTACATCCTCAATCCCGATCTATCCGA<br>GATCCGAGGAATATCGAAATCGGGGCGCGCCTGGTGTACCGAGAACGATCCTCTCAGTGCGAGTCTC<br>GACGATCCATATCGTTGCTTGGCAGTCAGCCAGTCGGAATCCAGCTTGGGACCCAGGAAGTCCAATC<br>GTCAGATATTGTACTCAAGCCTGGTCACGGCAGCGTACCGATCTGTTTAAACCTAGATATTGATAGT<br>CTGATCGGTCAACGTATAATCGAGTCCTAGCTTTTGCAAACATCTATCAAGAGACAGGATCAGCAGG<br>AGGCTTTCGCATGAGTATTCAACATTTCCGTGTCGCCCTTATTCCCTTTTTTGCGGCATTTTGCCTT<br>CCTGTTTTTGCTCACCCAGAAACGCTGGTGAAAGTAAAAGATGCTGAAGATCAGTTGGGTGCGCGAG<br>TGGGTTACATCGAACTGGATCTCAACAGCGGTAAGATCCTTGAGAGTTTTCGCCCCGAAGAACGCTT<br>TCCAATGATGAGCACTTTTAAAGTTCTGCTATGTGGCGCGGTATTATCCCGTATTGACGCCGGGCAA<br>GAGCAACTCGGTCGCCGCATACACTATTCTCAGAATGACTTGGTTGAGTATTCACCAGTCACAGAAA<br>AGCATCTTACGGATGGCATGACAGTAAGAGAATTATGCAGTGCTGCCATAACCATGAGTGATAACAC<br>TGCGGCCAACTTACTTCTGACAACGATTGGAGGACCGAAGGAGCTAACCGCTTTTTTGCACAACATG<br>GGGGATCATGTAACTCGCCTTGATCGTTGGGAACCGGAGCTGAATGAAGCCATACCAAACGACGAGC<br>GTGACACCACGATGCCTGTAGCAATGGCAACAACCTTGCGTAAACTATTAACTGGCGAACTACTTAC<br>TCTAGCTTCCCGGCAACAGTTGATAGACTGGATGGAGGCGGATAAAGTTGCAGGACCACTTCTGCGC<br>TCGGCCCTTCCGGCTGGCTGGTTTATTGCTGATAAATCTGGAGCCGGTGAGCGTGGGTCTCGCGGTA<br>TCATTGCAGCACTGGGGCCAGATGGTAAGCCCTCCCGTATCGTAGTTATCTACACGACGGGGAGTCA<br>GGCAACTATGGATGAACGAAATAGACAGATCGCTGAGATAGGTGCCTCACTGATTAAGCATTGGTAA<br>CCGATTCTAGGTGCATTGGCGCAGAAAAAAATGCCTGATGCGACGCTGCGCGTCTTATACTCCCACA<br>TATGCCAGATTCAGCAACGGATACGGCTTCCCCAACTTGCCCACTTCCATACGTGTCCTCCTTACCA<br>GAAATTTATCCTTAAGATCGTTTAAACTCGACTCTGGCTCTATCGAATCTCCGTCGTTTCGAGCTTA<br>CGCGAACAGCCGTGGCGCTCATTTGCTCGTCGGGCATCGAATCTCGTCAGCTATCGTCAGCTTACCT<br>TTTTGGCAGCGATCGCGGCTCCCGACATCTTGGACCATTAGCTCCACAGGTATCTTCTTCCCTCTAG<br>TGGTCATAACAGCAGCTTCAGCTACCTCTCAATTCAAAAAACCCCTCAAGACCCGTTTAGAGGCCCC<br>AAGGGGTTATGCTATCAATCGTTGCGTTACACACACAAAAAACCAACACACATCCATCTTCGATGGA<br>TAGCGATTTTATTATCTAACTGCTGATCGAGTGTAGCCAGATCTAGTAATCAATTACGGGGTCATTA<br>GTTCATAGCCCATATATGGAGTTCCGCGTTACATAACTTACGGTAAATGGCCCGCCTGGCTGACCGC<br>CCAACGACCCCCGCCCATTGACGTCAATAATGACGTATGTTCCCATAGTAACGCCAATAGGGACTTT<br>CCATTGACGTCAATGGGTGGAGTATTTACGGTAAACTGCCCACTTGGCAGTACATCAAGTGTATCAT<br>ATGCCAAGTACGCCCCCTATTGACGTCAATGACGGTAAATGGCCCGCCTGGCATTATGCCCAGTACA<br>TGACCTTATGGGACTTTCCTACTTGGCAGTACATCTACGTATTAGTCATCGCTATTACCATGCTGAT<br>GCGGTTTTGGCAGTACATCAATGGGCGTGGATAGCGGTTTGACTCACGGGGATTTCCAAGTCTCCAC<br>CCCATTGACGTCAATGGGAGTTTGTTTTGGCACCAAAATCAACGGGACTTTCCAAAATGTCGTAACA<br>ACTCCGCCCCATTGACGCAAATGGGCGGTAGGCGTGTACGGTGGGAGGTCTATATAAGCAGAGCTGG<br>TTTAGTGAACCGTCAGATCAGATCTTTGTCGATCCTACCATCCACTCGACACACCCGCCAGCGGCCG<br>CTAATACGACTCACTATAGGGAGAAGTACTGCCACCATGccaaagaagaagcggaaggtcGGCAAGA<br>AGCAAAATCGCAAGACGGGGAATTCCAAGACACAATCCGCTAGCCCACCACCTAAAGAGCGTTCTAG<br>CTCCCCTGCTACTGAGCAGTCCTGGATGGAAAACGACTTCGATGAACTCCGGGAAGAGGGATTTAGG<br>CGATCCAACTATTCAGAACTCCGCGAAGATATCCAGACAAAGGGGAAGGAAGTCGAGAATTTCGAGA<br>AGAACCTCGAGGAGTGCATCACCCGTATCACAAACACTGAGAAATGTCTCAAAGAACTCATGGAACT<br>TAAGACAAAAGCCAGGGAGCTTCGAGAGGAGTGTCGGAGTCTGAGATCCAGGTGTGACCAGCTCGAG<br>GAGCGCGTGAGCGCGATGGAAGACGAGATGAACGAGATGAAAAGAGAGGGCAAATTCAGGGAGAAGC<br>GCATTAAGAGGAACGAACAGAGTCTGCAGGAGATTTGGGATTACGTCAAGAGGCCTAACCTGCGGTT<br>GATCGGCGTCCCCGAGAGCGACGTAGAAAACGGGACTAAACTGGAGAATACACTTCAAGACATCATT<br>CAAGAAAATTTTCCAAACCTGGCTCGGCAAGCTAATGTGCAAATCCAAGAGATCCAACGCACACCCC<br>AGCGGTATAGCTCTCGGCGTGCCACCCCTAGGCATATTATCGTGCGCTTTACTAAGGTGGAGATGAA<br>AGAGAAGATGCTGCGAGCCGCTCGGGAAAAGGGAAGGGTGACTTTGAAGGGCAAACCTATTCGGCTG<br>ACGGTTGACCTTAGCGCCGAGACACTCCAGGCACGCCGGGAATGGGGCCCCATCTTTAATATCCTGA<br>AGGAGAAGAACTTCCAGCCACGAATCTCTTACCCTGCAAAGTTGAGTTTTATCTCCGAGGGTGAGAT<br>TAAGTATTTCATCGATAAACAGATGCTGCGAGACTTCGTGACAACTCGCCCAGCTCTCAAGGAACTG<br>CTCAAAGAGGCTCTTAATATGGAGCGCAATAATAGATATCAACCCTTGCAGAACCACGCAAAGATGT<br>GAGACAGCCGTCAGACCATCAAGACTAGGAAGAAACTGCATCAACTAATGAGCAAAATCACCAGCTA |

TABLE 13-continued

Exemplary plasmid sequences

| Name | Sequence |
|---|---|
| | ACATCATAGTATACATGACCGGCTCTAACTCACATATCACCATCCTTACACTTAACATTAACGGCCT |
| | CAACTCAGCTATCAAGCGCCATCGGCTGGCCAGCTGGATCAAATCACAGGATCCAAGCGTTTGTTGC |
| | ATCCAAGAGACCCACCTGACCTGTAGAGATACTCACCGCCTCAAGATCAAGGGATGGCGAAAGATTT |
| | ATCAGGCGAACGGTAAGCAGAAGAAAGCCGGAGTCGCAATTCTGGTCTCAGACAAGACGGATTTCAA |
| | GCCCACCAAAATTAAGCGTGATAAGGAAGGTCACTATATTATGGTGAAAGGCAGCATACAGCAGGAA |
| | GAACTTACCATATTGAACATCTACGCGCCAAACACCGGCGCACCTCGCTTTATCAAACAGGTCCTGT |
| | CCGATCTGCAGCGAGATCTGGATTCTCATACGTTGATTATGGGTGATTTCAATACACCATTGAGCAC |
| | CCTGGATCGCAGCACCAGGCAAAAGGTAAATAAAGACACGCAAGAGCTCAATAGCGCACTGCATCAG |
| | GCAGATCTCATTGATATTTATCGCACTCTTCATCCTAAGAGTACCGAGTACACATTCTTCAGCGCCC |
| | CACATCATACATACTCAAAGATCGATCATATCGTCGGCTCAAAGGCTCTGCTGTCAAAGTGCAAGCG |
| | CACAGAGATAATTACAAATTACCTGTCAGATCATAGCGCGATCAAGCTCGAGCTGAGAATCAAGAAC |
| | CTGACCCAGAGCCGGAGTACCACTTGGAAGCTTAATAACCTGCTGCTCAACGATTATTGGGTCCACA |
| | ATGAGATGAAGGCAGAGATTAAAATGTTCTTCGAAACAAATGAGAATAAGGATACTACCTATCAAAA |
| | CCTTTGGGATGCCTTTAAGGCCGTCTGCAGAGGCAAGTTCATCGCCCTCAACGCCTATAAAAGAAAA |
| | CAAGAGAGATCTAAGATCGATACTCTCACCTCTCAGCTGAAGGAGTTGGAGAAACAGGAACAGACCC |
| | ACTCCAAGGCGTCAAGACGGCAGGAGATCACAAAGATTCGCGCCGAGTTGAAAGAGATCGAAACCCA |
| | AAAGACTCTTCAGAAAATTAACGAGTCTCGTAGTTGGTTCTTCGAGCGGATTAATAAGATAGACAGA |
| | CCTCTGGCACGACTGATTAAGAAGAAGCGCGAAAAGAACCAGATTGATACCATCAAGAACGACAAGG |
| | GCGACATCACTACTGACCCGACCGAGATCCAGACCACTATTCGGGAGTATTATAAGCATTTGTATGC |
| | TAACAAGCTTGAGAACCTGGAAGAGATGGACACTTTTCTGGATACCTATACTCTGCCACGGCTTAAT |
| | CAAGAGGAAGTCGAGTCCCTCAACCGCCCAATTACAGGAAGCGAGATTGTGGCCATAATTAACTCCC |
| | TGCCGACAAAGAAATCTCCTGGTCCGGACGGGTTTACAGCTGAGTTTTATCAACGGTATATGGAAGA |
| | GCTTGTACCGTTTCTGCTCAAGCTCTTTCAGTCTATAGAAAAGGAAGGCATCTTGCCCAATTCCTTC |
| | TACGAAGCTTCTATAATACTTATTCCCAAACCAGGACGCGATACCACAAAGAAGGAAAACTTCCGGC |
| | CCATTAGTCTCATGAATATCGACGCTAAAATATTGAACAAGATTCTCGCCAACAGAATCCAACAACA |
| | TATTAAGAAATTGATACATCACGACCAGGTGGGGTTTATACCTGGCATGCAGGGCTGGTTTAACATC |
| | CGGAAGAGTATTAACGTCATTCAACACATTAATAGAGCTAAGGATAAGAATCATATGATCATCTCTA |
| | TAGACGCGGAAAAGGCATTCGATAAGATTCAGCAGCCATTTATGCTCAAGACTCTGAACAAACTCGG |
| | CATCGACGGAACATATTTTAAGATTATTCGCGCAATTTACGATAAGCCGACTGCTAACATTATCCTT |
| | AACGGCCAAAAGCTCGAGGCCTTTCCGCTCAAGACTGGAACCCGCCAAGGCTGTCCCCTCTCCCCGC |
| | TTTTGTTTAATATTGTACTCGAGGTGCTGGCTAGGGCTATTCGTCAAGAGAAAGAGATTAAAGGGAT |
| | ACAGCTCGGGAAGGAAGAGGTCAAGCTTTCCTTGTTCGCCGATGATATGATTGTGTACCTGGAGAAT |
| | CCTATTGTGTCTGCTCAGAACCTTCTTAAACTTATTTCTAACTTTAGCAAGGTCAGCGGCTATAAGA |
| | TTAACGTCCAGAAATCTCAGGCCTTTCTGTACACAAATAATCGACAGACCGAATCCCAGATAATGGG |
| | TGAGCTTCCGTTTGTCATAGCCAGCAAAAGGATAAAGTATCTCGGAATCCAGCTGACACGAGACGTT |
| | AAAGATTTGTTTAAGGAAAATTACAAGCCTCTCCTGAAAGAGATTAAGGAAGATACTAATAAGTGGA |
| | AGAATATCCCCTGTTCATGGGTTGGCAGAATCAACATAGTGAAGATGGCAATACTTCCTAAAGTGAT |
| | ATATCGCTTTAACGCCATCCCAATTAAACTGCCTATGACCTTCTTTACGGAGCTCGAGAAAACAACC |
| | CTTAAATTTATATGGAATCAAAAGAGAGCAAGAATAGCGAAGTCCATCTTGAGCCAGAAGAATAAGG |
| | CCGGTGGGATTACTTTGCCTGATTTTAAGTTGTATTATAAAGCCACAGTAACTAAGACAGCCTGGTA |
| | TTGGTATCAGAATAGAGACATCGACCAGTGGAATCGGACCGAACCATCAGAGATAATGCCCCACATC |
| | TATAATTACCTTATATTCGATAAGCCAGAAAAGAATAAACAGTGGGGCAAAGACAGCCTCTTCAACA |
| | AGTGGTGTTGGGAGAATTGGCTGGCCATATGCCGGAAACTCAAGCTCGACCCCTTTCTTACACCCTA |
| | CACTAAAATCAACAGTAGGTGGATCAAGGACTTGAATGTCAAGCCAAAGACTATAAAGACACTGGAA |
| | GAGAATCTTGGGATCACAATACAAGATATAGGCGTCGGCAAAGATTTTATGTCAAAGACGCCCAAGG |
| | CCATGGCCACTAAGGATAAGATTGATAAGTGGGACCTTATTAAGCTCAAAAGCTTCTGTACTGCCAA |
| | GGAGACCACGATCAGAGTTAATAGGCAGCCCACTACATGGGAAAAGATTTTCGCCACTTATTCATCA |
| | GATAAGGGGTTGATAAGCAGAATATATAACGAGCTGAAGCAGATCTACAAGAAGAAAACGAATAATC |
| | CCATCAAGAAGTGGGCAAAAGATATGAACAGGCATTTTAGCAAAGAGGATATCTACGCCGCGAAGAA |
| | GCATATGAAGAAGTGTAGTTCAAGCTTGGCCATTCGTGAGATGCAGATTAAGACGACCATGCGATAC |
| | CACCTTACCCCAGTGAGGATGGCAATTATCAAGAAATCTGGCAATAATAGATGTTGGCGGGGCTGTG |
| | GCGAGATTGGCACCCTGCTCCATTGCTGGTGGGATTGCAAGCTGGTGCAGCCGCTTTGGAAATCAGT |
| | CTGGCGCTTTCTGAGGGACCTCGAGCTTGAGATTCCCTTCGATCCCGCAATTCCCTTGCTCGGAATC |
| | TATCCTAACGAATACAAGAGCTGTTGTTACAAGGATACGTGTACCCGGATGTTCATCGCGGCCTTGT |
| | TTACGATAGCTAAGACGTGGAATCAGCCTAAGTGCCCCACAATGATCGATTGGATCAAGAAAATGTG |
| | GCATATTTATACCATGGAGTATTACGCAGCAATTAAGAATGACGAATTTATTTCCTTCGTTGGGACC |
| | TGGATGAAGCTGGAGACTATTATTCTGAGCAAGCTGTCTCAGGAGCAAAAGACAAAGCATAGAATCT |
| | TCTCTCTCATTGGTGGTAACGACTACAAAGACGATGACGACAAGTAAAGCGCTTCTAGAAGTTGTCT |
| | CCTCCTGCACTGACTGACTGATACAATCGATTTCTGGATCCGCAGGCCTAATCAACCTCTGGATTAC |
| | AAAATTTGTGAAAGATTGACTGGTATTCTTAACTATGTTGCTCCTTTTACGCTATGTGGATACGCTG |
| | CTTTAATGCCTTTGTATCATGCTATTGCTTCCCGTATGGCTTTCATTTTCTCCTCCTTGTATAAATC |
| | CTGGTTGCTGTCTCTTTATGAGGAGTTGTGGCCCGTTGTCAGGCAACGTGGCGTGGTGTGCACTGTG |
| | TTTGCTGACGCAACCCCCACTGGTTGGGGCATTGCCACCACCTGTCAGCTCCTTTCCGGGACTTTCG |
| | CTTTCCCCCTCCCTATTGCCACGGCGGAACTCATCGCCGCCTGCCTTGCCCGCTGCTGGACAGGGGC |
| | TCGGCTGTTGGGCACTGACAATTCCGTGGTGTTGTCGGGGAAGCTGACGTCCTTTCCATGGCTGCTC |
| | GCCTGTGTTGCCACCTGGATTCTGCGCGGGACGTCCTTCTGCTACGTCCCTTCGGCCCTCAATCCAG |
| | CGGACCTTCCTTCCCGCtgagagacacaaaaaattccaacacactattgcaatgaaaataaatttcc |
| | tttattagccagaagtcagatgctcaaggggcttcatgatgtccccataatttttggcagagggaaa |
| | aagatctcagtggtatttgtgagccagggcattggccttctgataggcagcctgcacctgaggagtg |
| | cggccgctttacttgtacagctcgtccatgccgagagtgatcccggcggcggtcacgaactccagca |
| | ggaccatgtgatcgcgcttctcgttggggtctttgctcagggcggactgggtgctcaggtagtggtt |
| | gtcgggcagcagcacggggccgtcgccgatgggggtgttctgctggtagtggtcggcgagctgcacg |
| | ctgccgtcctcgatgttgtggcggatcttgaagttcaccttgatgccgttcttctgcttgtcggcca |
| | tgatatagacgttgtggctgttgtagttgtactccagcttgtgccccaggatgttgccgtcctcctt |
| | gaagtcgatgcccttcagctcgatgcggttcaccagggtgtcgccctcgaacttcacctcggcgcgg |
| | gtcttgtagttgccgtcgtccttgaagaagatggtgcgctcctggacgtagccttcgggcatggcgg |

TABLE 13-continued

| Exemplary plasmid sequences | |
|---|---|
| Name | Sequence |
| | acttgaagaagtcgtgctgcttcatgtggtcggggtagcggctgaagcactgcacgccgtaggtcag ggtggtcacgagggtgggccagggcacgggcagcttgccggtggtgcagatgaacttcagggtcagc ttgccgtaggtggcatcgccctcgccctcgccggacacgctgaacttgtggccgtttacgtcgccgt ccagctcgaccaggatgggcaccaccccggtgaacagctcctcgcccttgctcaccatggtggcggg atctgacggttcactaaaccagctctgcttatatagacctcccaccgtacacgcctaccgcccattt gcgtcaatggggcggagttgttacgacattttggaaagtcccgttgattttggtgccaaaacaaact cccattgacgtcaatggggtggagacttggaaatccccgtgagtcaaaccgctatccacgcccattg atgtactgccaaaaccgcatcaccatggtaatagcgatgactaatacgtagatgtactgccaagtag gaaagtcccataaggtcatgtactgggcataatgccaggcgggccatttaccgtcattgacgtcaat agggggcgtacttggcatatgatacacttgatgtactgccaagtgggcagtttaccgtaaatactcc acccattgacgtcaatggaaagtccctattggcgttactatgggaacatacgtcattattgacgtca atgggcgggggtcgttgggcggtcagccaggcgggccatttaccgtaagttatgtaacgGGCCTGCT GCCGGCTCTGCGGCCTCTTCCGCGTCTTCGCCTTCGCCCTCAGACGAGTCGGATCTCCCTTTGGGCC GCCTCCCCGCCTGTCTAGCTTGACTGACTGAGATACAGCGTACCTTCAGCTCACAGACATGATAAGA TACATTGATGAGTTTGGACAAACCACAACTAGAATGCAGTGAAAAAAATGCTTTATTTGTGAAATTT GTGATGCTATTGCTTTATTTGTAACCATTATAAGCTGCAATAAACAAGTTAACAACAACAATTGCAT TCATTTTATGTTTCAGGTTCAGGGGGAGGTGTGGGAGGTTTTTTAAAGCAAGTAAAACCTCTACAAA TGTGGTATTGGCCCATCTCTATCGGTATCGTAGCATAACCCCTTGGGGCCTCTAAACGGGTCTTGAG GGGTTTTTTGTGCCCCTCGGGCCGGATTGCTATCTACCGGCATTGGCGCAGAAAAAAATGCCTGATG CGACGCTGCGCGTCTTATACTCCCACATATGCCAGATTCAGCAACGGATACGGCTTCCCCAACTTGC CCACTTCCATACGTGTCCTCCTTACCAGAAATTTATCCTTAAGGTCGTCAGCTATCCTGCAGGCGAT CTCTCGATTTCGATCAAGACATTCCTTTAATGGTCTTTTCTGGACACCACTAGGGGTCAGAAGTAGT TCATCAAACTTTCTTCCCTCCCTAATCTCATTGGTTACCTTGGGCTATCGAAACTTAATTAAGCGAT CTGCATCTCAATTAGTCAGCAACCATAGTCCCGCCCCTAACTCCGCCCATCCCGCCCCTAACTCCGC CCAGTTCCGCCCATTCTCCGCCCCATCGCTGACTAATTTTTTTTATTTATGCAGAGGCCGAGGCCGC CTCGGCCTCTGAGCTATTCCAGAAGTAGTGAGGAGGCTTTTTTGGAGGCCTAGGCTTTTGCAAAGGA GGTAGCCAACATGATTGAACAAGATGGATTGCACGCAGGTTCTCCCGCCGCTTGGGTGGAGAGGCTA TTCGGCTATGACTGGGCACAACAGACAATCGGCTGCTCTGATGCCGCCGTGTTCCGGCTGTCAGCGC AGGGGCGCCCGGTTCTTTTTGTCAAGACCGACCTGTCCGGTGCCCTGAATGAACTCCAGGACGAGGC AGCGCGGCTATCGTGGCTGGCCACGACGGGCGTTCCTTGCGCAGCTGTGCTCGACGTTGTCACTGAA GCGGGAAGGGACTGGCTGCTATTGGGCGAAGTGCCGGGGCAGGATCTCCTGTCATCTCACCTTGCTC CTGCCGAGAAAGTATCCATCATGGCTGATGCAATGCGGCGGCTGCATACGCTTGATCCGGCTACCTG CCCATTCGACCACCAAGCGAAACATCGCATCGAGCGAGCACGTACTCGGATGGAAGCCGGTCTTGTC GATCAGGATGATCTGGACGAAGAGCATCAGGGGCTCGCGCCAGCCGAACTGTTCGCCAGGCTCAAGG CGCGGATGCCCGACGGCGAGGATCTCGTCGTGACCCACGGCGATGCCTGCTTGCCGAATATCATGGT GGAAAATGGCCGCTTTTCTGGATTCATCGACTGTGGCCGGCTGGGTGTGGCGGACCGCTATCAGGAC ATAGCGTTGGCTACCCGTGATATTGCTGAAGAGCTTGGCGGCGAATGGGCTGACCGCTTCCTCGTGC TTTACGGTATCGCCGCTCCCGATTCGCAGCGCATCGCCTTCTATCGCCTTCTTGACGAGTTCTTCTA GTATGTAAGCCCTGTGCCTTCTAGTTGCCAGCCATCTGTTGTTTGCCCCTCCCCCGTGCCTTCCTTG ACCCTGGAAGGTGCCACTCCCACTGTCCTTTCCTAATAAAATGAGGAAATTGCATCGCATTGTCTGA GTAGGTGTCATTCTATTCTGGGGGGTGGGGTGGGGCAGGACAGCAAGGGGGAGGATTGGGAAGACAA TAGCAGGCATGCTGGGGATGCGGTGGGCTCTATGGTTAATTAACCAGTCAAGTCAGCTACTTGGCGA GATCGACTTGTCTGGGTTTCGACTACGCTCAGAATTGCGTCAGTCAAGTTCGATCTGGTCCTTGCTA TTGCACCCGTTCTCCGATTACGAGTTTCATTTAAATCATGTGAGCAAAAGGCCAGCAAAAGGCCAGG AACCGTAAAAAGGCCGCGTTGCTGGCGTTTTTCCATAGGCTCCGCCCCCCTGACGAGCATCACAAAA ATCGACGCTCAAGTCAGAGGTGGCGAAACCCGACAGGACTATAAAGATACCAGGCGTTTCCCCCTGG AAGCTCCCTCGTGCGCTCTCCTGTTCCGACCCTGCCGCTTACCGGATACCTGTCCGCCTTTCTCCCT TCGGGAAGCGTGGCGCTTTCTCATAGCTCACGCTGTAGGTATCTCAGTTCGGTGTAGGTCGTTCGCT CCAAGCTGGGCTGTGTGCACGAACCCCCCGTTCAGCCCGACCGCTGCGCCTTATCCGGTAACTATCG TCTTGAGTCCAACCCGGTAAGACACGACTTATCGCCACTGGCAGCAGCCACTGGTAACAGGATTAGC AGAGCGAGGTATGTAGGCGGTGCTACAGAGTTCTTGAAGTGGTGGCCTAACTACGGCTACACTAGAA GAACAGTATTTGGTATCTGCGCTCTGCTGAAGCCAGTTACCTTCGGAAAAAGAGTTGGTAGCTCTTG ATCCGGCAAACAAACCACCGCTGGTAGCGGTGGTTTTTTTGTTTGCAAGCAGCAGATTACGCGCAGA AAAAAAGGATCTCAAGAAGATCCTTTGATCTTTTCTACGGGGTCTGACGCTCAGTGGAACGAAAACT CACGTTAAGGGATTTTGGTCATGAGATTATCAAAAAGGATCTTCACCTAGATCCTTTTAAATTAAAA ATGAAGTTTTAAATCAATCTAAAGTATATATGAGTAAACTTGGTCTGACAGTTACCAATGCTTAATC AGTGAGGCACCTATCTCAGCGATCTGTCTATTTCGTTCATCCATAGTTGCATTTAAATTTCCGAACT CTCCAAGGCCCTC (SEQ ID NO: 96) |
| RET-007 LINE1-GFP ORF1-NSV40 NLS Linker | GGAAAATCTTCAAACCTTTCGTCCGATCCATCTTGCAGGCTACCTCTCGAACGAACTATCGCAAGTC TCTTGGCCGGCCTTGCGCCTTGGCTATTGCTTGGCAGCGCCTATCGCCAGGTATTACTCCAATCCCG AATATCCGAGATCGGGATCACCCGAGAGAAGTTCAACCTACATCCTCAATCCCGATCTATCCGAGAT CCGAGGAATATCGAAATCGGGGCGCGCCTGGTGTACCGAGAACGATCCTCTCAGTGCGAGTCTCGAC GATCCATATCGTTGCTTGGCAGTCAGCCAGTCGGAATCCAGCTTGGGACCCAGGAAGTCCAATCGTC AGATATTGTACTCAAGCCTGGTCACGGCAGCGTACCGATCTGTTTAAACCTAGATATTGATAGTCTG ATCGGTCAACGTATAATCGAGTCCTAGCTTTTGCAAACATCTATCAAGAGACAGGATCAGCAGGAGG CTTTCGCATGAGTATTCAACATTTCCGTGTCGCCCTTATTCCCTTTTTTGCGGCATTTTGCCTTCCT GTTTTTGCTCACCCAGAAACGCTGGTGAAAGTAAAAGATGCTGAAGATCAGTTGGGTGCGCGAGTGG GTTACATCGAACTGGATCTCAACAGCGGTAAGATCCTTGAGAGTTTTCGCCCCGAAGAACGCTTTCC AATGATGAGCACTTTTAAAGTTCTGCTATGTGGCGCGGTATTATCCCGTATTGACGCCGGGCAAGAG CAACTCGGTCGCCGCATACACTATTCTCAGAATGACTTGGTTGAGTATTCACCAGTCACAGAAAAGC ATCTTACGGATGGCATGACAGTAAGAGAATTATGCAGTGCTGCCATAACCATGAGTGATAACACTGC GGCCAACTTACTTCTGACAACGATTGGAGGACCGAAGGAGCTAACCGCTTTTTTGCACAACATGGGG GATCATGTAACTCGCCTTGATCGTTGGGAACCGGAGCTGAATGAAGCCATACCAAACGACGAGCGTG ACACCACGATGCCTGTAGCAATGGCAACAACCTTGCGTAAACTATTAACTGGCGAACTACTTACTCT AGCTTCCCGGCAACAGTTGATAGACTGGATGGAGGCGGATAAAGTTGCAGGACCACTTCTGCGCTCG |

TABLE 13-continued

Exemplary plasmid sequences

| Name | Sequence |
|---|---|
| | GCCCTTCCGGCTGGCTGGTTTATTGCTGATAAATCTGGAGCCGGTGAGCGTGGGTCTCGCGGTATCA |
| | TTGCAGCACTGGGGCCAGATGGTAAGCCCTCCCGTATCGTAGTTATCTACACGACGGGGAGTCAGGC |
| | AACTATGGATGAACGAAATAGACAGATCGCTGAGATAGGTGCCTCACTGATTAAGCATTGGTAACCG |
| | ATTCTAGGTGCATTGGCGCAGAAAAAAATGCCTGATGCGACGCTGCGCGTCTTATACTCCCACATAT |
| | GCCAGATTCAGCAACGGATACGGCTTCCCCAACTTGCCCACTTCCATACGTGTCCTCCTTACCAGAA |
| | ATTTATCCTTAAGATCGTTTAAACTCGACTCTGGCTCTATCGAATCTCCGTCGTTTCGAGCTTACGC |
| | GAACAGCCGTGGCGCTCATTTGCTCGTCGGGCATCGAATCTCGTCAGCTATCGTCAGCTTACCTTTT |
| | TGGCAGCGATCGCGGCTCCCGACATCTTGGACCATTAGCTCCACAGGTATCTTCTTCCCTCTAGTGG |
| | TCATAACAGCAGCTTCAGCTACCTCTCAATTCAAAAAACCCCTCAAGACCCGTTTAGAGGCCCCAAG |
| | GGGTTATGCTATCAATCGTTGCGTTACACACACAAAAAACCAACACACATCCATCTTCGATGGATAG |
| | CGATTTTATTATCTAACTGCTGATCGAGTGTAGCCAGATCTAGTAATCAATTACGGGGTCATTAGTT |
| | CATAGCCCATATATGGAGTTCCGCGTTACATAACTTACGGTAAATGGCCCGCCTGGCTGACCGCCCA |
| | ACGACCCCCGCCCATTGACGTCAATAATGACGTATGTTCCCATAGTAACGCCAATAGGGACTTTCCA |
| | TTGACGTCAATGGGTGGAGTATTTACGGTAAACTGCCCACTTGGCAGTACATCAAGTGTATCATATG |
| | CCAAGTACGCCCCCTATTGACGTCAATGACGGTAAATGGCCCGCCTGGCATTATGCCCAGTACATGA |
| | CCTTATGGGACTTTCCTACTTGGCAGTACATCTACGTATTAGTCATCGCTATTACCATGCTGATGCG |
| | GTTTTGGCAGTACATCAATGGGCGTGGATAGCGGTTTGACTCACGGGGATTTCCAAGTCTCCACCCC |
| | ATTGACGTCAATGGGAGTTTGTTTTGGCACCAAAATCAACGGGACTTTCCAAAATGTCGTAACAACT |
| | CCGCCCCATTGACGCAAATGGGCGGTAGGCGTGTACGGTGGGAGGTCTATATAAGCAGAGCTGGTTT |
| | AGTGAACCGTCAGATCAGATCTTTGTCGATCCTACCATCCACTCGACACACCCGCCAGCGGCCGCTA |
| | ATACGACTCACTATAGGGAGAAGTACTGCCACCATGccaaagaagaagcggaaggtcggcggcggca |
| | gcGGCAAGAAGCAAAATCGCAAGACGGGGAATTCCAAGACACAATCCGCTAGCCCACCACCTAAAGA |
| | GCGTTCTAGCTCCCCTGCTACTGAGCAGTCCTGGATGGAAAACGACTTCGATGAACTCCGGGAAGAG |
| | GGATTTAGGCGATCCAACTATTCAGAACTCCGCGAAGATATCCAGACAAAGGGGAAGGAAGTCGAGA |
| | ATTTCGAGAAGAACCTCGAGGAGTGCATCACCCGTATCACAAACACTGAGAAATGTCTCAAAGAACT |
| | CATGGAACTTAAGACAAAAGCCAGGGAGCTTCGAGAGGAGTGTCGGAGTCTGAGATCCAGGTGTGAC |
| | CAGCTCGAGGAGCGCGTGAGCGCGATGGAAGACGAGATGAACGAGATGAAAAGAGAGGGCAAATTCA |
| | GGGAGAAGCGCATTAAGAGGAACGAACAGAGTCTGCAGGAGATTTGGGATTACGTCAAGAGGCCTAA |
| | CCTGCGGTTGATCGGCGTCCCCGAGAGCGACGTAGAAAACGGGACTAAACTGGAGAATACACTTCAA |
| | GACATCATTCAAGAAAATTTTCCAAACCTGGCTCGGCAAGCTAATGTGCAAATCCAAGAGATCCAAC |
| | GCACACCCCAGCGGTATAGCTCTCGGCGTGCCACCCCTAGGCATATTATCGTGCGCTTTACTAAGGT |
| | GGAGATGAAAGAGAAGATGCTGCGAGCCGCTCGGGAAAAGGGAAGGGTGACTTTGAAGGGCAAACCT |
| | ATTCGGCTGACGGTTGACCTTAGCGCCGAGACACTCCAGGCACGCCGGGAATGGGGCCCCATCTTTA |
| | ATATCCTGAAGGAGAAGAACTTCCAGCCACGAATCTCTTACCCTGCAAAGTTGAGTTTTATCTCCGA |
| | GGGTGAGATTAAGTATTTCATCGATAAACAGATGCTGCGAGACTTCGTGACAACTCGCCCAGCTCTC |
| | AAGGAACTGCTCAAAGAGGCTCTTAATATGGAGCGCAATAATAGATATCAACCCTTGCAGAACCACG |
| | CAAAGATGTGAGACAGCCGTCAGACCATCAAGACTAGGAAGAAACTGCATCAACTAATGAGCAAAAT |
| | CACCAGCTAACATCATAGTATACATGACCGGCTCTAACTCACATATCACCATCCTTACACTTAACAT |
| | TAACGGCCTCAACTCAGCTATCAAGCGCCATCGGCTGGCCAGCTGGATCAAATCACAGGATCCAAGC |
| | GTTTGTTGCATCCAAGAGACCCACCTGACCTGTAGAGATACTCACCGCCTCAAGATCAAGGGATGGC |
| | GAAAGATTTATCAGGCGAACGGTAAGCAGAAGAAAGCCGGAGTCGCAATTCTGGTCTCAGACAAGAC |
| | GGATTTCAAGCCCACCAAAATTAAGCGTGATAAGGAAGGTCACTATATTATGGTGAAAGGCAGCATA |
| | CAGCAGGAAGAACTTACCATATTGAACATCTACGCGCCAAACACCGGCGCACCTCGCTTTATCAAAC |
| | AGGTCCTGTCCGATCTGCAGCGAGATCTGGATTCTCATACGTTGATTATGGGTGATTTCAATACACC |
| | ATTGAGCACCCTGGATCGCAGCACCAGGCAAAAGGTAAATAAAGACACGCAAGAGCTCAATAGCGCA |
| | CTGCATCAGGCAGATCTCATTGATATTTATCGCACTCTTCATCCTAAGAGTACCGAGTACACATTCT |
| | TCAGCGCCCCACATCATACATACTCAAAGATCGATCATATCGTCGGCTCAAAGGCTCTGCTGTCAAA |
| | GTGCAAGCGCACAGAGATAATTACAAATTACCTGTCAGATCATAGCGCGATCAAGCTCGAGCTGAGA |
| | ATCAAGAACCTGACCCAGAGCCGGAGTACCACTTGGAAGCTTAATAACCTGCTGCTCAACGATTATT |
| | GGGTCCACAATGAGATGAAGGCAGAGATTAAAATGTTCTTCGAAACAAATGAGAATAAGGATACTAC |
| | CTATCAAAACCTTTGGGATGCCTTTAAGGCCGTCTGCAGAGGCAAGTTCATCGCCCTCAACGCCTAT |
| | AAAAGAAAACAAGAGAGATCTAAGATCGATACTCTCACCTCTCAGCTGAAGGAGTTGGAGAAACAGG |
| | AACAGACCCACTCCAAGGCGTCAAGACGGCAGGAGATCACAAAGATTCGCGCCGAGTTGAAAGAGAT |
| | CGAAACCCAAAAGACTCTTCAGAAAATTAACGAGTCTCGTAGTTGGTTCTTCGAGCGGATTAATAAG |
| | ATAGACAGACCTCTGGCACGACTGATTAAGAAGAAGCGCGAAAAGAACCAGATTGATACCATCAAGA |
| | ACGACAAGGGCGACATCACTACTGACCCGACCGAGATCCAGACCACTATTCGGGAGTATTATAAGCA |
| | TTTGTATGCTAACAAGCTTGAGAACCTGGAAGAGATGGACACTTTTCTGGATACCTATACTCTGCCA |
| | CGGCTTAATCAAGAGGAAGTCGAGTCCCTCAACCGCCCAATTACAGGAAGCGAGATTGTGGCCATAA |
| | TTAACTCCCTGCCGACAAAGAAATCTCCTGGTCCGGACGGGTTTACAGCTGAGTTTTATCAACGGTA |
| | TATGGAAGAGCTTGTACCGTTTCTGCTCAAGCTCTTTCAGTCTATAGAAAAGGAAGGCATCTTGCCC |
| | AATTCCTTCTACGAAGCTTCTATAATACTTATTCCCAAACCAGGACGCGATACCACAAAGAAGGAAA |
| | ACTTCCGGCCCATTAGTCTCATGAATATCGACGCTAAAATATTGAACAAGATTCTCGCCAACAGAAT |
| | CCAACAACATATTAAGAAATTGATACATCACGACCAGGTGGGGTTTATACCTGGCATGCAGGGCTGG |
| | TTTAACATCCGGAAGAGTATTAACGTCATTCAACACATTAATAGAGCTAAGGATAAGAATCATATGA |
| | TCATCTCTATAGACGCGGAAAAGGCATTCGATAAGATTCAGCAGCCATTTATGCTCAAGACTCTGAA |
| | CAAACTCGGCATCGACGGAACATATTTTAAGATTATTCGCGCAATTTACGATAAGCCGACTGCTAAC |
| | ATTATCCTTAACGGCCAAAAGCTCGAGGCCTTTCCGCTCAAGACTGGAACCCGCCAAGGCTGTCCCC |
| | TCTCCCCGCTTTTGTTTAATATTGTACTCGAGGTGCTGGCTAGGGCTATTCGTCAAGAGAAAGAGAT |
| | TAAAGGGATACAGCTCGGGAAGGAAGAGGTCAAGCTTTCCTTGTTCGCCGATGATATGATTGTGTAC |
| | CTGGAGAATCCTATTGTGTCTGCTCAGAACCTTCTTAAACTTATTTCTAACTTTAGCAAGGTCAGCG |
| | GCTATAAGATTAACGTCCAGAAATCTCAGGCCTTTCTGTACACAAATAATCGAGAGACCGAATCCCA |
| | GATAATGGGTGAGCTTCCGTTTGTCATAGCCAGCAAAAGGATAAAGTATCTCGGAATCCAGCTGACA |
| | CGAGACGTTAAAGATTTGTTTAAGGAAAATTACAAGCCTCTCCTGAAAGAGATTAAGGAAGATACTA |
| | ATAAGTGGAAGAATATCCCCTGTTCATGGGTTGGCAGAATCAACATAGTGAAGATGGCAATACTTCC |
| | TAAAGTGATATATCGCTTTAACGCCATCCCAATTAAACTGCCTATGACCTTCTTTACGGAGCTCGAG |
| | AAAACAACCCTTAAATTTATATGGAATCAAAAGAGAGCAAGAATAGCGAAGTCCATCTTGAGCCAGA |

TABLE 13-continued

Exemplary plasmid sequences

| Name | Sequence |
| --- | --- |
| | AGAATAAGGCCGGTGGGATTACTTTGCCTGATTTTAAGTTGTATTATAAAGCCACAGTAACTAAGAC |
| | AGCCTGGTATTGGTATCAGAATAGAGACATCGACCAGTGGAATCGGACCGAACCATCAGAGATAATG |
| | CCCCACATCTATAATTACCTTATATTCGATAAGCCAGAAAAGAATAAACAGTGGGGCAAAGACAGCC |
| | TCTTCAACAAGTGGTGTTGGGAGAATTGGCTGGCCATATGCCGGAAACTCAAGCTCGACCCCTTTCT |
| | TACACCCTACACTAAAATCAACAGTAGGTGGATCAAGGACTTGAATGTCAAGCCAAAGACTATAAAG |
| | ACACTGGAAGAGAATCTTGGGATCACAATACAAGATATAGGCGTCGGCAAAGATTTTATGTCAAAGA |
| | CGCCCAAGGCCATGGCCACTAAGGATAAGATTGATAAGTGGGACCTTATTAAGCTCAAAAGCTTCTG |
| | TACTGCCAAGGAGACCACGATCAGAGTTAATAGGCAGCCCACTACATGGGAAAAGATTTTCGCCACT |
| | TATTCATCAGATAAGGGGTTGATAAGCAGAATATATAACGAGCTGAAGCAGATCTACAAGAAGAAAA |
| | CGAATAATCCCATCAAGAAGTGGGCAAAAGATATGAACAGGCATTTTAGCAAAGAGGATATCTACGC |
| | CGCGAAGAAGCATATGAAGAAGTGTAGTTCAAGCTTGGCCATTCGTGAGATGCAGATTAAGACGACC |
| | ATGCGATACCACCTTACCCCAGTGAGGATGGCAATTATCAAGAAATCTGGCAATAATAGATGTTGGC |
| | GGGGCTGTGGCGAGATTGGCACCCTGCTCCATTGCTGGTGGGATTGCAAGCTGGTGCAGCCGCTTTG |
| | GAAATCAGTCTGGCGCTTTCTGAGGGACCTCGAGCTTGAGATTCCCTTCGATCCCGCAATTCCCTTG |
| | CTCGGAATCTATCCTAACGAATACAAGAGCTGTTGTTACAAGGATACGTGTACCCGGATGTTCATCG |
| | CGGCCTTGTTTACGATAGCTAAGACGTGGAATCAGCCTAAGTGCCCCACAATGATCGATTGGATCAA |
| | GAAAATGTGGCATATTTATACCATGGAGTATTACGCAGCAATTAAGAATGACGAATTTATTTCCTTC |
| | GTTGGGACCTGGATGAAGCTGGAGACTATTATTCTGAGCAAGCTGTCTCAGGAGCAAAAGACAAAGC |
| | ATAGAATCTTCTCTCTCATTGGTGGTAACGACTACAAAGACGATGACGACAAGTAAAGCGCTTCTAG |
| | AAGTTGTCTCCTCCTGCACTGACTGACTGATACAATCGATTTCTGGATCCGCAGGCCTAATCAACCT |
| | CTGGATTACAAAATTTGTGAAAGATTGACTGGTATTCTTAACTATGTTGCTCCTTTTACGCTATGTG |
| | GATACGCTGCTTTAATGCCTTTGTATCATGCTATTGCTTCCCGTATGGCTTTCATTTTCTCCTCCTT |
| | GTATAAATCCTGGTTGCTGTCTCTTTATGAGGAGTTGTGGCCCGTTGTCAGGCAACGTGGCGTGGTG |
| | TGCACTGTGTTTGCTGACGCAACCCCCACTGGTTGGGGCATTGCCACCACCTGTCAGCTCCTTTCCG |
| | GGACTTTCGCTTTCCCCCTCCCTATTGCCACGGCGGAACTCATCGCCGCCTGCCTTGCCCGCTGCTG |
| | GACAGGGGCTCGGCTGTTGGGCACTGACAATTCCGTGGTGTTGTCGGGGAAGCTGACGTCCTTTCCA |
| | TGGCTGCTCGCCTGTGTTGCCACCTGGATTCTGCGCGGGACGTCCTTCTGCTACGTCCCTTCGGCCC |
| | TCAATCCAGCGGACCTTCCTTCCCGCtgagagacacaaaaaattccaacacactattgcaatgaaaa |
| | taaatttcctttattagccagaagtcagatgctcaaggggcttcatgatgtccccataatttttggc |
| | agagggaaaaagatctcagtggtatttgtgagccagggcattggccttctgataggcagcctgcacc |
| | tgaggagtgcggccgctttacttgtacagctcgtccatgccgagagtgatcccggcggcggtcacga |
| | actccagcaggaccatgtgatcgcgcttctcgttggggtctttgctcagggcggactgggtgctcag |
| | gtagtggttgtcgggcagcagcacggggccgtcgccgatgggggtgttctgctggtagtggtcggcg |
| | agctgcacgctgccgtcctcgatgttgtggcggatcttgaagttcaccttgatgccgttcttctgct |
| | tgtcggccatgatatagacgttgtggctgttgtagttgtactccagcttgtgccccaggatgttgcc |
| | gtcctccttgaagtcgatgcccttcagctcgatgcggttcaccagggtgtcgccctcgaacttcacc |
| | tcggcgcgggtcttgtagttgccgtcgtccttgaagaagatggtgcgctcctggacgtagccttcgg |
| | gcatggcggacttgaagaagtcgtgctgcttcatgtggtcggggtagcggctgaagcactgcacgcc |
| | gtaggtcagggtggtcacgagggtgggccagggcacgggcagcttgccggtggtgcagatgaacttc |
| | agggtcagcttgccgtaggtggcatcgccctcgccctcgccggacacgctgaacttgtggccgttta |
| | cgtcgccgtccagctcgaccaggatgggcaccaccccggtgaacagctcctcgcccttgctcaccat |
| | ggtggcgggatctgacggttcactaaaccagctctgcttatatagacctcccaccgtacacgcctac |
| | cgcccatttgcgtcaatggggcggagttgttacgacattttggaaagtcccgttgattttggtgcca |
| | aaacaaactcccattgacgtcaatggggtggagacttggaaatccccgtgagtcaaaccgctatcca |
| | cgcccattgatgtactgccaaaaccgcatcaccatggtaatagcgatgactaatacgtagatgtact |
| | gccaagtaggaaagtcccataaggtcatgtactgggcataatgccaggcgggccatttaccgtcatt |
| | gacgtcaatagggggcgtacttggcatatgatacacttgatgtactgccaagtgggcagtttaccgt |
| | aaatactccacccattgacgtcaatggaaagtccctattggcgttactatgggaacatacgtcatta |
| | ttgacgtcaatgggcgggggtcgttgggcggtcagccaggcgggccatttaccgtaagttatgtaac |
| | gGGCCTGCTGCCGGCTCTGCGGCCTCTTCCGCGTCTTCGCCTTCGCCCTCAGACGAGTCGGATCTCC |
| | CTTTGGGCCGCCTCCCCGCCTGTCTAGCTTGACTGACTGAGATACAGCGTACCTTCAGCTCACAGAC |
| | ATGATAAGATACATTGATGAGTTTGGACAAACCACAACTAGAATGCAGTGAAAAAAATGCTTTATTT |
| | GTGAAATTTGTGATGCTATTGCTTTATTTGTAACCATTATAAGCTGCAATAAACAAGTTAACAACAA |
| | CAATTGCATTCATTTTATGTTTCAGGTTCAGGGGGAGGTGTGGGAGGTTTTTTAAAGCAAGTAAAAC |
| | CTCTACAAATGTGGTATTGGCCCATCTCTATCGGTATCGTAGCATAACCCCTTGGGGCCTCTAAACG |
| | GGTCTTGAGGGGTTTTTTGTGCCCCTCGGGCCGGATTGCTATCTACCGGCATTGGCGCAGAAAAAAA |
| | TGCCTGATGCGACGCTGCGCGTCTTATACTCCCACATATGCCAGATTCAGCAACGGATACGGCTTCC |
| | CCAACTTGCCCACTTCCATACGTGTCCTCCTTACCAGAAATTTATCCTTAAGGTCGTCAGCTATCCT |
| | GCAGGCGATCTCTCGATTTCGATCAAGACATTCCTTTAATGGTCTTTTCTGGACACCACTAGGGGTC |
| | AGAAGTAGTTCATCAAACTTTCTTCCCTCCCTAATCTCATTGGTTACCTTGGGCTATCGAAACTTAA |
| | TTAAGCGATCTGCATCTCAATTAGTCAGCAACCATAGTCCCGCCCCTAACTCCGCCCATCCCGCCCC |
| | TAACTCCGCCCAGTTCCGCCCATTCTCCGCCCCATCGCTGACTAATTTTTTTTATTTATGCAGAGGC |
| | CGAGGCCGCCTCGGCCTCTGAGCTATTCCAGAAGTAGTGAGGAGGCTTTTTTGGAGGCCTAGGCTTT |
| | TGCAAAGGAGGTAGCCAACATGATTGAACAAGATGGATTGCACGCAGGTTCTCCCGCCGCTTGGGTG |
| | GAGAGGCTATTCGGCTATGACTGGGCACAACAGACAATCGGCTGCTCTGATGCCGCCGTGTTCCGGC |
| | TGTCAGCGCAGGGGCGCCCGGTTCTTTTTGTCAAGACCGACCTGTCCGGTGCCCTGAATGAACTCCA |
| | GGACGAGGCAGCGCGGCTATCGTGGCTGGCCACGACGGGCGTTCCTTGCGCAGCTGTGCTCGACGTT |
| | GTCACTGAAGCGGGAAGGGACTGGCTGCTATTGGGCGAAGTGCCGGGGCAGGATCTCCTGTCATCTC |
| | ACCTTGCTCCTGCCGAGAAAGTATCCATCATGGCTGATGCAATGCGGCGGCTGCATACGCTTGATCC |
| | GGCTACCTGCCCATTCGACCACCAAGCGAAACATCGCATCGAGCGAGCACGTACTCGGATGGAAGCC |
| | GGTCTTGTCGATCAGGATGATCTGGACGAAGAGCATCAGGGGCTCGCGCCAGCCGAACTGTTCGCCA |
| | GGCTCAAGGCGCGGATGCCCGACGGCGAGGATCTCGTCGTGACCCACGGCGATGCCTGCTTGCCGAA |
| | TATCATGGTGGAAAATGGCCGCTTTTCTGGATTCATCGACTGTGGCCGGCTGGGTGTGGCGGACCGC |
| | TATCAGGACATAGCGTTGGCTACCCGTGATATTGCTGAAGAGCTTGGCGGCGAATGGGCTGACCGCT |
| | TCCTCGTGCTTTACGGTATCGCCGCTCCCGATTCGCAGCGCATCGCCTTCTATCGCCTTCTTGACGA |
| | GTTCTTCTAGTATGTAAGCCCTGTGCCTTCTAGTTGCCAGCCATCTGTTGTTTGCCCCTCCCCCGTG |

TABLE 13-continued

| Exemplary plasmid sequences | |
|---|---|
| Name | Sequence |
| | CCTTCCTTGACCCTGGAAGGTGCCACTCCCACTGTCCTTTCCTAATAAAATGAGGAAATTGCATCGC<br>ATTGTCTGAGTAGGTGTCATTCTATTCTGGGGGGTGGGGTGGGGCAGGACAGCAAGGGGGAGGATTG<br>GGAAGACAATAGCAGGCATGCTGGGGATGCGGTGGGCTCTATGGTTAATTAACCAGTCAAGTCAGCT<br>ACTTGGCGAGATCGACTTGTCTGGGTTTCGACTACGCTCAGAATTGCGTCAGTCAAGTTCGATCTGG<br>TCCTTGCTATTGCACCCGTTCTCCGATTACGAGTTTCATTTAAATCATGTGAGCAAAAGGCCAGCAA<br>AAGGCCAGGAACCGTAAAAAGGCCGCGTTGCTGGCGTTTTTCCATAGGCTCCGCCCCCCTGACGAGC<br>ATCACAAAAATCGAGGCTCAAGTCAGAGGTGGCGAAACCCGACAGGACTATAAAGATACCAGGCGTT<br>TCCCCCTGGAAGCTCCCTCGTGCGCTCTCCTGTTCCGACCCTGCCGCTTACCGGATACCTGTCCGCC<br>TTTCTCCCTTCGGGAAGCGTGGCGCTTTCTCATAGCTCACGCTGTAGGTATCTCAGTTCGGTGTAGG<br>TCGTTCGCTCCAAGCTGGGCTGTGTGCACGAACCCCCCGTTCAGCCCGACCGCTGCGCCTTATCCGG<br>TAACTATCGTCTTGAGTCCAACCCGGTAAGACACGACTTATCGCCACTGGCAGCAGCCACTGGTAAC<br>AGGATTAGCAGAGCGAGGTATGTAGGCGGTGCTACAGAGTTCTTGAAGTGGTGGCCTAACTACGGCT<br>ACACTAGAAGAACAGTATTTGGTATCTGCGCTCTGCTGAAGCCAGTTACCTTCGGAAAAAGAGTTGG<br>TAGCTCTTGATCCGGCAAACAAACCACCGCTGGTAGCGGTGGTTTTTTTGTTTGCAAGCAGCAGATT<br>ACGCGCAGAAAAAAAGGATCTCAAGAAGATCCTTTGATCTTTTCTACGGGGTCTGACGCTCAGTGGA<br>ACGAAAACTCACGTTAAGGGATTTTGGTCATGAGATTATCAAAAAGGATCTTCACCTAGATCCTTTT<br>AAATTAAAAATGAAGTTTTAAATCAATCTAAAGTATATATGAGTAAACTTGGTCTGACAGTTACCAA<br>TGCTTAATCAGTGAGGCACCTATCTCAGCGATCTGTCTATTTCGTTCATCCATAGTTGCATTTAAAT<br>TTCCGAACTCTCCAAGGCCCTCGTC (SEQ ID NO: 97) |
| RET-008 LINE1-GFP ORF1-N Nucleo-plasmin NLS | GGAAAATCTTCAAACCTTTCGTCCGATCCATCTTGCAGGCTACCTCTCGAACGAACTATCGCAAGTC<br>TCTTGGCCGGCCTTGCGCCTTGGCTATTGCTTGGCAGCGCCTATCGCCAGGTATTACTCCAATCCCG<br>AATATCCGAGATCGGGATCACCCGAGAGAAGTTCAACCTACATCCTCAATCCCGATCTATCCGAGAT<br>CCGAGGAATATCGAAATCGGGGCGCGCCTGGTGTACCGAGAACGATCCTCTCAGTGCGAGTCTCGAC<br>GATCCATATCGTTGCTTGGCAGTCAGCCAGTCGGAATCCAGCTTGGGACCCAGGAAGTCCAATCGTC<br>AGATATTGTACTCAAGCCTGGTCACGGCAGCGTACCGATCTGTTTAAACCTAGATATTGATAGTCTG<br>ATCGGTCAACGTATAATCGAGTCCTAGCTTTTGCAAACATCTATCAAGAGACAGGATCAGCAGGAGG<br>CTTTCGCATGAGTATTCAACATTTCCGTGTCGCCCTTATTCCCTTTTTTGCGGCATTTTGCCTTCCT<br>GTTTTTGCTCACCCAGAAACGCTGGTGAAAGTAAAAGATGCTGAAGATCAGTTGGGTGCGCGAGTGG<br>GTTACATCGAACTGGATCTCAACAGCGGTAAGATCCTTGAGAGTTTTCGCCCCGAAGAACGCTTTCC<br>AATGATGAGCACTTTTAAAGTTCTGCTATGTGGCGCGGTATTATCCCGTATTGACGCCGGGCAAGAG<br>CAACTCGGTCGCCGCATACACTATTCTCAGAATGACTTGGTTGAGTATTCACCAGTCACAGAAAAGC<br>ATCTTACGGATGGCATGACAGTAAGAGAATTATGCAGTGCTGCCATAACCATGAGTGATAACACTGC<br>GGCCAACTTACTTCTGACAACGATTGGAGGACCGAAGGAGCTAACCGCTTTTTTGCACAACATGGGG<br>GATCATGTAACTCGCCTTGATCGTTGGGAACCGGAGCTGAATGAAGCCATACCAAACGACGAGCGTG<br>ACACCACGATGCCTGTAGCAATGGCAACAACCTTGCGTAAACTATTAACTGGCGAACTACTTACTCT<br>AGCTTCCCGGCAACAGTTGATAGACTGGATGGAGGCGGATAAAGTTGCAGGACCACTTCTGCGCTCG<br>GCCCTTCCGGCTGGCTGGTTTATTGCTGATAAATCTGGAGCCGGTGAGCGTGGGTCTCGCGGTATCA<br>TTGCAGCACTGGGGCCAGATGGTAAGCCCTCCCGTATCGTAGTTATCTACACGACGGGGAGTCAGGC<br>AACTATGGATGAACGAAATAGACAGATCGCTGAGATAGGTGCCTCACTGATTAAGCATTGGTAACCG<br>ATTCTAGGTGCATTGGCGCAGAAAAAAATGCCTGATGCGACGCTGCGCGTCTTATACTCCCACATAT<br>GCCAGATTCAGCAACGGATACGGCTTCCCCAACTTGCCCACTTCCATACGTGTCCTCCTTACCAGAA<br>ATTTATCCTTAAGATCGTTTAAACTCGACTCTGGCTCTATCGAATCTCCGTCGTTTCGAGCTTACGC<br>GAACAGCCGTGGCGCTCATTTGCTCGTCGGGCATCGAATCTCGTCAGCTATCGTCAGCTTACCTTTT<br>TGGCAGCGATCGCGGCTCCCGACATCTTGGACCATTAGCTCCACAGGTATCTTCTTCCCTCTAGTGG<br>TCATAACAGCAGCTTCAGCTACCTCTCAATTCAAAAAACCCCTCAAGACCCGTTTAGAGGCCCCAAG<br>GGGTTATGCTATCAATCGTTGCGTTACACACACAAAAAACCAACACACATCCATCTTCGATGGATAG<br>CGATTTTATTATCTAACTGCTGATCGAGTGTAGCCAGATCTAGTAATCAATTACGGGGTCATTAGTT<br>CATAGCCCATATATGGAGTTCCGCGTTACATAACTTACGGTAAATGGCCCGCCTGGCTGACCGCCCA<br>ACGACCCCCGCCCATTGACGTCAATAATGACGTATGTTCCCATAGTAACGCCAATAGGGACTTTCCA<br>TTGACGTCAATGGGTGGAGTATTTACGGTAAACTGCCCACTTGGCAGTACATCAAGTGTATCATATG<br>CCAAGTACGCCCCCTATTGACGTCAATGACGGTAAATGGCCCGCCTGGCATTATGCCCAGTACATGA<br>CCTTATGGGACTTTCCTACTTGGCAGTACATCTACGTATTAGTCATCGCTATTACCATGCTGATGCG<br>GTTTTGGCAGTACATCAATGGGCGTGGATAGCGGTTTGACTCACGGGGATTTCCAAGTCTCCACCCC<br>ATTGACGTCAATGGGAGTTTGTTTTGGCACCAAAATCAACGGGACTTTCCAAAATGTCGTAACAACT<br>CCGCCCCATTGACGCAAATGGGCGGTAGGCGTGTACGGTGGGAGGTCTATATAAGCAGAGCTGGTTT<br>AGTGAACCGTCAGATCAGATCTTTGTCGATCCTACCATCCACTCGACACACCCGCCAGCGGCCGCTA<br>ATACGACTCACTATAGGGAGAAGTACTGCCACCATGaaaaggccggcggccacgaaaaaggccggcc<br>aggcaaaaaagaaaaagGGCAAGAAGCAAAATCGCAAGACGGGGAATTCCAAGACACAATCCGCTAG<br>CCCACCACCTAAAGAGCGTTCTAGCTCCCCTGCTACTGAGCAGTCCTGGATGGAAAACGACTTCGAT<br>GAACTCCGGGAAGAGGGATTTAGGCGATCCAACTATTCAGAACTCCGCGAAGATATCCAGACAAAGG<br>GGAAGGAAGTCGAGAATTTCGAGAAGAACCTCGAGGAGTGCATCACCCGTATCACAAACACTGAGAA<br>ATGTCTCAAAGAACTCATGGAACTTAAGACAAAAGCCAGGGAGCTTCGAGAGGAGTGTCGGAGTCTG<br>AGATCCAGGTGTGACCAGCTCGAGGAGCGCGTGAGCGCGATGGAAGACGAGATGAACGAGATGAAAA<br>GAGAGGGCAAATTCAGGGAGAAGCGCATTAAGAGGAACGAACAGAGTCTGCAGGAGATTTGGGATTA<br>CGTCAAGAGGCCTAACCTGCGGTTGATCGGCGTCCCCGAGAGCGACGTAGAAAACGGGACTAAACTG<br>GAGAATACACTTCAAGACATCATTCAAGAAAATTTTCCAAACCTGGCTCGGCAAGCTAATGTGCAAA<br>TCCAAGAGATCCAACGCACACCCCAGCGGTATAGCTCTCGGCGTGCCACCCCTAGGCATATTATCGT<br>GCGCTTTACTAAGGTGGAGATGAAAGAGAAGATGCTGCGAGCCGCTCGGGAAAAGGGAAGGGTGACT<br>TTGAAGGGCAAACCTATTCGGCTGACGGTTGACCTTAGCGCCGAGACACTCCAGGCACGCCGGGAAT<br>GGGGCCCCATCTTTAATATCCTGAAGGAGAAGAACTTCCAGCCACGAATCTCTTACCCTGCAAAGTT<br>GAGTTTTATCTCCGAGGGTGAGATTAAGTATTTCATCGATAAACAGATGCTGCGAGACTTCGTGACA<br>ACTCGCCCAGCTCTCAAGGAACTGCTCAAAGAGGCTCTTAATATGGAGCGCAATAATAGATATCAAC<br>CCTTGCAGAACCACGCAAAGATGTGAGACAGCCGTCAGACCATCAAGACTAGGAAGAAACTGCATCA<br>ACTAATGAGCAAAATCACCAGCTAACATCATAGTATACATGACCGGCTCTAACTCACATATCACCAT<br>CCTTACACTTAACATTAACGGCCTCAACTCAGCTATCAAGCGCCATCGGCTGGCCAGCTGGATCAAA |

TABLE 13-continued

| Exemplary plasmid sequences | |
|---|---|
| Name | Sequence |
| | TCACAGGATCCAAGCGTTTGTTGCATCCAAGAGACCCACCTGACCTGTAGAGATACTCACCGCCTCA AGATCAAGGGATGGCGAAAGATTTATCAGGCGAACGGTAAGCAGAAGAAAGCCGGAGTCGCAATTCT GGTCTCAGACAAGACGGATTTCAAGCCCACCAAAATTAAGCGTGATAAGGAAGGTCACTATATTATG GTGAAAGGCAGCATACAGCAGGAAGAACTTACCATATTGAACATCTACGCGCCAAACACCGGCGCAC CTCGCTTTATCAAACAGGTCCTGTCCGATCTGCAGCGAGATCTGGATTCTCATACGTTGATTATGGG TGATTTCAATACACCATTGAGCACCCTGGATCGCAGCACCAGGCAAAAGGTAAATAAAGACACGCAA GAGCTCAATAGCGCACTGCATCAGGCAGATCTCATTGATATTTATCGCACTCTTCATCCTAAGAGTA CCGAGTACACATTCTTCAGCGCCCCACATCATACATACTCAAAGATCGATCATATCGTCGGCTCAAA GGCTCTGCTGTCAAAGTGCAAGCGCACAGAGATAATTACAAATTACCTGTCAGATCATAGCGCGATC AAGCTCGAGCTGAGAATCAAGAACCTGACCCAGAGCCGGAGTACCACTTGGAAGCTTAATAACCTGC TGCTCAACGATTATTGGGTCCACAATGAGATGAAGGCAGAGATTAAAATGTTCTTCGAAACAAATGA GAATAAGGATACTACCTATCAAAACCTTTGGGATGCCTTTAAGGCCGTCTGCAGAGGCAAGTTCATC GCCCTCAACGCCTATAAAAGAAAACAAGAGAGATCTAAGATCGATACTCTCACCTCTCAGCTGAAGG AGTTGGAGAAACAGGAACAGACCCACTCCAAGGCGTCAAGACGGCAGGAGATCACAAAGATTCGCGC CGAGTTGAAAGAGATCGAAACCCAAAAGACTCTTCAGAAAATTAACGAGTCTCGTAGTTGGTTCTTC GAGCGGATTAATAAGATAGACAGACCTCTGGCACGACTGATTAAGAAGAAGCGCGAAAAGAACCAGA TTGATACCATCAAGAACGACAAGGGCGACATCACTACTGACCCGACCGAGATCCAGACCACTATTCG GGAGTATTATAAGCATTTGTATGCTAACAAGCTTGAGAACCTGGAAGAGATGGACACTTTTCTGGAT ACCTATACTCTGCCACGGCTTAATCAAGAGGAAGTCGAGTCCCTCAACCGCCCAATTACAGGAAGCG AGATTGTGGCCATAATTAACTCCCTGCCGACAAAGAAATCTCCTGGTCCGGACGGGTTTACAGCTGA GTTTTATCAACGGTATATGGAAGAGCTTGTACCGTTTCTGCTCAAGCTCTTTCAGTCTATAGAAAAG GAAGGCATCTTGCCCAATTCCTTCTACGAAGCTTCTATAATACTTATTCCCAAACCAGGACGCGATA CCACAAAGAAGGAAAACTTCCGGCCCATTAGTCTCATGAATATCGACGCTAAAATATTGAACAAGAT TCTCGCCAACAGAATCCAACAACATATTAAGAAATTGATACATCACGACCAGGTGGGGTTTATACCT GGCATGCAGGGCTGGTTTAACATCCGGAAGAGTATTAACGTCATTCAACACATTAATAGAGCTAAGG ATAAGAATCATATGATCATCTCTATAGACGCGGAAAAGGCATTCGATAAGATTCAGCAGCCATTTAT GCTCAAGACTCTGAACAAACTCGGCATCGACGGAACATATTTTAAGATTATTCGCGCAATTTACGAT AAGCCGACTGCTAACATTATCCTTAACGGCCAAAAGCTCGAGGCCTTTCCGCTCAAGACTGGAACCC GCCAAGGCTGTCCCCTCTCCCCGCTTTTGTTTAATATTGTACTCGAGGTGCTGGCTAGGGCTATTCG TCAAGAGAAAGAGATTAAAGGGATACAGCTCGGGAAGGAAGAGGTCAAGCTTTCCTTGTTCGCCGAT GATATGATTGTGTACCTGGAGAATCCTATTGTGTCTGCTCAGAACCTTCTTAAACTTATTTCTAACT TTAGCAAGGTCAGCGGCTATAAGATTAACGTCCAGAAATCTCAGGCCTTTCTGTACACAAATAATCG ACAGACCGAATCCCAGATAATGGGTGAGCTTCCGTTTGTCATAGCCAGCAAAAGGATAAAGTATCTC GGAATCCAGCTGACACGAGACGTTAAAGATTTGTTTAAGGAAAATTACAAGCCTCTCCTGAAAGAGA TTAAGGAAGATACTAATAAGTGGAAGAATATCCCCTGTTCATGGGTTGGCAGAATCAACATAGTGAA GATGGCAATACTTCCTAAAGTGATATATCGCTTTAACGCCATCCCAATTAAACTGCCTATGACCTTC TTTACGGAGCTCGAGAAAACAACCCTTAAATTTATATGGAATCAAAAGAGAGCAAGAATAGCGAAGT CCATCTTGAGCCAGAAGAATAAGGCCGGTGGGATTACTTTGCCTGATTTTAAGTTGTATTATAAAGC CACAGTAACTAAGACAGCCTGGTATTGGTATCAGAATAGAGACATCGACCAGTGGAATCGGACCGAA CCATCAGAGATAATGCCCCACATCTATAATTACCTTATATTCGATAAGCCAGAAAAGAATAAACAGT GGGGCAAAGACAGCCTCTTCAACAAGTGGTGTTGGGAGAATTGGCTGGCCATATGCCGGAAACTCAA GCTCGACCCCTTTCTTACACCCTACACTAAAATCAACAGTAGGTGGATCAAGGACTTGAATGTCAAG CCAAAGACTATAAAGACACTGGAAGAGAATCTTGGGATCACAATACAAGATATAGGCGTCGGCAAAG ATTTTATGTCAAAGACGCCCAAGGCCATGGCCACTAAGGATAAGATTGATAAGTGGGACCTTATTAA GCTCAAAAGCTTCTGTACTGCCAAGGAGACCACGATCAGAGTTAATAGGCAGCCCACTACATGGGAA AAGATTTTCGCCACTTATTCATCAGATAAGGGGTTGATAAGCAGAATATATAACGAGCTGAAGCAGA TCTACAAGAAGAAAACGAATAATCCCATCAAGAAGTGGGCAAAAGATATGAACAGGCATTTTAGCAA AGAGGATATCTACGCCGCGAAGAAGCATATGAAGAAGTGTAGTTCAAGCTTGGCCATTCGTGAGATG CAGATTAAGACGACCATGCGATACCACCTTACCCCAGTGAGGATGGCAATTATCAAGAAATCTGGCA ATAATAGATGTTGGCGGGGCTGTGGCGAGATTGGCACCCTGCTCCATTGCTGGTGGGATTGCAAGCT GGTGCAGCCGCTTTGGAAATCAGTCTGGCGCTTTCTGAGGGACCTCGAGCTTGAGATTCCCTTCGAT CCCGCAATTCCCTTGCTCGGAATCTATCCTAACGAATACAAGAGCTGTTGTTACAAGGATACGTGTA CCCGGATGTTCATCGCGGCCTTGTTTACGATAGCTAAGACGTGGAATCAGCCTAAGTGCCCCACAAT GATCGATTGGATCAAGAAAATGTGGCATATTTATACCATGGAGTATTACGCAGCAATTAAGAATGAC GAATTTATTTCCTTCGTTGGGACCTGGATGAAGCTGGAGACTATTATTCTGAGCAAGCTGTCTCAGG AGCAAAAGACAAAGCATAGAATCTTCTCTCTCATTGGTGGTAACGACTACAAAGACGATGACGACAA GTAAAGCGCTTCTAGAAGTTGTCTCCTCCTGCACTGACTGACTGATACAATCGATTTCTGGATCCGC AGGCCTAATCAACCTCTGGATTACAAAATTTGTGAAAGATTGACTGGTATTCTTAACTATGTTGCTC CTTTTACGCTATGTGGATACGCTGCTTTAATGCCTTTGTATCATGCTATTGCTTCCCGTATGGCTTT CATTTTCTCCTCCTTGTATAAATCCTGGTTGCTGTCTCTTTATGAGGAGTTGTGGCCCGTTGTCAGG CAACGTGGCGTGGTGTGCACTGTGTTTGCTGACGCAACCCCCACTGGTTGGGGCATTGCCACCACCT GTCAGCTCCTTTCCGGGACTTTCGCTTTCCCCCTCCCTATTGCCACGGCGGAACTCATCGCCGCCTG CCTTGCCCGCTGCTGGACAGGGGCTCGGCTGTTGGGCACTGACAATTCCGTGGTGTTGTCGGGGAAG CTGACGTCCTTTCCATGGCTGCTCGCCTGTGTTGCCACCTGGATTCTGCGCGGGACGTCCTTCTGCT ACGTCCCTTCGGCCCTCAATCCAGCGGACCTTCCTTCCCGCtgagagacacaaaaaattccaacaca ctattgcaatgaaaataaatttcctttattagccagaagtcagatgctcaaggggcttcatgatgtc cccataatttttggcagagggaaaaagatctcagtggtatttgtgagccagggcattggccttctga taggcagcctgcacctgaggagtgcggccgctttacttgtacagctcgtccatgccgagagtgatcc cggcggcggtcacgaactccagcaggaccatgtgatcgcgcttctcgttggggtctttgctcagggc ggactgggtgctcaggtagtggttgtcgggcagcagcacggggccgtcgccgatgggggtgttctgc tggtagtggtcggcgagctgcacgctgccgtcctcgatgttgtggcggatcttgaagttcaccttga tgccgttcttctgcttgtcggccatgatatagacgttgtggctgttgtagttgtactccagcttgtg ccccaggatgttgccgtcctccttgaagtcgatgcccttcagctcgatgcggttcaccagggtgtcg ccctcgaacttcacctcggcgcgggtcttgtagttgccgtcgtccttgaagaagatggtgcgctcct ggacgtagccttcgggcatggcggacttgaagaagtcgtgctgcttcatgtggtcggggtagcggct gaagcactgcacgccgtaggtcagggtggtcacgagggtgggccagggcacgggcagcttgccggtg |

TABLE 13-continued

| Exemplary plasmid sequences | |
|---|---|
| Name | Sequence |
| | gtgcagatgaacttcagggtcagcttgccgtaggtggcatcgccctcgccctcgccggacacgctga<br>acttgtggccgtttacgtcgccgtccagctcgaccaggatgggcaccaccccggtgaacagctcctc<br>gcccttgctcaccatggtggcgggatctgacggttcactaaaccagctctgcttatatagacctccc<br>accgtacacgcctaccgcccatttgcgtcaatggggcggagttgttacgacattttggaaagtcccg<br>ttgattttggtgccaaaacaaactcccattgacgtcaatggggtggagacttggaaatccccgtgag<br>tcaaaccgctatccacgcccattgatgtactgccaaaaccgcatcaccatggtaatagcgatgacta<br>atacgtagatgtactgccaagtaggaaagtcccataaggtcatgtactgggcataatgccaggcggg<br>ccatttaccgtcattgacgtcaatagggggcgtacttggcatatgatacacttgatgtactgccaag<br>tgggcagtttaccgtaaatactccacccattgacgtcaatggaaagtccctattggcgttactatgg<br>gaacatacgtcattattgacgtcaatgggcgggggtcgttgggcggtcagccaggcgggccatttac<br>cgtaagttatgtaacgGGCCTGCTGCCGGCTCTGCGGCCTCTTCCGCGTCTTCGCCTTCGCCCTCAG<br>ACGAGTCGGATCTCCCTTTGGGCCGCCTCCCCGCCTGTCTAGCTTGACTGACTGAGATACAGCGTAC<br>CTTCAGCTCACAGACATGATAAGATACATTGATGAGTTTGGACAAACCACAACTAGAATGCAGTGAA<br>AAAAATGCTTTATTTGTGAAATTTGTGATGCTATTGCTTTATTTGTAACCATTATAAGCTGCAATAA<br>ACAAGTTAACAACAACAATTGCATTCATTTTATGTTTCAGGTTCAGGGGGAGGTGTGGGAGGTTTTT<br>TAAAGCAAGTAAAACCTCTACAAATGTGGTATTGGCCCATCTCTATCGGTATCGTAGCATAACCCCT<br>TGGGGCCTCTAAACGGGTCTTGAGGGGTTTTTTGTGCCCCTCGGGCCGGATTGCTATCTACCGGCAT<br>TGGCGCAGAAAAAAATGCCTGATGCGACGCTGCGCGTCTTATACTCCCACATATGCCAGATTCAGCA<br>ACGGATACGGCTTCCCCAACTTGCCCACTTCCATACGTGTCCTCCTTACCAGAAATTTATCCTTAAG<br>GTCGTCAGCTATCCTGCAGGCGATCTCTCGATTTCGATCAAGACATTCCTTTAATGGTCTTTTCTGG<br>ACACCACTAGGGGTCAGAAGTAGTTCATCAAACTTTCTTCCCTCCCTAATCTCATTGGTTACCTTGG<br>GCTATCGAAACTTAATTAAGCGATCTGCATCTCAATTAGTCAGCAACCATAGTCCCGCCCCTAACTC<br>CGCCCATCCCGCCCCTAACTCCGCCCAGTTCCGCCCATTCTCCGCCCCATCGCTGACTAATTTTTT<br>TATTTATGCAGAGGCCGAGGCCGCCTCGGCCTCTGAGCTATTCCAGAAGTAGTGAGGAGGCTTTTT<br>GGAGGCCTAGGCTTTTGCAAAGGAGGTAGCCAACATGATTGAACAAGATGGATTGCACGCAGGTTCT<br>CCCGCCGCTTGGGTGGAGAGGCTATTCGGCTATGACTGGGCACAACAGACAATCGGCTGCTCTGATG<br>CCGCCGTGTTCCGGCTGTCAGCGCAGGGGCGCCCGGTTCTTTTTGTCAAGACCGACCTGTCCGGTGC<br>CCTGAATGAACTCCAGGACGAGGCAGCGCGGCTATCGTGGCTGGCCACGACGGGCGTTCCTTGCGCA<br>GCTGTGCTCGACGTTGTCACTGAAGCGGGAAGGGACTGGCTGCTATTGGGCGAAGTGCCGGGGCAGG<br>ATCTCCTGTCATCTCACCTTGCTCCTGCCGAGAAAGTATCCATCATGGCTGATGCAATGCGGCGGCT<br>GCATACGCTTGATCCGGCTACCTGCCCATTCGACCACCAAGCGAAACATCGCATCGAGCGAGCACGT<br>ACTCGGATGGAAGCCGGTCTTGTCGATCAGGATGATCTGGACGAAGAGCATCAGGGGCTCGCGCCAG<br>CCGAACTGTTCGCCAGGCTCAAGGCGCGGATGCCCGACGGCGAGGATCTCGTCGTGACCCACGGCGA<br>TGCCTGCTTGCCGAATATCATGGTGGAAAATGGCCGCTTTTCTGGATTCATCGACTGTGGCCGGCTG<br>GGTGTGGCGGACCGCTATCAGGACATAGCGTTGGCTACCCGTGATATTGCTGAAGAGCTTGGCGGCG<br>AATGGGCTGACCGCTTCCTCGTGCTTTACGGTATCGCCGCTCCCGATTCGCAGCGCATCGCCTTCTA<br>TCGCCTTCTTGACGAGTTCTTCTAGTATGTAAGCCCTGTGCCTTCTAGTTGCCAGCCATCTGTTGTT<br>TGCCCCTCCCCCGTGCCTTCCTTGACCCTGGAAGGTGCCACTCCCACTGTCCTTTCCTAATAAAATG<br>AGGAAATTGCATCGCATTGTCTGAGTAGGTGTCATTCTATTCTGGGGGGTGGGGTGGGGCAGGACAG<br>CAAGGGGGAGGATTGGGAAGACAATAGCAGGCATGCTGGGGATGCGGTGGGCTCTATGGTTAATTAA<br>CCAGTCAAGTCAGCTACTTGGCGAGATCGACTTGTCTGGGTTTCGACTACGCTCAGAATTGCGTCAG<br>TCAAGTTCGATCTGGTCCTTGCTATTGCACCCGTTCTCCGATTACGAGTTTCATTTAAATCATGTGA<br>GCAAAAGGCCAGCAAAAGGCCAGGAACCGTAAAAAGGCCGCGTTGCTGGCGTTTTTCCATAGGCTCC<br>GCCCCCCTGACGAGCATCACAAAAATCGACGCTCAAGTCAGAGGTGGCGAAACCCGACAGGACTATA<br>AAGATACCAGGCGTTTCCCCCTGGAAGCTCCCTCGTGCGCTCTCCTGTTCCGACCCTGCCGCTTACC<br>GGATACCTGTCCGCCTTTCTCCCTTCGGGAAGCGTGGCGCTTTCTCATAGCTCACGCTGTAGGTATC<br>TCAGTTCGGTGTAGGTCGTTCGCTCCAAGCTGGGCTGTGTGCACGAACCCCCCGTTCAGCCCGACCG<br>CTGCGCCTTATCCGGTAACTATCGTCTTGAGTCCAACCCGGTAAGACACGACTTATCGCCACTGGCA<br>GCAGCCACTGGTAACAGGATTAGCAGAGCGAGGTATGTAGGCGGTGCTACAGAGTTCTTGAAGTGGT<br>GGCCTAACTACGGCTACACTAGAAGAACAGTATTTGGTATCTGCGCTCTGCTGAAGCCAGTTACCTT<br>CGGAAAAAGAGTTGGTAGCTCTTGATCCGGCAAACAAACCACCGCTGGTAGCGGTGGTTTTTTTGTT<br>TGCAAGCAGCAGATTACGCGCAGAAAAAAAGGATCTCAAGAAGATCCTTTGATCTTTTCTACGGGGT<br>CTGACGCTCAGTGGAACGAAAACTCACGTTAAGGGATTTTGGTCATGAGATTATCAAAAAGGATCTT<br>CACCTAGATCCTTTTAAATTAAAAATGAAGTTTTAAATCAATCTAAAGTATATATGAGTAAACTTGG<br>TCTGACAGTTACCAATGCTTAATCAGTGAGGCACCTATCTCAGCGATCTGTCTATTTCGTTCATCCA<br>TAGTTGCATTTAAATTTCCGAACTCTCCAAGGCCCTCGTC (SEQ ID NO: 98) |
| RET-009 LINE1-GFP ORF1-N Nucleo-plasmin NLS Linker | CAAACCTTTCGTCCGATCCATCTTGCAGGCTACCTCTCGAACGAACTATCGCAAGTCTCTTGGCCGG<br>CCTTGCGCCTTGGCTATTGCTTGGCAGCGCCTATCGCCAGGTATTACTCCAATCCCGAATATCCGAG<br>ATCGGGATCACCCGAGAGAAGTTCAACCTACATCCTCAATCCCGATCTATCCGAGATCCGAGGAATA<br>TCGAAATCGGGGCGCGCCTGGTGTACCGAGAACGATCCTCTCAGTGCGAGTCTCGACGATCCATATC<br>GTTGCTTGGCAGTCAGCCAGTCGGAATCCAGCTTGGGACCCAGGAAGTCCAATCGTCAGATATTGTA<br>CTCAAGCCTGGTCACGGCAGCGTACCGATCTGTTTAAACCTAGATATTGATAGTCTGATCGGTCAAC<br>GTATAATCGAGTCCTAGCTTTTGCAAACATCTATCAAGAGACAGGATCAGCAGGAGGCTTTCGCATG<br>AGTATTCAACATTTCCGTGTCGCCCTTATTCCCTTTTTTGCGGCATTTTGCCTTCCTGTTTTTGCTC<br>ACCCAGAAACGCTGGTGAAAGTAAAAGATGCTGAAGATCAGTTGGGTGCGCGAGTGGGTTACATCGA<br>ACTGGATCTCAACAGCGGTAAGATCCTTGAGAGTTTTCGCCCCGAAGAACGCTTTCCAATGATGAGC<br>ACTTTTAAAGTTCTGCTATGTGGCGCGGTATTATCCCGTATTGACGCCGGGCAAGAGCAACTCGGTC<br>GCCGCATACACTATTCTCAGAATGACTTGGTTGAGTATTCACCAGTCACAGAAAAGCATCTTACGGA<br>TGGCATGACAGTAAGAGAATTATGCAGTGCTGCCATAACCATGAGTGATAACACTGCGGCCAACTTA<br>CTTCTGACAACGATTGGAGGACCGAAGGAGCTAACCGCTTTTTTGCACAACATGGGGGATCATGTAA<br>CTCGCCTTGATCGTTGGGAACCGGAGCTGAATGAAGCCATACCAAACGACGAGCGTGACACCACGAT<br>GCCTGTAGCAATGGCAACAACCTTGCGTAAACTATTAACTGGCGAACTACTTACTCTAGCTTCCCGG<br>CAACAGTTGATAGACTGGATGGAGGCGGATAAAGTTGCAGGACCACTTCTGCGCTCGGCCCTTCCGG<br>CTGGCTGGTTTATTGCTGATAAATCTGGAGCCGGTGAGCGTGGGTCTCGCGGTATCATTGCAGCACT<br>GGGGCCAGATGGTAAGCCCTCCCGTATCGTAGTTATCTACACGACGGGGAGTCAGGCAACTATGGAT |

TABLE 13-continued

Exemplary plasmid sequences

| Name | Sequence |
|---|---|
| | GAACGAAATAGACAGATCGCTGAGATAGGTGCCTCACTGATTAAGCATTGGTAACCGATTCTAGGTG |
| | CATTGGCGCAGAAAAAAATGCCTGATGCGACGCTGCGCGTCTTATACTCCCACATATGCCAGATTCA |
| | GCAACGGATACGGCTTCCCCAACTTGCCCACTTCCATACGTGTCCTCCTTACCAGAAATTTATCCTT |
| | AAGATCGTTTAAACTCGACTCTGGCTCTATCGAATCTCCGTCGTTTCGAGCTTACGCGAACAGCCGT |
| | GGCGCTCATTTGCTCGTCGGGCATCGAATCTCGTCAGCTATCGTCAGCTTACCTTTTTGGCAGCGAT |
| | CGCGGCTCCCGACATCTTGGACCATTAGCTCCACAGGTATCTTCTTCCCTCTAGTGGTCATAACAGC |
| | AGCTTCAGCTACCTCTCAATTCAAAAAACCCCTCAAGACCCGTTTAGAGGCCCCAAGGGGTTATGCT |
| | ATCAATCGTTGCGTTACACACACAAAAAACCAACACACATCCATCTTCGATGGATAGCGATTTTATT |
| | ATCTAACTGCTGATCGAGTGTAGCCAGATCTAGTAATCAATTACGGGGTCATTAGTTCATAGCCCAT |
| | ATATGGAGTTCCGCGTTACATAACTTACGGTAAATGGCCCGCCTGGCTGACCGCCCAACGACCCCCG |
| | CCCATTGACGTCAATAATGACGTATGTTCCCATAGTAACGCCAATAGGGACTTTCCATTGACGTCAA |
| | TGGGTGGAGTATTTACGGTAAACTGCCCACTTGGCAGTACATCAAGTGTATCATATGCCAAGTACGC |
| | CCCCTATTGACGTCAATGACGGTAAATGGCCCGCCTGGCATTATGCCCAGTACATGACCTTATGGGA |
| | CTTTCCTACTTGGCAGTACATCTACGTATTAGTCATCGCTATTACCATGCTGATGCGGTTTTGGCAG |
| | TACATCAATGGGCGTGGATAGCGGTTTGACTCACGGGGATTTCCAAGTCTCCACCCCATTGACGTCA |
| | ATGGGAGTTTGTTTTGGCACCAAAATCAACGGGACTTTCCAAAATGTCGTAACAACTCCGCCCCATT |
| | GACGCAAATGGGCGGTAGGCGTGTACGGTGGGAGGTCTATATAAGCAGAGCTGGTTTAGTGAACCGT |
| | CAGATCAGATCTTTGTCGATCCTACCATCCACTCGACACACCCGCCAGCGGCCGCTAATACGACTCA |
| | CTATAGGGAGAAGTACTGCCACCATGaaaaggccggcggccacgaaaaaggccggccaggcaaaaaa |
| | gaaaaagggcggcggcagcGGCAAGAAGCAAAATCGCAAGACGGGGAATTCCAAGACACAATCCGCT |
| | AGCCCACCACCTAAAGAGCGTTCTAGCTCCCCTGCTACTGAGCAGTCCTGGATGGAAAACGACTTCG |
| | ATGAACTCCGGGAAGAGGGATTTAGGCGATCCAACTATTCAGAACTCCGCGAAGATATCCAGACAAA |
| | GGGGAAGGAAGTCGAGAATTTCGAGAAGAACCTCGAGGAGTGCATCACCCGTATCACAAACACTGAG |
| | AAATGTCTCAAAGAACTCATGGAACTTAAGACAAAAGCCAGGGAGCTTCGAGAGGAGTGTCGGAGTC |
| | TGAGATCCAGGTGTGACCAGCTCGAGGAGCGCGTGAGCGCGATGGAAGACGAGATGAACGAGATGAA |
| | AAGAGAGGGCAAATTCAGGGAGAAGCGCATTAAGAGGAACGAACAGAGTCTGCAGGAGATTTGGGAT |
| | TACGTCAAGAGGCCTAACCTGCGGTTGATCGGCGTCCCCGAGAGCGACGTAGAAAACGGGACTAAAC |
| | TGGAGAATACACTTCAAGACATCATTCAAGAAAATTTTCCAAACCTGGCTCGGCAAGCTAATGTGCA |
| | AATCCAAGAGATCCAACGCACACCCCAGCGGTATAGCTCTCGGCGTGCCACCCCTAGGCATATTATC |
| | GTGCGCTTTACTAAGGTGGAGATGAAAGAGAAGATGCTGCGAGCCGCTCGGGAAAAGGGAAGGGTGA |
| | CTTTGAAGGGCAAACCTATTCGGCTGACGGTTGACCTTAGCGCCGAGACACTCCAGGCACGCCGGGA |
| | ATGGGGCCCCATCTTTAATATCCTGAAGGAGAAGAACTTCCAGCCACGAATCTCTTACCCTGCAAAG |
| | TTGAGTTTTATCTCCGAGGGTGAGATTAAGTATTTCATCGATAAACAGATGCTGCGAGACTTCGTGA |
| | CAACTCGCCCAGCTCTCAAGGAACTGCTCAAAGAGGCTCTTAATATGGAGCGCAATAATAGATATCA |
| | ACCCTTGCAGAACCACGCAAAGATGTGAGACAGCCGTCAGACCATCAAGACTAGGAAGAAACTGCAT |
| | CAACTAATGAGCAAAATCACCAGCTAACATCATAGTATACATGACCGGCTCTAACTCACATATCACC |
| | ATCCTTACACTTAACATTAACGGCCTCAACTCAGCTATCAAGCGCCATCGGCTGGCCAGCTGGATCA |
| | AATCACAGGATCCAAGCGTTTGTTGCATCCAAGAGACCCACCTGACCTGTAGAGATACTCACCGCCT |
| | CAAGATCAAGGGATGGCGAAAGATTTATCAGGCGAACGGTAAGCAGAAGAAAGCCGGAGTCGCAATT |
| | CTGGTCTCAGACAAGACGGATTTCAAGCCCACCAAAATTAAGCGTGATAAGGAAGGTCACTATATTA |
| | TGGTGAAAGGCAGCATACAGCAGGAAGAACTTACCATATTGAACATCTACGCGCCAAACACCGGCGC |
| | ACCTCGCTTTATCAAACAGGTCCTGTCCGATCTGCAGCGAGATCTGGATTCTCATACGTTGATTATG |
| | GGTGATTTCAATACACCATTGAGCACCCTGGATCGCAGCACCAGGCAAAAGGTAAATAAAGACACGC |
| | AAGAGCTCAATAGCGCACTGCATCAGGCAGATCTCATTGATATTTATCGCACTCTTCATCCTAAGAG |
| | TACCGAGTACACATTCTTCAGCGCCCCACATCATACATACTCAAAGATCGATCATATCGTCGGCTCA |
| | AAGGCTCTGCTGTCAAAGTGCAAGCGCACAGAGATAATTACAAATTACCTGTCAGATCATAGCGCGA |
| | TCAAGCTCGAGCTGAGAATCAAGAACCTGACCCAGAGCCGGAGTACCACTTGGAAGCTTAATAACCT |
| | GCTGCTCAACGATTATTGGGTCCACAATGAGATGAAGGCAGAGATTAAAATGTTCTTCGAAACAAAT |
| | GAGAATAAGGATACTACCTATCAAAACCTTTGGGATGCCTTTAAGGCCGTCTGCAGAGGCAAGTTCA |
| | TCGCCCTCAACGCCTATAAAAGAAAACAAGAGAGATCTAAGATCGATACTCTCACCTCTCAGCTGAA |
| | GGAGTTGGAGAAACAGGAACAGACCCACTCCAAGGCGTCAAGACGGCAGGAGATCACAAAGATTCGC |
| | GCCGAGTTGAAAGAGATCGAAACCCAAAAGACTCTTCAGAAAATTAACGAGTCTCGTAGTTGGTTCT |
| | TCGAGCGGATTAATAAGATAGACAGACCTCTGGCACGACTGATTAAGAAGAAGCGCGAAAAGAACCA |
| | GATTGATACCATCAAGAACGACAAGGGCGACATCACTACTGACCCGACCGAGATCCAGACCACTATT |
| | CGGGAGTATTATAAGCATTTGTATGCTAACAAGCTTGAGAACCTGGAAGAGATGGACACTTTTCTGG |
| | ATACCTATACTCTGCCACGGCTTAATCAAGAGGAAGTCGAGTCCCTCAACCGCCCAATTACAGGAAG |
| | CGAGATTGTGGCCATAATTAACTCCCTGCCGACAAAGAAATCTCCTGGTCCGGACGGGTTTACAGCT |
| | GAGTTTTATCAACGGTATATGGAAGAGCTTGTACCGTTTCTGCTCAAGCTCTTTCAGTCTATAGAAA |
| | AGGAAGGCATCTTGCCCAATTCCTTCTACGAAGCTTCTATAATACTTATTCCCAAACCAGGACGCGA |
| | TACCACAAAGAAGGAAAACTTCCGGCCCATTAGTCTCATGAATATCGACGCTAAAATATTGAACAAG |
| | ATTCTCGCCAACAGAATCCAACAACATATTAAGAAATTGATACATCACGACCAGGTGGGGTTTATAC |
| | CTGGCATGCAGGGCTGGTTTAACATCCGGAAGAGTATTAACGTCATTCAACACATTAATAGAGCTAA |
| | GGATAAGAATCATATGATCATCTCTATAGACGCGGAAAAGGCATTCGATAAGATTCAGCAGCCATTT |
| | ATGCTCAAGACTCTGAACAAACTCGGCATCGACGGAACATATTTTAAGATTATTCGCGCAATTTACG |
| | ATAAGCCGACTGCTAACATTATCCTTAACGGCCAAAAGCTCGAGGCCTTTCCGCTCAAGACTGGAAC |
| | CCGCCAAGGCTGTCCCCTCTCCCCGCTTTTGTTTAATATTGTACTCGAGGTGCTGGCTAGGGCTATT |
| | CGTCAAGAGAAAGAGATTAAAGGGATACAGCTCGGGAAGGAAGAGGTCAAGCTTTCCTTGTTCGCCG |
| | ATGATATGATTGTGTACCTGGAGAATCCTATTGTGTCTGCTCAGAACCTTCTTAAACTTATTTCTAA |
| | CTTTAGCAAGGTCAGCGGCTATAAGATTAACGTCCAGAAATCTCAGGCCTTTCTGTACACAAATAAT |
| | CGACAGACCGAATCCCAGATAATGGGTGAGCTTCCGTTTGTCATAGCCAGCAAAAGGATAAAGTATC |
| | TCGGAATCCAGCTGACACGAGACGTTAAAGATTTGTTTAAGGAAAATTACAAGCCTCTCCTGAAAGA |
| | GATTAAGGAAGATACTAATAAGTGGAAGAATATCCCCTGTTCATGGGTTGGCAGAATCAACATAGTG |
| | AAGATGGCAATACTTCCTAAAGTGATATATCGCTTTAACGCCATCCCAATTAAACTGCCTATGACCT |
| | TCTTTACGGAGCTCGAGAAAACACCCCTTAAATTTATATGGAATCAAAAGAGAGCAAGAATAGCGAA |
| | GTCCATCTTGAGCCAGAAGAATAAGGCCGGTGGGATTACTTTGCCTGATTTTAAGTTGTATTATAAA |
| | GCCACAGTAACTAAGACAGCCTGGTATTGGTATCAGAATAGAGACATCGACCAGTGGAATCGGACCG |

TABLE 13-continued

| Exemplary plasmid sequences | |
|---|---|
| Name | Sequence |
| | AACCATCAGAGATAATGCCCCACATCTATAATTAGCTTATATTCGATAAGCCAGAAAAGAATAAACA GTGGGGCAAAGACAGCCTCTTCAACAAGTGGTGTTGGGAGAATTGGCTGGCCATATGCCGGAAACTC AAGCTCGACCCCTTTCTTACACCCTACACTAAAATCAACAGTAGGTGGATCAAGGACTTGAATGTCA AGCCAAAGACTATAAAGACACTGGAAGAGAATCTTGGGATCACAATACAAGATATAGGCGTCGGCAA AGATTTTATGTCAAAGACGCCCAAGGCCATGGCCACTAAGGATAAGATTGATAAGTGGGACCTTATT AAGCTCAAAAGCTTCTGTACTGCCAAGGAGACCACGATCAGAGTTAATAGGCAGCCCACTACATGGG AAAAGATTTTCGCCACTTATTCATCAGATAAGGGGTTGATAAGCAGAATATATAACGAGCTGAAGCA GATCTACAAGAAGAAAACGAATAATCCCATCAAGAAGTGGGCAAAAGATATGAACAGGCATTTTAGC AAAGAGGATATCTACGCCGCGAAGAAGCATATGAAGAAGTGTAGTTCAAGCTTGGCCATTCGTGAGA TGCAGATTAAGACGACCATGCGATACCACCTTACCCCAGTGAGGATGGCAATTATCAAGAAATCTGG CAATAATAGATGTTGGCGGGGCTGTGGCGAGATTGGCACCCTGCTCCATTGCTGGTGGGATTGCAAG CTGGTGCAGCCGCTTTGGAAATCAGTCTGGCGCTTTCTGAGGGACCTCGAGCTTGAGATTCCCTTCG ATCCCGCAATTCCCTTGCTCGGAATCTATCCTAACGAATACAAGAGCTGTTGTTACAAGGATACGTG TACCCGGATGTTCATCGCGGCCTTGTTTACGATAGCTAAGACGTGGAATCAGCCTAAGTGCCCCACA ATGATCGATTGGATCAAGAAAATGTGGCATATTTATACCATGGAGTATTACGCAGCAATTAAGAATG ACGAATTTATTTCCTTCGTTGGGACCTGGATGAAGCTGGAGACTATTATTCTGAGCAAGCTGTCTCA GGAGCAAAAGACAAAGCATAGAATCTTCTCTCTCATTGGTGGTAACGACTACAAAGACGATGACGAC AAGTAAAGCGCTTCTAGAAGTTGTCTCCTCCTGCACTGACTGACTGATACAATCGATTTCTGGATCC GCAGGCCTAATCAACCTCTGGATTACAAAATTTGTGAAAGATTGACTGGTATTCTTAACTATGTTGC TCCTTTTACGCTATGTGGATACGCTGCTTTAATGCCTTTGTATCATGCTATTGCTTCCCGTATGGCT TTCATTTTCTCCTCCTTGTATAAATCCTGGTTGCTGTCTCTTTATGAGGAGTTGTGGCCCGTTGTCA GGCAACGTGGCGTGGTGTGCACTGTGTTTGCTGACGCAACCCCCACTGGTTGGGGCATTGCCACCAC CTGTCAGCTCCTTTCCGGGACTTTCGCTTTCCCCCTCCCTATTGCCACGGCGGAACTCATCGCCGCC TGCCTTGCCCGCTGCTGGACAGGGGCTCGGCTGTTGGGCACTGACAATTCCGTGGTGTTGTCGGGGA AGCTGACGTCCTTTCCATGGCTGCTCGCCTGTGTTGCCACCTGGATTCTGCGCGGGACGTCCTTCTG CTACGTCCCTTCGGCCCTCAATCCAGCGGACCTTCCTTCCCGCtgagagacacaaaaaattccaaca cactattgcaatgaaaataaatttcctttattagccagaagtcagatgctcaaggggcttcatgatg tccccataattttggcagagggaaaaagatctcagtggtatttgtgagccagggcattggccttct gataggcagcctgcacctgaggagtgcggccgctttacttgtacagctcgtccatgccgagagtgat cccggcggcggtcacgaactccagcaggaccatgtgatcgcgcttctcgttggggtctttgctcagg gcggactgggtgctcaggtagtggttgtcgggcagcagcacggggccgtcgccgatgggggtgttct gctggtagtggtcggcgagctgcacgctgccgtcctcgatgttgtggcggatcttgaagttcacctt gatgccgttcttctgcttgtcggccatgatatagacgttgtggctgttgtagttgtactccagcttg tgccccaggatgttgccgtcctccttgaagtcgatgcccttcagctcgatgcggttcaccagggtgt cgccctcgaacttcacctcggcgcgggtcttgtagttgccgtcgtccttgaagaagatggtgcgctc ctggacgtagccttcgggcatggcggacttgaagaagtcgtgctgcttcatgtggtcggggtagcgg ctgaagcactgcacgccgtaggtcagggtggtcacgagggtgggccagggcacgggcagcttgccgg tggtgcagatgaacttcagggtcagcttgccgtaggtggcatcgccctcgccctcgccggacacgct gaacttgtggccgtttacgtcgccgtccagctcgaccaggatgggcaccaccccggtgaacagctcc tcgcccttgctcaccatggtggcgggatctgacggttcactaaaccagctctgcttatatagacctc ccaccgtacacgcctaccgcccatttgcgtcaatggggcggagttgttacgacattttggaaagtcc cgttgattttggtgccaaaacaaactcccattgacgtcaatggggtggagacttggaaatccccgtg agtcaaaccgctatccacgcccattgatgtactgccaaaaccgcatcaccatggtaatagcgatgac taatacgtagatgtactgccaagtaggaaagtcccataaggtcatgtactgggcataatgccaggcg ggccatttaccgtcattgacgtcaatagggggcgtacttggcatatgatacacttgatgtactgcca agtgggcagtttaccgtaaatactccacccattgacgtcaatggaaagtccctattggcgttactat gggaacatacgtcattattgacgtcaatgggcgggggtcgttgggcggtcagccaggcgggccattt accgtaagttatgtaacgGGCCTGCTGCCGGCTCTGCGGCCTCTTCCGCGTCTTCGCCTTCGCCCTC AGACGAGTCGGATCTCCCTTTGGGCCGCCTCCCCGCCTGTCTAGCTTGACTGACTGAGATACAGCGT ACCTTCAGCTCACAGACATGATAAGATACATTGATGAGTTTGGACAAACCACAACTAGAATGCAGTG AAAAAAATGCTTTATTTGTGAAATTTGTGATGCTATTGCTTTATTTGTAACCATTATAAGCTGCAAT AAACAAGTTAACAACAACAATTGCATTCATTTTATGTTTCAGGTTCAGGGGGAGGTGTGGGAGGTTT TTTAAAGCAAGTAAAACCTCTACAAATGTGGTATTGGCCCATCTCTATCGGTATCGTAGCATAACCC CTTGGGGCCTCTAAACGGGTCTTGAGGGGTTTTTTGTGCCCCTCGGGCCGGATTGCTATCTACCGGC ATTGGCGCAGAAAAAAATGCCTGATGCGACGCTGCGCGTCTTATACTCCCACATATGCCAGATTCAG CAACGGATACGGCTTCCCCAACTTGCCCACTTCCATACGTGTCCTCCTTACCAGAAATTTATCCTTA AGGTCGTCAGCTATCCTGCAGGCGATCTCTCGATTTCGATCAAGACATTCCTTTAATGGTCTTTTCT GGACACCACTAGGGGTCAGAAGTAGTTCATCAAACTTTCTTCCCTCCCTAATCTCATTGGTTACCTT GGGCTATCGAAACTTAATTAAGCGATCTGCATCTCAATTAGTCAGCAACCATAGTCCCGCCCCTAAC TCCGCCCATCCCGCCCCTAACTCCGCCCAGTTCCGCCCATTCTCCGCCCCATCGCTGACTAATTTTT TTTATTTATGCAGAGGCCGAGGCCGCCTCGGCCTCTGAGCTATTCCAGAAGTAGTGAGGAGGCTTTT TTGGAGGCCTAGGCTTTTGCAAAGGAGGTAGCCAACATGATTGAACAAGATGGATTGCACGCAGGTT CTCCCGCCGCTTGGGTGGAGAGGCTATTCGGCTATGACTGGGCACAACAGACAATCGGCTGCTCTGA TGCCGCCGTGTTCCGGCTGTCAGCGCAGGGGCGCCCGGTTCTTTTTGTCAAGACCGACCTGTCCGGT GCCCTGAATGAACTCCAGGACGAGGCAGCGCGGCTATCGTGGCTGGCCACGACGGGCGTTCCTTGCG CAGCTGTGCTCGACGTTGTCACTGAAGCGGGAAGGGACTGGCTGCTATTGGGCGAAGTGCCGGGGCA GGATCTCCTGTCATCTCACCTTGCTCCTGCCGAGAAAGTATCCATCATGGCTGATGCAATGCGGCGG CTGCATACGCTTGATCCGGCTACCTGCCCATTCGACCACCAAGCGAAACATCGCATCGAGCGAGCAC GTACTCGGATGGAAGCCGGTCTTGTCGATCAGGATGATCTGGACGAAGAGCATCAGGGGCTCGCGCC AGCCGAACTGTTCGCCAGGCTCAAGGCGCGGATGCCCGACGGCGAGGATCTCGTCGTGACCCACGGC GATGCCTGCTTGCCGAATATCATGGTGGAAAATGGCCGCTTTTCTGGATTCATCGACTGTGGCCGGC TGGGTGTGGCGGACCGCTATCAGGACATAGCGTTGGCTACCCGTGATATTGCTGAAGAGCTTGGCGG CGAATGGGCTGACCGCTTCCTCGTGCTTTACGGTATCGCCGCTCCCGATTCGCAGCGCATCGCCTTC TATCGCCTTCTTGACGAGTTCTTCTAGTATGTAAGCCCTGTGCCTTCTAGTTGCCAGCCATCTGTTG TTTGCCCCTCCCCCGTGCCTTCCTTGACCCTGGAAGGTGCCACTCCCACTGTCCTTTCCTAATAAAA TGAGGAAATTGCATCGCATTGTCTGAGTAGGTGTCATTCTATTCTGGGGGGTGGGGTGGGGCAGGAC |

TABLE 13-continued

Exemplary plasmid sequences

| Name | Sequence |
|---|---|
| | AGCAAGGGGGAGGATTGGGAAGACAATAGCAGGCATGCTGGGGATGCGGTGGGCTCTATGGTTAATT<br>AACCAGTCAAGTCAGCTACTTGGCGAGATCGACTTGTCTGGGTTTCGACTACGCTCAGAATTGCGTC<br>AGTCAAGTTCGATCTGGTCCTTGCTATTGCACCCGTTCTCCGATTACGAGTTTCATTTAAATCATGT<br>GAGCAAAAGGCCAGCAAAAGGCCAGGAACCGTAAAAAGGCCGCGTTGCTGGCGTTTTTCCATAGGCT<br>CCGCCCCCCTGACGAGCATCACAAAAATCGACGCTCAAGTCAGAGGTGGCGAAACCCGACAGGACTA<br>TAAAGATACCAGGCGTTTCCCCCTGGAAGCTCCCTCGTGCGCTCTCCTGTTCCGACCCTGCCGCTTA<br>CCGGATACCTGTCCGCCTTTCTCCCTTCGGGAAGCGTGGCGCTTTCTCATAGCTCACGCTGTAGGTA<br>TCTCAGTTCGGTGTAGGTCGTTCGCTCCAAGCTGGGCTGTGTGCACGAACCCCCCGTTCAGCCCGAC<br>CGCTGCGCCTTATCCGGTAACTATCGTCTTGAGTCCAACCCGGTAAGACACGACTTATCGCCACTGG<br>CAGCAGCCACTGGTAACAGGATTAGCAGAGCGAGGTATGTAGGCGGTGCTACAGAGTTCTTGAAGTG<br>GTGGCCTAACTACGGCTACACTAGAAGAACAGTATTTGGTATCTGCGCTCTGCTGAAGCCAGTTACC<br>TTCGGAAAAAGAGTTGGTAGCTCTTGATCCGGCAAACAAACCACCGCTGGTAGCGGTGGTTTTTTTG<br>TTTGCAAGCAGCAGATTACGCGCAGAAAAAAAGGATCTCAAGAAGATCCTTTGATCTTTTCTACGGG<br>GTCTGACGCTCAGTGGAACGAAAACTCACGTTAAGGGATTTTGGTCATGAGATTATCAAAAAGGATC<br>TTCACCTAGATCCTTTTAAATTAAAAATGAAGTTTTAAATCAATCTAAAGTATATATGAGTAAACTT<br>GGTCTGACAGTTACCAATGCTTAATCAGTGAGGCACCTATCTCAGCGATCTGTCTATTTCGTTCATC<br>CATAGTTGCATTTAAATTTCCGAACTCTCCAAGGCCCTCGTCGGAAAATCTT (SEQ ID NO: 99) |
| RET-010 LINE1-GFP ORF2-NSV40-NLS | GGGGCGCGCCTGGTGTACCGAGAACGATCCTCTCAGTGCGAGTCTCGACGATCCATATCGTTGCTTG<br>GCAGTCAGCCAGTCGGAATCCAGCTTGGGACCCAGGAAGTCCAATCGTCAGATATTGTACTCAAGCC<br>TGGTCACGGCAGCGTACCGATCTGTTTAAACCTAGATATTGATAGTCTGATCGGTCAACGTATAATC<br>GAGTCCTAGCTTTTGCAAACATCTATCAAGAGACAGGATCAGCAGGAGGCTTTCGCATGAGTATTCA<br>ACATTTCCGTGTCGCCCTTATTCCCTTTTTTGCGGCATTTTGCCTTCCTGTTTTTGCTCACCCAGAA<br>ACGCTGGTGAAAGTAAAAGATGCTGAAGATCAGTTGGGTGCGCGAGTGGGTTACATCGAACTGGATC<br>TCAACAGCGGTAAGATCCTTGAGAGTTTTCGCCCCGAAGAACGCTTTCCAATGATGAGCACTTTTAA<br>AGTTCTGCTATGTGGCGCGGTATTATCCCGTATTGACGCCGGGCAAGAGCAACTCGGTCGCCGCATA<br>CACTATTCTCAGAATGACTTGGTTGAGTATTCACCAGTCACAGAAAAGCATCTTACGGATGGCATGA<br>CAGTAAGAGAATTATGCAGTGCTGCCATAACCATGAGTGATAACACTGCGGCCAACTTAGTTCTGAC<br>AACGATTGGAGGACCGAAGGAGCTAACCGCTTTTTTGCACAACATGGGGGATCATGTAACTCGCCTT<br>GATCGTTGGGAACCGGAGCTGAATGAAGCCATACCAAACGACGAGCGTGACACCACGATGCCTGTAG<br>CAATGGCAACAACCTTGCGTAAACTATTAACTGGCGAACTACTTACTCTAGCTTCCCGGCAACAGTT<br>GATAGACTGGATGGAGGCGGATAAAGTTGCAGGACCACTTCTGCGCTCGGCCCTTCCGGCTGGCTGG<br>TTTATTGCTGATAAATCTGGAGCCGGTGAGCGTGGGTCTCGCGGTATCATTGCAGCACTGGGGCCAG<br>ATGGTAAGCCCTCCCGTATCGTAGTTATCTACACGACGGGGAGTCAGGCAACTATGGATGAACGAAA<br>TAGACAGATCGCTGAGATAGGTGCCTCACTGATTAAGCATTGGTAACCGATTCTAGGTGCATTGGCG<br>CAGAAAAAAATGCCTGATGCGACGCTGCGCGTCTTATACTCCCACATATGCCAGATTCAGCAACGGA<br>TACGGCTTCCCCAACTTGCCCACTTCCATACGTGTCCTCCTTACCAGAAATTTATCCTTAAGATCGT<br>TTAAACTCGACTCTGGCTCTATCGAATCTCCGTCGTTTCGAGCTTACGCGAACAGCCGTGGCGCTCA<br>TTTGCTCGTCGGGCATCGAATCTCGTCAGCTATCGTCAGCTTACCTTTTTGGCAGCGATCGCGGCTC<br>CCGACATCTTGGACCATTAGCTCCACAGGTATCTTCTTCCCTCTAGTGGTCATAACAGCAGCTTCAG<br>CTACCTCTCAATTCAAAAAACCCCTCAAGACCCGTTTAGAGGCCCCAAGGGGTTATGCTATCAATCG<br>TTGCGTTACACACACAAAAAACCAACACACATCCATCTTCGATGGATAGCGATTTTATTATCTAACT<br>GCTGATCGAGTGTAGCCAGATCTAGTAATCAATTACGGGGTCATTAGTTCATAGCCCATATATGGAG<br>TTCCGCGTTACATAACTTACGGTAAATGGCCCGCCTGGCTGACCGCCCAACGACCCCCGCCCATTGA<br>CGTCAATAATGACGTATGTTCCCATAGTAACGCCAATAGGGACTTTCCATTGACGTCAATGGGTGGA<br>GTATTTACGGTAAACTGCCCACTTGGCAGTACATCAAGTGTATCATATGCCAAGTACGCCCCCTATT<br>GACGTCAATGACGGTAAATGGCCCGCCTGGCATTATGCCCAGTACATGACCTTATGGGACTTTCCTA<br>CTTGGCAGTACATCTACGTATTAGTCATCGCTATTACCATGCTGATGCGGTTTTGGCAGTACATCAA<br>TGGGCGTGGATAGCGGTTTGACTCACGGGGATTTCCAAGTCTCCACCCCATTGACGTCAATGGGAGT<br>TTGTTTTGGCACCAAAATCAACGGGACTTTCCAAAATGTCGTAACAACTCCGCCCCATTGACGCAAA<br>TGGGCGGTAGGCGTGTACGGTGGGAGGTCTATATAAGCAGAGCTGGTTTAGTGAACCGTCAGATCAG<br>ATCTTTGTCGATCCTACCATCCACTCGACACACCCGCCAGCGGCCGCTAATACGACTCACTATAGGG<br>AGAAGTACTGCCACCATGGGCAAGAAGCAAAATCGCAAGACGGGGAATTCCAAGACACAATCCGCTA<br>GCCCACCACCTAAAGAGCGTTCTAGCTCCCCTGCTACTGAGCAGTCCTGGATGGAAAACGACTTCGA<br>TGAACTCCGGGAAGAGGGATTTAGGCGATCCAACTATTCAGAACTCCGCGAAGATATCCAGACAAAG<br>GGGAAGGAAGTCGAGAATTTCGAGAAGAACCTCGAGGAGTGCATCACCCGTATCACAAACACTGAGA<br>AATGTCTCAAAGAACTCATGGAACTTAAGACAAAAGCCAGGGAGCTTCGAGAGGAGTGTCGGAGTCT<br>GAGATCCAGGTGTGACCAGCTCGAGGAGCGCGTGAGCGCGATGGAAGACGAGATGAACGAGATGAAA<br>AGAGAGGGCAAATTCAGGGAGAAGCGCATTAAGAGGAACGAACAGAGTCTGCAGGAGATTTGGGATT<br>ACGTCAAGAGGCCTAACCTGCGGTTGATCGGCGTCCCCGAGAGCGACGTAGAAAACGGGACTAAACT<br>GGAGAATACACTTCAAGACATCATTCAAGAAAATTTTCCAAACCTGGCTCGGCAAGCTAATGTGCAA<br>ATCCAAGAGATCCAACGCACACCCCAGCGGTATAGCTCTCGGCGTGCCACCCCTAGGCATATTATCG<br>TGCGCTTTACTAAGGTGGAGATGAAAGAGAAGATGCTGCGAGCCGCTCGGGAAAAGGGAAGGGTGAC<br>TTTGAAGGGCAAACCTATTCGGCTGACGGTTGACCTTAGCGCCGAGACACTCCAGGCACGCCGGGAA<br>TGGGGCCCCATCTTTAATATCCTGAAGGAGAAGAACTTCCAGCCACGAATCTCTTACCCTGCAAAGT<br>TGAGTTTTATCTCCGAGGGTGAGATTAAGTATTTCATCGATAAACAGATGCTGCGAGACTTCGTGAC<br>AACTCGCCCAGCTCTCAAGGAACTGCTCAAAGAGGCTCTTAATATGGAGCGCAATAATAGATATCAA<br>CCCTTGCAGAACCACGCAAAGATGTGAGACAGCCGTCAGACCATCAAGACTAGGAAGAAACTGCATC<br>AACTAATGAGCAAAATCACCAGCTAACATCATAGTATACATGccaaagaagaagcggaaggtcACCG<br>GCTCTAACTCACATATCACCATCCTTACACTTAACATTAACGGCCTCAACTCAGCTATCAAGCGCCA<br>TCGGCTGGCCAGCTGGATCAAATCACAGGATCCAAGCGTTTGTTGCATCCAAGAGACCCACCTGACC<br>TGTAGAGATACTCACCGCCTCAAGATCAAGGGATGGCGAAAGATTTATCAGGCGAACGGTAAGCAGA<br>AGAAAGCCGGAGTCGCAATTCTGGTCTCAGACAAGACGGATTTCAAGCCCACCAAAATTAAGCGTGA<br>TAAGGAAGGTCACTATATTATGGTGAAAGGCAGCATACAGCAGGAAGAACTTACCATATTGAACATC<br>TACGCGCCAAACACCGGCGCACCTCGCTTTATCAAACAGGTCCTGTCCGATCTGCAGCGAGATCTGG |

TABLE 13-continued

Exemplary plasmid sequences

| Name | Sequence |
|---|---|
| | ATTCTCATACGTTGATTATGGGTGATTTCAATACACCATTGAGCACCCTGGATCGCAGCACCAGGCA |
| | AAAGGTAAATAAAGACACGCAAGAGCTCAATAGCGCACTGCATCAGGCAGATCTCATTGATATTTAT |
| | CGCACTCTTCATCCTAAGAGTACCGAGTACACATTCTTCAGCGCCCCACATCATACATACTCAAAGA |
| | TCGATCATATCGTCGGCTCAAAGGCTCTGCTGTCAAAGTGCAAGCGCACAGAGATAATTACAAATTA |
| | CCTGTCAGATCATAGCGCGATCAAGCTCGAGCTGAGAATCAAGAACCTGACCCAGAGCCGGAGTACC |
| | ACTTGGAAGCTTAATAACCTGCTGCTCAACGATTATTGGGTCCACAATGAGATGAAGGCAGAGATTA |
| | AAATGTTCTTCGAAACAAATGAGAATAAGGATACTACCTATCAAAACCTTTGGGATGCCTTTAAGGC |
| | CGTCTGCAGAGGCAAGTTCATCGCCCTCAACGCCTATAAAAGAAAACAAGAGAGATCTAAGATCGAT |
| | ACTCTCACCTCTCAGCTGAAGGAGTTGGAGAAACAGGAACAGACCCACTCCAAGGCGTCAAGACGGC |
| | AGGAGATCACAAAGATTCGCGCCGAGTTGAAAGAGATCGAAACCCAAAAGACTCTTCAGAAAATTAA |
| | CGAGTCTCGTAGTTGGTTCTTCGAGCGGATTAATAAGATAGACAGACCTCTGGCACGACTGATTAAG |
| | AAGAAGCGCGAAAAGAACCAGATTGATACCATCAAGAACGACAAGGGCGACATCACTACTGACCCGA |
| | CCGAGATCCAGACCACTATTCGGGAGTATTATAAGCATTTGTATGCTAACAAGCTTGAGAACCTGGA |
| | AGAGATGGACACTTTTCTGGATACCTATACTCTGCCACGGCTTAATCAAGAGGAAGTCGAGTCCCTC |
| | AACCGCCCAATTACAGGAAGCGAGATTGTGGCCATAATTAACTCCCTGCCGACAAAGAAATCTCCTG |
| | GTCCGGACGGGTTTACAGCTGAGTTTTATCAACGGTATATGGAAGAGCTTGTACCGTTTCTGCTCAA |
| | GCTCTTTCAGTCTATAGAAAAGGAAGGCATCTTGCCCAATTCCTTCTACGAAGCTTCTATAATACTT |
| | ATTCCCAAACCAGGACGCGATACCACAAAGAAGGAAAACTTCCGGCCCATTAGTCTCATGAATATCG |
| | ACGCTAAAATATTGAACAAGATTCTCGCCAACAGAATCCAACAACATATTAAGAAATTGATACATCA |
| | CGACCAGGTGGGGTTTATACCTGGCATGCAGGGCTGGTTTAACATCCGGAAGAGTATTAACGTCATT |
| | CAACACATTAATAGAGCTAAGGATAAGAATCATATGATCATCTCTATAGACGCGGAAAAGGCATTCG |
| | ATAAGATTCAGCAGCCATTTATGCTCAAGACTCTGAACAAACTCGGCATCGACGGAACATATTTTAA |
| | GATTATTCGCGCAATTTACGATAAGCCGACTGCTAACATTATCCTTAACGGCCAAAAGCTCGAGGCC |
| | TTTCCGCTCAAGACTGGAACCCGCCAAGGCTGTCCCCTCTCCCCGCTTTTGTTTAATATTGTACTCG |
| | AGGTGCTGGCTAGGGCTATTCGTCAAGAGAAAGAGATTAAAGGGATACAGCTCGGGAAGGAAGAGGT |
| | CAAGCTTTCCTTGTTCGCCGATGATATGATTGTGTACCTGGAGAATCCTATTGTGTCTGCTCAGAAC |
| | CTTCTTAAACTTATTTCTAACTTTAGCAAGGTCAGCGGCTATAAGATTAACGTCCAGAAATCTCAGG |
| | CCTTTCTGTACACAAATAATCGACAGACCGAATCCCAGATAATGGGTGAGCTTCCGTTTGTCATAGC |
| | CAGCAAAAGGATAAAGTATCTCGGAATCCAGCTGACACGAGACGTTAAAGATTTGTTTAAGGAAAAT |
| | TACAAGCCTCTCCTGAAAGAGATTAAGGAAGATACTAATAAGTGGAAGAATATCCCCTGTTCATGGG |
| | TTGGCAGAATCAACATAGTGAAGATGGCAATACTTCCTAAAGTGATATATCGCTTTAACGCCATCCC |
| | AATTAAACTGCCTATGACCTTCTTTACGGAGCTCGAGAAAACAACCCTTAAATTTATATGGAATCAA |
| | AAGAGAGCAAGAATAGCGAAGTCCATCTTGAGCCAGAAGAATAAGGCCGGTGGGATTACTTTGCCTG |
| | ATTTTAAGTTGTATTATAAAGCCACAGTAACTAAGACAGCCTGGTATTGGTATCAGAATAGAGACAT |
| | CGAGCAGTGGAATCGGACCGAACCATCAGAGATAATGCCCCACATCTATAATTACCTTATATTCGAT |
| | AAGCCAGAAAAGAATAAACAGTGGGGCAAAGACAGCCTCTTCAACAAGTGGTGTTGGGAGAATTGGC |
| | TGGCCATATGCCGGAAACTCAAGCTCGACCCCTTTCTTACACCCTACACTAAAATCAACAGTAGGTG |
| | GATCAAGGACTTGAATGTCAAGCCAAAGACTATAAAGACACTGGAAGAGAATCTTGGGATCACAATA |
| | CAAGATATAGGCGTCGGCAAAGATTTTATGTCAAAGACGCCCAAGGCCATGGCCACTAAGGATAAGA |
| | TTGATAAGTGGGACCTTATTAAGCTCAAAAGCTTCTGTACTGCCAAGGAGACCACGATCAGAGTTAA |
| | TAGGCAGCCCACTACATGGGAAAAGATTTTCGCCACTTATTCATCAGATAAGGGGTTGATAAGCAGA |
| | ATATATAACGAGCTGAAGCAGATCTACAAGAAGAAAACGAATAATCCCATCAAGAAGTGGGCAAAAG |
| | ATATGAACAGGCATTTTAGCAAAGAGGATATCTACGCCGCGAAGAAGCATATGAAGAAGTGTAGTTC |
| | AAGCTTGGCCATTCGTGAGATGCAGATTAAGACGACCATGCGATACCACCTTACCCCAGTGAGGATG |
| | GCAATTATCAAGAAATCTGGCAATAATAGATGTTGGCGGGGCTGTGGCGAGATTGGCACCCTGCTCC |
| | ATTGCTGGTGGGATTGCAAGCTGGTGCAGCCGCTTTGGAAATCAGTCTGGCGCTTTCTGAGGGACCT |
| | CGAGCTTGAGATTCCCTTCGATCCCGCAATTCCCTTGCTCGGAATCTATCCTAACGAATACAAGAGC |
| | TGTTGTTACAAGGATACGTGTACCCGGATGTTCATCGCGGCCTTGTTTACGATAGCTAAGACGTGGA |
| | ATCAGCCTAAGTGCCCCACAATGATCGATTGGATCAAGAAAATGTGGCATATTTATACCATGGAGTA |
| | TTACGCAGCAATTAAGAATGACGAATTTATTTCCTTCGTTGGGACCTGGATGAAGCTGGAGACTATT |
| | ATTCTGAGCAAGCTGTCTCAGGAGCAAAAGACAAAGCATAGAATCTTCTCTCTCATTGGTGGTAACG |
| | ACTACAAAGACGATGACGACAAGTAAAGCGCTTCTAGAAGTTGTCTCCTCCTGCACTGACTGACTGA |
| | TACAATCGATTTCTGGATCCGCAGGCCTAATCAACCTCTGGATTACAAAATTTGTGAAAGATTGACT |
| | GGTATTCTTAACTATGTTGCTCCTTTTACGCTATGTGGATACGCTGCTTTAATGCCTTTGTATCATG |
| | CTATTGCTTCCCGTATGGCTTTCATTTTCTCCTCCTTGTATAAATCCTGGTTGCTGTCTCTTTATGA |
| | GGAGTTGTGGCCCGTTGTCAGGCAACGTGGCGTGGTGTGCACTGTGTTTGCTGACGCAACCCCCACT |
| | GGTTGGGGCATTGCCACCACCTGTCAGCTCCTTTCCGGGACTTTCGCTTTCCCCCTCCCTATTGCCA |
| | CGGCGGAACTCATCGCCGCCTGCCTTGCCCGCTGCTGGACAGGGGCTCGGCTGTTGGGCACTGACAA |
| | TTCCGTGGTGTTGTCGGGGAAGCTGACGTCCTTTCCATGGCTGCTCGCCTGTGTTGCCACCTGGATT |
| | CTGCGCGGGACGTCCTTCTGCTACGTCCCTTCGGCCCTCAATCCAGCGGACCTTCCTTCCCGCtgag |
| | agacacaaaaaattccaacacactattgcaatgaaaataaatttcctttattagccagaagtcagat |
| | gctcaaggggcttcatgatgtccccataatttttggcagagggaaaaagatctcagtggtatttgtg |
| | agccagggcattggccttctgataggcagcctgcacctgaggagtgcggccgctttacttgtacagc |
| | tcgtccatgccgagagtgatcccggcggcggtcacgaactccagcaggaccatgtgatcgcgcttct |
| | cgttggggtctttgctcagggcggactgggtgctcaggtagtggttgtcgggcagcagcacggggcc |
| | gtcgccgatgggggtgttctgctggtagtggtcggcgagctgcacgctgccgtcctcgatgttgtgg |
| | cggatcttgaagttcaccttgatgccgttcttctgcttgtcggccatgatatagacgttgtggctgt |
| | tgtagttgtactccagcttgtgccccaggatgttgccgtcctccttgaagtcgatgcccttcagctc |
| | gatgcggttcaccagggtgtcgccctcgaacttcacctcggcgcgggtcttgtagttgccgtcgtcc |
| | ttgaagaagatggtgcgctcctggacgtagccttcgggcatggcggacttgaagaagtcgtgctgct |
| | tcatgtggtcggggtagcggctgaagcactgcacgccgtaggtcagggtggtcacgagggtgggcca |
| | gggcacgggcagcttgccggtggtgcagatgaacttcagggtcagcttgccgtaggtggcatcgccc |
| | tcgccctcgccggacacgctgaacttgtggccgtttacgtcgccgtccagctcgaccaggatgggca |
| | ccaccccggtgaacagctcctcgcccttgctcaccatggtggcgggatctgacggttcactaaacca |
| | gctctgcttatatagacctcccaccgtacacgcctaccgcccatttgcgtcaatggggcggagttgt |
| | tacgacattttggaaagtcccgttgattttggtgccaaaacaaactcccattgacgtcaatggggtg |

TABLE 13-continued

Exemplary plasmid sequences

| Name | Sequence |
|---|---|
| | gagacttggaaatccccgtgagtcaaaccgctatccacgcccattgatgtactgccaaaaccgcatc<br>accatggtaatagcgatgactaatacgtagatgtactgccaagtaggaaagtcccataaggtcatgt<br>actgggcataatgccaggcgggccatttaccgtcattgacgtcaatagggggcgtacttggcatatg<br>atacacttgatgtactgccaagtgggcagtttaccgtaaatactccacccattgacgtcaatggaaa<br>gtccctattggcgttactatgggaacatacgtcattattgacgtcaatgggcgggggtcgttgggcg<br>gtcagccaggcgggccatttaccgtaagttatgtaacgGGCCTGCTGCCGGCTCTGCGGCCTCTTCC<br>GCGTCTTCGCCTTCGCCCTCAGACGAGTCGGATCTCCCTTTGGGCCGCCTCCCCGCCTGTCTAGCTT<br>GACTGACTGAGATACAGCGTACCTTCAGCTCACAGACATGATAAGATACATTGATGAGTTTGGACAA<br>ACCACAACTAGAATGCAGTGAAAAAAATGCTTTATTTGTGAAATTTGTGATGCTATTGCTTTATTTG<br>TAACCATTATAAGCTGCAATAAACAAGTTAACAACAACAATTGCATTCATTTTATGTTTCAGGTTCA<br>GGGGGAGGTGTGGGAGGTTTTTTAAAGCAAGTAAAACCTCTACAAATGTGGTATTGGCCCATCTCTA<br>TCGGTATCGTAGCATAACCCCTTGGGGCCTCTAAACGGGTCTTGAGGGGTTTTTTGTGCCCCTCGGG<br>CCGGATTGCTATCTACCGGCATTGGCGCAGAAAAAAATGCCTGATGCGACGCTGCGCGTCTTATACT<br>CCCACATATGCCAGATTCAGCAACGGATACGGCTTCCCCAACTTGCCCACTTCCATACGTGTCCTCC<br>TTACCAGAAATTTATCCTTAAGGTCGTCAGCTATCCTGCAGGCGATCTCTCGATTTCGATCAAGACA<br>TTCCTTTAATGGTCTTTTCTGGACACCACTAGGGGTCAGAAGTAGTTCATCAAACTTTCTTCCCTCC<br>CTAATCTCATTGGTTACCTTGGGCTATCGAAACTTAATTAAGCGATCTGCATCTCAATTAGTCAGCA<br>ACCATAGTCCCGCCCCTAACTCCGCCCATCCCGCCCCTAACTCCGCCCAGTTCCGCCCATTCTCCGC<br>CCCATCGCTGACTAATTTTTTTTATTTATGCAGAGGCCGAGGCCGCCTCGGCCTCTGAGCTATTCCA<br>GAAGTAGTGAGGAGGCTTTTTTGGAGGCCTAGGCTTTTGCAAAGGAGGTAGCCAACATGATTGAACA<br>AGATGGATTGCACGCAGGTTCTCCCGCCGCTTGGGTGGAGAGGCTATTCGGCTATGACTGGGCACAA<br>CAGACAATCGGCTGCTCTGATGCCGCCGTGTTCCGGCTGTCAGCGCAGGGGCGCCCGGTTCTTTTTG<br>TCAAGACCGACCTGTCCGGTGCCCTGAATGAACTCCAGGACGAGGCAGCGCGGCTATCGTGGCTGGC<br>CACGACGGGCGTTCCTTGCGCAGCTGTGCTCGACGTTGTCACTGAAGCGGGAAGGGACTGGCTGCTA<br>TTGGGCGAAGTGCCGGGGCAGGATCTCCTGTCATCTCACCTTGCTCCTGCCGAGAAAGTATCCATCA<br>TGGCTGATGCAATGCGGCGGCTGCATACGCTTGATCCGGCTACCTGCCCATTCGACCACCAAGCGAA<br>ACATCGCATCGAGCGAGCACGTACTCGGATGGAAGCCGGTCTTGTCGATCAGGATGATCTGGACGAA<br>GAGCATCAGGGGCTCGCGCCAGCCGAACTGTTCGCCAGGCTCAAGGCGCGGATGCCCGACGGCGAGG<br>ATCTCGTCGTGACCCACGGCGATGCCTGCTTGCCGAATATCATGGTGGAAAATGGCCGCTTTTCTGG<br>ATTCATCGACTGTGGCCGGCTGGGTGTGGCGGACCGCTATCAGGACATAGCGTTGGCTACCCGTGAT<br>ATTGCTGAAGAGCTTGGCGGCGAATGGGCTGACCGCTTCCTCGTGCTTTACGGTATCGCCGCTCCCG<br>ATTCGCAGCGCATCGCCTTCTATCGCCTTCTTGACGAGTTCTTCTAGTATGTAAGCCCTGTGCCTTC<br>TAGTTGCCAGCCATCTGTTGTTTGCCCCTCCCCCGTGCCTTCCTTGACCCTGGAAGGTGCCACTCCC<br>ACTGTCCTTTCCTAATAAAATGAGGAAATTGCATCGCATTGTCTGAGTAGGTGTCATTCTATTCTGG<br>GGGGTGGGGTGGGGCAGGACAGCAAGGGGGAGGATTGGGAAGACAATAGCAGGCATGCTGGGGATGC<br>GGTGGGCTCTATGGTTAATTAACCAGTCAAGTCAGCTACTTGGCGAGATCGACTTGTCTGGGTTTCG<br>ACTACGCTCAGAATTGCGTCAGTCAAGTTCGATCTGGTCCTTGCTATTGCACCCGTTCTCCGATTAC<br>GAGTTTCATTTAAATCATGTGAGCAAAAGGCCAGCAAAAGGCCAGGAACCGTAAAAAGGCCGCGTTG<br>CTGGCGTTTTTCCATAGGCTCCGCCCCCCTGACGAGCATCACAAAAATCGACGCTCAAGTCAGAGGT<br>GGCGAAACCCGACAGGACTATAAAGATACCAGGCGTTTCCCCCTGGAAGCTCCCTCGTGCGCTCTCC<br>TGTTCCGACCCTGCCGCTTACCGGATACCTGTCCGCCTTTCTCCCTTCGGGAAGCGTGGCGCTTTCT<br>CATAGCTCACGCTGTAGGTATCTCAGTTCGGTGTAGGTCGTTCGCTCCAAGCTGGGCTGTGTGCACG<br>AACCCCCCGTTCAGCCCGACCGCTGCGCCTTATCCGGTAACTATCGTCTTGAGTCCAACCCGGTAAG<br>ACACGACTTATCGCCACTGGCAGCAGCCACTGGTAACAGGATTAGCAGAGCGAGGTATGTAGGCGGT<br>GCTACAGAGTTCTTGAAGTGGTGGCCTAACTACGGCTACACTAGAAGAACAGTATTTGGTATCTGCG<br>CTCTGCTGAAGCCAGTTACCTTCGGAAAAAGAGTTGGTAGCTCTTGATCCGGCAAACAAACCACCGC<br>TGGTAGCGGTGGTTTTTTTGTTTGCAAGCAGCAGATTACGCGCAGAAAAAAAGGATCTCAAGAAGAT<br>CCTTTGATCTTTTCTACGGGGTCTGACGCTCAGTGGAACGAAAACTCACGTTAAGGGATTTTGGTCA<br>TGAGATTATCAAAAAGGATCTTCACCTAGATCCTTTTAAATTAAAAATGAAGTTTTAAATCAATCTA<br>AAGTATATATGAGTAAACTTGGTCTGACAGTTACCAATGCTTAATCAGTGAGGCACCTATCTCAGCG<br>ATCTGTCTATTTCGTTCATCCATAGTTGCATTTAAATTTCCGAACTCTCCAAGGCCCTCGTCGGAAA<br>ATCTTCAAACCTTTCGTCCGATCCATCTTGCAGGCTACCTCTCGAACGAACTATCGCAAGTCTCTTG<br>GCCGGCCTTGCGCCTTGGCTATTGCTTGGCAGCGCCTATCGCCAGGTATTACTCCAATCCCGAATAT<br>CCGAGATCGGGATCACCCGAGAGAAGTTCAACCTACATCCTCAATCCCGATCTATCCGAGATCCGAG<br>GAATATCGAAATC (SEQ ID NO: 100) |
| ret-011-line1-gfp-orf2-n-sv40-nls-linker | TGGCCGGCCTTGCGCCTTGGCTATTGCTTGGCAGCGCCTATCGCCAGGTATTACTCCAATCCCGAAT<br>ATCCGAGATCGGGATCACCCGAGAGAAGTTCAACCTACATCCTCAATCCCGATCTATCCGAGATCCG<br>AGGAATATCGAAATCGGGGCGCGCCTGGTGTACCGAGAACGATCCTCTCAGTGCGAGTCTCGACGAT<br>CCATATCGTTGCTTGGCAGTCAGCCAGTCGGAATCCAGCTTGGGACCCAGGAAGTCCAATCGTCAGA<br>TATTGTACTCAAGCCTGGTCACGGCAGCGTACCGATCTGTTTAAACCTAGATATTGATAGTCTGATC<br>GGTCAACGTATAATCGAGTCCTAGCTTTTGCAAACATCTATCAAGAGACAGGATCAGCAGGAGGCTT<br>TCGCATGAGTATTCAACATTTCCGTGTCGCCCTTATTCCCTTTTTTGCGGCATTTTGCCTTCCTGTT<br>TTTGCTCACCCAGAAACGCTGGTGAAAGTAAAAGATGCTGAAGATCAGTTGGGTGCGCGAGTGGGTT<br>ACATCGAACTGGATCTCAACAGCGGTAAGATCCTTGAGAGTTTTCGCCCCGAAGAACGCTTTCCAAT<br>GATGAGCACTTTTAAAGTTCTGCTATGTGGCGCGGTATTATCCCGTATTGACGCCGGGCAAGAGCAA<br>CTCGGTCGCCGCATACACTATTCTCAGAATGACTTGGTTGAGTATTCACCAGTCACAGAAAAGCATC<br>TTACGGATGGCATGACAGTAAGAGAATTATGCAGTGCTGCCATAACCATGAGTGATAACACTGCGGC<br>CAACTTACTTCTGACAACGATTGGAGGACCGAAGGAGCTAACCGCTTTTTTGCACAACATGGGGGAT<br>CATGTAACTCGCCTTGATCGTTGGGAACCGGAGCTGAATGAAGCCATACCAAACGACGAGCGTGACA<br>CCACGATGCCTGTAGCAATGGCAACAACCTTGCGTAAACTATTAACTGGCGAACTACTTACTCTAGC<br>TTCCCGGCAACAGTTGATAGACTGGATGGAGGCGGATAAAGTTGCAGGACCACTTCTGCGCTCGGCC<br>CTTCCGGCTGGCTGGTTTATTGCTGATAAATCTGGAGCCGGTGAGCGTGGGTCTCGCGGTATCATTG<br>CAGCACTGGGGCCAGATGGTAAGCCCTCCCGTATCGTAGTTATCTACACGACGGGGAGTCAGGCAAC<br>TATGGATGAACGAAATAGACAGATCGCTGAGATAGGTGCCTCACTGATTAAGCATTGGTAACCGATT<br>CTAGGTGCATTGGCGCAGAAAAAAATGCCTGATGCGACGCTGCGCGTCTTATACTCCCACATATGCC |

TABLE 13-continued

Exemplary plasmid sequences

| Name | Sequence |
| --- | --- |
| | AGATTCAGCAACGGATACGGCTTCCCCAACTTGCCCACTTCCATACGTGTCCTCCTTACCAGAAATT |
| | TATCCTTAAGATCGTTTAAACTCGACTCTGGCTCTATCGAATCTCCGTCGTTTCGAGCTTACGCGAA |
| | CAGCCGTGGCGCTCATTTGCTCGTCGGGCATCGAATCTCGTCAGCTATCGTCAGCTTACCTTTTTGG |
| | CAGCGATCGCGGCTCCCGACATCTTGGACCATTAGCTCCACAGGTATCTTCTTCCCTCTAGTGGTCA |
| | TAACAGCAGCTTCAGCTACCTCTCAATTCAAAAAACCCCTCAAGACCCGTTTAGAGGCCCCAAGGGG |
| | TTATGCTATCAATCGTTGCGTTACACACACAAAAAACCAACACACATCCATCTTCGATGGATAGCGA |
| | TTTTATTATCTAACTGCTGATCGAGTGTAGCCAGATCTAGTAATCAATTACGGGGTCATTAGTTCAT |
| | AGCCCATATATGGAGTTCCGCGTTACATAACTTACGGTAAATGGCCCGCCTGGCTGACCGCCCAACG |
| | ACCCCCGCCCATTGACGTCAATAATGACGTATGTTCCCATAGTAACGCCAATAGGGACTTTCCATTG |
| | ACGTCAATGGGTGGAGTATTTACGGTAAACTGCCCACTTGGCAGTACATCAAGTGTATCATATGCCA |
| | AGTACGCCCCCTATTGACGTCAATGACGGTAAATGGCCCGCCTGGCATTATGCCCAGTACATGACCT |
| | TATGGGACTTTCCTACTTGGCAGTACATCTACGTATTAGTCATCGCTATTACCATGCTGATGCGGTT |
| | TTGGCAGTACATCAATGGGCGTGGATAGCGGTTTGACTCACGGGGATTTCCAAGTCTCCACCCCATT |
| | GACGTCAATGGGAGTTTGTTTTGGCACCAAAATCAACGGGACTTTCCAAAATGTCGTAACAACTCCG |
| | CCCCATTGACGCAAATGGGCGGTAGGCGTGTACGGTGGGAGGTCTATATAAGCAGAGCTGGTTTAGT |
| | GAACCGTCAGATCAGATCTTTGTCGATCCTACCATCCACTCGACACACCCGCCAGCGGCCGCTAATA |
| | CGACTCACTATAGGGAGAAGTACTGCCACCATGGGCAAGAAGCAAAATCGCAAGACGGGGAATTCCA |
| | AGACACAATCCGCTAGCCCACCACCTAAAGAGCGTTCTAGCTCCCCTGCTACTGAGCAGTCCTGGAT |
| | GGAAAACGACTTCGATGAACTCCGGGAAGAGGGATTTAGGCGATCCAACTATTCAGAACTCCGCGAA |
| | GATATCCAGACAAAGGGGAAGGAAGTCGAGAATTTCGAGAAGAACCTCGAGGAGTGCATCACCCGTA |
| | TCACAAACACTGAGAAATGTCTCAAAGAACTCATGGAACTTAAGACAAAAGCCAGGGAGCTTCGAGA |
| | GGAGTGTCGGAGTCTGAGATCCAGGTGTGACCAGCTCGAGGAGCGCGTGAGCGCGATGGAAGACGAG |
| | ATGAACGAGATGAAAAGAGAGGGCAAATTCAGGGAGAAGCGCATTAAGAGGAACGAACAGAGTCTGC |
| | AGGAGATTTGGGATTACGTCAAGAGGCCTAACCTGCGGTTGATCGGCGTCCCCGAGAGCGACGTAGA |
| | AAACGGGACTAAACTGGAGAATACACTTCAAGACATCATTCAAGAAAATTTTCCAAACCTGGCTCGG |
| | CAAGCTAATGTGCAAATCCAAGAGATCCAACGCACACCCCAGCGGTATAGCTCTCGGCGTGCCACCC |
| | CTAGGCATATTATCGTGCGCTTTACTAAGGTGGAGATGAAAGAGAAGATGCTGCGAGCCGCTCGGGA |
| | AAAGGGAAGGGTGACTTTGAAGGGCAAACCTATTCGGCTGACGGTTGACCTTAGCGCCGAGACACTC |
| | CAGGCACGCCGGGAATGGGGCCCCATCTTTAATATCCTGAAGGAGAAGAACTTCCAGCCACGAATCT |
| | CTTACCCTGCAAAGTTGAGTTTTATCTCCGAGGGTGAGATTAAGTATTTCATCGATAAACAGATGCT |
| | GCGAGACTTCGTGACAACTCGCCCAGCTCTCAAGGAACTGCTCAAAGAGGCTCTTAATATGGAGCGC |
| | AATAATAGATATCAACCCTTGCAGAACCACGCAAAGATGTGAGACAGCCGTCAGACCATCAAGACTA |
| | GGAAGAAACTGCATCAACTAATGAGCAAAATCACCAGCTAACATCATAGTATACATGccaaagaaga |
| | agcggaaggtcggcggcggcagcACCGGCTCTAACTCACATATCACCATCCTTACACTTAACATTAA |
| | CGGCCTCAACTCAGCTATCAAGCGCCATCGGCTGGCCAGCTGGATCAAATCACAGGATCCAAGCGTT |
| | TGTTGCATCCAAGAGACCCACCTGACCTGTAGAGATACTCACCGCCTCAAGATCAAGGGATGGCGAA |
| | AGATTTATCAGGCGAACGGTAAGCAGAAGAAAGCCGGAGTCGCAATTCTGGTCTCAGACAAGACGGA |
| | TTTCAAGCCCACCAAAATTAAGCGTGATAAGGAAGGTCACTATATTATGGTGAAAGGCAGCATACAG |
| | CAGGAAGAACTTACCATATTGAACATCTACGCGCCAAACACCGGCGCACCTCGCTTTATCAAACAGG |
| | TCCTGTCCGATCTGCAGCGAGATCTGGATTCTCATACGTTGATTATGGGTGATTTCAATACACCATT |
| | GAGCACCCTGGATCGCAGCACCAGGCAAAAGGTAAATAAAGACACGCAAGAGCTCAATAGCGCACTG |
| | CATCAGGCAGATCTCATTGATATTTATCGCACTCTTCATCCTAAGAGTACCGAGTACACATTCTTCA |
| | GCGCCCCACATCATACATACTCAAAGATCGATCATATCGTCGGCTCAAAGGCTCTGCTGTCAAAGTG |
| | CAAGCGCACAGAGATAATTACAAATTACCTGTCAGATCATAGCGCGATCAAGCTCGAGCTGAGAATC |
| | AAGAACCTGACCCAGAGCCGGAGTACCACTTGGAAGCTTAATAACCTGCTGCTCAACGATTATTGGG |
| | TCCACAATGAGATGAAGGCAGAGATTAAAATGTTCTTCGAAACAAATGAGAATAAGGATACTACCTA |
| | TCAAAACCTTTGGGATGCCTTTAAGGCCGTCTGCAGAGGCAAGTTCATCGCCCTCAACGCCTATAAA |
| | AGAAAACAAGAGAGATCTAAGATCGATACTCTCACCTCTCAGCTGAAGGAGTTGGAGAAACAGGAAC |
| | AGACCCACTCCAAGGCGTCAAGACGGCAGGAGATCACAAAGATTCGCGCCGAGTTGAAAGAGATCGA |
| | AACCCAAAAGACTCTTCAGAAAATTAACGAGTCTCGTAGTTGGTTCTTCGAGCGGATTAATAAGATA |
| | GACAGACCTCTGGCACGACTGATTAAGAAGAAGCGCGAAAAGAACCAGATTGATACCATCAAGAACG |
| | ACAAGGGCGACATCACTACTGACCCGACCGAGATCCAGACCACTATTCGGGAGTATTATAAGCATTT |
| | GTATGCTAACAAGCTTGAGAACCTGGAAGAGATGGACACTTTTCTGGATACCTATACTCTGCCACGG |
| | CTTAATCAAGAGGAAGTCGAGTCCCTCAACCGCCCAATTACAGGAAGCGAGATTGTGGCCATAATTA |
| | ACTCCCTGCCGACAAAGAAATCTCCTGGTCCGGACGGGTTTACAGCTGAGTTTTATCAACGGTATAT |
| | GGAAGAGCTTGTACCGTTTCTGCTCAAGCTCTTTCAGTCTATAGAAAAGGAAGGCATCTTGCCCAAT |
| | TCCTTCTACGAAGCTTCTATAATACTTATTCCCAAACCAGGACGCGATACCACAAAGAAGGAAAACT |
| | TCCGGCCCATTAGTCTCATGAATATCGACGCTAAAATATTGAACAAGATTCTCGCCAACAGAATCCA |
| | ACAACATATTAAGAAATTGATACATCACGACCAGGTGGGGTTTATACCTGGCATGCAGGGCTGGTTT |
| | AACATCCGGAAGAGTATTAACGTCATTCAACACATTAATAGAGCTAAGGATAAGAATCATATGATCA |
| | TCTCTATAGACGCGGAAAAGGCATTCGATAAGATTCAGCAGCCATTTATGCTCAAGACTCTGAACAA |
| | ACTCGGCATCGACGGAACATATTTTAAGATTATTCGCGCAATTTACGATAAGCCGACTGCTAACATT |
| | ATCCTTAACGGCCAAAAGCTCGAGGCCTTTCCGCTCAAGACTGGAACCCGCCAAGGCTGTCCCCTCT |
| | CCCCGCTTTTGTTTAATATTGTACTCGAGGTGCTGGCTAGGGCTATTCGTCAAGAGAAAGAGATTAA |
| | AGGGATACAGCTCGGGAAGGAAGAGGTCAAGCTTTCCTTGTTCGCCGATGATATGATTGTGTACCTG |
| | GAGAATCCTATTGTGTCTGCTCAGAACCTTCTTAAACTTATTTCTAACTTTAGCAAGGTCAGCGGCT |
| | ATAAGATTAACGTCCAGAAATCTCAGGCCTTTCTGTACACAAATAATCGACAGACCGAATCCCAGAT |
| | AATGGGTGAGCTTCCGTTTGTCATAGCCAGCAAAAGGATAAAGTATCTCGGAATCCAGCTGACACGA |
| | GACGTTAAAGATTTGTTTAAGGAAAATTACAAGCCTCTCCTGAAAGAGATTAAGGAAGATACTAATA |
| | AGTGGAAGAATATCCCCTGTTCATGGGTTGGCAGAATCAACATAGTGAAGATGGCAATACTTCCTAA |
| | AGTGATATATCGCTTTAACGCCATCCCAATTAAACTGCCTATGACCTTCTTTACGGAGCTCGAGAAA |
| | ACAACCCTTAAATTTATATGGAATCAAAAGAGAGCAAGAATAGCGAAGTCCATCTTGAGCCAGAAGA |
| | ATAAGGCCGGTGGGATTACTTTGCCTGATTTTAAGTTGTATTATAAAGCCACAGTAACTAAGACAGC |
| | CTGGTATTGGTATCAGAATAGAGACATCGACCAGTGGAATCGGACCGAACCATCAGAGATAATGCCC |
| | CACATCTATAATTACCTTATATTCGATAAGCCAGAAAAGAATAAACAGTGGGGCAAAGACAGCCTCT |
| | TCAACAAGTGGTGTTGGGAGAATTGGCTGGCCATATGCCGGAAACTCAAGCTCGACCCCTTTCTTAC |

TABLE 13-continued

Exemplary plasmid sequences

| Name | Sequence |
| --- | --- |
| | ACCCTACACTAAAATCAACAGTAGGTGGATCAAGGACTTGAATGTCAAGCCAAAGACTATAAAGACA<br>CTGGAAGAGAATCTTGGGATCACAATACAAGATATAGGCGTCGGCAAAGATTTTATGTCAAAGACGC<br>CCAAGGCCATGGCCACTAAGGATAAGATTGATAAGTGGGACCTTATTAAGCTCAAAAGCTTCTGTAC<br>TGCCAAGGAGACCACGATCAGAGTTAATAGGCAGCCCACTACATGGGAAAAGATTTTCGCCACTTAT<br>TCATCAGATAAGGGGTTGATAAGCAGAATATATAACGAGCTGAAGCAGATCTACAAGAAGAAAACGA<br>ATAATCCCATCAAGAAGTGGGCAAAAGATATGAACAGGCATTTTAGCAAAGAGGATATCTACGCCGC<br>GAAGAAGCATATGAAGAAGTGTAGTTCAAGCTTGGCCATTCGTGAGATGCAGATTAAGACGACCATG<br>CGATACCACCTTACCCCAGTGAGGATGGCAATTATCAAGAAATCTGGCAATAATAGATGTTGGCGGG<br>GCTGTGGCGAGATTGGCACCCTGCTCCATTGCTGGTGGGATTGCAAGCTGGTGCAGCCGCTTTGGAA<br>ATCAGTCTGGCGCTTTCTGAGGGACCTCGAGCTTGAGATTCCCTTCGATCCCGCAATTCCCTTGCTC<br>GGAATCTATCCTAACGAATACAAGAGCTGTTGTTACAAGGATACGTGTACCCGGATGTTCATCGCGG<br>CCTTGTTTACGATAGCTAAGACGTGGAATCAGCCTAAGTGCCCCACAATGATCGATTGGATCAAGAA<br>AATGTGGCATATTTATACCATGGAGTATTACGCAGCAATTAAGAATGACGAATTTATTTCCTTCGTT<br>GGGACCTGGATGAAGCTGGAGACTATTATTCTGAGCAAGCTGTCTCAGGAGCAAAAGACAAAGCATA<br>GAATCTTCTCTCTCATTGGTGGTAACGACTACAAAGACGATGACGACAAGTAAAGCGCTTCTAGAAG<br>TTGTCTCCTCCTGCACTGACTGACTGATACAATCGATTTCTGGATCCGCAGGCCTAATCAACCTCTG<br>GATTACAAAATTTGTGAAAGATTGACTGGTATTCTTAACTATGTTGCTCCTTTTACGCTATGTGGAT<br>ACGCTGCTTTAATGCCTTTGTATCATGCTATTGCTTCCCGTATGGCTTTCATTTTCTCCTCCTTGTA<br>TAAATCCTGGTTGCTGTCTCTTTATGAGGAGTTGTGGCCCGTTGTCAGGCAACGTGGCGTGGTGTGC<br>ACTGTGTTTGCTGACGCAACCCCCACTGGTTGGGGCATTGCCACCACCTGTCAGCTCCTTTCCGGGA<br>CTTTCGCTTTCCCCCTCCCTATTGCCACGGCGGAACTCATCGCCGCCTGCCTTGCCCGCTGCTGGAC<br>AGGGGCTCGGCTGTTGGGCACTGACAATTCCGTGGTGTTGTCGGGGAAGCTGACGTCCTTTCCATGG<br>CTGCTCGCCTGTGTTGCCACCTGGATTCTGCGCGGGACGTCCTTCTGCTACGTCCCTTCGGCCCTCA<br>ATCCAGCGGACCTTCCTTCCCGCtgagagacacaaaaaattccaacacactattgcaatgaaaataa<br>atttcctttattagccagaagtcagatgctcaaggggcttcatgatgtccccataatttttggcaga<br>gggaaaaagatctcagtggtatttgtgagccagggcattggccttctgataggcagcctgcacctga<br>ggagtgcggccgctttacttgtacagctcgtccatgccgagagtgatcccggcggcggtcacgaact<br>ccagcaggaccatgtgatcgcgcttctcgttggggtctttgctcagggcggactgggtgctcaggta<br>gtggttgtcgggcagcagcacggggccgtcgccgatgggggtgttctgctggtagtggtcggcgagc<br>tgcacgctgccgtcctcgatgttgtggcggatcttgaagttcaccttgatgccgttcttctgcttgt<br>cggccatgatatagacgttgtggctgttgtagttgtactccagcttgtgccccaggatgttgccgtc<br>ctccttgaagtcgatgcccttcagctcgatgcggttcaccagggtgtcgccctcgaacttcacctcg<br>gcgcgggtcttgtagttgccgtcgtccttgaagaagatggtgcgctcctggacgtagccttcgggca<br>tggcggacttgaagaagtcgtgctgcttcatgtggtcggggtagcggctgaagcactgcacgccgta<br>ggtcagggtggtcacgagggtgggccagggcacgggcagcttgccggtggtgcagatgaacttcagg<br>gtcagcttgccgtaggtggcatcgccctcgccctcgccggacacgctgaacttgtggccgtttacgt<br>cgccgtccagctcgaccaggatgggcaccaccccggtgaacagctcctcgcccttgctcaccatggt<br>ggcgggatctgacggttcactaaaccagctctgcttatatagacctcccaccgtacacgcctaccgc<br>ccatttgcgtcaatggggcggagttgttacgacattttggaaagtcccgttgattttggtgccaaaa<br>caaactcccattgacgtcaatggggtggagacttggaaatccccgtgagtcaaaccgctatccacgc<br>ccattgatgtactgccaaaaccgcatcaccatggtaatagcgatgactaatacgtagatgtactgcc<br>aagtaggaaagtcccataaggtcatgtactgggcataatgccaggcgggccatttaccgtcattgac<br>gtcaatagggggcgtacttggcatatgatacacttgatgtactgccaagtgggcagtttaccgtaaa<br>tactccacccattgacgtcaatggaaagtccctattggcgttactatgggaacatacgtcattattg<br>acgtcaatgggcgggggtcgttgggcggtcagccaggcgggccatttaccgtaagttatgtaacgGG<br>CCTGCTGCCGGCTCTGCGGCCTCTTCCGCGTCTTCGCCTTCGCCCTCAGACGAGTCGGATCTCCCTT<br>TGGGCCGCCTCCCCGCCTGTCTAGCTTGACTGACTGAGATACAGCGTACCTTCAGCTCACAGACATG<br>ATAAGATACATTGATGAGTTTGGACAAACCACAACTAGAATGCAGTGAAAAAAATGCTTTATTTGTG<br>AAATTTGTGATGCTATTGCTTTATTTGTAACCATTATAAGCTGCAATAAACAAGTTAACAACAACAA<br>TTGCATTCATTTTATGTTTCAGGTTCAGGGGGAGGTGTGGGAGGTTTTTTAAAGCAAGTAAAACCTC<br>TACAAATGTGGTATTGGCCCATCTCTATCGGTATCGTAGCATAACCCCTTGGGGCCTCTAAACGGGT<br>CTTGAGGGGTTTTTTGTGCCCCTCGGGCCGGATTGCTATCTACCGGCATTGGCGCAGAAAAAAATGC<br>CTGATGCGACGCTGCGCGTCTTATACTCCCACATATGCCAGATTCAGCAACGGATACGGCTTCCCCA<br>ACTTGCCCACTTCCATACGTGTCCTCCTTACCAGAAATTTATCCTTAAGGTCGTCAGCTATCCTGCA<br>GGCGATCTCTCGATTTCGATCAAGACATTCCTTTAATGGTCTTTTCTGGACACCACTAGGGGTCAGA<br>AGTAGTTCATCAAACTTTCTTCCCTCCCTAATCTCATTGGTTACCTTGGGCTATCGAAACTTAATTA<br>AGCGATCTGCATCTCAATTAGTCAGCAACCATAGTCCCGCCCCTAACTCCGCCCATCCCGCCCCTAA<br>CTCCGCCCAGTTCCGCCCATTCTCCGCCCCATCGCTGACTAATTTTTTTTATTTATGCAGAGGCCGA<br>GGCCGCCTCGGCCTCTGAGCTATTCCAGAAGTAGTGAGGAGGCTTTTTTGGAGGCCTAGGCTTTTGC<br>AAAGGAGGTAGCCAACATGATTGAACAAGATGGATTGCACGCAGGTTCTCCCGCCGCTTGGGTGGAG<br>AGGCTATTCGGCTATGACTGGGCACAACAGACAATCGGCTGCTCTGATGCCGCCGTGTTCCGGCTGT<br>CAGCGCAGGGGCGCCCGGTTCTTTTTGTCAAGACCGACCTGTCCGGTGCCCTGAATGAACTCCAGGA<br>CGAGGCAGCGCGGCTATCGTGGCTGGCCACGACGGGCGTTCCTTGCGCAGCTGTGCTCGACGTTGTC<br>ACTGAAGCGGGAAGGGACTGGCTGCTATTGGGCGAAGTGCCGGGGCAGGATCTCCTGTCATCTCACC<br>TTGCTCCTGCCGAGAAAGTATCCATCATGGCTGATGCAATGCGGCGGCTGCATACGCTTGATCCGGC<br>TACCTGCCCATTCGACCACCAAGCGAAACATCGCATCGAGCGAGCACGTACTCGGATGGAAGCCGGT<br>CTTGTCGATCAGGATGATCTGGACGAAGAGCATCAGGGGCTCGCGCCAGCCGAACTGTTCGCCAGGC<br>TCAAGGCGCGGATGCCCGACGGCGAGGATCTCGTCGTGACCCACGGCGATGCCTGCTTGCCGAATAT<br>CATGGTGGAAAATGGCCGCTTTTCTGGATTCATCGACTGTGGCCGGCTGGGTGTGGCGGACCGCTAT<br>CAGGACATAGCGTTGGCTACCCGTGATATTGCTGAAGAGCTTGGCGGCGAATGGGCTGACCGCTTCC<br>TCGTGCTTTACGGTATCGCCGCTCCCGATTCGCAGCGCATCGCCTTCTATCGCCTTCTTGACGAGTT<br>CTTCTAGTATGTAAGCCCTGTGCCTTCTAGTTGCCAGCCATCTGTTGTTTGCCCCTCCCCCGTGCCT<br>TCCTTGACCCTGGAAGGTGCCACTCCCACTGTCCTTTCCTAATAAAATGAGGAAATTGCATCGCATT<br>GTCTGAGTAGGTGTCATTCTATTCTGGGGGGTGGGGTGGGGCAGGACAGCAAGGGGGAGGATTGGGA<br>AGACAATAGCAGGCATGCTGGGGATGCGGTGGGCTCTATGGTTAATTAACCAGTCAAGTCAGCTACT<br>TGGCGAGATCGACTTGTCTGGGTTTCGACTACGCTCAGAATTGCGTCAGTCAAGTTCGATCTGGTCC |

TABLE 13-continued

Exemplary plasmid sequences

| Name | Sequence |
|---|---|
| | TTGCTATTGCACCCGTTCTCCGATTACGAGTTTCATTTAAATCATGTGAGCAAAAGGCCAGCAAAAG<br>GCCAGGAACCGTAAAAAGGCCGCGTTGCTGGCGTTTTTCCATAGGCTCCGCCCCCCTGACGAGCATC<br>ACAAAAATCGACGCTCAAGTCAGAGGTGGCGAAACCCGACAGGACTATAAAGATACCAGGCGTTTCC<br>CCCTGGAAGCTCCCTCGTGCGCTCTCCTGTTCCGACCCTGCCGCTTACCGGATACCTGTCCGCCTTT<br>CTCCCTTCGGGAAGCGTGGCGCTTTCTCATAGCTCACGCTGTAGGTATCTCAGTTCGGTGTAGGTCG<br>TTCGCTCCAAGCTGGGCTGTGTGCACGAACCCCCCGTTCAGCCCGACCGCTGCGCCTTATCCGGTAA<br>CTATCGTCTTGAGTCCAACCCGGTAAGACACGACTTATCGCCACTGGCAGCAGCCACTGGTAACAGG<br>ATTAGCAGAGCGAGGTATGTAGGCGGTGCTACAGAGTTCTTGAAGTGGTGGCCTAACTACGGCTACA<br>CTAGAAGAACAGTATTTGGTATCTGCGCTCTGCTGAAGCCAGTTACCTTCGGAAAAAGAGTTGGTAG<br>CTCTTGATCCGGCAAACAAACCACCGCTGGTAGCGGTGGTTTTTTTGTTTGCAAGCAGCAGATTACG<br>CGCAGAAAAAAAGGATCTCAAGAAGATCCTTTGATCTTTTCTACGGGGTCTGACGCTCAGTGGAACG<br>AAAACTCACGTTAAGGGATTTTGGTCATGAGATTATCAAAAAGGATCTTCACCTAGATCCTTTTAAA<br>TTAAAAATGAAGTTTTAAATCAATCTAAAGTATATATGAGTAAACTTGGTCTGACAGTTACCAATGC<br>TTAATCAGTGAGGCACCTATCTCAGCGATCTGTCTATTTCGTTCATCCATAGTTGCATTTAAATTTC<br>CGAACTCTCCAAGGCCCTCGTCGGAAAATCTTCAAACCTTTCGTCCGATCCATCTTGCAGGCTACCT<br>CTCGAACGAACTATCGCAAGTCTCT (SEQ ID NO: 101) |
| RET-<br>012<br>LINE1-<br>GFP<br>ORF2-N<br>Nucleo-<br>plasmin-<br>NLS | GACGATCCATATCGTTGCTTGGCAGTCAGCCAGTCGGAATCCAGCTTGGGACCCAGGAAGTCCAATC<br>GTCAGATATTGTACTCAAGCCTGGTCACGGCAGCGTACCGATCTGTTTAAACCTAGATATTGATAGT<br>CTGATCGGTCAACGTATAATCGAGTCCTAGCTTTTGCAAACATCTATCAAGAGACAGGATCAGCAGG<br>AGGCTTTCGCATGAGTATTCAACATTTCCGTGTCGCCCTTATTCCCTTTTTTGCGGCATTTTGCCTT<br>CCTGTTTTTGCTCACCCAGAAACGCTGGTGAAAGTAAAAGATGCTGAAGATCAGTTGGGTGCGCGAG<br>TGGGTTACATCGAACTGGATCTCAACAGCGGTAAGATCCTTGAGAGTTTTCGCCCCGAAGAACGCTT<br>TCCAATGATGAGCACTTTTAAAGTTCTGCTATGTGGCGCGGTATTATCCCGTATTGACGCCGGGCAA<br>GAGCAACTCGGTCGCCGCATACACTATTCTCAGAATGACTTGGTTGAGTATTCACCAGTCACAGAAA<br>AGCATCTTACGGATGGCATGACAGTAAGAGAATTATGCAGTGCTGCCATAACCATGAGTGATAACAC<br>TGCGGCCAACTTACTTCTGACAACGATTGGAGGACCGAAGGAGCTAACCGCTTTTTTGCACAACATG<br>GGGGATCATGTAACTCGCCTTGATCGTTGGGAACCGGAGCTGAATGAAGCCATACCAAACGACGAGC<br>GTGACACCACGATGCCTGTAGCAATGGCAACAACCTTGCGTAAACTATTAACTGGCGAACTACTTAC<br>TCTAGCTTCCCGGCAACAGTTGATAGACTGGATGGAGGCGGATAAAGTTGCAGGACCACTTCTGCGC<br>TCGGCCCTTCCGGCTGGCTGGTTTATTGCTGATAAATCTGGAGCCGGTGAGCGTGGGTCTCGCGGTA<br>TCATTGCAGCACTGGGGCCAGATGGTAAGCCCTCCCGTATCGTAGTTATCTACACGACGGGGAGTCA<br>GGCAACTATGGATGAACGAAATAGACAGATCGCTGAGATAGGTGCCTCACTGATTAAGCATTGGTAA<br>CCGATTCTAGGTGCATTGGCGCAGAAAAAAATGCCTGATGCGACGCTGCGCGTCTTATACTCCCACA<br>TATGCCAGATTCAGCAACGGATACGGCTTCCCCAACTTGCCCACTTCCATACGTGTCCTCCTTACCA<br>GAAATTTATCCTTAAGATCGTTTAAACTCGACTCTGGCTCTATCGAATCTCCGTCGTTTCGAGCTTA<br>CGCGAACAGCCGTGGCGCTCATTTGCTCGTCGGGCATCGAATCTCGTCAGCTATCGTCAGCTTACCT<br>TTTTGGCAGCGATCGCGGCTCCCGACATCTTGGACCATTAGCTCCACAGGTATCTTCTTCCCTCTAG<br>TGGTCATAACAGCAGCTTCAGCTACCTCTCAATTCAAAAAACCCCTCAAGACCCGTTTAGAGGCCCC<br>AAGGGGTTATGCTATCAATCGTTGCGTTACACACACAAAAAACCAACACACATCCATCTTCGATGGA<br>TAGCGATTTTATTATCTAACTGCTGATCGAGTGTAGCCAGATCTAGTAATCAATTACGGGGTCATTA<br>GTTCATAGCCCATATATGGAGTTCCGCGTTACATAACTTACGGTAAATGGCCCGCCTGGCTGACCGC<br>CCAACGACCCCCGCCCATTGACGTCAATAATGACGTATGTTCCCATAGTAACGCCAATAGGGACTTT<br>CCATTGACGTCAATGGGTGGAGTATTTACGGTAAACTGCCCACTTGGCAGTACATCAAGTGTATCAT<br>ATGCCAAGTACGCCCCCTATTGACGTCAATGACGGTAAATGGCCCGCCTGGCATTATGCCCAGTACA<br>TGACCTTATGGGACTTTCCTACTTGGCAGTACATCTACGTATTAGTCATCGCTATTACCATGCTGAT<br>GCGGTTTTGGCAGTACATCAATGGGCGTGGATAGCGGTTTGACTCACGGGGATTTCCAAGTCTCCAC<br>CCCATTGACGTCAATGGGAGTTTGTTTTGGCACCAAAATCAACGGGACTTTCCAAAATGTCGTAACA<br>ACTCCGCCCCATTGACGCAAATGGGCGGTAGGCGTGTACGGTGGGAGGTCTATATAAGCAGAGCTGG<br>TTTAGTGAACCGTCAGATCAGATCTTTGTCGATCCTACCATCCACTCGACACACCCGCCAGCGGCCG<br>CTAATACGACTCACTATAGGGAGAAGTACTGCCACCATGGGCAAGAAGCAAAATCGCAAGACGGGGA<br>ATTCCAAGACACAATCCGCTAGCCCACCACCTAAAGAGCGTTCTAGCTCCCCTGCTACTGAGCAGTC<br>CTGGATGGAAAACGACTTCGATGAACTCCGGGAAGAGGGATTTAGGCGATCCAACTATTCAGAACTC<br>CGCGAAGATATCCAGACAAAGGGGAAGGAAGTCGAGAATTTCGAGAAGAACCTCGAGGAGTGCATCA<br>CCCGTATCACAAACACTGAGAAATGTCTCAAAGAACTCATGGAACTTAAGACAAAAGCCAGGGAGCT<br>TCGAGAGGAGTGTCGGAGTCTGAGATCCAGGTGTGACCAGCTCGAGGAGCGCGTGAGCGCGATGGAA<br>GACGAGATGAACGAGATGAAAAGAGAGGGCAAATTCAGGGAGAAGCGCATTAAGAGGAACGAACAGA<br>GTCTGCAGGAGATTTGGGATTACGTCAAGAGGCCTAACCTGCGGTTGATCGGCGTCCCCGAGAGCGA<br>CGTAGAAAACGGGACTAAACTGGAGAATACACTTCAAGACATCATTCAAGAAAATTTTCCAAACCTG<br>GCTCGGCAAGCTAATGTGCAAATCCAAGAGATCCAACGCACACCCCAGCGGTATAGCTCTCGGCGTG<br>CCACCCCTAGGCATATTATCGTGCGCTTTACTAAGGTGGAGATGAAAGAGAAGATGCTGCGAGCCGC<br>TCGGGAAAAGGGAAGGGTGACTTTGAAGGGCAAACCTATTCGGCTGACGGTTGACCTTAGCGCCGAG<br>ACACTCCAGGCACGCCGGGAATGGGGCCCCATCTTTAATATCCTGAAGGAGAAGAACTTCCAGCCAC<br>GAATCTCTTACCCTGCAAAGTTGAGTTTTATCTCCGAGGGTGAGATTAAGTATTTCATCGATAAACA<br>GATGCTGCGAGACTTCGTGACAACTCGCCCAGCTCTCAAGGAACTGCTCAAAGAGGCTCTTAATATG<br>GAGCGCAATAATAGATATCAACCCTTGCAGAACCACGCAAAGATGTGAGACAGCCGTCAGACCATCA<br>AGACTAGGAAGAAACTGCATCAACTAATGAGCAAAATCACCAGCTAACATCATAGTATACATGaaaa<br>ggccggcggccacgaaaaaggccggccaggcaaaaaagaaaaagACCGGCTCTAACTCACATATCAC<br>CATCCTTACACTTAACATTAACGGCCTCAACTCAGCTATCAAGCGCCATCGGCTGGCCAGCTGGATC<br>AAATCACAGGATCCAAGCGTTTGTTGCATCCAAGAGACCCACCTGACCTGTAGAGATACTCACCGCC<br>TCAAGATCAAGGGATGGCGAAAGATTTATCAGGCGAACGGTAAGCAGAAGAAAGCCGGAGTCGCAAT<br>TCTGGTCTCAGACAAGACGGATTTCAAGCCCACCAAAATTAAGCGTGATAAGGAAGGTCACTATATT<br>ATGGTGAAAGGCAGCATACAGCAGGAAGAACTTACCATATTGAACATCTACGCGCCAAACACCGGCG<br>CACCTCGCTTTATCAAACAGGTCCTGTCCGATCTGCAGCGAGATCTGGATTCTCATACGTTGATTAT<br>GGGTGATTTCAATACACCATTGAGCACCCTGGATCGCAGCACCAGGCAAAAGGTAAATAAAGACACG<br>CAAGAGCTCAATAGCGCACTGCATCAGGCAGATCTCATTGATATTTATCGCACTCTTCATCCTAAGA |

TABLE 13-continued

Exemplary plasmid sequences

| Name | Sequence |
|---|---|
| | GTACCGAGTACACATTCTTCAGCGCCCCACATCATACATACTCAAAGATCGATCATATCGTCGGCTC<br>AAAGGCTCTGCTGTCAAAGTGCAAGCGCACAGAGATAATTACAAATTACCTGTCAGATCATAGCGCG<br>ATCAAGCTCGAGCTGAGAATCAAGAACCTGACCCAGAGCCGGAGTACCACTTGGAAGCTTAATAACC<br>TGCTGCTCAACGATTATTGGGTCCACAATGAGATGAAGGCAGAGATTAAAATGTTCTTCGAAACAAA<br>TGAGAATAAGGATACTACCTATCAAAACCTTTGGGATGCCTTTAAGGCCGTCTGCAGAGGCAAGTTC<br>ATCGCCCTCAACGCCTATAAAAGAAAACAAGAGAGATCTAAGATCGATACTCTCACCTCTCAGCTGA<br>AGGAGTTGGAGAAACAGGAACAGACCCACTCCAAGGCGTCAAGACGGCAGGAGATCACAAAGATTCG<br>CGCCGAGTTGAAAGAGATCGAAACCCAAAAGACTCTTCAGAAAATTAACGAGTCTCGTAGTTGGTTC<br>TTCGAGCGGATTAATAAGATAGACAGACCTCTGGCACGACTGATTAAGAAGAAGCGCGAAAAGAACC<br>AGATTGATACCATCAAGAACGACAAGGGCGACATCACTACTGACCCGACCGAGATCCAGACCACTAT<br>TCGGGAGTATTATAAGCATTTGTATGCTAACAAGCTTGAGAACCTGGAAGAGATGGACACTTTTCTG<br>GATACCTATACTCTGCCACGGCTTAATCAAGAGGAAGTCGAGTCCCTCAACCGCCCAATTACAGGAA<br>GCGAGATTGTGGCCATAATTAACTCCCTGCCGACAAAGAAATCTCCTGGTCCGGACGGGTTTACAGC<br>TGAGTTTTATCAACGGTATATGGAAGAGCTTGTACCGTTTCTGCTCAAGCTCTTTCAGTCTATAGAA<br>AAGGAAGGCATCTTGCCCAATTCCTTCTACGAAGCTTCTATAATACTTATTCCCAAACCAGGACGCG<br>ATACCACAAAGAAGGAAAACTTCCGGCCCATTAGTCTCATGAATATCGACGCTAAAATATTGAACAA<br>GATTCTCGCCAACAGAATCCAACAACATATTAAGAAATTGATACATCACGACCAGGTGGGGTTTATA<br>CCTGGCATGCAGGGCTGGTTTAACATCCGGAAGAGTATTAACGTCATTCAACACATTAATAGAGCTA<br>AGGATAAGAATCATATGATCATCTCTATAGACGCGGAAAAGGCATTCGATAAGATTCAGCAGCCATT<br>TATGCTCAAGACTCTGAACAAACTCGGCATCGACGGAACATATTTTAAGATTATTCGCGCAATTTAC<br>GATAAGCCGACTGCTAACATTATCCTTAACGGCCAAAAGCTCGAGGCCTTTCCGCTCAAGACTGGAA<br>CCCGCCAAGGCTGTCCCCTCTCCCCGCTTTTGTTTAATATTGTACTCGAGGTGCTGGCTAGGGCTAT<br>TCGTCAAGAGAAAGAGATTAAAGGGATACAGCTCGGGAAGGAAGAGGTCAAGCTTTCCTTGTTCGCC<br>GATGATATGATTGTGTACCTGGAGAATCCTATTGTGTCTGCTCAGAACCTTCTTAAACTTATTTCTA<br>ACTTTAGCAAGGTCAGCGGCTATAAGATTAACGTCCAGAAATCTCAGGCCTTTCTGTACACAAATAA<br>TCGACAGACCGAATCCCAGATAATGGGTGAGCTTCCGTTTGTCATAGCCAGCAAAAGGATAAAGTAT<br>CTCGGAATCCAGCTGACACGAGACGTTAAAGATTTGTTTAAGGAAAATTACAAGCCTCTCCTGAAAG<br>AGATTAAGGAAGATACTAATAAGTGGAAGAATATCCCCTGTTCATGGGTTGGCAGAATCAACATAGT<br>GAAGATGGCAATACTTCCTAAAGTGATATATCGCTTTAACGCCATCCCAATTAAACTGCCTATGACC<br>TTCTTTACGGAGCTCGAGAAAACAACCCTTAAATTTATATGGAATCAAAAGAGAGCAAGAATAGCGA<br>AGTCCATCTTGAGCCAGAAGAATAAGGCCGGTGGGATTACTTTGCCTGATTTTAAGTTGTATTATAA<br>AGCCACAGTAACTAAGACAGCCTGGTATTGGTATCAGAATAGAGACATCGACCAGTGGAATCGGACC<br>GAACCATCAGAGATAATGCCCCACATCTATAATTACCTTATATTCGATAAGCCAGAAAAGAATAAAC<br>AGTGGGGCAAAGACAGCCTCTTCAACAAGTGGTGTTGGGAGAATTGGCTGGCCATATGCCGGAAACT<br>CAAGCTCGACCCCTTTCTTACACCCTACACTAAAATCAACAGTAGGTGGATCAAGGACTTGAATGTC<br>AAGCCAAAGACTATAAAGACACTGGAAGAGAATCTTGGGATCACAATACAAGATATAGGCGTCGGCA<br>AAGATTTTATGTCAAAGACGCCCAAGGCCATGGCCACTAAGGATAAGATTGATAAGTGGGACCTTAT<br>TAAGCTCAAAAGCTTCTGTACTGCCAAGGAGACCACGATCAGAGTTAATAGGCAGCCCACTACATGG<br>GAAAAGATTTTCGCCACTTATTCATCAGATAAGGGGTTGATAAGCAGAATATATAACGAGCTGAAGC<br>AGATCTACAAGAAGAAAACGAATAATCCCATCAAGAAGTGGGCAAAAGATATGAACAGGCATTTTAG<br>CAAAGAGGATATCTACGCCGCGAAGAAGCATATGAAGAAGTGTAGTTCAAGCTTGGCCATTCGTGAG<br>ATGCAGATTAAGACGACCATGCGATACCACCTTACCCCAGTGAGGATGGCAATTATCAAGAAATCTG<br>GCAATAATAGATGTTGGCGGGGCTGTGGCGAGATTGGCACCCTGCTCCATTGCTGGTGGGATTGCAA<br>GCTGGTGCAGCCGCTTTGGAAATCAGTCTGGCGCTTTCTGAGGGACCTCGAGCTTGAGATTCCCTTC<br>GATCCCGCAATTCCCTTGCTCGGAATCTATCCTAACGAATACAAGAGCTGTTGTTACAAGGATACGT<br>GTACCCGGATGTTCATCGCGGCCTTGTTTACGATAGCTAAGACGTGGAATCAGCCTAAGTGCCCCAC<br>AATGATCGATTGGATCAAGAAAATGTGGCATATTTATACCATGGAGTATTACGCAGCAATTAAGAAT<br>GACGAATTTATTTCCTTCGTTGGGACCTGGATGAAGCTGGAGACTATTATTCTGAGCAAGCTGTCTC<br>AGGAGCAAAAGACAAAGCATAGAATCTTCTCTCTCATTGGTGGTAACGACTACAAAGACGATGACGA<br>CAAGTAAAGCGCTTCTAGAAGTTGTCTCCTCCTGCACTGACTGACTGATACAATCGATTTCTGGATC<br>CGCAGGCCTAATCAACCTCTGGATTACAAAATTTGTGAAAGATTGACTGGTATTCTTAACTATGTTG<br>CTCCTTTTACGCTATGTGGATACGCTGCTTTAATGCCTTTGTATCATGCTATTGCTTCCCGTATGGC<br>TTTCATTTTCTCCTCCTTGTATAAATCCTGGTTGCTGTCTCTTTATGAGGAGTTGTGGCCCGTTGTC<br>AGGCAACGTGGCGTGGTGTGCACTGTGTTTGCTGACGCAACCCCCACTGGTTGGGGCATTGCCACCA<br>CCTGTCAGCTCCTTTCCGGGACTTTCGCTTTCCCCCTCCCTATTGCCACGGCGGAACTCATCGCCGC<br>CTGCCTTGCCCGCTGCTGGACAGGGGCTCGGCTGTTGGGCACTGACAATTCCGTGGTGTTGTCGGGG<br>AAGCTGACGTCCTTTCCATGGCTGCTCGCCTGTGTTGCCACCTGGATTCTGCGCGGGACGTCCTTCT<br>GCTACGTCCCTTCGGCCCTCAATCCAGCGGACCTTCCTTCCCGCtgagagacacaaaaaattccaac<br>acactattgcaatgaaaataaatttcctttattagccagaagtcagatgctcaaggggcttcatgat<br>gtccccataatttttggcagagggaaaaagatctcagtggtatttgtgagccagggcattggccttc<br>tgataggcagcctgcacctgaggagtgcggccgctttacttgtacagctcgtccatgccgagagtga<br>tcccggcggcggtcacgaactccagcaggaccatgtgatcgcgcttctcgttggggtctttgctcag<br>ggcggactgggtgctcaggtagtggttgtcgggcagcagcacggggccgtcgccgatgggggtgttc<br>tgctggtagtggtcggcgagctgcacgctgccgtcctcgatgttgtggcggatcttgaagttcacct<br>tgatgccgttcttctgcttgtcggccatgatatagacgttgtggctgttgtagttgtactccagctt<br>gtgccccaggatgttgccgtcctccttgaagtcgatgcccttcagctcgatgcggttcaccagggtg<br>tcgccctcgaacttcacctcggcgcgggtcttgtagttgccgtcgtccttgaagaagatggtgcgct<br>cctggacgtagccttcgggcatggcggacttgaagaagtcgtgctgcttcatgtggtcggggtagcg<br>gctgaagcactgcacgccgtaggtcagggtggtcacgagggtgggccagggcacgggcagcttgccg<br>gtggtgcagatgaacttcagggtcagcttgccgtaggtggcatcgccctcgccctcgccggacacgc<br>tgaacttgtggccgtttacgtcgccgtccagctcgaccaggatgggcaccaccccggtgaacagctc<br>ctcgcccttgctcaccatggtggcgggatctgacggttcactaaaccagctctgcttatatagacct<br>cccaccgtacacgcctaccgcccatttgcgtcaatggggcggagttgttacgacattttggaaagtc<br>ccgttgattttggtgccaaaacaaactcccattgacgtcaatggggtggagacttggaaatccccgt<br>gagtcaaaccgctatccacgcccattgatgtactgccaaaaccgcatcaccatggtaatagcgatga<br>ctaatacgtagatgtactgccaagtaggaaagtcccataaggtcatgtactgggcataatgccaggc |

TABLE 13-continued

Exemplary plasmid sequences

| Name | Sequence |
| --- | --- |
| | gggccatttaccgtcattgacgtcaatagggggcgtacttggcatatgatacacttgatgtactgcc aagtgggcagtttaccgtaaatactccacccattgacgtcaatggaaagtccctattggcgttacta tgggaacatacgtcattattgacgtcaatgggcgggggtcgttgggcggtcagccaggcgggccatt taccgtaagttatgtaacgGGCCTGCTGCCGGCTCTGCGGCCTCTTCCGCGTCTTCGCCTTCGCCCT CAGACGAGTCGGATCTCCCTTTGGGCCGCCTCCCCGCCTGTCTAGCTTGACTGACTGAGATACAGCG TACCTTCAGCTCACAGACATGATAAGATACATTGATGAGTTTGGACAAACCACAACTAGAATGCAGT GAAAAAAATGCTTTATTTGTGAAATTTGTGATGCTATTGCTTTATTTGTAACCATTATAAGCTGCAA TAAACAAGTTAACAACAACAATTGCATTCATTTTATGTTTCAGGTTCAGGGGGAGGTGTGGGAGGTT TTTTAAAGCAAGTAAAACCTCTACAAATGTGGTATTGGCCCATCTCTATCGGTATCGTAGCATAACC CCTTGGGGCCTCTAAACGGGTCTTGAGGGGTTTTTTGTGCCCCTCGGGCCGGATTGCTATCTACCGG CATTGGCGCAGAAAAAAATGCCTGATGCGACGCTGCGCGTCTTATACTCCCACATATGCCAGATTCA GCAACGGATACGGCTTCCCCAACTTGCCCACTTCCATACGTGTCCTCCTTACCAGAAATTTATCCTT AAGGTCGTCAGCTATCCTGCAGGCGATCTCTCGATTTCGATCAAGACATTCCTTTAATGGTCTTTTC TGGACACCACTAGGGGTCAGAAGTAGTTCATCAAACTTTCTTCCCTCCCTAATCTCATTGGTTACCT TGGGCTATCGAAACTTAATTAAGCGATCTGCATCTCAATTAGTCAGCAACCATAGTCCCGCCCCTAA CTCCGCCCATCCCGCCCCTAACTCCGCCCAGTTCCGCCCATTCTCCGCCCCATCGCTGACTAATTTT TTTTATTTATGCAGAGGCCGAGGCCGCCTCGGCCTCTGAGCTATTCCAGAAGTAGTGAGGAGGCTTT TTTGGAGGCCTAGGCTTTTGCAAAGGAGGTAGCCAACATGATTGAACAAGATGGATTGCACGCAGGT TCTCCCGCCGCTTGGGTGGAGAGGCTATTCGGCTATGACTGGGCACAACAGACAATCGGCTGCTCTG ATGCCGCCGTGTTCCGGCTGTCAGCGCAGGGGCGCCCGGTTCTTTTTGTCAAGACCGACCTGTCCGG TGCCCTGAATGAACTCCAGGACGAGGCAGCGCGGCTATCGTGGCTGGCCACGACGGGCGTTCCTTGC GCAGCTGTGCTCGACGTTGTCACTGAAGCGGGAAGGGACTGGCTGCTATTGGGCGAAGTGCCGGGGC AGGATCTCCTGTCATCTCACCTTGCTCCTGCCGAGAAAGTATCCATCATGGCTGATGCAATGCGGCG GCTGCATACGCTTGATCCGGCTACCTGCCCATTCGACCACCAAGCGAAACATCGCATCGAGCGAGCA CGTACTCGGATGGAAGCCGGTCTTGTCGATCAGGATGATCTGGACGAAGAGCATCAGGGGCTCGCGC CAGCCGAACTGTTCGCCAGGCTCAAGGCGCGGATGCCCGACGGCGAGGATCTCGTCGTGACCCACGG CGATGCCTGCTTGCCGAATATCATGGTGGAAAATGGCCGCTTTTCTGGATTCATCGACTGTGGCCGG CTGGGTGTGGCGGACCGCTATCAGGACATAGCGTTGGCTACCCGTGATATTGCTGAAGAGCTTGGCG GCGAATGGGCTGACCGCTTCCTCGTGCTTTACGGTATCGCCGCTCCCGATTCGCAGCGCATCGCCTT CTATCGCCTTCTTGACGAGTTCTTCTAGTATGTAAGCCCTGTGCCTTCTAGTTGCCAGCCATCTGTT GTTTGCCCCTCCCCCGTGCCTTCCTTGACCCTGGAAGGTGCCACTCCCACTGTCCTTTCCTAATAAA ATGAGGAAATTGCATCGCATTGTCTGAGTAGGTGTCATTCTATTCTGGGGGGTGGGGTGGGGCAGGA CAGCAAGGGGGAGGATTGGGAAGACAATAGCAGGCATGCTGGGGATGCGGTGGGCTCTATGGTTAAT TAACCAGTCAAGTCAGCTACTTGGCGAGATCGACTTGTCTGGGTTTCGACTACGCTCAGAATTGCGT CAGTCAAGTTCGATCTGGTCCTTGCTATTGCACCCGTTCTCCGATTACGAGTTTCATTTAAATCATG TGAGCAAAAGGCCAGCAAAAGGCCAGGAACCGTAAAAAGGCCGCGTTGCTGGCGTTTTTCCATAGGC TCCGCCCCCCTGACGAGCATCACAAAAATCGACGCTCAAGTCAGAGGTGGCGAAACCCGACAGGACT ATAAAGATACCAGGCGTTTCCCCCTGGAAGCTCCCTCGTGCGCTCTCCTGTTCCGACCCTGCCGCTT ACCGGATACCTGTCCGCCTTTCTCCCTTCGGGAAGCGTGGCGCTTTCTCATAGCTCACGCTGTAGGT ATCTCAGTTCGGTGTAGGTCGTTCGCTCCAAGCTGGGCTGTGTGCACGAACCCCCCGTTCAGCCCGA CCGCTGCGCCTTATCCGGTAACTATCGTCTTGAGTCCAACCCGGTAAGACACGACTTATCGCCACTG GCAGCAGCCACTGGTAACAGGATTAGCAGAGCGAGGTATGTAGGCGGTGCTACAGAGTTCTTGAAGT GGTGGCCTAACTACGGCTACACTAGAAGAACAGTATTTGGTATCTGCGCTCTGCTGAAGCCAGTTAC CTTCGGAAAAAGAGTTGGTAGCTCTTGATCCGGCAAACAAACCACCGCTGGTAGCGGTGGTTTTTTT GTTTGCAAGCAGCAGATTACGCGCAGAAAAAAAGGATCTCAAGAAGATCCTTTGATCTTTTCTACGG GGTCTGACGCTCAGTGGAACGAAAACTCACGTTAAGGGATTTTGGTCATGAGATTATCAAAAAGGAT CTTCACCTAGATCCTTTTAAATTAAAAATGAAGTTTTAAATCAATCTAAAGTATATATGAGTAAACT TGGTCTGACAGTTACCAATGCTTAATCAGTGAGGCACCTATCTCAGCGATCTGTCTATTTCGTTCAT CCATAGTTGCATTTAAATTTCCGAACTCTCCAAGGCCCTCGTCGGAAAATCTTCAAACCTTTCGTCC GATCCATCTTGCAGGCTACCTCTCGAACGAACTATCGCAAGTCTCTTGGCCGGCCTTGCGCCTTGGC TATTGCTTGGCAGCGCCTATCGCCAGGTATTACTCCAATCCCGAATATCCGAGATCGGGATCACCCG AGAGAAGTTCAACCTACATCCTCAATCCCGATCTATCCGAGATCCGAGGAATATCGAAATCGGGGCG CGCCTGGTGTACCGAGAACGATCCTCTCAGTGCGAGTCTC (SEQ ID NO: 102) |
| RET-013 LINE1-GFP ORF2-N Nucleo-plasmin NLS Linker | AGATCCGAGGAATATCGAAATCGGGGCGCGCCTGGTGTACCGAGAACGATCCTCTCAGTGCGAGTCT CGACGATCCATATCGTTGCTTGGCAGTCAGCCAGTCGGAATCCAGCTTGGGACCCAGGAAGTCCAAT CGTCAGATATTGTACTCAAGCCTGGTCACGGCAGCGTACCGATCTGTTTAAACCTAGATATTGATAG TCTGATCGGTCAACGTATAATCGAGTCCTAGCTTTTGCAAACATCTATCAAGAGACAGGATCAGCAG GAGGCTTTCGCATGAGTATTCAACATTTCCGTGTCGCCCTTATTCCCTTTTTTGCGGCATTTTGCCT TCCTGTTTTTGCTCACCCAGAAACGCTGGTGAAAGTAAAAGATGCTGAAGATCAGTTGGGTGCGCGA GTGGGTTACATCGAACTGGATCTCAACAGCGGTAAGATCCTTGAGAGTTTTCGCCCCGAAGAACGCT TTCCAATGATGAGCACTTTTAAAGTTCTGCTATGTGGCGCGGTATTATCCCGTATTGACGCCGGGCA AGAGCAACTCGGTCGCCGCATACACTATTCTCAGAATGACTTGGTTGAGTATTCACCAGTCACAGAA AAGCATCTTACGGATGGCATGACAGTAAGAGAATTATGCAGTGCTGCCATAACCATGAGTGATAACA CTGCGGCCAACTTACTTCTGACAACGATTGGAGGACCGAAGGAGCTAACCGCTTTTTTGCACAACAT GGGGGATCATGTAACTCGCCTTGATCGTTGGGAACCGGAGCTGAATGAAGCCATACCAAACGACGAG CGTGACACCACGATGCCTGTAGCAATGGCAACAACCTTGCGTAAACTATTAACTGGCGAACTACTTA CTCTAGCTTCCCGGCAACAGTTGATAGACTGGATGGAGGCGGATAAAGTTGCAGGACCACTTCTGCG CTCGGCCCTTCCGGCTGGCTGGTTTATTGCTGATAAATCTGGAGCCGGTGAGCGTGGGTCTCGCGGT ATCATTGCAGCACTGGGGCCAGATGGTAAGCCCTCCCGTATCGTAGTTATCTACACGACGGGGAGTC AGGCAACTATGGATGAACGAAATAGACAGATCGCTGAGATAGGTGCCTCACTGATTAAGCATTGGTA ACCGATTCTAGGTGCATTGGCGCAGAAAAAAATGCCTGATGCGACGCTGCGCGTCTTATACTCCCAC ATATGCCAGATTCAGCAACGGATACGGCTTCCCCAACTTGCCCACTTCCATACGTGTCCTCCTTACC AGAAATTTATCCTTAAGATCGTTTAAACTCGACTCTGGCTCTATCGAATCTCCGTCGTTTCGAGCTT ACGCGAACAGCCGTGGCGCTCATTTGCTCGTCGGGCATCGAATCTCGTCAGCTATCGTCAGCTTACC TTTTTGGCAGCGATCGCGGCTCCCGACATCTTGGACCATTAGCTCCACAGGTATCTTCTTCCCTCTA |

TABLE 13-continued

Exemplary plasmid sequences

| Name | Sequence |
|---|---|
| | GTGGTCATAACAGCAGCTTCAGCTACCTCTCAATTCAAAAAACCCCTCAAGACCCGTTTAGAGGCCC |
| | CAAGGGGTTATGCTATCAATCGTTGCGTTACACACACAAAAAACCAACACACATCCATCTTCGATGG |
| | ATAGCGATTTTATTATCTAACTGCTGATCGAGTGTAGCCAGATCTAGTAATCAATTACGGGGTCATT |
| | AGTTCATAGCCCATATATGGAGTTCCGCGTTACATAACTTACGGTAAATGGCCCGCCTGGCTGACCG |
| | CCCAACGACCCCCGCCCATTGACGTCAATAATGACGTATGTTCCCATAGTAACGCCAATAGGGACTT |
| | TCCATTGACGTCAATGGGTGGAGTATTTACGGTAAACTGCCCACTTGGCAGTACATCAAGTGTATCA |
| | TATGCCAAGTACGCCCCCTATTGACGTCAATGACGGTAAATGGCCCGCCTGGCATTATGCCCAGTAC |
| | ATGACCTTATGGGACTTTCCTACTTGGCAGTACATCTACGTATTAGTCATCGCTATTACCATGCTGA |
| | TGCGGTTTTGGCAGTACATCAATGGGCGTGGATAGCGGTTTGACTCACGGGGATTTCCAAGTCTCCA |
| | CCCCATTGACGTCAATGGGAGTTTGTTTTGGCACCAAAATCAACGGGACTTTCCAAAATGTCGTAAC |
| | AACTCCGCCCCATTGACGCAAATGGGCGGTAGGCGTGTACGGTGGGAGGTCTATATAAGCAGAGCTG |
| | GTTTAGTGAACCGTCAGATCAGATCTTTGTCGATCCTACCATCCACTCGACACACCCGCCAGCGGCC |
| | GCTAATACGACTCACTATAGGGAGAAGTACTGCCACCATGGGCAAGAAGCAAAATCGCAAGACGGGG |
| | AATTCCAAGACACAATCCGCTAGCCCACCACCTAAAGAGCGTTCTAGCTCCCCTGCTACTGAGCAGT |
| | CCTGGATGGAAAACGACTTCGATGAACTCCGGGAAGAGGGATTTAGGCGATCCAACTATTCAGAACT |
| | CCGCGAAGATATCCAGACAAAGGGGAAGGAAGTCGAGAATTTCGAGAAGAACCTCGAGGAGTGCATC |
| | ACCCGTATCACAAACACTGAGAAATGTCTCAAAGAACTCATGGAACTTAAGACAAAAGCCAGGGAGC |
| | TTCGAGAGGAGTGTCGGAGTCTGAGATCCAGGTGTGACCAGCTCGAGGAGCGCGTGAGCGCGATGGA |
| | AGACGAGATGAACGAGATGAAAAGAGAGGGCAAATTCAGGGAGAAGCGCATTAAGAGGAACGAACAG |
| | AGTCTGCAGGAGATTTGGGATTACGTCAAGAGGCCTAACCTGCGGTTGATCGGCGTCCCCGAGAGCG |
| | ACGTAGAAAACGGGACTAAACTGGAGAATACACTTCAAGACATCATTCAAGAAAATTTTCCAAACCT |
| | GGCTCGGCAAGCTAATGTGCAAATCCAAGAGATCCAACGCACACCCCAGCGGTATAGCTCTCGGCGT |
| | GCCACCCCTAGGCATATTATCGTGCGCTTTACTAAGGTGGAGATGAAAGAGAAGATGCTGCGAGCCG |
| | CTCGGGAAAAGGGAAGGGTGACTTTGAAGGGCAAACCTATTCGGCTGACGGTTGACCTTAGCGCCGA |
| | GACACTCCAGGCACGCCGGGAATGGGGCCCCATCTTTAATATCCTGAAGGAGAAGAACTTCCAGCCA |
| | CGAATCTCTTACCCTGCAAAGTTGAGTTTTATCTCCGAGGGTGAGATTAAGTATTTCATCGATAAAC |
| | AGATGCTGCGAGACTTCGTGACAACTCGCCCAGCTCTCAAGGAACTGCTCAAAGAGGCTCTTAATAT |
| | GGAGCGCAATAATAGATATCAACCCTTGCAGAACCACGCAAAGATGTGAGACAGCCGTCAGACCATC |
| | AAGACTAGGAAGAAACTGCATCAACTAATGAGCAAAATCACCAGCTAACATCATAGTATACATGaaa |
| | aggccggcggccacgaaaaaggccggccaggcaaaaaagaaaaagggcggcggcagcACCGGCTCTA |
| | ACTCACATATCACCATCCTTACACTTAACATTAACGGCCTCAACTCAGCTATCAAGCGCCATCGGCT |
| | GGCCAGCTGGATCAAATCACAGGATCCAAGCGTTTGTTGCATCCAAGAGACCCACCTGACCTGTAGA |
| | GATACTCACCGCCTCAAGATCAAGGGATGGCGAAAGATTTATCAGGCGAACGGTAAGCAGAAGAAAG |
| | CCGGAGTCGCAATTCTGGTCTCAGACAAGACGGATTTCAAGCCCACCAAAATTAAGCGTGATAAGGA |
| | AGGTCACTATATTATGGTGAAAGGCAGCATACAGCAGGAAGAACTTACCATATTGAACATCTACGCG |
| | CCAAACACCGGCGCACCTCGCTTTATCAAACAGGTCCTGTCCGATCTGCAGCGAGATCTGGATTCTC |
| | ATACGTTGATTATGGGTGATTTCAATACACCATTGAGCACCCTGGATCGCAGCACCAGGCAAAAGGT |
| | AAATAAAGACACGCAAGAGCTCAATAGCGCACTGCATCAGGCAGATCTCATTGATATTTATCGCACT |
| | CTTCATCCTAAGAGTACCGAGTACACATTCTTCAGCGCCCCACATCATACATACTCAAAGATCGATC |
| | ATATCGTCGGCTCAAAGGCTCTGCTGTCAAAGTGCAAGCGCACAGAGATAATTACAAATTACCTGTC |
| | AGATCATAGCGCGATCAAGCTCGAGCTGAGAATCAAGAACCTGACCCAGAGCCGGAGTACCACTTGG |
| | AAGCTTAATAACCTGCTGCTCAACGATTATTGGGTCCACAATGAGATGAAGGCAGAGATTAAAATGT |
| | TCTTCGAAACAAATGAGAATAAGGATACTACCTATCAAAACCTTTGGGATGCCTTTAAGGCCGTCTG |
| | CAGAGGCAAGTTCATCGCCCTCAACGCCTATAAAAGAAAACAAGAGAGATCTAAGATCGATACTCTC |
| | ACCTCTCAGCTGAAGGAGTTGGAGAAACAGGAACAGACCCACTCCAAGGCGTCAAGACGGCAGGAGA |
| | TCACAAAGATTCGCGCCGAGTTGAAAGAGATCGAAACCCAAAAGACTCTTCAGAAAATTAACGAGTC |
| | TCGTAGTTGGTTCTTCGAGCGGATTAATAAGATAGACAGACCTCTGGCACGACTGATTAAGAAGAAG |
| | CGCGAAAAGAACCAGATTGATACCATCAAGAACGACAAGGGCGACATCACTACTGACCCGACCGAGA |
| | TCCAGACCACTATTCGGGAGTATTATAAGCATTTGTATGCTAACAAGCTTGAGAACCTGGAAGAGAT |
| | GGACACTTTTCTGGATACCTATACTCTGCCACGGCTTAATCAAGAGGAAGTCGAGTCCCTCAACCGC |
| | CCAATTACAGGAAGCGAGATTGTGGCCATAATTAACTCCCTGCCGACAAAGAAATCTCCTGGTCCGG |
| | ACGGGTTTACAGCTGAGTTTTATCAACGGTATATGGAAGAGCTTGTACCGTTTCTGCTCAAGCTCTT |
| | TCAGTCTATAGAAAAGGAAGGCATCTTGCCCAATTCCTTCTACGAAGCTTCTATAATACTTATTCCC |
| | AAACCAGGACGCGATACCACAAAGAAGGAAAACTTCCGGCCCATTAGTCTCATGAATATCGACGCTA |
| | AAATATTGAACAAGATTCTCGCCAACAGAATCCAACAACATATTAAGAAATTGATACATCACGACCA |
| | GGTGGGGTTTATACCTGGCATGCAGGGCTGGTTTAACATCCGGAAGAGTATTAACGTCATTCAACAC |
| | ATTAATAGAGCTAAGGATAAGAATCATATGATCATCTCTATAGACGCGGAAAAGGCATTCGATAAGA |
| | TTCAGCAGCCATTTATGCTCAAGACTCTGAACAAACTCGGCATCGACGGAACATATTTTAAGATTAT |
| | TCGCGCAATTTACGATAAGCCGACTGCTAACATTATCCTTAACGGCCAAAAGCTCGAGGCCTTTCCG |
| | CTCAAGACTGGAACCCGCCAAGGCTGTCCCCTCTCCCCGCTTTTGTTTAATATTGTACTCGAGGTGC |
| | TGGCTAGGGCTATTCGTCAAGAGAAAGAGATTAAAGGGATACAGCTCGGGAAGGAAGAGGTCAAGCT |
| | TTCCTTGTTCGCCGATGATATGATTGTGTACCTGGAGAATCCTATTGTGTCTGCTCAGAACCTTCTT |
| | AAACTTATTTCTAACTTTAGCAAGGTCAGCGGCTATAAGATTAACGTCCAGAAATCTCAGGCCTTTC |
| | TGTACACAAATAATCGACAGACCGAATCCCAGATAATGGGTGAGCTTCCGTTTGTCATAGCCAGCAA |
| | AAGGATAAAGTATCTCGGAATCCAGCTGACACGAGACGTTAAAGATTTGTTTAAGGAAAATTACAAG |
| | CCTCTCCTGAAAGAGATTAAGGAAGATACTAATAAGTGGAAGAATATCCCCTGTTCATGGGTTGGCA |
| | GAATCAACATAGTGAAGATGGCAATACTTCCTAAAGTGATATATCGCTTTAACGCCATCCCAATTAA |
| | ACTGCCTATGACCTTCTTTACGGAGCTCGAGAAAACAACCCTTAAATTTATATGGAATCAAAAGAGA |
| | GCAAGAATAGCGAAGTCCATCTTGAGCCAGAAGAATAAGGCCGGTGGGATTACTTTGCCTGATTTTA |
| | AGTTGTATTATAAAGCCACAGTAACTAAGACAGCCTGGTATTGGTATCAGAATAGAGACATCGACCA |
| | GTGGAATCGGACCGAACCATCAGAGATAATGCCCCACATCTATAATTACCTTATATTCGATAAGCCA |
| | GAAAAGAATAAACAGTGGGGCAAAGACAGCCTCTTCAACAAGTGGTGTTGGGAGAATTGGCTGGCCA |
| | TATGCCGGAAACTCAAGCTCGACCCCTTTCTTACACCCTACACTAAAATCAACAGTAGGTGGATCAA |
| | GGACTTGAATGTCAAGCCAAAGACTATAAAGACACTGGAAGAGAATCTTGGGATCACAATACAAGAT |
| | ATAGGCGTCGGCAAAGATTTTATGTCAAAGACGCCCAAGGCCATGGCCACTAAGGATAAGATTGATA |
| | AGTGGGACCTTATTAAGCTCAAAAGCTTCTGTACTGCCAAGGAGACCACGATCAGAGTTAATAGGCA |

TABLE 13-continued

Exemplary plasmid sequences

| Name | Sequence |
|---|---|
| | GCCCACTACATGGGAAAAGATTTTCGCCACTTATTCATCAGATAAGGGGTTGATAAGCAGAATATAT |
| | AACGAGCTGAAGCAGATCTACAAGAAGAAAACGAATAATCCCATCAAGAAGTGGGCAAAAGATATGA |
| | ACAGGCATTTTAGCAAAGAGGATATCTACGCCGCGAAGAAGCATATGAAGAAGTGTAGTTCAAGCTT |
| | GGCCATTCGTGAGATGCAGATTAAGACGACCATGCGATACCACCTTACCCCAGTGAGGATGGCAATT |
| | ATCAAGAAATCTGGCAATAATAGATGTTGGCGGGGCTGTGGCGAGATTGGCACCCTGCTCCATTGCT |
| | GGTGGGATTGCAAGCTGGTGCAGCCGCTTTGGAAATCAGTCTGGCGCTTTCTGAGGGACCTCGAGCT |
| | TGAGATTCCCTTCGATCCCGCAATTCCCTTGCTCGGAATCTATCCTAACGAATACAAGAGCTGTTGT |
| | TACAAGGATACGTGTACCCGGATGTTCATCGCGGCCTTGTTTACGATAGCTAAGACGTGGAATCAGC |
| | CTAAGTGCCCCACAATGATCGATTGGATCAAGAAAATGTGGCATATTTATACCATGGAGTATTACGC |
| | AGCAATTAAGAATGACGAATTTATTTCCTTCGTTGGGACCTGGATGAAGCTGGAGACTATTATTCTG |
| | AGCAAGCTGTCTCAGGAGCAAAAGACAAAGCATAGAATCTTCTCTCTCATTGGTGGTAACGACTACA |
| | AAGACGATGACGACAAGTAAAGCGCTTCTAGAAGTTGTCTCCTCCTGCACTGACTGACTGATACAAT |
| | CGATTTCTGGATCCGCAGGCCTAATCAACCTCTGGATTACAAAATTTGTGAAAGATTGACTGGTATT |
| | CTTAACTATGTTGCTCCTTTTACGCTATGTGGATACGCTGCTTTAATGCCTTTGTATCATGCTATTG |
| | CTTCCCGTATGGCTTTCATTTTCTCCTCCTTGTATAAATCCTGGTTGCTGTCTCTTTATGAGGAGTT |
| | GTGGCCCGTTGTCAGGCAACGTGGCGTGGTGTGCACTGTGTTTGCTGACGCAACCCCCACTGGTTGG |
| | GGCATTGCCACCACCTGTCAGCTCCTTTCCGGGACTTTCGCTTTCCCCCTCCCTATTGCCACGGCGG |
| | AACTCATCGCCGCCTGCCTTGCCCGCTGCTGGACAGGGGCTCGGCTGTTGGGCACTGACAATTCCGT |
| | GGTGTTGTCGGGGAAGCTGACGTCCTTTCCATGGCTGCTCGCCTGTGTTGCCACCTGGATTCTGCGC |
| | GGGACGTCCTTCTGCTACGTCCCTTCGGCCCTCAATCCAGCGGACCTTCCTTCCCGCtgagagacac |
| | aaaaaattccaacacactattgcaatgaaaataaatttcctttattagccagaagtcagatgctcaa |
| | ggggcttcatgatgtccccataatttttggcagagggaaaaagatctcagtggtatttgtgagccag |
| | ggcattggccttctgataggcagcctgcacctgaggagtgcggccgctttacttgtacagctcgtcc |
| | atgccgagagtgatcccggcggcggtcacgaactccagcaggaccatgtgatcgcgcttctcgttgg |
| | ggtctttgctcagggcggactgggtgctcaggtagtggttgtcgggcagcagcacggggccgtcgcc |
| | gatgggggtgttctgctggtagtggtcggcgagctgcacgctgccgtcctcgatgttgtggcggatc |
| | ttgaagttcaccttgatgccgttcttctgcttgtcggccatgatatagacgttgtggctgttgtagt |
| | tgtactccagcttgtgccccaggatgttgccgtcctccttgaagtcgatgcccttcagctcgatgcg |
| | gttcaccagggtgtcgccctcgaacttcacctcggcgcgggtcttgtagttgccgtcgtccttgaag |
| | aagatggtgcgctcctggacgtagccttcgggcatggcggacttgaagaagtcgtgctgcttcatgt |
| | ggtcggggtagcggctgaagcactgcacgccgtaggtcagggtggtcacgagggtgggccagggcac |
| | gggcagcttgccggtggtgcagatgaacttcagggtcagcttgccgtaggtggcatcgccctcgccc |
| | tcgccggacacgctgaacttgtggccgtttacgtcgccgtccagctcgaccaggatgggcaccaccc |
| | cggtgaacagctcctcgcccttgctcaccatggtggcgggatctgacggttcactaaaccagctctg |
| | cttatatagacctcccaccgtacacgcctaccgcccatttgcgtcaatggggcggagttgttacgac |
| | attttggaaagtcccgttgattttggtgccaaaacaaactcccattgacgtcaatggggtggagact |
| | tggaaatccccgtgagtcaaaccgctatccacgcccattgatgtactgccaaaaccgcatcaccatg |
| | gtaatagcgatgactaatacgtagatgtactgccaagtaggaaagtcccataaggtcatgtactggg |
| | cataatgccaggcgggccatttaccgtcattgacgtcaatagggggcgtacttggcatatgatacac |
| | ttgatgtactgccaagtgggcagtttaccgtaaatactccacccattgacgtcaatggaaagtccct |
| | attggcgttactatgggaacatacgtcattattgacgtcaatgggcgggggtcgttgggcggtcagc |
| | caggcgggccatttaccgtaagttatgtaacgGGCCTGCTGCCGGCTCTGCGGCCTCTTCCGCGTCT |
| | TCGCCTTCGCCCTCAGACGAGTCGGATCTCCCTTTGGGCCGCCTCCCCGCCTGTCTAGCTTGACTGA |
| | CTGAGATACAGCGTACCTTCAGCTCACAGACATGATAAGATACATTGATGAGTTTGGACAAACCACA |
| | ACTAGAATGCAGTGAAAAAAATGCTTTATTTGTGAAATTTGTGATGCTATTGCTTTATTTGTAACCA |
| | TTATAAGCTGCAATAAACAAGTTAACAACAACAATTGCATTCATTTTATGTTTCAGGTTCAGGGGGA |
| | GGTGTGGGAGGTTTTTTAAAGCAAGTAAAACCTCTACAAATGTGGTATTGGCCCATCTCTATCGGTA |
| | TCGTAGCATAACCCCTTGGGGCCTCTAAACGGGTCTTGAGGGGTTTTTTGTGCCCCTCGGGCCGGAT |
| | TGCTATCTACCGGCATTGGCGCAGAAAAAAATGCCTGATGCGACGCTGCGCGTCTTATACTCCCACA |
| | TATGCCAGATTCAGCAACGGATACGGCTTCCCCAACTTGCCCACTTCCATACGTGTCCTCCTTACCA |
| | GAAATTTATCCTTAAGGTCGTCAGCTATCCTGCAGGCGATCTCTCGATTTCGATCAAGACATTCCTT |
| | TAATGGTCTTTTCTGGACACCACTAGGGGTCAGAAGTAGTTCATCAAACTTTCTTCCCTCCCTAATC |
| | TCATTGGTTACCTTGGGCTATCGAAACTTAATTAAGCGATCTGCATCTCAATTAGTCAGCAACCATA |
| | GTCCCGCCCCTAACTCCGCCCATCCCGCCCCTAACTCCGCCCAGTTCCGCCCATTCTCCGCCCCATC |
| | GCTGACTAATTTTTTTTATTTATGCAGAGGCCGAGGCCGCCTCGGCCTCTGAGCTATTCCAGAAGTA |
| | GTGAGGAGGCTTTTTTGGAGGCCTAGGCTTTTGCAAAGGAGGTAGCCAACATGATTGAACAAGATGG |
| | ATTGCACGCAGGTTCTCCCGCCGCTTGGGTGGAGAGGCTATTCGGCTATGACTGGGCACAACAGACA |
| | ATCGGCTGCTCTGATGCCGCCGTGTTCCGGCTGTCAGCGCAGGGGCGCCCGGTTCTTTTTGTCAAGA |
| | CCGACCTGTCCGGTGCCCTGAATGAACTCCAGGACGAGGCAGCGCGGCTATCGTGGCTGGCCACGAC |
| | GGGCGTTCCTTGCGCAGCTGTGCTCGACGTTGTCACTGAAGCGGGAAGGGACTGGCTGCTATTGGGC |
| | GAAGTGCCGGGGCAGGATCTCCTGTCATCTCACCTTGCTCCTGCCGAGAAAGTATCCATCATGGCTG |
| | ATGCAATGCGGCGGCTGCATACGCTTGATCCGGCTACCTGCCCATTCGACCACCAAGCGAAACATCG |
| | CATCGAGCGAGCACGTACTCGGATGGAAGCCGGTCTTGTCGATCAGGATGATCTGGACGAAGAGCAT |
| | CAGGGGCTCGCGCCAGCCGAACTGTTCGCCAGGCTCAAGGCGCGGATGCCCGACGGCGAGGATCTCG |
| | TCGTGACCCACGGCGATGCCTGCTTGCCGAATATCATGGTGGAAAATGGCCGCTTTTCTGGATTCAT |
| | CGACTGTGGCCGGCTGGGTGTGGCGGACCGCTATCAGGACATAGCGTTGGCTACCCGTGATATTGCT |
| | GAAGAGCTTGGCGGCGAATGGGCTGACCGCTTCCTCGTGCTTTACGGTATCGCCGCTCCCGATTCGC |
| | AGCGCATCGCCTTCTATCGCCTTCTTGACGAGTTCTTCTAGTATGTAAGCCCTGTGCCTTCTAGTTG |
| | CCAGCCATCTGTTGTTTGCCCCTCCCCCGTGCCTTCCTTGACCCTGGAAGGTGCCACTCCCACTGTC |
| | CTTTCCTAATAAAATGAGGAAATTGCATCGCATTGTCTGAGTAGGTGTCATTCTATTCTGGGGGGTG |
| | GGGTGGGGCAGGACAGCAAGGGGGAGGATTGGGAAGACAATAGCAGGCATGCTGGGGATGCGGTGGG |
| | CTCTATGGTTAATTAACCAGTCAAGTCAGCTACTTGGCGAGATCGACTTGTCTGGGTTTCGACTACG |
| | CTCAGAATTGCGTCAGTCAAGTTCGATCTGGTCCTTGCTATTGCACCCGTTCTCCGATTACGAGTTT |
| | CATTTAAATCATGTGAGCAAAAGGCCAGCAAAAGGCCAGGAACCGTAAAAAGGCCGCGTTGCTGGCG |
| | TTTTTCCATAGGCTCCGCCCCCCTGACGAGCATCACAAAAATCGACGCTCAAGTCAGAGGTGGCGAA |
| | ACCCGACAGGACTATAAAGATACCAGGCGTTTCCCCCTGGAAGCTCCCTCGTGCGCTCTCCTGTTCC |

TABLE 13-continued

| Exemplary plasmid sequences | |
|---|---|
| Name | Sequence |
| | GACCCTGCCGCTTACCGGATACCTGTCCGCCTTTCTCCCTTCGGGAAGCGTGGCGCTTTCTCATAGC<br>TCACGCTGTAGGTATCTCAGTTCGGTGTAGGTCGTTCGCTCCAAGCTGGGCTGTGTGCACGAACCCC<br>CCGTTCAGCCCGACCGCTGCGCCTTATCCGGTAACTATCGTCTTGAGTCCAACCCGGTAAGACACGA<br>CTTATCGCCACTGGCAGCAGCCACTGGTAACAGGATTAGCAGAGCGAGGTATGTAGGCGGTGCTACA<br>GAGTTCTTGAAGTGGTGGCCTAACTACGGCTACACTAGAAGAACAGTATTTGGTATCTGCGCTCTGC<br>TGAAGCCAGTTACCTTCGGAAAAAGAGTTGGTAGCTCTTGATCCGGCAAACAAACCACCGCTGGTAG<br>CGGTGGTTTTTTTGTTTGCAAGCAGCAGATTACGCGCAGAAAAAAAGGATCTCAAGAAGATCCTTTG<br>ATCTTTTCTACGGGGTCTGACGCTCAGTGGAACGAAAACTCACGTTAAGGGATTTTGGTCATGAGAT<br>TATCAAAAAGGATCTTCACCTAGATCCTTTTAAATTAAAAATGAAGTTTTAAATCAATCTAAAGTAT<br>ATATGAGTAAACTTGGTCTGACAGTTACCAATGCTTAATCAGTGAGGCACCTATCTCAGCGATCTGT<br>CTATTTCGTTCATCCATAGTTGCATTTAAATTTCCGAACTCTCCAAGGCCCTCGTCGGAAAATCTTC<br>AAACCTTTCGTCCGATCCATCTTGCAGGCTACCTCTCGAACGAACTATCGCAAGTCTCTTGGCCGGC<br>CTTGCGCCTTGGCTATTGCTTGGCAGCGCCTATCGCCAGGTATTACTCCAATCCCGAATATCCGAGA<br>TCGGGATCACCCGAGAGAAGTTCAACCTACATCCTCAATCCCGATCTATCCG (SEQ ID NO:<br>103) |
| RET-<br>014<br>LINE1-<br>GFP<br>ORF2-<br>CSV40-<br>NLS | AGAACGATCCTCTCAGTGCGAGTCTCGACGATCCATATCGTTGCTTGGCAGTCAGCCAGTCGGAATC<br>CAGCTTGGGACCCAGGAAGTCCAATCGTCAGATATTGTACTCAAGCCTGGTCACGGCAGCGTACCGA<br>TCTGTTTAAACCTAGATATTGATAGTCTGATCGGTCAACGTATAATCGAGTCCTAGCTTTTGCAAAC<br>ATCTATCAAGAGACAGGATCAGCAGGAGGCTTTCGCATGAGTATTCAACATTTCCGTGTCGCCCTTA<br>TTCCCTTTTTTGCGGCATTTTGCCTTCCTGTTTTTGCTCACCCAGAAACGCTGGTGAAAGTAAAAGA<br>TGCTGAAGATCAGTTGGGTGCGCGAGTGGGTTACATCGAACTGGATCTCAACAGCGGTAAGATCCTT<br>GAGAGTTTTCGCCCCGAAGAACGCTTTCCAATGATGAGCACTTTTAAAGTTCTGCTATGTGGCGCGG<br>TATTATCCCGTATTGACGCCGGGCAAGAGCAACTCGGTCGCCGCATACACTATTCTCAGAATGACTT<br>GGTTGAGTATTCACCAGTCACAGAAAAGCATCTTACGGATGGCATGACAGTAAGAGAATTATGCAGT<br>GCTGCCATAACCATGAGTGATAACACTGCGGCCAACTTACTTCTGACAACGATTGGAGGACCGAAGG<br>AGCTAACCGCTTTTTTGCACAACATGGGGGATCATGTAACTCGCCTTGATCGTTGGGAACCGGAGCT<br>GAATGAAGCCATACCAAACGACGAGCGTGACACCACGATGCCTGTAGCAATGGCAACAACCTTGCGT<br>AAACTATTAACTGGCGAACTACTTACTCTAGCTTCCCGGCAACAGTTGATAGACTGGATGGAGGCGG<br>ATAAAGTTGCAGGACCACTTCTGCGCTCGGCCCTTCCGGCTGGCTGGTTTATTGCTGATAAATCTGG<br>AGCCGGTGAGCGTGGGTCTCGCGGTATCATTGCAGCACTGGGGCCAGATGGTAAGCCCTCCCGTATC<br>GTAGTTATCTACACGACGGGGAGTCAGGCAACTATGGATGAACGAAATAGACAGATCGCTGAGATAG<br>GTGCCTCACTGATTAAGCATTGGTAACCGATTCTAGGTGCATTGGCGCAGAAAAAAATGCCTGATGC<br>GACGCTGCGCGTCTTATACTCCCACATATGCCAGATTCAGCAACGGATACGGCTTCCCCAACTTGCC<br>CACTTCCATACGTGTCCTCCTTACCAGAAATTTATCCTTAAGATCGTTTAAACTCGACTCTGGCTCT<br>ATCGAATCTCCGTCGTTTCGAGCTTACGCGAACAGCCGTGGCGCTCATTTGCTCGTCGGGCATCGAA<br>TCTCGTCAGCTATCGTCAGCTTACCTTTTTGGCAGCGATCGCGGCTCCCGACATCTTGGACCATTAG<br>CTCCACAGGTATCTTCTTCCCTCTAGTGGTCATAACAGCAGCTTCAGCTACCTCTCAATTCAAAAAA<br>CCCCTCAAGACCCGTTTAGAGGCCCCAAGGGGTTATGCTATCAATCGTTGCGTTACACACACAAAAA<br>ACCAACACACATCCATCTTCGATGGATAGCGATTTTATTATCTAACTGCTGATCGAGTGTAGCCAGA<br>TCTAGTAATCAATTACGGGGTCATTAGTTCATAGCCCATATATGGAGTTCCGCGTTACATAACTTAC<br>GGTAAATGGCCCGCCTGGCTGACCGCCCAACGACCCCCGCCCATTGACGTCAATAATGACGTATGTT<br>CCCATAGTAACGCCAATAGGGACTTTCCATTGACGTCAATGGGTGGAGTATTTACGGTAAACTGCCC<br>ACTTGGCAGTACATCAAGTGTATCATATGCCAAGTACGCCCCCTATTGACGTCAATGACGGTAAATG<br>GCCCGCCTGGCATTATGCCCAGTACATGACCTTATGGGACTTTCCTACTTGGCAGTACATCTACGTA<br>TTAGTCATCGCTATTACCATGCTGATGCGGTTTTGGCAGTACATCAATGGGCGTGGATAGCGGTTTG<br>ACTCACGGGGATTTCCAAGTCTCCACCCCATTGACGTCAATGGGAGTTTGTTTTGGCACCAAAATCA<br>ACGGGACTTTCCAAAATGTCGTAACAACTCCGCCCCATTGACGCAAATGGGCGGTAGGCGTGTACGG<br>TGGGAGGTCTATATAAGCAGAGCTGGTTTAGTGAACCGTCAGATCAGATCTTTGTCGATCCTACCAT<br>CCACTCGACACACCCGCCAGCGGCCGCTAATACGACTCACTATAGGGAGAAGTACTGCCACCATGGG<br>CAAGAAGCAAAATCGCAAGACGGGGAATTCCAAGACACAATCCGCTAGCCCACCACCTAAAGAGCGT<br>TCTAGCTCCCCTGCTACTGAGCAGTCCTGGATGGAAAACGACTTCGATGAACTCCGGGAAGAGGGAT<br>TTAGGCGATCCAACTATTCAGAACTCCGCGAAGATATCCAGACAAAGGGGAAGGAAGTCGAGAATTT<br>CGAGAAGAACCTCGAGGAGTGCATCACCCGTATCACAAACACTGAGAAATGTCTCAAAGAACTCATG<br>GAACTTAAGACAAAAGCCAGGGAGCTTCGAGAGGAGTGTCGGAGTCTGAGATCCAGGTGTGACCAGC<br>TCGAGGAGCGCGTGAGCGCGATGGAAGACGAGATGAACGAGATGAAAAGAGAGGGCAAATTCAGGGA<br>GAAGCGCATTAAGAGGAACGAACAGAGTCTGCAGGAGATTTGGGATTACGTCAAGAGGCCTAACCTG<br>CGGTTGATCGGCGTCCCCGAGAGCGACGTAGAAAACGGGACTAAACTGGAGAATACACTTCAAGACA<br>TCATTCAAGAAAATTTTCCAAACCTGGCTCGGCAAGCTAATGTGCAAATCCAAGAGATCCAACGCAC<br>ACCCCAGCGGTATAGCTCTCGGCGTGCCACCCCTAGGCATATTATCGTGCGCTTTACTAAGGTGGAG<br>ATGAAAGAGAAGATGCTGCGAGCCGCTCGGGAAAAGGGAAGGGTGACTTTGAAGGGCAAACCTATTC<br>GGCTGACGGTTGACCTTAGCGCCGAGACACTCCAGGCACGCCGGGAATGGGGCCCCATCTTTAATAT<br>CCTGAAGGAGAAGAACTTCCAGCCACGAATCTCTTACCCTGCAAAGTTGAGTTTTATCTCCGAGGGT<br>GAGATTAAGTATTTCATCGATAAACAGATGCTGCGAGACTTCGTGACAACTCGCCCAGCTCTCAAGG<br>AACTGCTCAAAGAGGCTCTTAATATGGAGCGCAATAATAGATATCAACCCTTGCAGAACCACGCAAA<br>GATGTGAGACAGCCGTCAGACCATCAAGACTAGGAAGAAACTGCATCAACTAATGAGCAAAATCACC<br>AGCTAACATCATAGTATACATGACCGGCTCTAACTCACATATCACCATCCTTACACTTAACATTAAC<br>GGCCTCAACTCAGCTATCAAGCGCCATCGGCTGGCCAGCTGGATCAAATCACAGGATCCAAGCGTTT<br>GTTGCATCCAAGAGACCCACCTGACCTGTAGAGATACTCACCGCCTCAAGATCAAGGGATGGCGAAA<br>GATTTATCAGGCGAACGGTAAGCAGAAGAAAGCCGGAGTCGCAATTCTGGTCTCAGACAAGACGGAT<br>TTCAAGCCCACCAAAATTAAGCGTGATAAGGAAGGTCACTATATTATGGTGAAAGGCAGCATACAGC<br>AGGAAGAACTTACCATATTGAACATCTACGCGCCAAACACCGGCGCACCTCGCTTTATCAAACAGGT<br>CCTGTCCGATCTGCAGCGAGATCTGGATTCTCATACGTTGATTATGGGTGATTTCAATACACCATTG<br>AGCACCCTGGATCGCAGCACCAGGCAAAAGGTAAATAAAGACACGCAAGAGCTCAATAGCGCACTGC<br>ATCAGGCAGATCTCATTGATATTTATCGCACTCTTCATCCTAAGAGTACCGAGTACACATTCTTCAG<br>CGCCCCACATCATACATACTCAAAGATCGATCATATCGTCGGCTCAAAGGCTCTGCTGTCAAAGTGC |

TABLE 13-continued

Exemplary plasmid sequences

| Name | Sequence |
| --- | --- |
| | AAGCGCACAGAGATAATTACAAATTACCTGTCAGATCATAGCGCGATCAAGCTCGAGCTGAGAATCA |
| | AGAACCTGACCCAGAGCCGGAGTACCACTTGGAAGCTTAATAACCTGCTGCTCAACGATTATTGGGT |
| | CCACAATGAGATGAAGGGAGAGATTAAAATGTTCTTCGAAACAAATGAGAATAAGGATACTACCTAT |
| | CAAAACCTTTGGGATGCCTTTAAGGCCGTCTGCAGAGGCAAGTTCATCGCCCTCAACGCCTATAAAA |
| | GAAAACAAGAGAGATCTAAGATCGATACTCTCACCTCTCAGCTGAAGGAGTTGGAGAAACAGGAACA |
| | GACCCACTCCAAGGCGTCAAGACGGCAGGAGATCACAAAGATTCGCGCCGAGTTGAAAGAGATCGAA |
| | ACCCAAAAGACTCTTCAGAAAATTAACGAGTCTCGTAGTTGGTTCTTCGAGCGGATTAATAAGATAG |
| | ACAGACCTCTGGCACGACTGATTAAGAAGAAGCGCGAAAAGAACCAGATTGATACCATCAAGAACGA |
| | CAAGGGCGACATCACTACTGACCCGACCGAGATCCAGACCACTATTCGGGAGTATTATAAGCATTTG |
| | TATGCTAACAAGCTTGAGAACCTGGAAGAGATGGACACTTTTCTGGATACCTATACTCTGCCACGGC |
| | TTAATCAAGAGGAAGTCGAGTCCCTCAACCGCCCAATTACAGGAAGCGAGATTGTGGCCATAATTAA |
| | CTCCCTGCCGACAAAGAAATCTCCTGGTCCGGACGGGTTTACAGCTGAGTTTTATCAACGGTATATG |
| | GAAGAGCTTGTACCGTTTCTGCTCAAGCTCTTTCAGTCTATAGAAAAGGAAGGCATCTTGCCCAATT |
| | CCTTCTACGAAGCTTCTATAATACTTATTCCCAAACCAGGACGCGATACCACAAAGAAGGAAAACTT |
| | CCGGCCCATTAGTCTCATGAATATCGACGCTAAAATATTGAACAAGATTCTCGCCAACAGAATCCAA |
| | CAACATATTAAGAAATTGATACATCACGACCAGGTGGGGTTTATACCTGGCATGCAGGGCTGGTTTA |
| | ACATCCGGAAGAGTATTAACGTCATTCAACACATTAATAGAGCTAAGGATAAGAATCATATGATCAT |
| | CTCTATAGACGCGGAAAAGGCATTCGATAAGATTCAGCAGCCATTTATGCTCAAGACTCTGAACAAA |
| | CTCGGCATCGACGGAACATATTTTAAGATTATTCGCGCAATTTACGATAAGCCGACTGCTAACATTA |
| | TCCTTAACGGCCAAAAGCTCGAGGCCTTTCCGCTCAAGACTGGAACCCGCCAAGGCTGTCCCCTCTC |
| | CCCGCTTTTGTTTAATATTGTACTCGAGGTGCTGGCTAGGGCTATTCGTCAAGAGAAAGAGATTAAA |
| | GGGATACAGCTCGGGAAGGAAGAGGTCAAGCTTTCCTTGTTCGCCGATGATATGATTGTGTACCTGG |
| | AGAATCCTATTGTGTCTGCTCAGAACCTTCTTAAACTTATTTCTAACTTTAGCAAGGTCAGCGGCTA |
| | TAAGATTAACGTCCAGAAATCTCAGGCCTTTCTGTACACAAATAATCGACAGACCGAATCCCAGATA |
| | ATGGGTGAGCTTCCGTTTGTCATAGCCAGCAAAAGGATAAAGTATCTCGGAATCCAGCTGACACGAG |
| | ACGTTAAAGATTTGTTTAAGGAAAATTACAAGCCTCTCCTGAAAGAGATTAAGGAAGATACTAATAA |
| | GTGGAAGAATATCCCCTGTTCATGGGTTGGCAGAATCAACATAGTGAAGATGGCAATACTTCCTAAA |
| | GTGATATATCGCTTTAACGCCATCCCAATTAAACTGCCTATGACCTTCTTTACGGAGCTCGAGAAAA |
| | CAACCCTTAAATTTATATGGAATCAAAAGAGAGCAAGAATAGCGAAGTCCATCTTGAGCCAGAAGAA |
| | TAAGGCCGGTGGGATTACTTTGCCTGATTTTAAGTTGTATTATAAAGCCACAGTAACTAAGACAGCC |
| | TGGTATTGGTATCAGAATAGAGACATCGACCAGTGGAATCGGACCGAACCATCAGAGATAATGCCCC |
| | ACATCTATAATTACCTTATATTCGATAAGCCAGAAAAGAATAAACAGTGGGGCAAAGACAGCCTCTT |
| | CAACAAGTGGTGTTGGGAGAATTGGCTGGCCATATGCCGGAAACTCAAGCTCGACCCCTTTCTTACA |
| | CCCTACACTAAAATCAACAGTAGGTGGATCAAGGACTTGAATGTCAAGCCAAAGACTATAAAGACAC |
| | TGGAAGAGAATCTTGGGATCACAATACAAGATATAGGCGTCGGCAAAGATTTTATGTCAAAGACGCC |
| | CAAGGCCATGGCCACTAAGGATAAGATTGATAAGTGGGACCTTATTAAGCTCAAAAGCTTCTGTACT |
| | GCCAAGGAGACCACGATCAGAGTTAATAGGCAGCCCACTACATGGGAAAAGATTTTCGCCACTTATT |
| | CATCAGATAAGGGGTTGATAAGCAGAATATATAACGAGCTGAAGCAGATCTACAAGAAGAAAACGAA |
| | TAATCCCATCAAGAAGTGGGCAAAAGATATGAACAGGCATTTTAGCAAAGAGGATATCTACGCCGCG |
| | AAGAAGCATATGAAGAAGTGTAGTTCAAGCTTGGCCATTCGTGAGATGCAGATTAAGACGACCATGC |
| | GATACCACCTTACCCCAGTGAGGATGGCAATTATCAAGAAATCTGGCAATAATAGATGTTGGCGGGG |
| | CTGTGGCGAGATTGGCACCCTGCTCCATTGCTGGTGGGATTGCAAGCTGGTGCAGCCGCTTTGGAAA |
| | TCAGTCTGGCGCTTTCTGAGGGACCTCGAGCTTGAGATTCCCTTCGATCCCGCAATTCCCTTGCTCG |
| | GAATCTATCCTAACGAATACAAGAGCTGTTGTTACAAGGATACGTGTACCCGGATGTTCATCGCGGC |
| | CTTGTTTACGATAGCTAAGACGTGGAATCAGCCTAAGTGCCCCACAATGATCGATTGGATCAAGAAA |
| | ATGTGGCATATTTATACCATGGAGTATTACGCAGCAATTAAGAATGACGAATTTATTTCCTTCGTTG |
| | GGACCTGGATGAAGCTGGAGACTATTATTCTGAGCAAGCTGTCTCAGGAGCAAAAGACAAAGCATAG |
| | AATCTTCTCTCTCATTGGTGGTAACGACTACAAAGACGATGACGACAAGccaaagaagaagcggaag |
| | gtcTAAAGCGCTTCTAGAAGTTGTCTCCTCCTGCACTGACTGACTGATACAATCGATTTCTGGATCC |
| | GCAGGCCTAATCAACCTCTGGATTACAAAATTTGTGAAAGATTGACTGGTATTCTTAACTATGTTGC |
| | TCCTTTTACGCTATGTGGATACGCTGCTTTAATGCCTTTGTATCATGCTATTGCTTCCCGTATGGCT |
| | TTCATTTTCTCCTCCTTGTATAAATCCTGGTTGCTGTCTCTTTATGAGGAGTTGTGGCCCGTTGTCA |
| | GGCAACGTGGCGTGGTGTGCACTGTGTTTGCTGACGCAACCCCCACTGGTTGGGGCATTGCCACCAC |
| | CTGTCAGCTCCTTTCCGGGACTTTCGCTTTCCCCCTCCCTATTGCCACGGCGGAACTCATCGCCGCC |
| | TGCCTTGCCCGCTGCTGGACAGGGGCTCGGCTGTTGGGCACTGACAATTCCGTGGTGTTGTCGGGGA |
| | AGCTGACGTCCTTTCCATGGCTGCTCGCCTGTGTTGCCACCTGGATTCTGCGCGGGACGTCCTTCTG |
| | CTACGTCCCTTCGGCCCTCAATCCAGCGGACCTTCCTTCCCGCtgagagacacaaaaaattccaaca |
| | cactattgcaatgaaaataaatttcctttattagccagaagtcagatgctcaaggggcttcatgatg |
| | tccccataatttttggcagagggaaaaagatctcagtggtatttgtgagccagggcattggccttct |
| | gataggcagcctgcacctgaggagtgcggccgctttacttgtacagctcgtccatgccgagagtgat |
| | cccggcggcggtcacgaactccagcaggaccatgtgatcgcgcttctcgttggggtctttgctcagg |
| | gcggactgggtgctcaggtagtggttgtcgggcagcagcacggggccgtcgccgatgggggtgttct |
| | gctggtagtggtcggcgagctgcacgctgccgtcctcgatgttgtggcggatcttgaagttcacctt |
| | gatgccgttcttctgcttgtcggccatgatatagacgttgtggctgttgtagttgtactccagcttg |
| | tgccccaggatgttgccgtcctccttgaagtcgatgcccttcagctcgatgcggttcaccagggtgt |
| | cgccctcgaacttcacctcggcgcgggtcttgtagttgccgtcgtccttgaagaagatggtgcgctc |
| | ctggacgtagccttcgggcatggcggacttgaagaagtcgtgctgcttcatgtggtcggggtagcgg |
| | ctgaagcactgcacgccgtaggtcagggtggtcacgagggtgggccagggcacgggcagcttgccgg |
| | tggtgcagatgaacttcagggtcagcttgccgtaggtggcatcgccctcgccctcgccggacacgct |
| | gaacttgtggccgtttacgtcgccgtccagctcgaccaggatgggcaccaccccggtgaacagctcc |
| | tcgcccttgctcaccatggtggcgggatctgacggttcactaaaccagctctgcttatatagacctc |
| | ccaccgtacacgcctaccgcccatttgcgtcaatggggcggagttgttacgacattttggaaagtcc |
| | cgttgattttggtgccaaaacaaactcccattgacgtcaatggggtggagacttggaaatccccgtg |
| | agtcaaaccgctatccacgcccattgatgtactgccaaaaccgcatcaccatggtaatagcgatgac |
| | taatacgtagatgtactgccaagtaggaaagtcccataaggtcatgtactgggcataatgccaggcg |
| | ggccatttaccgtcattgacgtcaatagggggcgtacttggcatatgatacacttgatgtactgcca |

TABLE 13-continued

Exemplary plasmid sequences

| Name | Sequence |
|---|---|
| | agtgggcagtttaccgtaaatactccacccattgacgtcaatggaaagtccctattggcgttactat<br>gggaacatacgtcattattgacgtcaatgggcgggggtcgttgggcggtcagccaggcgggccattt<br>accgtaagttatgtaacgGGCCTGCTGCCGGCTCTGCGGCCTCTTCCGCGTCTTCGCCTTCGCCCTC<br>AGACGAGTCGGATCTCCCTTTGGGCCGCCTCCCCGCCTGTCTAGCTTGACTGACTGAGATACAGCGT<br>ACCTTCAGCTCACAGACATGATAAGATACATTGATGAGTTTGGACAAACCACAACTAGAATGCAGTG<br>AAAAAAATGCTTTATTTGTGAAATTTGTGATGCTATTGCTTTATTTGTAACCATTATAAGCTGCAAT<br>AAACAAGTTAACAACAACAATTGCATTCATTTTATGTTTCAGGTTCAGGGGGAGGTGTGGGAGGTTT<br>TTTAAAGCAAGTAAAACCTCTACAAATGTGGTATTGGCCCATCTCTATCGGTATCGTAGCATAACCC<br>CTTGGGGCCTCTAAACGGGTCTTGAGGGGTTTTTTGTGCCCCTCGGGCCGGATTGCTATCTACCGGC<br>ATTGGCGCAGAAAAAAATGCCTGATGCGACGCTGCGCGTCTTATACTCCCACATATGCCAGATTCAG<br>CAACGGATACGGCTTCCCCAACTTGCCCACTTCCATACGTGTCCTCCTTACCAGAAATTTATCCTTA<br>AGGTCGTCAGCTATCCTGCAGGCGATCTCTCGATTTCGATCAAGACATTCCTTTAATGGTCTTTTCT<br>GGACACCACTAGGGGTCAGAAGTAGTTCATCAAACTTTCTTCCCTCCCTAATCTCATTGGTTACCTT<br>GGGCTATCGAAACTTAATTAAGCGATCTGCATCTCAATTAGTCAGCAACCATAGTCCCGCCCCTAAC<br>TCCGCCCATCCCGCCCCTAACTCCGCCCAGTTCCGCCCATTCTCCGCCCCATCGCTGACTAATTTTT<br>TTTATTTATGCAGAGGCCGAGGCCGCCTCGGCCTCTGAGCTATTCCAGAAGTAGTGAGGAGGCTTTT<br>TTGGAGGCCTAGGCTTTTGCAAAGGAGGTAGCCAACATGATTGAACAAGATGGATTGCACGCAGGTT<br>CTCCCGCCGCTTGGGTGGAGAGGCTATTCGGCTATGACTGGGCACAACAGACAATCGGCTGCTCTGA<br>TGCCGCCGTGTTCCGGCTGTCAGCGCAGGGGCGCCCGGTTCTTTTTGTCAAGACCGACCTGTCCGGT<br>GCCCTGAATGAACTCCAGGACGAGGCAGCGCGGCTATCGTGGCTGGCCACGACGGGCGTTCCTTGCG<br>CAGCTGTGCTCGACGTTGTCACTGAAGCGGGAAGGGACTGGCTGCTATTGGGCGAAGTGCCGGGGCA<br>GGATCTCCTGTCATCTCACCTTGCTCCTGCCGAGAAAGTATCCATCATGGCTGATGCAATGCGGCGG<br>CTGCATACGCTTGATCCGGCTACCTGCCCATTCGACCACCAAGCGAAACATCGCATCGAGCGAGCAC<br>GTACTCGGATGGAAGCCGGTCTTGTCGATCAGGATGATCTGGACGAAGAGCATCAGGGGCTCGCGCC<br>AGCCGAACTGTTCGCCAGGCTCAAGGCGCGGATGCCCGACGGCGAGGATCTCGTCGTGACCCACGGC<br>GATGCCTGCTTGCCGAATATCATGGTGGAAAATGGCCGCTTTTCTGGATTCATCGACTGTGGCCGGC<br>TGGGTGTGGCGGACCGCTATCAGGACATAGCGTTGGCTACCCGTGATATTGCTGAAGAGCTTGGCGG<br>CGAATGGGCTGACCGCTTCCTCGTGCTTTACGGTATCGCCGCTCCCGATTCGCAGCGCATCGCCTTC<br>TATCGCCTTCTTGACGAGTTCTTCTAGTATGTAAGCCCTGTGCCTTCTAGTTGCCAGCCATCTGTTG<br>TTTGCCCCTCCCCCGTGCCTTCCTTGACCCTGGAAGGTGCCACTCCCACTGTCCTTTCCTAATAAAA<br>TGAGGAAATTGCATCGCATTGTCTGAGTAGGTGTCATTCTATTCTGGGGGGTGGGGTGGGGCAGGAC<br>AGCAAGGGGGAGGATTGGGAAGACAATAGCAGGCATGCTGGGGATGCGGTGGGCTCTATGGTTAATT<br>AACCAGTCAAGTCAGCTACTTGGCGAGATCGACTTGTCTGGGTTTCGACTACGCTCAGAATTGCGTC<br>AGTCAAGTTCGATCTGGTCCTTGCTATTGCACCCGTTCTCCGATTACGAGTTTCATTTAAATCATGT<br>GAGCAAAAGGCCAGCAAAAGGCCAGGAACCGTAAAAAGGCCGCGTTGCTGGCGTTTTTCCATAGGCT<br>CCGCCCCCCTGACGAGCATCACAAAAATCGACGCTCAAGTCAGAGGTGGCGAAACCCGACAGGACTA<br>TAAAGATACCAGGCGTTTCCCCCTGGAAGCTCCCTCGTGCGCTCTCCTGTTCCGACCCTGCCGCTTA<br>CCGGATACCTGTCCGCCTTTCTCCCTTCGGGAAGCGTGGCGCTTTCTCATAGCTCACGCTGTAGGTA<br>TCTCAGTTCGGTGTAGGTCGTTCGCTCCAAGCTGGGCTGTGTGCACGAACCCCCCGTTCAGCCCGAC<br>CGCTGCGCCTTATCCGGTAACTATCGTCTTGAGTCCAACCCGGTAAGACACGACTTATCGCCACTGG<br>CAGCAGCCACTGGTAACAGGATTAGCAGAGCGAGGTATGTAGGCGGTGCTACAGAGTTCTTGAAGTG<br>GTGGCCTAACTACGGCTACACTAGAAGAACAGTATTTGGTATCTGCGCTCTGCTGAAGCCAGTTACC<br>TTCGGAAAAAGAGTTGGTAGCTCTTGATCCGGCAAACAAACCACCGCTGGTAGCGGTGGTTTTTTTG<br>TTTGCAAGCAGCAGATTACGCGCAGAAAAAAAGGATCTCAAGAAGATCCTTTGATCTTTTCTACGGG<br>GTCTGACGCTCAGTGGAACGAAAACTCACGTTAAGGGATTTTGGTCATGAGATTATCAAAAAGGATC<br>TTCACCTAGATCCTTTTAAATTAAAAATGAAGTTTTAAATCAATCTAAAGTATATATGAGTAAACTT<br>GGTCTGACAGTTACCAATGCTTAATCAGTGAGGCACCTATCTCAGCGATCTGTCTATTTCGTTCATC<br>CATAGTTGCATTTAAATTTCCGAACTCTCCAAGGCCCTCGTCGGAAAATCTTCAAACCTTTCGTCCG<br>ATCCATCTTGCAGGCTACCTCTCGAACGAACTATCGCAAGTCTCTTGGCCGGCCTTGCGCCTTGGCT<br>ATTGCTTGGCAGCGCCTATCGCCAGGTATTACTCCAATCCCGAATATCCGAGATCGGGATCACCCGA<br>GAGAAGTTCAACCTACATCCTCAATCCCGATCTATCCGAGATCCGAGGAATATCGAAATCGGGGCGC<br>GCCTGGTGTACCG (SEQ ID NO: 104) |
| RET-<br>015<br>LINE1-<br>GFP<br>ORF2-<br>C_Linker_<br>SV40-<br>NLS | TCGACGATCCATATCGTTGCTTGGCAGTCAGCCAGTCGGAATCCAGCTTGGGACCCAGGAAGTCCAA<br>TCGTCAGATATTGTACTCAAGCCTGGTCACGGCAGCGTACCGATCTGTTTAAACCTAGATATTGATA<br>GTCTGATCGGTCAACGTATAATCGAGTCCTAGCTTTTGCAAACATCTATCAAGAGACAGGATCAGCA<br>GGAGGCTTTCGCATGAGTATTCAACATTTCCGTGTCGCCCTTATTCCCTTTTTTGCGGCATTTTGCC<br>TTCCTGTTTTTGCTCACCCAGAAACGCTGGTGAAAGTAAAAGATGCTGAAGATCAGTTGGGTGCGCG<br>AGTGGGTTACATCGAACTGGATCTCAACAGCGGTAAGATCCTTGAGAGTTTTCGCCCCGAAGAACGC<br>TTTCCAATGATGAGCACTTTTAAAGTTCTGCTATGTGGCGCGGTATTATCCCGTATTGACGCCGGGC<br>AAGAGCAACTCGGTCGCCGCATACACTATTCTCAGAATGACTTGGTTGAGTATTCACCAGTCACAGA<br>AAAGCATCTTACGGATGGCATGACAGTAAGAGAATTATGCAGTGCTGCCATAACCATGAGTGATAAC<br>ACTGCGGCCAACTTACTTCTGACAACGATTGGAGGACCGAAGGAGCTAACCGCTTTTTTGCACAACA<br>TGGGGGATCATGTAACTCGCCTTGATCGTTGGGAACCGGAGCTGAATGAAGCCATACCAAACGACGA<br>GCGTGACACCACGATGCCTGTAGCAATGGCAACAACCTTGCGTAAACTATTAACTGGCGAACTACTT<br>ACTCTAGCTTCCCGGCAACAGTTGATAGACTGGATGGAGGCGGATAAAGTTGCAGGACCACTTCTGC<br>GCTCGGCCCTTCCGGCTGGCTGGTTTATTGCTGATAAATCTGGAGCCGGTGAGCGTGGGTCTCGCGG<br>TATCATTGCAGCACTGGGGCCAGATGGTAAGCCCTCCCGTATCGTAGTTATCTACACGACGGGGAGT<br>CAGGCAACTATGGATGAACGAAATAGACAGATCGCTGAGATAGGTGCCTCACTGATTAAGCATTGGT<br>AACCGATTCTAGGTGCATTGGCGCAGAAAAAAATGCCTGATGCGACGCTGCGCGTCTTATACTCCCA<br>CATATGCCAGATTCAGCAACGGATACGGCTTCCCCAACTTGCCCACTTCCATACGTGTCCTCCTTAC<br>CAGAAATTTATCCTTAAGATCGTTTAAACTCGACTCTGGCTCTATCGAATCTCCGTCGTTTCGAGCT<br>TACGCGAACAGCCGTGGCGCTCATTTGCTCGTCGGGCATCGAATCTCGTCAGCTATCGTCAGCTTAC<br>CTTTTTGGCAGCGATCGCGGCTCCCGACATCTTGGACCATTAGCTCCACAGGTATCTTCTTCCCTCT<br>AGTGGTCATAACAGCAGCTTCAGCTACCTCTCAATTCAAAAAACCCCTCAAGACCCGTTTAGAGGCC<br>CCAAGGGGTTATGCTATCAATCGTTGCGTTACACACACAAAAAACCAACACACATCCATCTTCGATG |

TABLE 13-continued

Exemplary plasmid sequences

| Name | Sequence |
|---|---|
| | GATAGCGATTTTATTATCTAACTGCTGATCGAGTGTAGCCAGATCTAGTAATCAATTACGGGGTCAT |
| | TAGTTCATAGCCCATATATGGAGTTCCGCGTTACATAACTTACGGTAAATGGCCCGCCTGGCTGACC |
| | GCCCAACGACCCCCGCCCATTGACGTCAATAATGACGTATGTTCCCATAGTAACGCCAATAGGGACT |
| | TTCCATTGACGTCAATGGGTGGAGTATTTACGGTAAACTGCCCACTTGGCAGTACATCAAGTGTATC |
| | ATATGCCAAGTACGCCCCCTATTGACGTCAATGACGGTAAATGGCCCGCCTGGCATTATGCCCAGTA |
| | CATGACCTTATGGGACTTTCCTACTTGGCAGTACATCTACGTATTAGTCATCGCTATTACCATGCTG |
| | ATGCGGTTTTGGCAGTACATCAATGGGCGTGGATAGCGGTTTGACTCACGGGGATTTCCAAGTCTCC |
| | ACCCCATTGACGTCAATGGGAGTTTGTTTTGGCACCAAAATCAACGGGACTTTCCAAAATGTCGTAA |
| | CAACTCCGCCCCATTGACGCAAATGGGCGGTAGGCGTGTACGGTGGGAGGTCTATATAAGCAGAGCT |
| | GGTTTAGTGAACCGTCAGATCAGATCTTTGTCGATCCTACCATCCACTCGACACACCCGCCAGCGGC |
| | CGCTAATACGACTCACTATAGGGAGAAGTACTGCCACCATGGGCAAGAAGCAAAATCGCAAGACGGG |
| | GAATTCCAAGACACAATCCGCTAGCCCACCACCTAAAGAGCGTTCTAGCTCCCCTGCTACTGAGCAG |
| | TCCTGGATGGAAAACGACTTCGATGAACTCCGGGAAGAGGGATTTAGGCGATCCAACTATTCAGAAC |
| | TCCGCGAAGATATCCAGACAAAGGGGAAGGAAGTCGAGAATTTCGAGAAGAACCTCGAGGAGTGCAT |
| | CACCCGTATCACAAACACTGAGAAATGTCTCAAAGAACTCATGGAACTTAAGACAAAAGCCAGGGAG |
| | CTTCGAGAGGAGTGTCGGAGTCTGAGATCCAGGTGTGACCAGCTCGAGGAGCGCGTGAGCGCGATGG |
| | AAGACGAGATGAACGAGATGAAAAGAGAGGGCAAATTCAGGGAGAAGCGCATTAAGAGGAACGAACA |
| | GAGTCTGCAGGAGATTTGGGATTACGTCAAGAGGCCTAACCTGCGGTTGATCGGCGTCCCCGAGAGC |
| | GACGTAGAAAACGGGACTAAACTGGAGAATACACTTCAAGACATCATTCAAGAAAATTTTCCAAACC |
| | TGGCTCGGCAAGCTAATGTGCAAATCCAAGAGATCCAACGCACACCCCAGCGGTATAGCTCTCGGCG |
| | TGCCACCCCTAGGCATATTATCGTGCGCTTTACTAAGGTGGAGATGAAAGAGAAGATGCTGCGAGCC |
| | GCTCGGGAAAAGGGAAGGGTGACTTTGAAGGGCAAACCTATTCGGCTGACGGTTGACCTTAGCGCCG |
| | AGACACTCCAGGCACGCCGGGAATGGGGCCCCATCTTTAATATCCTGAAGGAGAAGAACTTCCAGCC |
| | ACGAATCTCTTACCCTGCAAAGTTGAGTTTTATCTCCGAGGGTGAGATTAAGTATTTCATCGATAAA |
| | CAGATGCTGCGAGACTTCGTGACAACTCGCCCAGCTCTCAAGGAACTGCTCAAAGAGGCTCTTAATA |
| | TGGAGCGCAATAATAGATATCAACCCTTGCAGAACCACGCAAAGATGTGAGACAGCCGTCAGACCAT |
| | CAAGACTAGGAAGAAACTGCATCAACTAATGAGCAAAATCACCAGCTAACATCATAGTATACATGAC |
| | CGGCTCTAACTCACATATCACCATCCTTACACTTAACATTAACGGCCTCAACTCAGCTATCAAGCGC |
| | CATCGGCTGGCCAGCTGGATCAAATCACAGGATCCAAGCGTTTGTTGCATCCAAGAGACCCACCTGA |
| | CCTGTAGAGATACTCACCGCCTCAAGATCAAGGGATGGCGAAAGATTTATCAGGCGAACGGTAAGCA |
| | GAAGAAAGCCGGAGTCGCAATTCTGGTCTCAGACAAGACGGATTTCAAGCCCACCAAAATTAAGCGT |
| | GATAAGGAAGGTCACTATATTATGGTGAAAGGCAGCATACAGCAGGAAGAACTTACCATATTGAACA |
| | TCTACGCGCCAAACACCGGCGCACCTCGCTTTATCAAACAGGTCCTGTCCGATCTGCAGCGAGATCT |
| | GGATTCTCATACGTTGATTATGGGTGATTTCAATACACCATTGAGCACCCTGGATCGCAGCACCAGG |
| | CAAAAGGTAAATAAAGACACGCAAGAGCTCAATAGCGCACTGCATCAGGCAGATCTCATTGATATTT |
| | ATCGCACTCTTCATCCTAAGAGTACCGAGTACACATTCTTCAGCGCCCCACATCATACATACTCAAA |
| | GATCGATCATATCGTCGGCTCAAAGGCTCTGCTGTCAAAGTGCAAGCGCACAGAGATAATTACAAAT |
| | TACCTGTCAGATCATAGCGCGATCAAGCTCGAGCTGAGAATCAAGAACCTGACCCAGAGCCGGAGTA |
| | CCACTTGGAAGCTTAATAACCTGCTGCTCAACGATTATTGGGTCCACAATGAGATGAAGGCAGAGAT |
| | TAAAATGTTCTTCGAAACAAATGAGAATAAGGATACTACCTATCAAAACCTTTGGGATGCCTTTAAG |
| | GCCGTCTGCAGAGGCAAGTTCATCGCCCTCAACGCCTATAAAAGAAAACAAGAGAGATCTAAGATCG |
| | ATACTCTCACCTCTCAGCTGAAGGAGTTGGAGAAACAGGAACAGACCCACTCCAAGGCGTCAAGACG |
| | GCAGGAGATCACAAAGATTCGCGCCGAGTTGAAAGAGATCGAAACCCAAAAGACTCTTCAGAAAATT |
| | AACGAGTCTCGTAGTTGGTTCTTCGAGCGGATTAATAAGATAGACAGACCTCTGGCACGACTGATTA |
| | AGAAGAAGCGCGAAAAGAACCAGATTGATACCATCAAGAACGACAAGGGCGACATCACTACTGACCC |
| | GACCGAGATCCAGACCACTATTCGGGAGTATTATAAGCATTTGTATGCTAACAAGCTTGAGAACCTG |
| | GAAGAGATGGACACTTTTCTGGATACCTATACTCTGCCACGGCTTAATCAAGAGGAAGTCGAGTCCC |
| | TCAACCGCCCAATTACAGGAAGCGAGATTGTGGCCATAATTAACTCCCTGCCGACAAAGAAATCTCC |
| | TGGTCCGGACGGGTTTACAGCTGAGTTTTATCAACGGTATATGGAAGAGCTTGTACCGTTTCTGCTC |
| | AAGCTCTTTCAGTCTATAGAAAAGGAAGGCATCTTGCCCAATTCCTTCTACGAAGCTTCTATAATAC |
| | TTATTCCCAAACCAGGACGCGATACCACAAAGAAGGAAAACTTCCGGCCCATTAGTCTCATGAATAT |
| | CGACGCTAAAATATTGAACAAGATTCTCGCCAACAGAATCCAACAACATATTAAGAAATTGATACAT |
| | CACGACCAGGTGGGGTTTATACCTGGCATGCAGGGCTGGTTTAACATCCGGAAGAGTATTAACGTCA |
| | TTCAACACATTAATAGAGCTAAGGATAAGAATCATATGATCATCTCTATAGACGCGGAAAAGGCATT |
| | CGATAAGATTCAGCAGCCATTTATGCTCAAGACTCTGAACAAACTCGGCATCGACGGAACATATTTT |
| | AAGATTATTCGCGCAATTTACGATAAGCCGACTGCTAACATTATCCTTAACGGCCAAAAGCTCGAGG |
| | CCTTTCCGCTCAAGACTGGAACCCGCCAAGGCTGTCCCCTCTCCCCGCTTTTGTTTAATATTGTACT |
| | CGAGGTGCTGGCTAGGGCTATTCGTCAAGAGAAAGAGATTAAAGGGATACAGCTCGGGAAGGAAGAG |
| | GTCAAGCTTTCCTTGTTCGCCGATGATATGATTGTGTACCTGGAGAATCCTATTGTGTCTGCTCAGA |
| | ACCTTCTTAAACTTATTTCTAACTTTAGCAAGGTCAGCGGCTATAAGATTAACGTCCAGAAATCTCA |
| | GGCCTTTCTGTACACAAATAATCGACAGACCGAATCCCAGATAATGGGTGAGCTTCCGTTTGTCATA |
| | GCCAGCAAAAGGATAAAGTATCTCGGAATCCAGCTGACACGAGACGTTAAAGATTTGTTTAAGGAAA |
| | ATTACAAGCCTCTCCTGAAAGAGATTAAGGAAGATACTAATAAGTGGAAGAATATCCCCTGTTCATG |
| | GGTTGGCAGAATCAACATAGTGAAGATGGCAATACTTCCTAAAGTGATATATCGCTTTAACGCCATC |
| | CCAATTAAACTGCCTATGACCTTCTTTACGGAGCTCGAGAAAACAACCCTTAAATTTATATGGAATC |
| | AAAAGAGAGCAAGAATAGCGAAGTCCATCTTGAGCCAGAAGAATAAGGCCGGTGGGATTACTTTGCC |
| | TGATTTTAAGTTGTATTATAAAGCCACAGTAACTAAGACAGCCTGGTATTGGTATCAGAATAGAGAC |
| | ATCGACCAGTGGAATCGGACCGAACCATCAGAGATAATGCCCCACATCTATAATTACCTTATATTCG |
| | ATAAGCCAGAAAAGAATAAACAGTGGGGCAAAGACAGCCTCTTCAACAAGTGGTGTTGGGAGAATTG |
| | GCTGGCCATATGCCGGAAACTCAAGCTCGACCCCTTTCTTACACCCTACACTAAAATCAACAGTAGG |
| | TGGATCAAGGACTTGAATGTCAAGCCAAAGACTATAAAGACACTGGAAGAGAATCTTGGGATCACAA |
| | TACAAGATATAGGCGTCGGCAAAGATTTTATGTCAAAGACGCCCAAGGCCATGGCCACTAAGGATAA |
| | GATTGATAAGTGGGACCTTATTAAGCTCAAAAGCTTCTGTACTGCCAAGGAGACCACGATCAGAGTT |
| | AATAGGCAGCCCACTACATGGGAAAAGATTTTCGCCACTTATTCATCAGATAAGGGGTTGATAAGCA |
| | GAATATATAACGAGCTGAAGCAGATCTACAAGAAGAAAACGAATAATCCCATCAAGAAGTGGGCAAA |
| | AGATATGAACAGGCATTTTAGCAAAGAGGATATCTACGCCGCGAAGAAGCATATGAAGAAGTGTAGT |

TABLE 13-continued

Exemplary plasmid sequences

| Name | Sequence |
|---|---|
| | TCAAGCTTGGCCATTCGTGAGATGCAGATTAAGACGACCATGCGATACCACCTTACCCCAGTGAGGA<br>TGGCAATTATCAAGAAATCTGGCAATAATAGATGTTGGCGGGGCTGTGGCGAGATTGGCACCCTGCT<br>CCATTGCTGGTGGGATTGCAAGCTGGTGCAGCCGCTTTGGAAATCAGTCTGGCGCTTTCTGAGGGAC<br>CTCGAGCTTGAGATTCCCTTCGATCCCGCAATTCCCTTGCTCGGAATCTATCCTAACGAATACAAGA<br>GCTGTTGTTACAAGGATACGTGTACCCGGATGTTCATCGCGGCCTTGTTTACGATAGCTAAGACGTG<br>GAATCAGCCTAAGTGCCCCACAATGATCGATTGGATCAAGAAAATGTGGCATATTTATACCATGGAG<br>TATTACGCAGCAATTAAGAATGACGAATTTATTTCCTTCGTTGGGACCTGGATGAAGCTGGAGACTA<br>TTATTCTGAGCAAGCTGTCTCAGGAGCAAAAGACAAAGCATAGAATCTTCTCTCTCATTGGTGGTAA<br>CGACTACAAAGACGATGACGACAAGggcggcggcagcccaaagaagaagcggaaggtcTAAAGCGCT<br>TCTAGAAGTTGTCTCCTCCTGCACTGACTGACTGATACAATCGATTTCTGGATCCGCAGGCCTAATC<br>AACCTCTGGATTACAAAATTTGTGAAAGATTGACTGGTATTCTTAACTATGTTGCTCCTTTTACGCT<br>ATGTGGATACGCTGCTTTAATGCCTTTGTATCATGCTATTGCTTCCCGTATGGCTTTCATTTTCTCC<br>TCCTTGTATAAATCCTGGTTGCTGTCTCTTTATGAGGAGTTGTGGCCCGTTGTCAGGCAACGTGGCG<br>TGGTGTGCACTGTGTTTGCTGACGCAACCCCCACTGGTTGGGGCATTGCCACCACCTGTCAGCTCCT<br>TTCCGGGACTTTCGCTTTCCCCCTCCCTATTGCCACGGCGGAACTCATCGCCGCCTGCCTTGCCCGC<br>TGCTGGACAGGGGCTCGGCTGTTGGGCACTGACAATTCCGTGGTGTTGTCGGGGAAGCTGACGTCCT<br>TTCCATGGCTGCTCGCCTGTGTTGCCACCTGGATTCTGCGCGGGACGTCCTTCTGCTACGTCCCTTC<br>GGCCCTCAATCCAGCGGACCTTCCTTCCCGCtgagagacacaaaaaattccaacacactattgcaat<br>gaaaataaatttcctttattagccagaagtcagatgctcaaggggcttcatgatgtccccataattt<br>ttggcagagggaaaaagatctcagtggtatttgtgagccagggcattggccttctgataggcagcct<br>gcacctgaggagtgcggccgctttacttgtacagctcgtccatgccgagagtgatcccggcggcggt<br>cacgaactccagcaggaccatgtgatcgcgcttctcgttggggtctttgctcagggcggactgggtg<br>ctcaggtagtggttgtcgggcagcagcacggggccgtcgccgatgggggtgttctgctggtagtggt<br>cggcgagctgcacgctgccgtcctcgatgttgtggcggatcttgaagttcaccttgatgccgttctt<br>ctgcttgtcggccatgatatagacgttgtggctgttgtagttgtactccagcttgtgccccaggatg<br>ttgccgtcctccttgaagtcgatgcccttcagctcgatgcggttcaccagggtgtcgccctcgaact<br>tcacctcggcgcgggtcttgtagttgccgtcgtccttgaagaagatggtgcgctcctggacgtagcc<br>ttcgggcatggcggacttgaagaagtcgtgctgcttcatgtggtcggggtagcggctgaagcactgc<br>acgccgtaggtcagggtggtcacgagggtgggccagggcacgggcagcttgccggtggtgcagatga<br>acttcagggtcagcttgccgtaggtggcatcgccctcgccctcgccggacacgctgaacttgtggcc<br>gtttacgtcgccgtccagctcgaccaggatgggcaccaccccggtgaacagctcctcgcccttgctc<br>accatggtggcgggatctgacggttcactaaaccagctctgcttatatagacctcccaccgtacacg<br>cctaccgcccatttgcgtcaatggggcggagttgttacgacattttggaaagtcccgttgattttgg<br>tgccaaaacaaactcccattgacgtcaatggggtggagacttggaaatccccgtgagtcaaaccgct<br>atccacgcccattgatgtactgccaaaaccgcatcaccatggtaatagcgatgactaatacgtagat<br>gtactgccaagtaggaaagtcccataaggtcatgtactgggcataatgccaggcgggccatttaccg<br>tcattgacgtcaatagggggcgtacttggcatatgatacacttgatgtactgccaagtgggcagttt<br>accgtaaatactccacccattgacgtcaatggaaagtccctattggcgttactatgggaacatacgt<br>cattattgacgtcaatgggcgggggtcgttgggcggtcagccaggcgggccatttaccgtaagttat<br>gtaacgGGCCTGCTGCCGGCTCTGCGGCCTCTTCCGCGTCTTCGCCTTCGCCCTCAGACGAGTCGGA<br>TCTCCCTTTGGGCCGCCTCCCCGCCTGTCTAGCTTGACTGACTGAGATACAGCGTACCTTCAGCTCA<br>CAGACATGATAAGATACATTGATGAGTTTGGACAAACCACAACTAGAATGCAGTGAAAAAAATGCTT<br>TATTTGTGAAATTTGTGATGCTATTGCTTTATTTGTAACCATTATAAGCTGCAATAAACAAGTTAAC<br>AACAACAATTGCATTCATTTTATGTTTCAGGTTCAGGGGGAGGTGTGGGAGGTTTTTTAAAGCAAGT<br>AAAACCTCTACAAATGTGGTATTGGCCCATCTCTATCGGTATCGTAGCATAACCCCTTGGGGCCTCT<br>AAACGGGTCTTGAGGGGTTTTTTGTGCCCCTCGGGCCGGATTGCTATCTACCGGCATTGGCGCAGAA<br>AAAAATGCCTGATGCGACGCTGCGCGTCTTATACTCCCACATATGCCAGATTCAGCAACGGATACGG<br>CTTCCCCAACTTGCCCACTTCCATACGTGTCCTCCTTACCAGAAATTTATCCTTAAGGTCGTCAGCT<br>ATCCTGCAGGCGATCTCTCGATTTCGATCAAGACATTCCTTTAATGGTCTTTTCTGGACACCACTAG<br>GGGTCAGAAGTAGTTCATCAAACTTTCTTCCCTCCCTAATCTCATTGGTTACCTTGGGCTATCGAAA<br>CTTAATTAAGCGATCTGCATCTCAATTAGTCAGCAACCATAGTCCCGCCCCTAACTCCGCCCATCCC<br>GCCCCTAACTCCGCCCAGTTCCGCCCATTCTCCGCCCCATCGCTGACTAATTTTTTTTATTTATGCA<br>GAGGCCGAGGCCGCCTCGGCCTCTGAGCTATTCCAGAAGTAGTGAGGAGGCTTTTTTGGAGGCCTAG<br>GCTTTTGCAAAGGAGGTAGCCAACATGATTGAACAAGATGGATTGCACGCAGGTTCTCCCGCCGCTT<br>GGGTGGAGAGGCTATTCGGCTATGACTGGGCACAACAGACAATCGGCTGCTCTGATGCCGCCGTGTT<br>CCGGCTGTCAGCGCAGGGGCGCCCGGTTCTTTTTGTCAAGACCGACCTGTCCGGTGCCCTGAATGAA<br>CTCCAGGACGAGGCAGCGCGGCTATCGTGGCTGGCCACGACGGGCGTTCCTTGCGCAGCTGTGCTCG<br>ACGTTGTCACTGAAGCGGGAAGGGACTGGCTGCTATTGGGCGAAGTGCCGGGGCAGGATCTCCTGTC<br>ATCTCACCTTGCTCCTGCCGAGAAAGTATCCATCATGGCTGATGCAATGCGGCGGCTGCATACGCTT<br>GATCCGGCTACCTGCCCATTCGACCACCAAGCGAAACATCGCATCGAGCGAGCACGTACTCGGATGG<br>AAGCCGGTCTTGTCGATCAGGATGATCTGGACGAAGAGCATCAGGGGCTCGCGCCAGCCGAACTGTT<br>CGCCAGGCTCAAGGCGCGGATGCCCGACGGCGAGGATCTCGTCGTGACCCACGGCGATGCCTGCTTG<br>CCGAATATCATGGTGGAAAATGGCCGCTTTTCTGGATTCATCGACTGTGGCCGGCTGGGTGTGGCGG<br>ACCGCTATCAGGACATAGCGTTGGCTACCCGTGATATTGCTGAAGAGCTTGGCGGCGAATGGGCTGA<br>CCGCTTCCTCGTGCTTTACGGTATCGCCGCTCCCGATTCGCAGCGCATCGCCTTCTATCGCCTTCTT<br>GACGAGTTCTTCTAGTATGTAAGCCCTGTGCCTTCTAGTTGCCAGCCATCTGTTGTTTGCCCCTCCC<br>CCGTGCCTTCCTTGACCCTGGAAGGTGCCACTCCCACTGTCCTTTCCTAATAAAATGAGGAAATTGC<br>ATCGCATTGTCTGAGTAGGTGTCATTCTATTCTGGGGGGTGGGGTGGGGCAGGACAGCAAGGGGGAG<br>GATTGGGAAGACAATAGCAGGCATGCTGGGGATGCGGTGGGCTCTATGGTTAATTAACCAGTCAAGT<br>CAGCTACTTGGCGAGATCGACTTGTCTGGGTTTCGACTACGCTCAGAATTGCGTCAGTCAAGTTCGA<br>TCTGGTCCTTGCTATTGCACCCGTTCTCCGATTACGAGTTTCATTTAAATCATGTGAGCAAAAGGCC<br>AGCAAAAGGCCAGGAACCGTAAAAAGGCCGCGTTGCTGGCGTTTTTCCATAGGCTCCGCCCCCCTGA<br>CGAGCATCACAAAAATCGACGCTCAAGTCAGAGGTGGCGAAACCCGACAGGACTATAAAGATACCAG<br>GCGTTTCCCCCTGGAAGCTCCCTCGTGCGCTCTCCTGTTCCGACCCTGCCGCTTACCGGATACCTGT<br>CCGCCTTTCTCCCTTCGGGAAGCGTGGCGCTTTCTCATAGCTCACGCTGTAGGTATCTCAGTTCGGT<br>GTAGGTCGTTCGCTCCAAGCTGGGCTGTGTGCACGAACCCCCCGTTCAGCCCGACCGCTGCGCCTTA |

TABLE 13-continued

Exemplary plasmid sequences

| Name | Sequence |
|---|---|
| | TCCGGTAACTATCGTCTTGAGTCCAACCCGGTAAGACACGACTTATCGCCACTGGCAGCAGCCACTG<br>GTAACAGGATTAGCAGAGCGAGGTATGTAGGCGGTGCTACAGAGTTCTTGAAGTGGTGGCCTAACTA<br>CGGCTACACTAGAAGAACAGTATTTGGTATCTGCGCTCTGCTGAAGCCAGTTACCTTCGGAAAAAGA<br>GTTGGTAGCTCTTGATCCGGCAAACAAACCACCGCTGGTAGCGGTGGTTTTTTTGTTTGCAAGCAGC<br>AGATTACGCGCAGAAAAAAAGGATCTCAAGAAGATCCTTTGATCTTTTCTACGGGGTCTGACGCTCA<br>GTGGAACGAAAACTCACGTTAAGGGATTTTGGTCATGAGATTATCAAAAAGGATCTTCACCTAGATC<br>CTTTTAAATTAAAAATGAAGTTTTAAATCAATCTAAAGTATATATGAGTAAACTTGGTCTGACAGTT<br>ACCAATGCTTAATCAGTGAGGCACCTATCTCAGCGATCTGTCTATTTCGTTCATCCATAGTTGCATT<br>TAAATTTCCGAACTCTCCAAGGCCCTCGTCGGAAAATCTTCAAACCTTTCGTCCGATCCATCTTGCA<br>GGCTACCTCTCGAACGAACTATCGCAAGTCTCTTGGCCGGCCTTGCGCCTTGGCTATTGCTTGGCAG<br>CGCCTATCGCCAGGTATTACTCCAATCCCGAATATCCGAGATCGGGATCACCCGAGAGAAGTTCAAC<br>CTACATCCTCAATCCCGATCTATCCGAGATCCGAGGAATATCGAAATCGGGGCGCGCCTGGTGTACC<br>GAGAACGATCCTCTCAGTGCGAGTC (SEQ ID NO: 105) |
| ret-016-line1-gfp-orf-c_nucleo-plasmin-nls | ACCGAGAACGATCCTCTCAGTGCGAGTCTCGACGATCCATATCGTTGCTTGGCAGTCAGCCAGTCGG<br>AATCCAGCTTGGGACCCAGGAAGTCCAATCGTCAGATATTGTACTCAAGCCTGGTCACGGCAGCGTA<br>CCGATCTGTTTAAACCTAGATATTGATAGTCTGATCGGTCAACGTATAATCGAGTCCTAGCTTTTGC<br>AAACATCTATCAAGAGACAGGATCAGCAGGAGGCTTTCGCATGAGTATTCAACATTTCCGTGTCGCC<br>CTTATTCCCTTTTTTGCGGCATTTTGCCTTCCTGTTTTTGCTCACCCAGAAACGCTGGTGAAAGTAA<br>AAGATGCTGAAGATCAGTTGGGTGCGCGAGTGGGTTACATCGAACTGGATCTCAACAGCGGTAAGAT<br>CCTTGAGAGTTTTCGCCCCGAAGAACGCTTTCCAATGATGAGCACTTTTAAAGTTCTGCTATGTGGC<br>GCGGTATTATCCCGTATTGACGCCGGGCAAGAGCAACTCGGTCGCCGCATACACTATTCTCAGAATG<br>ACTTGGTTGAGTATTCACCAGTCACAGAAAAGCATCTTACGGATGGCATGACAGTAAGAGAATTATG<br>CAGTGCTGCCATAACCATGAGTGATAACACTGCGGCCAACTTACTTCTGACAACGATTGGAGGACCG<br>AAGGAGCTAACCGCTTTTTTGCACAACATGGGGGATCATGTAACTCGCCTTGATCGTTGGGAACCGG<br>AGCTGAATGAAGCCATACCAAACGACGAGCGTGACACCACGATGCCTGTAGCAATGGCAACAACCTT<br>GCGTAAACTATTAACTGGCGAACTACTTACTCTAGCTTCCCGGCAACAGTTGATAGACTGGATGGAG<br>GCGGATAAAGTTGCAGGACCACTTCTGCGCTCGGCCCTTCCGGCTGGCTGGTTTATTGCTGATAAAT<br>CTGGAGCCGGTGAGCGTGGGTCTCGCGGTATCATTGCAGCACTGGGGCCAGATGGTAAGCCCTCCCG<br>TATCGTAGTTATCTACACGACGGGGAGTCAGGCAACTATGGATGAACGAAATAGACAGATCGCTGAG<br>ATAGGTGCCTCACTGATTAAGCATTGGTAACCGATTCTAGGTGCATTGGCGCAGAAAAAAATGCCTG<br>ATGCGACGCTGCGCGTCTTATACTCCCACATATGCCAGATTCAGCAACGGATACGGCTTCCCCAACT<br>TGCCCACTTCCATACGTGTCCTCCTTACCAGAAATTTATCCTTAAGATCGTTTAAACTCGACTCTGG<br>CTCTATCGAATCTCCGTCGTTTCGAGCTTACGCGAACAGCCGTGGCGCTCATTTGCTCGTCGGGCAT<br>CGAATCTCGTCAGCTATCGTCAGCTTACCTTTTTGGCAGCGATCGCGGCTCCCGACATCTTGGACCA<br>TTAGCTCCACAGGTATCTTCTTCCCTCTAGTGGTCATAACAGCAGCTTCAGCTACCTCTCAATTCAA<br>AAAACCCCTCAAGACCCGTTTAGAGGCCCCAAGGGGTTATGCTATCAATCGTTGCGTTACACACACA<br>AAAAACCAACACACATCCATCTTCGATGGATAGCGATTTTATTATCTAACTGCTGATCGAGTGTAGC<br>CAGATCTAGTAATCAATTACGGGGTCATTAGTTCATAGCCCATATATGGAGTTCCGCGTTACATAAC<br>TTACGGTAAATGGCCCGCCTGGCTGACCGCCCAACGACCCCCGCCCATTGACGTCAATAATGACGTA<br>TGTTCCCATAGTAACGCCAATAGGGACTTTCCATTGACGTCAATGGGTGGAGTATTTACGGTAAACT<br>GCCCACTTGGCAGTACATCAAGTGTATCATATGCCAAGTACGCCCCCTATTGACGTCAATGACGGTA<br>AATGGCCCGCCTGGCATTATGCCCAGTACATGACCTTATGGGACTTTCCTACTTGGCAGTACATCTA<br>CGTATTAGTCATCGCTATTACCATGCTGATGCGGTTTTGGCAGTACATCAATGGGCGTGGATAGCGG<br>TTTGACTCACGGGGATTTCCAAGTCTCCACCCCATTGACGTCAATGGGAGTTTGTTTTGGCACCAAA<br>ATCAACGGGACTTTCCAAAATGTCGTAACAACTCCGCCCCATTGACGCAAATGGGCGGTAGGCGTGT<br>ACGGTGGGAGGTCTATATAAGCAGAGCTGGTTTAGTGAACCGTCAGATCAGATCTTTGTCGATCCTA<br>CCATCCACTCGACACACCCGCCAGCGGCCGCTAATACGACTCACTATAGGGAGAAGTACTGCCACCA<br>TGGGCAAGAAGCAAAATCGCAAGACGGGGAATTCCAAGACACAATCCGCTAGCCCACCACCTAAAGA<br>GCGTTCTAGCTCCCCTGCTACTGAGCAGTCCTGGATGGAAAACGACTTCGATGAACTCCGGGAAGAG<br>GGATTTAGGCGATCCAACTATTCAGAACTCCGCGAAGATATCCAGACAAAGGGGAAGGAAGTCGAGA<br>ATTTCGAGAAGAACCTCGAGGAGTGCATCACCCGTATCACAAACACTGAGAAATGTCTCAAAGAACT<br>CATGGAACTTAAGACAAAAGCCAGGGAGCTTCGAGAGGAGTGTCGGAGTCTGAGATCCAGGTGTGAC<br>CAGCTCGAGGAGCGCGTGAGCGCGATGGAAGACGAGATGAACGAGATGAAAAGAGAGGGCAAATTCA<br>GGGAGAAGCGCATTAAGAGGAACGAACAGAGTCTGCAGGAGATTTGGGATTACGTCAAGAGGCCTAA<br>CCTGCGGTTGATCGGCGTCCCCGAGAGCGACGTAGAAAACGGGACTAAACTGGAGAATACACTTCAA<br>GACATCATTCAAGAAAATTTTCCAAACCTGGCTCGGCAAGCTAATGTGCAAATCCAAGAGATCCAAC<br>GCACACCCCAGCGGTATAGCTCTCGGCGTGCCACCCCTAGGCATATTATCGTGCGCTTTACTAAGGT<br>GGAGATGAAAGAGAAGATGCTGCGAGCCGCTCGGGAAAAGGGAAGGGTGACTTTGAAGGGCAAACCT<br>ATTCGGCTGACGGTTGACCTTAGCGCCGAGACACTCCAGGCACGCCGGGAATGGGGCCCCATCTTTA<br>ATATCCTGAAGGAGAAGAACTTCCAGCCACGAATCTCTTACCCTGCAAAGTTGAGTTTTATCTCCGA<br>GGGTGAGATTAAGTATTTCATCGATAAACAGATGCTGCGAGACTTCGTGACAACTCGCCCAGCTCTC<br>AAGGAACTGCTCAAAGAGGCTCTTAATATGGAGCGCAATAATAGATATCAACCCTTGCAGAACCACG<br>CAAAGATGTGAGACAGCCGTCAGACCATCAAGACTAGGAAGAAACTGCATCAACTAATGAGCAAAAT<br>CACCAGCTAACATCATAGTATACATGACCGGCTCTAACTCACATATCACCATCCTTACACTTAACAT<br>TAACGGCCTCAACTCAGCTATCAAGCGCCATCGGCTGGCCAGCTGGATCAAATCACAGGATCCAAGC<br>GTTTGTTGCATCCAAGAGACCCACCTGACCTGTAGAGATACTCACCGCCTCAAGATCAAGGGATGGC<br>GAAAGATTTATCAGGCGAACGGTAAGCAGAAGAAAGCCGGAGTCGCAATTCTGGTCTCAGACAAGAC<br>GGATTTCAAGCCCACCAAAATTAAGCGTGATAAGGAAGGTCACTATATTATGGTGAAAGGCAGCATA<br>CAGCAGGAAGAACTTACCATATTGAACATCTACGCGCCAAACACCGGCGCACCTCGCTTTATCAAAC<br>AGGTCCTGTCCGATCTGCAGCGAGATCTGGATTCTCATACGTTGATTATGGGTGATTTCAATACACC<br>ATTGAGCACCCTGGATCGCAGCACCAGGCAAAAGGTAAATAAAGACACGCAAGAGCTCAATAGCGCA<br>CTGCATCAGGCAGATCTCATTGATATTTATCGCACTCTTCATCCTAAGAGTACCGAGTACACATTCT<br>TCAGCGCCCCACATCATACATACTCAAAGATCGATCATATCGTCGGCTCAAAGGCTCTGCTGTCAAA<br>GTGCAAGCGCACAGAGATAATTACAAATTACCTGTCAGATCATAGCGCGATCAAGCTCGAGCTGAGA<br>ATCAAGAACCTGACCCAGAGCCGGAGTACCACTTGGAAGCTTAATAACCTGCTGCTCAACGATTATT |

TABLE 13-continued

Exemplary plasmid sequences

| Name | Sequence |
| --- | --- |
| | GGGTCCACAATGAGATGAAGGCAGAGATTAAAATGTTCTTCGAAACAAATGAGAATAAGGATACTAC<br>CTATCAAAACCTTTGGGATGCCTTTAAGGCCGTCTGCAGAGGCAAGTTCATCGCCCTCAACGCCTAT<br>AAAAGAAAACAAGAGAGATCTAAGATCGATACTCTCACCTCTCAGCTGAAGGAGTTGGAGAAACAGG<br>AACAGACCCACTCCAAGGCGTCAAGACGGCAGGAGATCACAAAGATTCGCGCCGAGTTGAAAGAGAT<br>CGAAACCCAAAAGACTCTTCAGAAAATTAACGAGTCTCGTAGTTGGTTCTTCGAGCGGATTAATAAG<br>ATAGACAGACCTCTGGCACGACTGATTAAGAAGAAGCGCGAAAAGAACCAGATTGATACCATCAAGA<br>ACGACAAGGGCGACATCACTACTGACCCGACCGAGATCCAGACCACTATTCGGGAGTATTATAAGCA<br>TTTGTATGCTAACAAGCTTGAGAACCTGGAAGAGATGGACACTTTTCTGGATACCTATACTCTGCCA<br>CGGCTTAATCAAGAGGAAGTCGAGTCCCTCAACCGCCCAATTACAGGAAGCGAGATTGTGGCCATAA<br>TTAACTCCCTGCCGACAAAGAAATCTCCTGGTCCGGACGGGTTTACAGCTGAGTTTTATCAACGGTA<br>TATGGAAGAGCTTGTACCGTTTCTGCTCAAGCTCTTTCAGTCTATAGAAAAGGAAGGCATCTTGCCC<br>AATTCCTTCTACGAAGCTTCTATAATACTTATTCCCAAACCAGGACGCGATACCACAAAGAAGGAAA<br>ACTTCCGGCCCATTAGTCTCATGAATATCGACGCTAAAATATTGAACAAGATTCTCGCCAACAGAAT<br>CCAACAACATATTAAGAAATTGATACATCACGACCAGGTGGGGTTTATACCTGGCATGCAGGGCTGG<br>TTTAACATCCGGAAGAGTATTAACGTCATTCAACACATTAATAGAGCTAAGGATAAGAATCATATGA<br>TCATCTCTATAGACGCGGAAAAGGCATTCGATAAGATTCAGCAGCCATTTATGCTCAAGACTCTGAA<br>CAAACTCGGCATCGACGGAACATATTTTAAGATTATTCGCGCAATTTACGATAAGCCGACTGCTAAC<br>ATTATCCTTAACGGCCAAAAGCTCGAGGCCTTTCCGCTCAAGACTGGAACCCGCCAAGGCTGTCCCC<br>TCTCCCCGCTTTTGTTTAATATTGTACTCGAGGTGCTGGCTAGGGCTATTCGTCAAGAGAAAGAGAT<br>TAAAGGGATACAGCTCGGGAAGGAAGAGGTCAAGCTTTCCTTGTTCGCCGATGATATGATTGTGTAC<br>CTGGAGAATCCTATTGTGTCTGCTCAGAACCTTCTTAAACTTATTTCTAACTTTAGCAAGGTCAGCG<br>GCTATAAGATTAACGTCCAGAAATCTCAGGCCTTTCTGTACACAAATAATCGACAGACCGAATCCCA<br>GATAATGGGTGAGCTTCCGTTTGTCATAGCCAGCAAAAGGATAAAGTATCTCGGAATCCAGCTGACA<br>CGAGACGTTAAAGATTTGTTTAAGGAAAATTACAAGCCTCTCCTGAAAGAGATTAAGGAAGATACTA<br>ATAAGTGGAAGAATATCCCCTGTTCATGGGTTGGCAGAATCAACATAGTGAAGATGGCAATACTTCC<br>TAAAGTGATATATCGCTTTAACGCCATCCCAATTAAACTGCCTATGACCTTCTTTACGGAGCTCGAG<br>AAAACAACCCTTAAATTTATATGGAATCAAAAGAGAGCAAGAATAGCGAAGTCCATCTTGAGCCAGA<br>AGAATAAGGCCGGTGGGATTACTTTGCCTGATTTTAAGTTGTATTATAAAGCCACAGTAACTAAGAC<br>AGCCTGGTATTGGTATCAGAATAGAGACATCGACCAGTGGAATCGGACCGAACCATCAGAGATAATG<br>CCCCACATCTATAATTACCTTATATTCGATAAGCCAGAAAAGAATAAACAGTGGGGCAAAGACAGCC<br>TCTTCAACAAGTGGTGTTGGGAGAATTGGCTGGCCATATGCCGGAAACTCAAGCTCGACCCCTTTCT<br>TACACCCTACACTAAAATCAACAGTAGGTGGATCAAGGACTTGAATGTCAAGCCAAAGACTATAAAG<br>ACACTGGAAGAGAATCTTGGGATCACAATACAAGATATAGGCGTCGGCAAAGATTTTATGTCAAAGA<br>CGCCCAAGGCCATGGCCACTAAGGATAAGATTGATAAGTGGGACCTTATTAAGCTCAAAAGCTTCTG<br>TACTGCCAAGGAGACCACGATCAGAGTTAATAGGCAGCCCACTACATGGAAAAGATTTTCGCCACT<br>TATTCATCAGATAAGGGGTTGATAAGCAGAATATATAACGAGCTGAAGCAGATCTACAAGAAGAAAA<br>CGAATAATCCCATCAAGAAGTGGGCAAAAGATATGAACAGGCATTTTAGCAAAGAGGATATCTACGC<br>CGCGAAGAAGCATATGAAGAAGTGTAGTTCAAGCTTGGCCATTCGTGAGATGCAGATTAAGACGACC<br>ATGCGATACCACCTTACCCCAGTGAGGATGGCAATTATCAAGAAATCTGGCAATAATAGATGTTGGC<br>GGGGCTGTGGCGAGATTGGCACCCTGCTCCATTGCTGGTGGGATTGCAAGCTGGTGCAGCCGCTTTG<br>GAAATCAGTCTGGCGCTTTCTGAGGGACCTCGAGCTTGAGATTCCCTTCGATCCCGCAATTCCCTTG<br>CTCGGAATCTATCCTAACGAATACAAGAGCTGTTGTTACAAGGATACGTGTACCCGGATGTTCATCG<br>CGGCCTTGTTTACGATAGCTAAGACGTGGAATCAGCCTAAGTGCCCCACAATGATCGATTGGATCAA<br>GAAAATGTGGCATATTTATACCATGGAGTATTACGCAGCAATTAAGAATGACGAATTTATTTCCTTC<br>GTTGGGACCTGGATGAAGCTGGAGACTATTATTCTGAGCAAGCTGTCTCAGGAGCAAAAGACAAAGC<br>ATAGAATCTTCTCTCTCATTGGTGGTAACGACTACAAAGACGATGACGACAAGaaaaggccggcggc<br>cacgaaaaaggccggccaggcaaaaaagaaaaagTAAAGCGCTTCTAGAAGTTGTCTCCTCCTGCAC<br>TGACTGACTGATACAATCGATTTCTGGATCCGCAGGCCTAATCAACCTCTGGATTACAAAATTTGTG<br>AAAGATTGACTGGTATTCTTAACTATGTTGCTCCTTTTACGCTATGTGGATACGCTGCTTTAATGCC<br>TTTGTATCATGCTATTGCTTCCCGTATGGCTTTCATTTTCTCCTCCTTGTATAAATCCTGGTTGCTG<br>TCTCTTTATGAGGAGTTGTGGCCCGTTGTCAGGCAACGTGGCGTGGTGTGCACTGTGTTTGCTGACG<br>CAACCCCCACTGGTTGGGGCATTGCCACCACCTGTCAGCTCCTTTCCGGGACTTTCGCTTTCCCCCT<br>CCCTATTGCCACGGCGGAACTCATCGCCGCCTGCCTTGCCCGCTGCTGGACAGGGGCTCGGCTGTTG<br>GGCACTGACAATTCCGTGGTGTTGTCGGGGAAGCTGACGTCCTTTCCATGGCTGCTCGCCTGTGTTG<br>CCACCTGGATTCTGCGCGGGACGTCCTTCTGCTACGTCCCTTCGGCCCTCAATCCAGCGGACCTTCC<br>TTCCCGCtgagagacacaaaaaattccaacacactattgcaatgaaaataaatttcctttattagcc<br>agaagtcagatgctcaaggggcttcatgatgtccccataatttttggcagagggaaaaagatctcag<br>tggtatttgtgagccagggcattggccttctgataggcagcctgcacctgaggagtgcggccgcttt<br>acttgtacagctcgtccatgccgagagtgatcccggcggcggtcacgaactccagcaggaccatgtg<br>atcgcgcttctcgttggggtctttgctcagggcggactgggtgctcaggtagtggttgtcgggcagc<br>agcacggggccgtcgccgatgggggtgttctgctggtagtggtcggcgagctgcacgctgccgtcct<br>cgatgttgtggcggatcttgaagttcaccttgatgccgttcttctgcttgtcggccatgatatagac<br>gttgtggctgttgtagttgtactccagcttgtgccccaggatgttgccgtcctccttgaagtcgatg<br>cccttcagctcgatgcggttcaccagggtgtcgccctcgaacttcacctcggcgcgggtcttgtagt<br>tgccgtcgtccttgaagaagatggtgcgctcctggacgtagccttcgggcatggcggacttgaagaa<br>gtcgtgctgcttcatgtggtcggggtagcggctgaagcactgcacgccgtaggtcagggtggtcacg<br>agggtgggccagggcacgggcagcttgccggtggtgcagatgaacttcagggtcagcttgccgtagg<br>tggcatcgccctcgccctcgccggacacgctgaacttgtggccgtttacgtcgccgtccagctcgac<br>caggatgggcaccaccccggtgaacagctcctcgcccttgctcaccatggtggcgggatctgacggt<br>tcactaaaccagctctgcttatatagacctcccaccgtacacgcctaccgcccatttgcgtcaatgg<br>ggcggagttgttacgacattttggaaagtcccgttgattttggtgccaaaacaaactcccattgacg<br>tcaatggggtggagacttggaaatccccgtgagtcaaaccgctatccacgcccattgatgtactgcc<br>aaaaccgcatcaccatggtaatagcgatgactaatacgtagatgtactgccaagtaggaaagtccca<br>taaggtcatgtactgggcataatgccaggcgggccatttaccgtcattgacgtcaatagggggcgta<br>cttggcatatgatacacttgatgtactgccaagtgggcagtttaccgtaaatactccacccattgac<br>gtcaatggaaagtccctattggcgttactatgggaacatacgtcattattgacgtcaatgggcgggg |

TABLE 13-continued

| Exemplary plasmid sequences | |
|---|---|
| Name | Sequence |
| | gtcgttgggcggtcagccaggcgggccatttaccgtaagttatgtaacgGGCCTGCTGCCGGCTCTG CGGCCTCTTCCGCGTCTTCGCCTTCGCCCTCAGACGAGTCGGATCTCCCTTTGGGCCGCCTCCCCGC CTGTCTAGCTTGACTGACTGAGATACAGCGTACCTTCAGCTCACAGACATGATAAGATACATTGATG AGTTTGGACAAACCACAACTAGAATGCAGTGAAAAAAATGCTTTATTTGTGAAATTTGTGATGCTAT TGCTTTATTTGTAACCATTATAAGCTGCAATAAACAAGTTAACAACAACAATTGCATTCATTTTATG TTTCAGGTTCAGGGGGAGGTGTGGGAGGTTTTTTAAAGCAAGTAAAACCTCTACAAATGTGGTATTG GCCCATCTCTATCGGTATCGTAGCATAACCCCTTGGGGCCTCTAAACGGGTCTTGAGGGGTTTTTTG TGCCCCTCGGGCCGGATTGCTATCTACCGGCATTGGCGCAGAAAAAAATGCCTGATGCGACGCTGCG CGTCTTATACTCCCACATATGCCAGATTCAGCAACGGATACGGCTTCCCCAACTTGCCCACTTCCAT ACGTGTCCTCCTTACCAGAAATTTATCCTTAAGGTCGTCAGCTATCCTGCAGGCGATCTCTCGATTT CGATCAAGACATTCCTTTAATGGTCTTTTCTGGACACCACTAGGGGTCAGAAGTAGTTCATCAAACT TTCTTCCCTCCCTAATCTCATTGGTTACCTTGGGCTATCGAAACTTAATTAAGCGATCTGCATCTCA ATTAGTCAGCAACCATAGTCCCGCCCCTAACTCCGCCCATCCCGCCCCTAACTCCGCCCAGTTCCGC CCATTCTCCGCCCCATCGCTGACTAATTTTTTTTATTTATGCAGAGGCCGAGGCCGCCTCGGCCTCT GAGCTATTCCAGAAGTAGTGAGGAGGCTTTTTTGGAGGCCTAGGCTTTTGCAAAGGAGGTAGCCAAC ATGATTGAACAAGATGGATTGCACGCAGGTTCTCCCGCCGCTTGGGTGGAGAGGCTATTCGGCTATG ACTGGGCACAACAGACAATCGGCTGCTCTGATGCCGCCGTGTTCCGGCTGTCAGCGCAGGGGCGCCC GGTTCTTTTTGTCAAGACCGACCTGTCCGGTGCCCTGAATGAACTCCAGGACGAGGCAGCGCGGCTA TCGTGGCTGGCCACGACGGGCGTTCCTTGCGCAGCTGTGCTCGACGTTGTCACTGAAGCGGGAAGGG ACTGGCTGCTATTGGGCGAAGTGCCGGGGCAGGATCTCCTGTCATCTCACCTTGCTCCTGCCGAGAA AGTATCCATCATGGCTGATGCAATGCGGCGGCTGCATACGCTTGATCCGGCTACCTGCCCATTCGAC CACCAAGCGAAACATCGCATCGAGCGAGCACGTACTCGGATGGAAGCCGGTCTTGTCGATCAGGATG ATCTGGACGAAGAGCATCAGGGGCTCGCGCCAGCCGAACTGTTCGCCAGGCTCAAGGCGCGGATGCC CGACGGCGAGGATCTCGTCGTGACCCACGGCGATGCCTGCTTGCCGAATATCATGGTGGAAAATGGC CGCTTTTCTGGATTCATCGACTGTGGCCGGCTGGGTGTGGCGGACCGCTATCAGGACATAGCGTTGG CTACCCGTGATATTGCTGAAGAGCTTGGCGGCGAATGGGCTGACCGCTTCCTCGTGCTTTACGGTAT CGCCGCTCCCGATTCGCAGCGCATCGCCTTCTATCGCCTTCTTGACGAGTTCTTCTAGTATGTAAGC CCTGTGCCTTCTAGTTGCCAGCCATCTGTTGTTTGCCCCTCCCCCGTGCCTTCCTTGACCCTGGAAG GTGCCACTCCCACTGTCCTTTCCTAATAAAATGAGGAAATTGCATCGCATTGTCTGAGTAGGTGTCA TTCTATTCTGGGGGGTGGGGTGGGGCAGGACAGCAAGGGGGAGGATTGGGAAGACAATAGCAGGCAT GCTGGGGATGCGGTGGGCTCTATGGTTAATTAACCAGTCAAGTCAGCTACTTGGCGAGATCGACTTG TCTGGGTTTCGACTACGCTCAGAATTGCGTCAGTCAAGTTCGATCTGGTCCTTGCTATTGCACCCGT TCTCCGATTACGAGTTTCATTTAAATCATGTGAGCAAAAGGCCAGCAAAAGGCCAGGAACCGTAAAA AGGCCGCGTTGCTGGCGTTTTTCCATAGGCTCCGCCCCCCTGACGAGCATCACAAAAATCGACGCTC AAGTCAGAGGTGGCGAAACCCGACAGGACTATAAAGATACCAGGCGTTTCCCCCTGGAAGCTCCCTC GTGCGCTCTCCTGTTCCGACCCTGCCGCTTACCGGATACCTGTCCGCCTTTCTCCCTTCGGGAAGCG TGGCGCTTTCTCATAGCTCACGCTGTAGGTATCTCAGTTCGGTGTAGGTCGTTCGCTCCAAGCTGGG CTGTGTGCACGAACCCCCCGTTCAGCCCGACCGCTGCGCCTTATCCGGTAACTATCGTCTTGAGTCC AACCCGGTAAGACACGACTTATCGCCACTGGCAGCAGCCACTGGTAACAGGATTAGCAGAGCGAGGT ATGTAGGCGGTGCTACAGAGTTCTTGAAGTGGTGGCCTAACTACGGCTACACTAGAAGAACAGTATT TGGTATCTGCGCTCTGCTGAAGCCAGTTACCTTCGGAAAAAGAGTTGGTAGCTCTTGATCCGGCAAA CAAACCACCGCTGGTAGCGGTGGTTTTTTTGTTTGCAAGCAGCAGATTACGCGCAGAAAAAAAGGAT CTCAAGAAGATCCTTTGATCTTTTCTACGGGGTCTGACGCTCAGTGGAACGAAAACTCACGTTAAGG GATTTTGGTCATGAGATTATCAAAAAGGATCTTCACCTAGATCCTTTTAAATTAAAAATGAAGTTTT AAATCAATCTAAAGTATATATGAGTAAACTTGGTCTGACAGTTACCAATGCTTAATCAGTGAGGCAC CTATCTCAGCGATCTGTCTATTTCGTTCATCCATAGTTGCATTTAAATTTCCGAACTCTCCAAGGCC CTCGTCGGAAAATCTTCAAACCTTTCGTCCGATCCATCTTGCAGGCTACCTCTCGAACGAACTATCG CAAGTCTCTTGGCCGGCCTTGCGCCTTGGCTATTGCTTGGCAGCGCCTATCGCCAGGTATTACTCCA ATCCCGAATATCCGAGATCGGGATCACCCGAGAGAAGTTCAACCTACATCCTCAATCCCGATCTATC CGAGATCCGAGGAATATCGAAATCGGGGCGCGCCTGGTGT (SEQ ID NO: 106) |
| RET-017 LINE1-GFP ORF2-C_Linker_Nucleo-plasmin-NLS | CCGAGAACGATCCTCTCAGTGCGAGTCTCGACGATCCATATCGTTGCTTGGCAGTCAGCCAGTCGGA ATCCAGCTTGGGACCCAGGAAGTCCAATCGTCAGATATTGTACTCAAGCCTGGTCACGGCAGCGTAC CGATCTGTTTAAACCTAGATATTGATAGTCTGATCGGTCAACGTATAATCGAGTCCTAGCTTTTGCA AACATCTATCAAGAGACAGGATCAGCAGGAGGCTTTCGCATGAGTATTCAACATTTCCGTGTCGCCC TTATTCCCTTTTTTGCGGCATTTTGCCTTCCTGTTTTTGCTCACCCAGAAACGCTGGTGAAAGTAAA AGATGCTGAAGATCAGTTGGGTGCGCGAGTGGGTTACATCGAACTGGATCTCAACAGCGGTAAGATC CTTGAGAGTTTTCGCCCCGAAGAACGCTTTCCAATGATGAGCACTTTTAAAGTTCTGCTATGTGGCG CGGTATTATCCCGTATTGACGCCGGGCAAGAGCAACTCGGTCGCCGCATACACTATTCTCAGAATGA CTTGGTTGAGTATTCACCAGTCACAGAAAAGCATCTTACGGATGGCATGACAGTAAGAGAATTATGC AGTGCTGCCATAACCATGAGTGATAACACTGCGGCCAACTTACTTCTGACAACGATTGGAGGACCGA AGGAGCTAACCGCTTTTTTGCACAACATGGGGGATCATGTAACTCGCCTTGATCGTTGGGAACCGGA GCTGAATGAAGCCATACCAAACGACGAGCGTGACACCACGATGCCTGTAGCAATGGCAACAACCTTG CGTAAACTATTAACTGGCGAACTACTTACTCTAGCTTCCCGGCAACAGTTGATAGACTGGATGGAGG CGGATAAAGTTGCAGGACCACTTCTGCGCTCGGCCCTTCCGGCTGGCTGGTTTATTGCTGATAAATC TGGAGCCGGTGAGCGTGGGTCTCGCGGTATCATTGCAGCACTGGGGCCAGATGGTAAGCCCTCCCGT ATCGTAGTTATCTACACGACGGGGAGTCAGGCAACTATGGATGAACGAAATAGACAGATCGCTGAGA TAGGTGCCTCACTGATTAAGCATTGGTAACCGATTCTAGGTGCATTGGCGCAGAAAAAAATGCCTGA TGCGACGCTGCGCGTCTTATACTCCCACATATGCCAGATTCAGCAACGGATACGGCTTCCCCAACTT GCCCACTTCCATACGTGTCCTCCTTACCAGAAATTTATCCTTAAGATCGTTTAAACTCGACTCTGGC TCTATCGAATCTCCGTCGTTTCGAGCTTACGCGAACAGCCGTGGCGCTCATTTGCTCGTCGGGCATC GAATCTCGTCAGCTATCGTCAGCTTACCTTTTTGGCAGCGATCGCGGCTCCCGACATCTTGGACCAT TAGCTCCACAGGTATCTTCTTCCCTCTAGTGGTCATAACAGCAGCTTCAGCTACCTCTCAATTCAAA AAACCCCTCAAGACCCGTTTAGAGGCCCCAAGGGGTTATGCTATCAATCGTTGCGTTACACACACAA AAAACCAACACACATCCATCTTCGATGGATAGCGATTTTATTATCTAACTGCTGATCGAGTGTAGCC AGATCTAGTAATCAATTACGGGGTCATTAGTTCATAGCCCATATATGGAGTTCCGCGTTACATAACT |

TABLE 13-continued

Exemplary plasmid sequences

| Name | Sequence |
|---|---|
| | TACGGTAAATGGCCCGCCTGGCTGACCGCCCAACGACCCCCGCCCATTGACGTCAATAATGACGTAT |
| | GTTCCCATAGTAACGCCAATAGGGACTTTCCATTGACGTCAATGGGTGGAGTATTTACGGTAAACTG |
| | CCCACTTGGCAGTACATCAAGTGTATCATATGCCAAGTACGCCCCCTATTGACGTCAATGACGGTAA |
| | ATGGCCCGCCTGGCATTATGCCCAGTACATGACCTTATGGGACTTTCCTACTTGGCAGTACATCTAC |
| | GTATTAGTCATCGCTATTACCATGCTGATGCGGTTTTGGCAGTACATCAATGGGCGTGGATAGCGGT |
| | TTGACTCACGGGGATTTCCAAGTCTCCACCCCATTGACGTCAATGGGAGTTTGTTTTGGCACCAAAA |
| | TCAACGGGACTTTCCAAAATGTCGTAACAACTCCGCCCCATTGACGCAAATGGGCGGTAGGCGTGTA |
| | CGGTGGGAGGTCTATATAAGCAGAGCTGGTTTAGTGAACCGTCAGATCAGATCTTTGTCGATCCTAC |
| | CATCCACTCGACACACCCGCCAGCGGCCGCTAATACGACTCACTATAGGGAGAAGTACTGCCACCAT |
| | GGGCAAGAAGCAAAATCGCAAGACGGGGAATTCCAAGACACAATCCGCTAGCCCACCACCTAAAGAG |
| | CGTTCTAGCTCCCCTGCTACTGAGCAGTCCTGGATGGAAAACGACTTCGATGAACTCCGGGAAGAGG |
| | GATTTAGGCGATCCAACTATTCAGAACTCCGCGAAGATATCCAGACAAAGGGGAAGGAAGTCGAGAA |
| | TTTCGAGAAGAACCTCGAGGAGTGCATCACCCGTATCACAAACACTGAGAAATGTCTCAAAGAACTC |
| | ATGGAACTTAAGACAAAAGCCAGGGAGCTTCGAGAGGAGTGTCGGAGTCTGAGATCCAGGTGTGACC |
| | AGCTCGAGGAGCGCGTGAGCGCGATGGAAGACGAGATGAACGAGATGAAAAGAGAGGGCAAATTCAG |
| | GGAGAAGCGCATTAAGAGGAACGAACAGAGTCTGCAGGAGATTTGGGATTACGTCAAGAGGCCTAAC |
| | CTGCGGTTGATCGGCGTCCCCGAGAGCGACGTAGAAAACGGGACTAAACTGGAGAATACACTTCAAG |
| | ACATCATTCAAGAAAATTTTCCAAACCTGGCTCGGCAAGCTAATGTGCAAATCCAAGAGATCCAACG |
| | CACACCCCAGCGGTATAGCTCTCGGCGTGCCACCCCTAGGCATATTATCGTGCGCTTTACTAAGGTG |
| | GAGATGAAAGAGAAGATGCTGCGAGCCGCTCGGGAAAAGGGAAGGGTGACTTTGAAGGGCAAACCTA |
| | TTCGGCTGACGGTTGACCTTAGCGCCGAGACACTCCAGGCACGCCGGGAATGGGGCCCCATCTTTAA |
| | TATCCTGAAGGAGAAGAACTTCCAGCCACGAATCTCTTACCCTGCAAAGTTGAGTTTTATCTCCGAG |
| | GGTGAGATTAAGTATTTCATCGATAAACAGATGCTGCGAGACTTCGTGACAACTCGCCCAGCTCTCA |
| | AGGAACTGCTCAAAGAGGCTCTTAATATGGAGCGCAATAATAGATATCAACCCTTGCAGAACCACGC |
| | AAAGATGTGAGACAGCCGTCAGACCATCAAGACTAGGAAGAAACTGCATCAACTAATGAGCAAAATC |
| | ACCAGCTAACATCATAGTATACATGACCGGCTCTAACTCACATATCACCATCCTTACACTTAACATT |
| | AACGGCCTCAACTCAGCTATCAAGCGCCATCGGCTGGCCAGCTGGATCAAATCACAGGATCCAAGCG |
| | TTTGTTGCATCCAAGAGACCCACCTGACCTGTAGAGATACTCACCGCCTCAAGATCAAGGGATGGCG |
| | AAAGATTTATCAGGCGAACGGTAAGCAGAAGAAAGCCGGAGTCGCAATTCTGGTCTCAGACAAGACG |
| | GATTTCAAGCCCACCAAAATTAAGCGTGATAAGGAAGGTCACTATATTATGGTGAAAGGCAGCATAC |
| | AGCAGGAAGAACTTACCATATTGAACATCTACGCGCCAAACACCGGCGCACCTCGCTTTATCAAACA |
| | GGTCCTGTCCGATCTGCAGCGAGATCTGGATTCTCATACGTTGATTATGGGTGATTTCAATACACCA |
| | TTGAGCACCCTGGATCGCAGCACCAGGCAAAAGGTAAATAAAGACACGCAAGAGCTCAATAGCGCAC |
| | TGCATCAGGCAGATCTCATTGATATTTATCGCACTCTTCATCCTAAGAGTACCGAGTACACATTCTT |
| | CAGCGCCCCACATCATACATACTCAAAGATCGATCATATCGTCGGCTCAAAGGCTCTGCTGTCAAAG |
| | TGCAAGCGCACAGAGATAATTACAAATTACCTGTCAGATCATAGCGCGATCAAGCTCGAGCTGAGAA |
| | TCAAGAACCTGACCCAGAGCCGGAGTACCACTTGGAAGCTTAATAACCTGCTGCTCAACGATTATTG |
| | GGTCCACAATGAGATGAAGGCAGAGATTAAAATGTTCTTCGAAACAAATGAGAATAAGGATACTACC |
| | TATCAAAACCTTTGGGATGCCTTTAAGGCCGTCTGCAGAGGCAAGTTCATCGCCCTCAACGCCTATA |
| | AAAGAAAACAAGAGAGATCTAAGATCGATACTCTCACCTCTCAGCTGAAGGAGTTGGAGAAACAGGA |
| | ACAGACCCACTCCAAGGCGTCAAGACGGCAGGAGATCACAAAGATTCGCGCCGAGTTGAAAGAGATC |
| | GAAACCCAAAAGACTCTTCAGAAAATTAACGAGTCTCGTAGTTGGTTCTTCGAGCGGATTAATAAGA |
| | TAGACAGACCTCTGGCACGACTGATTAAGAAGAAGCGCGAAAAGAACCAGATTGATACCATCAAGAA |
| | CGACAAGGGCGACATCACTACTGACCCGACCGAGATCCAGACCACTATTCGGGAGTATTATAAGCAT |
| | TTGTATGCTAACAAGCTTGAGAACCTGGAAGAGATGGACACTTTTCTGGATACCTATACTCTGCCAC |
| | GGCTTAATCAAGAGGAAGTCGAGTCCCTCAACCGCCCAATTACAGGAAGCGAGATTGTGGCCATAAT |
| | TAACTCCCTGCCGACAAAGAAATCTCCTGGTCCGGACGGGTTTACAGCTGAGTTTTATCAACGGTAT |
| | ATGGAAGAGCTTGTACCGTTTCTGCTCAAGCTCTTTCAGTCTATAGAAAAGGAAGGCATCTTGCCCA |
| | ATTCCTTCTACGAAGCTTCTATAATACTTATTCCCAAACCAGGACGCGATACCACAAAGAAGGAAAA |
| | CTTCCGGCCCATTAGTCTCATGAATATCGACGCTAAAATATTGAACAAGATTCTCGCCAACAGAATC |
| | CAACAACATATTAAGAAATTGATACATCACGACCAGGTGGGGTTTATACCTGGCATGCAGGGCTGGT |
| | TTAACATCCGGAAGAGTATTAACGTCATTCAACACATTAATAGAGCTAAGGATAAGAATCATATGAT |
| | CATCTCTATAGACGCGGAAAAGGCATTCGATAAGATTCAGCAGCCATTTATGCTCAAGACTCTGAAC |
| | AAACTCGGCATCGACGGAACATATTTAAGATTATTCGCGCAATTTACGATAAGCCGACTGCTAACA |
| | TTATCCTTAACGGCCAAAAGCTCGAGGCCTTTCCGCTCAAGACTGGAACCCGCCAAGGCTGTCCCCT |
| | CTCCCCGCTTTTGTTTAATATTGTACTCGAGGTGCTGGCTAGGGCTATTCGTCAAGAGAAAGAGATT |
| | AAAGGGATACAGCTCGGGAAGGAAGAGGTCAAGCTTTCCTTGTTCGCCGATGATATGATTGTGTACC |
| | TGGAGAATCCTATTGTGTCTGCTCAGAACCTTCTTAAACTTATTTCTAACTTTAGCAAGGTCAGCGG |
| | CTATAAGATTAACGTCCAGAAATCTCAGGCCTTTCTGTACACAAATAATCGACAGACCGAATCCCAG |
| | ATAATGGGTGAGCTTCCGTTTGTCATAGCCAGCAAAAGGATAAAGTATCTCGGAATCCAGCTGACAC |
| | GAGACGTTAAAGATTTGTTTAAGGAAAATTACAAGCCTCTCCTGAAAGAGATTAAGGAAGATACTAA |
| | TAAGTGGAAGAATATCCCCTGTTCATGGGTTGGCAGAATCAACATAGTGAAGATGGCAATACTTCCT |
| | AAAGTGATATATCGCTTTAACGCCATCCCAATTAAACTGCCTATGACCTTCTTTACGGAGCTCGAGA |
| | AAACAACCCTTAAATTTATATGGAATCAAAAGAGAGCAAGAATAGCGAAGTCCATCTTGAGCCAGAA |
| | GAATAAGGCCGGTGGGATTACTTTGCCTGATTTTAAGTTGTATTATAAAGCCACAGTAACTAAGACA |
| | GCCTGGTATTGGTATCAGAATAGAGACATCGACCAGTGGAATCGGACCGAACCATCAGAGATAATGC |
| | CCCACATCTATAATTACCTTATATTCGATAAGCCAGAAAAGAATAAACAGTGGGGCAAAGACAGCCT |
| | CTTCAACAAGTGGTGTTGGGAGAATTGGCTGGCCATATGCCGGAAACTCAAGCTCGACCCCTTTCTT |
| | ACACCCTACACTAAAATCAACAGTAGGTGGATCAAGGACTTGAATGTCAAGCCAAAGACTATAAAGA |
| | CACTGGAAGAGAATCTTGGGATCACAATACAAGATATAGGCGTCGGCAAAGATTTTATGTCAAAGAC |
| | GCCCAAGGCCATGGCCACTAAGGATAAGATTGATAAGTGGGACCTTATTAAGCTCAAAAGCTTCTGT |
| | ACTGCCAAGGAGACCACGATCAGAGTTAATAGGCAGCCCACTACATGGGAAAAGATTTTCGCCACTT |
| | ATTCATCAGATAAGGGGTTGATAAGCAGAATATATAACGAGCTGAAGCAGATCTACAAGAAGAAAAC |
| | GAATAATCCCATCAAGAAGTGGGCAAAAGATATGAACAGGCATTTTAGCAAAGAGGATATCTACGCC |
| | GCGAAGAAGCATATGAAGAAGTGTAGTTCAAGCTTGGCCATTCGTGAGATGCAGATTAAGACGACCA |
| | TGCGATACCACCTTACCCCAGTGAGGATGGCAATTATCAAGAAATCTGGCAATAATAGATGTTGGCG |

TABLE 13-continued

Exemplary plasmid sequences

| Name | Sequence |
|---|---|
| | GGGCTGTGGCGAGATTGGCACCCTGCTCCATTGCTGGTGGGATTGCAAGCTGGTGCAGCCGCTTTGG<br>AAATCAGTCTGGCGCTTTCTGAGGGACCTCGAGCTTGAGATTCCCTTCGATCCCGCAATTCCCTTGC<br>TCGGAATCTATCCTAACGAATACAAGAGCTGTTGTTACAAGGATACGTGTACCCGGATGTTCATCGC<br>GGCCTTGTTTACGATAGCTAAGACGTGGAATCAGCCTAAGTGCCCCACAATGATCGATTGGATCAAG<br>AAAATGTGGCATATTTATACCATGGAGTATTACGCAGCAATTAAGAATGACGAATTTATTTCCTTCG<br>TTGGGACCTGGATGAAGCTGGAGACTATTATTCTGAGCAAGCTGTCTCAGGAGCAAAAGACAAAGCA<br>TAGAATCTTCTCTCTCATTGGTGGTAACGACTACAAAGACGATGACGACAAGggcggcggcagcaaa<br>aggccggcggccacgaaaaaggccggccaggcaaaaaagaaaaagTAAAGCGCTTCTAGAAGTTGTC<br>TCCTCCTGCACTGACTGACTGATACAATCGATTTCTGGATCCGCAGGCCTAATCAACCTCTGGATTA<br>CAAAATTTGTGAAAGATTGACTGGTATTCTTAACTATGTTGCTCCTTTTACGCTATGTGGATACGCT<br>GCTTTAATGCCTTTGTATCATGCTATTGCTTCCCGTATGGCTTTCATTTTCTCCTCCTTGTATAAAT<br>CCTGGTTGCTGTCTCTTTATGAGGAGTTGTGGCCCGTTGTCAGGCAACGTGGCGTGGTGTGCACTGT<br>GTTTGCTGACGCAACCCCCACTGGTTGGGGCATTGCCACCACCTGTCAGCTCCTTTCCGGGACTTTC<br>GCTTTCCCCCTCCCTATTGCCACGGCGGAACTCATCGCCGCCTGCCTTGCCCGCTGCTGGACAGGGG<br>CTCGGCTGTTGGGCACTGACAATTCCGTGGTGTTGTCGGGGAAGCTGACGTCCTTTCCATGGCTGCT<br>CGCCTGTGTTGCCACCTGGATTCTGCGCGGGACGTCCTTCTGCTACGTCCCTTCGGCCCTCAATCCA<br>GCGGACCTTCCTTCCCGCtgagagacacaaaaaattccaacacactattgcaatgaaaataaatttc<br>ctttattagccagaagtcagatgctcaaggggcttcatgatgtccccataatttttggcagagggaa<br>aaagatctcagtggtatttgtgagccagggcattggccttctgataggcagcctgcacctgaggagt<br>gcggccgctttacttgtacagctcgtccatgccgagagtgatcccggcggcggtcacgaactccagc<br>aggaccatgtgatcgcgcttctcgttggggtctttgctcagggcggactgggtgctcaggtagtggt<br>tgtcgggcagcagcacggggccgtcgccgatgggggtgttctgctggtagtggtcggcgagctgcac<br>gctgccgtcctcgatgttgtggcggatcttgaagttcaccttgatgccgttcttctgcttgtcggcc<br>atgatatagacgttgtggctgttgtagttgtactccagcttgtgccccaggatgttgccgtcctcct<br>tgaagtcgatgcccttcagctcgatgcggttcaccagggtgtcgccctcgaacttcacctcggcgcg<br>ggtcttgtagttgccgtcgtccttgaagaagatggtgcgctcctggacgtagccttcgggcatggcg<br>gacttgaagaagtcgtgctgcttcatgtggtcggggtagcggctgaagcactgcacgccgtaggtca<br>gggtggtcacgagggtgggccagggcacgggcagcttgccggtggtgcagatgaacttcagggtcag<br>cttgccgtaggtggcatcgccctcgccctcgccggacacgctgaacttgtggccgtttacgtcgccg<br>tccagctcgaccaggatgggcaccaccccggtgaacagctcctcgcccttgctcaccatggtggcgg<br>gatctgacggttcactaaaccagctctgcttatatagacctcccaccgtacacgcctaccgcccatt<br>tgcgtcaatggggcggagttgttacgacattttggaaagtcccgttgattttggtgccaaaacaaac<br>tcccattgacgtcaatggggtggagacttggaaatccccgtgagtcaaaccgctatccacgcccatt<br>gatgtactgccaaaaccgcatcaccatggtaatagcgatgactaatacgtagatgtactgccaagta<br>ggaaagtcccataaggtcatgtactgggcataatgccaggcgggccatttaccgtcattgacgtcaa<br>taggggggcgtacttggcatatgatacacttgatgtactgccaagtgggcagtttaccgtaaatactc<br>cacccattgacgtcaatggaaagtccctattggcgttactatgggaacatacgtcattattgacgtc<br>aatgggcgggggtcgttgggcggtcagccaggcgggccatttaccgtaagttatgtaacgGGCCTGC<br>TGCCGGCTCTGCGGCCTCTTCCGCGTCTTCGCCTTCGCCCTCAGACGAGTCGGATCTCCCTTTGGGC<br>CGCCTCCCCGCCTGTCTAGCTTGACTGACTGAGATACAGCGTACCTTCAGCTCACAGACATGATAAG<br>ATACATTGATGAGTTTGGACAAACCACAACTAGAATGCAGTGAAAAAAATGCTTTATTTGTGAAATT<br>TGTGATGCTATTGCTTTATTTGTAACCATTATAAGCTGCAATAAACAAGTTAACAACAACAATTGCA<br>TTCATTTTATGTTTCAGGTTCAGGGGGAGGTGTGGGAGGTTTTTTAAAGCAAGTAAAACCTCTACAA<br>ATGTGGTATTGGCCCATCTCTATCGGTATCGTAGCATAACCCCTTGGGGCCTCTAAACGGGTCTTGA<br>GGGGTTTTTTGTGCCCCTCGGGCCGGATTGCTATCTACCGGCATTGGCGCAGAAAAAAATGCCTGAT<br>GCGACGCTGCGCGTCTTATACTCCCACATATGCCAGATTCAGCAACGGATACGGCTTCCCCAACTTG<br>CCCACTTCCATACGTGTCCTCCTTACCAGAAATTTATCCTTAAGGTCGTCAGCTATCCTGCAGGCGA<br>TCTCTCGATTTCGATCAAGACATTCCTTTAATGGTCTTTTCTGGACACCACTAGGGGTCAGAAGTAG<br>TTCATCAAACTTTCTTCCCTCCCTAATCTCATTGGTTACCTTGGGCTATCGAAACTTAATTAAGCGA<br>TCTGCATCTCAATTAGTCAGCAACCATAGTCCCGCCCCTAACTCCGCCCATCCCGCCCCTAACTCCG<br>CCCAGTTCCGCCCATTCTCCGCCCCATCGCTGACTAATTTTTTTTATTTATGCAGAGGCCGAGGCCG<br>CCTCGGCCTCTGAGCTATTCCAGAAGTAGTGAGGAGGCTTTTTTGGAGGCCTAGGCTTTTGCAAAGG<br>AGGTAGCCAACATGATTGAACAAGATGGATTGCACGCAGGTTCTCCCGCCGCTTGGGTGGAGAGGCT<br>ATTCGGCTATGACTGGGCACAACAGACAATCGGCTGCTCTGATGCCGCCGTGTTCCGGCTGTCAGCG<br>CAGGGGCGCCCGGTTCTTTTTGTCAAGACCGACCTGTCCGGTGCCCTGAATGAACTCCAGGACGAGG<br>CAGCGCGGCTATCGTGGCTGGCCACGACGGGCGTTCCTTGCGCAGCTGTGCTCGACGTTGTCACTGA<br>AGCGGGAAGGGACTGGCTGCTATTGGGCGAAGTGCCGGGGCAGGATCTCCTGTCATCTCACCTTGCT<br>CCTGCCGAGAAAGTATCCATCATGGCTGATGCAATGCGGCGGCTGCATACGCTTGATCCGGCTACCT<br>GCCCATTCGACCACCAAGCGAAACATCGCATCGAGCGAGCACGTACTCGGATGGAAGCCGGTCTTGT<br>CGATCAGGATGATCTGGACGAAGAGCATCAGGGGCTCGCGCCAGCCGAACTGTTCGCCAGGCTCAAG<br>GCGCGGATGCCCGACGGCGAGGATCTCGTCGTGACCCACGGCGATGCCTGCTTGCCGAATATCATGG<br>TGGAAAATGGCCGCTTTTCTGGATTCATCGACTGTGGCCGGCTGGGTGTGGCGGACCGCTATCAGGA<br>CATAGCGTTGGCTACCCGTGATATTGCTGAAGAGCTTGGCGGCGAATGGGCTGACCGCTTCCTCGTG<br>CTTTACGGTATCGCCGCTCCCGATTCGCAGCGCATCGCCTTCTATCGCCTTCTTGACGAGTTCTTCT<br>AGTATGTAAGCCCTGTGCCTTCTAGTTGCCAGCCATCTGTTGTTTGCCCCTCCCCCGTGCCTTCCTT<br>GACCCTGGAAGGTGCCACTCCCACTGTCCTTTCCTAATAAAATGAGGAAATTGCATCGCATTGTCTG<br>AGTAGGTGTCATTCTATTCTGGGGGGTGGGGTGGGGCAGGACAGCAAGGGGGAGGATTGGGAAGACA<br>ATAGCAGGCATGCTGGGGATGCGGTGGGCTCTATGGTTAATTAACCAGTCAAGTCAGCTACTTGGCG<br>AGATCGACTTGTCTGGGTTTCGACTACGCTCAGAATTGCGTCAGTCAAGTTCGATCTGGTCCTTGCT<br>ATTGCACCCGTTCTCCGATTACGAGTTTCATTTAAATCATGTGAGCAAAAGGCCAGCAAAAGGCCAG<br>GAACCGTAAAAAGGCCGCGTTGCTGGCGTTTTTCCATAGGCTCCGCCCCCCTGACGAGCATCACAAA<br>AATCGACGCTCAAGTCAGAGGTGGCGAAACCCGACAGGACTATAAAGATACCAGGCGTTTCCCCCTG<br>GAAGCTCCCTCGTGCGCTCTCCTGTTCCGACCCTGCCGCTTACCGGATACCTGTCCGCCTTTCTCCC<br>TTCGGGAAGCGTGGCGCTTTCTCATAGCTCACGCTGTAGGTATCTCAGTTCGGTGTAGGTCGTTCGC<br>TCCAAGCTGGGCTGTGTGCACGAACCCCCCGTTCAGCCCGACCGCTGCGCCTTATCCGGTAACTATC<br>GTCTTGAGTCCAACCCGGTAAGACACGACTTATCGCCACTGGCAGCAGCCACTGGTAACAGGATTAG |

TABLE 13-continued

Exemplary plasmid sequences

| Name | Sequence |
|---|---|
| | CAGAGCGAGGTATGTAGGCGGTGCTACAGAGTTCTTGAAGTGGTGGCCTAACTACGGCTACACTAGA<br>AGAACAGTATTTGGTATCTGCGCTCTGCTGAAGCCAGTTACCTTCGGAAAAAGAGTTGGTAGCTCTT<br>GATCCGGCAAACAAACCACCGCTGGTAGCGGTGGTTTTTTTGTTTGCAAGCAGCAGATTACGCGCAG<br>AAAAAAAGGATCTCAAGAAGATCCTTTGATCTTTTCTACGGGGTCTGACGCTCAGTGGAACGAAAAC<br>TCACGTTAAGGGATTTTGGTCATGAGATTATCAAAAAGGATCTTCACCTAGATCCTTTTAAATTAAA<br>AATGAAGTTTTAAATCAATCTAAAGTATATATGAGTAAACTTGGTCTGACAGTTACCAATGCTTAAT<br>CAGTGAGGCACCTATCTCAGCGATCTGTCTATTTCGTTCATCCATAGTTGCATTTAAATTTCCGAAC<br>TCTCCAAGGCCCTCGTCGGAAAATCTTCAAACCTTTCGTCCGATCCATCTTGCAGGCTACCTCTCGA<br>ACGAACTATCGCAAGTCTCTTGGCCGGCCTTGCGCCTTGGCTATTGCTTGGCAGCGCCTATCGCCAG<br>GTATTACTCCAATCCCGAATATCCGAGATCGGGATCACCCGAGAGAAGTTCAACCTACATCCTCAAT<br>CCCGATCTATCCGAGATCCGAGGAATATCGAAATCGGGGCGCGCCTGGTGTA (SEQ ID NO:<br>107) |
| RET-<br>018<br>LINE1-<br>GFP<br>ORF2-<br>NSV40<br>_NLS_<br>Linker<br>ORF2-<br>C_Nucleo-<br>plasmin_<br>NLS | TGGCCGGCCTTGCGCCTTGGCTATTGCTTGGCAGCGCCTATCGCCAGGTATTACTCCAATCCCGAAT<br>ATCCGAGATCGGGATCACCCGAGAGAAGTTCAACCTACATCCTCAATCCCGATCTATCCGAGATCCG<br>AGGAATATCGAAATCGGGGCGCGCCTGGTGTACCGAGAACGATCCTCTCAGTGCGAGTCTCGACGAT<br>CCATATCGTTGCTTGGCAGTCAGCCAGTCGGAATCCAGCTTGGGACCCAGGAAGTCCAATCGTCAGA<br>TATTGTACTCAAGCCTGGTCACGGCAGCGTACCGATCTGTTTAAACCTAGATATTGATAGTCTGATC<br>GGTCAACGTATAATCGAGTCCTAGCTTTTGCAAACATCTATCAAGAGACAGGATCAGCAGGAGGCTT<br>TCGCATGAGTATTCAACATTTCCGTGTCGCCCTTATTCCCTTTTTTGCGGCATTTTGCCTTCCTGTT<br>TTTGCTCACCCAGAAACGCTGGTGAAAGTAAAAGATGCTGAAGATCAGTTGGGTGCGCGAGTGGGTT<br>ACATCGAACTGGATCTCAACAGCGGTAAGATCCTTGAGAGTTTTCGCCCCGAAGAACGCTTTCCAAT<br>GATGAGCACTTTTAAAGTTCTGCTATGTGGCGCGGTATTATCCCGTATTGACGCCGGGCAAGAGCAA<br>CTCGGTCGCCGCATACACTATTCTCAGAATGACTTGGTTGAGTATTCACCAGTCACAGAAAAGCATC<br>TTACGGATGGCATGACAGTAAGAGAATTATGCAGTGCTGCCATAACCATGAGTGATAACACTGCGGC<br>CAACTTACTTCTGACAACGATTGGAGGACCGAAGGAGCTAACCGCTTTTTTGCACAACATGGGGGAT<br>CATGTAACTCGCCTTGATCGTTGGGAACCGGAGCTGAATGAAGCCATACCAAACGACGAGCGTGACA<br>CCACGATGCCTGTAGCAATGGCAACAACCTTGCGTAAACTATTAACTGGCGAACTACTTACTCTAGC<br>TTCCCGGCAACAGTTGATAGACTGGATGGAGGCGGATAAAGTTGCAGGACCACTTCTGCGCTCGGCC<br>CTTCCGGCTGGCTGGTTTATTGCTGATAAATCTGGAGCCGGTGAGCGTGGGTCTCGCGGTATCATTG<br>CAGCACTGGGGCCAGATGGTAAGCCCTCCCGTATCGTAGTTATCTACACGACGGGGAGTCAGGCAAC<br>TATGGATGAACGAAATAGACAGATCGCTGAGATAGGTGCCTCACTGATTAAGCATTGGTAACCGATT<br>CTAGGTGCATTGGCGCAGAAAAAAATGCCTGATGCGACGCTGCGCGTCTTATACTCCCACATATGCC<br>AGATTCAGCAACGGATACGGCTTCCCCAACTTGCCCACTTCCATACGTGTCCTCCTTACCAGAAATT<br>TATCCTTAAGATCGTTTAAACTCGACTCTGGCTCTATCGAATCTCCGTCGTTTCGAGCTTACGCGAA<br>CAGCCGTGGCGCTCATTTGCTCGTCGGGCATCGAATCTCGTCAGCTATCGTCAGCTTACCTTTTTGG<br>CAGCGATCGCGGCTCCCGACATCTTGGACCATTAGCTCCACAGGTATCTTCTTCCCTCTAGTGGTCA<br>TAACAGCAGCTTCAGCTACCTCTCAATTCAAAAAACCCCTCAAGACCCGTTTAGAGGCCCCAAGGGG<br>TTATGCTATCAATCGTTGCGTTACACACACAAAAAACCAACACACATCCATCTTCGATGGATAGCGA<br>TTTTATTATCTAACTGCTGATCGAGTGTAGCCAGATCTAGTAATCAATTACGGGGTCATTAGTTCAT<br>AGCCCATATATGGAGTTCCGCGTTACATAACTTACGGTAAATGGCCCGCCTGGCTGACCGCCCAACG<br>ACCCCCGCCCATTGACGTCAATAATGACGTATGTTCCCATAGTAACGCCAATAGGGACTTTCCATTG<br>ACGTCAATGGGTGGAGTATTTACGGTAAACTGCCCACTTGGCAGTACATCAAGTGTATCATATGCCA<br>AGTACGCCCCCTATTGACGTCAATGACGGTAAATGGCCCGCCTGGCATTATGCCCAGTACATGACCT<br>TATGGGACTTTCCTACTTGGCAGTACATCTACGTATTAGTCATCGCTATTACCATGCTGATGCGGTT<br>TTGGCAGTACATCAATGGGCGTGGATAGCGGTTTGACTCACGGGGATTTCCAAGTCTCCACCCCATT<br>GACGTCAATGGGAGTTTGTTTTGGCACCAAAATCAACGGGACTTTCCAAAATGTCGTAACAACTCCG<br>CCCCATTGACGCAAATGGGCGGTAGGCGTGTACGGTGGGAGGTCTATATAAGCAGAGCTGGTTTAGT<br>GAACCGTCAGATCAGATCTTTGTCGATCCTACCATCCACTCGACACACCCGCCAGCGGCCGCTAATA<br>CGACTCACTATAGGGAGAAGTACTGCCACCATGGGCAAGAAGCAAAATCGCAAGACGGGGAATTCCA<br>AGACACAATCCGCTAGCCCACCACCTAAAGAGCGTTCTAGCTCCCCTGCTACTGAGCAGTCCTGGAT<br>GGAAAACGACTTCGATGAACTCCGGGAAGAGGGATTTAGGCGATCCAACTATTCAGAACTCCGCGAA<br>GATATCCAGACAAAGGGGAAGGAAGTCGAGAATTTCGAGAAGAACCTCGAGGAGTGCATCACCCGTA<br>TCACAAACACTGAGAAATGTCTCAAAGAACTCATGGAACTTAAGACAAAAGCCAGGGAGCTTCGAGA<br>GGAGTGTCGGAGTCTGAGATCCAGGTGTGACCAGCTCGAGGAGCGCGTGAGCGCGATGGAAGACGAG<br>ATGAACGAGATGAAAAGAGAGGGCAAATTCAGGGAGAAGCGCATTAAGAGGAACGAACAGAGTCTGC<br>AGGAGATTTGGGATTACGTCAAGAGGCCTAACCTGCGGTTGATCGGCGTCCCCGAGAGCGACGTAGA<br>AAACGGGACTAAACTGGAGAATACACTTCAAGACATCATTCAAGAAAATTTTCCAAACCTGGCTCGG<br>CAAGCTAATGTGCAAATCCAAGAGATCCAACGCACACCCCAGCGGTATAGCTCTCGGCGTGCCACCC<br>CTAGGCATATTATCGTGCGCTTTACTAAGGTGGAGATGAAAGAGAAGATGCTGCGAGCCGCTCGGGA<br>AAAGGGAAGGGTGACTTTGAAGGGCAAACCTATTCGGCTGACGGTTGACCTTAGCGCCGAGACACTC<br>CAGGCACGCCGGGAATGGGGCCCCATCTTTAATATCCTGAAGGAGAAGAACTTCCAGCCACGAATCT<br>CTTACCCTGCAAAGTTGAGTTTTATCTCCGAGGGTGAGATTAAGTATTTCATCGATAAACAGATGCT<br>GCGAGACTTCGTGACAACTCGCCCAGCTCTCAAGGAACTGCTCAAAGAGGCTCTTAATATGGAGCGC<br>AATAATAGATATCAACCCTTGCAGAACCACGCAAAGATGTGAGACAGCCGTCAGACCATCAAGACTA<br>GGAAGAAACTGCATCAACTAATGAGCAAAATCACCAGCTAACATCATAGTATACATGccaaagaaga<br>agcggaaggtcggcggcggcagcACCGGCTCTAACTCACATATCACCATCCTTACACTTAACATTAA<br>CGGCCTCAACTCAGCTATCAAGCGCCATCGGCTGGCCAGCTGGATCAAATCACAGGATCCAAGCGTT<br>TGTTGCATCCAAGAGACCCACCTGACCTGTAGAGATACTCACCGCCTCAAGATCAAGGGATGGCGAA<br>AGATTTATCAGGCGAACGGTAAGCAGAAGAAAGCCGGAGTCGCAATTCTGGTCTCAGACAAGACGGA<br>TTTCAAGCCCACCAAAATTAAGCGTGATAAGGAAGGTCACTATATTATGGTGAAAGGCAGCATACAG<br>CAGGAAGAACTTACCATATTGAACATCTACGCGCCAAACACCGGCGCACCTCGCTTTATCAAACAGG<br>TCCTGTCCGATCTGCAGCGAGATCTGGATTCTCATACGTTGATTATGGGTGATTTCAATACACCATT<br>GAGCACCCTGGATCGCAGCACCAGGCAAAAGGTAAATAAAGACACGCAAGAGCTCAATAGCGCACTG<br>CATCAGGCAGATCTCATTGATATTTATCGCACTCTTCATCCTAAGAGTACCGAGTACACATTCTTCA<br>GCGCCCCACATCATACATACTCAAAGATCGATCATATCGTCGGCTCAAAGGCTCTGCTGTCAAAGTG |

TABLE 13-continued

Exemplary plasmid sequences

| Name | Sequence |
|---|---|
| | CAAGCGCACAGAGATAATTACAAATTACCTGTCAGATCATAGCGCGATCAAGCTCGAGCTGAGAATC |
| | AAGAACCTGACCCAGAGCCGGAGTACCACTTGGAAGCTTAATAACCTGCTGCTCAACGATTATTGGG |
| | TCCACAATGAGATGAAGGCAGAGATTAAAATGTTCTTCGAAACAAATGAGAATAAGGATACTACCTA |
| | TCAAAACCTTTGGGATGCCTTTAAGGCCGTCTGCAGAGGCAAGTTCATCGCCCTCAACGCCTATAAA |
| | AGAAAACAAGAGAGATCTAAGATCGATACTCTCACCTCTCAGCTGAAGGAGTTGGAGAAACAGGAAC |
| | AGACCCACTCCAAGGCGTCAAGACGGCAGGAGATCACAAAGATTCGCGCCGAGTTGAAAGAGATCGA |
| | AACCCAAAAGACTCTTCAGAAAATTAACGAGTCTCGTAGTTGGTTCTTCGAGCGGATTAATAAGATA |
| | GACAGACCTCTGGCACGACTGATTAAGAAGAAGCGCGAAAAGAACCAGATTGATACCATCAAGAACG |
| | ACAAGGGCGACATCACTACTGACCCGACCGAGATCCAGACCACTATTCGGGAGTATTATAAGCATTT |
| | GTATGCTAACAAGCTTGAGAACCTGGAAGAGATGGACACTTTTCTGGATACCTATACTCTGCCACGG |
| | CTTAATCAAGAGGAAGTCGAGTCCCTCAACCGCCCAATTACAGGAAGCGAGATTGTGGCCATAATTA |
| | ACTCCCTGCCGACAAAGAAATCTCCTGGTCCGGACGGGTTTACAGCTGAGTTTTATCAACGGTATAT |
| | GGAAGAGCTTGTACCGTTTCTGCTCAAGCTCTTTCAGTCTATAGAAAAGGAAGGCATCTTGCCCAAT |
| | TCCTTCTACGAAGCTTCTATAATACTTATTCCCAAACCAGGACGCGATACCACAAAGAAGGAAAACT |
| | TCCGGCCCATTAGTCTCATGAATATCGACGCTAAAATATTGAACAAGATTCTCGCCAACAGAATCCA |
| | ACAACATATTAAGAAATTGATACATCACGACCAGGTGGGGTTTATACCTGGCATGCAGGGCTGGTTT |
| | AACATCCGGAAGAGTATTAACGTCATTCAACACATTAATAGAGCTAAGGATAAGAATCATATGATCA |
| | TCTCTATAGACGCGGAAAAGGCATTCGATAAGATTCAGCAGCCATTTATGCTCAAGACTCTGAACAA |
| | ACTCGGCATCGACGGAACATATTTTAAGATTATTCGCGCAATTTACGATAAGCCGACTGCTAACATT |
| | ATCCTTAACGGCCAAAAGCTCGAGGCCTTTCCGCTCAAGACTGGAACCCGCCAAGGCTGTCCCCTCT |
| | CCCCGCTTTTGTTTAATATTGTACTCGAGGTGCTGGCTAGGGCTATTCGTCAAGAGAAAGAGATTAA |
| | AGGGATACAGCTCGGGAAGGAAGAGGTCAAGCTTTCCTTGTTCGCCGATGATATGATTGTGTACCTG |
| | GAGAATCCTATTGTGTCTGCTCAGAACCTTCTTAAACTTATTTCTAACTTTAGCAAGGTCAGCGGCT |
| | ATAAGATTAACGTCCAGAAATCTCAGGCCTTTCTGTACACAAATAATCGACAGACCGAATCCCAGAT |
| | AATGGGTGAGCTTCCGTTTGTCATAGCCAGCAAAAGGATAAAGTATCTCGGAATCCAGCTGACACGA |
| | GACGTTAAAGATTTGTTTAAGGAAAATTACAAGCCTCTCCTGAAAGAGATTAAGGAAGATACTAATA |
| | AGTGGAAGAATATCCCCTGTTCATGGGTTGGCAGAATCAACATAGTGAAGATGGCAATACTTCCTAA |
| | AGTGATATATCGCTTTAACGCCATCCCAATTAAACTGCCTATGACCTTCTTTACGGAGCTCGAGAAA |
| | ACAACCCTTAAATTTATATGGAATCAAAAGAGAGCAAGAATAGCGAAGTCCATCTTGAGCCAGAAGA |
| | ATAAGGCCGGTGGGATTACTTTGCCTGATTTTAAGTTGTATTATAAAGCCACAGTAACTAAGACAGC |
| | CTGGTATTGGTATCAGAATAGAGACATCGACCAGTGGAATCGGACCGAACCATCAGAGATAATGCCC |
| | CACATCTATAATTACCTTATATTCGATAAGCCAGAAAAGAATAAACAGTGGGGCAAAGACAGCCTCT |
| | TCAACAAGTGGTGTTGGGAGAATTGGCTGGCCATATGCCGGAAACTCAAGCTCGACCCCTTTCTTAC |
| | ACCCTACACTAAAATCAACAGTAGGTGGATCAAGGACTTGAATGTCAAGCCAAAGACTATAAAGACA |
| | CTGGAAGAGAATCTTGGGATCACAATACAAGATATAGGCGTCGGCAAAGATTTTATGTCAAAGACGC |
| | CCAAGGCCATGGCCACTAAGGATAAGATTGATAAGTGGGACCTTATTAAGCTCAAAAGCTTCTGTAC |
| | TGCCAAGGAGACCACGATCAGAGTTAATAGGCAGCCCACTACATGGGAAAAGATTTTCGCCACTTAT |
| | TCATCAGATAAGGGGTTGATAAGCAGAATATATAACGAGCTGAAGCAGATCTACAAGAAGAAAACGA |
| | ATAATCCCATCAAGAAGTGGGCAAAAGATATGAACAGGCATTTTAGCAAAGAGGATATCTACGCCGC |
| | GAAGAAGCATATGAAGAAGTGTAGTTCAAGCTTGGCCATTCGTGAGATGCAGATTAAGACGACCATG |
| | CGATACCACCTTACCCCAGTGAGGATGGCAATTATCAAGAAATCTGGCAATAATAGATGTTGGCGGG |
| | GCTGTGGCGAGATTGGCACCCTGCTCCATTGCTGGTGGGATTGCAAGCTGGTGCAGCCGCTTTGGAA |
| | ATCAGTCTGGCGCTTTCTGAGGGACCTCGAGCTTGAGATTCCCTTCGATCCCGCAATTCCCTTGCTC |
| | GGAATCTATCCTAACGAATACAAGAGCTGTTGTTACAAGGATACGTGTACCCGGATGTTCATCGCGG |
| | CCTTGTTTACGATAGCTAAGACGTGGAATCAGCCTAAGTGCCCCACAATGATCGATTGGATCAAGAA |
| | AATGTGGCATATTTATACCATGGAGTATTACGCAGCAATTAAGAATGACGAATTTATTTCCTTCGTT |
| | GGGACCTGGATGAAGCTGGAGACTATTATTCTGAGCAAGCTGTCTCAGGAGCAAAAGACAAAGCATA |
| | GAATCTTCTCTCTCATTGGTGGTAACGACTACAAAGACGATGACGACAAGaaaaggccggcggccac |
| | gaaaaaggccggccaggcaaaaaagaaaaagTAAAGCGCTTCTAGAAGTTGTCTCCTCCTGCACTGA |
| | CTGACTGATACAATCGATTTCTGGATCCGCAGGCCTAATCAACCTCTGGATTACAAAATTTGTGAAA |
| | GATTGACTGGTATTCTTAACTATGTTGCTCCTTTTACGCTATGTGGATACGCTGCTTTAATGCCTTT |
| | GTATCATGCTATTGCTTCCCGTATGGCTTTCATTTTCTCCTCCTTGTATAAATCCTGGTTGCTGTCT |
| | CTTTATGAGGAGTTGTGGCCCGTTGTCAGGCAACGTGGCGTGGTGTGCACTGTGTTTGCTGACGCAA |
| | CCCCCACTGGTTGGGGCATTGCCACCACCTGTCAGCTCCTTTCCGGGACTTTCGCTTTCCCCCTCCC |
| | TATTGCCACGGCGGAACTCATCGCCGCCTGCCTTGCCCGCTGCTGGACAGGGGCTCGGCTGTTGGGC |
| | ACTGACAATTCCGTGGTGTTGTCGGGGAAGCTGACGTCCTTTCCATGGCTGCTCGCCTGTGTTGCCA |
| | CCTGGATTCTGCGCGGGACGTCCTTCTGCTACGTCCCTTCGGCCCTCAATCCAGCGGACCTTCCTTC |
| | CCGCtgagagacacaaaaaattccaacacactattgcaatgaaaataaatttcctttattagccaga |
| | agtcagatgctcaaggggcttcatgatgtccccataattttggcagagggaaaaagatctcagtgg |
| | tatttgtgagccagggcattggccttctgataggcagcctgcacctgaggagtgcggccgctttact |
| | tgtacagctcgtccatgccgagagtgatcccggcggcggtcacgaactccagcaggaccatgtgatc |
| | gcgcttctcgttggggtctttgctcagggcggactgggtgctcaggtagtggttgtcgggcagcagc |
| | acggggccgtcgccgatgggggtgttctgctggtagtggtcggcgagctgcacgctgccgtcctcga |
| | tgttgtggcggatcttgaagttcaccttgatgccgttcttctgcttgtcggccatgatatagacgtt |
| | gtggctgttgtagttgtactccagcttgtgccccaggatgttgccgtcctccttgaagtcgatgccc |
| | ttcagctcgatgcggttcaccagggtgtcgccctcgaacttcacctcggcgcgggtcttgtagttgc |
| | cgtcgtccttgaagaagatggtgcgctcctggacgtagccttcgggcatggcggacttgaagaagtc |
| | gtgctgcttcatgtggtcggggtagcggctgaagcactgcacgccgtaggtcagggtggtcacgagg |
| | gtgggccagggcacgggcagcttgccggtggtgcagatgaacttcagggtcagcttgccgtaggtgg |
| | catcgccctcgccctcgccggacacgctgaacttgtggccgtttacgtcgccgtccagctcgaccag |
| | gatgggcaccaccccggtgaacagctcctcgcccttgctcaccatggtggcgggatctgacggttca |
| | ctaaaccagctctgcttatatagacctcccaccgtacacgcctaccgcccatttgcgtcaatggggc |
| | ggagttgttacgacattttggaaagtcccgttgattttggtgccaaaacaaactcccattgacgtca |
| | atggggtggagacttggaaatccccgtgagtcaaaccgctatccacgcccattgatgtactgccaaa |
| | accgcatcaccatggtaatagcgatgactaatacgtagatgtactgccaagtaggaaagtcccataa |
| | ggtcatgtactgggcataatgccaggcgggccatttaccgtcattgacgtcaatagggggcgtactt |

TABLE 13-continued

Exemplary plasmid sequences

| Name | Sequence |
|---|---|
| | ggcatatgatacacttgatgtactgccaagtgggcagtttaccgtaaatactccacccattgacgtc<br>aatggaaagtccctattggcgttactatgggaacatacgtcattattgacgtcaatgggcgggggtc<br>gttgggcggtcagccaggcgggccatttaccgtaagttatgtaacgGGCCTGCTGCCGGCTCTGCGG<br>CCTCTTCCGCGTCTTCGCCTTCGCCCTCAGACGAGTCGGATCTCCCTTTGGGCCGCCTCCCCGCCTG<br>TCTAGCTTGACTGACTGAGATACAGCGTACCTTCAGCTCACAGACATGATAAGATACATTGATGAGT<br>TTGGACAAACCACAACTAGAATGCAGTGAAAAAAATGCTTTATTTGTGAAATTTGTGATGCTATTGC<br>TTTATTTGTAACCATTATAAGCTGCAATAAACAAGTTAACAACAACAATTGCATTCATTTTATGTTT<br>CAGGTTCAGGGGGAGGTGTGGGAGGTTTTTTAAAGCAAGTAAAACCTCTACAAATGTGGTATTGGCC<br>CATCTCTATCGGTATCGTAGCATAACCCCTTGGGGCCTCTAAACGGGTCTTGAGGGGTTTTTTGTGC<br>CCCTCGGGCCGGATTGCTATCTACCGGCATTGGCGCAGAAAAAAATGCCTGATGCGACGCTGCGCGT<br>CTTATACTCCCACATATGCCAGATTCAGCAACGGATACGGCTTCCCCAACTTGCCCACTTCCATACG<br>TGTCCTCCTTACCAGAAATTTATCCTTAAGGTCGTCAGCTATCCTGCAGGCGATCTCTCGATTTCGA<br>TCAAGACATTCCTTTAATGGTCTTTTCTGGACACCACTAGGGGTCAGAAGTAGTTCATCAAACTTTC<br>TTCCCTCCCTAATCTCATTGGTTACCTTGGGCTATCGAAACTTAATTAAGCGATCTGCATCTCAATT<br>AGTCAGCAACCATAGTCCCGCCCCTAACTCCGCCCATCCCGCCCCTAACTCCGCCCAGTTCCGCCCA<br>TTCTCCGCCCCATCGCTGACTAATTTTTTTTATTTATGCAGAGGCCGAGGCCGCCTCGGCCTCTGAG<br>CTATTCCAGAAGTAGTGAGGAGGCTTTTTTGGAGGCCTAGGCTTTTGCAAAGGAGGTAGCCAACATG<br>ATTGAACAAGATGGATTGCACGCAGGTTCTCCCGCCGCTTGGGTGGAGAGGCTATTCGGCTATGACT<br>GGGCACAACAGACAATCGGCTGCTCTGATGCCGCCGTGTTCCGGCTGTCAGCGCAGGGGCGCCCGGT<br>TCTTTTTGTCAAGACCGACCTGTCCGGTGCCCTGAATGAACTCCAGGACGAGGCAGCGCGGCTATCG<br>TGGCTGGCCACGACGGGCGTTCCTTGCGCAGCTGTGCTCGACGTTGTCACTGAAGCGGGAAGGGACT<br>GGCTGCTATTGGGCGAAGTGCCGGGGCAGGATCTCCTGTCATCTCACCTTGCTCCTGCCGAGAAAGT<br>ATCCATCATGGCTGATGCAATGCGGCGGCTGCATACGCTTGATCCGGCTACCTGCCCATTCGACCAC<br>CAAGCGAAACATCGCATCGAGCGAGCACGTACTCGGATGGAAGCCGGTCTTGTCGATCAGGATGATC<br>TGGACGAAGAGCATCAGGGGCTCGCGCCAGCCGAACTGTTCGCCAGGCTCAAGGCGCGGATGCCCGA<br>CGGCGAGGATCTCGTCGTGACCCACGGCGATGCCTGCTTGCCGAATATCATGGTGGAAAATGGCCGC<br>TTTTCTGGATTCATCGACTGTGGCCGGCTGGGTGTGGCGGACCGCTATCAGGACATAGCGTTGGCTA<br>CCCGTGATATTGCTGAAGAGCTTGGCGGCGAATGGGCTGACCGCTTCCTCGTGCTTTACGGTATCGC<br>CGCTCCCGATTCGCAGCGCATCGCCTTCTATCGCCTTCTTGACGAGTTCTTCTAGTATGTAAGCCCT<br>GTGCCTTCTAGTTGCCAGCCATCTGTTGTTTGCCCCTCCCCCGTGCCTTCCTTGACCCTGGAAGGTG<br>CCACTCCCACTGTCCTTTCCTAATAAAATGAGGAAATTGCATCGCATTGTCTGAGTAGGTGTCATTC<br>TATTCTGGGGGGTGGGGTGGGGCAGGACAGCAAGGGGGAGGATTGGGAAGACAATAGCAGGCATGCT<br>GGGGATGCGGTGGGCTCTATGGTTAATTAACCAGTCAAGTCAGCTACTTGGCGAGATCGACTTGTCT<br>GGGTTTCGACTACGCTCAGAATTGCGTCAGTCAAGTTCGATCTGGTCCTTGCTATTGCACCCGTTCT<br>CCGATTAGGAGTTTCATTTAAATCATGTGAGCAAAAGGCCAGCAAAAGGCCAGGAACCGTAAAAAGG<br>CCGCGTTGCTGGCGTTTTTCCATAGGCTCCGCCCCCCTGACGAGCATCACAAAAATCGACGCTCAAG<br>TCAGAGGTGGCGAAACCCGACAGGACTATAAAGATACCAGGCGTTTCCCCCTGGAAGCTCCCTCGTG<br>CGCTCTCCTGTTCCGACCCTGCCGCTTACCGGATACCTGTCCGCCTTTCTCCCTTCGGGAAGCGTGG<br>CGCTTTCTCATAGCTCACGCTGTAGGTATCTCAGTTCGGTGTAGGTCGTTCGCTCCAAGCTGGGCTG<br>TGTGCACGAACCCCCCGTTCAGCCCGACCGCTGCGCCTTATCCGGTAACTATCGTCTTGAGTCCAAC<br>CCGGTAAGACACGACTTATCGCCACTGGCAGCAGCCACTGGTAACAGGATTAGCAGAGCGAGGTATG<br>TAGGCGGTGCTACAGAGTTCTTGAAGTGGTGGCCTAACTACGGCTACACTAGAAGAACAGTATTTGG<br>TATCTGCGCTCTGCTGAAGCCAGTTACCTTCGGAAAAAGAGTTGGTAGCTCTTGATCCGGCAAACAA<br>ACCACCGCTGGTAGCGGTGGTTTTTTTGTTTGCAAGCAGCAGATTACGCGCAGAAAAAAAGGATCTC<br>AAGAAGATCCTTTGATCTTTTCTACGGGGTCTGACGCTCAGTGGAACGAAAACTCACGTTAAGGGAT<br>TTTGGTCATGAGATTATCAAAAAGGATCTTCACCTAGATCCTTTTAAATTAAAAATGAAGTTTTAAA<br>TCAATCTAAAGTATATATGAGTAAACTTGGTCTGACAGTTACCAATGCTTAATCAGTGAGGCACCTA<br>TCTCAGCGATCTGTCTATTTCGTTCATCCATAGTTGCATTTAAATTTCCGAACTCTCCAAGGCCCTC<br>GTCGGAAAATCTTCAAACCTTTCGTCCGATCCATCTTGCAGGCTACCTCTCGAACGAACTATCGCAA<br>GTCTCT (SEQ ID NO: 108) |
| ret-028-<br>line1-<br>orf1-t2a-<br>orf2-<br>n_sv40_<br>nls_linker-<br>gfp | TGGCCGGCCTTGCGCCTTGGCTATTGCTTGGCAGCGCCTATCGCCAGGTATTACTCCAATCCCGAAT<br>ATCCGAGATCGGGATCACCCGAGAGAAGTTCAACCTACATCCTCAATCCCGATCTATCCGAGATCCG<br>AGGAATATCGAAATCGGGGCGCGCCTGGTGTACCGAGAACGATCCTCTCAGTGCGAGTCTCGACGAT<br>CCATATCGTTGCTTGGCAGTCAGCCAGTCGGAATCCAGCTTGGGACCCAGGAAGTCCAATCGTCAGA<br>TATTGTACTCAAGCCTGGTCACGGCAGCGTACCGATCTGTTTAAACCTAGATATTGATAGTCTGATC<br>GGTCAACGTATAATCGAGTCCTAGCTTTTGCAAACATCTATCAAGAGACAGGATCAGCAGGAGGCTT<br>TCGCATGAGTATTCAACATTTCCGTGTCGCCCTTATTCCCTTTTTTGCGGCATTTTGCCTTCCTGTT<br>TTTGCTCACCCAGAAACGCTGGTGAAAGTAAAAGATGCTGAAGATCAGTTGGGTGCGCGAGTGGGTT<br>ACATCGAACTGGATCTCAACAGCGGTAAGATCCTTGAGAGTTTTCGCCCCGAAGAACGCTTTCCAAT<br>GATGAGCACTTTTAAAGTTCTGCTATGTGGCGCGGTATTATCCCGTATTGACGCCGGGCAAGAGCAA<br>CTCGGTCGCCGCATACACTATTCTCAGAATGACTTGGTTGAGTATTCACCAGTCACAGAAAAGCATC<br>TTACGGATGGCATGACAGTAAGAGAATTATGCAGTGCTGCCATAACCATGAGTGATAACACTGCGGC<br>CAACTTACTTCTGACAACGATTGGAGGACCGAAGGAGCTAACCGCTTTTTTGCACAACATGGGGGAT<br>CATGTAACTCGCCTTGATCGTTGGGAACCGGAGCTGAATGAAGCCATACCAAACGACGAGCGTGACA<br>CCACGATGCCTGTAGCAATGGCAACAACCTTGCGTAAACTATTAACTGGCGAACTACTTACTCTAGC<br>TTCCCGGCAACAGTTGATAGACTGGATGGAGGCGGATAAAGTTGCAGGACCACTTCTGCGCTCGGCC<br>CTTCCGGCTGGCTGGTTTATTGCTGATAAATCTGGAGCCGGTGAGCGTGGGTCTCGCGGTATCATTG<br>CAGCACTGGGGCCAGATGGTAAGCCCTCCCGTATCGTAGTTATCTACACGACGGGGAGTCAGGCAAC<br>TATGGATGAACGAAATAGACAGATCGCTGAGATAGGTGCCTCACTGATTAAGCATTGGTAACCGATT<br>CTAGGTGCATTGGCGCAGAAAAAAATGCCTGATGCGACGCTGCGCGTCTTATACTCCCACATATGCC<br>AGATTCAGCAACGGATACGGCTTCCCCAACTTGCCCACTTCCATACGTGTCCTCCTTACCAGAAATT<br>TATCCTTAAGATCGTTTAAACTCGACTCTGGCTCTATCGAATCTCCGTCGTTTCGAGCTTACGCGAA<br>CAGCCGTGGCGCTCATTTGCTCGTCGGGCATCGAATCTCGTCAGCTATCGTCAGCTTACCTTTTTGG<br>CAGCGATCGCGGCTCCCGACATCTTGGACCATTAGCTCCACAGGTATCTTCTTCCCTCTAGTGGTCA<br>TAACAGCAGCTTCAGCTACCTCTCAATTCAAAAACCCCTCAAGACCCGTTTAGAGGCCCCAAGGGG |

TABLE 13-continued

Exemplary plasmid sequences

| Name | Sequence |
|---|---|
| | TTATGCTATCAATCGTTGCGTTACACACACAAAAAACCAACACACATCCATCTTCGATGGATAGCGA |
| | TTTTATTATCTAACTGCTGATCGAGTGTAGCCAGATCTAGTAATCAATTACGGGGTCATTAGTTCAT |
| | AGCCCATATATGGAGTTCCGCGTTACATAACTTACGGTAAATGGCCCGCCTGGCTGACCGCCCAACG |
| | ACCCCCGCCCATTGACGTCAATAATGACGTATGTTCCCATAGTAACGCCAATAGGGACTTTCCATTG |
| | ACGTCAATGGGTGGAGTATTTACGGTAAACTGCCCACTTGGCAGTACATCAAGTGTATCATATGCCA |
| | AGTACGCCCCCTATTGACGTCAATGACGGTAAATGGCCCGCCTGGCATTATGCCCAGTACATGACCT |
| | TATGGGACTTTCCTACTTGGCAGTACATCTACGTATTAGTCATCGCTATTACCATGCTGATGCGGTT |
| | TTGGCAGTACATCAATGGGCGTGGATAGCGGTTTGACTCACGGGGATTTCCAAGTCTCCACCCCATT |
| | GACGTCAATGGGAGTTTGTTTTGGCACCAAAATCAACGGGACTTTCCAAAATGTCGTAACAACTCCG |
| | CCCCATTGACGCAAATGGGCGGTAGGCGTGTACGGTGGGAGGTCTATATAAGCAGAGCTGGTTTAGT |
| | GAACCGTCAGATCAGATCTTTGTCGATCCTACCATCCACTCGACACACCCGCCAGCGGCCGCTAATA |
| | CGACTCACTATAGGGAGAAGTACTGCCACCATGGGCAAGAAGCAAAATCGCAAGACGGGGAATTCCA |
| | AGACACAATCCGCTAGCCCACCACCTAAAGAGCGTTCTAGCTCCCCTGCTACTGAGCAGTCCTGGAT |
| | GGAAAACGACTTCGATGAACTCCGGGAAGAGGGATTTAGGCGATCCAACTATTCAGAACTCCGCGAA |
| | GATATCCAGACAAAGGGGAAGGAAGTCGAGAATTTCGAGAAGAACCTCGAGGAGTGCATCACCCGTA |
| | TCACAAACACTGAGAAATGTCTCAAAGAACTCATGGAACTTAAGACAAAAGCCAGGGAGCTTCGAGA |
| | GGAGTGTCGGAGTCTGAGATCCAGGTGTGACCAGCTCGAGGAGCGCGTGAGCGCGATGGAAGACGAG |
| | ATGAACGAGATGAAAAGAGAGGGCAAATTCAGGGAGAAGCGCATTAAGAGGAACGAACAGAGTCTGC |
| | AGGAGATTTGGGATTACGTCAAGAGGCCTAACCTGCGGTTGATCGGCGTCCCCGAGAGCGACGTAGA |
| | AAACGGGACTAAACTGGAGAATACACTTCAAGACATCATTCAAGAAAATTTTCCAAACCTGGCTCGG |
| | CAAGCTAATGTGCAAATCCAAGAGATCCAACGCACACCCCAGCGGTATAGCTCTCGGCGTGCCACCC |
| | CTAGGCATATTATCGTGCGCTTTACTAAGGTGGAGATGAAAGAGAAGATGCTGCGAGCCGCTCGGGA |
| | AAAGGGAAGGGTGACTTTGAAGGGCAAACCTATTCGGCTGACGGTTGACCTTAGCGCCGAGACACTC |
| | CAGGCACGCCGGGAATGGGGCCCCATCTTTAATATCCTGAAGGAGAAGAACTTCCAGCCACGAATCT |
| | CTTACCCTGCAAAGTTGAGTTTTATCTCCGAGGGTGAGATTAAGTATTTCATCGATAAACAGATGCT |
| | GCGAGACTTCGTGACAACTCGCCCAGCTCTCAAGGAACTGCTCAAAGAGGCTCTTAATATGGAGCGC |
| | AATAATAGATATCAACCCTTGCAGAACCACGCAAAGATGggctccggcgagggcaggggaagCcttc |
| | taacatgcggggacgtggaggaaaatcccggcccaGGTAGCGGCccaaagaagaagcggaaggtcgg |
| | cggcggcagcACCGGCTCTAACTCACATATCACCATCCTTACACTTAACATTAACGGCCTCAACTCA |
| | GCTATCAAGCGCCATCGGCTGGCCAGCTGGATCAAATCACAGGATCCAAGCGTTTGTTGCATCCAAG |
| | AGACCCACCTGACCTGTAGAGATACTCACCGCCTCAAGATCAAGGGATGGCGAAAGATTTATCAGGC |
| | GAACGGTAAGCAGAAGAAAGCCGGAGTCGCAATTCTGGTCTCAGACAAGACGGATTTCAAGCCCACC |
| | AAAATTAAGCGTGATAAGGAAGGTCACTATATTATGGTGAAAGGCAGCATACAGCAGGAAGAACTTA |
| | CCATATTGAACATCTACGCGCCAAACACCGGCGCACCTCGCTTTATCAAACAGGTCCTGTCCGATCT |
| | GCAGCGAGATCTGGATTCTCATACGTTGATTATGGGTGATTTCAATACACCATTGAGCACCCTGGAT |
| | CGCAGCACCAGGCAAAAGGTAAATAAAGACACGCAAGAGCTCAATAGCGCACTGCATCAGGCAGATC |
| | TCATTGATATTTATCGCACTCTTCATCCTAAGAGTACCGAGTACACATTCTTCAGCGCCCCACATCA |
| | TACATACTCAAAGATCGATCATATCGTCGGCTCAAAGGCTCTGCTGTCAAAGTGCAAGCGCACAGAG |
| | ATAATTACAAATTAGCTGTCAGATCATAGCGCGATCAAGCTCGAGCTGAGAATCAAGAACCTGACCC |
| | AGAGCCGGAGTACCACTTGGAAGCTTAATAACCTGCTGCTCAACGATTATTGGGTCCACAATGAGAT |
| | GAAGGCAGAGATTAAAATGTTCTTCGAAACAAATGAGAATAAGGATACTACCTATCAAAACCTTTGG |
| | GATGCCTTTAAGGCCGTCTGCAGAGGCAAGTTCATCGCCCTCAACGCCTATAAAAGAAAACAAGAGA |
| | GATCTAAGATCGATACTCTCACCTCTCAGCTGAAGGAGTTGGAGAAACAGGAACAGACCCACTCCAA |
| | GGCGTCAAGACGGCAGGAGATCACAAAGATTCGCGCCGAGTTGAAAGAGATCGAAACCCAAAAGACT |
| | CTTCAGAAAATTAACGAGTCTCGTAGTTGGTTCTTCGAGCGGATTAATAAGATAGACAGACCTCTGG |
| | CACGACTGATTAAGAAGAAGCGCGAAAAGAACCAGATTGATACCATCAAGAACGACAAGGGCGACAT |
| | CACTACTGACCCGACCGAGATCCAGACCACTATTCGGGAGTATTATAAGCATTTGTATGCTAACAAG |
| | CTTGAGAACCTGGAAGAGATGGACACTTTTCTGGATACCTATACTCTGCCACGGCTTAATCAAGAGG |
| | AAGTCGAGTCCCTCAACCGCCCAATTACAGGAAGCGAGATTGTGGCCATAATTAACTCCCTGCCGAC |
| | AAAGAAATCTCCTGGTCCGGACGGGTTTACAGCTGAGTTTTATCAACGGTATATGGAAGAGCTTGTA |
| | CCGTTTCTGCTCAAGCTCTTTCAGTCTATAGAAAAGGAAGGCATCTTGCCCAATTCCTTCTACGAAG |
| | CTTCTATAATACTTATTCCCAAACCAGGACGCGATACCACAAAGAAGGAAAACTTCCGGCCCATTAG |
| | TCTCATGAATATCGACGCTAAAATATTGAACAAGATTCTCGCCAACAGAATCCAACAACATATTAAG |
| | AAATTGATACATCACGACCAGGTGGGGTTTATACCTGGCATGCAGGGCTGGTTTAACATCCGGAAGA |
| | GTATTAACGTCATTCAACACATTAATAGAGCTAAGGATAAGAATCATATGATCATCTCTATAGACGC |
| | GGAAAAGGCATTCGATAAGATTCAGCAGCCATTTATGCTCAAGACTCTGAACAAACTCGGCATCGAC |
| | GGAACATATTTTAAGATTATTCGCGCAATTTACGATAAGCCGACTGCTAACATTATCCTTAACGGCC |
| | AAAAGCTCGAGGCCTTTCCGCTCAAGACTGGAACCCGCCAAGGCTGTCCCCTCTCCCCGCTTTTGTT |
| | TAATATTGTACTCGAGGTGCTGGCTAGGGCTATTCGTCAAGAGAAAGAGATTAAAGGGATACAGCTC |
| | GGGAAGGAAGAGGTCAAGCTTTCCTTGTTCGCCGATGATATGATTGTGTACCTGGAGAATCCTATTG |
| | TGTCTGCTCAGAACCTTCTTAAACTTATTTCTAACTTTAGCAAGGTCAGCGGCTATAAGATTAACGT |
| | CCAGAAATCTCAGGCCTTTCTGTACACAAATAATCGACAGACCGAATCCCAGATAATGGGTGAGCTT |
| | CCGTTTGTCATAGCCAGCAAAAGGATAAAGTATCTCGGAATCCAGCTGACACGAGACGTTAAAGATT |
| | TGTTTAAGGAAAATTACAAGCCTCTCCTGAAAGAGATTAAGGAAGATACTAATAAGTGGAAGAATAT |
| | CCCCTGTTCATGGGTTGGCAGAATCAACATAGTGAAGATGGCAATACTTCCTAAAGTGATATATCGC |
| | TTTAACGCCATCCCAATTAAACTGCCTATGACCTTCTTTACGGAGCTCGAGAAAACAACCCTTAAAT |
| | TTATATGGAATCAAAAGAGAGCAAGAATAGCGAAGTCCATCTTGAGCCAGAAGAATAAGGCCGGTGG |
| | GATTACTTTGCCTGATTTTAAGTTGTATTATAAAGCCACAGTAACTAAGACAGCCTGGTATTGGTAT |
| | CAGAATAGAGACATCGACCAGTGGAATCGGACCGAACCATCAGAGATAATGCCCCACATCTATAATT |
| | ACCTTATATTCGATAAGCCAGAAAAGAATAAACAGTGGGGCAAAGACAGCCTCTTCAACAAGTGGTG |
| | TTGGGAGAATTGGCTGGCCATATGCCGGAAACTCAAGCTCGACCCCTTTCTTACACCCTACACTAAA |
| | ATCAACAGTAGGTGGATCAAGGACTTGAATGTCAAGCCAAAGACTATAAAGACACTGGAAGAGAATC |
| | TTGGGATCACAATACAAGATATAGGCGTCGGCAAAGATTTTATGTCAAAGACGCCCAAGGCCATGGC |
| | CACTAAGGATAAGATTGATAAGTGGGACCTTATTAAGCTCAAAAGCTTCTGTACTGCCAAGGAGACC |
| | ACGATCAGAGTTAATAGGCAGCCCACTACATGGGAAAAGATTTTCGCCACTTATTCATCAGATAAGG |
| | GGTTGATAAGCAGAATATATAACGAGCTGAAGCAGATCTACAAGAAGAAAACGAATAATCCCATCAA |

TABLE 13-continued

Exemplary plasmid sequences

| Name | Sequence |
| --- | --- |
| | GAAGTGGGCAAAAGATATGAACAGGCATTTTAGCAAAGAGGATATCTACGCCGCGAAGAAGCATATG<br>AAGAAGTGTAGTTCAAGCTTGGCCATTCGTGAGATGCAGATTAAGACGACCATGCGATACCACCTTA<br>CCCCAGTGAGGATGGCAATTATCAAGAAATCTGGCAATAATAGATGTTGGCGGGGCTGTGGCGAGAT<br>TGGCACCCTGCTCCATTGCTGGTGGGATTGCAAGCTGGTGCAGCCGCTTTGGAAATCAGTCTGGCGC<br>TTTCTGAGGGACCTCGAGCTTGAGATTCCCTTCGATCCCGCAATTCCCTTGCTCGGAATCTATCCTA<br>ACGAATACAAGAGCTGTTGTTACAAGGATACGTGTACCCGGATGTTCATCGCGGCCTTGTTTACGAT<br>AGCTAAGACGTGGAATCAGCCTAAGTGCCCCACAATGATCGATTGGATCAAGAAAATGTGGCATATT<br>TATACCATGGAGTATTACGCAGCAATTAAGAATGACGAATTTATTTCCTTCGTTGGGACCTGGATGA<br>AGCTGGAGACTATTATTCTGAGCAAGCTGTCTCAGGAGCAAAAGACAAAGCATAGAATCTTCTCTCT<br>CATTGGTGGTAACGACTACAAAGACGATGACGACAAGTAAAGCGCTTCTAGAAGTTGTCTCCTCCTG<br>CACTGACTGACTGATACAATCGATTTCTGGATCCGCAGGCCTAATCAACCTCTGGATTACAAAATTT<br>GTGAAAGATTGACTGGTATTCTTAACTATGTTGCTCCTTTTACGCTATGTGGATACGCTGCTTTAAT<br>GCCTTTGTATCATGCTATTGCTTCCCGTATGGCTTTCATTTTCTCCTCCTTGTATAAATCCTGGTTG<br>CTGTCTCTTTATGAGGAGTTGTGGCCCGTTGTCAGGCAACGTGGCGTGGTGTGCACTGTGTTTGCTG<br>ACGCAACCCCCACTGGTTGGGGCATTGCCACCACCTGTCAGCTCCTTTCCGGGACTTTCGCTTTCCC<br>CCTCCCTATTGCCACGGCGGAACTCATCGCCGCCTGCCTTGCCCGCTGCTGGACAGGGGCTCGGCTG<br>TTGGGCACTGACAATTCCGTGGTGTTGTCGGGGAAGCTGACGTCCTTTCCATGGCTGCTCGCCTGTG<br>TTGCCACCTGGATTCTGCGCGGGACGTCCTTCTGCTACGTCCCTTCGGCCCTCAATCCAGCGGACCT<br>TCCTTCCCGCtgagagacacaaaaaattccaacacactattgcaatgaaaataaatttcctttatta<br>gccagaagtcagatgctcaaggggcttcatgatgtccccataatttttggcagagggaaaaagatct<br>cagtggtatttgtgagccagggcattggccttctgataggcagcctgcacctgaggagtgcggccgc<br>tttacttgtacagctcgtccatgccgagagtgatcccggcggcggtcacgaactccagcaggaccat<br>gtgatcgcgcttctcgttggggtctttgctcagggcggactgggtgctcaggtagtggttgtcgggc<br>agcagcacggggccgtcgccgatgggggtgttctgctggtagtggtcggcgagctgcacgctgccgt<br>cctcgatgttgtggcggatcttgaagttcaccttgatgccgttcttctgcttgtcggccatgatata<br>gacgttgtggctgttgtagttgtactccagcttgtgccccaggatgttgccgtcctccttgaagtcg<br>atgcccttcagctcgatgcggttcaccagggtgtcgccctcgaacttcacctcggcgcgggtcttgt<br>agttgccgtcgtccttgaagaagatggtgcgctcctggacgtagccttcgggcatggcggacttgaa<br>gaagtcgtgctgcttcatgtggtcggggtagcggctgaagcactgcacgccgtaggtcagggtggtc<br>acgagggtgggccagggcacgggcagcttgccggtggtgcagatgaacttcagggtcagcttgccgt<br>aggtggcatcgccctcgccctcgccggacacgctgaacttgtggccgtttacgtcgccgtccagctc<br>gaccaggatgggcaccaccccggtgaacagctcctcgcccttgctcaccatggtggcgggatctgac<br>ggttcactaaaccagctctgcttatatagacctcccaccgtacacgcctaccgcccatttgcgtcaa<br>tggggcggagttgttacgacattttggaaagtcccgttgattttggtgccaaaacaaactcccattg<br>acgtcaatggggtggagacttggaaatccccgtgagtcaaaccgctatccacgcccattgatgtact<br>gccaaaaccgcatcaccatggtaatagcgatgactaatacgtagatgtactgccaagtaggaaagtc<br>ccataaggtcatgtactgggcataatgccaggcgggccatttaccgtcattgacgtcaataggggc<br>gtacttggcatatgatacacttgatgtactgccaagtgggcagtttaccgtaaatactccacccatt<br>gacgtcaatggaaagtccctattggcgttactatgggaacatacgtcattattgacgtcaatgggcg<br>ggggtcgttgggcggtcagccaggcgggccatttaccgtaagttatgtaacgGGCCTGCTGCCGGCT<br>CTGCGGCCTCTTCCGCGTCTTCGCCTTCGCCCTCAGACGAGTCGGATCTCCCTTTGGGCCGCCTCCC<br>CGCCTGTCTAGCTTGACTGACTGAGATACAGCGTACCTTCAGCTCACAGACATGATAAGATACATTG<br>ATGAGTTTGGACAAACCACAACTAGAATGCAGTGAAAAAAATGCTTTATTTGTGAAATTTGTGATGC<br>TATTGCTTTATTTGTAACCATTATAAGCTGCAATAAACAAGTTAACAACAACAATTGCATTCATTTT<br>ATGTTTCAGGTTCAGGGGGAGGTGTGGGAGGTTTTTTAAAGCAAGTAAAACCTCTACAAATGTGGTA<br>TTGGCCCATCTCTATCGGTATCGTAGCATAACCCCTTGGGGCCTCTAAACGGGTCTTGAGGGGTTTT<br>TTGTGCCCCTCGGGCCGGATTGCTATCTACCGGCATTGGCGCAGAAAAAAATGCCTGATGCGACGCT<br>GCGCGTCTTATACTCCCACATATGCCAGATTCAGCAACGGATACGGCTTCCCCAACTTGCCCACTTC<br>CATACGTGTCCTCCTTACCAGAAATTTATCCTTAAGGTCGTCAGCTATCCTGCAGGCGATCTCTCGA<br>TTTCGATCAAGACATTCCTTTAATGGTCTTTTCTGGACACCACTAGGGGTCAGAAGTAGTTCATCAA<br>ACTTTCTTCCCTCCCTAATCTCATTGGTTACCTTGGGCTATCGAAACTTAATTAAGCGATCTGCATC<br>TCAATTAGTCAGCAACCATAGTCCCGCCCCTAACTCCGCCCATCCCGCCCCTAACTCCGCCCAGTTC<br>CGCCCATTCTCCGCCCCATCGCTGACTAATTTTTTTTATTTATGCAGAGGCCGAGGCCGCCTCGGCC<br>TCTGAGCTATTCCAGAAGTAGTGAGGAGGCTTTTTTGGAGGCCTAGGCTTTTGCAAAGGAGGTAGCC<br>AACATGATTGAACAAGATGGATTGCACGCAGGTTCTCCGGCCGCTTGGGTGGAGAGGCTATTCGGCT<br>ATGACTGGGCACAACAGACAATCGGCTGCTCTGATGCCGCCGTGTTCCGGCTGTCAGCGCAGGGGCG<br>CCCGGTTCTTTTTGTCAAGACCGACCTGTCCGGTGCCCTGAATGAACTCCAGGACGAGGCAGCGCGG<br>CTATCGTGGCTGGCCACGACGGGCGTTCCTTGCGCAGCTGTGCTCGACGTTGTCACTGAAGCGGGAA<br>GGGACTGGCTGCTATTGGGCGAAGTGCCGGGGCAGGATCTCCTGTCATCTCACCTTGCTCCTGCCGA<br>GAAAGTATCCATCATGGCTGATGCAATGCGGCGGCTGCATACGCTTGATCCGGCTACCTGCCCATTC<br>GACCACCAAGCGAAACATCGCATCGAGCGAGCACGTACTCGGATGGAAGCCGGTCTTGTCGATCAGG<br>ATGATCTGGACGAAGAGCATCAGGGGCTCGCGCCAGCCGAACTGTTCGCCAGGCTCAAGGCGCGGAT<br>GCCCGACGGCGAGGATCTCGTCGTGACCCACGGCGATGCCTGCTTGCCGAATATCATGGTGGAAAAT<br>GGCCGCTTTTCTGGATTCATCGACTGTGGCCGGCTGGGTGTGGCGGACCGCTATCAGGACATAGCGT<br>TGGCTACCCGTGATATTGCTGAAGAGCTTGGCGGCGAATGGGCTGACCGCTTCCTCGTGCTTTACGG<br>TATCGCCGCTCCCGATTCGCAGCGCATCGCCTTCTATCGCCTTCTTGACGAGTTCTTCTAGTATGTA<br>AGCCCTGTGCCTTCTAGTTGCCAGCCATCTGTTGTTTGCCCCTCCCCCGTGCCTTCCTTGACCCTGG<br>AAGGTGCCACTCCCACTGTCCTTTCCTAATAAAATGAGGAAATTGCATCGCATTGTCTGAGTAGGTG<br>TCATTCTATTCTGGGGGGTGGGGTGGGGCAGGACAGCAAGGGGGAGGATTGGGAAGACAATAGCAGG<br>CATGCTGGGGATGCGGTGGGCTCTATGGTTAATTAACCAGTCAAGTCAGCTACTTGGCGAGATCGAC<br>TTGTCTGGGTTTCGACTACGCTCAGAATTGCGTCAGTCAAGTTCGATCTGGTCCTTGCTATTGCACC<br>CGTTCTCCGATTACGAGTTTCATTTAAATCATGTGAGCAAAAGGCCAGCAAAAGGCCAGGAACCGTA<br>AAAAGGCCGCGTTGCTGGCGTTTTTCCATAGGCTCCGCCCCCCTGACGAGCATCACAAAAATCGACG<br>CTCAAGTCAGAGGTGGCGAAACCCGACAGGACTATAAAGATACCAGGCGTTTCCCCCTGGAAGCTCC<br>CTCGTGCGCTCTCCTGTTCCGACCCTGCCGCTTACCGGATACCTGTCCGCCTTTCTCCCTTCGGGAA<br>GCGTGGCGCTTTCTCATAGCTCACGCTGTAGGTATCTCAGTTCGGTGTAGGTCGTTCGCTCCAAGCT |

TABLE 13-continued

Exemplary plasmid sequences

| Name | Sequence |
|---|---|
| | GGGCTGTGTGCACGAACCCCCCGTTCAGCCCGACCGCTGCGCCTTATCCGGTAACTATCGTCTTGAG<br>TCCAACCCGGTAAGACACGACTTATCGCCACTGGCAGCAGCCACTGGTAACAGGATTAGCAGAGCGA<br>GGTATGTAGGCGGTGCTACAGAGTTCTTGAAGTGGTGGCCTAACTACGGCTACACTAGAAGAACAGT<br>ATTTGGTATCTGCGCTCTGCTGAAGCCAGTTACCTTCGGAAAAAGAGTTGGTAGCTCTTGATCCGGC<br>AAACAAACCACCGCTGGTAGCGGTGGTTTTTTTGTTTGCAAGCAGCAGATTACGCGCAGAAAAAAAG<br>GATCTCAAGAAGATCCTTTGATCTTTTCTACGGGGTCTGACGCTCAGTGGAACGAAAACTCACGTTA<br>AGGGATTTTGGTCATGAGATTATCAAAAAGGATCTTCACCTAGATCCTTTTAAATTAAAAATGAAGT<br>TTTAAATCAATCTAAAGTATATATGAGTAAACTTGGTCTGACAGTTACCAATGCTTAATCAGTGAGG<br>CACCTATCTCAGCGATCTGTCTATTTCGTTCATCCATAGTTGCATTTAAATTTCCGAACTCTCCAAG<br>GCCCTCGTCGGAAAATCTTCAAACCTTTCGTCCGATCCATCTTGCAGGCTACCTCTCGAACGAACTA<br>TCGCAAGTCTCT (SEQ ID NO: 109) |
| ret-029-line1-orf1-t2a-orf-c_nucleo-plasmin_nls-gfp | ACCGAGAACGATCCTCTCAGTGCGAGTCTCGACGATCCATATCGTTGCTTGGCAGTCAGCCAGTCGG<br>AATCCAGCTTGGGACCCAGGAAGTCCAATCGTCAGATATTGTACTCAAGCCTGGTCACGGCAGCGTA<br>CCGATCTGTTTAAACCTAGATATTGATAGTCTGATCGGTCAACGTATAATCGAGTCCTAGCTTTTGC<br>AAACATCTATCAAGAGACAGGATCAGCAGGAGGCTTTCGCATGAGTATTCAACATTTCCGTGTCGCC<br>CTTATTCCCTTTTTTGCGGCATTTTGCCTTCCTGTTTTTGCTCACCCAGAAACGCTGGTGAAAGTAA<br>AAGATGCTGAAGATCAGTTGGGTGCGCGAGTGGGTTACATCGAACTGGATCTCAACAGCGGTAAGAT<br>CCTTGAGAGTTTTCGCCCCGAAGAACGCTTTCCAATGATGAGCACTTTTAAAGTTCTGCTATGTGGC<br>GCGGTATTATCCCGTATTGACGCCGGGCAAGAGCAACTCGGTCGCCGCATACACTATTCTCAGAATG<br>ACTTGGTTGAGTATTCACCAGTCACAGAAAAGCATCTTACGGATGGCATGACAGTAAGAGAATTATG<br>CAGTGCTGCCATAACCATGAGTGATAACACTGCGGCCAACTTACTTCTGACAACGATTGGAGGACCG<br>AAGGAGCTAACCGCTTTTTTGCACAACATGGGGGATCATGTAACTCGCCTTGATCGTTGGGAACCGG<br>AGCTGAATGAAGCCATACCAAACGACGAGCGTGACACCACGATGCCTGTAGCAATGGCAACAACCTT<br>GCGTAAACTATTAACTGGCGAACTACTTACTCTAGCTTCCCGGCAACAGTTGATAGACTGGATGGAG<br>GCGGATAAAGTTGCAGGACCACTTCTGCGCTCGGCCCTTCCGGCTGGCTGGTTTATTGCTGATAAAT<br>CTGGAGCCGGTGAGCGTGGGTCTCGCGGTATCATTGCAGCACTGGGGCCAGATGGTAAGCCCTCCCG<br>TATCGTAGTTATCTACACGACGGGGAGTCAGGCAACTATGGATGAACGAAATAGACAGATCGCTGAG<br>ATAGGTGCCTCACTGATTAAGCATTGGTAACCGATTCTAGGTGCATTGGCGCAGAAAAAAATGCCTG<br>ATGCGACGCTGCGCGTCTTATACTCCCACATATGCCAGATTCAGCAACGGATACGGCTTCCCCAACT<br>TGCCCACTTCCATACGTGTCCTCCTTACCAGAAATTTATCCTTAAGATCGTTTAAACTCGACTCTGG<br>CTCTATCGAATCTCCGTCGTTTCGAGCTTACGCGAACAGCCGTGGCGCTCATTTGCTCGTCGGGCAT<br>CGAATCTCGTCAGCTATCGTCAGCTTACCTTTTTGGCAGCGATCGCGGCTCCCGACATCTTGGACCA<br>TTAGCTCCACAGGTATCTTCTTCCCTCTAGTGGTCATAACAGCAGCTTCAGCTACCTCTCAATTCAA<br>AAAACCCCTCAAGACCCGTTTAGAGGCCCCAAGGGGTTATGCTATCAATCGTTGCGTTACACACACA<br>AAAAACCAACACACATCCATCTTCGATGGATAGCGATTTTATTATCTAACTGCTGATCGAGTGTAGC<br>CAGATCTAGTAATCAATTACGGGGTCATTAGTTCATAGCCCATATATGGAGTTCCGCGTTACATAAC<br>TTACGGTAAATGGCCCGCCTGGCTGACCGCCCAACGACCCCCGCCCATTGACGTCAATAATGACGTA<br>TGTTCCCATAGTAACGCCAATAGGGACTTTCCATTGACGTCAATGGGTGGAGTATTTACGGTAAACT<br>GCCCACTTGGCAGTACATCAAGTGTATCATATGCCAAGTACGCCCCCTATTGACGTCAATGACGGTA<br>AATGGCCCGCCTGGCATTATGCCCAGTACATGACCTTATGGGACTTTCCTACTTGGCAGTACATCTA<br>CGTATTAGTCATCGCTATTACCATGCTGATGCGGTTTTGGCAGTACATCAATGGGCGTGGATAGCGG<br>TTTGACTCACGGGGATTTCCAAGTCTCCACCCCATTGACGTCAATGGGAGTTTGTTTTGGCACCAAA<br>ATCAACGGGACTTTCCAAAATGTCGTAACAACTCCGCCCCATTGACGCAAATGGGCGGTAGGCGTGT<br>ACGGTGGGAGGTCTATATAAGCAGAGCTGGTTTAGTGAACCGTCAGATCAGATCTTTGTCGATCCTA<br>CCATCCACTCGACACACCCGCCAGCGGCCGCTAATACGACTCACTATAGGGAGAAGTACTGCCACCA<br>TGGGCAAGAAGCAAAATCGCAAGACGGGGAATTCCAAGACACAATCCGCTAGCCCACCACCTAAAGA<br>GCGTTCTAGCTCCCCTGCTACTGAGCAGTCCTGGATGGAAAACGACTTCGATGAACTCCGGGAAGAG<br>GGATTTAGGCGATCCAACTATTCAGAACTCCGCGAAGATATCCAGACAAAGGGGAAGGAAGTCGAGA<br>ATTTCGAGAAGAACCTCGAGGAGTGCATCACCCGTATCACAAACACTGAGAAATGTCTCAAAGAACT<br>CATGGAACTTAAGACAAAAGCCAGGGAGCTTCGAGAGGAGTGTCGGAGTCTGAGATCCAGGTGTGAC<br>CAGCTCGAGGAGCGCGTGAGCGCGATGGAAGACGAGATGAACGAGATGAAAAGAGAGGGCAAATTCA<br>GGGAGAAGCGCATTAAGAGGAACGAACAGAGTCTGCAGGAGATTTGGGATTACGTCAAGAGGCCTAA<br>CCTGCGGTTGATCGGCGTCCCCGAGAGCGACGTAGAAAACGGGACTAAACTGGAGAATACACTTCAA<br>GACATCATTCAAGAAAATTTTCCAAACCTGGCTCGGCAAGCTAATGTGCAAATCCAAGAGATCCAAC<br>GCACACCCCAGCGGTATAGCTCTCGGCGTGCCACCCCTAGGCATATTATCGTGCGCTTTACTAAGGT<br>GGAGATGAAAGAGAAGATGCTGCGAGCCGCTCGGGAAAAGGGAAGGGTGACTTTGAAGGGCAAACCT<br>ATTCGGCTGACGGTTGACCTTAGCGCCGAGACACTCCAGGCACGCCGGGAATGGGGCCCCATCTTTA<br>ATATCCTGAAGGAGAAGAACTTCCAGCCACGAATCTCTTACCCTGCAAAGTTGAGTTTTATCTCCGA<br>GGGTGAGATTAAGTATTTCATCGATAAACAGATGCTGCGAGACTTCGTGACAACTCGCCCAGCTCTC<br>AAGGAACTGCTCAAAGAGGCTCTTAATATGGAGCGCAATAATAGATATCAACCCTTGCAGAACCACG<br>CAAAGATGggctccggcgagggcaggggaagCcttctaacatgcggggacgtggaggaaaatcccgg<br>cccaGGTAGCGGCACCGGCTCTAACTCACATATCACCATCCTTACACTTAACATTAACGGCCTCAAC<br>TCAGCTATCAAGCGCCATCGGCTGGCCAGCTGGATCAAATCACAGGATCCAAGCGTTTGTTGCATCC<br>AAGAGACCCACCTGACCTGTAGAGATACTCACCGCCTCAAGATCAAGGGATGGCGAAAGATTTATCA<br>GGCGAACGGTAAGCAGAAGAAAGCCGGAGTCGCAATTCTGGTCTCAGACAAGACGGATTTCAAGCCC<br>ACCAAAATTAAGCGTGATAAGGAAGGTCACTATATTATGGTGAAAGGCAGCATACAGCAGGAAGAAC<br>TTACCATATTGAACATCTACGCGCCAAACACCGGCGCACCTCGCTTTATCAAACAGGTCCTGTCCGA<br>TCTGCAGCGAGATCTGGATTCTCATACGTTGATTATGGGTGATTTCAATACACCATTGAGCACCCTG<br>GATCGCAGCACCAGGCAAAAGGTAAATAAAGACACGCAAGAGCTCAATAGCGCACTGCATCAGGCAG<br>ATCTCATTGATATTTATCGCACTCTTCATCCTAAGAGTACCGAGTACACATTCTTCAGCGCCCCACA<br>TCATACATACTCAAAGATCGATCATATCGTCGGCTCAAAGGCTCTGCTGTCAAAGTGCAAGCGCACA<br>GAGATAATTACAAATTACCTGTCAGATCATAGCGCGATCAAGCTCGAGCTGAGAATCAAGAACCTGA<br>CCCAGAGCCGGAGTACCACTTGGAAGCTTAATAACCTGCTGCTCAACGATTATTGGGTCCACAATGA<br>GATGAAGGCAGAGATTAAAATGTTCTTCGAAACAAATGAGAATAAGGATACTACCTATCAAAACCTT<br>TGGGATGCCTTTAAGGCCGTCTGCAGAGGCAAGTTCATCGCCCTCAACGCCTATAAAAGAAAACAAG |

TABLE 13-continued

Exemplary plasmid sequences

| Name | Sequence |
|---|---|
| | AGAGATCTAAGATCGATACTCTCACCTCTCAGCTGAAGGAGTTGGAGAAACAGGAACAGACCCACTC<br>CAAGGCGTCAAGACGGCAGGAGATCACAAAGATTCGCGCCGAGTTGAAAGAGATCGAAACCCAAAAG<br>ACTCTTCAGAAAATTAACGAGTCTCGTAGTTGGTTCTTCGAGCGGATTAATAAGATAGACAGACCTC<br>TGGCACGACTGATTAAGAAGAAGCGCGAAAAGAACCAGATTGATACCATCAAGAACGACAAGGGCGA<br>CATCACTACTGACCCGACCGAGATCCAGACCACTATTCGGGAGTATTATAAGCATTTGTATGCTAAC<br>AAGCTTGAGAACCTGGAAGAGATGGACACTTTTCTGGATACCTATACTCTGCCACGGCTTAATCAAG<br>AGGAAGTCGAGTCCCTCAACCGCCCAATTACAGGAAGCGAGATTGTGGCCATAATTAACTCCCTGCC<br>GACAAAGAAATCTCCTGGTCCGGACGGGTTTACAGCTGAGTTTTATCAACGGTATATGGAAGAGCTT<br>GTACCGTTTCTGCTCAAGCTCTTTCAGTCTATAGAAAAGGAAGGCATCTTGCCCAATTCCTTCTACG<br>AAGCTTCTATAATACTTATTCCCAAACCAGGACGCGATACCACAAAGAAGGAAAACTTCCGGCCCAT<br>TAGTCTCATGAATATCGACGCTAAAATATTGAACAAGATTCTCGCCAACAGAATCCAACAACATATT<br>AAGAAATTGATACATCACGACCAGGTGGGGTTTATACCTGGCATGCAGGGCTGGTTTAACATCCGGA<br>AGAGTATTAACGTCATTCAACACATTAATAGAGCTAAGGATAAGAATCATATGATCATCTCTATAGA<br>CGCGGAAAAGGCATTCGATAAGATTCAGCAGCCATTTATGCTCAAGACTCTGAACAAACTCGGCATC<br>GACGGAACATATTTTAAGATTATTCGCGCAATTTACGATAAGCCGACTGCTAACATTATCCTTAACG<br>GCCAAAAGCTCGAGGCCTTTCCGCTCAAGACTGGAACCCGCCAAGGCTGTCCCCTCTCCCCGCTTTT<br>GTTTAATATTGTACTCGAGGTGCTGGCTAGGGCTATTCGTCAAGAGAAAGAGATTAAAGGGATACAG<br>CTCGGGAAGGAAGAGGTCAAGCTTTCCTTGTTCGCCGATGATATGATTGTGTACCTGGAGAATCCTA<br>TTGTGTCTGCTCAGAACCTTCTTAAACTTATTTCTAACTTTAGCAAGGTCAGCGGCTATAAGATTAA<br>CGTCCAGAAATCTCAGGCCTTTCTGTACACAAATAATCGACAGACCGAATCCCAGATAATGGGTGAG<br>CTTCCGTTTGTCATAGCCAGCAAAAGGATAAAGTATCTCGGAATCCAGCTGACACGAGACGTTAAAG<br>ATTTGTTTAAGGAAAATTACAAGCCTCTCCTGAAAGAGATTAAGGAAGATACTAATAAGTGGAAGAA<br>TATCCCCTGTTCATGGGTTGGCAGAATCAACATAGTGAAGATGGCAATACTTCCTAAAGTGATATAT<br>CGCTTTAACGCCATCCCAATTAAACTGCCTATGACCTTCTTTACGGAGCTCGAGAAAACAACCCTTA<br>AATTTATATGGAATCAAAAGAGAGCAAGAATAGCGAAGTCCATCTTGAGCCAGAAGAATAAGGCCGG<br>TGGGATTACTTTGCCTGATTTTAAGTTGTATTATAAAGCCACAGTAACTAAGACAGCCTGGTATTGG<br>TATCAGAATAGAGACATCGACCAGTGGAATCGGACCGAACCATCAGAGATAATGCCCCACATCTATA<br>ATTACCTTATATTCGATAAGCCAGAAAAGAATAAACAGTGGGGCAAAGACAGCCTCTTCAACAAGTG<br>GTGTTGGGAGAATTGGCTGGCCATATGCCGGAAACTCAAGCTCGACCCCTTTCTTACACCCTACACT<br>AAAATCAACAGTAGGTGGATCAAGGACTTGAATGTCAAGCCAAAGACTATAAAGACACTGGAAGAGA<br>ATCTTGGGATCACAATACAAGATATAGGCGTCGGCAAAGATTTTATGTCAAAGACGCCCAAGGCCAT<br>GGCCACTAAGGATAAGATTGATAAGTGGGACCTTATTAAGCTCAAAAGCTTCTGTACTGCCAAGGAG<br>ACCACGATCAGAGTTAATAGGCAGCCCACTACATGGGAAAAGATTTTCGCCACTTATTCATCAGATA<br>AGGGGTTGATAAGCAGAATATATAACGAGCTGAAGCAGATCTACAAGAAGAAAACGAATAATCCCAT<br>CAAGAAGTGGGCAAAAGATATGAACAGGCATTTTAGCAAAGAGGATATCTACGCCGCGAAGAAGCAT<br>ATGAAGAAGTGTAGTTCAAGCTTGGCCATTCGTGAGATGCAGATTAAGACGACCATGCGATACCACC<br>TTACCCCAGTGAGGATGGCAATTATCAAGAAATCTGGCAATAATAGATGTTGGCGGGGCTGTGGCGA<br>GATTGGCACCCTGCTCCATTGCTGGTGGGATTGCAAGCTGGTGCAGCCGCTTTGGAAATCAGTCTGG<br>CGCTTTCTGAGGGACCTCGAGCTTGAGATTCCCTTCGATCCCGCAATTCCCTTGCTCGGAATCTATC<br>CTAACGAATACAAGAGCTGTTGTTACAAGGATACGTGTACCCGGATGTTCATCGCGGCCTTGTTTAC<br>GATAGCTAAGACGTGGAATCAGCCTAAGTGCCCCACAATGATCGATTGGATCAAGAAAATGTGGCAT<br>ATTTATACCATGGAGTATTACGCAGCAATTAAGAATGACGAATTTATTTCCTTCGTTGGGACCTGGA<br>TGAAGCTGGAGACTATTATTCTGAGCAAGCTGTCTCAGGAGCAAAAGACAAAGCATAGAATCTTCTC<br>TCTCATTGGTGGTAACGACTACAAAGACGATGACGACAAGaaaaggccggcggccacgaaaaaggcc<br>ggccaggcaaaaaagaaaaagTAAAGCGCTTCTAGAAGTTGTCTCCTCCTGCACTGACTGACTGATA<br>CAATCGATTTCTGGATCCGCAGGCCTAATCAACCTCTGGATTACAAAATTTGTGAAAGATTGACTGG<br>TATTCTTAACTATGTTGCTCCTTTTACGCTATGTGGATACGCTGCTTTAATGCCTTTGTATCATGCT<br>ATTGCTTCCCGTATGGCTTTCATTTTCTCCTCCTTGTATAAATCCTGGTTGCTGTCTCTTTATGAGG<br>AGTTGTGGCCCGTTGTCAGGCAACGTGGCGTGGTGTGCACTGTGTTTGCTGACGCAACCCCCACTGG<br>TTGGGGCATTGCCACCACCTGTCAGCTCCTTTCCGGGACTTTCGCTTTCCCCCTCCCTATTGCCACG<br>GCGGAACTCATCGCCGCCTGCCTTGCCCGCTGCTGGACAGGGGCTCGGCTGTTGGGCACTGACAATT<br>CCGTGGTGTTGTCGGGGAAGCTGACGTCCTTTCCATGGCTGCTCGCCTGTGTTGCCACCTGGATTCT<br>GCGCGGGACGTCCTTCTGCTACGTCCCTTCGGCCCTCAATCCAGCGGACCTTCCTTCCCGCtgagag<br>acacaaaaaattccaacacactattgcaatgaaaataaatttcctttattagccagaagtcagatgc<br>tcaaggggcttcatgatgtccccataattttggcagagggaaaaagatctcagtggtatttgtgag<br>ccagggcattggccttctgataggcagcctgcacctgaggagtgcggccgctttacttgtacagctc<br>gtccatgccgagagtgatcccggcggcggtcacgaactccagcaggaccatgtgatcgcgcttctcg<br>ttggggtctttgctcagggcggactgggtgctcaggtagtggttgtcgggcagcagcacggggccgt<br>cgccgatgggggtgttctgctggtagtggtcggcgagctgcacgctgccgtcctcgatgttgtggcg<br>gatcttgaagttcaccttgatgccgttcttctgcttgtcggccatgatatagacgttgtggctgttg<br>tagttgtactccagcttgtgccccaggatgttgccgtcctccttgaagtcgatgcccttcagctcga<br>tgcggttcaccagggtgtcgccctcgaacttcacctcggcgcgggtcttgtagttgccgtcgtcctt<br>gaagaagatggtgcgctcctggacgtagccttcgggcatggcggacttgaagaagtcgtgctgcttc<br>atgtggtcggggtagcggctgaagcactgcacgccgtaggtcagggtggtcacgagggtgggccagg<br>gcacgggcagcttgccggtggtgcagatgaacttcagggtcagcttgccgtaggtggcatcgccctc<br>gccctcgccggacacgctgaacttgtggccgtttacgtcgccgtccagctcgaccaggatgggcacc<br>accccggtgaacagctcctcgcccttgctcaccatggtggcgggatctgacggttcactaaaccagc<br>tctgcttatatagacctcccaccgtacacgcctaccgcccatttgcgtcaatggggcggagttgtta<br>cgacattttggaaagtcccgttgattttggtgccaaaacaaactcccattgacgtcaatggggtgga<br>gacttggaaatccccgtgagtcaaaccgctatccacgcccattgatgtactgccaaaaccgcatcac<br>catggtaatagcgatgactaatacgtagatgtactgccaagtaggaaagtcccataaggtcatgtac<br>tgggcataatgccaggcgggccatttaccgtcattgacgtcaataggggggcgtacttggcatatgat<br>acacttgatgtactgccaagtgggcagtttaccgtaaatactccacccattgacgtcaatggaaagt<br>ccctattggcgttactatgggaacatacgtcattattgacgtcaatgggcgggggtcgttgggcggt<br>cagccaggcgggccatttaccgtaagttatgtaacgGGCCTGCTGCCGGCTCTGCGGCCTCTTCCGC<br>GTCTTCGCCTTCGCCCTCAGACGAGTCGGATCTCCCTTTGGGCCGCCTCCCCGCCTGTCTAGCTTGA |

TABLE 13-continued

| Exemplary plasmid sequences | |
|---|---|
| Name | Sequence |
| | CTGACTGAGATACAGCGTACCTTCAGCTCACAGACATGATAAGATACATTGATGAGTTTGGACAAAC CACAACTAGAATGCAGTGAAAAAAATGCTTTATTTGTGAAATTTGTGATGCTATTGCTTTATTTGTA ACCATTATAAGCTGCAATAAACAAGTTAACAACAACAATTGCATTCATTTTATGTTTCAGGTTCAGG GGGAGGTGTGGGAGGTTTTTTAAAGCAAGTAAAACCTCTACAAATGTGGTATTGGCCCATCTCTATC GGTATCGTAGCATAACCCCTTGGGGCCTCTAAACGGGTCTTGAGGGGTTTTTTGTGCCCCTCGGGCC GGATTGCTATCTACCGGCATTGGCGCAGAAAAAAATGCCTGATGCGACGCTGCGCGTCTTATACTCC CACATATGCCAGATTCAGCAACGGATACGGCTTCCCCAACTTGCCCACTTCCATACGTGTCCTCCTT ACCAGAAATTTATCCTTAAGGTCGTCAGCTATCCTGCAGGCGATCTCTCGATTTCGATCAAGACATT CCTTTAATGGTCTTTTCTGGACACCACTAGGGGTCAGAAGTAGTTCATCAAACTTTCTTCCCTCCCT AATCTCATTGGTTACCTTGGGCTATCGAAACTTAATTAAGCGATCTGCATCTCAATTAGTCAGCAAC CATAGTCCCGCCCCTAACTCCGCCCATCCCGCCCCTAACTCCGCCCAGTTCCGCCCATTCTCCGCCC CATCGCTGACTAATTTTTTTTATTTATGCAGAGGCCGAGGCCGCCTCGGCCTCTGAGCTATTCCAGA AGTAGTGAGGAGGCTTTTTTGGAGGCCTAGGCTTTTGCAAAGGAGGTAGCCAACATGATTGAACAAG ATGGATTGCACGCAGGTTCTCCCGCCGCTTGGGTGGAGAGGCTATTCGGCTATGACTGGGCACAACA GACAATCGGCTGCTCTGATGCCGCCGTGTTCCGGCTGTCAGCGCAGGGGCGCCCGGTTCTTTTTGTC AAGACCGACCTGTCCGGTGCCCTGAATGAACTCCAGGACGAGGCAGCGCGGCTATCGTGGCTGGCCA CGACGGGCGTTCCTTGCGCAGCTGTGCTCGACGTTGTCACTGAAGCGGGAAGGGACTGGCTGCTATT GGGCGAAGTGCCGGGGCAGGATCTCCTGTCATCTCACCTTGCTCCTGCCGAGAAAGTATCCATCATG GCTGATGCAATGCGGCGGCTGCATACGCTTGATCCGGCTACCTGCCCATTCGACCACCAAGCGAAAC ATCGCATCGAGCGAGCACGTACTCGGATGGAAGCCGGTCTTGTCGATCAGGATGATCTGGACGAAGA GCATCAGGGGCTCGCGCCAGCCGAACTGTTCGCCAGGCTCAAGGCGCGGATGCCCGACGGCGAGGAT CTCGTCGTGACCCACGGCGATGCCTGCTTGCCGAATATCATGGTGGAAAATGGCCGCTTTTCTGGAT TCATCGACTGTGGCCGGCTGGGTGTGGCGGACCGCTATCAGGACATAGCGTTGGCTACCCGTGATAT TGCTGAAGAGCTTGGCGGCGAATGGGCTGACCGCTTCCTCGTGCTTTACGGTATCGCCGCTCCCGAT TCGCAGCGCATCGCCTTCTATCGCCTTCTTGACGAGTTCTTCTAGTATGTAAGCCCTGTGCCTTCTA GTTGCCAGCCATCTGTTGTTTGCCCCTCCCCCGTGCCTTCCTTGACCCTGGAAGGTGCCACTCCCAC TGTCCTTTCCTAATAAAATGAGGAAATTGCATCGCATTGTCTGAGTAGGTGTCATTCTATTCTGGGG GGTGGGGTGGGGCAGGACAGCAAGGGGGAGGATTGGGAAGACAATAGCAGGCATGCTGGGGATGCGG TGGGCTCTATGGTTAATTAACCAGTCAAGTCAGCTACTTGGCGAGATCGACTTGTCTGGGTTTCGAC TACGCTCAGAATTGCGTCAGTCAAGTTCGATCTGGTCCTTGCTATTGCACCCGTTCTCCGATTACGA GTTTCATTTAAATCATGTGAGCAAAAGGCCAGCAAAAGGCCAGGAACCGTAAAAAGGCCGCGTTGCT GGCGTTTTTCCATAGGCTCCGCCCCCCTGACGAGCATCACAAAAATCGACGCTCAAGTCAGAGGTGG CGAAACCCGACAGGACTATAAAGATACCAGGCGTTTCCCCCTGGAAGCTCCCTCGTGCGCTCTCCTG TTCCGACCCTGCCGCTTACCGGATACCTGTCCGCCTTTCTCCCTTCGGGAAGCGTGGCGCTTTCTCA TAGCTCACGCTGTAGGTATCTCAGTTCGGTGTAGGTCGTTCGCTCCAAGCTGGGCTGTGTGCACGAA CCCCCCGTTCAGCCCGACCGCTGCGCCTTATCCGGTAACTATCGTCTTGAGTCCAACCCGGTAAGAC ACGACTTATCGCCACTGGCAGCAGCCACTGGTAACAGGATTAGCAGAGCGAGGTATGTAGGCGGTGC TACAGAGTTCTTGAAGTGGTGGCCTAACTACGGCTACACTAGAAGAACAGTATTTGGTATCTGCGCT CTGCTGAAGCCAGTTACCTTCGGAAAAAGAGTTGGTAGCTCTTGATCCGGCAAACAAACCACCGCTG GTAGCGGTGGTTTTTTTGTTTGCAAGCAGCAGATTACGCGCAGAAAAAAAGGATCTCAAGAAGATCC TTTGATCTTTTCTACGGGGTCTGACGCTCAGTGGAACGAAAACTCACGTTAAGGGATTTTGGTCATG AGATTATCAAAAAGGATCTTCACCTAGATCCTTTTAAATTAAAAATGAAGTTTTAAATCAATCTAAA GTATATATGAGTAAACTTGGTCTGACAGTTACCAATGCTTAATCAGTGAGGCACCTATCTCAGCGAT CTGTCTATTTCGTTCATCCATAGTTGCATTTAAATTTCCGAACTCTCCAAGGCCCTCGTCGGAAAAT CTTCAAACCTTTCGTCCGATCCATCTTGCAGGCTACCTCTCGAACGAACTATCGCAAGTCTCTTGGC CGGCCTTGCGCCTTGGCTATTGCTTGGCAGCGCCTATCGCCAGGTATTACTCCAATCCCGAATATCC GAGATCGGGATCACCCGAGAGAAGTTCAACCTACATCCTCAATCCCGATCTATCCGAGATCCGAGGA ATATCGAAATCGGGGCGCGCCTGGTGT (SEQ ID NO: 110) |

Example 22. Effects of Introducing a Nuclear Export Signal on Retrotransposition by Human LINE1 Constructs In this example, addition of a nuclear export sequence is tested for improving translation of the cargo sequence. Addition of an NES at the C terminal or N terminal of the GFP is tested for increase in expression. Addition of multiple NESs at the C terminal or N terminal of the GFP is tested for increase in expression. Larger cargo (larger than 5 kB coding sequence, or larger than 7.5 kB coding sequence), will be tested to see if NES has effect on cargo of certain sizes. Additional cargo may be tested that specifically require trans-golgi or ER localization, e.g., cargo having a transmembrane domain.

Example 23. Screen for Efficient LINE1 System for Retrotransposition of Various Human Cells In this example, a phylogenetic screen is undertaken across a large number of organisms using bioinformatics followed by laboratory testing, for selecting one or more hyperactive retrotransposon element that can efficiently move within human genome. Over 10 million LINE-1 sequences from 503 different genomes were identified (Ivancevic et al., 2016), including ORF1 and ORF2 proteins with novel domain variations. Among these, the 'hyperactive'LINE-1 species were shown to display retrotransposition activity superior to that of human, rat and mouse. These elements will be cloned into LINE-1-GFPai plasmid and screened in HEK293T cells. Test mRNA constructs comprising a sequence encoding GFP along with a promoter and a poly A sequence, inserted in reverse orientation relative to the ORF1/2 genes in the retrotransposon complex as described elsewhere in the specification are used for electroporating the cells. Efficiency of integration is determined by flow cytometry and PCR. As above, GFP is measured in negative control and positive control to set gates for flow cytometry. As above, an exemplary negative control used will be set at <0.1% GFP+. As above, an exemplary positive control used will be set at >90% GFP+. Integration will be tested using PCR. An exemplary measurement indicative of successful integration is measurement of GFP expression, as determined by flow cytometry, in >10% of cells by day 10 post retrotransposition.

Example 24. Improvement of Cargo Gene Expression

To improve the cargo gene expression, various cargo gene promoters and poly(A) signals will be tested. To improve the cargo gene expression, various insertions of a short constitutively spliced introns will also be tested. To improve the cargo gene expression, codon optimized sequences, such as those generated using various alternative codon algorithms, will also be tested. As above, GFP is measured in negative control and positive control to set gates for flow cytometry. As above, an exemplary negative control used will be set at <0.1% GFP+. As above, an exemplary positive control used will be set at >90% GFP+. An exemplary measurement indicative of successful cargo gene expression is measurement of increased GFP expression, as determined by flow cytometry, in >10% of cells by day 10 post retrotransposition.

Example 25. Adapting Efficiency-Optimized Retrotransposon System for In Vivo Cargo Gene Delivery The retrotransposon mRNA will be engineered for in vivo delivery using liver-targeting LNPs to detect an intracellular or secreted protein, in mice. Cell-type specific miRNA targets in the 3' UTR of the cargo gene mRNA will be applied to target it for degradation in undesirable cell types. LNPs will be tested for efficient delivery in vivo. Mice will be administered the LNP encapsulated mRNA constructs that comprise a sequence encoding GFP along with a promoter and a poly A sequence flanking the GFP encoding sequence. The GFP gene is inserted in reverse orientation relative to the ORF1/2 genes in the retrotransposon complex as described elsewhere in the specification. Protein expression will be examined by imaging and test mice will be sacrificed and tissues harvested for histological analysis and PCR at determined time points.

Cell-specific targeting is achieved following systemic administration of the LNP encapsulated mRNA wherein the LNPs comprise surface modification to display antibodies or ligands that recognize cognate counterparts in the target cell.

Cell specific targeting is tested following designing specific constructs, wherein the UTRs are modified to encode one or more cell-type specific miRNA. When the recombinant mRNA is taken up by a cell that is not the intended target cell, miRNA present in the cell will bind to and destroy the mRNA. Hence the mRNA can express in the intended cell type.

An exemplary measurement indicative of successful in vivo mRNA delivery to liver measurement of GFP expression, as determined by flow cytometry or histology in hepatocytes.

Example 26. Targeting Retrotransposition to Specific Genomic Locations

In this example, retrotransposition design modifications are undertaken for increasing specificity of targeting at specific genomic locations. Retrotransposon fusion constructs are generated in which a targeting moiety is incorporated to ensure increase in targeting specificity of the ORF2p. One method is to retarget LINE1 elements with cargo to specifically integrate into one of the genomic safe harbor (GHS) sites with a high and sustainable transcriptional activity. AAVS1, CCR5 and ROSA26 are some of the GHS sites. As described above, specific LINE1 elements are selected after suitable screen for identifying an efficient LINE1 element that readily transposes in human. The selected LINE1 can be one that integrates into one of the GHS loci.

Another method is that the retrotransposon ORF2 is engineered bearing fusion of ORF2 with Cas9 and its mutants. Other candidates elements having a heterologous DNA binding domain with or without endonuclease activity are Cpf1, zinc finger element, TAL effector, Cas6-8 'cascade', restriction endonuclease) which will either replace or complement the endonuclease domain of ORF2p.

The addition of homology arms of different length around the mRNA cargo will also be tested.

An exemplary construct is designed, comprising sequences encoding: ORF1; RT and dCas9; the cargo gene in antisense orientation, and a guide RNA to target site for priming RT activity. In one exemplary construct use of two guide RNA is tested, each fused to a dCas9 nickase, to determine if introducing nicks upstream and downstream of targeted locations improves site-specific integration and orientation of gene cargo.

Exemplary constructs are designed and tested in which the ORF2p lacks an EN (deleted), and is fused with a Cas 9 or its mutants, a Cas 12a (Cpf1), a Cas6-8 'cascade', a Meganuclease, a Zinc-finger nuclease, a TALEN, or a restriction endonuclease, which directs the specificity and introduces the nicks on the genomic DNA.

Exemplary constructs are designed and tested in which the ORF2p comprises a mutant EN that has reduced or altered activity, and is fused with a Cas 9 or its mutants, a Cas 12a (Cpf1), a Cas6-8 'cascade', a Meganuclease, a Zinc-finger nuclease, a TALEN, or a restriction endonuclease, which directs the specificity and introduces the nicks on the genomic DNA. For example, constructs are designed and tested in which retrotransposon plasmids will be engineered that encode a fusion of ORF2 protein with Cas9 and Cas9 mutants. mRNA containing ORF1, and mRNA encoding RT and dCas9 and the cargo gene in antisense orientation, and pegRNA will be delivered to target sites for priming RT activity. The use of two sgRNA, each fused to a dCas9 nickase, may be evaluated to determine if introducing nicks upstream and downstream of targeted locations improves site-specific integration and orientation of gene cargo. If modified LINE-1 RT fusion protein can bind its own mRNA and transport to nucleus, pegRNA could target genomic region and prime RT activity (via dCas9 nickase activity) so the LINE-1 RT can reverse transcribe mRNA gene cargo for integration into genomic DNA.

Efficiency of integration will be determined by flow cytometry. above, GFP is measured in negative control and positive control to set gates for flow cytometry. As above, an exemplary negative control used will be set at <0.1% GFP+. As above, an exemplary positive control used will be set at >90% GFP+. Integration will be confirmed by PCR. The sites of genomic integration are analyzed using NGS. Any construct with preferential integration in the specific genome location is subjected to several cycles of directed evolution to improve its efficiency and/or integration precision. An exemplary measurement indicative of successful gene integration and expression is 90% of cargo gene integrations detected in a specific genome location and GFP expression, as determined by flow cytometry, in >2% of cells by day 10 post retrotransposition.

What is claimed is:

1. A method of expressing an exogenous human therapeutic polypeptide encoded by an exogenous sequence from a site-specifically integrated genomic DNA sequence of target human cells, the method comprising:

(a) contacting a composition to the target human cells, the composition comprising one or more nanoparticle delivery vehicles encapsulating:

(I) an RNA molecule encoding a Cas nickase, (II) a first guide RNA or a polynucleic acid encoding the first guide RNA, wherein the first guide RNA specifically targets a sequence upstream of a genomic DNA target site of the target human cells, (III) a second guide RNA or a polynucleic acid encoding the second guide RNA, wherein the second guide RNA specifically targets a sequence downstream of the genomic DNA target site of the target human cells, and (IV) one or more RNA molecules, wherein the one or more RNA molecules comprise a first RNA molecule comprising:

(i) a sequence that is a reverse complement of a DNA sequence that encodes the exogenous human therapeutic polypeptide; and (ii) a mobile genetic element, wherein the mobile genetic element comprises an RNA sequence encoding a polypeptide with target-primed reverse transcription (TPRT) activity, wherein the polypeptide with TPRT activity comprises an endonuclease domain with a mutation that abrogates endonuclease activity of the endonuclease domain, wherein the polypeptide with TPRT activity comprises a human ORF2p polypeptide having an amino acid sequence with at least 90% sequence identity to the amino acid sequence of SEQ ID NO: 59, and wherein the human ORF2p has a mutation at D205 of SEQ ID NO: 59 that abrogates endonuclease activity of the endonuclease;

wherein the target human cells uptake the one or more nanoparticle delivery vehicles;

(b) translating the RNA sequence encoding the polypeptide with TPRT activity and translating the RNA sequence encoding the Cas nickase;

(c) introducing nicks upstream and downstream of the genomic DNA target site of the target human cells via the Cas nickase translated in (b) guided by the first guide RNA and the second guide RNA;

(d) reverse transcribing the sequence that is the reverse complement of the DNA sequence that encodes the human therapeutic polypeptide via the TPRT activity of the polypeptide with TPRT activity translated in (b), thereby producing a DNA sequence encoding the exogenous human therapeutic polypeptide;

(e) integrating the DNA sequence encoding the exogenous human therapeutic polypeptide produced in step (d) into nicked genomic DNA target site of the target human cells, wherein the nicked genomic DNA target site of the target human cells is a non-ribosomal genomic DNA target site; and (f) expressing the exogenous human therapeutic polypeptide in the target human cells, wherein the exogenous human therapeutic polypeptide is expressed from the DNA sequence integrated into the genomic DNA of the target human cells in step (e);

wherein the DNA sequence encoding the exogenous human therapeutic polypeptide produced in (d) that is integrated into the genomic DNA target site of the target human cells in (e) is less than 7.5 kb in length.

2. The method of claim 1, wherein the polypeptide with TPRT activity comprises an amino acid sequence with at least 95% sequence identity to the amino acid sequence of SEQ ID NO: 59.

3. The method of claim 1, wherein the one or more RNA molecules further comprise a second RNA molecule comprising a sequence encoding a LINE1 ORF1p polypeptide with at least 90% sequence identity to the amino acid sequence of SEQ ID NO: 57.

4. The method of claim 2, wherein the RNA sequence encoding the polypeptide with TPRT activity comprises a sequence having at least 80% sequence identity to SEQ ID NO: 60.

5. The method of claim 1, wherein the polypeptide with TPRT activity comprises the amino acid sequence of SEQ ID NO: 59, with the proviso that amino acid D205 of SEQ ID NO: 59 is mutated.

6. The method of claim 1, wherein the polynucleic acid encoding the first guide RNA and the second guide RNA is a DNA.

7. The method of claim 1, wherein the Cas nickase is a Cas9 nickase, and wherein each of the first guide RNA and the second guide RNA is fused to a Cas9 nickase.

8. The method of claim 1, wherein the DNA sequence encoding the exogenous human therapeutic polypeptide produced in (d) that is integrated into the genomic DNA target site of the target human cells in (e) is from 1 kb to 5 kb in length.

9. The method of claim 1, wherein the target human cells are primary cells.

10. The method of claim 1, wherein the first RNA molecule comprises a homology arm complementary to a sequence comprising the target site in the genomic DNA.

11. The method of claim 1, wherein (e) does not comprise integrating the DNA sequence encoding the exogenous human therapeutic polypeptide produced in step (c) into the genomic DNA at a poly T site.

12. The method of claim 5, wherein the first RNA molecule has a total length of from 3 kb to 20 kb.

13. The method of claim 1, wherein the exogenous human therapeutic polypeptide is selected from the group consisting of a ligand, an antibody, a receptor, an enzyme, a transport protein, a structural protein, a hormone, a contractile protein, a storage protein and a transcription factor.

14. The method of claim 13, wherein the exogenous human therapeutic polypeptide is a receptor selected from the group consisting of a chimeric antigen receptor (CAR) and a T cell receptor (TCR).

15. The method of claim 1, wherein the composition is a pharmaceutical composition formulated for systemic administration to a human subject.

16. The method of claim 5, wherein the human ORF2p polypeptide is fused to a nuclear localization signal (NLS).

17. The method of claim 1, wherein the second first RNA molecule lacks a 3' UTR sequence.

18. The method of claim 1, wherein the DNA sequence encoding the exogenous human therapeutic polypeptide does not comprise introns.

19. The method of claim 1, wherein the target human cells are immune cells selected from the group consisting of T cells, B cells, myeloid cells, monocytes, macrophages and dendritic cells.

20. The method of claim 1, wherein the one or more RNA molecules (i) is formulated in a nanoparticle selected from the group consisting of a lipid nanoparticle and a polymeric nanoparticle; and/or (ii) comprise a glycosylated RNA molecule, a circular RNA molecule or a self-replicating RNA molecule.

21. The method of claim 1, wherein the first RNA molecule comprises:

an RNA sequence encoding human ORF1p with at least 95% sequence identity to the amino acid sequence of SEQ ID NO: 57, and an RNA sequence encoding a human ORF2p with at least 95% sequence identity to the amino acid sequence of SEQ ID NO: 59 and;

wherein the Cas nickase is a Cas9 nickase.

* * * * *